(12) United States Patent
Kuhn et al.

(10) Patent No.: US 9,585,392 B2
(45) Date of Patent: Mar. 7, 2017

(54) 3-PHENYLISOXAZOLIN DERIVATIVES WITH HERBICIDAL ACTION

(71) Applicant: BAYER CROPSCIENCE AG, Monheim (DE)

(72) Inventors: Birgit Kuhn, Kelkheim (DE); Lothar Willms, Hofheim (DE); Thomas Frenzel, Cologne (DE); Klaus Bernhard Haaf, Kelkheim (DE); Stephen David Lindell, Kelkheim (DE); Hansjörg Dietrich, Liederbach am Taunus (DE); Dirk Schmutzler, Hattersheim (DE); Elmar Gatzweiler, Bad Nauheim (DE); Christopher Hugh Rosinger, Hofheim (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/430,018

(22) PCT Filed: Sep. 19, 2013

(86) PCT No.: PCT/EP2013/069453
§ 371 (c)(1),
(2) Date: Mar. 20, 2015

(87) PCT Pub. No.: WO2014/048827
PCT Pub. Date: Apr. 3, 2014

(65) Prior Publication Data
US 2015/0245615 A1    Sep. 3, 2015

(30) Foreign Application Priority Data
Sep. 25, 2012    (EP) .................................... 12185768

(51) Int. Cl.
*A01N 43/80*    (2006.01)
*C07D 261/04*    (2006.01)

(52) U.S. Cl.
CPC ........... *A01N 43/80* (2013.01); *C07D 261/04* (2013.01)

(58) Field of Classification Search
None
See application file for complete search history.

(56) References Cited

U.S. PATENT DOCUMENTS

| | | | |
|---|---|---|---|
| 5,939,418 A | 8/1999 | Quan et al. | |
| 6,150,303 A | 11/2000 | Menke et al. | |
| 9,078,442 B2 | 7/2015 | Willms et al. | |
| 2015/0223461 A1 | 8/2015 | Frenzel et al. | |
| 2015/0245616 A1 | 9/2015 | Haaf et al. | |

FOREIGN PATENT DOCUMENTS

| | | |
|---|---|---|
| EP | 0174685 A2 | 3/1986 |
| WO | 9203053 A1 | 3/1992 |
| WO | 95/14680 | 6/1995 |
| WO | 9514680 A1 | 6/1995 |
| WO | 9905130 A1 | 2/1999 |
| WO | 2005021515 A2 | 3/2005 |
| WO | 2005021516 A1 | 3/2005 |
| WO | 2005051931 A2 | 6/2005 |
| WO | 2008035315 A2 | 3/2008 |

OTHER PUBLICATIONS

Priya et al., "Isoxazoline Derivatives As Antimicrobials" Heterocyclic Communications. vol. 12, No. 1: 35-42, (2006).
Gucma et al., "Synthesis and fungicidal activity of substituted isoxazolecarboxamides" Pesticides. pp. 21-31, (2010).
Quan et al., "Design and Synthesis of Isoxazoline Derivatives as Factor Xa Inhibitors" J. Med. Chem. vol. 42: 2760-2773, (1999).
Nagarajan et al., "Synthesis of some isoxazolines and evaluation of carbon-13 NMR substituent parameters for 5-methyl substitution" Indian Journal of Chemistry. vol. 32B: 938-941, (1993).
Bannikov et al., "Some heterocyclic derivatives of sterically hindered phenols" Russian Chemical Bulletin. vol. 45, No. 2: 410-413, (1996).
International Search Report from corresponding PCT/EP2013/069453, mailed Nov. 29, 2013.
Gucma et al., "Synthesis and Fungicidal Activity of Substituted Isoxazolecarboxamides", XP008159982, Pestycydy/Pesticides, 2010, (1-4), pp. 21-31.
Bannikov et al., "Some Heterocyclic Derivatives of Sterically Hindered Phenols", Russian Chemical Bulletin, vol. 45, No. 2, Feb. 1996, Moscow, Russian Federation, pp. 410-413.
Nagarajan et al., "Synthesis of Some Isoxazolines and Evaluatio of Carbon-13 NMR Substituent Parameters for 5- methyl substitution", Indian Journal of Chemistry, vol. 32B, Sep. 1993, Tamil Nadu, India, pp. 938-941.
Priya, et al., "Isoxazoline Derivatives as Antimicrobials", vol. 12, No. 1, 2006, Department of Studies of Chemistry, University of Mysore, Mysore, India, pp. 35-42.
Quan, et al., "Design and Synthesis of Isoxazoline Derivatives as Factor Xa Inhibitors", XP002213660, J. Med. Chem. 1999, 42, pp. 2760-2773.

(Continued)

*Primary Examiner* — Kamal Saeed
(74) *Attorney, Agent, or Firm* — McBee Moore Woodward Vanik IP LLC

(57) ABSTRACT

3-Phenylisoxazoline derivatives of the formula (I), and the use thereof as herbicides, are described.

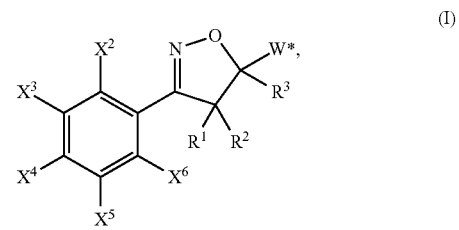

(I)

In this formula (I), $X^2$ to $X^6$ and $R^1$ to $R^3$ are radicals such as hydrogen, halogen, and organic radicals such as substituted alkyl. $W^*$ is carboxyl, cyano or CHO.

32 Claims, No Drawings

(56) References Cited

OTHER PUBLICATIONS

M.L. Quan et al. "Bisbenzamidine Isoxazoline Derivatives as Factor Xa Inhibitors", (1997) Bioorganic & Medical Chemistry Letters, vol. 7, No. 21, pp. 2813-2818.

Mimi L. Quan et al. Design and Synthesis of Isoxazoline Derivatives as Factor Xa Inhibitors. 2., (1998), J. Med. Chem. vol. 42, pp. 2760-2773.

Nagarajan et al. "An Improved Synthesis of Isoxazolines Based on Torssell's Procedure", (1993), Indian Journal of Chemistry vol. 32B, Apr. 1993 pp. 471-474.

U.S. Appl. No. 14/430,066, filed Mar. 20, 2015.

U.S. Appl. No. 14/429,914, filed Mar. 20, 2015.

3-PHENYLISOXAZOLIN DERIVATIVES WITH HERBICIDAL ACTION

CROSS REFERENCE TO RELATED APPLICATIONS

This application is a §371 National Stage Application of PCT/EP2013/069453, filed Sep. 19, 2013, which claims priority to EP 12185768.4, filed Sep. 25, 2012.

BACKGROUND

Field of the Invention

The invention relates to the technical field of herbicides, especially that of herbicides for selective control of broadleaved weeds and weed grasses in crops of useful plants.

Description of Related Art

WO1999/05130 A1 discloses herbicidally active 3-phenylisoxazolines substituted in the 5 position by a hydroxyl and trifluoromethyl group inter alia. WO2005/021516 A1, WO1995/014680 A1, WO 2008/035315 A1, WO2005/051931 A1 and WO2005/021515 A1 each describe, inter alia, 3-phenylisoxazoline-5-carboxylic acids, -carboxylic esters and -carbaldehydes substituted on the phenyl ring in the 3 and 4 positions by alkoxy radicals. These compounds are described as precursors for preparation of pharmacologically active 3-arylisoxazoline-5-carboxamides. J. Med. Chem. 42 (1999) 2760 described the compounds methyl 3-(3-cyanophenyl)-5-methyl-4,5-dihydro-1,2-oxazole-5-carboxylate, ethyl 3-(3-cyanophenyl)-5-methyl-4,5-dihydro-1,2-oxazole-5-carboxylate, 3-(3-cyanophenyl)-5-methyl-4,5-dihydro-1,2-oxazole-5-carboxylic acid and methyl 3-(3-cyanophenyl)-5-(methoxymethyl)-4,5-dihydro-1,2-oxazole-5-carboxylate as pharmacologically active. Indian Journal of Chemistry, Section B: Organic Chemistry Including Medicinal Chemistry (1993), 32B(9), 938-41 discloses the compound methyl 5-methyl-3-(3-nitrophenyl)-4,5-dihydro-1,2-oxazole-5-carboxylate. Izvestiya Akademii Nauk, Seriya Khimicheskaya (1996), (2), 426-429 mentions the compound methyl 3-(3,5-di-tert-butyl-4-hydroxyphenyl)-5-methyl-4,5-dihydro-1,2-oxazole-5-carboxylate. Under the following CAS numbers, the compounds which follow each one are known:

1326815-55-7: 3-(3-bromophenyl)-5-methyl-4,5-dihydro-1,2-oxazole-5-carboxylic acid,
1326814-80-5: 3-(5-bromo-2-fluorophenyl)-5-methyl-4,5-dihydro-1,2-oxazole-5-carboxylic acid,
1326811-51-1: 3-(5-bromo-2-methoxyphenyl)-5-methyl-4,5-dihydro-1,2-oxazole-5-carboxylic acid,
1326813-57-3: 3-(3-bromo-4-methoxyphenyl)-5-methyl-4,5-dihydro-1,2-oxazole-5-carboxylic acid,
1326814-71-4: ethyl 3-(3-chlorophenyl)-5-methyl-4,5-dihydro-1,2-oxazole-5-carboxylate,
1326810-45-0: 3-(3,4-dichlorophenyl)-5-methyl-4,5-dihydro-1,2-oxazole-5-carboxylic acid,
1326815-81-9: 3-(2,5-dichlorophenyl)-5-methyl-4,5-dihydro-1,2-oxazole-5-carboxylic acid,
1326813-44-8: 3-(4-chloro-3-nitrophenyl)-5-methyl-4,5-dihydro-1,2-oxazole-5-carboxylic acid,
1326810-59-6: 3-(2-chloro-5-nitrophenyl)-5-methyl-4,5-dihydro-1,2-oxazole-5-carboxylic acid,
1326814-16-7: 3-(3-chloro-4-fluorophenyl)-5-methyl-4,5-dihydro-1,2-oxazole-5-carboxylic acid,
1326815-03-5: 3-(3-fluorophenyl)-5-methyl-4,5-dihydro-1,2-oxazole-5-carboxylic acid,
1326810-73-4: 3-(3,4-difluorophenyl)-5-methyl-4,5-dihydro-1,2-oxazole-5-carboxylic acid,
1326811-86-2: 3-(2,5-difluorophenyl)-5-methyl-4,5-dihydro-1,2-oxazole-5-carboxylic acid,
1326811-50-0: 3-(2,3-difluorophenyl)-5-methyl-4,5-dihydro-1,2-oxazole-5-carboxylic acid,
1326813-45-9: 3-(4-fluoro-3-methoxyphenyl)-5-methyl-4,5-dihydro-1,2-oxazole-5-carboxylic acid,
1326813-37-9: 3-[2-fluoro-5-(trifluoromethyl)phenyl]-5-methyl-4,5-dihydro-1,2-oxazole-5-carboxylic acid,
1326811-79-3: 3-(3-methoxyphenyl)-5-methyl-4,5-dihydro-1,2-oxazole-5-carboxylic acid
1326811-74-8: 3-(2,5-dimethoxyphenyl)-5-methyl-4,5-dihydro-1,2-oxazole-5-carboxylic acid,
1326814-78-1: 3-(3-methylphenyl)-5-methyl-4,5-dihydro-1,2-oxazole-5-carboxylic acid
1326813-55-1: 3-(2,5-dimethylphenyl)-5-methyl-4,5-dihydro-1,2-oxazole-5-carboxylic acid,
1326815-05-7: 5-methyl-3-(3-nitrophenyl)-4,5-dihydro-1,2-oxazole-5-carboxylic acid,
1326812-83-2: 5-methyl-3-[3-(trifluoromethyl)phenyl]-4,5-dihydro-1,2-oxazole-5-carboxylic acid,
1027426-25-0: methyl 3-(3-cyanophenyl)-5-(ethoxymethyl)-4,5-dihydro-1,2-oxazole-5-carboxylate,
1026410-22-9: methyl 3-(3-cyanophenyl)-5-(isopropoxymethyl)-4,5-dihydro-1,2-oxazole-5-carboxylate,
1027205-06-6: methyl 5-(butoxymethyl)-3-(3-cyanophenyl)-4,5-dihydro-1,2-oxazole-5-carboxylate,
231300-28-0: methyl 3-(3-cyanophenyl)-5-(2-methoxyethyl)-4,5-dihydro-1,2-oxazole-5-carboxylate, and
1026948-50-4: 3-(3-cyanophenyl)-5-(trifluoromethyl)-4,5-dihydro-1,2-oxazole-5-carboxylic acid.

No herbicidal effect of the compounds known by their CAS numbers has been disclosed.

SUMMARY

It is an object of the present invention to provide herbicidally active compounds which are additionally also suitable as precursors for preparation of further herbicidally active compounds.

It has been found that particular 3-phenylisoxazoline derivatives are of particularly good suitability for this purpose. The present invention provides 3-phenylisoxazoline derivatives, or salts thereof, of the formula (I)

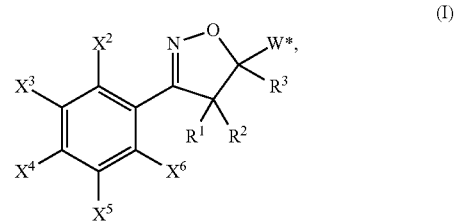

in which
$R^1$ and $R^2$ are each independently hydrogen, fluorine, chlorine, bromine, iodine, cyano, or $(C_1-C_4)$-alkyl or $(C_1-C_4)$-alkoxy each substituted by m radicals from the group consisting of fluorine, chlorine, bromine, iodine and cyano, or
$R^1$ and $R^2$ together with the carbon atom to which they are bonded form a saturated or partly or fully unsaturated three-, four- or five-membered ring formed from q carbon atoms and p oxygen atoms;
$R^3$ is fluorine, chlorine, cyano, $(C_1-C_3)$-alkylcarbonyloxy or $S(O)_n R^5$, or $(C_1-C_6)$-alkyl, $(C_3-C_6)$-cycloalkyl, $(C_2-C_6)$-alkenyl or $(C_2-C_6)$-alkynyl each substituted by m radicals from the group consisting of fluorine, chlorine, bromine, iodine, cyano, $(C_1-C_4)$-alkoxy and hydroxyl, or $(C_1-C_6)$-alkylcarbonyl, $(C_2-C_6)$-alkenylcarbonyl or $(C_3-C_6)$-cycloalkylcarbonyl each substituted by m radicals from the group consisting of fluorine, chlorine, bromine, iodine, cyano and $(C_1-C_6)$-alkoxy;

$R^5$ is $(C_1-C_6)$-alkyl or $(C_3-C_6)$-cycloalkyl each substituted by m radicals from the group consisting of fluorine, chlorine, bromine, iodine, cyano and hydroxyl;

$R^6$ is hydrogen or $R^5$;

$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;

$R^8$ is $R^7$;

W* is COOH, COOY, CN or CHO;

Y is $(C_1-C_8)$-alkyl which is substituted by m radicals from the group consisting of fluorine, chlorine, bromine, cyano, hydroxyl and COO—$(C_1-C_8)$-alkyl and which is interrupted by n heteroatoms from the group consisting of oxygen, sulfur and nitrogen, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

m is 0, 1, 2, 3, 4 or 5;

n is 0, 1 or 2;

p is 0 or 1;

q is 3, 4 or 5;

with the proviso that a) $X^3$ and $X^4$ are not both substituted or unsubstituted alkoxy, b) in the compounds in which $R^3$ is methyl and W* is COOH, $X^5$ is not hydrogen, and c) the compounds methyl 3-(3-cyanophenyl)-5-(isopropoxymethyl)-4,5-dihydro-1,2-oxazole-5-carboxylate, methyl 5-(butoxymethyl)-3-(3-cyanophenyl)-4,5-dihydro-1,2-oxazole-5-carboxylate, methyl 3-(3-cyanophenyl)-5-(methoxymethyl)-4,5-dihydro-1,2-oxazole-5-carboxylate, methyl 3-(3-cyanophenyl)-5-(2-methoxyethyl)-4,5-dihydro-1,2-oxazole-5-carboxylate, 3-(3-cyanophenyl)-5-(trifluoromethyl)-4,5-dihydro-1,2-oxazole-5-carboxylic acid, methyl 3-(3-cyanophenyl)-5-methyl-4,5-dihydro-1,2-oxazole-5-carboxylate, ethyl 3-(3-cyanophenyl)-5-methyl-4,5-dihydro-1,2-oxazole-5-carboxylate, methyl 5-methyl-3-(3-nitrophenyl)-4,5-dihydro-1,2-oxazole-5-carboxylate, methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

DETAILED DESCRIPTION OF A PREFERRED EMBODIMENT

Alkyl means saturated straight-chain or branched hydrocarbyl radicals having the number of carbon atoms specified in each case, e.g. $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl means straight-chain or branched alkyl groups where some or all of the hydrogen atoms in these groups may be replaced by halogen atoms, e.g. $C_1-C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-1,2-difluoroethyl, 2,2-dichloro-2-fluoroethyl, 2,2,2-trichloroethyl, pentafluoroethyl and 1,1,1-trifluoroprop-2-yl.

Alkenyl means unsaturated straight-chain or branched hydrocarbyl radicals having the number of carbon atoms specified in each case and one double bond in any position, e.g. $C_2-C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl means straight-chain or branched hydrocarbyl radicals having the number of carbon atoms specified in each case and one triple bond in any position, e.g. $C_2$-$C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Alkoxy means saturated straight-chain or branched alkoxy radicals having the number of carbon atoms stated in each case, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy means straight-chain or branched alkoxy radicals having the number of carbon atoms specified in each case, where some or all of the hydrogen atoms in these groups may be replaced by halogen atoms as specified above, e.g. $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-1,2-difluoroethoxy, 2,2-dichloro-2-fluoroethoxy, 2,2,2-trichloroethoxy, pentafluoroethoxy and 1,1,1-trifluoroprop-2-oxy.

According to the nature of the substituents and the way in which they are joined, the compounds of the formula (I) may be present as stereoisomers. If, for example, one or more asymmetrically substituted carbon atoms and/or sulfoxides are present, enantiomers and diastereomers may occur. Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or assistants. The invention also relates to all stereoisomers and mixtures thereof which are encompassed by the formula (I) but not defined specifically. For the sake of simplicity, however, reference is always made hereinafter to compounds of the formula (I), even though this means both the pure compounds and, if appropriate, mixtures having different proportions of isomeric compounds.

According to the nature of the substituents defined above, the compounds of the formula (I) have acidic properties and can form salts, and if appropriate also internal salts, or adducts with inorganic or organic bases or with metal ions.

If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

If a group is polysubstituted by radicals, this means that this group is substituted by one or more identical or different radicals from those mentioned.

In all the formulae specified hereinafter, the substituents and symbols have the same definition as in formula (I), unless defined differently. Arrows in a chemical formula denote the points at which it is joined to the rest of the molecule.

Preference is given to 3-phenylisoxazoline derivatives of the formula (I) in which
$R^1$ and $R^2$ are each hydrogen,
$R^3$ is $(C_1$-$C_6)$-alkyl, $(C_1$-$C_4)$-alkoxy-$(C_1$-$C_4)$-alkyl, $(C_2$-$C_6)$-alkenyl, $(C_2$-$C_6)$-alkynyl halo-$(C_1$-$C_6)$-alkyl or halo-$(C_2$-$C_6)$-alkenyl;
$R^5$ is $(C_1$-$C_6)$-alkyl or $(C_3$-$C_6)$-cycloalkyl each substituted by m radicals from the group consisting of fluorine, chlorine, bromine, iodine, cyano and hydroxyl;
$R^6$ is hydrogen or $R^5$;
$R^7$ is hydrogen or $(C_1$-$C_6)$-alkyl, $(C_3$-$C_6)$-cycloalkyl, $(C_2$-$C_4)$-alkenyl or $(C_2$-$C_4)$-alkynyl each substituted by m radicals from the group consisting of fluorine, chlorine, bromine, cyano and $(C_1$-$C_2)$-alkoxy;
$R^8$ is $R^7$;
W* is COOH or COOY;
Y is $(C_1$-$C_6)$-alkyl which is substituted by m radicals from the group consisting of fluorine, chlorine, bromine, cyano, hydroxyl and COO—$(C_1$-$C_4)$-alkyl and which is interrupted by n oxygen atoms, or
a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro,
or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;

$X^3$ is fluorine, chlorine, bromine, iodine, hydroxyl, cyano, nitro, $SF_5$, $CONR^8SO_2R^5$, $CONR^6R^8$, $COR^E$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$,
or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano,
or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^E$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$,
or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano,
or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

m is 0, 1, 2, 3, 4 or 5;
n is 0, 1 or 2;
with the proviso that
a) $X^3$ and $X^4$ are not both substituted or unsubstituted alkoxy,
b) in the compounds in which $R^3$ is methyl and W* is COOH, $X^5$ is not hydrogen, and
c) the compounds
methyl 3-(3-cyanophenyl)-5-(isopropoxymethyl)-4,5-dihydro-1,2-oxazole-5-carboxylate, methyl 5-(butoxymethyl)-3-(3-cyanophenyl)-4,5-dihydro-1,2-oxazole-5-carboxylate, methyl 3-(3-cyanophenyl)-5-(methoxymethyl)-4,5-dihydro-1,2-oxazole-5-carboxylate, methyl 3-(3-cyanophenyl)-5-(2-methoxyethyl)-4,5-dihydro-1,2-oxazole-5-carboxylate,
3-(3-cyanophenyl)-5-(trifluoromethyl)-4,5-dihydro-1,2-oxazole-5-carboxylic acid,
methyl 3-(3-cyanophenyl)-5-methyl-4,5-dihydro-1,2-oxazole-5-carboxylate,
ethyl 3-(3-cyanophenyl)-5-methyl-4,5-dihydro-1,2-oxazole-5-carboxylate,
methyl 5-methyl-3-(3-nitrophenyl)-4,5-dihydro-1,2-oxazole-5-carboxylate,
methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

Particular preference is given to 3-phenylisoxazoline derivatives of the formula (I) in which $R^1$ and $R^2$ are each hydrogen,
$R^3$ is $(C_1-C_4)$-alkyl, $(C_1-C_4)$-alkoxy-$(C_1-C_4)$-alkyl, vinyl, $(C_2-C_4)$-alkynyl, halo-$(C_1-C_4)$-alkyl or halo-$(C_2-C_4)$-alkenyl;
$R^5$ is methyl or ethyl;
$R^6$ is hydrogen or $R^5$;
$R^7$ is hydrogen or $(C_1-C_6)$-alkyl substituted by m radicals from the group consisting of fluorine and chlorine;
$R^8$ is $R^7$;
W* is COOH or COOY;
Y is $(C_1-C_6)$-alkyl which is substituted by m radicals from the group consisting of fluorine, chlorine, bromine, cyano, hydroxyl and COO—$(C_1-C_4)$-alkyl and which is interrupted by n oxygen atoms, or
a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, or chlorine,
or $(C_1-C_4)$-alkyl or $(C_1-C_4)$-alkoxy each substituted by m radicals from the group consisting of fluorine, chlorine, cyano and $(C_1-C_4)$-alkoxy;

$X^3$ is fluorine, chlorine, bromine, cyano,
or $(C_1-C_6)$-alkyl substituted by m radicals from the group consisting of fluorine and chlorine,
or $(C_1-C_6)$-alkoxy substituted by m radicals from the group consisting of fluorine and chlorine;

$X^5$ is hydrogen, fluorine, chlorine, bromine, cyano,
or $(C_1-C_6)$-alkyl substituted by m radicals from the group consisting of fluorine and chlorine,
or $(C_1-C_6)$-alkoxy substituted by m radicals from the group consisting of fluorine and chlorine;

m is 0, 1, 2 or 3;
n is 0, 1 or 2;
with the proviso that
a) $X^3$ and $X^4$ are not both substituted or unsubstituted alkoxy,
b) in the compounds in which $R^3$ is methyl and W* is COOH, $X^5$ is not hydrogen, and
c) the compounds
methyl 3-(3-cyanophenyl)-5-(isopropoxymethyl)-4,5-dihydro-1,2-oxazole-5-carboxylate,
methyl 5-(butoxymethyl)-3-(3-cyanophenyl)-4,5-dihydro-1,2-oxazole-5-carboxylate,
methyl 3-(3-cyanophenyl)-5-(methoxymethyl)-4,5-dihydro-1,2-oxazole-5-carboxylate,
methyl 3-(3-cyanophenyl)-5-(2-methoxyethyl)-4,5-dihydro-1,2-oxazole-5-carboxylate,
3-(3-cyanophenyl)-5-(trifluoromethyl)-4,5-dihydro-1,2-oxazole-5-carboxylic acid,
methyl 3-(3-cyanophenyl)-5-methyl-4,5-dihydro-1,2-oxazole-5-carboxylate,
ethyl 3-(3-cyanophenyl)-5-methyl-4,5-dihydro-1,2-oxazole-5-carboxylate,
methyl 5-methyl-3-(3-nitrophenyl)-4,5-dihydro-1,2-oxazole-5-carboxylate,
methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

Very particular preference is given to 3-phenylisoxazoline derivatives of the formula (I) in which
$R^1$ and $R^2$ are each hydrogen,
$R^3$ is $(C_1-C_4)$-alkyl, $(C_1-C_4)$-alkoxy-$(C_1-C_4)$-alkyl, vinyl, $(C_2-C_4)$-alkynyl, halo-$(C_1-C_4)$-alkyl or halo-$(C_2-C_4)$-alkenyl;
$R^5$ is methyl or ethyl;
$R^6$ is hydrogen or $R^5$;
$R^7$ is hydrogen or $(C_1-C_6)$-alkyl substituted by m radicals from the group consisting of fluorine and chlorine;
$R^8$ is $R^7$;
W* is COOH or COOY;
Y is $(C_1-C_6)$-alkyl which is substituted by m radicals from the group consisting of fluorine, chlorine, bromine, cyano, hydroxyl and COO—$(C_1-C_4)$-alkyl and which is interrupted by n oxygen atoms, or
a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;
$X^2$, $X^4$ and $X^6$ are each independently hydrogen, fluorine, or chlorine,
or $(C_1-C_4)$-alkyl or $(C_1-C_4)$-alkoxy each substituted by m radicals from the group consisting of fluorine, chlorine, cyano and $C_1-C_4)$-alkoxy;
$X^3$ is fluorine, chlorine, bromine, cyano,
or $(C_1-C_6)$-alkyl substituted by m radicals from the group consisting of fluorine and chlorine,
or $(C_1-C_6)$-alkoxy substituted by m radicals from the group consisting of fluorine and chlorine;
$X^5$ is fluorine, chlorine, bromine, cyano,
or $(C_1-C_6)$-alkyl substituted by m radicals from the group consisting of fluorine and chlorine,
or $(C_1-C_6)$-alkoxy substituted by m radicals from the group consisting of fluorine and chlorine;
m is 0, 1, 2 or 3;
n is 0, 1 or 2;
with the proviso that
a) $X^3$ and $X^4$ are not both substituted or unsubstituted alkoxy,
b) in the compounds in which $R^3$ is methyl and W* is COOH, $X^5$ is not hydrogen, and
c) the compounds
methyl 3-(3-cyanophenyl)-5-(isopropoxymethyl)-4,5-dihydro-1,2-oxazole-5-carboxylate,
methyl 5-(butoxymethyl)-3-(3-cyanophenyl)-4,5-dihydro-1,2-oxazole-5-carboxylate,
methyl 3-(3-cyanophenyl)-5-(methoxymethyl)-4,5-dihydro-1,2-oxazole-5-carboxylate,
methyl 3-(3-cyanophenyl)-5-(2-methoxyethyl)-4,5-dihydro-1,2-oxazole-5-carboxylate,
3-(3-cyanophenyl)-5-(trifluoromethyl)-4,5-dihydro-1,2-oxazole-5-carboxylic acid,
methyl 3-(3-cyanophenyl)-5-methyl-4,5-dihydro-1,2-oxazole-5-carboxylate,
ethyl 3-(3-cyanophenyl)-5-methyl-4,5-dihydro-1,2-oxazole-5-carboxylate,
methyl 5-methyl-3-(3-nitrophenyl)-4,5-dihydro-1,2-oxazole-5-carboxylate,
methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

The compounds described in the documents cited above have not only pharmacological action but also, surprisingly, herbicidal action. Furthermore, they are outstandingly suitable as intermediates for preparation of herbicidally active 3-phenylisoxazoline-5-carboxamides and 3-phenylisoxazoline-5-thioamides. The present invention therefore further provides for the use of 3-phenylisoxazoline derivatives of the formula (Ia) as herbicides. The present invention therefore further provides for the use of 3-phenylisoxazoline derivatives of the formula (Ia) as intermediates for preparation of herbicidally active 3-phenylisoxazoline-5-carboxamides and 3-phenylisoxazoline-5-thioamides.

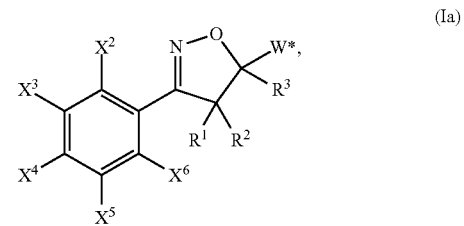

(Ia)

In formula (Ia), the radicals and indices are defined as follows:
$R^1$ and $R^2$ are each independently hydrogen, fluorine, chlorine, bromine, iodine, cyano, or $(C_1-C_4)$-alkyl or $(C_1-C_4)$-alkoxy each substituted by m radicals from the group consisting of fluorine, chlorine, bromine, iodine and cyano, or
$R^1$ and $R^2$ together with the carbon atom to which they are bonded form a saturated or partly or fully unsaturated three-, four- or five-membered ring formed from q carbon atoms and p oxygen atoms;
$R^3$ is fluorine, chlorine, cyano, $(C_1-C_3)$-alkylcarbonyloxy or $S(O)_nR^5$,
or $(C_1-C_6)$-alkyl, $(C_3-C_6)$-cycloalkyl, $(C_2-C_6)$-alkenyl or $(C_2-C_6)$-alkynyl each substituted by m radicals from the group consisting of fluorine, chlorine, bromine, iodine, cyano, $(C_1-C_4)$-alkoxy and hydroxyl,
or $(C_1-C_6)$-alkylcarbonyl, $(C_2-C_6)$-alkenylcarbonyl or $(C_3-C_6)$-cycloalkylcarbonyl each substituted by m radicals from the group consisting of fluorine, chlorine, bromine, iodine, cyano and $(C_1-C_6)$-alkoxy;
$R^5$ is $(C_1-C_6)$-alkyl or $(C_3-C_6)$-cycloalkyl each substituted by m radicals from the group consisting of fluorine, chlorine, bromine, iodine, cyano and hydroxyl;
$R^6$ is hydrogen or $R^5$;
$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;
$R^8$ is $R^7$;
W* is COOH, COOY, CN or CHO;
Y is $(C_1-C_8)$-alkyl which is substituted by m radicals from the group consisting of fluorine, chlorine, bromine, cyano, hydroxyl and COO—$(C_1-C_8)$-alkyl and which is interrupted by n heteroatoms from the group consisting of oxygen, sulfur and nitrogen, or
a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or $(C_1$-$C_4)$-alkyl, $(C_3$-$C_5)$-cycloalkyl, $(C_2$-$C_4)$-alkenyl, $(C_2$-$C_4)$-alkynyl, $(C_1$-$C_4)$-alkoxy, $(C_2$-$C_4)$-alkenyloxy, $(C_2$-$C_4)$-alkynyloxy or $(C_1$-$C_4)$-alkylcarbonyl each substituted by m radicals from the group consisting of fluorine, chlorine, bromine, iodine, cyano and $(C_1$-$C_4)$-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1$-$C_6)$-alkyl, $(C_3$-$C_5)$-cycloalkyl, $(C_2$-$C_6)$-alkenyl, $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1$-$C_6)$-alkyl, $(C_3$-$C_5)$-cycloalkyl, $(C_2$-$C_6)$-alkenyl, $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

m is 0, 1, 2, 3, 4 or 5;
n is 0, 1 or 2;
p is 0 or 1;
q is 3, 4 or 5.

Preferentially suitable as herbicides and intermediates are 3-phenylisoxazoline derivatives of the formula (Ia) in which $R^1$ and $R^2$ are each hydrogen, $R^3$ is $(C_1$-$C_6)$-alkyl, $(C_1$-$C_4)$-alkoxy-$(C_1$-$C_4)$-alkyl, $(C_2$-$C_6)$-alkenyl, $(C_2$-$C_6)$-alkynyl, halo-$(C_1$-$C_6)$-alkyl or halo-$(C_2$-$C_6)$-alkenyl;

$R^5$ is $(C_1$-$C_6)$-alkyl or $(C_3$-$C_6)$-cycloalkyl each substituted by m radicals from the group consisting of fluorine, chlorine, bromine, iodine, cyano and hydroxyl;

$R^6$ is hydrogen or $R^5$;

$R^7$ is hydrogen or $(C_1$-$C_6)$-alkyl, $(C_3$-$C_6)$-cycloalkyl, $(C_2$-$C_4)$-alkenyl or $(C_2$-$C_4)$-alkynyl each substituted by m radicals from the group consisting of fluorine, chlorine, bromine, cyano and $(C_1$-$C_2)$-alkoxy;

$R^8$ is $R^7$;

W* is COOH or COOY;

Y is $(C_1$-$C_6)$-alkyl which is substituted by m radicals from the group consisting of fluorine, chlorine, bromine, cyano, hydroxyl and COO—$(C_1$-$C_4)$-alkyl and which is interrupted by n oxygen atoms, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or $(C_1$-$C_4)$-alkyl, $(C_3$-$C_5)$-cycloalkyl, $(C_2$-$C_4)$-alkenyl, $(C_2$-$C_4)$-alkynyl, $(C_1$-$C_4)$-alkoxy, $(C_2$-$C_4)$-alkenyloxy, $(C_2$-$C_4)$-alkynyloxy or $(C_1$-$C_4)$-alkylcarbonyl each substituted by m radicals from the group consisting of fluorine, chlorine, bromine, iodine, cyano and $(C_1$-$C_4)$-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1$-$C_6)$-alkyl, $(C_3$-$C_5)$-cycloalkyl, $(C_2$-$C_6)$-alkenyl, $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1$-$C_6)$-alkyl, $(C_3$-$C_5)$-cycloalkyl, $(C_2$-$C_6)$-alkenyl, $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

m is 0, 1, 2, 3, 4 or 5;
n is 0, 1 or 2.

More preferentially suitable as herbicides and intermediates are 3-phenylisoxazoline derivatives of the formula (Ia) in which $R^1$ and $R^2$ are each hydrogen, $R^3$ is $(C_1$-$C_4)$-alkyl, $(C_1$-$C_4)$-alkoxy-$(C_1$-$C_4)$-alkyl, vinyl, $(C_2$-$C_4)$-alkynyl, halo-$(C_1$-$C_6)$-alkyl or halo-$(C_2$-$C_6)$-alkenyl;

$R^5$ is methyl or ethyl;

$R^6$ is hydrogen or $R^5$;

$R^7$ is hydrogen or $(C_1$-$C_6)$-alkyl substituted by m radicals from the group consisting of fluorine and chlorine;

$R^8$ is $R^7$;

W* is COOH or COOY;

Y is $(C_1$-$C_6)$-alkyl which is substituted by m radicals from the group consisting of fluorine, chlorine, bromine, cyano, hydroxyl and COO—$(C_1$-$C_4)$-alkyl and which is interrupted by n oxygen atoms, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, or chlorine, or $(C_1-C_4)$-alkyl or $(C_1-C_4)$-alkoxy each substituted by m radicals from the group consisting of fluorine, chlorine, cyano and $(C_1-C_4)$-alkoxy;

$X^3$ is fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine;

$X^5$ is hydrogen, fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine;

m is 0, 1, 2 or 3;

n is 0, 1 or 2.

Most preferentially suitable as herbicides and intermediates are 3-phenylisoxazoline derivatives of the formula (Ia) in which $R^1$ and $R^2$ are each hydrogen, $R^3$ is $(C_1-C_4)$-alkyl, $(C_1-C_4)$-alkoxy-$(C_1-C_4)$-alkyl, vinyl, $(C_2-C_4)$-alkynyl, halo-$(C_1-C_6)$-alkyl or halo-$(C_2-C_6)$-alkenyl;

$R^5$ is methyl or ethyl;

$R^6$ is hydrogen or $R^5$;

$R^7$ is hydrogen or $(C_1-C_6)$-alkyl substituted by m radicals from the group consisting of fluorine and chlorine;

$R^8$ is $R^7$;

W* is COOH or COOY;

Y is $(C_1-C_6)$-alkyl which is substituted by m radicals from the group consisting of fluorine, chlorine, bromine, cyano, hydroxyl and COO—$(C_1-C_4)$-alkyl and which is interrupted by n oxygen atoms, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl, ((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, or chlorine, or $(C_1-C_4)$-alkyl or $(C_1-C_4)$-alkoxy each substituted by m radicals from the group consisting of fluorine, chlorine, cyano and $(C_1-C_4)$-alkoxy;

$X^3$ is fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine;

$X^5$ is hydrogen, fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine;

m is 0, 1, 2 or 3;

n is 0, 1 or 2.

Inventive compounds in which W* is COOH can be prepared by reactions known per se to those skilled in the art, for example by the reaction sequence shown in scheme 1.

Scheme 1:

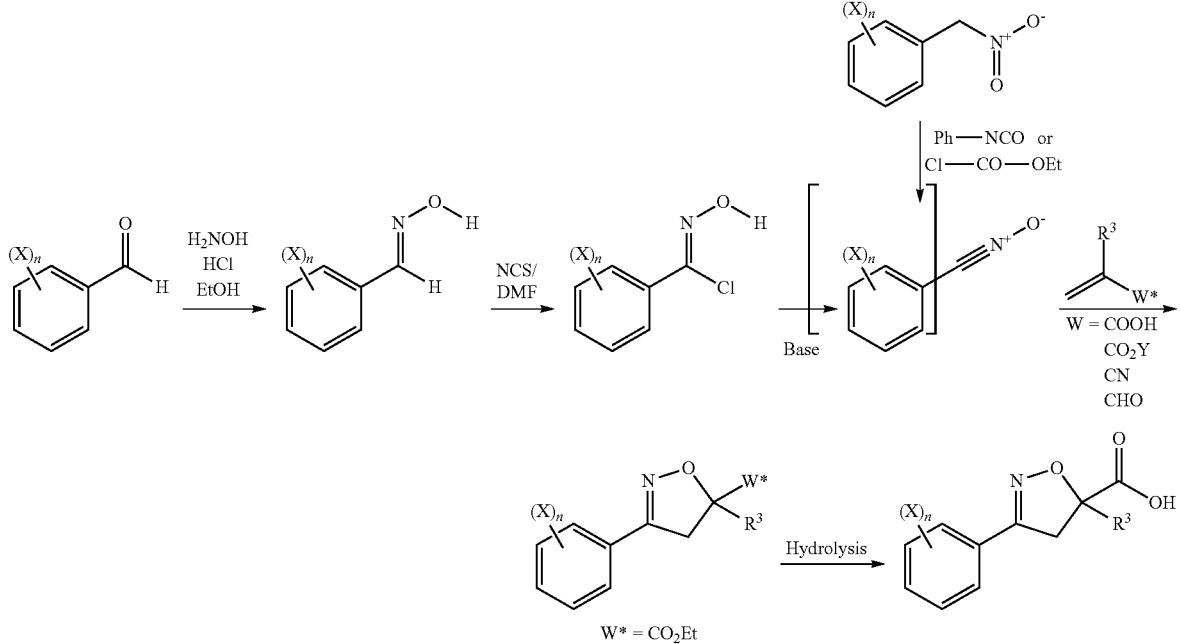

In scheme 1 and the schemes which follow, $(X)_n$ represents the substituents $X^2$, $X^3$, $X^4$, $X^5$ and $X^6$. Such 1,3-dipolar cycloadditions of nitrile oxides with suitable dipolarophiles are described, for example, in reviews: 1,3 dipolar Cycloaddition Chemistry, Padwa (editor), Wiley, New York, 1984; Kanemasa and Tsuge, Heterocycles 1990, 30, 719 and H. Feurer, Nitrones and Nitronates in Organic Synthesis, Second Edition, 1-129, Hoboken, N.J. 2008.

The cycloadditions can be performed in a one-pot reaction without isolation of the dipole precursor or with isolation of the dipole precursor.

Inventive compounds substituted in the 4 and 5 positions of the isoxazoline ring system can likewise be prepared by 1,3-dipolar cycloaddition by using suitably 1,2-disubstituted olefins as dipolarophiles. Usually, this reaction gives diastereomer mixtures which can be separated by column chromatography. Optically active isoxazolines can be obtained by chiral HPLC of suitable precursors or end products, and likewise by enantioselective reactions, for example enzymatic ester or amide cleavage or through the use of chiral auxiliaries on the dipolarophile, as described by Olssen (J. Org. Chem. 1988, 53, 2468). As well as the inventive acids (W*=COOH), salts thereof are also claimed, these being preparable by the customary route through reaction with an inorganic or organic base (scheme 2). In this scheme, Me⁺ represents a metal cation.

Scheme 2:

Inventive compounds in which W* is COOH can also be prepared by the methods specified in scheme 3a, by hydrolysis of anhydrides or hydrolysis of nitriles, or by the methods specified in scheme 3ba, by oxidation of alcohols or aldehydes.

Scheme 3a:

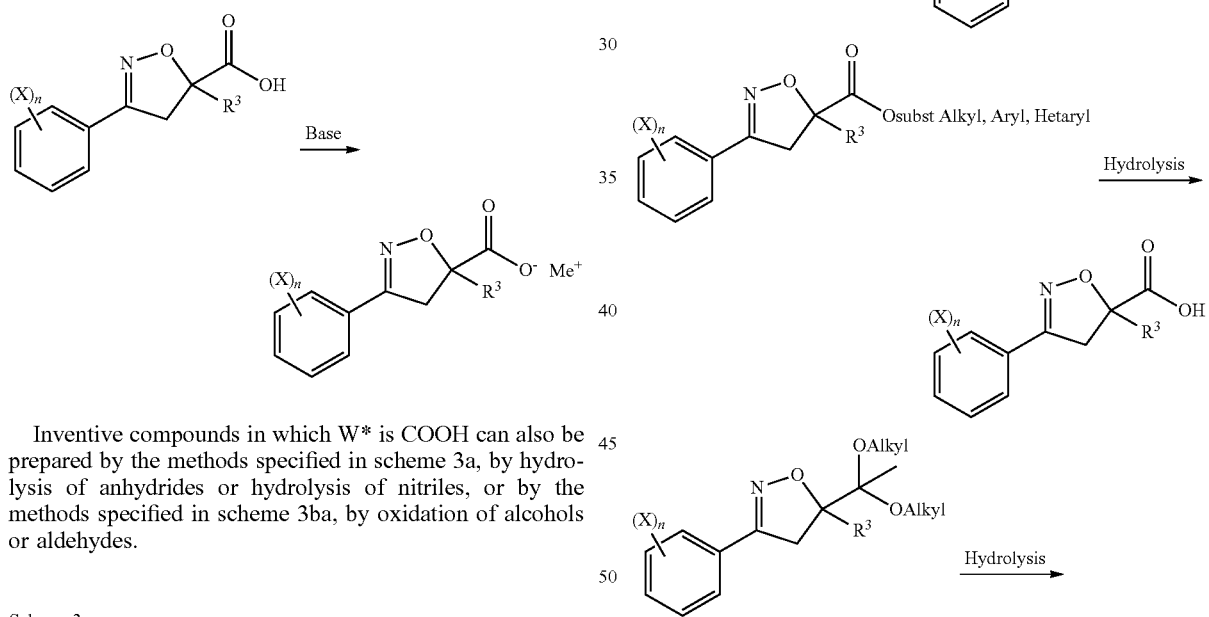

-continued

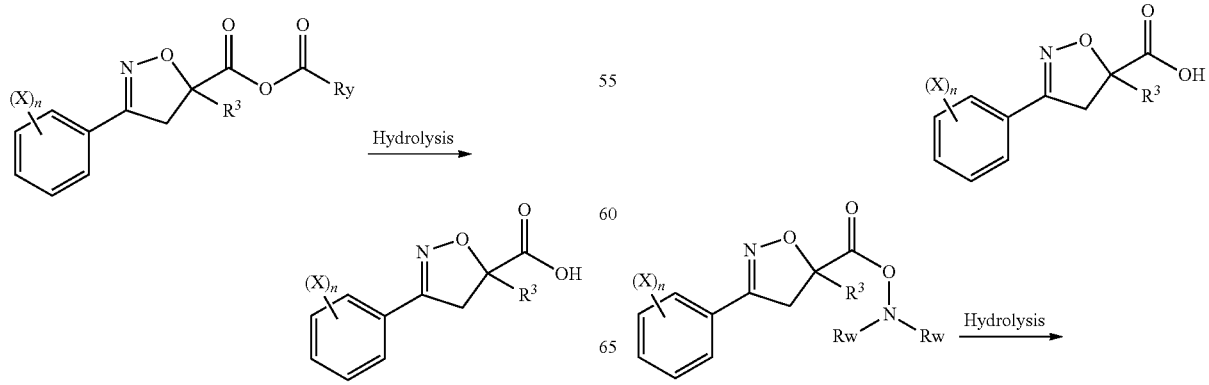

Scheme 3b:

Inventive compounds in which W* is COOY can be prepared, for example, according to scheme 4, by conversion of inventive compounds in which W* is COOH with addition of mineral acids and an appropriate alcohol, or by reaction of the particular acid halide with the respective alcohol or by coupling of the particular acid with coupling reagents.

Scheme 4:

Inventive compounds in which W* is CN can be prepared, for example, according to scheme 5 by cycloaddition or with dehydrating agents from a carboxamide or an aldoxime (The Chemistry of the Cyano Group, pp. 92-96, pp. 1345-1390, Interscience, New York, 1970).

Scheme 5:

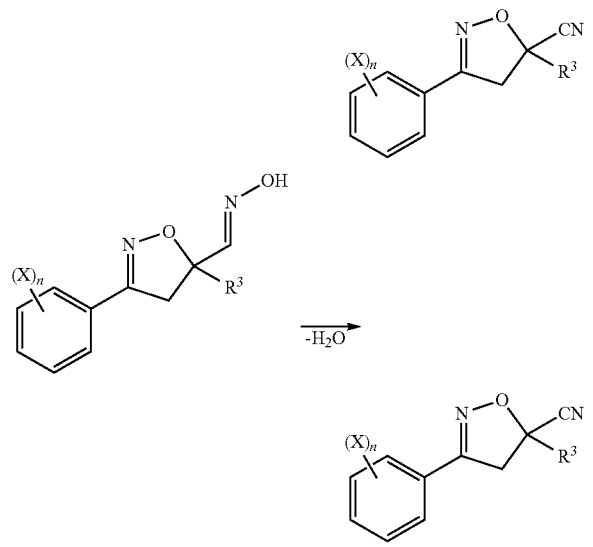

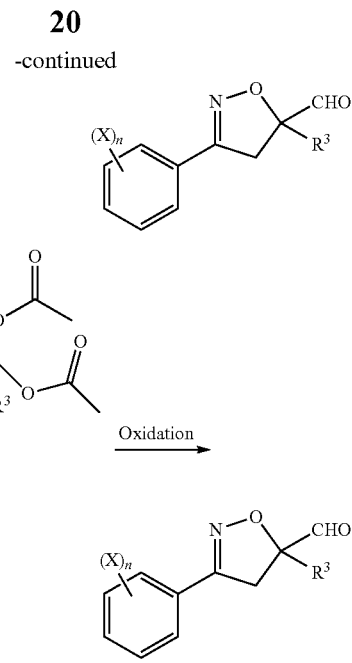

Inventive compounds in which W* is CHO can be prepared, for example, according to scheme 6 by selective reduction of carboxylic acids, carboxylic esters, carbonyl halides, or of Weinreb amides, or by oxidation of alcohols or hydrolysis of Scheme 6:

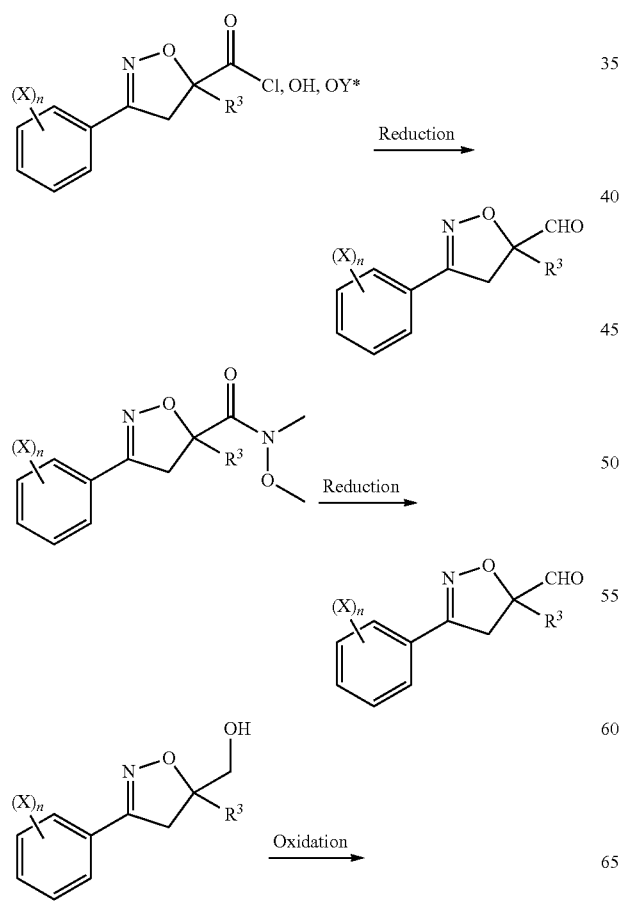

A general synthesis option for preparation of the inventive compounds 1 is the cycloaddition described in scheme 7 with dihaloformoximes (dichloroformoxime: Wade, Peter A.; Singh, Shankar M.; Pillay, M. Krishna, Tetrahedron (1984), 40(3), 601-11 and dibromoformoxime: DE 3612278) and subsequent introduction of the phenyl ring by means of Suzuki coupling (EP 0 792 870 A1) or Stille reaction (WO 2004/029066 A1).

Scheme 7:

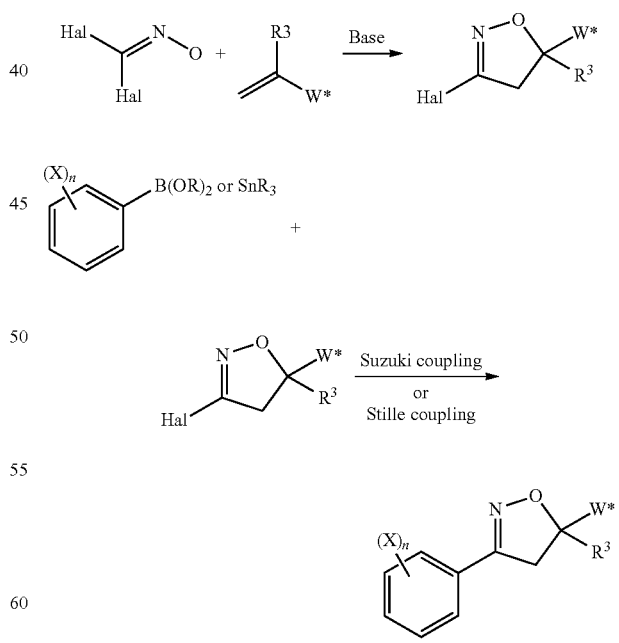

Transformations of the functional group $R^3$ are possible either at the alkene stage or at the isoxazoline stage. Scheme 8 describes preparation methods for different inventive 3-phenyl isoxazoline derivatives.

Scheme 8:

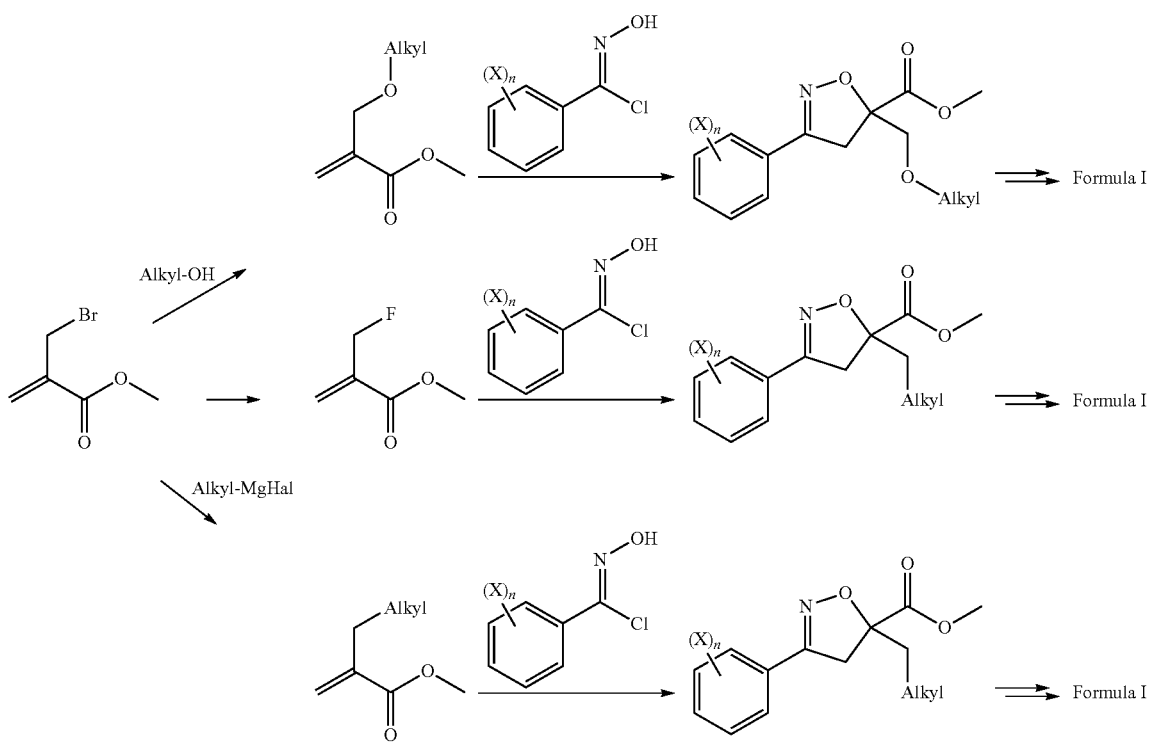

Commercially available methyl 2-bromomethylacrylate can be reacted under basic conditions with alcohols to give methyl 2-alkoxymethylacrylates, which then react with chloroximes via the nitrile oxides to give 3-phenyl-5-methoxymethylisoxazolines. Various 2-alkylacrylic esters can be prepared proceeding from methyl 2-bromomethyl-acrylate, for example by reaction with organometallic reagents. Such methods are described, for example, in Metzger, Albrecht; Piller, Fabian M.; Knochel, Paul; Chemical Communications, 2008, 44, pp. 5824-5826, and are also known from WO2006/33551.

Chem. Ber., 1963, 96, 1373; Tanoury, G. J.; Chen, M.; Dong, Y.; Forslund, R. E.; Magdziak, D.; Organic Letters, 2008, 10, 185.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Gunther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Gunther Jung), Wiley, 1999. The use of solid phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Either on a solid phase or in the liquid phase, the performance of single or multiple synthesis steps can be supported by the use of microwave technology. The technical literature describes a number of experimental protocols, for example in Microwaves in Organic and Medicinal Chemistry (editors: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), collectively referred to hereinafter as "inventive compounds", have excellent herbicidal efficacy against a broad spectrum of economically important monocotyledonous and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example harmful plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

When the inventive compounds are applied to the soil surface before germination, either the weed seedlings are prevented completely from emerging or the weeds grow until they have reached the cotyledon stage, but then stop growing and eventually, after three to four weeks have elapsed, die completely.

If the active ingredients are applied post-emergence to the green parts of the plants, growth stops after the treatment, and the harmful plants remain at the growth stage of the time of application, or die completely after a certain time, such that competition by the weeds, which is harmful to the crop plants, is thus eliminated very early and in a lasting manner.

Although the inventive compounds have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, especially *Zea* and *Triticum*, are damaged only to an insignificant extent, if at all, depending on the structure of the respective inventive compound and the application rate thereof. For these reasons, the present compounds are very suitable for selective control of unwanted plant growth in plant crops such as agriculturally useful plants or ornamentals.

Furthermore, the inventive compounds (depending on their particular structure and the application rate applied) have outstanding growth-regulating properties in crop plants. They intervene to regulate the plant's metabolism and can thus be used for controlled influence on plant constituents and to facilitate harvesting, for example by triggering desiccation and stunted growth. In addition, they are also suitable for general control and inhibition of unwanted vegetative growth without killing the plants. Inhibiting vegetative growth plays a major role for many monocotyledonous and dicotyledonous crops, since, for example, this can reduce or completely prevent lodging.

Because of their herbicidal and plant growth-regulating properties, the active ingredients can also be used to control harmful plants in crops of known genetically modified plants or of those yet to be developed. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other special properties relate, for example, to the harvested material with regard to quantity, quality, storability, composition and specific constituents. Thus, transgenic plants are known whose starch content is increased, or whose starch quality is altered, or those where the harvested material has a different fatty acid composition. Further special properties may be tolerance or resistance to abiotic stress factors, for example heat, cold, drought, salinity and ultraviolet radiation.

Preference is given to the use of the inventive compounds of the formula (I) or salts thereof in economically important transgenic crops of useful plants and ornamental plants, for example of cereals such as wheat, barley, rye, oats, sorghum and millet, rice, cassava and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044, EP 0131624). For example, there have been descriptions of several cases of genetic modifications of crop plants for the purpose of modifying the starch synthesized in the plants (e.g. WO 92/011376 A, WO 92/014827 A, WO 91/019806 A), transgenic crop plants resistant to particular herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soybean with the tradename or the designation Optimum™ GAT™ (Glyphosate ALS Tolerant), transgenic crop plants, for example cotton, capable of producing *Bacillus thuringiensis* toxins (Bt toxins), which make the plants resistant to particular pests (EP-A-0142924, EP-A-0193259), transgenic crop plants having a modified fatty acid composition (WO 91/013972 A), genetically modified crop plants having novel constituents or secondary metabolites, for example novel phytoalexins, which cause an increase in disease resistance (EP 0309862 A, EP 0464461 A), genetically modified crop plants having reduced photorespiration, which have higher yields and higher stress tolerance (EP 0305398 A), transgenic crop plants which produce pharmaceutically or diagnostically important proteins ("molecular pharming"), transgenic crop plants which are notable for higher yields or better quality, transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.), Gene Transfer to Plants, Springer Lab Manual (1995), Springer Verlag Berlin, Heidelberg or Christou, "Trends in Plant Science" 1 (1996) 423-431).

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim, 2nd edition, 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product. For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants. Thus, it is possible to obtain transgenic plants whose properties are altered by overexpression, suppression or inhibition of homologous (=natural) genes or gene sequences, or expression of heterologous (=foreign) genes or gene sequences.

The inventive compounds (I) can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients, or to any desired combinations of these active ingredients.

The inventive compounds can be used with particular preference in transgenic crop plants which are resistant to a combination of glyphosates and glufosinates, glyphosates and sulfonylureas or imidazolinones. The inventive compounds can be used with very particular preference in transgenic crop plants, for example corn or soybeans with the trade name or the designation Optimum™ GAT™ (Glyphosate ALS Tolerant).

On employment of the inventive active ingredients in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds of the formula (I) and of the compounds of the formula (Ia) as herbicides for control of harmful plants in transgenic crop plants.

The inventive compounds can be applied in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes. These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schonfeldt, "Grenzflächenaktive Äthylenoxidaddukte" [Interface-active Ethylene Oxide Adducts], Wiss. Verlagsgesell., Stuttgart 1976, Winnacker-Kuchler, "Chemische Technologie", Volume 7, C. Hanser Verlag Munich, 4th ed. 1986.

On the basis of these formulations, it is also possible to produce combinations with other active ingredients, for example insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl, benoxacor and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2' dinaphthylmethane-6,6'-disulfonate, sodium dibutylnaphthalenesulfonate or else sodium oleoyl-methyltaurinate. To produce the wettable powders, the herbicidal active ingredients are ground finely, for example in customary apparatus such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene or else relatively high-boiling aromatics or hydrocarbons or mixtures of the organic solvents, with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granulated inert material or by applying active ingredient concentrates by means of adhesives, for example polyvinyl alcohol, sodium polyacrylate or mineral oils, to the surface of carrier substances, such as sand, kaolinites or granulated inert material. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1 to 99% by weight, especially 0.1 to 95% by weight, of inventive compounds. In wettable powders, the active compound concentration is, for example, from about 10 to 90% by weight, the remainder to 100% by weight consisting of customary formulation components. In emulsifiable concentrates, the active ingredient concentration may be about 1 to 90% and preferably 5 to 80% by weight. Dust-type formulations contain 1 to 30% by weight of active ingredient, preferably usually 5 to 20% by weight of active ingredient; sprayable solutions contain about 0.05 to 80% by weight, preferably from 2 to 50% by weight, of active ingredient. In the case of water-dispersible granules, the active ingredient content depends partly on whether the active compound is present in liquid or solid form and on which granulation assistants, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2009 and literature cited therein. Examples of known herbicides or plant growth regulators which can be combined with the inventive compounds include the active ingredients which follow (the compounds are designated either by the "common name" according to the International Organization for Standardization (ISO) or by the chemical name or by the code number) and always encompass all use forms, such as acids, salts, esters and isomers, such as stereoisomers and optical isomers.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It may vary within wide limits, for example between 0.001 and 1.0 kg/ha or more of active substance; however, preferably it is between 0.005 and 750 g/ha.

The inventive compositions may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 per cent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes. In general, the inventive compositions and formulations contain between 0.05 and 99% by weight, 0.01 and 98% by weight, preferably between 0.1 and 95% by weight and more preferably between 0.5 and 90% by weight active ingredient, most preferably between 10 and 70 percent by weight. The inventive active ingredients or compositions can be used as such or, depending on their respective physical and/or chemical properties, in the form of the formulations thereof or the use forms prepared therefrom, such as aerosols, capsule suspensions, cold-fogging concentrates, warm-fogging concentrates, encapsulated granules, fine granules, free-flowing concentrates for the treatment of seed, ready-to-use solutions, dustable powders, emulsifiable concentrates, oil-in-water emulsions, water-in-oil emulsions, macrogranules, microgranules, oil-dispersible powders, oil-miscible free-flowing concentrates, oil-miscible liquids, foams, pastes, pesticide-coated seed, suspension concentrates, suspoemulsion concentrates, soluble concentrates, suspensions, spray powders, soluble powders, dusts and granules, water-soluble granules or tablets, water-soluble powders for seed treatment, wettable powders, active ingredient-impregnated natural products and synthetic substances, and also microencapsulations in polymeric substances and in coating materials for seed, and also ULV cold-fogging and warm-fogging formulations.

The formulations mentioned can be produced in a manner known per se, for example by mixing the active ingredients with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The inventive compositions include not only formulations which are already ready for use and can be deployed with a suitable apparatus onto the plant or the seed, but also commercial concentrates which have to be diluted with water prior to use. The inventive active ingredients may be present as such or in their (commercial standard) formulations, or else in the use forms prepared from these formulations as a mixture with other (known) active ingredients, such as insecticides, attractants, sterilants, bactericides, acaricides, nematicides, fungicides, growth regulators, herbicides, fertilizers, safeners or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation/the active ingredient itself into the soil.

The examples which follow illustrate the invention in detail.

A. CHEMICAL EXAMPLES

1. Preparation of ethyl 3-(2,3-difluorophenyl)-5-methyl-4,5-dihydro-1,2-oxazole-5-carboxylate Example No. 2.1.056

To this end, 3.320 g (21.13 mmol) of 2,3-difluorobenzaldehyde oxime are initially charged in 25 ml of dimethylformamide, and 2.822 g (21.13 mmol) of N-chlorosuccinimide are added thereto, in the course of which the temperature rises to 79° C. Subsequently, the mixture is heated to 40° C. for 1 h, another spatula-tip of N-chlorosuccinimide is added, 15 minutes later the mixture is cooled to room temperature (RT), then 3.618 g (31.70 mmol) of ethyl methacrylate and 4.097 g (31.70 mmol) of N,N-diisopropylethylamine are added dropwise. After cooling to RT, the mixture is stirred for another 15 minutes, the flask contents are added to 50 ml of water, and the mixture is acidified with 1 M sulfuric acid and extracted repeatedly with methyl t-butyl ether. The combined organic phases are washed once with water and with sodium chloride solution, dried over sodium sulfate and filtered off, and the filtrate is concentrated under reduced pressure. This gives 6.06 g of yellow oil, which was chromatographed on silica gel using an ethyl acetate/heptane gradient. This gives 5.140 g (90%) of colorless oil.

$^1$H NMR [CDCl$_3$]: δ=1.31 (t, 3H); 1.72 (s, 3H); 3.33 (d, 1H); 3.95 (d, 1H); 4.36 (q, 2H); 7.12 (m, 1H); 7.23 (m, 1H); 7.53 (m, 1H).

2. Preparation of isopropyl 5-cyano-3-(3,5-difluorophenyl)-4,5-dihydro-1,2-oxazole-5-carboxylate Example No. 2.2.475

1.00 g (6.37 mmol) of 3,5-difluorobenzaldehyde oxime is dissolved in 25 ml of dichloromethane and cooled to 0° C., and 1.195 g (9.55 mmol) of ethyl 2-cyanoacrylate are added. Then 2.050 g (6.37 mmol) of iodosobenzene are added and the mixture is warmed to RT. After the reaction has ended, the solution is admixed with thiosulfate solution, extracted with ethyl acetate and dried over sodium sulfate. After purification by chromatography using silica gel, this gives 1.010 g (54%) of the desired product.

$^1$H NMR [DMSO]: δ=1.30 (t, 3H); 4.11 (d, 1H); 4.32 (q, 2H); 4.48 (d, 1H); 7.48 (m, 3H).

3. Preparation of ethyl 3-(3,5-difluorophenyl)-5-ethyl-4,5-dihydro-1,2-oxazole-5-carboxylate Example No. 2.1.471

Intermediate: 3,5-difluoro-N-hydroxybenzenecarboximidoyl chloride 19.000 g (259.94 mmol) of 3,5-difluorobenzaldehyde oxime are initially charged in 20 ml of dry DMF under nitrogen, and 510 mg (3.81 mmol) of N-chlorosuccinimide are added first. Subsequently, gaseous hydrochloric acid is introduced into the reaction solution until the reaction temperature has risen to 35° C. Then the remaining 1.990 g (15.28 mmol) of N-chlorosuccinimide are metered in, such that the internal temperature of 40° C. is not exceeded. After cooling to RT, ice-water is added, the mixture is diluted with diethyl ether, and the organic phase is extracted twice with ice-water. After drying over sodium sulfate, the solvent is removed under reduced pressure. This gives 3.177 g (87%) of colorless solid.

2.000 g (10.44 mmol) of 3,5-difluoro-N-hydroxybenzenecarboximidoyl chloride are dissolved in 117 g of isopropanol. Then 1.606 g (9.39 mmol) of 75% ethyl 2-methylenebutanoate are added thereto, and the mixture is admixed with 4.385 g (52.20 mmol) of sodium hydrogencarbonate and stirred at RT. After 12 h, undissolved material is filtered off, and the mother liquor is concentrated and separated on silica gel with ethyl acetate/heptane. This gives 1.900 g (61%) of the desired product.

$^1$H NMR [CDCl$_3$]: δ=1.00 (t, 3H); 1.32 (t, 3H); 2.06 (q, 2H); 3.18 (d, 1H); 3.88 (d, 1H); 4.27 (M, 2H); 6.85 (m, 1H), 7.18 (m, 2H).

4. Preparation of 3-[3-chloro-5-(trifluoromethoxy)phenyl]-5-methyl-4,5-dihydro-1,2-oxazole-5-carboxylic acid Example No. 1.1.554

3.878 g (11.03 mmol) of ethyl 3-[3-chloro-5-(trifluoromethoxy)phenyl]-5-methyl-4,5-dihydro-1,2-oxazole-5-carboxylate are initially charged in 50 ml of THF and stirred with 33.1 ml (33.079 mmol) of 1 M sodium hydroxide solution at RT for 16 h. Subsequently, the mixture is acidified with dilute sulfuric acid, sodium chloride solution is added and the mixture is extracted repeatedly with ethyl acetate. This gives 2.323 g (65%) of the above compound after chromatographic purification on silica gel with ethyl acetate/heptane mixtures.

$^1$H NMR [DMSO]: δ=1.58 (s, 3H); 3.3 (OH); 3.32 (d, 1H); 3.84 (d; 1H); 7.61 (m, 1H); 7.70 (s, 1H); 7.78 (m, 1H).

5. Preparation of 3-methoxy-3-oxopropyl-3-(3,5-difluorophenyl)-5-ethyl-4,5-dihydro-1,2-oxazole-5-carboxylate Example No. 2.6.486

Intermediate: 3-(3,5-difluorophenyl)-5-ethyl-4,5-dihydro-1,2-oxazole-5-carbonyl chloride 2.000 g (7.84 mmol) of 3-(3,5-difluorophenyl)-5-ethyl-4,5-dihydro-1,2-oxazole-5-carboxylic acid are dissolved in 50 ml of dichloromethane, and 29.0 mg (73.10 mmol) of dimethylformamide are added thereto. Then the reaction solution is admixed with 1.492 g (11.76 mmol) of oxalyl chloride and stirred at RT. After 1 h, the reaction mixture is concentrated by rotary evaporation, and twice more admixed with toluene and concentrated by rotary evaporation. This gives 2.30 g (97%) of the above carbonyl chloride, which is reacted without further purification.

200.0 mg (0.73 mmol) of 3-(3,5-difluorophenyl)-5-ethyl-4,5-dihydro-1,2-oxazole-5-carbonyl chloride are initially charged in 5 ml of dichloromethane, then 221.86 mg (2.19 mmol) of triethylamine are added thereto, and finally 91.3 mg (0.88 mmol) of methyl 3-hydroxypropanoate in 5 ml of dichloromethane are added thereto. After 1 h, the reaction solution is concentrated by rotary evaporation and separated on silica gel with a heptane/ethyl acetate mixture. This gives 134 mg (51%) of the above compound as a colorless oil.

$^1$H NMR [CDCl$_3$]: δ=0.99 (t, 3H); 2.01-2.07 (m, 2H); 2.72 (t, 2H); 3.17 (d, 1H); 3.68 (s, 3H); 3.75 (d, 1H); 4.41-4.53 (m, 2H); 6.86 (t, 1H); 7.18 (d, 2H).

6. Preparation of 3-(3,5-dichlorophenyl)-5-methyl-4,5-dihydro-1,2-oxazole-5-carbonitrile Example No. 3.417

0.700 g (3.68 mmol) of 3,5-dichlorobenzaldehyde oxime is initially charged in 50 ml of DMF, then 0.516 g (3.87 mmol) of N-chlorosuccinimide is added thereto and the mixture is left to stir at RT for 4 h. Subsequently, 0.371 g (5.53 mmol) of methacrylonitrile and 0.559 g (5.53 mmol) of triethylamine are added thereto and the mixture is left to stir at RT for another 18 h. The mixture is concentrated by rotary evaporation under reduced pressure and separated on preparative HPLC (RP phase). This gives 110 mg (12%) of the desired product as a colorless oil.

$^1$H NMR [CDCl$_3$]: δ=[CDCl$_3$] 1.91 (s, 3H); 3.38 (d, 1H); 3.80 (d, 1H); 7.45 (s, 1H); 7.52 (s, 1H).

7. Preparation of methyl 4-bromo-3-(3,5-difluorophenyl)-5-methyl-4,5-dihydro-1,2-oxazole-5-carboxylate Example No. 2.1.470

1.000 g (5.22 mmol) of 3,5-difluoro-N-hydroxybenzenecarboximidoyl chloride is dissolved in 20 ml of isopropanol, then 1121 mg (6.26 mmol) of methyl 3-bromo-2-methylacrylate are added thereto, and 1754.1 mg (20.88 mmol) of solid sodium hydrogencarbonate. The mixture is left to stir at RT for 2 d and the crude mixture obtained is purified using silica gel with ethyl acetate/heptane. This gives 540 mg (31%) of a yellow oil.

$^1$H NMR [CDCl$_3$]: δ=D1=1.58 (s, 3H); 3.82 (s, 3H); 5.50 (s, 1H); D2=1.85 (s, 3H); 3.72 (s, 3H); 5.78 (s, 1H); 6.8-7.5 (m, 3H).

8. Preparation of methyl 3-(3,5-difluorophenyl)-5-fluoro-4,5-dihydro-1,2-oxazole-5-carboxylate Example No. 2.2.468

1.000 g (5.22 mmol) of 3,5-difluoro-N-hydroxybenzenecarboximidoyl chloride is dissolved in 23 ml of isopropanol, then 1086.6 mg (10.44 mmol) of methyl 2-fluoroacrylate are added thereto, and then the mixture is admixed with 2.192 g (26.10 mmol) of sodium hydrogencarbonate. The mixture is left to stir at 40° C. for 1 h, taken up in water and extracted with ethyl acetate to obtain 1.230 g (91%) of the above compound in solid form.

$^1$H NMR [CDCl$_3$]: δ=3.65 (dd, 1H); 3.96 (s, 3H); 4.12 (dd, 1H); 6.96 (t, 1H); 7.22 (d, 2H).

9. Preparation of 5-(fluoromethyl)-3-(3-fluorophenyl)-4,5-dihydro-1,2-oxazole-5-carboxylic acid Example No. 1.2.001

3.00 g (11.14 mmol) of ethyl 5-(fluoromethyl)-3-(3-fluorophenyl)-4,5-dihydro-1,2-oxazole-5-carboxylate are dissolved in 150 ml of THF, and 0.543 g (22.28 mmol) of lithium hydroxide is added at RT. After 20 h, the mixture is concentrated by rotary evaporation under reduced pressure, and the residue is taken up with dichloromethane and extracted with saturated sodium hydrogencarbonate solution. The aqueous phase is subsequently adjusted to pH 1-2 and the mixture is extracted with ethyl acetate. This gives 2.530 g (89%) of the carboxylic acid.

$^1$H NMR [CDCl$_3$]: δ=3.56 (d, 1H); 3.80 (d, 1H); 4.71 (d, 1H); 4.83 (d, 1H); 7.18 (m, 1H); 7.41 (m, 3H).

10. Preparation of methyl 3-(3-chloro-4-fluorophenyl)-5-(trifluoromethyl)-4,5-dihydro-1,2-oxazole-5-carboxylate Example No. 2.2.1208

1.500 g (8.64 mmol) of 3-chloro-4-fluorobenzaldehyde oxime are initially charged in 47.5 g of DMF and cyclized with 1.212 g (9.07 mmol) of N-chlorosuccinimide, 1.312 g (12.96 mmol) and 2.179 g (12.96 mmol) of methyl 2-(trifluoromethyl)acrylate. After purification on silica gel with ethyl acetate/heptane as a solvent mixture, 1.300 g (43%) of the above product are obtained.

$^1$H NMR [CDCl$_3$]: δ=1.52 8s, 3H); 3.74 (d, 1H); 3.94 (s, 3H); 4.03 (d, 1H); 7.22 (m, 1H); 7.58 (m, 1H); 7.72 (m, 1H).

11. Preparation of 3-(3-chloro-4-fluorophenyl)-5-(trifluoromethyl)-4,5-dihydro-1,2-oxazole-5-carboxylic acid Example No. 1.2.1205

2.000 g (6.14 mmol) of the ester methyl 3-(3-chloro-4-fluorophenyl)-5-(trifluoromethyl)-4,5-dihydro-1,2-oxazole-5-carboxylate are dissolved in 20 ml of THF, 0.295 g (7.37 mmol) of sodium hydroxide in water are added and the mixture is stirred at RT. After 18 h, the solvent is removed by rotary evaporation, water is added, the mixture is washed once with dichloromethane and the water phase is acidified with dilute hydrochloric acid. The latter is extracted twice more with dichloromethane. The mixture is dried over magnesium sulfate to obtain 1.740 g (85%) of the carboxylic acid.

$^1$H NMR [CDCl$_3$]: δ=3.81 (d, 1H); 4.00 (d, 1H); 7.22 (m, 1H); 7.58 (m, 1H); 7.74 (m, 1H).

12. Preparation of methyl 3-(3,5-dichlorophenyl)-5-(methoxymethyl)-4,5-dihydro-1,2-oxazole-5-carboxylate Example No. 2.5.544

1.156 g (6.08 mmol) of 3,5-dichlorobenzaldehyde oxime are cyclized with 0.950 g (7.30 mmol) of methyl 2-(methoxymethyl)acrylate, 0.853 g (6.39 mmol) of N-chlorosuccinimide and 0.923 g (9.13 mmol) of triethylamine in 47.5 g of dimethylformamide. After chromatographic purification on silica gel, 0.150 g (7.34%) of the above compound is obtained as a yellowish oil.

$^1$H NMR [CDCl$_3$]: δ=3.43 (s, 3H); 3.50 (d, 1H); 3.72 (d, 1H); 3.80 (mc, 2H); 3.82 (s, 3H); 7.41 (m, 1H); 7.55 (s, 2H).

13. Preparation of 3-(3,5-dichlorophenyl)-5-(methoxymethyl)-4,5-dihydro-1,2-oxazole-5-carboxylic acid Example No. 1.5.544

100.0 mg (0.31 mmol) of methyl 3-(3,5-dichlorophenyl)-5-(methoxymethyl)-4,5-dihydro-1,2-oxazole-5-carboxylate are dissolved in 5 ml of THF, 40.0 mg (0.47 mmol) of sodium hydroxide in 2 ml of water are added and the mixture is stirred at RT for 18 h.

After removing the solvent, the mixture is diluted with water, the water phase is washed with dichloromethane, then the water phase is acidified with dilute hydrochloric acid and washed once again with dichloromethane. The latter dichloromethane phase is dried. This gives 100 mg (100%) of the above acid as a colorless oil.

$^1$H NMR [CDCl$_3$]: δ=3.48 (s, 3H); 3.50 (d, 1H); 3.72 8d, 1H); 3.85 (q, 2H); 7.42 (m, 1H); 7.55 (m, 2H).

14. Preparation of methyl 3-(3-fluoro-5-methylphenyl)-5-(1-hydroxyethyl)-4,5-dihydro-1,2-oxazole-5-carboxylate Example No. 2.5.498

10.0 g (53.31 mmol) of 3-fluoro-N-hydroxy-5-methylbenzenecarboximidoyl chloride are reacted with 7.631 g (58.64 mmol) of methyl 3-hydroxy-2-methylenebutanoate and 22.390 g (22.54 mmol) of sodium hydrogencarbonate according to method C overnight. After filtration of the reaction solution, it is chromatographed on silica gel. This gives 15.00 g (95%) of the above compound as an oil.

$^1$H NMR [CDCl$_3$]: δ=D1 1.20 (d, 3H); 2.37 (d, 1H); 2.38 (s, 3H); 3.54 (d, 1H); 3.69 (d, 1H); 3.83 (s, 3H); 4.33 (m, 1H); 6.96 (s, 1H); 7.23 (s, 1H); 7.25 (s, 1H). D2 1.26 (d, 3H); 2.18 (d, 1H); 2.38 (s, 3H); 3.60 (d, 1H); 3.72 (d, 1H); 3.83 (s, 3H); 4.22 (m, 1H); 6.93 (s, 1H); 7.21 (s, 1H); 7.25 (s, 1H)

15. Preparation of 3-(3,5-difluorophenyl)-5-(1-hydroxyethyl)-4,5-dihydro-1,2-oxazole-5-carboxylic acid Example No. 1.5.479

1.5 g (5.26 mmol) of methyl 3-(3,5-difluorophenyl)-5-(1-hydroxyethyl)-4,5-dihydro-1,2-oxazole-5-carboxylate in 75 ml THF are hydrolyzed with 0.151 g (6.31 mmol) of LiOH at RT. After 1 h, the solvent is removed under reduced pressure, the pH is brought to 1-2 with hydrochloric acid and extraction is effected with ethyl acetate. This gives 1.50 g (99%) of the above acid.

$^1$H NMR [CDCl$_3$]: δ=D1 1.25 (d, 3H); 1.36 (d, 1H); 3.60 (d, 1H); 3.70 (d, 1H); 4.29 (m, 1H); 6.91 (t, 1H); 7.20 (d, 2H). D2 1.29 (d, 3H); 1.42 (d, 1H); 3.60 (d, 1H); 3.69 (d, 1H); 4.22 (m, 1H); 6.91 (t, 1H); 7.20 (d, 2H).

16. Preparation of methyl 5-acetyl-3-(3,5-difluorophenyl)-4,5-dihydro-1,2-oxazole-5-carboxylate Example No. 2.4.462

To this end, 2.000 g (7.01 mmol) of methyl 3-(3,5-difluorophenyl)-5-(1-hydroxyethyl)-4,5-dihydro-1,2-oxazole-5-carboxylate are stirred with 6.048 g (28.05 mmol) of pyridinium chlorochromate and molecular sieve in 75 ml of dichloromethane at RT for 5 h. The reaction solution is filtered with diethyl ether through an SPE cartridge and concentrated by rotary evaporation. This gives 2.000 g (96%) of the above compound in solid form.

$^1$H NMR [CDCl$_3$]: δ=2.44 (s, 3H); 3.80 (d, 1H); 3.86 (s, 3H); 3.89 (d, 1H); 6.90 (m, 1H); 7.19 (d, 2H).

17. Preparation of methyl 3-(3-chloro-5-fluorophenyl)-5-vinyl-4,5-dihydro-1,2-oxazole-5-carboxylate Example No. 2.3.572

4.400 g (15.76 mmol) of methyl 3-(3-bromo-5-methylphenyl)-5-(1-{[(trifluoromethyl)-sulfonyl]oxy}ethyl)-4,5-dihydro-1,2-oxazole-5-carboxylate, prepared from the corresponding alcohol, trifluoromethanesulfonic anhydride and pyridine (62% yield), are converted together with 600.29 mg (3.94 mmol) of DBU. After 2 days, the reaction mixture is diluted with water, acidified with dilute hydrochloric acid up to pH 4-5 and finally extracted with dichloromethane. Subsequently, the mixture is chromatographed on silica gel with ethyl acetate/heptane. This gives 450 mg (57%) of the above compound as a colorless oil.

$^1$H NMR [CDCl$_3$]: δ=2.35 (s, 3H), 3.35 (d, 1H); 3.83 (s, 3H); 3.93 (d, 1H); 5.35 (d, 1H), 5.55 (d, 1H); 6.13 (dd, 1H); 7.38 (s, 1H), 7.42 (s, 1H); 7.58 (s, 1H).

18. Preparation of methyl 5-(1-chlorovinyl)-3-(3,5-difluorophenyl)-4,5-dihydro-1,2-oxazole-5-carboxylate Example No. 2.3.473

730 mg (2.58 mmol) of methyl 5-acetyl-3-(3,5-difluorophenyl)-4,5-dihydro-1,2-oxazole-5-carboxylate are dissolved in 20 ml of dichloromethane, one drop of DMF is added and the mixture is heated with 590 mg (2.84 mmol) of phosphorus pentachloride at 100° C. in a microwave for 6 h. Subsequently, the reaction mixture is added to a mixture of warm water (about 35° C.) and dichloromethane and stirred at the temperature for 1 h. The water phase (pH 2) is removed. The dichloromethane phase is washed with saturated sodium carbonate solution and dried over sodium sulfate. Subsequently, the mixture is chromatographed using silica gel (ethyl acetate/heptane). This gives 230 mg (25%) of the above compound in solid form.

$^1$H NMR [CDCl$_3$]: δ=3.53 (d, 1H); 3.88 (s, 3H); 4.22 (d, 1H); 5.55 (s, 1H); 5.93 (s, 1H); 6.90 (m, 1H); 7.20 (d, 2H).

In analogy to the preparation of the abovementioned compounds and in accordance with the general details of the preparation, the compounds specified in the following tables are obtainable. The NMR data of the examples disclosed in these tables are given either in conventional form (δ values, number of hydrogen atoms, multiplet splitting) or as NMR peak lists. In the NMR peak list method, the NMR data of selected examples are stated in the form of NMR peak lists, giving, for each signal peak, first the δ value in ppm and then the signal intensity separated by a space. The δ value/signal intensity number pairs for different signal peaks are listed separated from one another by semicolons.

The abbreviations used mean:

| Ac | acetoxy | Bu | butyl | Et | ethyl | Me | methyl |
|---|---|---|---|---|---|---|---|
| Pr | propyl | Pen | pentyl | Hex | hexyl | Ph | phenyl |
| c | cyclo | s | secondary | i | iso | t | tertiary |
| THF | tetrahydrofuran | | | | | | |

D1, D2 denote diastereomers of a diastereomer pair present as a racemate of two enantiomers.

TABLE 1.1

Inventive compounds of the general formula (I) in which W* is COOH, R¹ is hydrogen, and aryl is the radical.

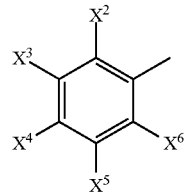

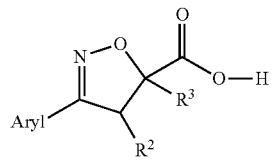

| No. | Aryl | R² | R³ | Physical data |
|---|---|---|---|---|
| 1.1.1 | 3-fluorophenyl | H | methyl | [CDCl₃] 1.78 (s, 3H); 3.29 (d, 1H); 3.85 (d, 1H); 7.12 (m, 1H); 7.40 (m, 2H). |
| 1.1.2 | 3-fluorophenyl | H | ethyl | [CDCl₃] 1.08 (t, 3H); 2.14 (mc; 2H); 3.32 (d, 1H); 3.30 (d, 1H); 7.15 (m, 1H); 7.40 (m, 2H). |
| 1.1.3 | 3-fluorophenyl | H | propyl | |
| 1.1.4 | 3-fluorophenyl | H | cyclopropyl | |
| 1.1.5 | 3-chlorophenyl | H | methyl | [CDCl₃] 1.78 (s, 3H); 3.28 (d, 1H); 3.86 (d, 1H); 7.35 (m, 1H); 7.42 (m, 1H); 7.51 (m, 1H); 7.65 (m, 1H). |
| 1.1.6 | 3-chlorophenyl | H | ethyl | |
| 1.1.7 | 3-chlorophenyl | H | propyl | |
| 1.1.8 | 3-chlorophenyl | H | cyclopropyl | |
| 1.1.9 | 3-bromophenyl | H | methyl | [CDCl₃] 1.72 (s, 3H); 3.19 (d, 1H); 3.82 (s, 3H); 3.86 (d, 1H); 7.28 (t, 1H); 7.55 (m, 1H); 7.59 (m, 1H); 7.80 (t, 1 H). |
| 1.1.10 | 3-bromophenyl | H | ethyl | |
| 1.1.11 | 3-iodophenyl | H | methyl | |
| 1.1.12 | 3-iodophenyl | H | ethyl | |
| 1.1.13 | 3-methylphenyl | H | methyl | [DMSO] 1.55 (s, 3H); 2.32 (s, 3H); 3.35 (d, 1H); 3.76 (d, 1H); 7.20-7.50 (m, 4H). |
| 1.1.14 | 3-methylphenyl | H | ethyl | |
| 1.1.15 | 3-ethylphenyl | H | methyl | [DMSO] 1.20 (t, 3H); 1.55 (s, 3H); 2.65 (q, 2H); 3.38 (d, 1H); 3.80 (d, 1H); 7.28-7.50 (m, 4H). |
| 1.1.16 | 3-propylphenyl | H | methyl | |
| 1.1.17 | 3-isopropylphenyl | H | methyl | [DMSO] 1.20 (d, 6H); 1.55 (s, 3H); 2.94 (m, 1H); 3.40 (d, 1H); 3.80 (d, 1H); 7.35 (m, 2H); 7.48 (m, 1H); 7.55 (s, 1H). |
| 1.1.18 | 3-n-butylphenyl | H | methyl | |
| 1.1.19 | 3-i-butylphenyl | H | methyl | |
| 1.1.20 | 3-tert-butylphenyl | H | methyl | |
| 1.1.21 | 3-cyclopropylphenyl | H | methyl | |
| 1.1.22 | 3-cyclobutylphenyl | H | methyl | |
| 1.1.23 | 3-cyclopentylphenyl | H | methyl | |
| 1.1.24 | 3-vinylphenyl | H | methyl | |
| 1.1.25 | 3-ethynylphenyl | H | methyl | [CDCl₃] 1.78 (s, 1H); 3.10 (s, 1H); 3.30 (d, 1H); 3.87 (d, 1H); 7.35 (m, 1H); 7.52 (m, 1H); 7.68 (m, 1H); 7.75 (s, 1H). |
| 1.1.26 | 3-cyanophenyl | H | methyl | [CDCl₃] 1.80 (s, 3H); 3.29 (d, 1H); 3.89 (d, 1H); 7.55 (m, 1H); 7.72 (m, 1H); 7.90 (m, 2H). |
| 1.1.27 | 3-trifluoromethyl-phenyl | H | methyl | [CDCl₃] 1.80 (s, 3H); 3.32 (d, 1H); 3.91 (d, 1H); 7.56 (m, 1H); 7.69 (m, 1H); 7.88 (m, 2H). |
| 1.1.28 | 3-difluoromethyl-phenyl | H | methyl | |

TABLE 1.1-continued

Inventive compounds of the general formula (I) in which W* is COOH, R¹ is hydrogen, and aryl is the radical.

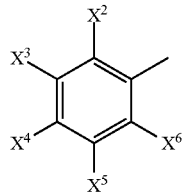

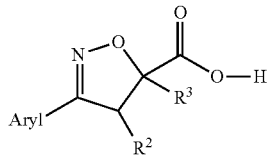

| No. | Aryl | R² | R³ | Physical data |
|---|---|---|---|---|
| 1.1.29 | 3-(hydroxycarbonyl)-phenyl | H | methyl | [DMSO] 1.58 (s, 3H); 3.42 (d, 1H);3.82 (d, 1H); 7.60 (t, 1H); 7.90 (d, 1H); 8.03 (d, 1H); 8.20 (s, 1H). 13.2 (bs, 1H) |
| 1.1.30 | 3-(methoxycarbonyl)-phenyl | H | methyl | |
| 1.1.31 | 3-(ethoxycarbonyl)-phenyl | H | methyl | |
| 1.1.32 | 3-hydroxymethyl-phenyl | H | methyl | |
| 1.1.33 | 3-carbamoylphenyl | H | methyl | [DMSO] 1.58 (s, 3H); 3.40 (d, 1H); 3.85 (d, 1H); 7.43 (bs, 1H); 7.53 t, 1H); 7.85 (d, 1H); 7.95 (d, 1H); 8.08 (bs, 1H); 8.11 (s, 1H). |
| 1.1.34 | 3-hydroxyphenyl | H | methyl | [DMSO] 1.52 (s, 3H); 3.32 (d, 1H); 3.71 (d, 1H); 6.85 (d, 1H); 7.08 (m, 2H); 7.24 /t, 1H); 9.65 (s, 1H); 13.2 (bs, 1H). |
| 1.1.35 | 3-methoxyphenyl | H | methyl | [CDCl₃] 1.75 (s, 3H); 3.30 (d, 1H); 3.85 (s, 3H); 3.89 (d, 1H); 7.00 (m, 1H); 7.16 (m, 1H); 7.25 (m, 1H); 7.35 (m, 1H). |
| 1.1.36 | 3-ethoxyphenyl | H | methyl | [CDCl₃] 1.41 (t, 1H), 1.75 (s, 1H); 3.25 (d, 1H); 3.83 (d, 1H); 4.05 (q, 2H); 6.95 (m, 1H); 7.15 (m, 1H); 7.20-7.32 (m, 2H). |
| 1.1.37 | 3-propyloxyphenyl | H | methyl | |
| 1.1.38 | 3-isopropyloxyphenyl | H | methyl | |
| 1.1.39 | 3-n-butyloxyphenyl | H | methyl | |
| 1.1.40 | 3-i-butyloxyphenyl | H | methyl | |
| 1.1.41 | 3-t-butyloxyphenyl | H | methyl | |
| 1.1.42 | 3-difluoromethoxy-phenyl | H | methyl | [CDCl₃] 1.78 (s, 3H); 3.38 (d, 1H); 3.86 (d, 1H); 6.52 (t, 1H); 7.21 (m, 1H); 7.43 (m, 2H). |
| 1.1.43 | 3-trifluoromethoxy-phenyl | H | methyl | [CDCl₃] 1.80 (s, 3H); 3.30 (d, 1H); 3.88 (d, 1H); 7.25 (m, 1H); 7.45 (m, 1H); 7.55 (m, 2H). |
| 1.1.44 | 3-(2,2,2-trifluoro-ethoxy)phenyl | H | methyl | |
| 1.1.45 | 3-(2-chloroethoxy)-phenyl | H | methyl | |
| 1.1.46 | 3-(2-hydroxyethoxy)-phenyl | H | methyl | |
| 1.1.47 | 3-(2-methoxyethoxy)-phenyl | H | methyl | [CDCl₃] 1.75 (s, 3H); 3.35 (d, 1H); 3.43 (s, 3H); 3.75 (dd, 2H); 3.85 (d, 1H); 4.14 (dd, 2H); 7.04 (d, 1H); 7.15 (d, 1H); 7.25-7.40 (m, 2H). |
| 1.1.48 | 3-[(tert-butoxy-carbonyl)oxy]phenyl | H | methyl | |
| 1.1.49 | 3-nitrophenyl | H | methyl | [DMSO] 1.52 (s, 3H); 3.40 (d, 1H); 3.85 (d, 1H); 7.75 (t, 1H); 8.08 (d, 1H); 8.29 (d, 1H); 8.4 (s, 1H). |

TABLE 1.1-continued

Inventive compounds of the general formula (I) in which W* is COOH, $R^1$ is hydrogen, and aryl is the radical.

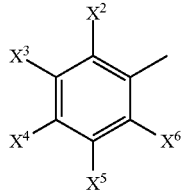

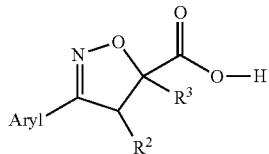

| No. | Aryl | $R^2$ | $R^3$ | Physical data |
|---|---|---|---|---|
| 1.1.50 | 3-acetoxyphenyl | H | methyl | |
| 1.1.51 | {3-[(tert-butoxycarbonyl)-amino]phenyl} | H | methyl | [CDCl$_3$] 1.50 (s, 9H); 1.75 (s, 3H); 3.30 (d, 1H); 3.90 (d, 1H); 6.70 (bs, 1H); 7.30 (s, 2H), 7.40 (s, 1H), 7.70 (s, 1H). |
| 1.1.52 | 3-methylsulfanyl-phenyl | H | methyl | |
| 1.1.53 | 3-ethylsulfanylphenyl | H | methyl | |
| 1.1.54 | 3-(pentafluoro-lambda$^6$-sulfanyl)-phenyl | H | methyl | [CDCl$_3$] 1.80 (s, 3H); 3.30 (d, 1H); 3.90 (d, 1H); 7.51 (t, 1H); 7.80 (2d, 2H); 8.00 (s, 1H). |
| 1.1.55 | 2,3-difluorophenyl | H | methyl | [CDCl$_3$] 1.78 (s, 3H); 3.40 (dd, 1H); 3.95 (dd, 1H); 7.13 (m, 1H); 7.22 (m, 2H); 7.61 (t, 1H). |
| 1.1.56 | 2,3-difluorophenyl | H | ethyl | |
| 1.1.57 | 2,3-difluorophenyl | H | propyl | |
| 1.1.58 | 2,3-difluorophenyl | H | cyclopropyl | |
| 1.1.59 | 2-chloro-3-fluorophenyl | H | methyl | |
| 1.1.60 | 2-bromo-3-fluorophenyl | H | methyl | |
| 1.1.61 | 2-methyl-3-fluorophenyl | H | methyl | |
| 1.1.62 | 2-ethyl-3-fluorophenyl | H | methyl | |
| 1.1.63 | 2-cyclopropyl-3-fluorophenyl | H | methyl | |
| 1.1.64 | 2-vinyl-3-fluorophenyl | H | methyl | |
| 1.1.65 | 2-ethynyl-3-fluorophenyl | H | methyl | |
| 1.1.66 | 2-cyano-3-fluorophenyl | H | methyl | |
| 1.1.67 | 2-methoxy-3-fluorophenyl | H | methyl | |
| 1.1.68 | 2-ethoxy-3-fluorophenyl | H | methyl | |
| 1.1.69 | 2-trifluoromethoxy-3-fluorophenyl | H | methyl | |
| 1.1.70 | 2-nitro-3-fluorophenyl | H | methyl | |
| 1.1.71 | 2-fluoro-3-chlorophenyl | H | methyl | |
| 1.1.72 | 2,3-dichlorophenyl | H | methyl | [CDCl$_3$] 1.80 (s, 3H); 3.50 (d, 1H); 3.95 (d, 1H); 7.25 (m, 1 H); 7.26 (m, 1H); 7.50 (m, 1H); 7.58 (m, 1H). |
| 1.1.73 | 2,3-dichlorophenyl | H | ethyl | |
| 1.1.74 | 2,3-dichlorophenyl | H | propyl | |
| 1.1.75 | 2,3-dichlorophenyl | H | cyclopropyl | |
| 1.1.76 | 2-bromo-3-chlorophenyl | H | methyl | |
| 1.1.77 | 2-methyl-3-chlorophenyl | H | methyl | |
| 1.1.78 | 2-ethyl-3-chlorophenyl | H | methyl | |

TABLE 1.1-continued

Inventive compounds of the general formula (I) in which W* is COOH, R¹ is hydrogen, and aryl is the radical.

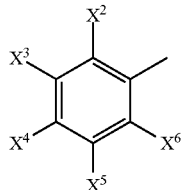

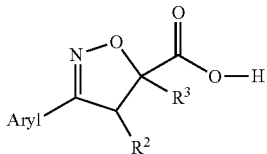

| No. | Aryl | R² | R³ | Physical data |
|---|---|---|---|---|
| 1.1.79 | 2-cyclopropyl-3-chlorophenyl | H | methyl | |
| 1.1.80 | 2-vinyl-3-chlorophenyl | H | methyl | |
| 1.1.81 | 2-ethynyl-3-chlorophenyl | H | methyl | |
| 1.1.82 | 2-cyano-3-chlorophenyl | H | methyl | |
| 1.1.83 | 2-trifluoromethyl-2-chlorophenyl | H | methyl | |
| 1.1.84 | 2-methoxy-3-chlorophenyl | H | methyl | |
| 1.1.85 | 2-ethoxy-3-chlorophenyl | H | methyl | |
| 1.1.86 | 2-trifluoromethoxy-3-chlorophenyl | H | methyl | |
| 1.1.87 | 2-nitro-3-chlorophenyl | H | methyl | |
| 1.1.88 | 2-fluoro-3-bromophenyl | H | methyl | |
| 1.1.89 | 2-chloro-3-bromophenyl | H | methyl | |
| 1.1.90 | 2,3-dibromophenyl | H | methyl | |
| 1.1.91 | 2-methyl-3-bromophenyl | H | methyl | |
| 1.1.92 | 2-ethyl-3-bromophenyl | H | methyl | |
| 1.1.93 | 2-cyclopropyl-3-bromophenyl | H | methyl | |
| 1.1.94 | 2-vinyl-3-bromophenyl | H | methyl | |
| 1.1.95 | 2-ethynyl-3-bromophenyl | H | methyl | |
| 1.1.96 | 2-cyano-3-bromophenyl | H | methyl | |
| 1.1.97 | 2-trifluoromethyl-3-bromophenyl | H | methyl | |
| 1.1.98 | 2-methoxy-3-phenyl | H | methyl | |
| 1.1.99 | 2-ethoxy-3-bromophenyl | H | methyl | |
| 1.1.100 | 2-trifluoromethoxy-3-bromophenyl | H | methyl | |
| 1.1.101 | 2-nitro-3-bromophenyl | H | methyl | |
| 1.1.102 | 2-fluoro-3-iodophenyl | H | methyl | |
| 1.1.103 | 2-chloro-3-iodophenyl | H | methyl | |
| 1.1.104 | 2-bromo-3-iodophenyl | H | methyl | |
| 1.1.105 | 2-methyl-3-iodophenyl | H | methyl | |
| 1.1.106 | 2-ethyl-3-iodophenyl | H | methyl | |
| 1.1.107 | 2-cyclopropyl-3-iodophenyl | H | methyl | |
| 1.1.108 | 2-vinyl-3-iodophenyl | H | methyl | |

TABLE 1.1-continued

Inventive compounds of the general formula (I) in which W* is COOH, R¹ is hydrogen, and aryl is the radical.

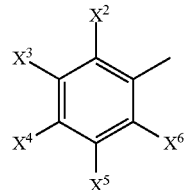

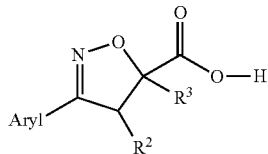

| No. | Aryl | R² | R³ | Physical data |
|---|---|---|---|---|
| 1.1.109 | 2-ethynyl-3-iodophenyl | H | methyl | |
| 1.1.110 | 2-cyano-3-iodophenyl | H | methyl | |
| 1.1.111 | 2-trifluoromethyl-3-iodophenyl | H | methyl | |
| 1.1.112 | 2-methoxy-3-iodophenyl | H | methyl | |
| 1.1.113 | 2-ethoxy-3-iodophenyl | H | methyl | |
| 1.1.114 | 2-trifluoromethoxy-3-iodophenyl | H | methyl | |
| 1.1.115 | 2-nitro-3-iodophenyl | H | methyl | |
| 1.1.116 | 2-fluoro-3-methylphenyl | H | methyl | [CDCl$_3$] 1.56 (s, 3H); 2.25 (s, 3H); 3.35 (d, 1H); 3.80 (d, 1H); 7.15 (t, 1H); 7.40 (t, 1H); 7.51 (t, 1H). |
| 1.1.117 | 2-fluoro-3-methylphenyl | H | ethyl | |
| 1.1.118 | 2-fluoro-3-methylphenyl | H | propyl | |
| 1.1.119 | 2-fluoro-3-methylphenyl | H | cyclopropyl | |
| 1.1.120 | 2-chloro-3-methylphenyl | H | methyl | |
| 1.1.121 | 2-chloro-3-methylphenyl | H | ethyl | |
| 1.1.122 | 2-chloro-3-methylphenyl | H | propyl | |
| 1.1.123 | 2-chloro-3-methylphenyl | H | cyclopropyl | |
| 1.1.124 | 2-bromo-3-methylphenyl | H | methyl | |
| 1.1.125 | 2,3-dimethylphenyl | H | methyl | |
| 1.1.126 | 2,3-dimethylphenyl | H | ethyl | |
| 1.1.127 | 2,3-dimethylphenyl | H | propyl | |
| 1.1.128 | 2,3-dimethylphenyl | H | cyclopropyl | |
| 1.1.129 | 2-ethyl-3-methylphenyl | H | methyl | |
| 1.1.130 | 2-cyclopropyl-3-methylphenyl | H | methyl | |
| 1.1.131 | 2-vinyl-3-methylphenyl | H | methyl | |
| 1.1.132 | 2-ethynyl-3-methylphenyl | H | methyl | |
| 1.1.133 | 2-cyano-3-methylphenyl | H | methyl | |
| 1.1.134 | 2-trifluoromethyl-3-methylphenyl | H | methyl | |
| 1.1.135 | 2-methoxy-3-methylphenyl | H | methyl | |
| 1.1.136 | 2-ethoxy-3-methylphenyl | H | methyl | |
| 1.1.137 | 2-trifluoromethoxy-3-methylphenyl | H | methyl | |

TABLE 1.1-continued

Inventive compounds of the general formula (I) in which W* is COOH, R¹ is hydrogen, and aryl is the radical.

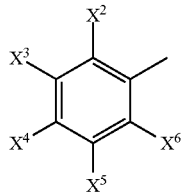

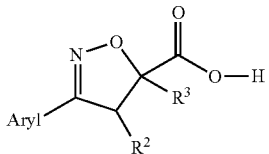

| No. | Aryl | R² | R³ | Physical data |
|---|---|---|---|---|
| 1.1.138 | 2-nitro-3-methylphenyl | H | methyl | |
| 1.1.139 | 2-fluoro-3-ethylphenyl | H | methyl | |
| 1.1.140 | 2-chloro-3-ethylphenyl | H | methyl | |
| 1.1.141 | 2-bromo-3-ethylphenyl | H | methyl | |
| 1.1.142 | 2-methyl-3-ethylphenyl | H | methyl | |
| 1.1.143 | 2,3-diethylphenyl | H | methyl | |
| 1.1.144 | 2-cyclopropyl-3-ethylphenyl | H | methyl | |
| 1.1.145 | 2-vinyl-3-ethylphenyl | H | methyl | |
| 1.1.146 | 2-ethynyl-3-ethylphenyl | H | methyl | |
| 1.1.147 | 2-cyano-3-ethylphenyl | H | methyl | |
| 1.1.148 | 2-trifluoromethyl-3-ethylphenyl | H | methyl | |
| 1.1.149 | 2-methoxy-3-ethylphenyl | H | methyl | |
| 1.1.150 | 2-ethoxy-3-ethylphenyl | H | methyl | |
| 1.1.151 | 2-trifluoromethoxy-3-ethylphenyl | H | methyl | |
| 1.1.152 | 2-nitro-3-ethylphenyl | H | methyl | |
| 1.1.153 | 2-fluoro-3-propylphenyl | H | methyl | |
| 1.1.154 | 2-chloro-3-propylphenyl | H | methyl | |
| 1.1.155 | 2-bromo-3-propylphenyl | H | methyl | |
| 1.1.156 | 2-methyl-3-propylphenyl | H | methyl | |
| 1.1.157 | 2-methyl-3-propylphenyl | H | methyl | |
| 1.1.158 | 2-cyclopropyl-3-propylphenyl | H | methyl | |
| 1.1.159 | 2-vinyl-3-propylphenyl | H | methyl | |
| 1.1.160 | 2-ethynyl-3propylphenyl | H | methyl | |
| 1.1.161 | 2-cyano-3-propylphenyl | H | methyl | |
| 1.1.162 | 2-trifluoromethyl-3-propylphenyl | H | methyl | |
| 1.1.163 | 2-methoxy-3-propylphenyl | H | methyl | |
| 1.1.164 | 2-ethoxy-3-propylphenyl | H | methyl | |
| 1.1.165 | 2-trifluoromethoxy-3-propylphenyl | H | methyl | |
| 1.1.166 | 2-nitro-3-propylphenyl | H | methyl | |

TABLE 1.1-continued

Inventive compounds of the general formula (I) in which W* is COOH, R¹ is hydrogen, and aryl is the radical.

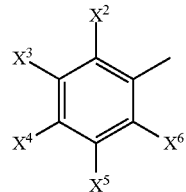

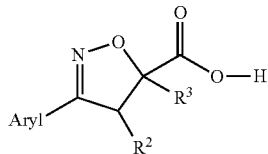

| No. | Aryl | R² | R³ | Physical data |
|---|---|---|---|---|
| 1.1.167 | 2-fluoro-3-isopropylphenyl | H | methyl | |
| 1.1.168 | 2-chloro-3-isopropylphenyl | H | methyl | |
| 1.1.169 | 2-bromo-3-isopropylphenyl | H | methyl | |
| 1.1.170 | 2-methyl-3-isopropylphenyl | H | methyl | |
| 1.1.171 | 2-ethyl-3-isopropylphenyl | H | methyl | |
| 1.1.172 | 2-cyclopropyl-3-isopropylphenyl | H | methyl | |
| 1.1.173 | 2-vinyl-3-isopropylphenyl | H | methyl | |
| 1.1.174 | 2-ethynyl-3-isopropylphenyl | H | methyl | |
| 1.1.175 | 2-cyano-3-isopropylphenyl | H | methyl | |
| 1.1.176 | 2-trifluoromethyl-3-isopropylphenyl | H | methyl | |
| 1.1.177 | 2-methoxy-3-isopropylphenyl | H | methyl | |
| 1.1.178 | 2-thoxy-3-isopreopylphenyl | H | methyl | |
| 1.1.179 | 2-trifluoromethoxy-3-isopropylphenyl | H | methyl | |
| 1.1.180 | 2-nitro-3-isopropylphenyl | H | methyl | |
| 1.1.181 | 2-fluoro-3-tert-butylphenyl | H | methyl | |
| 1.1.182 | 2-chloro-3-tert-butylphenyl | H | methyl | |
| 1.1.183 | 2-bromo-3-tert-butylphenyl | H | methyl | |
| 1.1.184 | 2-methyl-3-tert-butylphenyl | H | methyl | |
| 1.1.185 | 2-ethyl-3-tert-butylphenyl | H | methyl | |
| 1.1.186 | 2-cyclopropyl-3-tert-butylphenyl | H | methyl | |
| 1.1.187 | 2-vinyl-3-tert-butylphenyl | H | methyl | |
| 1.1.188 | 2-ethynyl-3-tert-butylphenyl | H | methyl | |
| 1.1.189 | 2-cyano-3-tert-butylphenyl | H | methyl | |
| 1.1.190 | 2-trifluoromethyl-3-tert-butylphenyl | H | methyl | |
| 1.1.191 | 2-methoxy-3-tert-butylphenyl | H | methyl | |
| 1.1.192 | 2-ethoxy-3-tert-butylphenyl | H | methyl | |
| 1.1.193 | 2-trifluoromethoxy-3-tert-butylphenyl | H | methyl | |

TABLE 1.1-continued

Inventive compounds of the general formula (I) in which W* is COOH, R¹ is hydrogen, and aryl is the radical.

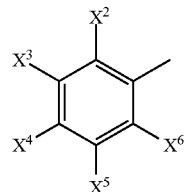

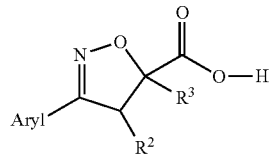

| No. | Aryl | R² | R³ | Physical data |
|---|---|---|---|---|
| 1.1.194 | 2-nitro-3-tert-butylphenyl | H | methyl | |
| 1.1.195 | 2-fluoro-3-hydroxymethylphenyl | H | methyl | |
| 1.1.196 | 2-chloro-3-hydroxymethylphenyl | H | methyl | |
| 1.1.197 | 2-bromo-3-hydroxymethylphenyl | H | methyl | |
| 1.1.198 | 2-methyl-3-hydroxymethylphenyl | H | methyl | |
| 1.1.199 | 2-ethyl-3-hydroxymethylphenyl | H | methyl | |
| 1.1.200 | 2-cyclopropyl-3-hydroxymethylphenyl | H | methyl | |
| 1.1.201 | 2-vinyl-3-hydroxymethylphenyl | H | methyl | |
| 1.1.202 | 2-ethynyl-3-hydroxymethylphenyl | H | methyl | |
| 1.1.203 | 2-cyano-3-hydroxymethylphenyl | H | methyl | |
| 1.1.204 | 2-trifluoromethyl-3-hydroxymethylphenyl | H | methyl | |
| 1.1.205 | 2-methoxy-3-hydroxymethylphenyl | H | methyl | |
| 1.1.206 | 2-ethoxy-3-hydroxymethylphenyl | H | methyl | |
| 1.1.207 | 2-trifluoromethoxy-3-hydroxymethylphenyl | H | methyl | |
| 1.1.208 | 2-nitro-3-hydroxymethylphenyl | H | methyl | |
| 1.1.209 | 2-fluoro-3-cyclopropylphenyl | H | methyl | |
| 1.1.210 | 2-chloro-3-cyclopropylphenyl | H | methyl | |
| 1.1.211 | 2-bromo-3-cyclopropylphenyl | H | methyl | |
| 1.1.212 | 2-methyl-3-cyclopropylphenyl | H | methyl | |
| 1.1.213 | 2-ethyl-3-cyclopropylphenyl | H | methyl | |
| 1.1.214 | 2-cyclopropyl-3-cyclopropylphenyl | H | methyl | |
| 1.1.215 | 2-vinyl-3-cyclopropylphenyl | H | methyl | |
| 1.1.216 | 2-ethynyl-3-cyclopropylphenyl | H | methyl | |
| 1.1.217 | 2-cyano-3-cyclopropylphenyl | H | methyl | |
| 1.1.218 | 2-trifluoromethyl-3-cyclopropylphenyl | H | methyl | |
| 1.1.219 | 2-methoxy-3-cyclopropylphenyl | H | methyl | |
| 1.1.220 | 2-ethoxy-3-cyclopropylphenyl | H | methyl | |

TABLE 1.1-continued

Inventive compounds of the general formula (I) in which W* is COOH, $R^1$ is hydrogen, and aryl is the radical.

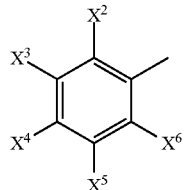

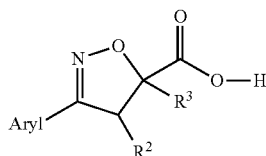

| No. | Aryl | $R^2$ | $R^3$ | Physical data |
|---|---|---|---|---|
| 1.1.221 | 2-trifluoromethoxy-3-cyclopropylphenyl | H | methyl | |
| 1.1.222 | 2-fluoro-3-methoxy-carbonylphenyl | H | methyl | |
| 1.1.223 | 2-chloro-3-methoxy-carbonylphenyl | H | methyl | |
| 1.1.224 | 2-bromo-3-methoxy-carbonylphenyl | H | methyl | |
| 1.1.225 | 2-methyl-3-methoxy-carbonylphenyl | H | methyl | |
| 1.1.226 | 2-ethyl-3-methoxy-carbonylphenyl | H | methyl | |
| 1.1.227 | 2-cyclopropyl-3-methoxycarbonyl-phenyl | H | methyl | |
| 1.1.228 | 2-vinyl-3-methoxy-carbonylphenyl | H | methyl | |
| 1.1.229 | 2-ethynyl-3-methoxy-carbonylphenyl | H | methyl | |
| 1.1.230 | 2-cyano-3-methoxy-carbonylphenyl | H | methyl | |
| 1.1.231 | 2-trifluoromethyl-3-methoxycarbonyl-phenyl | H | methyl | |
| 1.1.232 | 2-methoxy-3-methoxycarbonyl-phenyl | H | methyl | |
| 1.1.233 | 2-ethoxy-3-methoxy-carbonylphenyl | H | methyl | |
| 1.1.234 | 2-trifluoromethoxy-3-methoxycarbonyl-phenyl | H | methyl | |
| 1.1.235 | 2-nitro-3-methoxy-carbonylphenyl | H | methyl | |
| 1.1.236 | 2-fluoro-3-vinylphenyl | H | methyl | |
| 1.1.237 | 2-chloro-3-vinylphenyl | H | methyl | |
| 1.1.238 | 2-bromo-3-vinylphenyl | H | methyl | |
| 1.1.239 | 2-methyl-3-vinylphenyl | H | methyl | |
| 1.1.240 | 2-ethyl-3-vinylphenyl | H | methyl | |
| 1.1.241 | 2-cyclopropyl-3-vinylphenyl | H | methyl | |
| 1.1.242 | 2-vinyl-3-vinylphenyl | H | methyl | |
| 1.1.243 | 2-ethynyl-3-vinylphenyl | H | methyl | |
| 1.1.244 | 2-cyano-3-vinylphenyl | H | methyl | |
| 1.1.245 | 2-trifluoromethyl-3-vinylphenyl | H | methyl | |

TABLE 1.1-continued

Inventive compounds of the general formula (I) in which W* is COOH, R¹ is hydrogen, and aryl is the radical.

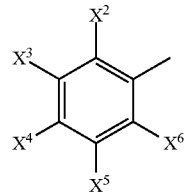

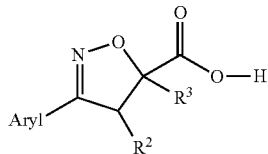

| No. | Aryl | R² | R³ | Physical data |
|---|---|---|---|---|
| 1.1.246 | 2-methoxy-3-vinylphenyl | H | methyl | |
| 1.1.247 | 2-ethoxy-3-vinylphenyl | H | methyl | |
| 1.1.248 | 2-trifluoromethoxy-3-vinylphenyl | H | methyl | |
| 1.1.249 | 2-nitro-3-vinylphenyl | H | methyl | |
| 1.1.250 | 2-fluoro-3-ethynylphenyl | H | methyl | |
| 1.1.251 | 2-chloro-3-ethynylphenyl | H | methyl | |
| 1.1.252 | 2-bromo-3-ethynylphenyl | H | methyl | |
| 1.1.253 | 2-methyl-3-ethynylphenyl | H | methyl | |
| 1.1.254 | 2-ethyl-3-ethynylphenyl | H | methyl | |
| 1.1.255 | 2-cyclopropyl-3-ethynylphenyl | H | methyl | |
| 1.1.256 | 2-vinyl-3-ethynylphenyl | H | methyl | |
| 1.1.257 | 2-cyano-3-ethynylphenyl | H | methyl | |
| 1.1.258 | 2-trifluoromethyl-3-ethynylphenyl | H | methyl | |
| 1.1.259 | 2-methoxy-3-ethynylphenyl | H | methyl | |
| 1.1.260 | 2-ethoxy-3-ethynylphenyl | H | methyl | |
| 1.1.261 | 2-trifluoromethoxy-3-ethynylphenyl | H | methyl | |
| 1.1.262 | 2-nitro-3-ethynylphenyl | H | methyl | |
| 1.1.263 | 2-fluoro-3-ethynylphenyl | H | methyl | |
| 1.1.264 | 2-fluoro-3-cyanophenyl | H | methyl | |
| 1.1.265 | 2-chloro-3-cyanophenyl | H | methyl | |
| 1.1.266 | 2-bromo-3-cyanophenyl | H | methyl | |
| 1.1.267 | 2-methyl-3-cyanophenyl | H | methyl | |
| 1.1.268 | 2-ethyl-3-cyanophenyl | H | methyl | |
| 1.1.269 | 2-ethyl-3-cyanophenyl | H | ethyl | |
| 1.1.270 | 2-ethyl-3-cyanophenyl | H | propyl | |
| 1.1.271 | 2-ethyl-3-cyanophenyl | H | cyclopropyl | |
| 1.1.272 | 2-cyclopropyl-3-cyanophenyl | H | methyl | |
| 1.1.273 | 2-vinyl-3-cyanophenyl | H | methyl | |

TABLE 1.1-continued

Inventive compounds of the general formula (I) in which W* is COOH, R¹ is hydrogen, and aryl is the radical.

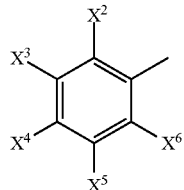

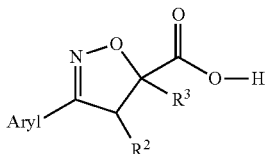

| No. | Aryl | R² | R³ | Physical data |
|---|---|---|---|---|
| 1.1.274 | 2-ethynyl-3-cyanophenyl | H | methyl | |
| 1.1.275 | 2-cyano-3-cyanophenyl | H | methyl | |
| 1.1.276 | 2-trifluoromethyl-3-cyanophenyl | H | methyl | |
| 1.1.277 | 2-methoxy-3-cyanophenyl | H | methyl | |
| 1.1.278 | 2-ethoxy-3-cyanophenyl | H | methyl | |
| 1.1.279 | 2-trifluoromethoxy-3-cyanophenyl | H | methyl | |
| 1.1.280 | 2-nitro-3-cyanophenyl | H | methyl | |
| 1.1.281 | 2-fluoro-3-hydroxyphenyl | H | methyl | |
| 1.1.282 | 2-chloro-3-hydroxyphenyl | H | methyl | |
| 1.1.283 | 2-bromo-3-hydroxyphenyl | H | methyl | |
| 1.1.284 | 2-methyl-3-hydroxyphenyl | H | methyl | |
| 1.1.285 | 2-ethyl-3-hydroxyphenyl | H | methyl | |
| 1.1.286 | 2-cyclopropyl-3-hydroxyphenyl | H | methyl | |
| 1.1.287 | 2-vinyl-3-hydroxyphenyl | H | methyl | |
| 1.1.288 | 2-ethynyl-3-hydroxyphenyl | H | methyl | |
| 1.1.289 | 2-cyano-3-hydroxyphenyl | H | methyl | |
| 1.1.290 | 2-trifluoromethyl-3-hydroxyphenyl | H | methyl | |
| 1.1.291 | 2-methoxy-3-hydroxyphenyl | H | methyl | |
| 1.1.292 | 2-ethoxy-3-hydroxyphenyl | H | methyl | |
| 1.1.293 | 2-trifluoromethoxy-3-hydroxyphenyl | H | methyl | |
| 1.1.294 | 2-nitro-3-hydroxyphenyl | H | methyl | |
| 1.1.295 | 2-fluoro-3-methoxyphenyl | H | methyl | |
| 1.1.296 | 2-chloro-3-methoxyphenyl | H | methyl | |
| 1.1.297 | 2-bromo-3-methoxyphenyl | H | methyl | |
| 1.1.298 | 2-methyl-3-methoxyphenyl | H | methyl | |
| 1.1.299 | 2-ethyl-3-methoxyphenyl | H | methyl | |

TABLE 1.1-continued

Inventive compounds of the general formula (I) in which W* is COOH, R¹ is hydrogen, and aryl is the radical.

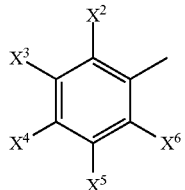

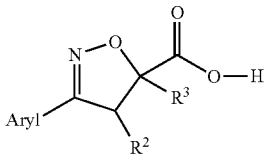

| No. | Aryl | R² | R³ | Physical data |
|---|---|---|---|---|
| 1.1.300 | 2-cyclopropyl-3-methoxyphenyl | H | methyl | |
| 1.1.301 | 2-vinyl-3-methoxyphenyl | H | methyl | |
| 1.1.302 | 2-ethynyl-3-methoxyphenyl | H | methyl | |
| 1.1.303 | 2-cyano-3-methoxyphenyl | H | methyl | |
| 1.1.304 | 2-trifluoromethyl-3-methoxyphenyl | H | methyl | |
| 1.1.305 | 2,3-dimethoxy-phenyl | H | methyl | |
| 1.1.306 | 2-ethoxy-3-methoxyphenyl | H | methyl | |
| 1.1.307 | 2-trifluoromethoxy-3-methoxyphenyl | H | methyl | |
| 1.1.308 | 2-nitro-3-methoxyphenyl | H | methyl | |
| 1.1.309 | 2-fluoro-3-ethoxyphenyl | H | methyl | |
| 1.1.310 | 2-chloro-3-ethoxyphenyl | H | methyl | |
| 1.1.311 | 2-bromo-3-ethoxyphenyl | H | methyl | |
| 1.1.312 | 2-methyl-3-ethoxyphenyl | H | methyl | |
| 1.1.313 | 2-ethyl-3-ethoxyphenyl | H | methyl | |
| 1.1.314 | 2-cyclopropyl-3-ethoxyphenyl | H | methyl | |
| 1.1.315 | 2-vinyl-3-ethoxyphenyl | H | methyl | |
| 1.1.316 | 2-ethynyl-3-ethoxyphenyl | H | methyl | |
| 1.1.317 | 2-cyano-3-ethoxyphenyl | H | methyl | |
| 1.1.318 | 2-trifluoromethyl-3-ethoxyphenyl | H | methyl | |
| 1.1.319 | 2-methoxy-3-ethoxyphenyl | H | methyl | |
| 1.1.320 | 2,3-diethoxyphenyl | H | methyl | |
| 1.1.321 | 2-trifluoromethoxy-3-ethoxyphenyl | H | methyl | |
| 1.1.322 | 2-nitro-3-ethoxyphenyl | H | methyl | |
| 1.1.323 | 2-fluoro-3-propoxyphenyl | H | methyl | |
| 1.1.324 | 2-chloro-3-propoxyphenyl | H | methyl | |
| 1.1.325 | 2-bromo-3-propoxyphenyl | H | methyl | |
| 1.1.326 | 2-methyl-3-propoxyphenyl | H | methyl | |
| 1.1.327 | 2-ethyl-3-propoxyphenyl | H | methyl | |

TABLE 1.1-continued

Inventive compounds of the general formula (I) in which W* is COOH, $R^1$ is hydrogen, and aryl is the radical.

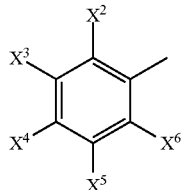

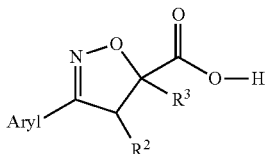

1

| No. | Aryl | $R^2$ | $R^3$ | Physical data |
|---|---|---|---|---|
| 1.1.328 | 2-cyclopropyl-3-propoxyphenyl | H | methyl | |
| 1.1.329 | 2-vinyl-3-propoxyphenyl | H | methyl | |
| 1.1.330 | 2-ethynyl-3-propoxyphenyl | H | methyl | |
| 1.1.331 | 2-cyano-3-propoxyphenyl | H | methyl | |
| 1.1.332 | 2-trifluoromethyl-3-propoxyphenyl | H | methyl | |
| 1.1.333 | 2-methoxy-3-propoxyphenyl | H | methyl | |
| 1.1.334 | 2-ethoxy-3-propoxyphenyl | H | methyl | |
| 1.1.335 | 2-trifluoromethoxy-3-propoxyphenyl | H | methyl | |
| 1.1.336 | 2-nitro-3-propoxyphenyl | H | methyl | |
| 1.1.337 | 2-fluoro-3-isopropoxyphenyl | H | methyl | |
| 1.1.338 | 2-chloro-3-isopropoxyphenyl | H | methyl | |
| 1.1.339 | 2-bromo-3-isopropoxyphenyl | H | methyl | |
| 1.1.340 | 2-methyl-3-isopropoxyphenyl | H | methyl | |
| 1.1.341 | 2-ethyl-3-isopropoxyphenyl | H | methyl | |
| 1.1.342 | 2-cyclopropyl-3-isopropoxyphenyl | H | methyl | |
| 1.1.343 | 2-vinyl-3-isopropoxyphenyl | H | methyl | |
| 1.1.344 | 2-ethynyl-3-isopropoxyphenyl | H | methyl | |
| 1.1.345 | 2-cyano-3-isopropoxyphenyl | H | methyl | |
| 1.1.346 | 2-trifluoromethyl-3-isopropoxyphenyl | H | methyl | |
| 1.1.347 | 2-methoxy-3-isopropoxyphenyl | H | methyl | |
| 1.1.348 | 2-ethoxy-3-isopropoxyphenyl | H | methyl | |
| 1.1.349 | 2-trifluoromethoxy-3-isopropoxyphenyl | H | methyl | |
| 1.1.350 | 2-nitro-3-isopropoxyphenyl | H | methyl | |
| 1.1.351 | 2-fluoro-3-tert-butoxyphenyl | H | methyl | |
| 1.1.352 | 2-chloro-3-tert-butoxyphenyl | H | methyl | |
| 1.1.353 | 2-bromo-3-tert-butoxyphenyl | H | methyl | |

TABLE 1.1-continued

Inventive compounds of the general formula (I) in which W* is COOH, $R^1$ is hydrogen, and aryl is the radical.

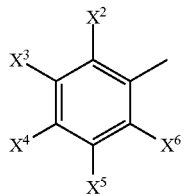

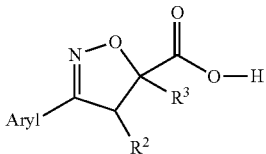

| No. | Aryl | $R^2$ | $R^3$ | Physical data |
|---|---|---|---|---|
| 1.1.354 | 2-methyl-3-tert-butoxyphenyl | H | methyl | |
| 1.1.355 | 2-ethyl-3-tert-butoxyphenyl | H | methyl | |
| 1.1.356 | 2-cyclopropyl-3-tert-butoxyphenyl | H | methyl | |
| 1.1.357 | 2-vinyl-3-tert-butoxyphenyl | H | methyl | |
| 1.1.358 | 2-ethynyl-3-tert-butoxyphenyl | H | methyl | |
| 1.1.359 | 2-cyano-3-tert-butoxyphenyl | H | methyl | |
| 1.1.360 | 2-trifluoromethyl-3-tert-butoxyphenyl | H | methyl | |
| 1.1.361 | 2-methoxy-3-tert-butoxyphenyl | H | methyl | |
| 1.1.362 | 2-ethoxy-3-tert-butoxyphenyl | H | methyl | |
| 1.1.363 | 2-trifluoromethoxy-3-tert-butoxyphenyl | H | methyl | |
| 1.1.364 | 2-nitro-3-tert-butoxyphenyl | H | methyl | |
| 1.1.365 | 2-fluoro-3-trifluoromethoxyphenyl | H | methyl | |
| 1.1.366 | 2-chloro-3-trifluoromethoxyphenyl | H | methyl | |
| 1.1.367 | 2-bromo-3-trifluoromethoxyphenyl | H | methyl | |
| 1.1.368 | 2-methyl-3-trifluoromethoxyphenyl | H | methyl | |
| 1.1.369 | 2-ethyl-3-trifluoromethoxyphenyl | H | methyl | |
| 1.1.370 | 2-cyclopropyl-3-trifluoromethoxyphenyl | H | methyl | |
| 1.1.371 | 2-vinyl-3-trifluoromethoxyphenyl | H | methyl | |
| 1.1.372 | 2-ethynyl-3-trifluoromethoxyphenyl | H | methyl | |
| 1.1.373 | 2-cyano-3-trifluoromethoxyphenyl | H | methyl | |
| 1.1.374 | 2-trifluoromethyl-3-trifluoromethoxyphenyl | H | methyl | |
| 1.1.375 | 2-methoxy-3-trifluoromethoxyphenyl | H | methyl | |
| 1.1.376 | 2-ethoxy-3-trifluoromethoxyphenyl | H | methyl | |
| 1.1.377 | 2,3-bis(trifluoromethoxy)phenyl | H | methyl | |
| 1.1.378 | 2-nitro-3-trifluoromethoxyphenyl | H | methyl | |

TABLE 1.1-continued

Inventive compounds of the general formula (I) in which W* is COOH, R¹ is hydrogen, and aryl is the radical.

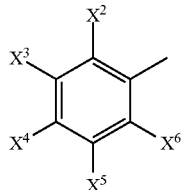

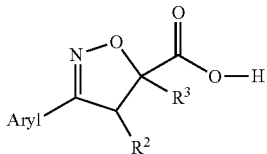

| No. | Aryl | R² | R³ | Physical data |
|---|---|---|---|---|
| 1.1.379 | 2-fluoro-3-(2,2,2-trifluoroethoxy)-phenyl | H | methyl | |
| 1.1.380 | 2-chloro-3-(2,2,2-trifluoroethoxy)-phenyl | H | methyl | |
| 1.1.381 | 2-bromo-3-(2,2,2-trifluoroethoxy)-phenyl | H | methyl | |
| 1.1.382 | 2-methyl-3-(2,2,2-trifluoroethoxy)-phenyl | H | methyl | |
| 1.1.383 | 2-ethyl-3-(2,2,2-trifluoroethoxy)-phenyl | H | methyl | |
| 1.1.384 | 2-cyclopropyl-3-(2,2,2-trifluoroethoxy)phenyl | H | methyl | |
| 1.1.385 | 2-vinyl-3-(2,2,2-trifluoroethoxy)-phenyl | H | methyl | |
| 1.1.386 | 2-ethynyl-3-(2,2,2-trifluoroethoxyphenyl | H | methyl | |
| 1.1.387 | 2-cyano-3-(2,2,2-trifluoroethoxy)-phenyl | H | methyl | |
| 1.1.388 | 2-trifluoromethyl-3-(2,2,2-trifluoroethoxy)phenyl | H | methyl | |
| 1.1.389 | 2-methoxy-3-(2,2,2-trifluoroethoxy)-phenyl | H | methyl | |
| 1.1.390 | 2-ethoxy-3-(2,2,2-trifluoroethoxy)-phenyl | H | methyl | |
| 1.1.391 | 2-trifluoromethoxy-3-(2,2,2-trifluoroethoxy)phenyl | H | methyl | |
| 1.1.392 | 2-nitro-3-(2,2,2-trifluoroethoxy)-phenyl | H | methyl | |
| 1.1.393 | 2-fluoro-3-difluoromethoxy-phenyl | H | methyl | |
| 1.1.394 | 2-chloro-3-difluoromethoxy-phenyl | H | methyl | |
| 1.1.395 | 2-bromo-3-difluoromethoxy-phenyl | H | methyl | |
| 1.1.396 | 2-methyl-3-difluoromethoxy-phenyl | H | methyl | |

TABLE 1.1-continued

Inventive compounds of the general formula (I) in which W* is COOH, $R^1$ is hydrogen, and aryl is the radical.

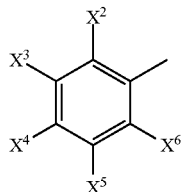

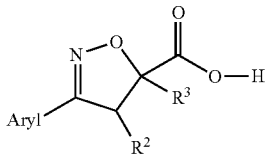

| No. | Aryl | $R^2$ | $R^3$ | Physical data |
|---|---|---|---|---|
| 1.1.397 | 2-ethyl-3-difluoromethoxy-phenyl | H | methyl | |
| 1.1.398 | 2-cyclopropyl-3-difluoromethoxy-phenyl | H | methyl | |
| 1.1.399 | 2-vinyl-3-difluoromethoxy-phenyl | H | methyl | |
| 1.1.400 | 2-ethynyl-3-difluoromethoxy-phenyl | H | methyl | |
| 1.1.401 | 2-cyano-3-difluoro-methoxyphenyl | H | methyl | |
| 1.1.402 | 2-trifluoromethyl-3-difluoromethoxy-phenyl | H | methyl | |
| 1.1.403 | 2-methoxy-3-difluoro-methoxyphenyl | H | methyl | |
| 1.1.404 | 2-ethoxy-3-difluoro-methoxyphenyl | H | methyl | |
| 1.1.405 | 2-trifluoromethoxy-3-difluoromethoxy-phenyl | H | methyl | |
| 1.1.406 | 2-nitro-3-difluoro-methoxyphenyl | H | methyl | |
| 1.1.407 | 2-fluoro-3-(2-methoxyethoxy)-phenyl | H | methyl | |
| 1.1.408 | 2-chloro-3-(2-methoxyethoxy)-phenyl | H | methyl | |
| 1.1.409 | 2-bromo-3-(2-methoxyethoxy)-phenyl | H | methyl | |
| 1.1.410 | 2-methyl-3-(2-methoxyethoxy)-phenyl | H | methyl | |
| 1.1.411 | 2-ethyl-3-(2-methoxyethoxy)-phenyl | H | methyl | |
| 1.1.412 | 2-cyclopropyl-3-(2-methoxyethoxy)-phenyl | H | methyl | |
| 1.1.413 | 2-vinyl-3-(2-methoxy-ethoxy)phenyl | H | methyl | |
| 1.1.414 | 2-ethynyl-3-(2-methoxyethoxy)-phenyl | H | methyl | |
| 1.1.415 | 2-cyano-3-(2-methoxyethoxy)-phenyl | H | methyl | |
| 1.1.416 | 2-trifluoromethyl-3-(2-methoxyethoxy)-phenyl | H | methyl | |

TABLE 1.1-continued

Inventive compounds of the general formula (I) in which W* is COOH, R¹ is hydrogen, and aryl is the radical.

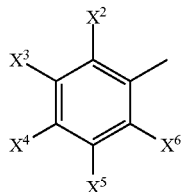

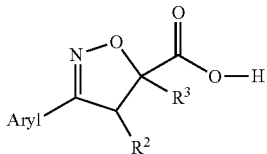

| No. | Aryl | R² | R³ | Physical data |
|---|---|---|---|---|
| 1.1.417 | 2-methoxy-3-(2-methoxyethoxy)-phenyl | H | methyl | |
| 1.1.418 | 2-ethoxy-3-(2-methoxyethoxy)-phenyl | H | methyl | |
| 1.1.419 | 2-trifluoromethoxy-(2-methoxyethoxy)-phenyl | H | methyl | |
| 1.1.420 | 2-nitro-3-(2-methoxy-ethoxy)phenyl | H | methyl | |
| 1.1.421 | 2-fluoro-3-(tert-butoxycarbonyloxy)-phenyl | H | methyl | |
| 1.1.422 | 2-chloro-3-(tert-butoxycarbonyloxy)-phenyl | H | methyl | |
| 1.1.423 | 2-bromo-3-(tert-butoxycarbonyl-oxy)phenyl | H | methyl | |
| 1.1.424 | 2-methyl-3-(tert-butoxycarbonyl-oxy)phenyl | H | methyl | |
| 1.1.425 | 2-ethyl-3-(tert-butoxycarbonyloxy)-phenyl | H | methyl | |
| 1.1.426 | 2-cyclopropyl-3-(tert-butoxycarbonyl-oxy)phenyl | H | methyl | |
| 1.1.427 | 2-vinyl-3-(tert-butoxycarbonyloxy)-phenyl | H | methyl | |
| 1.1.428 | 2-ethynyl-3-(tert-butoxycarbonyl-oxy)phenyl | H | methyl | |
| 1.1.429 | 2-cyano-3-(tert-butoxycarbonyloxy)-phenyl | H | methyl | |
| 1.1.430 | 2-trifluoromethyl-3-(tert-butoxycarbonyl-oxy)phenyl | H | methyl | |
| 1.1.431 | 2-methoxy-3-(tert-butoxycarbonyloxy)-phenyl | H | methyl | |
| 1.1.432 | 2-ethoxy-3-(tert-butoxycarbonyloxy)-phenyl | H | methyl | |
| 1.1.433 | 2-trifluoromethoxy-3-(tert-butoxycarbonyl-oxy)phenyl | H | methyl | |
| 1.1.434 | 2-nitro-3-(tert-butoxycarbonyloxy)-phenyl | H | methyl | |

TABLE 1.1-continued

Inventive compounds of the general formula (I) in which W* is COOH, R¹ is hydrogen, and aryl is the radical.

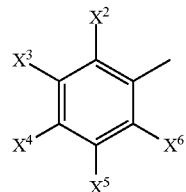

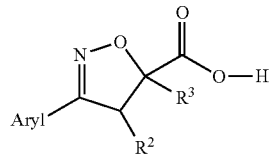

| No. | Aryl | R² | R³ | Physical data |
|---|---|---|---|---|
| 1.1.435 | 2-fluoro-3-nitrophenyl | H | methyl | |
| 1.1.436 | 2-chloro-3-nitrophenyl | H | methyl | |
| 1.1.437 | 2-bromo-3-nitrophenyl | H | methyl | |
| 1.1.438 | 2-methyl-3-nitrophenyl | H | methyl | |
| 1.1.439 | 2-ethyl-3-nitrophenyl | H | methyl | |
| 1.1.440 | 2-cyclopropyl-3-nitrophenyl | H | methyl | |
| 1.1.441 | 2-vinyl-3-nitrophenyl | H | methyl | |
| 1.1.442 | 2-ethynyl-3-nitrophenyl | H | methyl | |
| 1.1.443 | 2-cyano-3-nitrophenyl | H | methyl | |
| 1.1.444 | 2-trifluoromethyl-3-nitrophenyl | H | methyl | |
| 1.1.445 | 2-methoxy-3-nitrophenyl | H | methyl | |
| 1.1.446 | 2-ethoxy-3-nitrophenyl | H | methyl | |
| 1.1.447 | 2-trifluoromethoxy-3-nitrophenyl | H | methyl | |
| 1.1.448 | 2-fluoro-3-methylsulfanylphenyl | H | methyl | |
| 1.1.449 | 2-chloro-3-methylsulfanylphenyl | H | methyl | |
| 1.1.450 | 2-bromo-3-methylsulfanylphenyl | H | methyl | |
| 1.1.451 | 2-methyl-3-methylsulfanylphenyl | H | methyl | |
| 1.1.452 | 2-ethyl-3-methylsulfanylphenyl | H | methyl | |
| 1.1.453 | 2-cyclopropyl-3-methylsulfanylphenyl | H | methyl | |
| 1.1.454 | 2-vinyl-3-methylsulfanylphenyl | H | methyl | |
| 1.1.455 | 2-ethynyl-3-methylsulfanylphenyl | H | methyl | |
| 1.1.456 | 2-cyano-3-methylsulfanylphenyl | H | methyl | |
| 1.1.457 | 2-trifluoromethyl-3-methylsulfanylphenyl | H | methyl | |
| 1.1.458 | 2-methoxy-3-methylsulfanylphenyl | H | methyl | |
| 1.1.459 | 2-ethoxy-3-methylsulfanylphenyl | H | methyl | |
| 1.1.460 | 2-trifluoromethoxy-3-methylsulfanylphenyl | H | methyl | |
| 1.1.461 | 2-nitro-3-methylsulfanylphenyl | H | methyl | |
| 1.1.462 | 3,5-difluorophenyl | H | methyl | [CDCl₃] 1.80 (s, 3H); 3.25 (d, 1H); 3.83 (d, 1H); 6.90 (m, 1H); 7.15 (m, 2H). |

TABLE 1.1-continued

Inventive compounds of the general formula (I) in which W* is COOH, R¹ is hydrogen, and aryl is the radical.

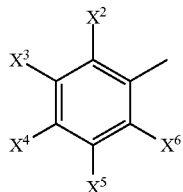

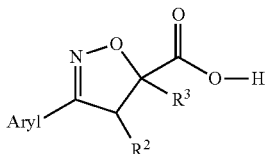

| No. | Aryl | R² | R³ | Physical data |
|---|---|---|---|---|
| 1.1.463 | (R)-3,5-difluorophenyl | H | methyl | [CDCl₃] 1.79 (s, 3H); 1.90 (s br, 1H); 3.26 (d, 1H); 3.84 (d, 1H), 6.90 (t, 1H); 7.18 (d, 2H). |
| 1.1.464 | (S)-3,5-difluorophenyl | H | methyl | [CDCl₃] 1.79 (s, 3H); 3.25 (d, 1H); 3.83 (d, 1H), 6.89 (t, 1H); 7.18 (d, 2H). |
| 1.1.465 | rel-(4R,5R)-3,5-difluorophenyl | methyl | methyl | |
| 1.1.466 | rel-(4R,5R)-3,5-difluorophenyl | ethyl | methyl | [CDCl₃] 0.93 (t, 3H); 1.61 (s, 3H); 1.75 (m, 2H); 3.84 (dd, 1H); 6.90 (m, 1H); 7.21 (m, 2H). |
| 1.1.467 | 3,5-difluorophenyl | Br | methyl | |
| 1.1.468 | 3,5-difluorophenyl | H | ethyl | [CDCl₃] 1.09 (t, 3H); 2.12 (mc, 2H); 3.30 (d, 1H); 3.75 (d, 1H); 6.90 (m, 1H); 7.18 (m, 2H). |
| 1.1.469 | 3,5-difluorophenyl | H | isopropyl | [CDCl₃] 1.06 (m, 6H); 2.40 (m, 1H); 3.30 (d, 1H); 3.70 (d, 1H); 6.90 (m, 1H); 7.19 (m, 2H). |
| 1.1.470 | 3,5-difluorophenyl | H | cyclopropyl | |
| 1.1.471 | 3-chloro-5-fluorophenyl | H | methyl | [CDCl₃] 1.76 (s, 3H); 3.25 (d, 1H); 3.82 (d, 1H); 7.16 (m, 1H); 7.30 (m, 1H); 7.4 (bs, 1H). |
| 1.1.472 | 3-chloro-5-fluorophenyl | H | ethyl | [CDCl₃] 1.05 (t, 3H); 2.11 (mc, 2H); 3.28 (d, 1H); 3.75 (d, 1H); 7.18 (m, 1H); 7.28 (m, 1H); 7.40 (1H). |
| 1.1.473 | 3-chloro-5-fluorophenyl | H | isopropyl | |
| 1.1.474 | 3-chloro-5-fluorophenyl | H | cyclopropyl | |
| 1.1.475 | 3-bromo-5-fluorophenyl | H | methyl | [CDCl₃] 1.70 (s, 3H); 3.25 (d, 1H); 3.85 (d, 1H); 7.35 (m, 2H); 7.56 (m, 1H). |
| 1.1.476 | 3-bromo-5-fluorophenyl | H | ethyl | |
| 1.1.477 | 3-bromo-5-fluorophenyl | H | isopropyl | |
| 1.1.478 | 3-bromo-5-fluorophenyl | H | cyclopropyl | |
| 1.1.479 | 3-iodo-5-fluorophenyl | H | methyl | |
| 1.1.480 | 3-methyl-5-fluorophenyl | H | methyl | [DMSO] 1.51 (s, 3H); 2.35 (s, 3H); 3.31 (d, 1H); 3.76 (d, 1H); 7.14 (d, 1H); 7.25 (d, 1H); 7.35 (s, 1H). |
| 1.1.481 | 3-methyl-5-fluorophenyl | H | ethyl | |
| 1.1.482 | 3-methyl-5-fluorophenyl | H | propyl | |
| 1.1.483 | 3-methyl-5-fluorophenyl | H | cyclopropyl | |
| 1.1.484 | 3-ethyl-5-fluorophenyl | H | methyl | [DMSO] 1.20 (t, 3H); 1.55 (s, 3H); 2.65 (q, 2H); 3.38 (d, 1H); 3.80 (d, 1H); 7.15 (d, 1H); 7.38 (d, 1H); 7.39 (s, 1H). |

TABLE 1.1-continued

Inventive compounds of the general formula (I) in which W* is COOH, R¹ is hydrogen, and aryl is the radical.

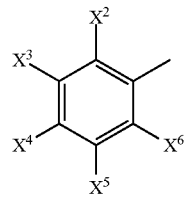

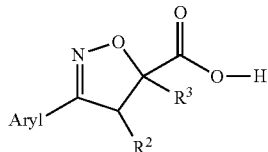

| No. | Aryl | R² | R³ | Physical data |
|---|---|---|---|---|
| 1.1.485 | 3-propyl-5-fluorophenyl | H | methyl | |
| 1.1.486 | 3-i-propyl-5-fluorophenyl | H | methyl | |
| 1.1.487 | 3-n-butyl-5-fluorophenyl | H | methyl | |
| 1.1.488 | 3-isobutyl-5-fluorophenyl | H | methyl | |
| 1.1.489 | 3-tert-butyl-5-fluorophenyl | H | methyl | |
| 1.1.490 | 3-cyclopropyl-5-fluorophenyl | H | methyl | [CDCl$_3$] 0.71 (m, 2H); 1.03 (m, 2H); 1.75 (s, 3H); 1.91 (m, 1H); 3.26 (d, 1H); 3.85 (d, 1H); 6.81 (dd, 1H); 7.13 (dd, 2H). |
| 1.1.491 | 3-vinyl-5-fluorophenyl | H | methyl | [CDCl$_3$] 1.80 (s, 3H); 3.27 (d, 1H); 3.86 (d, 1H); 5.39 (d, 1H); 5.8 (d, 1H); 6.69 (dd, 1H); 7.19 (m, 1H); 7.25 (m, 1H); 7.40 (bs, 1H). |
| 1.1.492 | 3-ethynyl-5-fluorophenyl | H | methyl | |
| 1.1.493 | 3-cyano-5-fluorophenyl | H | methyl | |
| 1.1.494 | 3-trifluoromethyl-5-fluorophenyl | H | methyl | [CDCl$_3$] 1.80 (s, 3H); 3.29 (d, 1H); 3.90 (d, 1H); 7.40 (m, 1H); 7.59 (m, 1H); 7.66 (s, 1H). |
| 1.1.495 | 3-trifluoromethyl-5-fluorophenyl | H | ethyl | |
| 1.1.496 | 3-trifluoromethyl-5-fluorophenyl | H | propyl | |
| 1.1.497 | 3-trifluoromethyl-5-fluorophenyl | H | cyclopropyl | |
| 1.1.498 | 3-(methoxycarbonyl)-5-fluorophenyl | H | methyl | |
| 1.1.499 | 3-hydroxymethyl-5-fluorophenyl | H | methyl | |
| 1.1.500 | 3-carbamoyl-5-fluorophenyl | H | methyl | |
| 1.1.501 | 3-hydroxy-5-fluorophenyl | H | methyl | |
| 1.1.502 | 3-methoxy-5-fluorophenyl | H | methyl | [CDCl$_3$] 1.78 (s, 3H); 3.25 (d, 1H); 3.82 (s, 3H); 3.88 (d, 1H); 6.7 (dd, 1H); 6.92 (dd, 1H); 7.05 (bs, 1H). |
| 1.1.503 | 3-ethoxy-5-fluorophenyl | H | methyl | |
| 1.1.504 | 3-n-propoxy-5-fluorophenyl | H | methyl | |
| 1.1.505 | 3-isopropoxy-5-fluorophenyl | H | methyl | |
| 1.1.506 | 3-n-butoxy-5-fluorophenyl | H | methyl | |
| 1.1.507 | 3-isobutoxy-5-fluorophenyl | H | methyl | |
| 1.1.508 | 3-tert-butoxy-5-fluorophenyl | H | methyl | |

TABLE 1.1-continued

Inventive compounds of the general formula (I) in which W* is COOH, R¹ is hydrogen, and aryl is the radical.

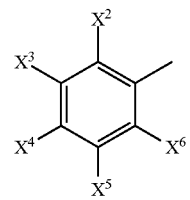

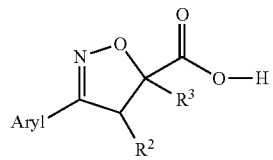

| No. | Aryl | R² | R³ | Physical data |
|---|---|---|---|---|
| 1.1.509 | 3-difluoromethoxy-5-fluorophenyl | H | methyl | |
| 1.1.510 | 3-trifluoromethoxy-5-fluorophenyl | H | methyl | |
| 1.1.511 | 3-(2,2,2-trifluoroethoxy)-5-fluorophenyl | H | methyl | |
| 1.1.512 | 3-(2-chloroethoxy)-5-fluorophenyl | H | methyl | |
| 1.1.513 | 3-(2-hydroxyethoxy)-5-fluorophenyl | H | methyl | |
| 1.1.514 | 3-[(tert-butoxy-carbonyl)oxy]-5-fluorophenyl | H | methyl | |
| 1.1.515 | 3-nitro-5-fluorophenyl | H | methyl | |
| 1.1.516 | 3-acetoxy-5-fluorophenyl | H | methyl | |
| 1.1.517 | {3-[(tert-butoxy-carbonyl)amino]-5-fluorophenyl} | H | methyl | |
| 1.1.518 | 3-methylsulfanyl-5-fluorophenyl | H | methyl | |
| 1.1.519 | 3,5-dichlorophenyl | H | methyl | [CDCl₃] 1.79 (s, 3H); 3.25 (d, 1H), 3.83 (d, 1H); 7.41 (s, 1H); 7.53 (s, 2H). |
| 1.1.520 | (R)-3,5-dichlorophenyl | H | methyl | [CDCl₃] 1.78 (s, 3H); 3.25 (d, 1H); 3.83 (d, 1H); 5.3 (s br, 1H); 7.42 (s, 1H); 7.52 (s, 2H). |
| 1.1.521 | (S)-3,5-dichlorophenyl | H | methyl | [CDCl₃] 1.78 (s, 3H); 3.25 (d, 1H), 3.83 (d, 1H); 5.3 (s br, 1H); 7.42 (s, 1H); 7.52 (s, 2H). |
| 1.1.522 | rel-(4R,5S)-3,5-dichlorophenyl | methyl | methyl | [CDCl₃] 1.30 (d, 3H); 1.70 (s, 3H); 3.55 (q, 1H); 7.44 (m, 1H); 7.55 (m, 2H). |
| 1.1.523 | rel-(4R,5R)-3,5-dichlorophenyl | methyl | methyl | [CDCl₃] 1.25 (d, 3H); 1.70 (s, 3H); 3.95 (q, 2H); 7.42 (m, 1H); 7.58 (m, 2H). |
| 1.1.524 | 3,5-dichlorophenyl | H | ethyl | [CDCl₃] 1.18 (dq, 3H); 2.11 (m, 2H); 3.30 (d, 1H); 3.75 (d, 1H); 7.42 (s, 1H), 7.72 (s, 1H). |
| 1.1.525 | 3,5-dichlorophenyl | H | isopropyl | [CDCl₃] 1.18 (dd, 6H); 2.40 (dq, 1H); 3.32 (d, 1H); 3.70 (d, 1H); 7.41 (bs, 1H); 7.55 (bs, 2H). |
| 1.1.526 | 3,5-dichlorophenyl | H | cyclopropyl | [CDCl₃] 0.45-0.80 (m, 4H); 1.51 (m, 1H); 3.39 (d, 1H); 3.82 (d, 1H); 7.42 (m, 1H); 7.50 (m, m, 2H). |
| 1.1.527 | 3-bromo-5-chlorophenyl | H | methyl | [CDCl₃] 1.79 (s, 3H); 3.25 (d, 1H); 3.85 (d, 1H); 7.60 (s, 2H); 7.70 (s, 1H). |
| 1.1.528 | 3-iodo-5-chlorophenyl | H | methyl | |
| 1.1.529 | 3-methyl-5-chlorophenyl | H | methyl | [DMSO] 1.55 (s, 3H); 2.35 (s, 3H); 3.38 (d, 1H); 3.77 (d, 1H); 7.38 (s, 1H); 7.50 (d, 1H). |

TABLE 1.1-continued

Inventive compounds of the general formula (I) in which W* is COOH, R¹ is hydrogen, and aryl is the radical.

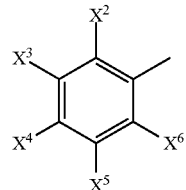

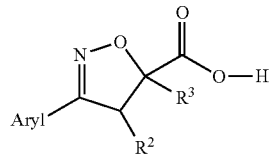

| No. | Aryl | R² | R³ | Physical data |
|---|---|---|---|---|
| 1.1.530 | 3-ethyl-5-chlorophenyl | H | methyl | [CDCl₃] 1.25 (7. 3H); 1.80 (s, 3H); 2.68 (q, 2H); 3.27 (d, 1H); 3.85 (d, 1H); 7.28 (m, 1H); 3.38 (s, 1H); 7.43 (s, 1H). |
| 1.1.531 | 3-propyl-5-chlorophenyl | H | methyl | |
| 1.1.532 | 3-isopropyl-5-chlorophenyl | H | methyl | |
| 1.1.533 | 3-n-butyl-5-chlorophenyl | H | methyl | |
| 1.1.534 | 3-isobutyl-5-chlorophenyl | H | methyl | |
| 1.1.535 | 3-tert-butyl-5-chlorophenyl | H | methyl | |
| 1.1.536 | 3-cyclopropyl-5-chlorophenyl | H | methyl | |
| 1.1.537 | 3-vinyl-5-chlorophenyl | H | methyl | |
| 1.1.538 | 3-ethynyl-5-chlorophenyl | H | methyl | |
| 1.1.539 | 3-cyano-5-chlorophenyl | H | methyl | |
| 1.1.540 | 3-trifluoromethyl-5-chlorophenyl | H | methyl | [CDCl₃] 1.80 (s, 3H); 3.30 (d, 1H); 3.89 (d, 1H); 7.69 (s, 1H); 7.78 (s, 1 H); 7.82 (s, 1 H). |
| 1.1.541 | 3-(hydroxycarbonyl)-5-chlorophenyl | H | methyl | |
| 1.1.542 | 3-(methoxycarbonyl)-5-chlorophenyl | H | methyl | |
| 1.1.543 | 3-hydroxymethyl-5-chlorophenyl | H | methyl | |
| 1.1.544 | 3-carbamoyl-5-chlorophenyl | H | methyl | |
| 1.1.545 | 3-hydroxy-5-chlorophenyl | H | methyl | |
| 1.1.546 | 3-methoxy-5-chlorophenyl | H | methyl | [CDCl₃] 1.77 (s, 3H); 3.25 (d, 1H); 3.71 (s, 3H); 3.82 (d, 1H); 6.95-7.18 (m, Ar, 3H) |
| 1.1.547 | 3-ethoxy-5-chlorophenyl | H | methyl | |
| 1.1.548 | 3-n-propoxy-5-chlorophenyl | H | methyl | |
| 1.1.549 | 3-isopropoxy-5-chlorophenyl | H | methyl | |
| 1.1.550 | 3-n-butoxy-5-chlorophenyl | H | methyl | |
| 1.1.551 | 3-isobutoxy-5-chlorophenyl | H | methyl | |
| 1.1.552 | 3-tert-butoxy-5-chlorophenyl | H | methyl | |
| 1.1.553 | 3-difluoromethoxy-5-chlorophenyl | H | methyl | |
| 1.1.554 | 3-trifluoromethoxy-5-chlorophenyl | H | methyl | [DMSO] 1.59 (s, 3H); 3.43 (d, 1H); 3.85 (d, 1H); 7.63 (s, 1H); 7.69 (s, 1H); 6.78 (s, 1H). |

TABLE 1.1-continued

Inventive compounds of the general formula (I) in which W* is COOH, R¹ is hydrogen, and aryl is the radical.

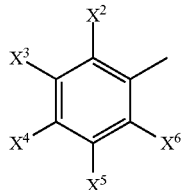

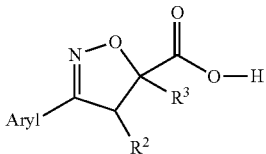

| No. | Aryl | R² | R³ | Physical data |
|---|---|---|---|---|
| 1.1.555 | 3-(2,2,2-trifluoroethoxy)-5-chlorophenyl | H | methyl | |
| 1.1.556 | 3-(2-chloroethoxy)-5-chlorophenyl | H | methyl | |
| 1.1.557 | 3-(2-hydroxyethoxy)-5-chlorophenyl | H | methyl | |
| 1.1.558 | 3-[(tert-butoxy-carbonyl)oxy]-5-chlorophenyl | H | methyl | |
| 1.1.559 | 3-nitro-5-chlorophenyl | H | methyl | |
| 1.1.560 | 3-acetoxy-5-chlorophenyl | H | methyl | |
| 1.1.561 | {3-[(tert-butoxy-carbonyl)amino]-5-chlorophenyl} | H | methyl | |
| 1.1.562 | 3-methylsulfanyl-5-chlorophenyl | H | methyl | |
| 1.1.563 | 3,5-dibromophenyl | H | methyl | [CDCl$_3$] 1.80 (s, 3H); 3.25 (d, 1H); 3.85 (d, 1H); 7.73 (s, 3H). |
| 1.1.564 | 3,5-dibromophenyl | H | ethyl | [CDCl$_3$] 1.08 (t, 3H); 2.10 (m, 2H); 3.25 (d, 1H); 3.75 (d, 1H); 7.72 (s, 3H). |
| 1.1.565 | 3-iodo-5-bromophenyl | H | methyl | |
| 1.1.566 | 3-methyl-5-bromophenyl | H | methyl | [CDCl$_3$] 1.78 (s, 3H); 2.36 (s, 3H); 3.27 (d, 1H); 3.84 (d, 1H); 7.40 (s, 2H); 7.57 (s, 1H). |
| 1.1.567 | 3-methyl-5-bromophenyl | H | ethyl | |
| 1.1.568 | 3-methyl-5-bromophenyl | H | isopropyl | |
| 1.1.569 | 3-methyl-5-bromophenyl | H | cyclopropyl | |
| 1.1.570 | 3-ethyl-5-bromophenyl | H | methyl | |
| 1.1.571 | 3-propyl-5-bromophenyl | H | methyl | |
| 1.1.572 | 3-isopropyl-5-bromophenyl | H | methyl | |
| 1.1.573 | 3-n-butyl-5-bromophenyl | H | methyl | |
| 1.1.574 | 3-isobutyl-5-bromophenyl | H | methyl | |
| 1.1.575 | 3-tert-butyl-5-bromophenyl | H | methyl | |
| 1.1.576 | 3-cyclopropyl-5-bromophenyl | H | methyl | |
| 1.1.577 | 3-vinyl-5-bromophenyl | H | methyl | |
| 1.1.578 | 3-ethynyl-5-bromophenyl | H | methyl | |
| 1.1.579 | 3-cyano-5-bromophenyl | H | methyl | |

TABLE 1.1-continued

Inventive compounds of the general formula (I) in which W* is COOH, R¹ is hydrogen, and aryl is the radical.

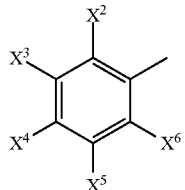

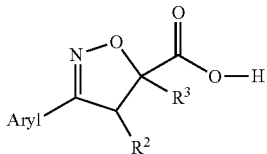

| No. | Aryl | R² | R³ | Physical data |
|---|---|---|---|---|
| 1.1.580 | 3-trifluoromethyl-5-bromophenyl | H | methyl | [CDCl$_3$] 1.80 (s, 3H); 3.30 (d, 1H); 3.90 (d, 1H); 7.81 (s, 2H); 8.0 (s, 1H). |
| 1.1.581 | 3-(hydroxycarbonyl)-5-bromophenyl | H | methyl | |
| 1.1.582 | 3-(methoxycarbonyl)-5-bromophenyl | H | methyl | |
| 1.1.583 | 3-hydroxymethyl-5-bromophenyl | H | methyl | |
| 1.1.584 | 3-carbamoyl-5-bromophenyl | H | methyl | |
| 1.1.585 | 3-hydroxy-5-bromophenyl | H | methyl | |
| 1.1.586 | 3-methoxy-5-bromophenyl | H | methyl | |
| 1.1.587 | 3-ethoxy-5-bromophenyl | H | methyl | |
| 1.1.588 | 3-n-propoxy-5-bromophenyl | H | methyl | |
| 1.1.589 | 3-isopropoxy-5-bromophenyl | H | methyl | |
| 1.1.590 | 3-n-butoxy-5-bromophenyl | H | methyl | |
| 1.1.591 | 3-isobutoxy-5-bromophenyl | H | methyl | |
| 1.1.592 | 3-tert-butoxy-5-bromophenyl | H | methyl | |
| 1.1.593 | 3-difluoromethoxy-5-bromophenyl | H | methyl | |
| 1.1.594 | 3-trifluoromethoxy-5-bromophenyl | H | methyl | |
| 1.1.595 | 3-(2,2,2-trifluoroethoxy)-5-bromophenyl | H | methyl | |
| 1.1.596 | 3-(2-chloroethoxy)-5-bromophenyl | H | methyl | |
| 1.1.597 | 3-(2-hydroxyethoxy)-5-bromophenyl | H | methyl | |
| 1.1.598 | 3-[(tert-butoxycarbonyl)oxy]-5-bromophenyl | H | methyl | |
| 1.1.599 | 3-nitro-5-bromophenyl | H | methyl | |
| 1.1.600 | 3-acetoxy-5-bromophenyl | H | methyl | |
| 1.1.601 | {3-[(tert-butoxycarbonyl)amino]-5-bromophenyl} | H | methyl | |
| 1.1.602 | 3-methylsulfanyl-5-bromophenyl | H | methyl | |
| 1.1.603 | 3,5-diiodophenyl | H | methyl | [CDCl$_3$] 1.75 (s, 3H); 3.23 (d; 1H); 3.80 (d, 1H); 7.91 (s, 2H); 8.10 (s, 1H): |
| 1.1.604 | 3-methyl-5-iodophenyl | H | methyl | |

TABLE 1.1-continued

Inventive compounds of the general formula (I) in which W* is COOH, R¹ is hydrogen, and aryl is the radical.

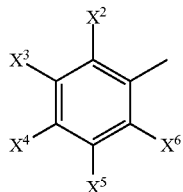

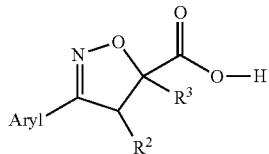

| No. | Aryl | R² | R³ | Physical data |
|---|---|---|---|---|
| 1.1.605 | 3-ethyl-5-iodophenyl | H | methyl | |
| 1.1.606 | 3-propyl-5-iodophenyl | H | methyl | |
| 1.1.607 | 3-isopropyl-5-iodophenyl | H | methyl | |
| 1.1.608 | 3-n-butyl-5-iodophenyl | H | methyl | |
| 1.1.609 | 3-isobutyl-5-iodophenyl | H | methyl | |
| 1.1.610 | 3-tert-butyl-5-iodophenyl | H | methyl | |
| 1.1.611 | 3-cyclopropyl-5-iodophenyl | H | methyl | |
| 1.1.612 | 3-vinyl-5-iodophenyl | H | methyl | |
| 1.1.613 | 3-ethynyl-5-iodophenyl | H | methyl | |
| 1.1.614 | 3-cyano-5-iodophenyl | H | methyl | |
| 1.1.615 | 3-trifluoromethyl-5-iodophenyl | H | methyl | |
| 1.1.616 | 3-(hydroxycarbonyl)-5-iodophenyl | H | methyl | |
| 1.1.617 | 3-(methoxycarbonyl)-5-iodophenyl | H | methyl | |
| 1.1.618 | 3-hydroxymethyl-5-iodophenyl | H | methyl | |
| 1.1.619 | 3-carbamoyl-5-iodophenyl | H | methyl | |
| 1.1.620 | 3-hydroxy-5-iodophenyl | H | methyl | |
| 1.1.621 | 3-methoxy-5-iodophenyl | H | methyl | |
| 1.1.622 | 3-ethoxy-5-iodophenyl | H | methyl | |
| 1.1.623 | 3-n-propoxy-5-iodophenyl | H | methyl | |
| 1.1.624 | 3-isopropoxy-5-iodophenyl | H | methyl | |
| 1.1.625 | 3-n-butoxy-5-iodophenyl | H | methyl | |
| 1.1.626 | 3-isobutoxy-5-iodophenyl | H | methyl | |
| 1.1.627 | 3-tert-butoxy-5-iodophenyl | H | methyl | |
| 1.1.628 | 3-difluoromethoxy-5-iodophenyl | H | methyl | |
| 1.1.629 | 3-trifluoromethoxy-5-iodophenyl | H | methyl | |
| 1.1.630 | 3-(2,2,2-trifluoroethoxy)-5-iodophenyl | H | methyl | |
| 1.1.631 | 3-(2-chloroethoxy)-5-iodophenyl | H | methyl | |
| 1.1.632 | 3-(2-hydroxyethoxy)-5-iodophenyl | H | methyl | |

TABLE 1.1-continued

Inventive compounds of the general formula (I) in which W* is COOH, R¹ is hydrogen, and aryl is the radical.

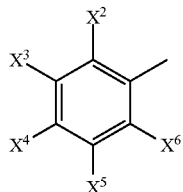

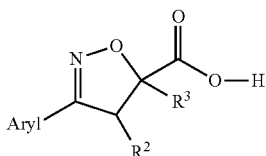

| No. | Aryl | R² | R³ | Physical data |
|---|---|---|---|---|
| 1.1.633 | 3-[(tert-butoxy-carbonyl)oxy]-5-iodophenyl | H | methyl | |
| 1.1.634 | 3-nitro-5-iodophenyl | H | methyl | |
| 1.1.635 | 3-acetoxy-5-iodophenyl | H | methyl | |
| 1.1.636 | {3-[(tert-butoxy-carbonyl)amino]-5-iodophenyl} | H | methyl | |
| 1.1.637 | 3-methylsulfanyl-5-iodophenyl | H | methyl | |
| 1.1.638 | 3,5-dimethylphenyl | H | methyl | [CDCl$_3$] 1.75 (s, 3H);, 2.32 (s, 6H); 3.3 (d, 1H); 3.85 (d. 1H); 7.09 (s, 1H); 7.35 (s, 2H). |
| 1.1.639 | 3-ethyl-5-methylphenyl | H | methyl | |
| 1.1.640 | 3-propyl-5-methylphenyl | H | methyl | |
| 1.1.641 | 3-isopropyl-5-methylphenyl | H | methyl | |
| 1.1.642 | 3-n-butyl-5-methylphenyl | H | methyl | |
| 1.1.643 | 3-isobutyl-5-methylphenyl | H | methyl | |
| 1.1.644 | 3-tert-butyl-5-methylphenyl | H | methyl | |
| 1.1.645 | 3-cyclopropyl-5-methylphenyl | H | methyl | |
| 1.1.646 | 3-vinyl-5-methylphenyl | H | methyl | |
| 1.1.647 | 3-ethynyl-5-methylphenyl | H | methyl | |
| 1.1.648 | 3-cyano-5-methylphenyl | H | methyl | |
| 1.1.649 | 3-trifluoromethyl-5-methylphenyl | H | methyl | |
| 1.1.650 | 3-(hydroxycarbonyl)-5-methylphenyl | H | methyl | |
| 1.1.651 | 3-(methoxycarbonyl)-5-methylphenyl | H | methyl | |
| 1.1.652 | 3-hydroxymethyl-5-methylphenyl | H | methyl | |
| 1.1.653 | 3-carbamoyl-5-methylphenyl | H | methyl | |
| 1.1.654 | 3-hydroxy-5-methylphenyl | H | methyl | |
| 1.1.655 | 3-methoxy-5-methylphenyl | H | methyl | |
| 1.1.656 | 3-ethoxy-5-methylphenyl | H | methyl | |
| 1.1.657 | 3-n-propoxy-5-methylphenyl | H | methyl | |

TABLE 1.1-continued

Inventive compounds of the general formula (I) in which W* is COOH, $R^1$ is hydrogen, and aryl is the radical.

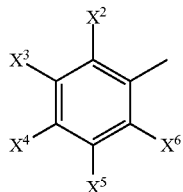

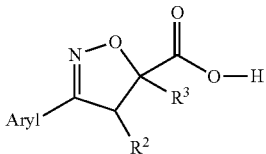

1

| No. | Aryl | $R^2$ | $R^3$ | Physical data |
|---|---|---|---|---|
| 1.1.658 | 3-n-butoxy-5-methylphenyl | H | methyl | |
| 1.1.659 | 3-isobutoxy-5-methylphenyl | H | methyl | |
| 1.1.660 | 3-tert-butoxy-5-methylphenyl | H | methyl | |
| 1.1.661 | 3-difluoromethoxy-5-methylphenyl | H | methyl | |
| 1.1.662 | 3-trifluoromethoxy-5-methylphenyl | H | methyl | |
| 1.1.663 | 3-(2,2,2-trifluoroethoxy)-5-methylphenyl | H | methyl | |
| 1.1.664 | 3-(2-chloroethoxy)-5-methylphenyl | H | methyl | |
| 1.1.665 | 3-(2-hydroxyethoxy)-5-methylphenyl | H | methyl | |
| 1.1.666 | 3-[(tert-butoxy-carbonyl)oxy]-5-methylphenyl | H | methyl | |
| 1.1.667 | 3-nitro-5-methylphenyl | H | methyl | |
| 1.1.668 | 3-acetoxy-5-methylphenyl | H | methyl | |
| 1.1.669 | {3-[(tert-butoxy-carbonyl)amino]-5-methylphenyl} | H | methyl | |
| 1.1.670 | 3-methylsulfanyl-5-methylphenyl | H | methyl | |
| 1.1.671 | 3,5-diethylphenyl | H | methyl | |
| 1.1.672 | 3-propyl-5-ethylphenyl | H | methyl | |
| 1.1.673 | 3-isopropyl-5-ethylphenyl | H | methyl | |
| 1.1.674 | 3-n-butyl-5-ethylphenyl | H | methyl | |
| 1.1.675 | 3-isobutyl-5-ethylphenyl | H | methyl | |
| 1.1.676 | 3-tert-butyl-5-ethylphenyl | H | methyl | |
| 1.1.677 | 3-cyclopropyl-5-ethylphenyl | H | methyl | |
| 1.1.678 | 3-vinyl-5-ethylphenyl | H | methyl | |
| 1.1.679 | 3-ethynyl-5-ethylphenyl | H | methyl | |
| 1.1.680 | 3-cyano-5-ethylphenyl | H | methyl | |
| 1.1.681 | 3-trifluoromethyl-5-ethylphenyl | H | methyl | |
| 1.1.682 | 3-(hydroxycarbonyl)-5-ethylphenyl | H | methyl | |
| 1.1.683 | 3-(methoxycarbonyl)-5-ethylphenyl | H | methyl | |
| 1.1.684 | 3-hydroxymethyl-5-ethylphenyl | H | methyl | |

TABLE 1.1-continued

Inventive compounds of the general formula (I) in which W* is COOH, $R^1$ is hydrogen, and aryl is the radical.

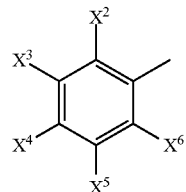

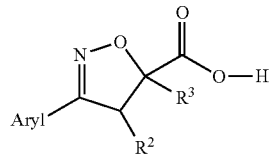

| No. | Aryl | $R^2$ | $R^3$ | Physical data |
|---|---|---|---|---|
| 1.1.685 | 3-carbamoyl-5-ethylphenyl | H | methyl | |
| 1.1.686 | 3-hydroxy-5-ethylphenyl | H | methyl | |
| 1.1.687 | 3-methoxy-5-ethylphenyl | H | methyl | |
| 1.1.688 | 3-ethoxy-5-ethylphenyl | H | methyl | |
| 1.1.689 | 3-n-propoxy-5-ethylphenyl | H | methyl | |
| 1.1.690 | 3-n-butoxy-5-ethylphenyl | H | methyl | |
| 1.1.691 | 3-isobutoxy-5-ethylphenyl | H | methyl | |
| 1.1.692 | 3-tert-butoxy-5-ethylphenyl | H | methyl | |
| 1.1.693 | 3-difluoromethoxy-5-ethylphenyl | H | methyl | |
| 1.1.694 | 3-trifluoromethoxy-5-ethylphenyl | H | methyl | |
| 1.1.695 | 3-(2,2,2-trifluoroethoxy)-5-ethylphenyl | H | methyl | |
| 1.1.696 | 3-(2-chloroethoxy)-5-ethylphenyl | H | methyl | |
| 1.1.697 | 3-(2-hydroxyethoxy)-5-ethylphenyl | H | methyl | |
| 1.1.698 | 3-[(tert-butoxy-carbonyl)oxy]-5-ethylphenyl | H | methyl | |
| 1.1.699 | 3-nitro-5-ethylphenyl | H | methyl | |
| 1.1.700 | 3-acetoxy-5-ethylphenyl | H | methyl | |
| 1.1.701 | {3-[(tert-butoxy-carbonyl)amino]-5-ethylphenyl} | H | methyl | |
| 1.1.702 | 3-methylsulfanyl-5-ethylphenyl | H | methyl | |
| 1.1.703 | 3,5-dipropylphenyl | H | methyl | |
| 1.1.704 | 3-isopropyl-5-propylphenyl | H | methyl | |
| 1.1.705 | 3-n-butyl-5-propylphenyl | H | methyl | |
| 1.1.706 | 3-isobutyl-5-propylphenyl | H | methyl | |
| 1.1.707 | 3-tert-butyl-5-propylphenyl | H | methyl | |
| 1.1.708 | 3-cyclopropyl-5-propylphenyl | H | methyl | |
| 1.1.709 | 3-vinyl-5-propylphenyl | H | methyl | |
| 1.1.710 | 3-ethynyl-5-propylphenyl | H | methyl | |
| 1.1.711 | 3-cyano-5-propylphenyl | H | methyl | |

TABLE 1.1-continued

Inventive compounds of the general formula (I) in which W* is COOH, R¹ is hydrogen, and aryl is the radical.

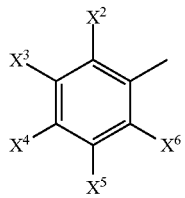

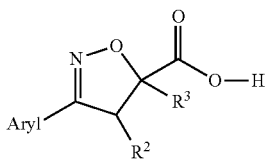

| No. | Aryl | R² | R³ | Physical data |
|---|---|---|---|---|
| 1.1.712 | 3-trifluoromethyl-5-propylphenyl | H | methyl | |
| 1.1.713 | 3-(hydroxycarbonyl)-5-propylphenyl | H | methyl | |
| 1.1.714 | 3-(methoxycarbonyl)-5-propylphenyl | H | methyl | |
| 1.1.715 | 3-hydroxymethyl-5-propylphenyl | H | methyl | |
| 1.1.716 | 3-carbamoyl-5-propylphenyl | H | methyl | |
| 1.1.717 | 3-hydroxy-5-propylphenyl | H | methyl | |
| 1.1.718 | 3-methoxy-5-propylphenyl | H | methyl | |
| 1.1.719 | 3-ethoxy-5-propylphenyl | H | methyl | |
| 1.1.720 | 3-n-propoxy-5-propylphenyl | H | methyl | |
| 1.1.721 | 3-n-butoxy-5-propylphenyl | H | methyl | |
| 1.1.722 | 3-isobutoxy-5-propylphenyl | H | methyl | |
| 1.1.723 | 3-tert-butoxy-5-propylphenyl | H | methyl | |
| 1.1.724 | 3-difluoromethoxy-5-propylphenyl | H | methyl | |
| 1.1.725 | 3-trifluoromethoxy-5-ethylphenyl | H | methyl | |
| 1.1.726 | 3-(2,2,2-trifluoroethoxy)-5-propylphenyl | H | methyl | |
| 1.1.727 | 3-(2-chloroethoxy)-5-propylphenyl | H | methyl | |
| 1.1.728 | 3-(2-hydroxyethoxy)-5-propylphenyl | H | methyl | |
| 1.1.729 | 3-[(tert-butoxy-carbonyl)oxy]-5-propylphenyl | H | methyl | |
| 1.1.730 | 3-nitro-5-propylphenyl | H | methyl | |
| 1.1.731 | 3-acetoxy-5-propylphenyl | H | methyl | |
| 1.1.732 | {3-[(tert-butoxy-carbonyl)amino]-5-propylphenyl} | H | methyl | |
| 1.1.733 | 3-methylsulfanyl-5-propylphenyl | H | methyl | |
| 1.1.734 | 3,5-diisopropylphenyl | H | methyl | |
| 1.1.735 | 3-n-butyl-5-isopropylphenyl | H | methyl | |
| 1.1.736 | 3-isobutyl-5-isopropylphenyl | H | methyl | |

TABLE 1.1-continued

Inventive compounds of the general formula (I) in which W* is COOH, R¹ is hydrogen, and aryl is the radical.

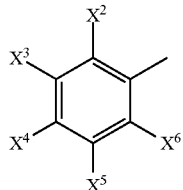

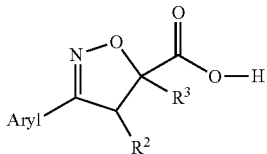

| No. | Aryl | R² | R³ | Physical data |
|---|---|---|---|---|
| 1.1.737 | 3-tert-butyl-5-isopropylphenyl | H | methyl | |
| 1.1.738 | 3-cyclopropyl-5-isopropylphenyl | H | methyl | |
| 1.1.739 | 3-vinyl-5-isopropylphenyl | H | methyl | |
| 1.1.740 | 3-thynyl-5-isopreopylphenyl | H | methyl | |
| 1.1.741 | 3-cyano-5-isopropylphenyl | H | methyl | |
| 1.1.742 | 3-trifluoromethyl-5-isopropylphenyl | H | methyl | |
| 1.1.743 | 3-(hydroxycarbonyl)-5-isopropylphenyl | H | methyl | |
| 1.1.744 | 3-(methoxycarbonyl)-5-isopropylphenyl | H | methyl | |
| 1.1.745 | 3-hydroxymethyl-5-isopropylphenyl | H | methyl | |
| 1.1.746 | 3-carbamoyl-5-isopropylphenyl | H | methyl | |
| 1.1.747 | 3-hydroxy-5-isopropylphenyl | H | methyl | |
| 1.1.748 | 3-methoxy-5-isopropylphenyl | H | methyl | |
| 1.1.749 | 3-thoxy-5-isopropylphenyl | H | methyl | |
| 1.1.750 | 3-n-propoxy-5-isopropylphenyl | H | methyl | |
| 1.1.751 | 3-n-butoxy-5-isopropylphenyl | H | methyl | |
| 1.1.752 | 3-isobutoxy-5-isopropylphenyl | H | methyl | |
| 1.1.753 | 3-tert-butoxy-5-isopropylphenyl | H | methyl | |
| 1.1.754 | 3-difluoromethoxy-5-isopropylphenyl | H | methyl | |
| 1.1.755 | 3-trifluoromethoxy-5-isopropylphenyl | H | methyl | |
| 1.1.756 | 3-(2,2,2-trifluoroethoxy)-5-isopropylphenyl | H | methyl | |
| 1.1.757 | 3-(2-chloroethoxy)-5-isopropylphenyl | H | methyl | |
| 1.1.758 | 3-(2-hydroxyethoxy)-5-propylphenyl | H | methyl | |
| 1.1.759 | 3-[(tert-butoxy-carbonyl)oxy]-5-isopropylphenyl | H | methyl | |
| 1.1.760 | 3-nitro-5-isopropylphenyl | H | methyl | |
| 1.1.761 | 3-acetoxy-5-isopropylphenyl | H | methyl | |
| 1.1.762 | {3-[(tert-butoxy-carbonyl)amino]-5-isopropylphenyl} | H | methyl | |

TABLE 1.1-continued

Inventive compounds of the general formula (I) in which W* is COOH, $R^1$ is hydrogen, and aryl is the radical.

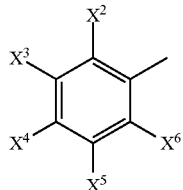

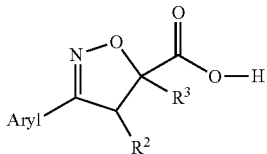

| No. | Aryl | $R^2$ | $R^3$ | Physical data |
|---|---|---|---|---|
| 1.1.763 | 3-methylsulfanyl-5-isopropylphenyl | H | methyl | |
| 1.1.764 | 3,5-dibutylphenyl | H | methyl | |
| 1.1.765 | 3-isobutyl-5-butylphenyl | H | methyl | |
| 1.1.766 | 3-tert-butyl-5-butylphenyl | H | methyl | |
| 1.1.767 | 3-cyclopropyl-5-butylphenyl | H | methyl | |
| 1.1.768 | 3-vinyl-5-butylphenyl | H | methyl | |
| 1.1.769 | 3-ethynyl-5-butylphenyl | H | methyl | |
| 1.1.770 | 3-cyano-5-butylphenyl | H | methyl | |
| 1.1.771 | 3-trifluoromethyl-5-butylphenyl | H | methyl | |
| 1.1.772 | 3-(hydroxycarbonyl)-5-butylphenyl | H | methyl | |
| 1.1.773 | 3-(methoxycarbonyl)-5-butylphenyl | H | methyl | |
| 1.1.774 | 3-hydroxymethyl-5-butylphenyl | H | methyl | |
| 1.1.775 | 3-carbamoyl-5-butylphenyl | H | methyl | |
| 1.1.776 | 3-hydroxy-5-butylphenyl | H | methyl | |
| 1.1.777 | 3-methoxy-5-butylphenyl | H | methyl | |
| 1.1.778 | 3-ethoxy-5-butylphenyl | H | methyl | |
| 1.1.779 | 3-n-propoxy-5-butylphenyl | H | methyl | |
| 1.1.780 | 3-n-butoxy-5-butylphenyl | H | methyl | |
| 1.1.781 | 3-isobutoxy-5-butylphenyl | H | methyl | |
| 1.1.782 | 3-tert-butoxy-5-butylphenyl | H | methyl | |
| 1.1.783 | 3-difluoromethoxy-5-butylphenyl | H | methyl | |
| 1.1.784 | 3-trifluoromethoxy-5-butylphenyl | H | methyl | |
| 1.1.785 | 3-(2,2,2-trifluoroethoxy)-5-butylphenyl | H | methyl | |
| 1.1.786 | 3-(2-chloroethoxy)-5-butylphenyl | H | methyl | |
| 1.1.787 | 3-(2-hydroxyethoxy)-5-butylphenyl | H | methyl | |
| 1.1.788 | 3-[(tert-butoxy-carbonyl)oxy]-5-butylphenyl | H | methyl | |
| 1.1.789 | 3-nitro-5-butylphenyl | H | methyl | |
| 1.1.790 | 3-acetoxy-5-butylphenyl | H | methyl | |

TABLE 1.1-continued

Inventive compounds of the general formula (I) in which W* is COOH, R¹ is hydrogen, and aryl is the radical.

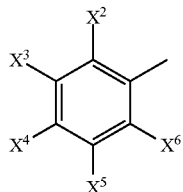

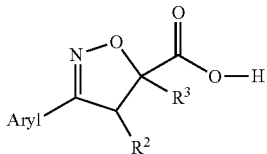

| No. | Aryl | $R^2$ | $R^3$ | Physical data |
|---|---|---|---|---|
| 1.1.791 | {3-[(tert-butoxy-carbonyl)amino]-5-butylphenyl} | H | methyl | |
| 1.1.792 | 3-methylsulfanyl-5-butylphenyl | H | methyl | |
| 1.1.793 | 3,5-diisobutylphenyl | H | methyl | |
| 1.1.794 | 3-tert-butyl-5-isobutylphenyl | H | methyl | |
| 1.1.795 | 3-cyclopropyl-5-isobutylphenyl | H | methyl | |
| 1.1.796 | 3-vinyl-5-isobutylphenyl | H | methyl | |
| 1.1.797 | 3-ethynyl-5-isobutylphenyl | H | methyl | |
| 1.1.798 | 3-cyano-5-isobutylphenyl | H | methyl | |
| 1.1.799 | 3-trifluoromethyl-5-isobutylphenyl | H | methyl | |
| 1.1.800 | 3-(hydroxycarbonyl)-5-isobutylphenyl | H | methyl | |
| 1.1.801 | 3-(methoxycarbonyl)-5-isobutylphenyl | H | methyl | |
| 1.1.802 | 3-hydroxymethyl-5-isobutylphenyl | H | methyl | |
| 1.1.803 | 3-carbamoyl-5-isobutylphenyl | H | methyl | |
| 1.1.804 | 3-hydroxy-5-isobutylphenyl | H | methyl | |
| 1.1.805 | 3-methoxy-5-isobutylphenyl | H | methyl | |
| 1.1.806 | 3-ethoxy-5-isobutylphenyl | H | methyl | |
| 1.1.807 | 3-n-propoxy-5-isobutylphenyl | H | methyl | |
| 1.1.808 | 3-n-butoxy-5-isobutylphenyl | H | methyl | |
| 1.1.809 | 3-isobutoxy-5-isobutylphenyl | H | methyl | |
| 1.1.810 | 3-tert-butoxy-5-isobutylphenyl | H | methyl | |
| 1.1.811 | 3-difluoromethoxy-5-isobutylphenyl | H | methyl | |
| 1.1.812 | 3-trifluoromethoxy-5-isobutylphenyl | H | methyl | |
| 1.1.813 | 3-(2,2,2-trifluoroethoxy)-5-isobutylphenyl | H | methyl | |
| 1.1.814 | 3-(2-chloroethoxy)-5-isobutylphenyl | H | methyl | |
| 1.1.815 | 3-(2-hydroxyethoxy)-5-isobutylphenyl | H | methyl | |
| 1.1.816 | 3-[(tert-butoxy-carbonyl)oxy]-5-isobutylphenyl | H | methyl | |

TABLE 1.1-continued

Inventive compounds of the general formula (I) in which W* is COOH, R¹ is hydrogen, and aryl is the radical.

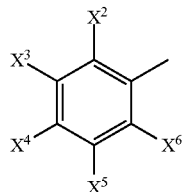

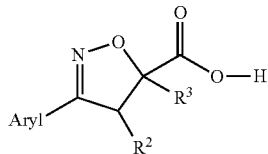

| No. | Aryl | R² | R³ | Physical data |
|---|---|---|---|---|
| 1.1.817 | 3-nitro-5-isobutylphenyl | H | methyl | |
| 1.1.818 | 3-acetoxy-5-isobutylphenyl | H | methyl | |
| 1.1.819 | {3-[(tert-butoxy-carbonyl)amino]-5-isobutylphenyl} | H | methyl | |
| 1.1.820 | 3-methylsulfanyl-5-isobutylphenyl | H | methyl | |
| 1.1.821 | 3,5-di(tert-butylphenyl | H | methyl | [DMSO] 1.30 (s, 9H); 1.56 (s, 3H); 3.41 (d, 1H); 3.82 (d, 1H); 7.48 (s, 2H); 7.5 (s, 1H). |
| 1.1.822 | 3-cyclopropyl-5-tert-butylphenyl | H | methyl | |
| 1.1.823 | 3-vinyl-5-tert-butylphenyl | H | methyl | |
| 1.1.824 | 3-ethynyl-5-tert-butylphenyl | H | methyl | |
| 1.1.825 | 3-cyano-5-tert-butylphenyl | H | methyl | |
| 1.1.826 | 3-trifluoromethyl-5-tert-butylphenyl | H | methyl | |
| 1.1.827 | 3-(hydroxycarbonyl)-5-tert-butylphenyl | H | methyl | |
| 1.1.828 | 3-(methoxycarbonyl)-5-tert-butylphenyl | H | methyl | |
| 1.1.829 | 3-hydroxymethyl-5-tert-butylphenyl | H | methyl | |
| 1.1.830 | 3-carbamoyl-5-tert-butylphenyl | H | methyl | |
| 1.1.831 | 3-hydroxy-5-tert-butylphenyl | H | methyl | |
| 1.1.832 | 3-methoxy-5-tert-butylphenyl | H | methyl | |
| 1.1.833 | 3-ethoxy-5-tert-butylphenyl | H | methyl | |
| 1.1.834 | 3-n-propoxy-5-tert-butylphenyl | H | methyl | |
| 1.1.835 | 3-n-butoxy-5-tert-butylphenyl | H | methyl | |
| 1.1.836 | 3-isobutoxy-5-tert-butylphenyl | H | methyl | |
| 1.1.837 | 3-tert-butoxy-5-tert-butylphenyl | H | methyl | |
| 1.1.838 | 3-difluoromethoxy-5-tert-butylphenyl | H | methyl | |
| 1.1.839 | 3-trifluoromethoxy-5-tert-butylphenyl | H | methyl | |
| 1.1.840 | 3-(2,2,2-trifluoroethoxy)-5-tert-butylphenyl | H | methyl | |
| 1.1.841 | 3-(2-chloroethoxy)-5-tert-butylphenyl | H | methyl | |
| 1.1.842 | 3-(2-hydroxyethoxy)-5-tert-butylphenyl | H | methyl | |

TABLE 1.1-continued

Inventive compounds of the general formula (I) in which W* is COOH, R¹ is hydrogen, and aryl is the radical.

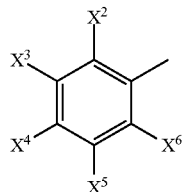

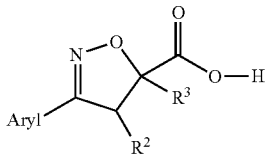

1

| No. | Aryl | R² | R³ | Physical data |
|---|---|---|---|---|
| 1.1.843 | 3-[(tert-butoxy-carbonyl)oxy]-5-tert-butylphenyl | H | methyl | |
| 1.1.844 | 3-nitro-5-tert-butylphenyl | H | methyl | |
| 1.1.845 | 3-acetoxy-5-tert-butylphenyl | H | methyl | |
| 1.1.846 | {3-[(tert-butoxy-carbonyl)amino]-5-tert-butylphenyl} | H | methyl | |
| 1.1.847 | 3-methylsulfanyl-5-tert-butylphenyl | H | methyl | |
| 1.1.848 | 3-tert-butyl-5-cyclopropylphenyl | H | methyl | |
| 1.1.849 | 3,5-dicyclopropyl-phenyl | H | methyl | |
| 1.1.850 | 3-vinyl-5-cyclopropylphenyl | H | methyl | |
| 1.1.851 | 3-ethynyl-5-cyclopropylphenyl | H | methyl | |
| 1.1.852 | 3-cyano-5-cyclopropylphenyl | H | methyl | |
| 1.1.853 | 3-trifluoromethyl-5-cyclopropylphenyl | H | methyl | |
| 1.1.854 | 3-(hydroxycarbonyl)-5-cyclopropylphenyl | H | methyl | |
| 1.1.855 | 3-(methoxycarbonyl)-5-cyclopropylphenyl | H | methyl | |
| 1.1.856 | 3-hydroxymethyl-5-cyclopropylphenyl | H | methyl | |
| 1.1.857 | 3-carbamoyl-5-cyclopropylphenyl | H | methyl | |
| 1.1.858 | 3-hydroxy-5-cyclopropylphenyl | H | methyl | |
| 1.1.859 | 3-methoxy-5-cyclopropylphenyl | H | methyl | |
| 1.1.860 | 3-ethoxy-5-cyclopropylphenyl | H | methyl | |
| 1.1.861 | 3-n-propoxy-5-cyclopropylphenyl | H | methyl | |
| 1.1.862 | 3-n-butoxy-5-cyclopropylphenyl | H | methyl | |
| 1.1.863 | 3-isobutoxy-5-cyclopropylphenyl | H | methyl | |
| 1.1.864 | 3-tert-butoxy-5-cyclopropylphenyl | H | methyl | |
| 1.1.865 | 3-difluoromethoxy-5-cyclopropylphenyl | H | methyl | |
| 1.1.866 | 3-trifluoromethoxy-5-cyclopropylphenyl | H | methyl | |
| 1.1.867 | 3-(2,2,2-trifluoroethoxy)-5-cyclopropylphenyl | H | methyl | |
| 1.1.868 | 3-(2-chloroethoxy)-5-cyclopropylphenyl | H | methyl | |

TABLE 1.1-continued

Inventive compounds of the general formula (I) in which W* is COOH, $R^1$ is hydrogen, and aryl is the radical.

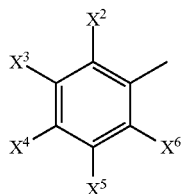

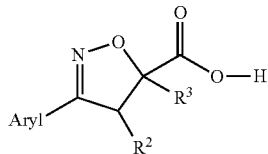

| No. | Aryl | $R^2$ | $R^3$ | Physical data |
|---|---|---|---|---|
| 1.1.869 | 3-(2-hydroxyethoxy)-5-cyclopropylphenyl | H | methyl | |
| 1.1.870 | 3-[(tert-butoxy-carbonyl)oxy]-5-cyclopropylphenyl | H | methyl | |
| 1.1.871 | 3-nitro-5-cyclopropylphenyl | H | methyl | |
| 1.1.872 | 3-acetoxy-5-cyclopropylphenyl | H | methyl | |
| 1.1.873 | {3-[(tert-butoxy-carbonyl)amino]-5-cyclopropylphenyl} | H | methyl | |
| 1.1.874 | 3-methylsulfanyl-5-cyclopropylphenyl | H | methyl | |
| 1.1.875 | 3,5-divinylphenyl | H | methyl | |
| 1.1.876 | 3-ethynyl-5-vinylphenyl | H | methyl | |
| 1.1.877 | 3-cyano-5-vinylphenyl | H | methyl | |
| 1.1.878 | 3-trifluoromethyl-5-vinylphenyl | H | methyl | |
| 1.1.879 | 3-(hydroxycarbonyl)-5-vinylphenyl | H | methyl | |
| 1.1.880 | 3-(methoxycarbonyl)-5-vinylphenyl | H | methyl | |
| 1.1.881 | 3-hydroxymethyl-5-vinylphenyl | H | methyl | |
| 1.1.882 | 3-carbamoyl-5-vinylphenyl | H | methyl | |
| 1.1.883 | 3-hydroxy-5-vinylphenyl | H | methyl | |
| 1.1.884 | 3-methoxy-5-vinylphenyl | H | methyl | |
| 1.1.885 | 3-ethoxy-5-vinylphenyl | H | methyl | |
| 1.1.886 | 3-n-propoxy-5-vinylphenyl | H | methyl | |
| 1.1.887 | 3-n-butoxy-5-vinylphenyl | H | methyl | |
| 1.1.888 | 3-isobutoxy-5-vinylphenyl | H | methyl | |
| 1.1.889 | 3-tert-butoxy-5-vinylphenyl | H | methyl | |
| 1.1.890 | 3-difluoromethoxy-5-vinylphenyl | H | methyl | |
| 1.1.891 | 3-trifluoromethoxy-5-vinylphenyl | H | methyl | |
| 1.1.892 | 3-(2,2,2-trifluoroethoxy)-5-vinylphenyl | H | methyl | |
| 1.1.893 | 3-(2-chloroethoxy)-5-vinylphenyl | H | methyl | |
| 1.1.894 | 3-(2-hydroxyethoxy)-5-vinylphenyl | H | methyl | |

TABLE 1.1-continued

Inventive compounds of the general formula (I) in which W* is COOH, $R^1$ is hydrogen, and aryl is the radical.

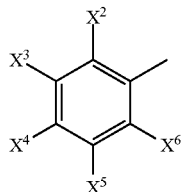

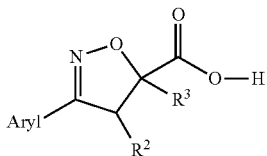

| No. | Aryl | $R^2$ | $R^3$ | Physical data |
|---|---|---|---|---|
| 1.1.895 | 3-[(tert-butoxy-carbonyl)oxy]-5-vinylphenyl | H | methyl | |
| 1.1.896 | 3-nitro-5-vinylphenyl | H | methyl | |
| 1.1.897 | 3-acetoxy-5-vinylphenyl | H | methyl | |
| 1.1.898 | {3-[(tert-butoxy-carbonyl)amino]-5-vinylphenyl} | H | methyl | |
| 1.1.899 | 3-methylsulfanyl-5-vinylphenyl | H | methyl | |
| 1.1.900 | 3,5-diethynylphenyl | H | methyl | |
| 1.1.901 | 3-cyano-5-ethynylphenyl | H | methyl | |
| 1.1.902 | 3-trifluoromethyl-5-ethynylphenyl | H | methyl | |
| 1.1.903 | 3-(hydroxycarbonyl)-5-ethynylphenyl | H | methyl | |
| 1.1.904 | 3-(methoxycarbonyl)-5-ethynylphenyl | H | methyl | |
| 1.1.905 | 3-hydroxymethyl-5-ethynylphenyl | H | methyl | |
| 1.1.906 | 3-carbamoyl-5-ethynylphenyl | H | methyl | |
| 1.1.907 | 3-hydroxy-5-ethynylphenyl | H | methyl | |
| 1.1.908 | 3-methoxy-5-ethynylphenyl | H | methyl | |
| 1.1.909 | 3-ethoxy-5-ethynylphenyl | H | methyl | |
| 1.1.910 | 3-n-propoxy-5-ethynylphenyl | H | methyl | |
| 1.1.911 | 3-n-butoxy-5-ethynylphenyl | H | methyl | |
| 1.1.912 | 3-isobutoxy-5-ethynylphenyl | H | methyl | |
| 1.1.913 | 3-tert-butoxy-5-ethynylphenyl | H | methyl | |
| 1.1.914 | 3-difluoromethoxy-5-ethynylphenyl | H | methyl | |
| 1.1.915 | 3-trifluoromethoxy-5-ethynylphenyl | H | methyl | |
| 1.1.916 | 3-(2,2,2-trifluoroethoxy)-5-ethynylphenyl | H | methyl | |
| 1.1.917 | 3-(2-chloroethoxy)-5-ethynylphenyl | H | methyl | |
| 1.1.918 | 3-(2-hydroxyethoxy)-5-ethynylphenyl | H | methyl | |
| 1.1.919 | 3-[(tert-butoxy-carbonyl)oxy]-5-ethynylphenyl | H | methyl | |

TABLE 1.1-continued

Inventive compounds of the general formula (I) in which W* is COOH, $R^1$ is hydrogen, and aryl is the radical.

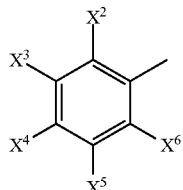

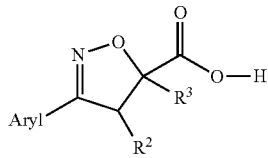

| No. | Aryl | $R^2$ | $R^3$ | Physical data |
|---|---|---|---|---|
| 1.1.920 | 3-nitro-5-ethynylphenyl | H | methyl | |
| 1.1.921 | 3-acetoxy-5-ethynylphenyl | H | methyl | |
| 1.1.922 | {3-[(tert-butoxy-carbonyl)amino]-5-ethynylphenyl} | H | methyl | |
| 1.1.923 | 3-methylsulfanyl-5-ethynylphenyl | H | methyl | |
| 1.1.924 | 3,5-dicyanophenyl | H | methyl | [CDCl$_3$] 1.80 (s, 3H); 3.28 (d, 1H); 3.90 (d, 1H); 7.98 (s, 1H); 8.15 (s, 2H). |
| 1.1.925 | 3-trifluoromethyl-5-cyanophenyl | H | methyl | [CDCl$_3$] 1.81 (s, 3H); 3.30 (d, 1H); 3.91 (d, 1H); 7.92 (s, 1H); 8.11 (d, 2H). |
| 1.1.926 | 3-(hydroxycarbonyl)-5-cyanophenyl | H | methyl | |
| 1.1.927 | 3-(methoxycarbonyl)-5-cyanophenyl | H | methyl | |
| 1.1.928 | 3-hydroxymethyl-5-cyanophenyl | H | methyl | |
| 1.1.929 | 3-carbamoyl-5-cyanophenyl | H | methyl | |
| 1.1.930 | 3-hydroxy-5-cyanophenyl | H | methyl | |
| 1.1.931 | 3-methoxy-5-cyanophenyl | H | methyl | |
| 1.1.932 | 3-ethoxy-5-cyanophenyl | H | methyl | |
| 1.1.933 | 3-n-propoxy-5-cyanophenyl | H | methyl | |
| 1.1.934 | 3-n-butoxy-5-cyanophenyl | H | methyl | |
| 1.1.935 | 3-isobutoxy-5-cyanophenyl | H | methyl | |
| 1.1.936 | 3-tert-butoxy-5-cyanophenyl | H | methyl | |
| 1.1.937 | 3-difluoromethoxy-5-cyanophenyl | H | methyl | |
| 1.1.938 | 3-trifluoromethoxy-5-cyanophenyl | H | methyl | |
| 1.1.939 | 3-(2,2,2-trifluoroethoxy)-5-cyanophenyl | H | methyl | |
| 1.1.940 | 3-(2-chloroethoxy)-5-cyanophenyl | H | methyl | |
| 1.1.941 | 3-(2-hydroxyethoxy)-5-cyanophenyl | H | methyl | |
| 1.1.942 | 3-[(tert-butoxy-carbonyl)oxy]-5-cyanophenyl | H | methyl | |
| 1.1.943 | 3-nitro-5-cyanophenyl | H | methyl | |
| 1.1.944 | 3-acetoxy-5-cyanophenyl | H | methyl | |

TABLE 1.1-continued

Inventive compounds of the general formula (I) in which W* is COOH, $R^1$ is hydrogen, and aryl is the radical.

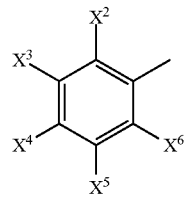

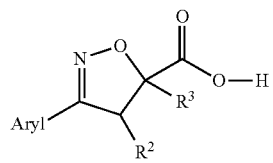

| No. | Aryl | $R^2$ | $R^3$ | Physical data |
|---|---|---|---|---|
| 1.1.945 | {3-[(tert-butoxy-carbonyl)amino]-5-cyanophenyl} | H | methyl | |
| 1.1.946 | 3-methylsulfanyl-5-cyanophenyl | H | methyl | |
| 1.1.947 | 3,5-di(trifluoromethyl)-phenyl | H | methyl | [CDCl$_3$] 1.81 (s, 3H); 3.35 (d, 1H); 3.95 (d, 1H); 7.92 (s, 1H); 8.08 (s, 2H). |
| 1.1.948 | 3-(hydroxycarbonyl)-5-trifluoromethyl-phenyl | H | methyl | |
| 1.1.949 | 3-(methoxycarbonyl)-5-trifluoromethyl-phenyl | H | methyl | |
| 1.1.950 | 3-hydroxymethyl-5-trifluoromethylphenyl | H | methyl | |
| 1.1.951 | 3-carbamoyl-5-trifluoromethylphenyl | H | methyl | |
| 1.1.952 | 3-hydroxy-5-trifluoromethylphenyl | H | methyl | |
| 1.1.953 | 3-methoxy-5-trifluoromethylphenyl | H | methyl | |
| 1.1.954 | 3-ethoxy-5-trifluoromethylphenyl | H | methyl | |
| 1.1.955 | 3-n-propoxy-5-trifluoromethylphenyl | H | methyl | |
| 1.1.956 | 3-n-butoxy-5-trifluoromethylphenyl | H | methyl | |
| 1.1.957 | 3-isobutoxy-5-trifluoromethylphenyl | H | methyl | |
| 1.1.958 | 3-tert-butoxy-5-trifluoromethylphenyl | H | methyl | |
| 1.1.959 | 3-difluoromethoxy-5-trifluoromethylphenyl | H | methyl | |
| 1.1.960 | 3-trifluoromethoxy-5-trifluoromethylphenyl | H | methyl | |
| 1.1.961 | 3-(2,2,2-trifluoro-ethoxy)-5-trifluoro-methylphenyl | H | methyl | |
| 1.1.962 | 3-(2-chloroethoxy)-5-trifluoromethyl-phenyl | H | methyl | |
| 1.1.963 | 3-(2-hydroxyethoxy)-5-trifluoromethyl-phenyl | H | methyl | |
| 1.1.964 | 3-[(tert-butoxy-carbonyl)oxy]-5-trifluoromethylphenyl | H | methyl | |
| 1.1.965 | 3-nitro-5-trifluoromethylphenyl | H | methyl | |
| 1.1.966 | 3-acetoxy-5-trifluoromethylphenyl | H | methyl | |

TABLE 1.1-continued

Inventive compounds of the general formula (I) in which W* is COOH, $R^1$ is hydrogen, and aryl is the radical.

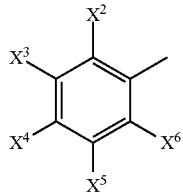

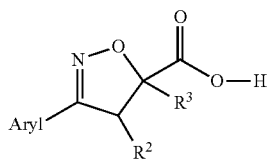

| No. | Aryl | $R^2$ | $R^3$ | Physical data |
|---|---|---|---|---|
| 1.1.967 | {3-[(tert-butoxy-carbonyl)amino]-5-trifluoromethyl-phenyl} | H | methyl | |
| 1.1.968 | 3-methylsulfanyl-5-trifluoromethylphenyl | H | methyl | |
| 1.1.969 | 3,5-bis(hydroxy-carbonyl)phenyl | H | methyl | |
| 1.1.970 | 3-(methoxycarbonyl)-5-(hydroxycarbonyl)-phenyl | H | methyl | |
| 1.1.971 | 3-hydroxymethyl-5-(hydroxycarbonyl)-phenyl | H | methyl | |
| 1.1.972 | 3-carbamoyl-5-(hydroxycarbonyl)-phenyl | H | methyl | |
| 1.1.973 | 3-hydroxy-5-(hydroxycarbonyl)-phenyl | H | methyl | |
| 1.1.974 | 3-methoxy-5-(hydroxycarbonyl)-phenyl | H | methyl | |
| 1.1.975 | 3-ethoxy-5-(hydroxycarbonyl)-phenyl | H | methyl | |
| 1.1.976 | 3-n-propoxy-5-(hydroxycarbonyl)-phenyl | H | methyl | |
| 1.1.977 | 3-n-butoxy-5-(hydroxycarbonyl)-phenyl | H | methyl | |
| 1.1.978 | 3-isobutoxy-5-(hydroxycarbonyl)-phenyl | H | methyl | |
| 1.1.979 | 3-tert-butoxy-5-(hydroxycarbonyl)-phenyl | H | methyl | |
| 1.1.980 | 3-difluoromethoxy-5-(hydroxycarbonyl)-phenyl | H | methyl | |
| 1.1.981 | 3-trifluoromethoxy-5-(hydroxycarbonyl)-phenyl | H | methyl | |
| 1.1.982 | 3-(2,2,2-trifluoro-ethoxy)-5-(hydroxy-carbonyl)phenyl | H | methyl | |
| 1.1.983 | 3-(2-chloroethoxy)-5-(hydroxycarbonyl)-phenyl | H | methyl | |

TABLE 1.1-continued

Inventive compounds of the general formula (I) in which W* is COOH, $R^1$ is hydrogen, and aryl is the radical.

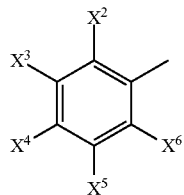

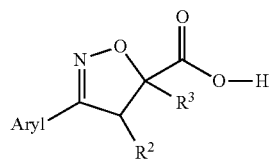

1

| No. | Aryl | $R^2$ | $R^3$ | Physical data |
|---|---|---|---|---|
| 1.1.984 | 3-(2-hydroxyethoxy)-5-(hydroxycarbonyl)-phenyl | H | methyl | |
| 1.1.985 | 3-[(tert-butoxy-(hydroxycarbonyl)-phenyl | H | methyl | |
| 1.1.986 | 3-nitro-5-(hydroxycarbonyl)-phenyl | H | methyl | |
| 1.1.987 | 3-acetoxy-5-(hydroxycarbonyl)-phenyl | H | methyl | |
| 1.1.988 | {3-[(tert-butoxy-carbonyl)amino]-5-(hydroxycarbonyl)-phenyl) | H | methyl | |
| 1.1.989 | 3-methylsulfanyl-5-(hydroxycarbonyl)-phenyl | H | methyl | |
| 1.1.990 | 3,5-di(methoxy-carbonyl)phenyl | H | methyl | |
| 1.1.991 | 3-hydroxymethyl-5-(methoxycarbonyl)-phenyl | H | methyl | |
| 1.1.992 | 3-carbamoyl-5-(methoxycarbonyl)-phenyl | H | methyl | |
| 1.1.993 | 3-hydroxy-5-(methoxycarbonyl)-phenyl | H | methyl | |
| 1.1.994 | 3-methoxy-5-(methoxycarbonyl)-phenyl | H | methyl | |
| 1.1.995 | 3-ethoxy-5-(methoxycarbonyl)-phenyl | H | methyl | |
| 1.1.996 | 3-n-propoxy-5-(methoxycarbonyl)-phenyl | H | methyl | |
| 1.1.997 | 3-n-butoxy-5-(methoxycarbonyl)-phenyl | H | methyl | |
| 1.1.998 | 3-isobutoxy-5-(methoxycarbonyl)-phenyl | H | methyl | |
| 1.1.999 | 3-tert-butoxy-5-(methoxycarbonyl)-phenyl | H | methyl | |
| 1.1.1000 | 3-difluoromethoxy-5-(methoxycarbonyl)-phenyl | H | methyl | |

TABLE 1.1-continued

Inventive compounds of the general formula (I) in which W* is COOH, R¹ is hydrogen, and aryl is the radical.

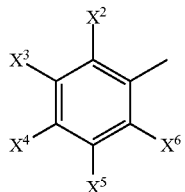

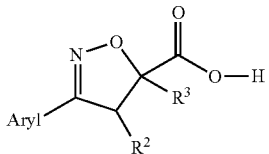

| No. | Aryl | R² | R³ | Physical data |
|---|---|---|---|---|
| 1.1.1001 | 3-trifluoromethoxy-5-(methoxycarbonyl)phenyl | H | methyl | |
| 1.1.1002 | 3-(2,2,2-trifluoroethoxy)-5-(methoxycarbonyl)phenyl | H | methyl | |
| 1.1.1003 | 3-(2-chloroethoxy)-5-(methoxycarbonyl)phenyl | H | methyl | |
| 1.1.1004 | 3-(2-hydroxyethoxy)-5-(methoxycarbonyl)phenyl | H | methyl | |
| 1.1.1005 | 3-[(tert-butoxycarbonyl)oxy]-5-methoxycarbonyl)phenyl | H | methyl | |
| 1.1.1006 | 3-nitro-5-(methoxycarbonyl)phenyl | H | methyl | |
| 1.1.1007 | 3-acetoxy-5-(methoxycarbonyl)phenyl | H | methyl | |
| 1.1.1008 | (3-[(tert-butoxycarbonyl)amino]-5-(methoxycarbonyl)phenyl) | H | methyl | |
| 1.1.1009 | 3-methylsulfanyl-5-(methoxycarbonyl)phenyl | H | methyl | |
| 1.1.1010 | 3,5-di(hydroxymethyl)phenyl | H | methyl | |
| 1.1.1011 | 3-carbamoyl-5-hydroxymethylphenyl | H | methyl | |
| 1.1.1012 | 3-hydroxy-5-hydroxymethylphenyl | H | methyl | |
| 1.1.1013 | 3-methoxy-5-hydroxymethylphenyl | H | methyl | |
| 1.1.1014 | 3-ethoxy-5-hydroxymethylphenyl | H | methyl | |
| 1.1.1015 | 3-n-propoxy-5-hydroxymethylphenyl | H | methyl | |
| 1.1.1016 | 3-n-butoxy-5-hydroxymethylphenyl | H | methyl | |
| 1.1.1017 | 3-isobutoxy-5-hydroxymethylphenyl | H | methyl | |
| 1.1.1018 | 3-tert-butoxy-5-hydroxymethylphenyl | H | methyl | |
| 1.1.1019 | 3-difluoromethoxy-5-hydroxymethylphenyl | H | methyl | |
| 1.1.1020 | 3-trifluoromethoxy-5-hydroxymethylphenyl | H | methyl | |
| 1.1.1021 | 3-(2,2,2-trifluoroethoxy)-5-hydroxymethylphenyl | H | methyl | |
| 1.1.1022 | 3-(2-chloroethoxy)-5-hydroxymethylphenyl | H | methyl | |

TABLE 1.1-continued

Inventive compounds of the general formula (I) in which W* is COOH, $R^1$ is hydrogen, and aryl is the radical.

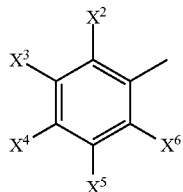

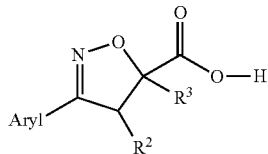

| No. | Aryl | $R^2$ | $R^3$ | Physical data |
|---|---|---|---|---|
| 1.1.1023 | 3-(2-hydroxyethoxy)-5-hydroxymethyl-phenyl | H | methyl | |
| 1.1.1024 | 3-[(tert-butoxy-carbonyl)oxy]-5-hydroxymethylphenyl | H | methyl | |
| 1.1.1025 | 3-nitro-5-hydroxymethylphenyl | H | methyl | |
| 1.1.1026 | 3-acetoxy-5-hydroxymethylphenyl | H | methyl | |
| 1.1.1027 | (3-[(tert-butoxy-carbonyl)amino]-5-hydroxymethyl-phenyl} | H | methyl | |
| 1.1.1028 | 3-methylsulfanyl-5-hydroxymethylphenyl | H | methyl | |
| 1.1.1029 | 3,5-dicarbamoyl-5-carbamoylphenyl | H | methyl | |
| 1.1.1030 | 3-hydroxy-5-carbamoylphenyl | H | methyl | |
| 1.1.1031 | 3-methoxy-5-carbamoylphenyl | H | methyl | |
| 1.1.1032 | 3-ethoxy-5-carbamoylphenyl | H | methyl | |
| 1.1.1033 | 3-n-propoxy-5-carbamoylphenyl | H | methyl | |
| 1.1.1034 | 3-n-butoxy-5-carbamoylphenyl | H | methyl | |
| 1.1.1035 | 3-isobutoxy-5-arbamoylphenyl | H | methyl | |
| 1.1.1036 | 3-tert-butoxy-5-carbamoylphenyl | H | methyl | |
| 1.1.1037 | 3-difluoromethoxy-5-carbamoylphenyl | H | methyl | |
| 1.1.1038 | 3-trifluoromethoxy-5-carbamoylphenyl | H | methyl | |
| 1.1.1039 | 3-(2,2,2-trifluoroethoxy)-5-carbamoylphenyl | H | methyl | |
| 1.1.1040 | 3-(2-chloroethoxy)-5-carbamoylphenyl | H | methyl | |
| 1.1.1041 | 3-(2-hydroxyethoxy)-5-carbamoylphenyl | H | methyl | |
| 1.1.1042 | 3-[(tert-butoxy-carbonyl)oxy]-5-carbamoylphenyl | H | methyl | |
| 1.1.1043 | 3-nitro-5-carbamoylphenyl | H | methyl | |
| 1.1.1044 | 3-acetoxy-5-carbamoylphenyl | H | methyl | |
| 1.1.1045 | {3-[(tert-butoxy-carbonyl)amino]-5-carbamoylphenyl} | H | methyl | |
| 1.1.1046 | 3-methylsulfanyl-5-carbamoylphenyl | H | methyl | |

TABLE 1.1-continued

Inventive compounds of the general formula (I) in which W* is COOH, $R^1$ is hydrogen, and aryl is the radical.

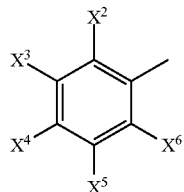

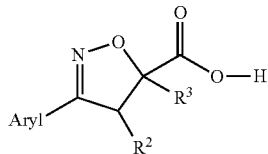

| No. | Aryl | $R^2$ | $R^3$ | Physical data |
|---|---|---|---|---|
| 1.1.1047 | 3,5-dihydroxyphenyl | H | methyl | |
| 1.1.1048 | 3-methoxy-5-hydroxyphenyl | H | methyl | |
| 1.1.1049 | 3-ethoxy-5-hydroxyphenyl | H | methyl | |
| 1.1.1050 | 3-n-propoxy-5-hydroxyphenyl | H | methyl | |
| 1.1.1051 | 3-n-butoxy-5-hydroxyphenyl | H | methyl | |
| 1.1.1052 | 3-isobutoxy-5-hydroxyphenyl | H | methyl | |
| 1.1.1053 | 3-tert-butoxy-5-hydroxyphenyl | H | methyl | |
| 1.1.1054 | 3-difluoromethoxy-5-hydroxyphenyl | H | methyl | |
| 1.1.1055 | 3-trifluoromethoxy-5-hydroxyphenyl | H | methyl | |
| 1.1.1056 | 3-(2,2,2-trifluoroethoxy)-5-hydroxyphenyl | H | methyl | |
| 1.1.1057 | 3-(2-chloroethoxy)-5-hydroxyphenyl | H | methyl | |
| 1.1.1058 | 3-(2-hydroxyethoxy)-5-hydroxyphenyl | H | methyl | |
| 1.1.1059 | 3-[(tert-butoxy-carbonyl)oxy]-5-hydroxyphenyl | H | methyl | |
| 1.1.1060 | 3-nitro-5-hydroxyphenyl | H | methyl | |
| 1.1.1061 | 3-acetoxy-5-hydroxyphenyl | H | methyl | |
| 1.1.1062 | {3-[(tert-butoxy-carbonyl)amino]-5-hydroxyphenyl} | H | methyl | |
| 1.1.1063 | 3-methylsulfanyl-5-hydroxyphenyl | H | methyl | |
| 1.1.1064 | 3,5-dimethoxyphenyl | H | methyl | |
| 1.1.1065 | 3-ethoxy-5-methoxyphenyl | H | methyl | |
| 1.1.1066 | 3-n-propoxy-5-methoxyphenyl | H | methyl | |
| 1.1.1067 | 3-n-butoxy-5-methoxyphenyl | H | methyl | |
| 1.1.1068 | 3-isobutoxy-5-methoxyphenyl | H | methyl | |
| 1.1.1069 | 3-tert-butoxy-5-methoxyphenyl | H | methyl | |
| 1.1.1070 | 3-difluoromethoxy-5-methoxyphenyl | H | methyl | |
| 1.1.1071 | 3-trifluoromethoxy-5-methoxyphenyl | H | methyl | |
| 1.1.1072 | 3-(2,2,2-trifluoroethoxy)-5-methoxyphenyl | H | methyl | |

TABLE 1.1-continued

Inventive compounds of the general formula (I) in which W* is COOH, R¹ is hydrogen, and aryl is the radical.

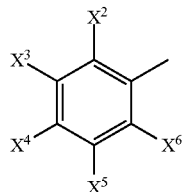

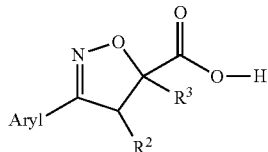

| No. | Aryl | R² | R³ | Physical data |
|---|---|---|---|---|
| 1.1.1073 | 3-(2-chloroethoxy)-5-methoxyphenyl | H | methyl | |
| 1.1.1074 | 3-(2-hydroxyethoxy)-5-methoxyphenyl | H | methyl | |
| 1.1.1075 | 3-[(tert-butoxy-carbonyl)oxy]-5-methoxyphenyl | H | methyl | |
| 1.1.1076 | 3-nitro-5-methoxyphenyl | H | methyl | |
| 1.1.1077 | 3-acetoxy-5-methoxyphenyl | H | methyl | |
| 1.1.1078 | {3-[(tert-butoxy-carbonyl)amino]-5-methoxyphenyl} | H | methyl | |
| 1.1.1079 | 3-methylsulfanyl-5-methoxyphenyl | H | methyl | |
| 1.1.1080 | 3,5-diethoxyphenyl | H | methyl | |
| 1.1.1081 | 3-n-propoxy-5-ethoxyphenyl | H | methyl | |
| 1.1.1082 | 3-n-butoxy-5-ethoxyphenyl | H | methyl | |
| 1.1.1083 | 3-isobutoxy-5-ethoxyphenyl | H | methyl | |
| 1.1.1084 | 3-tert-butoxy-5-ethoxyphenyl | H | methyl | |
| 1.1.1085 | 3-difluoromethoxy-5-ethoxyphenyl | H | methyl | |
| 1.1.1086 | 3-trifluoromethoxy-5-ethoxyphenyl | H | methyl | |
| 1.1.1087 | 3-(2,2,2-trifluoroethoxy)-5-ethoxyphenyl | H | methyl | |
| 1.1.1088 | 3-(2-chloroethoxy)-5-ethoxyphenyl | H | methyl | |
| 1.1.1089 | 3-(2-hydroxyethoxy)-5-ethoxyphenyl | H | methyl | |
| 1.1.1090 | 3-[(tert-butoxy-carbonyl)oxy]-5-ethoxyphenyl | H | methyl | |
| 1.1.1091 | 3-nitro-5-ethoxyphenyl | H | methyl | |
| 1.1.1092 | 3-acetoxy-5-ethoxyphenyl | H | methyl | |
| 1.1.1093 | {3-[(tert-butoxy-carbonyl)amino]-5-ethoxyphenyl} | H | methyl | |
| 1.1.1094 | 3-methylsulfanyl-5-ethoxyphenyl | H | methyl | |
| 1.1.1095 | 3,5-dipropoxyphenyl | H | methyl | |
| 1.1.1096 | 3-n-butoxy-5-propoxyphenyl | H | methyl | |
| 1.1.1097 | 3-isobutoxy-5-propoxyphenyl | H | methyl | |
| 1.1.1098 | 3-tert-butoxy-5-propoxyphenyl | H | methyl | |

TABLE 1.1-continued

Inventive compounds of the general formula (I) in which W* is COOH, $R^1$ is hydrogen, and aryl is the radical.

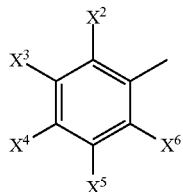

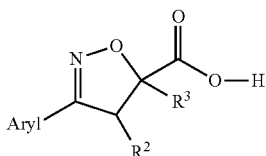

| No. | Aryl | $R^2$ | $R^3$ | Physical data |
|---|---|---|---|---|
| 1.1.1099 | 3-difluoromethoxy-5-propoxyphenyl | H | methyl | |
| 1.1.1100 | 3-trifluoromethoxy-5-propoxyphenyl | H | methyl | |
| 1.1.1101 | 3-(2,2,2-trifluoroethoxy)-5-propoxyphenyl | H | methyl | |
| 1.1.1102 | 3-(2-chloroethoxy)-5-propoxyphenyl | H | methyl | |
| 1.1.1103 | 3-(2-hydroxyethoxy)-5-propoxyphenyl | H | methyl | |
| 1.1.1104 | 3-[(tert-butoxy-carbonyl)oxy]-5-propoxyphenyl | H | methyl | |
| 1.1.1105 | 3-nitro-5-propoxyphenyl | H | methyl | |
| 1.1.1106 | 3-acetoxy-5-propoxyphenyl | H | methyl | |
| 1.1.1107 | {3-[(tert-butoxy-carbonyl)amino]-5-propoxyphenyl} | H | methyl | |
| 1.1.1108 | 3-methylsulfanyl-5-propoxyphenyl | H | methyl | |
| 1.1.1109 | 3,5-di(isopropoxy)phenyl | H | methyl | |
| 1.1.1110 | 3-n-butoxy-5-isopropoxyphenyl | H | methyl | |
| 1.1.1111 | 3-isobutoxy-5-isopropoxyphenyl | H | methyl | |
| 1.1.1112 | 3-tert-butoxy-5-isopropoxyphenyl | H | methyl | |
| 1.1.1113 | 3-difluoromethoxy-5-isopropoxyphenyl | H | methyl | |
| 1.1.1114 | 3-trifluoromethoxy-5-isopropoxyphenyl | H | methyl | |
| 1.1.1115 | 3-(2,2,2-trifluoroethoxy)-5-isopropoxyphenyl | H | methyl | |
| 1.1.1116 | 3-(2-chloroethoxy)-5-isopropoxyphenyl | H | methyl | |
| 1.1.1117 | 3-(2-hydroxyethoxy)-5-isopropoxyphenyl | H | methyl | |
| 1.1.1118 | 3-[(tert-butoxy-carbonyl)oxy]-5-isopropoxyphenyl | H | methyl | |
| 1.1.1119 | 3-nitro-5-isopropoxyphenyl | H | methyl | |
| 1.1.1120 | 3-acetoxy-5-isopropoxyphenyl | H | methyl | |
| 1.1.1121 | {3-[(tert-butoxy-carbonyl)amino]-5-isopropoxyphenyl} | H | methyl | |

TABLE 1.1-continued

Inventive compounds of the general formula (I) in which W* is COOH, $R^1$ is hydrogen, and aryl is the radical.

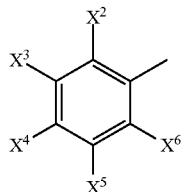

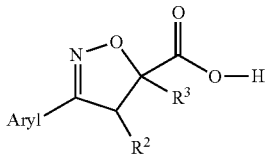

| No. | Aryl | $R^2$ | $R^3$ | Physical data |
|---|---|---|---|---|
| 1.1.1122 | 3-methylsulfanyl-5-isopropoxyphenyl | H | methyl | |
| 1.1.1123 | 3,5-di(tert-butoxy)-phenyl | H | methyl | |
| 1.1.1124 | 3-difluoromethoxy-5-tert-butoxyphenyl | H | methyl | |
| 1.1.1125 | 3-trifluoromethoxy-5-tert-butoxyphenyl | H | methyl | |
| 1.1.1126 | 3-(2,2,2-trifluoroethoxy)-5-tert-butoxyphenyl | H | methyl | |
| 1.1.1127 | 3-(2-chloroethoxy)-5-tert-butoxylphenyl | H | methyl | |
| 1.1.1128 | 3-(2-hydroxyethoxy)-5-tert-butoxyphenyl | H | methyl | |
| 1.1.1129 | 3-[(tert-butoxy-carbonyl)oxy]-5-tert-butoxyphenyl | H | methyl | |
| 1.1.1130 | 3-nitro-5-tert-butoxyphenyl | H | methyl | |
| 1.1.1131 | 3-acetoxy-5-tert-butoxyphenyl | H | methyl | |
| 1.1.1132 | {3-[(tert-butoxy-carbonyl)amino]-5-tert-butoxyphenyl} | H | methyl | |
| 1.1.1133 | 3-methylsulfanyl-5-tert-butoxyphenyl | H | methyl | |
| 1.1.1134 | 3,5-di(trifluoro-methoxy)phenyl | H | methyl | |
| 1.1.1135 | 3-(2,2,2-trifluoro-ethoxy)-5-trifluoro-methoxyphenyl | H | methyl | |
| 1.1.1136 | 3-(2-chloroethoxy)-5-trifluoromethoxy-phenyl | H | methyl | |
| 1.1.1137 | 3-(2-hydroxyethoxy)-5-trifluoromethoxy-phenyl | H | methyl | |
| 1.1.1138 | 3-[(tert-butoxy-carbonyl)oxy]-5-trifluoromethoxy-phenyl | H | methyl | |
| 1.1.1139 | 3-nitro-5-trifluoro-methoxyphenyl | H | methyl | |
| 1.1.1140 | 3-acetoxy-5-tert-butoxyphenyl | H | methyl | |
| 1.1.1141 | (3-[(tert-butoxy-carbonyl)amino]-5-trifluoromethoxy-phenyl} | H | methyl | |
| 1.1.1142 | 3-methylsulfanyl-5-trifluoromethoxy-phenyl | H | methyl | |
| 1.1.1143 | 3,5-bis(difluoro-methoxy)phenyl | H | methyl | |

TABLE 1.1-continued

Inventive compounds of the general formula (I) in which W* is COOH, R¹ is hydrogen, and aryl is the radical.

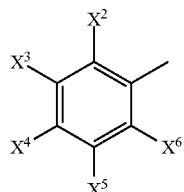

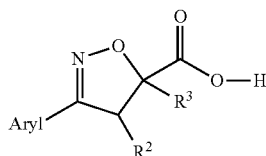

| No. | Aryl | R² | R³ | Physical data |
|---|---|---|---|---|
| 1.1.1144 | 3,5-bis(difluoro-methoxy)phenyl | H | ethyl | |
| 1.1.1145 | 3,5-bis(difluoro-methoxy)phenyl | H | isopropyl | |
| 1.1.1146 | 3,5-bis(difluoro-methoxy)phenyl | H | cyclopropyl | |
| 1.1.1147 | 3-trifluoromethoxy-5-difluoromethoxy-phenyl | H | methyl | |
| 1.1.1148 | 3-(2,2,2-trifluoro-ethoxy)-5-difluoro-methoxyphenyl | H | methyl | |
| 1.1.1149 | 3-(2-chloroethoxy)-5-difluoromethoxy-phenyl | H | methyl | |
| 1.1.1150 | 3-(2-hydroxyethoxy)-5-difluoromethoxy-phenyl | H | methyl | |
| 1.1.1151 | 3-[(tert-butoxy-carbonyl)oxy]-5-difluoromethoxy-phenyl | H | methyl | |
| 1.1.1152 | 3-nitro-5-difluoro-methoxyphenyl | H | methyl | |
| 1.1.1153 | 3-acetoxy-5-difluoro-methoxyphenyl | H | methyl | |
| 1.1.1154 | {3-[(tert-butoxy-carbonyl)amino]-5-difluoromethoxy-phenyl} | H | methyl | |
| 1.1.1155 | 3-methylsulfanyl-5-difluoromethoxy-phenyl | H | methyl | |
| 1.1.1156 | 3,5-bis(2,2,2-trifluoroethoxy)-phenyl | H | methyl | |
| 1.1.1157 | 3-(2-chloroethoxy)-5-(2,2,2-trifluoro-ethoxy)phenyl | H | methyl | |
| 1.1.1158 | 3-(2-hydroxyethoxy)-5-(2,2,2-trifluoro-ethoxy)phenyl | H | methyl | |
| 1.1.1159 | 3-[(tert-butoxy-carbonyl)oxy]-5-(2,2,2-trifluoro-ethoxy)phenyl | H | methyl | |
| 1.1.1160 | 3-nitro-5-(2,2,2-trifluoroethoxy)-phenyl | H | methyl | |
| 1.1.1161 | 3-acetoxy-5-(2,2,2-trifluoroethoxy)-phenyl | H | methyl | |

TABLE 1.1-continued

Inventive compounds of the general formula (I) in which W* is COOH, $R^1$ is hydrogen, and aryl is the radical.

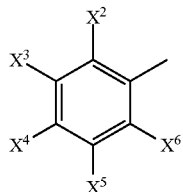

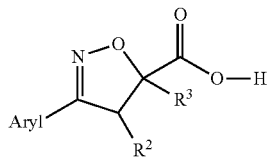

| No. | Aryl | $R^2$ | $R^3$ | Physical data |
|---|---|---|---|---|
| 1.1.1162 | {3-[(tert-butoxy-carbonyl)amino]-5-(2,2,2-trifluoro-ethoxy)phenyl} | H | methyl | |
| 1.1.1163 | 3-methylsulfanyl-5-(2,2,2-trifluoro-ethoxy)phenyl | H | methyl | |
| 1.1.1164 | 3,5-bis(2-chloroethoxy)phenyl | H | methyl | |
| 1.1.1165 | 3-(2-hydroxyethoxy)-5-(2-chloroethoxy)-phenyl | H | methyl | |
| 1.1.1166 | 3-[(tert-butoxy-carbonyl)oxy]-5-(2-chloroethoxy)phenyl | H | methyl | |
| 1.1.1167 | 3-nitro-5-(2-chloroethoxy)phenyl | H | methyl | |
| 1.1.1168 | 3-acetoxy-5-(2-chloroethoxy)phenyl | H | methyl | |
| 1.1.1169 | {3-[(tert-butoxy-carbonyl)amino]-5-(2-chloroethoxy)-phenyl} | H | methyl | |
| 1.1.1170 | 3-methylsulfanyl-5-(2-chloroethoxy)-phenyl | H | methyl | |
| 1.1.1171 | 3,5-bis(2-hydroxy-ethoxy)phenyl | H | methyl | |
| 1.1.1172 | 3-[(tert-butoxy-carbonyl)oxy]-5-(2-hydroxyethoxy)-phenyl | H | methyl | |
| 1.1.1173 | 3-nitro-5-(2-hydroxy-ethoxy)phenyl | H | methyl | |
| 1.1.1174 | 3-acetoxy-5-(2-hydroxyethoxy)-phenyl | H | methyl | |
| 1.1.1175 | 3-[(tert-butoxy-carbonyl)amino]-5-(2-hydroxyethoxy)-phenyl | H | methyl | |
| 1.1.1176 | 3-methylsulfanyl-5-(2-hydroxyethoxy)-phenyl | H | methyl | |
| 1.1.1177 | 3,5-bis[(tert-butoxy-carbonyl)oxy]phenyl | H | methyl | |
| 1.1.1178 | 3-nitro-5-[(tert-butoxycarbonyl)-oxy]phenyl | H | methyl | |
| 1.1.1179 | 3-acetoxy-5-[(tert-butoxycarbonyl)oxy]-phenyl | H | methyl | |

TABLE 1.1-continued

Inventive compounds of the general formula (I) in which W* is COOH, R¹ is hydrogen, and aryl is the radical.

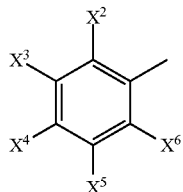

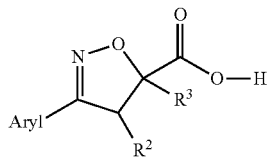

| No. | Aryl | R² | R³ | Physical data |
|---|---|---|---|---|
| 1.1.1180 | {3-[(tert-butoxy-carbonyl)amino]-5-[(tert-butoxy-carbonyl)oxy]phenyl} | H | methyl | |
| 1.1.1181 | 3,5-bis(acetoxy)phenyl | H | methyl | |
| 1.1.1182 | {3-[(tert-butoxy-carbonyl)amino]-5-acetoxyphenyl} | H | methyl | |
| 1.1.1183 | 3-methylsulfanyl-5-acetoxyphenyl | H | methyl | |
| 1.1.1184 | 3,5-dinitrophenyl | H | methyl | |
| 1.1.1185 | 3-acetoxy-5-nitrophenyl | H | methyl | |
| 1.1.1186 | {3-[(tert-butoxy-carbonyl)amino]-5-nitrophenyl} | H | methyl | |
| 1.1.1187 | 3-methylsulfanyl-5-nitrophenyl | H | methyl | |
| 1.1.1188 | 3,5-bis[(tert-butoxycarbonyl)-amino]phenyl | H | methyl | |
| 1.1.1189 | 3-methylsulfanyl-5-[(tert-butoxy-carbonyl)amino]phenyl | H | methyl | |
| 1.1.1190 | 3,5-di(methylsulfanyl)phenyl | H | methyl | |
| 1.1.1191 | 3,4-difluorophenyl | H | methyl | [CDCl₃] 1.80 (s, 3H); 3.25 (d, 1H); 3.85 (d, 1H); 7.22 (m, 1H); 7.30 (m, 1H); 7.55 (m, 1H). |
| 1.1.1192 | 3,4-difluorophenyl | H | ethyl | [CDCl₃] 1.09 (t, 3H); 2.12 (mc, 2H); 3.29 (d, 1H); 3.25 (d, 1H); 7.22 (m, 1H); 7.35 (m, 1H); 7.55 (m, 1H). |
| 1.1.1193 | 3,4-difluorophenyl | H | isopropyl | |
| 1.1.1194 | 3,4-difluorophenyl | H | cyclopropyl | |
| 1.1.1195 | 3-chloro-4-fluorophenyl | H | methyl | [CDCl₃] 1.81 (s, 3H); 3.28 (d, 1H); 3.85 (d, 1H), 7.21 (m, 1H); 7.52 (m, 1H); 7.72 (m, 1H). |
| 1.1.1196 | 3-chloro-4-fluorophenyl | H | ethyl | |
| 1.1.1197 | 3-chloro-4-fluorophenyl | H | isopropyl | |
| 1.1.1198 | 3-chloro-4-fluorophenyl | H | cyclopropyl | |
| 1.1.1199 | 3-bromo-4-fluorophenyl | H | methyl | |
| 1.1.1200 | 3-methyl-4-fluorophenyl | H | methyl | |
| 1.1.1201 | 3-methyl-4-fluorophenyl | H | ethyl | |
| 1.1.1202 | 3-ethyl-4-fluorophenyl | H | methyl | |

TABLE 1.1-continued

Inventive compounds of the general formula (I) in which W* is COOH, $R^1$ is hydrogen, and aryl is the radical.

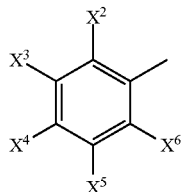

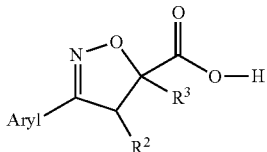

| No. | Aryl | $R^2$ | $R^3$ | Physical data |
| --- | --- | --- | --- | --- |
| 1.1.1203 | 3-cyclopropyl-4-fluorophenyl | H | methyl | |
| 1.1.1204 | 3-vinyl-4-fluorophenyl | H | methyl | |
| 1.1.1205 | 3-ethynyl-4-fluorophenyl | H | methyl | |
| 1.1.1206 | 3-cyano-4-fluorophenyl | H | methyl | |
| 1.1.1207 | 3-methoxy-4-fluorophenyl | H | methyl | |
| 1.1.1208 | 3-ethoxy-4-fluorophenyl | H | methyl | |
| 1.1.1209 | 3-trifluoromethoxy-4-fluorophenyl | H | methyl | |
| 1.1.1210 | 3-nitro-4-fluorophenyl | H | methyl | |
| 1.1.1211 | 3-fluoro-4-chlorophenyl | H | methyl | [CDCl$_3$] 1.71 (s, 3H); 3.25 (d, 1H); 3.82 (d, 1H); 7.35 (m, 1H); 7.48 (m, 1H). |
| 1.1.1212 | 3,4-dichlorophenyl | H | methyl | [CDCl$_3$] 1.8 (s, 3H); 3.25 (d, 1H); 3.83 (d, 1H); 7.5 (s, 2H); 7.72 (s, 1H). |
| 1.1.1213 | 3-bromo-4-chlorophenyl | H | methyl | |
| 1.1.1214 | 3-methyl-4-chlorophenyl | H | methyl | |
| 1.1.1215 | 3-ethyl-4-chlorophenyl | H | methyl | |
| 1.1.1216 | 3-cyclopropyl-4-chlorophenyl | H | methyl | |
| 1.1.1217 | 3-vinyl-4-chlorophenyl | H | methyl | |
| 1.1.1218 | 3-ethynyl-4-chlorophenyl | H | methyl | |
| 1.1.1219 | 3-cyano-4-chlorophenyl | H | methyl | |
| 1.1.1220 | 3-trifluoromethyl-4-chlorophenyl | H | methyl | |
| 1.1.1221 | 3-methoxy-4-chlorophenyl | H | methyl | |
| 1.1.1222 | 3-ethoxy-4-chlorophenyl | H | methyl | |
| 1.1.1223 | 3-trifluoromethoxy-4-chlorophenyl | H | methyl | |
| 1.1.1224 | 3-nitro-4-chlorophenyl | H | methyl | |
| 1.1.1225 | 3-fluoro-4-bromophenyl | H | methyl | |
| 1.1.1226 | 3-chloro-4-bromophenyl | H | methyl | |
| 1.1.1227 | 3,4-dibromophenyl | H | methyl | |
| 1.1.1228 | 3-methyl-4-bromophenyl | H | methyl | |
| 1.1.1229 | 3-ethyl-4-bromophenyl | H | methyl | |

TABLE 1.1-continued

Inventive compounds of the general formula (I) in which W* is COOH, R¹ is hydrogen, and aryl is the radical.

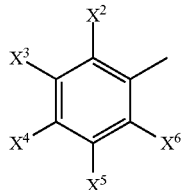

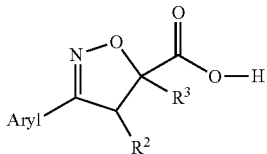

1

| No. | Aryl | R² | R³ | Physical data |
|---|---|---|---|---|
| 1.1.1230 | 3-cyclopropyl-4-bromophenyl | H | methyl | |
| 1.1.1231 | 3-vinyl-4-bromophenyl | H | methyl | |
| 1.1.1232 | 3-ethynyl-4-bromophenyl | H | methyl | |
| 1.1.1233 | 3-cyano-4-bromophenyl | H | methyl | |
| 1.1.1234 | 3-trifluoromethyl-4-bromophenyl | H | methyl | |
| 1.1.1235 | 3-methoxy-4-phenyl | H | methyl | |
| 1.1.1236 | 3-ethoxy-4-bromophenyl | H | methyl | |
| 1.1.1237 | 3-trifluoromethoxy-4-bromophenyl | H | methyl | |
| 1.1.1238 | 3-nitro-4-bromophenyl | H | methyl | |
| 1.1.1239 | 3-fluoro-4-iodophenyl | H | methyl | |
| 1.1.1240 | 3-chloro-4-iodophenyl | H | methyl | |
| 1.1.1241 | 3-bromo-4-iodophenyl | H | methyl | |
| 1.1.1242 | 3-methyl-4-iodophenyl | H | methyl | |
| 1.1.1243 | 3-ethyl-4-iodophenyl | H | methyl | |
| 1.1.1244 | 3-cyclopropyl-4-iodophenyl | H | methyl | |
| 1.1.1245 | 3-vinyl-4-iodophenyl | H | methyl | |
| 1.1.1246 | 3-ethynyl-4-iodophenyl | H | methyl | |
| 1.1.1247 | 3-cyano-4-iodophenyl | H | methyl | |
| 1.1.1248 | 3-trifluoromethyl-4-iodophenyl | H | methyl | |
| 1.1.1249 | 3-methoxy-4-iodophenyl | H | methyl | |
| 1.1.1250 | 3-ethoxy-4-iodophenyl | H | methyl | |
| 1.1.1251 | 3-trifluoromethoxy-4-iodophenyl | H | methyl | |
| 1.1.1252 | 3-nitro-4-iodophenyl | H | methyl | |
| 1.1.1253 | 3-fluoro-4-methylphenyl | H | methyl | |
| 1.1.1254 | 3-chloro-4-methylphenyl | H | methyl | [CDCl₃] 1.75 (s, 3H); 2.42 (s, 3H); 3.29 (d, 1H); 3.85 (d, 1H); 7.25 (m, 1H); 7.41 (m, 1H); 7.51 (m, 1H). |
| 1.1.1255 | 3-bromo-4-methylphenyl | H | methyl | |
| 1.1.1256 | 3,4-dimethylphenyl | H | methyl | |
| 1.1.1257 | 3,4-dimethylphenyl | H | ethyl | |
| 1.1.1258 | 3,4-dimethylphenyl | H | isopropyl | |
| 1.1.1259 | 3,4-dimethylphenyl | H | cyclopropyl | |
| 1.1.1260 | 3-ethyl-4-methylphenyl | H | methyl | |

TABLE 1.1-continued

Inventive compounds of the general formula (I) in which W* is COOH, $R^1$ is hydrogen, and aryl is the radical.

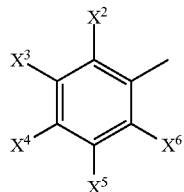

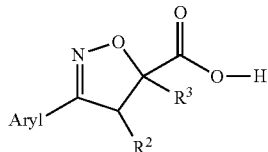

1

| No. | Aryl | $R^2$ | $R^3$ | Physical data |
|---|---|---|---|---|
| 1.1.1261 | 3-cyclopropyl-4-methylphenyl | H | methyl | |
| 1.1.1262 | 3-vinyl-4-methylphenyl | H | methyl | |
| 1.1.1263 | 3-ethynyl-4-methylphenyl | H | methyl | |
| 1.1.1264 | 3-cyano-4-methylphenyl | H | methyl | |
| 1.1.1265 | 3-trifluoromethyl-4-methylphenyl | H | methyl | |
| 1.1.1266 | 3-methoxy-4-methylphenyl | H | methyl | |
| 1.1.1267 | 3-ethoxy-4-methylphenyl | H | methyl | |
| 1.1.1268 | 3-trifluoromethoxy-4-methylphenyl | H | methyl | |
| 1.1.1269 | 3-nitro-4-methylphenyl | H | methyl | |
| 1.1.1270 | 3-fluoro-4-ethylphenyl | H | methyl | |
| 1.1.1271 | 3-chloro-4-ethylphenyl | H | methyl | |
| 1.1.1272 | 3-bromo-4-ethylphenyl | H | methyl | |
| 1.1.1273 | 3-methyl-4-ethylphenyl | H | methyl | |
| 1.1.1274 | 3,4-diethylphenyl | H | methyl | |
| 1.1.1275 | 3-cyclopropyl-4-ethylphenyl | H | methyl | |
| 1.1.1276 | 3-vinyl-4-ethylphenyl | H | methyl | |
| 1.1.1277 | 3-ethynyl-4-ethylphenyl | H | methyl | |
| 1.1.1278 | 3-cyano-4-ethylphenyl | H | methyl | |
| 1.1.1279 | 3-trifluoromethyl-4-ethylphenyl | H | methyl | |
| 1.1.1280 | 3-methoxy-4-ethylphenyl | H | methyl | |
| 1.1.1281 | 3-ethoxy-4-ethylphenyl | H | methyl | |
| 1.1.1282 | 3-trifluoromethoxy-4-ethylphenyl | H | methyl | |
| 1.1.1283 | 3-nitro-4-ethylphenyl | H | methyl | |
| 1.1.1284 | 3-fluoro-4-propylphenyl | H | methyl | |
| 1.1.1285 | 3-chloro-4-propylphenyl | H | methyl | |
| 1.1.1286 | 3-bromo-4-propylphenyl | H | methyl | |
| 1.1.1287 | 3-methyl-4-propylphenyl | H | methyl | |
| 1.1.1288 | 3-methyl-4-propylphenyl | H | methyl | |
| 1.1.1289 | 3-cyclopropyl-4-propylphenyl | H | methyl | |

TABLE 1.1-continued

Inventive compounds of the general formula (I) in which W* is COOH, R¹ is hydrogen, and aryl is the radical.

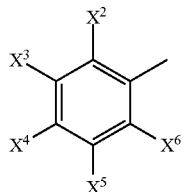

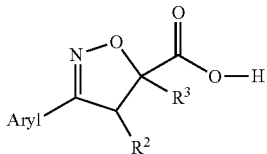

| No. | Aryl | R² | R³ | Physical data |
|---|---|---|---|---|
| 1.1.1290 | 3-vinyl-4-propylphenyl | H | methyl | |
| 1.1.1291 | 3-ethynyl-4-propylphenyl | H | methyl | |
| 1.1.1292 | 3-cyano-4-propylphenyl | H | methyl | |
| 1.1.1293 | 3-trifluoromethyl-4-propylphenyl | H | methyl | |
| 1.1.1294 | 3-methoxy-4-propylphenyl | H | methyl | |
| 1.1.1295 | 3-ethoxy-4-propylphenyl | H | methyl | |
| 1.1.1296 | 3-trifluoromethoxy-4-propylphenyl | H | methyl | |
| 1.1.1297 | 3-nitro-4-propylphenyl | H | methyl | |
| 1.1.1298 | 3-fluoro-4-isopropylphenyl | H | methyl | |
| 1.1.1299 | 3-chloro-4-isopropylphenyl | H | methyl | |
| 1.1.1300 | 3-bromo-4-isopropylphenyl | H | methyl | |
| 1.1.1301 | 3-methyl-4-isopropylphenyl | H | methyl | |
| 1.1.1302 | 3-ethyl-4-isopropylphenyl | H | methyl | |
| 1.1.1303 | 3-cyclopropyl-4-isopropylphenyl | H | methyl | |
| 1.1.1304 | 3-vinyl-4-isopropylphenyl | H | methyl | |
| 1.1.1305 | 3-thynyl-4-isopreopylphenyl | H | methyl | |
| 1.1.1306 | 3-cyano-4-isopropylphenyl | H | methyl | |
| 1.1.1307 | 3-trifluoromethyl-4-isopropylphenyl | H | methyl | |
| 1.1.1308 | 3-methoxy-4-isopropylphenyl | H | methyl | |
| 1.1.1309 | 3-ethoxy-4-isopropylphenyl | H | methyl | |
| 1.1.1310 | 3-trifluoromethoxy-4-isopropylphenyl | H | methyl | |
| 1.1.1311 | 3-nitro-4-isopropylphenyl | H | methyl | |
| 1.1.1312 | 3-fluoro-4-tert-butylphenyl | H | methyl | |
| 1.1.1313 | 3-chloro-4-tert-butylphenyl | H | methyl | |
| 1.1.1314 | 3-bromo-4-tert-butylphenyl | H | methyl | |
| 1.1.1315 | 3-methyl-4-tert-butylphenyl | H | methyl | |
| 1.1.1316 | 3-ethyl-4-tert-butylphenyl | H | methyl | |

TABLE 1.1-continued

Inventive compounds of the general formula (I) in which W* is COOH, $R^1$ is hydrogen, and aryl is the radical.

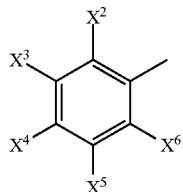

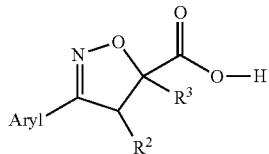

| No. | Aryl | $R^2$ | $R^3$ | Physical data |
|---|---|---|---|---|
| 1.1.1317 | 3-cyclopropyl-4-tert-butylphenyl | H | methyl | |
| 1.1.1318 | 3-vinyl-4-tert-butylphenyl | H | methyl | |
| 1.1.1319 | 3-ethynyl-4-tert-butylphenyl | H | methyl | |
| 1.1.1320 | 3-cyano-4-tert-butylphenyl | H | methyl | |
| 1.1.1321 | 3-trifluoromethyl-4-tert-butylphenyl | H | methyl | |
| 1.1.1322 | 3-trifluoromethyl-4-tert-butylphenyl | H | ethyl | |
| 1.1.1323 | 3-trifluoromethyl-4-tert-butylphenyl | H | isopropyl | |
| 1.1.1324 | 3-trifluoromethyl-4-tert-butylphenyl | H | cyclopropyl | |
| 1.1.1325 | 3-methoxy-4-tert-butylphenyl | H | methyl | |
| 1.1.1326 | 3-ethoxy-4-tert-butylphenyl | H | methyl | |
| 1.1.1327 | 3-trifluoromethoxy-4-tert-butylphenyl | H | methyl | |
| 1.1.1328 | 3-nitro-4-tert-butylphenyl | H | methyl | |
| 1.1.1329 | 3-fluoro-4-hydroxymethylphenyl | H | methyl | |
| 1.1.1330 | 3-chloro-4-hydroxymethylphenyl | H | methyl | |
| 1.1.1331 | 3-bromo-4-hydroxymethylphenyl | H | methyl | |
| 1.1.1332 | 3-methyl-4-hydroxymethylphenyl | H | methyl | |
| 1.1.1333 | 3-ethyl-4-hydroxymethylphenyl | H | methyl | |
| 1.1.1334 | 3-cyclopropyl-4-hydroxymethylphenyl | H | methyl | |
| 1.1.1335 | 3-vinyl-4-hydroxymethylphenyl | H | methyl | |
| 1.1.1336 | 3-ethynyl-4-hydroxymethylphenyl | H | methyl | |
| 1.1.1337 | 3-cyano-4-hydroxymethylphenyl | H | methyl | |
| 1.1.1338 | 3-trifluoromethyl-4-hydroxymethylphenyl | H | methyl | |
| 1.1.1339 | 3-methoxy-4-hydroxymethylphenyl | H | methyl | |
| 1.1.1340 | 3-ethoxy-4-hydroxymethylphenyl | H | methyl | |
| 1.1.1341 | 3-trifluoromethoxy-4-hydroxymethylphenyl | H | methyl | |
| 1.1.1342 | 3-nitro-4-hydroxymethylphenyl | H | methyl | |
| 1.1.1343 | 3-fluoro-4-cyclopropylphenyl | H | methyl | |

TABLE 1.1-continued

Inventive compounds of the general formula (I) in which W* is COOH, $R^1$ is hydrogen, and aryl is the radical.

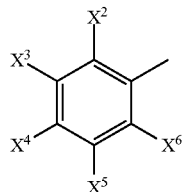

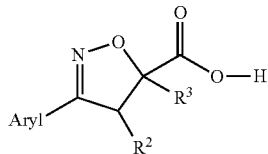

| No. | Aryl | $R^2$ | $R^3$ | Physical data |
|---|---|---|---|---|
| 1.1.1344 | 3-chloro-4-cyclopropylphenyl | H | methyl | |
| 1.1.1345 | 3-bromo-4-cyclopropylphenyl | H | methyl | |
| 1.1.1346 | 3-methyl-4-cyclopropylphenyl | H | methyl | |
| 1.1.1347 | 3-ethyl-4-cyclopropylphenyl | H | methyl | |
| 1.1.1348 | 3-cyclopropyl-4-cyclopropylphenyl | H | methyl | |
| 1.1.1349 | 3-vinyl-4-cyclopropylphenyl | H | methyl | |
| 1.1.1350 | 3-ethynyl-4-cyclopropylphenyl | H | methyl | |
| 1.1.1351 | 3-cyano-4-cyclopropylphenyl | H | methyl | |
| 1.1.1352 | 3-trifluoromethyl-4-cyclopropylphenyl | H | methyl | |
| 1.1.1353 | 3-methoxy-4-cyclopropylphenyl | H | methyl | |
| 1.1.1354 | 3-ethoxy-4-cyclopropylphenyl | H | methyl | |
| 1.1.1355 | 3-trifluoromethoxy-4-cyclopropylphenyl | H | methyl | |
| 1.1.1356 | 3-fluoro-4-methoxycarbonyl-phenyl | H | methyl | |
| 1.1.1357 | 3-chloro-4-methoxy-carbonylphenyl | H | methyl | |
| 1.1.1358 | 3-bromo-4-methoxy-carbonylphenyl | H | methyl | |
| 1.1.1359 | 3-methyl-4-methoxy-carbonylphenyl | H | methyl | |
| 1.1.1360 | 3-ethyl-4-methoxy-carbonylphenyl | H | methyl | |
| 1.1.1361 | 3-cyclopropyl-4-methoxycarbonyl-phenyl | H | methyl | |
| 1.1.1362 | 3-vinyl-4-methoxy-carbonylphenyl | H | methyl | |
| 1.1.1363 | 3-ethynyl-4-methoxy-carbonylphenyl | H | methyl | |
| 1.1.1364 | 3-cyano-4-methoxycarbonylphenyl | H | methyl | |
| 1.1.1365 | 3-trifluoromethyl-4-methoxycarbonyl-phenyl | H | methyl | |
| 1.1.1366 | 3-methoxy-4-methoxycarbonyl-phenyl | H | methyl | |
| 1.1.1367 | 3-ethoxy-4-methoxycarbonyl-phenyl | H | methyl | |

TABLE 1.1-continued

Inventive compounds of the general formula (I) in which W* is COOH, R¹ is hydrogen, and aryl is the radical.

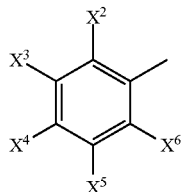

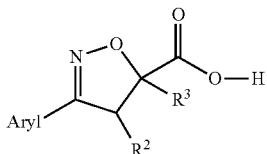

| No. | Aryl | R² | R³ | Physical data |
|---|---|---|---|---|
| 1.1.1368 | 3-trifluoromethoxy-4-methoxycarbonyl-phenyl | H | methyl | |
| 1.1.1369 | 3-nitro-4-methoxy-carbonylphenyl | H | methyl | |
| 1.1.1370 | 3-fluoro-4-vinylphenyl | H | methyl | |
| 1.1.1371 | 3-chloro-4-vinylphenyl | H | methyl | |
| 1.1.1372 | 3-bromo-4-vinylphenyl | H | methyl | |
| 1.1.1373 | 3-methyl-4-vinylphenyl | H | methyl | |
| 1.1.1374 | 3-ethyl-4-vinylphenyl | H | methyl | |
| 1.1.1375 | 3-cyclopropyl-4-vinylphenyl | H | methyl | |
| 1.1.1376 | 3,4-divinylphenyl | H | methyl | |
| 1.1.1377 | 3-ethynyl-4-vinylphenyl | H | methyl | |
| 1.1.1378 | 3-cyano-4-vinylphenyl | H | methyl | |
| 1.1.1379 | 3-trifluoromethyl-4-vinylphenyl | H | methyl | |
| 1.1.1380 | 3-methoxy-4-vinylphenyl | H | methyl | |
| 1.1.1381 | 3-ethoxy-4-vinylphenyl | H | methyl | |
| 1.1.1382 | 3-trifluoromethoxy-4-vinylphenyl | H | methyl | |
| 1.1.1383 | 3-nitro-4-vinylphenyl | H | methyl | |
| 1.1.1384 | 3-fluoro-4-ethynylphenyl | H | methyl | |
| 1.1.1385 | 3-chloro-4-ethynylphenyl | H | methyl | |
| 1.1.1386 | 3-bromo-4-ethynylphenyl | H | methyl | |
| 1.1.1387 | 3-methyl-4-ethynylphenyl | H | methyl | |
| 1.1.1388 | 3-ethyl-4-ethynylphenyl | H | methyl | |
| 1.1.1389 | 3-cyclopropyl-4-ethynylphenyl | H | methyl | |
| 1.1.1390 | 3-vinyl-4-ethynylphenyl | H | methyl | |
| 1.1.1391 | 3-cyano-4-ethynylphenyl | H | methyl | |
| 1.1.1392 | 3-trifluoromethyl-4-ethynylphenyl | H | methyl | |
| 1.1.1393 | 3-methoxy-4-ethynylphenyl | H | methyl | |
| 1.1.1394 | 3-ethoxy-4-ethynylphenyl | H | methyl | |

TABLE 1.1-continued

Inventive compounds of the general formula (I) in which W* is COOH, R¹ is hydrogen, and aryl is the radical.

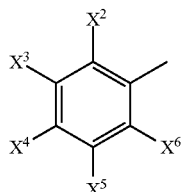

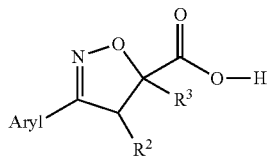

| No. | Aryl | R² | R³ | Physical data |
|---|---|---|---|---|
| 1.1.1395 | 3-trifluoromethoxy-4-ethynylphenyl | H | methyl | |
| 1.1.1396 | 3-nitro-4-ethynylphenyl | H | methyl | |
| 1.1.1397 | 3-fluoro-4-ethynylphenyl | H | methyl | |
| 1.1.1398 | 3-fluoro-4-cyanophenyl | H | methyl | |
| 1.1.1399 | 3-chloro-4-cyanophenyl | H | methyl | |
| 1.1.1400 | 3-bromo-4-cyanophenyl | H | methyl | |
| 1.1.1401 | 3-methyl-4-cyanophenyl | H | methyl | |
| 1.1.1402 | 3-ethyl-4-cyanophenyl | H | methyl | |
| 1.1.1403 | 3-cyclopropyl-4-cyanophenyl | H | methyl | |
| 1.1.1404 | 3-vinyl-4-cyanophenyl | H | methyl | |
| 1.1.1405 | 3-ethynyl-4-cyanophenyl | H | methyl | |
| 1.1.1406 | 3,4-dicyanophenyl | H | methyl | |
| 1.1.1407 | 3-trifluoromethyl-4-cyanophenyl | H | methyl | |
| 1.1.1408 | 3-trifluoromethyl-4-cyanophenyl | H | ethyl | |
| 1.1.1409 | 3-trifluoromethyl-4-cyanophenyl | H | isopropyl | |
| 1.1.1410 | 3-trifluoromethyl-4-cyanophenyl | H | cyclopropyl | |
| 1.1.1411 | 3-methoxy-4-cyanophenyl | H | methyl | |
| 1.1.1412 | 3-ethoxy-4-cyanophenyl | H | methyl | |
| 1.1.1413 | 3-trifluoromethoxy-4-cyanophenyl | H | methyl | |
| 1.1.1414 | 3-nitro-4-cyanophenyl | H | methyl | |
| 1.1.1415 | 3-fluoro-4-hydroxyphenyl | H | methyl | |
| 1.1.1416 | 3-chloro-4-hydroxyphenyl | H | methyl | |
| 1.1.1417 | 3-bromo-4-hydroxyphenyl | H | methyl | |
| 1.1.1418 | 3-methyl-4-hydroxyphenyl | H | methyl | |
| 1.1.1419 | 3-ethyl-4-hydroxyphenyl | H | methyl | |
| 1.1.1420 | 3-cyclopropyl-4-hydroxyphenyl | H | methyl | |
| 1.1.1421 | 3-vinyl-4-hydroxyphenyl | H | methyl | |
| 1.1.1422 | 3-ethynyl-4-hydroxyphenyl | H | methyl | |

TABLE 1.1-continued

Inventive compounds of the general formula (I) in which W* is COOH, R¹ is hydrogen, and aryl is the radical.

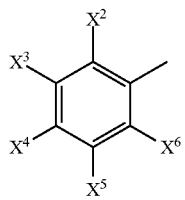

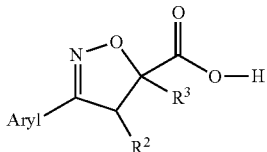

| No. | Aryl | R² | R³ | Physical data |
|---|---|---|---|---|
| 1.1.1423 | 3-cyano-4-hydroxyphenyl | H | methyl | |
| 1.1.1424 | 3-trifluoromethyl-4-hydroxyphenyl | H | methyl | |
| 1.1.1425 | 3-methoxy-4-hydroxyphenyl | H | methyl | |
| 1.1.1426 | 3-ethoxy-4-hydroxyphenyl | H | methyl | |
| 1.1.1427 | 3-trifluoromethoxy-4-hydroxyphenyl | H | methyl | |
| 1.1.1428 | 3-nitro-4-hydroxyphenyl | H | methyl | |
| 1.1.1429 | 3-fluoro-4-methoxyphenyl | H | methyl | |
| 1.1.1430 | 3-chloro-4-methoxyphenyl | H | methyl | |
| 1.1.1431 | 3-bromo-4-methoxyphenyl | H | methyl | |
| 1.1.1432 | 3-methyl-4-methoxyphenyl | H | methyl | |
| 1.1.1433 | 3-ethyl-4-methoxyphenyl | H | methyl | |
| 1.1.1434 | 3-cyclopropyl-4-methoxyphenyl | H | methyl | |
| 1.1.1435 | 3-vinyl-4-methoxyphenyl | H | methyl | |
| 1.1.1436 | 3-ethynyl-4-methoxyphenyl | H | methyl | |
| 1.1.1437 | 3-cyano-4-methoxyphenyl | H | methyl | |
| 1.1.1438 | 3-trifluoromethyl-4-methoxyphenyl | H | methyl | |
| 1.1.1439 | 3,4-dimethoxyphenyl | H | methyl | |
| 1.1.1440 | 3-ethoxy-4-methoxyphenyl | H | methyl | |
| 1.1.1441 | 3-trifluoromethoxy-4-methoxyphenyl | H | methyl | |
| 1.1.1442 | 3-nitro-4-methoxyphenyl | H | methyl | |
| 1.1.1443 | 3-fluoro-4-ethoxyphenyl | H | methyl | |
| 1.1.1444 | 3-chloro-4-ethoxyphenyl | H | methyl | |
| 1.1.1445 | 3-chloro-4-ethoxyphenyl | H | ethyl | |
| 1.1.1446 | 3-chloro-4-ethoxyphenyl | H | isopropyl | |
| 1.1.1447 | 3-chloro-4-ethoxyphenyl | H | cyclopropyl | |
| 1.1.1448 | 3-bromo-4-ethoxyphenyl | H | methyl | |
| 1.1.1449 | 3-methyl-4-ethoxyphenyl | H | methyl | |
| 1.1.1450 | 3-ethyl-4-ethoxyphenyl | H | methyl | |

TABLE 1.1-continued

Inventive compounds of the general formula (I) in which W* is COOH, $R^1$ is hydrogen, and aryl is the radical.

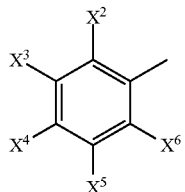

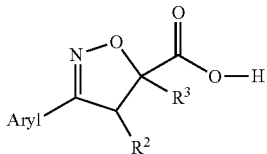

| No. | Aryl | $R^2$ | $R^3$ | Physical data |
|---|---|---|---|---|
| 1.1.1451 | 3-cyclopropyl-4-ethoxyphenyl | H | methyl | |
| 1.1.1452 | 3-vinyl-4-ethoxyphenyl | H | methyl | |
| 1.1.1453 | 3-ethynyl-4-ethoxyphenyl | H | methyl | |
| 1.1.1454 | 3-cyano-4-ethoxyphenyl | H | methyl | |
| 1.1.1455 | 3-trifluoromethyl-4-ethoxyphenyl | H | methyl | |
| 1.1.1456 | 3-methoxy-4-ethoxyphenyl | H | methyl | |
| 1.1.1457 | 2,4-diethoxyphenyl | H | methyl | |
| 1.1.1458 | 3-trifluoromethoxy-4-ethoxyphenyl | H | methyl | |
| 1.1.1459 | 3-nitro-4-ethoxyphenyl | H | methyl | |
| 1.1.1460 | 3-fluoro-4-propoxyphenyl | H | methyl | |
| 1.1.1461 | 3-chloro-4-propoxyphenyl | H | methyl | |
| 1.1.1462 | 3-bromo-4-propoxyphenyl | H | methyl | |
| 1.1.1463 | 3-methyl-4-propoxyphenyl | H | methyl | |
| 1.1.1464 | 3-ethyl-4-propoxyphenyl | H | methyl | |
| 1.1.1465 | 3-cyclopropyl-4-propoxyphenyl | H | methyl | |
| 1.1.1466 | 3-vinyl-4-propoxyphenyl | H | methyl | |
| 1.1.1467 | 3-ethynyl-4-propoxyphenyl | H | methyl | |
| 1.1.1468 | 3-cyano-4-propoxyphenyl | H | methyl | |
| 1.1.1469 | 3-trifluoromethyl-4-propoxyphenyl | H | methyl | |
| 1.1.1470 | 3-methoxy-4-propoxy-phenyl | H | methyl | |
| 1.1.1471 | 3-ethoxy-4-propoxyphenyl | H | methyl | |
| 1.1.1472 | 3-trifluoromethoxy-4-propoxyphenyl | H | methyl | |
| 1.1.1473 | 3-nitro-4-propoxyphenyl | H | methyl | |
| 1.1.1474 | 3-fluoro-4-isopropoxyphenyl | H | methyl | |
| 1.1.1475 | 3-chloro-4-isopropoxyphenyl | H | methyl | |
| 1.1.1476 | 3-bromo-4-isopropoxyphenyl | H | methyl | |
| 1.1.1477 | 3-methyl-4-isopropoxyphenyl | H | methyl | |
| 1.1.1478 | 3-ethyl-4-isopropoxyphenyl | H | methyl | |

TABLE 1.1-continued

Inventive compounds of the general formula (I) in which W* is COOH, $R^1$ is hydrogen, and aryl is the radical.

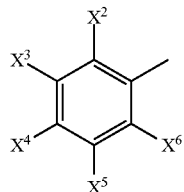

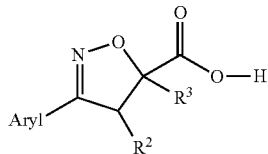

| No. | Aryl | $R^2$ | $R^3$ | Physical data |
|---|---|---|---|---|
| 1.1.1479 | 3-cyclopropyl-4-isopropoxyphenyl | H | methyl | |
| 1.1.1480 | 3-vinyl-4-isopropoxyphenyl | H | methyl | |
| 1.1.1481 | 3-ethynyl-4-isopropoxyphenyl | H | methyl | |
| 1.1.1482 | 3-cyano-4-isopropoxyphenyl | H | methyl | |
| 1.1.1483 | 3-trifluoromethyl-4-isopropoxyphenyl | H | methyl | |
| 1.1.1484 | 3-methoxy-4-isopropoxyphenyl | H | methyl | |
| 1.1.1485 | 3-ethoxy-4-isopropoxyphenyl | H | methyl | |
| 1.1.1486 | 3-trifluoromethoxy-4-isopropoxyphenyl | H | methyl | |
| 1.1.1487 | 3-nitro-4-isopropoxyphenyl | H | methyl | |
| 1.1.1488 | 3-fluoro-4-tert-butoxyphenyl | H | methyl | |
| 1.1.1489 | 3-chloro-4-tert-butoxyphenyl | H | methyl | |
| 1.1.1490 | 3-bromo-4-tert-butoxyphenyl | H | methyl | |
| 1.1.1491 | 3-methyl-4-tert-butoxyphenyl | H | methyl | |
| 1.1.1492 | 3-ethyl-4-tert-butoxyphenyl | H | methyl | |
| 1.1.1493 | 3-cyclopropyl-4-tert-butoxyphenyl | H | methyl | |
| 1.1.1494 | 3-vinyl-4-tert-butoxyphenyl | H | methyl | |
| 1.1.1495 | 3-ethynyl-4-tert-butoxyphenyl | H | methyl | |
| 1.1.1496 | 3-cyano-4-tert-butoxyphenyl | H | methyl | |
| 1.1.1497 | 3-trifluoromethyl-4-tert-butoxyphenyl | H | methyl | |
| 1.1.1498 | 3-methoxy-4-tert-butoxyphenyl | H | methyl | |
| 1.1.1499 | 3-ethoxy-4-tert-butoxyphenyl | H | methyl | |
| 1.1.1500 | 3-trifluoromethoxy-4-tert-butoxyphenyl | H | methyl | |
| 1.1.1501 | 3-nitro-4-tert-butoxyphenyl | H | methyl | |
| 1.1.1502 | 3-fluoro-4-trifluoromethoxyphenyl | H | methyl | |
| 1.1.1503 | 3-chloro-4-trifluoromethoxyphenyl | H | methyl | |
| 1.1.1504 | 3-bromo-4-trifluoromethoxyphenyl | H | methyl | |
| 1.1.1505 | 3-methyl-4-trifluoromethoxyphenyl | H | methyl | |

TABLE 1.1-continued

Inventive compounds of the general formula (I) in which W* is COOH, R¹ is hydrogen, and aryl is the radical.

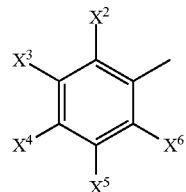

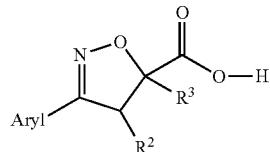

| No. | Aryl | R² | R³ | Physical data |
|---|---|---|---|---|
| 1.1.1506 | 3-ethyl-4-trifluoro-methoxyphenyl | H | methyl | |
| 1.1.1507 | 3-cyclopropyl-4-trifluoromethoxy-phenyl | H | methyl | |
| 1.1.1508 | 3-vinyl-4-trifluoro-methoxyphenyl | H | methyl | |
| 1.1.1509 | 3-ethynyl-4-trifluoro-methoxyphenyl | H | methyl | |
| 1.1.1510 | 3-cyano-4-trifluoro-methoxyphenyl | H | methyl | |
| 1.1.1511 | 3-trifluoromethyl-4-trifluoromethoxy-phenyl | H | methyl | |
| 1.1.1512 | 3-methoxy-4-trifluoromethoxy-phenyl | H | methyl | |
| 1.1.1513 | 3-ethoxy-4-trifluoro-methoxyphenyl | H | methyl | |
| 1.1.1514 | 3,4-bis(trifluoro-methoxy)phenyl | H | methyl | |
| 1.1.1515 | 3-nitro-4-trifluoro-methoxyphenyl | H | methyl | |
| 1.1.1516 | 3-fluoro-4-(2,2,2-trifluoroethoxy)-phenyl | H | methyl | |
| 1.1.1517 | 3-chloro-4-(2,2,2-trifluoroethoxy)-phenyl | H | methyl | |
| 1.1.1518 | 3-bromo-4-(2,2,2-trifluoroethoxy)-phenyl | H | methyl | |
| 1.1.1519 | 3-methyl-4-(2,2,2-trifluoroethoxy)-phenyl | H | methyl | |
| 1.1.1520 | 3-ethyl-4-(2,2,2-trifluoroethoxy)-phenyl | H | methyl | |
| 1.1.1521 | 3-cyclopropyl-4-(2,2,2-trifluoro-ethoxy)phenyl | H | methyl | |
| 1.1.1522 | 3-vinyl-4-(2,2,2-trifluoroethoxy)-phenyl | H | methyl | |
| 1.1.1523 | 3-ethynyl-4-(2,2,2-trifluoroethoxyphenyl | H | methyl | |
| 1.1.1524 | 3-cyano-4-(2,2,2-trifluoroethoxy)-phenyl | H | methyl | |
| 1.1.1525 | 3-trifluoromethyl-4-(2,2,2-trifluoro-ethoxy)phenyl | H | methyl | |
| 1.1.1526 | 3-methoxy-4-(2,2,2-trifluoroethoxy)-phenyl | H | methyl | |

TABLE 1.1-continued

Inventive compounds of the general formula (I) in which W* is COOH, $R^1$ is hydrogen, and aryl is the radical.

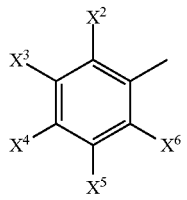

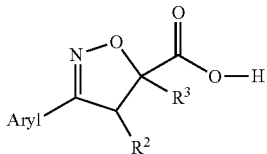

| No. | Aryl | $R^2$ | $R^3$ | Physical data |
|---|---|---|---|---|
| 1.1.1527 | 3-ethoxy-4-(2,2,2-trifluoroethoxy)-phenyl | H | methyl | |
| 1.1.1528 | 3-trifluoromethoxy-4-(2,2,2-trifluoroethoxy)phenyl | H | methyl | |
| 1.1.1529 | 3-nitro-4-(2,2,2-trifluoroethoxy)-phenyl | H | methyl | |
| 1.1.1530 | 3-fluoro-4-difluoromethoxyphenyl | H | methyl | |
| 1.1.1531 | 3-chloro-4-difluoromethoxyphenyl | H | methyl | |
| 1.1.1532 | 3-bromo-4-difluoromethoxyphenyl | H | methyl | |
| 1.1.1533 | 3-methyl-4-difluoromethoxyphenyl | H | methyl | |
| 1.1.1534 | 3-ethyl-4-difluoromethoxyphenyl | H | methyl | |
| 1.1.1535 | 3-cyclopropyl-4-difluoromethoxyphenyl | H | methyl | |
| 1.1.1536 | 3-vinyl-4-difluoromethoxyphenyl | H | methyl | |
| 1.1.1537 | 3-ethynyl-4-difluoromethoxyphenyl | H | methyl | |
| 1.1.1538 | 3-cyano-4-difluoromethoxyphenyl | H | methyl | |
| 1.1.1539 | 3-trifluoromethyl-4-difluoromethoxyphenyl | H | methyl | |
| 1.1.1540 | 3-methoxy-4-difluoromethoxyphenyl | H | methyl | |
| 1.1.1541 | 3-ethoxy-4-difluoromethoxyphenyl | H | methyl | |
| 1.1.1542 | 3-trifluoromethoxy-4-difluoromethoxyphenyl | H | methyl | |
| 1.1.1543 | 3-nitro-4-difluoromethoxyphenyl | H | methyl | |
| 1.1.1544 | 3-fluoro-4-(2-methoxyethoxy)-phenyl | H | methyl | |
| 1.1.1545 | 3-chloro-4-(2-methoxyethoxy)-phenyl | H | methyl | |
| 1.1.1546 | 3-bromo-4-(2-methoxyethoxy)-phenyl | H | methyl | |
| 1.1.1547 | 3-methyl-4-(2-methoxyethoxy)-phenyl | H | methyl | |
| 1.1.1548 | 3-ethyl-4-(2-methoxyethoxy)-phenyl | H | methyl | |

TABLE 1.1-continued

Inventive compounds of the general formula (I) in which W* is COOH, R¹ is hydrogen, and aryl is the radical.

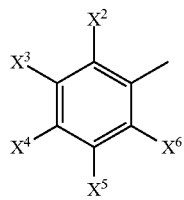

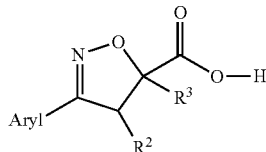

| No. | Aryl | R² | R³ | Physical data |
|---|---|---|---|---|
| 1.1.1549 | 3-cyclopropyl-4-(2-methoxyethoxy)-phenyl | H | methyl | |
| 1.1.1550 | 3-vinyl-4-(2-methoxyethoxy)-phenyl | H | methyl | |
| 1.1.1551 | 3-ethynyl-4-(2-methoxyethoxy)-phenyl | H | methyl | |
| 1.1.1552 | 3-cyano-4-(2-methoxyethoxy)-phenyl | H | methyl | |
| 1.1.1553 | 3-trifluoromethyl-4-(2-methoxyethoxy)-phenyl | H | methyl | |
| 1.1.1554 | 3-methoxy-4-(2-methoxyethoxy)-phenyl | H | methyl | |
| 1.1.1555 | 3-ethoxy-4-(2-methoxyethoxy)-phenyl | H | methyl | |
| 1.1.1556 | 3-trifluoromethoxy-(2-methoxyethoxy)-phenyl | H | methyl | |
| 1.1.1557 | 3-nitro-4-(2-methoxy-ethoxy)phenyl | H | methyl | |
| 1.1.1558 | 3-fluoro-4-(tert-butoxycarbonyloxy)-phenyl | H | methyl | |
| 1.1.1559 | 3-chloro-4-(tert-butoxycarbonyloxy)-phenyl | H | methyl | |
| 1.1.1560 | 3-bromo-4-(tert-butoxycarbonyloxy)-phenyl | H | methyl | |
| 1.1.1561 | 3-methyl-4-(tert-butoxycarbonyloxy)-phenyl | H | methyl | |
| 1.1.1562 | 3-ethyl-4-(tert-butoxycarbonyloxy)-phenyl | H | methyl | |
| 1.1.1563 | 3-cyclopropyl-4-(tert-butoxycarbonyloxy)-phenyl | H | methyl | |
| 1.1.1564 | 3-vinyl-4-(tert-butoxycarbonyloxy)-phenyl | H | methyl | |
| 1.1.1565 | 3-ethynyl-4-(tert-butoxycarbonyloxy)-phenyl | H | methyl | |
| 1.1.1566 | 3-cyano-4-(tert-butoxycarbonyloxy)-phenyl | H | methyl | |

TABLE 1.1-continued

Inventive compounds of the general formula (I) in which W* is COOH, R¹ is hydrogen, and aryl is the radical.

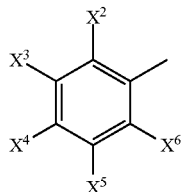

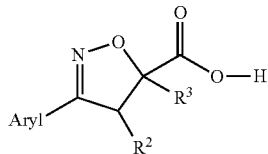

| No. | Aryl | R² | R³ | Physical data |
|---|---|---|---|---|
| 1.1.1567 | 3-trifluoromethyl-4-(tert-butoxycarbonyloxy)phenyl | H | methyl | |
| 1.1.1568 | 3-methoxy-4-(tert-butoxycarbonyloxy)-phenyl | H | methyl | |
| 1.1.1569 | 3-ethoxy-4-(tert-butoxycarbonyloxy)-phenyl | H | methyl | |
| 1.1.1570 | 3-trifluoromethoxy-4-(tert-butoxycarbonyloxy)phenyl | H | methyl | |
| 1.1.1571 | 2-nitro-4-(tert-butoxycarbonyloxy)-phenyl | H | methyl | |
| 1.1.1572 | 3-fluoro-4-nitrophenyl | H | methyl | |
| 1.1.1573 | 3-chloro-4-nitrophenyl | H | methyl | |
| 1.1.1574 | 3-bromo-4-nitrophenyl | H | methyl | |
| 1.1.1575 | 3-methyl-4-nitrophenyl | H | methyl | |
| 1.1.1576 | 3-ethyl-4-nitrophenyl | H | methyl | |
| 1.1.1577 | 3-cyclopropyl-4-nitrophenyl | H | methyl | |
| 1.1.1578 | 3-vinyl-4-nitrophenyl | H | methyl | |
| 1.1.1579 | 3-ethynyl-4-nitrophenyl | H | methyl | |
| 1.1.1580 | 3-cyano-4-nitrophenyl | H | methyl | |
| 1.1.1581 | 3-trifluoromethyl-4-nitrophenyl | H | methyl | |
| 1.1.1582 | 3-methoxy-4-nitrophenyl | H | methyl | |
| 1.1.1583 | 3-ethoxy-4-nitrophenyl | H | methyl | |
| 1.1.1584 | 3-trifluoromethoxy-4-nitrophenyl | H | methyl | |
| 1.1.1585 | 3-fluoro-4-methylsulfanylphenyl | H | methyl | |
| 1.1.1586 | 3-chloro-4-methylsulfanylphenyl | H | methyl | |
| 1.1.1587 | 3-bromo-4-methylsulfanylphenyl | H | methyl | |
| 1.1.1588 | 3-methyl-4-methylsulfanylphenyl | H | methyl | |
| 1.1.1589 | 3-ethyl-4-methylsulfanylphenyl | H | methyl | |
| 1.1.1590 | 3-cyclopropyl-4-methylsulfanylphenyl | H | methyl | |
| 1.1.1591 | 3-vinyl-4-methylsulfanylphenyl | H | methyl | |
| 1.1.1592 | 3-ethynyl-4-methylsulfanylphenyl | H | methyl | |

TABLE 1.1-continued

Inventive compounds of the general formula (I) in which W* is COOH, R¹ is hydrogen, and aryl is the radical.

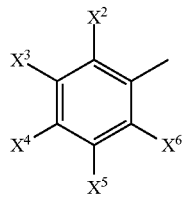

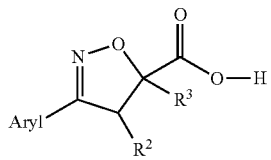

| No. | Aryl | R² | R³ | Physical data |
|---|---|---|---|---|
| 1.1.1593 | 3-cyano-4-methylsulfanylphenyl | H | methyl | |
| 1.1.1594 | 3-trifluoromethyl-4-methylsulfanylphenyl | H | methyl | |
| 1.1.1595 | 3-methoxy-4-methylsulfanylphenyl | H | methyl | |
| 1.1.1596 | 3-ethoxy-4-methylsulfanylphenyl | H | methyl | |
| 1.1.1597 | 3-trifluoromethoxy-4-methylsulfanylphenyl | H | methyl | |
| 1.1.1598 | 3-nitro-4-methylsulfanylphenyl | H | methyl | |
| 1.1.1599 | 3,6-difluorophenyl | H | methyl | [CDCl₃] 1.78 (s, 3H); 3.39 (d, 1H); 3.91 (dd, 1H); 7.09 (m, 2H); 7.59 (m, 1H). |
| 1.1.1600 | 3,6-difluorophenyl | H | ethyl | |
| 1.1.1601 | 3,6-difluorophenyl | H | isopropyl | |
| 1.1.1602 | 3,6-difluorophenyl | H | cyclopropyl | |
| 1.1.1603 | 3-chloro-6-fluorophenyl | H | methyl | |
| 1.1.1604 | 3-bromo-6-fluorophenyl | H | methyl | [CDCl₃] 1.75 (s, 3H); 3.35 (d, 1H); 3.90 (d, 1H); 7.00 (t, 3H); 7.51 (m, 1H); 8.0 (m, 1H). |
| 1.1.1605 | 3-methyl-6-fluorophenyl | H | methyl | |
| 1.1.1606 | 3-ethyl-6-fluorophenyl | H | methyl | |
| 1.1.1607 | 3-cyclopropyl-6-fluorophenyl | H | methyl | |
| 1.1.1608 | 3-vinyl-6-fluorophenyl | H | methyl | |
| 1.1.1609 | 3-ethynyl-6-fluorophenyl | H | methyl | |
| 1.1.1610 | 3-cyano-6-fluorophenyl | H | methyl | |
| 1.1.1611 | 3-methoxy-6-fluorophenyl | H | methyl | [DMSO] 1.53 (s, 3H); 3.39 (d, 1H); 3.75 (s, 3H); 3.81 (d, 1H); 7.06 (m, 1H); 7.18 (m, 1H); 7.38 (t, 1H). |
| 1.1.1612 | 3-ethoxy-6-fluorophenyl | H | methyl | |
| 1.1.1613 | 3-trifluoromethoxy-6-fluorophenyl | H | methyl | |
| 1.1.1614 | 3-nitro-6-fluorophenyl | H | methyl | |
| 1.1.1615 | 3-fluoro-6-chlorophenyl | H | methyl | [CDCl₃] 1.80 (s, 3H); 3.50 (d, 1H); 4.02 (d, 1H); 7.10 (m, 1H); 7.40 (m, 2H). |
| 1.1.1616 | 3-fluoro-6-chlorophenyl | H | ethyl | |
| 1.1.1617 | 3-fluoro-6-chlorophenyl | H | isopropyl | |
| 1.1.1618 | 3-fluoro-6-chlorophenyl | H | cyclopropyl | |
| 1.1.1619 | 3,6-dichlorophenyl | H | methyl | [CDCl₃] 1.78 (s, 3H); 3.48 (d, 1H); 3.97 (d, 1H); 7.35 (m, 2H); 7.67 (m, 1H). |

TABLE 1.1-continued

Inventive compounds of the general formula (I) in which W* is COOH, R¹ is hydrogen, and aryl is the radical.

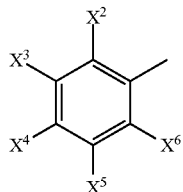

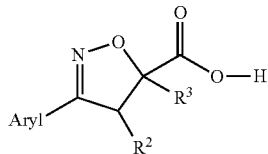

| No. | Aryl | R² | R³ | Physical data |
|---|---|---|---|---|
| 1.1.1620 | 3,6-dichlorophenyl | H | ethyl | |
| 1.1.1621 | 3,6-dichlorophenyl | H | isopropyl | |
| 1.1.1622 | 3,6-dichlorophenyl | H | cyclopropyl | |
| 1.1.1623 | 3-bromo-6-chlorophenyl | H | methyl | |
| 1.1.1624 | 3-methyl-6-chlorophenyl | H | methyl | |
| 1.1.1625 | 3-ethyl-6-chlorophenyl | H | methyl | |
| 1.1.1626 | 3-cyclopropyl-6-chlorophenyl | H | methyl | |
| 1.1.1627 | 3-vinyl-6-chlorophenyl | H | methyl | |
| 1.1.1628 | 3-ethynyl-6-chlorophenyl | H | methyl | |
| 1.1.1629 | 3-cyano-6-chlorophenyl | H | methyl | |
| 1.1.1630 | 3-trifluoromethyl-6-chlorophenyl | H | methyl | |
| 1.1.1631 | 3-methoxy-6-chlorophenyl | H | methyl | |
| 1.1.1632 | 3-ethoxy-6-chlorophenyl | H | methyl | |
| 1.1.1633 | 3-trifluoromethoxy-6-chlorophenyl | H | methyl | |
| 1.1.1634 | 3-nitro-6-chlorophenyl | H | methyl | |
| 1.1.1635 | 3-fluoro-6-bromophenyl | H | methyl | |
| 1.1.1636 | 3-chloro-6-bromophenyl | H | methyl | |
| 1.1.1637 | 3,6-dibromophenyl | H | methyl | |
| 1.1.1638 | 3-methyl-6-bromophenyl | H | methyl | |
| 1.1.1639 | 3-ethyl-6-bromophenyl | H | methyl | |
| 1.1.1640 | 3-cyclopropyl-6-bromophenyl | H | methyl | |
| 1.1.1641 | 3-vinyl-6-bromophenyl | H | methyl | |
| 1.1.1642 | 3-ethynyl-6-bromophenyl | H | methyl | |
| 1.1.1643 | 3-cyano-6-bromophenyl | H | methyl | |
| 1.1.1644 | 3-trifluoromethyl-6-bromophenyl | H | methyl | |
| 1.1.1645 | 3-methoxy-6-phenyl | H | methyl | |
| 1.1.1646 | 3-ethoxy-6-bromophenyl | H | methyl | |
| 1.1.1647 | 3-trifluoromethoxy-6-bromophenyl | H | methyl | |
| 1.1.1648 | 3-nitro-6-bromophenyl | H | methyl | |

TABLE 1.1-continued

Inventive compounds of the general formula (I) in which W* is COOH, R¹ is hydrogen, and aryl is the radical.

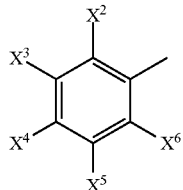

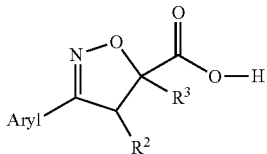

| No. | Aryl | R² | R³ | Physical data |
|---|---|---|---|---|
| 1.1.1649 | 3-fluoro-6-iodophenyl | H | methyl | |
| 1.1.1650 | 3-chloro-6-iodophenyl | H | methyl | |
| 1.1.1651 | 3-bromo-6-iodophenyl | H | methyl | |
| 1.1.1652 | 3-methyl-6-iodophenyl | H | methyl | |
| 1.1.1653 | 3-ethyl-6-iodophenyl | H | methyl | |
| 1.1.1654 | 3-cyclopropyl-6-iodophenyl | H | methyl | |
| 1.1.1655 | 3-vinyl-6-iodophenyl | H | methyl | |
| 1.1.1656 | 3-ethynyl-6-iodophenyl | H | methyl | |
| 1.1.1657 | 3-cyano-6-iodophenyl | H | methyl | |
| 1.1.1658 | 3-trifluoromethyl-6-iodophenyl | H | methyl | |
| 1.1.1659 | 3-methoxy-6-iodophenyl | H | methyl | |
| 1.1.1660 | 3-ethoxy-6-iodophenyl | H | methyl | |
| 1.1.1661 | 3-trifluoromethoxy-6-iodophenyl | H | methyl | |
| 1.1.1662 | 3-nitro-6-iodophenyl | H | methyl | |
| 1.1.1663 | 3-fluoro-6-methylphenyl | H | methyl | |
| 1.1.1664 | 3-chloro-6-methylphenyl | H | methyl | |
| 1.1.1665 | 3-bromo-6-methylphenyl | H | methyl | |
| 1.1.1666 | 3,6-dimethylphenyl | H | methyl | [DMSO] 1.56 (s, 3H); 2.28 (s, 3H); 2.40 (s, 3H); 3.38 (d, 1H); 3.80 (d, 1H); 7.15 (m, 2H); 7.25 (d, 1H). |
| 1.1.1667 | 3-ethyl-6-methylphenyl | H | methyl | |
| 1.1.1668 | 3-cyclopropyl-6-methylphenyl | H | methyl | |
| 1.1.1669 | 3-vinyl-6-methylphenyl | H | methyl | |
| 1.1.1670 | 3-ethynyl-6-methylphenyl | H | methyl | |
| 1.1.1671 | 3-cyano-6-methylphenyl | H | methyl | |
| 1.1.1672 | 3-trifluoromethyl-6-methylphenyl | H | methyl | |
| 1.1.1673 | 3-methoxy-6-methylphenyl | H | methyl | |
| 1.1.1674 | 3-ethoxy-6-methylphenyl | H | methyl | |
| 1.1.1675 | 3-trifluoromethoxy-6-methylphenyl | H | methyl | |
| 1.1.1676 | 3-nitro-6-methylphenyl | H | methyl | |
| 1.1.1677 | 3-fluoro-6-ethylphenyl | H | methyl | |

TABLE 1.1-continued

Inventive compounds of the general formula (I) in which W* is COOH, $R^1$ is hydrogen, and aryl is the radical.

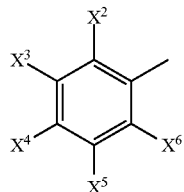

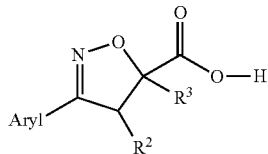

| No. | Aryl | $R^2$ | $R^3$ | Physical data |
|---|---|---|---|---|
| 1.1.1678 | 3-chloro-6-ethylphenyl | H | methyl | |
| 1.1.1679 | 3-bromo-6-ethylphenyl | H | methyl | |
| 1.1.1680 | 3-methyl-6-ethylphenyl | H | methyl | |
| 1.1.1681 | 3,6-diethylphenyl | H | methyl | |
| 1.1.1682 | 3-cyclopropyl-6-ethylphenyl | H | methyl | |
| 1.1.1683 | 3-vinyl-6-ethylphenyl | H | methyl | |
| 1.1.1684 | 3-ethynyl-6-ethylphenyl | H | methyl | |
| 1.1.1685 | 3-cyano-6-ethylphenyl | H | methyl | |
| 1.1.1686 | 3-trifluoromethyl-6-ethylphenyl | H | methyl | |
| 1.1.1687 | 3-methoxy-6-ethylphenyl | H | methyl | |
| 1.1.1688 | 3-ethoxy-6-ethylphenyl | H | methyl | |
| 1.1.1689 | 3-trifluoromethoxy-6-ethylphenyl | H | methyl | |
| 1.1.1690 | 3-nitro-6-ethylphenyl | H | methyl | |
| 1.1.1691 | 3-fluoro-6-propylphenyl | H | methyl | |
| 1.1.1692 | 3-chloro-6-propylphenyl | H | methyl | |
| 1.1.1693 | 3-bromo-6-propylphenyl | H | methyl | |
| 1.1.1694 | 3-methyl-6-propylphenyl | H | methyl | |
| 1.1.1695 | 3-methyl-6-propylphenyl | H | methyl | |
| 1.1.1696 | 3-cyclopropyl-6-propylphenyl | H | methyl | |
| 1.1.1697 | 3-vinyl-6-propylphenyl | H | methyl | |
| 1.1.1698 | 3-ethynyl-6-propylphenyl | H | methyl | |
| 1.1.1699 | 3-cyano-6-propylphenyl | H | methyl | |
| 1.1.1700 | 3-trifluoromethyl-6-propylphenyl | H | methyl | |
| 1.1.1701 | 3-methoxy-6-propylphenyl | H | methyl | |
| 1.1.1702 | 3-ethoxy-6-propylphenyl | H | methyl | |
| 1.1.1703 | 3-trifluoromethoxy-6-propylphenyl | H | methyl | |
| 1.1.1704 | 3-nitro-6-propylphenyl | H | methyl | |
| 1.1.1705 | 3-fluoro-6-isopropylphenyl | H | methyl | |
| 1.1.1706 | 3-chloro-6-isopropylphenyl | H | methyl | |

TABLE 1.1-continued

Inventive compounds of the general formula (I) in which W* is COOH, R¹ is hydrogen, and aryl is the radical.

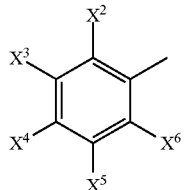

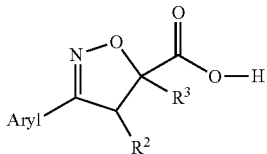

| No. | Aryl | R² | R³ | Physical data |
|---|---|---|---|---|
| 1.1.1707 | 3-bromo-6-isopropylphenyl | H | methyl | |
| 1.1.1708 | 3-methyl-6-isopropylphenyl | H | methyl | |
| 1.1.1709 | 3-ethyl-6-isopropylphenyl | H | methyl | |
| 1.1.1710 | 3-cyclopropyl-6-isopropylphenyl | H | methyl | |
| 1.1.1711 | 3-vinyl-6-isopropylphenyl | H | methyl | |
| 1.1.1712 | 3-ethynyl-6-isopropylphenyl | H | methyl | |
| 1.1.1713 | 3-cyano-6-isopropylphenyl | H | methyl | |
| 1.1.1714 | 3-trifluoromethyl-6-isopropylphenyl | H | methyl | |
| 1.1.1715 | 3-methoxy-6-isopropylphenyl | H | methyl | |
| 1.1.1716 | 3-ethoxy-6-isopropylphenyl | H | methyl | |
| 1.1.1717 | 3-trifluoromethoxy-6-isopropylphenyl | H | methyl | |
| 1.1.1718 | 3-nitro-6-isopropylphenyl | H | methyl | |
| 1.1.1719 | 3-fluoro-6-tert-butylphenyl | H | methyl | |
| 1.1.1720 | 3-chloro-6-tert-butylphenyl | H | methyl | |
| 1.1.1721 | 3-bromo-6-tert-butylphenyl | H | methyl | |
| 1.1.1722 | 3-methyl-6-tert-butylphenyl | H | methyl | |
| 1.1.1723 | 3-ethyl-6-tert-butylphenyl | H | methyl | |
| 1.1.1724 | 3-cyclopropyl-6-tert-butylphenyl | H | methyl | |
| 1.1.1725 | 3-vinyl-6-tert-butylphenyl | H | methyl | |
| 1.1.1726 | 3-ethynyl-6-tert-butylphenyl | H | methyl | |
| 1.1.1727 | 3-cyano-6-tert-butylphenyl | H | methyl | |
| 1.1.1728 | 3-trifluoromethyl-6-tert-butylphenyl | H | methyl | |
| 1.1.1729 | 3-methoxy-6-tert-butylphenyl | H | methyl | |
| 1.1.1730 | 3-ethoxy-6-tert-butylphenyl | H | methyl | |
| 1.1.1731 | 3-trifluoromethoxy-6-tert-butylphenyl | H | methyl | |
| 1.1.1732 | 3-nitro-6-tert-butylphenyl | H | methyl | |
| 1.1.1733 | 3-fluoro-6-hydroxymethylphenyl | H | methyl | |

TABLE 1.1-continued

Inventive compounds of the general formula (I) in which W* is COOH, R¹ is hydrogen, and aryl is the radical.

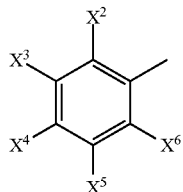

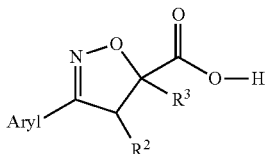

| No. | Aryl | R² | R³ | Physical data |
|---|---|---|---|---|
| 1.1.1734 | 3-chloro-6-hydroxymethylphenyl | H | methyl | |
| 1.1.1735 | 3-bromo-6-hydroxymethylphenyl | H | methyl | |
| 1.1.1736 | 3-methyl-6-hydroxymethylphenyl | H | methyl | |
| 1.1.1737 | 3-ethyl-6-hydroxymethylphenyl | H | methyl | |
| 1.1.1738 | 3-cyclopropyl-6-hydroxymethylphenyl | H | methyl | |
| 1.1.1739 | 3-vinyl-6-hydroxymethylphenyl | H | methyl | |
| 1.1.1740 | 3-ethynyl-6-hydroxymethylphenyl | H | methyl | |
| 1.1.1741 | 3-cyano-6-hydroxymethylphenyl | H | methyl | |
| 1.1.1742 | 3-trifluoromethyl-6-hydroxymethylphenyl | H | methyl | |
| 1.1.1743 | 3-methoxy-6-hydroxymethylphenyl | H | methyl | |
| 1.1.1744 | 3-ethoxy-6-hydroxymethylphenyl | H | methyl | |
| 1.1.1745 | 3-trifluoromethoxy-6-hydroxymethylphenyl | H | methyl | |
| 1.1.1746 | 3-nitro-6-hydroxymethylphenyl | H | methyl | |
| 1.1.1747 | 3-fluoro-6-cyclopropylphenyl | H | methyl | |
| 1.1.1748 | 3-chloro-6-cyclopropylphenyl | H | methyl | |
| 1.1.1749 | 3-bromo-6-cyclopropylphenyl | H | methyl | |
| 1.1.1750 | 3-methyl-6-cyclopropylphenyl | H | methyl | |
| 1.1.1751 | 3-ethyl-6-cyclopropylphenyl | H | methyl | |
| 1.1.1752 | 3-cyclopropyl-6-cyclopropylphenyl | H | methyl | |
| 1.1.1753 | 3-vinyl-6-cyclopropylphenyl | H | methyl | |
| 1.1.1754 | 3-ethynyl-6-cyclopropylphenyl | H | methyl | |
| 1.1.1755 | 3-cyano-6-cyclopropylphenyl | H | methyl | |
| 1.1.1756 | 3-trifluoromethyl-6-cyclopropylphenyl | H | methyl | |
| 1.1.1757 | 3-methoxy-6-cyclopropylphenyl | H | methyl | |
| 1.1.1758 | 3-ethoxy-6-cyclopropylphenyl | H | methyl | |
| 1.1.1759 | 3-trifluoromethoxy-6-cyclopropylphenyl | H | methyl | |

TABLE 1.1-continued

Inventive compounds of the general formula (I) in which W* is COOH, $R^1$ is hydrogen, and aryl is the radical.

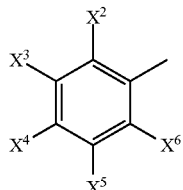

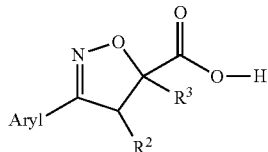

| No. | Aryl | $R^2$ | $R^3$ | Physical data |
|---|---|---|---|---|
| 1.1.1760 | 3-fluoro-6-methoxy-carbonylphenyl | H | methyl | |
| 1.1.1761 | 3-chloro-6-methoxy-carbonylphenyl | H | methyl | |
| 1.1.1762 | 3-bromo-6-methoxy-carbonylphenyl | H | methyl | |
| 1.1.1763 | 3-methyl-6-methoxy-carbonylphenyl | H | methyl | |
| 1.1.1764 | 3-ethyl-6-methoxy-carbonylphenyl | H | methyl | |
| 1.1.1765 | 3-cyclopropyl-6-methoxycarbonyl-phenyl | H | methyl | |
| 1.1.1766 | 3-vinyl-6-methoxy-carbonylphenyl | H | methyl | |
| 1.1.1767 | 3-ethynyl-6-methoxy-carbonylphenyl | H | methyl | |
| 1.1.1768 | 3-cyano-6-methoxy-carbonylphenyl | H | methyl | |
| 1.1.1769 | 3-trifluoromethyl-6-methoxycarbonyl-phenyl | H | methyl | |
| 1.1.1770 | 3-methoxy-6-methoxycarbonyl-phenyl | H | methyl | |
| 1.1.1771 | 3-ethoxy-6-methoxycarbonyl-phenyl | H | methyl | |
| 1.1.1772 | 3-trifluoromethoxy-6-methoxycarbonyl-phenyl | H | methyl | |
| 1.1.1773 | 3-nitro-6-methoxy-carbonylphenyl | H | methyl | |
| 1.1.1774 | 3-fluoro-6-vinylphenyl | H | methyl | |
| 1.1.1775 | 3-chloro-6-vinylphenyl | H | methyl | |
| 1.1.1776 | 3-bromo-6-vinylphenyl | H | methyl | |
| 1.1.1777 | 3-methyl-6-vinylphenyl | H | methyl | |
| 1.1.1778 | 3-ethyl-6-vinylphenyl | H | methyl | |
| 1.1.1779 | 3-cyclopropyl-6-vinylphenyl | H | methyl | |
| 1.1.1780 | 3,6-divinylphenyl | H | methyl | |
| 1.1.1781 | 3-ethynyl-6-vinylphenyl | H | methyl | |
| 1.1.1782 | 3-cyano-6-vinylphenyl | H | methyl | |
| 1.1.1783 | 3-trifluoromethyl-6-vinylphenyl | H | methyl | |
| 1.1.1784 | 3-methoxy-6-vinylphenyl | H | methyl | |
| 1.1.1785 | 3-ethoxy-6-vinylphenyl | H | methyl | |

TABLE 1.1-continued

Inventive compounds of the general formula (I) in which W* is COOH, $R^1$ is hydrogen, and aryl is the radical.

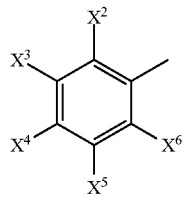

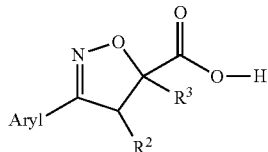

1

| No. | Aryl | $R^2$ | $R^3$ | Physical data |
|---|---|---|---|---|
| 1.1.1786 | 3-trifluoromethoxy-6-vinylphenyl | H | methyl | |
| 1.1.1787 | 3-nitro-6-vinylphenyl | H | methyl | |
| 1.1.1788 | 3-fluoro-6-ethynylphenyl | H | methyl | |
| 1.1.1789 | 3-chloro-6-ethynylphenyl | H | methyl | |
| 1.1.1790 | 3-bromo-6-ethynylphenyl | H | methyl | |
| 1.1.1791 | 3-methy-6-ethynylphenyl | H | methyl | |
| 1.1.1792 | 3-ethyl-6-ethynylphenyl | H | methyl | |
| 1.1.1793 | 3-cyclopropyl-6-ethynylphenyl | H | methyl | |
| 1.1.1794 | 3-vinyl-6-ethynylphenyl | H | methyl | |
| 1.1.1795 | 3-cyano-6-ethynylphenyl | H | methyl | |
| 1.1.1796 | 3-trifluoromethyl-6-ethynylphenyl | H | methyl | |
| 1.1.1797 | 3-methoxy-6-ethynylphenyl | H | methyl | |
| 1.1.1798 | 3-ethoxy-6-ethynylphenyl | H | methyl | |
| 1.1.1799 | 3-trifluoromethoxy-6-ethynylphenyl | H | methyl | |
| 1.1.1800 | 3-nitro-6-ethynylphenyl | H | methyl | |
| 1.1.1801 | 3-fluoro-6-ethynylphenyl | H | methyl | |
| 1.1.1802 | 3-fluoro-6-cyanophenyl | H | methyl | |
| 1.1.1803 | 3-chloro-6-cyanophenyl | H | methyl | |
| 1.1.1804 | 3-bromo-6-cyanophenyl | H | methyl | |
| 1.1.1805 | 3-methyl-6-cyanophenyl | H | methyl | |
| 1.1.1806 | 3-ethyl-6-cyanophenyl | H | methyl | |
| 1.1.1807 | 3-cyclopropyl-6-cyanophenyl | H | methyl | |
| 1.1.1808 | 3-vinyl-6-cyanophenyl | H | methyl | |
| 1.1.1809 | 3-ethynyl-6-cyanophenyl | H | methyl | |
| 1.1.1810 | 3-cyano-6-cyanophenyl | H | methyl | |
| 1.1.1811 | 3-trifluoromethyl-6-cyanophenyl | H | methyl | |
| 1.1.1812 | 3-methoxy-6-cyanophenyl | H | methyl | |
| 1.1.1813 | 3-ethoxy-6-cyanophenyl | H | methyl | |

TABLE 1.1-continued

Inventive compounds of the general formula (I) in which W* is COOH, R¹ is hydrogen, and aryl is the radical.

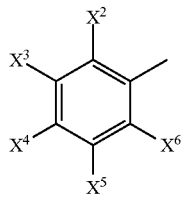

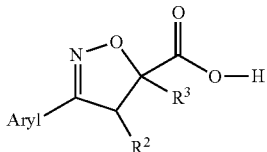

| No. | Aryl | R² | R³ | Physical data |
|---|---|---|---|---|
| 1.1.1814 | 3-trifluoromethoxy-6-cyanophenyl | H | methyl | |
| 1.1.1815 | 3-nitro-6-cyanophenyl | H | methyl | |
| 1.1.1816 | 3-fluoro-6-hydroxyphenyl | H | methyl | |
| 1.1.1817 | 3-chloro-6-hydroxyphenyl | H | methyl | |
| 1.1.1818 | 3-bromo-6-hydroxyphenyl | H | methyl | |
| 1.1.1819 | 3-methyl-6-hydroxyphenyl | H | methyl | |
| 1.1.1820 | 3-ethyl-6-hydroxyphenyl | H | methyl | |
| 1.1.1821 | 3-cyclopropyl-6-hydroxyphenyl | H | methyl | |
| 1.1.1822 | 3-vinyl-6-hydroxyphenyl | H | methyl | |
| 1.1.1823 | 3-ethynyl-6-hydroxyphenyl | H | methyl | |
| 1.1.1824 | 3-cyano-6-hydroxyphenyl | H | methyl | |
| 1.1.1825 | 3-trifluoromethyl-6-hydroxyphenyl | H | methyl | |
| 1.1.1826 | 3-methoxy-6-hydroxyphenyl | H | methyl | |
| 1.1.1827 | 3-ethoxy-6-hydroxyphenyl | H | methyl | |
| 1.1.1828 | 3-trifluoromethoxy-6-hydroxyphenyl | H | methyl | |
| 1.1.1829 | 3-nitro-6-hydroxyphenyl | H | methyl | |
| 1.1.1830 | 3-fluoro-6-methoxyphenyl | H | methyl | |
| 1.1.1831 | 3-chloro-6-methoxyphenyl | H | methyl | |
| 1.1.1832 | 3-bromo-6-methoxyphenyl | H | methyl | |
| 1.1.1833 | 3-methyl-6-methoxyphenyl | H | methyl | |
| 1.1.1834 | 3-ethyl-6-methoxyphenyl | H | methyl | |
| 1.1.1835 | 3-cyclopropyl-6-methoxyphenyl | H | methyl | |
| 1.1.1836 | 3-vinyl-6-methoxyphenyl | H | methyl | |
| 1.1.1837 | 3-ethynyl-6-methoxyphenyl | H | methyl | |
| 1.1.1838 | 3-cyano-6-methoxyphenyl | H | methyl | |
| 1.1.1839 | 3-trifluoromethyl-6-methoxyphenyl | H | methyl | |
| 1.1.1840 | 3,6-dimethoxy-phenyl | H | methyl | |

TABLE 1.1-continued

Inventive compounds of the general formula (I) in which W* is COOH, R¹ is hydrogen, and aryl is the radical.

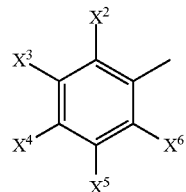

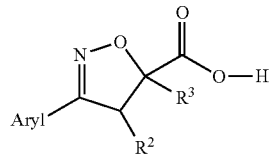

| No. | Aryl | R² | R³ | Physical data |
|---|---|---|---|---|
| 1.1.1841 | 3-ethoxy-6-methoxyphenyl | H | methyl | |
| 1.1.1842 | 3-trifluoromethoxy-6-methoxyphenyl | H | methyl | |
| 1.1.1843 | 3-nitro-6-methoxyphenyl | H | methyl | |
| 1.1.1844 | 3-fluoro-6-ethoxyphenyl | H | methyl | |
| 1.1.1845 | 3-chloro-6-ethoxyphenyl | H | methyl | |
| 1.1.1846 | 3-bromo-6-ethoxyphenyl | H | methyl | |
| 1.1.1847 | 3-methyl-6-ethoxyphenyl | H | methyl | |
| 1.1.1848 | 3-ethyl-6-ethoxyphenyl | H | methyl | |
| 1.1.1849 | 3-cyclopropyl-6-ethoxyphenyl | H | methyl | |
| 1.1.1850 | 3-vinyl-6-ethoxyphenyl | H | methyl | |
| 1.1.1851 | 3-ethynyl-6-ethoxyphenyl | H | methyl | |
| 1.1.1852 | 3-cyano-6-ethoxyphenyl | H | methyl | |
| 1.1.1853 | 3-trifluoromethyl-6-ethoxyphenyl | H | methyl | |
| 1.1.1854 | 3-methoxy-6-ethoxyphenyl | H | methyl | |
| 1.1.1855 | 2,6-diethoxyphenyl | H | methyl | |
| 1.1.1856 | 3-trifluoromethoxy-6-ethoxyphenyl | H | methyl | |
| 1.1.1857 | 3-nitro-6-ethoxyphenyl | H | methyl | |
| 1.1.1858 | 3-fluoro-6-propoxyphenyl | H | methyl | |
| 1.1.1859 | 3-chloro-6-propoxyphenyl | H | methyl | |
| 1.1.1860 | 3-bromo-6-propoxyphenyl | H | methyl | |
| 1.1.1861 | 3-methyl-6-propoxyphenyl | H | methyl | |
| 1.1.1862 | 3-ethyl-6-propoxyphenyl | H | methyl | |
| 1.1.1863 | 3-cyclopropyl-6-propoxyphenyl | H | methyl | |
| 1.1.1864 | 3-vinyl-6-propoxyphenyl | H | methyl | |
| 1.1.1865 | 3-ethynyl-6-propoxyphenyl | H | methyl | |
| 1.1.1866 | 3-cyano-6-propoxyphenyl | H | methyl | |
| 1.1.1867 | 3-trifluoromethyl-6-propoxyphenyl | H | methyl | |
| 1.1.1868 | 3-methoxy-6-propoxyphenyl | H | methyl | |

TABLE 1.1-continued

Inventive compounds of the general formula (I) in which W* is COOH, $R^1$ is hydrogen, and aryl is the radical.

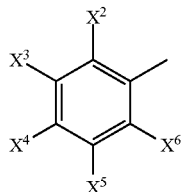

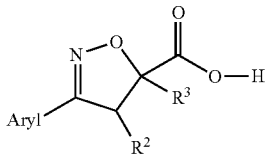

| No. | Aryl | $R^2$ | $R^3$ | Physical data |
|---|---|---|---|---|
| 1.1.1869 | 3-ethoxy-6-propoxyphenyl | H | methyl | |
| 1.1.1870 | 3-trifluoromethoxy-6-propoxyphenyl | H | methyl | |
| 1.1.1871 | 3-nitro-6-propoxyphenyl | H | methyl | |
| 1.1.1872 | 3-fluoro-6-isopropoxyphenyl | H | methyl | |
| 1.1.1873 | 3-chloro-6-isopropoxyphenyl | H | methyl | |
| 1.1.1874 | 3-bromo-6-isopropoxyphenyl | H | methyl | |
| 1.1.1875 | 3-methyl-6-isopropoxyphenyl | H | methyl | |
| 1.1.1876 | 3-ethyl-6-isopropoxyphenyl | H | methyl | |
| 1.1.1877 | 3-cyclopropyl-6-isopropoxyphenyl | H | methyl | |
| 1.1.1878 | 3-vinyl-6-isopropoxyphenyl | H | methyl | |
| 1.1.1879 | 3-ethynyl-6-isopropoxyphenyl | H | methyl | |
| 1.1.1880 | 3-cyano-6-isopropoxyphenyl | H | methyl | |
| 1.1.1881 | 3-trifluoromethyl-6-isopropoxyphenyl | H | methyl | |
| 1.1.1882 | 3-methoxy-6-isopropoxyphenyl | H | methyl | |
| 1.1.1883 | 3-ethoxy-6-isopropoxyphenyl | H | methyl | |
| 1.1.1884 | 3-trifluoromethoxy-6-isopropoxyphenyl | H | methyl | |
| 1.1.1885 | 3-nitro-6-isopropoxyphenyl | H | methyl | |
| 1.1.1886 | 3-fluoro-6-tert-butoxyphenyl | H | methyl | |
| 1.1.1887 | 3-chloro-6-tert-butoxyphenyl | H | methyl | |
| 1.1.1888 | 3-bromo-6-tert-butoxyphenyl | H | methyl | |
| 1.1.1889 | 3-methyl-6-tert-butoxyphenyl | H | methyl | |
| 1.1.1890 | 3-ethyl-6-tert-butoxyphenyl | H | methyl | |
| 1.1.1891 | 3-cyclopropyl-6-tert-butoxyphenyl | H | methyl | |
| 1.1.1892 | 3-vinyl-6-tert-butoxyphenyl | H | methyl | |
| 1.1.1893 | 3-ethynyl-6-tert-butoxyphenyl | H | methyl | |
| 1.1.1894 | 3-cyano-6-tert-butoxyphenyl | H | methyl | |
| 1.1.1895 | 3-trifluoromethyl-6-tert-butoxyphenyl | H | methyl | |

TABLE 1.1-continued

Inventive compounds of the general formula (I) in which W* is COOH, R¹ is hydrogen, and aryl is the radical.

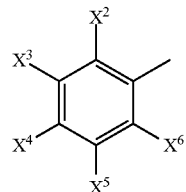

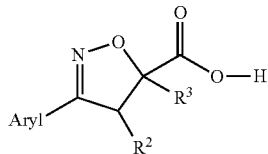

| No. | Aryl | R² | R³ | Physical data |
|---|---|---|---|---|
| 1.1.1896 | 3-methoxy-6-tert-butoxyphenyl | H | methyl | |
| 1.1.1897 | 3-ethoxy-6-tert-butoxyphenyl | H | methyl | |
| 1.1.1898 | 3-trifluoromethoxy-6-tert-butoxyphenyl | H | methyl | |
| 1.1.1899 | 3-nitro-6-tert-butoxyphenyl | H | methyl | |
| 1.1.1900 | 3-fluoro-6-trifluoromethoxyphenyl | H | methyl | |
| 1.1.1901 | 3-chloro-6-trifluoromethoxyphenyl | H | methyl | |
| 1.1.1902 | 3-bromo-6-trifluoromethoxyphenyl | H | methyl | |
| 1.1.1903 | 3-methyl-6-trifluoromethoxyphenyl | H | methyl | |
| 1.1.1904 | 3-ethyl-6-trifluoromethoxyphenyl | H | methyl | |
| 1.1.1905 | 3-cyclopropyl-6-trifluoromethoxyphenyl | H | methyl | |
| 1.1.1906 | 3-vinyl-6-trifluoromethoxyphenyl | H | methyl | |
| 1.1.1907 | 3-ethynyl-6-trifluoromethoxyphenyl | H | methyl | |
| 1.1.1908 | 3-cyano-6-trifluoromethoxyphenyl | H | methyl | |
| 1.1.1909 | 3-trifluoromethyl-6-trifluoromethoxyphenyl | H | methyl | |
| 1.1.1910 | 3-methoxy-6-trifluoromethoxyphenyl | H | methyl | |
| 1.1.1911 | 3-ethoxy-6-trifluoromethoxyphenyl | H | methyl | |
| 1.1.1912 | 3,6-bis(trifluoromethoxy)phenyl | H | methyl | |
| 1.1.1913 | 3-nitro-6-trifluoromethoxyphenyl | H | methyl | |
| 1.1.1914 | 3-fluoro-6-(2,2,2-trifluoroethoxy)-phenyl | H | methyl | |
| 1.1.1915 | 3-chloro-6-(2,2,2-trifluoroethoxy)-phenyl | H | methyl | |
| 1.1.1916 | 3-bromo-6-(2,2,2-trifluoroethoxy)-phenyl | H | methyl | |
| 1.1.1917 | 3-methyl-6-(2,2,2-trifluoroethoxy)-phenyl | H | methyl | |
| 1.1.1918 | 3-ethyl-6-(2,2,2-trifluoroethoxy)-phenyl | H | methyl | |

TABLE 1.1-continued

Inventive compounds of the general formula (I) in which W* is COOH, R¹ is hydrogen, and aryl is the radical.

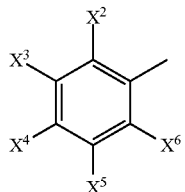

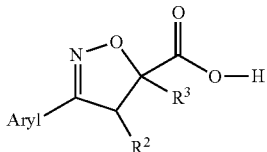

| No. | Aryl | R² | R³ | Physical data |
|---|---|---|---|---|
| 1.1.1919 | 3-cyclopropyl-6-(2,2,2-trifluoro-ethoxy)phenyl | H | methyl | |
| 1.1.1920 | 3-vinyl-6-(2,2,2-trifluoroethoxy)-phenyl | H | methyl | |
| 1.1.1921 | 3-ethynyl-6-(2,2,2-trifluoroethoxyphenyl | H | methyl | |
| 1.1.1922 | 3-cyano-6-(2,2,2-trifluoroethoxy)-phenyl | H | methyl | |
| 1.1.1923 | 3-trifluoromethyl-6-(2,2,2-trifluoro-ethoxy)phenyl | H | methyl | |
| 1.1.1924 | 3-methoxy-6-(2,2,2-trifluoroethoxy)-phenyl | H | methyl | |
| 1.1.1925 | 3-ethoxy-6-(2,2,2-trifluoroethoxy)-phenyl | H | methyl | |
| 1.1.1926 | 3-trifluoromethoxy-6-(2,2,2-trifluoro-ethoxy)phenyl | H | methyl | |
| 1.1.1927 | 3-nitro-6-(2,2,2-trifluoroethoxy)-phenyl | H | methyl | |
| 1.1.1928 | 3-fluoro-6-difluoro-methoxyphenyl | H | methyl | |
| 1.1.1929 | 3-chloro-6-difluoro-methoxyphenyl | H | methyl | |
| 1.1.1930 | 3-bromo-6-difluoro-methoxyphenyl | H | methyl | |
| 1.1.1931 | 3-methyl-6-difluoro-methoxyphenyl | H | methyl | |
| 1.1.1932 | 3-ethyl-6-difluoro-methoxyphenyl | H | methyl | |
| 1.1.1933 | 3-cyclopropyl-6-difluoromethoxy-phenyl | H | methyl | |
| 1.1.1934 | 3-vinyl-6-difluoro-methoxyphenyl | H | methyl | |
| 1.1.1935 | 3-ethynyl-6-difluoro-methoxyphenyl | H | methyl | |
| 1.1.1936 | 3-cyano-6-difluoro-methoxyphenyl | H | methyl | |
| 1.1.1937 | 3-trifluoromethyl-6-difluoromethoxy-phenyl | H | methyl | |
| 1.1.1938 | 3-methoxy-6-difluoro-methoxyphenyl | H | methyl | |
| 1.1.1939 | 3-ethoxy-6-difluoro-methoxyphenyl | H | methyl | |
| 1.1.1940 | 3-trifluoromethoxy-6-difluoromethoxy-phenyl | H | methyl | |

TABLE 1.1-continued

Inventive compounds of the general formula (I) in which W* is COOH, $R^1$ is hydrogen, and aryl is the radical.

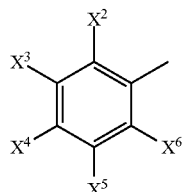

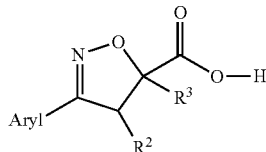

| No. | Aryl | $R^2$ | $R^3$ | Physical data |
|---|---|---|---|---|
| 1.1.1941 | 3-nitro-6-difluoro-methoxyphenyl | H | methyl | |
| 1.1.1942 | 3-fluoro-6-(2-methoxyethoxy)-phenyl | H | methyl | |
| 1.1.1943 | 3-chloro-6-(2-methoxyethoxy)-phenyl | H | methyl | |
| 1.1.1944 | 3-bromo-6-(2-methoxyethoxy)-phenyl | H | methyl | |
| 1.1.1945 | 3-methyl-6-(2-methoxyethoxy)-phenyl | H | methyl | |
| 1.1.1946 | 3-ethyl-6-(2-methoxyethoxy)-phenyl | H | methyl | |
| 1.1.1947 | 3-cyclopropyl-6-(2-methoxyethoxy)-phenyl | H | methyl | |
| 1.1.1948 | 3-vinyl-6-(2-methoxyethoxy)-phenyl | H | methyl | |
| 1.1.1949 | 3-ethynyl-6-(2-methoxyethoxy)-phenyl | H | methyl | |
| 1.1.1950 | 3-cyano-6-(2-methoxyethoxy)-phenyl | H | methyl | |
| 1.1.1951 | 3-trifluoromethyl-6-(2-methoxyethoxy)-phenyl | H | methyl | |
| 1.1.1952 | 3-methoxy-6-(2-methoxyethoxy)-phenyl | H | methyl | |
| 1.1.1953 | 3-ethoxy-6-(2-methoxyethoxy)-phenyl | H | methyl | |
| 1.1.1954 | 3-trifluoromethoxy-(2-methoxyethoxy)-phenyl | H | methyl | |
| 1.1.1955 | 3-nitro-6-(2-methoxyethoxy)-phenyl | H | methyl | |
| 1.1.1956 | 3-fluoro-6-(tert-butoxycarbonyloxy)-phenyl | H | methyl | |
| 1.1.1957 | 3-chloro-6-(tert-butoxycarbonyloxy)-phenyl | H | methyl | |
| 1.1.1958 | 3-bromo-6-(tert-butoxycarbonyloxy)-phenyl | H | methyl | |

TABLE 1.1-continued

Inventive compounds of the general formula (I) in which W* is COOH, $R^1$ is hydrogen, and aryl is the radical.

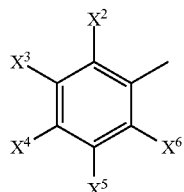

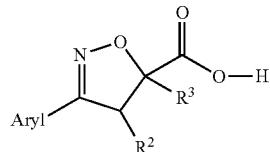

| No. | Aryl | $R^2$ | $R^3$ | Physical data |
|---|---|---|---|---|
| 1.1.1959 | 3-methyl-6-(tert-butoxycarbonyloxy)-phenyl | H | methyl | |
| 1.1.1960 | 3-ethyl-6-(tert-butoxycarbonyloxy)-phenyl | H | methyl | |
| 1.1.1961 | 3-cyclopropyl-6-(tert-butoxycarbonyloxy)-phenyl | H | methyl | |
| 1.1.1962 | 3-vinyl-6-(tert-butoxycarbonyloxy)-phenyl | H | methyl | |
| 1.1.1963 | 3-ethynyl-6-(tert-butoxycarbonyloxy)-phenyl | H | methyl | |
| 1.1.1964 | 3-cyano-6-(tert-butoxycarbonyloxy)-phenyl | H | methyl | |
| 1.1.1965 | 3-trifluoromethyl-6-(tert-butoxycarbonyloxy)-phenyl | H | methyl | |
| 1.1.1966 | 3-methoxy-6-(tert-butoxycarbonyloxy)-phenyl | H | methyl | |
| 1.1.1967 | 3-ethoxy-6-(tert-butoxycarbonyloxy)-phenyl | H | methyl | |
| 1.1.1968 | 3-trifluoromethoxy-6-(tert-butoxycarbonyloxy)phenyl | H | methyl | |
| 1.1.1969 | 2-nitro-6-(tert-butoxycarbonyloxy)-phenyl | H | methyl | |
| 1.1.1970 | 3-fluoro-6-nitrophenyl | H | methyl | |
| 1.1.1971 | 3-chloro-6-nitrophenyl | H | methyl | |
| 1.1.1972 | 3-bromo-6-nitrophenyl | H | methyl | |
| 1.1.1973 | 3-methyl-6-nitrophenyl | H | methyl | |
| 1.1.1974 | 3-ethyl-6-nitrophenyl | H | methyl | |
| 1.1.1975 | 3-cyclopropyl-6-nitrophenyl | H | methyl | |
| 1.1.1976 | 3-vinyl-6-nitrophenyl | H | methyl | |
| 1.1.1977 | 3-ethynyl-6-nitrophenyl | H | methyl | |
| 1.1.1978 | 3-cyano-6-nitrophenyl | H | methyl | |
| 1.1.1979 | 3-trifluoromethyl-6-nitrophenyl | H | methyl | |
| 1.1.1980 | 3-methoxy-6-nitrophenyl | H | methyl | |
| 1.1.1981 | 3-ethoxy-6-nitrophenyl | H | methyl | |

TABLE 1.1-continued

Inventive compounds of the general formula (I) in which W* is COOH, $R^1$ is hydrogen, and aryl is the radical.

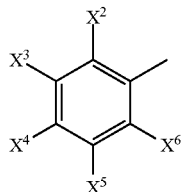

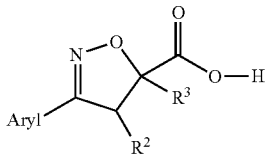

| No. | Aryl | $R^2$ | $R^3$ | Physical data |
|---|---|---|---|---|
| 1.1.1982 | 3-trifluoromethoxy-6-nitrophenyl | H | methyl | |
| 1.1.1983 | 3-fluoro-6-methylsulfanylphenyl | H | methyl | |
| 1.1.1984 | 3-chloro-6-methylsulfanylphenyl | H | methyl | |
| 1.1.1985 | 3-bromo-6-methylsulfanylphenyl | H | methyl | |
| 1.1.1986 | 3-methyl-6-methylsulfanylphenyl | H | methyl | |
| 1.1.1987 | 3-ethyl-6-methylsulfanylphenyl | H | methyl | |
| 1.1.1988 | 3-cyclopropyl-6-methylsulfanylphenyl | H | methyl | |
| 1.1.1989 | 3-vinyl-6-methylsulfanylphenyl | H | methyl | |
| 1.1.1990 | 3-ethynyl-6-methylsulfanylphenyl | H | methyl | |
| 1.1.1991 | 3-cyano-6-methylsulfanylphenyl | H | methyl | |
| 1.1.1992 | 3-trifluoromethyl-6-methylsulfanylphenyl | H | methyl | |
| 1.1.1993 | 3-methoxy-6-methylsulfanylphenyl | H | methyl | |
| 1.1.1994 | 3-ethoxy-6-methylsulfanylphenyl | H | methyl | |
| 1.1.1995 | 3-trifluoromethoxy-6-methylsulfanylphenyl | H | methyl | |
| 1.1.1996 | 3-nitro-6-methylsulfanylphenyl | H | methyl | |
| 1.1.1997 | 2,3,4-trifluorophenyl | H | methyl | [CDCl$_3$] 1.78 (s, 3H); 3.35 (dd, 1H); 3.90 (dd, 1H); 7.03 (m, 1H); 7.60 (m, 1H). |
| 1.1.1998 | 2,3,4-trichlorophenyl | H | methyl | |
| 1.1.1999 | 2,3,4-trimethylphenyl | H | methyl | |
| 1.1.2000 | 2-fluoro-2-chloro-5-trifluoromethylphenyl | H | methyl | |
| 1.1.2001 | 2,3,5-trifluorophenyl | H | methyl | [DMSO] 1.58 (s, 3H); 3.41 (d, 1H); 3.71 (d, 1H); 7.41 (m, 1H); 7.71 (m, 1H). |
| 1.1.2002 | 2,3,5-trichlorophenyl | H | methyl | |
| 1.1.2003 | 2,3,5-trimethylphenyl | H | methyl | |
| 1.1.2004 | 2,3-dichloro-5-methoxyphenyl | H | methyl | [CDCl$_3$] 1.7.(s, 3H); 3,5 (d, 1H); 3.7 (s, 3H); 3,95 (d, 1H); 7.02-7.13 (m, 2H). |
| 1.1.2005 | 2,3,6-trifluorophenyl | H | methyl | |
| 1.1.2006 | 2,3,6-trichlorophenyl | H | methyl | [CDCl$_3$] 1.85 (s, 3H); 3.26 (d, 1H); 3.78 (d, 1H); 7.33 (d, 1H); 7.49 (d, 1H). |
| 1.1.2007 | 2,3,6-trimethylphenyl | H | methyl | |
| 1.1.2008 | 3,4,5-trifluorophenyl | H | methyl | [CDCl$_3$] 1.80 (s, 3H); 3.22 (d, 1H); 3.80 (d, 1H); 7.30 (m, 2H). |
| 1.1.2009 | 3,4,5-trichlorophenyl | H | methyl | [CDCl$_3$] 1.80 (s, 3H); 3.25 (d, 1H); 3.85 (d, 1H); 7.65 (, 2H). |

TABLE 1.1-continued

Inventive compounds of the general formula (I) in which W* is COOH, R¹ is hydrogen, and aryl is the radical.

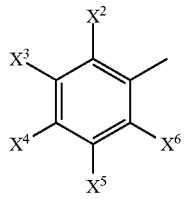

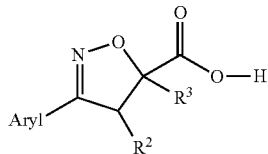

| No. | Aryl | R² | R³ | Physical data |
|---|---|---|---|---|
| 1.1.2010 | 3,4,5-trimethylphenyl | H | methyl | |
| 1.1.2011 | 3,5-dimethyl-4-fluorophenyl | H | methyl | |
| 1.1.2012 | 3,5-dichloro-4-methoxyphenyl | H | methyl | [CDCl₃] 1.81 (s, 3H); 3.25 (d, 1H); 3.82 (d, 1H); 3.95 (s, 3H); 7.60 (s, 2H). |
| 1.1.2013 | 3,5-difluoro-4-chlorophenyl | H | methyl | [CDCl₃] 1.81 (s, 3H); 3.24 (d, 1H); 3.83 (d, 1H); 7.27 (m, 3H). |
| 1.1.2014 | 3,5-dichloro-4-hydroxyphenyl | H | methyl | [CDCl₃] 1.79 (s, 3H); 3.25 (d, 1H); 3.80 (d, 1H); 7.59 (s, 2H). |
| 1.1.2015 | 3,5-trifluoromethyl-4-chlorophenyl | H | methyl | |
| 1.1.2016 | 3,4,6-trifluorophenyl | H | methyl | |
| 1.1.2017 | 3,4,6-trichlorophenyl | H | methyl | |
| 1.1.2018 | 3,4,6-trimethylphenyl | H | methyl | |
| 1.1.2019 | pentafluorophenyl | H | methyl | [CDCl₃] 1.80 (s, 3H); 3.34 (d, 1H); 3.9 (d, 1H). |

TABLE 1.2

Inventive compounds of the general formula (I) in which W* is COOH, R¹ and R² are each hydrogen, and aryl is the radical.

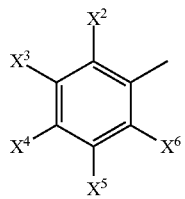

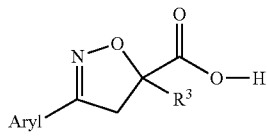

| No. | Aryl | R³ | Physical data |
|---|---|---|---|
| 1.2.1 | 3-fluorophenyl | fluoromethyl | [CDCl₃] 3.56 (d,1H); 3.80 (d,1H); 4.71 (d,1H); 4.83 (d,1H); 7.18 (m,1H); 7.41 (m,3H). |
| 1.2.2 | 3-fluorophenyl | chloromethyl | [CDCl₃] 3.62 (d,1H); 3.90 (m,2H); 4.03 (d,1H); 7.17 (m,1H); 7.41 (m,3H). |
| 1.2.3 | 3-fluorophenyl | bromomethyl | |
| 1.2.4 | 3-fluorophenyl | difluoromethyl | |
| 1.2.5 | 3-fluorophenyl | trifluoromethyl | |
| 1.2.6 | 3-fluorophenyl | cyano | |

TABLE 1.2-continued

Inventive compounds of the general formula (I) in which W* is COOH, $R^1$ and $R^2$ are each hydrogen, and aryl is the radical.

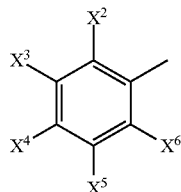

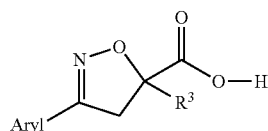

| No. | Aryl | $R^3$ | Physical data |
|---|---|---|---|
| 1.2.7 | 3-chlorophenyl | fluoromethyl | |
| 1.2.8 | 3-chlorophenyl | chloromethyl | |
| 1.2.9 | 3-chlorophenyl | bromomethyl | |
| 1.2.10 | 3-chlorophenyl | difluoromethyl | |
| 1.2.11 | 3-chlorophenyl | trifluoromethyl | |
| 1.2.12 | 3-chlorophenyl | cyano | |
| 1.2.13 | 3-bromophenyl | fluoromethyl | |
| 1.2.14 | 3-bromophenyl | chloromethyl | |
| 1.2.15 | 3-iodophenyl | fluoromethyl | |
| 1.2.16 | 3-iodophenyl | chloromethyl | |
| 1.2.17 | 3-methylphenyl | fluoromethyl | |
| 1.2.18 | 3-methylphenyl | chloromethyl | |
| 1.2.19 | 3-ethylphenyl | fluoromethyl | |
| 1.2.20 | 3-propylphenyl | fluoromethyl | |
| 1.2.21 | 3-isopropylphenyl | fluoromethyl | |
| 1.2.22 | 3-n-butylphenyl | fluoromethyl | |
| 1.2.23 | 3-i-butylphenyl | fluoromethyl | |
| 1.2.24 | 3-tert-butylphenyl | fluoromethyl | |
| 1.2.25 | 3-cyclopropylphenyl | fluoromethyl | |
| 1.2.26 | 3-cyclobutylphenyl | fluoromethyl | |
| 1.2.27 | 3-cyclopentylphenyl | fluoromethyl | |
| 1.2.28 | 3-vinylphenyl | fluoromethyl | |
| 1.2.29 | 3-ethynylphenyl | fluoromethyl | |
| 1.2.30 | 3-cyanophenyl | fluoromethyl | |
| 1.2.31 | 3-trifluoromethylphenyl | fluoromethyl | |
| 1.2.32 | 3-difluoromethylphenyl | fluoromethyl | |
| 1.2.33 | 3-(hydroxycarbonyl)phenyl | fluoromethyl | |
| 1.2.34 | 3-(methoxycarbonyl)phenyl | fluoromethyl | |
| 1.2.35 | 3-(ethoxycarbonyl)phenyl | fluoromethyl | |
| 1.2.36 | 3-hydroxymethylphenyl | fluoromethyl | |
| 1.2.37 | 3-carbamoylphenyl | fluoromethyl | |
| 1.2.38 | 3-hydroxyphenyl | fluoromethyl | |
| 1.2.39 | 3-methoxyphenyl | fluoromethyl | |
| 1.2.40 | 3-ethoxyphenyl | fluoromethyl | |
| 1.2.41 | 3-propyloxyphenyl | fluoromethyl | |
| 1.2.42 | 3-isopropyloxyphenyl | fluoromethyl | |
| 1.2.43 | 3-n-butyloxyphenyl | fluoromethyl | |
| 1.2.44 | 3-i-butyloxyphenyl | fluoromethyl | |
| 1.2.45 | 3-t-butyloxyphenyl | fluoromethyl | |
| 1.2.46 | 3-difluoromethoxyphenyl | fluoromethyl | |
| 1.2.47 | 3-trifluoromethoxyphenyl | fluoromethyl | |
| 1.2.48 | 3-(2,2,2-trifluoroethoxy)-phenyl | fluoromethyl | |
| 1.2.49 | 3-(2-chloroethoxy)-phenyl | fluoromethyl | |
| 1.2.50 | 3-(2-hydroxyethoxy)-phenyl | fluoromethyl | |
| 1.2.51 | 3-(2-methoxyethoxy)-phenyl | fluoromethyl | |
| 1.2.52 | 3-[(tert-butoxycarbonyl)oxy]phenyl | fluoromethyl | |
| 1.2.53 | 3-nitrophenyl | fluoromethyl | |
| 1.2.54 | 3-acetoxyphenyl | fluoromethyl | |
| 1.2.55 | {3-[(tert-butoxycarbonyl)amino]phenyl} | fluoromethyl | |
| 1.2.56 | 3-methylsulfanylphenyl | fluoromethyl | |
| 1.2.57 | 3-ethylsulfanylphenyl | fluoromethyl | |
| 1.2.58 | 3-(pentafluoro-lambda$^6$-sulfanyl)-phenyl | fluoromethyl | |
| 1.2.59 | 2,3-difluorophenyl | fluoromethyl | |
| 1.2.60 | 2,3-difluorophenyl | chloromethyl | |
| 1.2.61 | 2,3-difluorophenyl | bromomethyl | |

TABLE 1.2-continued

Inventive compounds of the general formula (I) in which W* is COOH, $R^1$ and $R^2$ are each hydrogen, and aryl is the radical.

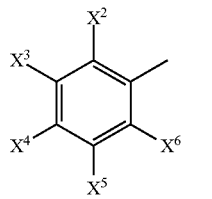

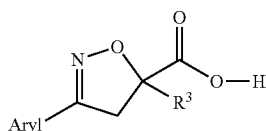

| No. | Aryl | $R^3$ | Physical data |
|---|---|---|---|
| 1.2.62 | 2,3-difluorophenyl | difluoromethyl | |
| 1.2.63 | 2,3-difluorophenyl | trifluoromethyl | |
| 1.2.64 | 2,3-difluorophenyl | cyano | |
| 1.2.65 | 2-chloro-3-fluorophenyl | fluoromethyl | |
| 1.2.66 | 2-bromo-3-fluorophenyl | fluoromethyl | |
| 1.2.67 | 2-methyl-3-fluorophenyl | fluoromethyl | |
| 1.2.68 | 2-ethyl-3-fluorophenyl | fluoromethyl | |
| 1.2.69 | 2-cyclopropyl-3-fluorophenyl | fluoromethyl | |
| 1.2.70 | 2-vinyl-3-fluorophenyl | fluoromethyl | |
| 1.2.71 | 2-ethynyl-3-fluorophenyl | fluoromethyl | |
| 1.2.72 | 2-cyano-3-fluorophenyl | fluoromethyl | |
| 1.2.73 | 2-methoxy-3-fluorophenyl | fluoromethyl | |
| 1.2.74 | 2-ethoxy-3-fluorophenyl | fluoromethyl | |
| 1.2.75 | 2-trifluoromethoxy-3-fluorophenyl | fluoromethyl | |
| 1.2.76 | 2-nitro-3-fluorophenyl | fluoromethyl | |
| 1.2.77 | 2-fluoro-3-chlorophenyl | fluoromethyl | |
| 1.2.78 | 2,3-dichlorophenyl | fluoromethyl | |
| 1.2.79 | 2,3-dichlorophenyl | chloromethyl | |
| 1.2.80 | 2,3-dichlorophenyl | bromomethyl | |
| 1.2.81 | 2,3-dichlorophenyl | difluoromethyl | |
| 1.2.82 | 2-bromo-3-chlorophenyl | fluoromethyl | |
| 1.2.83 | 2-methyl-3-chlorophenyl | fluoromethyl | |
| 1.2.84 | 2-ethyl-3-chlorophenyl | fluoromethyl | |
| 1.2.85 | 2-cyclopropyl-3-chlorophenyl | fluoromethyl | |
| 1.2.86 | 2-vinyl-3-chlorophenyl | fluoromethyl | |
| 1.2.87 | 2-ethynyl-3-chlorophenyl | fluoromethyl | |
| 1.2.88 | 2-cyano-3-chlorophenyl | fluoromethyl | |
| 1.2.89 | 2-trifluoromethyl-2-chlorophenyl | fluoromethyl | |
| 1.2.90 | 2-methoxy-3-chlorophenyl | fluoromethyl | |
| 1.2.91 | 2-ethoxy-3-chlorophenyl | fluoromethyl | |
| 1.2.92 | 2-trifluoromethoxy-3-chlorophenyl | fluoromethyl | |
| 1.2.93 | 2-nitro-3-chlorophenyl | fluoromethyl | |
| 1.2.94 | 2-fluoro-3-bromophenyl | fluoromethyl | |
| 1.2.95 | 2-chloro-3-bromophenyl | fluoromethyl | |
| 1.2.96 | 2,3-dibromophenyl | fluoromethyl | |
| 1.2.97 | 2-methyl-3-bromophenyl | fluoromethyl | |
| 1.2.98 | 2-ethyl-3-bromophenyl | fluoromethyl | |
| 1.2.99 | 2-cyclopropyl-3-bromophenyl | fluoromethyl | |
| 1.2.100 | 2-vinyl-3-bromophenyl | fluoromethyl | |
| 1.2.101 | 2-ethynyl-3-bromophenyl | fluoromethyl | |
| 1.2.102 | 2-cyano-3-bromophenyl | fluoromethyl | |
| 1.2.103 | 2-trifluoromethyl-3-bromophenyl | fluoromethyl | |
| 1.2.104 | 2-methoxy-3-phenyl | fluoromethyl | |
| 1.2.105 | 2-ethoxy-3-bromophenyl | fluoromethyl | |
| 1.2.106 | 2-trifluoromethoxy-3-bromophenyl | fluoromethyl | |
| 1.2.107 | 2-nitro-3-bromophenyl | fluoromethyl | |
| 1.2.108 | 2-fluoro-3-iodophenyl | fluoromethyl | |
| 1.2.109 | 2-chloro-3-iodophenyl | fluoromethyl | |
| 1.2.110 | 2-bromo-3-iodophenyl | fluoromethyl | |
| 1.2.111 | 2-methyl-3-iodophenyl | fluoromethyl | |
| 1.2.112 | 2-ethyl-3-iodophenyl | fluoromethyl | |
| 1.2.113 | 2-cyclopropyl-3-iodophenyl | fluoromethyl | |
| 1.2.114 | 2-vinyl-3-iodophenyl | fluoromethyl | |
| 1.2.115 | 2-ethynyl-3-iodophenyl | fluoromethyl | |
| 1.2.116 | 2-cyano-3-iodophenyl | fluoromethyl | |
| 1.2.117 | 2-trifluoromethyl-3-iodophenyl | fluoromethyl | |
| 1.2.118 | 2-methoxy-3-iodophenyl | fluoromethyl | |

TABLE 1.2-continued

Inventive compounds of the general formula (I) in which W* is COOH, $R^1$ and $R^2$ are each hydrogen, and aryl is the radical.

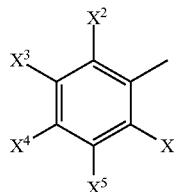

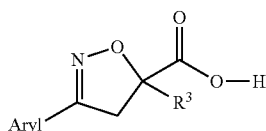

| No. | Aryl | $R^3$ | Physical data |
|---|---|---|---|
| 1.2.119 | 2-ethoxy-3-iodophenyl | fluoromethyl | |
| 1.2.120 | 2-trifluoromethoxy-3-iodophenyl | fluoromethyl | |
| 1.2.121 | 2-nitro-3-iodophenyl | fluoromethyl | |
| 1.2.122 | 2-fluoro-3-methylphenyl | fluoromethyl | |
| 1.2.123 | 2-fluoro-3-methylphenyl | chloromethyl | |
| 1.2.124 | 2-fluoro-3-methylphenyl | bromomethyl | |
| 1.2.125 | 2-fluoro-3-methylphenyl | difluoromethyl | |
| 1.2.126 | 2-chloro-3-methylphenyl | fluoromethyl | |
| 1.2.127 | 2-chloro-3-methylphenyl | chloromethyl | |
| 1.2.128 | 2-chloro-3-methylphenyl | bromomethyl | |
| 1.2.129 | 2-chloro-3-methylphenyl | difluoromethyl | |
| 1.2.130 | 2-bromo-3-methylphenyl | fluoromethyl | |
| 1.2.131 | 2,3-dimethylphenyl | fluoromethyl | |
| 1.2.132 | 2,3-dimethylphenyl | chloromethyl | |
| 1.2.133 | 2,3-dimethylphenyl | bromomethyl | |
| 1.2.134 | 2,3-dimethylphenyl | difluoromethyl | |
| 1.2.135 | 2-ethyl-3-methylphenyl | fluoromethyl | |
| 1.2.136 | 2-cyclopropyl-3-methylphenyl | fluoromethyl | |
| 1.2.137 | 2-vinyl-3-methylphenyl | fluoromethyl | |
| 1.2.138 | 2-ethynyl-3-methylphenyl | fluoromethyl | |
| 1.2.139 | 2-cyano-3-methylphenyl | fluoromethyl | |
| 1.2.140 | 2-trifluoromethyl-3-methylphenyl | fluoromethyl | |
| 1.2.141 | 2-methoxy-3-methylphenyl | fluoromethyl | |
| 1.2.142 | 2-ethoxy-3-methylphenyl | fluoromethyl | |
| 1.2.143 | 2-trifluoromethoxy-3-methylphenyl | fluoromethyl | |
| 1.2.144 | 2-nitro-3-methylphenyl | fluoromethyl | |
| 1.2.145 | 2-fluoro-3-ethylphenyl | fluoromethyl | |
| 1.2.146 | 2-chloro-3-ethylphenyl | fluoromethyl | |
| 1.2.147 | 2-bromo-3-ethylphenyl | fluoromethyl | |
| 1.2.148 | 2-methyl-3-ethylphenyl | fluoromethyl | |
| 1.2.149 | 2,3-diethylphenyl | fluoromethyl | |
| 1.2.150 | 2-cyclopropyl-3-ethylphenyl | fluoromethyl | |
| 1.2.151 | 2-vinyl-3-ethylphenyl | fluoromethyl | |
| 1.2.152 | 2-ethynyl-3-ethylphenyl | fluoromethyl | |
| 1.2.153 | 2-cyano-3-ethylphenyl | fluoromethyl | |
| 1.2.154 | 2-trifluoromethyl-3-ethylphenyl | fluoromethyl | |
| 1.2.155 | 2-methoxy-3-ethylphenyl | fluoromethyl | |
| 1.2.156 | 2-ethoxy-3-ethylphenyl | fluoromethyl | |
| 1.2.157 | 2-trifluoromethoxy-3-ethylphenyl | fluoromethyl | |
| 1.2.158 | 2-nitro-3-ethylphenyl | fluoromethyl | |
| 1.2.159 | 2-fluoro-3-propylphenyl | fluoromethyl | |
| 1.2.160 | 2-chloro-3-propylphenyl | fluoromethyl | |
| 1.2.161 | 2-bromo-3-propylphenyl | fluoromethyl | |
| 1.2.162 | 2-methyl-3-propylphenyl | fluoromethyl | |
| 1.2.163 | 2-methyl-3-propylphenyl | fluoromethyl | |
| 1.2.164 | 2-cyclopropyl-3-propylphenyl | fluoromethyl | |
| 1.2.165 | 2-vinyl-3-propylphenyl | fluoromethyl | |
| 1.2.166 | 2-ethynyl-3propylphenyl | fluoromethyl | |
| 1.2.167 | 2-cyano-3-propylphenyl | fluoromethyl | |
| 1.2.168 | 2-trifluoromethyl-3-propylphenyl | fluoromethyl | |
| 1.2.169 | 2-methoxy-3-propylphenyl | fluoromethyl | |
| 1.2.170 | 2-ethoxy-3-propylphenyl | fluoromethyl | |
| 1.2.171 | 2-trifluoromethoxy-3-propylphenyl | fluoromethyl | |
| 1.2.172 | 2-nitro-3-propylphenyl | fluoromethyl | |
| 1.2.173 | 2-fluoro-3-isopropylphenyl | fluoromethyl | |
| 1.2.174 | 2-chloro-3-isopropylphenyl | fluoromethyl | |
| 1.2.175 | 2-bromo-3-isopropylphenyl | fluoromethyl | |

TABLE 1.2-continued

Inventive compounds of the general formula (I) in which W* is COOH, $R^1$ and $R^2$ are each hydrogen, and aryl is the radical.

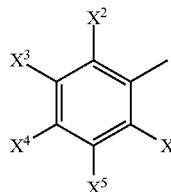

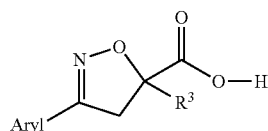

| No. | Aryl | $R^3$ | Physical data |
|---|---|---|---|
| 1.2.176 | 2-methyl-3-isopropylphenyl | fluoromethyl | |
| 1.2.177 | 2-ethyl-3-isopropylphenyl | fluoromethyl | |
| 1.2.178 | 2-cyclopropyl-3-isopropylphenyl | fluoromethyl | |
| 1.2.179 | 2-vinyl-3-isopropylphenyl | fluoromethyl | |
| 1.2.180 | 2-ethynyl-3-isopropylphenyl | fluoromethyl | |
| 1.2.181 | 2-cyano-3-isopropylphenyl | fluoromethyl | |
| 1.2.182 | 2-trifluoromethyl-3-isopropylphenyl | fluoromethyl | |
| 1.2.183 | 2-methoxy-3-isopropylphenyl | fluoromethyl | |
| 1.2.184 | 2-ethoxy-3-isopropylphenyl | fluoromethyl | |
| 1.2.185 | 2-trifluoromethoxy-3-isopropylphenyl | fluoromethyl | |
| 1.2.186 | 2-nitro-3-isopropylphenyl | fluoromethyl | |
| 1.2.187 | 2-fluoro-3-tert-butylphenyl | fluoromethyl | |
| 1.2.188 | 2-chloro-3-tert-butylphenyl | fluoromethyl | |
| 1.2.189 | 2-bromo-3-tert-butylphenyl | fluoromethyl | |
| 1.2.190 | 2-methyl-3-tert-butylphenyl | fluoromethyl | |
| 1.2.191 | 2-ethyl-3-tert-butylphenyl | fluoromethyl | |
| 1.2.192 | 2-cyclopropyl-3-tert-butylphenyl | fluoromethyl | |
| 1.2.193 | 2-vinyl-3-tert-butylphenyl | fluoromethyl | |
| 1.2.194 | 2-ethynyl-3-tert-butylphenyl | fluoromethyl | |
| 1.2.195 | 2-cyano-3-tert-butylphenyl | fluoromethyl | |
| 1.2.196 | 2-trifluoromethyl-3-tert-butylphenyl | fluoromethyl | |
| 1.2.197 | 2-methoxy-3-tert-butylphenyl | fluoromethyl | |
| 1.2.198 | 2-ethoxy-3-tert-butylphenyl | fluoromethyl | |
| 1.2.199 | 2-trifluoromethoxy-3-tert-butylphenyl | fluoromethyl | |
| 1.2.200 | 2-nitro-3-tert-butylphenyl | fluoromethyl | |
| 1.2.201 | 2-fluoro-3-hydroxymethylphenyl | fluoromethyl | |
| 1.2.202 | 2-chloro-3-hydroxymethylphenyl | fluoromethyl | |
| 1.2.203 | 2-bromo-3-hydroxymethylphenyl | fluoromethyl | |
| 1.2.204 | 2-methyl-3-hydroxymethylphenyl | fluoromethyl | |
| 1.2.205 | 2-ethyl-3-hydroxymethylphenyl | fluoromethyl | |
| 1.2.206 | 2-cyclopropyl-3-hydroxymethylphenyl | fluoromethyl | |
| 1.2.207 | 2-vinyl-3-hydroxymethylphenyl | fluoromethyl | |
| 1.2.208 | 2-ethynyl-3-hydroxymethylphenyl | fluoromethyl | |
| 1.2.209 | 2-cyano-3-hydroxymethylphenyl | fluoromethyl | |
| 1.2.210 | 2-trifluoromethyl-3-hydroxymethylphenyl | fluoromethyl | |
| 1.2.211 | 2-methoxy-3-hydroxymethylphenyl | fluoromethyl | |
| 1.2.212 | 2-ethoxy-3-hydroxymethylphenyl | fluoromethyl | |
| 1.2.213 | 2-trifluoromethoxy-3-hydroxymethylphenyl | fluoromethyl | |
| 1.2.214 | 2-nitro-3-hydroxymethylphenyl | fluoromethyl | |
| 1.2.215 | 2-fluoro-3-cyclopropylphenyl | fluoromethyl | |
| 1.2.216 | 2-chloro-3-cyclopropylphenyl | fluoromethyl | |
| 1.2.217 | 2-bromo-3-cyclopropylphenyl | fluoromethyl | |
| 1.2.218 | 2-methyl-3-cyclopropylphenyl | fluoromethyl | |
| 1.2.219 | 2-ethyl-3-cyclopropylphenyl | fluoromethyl | |
| 1.2.220 | 2-cyclopropyl-3-cyclopropylphenyl | fluoromethyl | |
| 1.2.221 | 2-vinyl-3-cyclopropylphenyl | fluoromethyl | |
| 1.2.222 | 2-ethynyl-3-cyclopropylphenyl | fluoromethyl | |
| 1.2.223 | 2-cyano-3-cyclopropylphenyl | fluoromethyl | |
| 1.2.224 | 2-trifluoromethyl-3-cyclopropylphenyl | fluoromethyl | |
| 1.2.225 | 2-methoxy-3-cyclopropylphenyl | fluoromethyl | |
| 1.2.226 | 2-ethoxy-3-cyclopropylphenyl | fluoromethyl | |

TABLE 1.2-continued

Inventive compounds of the general formula (I) in which W* is COOH, $R^1$ and $R^2$ are each hydrogen, and aryl is the radical.

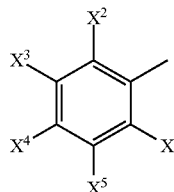

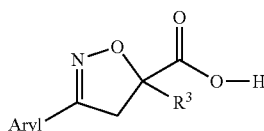

| No. | Aryl | $R^3$ | Physical data |
|---|---|---|---|
| 1.2.227 | 2-trifluoromethoxy-3-cyclopropylphenyl | fluoromethyl | |
| 1.2.228 | 2-fluoro-3-methoxycarbonylphenyl | fluoromethyl | |
| 1.2.229 | 2-chloro-3-methoxycarbonylphenyl | fluoromethyl | |
| 1.2.230 | 2-bromo-3-methoxycarbonylphenyl | fluoromethyl | |
| 1.2.231 | 2-methyl-3-methoxycarbonylphenyl | fluoromethyl | |
| 1.2.232 | 2-ethyl-3-methoxycarbonylphenyl | fluoromethyl | |
| 1.2.233 | 2-cyclopropyl-3-methoxycarbonylphenyl | fluoromethyl | |
| 1.2.234 | 2-vinyl-3-methoxycarbonylphenyl | fluoromethyl | |
| 1.2.235 | 2-ethynyl-3-methoxycarbonylphenyl | fluoromethyl | |
| 1.2.236 | 2-cyano-3-methoxycarbonylphenyl | fluoromethyl | |
| 1.2.237 | 2-trifluoromethyl-3-methoxycarbonylphenyl | fluoromethyl | |
| 1.2.238 | 2-methoxy-3-methoxycarbonylphenyl | fluoromethyl | |
| 1.2.239 | 2-ethoxy-3-methoxycarbonylphenyl | fluoromethyl | |
| 1.2.240 | 2-trifluoromethoxy-3-methoxycarbonylphenyl | fluoromethyl | |
| 1.2.241 | 2-nitro-3-methoxycarbonylphenyl | fluoromethyl | |
| 1.2.242 | 2-fluoro-3-vinylphenyl | fluoromethyl | |
| 1.2.243 | 2-chloro-3-vinylphenyl | fluoromethyl | |
| 1.2.244 | 2-bromo-3-vinylphenyl | fluoromethyl | |
| 1.2.245 | 2-methyl-3-vinylphenyl | fluoromethyl | |
| 1.2.246 | 2-ethyl-3-vinylphenyl | fluoromethyl | |
| 1.2.247 | 2-cyclopropyl-3-vinylphenyl | fluoromethyl | |
| 1.2.248 | 2-vinyl-3-vinylphenyl | fluoromethyl | |
| 1.2.249 | 2-ethynyl-3-vinylphenyl | fluoromethyl | |
| 1.2.250 | 2-cyano-3-vinylphenyl | fluoromethyl | |
| 1.2.251 | 2-trifluoromethyl-3-vinylphenyl | fluoromethyl | |
| 1.2.252 | 2-methoxy-3-vinylphenyl | fluoromethyl | |
| 1.2.253 | 2-ethoxy-3-vinylphenyl | fluoromethyl | |
| 1.2.254 | 2-trifluoromethoxy-3-vinylphenyl | fluoromethyl | |
| 1.2.255 | 2-nitro-3-vinylphenyl | fluoromethyl | |
| 1.2.256 | 2-fluoro-3-ethynylphenyl | fluoromethyl | |
| 1.2.257 | 2-chloro-3-ethynylphenyl | fluoromethyl | |
| 1.2.258 | 2-bromo-3-ethynylphenyl | fluoromethyl | |
| 1.2.259 | 2-methyl-3-ethynylphenyl | fluoromethyl | |
| 1.2.260 | 2-ethyl-3-ethynylphenyl | fluoromethyl | |
| 1.2.261 | 2-cyclopropyl-3-ethynylphenyl | fluoromethyl | |
| 1.2.262 | 2-vinyl-3-ethynylphenyl | fluoromethyl | |
| 1.2.263 | 2-cyano-3-ethynylphenyl | fluoromethyl | |
| 1.2.264 | 2-trifluoromethyl-3-ethynylphenyl | fluoromethyl | |
| 1.2.265 | 2-methoxy-3-ethynylphenyl | fluoromethyl | |
| 1.2.266 | 2-ethoxy-3-ethynylphenyl | fluoromethyl | |
| 1.2.267 | 2-trifluoromethoxy-3-ethynylphenyl | fluoromethyl | |
| 1.2.268 | 2-nitro-3-ethynylphenyl | fluoromethyl | |
| 1.2.269 | 2-fluoro-3-ethynylphenyl | fluoromethyl | |
| 1.2.270 | 2-fluoro-3-cyanophenyl | fluoromethyl | |
| 1.2.271 | 2-chloro-3-cyanophenyl | fluoromethyl | |
| 1.2.272 | 2-bromo-3-cyanophenyl | fluoromethyl | |
| 1.2.273 | 2-methyl-3-cyanophenyl | fluoromethyl | |
| 1.2.274 | 2-ethyl-3-cyanophenyl | fluoromethyl | |
| 1.2.275 | 2-ethyl-3-cyanophenyl | chloromethyl | |
| 1.2.276 | 2-ethyl-3-cyanophenyl | bromomethyl | |
| 1.2.277 | 2-ethyl-3-cyanophenyl | difluoromethyl | |

TABLE 1.2-continued

Inventive compounds of the general formula (I) in which W* is COOH, R¹ and R² are each hydrogen, and aryl is the radical.

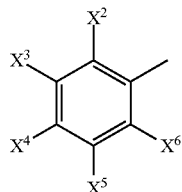

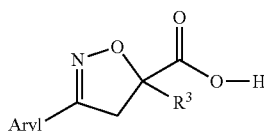

| No. | Aryl | R³ | Physical data |
|---|---|---|---|
| 1.2.278 | 2-cyclopropyl-3-cyanophenyl | fluoromethyl | |
| 1.2.279 | 2-vinyl-3-cyanophenyl | fluoromethyl | |
| 1.2.280 | 2-ethynyl-3-cyanophenyl | fluoromethyl | |
| 1.2.281 | 2-cyano-3-cyanophenyl | fluoromethyl | |
| 1.2.282 | 2-trifluoromethyl-3-cyanophenyl | fluoromethyl | |
| 1.2.283 | 2-methoxy-3-cyanophenyl | fluoromethyl | |
| 1.2.284 | 2-ethoxy-3-cyanophenyl | fluoromethyl | |
| 1.2.285 | 2-trifluoromethoxy-3-cyanophenyl | fluoromethyl | |
| 1.2.286 | 2-nitro-3-cyanophenyl | fluoromethyl | |
| 1.2.287 | 2-fluoro-3-hydroxyphenyl | fluoromethyl | |
| 1.2.288 | 2-chloro-3-hydroxyphenyl | fluoromethyl | |
| 1.2.289 | 2-bromo-3-hydroxyphenyl | fluoromethyl | |
| 1.2.290 | 2-methyl-3-hydroxyphenyl | fluoromethyl | |
| 1.2.291 | 2-ethyl-3-hydroxyphenyl | fluoromethyl | |
| 1.2.292 | 2-cyclopropyl-3-hydroxyphenyl | fluoromethyl | |
| 1.2.293 | 2-vinyl-3-hydroxyphenyl | fluoromethyl | |
| 1.2.294 | 2-ethynyl-3-hydroxyphenyl | fluoromethyl | |
| 1.2.295 | 2-cyano-3-hydroxyphenyl | fluoromethyl | |
| 1.2.296 | 2-trifluoromethyl-3-hydroxyphenyl | fluoromethyl | |
| 1.2.297 | 2-methoxy-3-hydroxyphenyl | fluoromethyl | |
| 1.2.298 | 2-ethoxy-3-hydroxyphenyl | fluoromethyl | |
| 1.2.299 | 2-trifluoromethoxy-3-hydroxyphenyl | fluoromethyl | |
| 1.2.300 | 2-nitro-3-hydroxyphenyl | fluoromethyl | |
| 1.2.301 | 2-fluoro-3-methoxyphenyl | fluoromethyl | |
| 1.2.302 | 2-chloro-3-methoxyphenyl | fluoromethyl | |
| 1.2.303 | 2-bromo-3-methoxyphenyl | fluoromethyl | |
| 1.2.304 | 2-methyl-3-methoxyphenyl | fluoromethyl | |
| 1.2.305 | 2-ethyl-3-methoxyphenyl | fluoromethyl | |
| 1.2.306 | 2-cyclopropyl-3-methoxyphenyl | fluoromethyl | |
| 1.2.307 | 2-vinyl-3-methoxyphenyl | fluoromethyl | |
| 1.2.308 | 2-ethynyl-3-methoxyphenyl | fluoromethyl | |
| 1.2.309 | 2-cyano-3-methoxyphenyl | fluoromethyl | |
| 1.2.310 | 2-trifluoromethyl-3-methoxyphenyl | fluoromethyl | |
| 1.2.311 | 2,3-dimethoxy--phenyl | fluoromethyl | |
| 1.2.312 | 2-ethoxy-3-methoxyphenyl | fluoromethyl | |
| 1.2.313 | 2-trifluoromethoxy-3-methoxyphenyl | fluoromethyl | |
| 1.2.314 | 2-nitro-3-methoxyphenyl | fluoromethyl | |
| 1.2.315 | 2-fluoro-3-ethoxyphenyl | fluoromethyl | |
| 1.2.316 | 2-chloro-3-ethoxyphenyl | fluoromethyl | |
| 1.2.317 | 2-bromo-3-ethoxyphenyl | fluoromethyl | |
| 1.2.318 | 2-methyl-3-ethoxyphenyl | fluoromethyl | |
| 1.2.319 | 2-ethyl-3-ethoxyphenyl | fluoromethyl | |
| 1.2.320 | 2-cyclopropyl-3-ethoxyphenyl | fluoromethyl | |
| 1.2.321 | 2-vinyl-3-ethoxyphenyl | fluoromethyl | |
| 1.2.322 | 2-ethynyl-3-ethoxyphenyl | fluoromethyl | |
| 1.2.323 | 2-cyano-3-ethoxyphenyl | fluoromethyl | |
| 1.2.324 | 2-trifluoromethyl-3-ethoxyphenyl | fluoromethyl | |
| 1.2.325 | 2-methoxy-3-ethoxyphenyl | fluoromethyl | |
| 1.2.326 | 2,3-diethoxy--phenyl | fluoromethyl | |
| 1.2.327 | 2-trifluoromethoxy-3-ethoxyphenyl | fluoromethyl | |
| 1.2.328 | 2-nitro-3-ethoxyphenyl | fluoromethyl | |
| 1.2.329 | 2-fluoro-3-propoxyphenyl | fluoromethyl | |
| 1.2.330 | 2-chloro-3-propoxyphenyl | fluoromethyl | |
| 1.2.331 | 2-bromo-3-propoxyphenyl | fluoromethyl | |
| 1.2.332 | 2-methyl-3-propoxyphenyl | fluoromethyl | |
| 1.2.333 | 2-ethyl-3-propoxyphenyl | fluoromethyl | |

TABLE 1.2-continued

Inventive compounds of the general formula (I) in which W* is COOH, $R^1$ and $R^2$ are each hydrogen, and aryl is the radical.

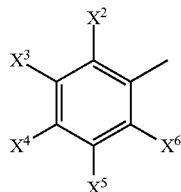

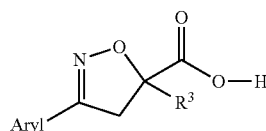

| No. | Aryl | $R^3$ | Physical data |
|---|---|---|---|
| 1.2.334 | 2-cyclopropyl-3-propoxyphenyl | fluoromethyl | |
| 1.2.335 | 2-vinyl-3-propoxyphenyl | fluoromethyl | |
| 1.2.336 | 2-ethynyl-3-propoxyphenyl | fluoromethyl | |
| 1.2.337 | 2-cyano-3-propoxyphenyl | fluoromethyl | |
| 1.2.338 | 2-trifluoromethyl-3-propoxyphenyl | fluoromethyl | |
| 1.2.339 | 2-methoxy-3-propoxyphenyl | fluoromethyl | |
| 1.2.340 | 2-ethoxy-3-propoxyphenyl | fluoromethyl | |
| 1.2.341 | 2-trifluoromethoxy-3-propoxyphenyl | fluoromethyl | |
| 1.2.342 | 2-nitro-3-propoxyphenyl | fluoromethyl | |
| 1.2.343 | 2-fluoro-3-isopropoxyphenyl | fluoromethyl | |
| 1.2.344 | 2-chloro-3-isopropoxyphenyl | fluoromethyl | |
| 1.2.345 | 2-bromo-3-isopropoxyphenyl | fluoromethyl | |
| 1.2.346 | 2-methyl-3-isopropoxyphenyl | fluoromethyl | |
| 1.2.347 | 2-ethyl-3-isopropoxyphenyl | fluoromethyl | |
| 1.2.348 | 2-cyclopropyl-3-isopropoxyphenyl | fluoromethyl | |
| 1.2.349 | 2-vinyl-3-isopropoxyphenyl | fluoromethyl | |
| 1.2.350 | 2-ethynyl-3-isopropoxyphenyl | fluoromethyl | |
| 1.2.351 | 2-cyano-3-isopropoxyphenyl | fluoromethyl | |
| 1.2.352 | 2-trifluoromethyl-3-isopropoxyphenyl | fluoromethyl | |
| 1.2.353 | 2-methoxy-3-isopropoxyphenyl | fluoromethyl | |
| 1.2.354 | 2-ethoxy-3-isopropoxyphenyl | fluoromethyl | |
| 1.2.355 | 2-trifluoromethoxy-3-isopropoxyphenyl | fluoromethyl | |
| 1.2.356 | 2-nitro-3-isopropoxyphenyl | fluoromethyl | |
| 1.2.357 | 2-fluoro-3-tert-butoxyphenyl | fluoromethyl | |
| 1.2.358 | 2-chloro-3-tert-butoxyphenyl | fluoromethyl | |
| 1.2.359 | 2-bromo-3-tert-butoxyphenyl | fluoromethyl | |
| 1.2.360 | 2-methyl-3-tert-butoxyphenyl | fluoromethyl | |
| 1.2.361 | 2-ethyl-3-tert-butoxyphenyl | fluoromethyl | |
| 1.2.362 | 2-cyclopropyl-3-tert-butoxyphenyl | fluoromethyl | |
| 1.2.363 | 2-vinyl-3-tert-butoxyphenyl | fluoromethyl | |
| 1.2.364 | 2-ethynyl-3-tert-butoxyphenyl | fluoromethyl | |
| 1.2.365 | 2-cyano-3-tert-butoxyphenyl | fluoromethyl | |
| 1.2.366 | 2-trifluoromethyl-3-tert-butoxyphenyl | fluoromethyl | |
| 1.2.367 | 2-methoxy-3-tert-butoxyphenyl | fluoromethyl | |
| 1.2.368 | 2-ethoxy-3-tert-butoxyphenyl | fluoromethyl | |
| 1.2.369 | 2-trifluoromethoxy-3-tert-butoxyphenyl | fluoromethyl | |
| 1.2.370 | 2-nitro-3-tert-butoxyphenyl | fluoromethyl | |
| 1.2.371 | 2-fluoro-3-trifluoromethoxyphenyl | fluoromethyl | |
| 1.2.372 | 2-chloro-3-trifluoromethoxyphenyl | fluoromethyl | |
| 1.2.373 | 2-bromo-3-trifluoromethoxyphenyl | fluoromethyl | |
| 1.2.374 | 2-methyl-3-trifluoromethoxyphenyl | fluoromethyl | |
| 1.2.375 | 2-ethyl-3-trifluoromethoxyphenyl | fluoromethyl | |
| 1.2.376 | 2-cyclopropyl-3-trifluoromethoxyphenyl | fluoromethyl | |
| 1.2.377 | 2-vinyl-3-trifluoromethoxyphenyl | fluoromethyl | |
| 1.2.378 | 2-ethynyl-3-trifluoromethoxyphenyl | fluoromethyl | |
| 1.2.379 | 2-cyano-3-trifluoromethoxyphenyl | fluoromethyl | |
| 1.2.380 | 2-trifluoromethyl-3-trifluoromethoxyphenyl | fluoromethyl | |
| 1.2.381 | 2-methoxy-3-trifluoromethoxyphenyl | fluoromethyl | |
| 1.2.382 | 2-ethoxy-3-trifluoromethoxyphenyl | fluoromethyl | |
| 1.2.383 | 2,3-bis(trifluoromethoxy)phenyl | fluoromethyl | |

TABLE 1.2-continued

Inventive compounds of the general formula (I) in which W* is COOH, $R^1$ and $R^2$ are each hydrogen, and aryl is the radical.

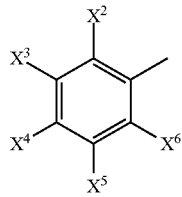

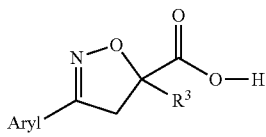

| No. | Aryl | $R^3$ | Physical data |
|---|---|---|---|
| 1.2.384 | 2-nitro-3-trifluoromethoxyphenyl | fluoromethyl | |
| 1.2.385 | 2-fluoro-3-(2,2,2-trifluoroethoxy)-phenyl | fluoromethyl | |
| 1.2.386 | 2-chloro-3-(2,2,2-trifluoroethoxy)-phenyl | fluoromethyl | |
| 1.2.387 | 2-bromo-3-(2,2,2-trifluoroethoxy)-phenyl | fluoromethyl | |
| 1.2.388 | 2-methyl-3-(2,2,2-trifluoroethoxy)-phenyl | fluoromethyl | |
| 1.2.389 | 2-ethyl-3-(2,2,2(2,2,2-trifluoroethoxy)-phenyl | fluoromethyl | |
| 1.2.390 | 2-cyclopropyl-3-(2,2,2-trifluoro-ethoxy)phenyl | fluoromethyl | |
| 1.2.391 | 2-vinyl-3-(2,2,2-trifluoroethoxy)-phenyl | fluoromethyl | |
| 1.2.392 | 2-ethynyl-3-(2,2,2-trifluoroethoxyphenyl | fluoromethyl | |
| 1.2.393 | 2-cyano-3-(2,2,2-trifluoroethoxy)-phenyl | fluoromethyl | |
| 1.2.394 | 2-trifluoromethyl-3-(2,2,2-trifluoro-ethoxy)phenyl | fluoromethyl | |
| 1.2.395 | 2-methoxy-3-(2,2,2-trifluoroethoxy)-phenyl | fluoromethyl | |
| 1.2.396 | 2-ethoxy-3-(2,2,2-trifluoroethoxy)-phenyl | fluoromethyl | |
| 1.2.397 | 2-trifluoromethoxy-3-(2,2,2-trifluoro-ethoxy)phenyl | fluoromethyl | |
| 1.2.398 | 2-nitro-3-(2,2,2-trifluoroethoxy)-phenyl | fluoromethyl | |
| 1.2.399 | 2-fluoro-3-difluoromethoxyphenyl | fluoromethyl | |
| 1.2.400 | 2-chloro-3-difluoromethoxyphenyl | fluoromethyl | |
| 1.2.401 | 2-bromo-3-difluoromethoxyphenyl | fluoromethyl | |
| 1.2.402 | 2-methyl-3-difluoromethoxyphenyl | fluoromethyl | |
| 1.2.403 | 2-ethyl-3-difluoromethoxyphenyl | fluoromethyl | |
| 1.2.404 | 2-cyclopropyl-3-difluoromethoxy-phenyl | fluoromethyl | |
| 1.2.405 | 2-vinyl-3-difluoromethoxyphenyl | fluoromethyl | |
| 1.2.406 | 2-ethynyl-3-difluoromethoxyphenyl | fluoromethyl | |
| 1.2.407 | 2-cyano-3-difluoromethoxyphenyl | fluoromethyl | |
| 1.2.408 | 2-trifluoromethyl-3-difluoromethoxy-phenyl | fluoromethyl | |
| 1.2.409 | 2-methoxy-3-difluoromethoxy-phenyl | fluoromethyl | |
| 1.2.410 | 2-ethoxy-3-difluoromethoxyphenyl | fluoromethyl | |
| 1.2.411 | 2-trifluoromethoxy-3-difluoromethoxyphenyl | fluoromethyl | |
| 1.2.412 | 2-nitro-3-difluoromethoxyphenyl | fluoromethyl | |
| 1.2.413 | 2-fluoro-3-(2-methoxyethoxy)-phenyl | fluoromethyl | |
| 1.2.414 | 2-chloro-3-(2-methoxyethoxy)-phenyl | fluoromethyl | |
| 1.2.415 | 2-bromo-3-(2-methoxyethoxy)-phenyl | fluoromethyl | |
| 1.2.416 | 2-methyl-3-(2-methoxyethoxy)-phenyl | fluoromethyl | |
| 1.2.417 | 2-ethyl-3-(2-methoxyethoxy)phenyl | fluoromethyl | |

TABLE 1.2-continued

Inventive compounds of the general formula (I) in which W* is COOH, $R^1$ and $R^2$ are each hydrogen, and aryl is the radical.

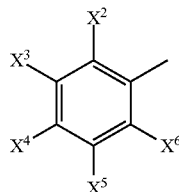

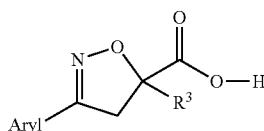

| No. | Aryl | $R^3$ | Physical data |
|---|---|---|---|
| 1.2.418 | 2-cyclopropyl-3-(2-methoxyethoxy)-phenyl | fluoromethyl | |
| 1.2.419 | 2-vinyl-3-(2-methoxyethoxy)phenyl | fluoromethyl | |
| 1.2.420 | 2-ethynyl-3-(2-methoxyethoxy)-phenyl | fluoromethyl | |
| 1.2.421 | 2-cyano-3-(2-methoxyethoxy)-phenyl | fluoromethyl | |
| 1.2.422 | 2-trifluoromethyl-3-(2-methoxyethoxy)-phenyl | fluoromethyl | |
| 1.2.423 | 2-methoxy-3-(2-methoxyethoxy)-phenyl | fluoromethyl | |
| 1.2.424 | 2-ethoxy-3-(2-methoxyethoxy)-phenyl | fluoromethyl | |
| 1.2.425 | 2-trifluoromethoxy-(2-methoxyethoxy)-phenyl | fluoromethyl | |
| 1.2.426 | 2-nitro-3-(2-methoxyethoxy)phenyl | fluoromethyl | |
| 1.2.427 | 2-fluoro-3-(tert-butoxycarbonyloxy)-phenyl | fluoromethyl | |
| 1.2.428 | 2-chloro-3-(tert-butoxycarbonyloxy)-phenyl | fluoromethyl | |
| 1.2.429 | 2-bromo-3-(tert-butoxycarbonyl-oxy)phenyl | fluoromethyl | |
| 1.2.430 | 2-methyl-3-(tert-butoxycarbonyl-oxy)phenyl | fluoromethyl | |
| 1.2.431 | 2-ethyl-3-(tert-butoxycarbonyloxy)-phenyl | fluoromethyl | |
| 1.2.432 | 2-cyclopropyl-3-(tert-butoxy-carbonyloxy)phenyl | fluoromethyl | |
| 1.2.433 | 2-vinyl-3-(tert-butoxycarbonyloxy)-phenyl | fluoromethyl | |
| 1.2.434 | 2-ethynyl-3-(tert-butoxycarbonyl-oxy)phenyl | fluoromethyl | |
| 1.2.435 | 2-cyano-3-(tert-butoxycarbonyloxy)-phenyl | fluoromethyl | |
| 1.2.436 | 2-trifluoromethyl-3-(tert-butoxy-carbonyloxy)phenyl | fluoromethyl | |
| 1.2.437 | 2-methoxy-3-(tert-butoxycarbonyl-oxy)phenyl | fluoromethyl | |
| 1.2.438 | 2-ethoxy-3-(tert-butoxycarbonyl-oxy)phenyl | fluoromethyl | |
| 1.2.439 | 2-trifluoromethoxy-3-(tert-butoxycarbonyl-oxy)phenyl | fluoromethyl | |
| 1.2.440 | 2-nitro-3-(tert-butoxycarbonyloxy)-phenyl | fluoromethyl | |
| 1.2.441 | 2-fluoro-3-nitrophenyl | fluoromethyl | |
| 1.2.442 | 2-chloro-3-nitrophenyl | fluoromethyl | |
| 1.2.443 | 2-bromo-3-nitrophenyl | fluoromethyl | |
| 1.2.444 | 2-methyl-3-nitrophenyl | fluoromethyl | |
| 1.2.445 | 2-ethyl-3-nitrophenyl | fluoromethyl | |
| 1.2.446 | 2-cyclopropyl-3-nitrophenyl | fluoromethyl | |
| 1.2.447 | 2-vinyl-3-nitrophenyl | fluoromethyl | |
| 1.2.448 | 2-ethynyl-3-nitrophenyl | fluoromethyl | |
| 1.2.449 | 2-cyano-3-nitrophenyl | fluoromethyl | |
| 1.2.450 | 2-trifluoromethyl-3-nitrophenyl | fluoromethyl | |
| 1.2.451 | 2-methoxy-3-nitrophenyl | fluoromethyl | |
| 1.2.452 | 2-ethoxy-3-nitrophenyl | fluoromethyl | |
| 1.2.453 | 2-trifluoromethoxy-3-nitrophenyl | fluoromethyl | |
| 1.2.454 | 2-fluoro-3-methylsulfanylphenyl | fluoromethyl | |

TABLE 1.2-continued

Inventive compounds of the general formula (I) in which W* is COOH, $R^1$ and $R^2$ are each hydrogen, and aryl is the radical.

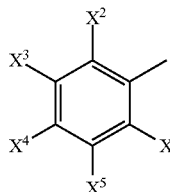

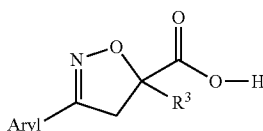

| No. | Aryl | $R^3$ | Physical data |
|---|---|---|---|
| 1.2.455 | 2-chloro-3-methylsulfanylphenyl | fluoromethyl | |
| 1.2.456 | 2-bromo-3-methylsulfanylphenyl | fluoromethyl | |
| 1.2.457 | 2-methyl-3-methylsulfanylphenyl | fluoromethyl | |
| 1.2.458 | 2-ethyl-3-methylsulfanylphenyl | fluoromethyl | |
| 1.2.459 | 2-cyclopropyl-3-methylsulfanylphenyl | fluoromethyl | |
| 1.2.460 | 2-vinyl-3-methylsulfanylphenyl | fluoromethyl | |
| 1.2.461 | 2-ethynyl-3-methylsulfanylphenyl | fluoromethyl | |
| 1.2.462 | 2-cyano-3-methylsulfanylphenyl | fluoromethyl | |
| 1.2.463 | 2-trifluoromethyl-3-methylsulfanylphenyl | fluoromethyl | |
| 1.2.464 | 2-methoxy-3-methylsulfanylphenyl | fluoromethyl | |
| 1.2.465 | 2-ethoxy-3-methylsulfanylphenyl | fluoromethyl | |
| 1.2.466 | 2-trifluoromethoxy-3-methylsulfanylphenyl | fluoromethyl | |
| 1.2.467 | 2-nitro-3-methylsulfanylphenyl | fluoromethyl | |
| 1.2.468 | 3,5-difluorophenyl | fluoromethyl | [CDCl3] 3.56 (d,1H); 3.80 (d,1H); 4.72 (s, 1H); 4.84 (s,1H); 6.0 (s br, 1H); 6.92 (t,1H); 7.19 (d,2H). |
| 1.2.469 | 3,5-difluorophenyl | chloromethyl | [CDCl$_3$] 3.57 (d,1H); 3.88 ( s,1H), 3.92 (d, 1H); 4.03 (d,1H), 6.93 (t,1H); 7.21 (d,2H). |
| 1.2.470 | 3,5-difluorophenyl | bromomethyl | [CDCl$_3$] 3.56 (d,1H); 3.71 (d,1H); 3.91 (d,1H); 3.96 (d,1H); 6.91 (t,1H); 7.18 (d,2H). |
| 1.2.471 | 3,5-difluorophenyl | difluoromethyl | [CDCl$_3$] 3.69 (d,1H); 3.91 (d,1H); 6.10-6.40 (s,1H); 6.92 (m,1H); 7.22 (m,2H). |
| 1.2.472 | 3,5-difluorophenyl | trifluoromethyl | |
| 1.2.473 | 3,5-difluorophenyl | 1,1-dichloroethyl | [CDCl$_3$] 2.40 (s,3H); 3.93 (d,1H, 4.00 (d,1H); 6.94 (t,1H) 7.21 (d,2H). |
| 1.2.474 | 3,5-difluorophenyl | CN | [CDCl$_3$] 3.97 (d,1H); 4.14 (d,1H); 6.97 (m,1H); 7.21 (m,2H). |
| 1.2.475 | 3-chloro-5-fluorophenyl | fluoromethyl | |
| 1.2.476 | 3-chloro-5-fluorophenyl | chloromethyl | |
| 1.2.477 | 3-chloro-5-fluorophenyl | bromomethyl | |
| 1.2.478 | 3-chloro-5-fluorophenyl | difluoromethyl | |
| 1.2.479 | 3-bromo-5-fluorophenyl | fluoromethyl | |
| 1.2.480 | 3-bromo-5-fluorophenyl | chloromethyl | |
| 1.2.481 | 3-bromo-5-fluorophenyl | bromomethyl | |
| 1.2.482 | 3-bromo-5-fluorophenyl | difluoromethyl | |
| 1.2.483 | 3-iodo-5-fluorophenyl | fluoromethyl | |
| 1.2.484 | 3-methyl-5-fluorophenyl | fluoromethyl | |
| 1.2.485 | 3-methyl-5-fluorophenyl | chloromethyl | |
| 1.2.486 | 3-methyl-5-fluorophenyl | bromomethyl | |
| 1.2.487 | 3-methyl-5-fluorophenyl | difluoromethyl | |
| 1.2.488 | 3-ethyl-5-fluorophenyl | fluoromethyl | |
| 1.2.489 | 3-propyl-5-fluorophenyl | fluoromethyl | |
| 1.2.490 | 3-i-propyl-5-fluorophenyl | fluoromethyl | |
| 1.2.491 | 3-n-butyl-5-fluorophenyl | fluoromethyl | |
| 1.2.492 | 3-isobutyl-5-fluorophenyl | fluoromethyl | |
| 1.2.493 | 3-tert-butyl-5-fluorophenyl | fluoromethyl | |

TABLE 1.2-continued

Inventive compounds of the general formula (I) in which W* is COOH, $R^1$ and $R^2$ are each hydrogen, and aryl is the radical.

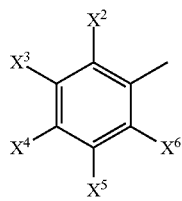

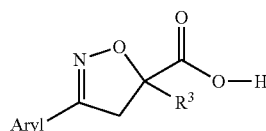

| No. | Aryl | $R^3$ | Physical data |
|---|---|---|---|
| 1.2.494 | 3-cyclopropyl-5-fluorophenyl | fluoromethyl | |
| 1.2.495 | 3-vinyl-5-fluorophenyl | fluoromethyl | |
| 1.2.496 | 3-ethynyl-5-fluorophenyl | fluoromethyl | |
| 1.2.497 | 3-cyano-5-fluorophenyl | fluoromethyl | |
| 1.2.498 | 3-trifluoromethyl-5-fluorophenyl | fluoromethyl | |
| 1.2.499 | 3-trifluoromethyl-5-fluorophenyl | chloromethyl | |
| 1.2.500 | 3-trifluoromethyl-5-fluorophenyl | bromomethyl | |
| 1.2.501 | 3-trifluoromethyl-5-fluorophenyl | difluoromethyl | |
| 1.2.502 | 3-(methoxycarbonyl)-5-fluorophenyl | fluoromethyl | |
| 1.2.503 | 3-hydroxymethyl-5-fluorophenyl | fluoromethyl | |
| 1.2.504 | 3-carbamoyl-5-fluorophenyl | fluoromethyl | |
| 1.2.505 | 3-hydroxy-5-fluorophenyl | fluoromethyl | |
| 1.2.506 | 3-methoxy-5-fluorophenyl | fluoromethyl | |
| 1.2.507 | 3-ethoxy-5-fluorophenyl | fluoromethyl | |
| 1.2.508 | 3-n-propoxy-5-fluorophenyl | fluoromethyl | |
| 1.2.509 | 3-isopropoxy-5-fluorophenyl | fluoromethyl | |
| 1.2.510 | 3-n-butoxy-5-fluorophenyl | fluoromethyl | |
| 1.2.511 | 3-isobutoxy-5-fluorophenyl | fluoromethyl | |
| 1.2.512 | 3-tert-butoxy-5-fluorophenyl | fluoromethyl | |
| 1.2.513 | 3-difluoromethoxy-5-fluorophenyl | fluoromethyl | |
| 1.2.514 | 3-trifluoromethoxy-5-fluorophenyl | fluoromethyl | |
| 1.2.515 | 3-(2,2,2-trifluoroethoxy)-5-fluorophenyl | fluoromethyl | |
| 1.2.516 | 3-(2-chloroethoxy)-5-fluorophenyl | fluoromethyl | |
| 1.2.517 | 3-(2-hydroxyethoxy)-5-fluorophenyl | fluoromethyl | |
| 1.2.518 | 3-[(tert-butoxycarbonyl)oxy]-5-fluorophenyl | fluoromethyl | |
| 1.2.519 | 3-nitro-5-fluorophenyl | fluoromethyl | |
| 1.2.520 | 3-acetoxy-5-fluorophenyl | fluoromethyl | |
| 1.2.521 | {3-[(tert-butoxycarbonyl)amino]-5-fluorophenyl} | fluoromethyl | |
| 1.2.522 | 3-methylsulfanyl-5-fluorophenyl | fluoromethyl | |
| 1.2.523 | 3,5-dichlorophenyl | fluoromethyl | |
| 1.2.524 | 3,5-dichlorophenyl | chloromethyl | [CDCl$_3$] 3.59 (d, 1H); 3.88 (d, 1H); 3.91 (d, 1H); 4.03 (d, 1H); 7.45 (m, 1H); 7.58 (m, 1H). |
| 1.2.525 | 3,5-dichlorophenyl | bromomethyl | [CDCl$_3$] 3.55 (d, 1H); 3.71 (d, 1H); 3.90 (d, 1H); 3.96 (d, 1H); 7.45 (s, 1H); 7.55 (s, 2H). |
| 1.2.526 | 3,5-dichlorophenyl | difluoromethyl | |
| 1.2.527 | 3,5-dichlorophenyl | trifluoromethyl | [CDCl$_3$] 3.8 (d, 1H); 4.0 (d, 1H); 7.45 (m, 1H); 7.55 (m, 1H). |
| 1.2.528 | 3,5-dichlorophenyl | cyano | [DMSO] 3.87 (d, 1H); 4.02 (d, 1H); 7.74 (m, 3H). |
| 1.2.529 | 3-bromo-5-chlorophenyl | fluoromethyl | |
| 1.2.530 | 3-iodo-5-chlorophenyl | fluoromethyl | |
| 1.2.531 | 3-methyl-5-chlorophenyl | fluoromethyl | |
| 1.2.532 | 3-ethyl-5-chlorophenyl | fluoromethyl | |
| 1.2.533 | 3-propyl-5-chlorophenyl | fluoromethyl | |
| 1.2.534 | 3-isopropyl-5-chlorophenyl | fluoromethyl | |
| 1.2.535 | 3-n-butyl-5-chlorophenyl | fluoromethyl | |
| 1.2.536 | 3-isobutyl-5-chlorophenyl | fluoromethyl | |
| 1.2.537 | 3-tert-butyl-5-chlorophenyl | fluoromethyl | |
| 1.2.538 | 3-cyclopropyl-5-chlorophenyl | fluoromethyl | |

TABLE 1.2-continued

Inventive compounds of the general formula (I) in which W* is COOH, $R^1$ and $R^2$ are each hydrogen, and aryl is the radical.

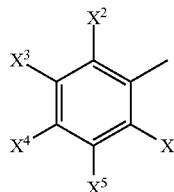

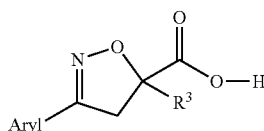

| No. | Aryl | $R^3$ | Physical data |
|---|---|---|---|
| 1.2.539 | 3-vinyl-5-chlorophenyl | fluoromethyl | |
| 1.2.540 | 3-ethynyl-5-chlorophenyl | fluoromethyl | |
| 1.2.541 | 3-cyano-5-chlorophenyl | fluoromethyl | |
| 1.2.542 | 3-trifluoromethyl-5-chlorophenyl | fluoromethyl | |
| 1.2.543 | 3-(hydroxycarbonyl)-5-chlorophenyl | fluoromethyl | |
| 1.2.544 | 3-(methoxycarbonyl)-5-chlorophenyl | fluoromethyl | |
| 1.2.545 | 3-hydroxymethyl-5-chlorophenyl | fluoromethyl | |
| 1.2.546 | 3-carbamoyl-5-chlorophenyl | fluoromethyl | |
| 1.2.547 | 3-hydroxy-5-chlorophenyl | fluoromethyl | |
| 1.2.548 | 3-methoxy-5-chlorophenyl | fluoromethyl | |
| 1.2.549 | 3-ethoxy-5-chlorophenyl | fluoromethyl | |
| 1.2.550 | 3-n-propoxy-5-chlorophenyl | fluoromethyl | |
| 1.2.551 | 3-isopropoxy-5-chlorophenyl | fluoromethyl | |
| 1.2.552 | 3-n-butoxy-5-chlorophenyl | fluoromethyl | |
| 1.2.553 | 3-isobutoxy-5-chlorophenyl | fluoromethyl | |
| 1.2.554 | 3-tert-butoxy-5-chlorophenyl | fluoromethyl | |
| 1.2.555 | 3-difluoromethoxy-5-chlorophenyl | fluoromethyl | |
| 1.2.556 | 3-trifluoromethoxy-5-chlorophenyl | fluoromethyl | |
| 1.2.557 | 3-(2,2,2-trifluoroethoxy)-5-chlorophenyl | fluoromethyl | |
| 1.2.558 | 3-(2-chloroethoxy)-5-chlorophenyl | fluoromethyl | |
| 1.2.559 | 3-(2-hydroxyethoxy)-5-chlorophenyl | fluoromethyl | |
| 1.2.560 | 3-[(tert-butoxycarbonyl)oxy]-5-chlorophenyl | fluoromethyl | |
| 1.2.561 | 3-nitro-5-chlorophenyl | fluoromethyl | |
| 1.2.562 | 3-acetoxy-5-chlorophenyl | fluoromethyl | |
| 1.2.563 | {3-[(tert-butoxycarbonyl)amino]-5-chlorophenyl} | fluoromethyl | |
| 1.2.564 | 3-methylsulfanyl-5-chlorophenyl | fluoromethyl | |
| 1.2.565 | 3,5-dibromophenyl | fluoromethyl | |
| 1.2.566 | 3,5-dibromophenyl | chloromethyl | |
| 1.2.567 | 3-iodo-5-bromophenyl | fluoromethyl | |
| 1.2.568 | 3-methyl-5-bromophenyl | fluoromethyl | |
| 1.2.569 | 3-methyl-5-bromophenyl | chloromethyl | |
| 1.2.570 | 3-methyl-5-bromophenyl | bromomethyl | |
| 1.2.571 | 3-methyl-5-bromophenyl | difluoromethyl | |
| 1.2.572 | 3-methyl-5-bromophenyl | trifluoromethyl | |
| 1.2.573 | 3-methyl-5-bromophenyl | cyano | |
| 1.2.574 | 3-ethyl-5-bromophenyl | fluoromethyl | |
| 1.2.575 | 3-propyl-5-bromophenyl | fluoromethyl | |
| 1.2.576 | 3-isopropyl-5-bromophenyl | fluoromethyl | |
| 1.2.577 | 3-n-butyl-5-bromophenyl | fluoromethyl | |
| 1.2.578 | 3-isobutyl-5-bromophenyl | fluoromethyl | |
| 1.2.579 | 3-tert-butyl-5-bromophenyl | fluoromethyl | |
| 1.2.580 | 3-cyclopropyl-5-bromophenyl | fluoromethyl | |
| 1.2.581 | 3-vinyl-5-bromophenyl | fluoromethyl | |
| 1.2.582 | 3-ethynyl-5-bromophenyl | fluoromethyl | |
| 1.2.583 | 3-cyano-5-bromophenyl | fluoromethyl | |
| 1.2.584 | 3-trifluoromethyl-5-bromophenyl | fluoromethyl | |
| 1.2.585 | 3-(hydroxycarbonyl)-5-bromophenyl | fluoromethyl | |
| 1.2.586 | 3-(methoxycarbonyl)-5-bromophenyl | fluoromethyl | |
| 1.2.587 | 3-hydroxymethyl-5-bromophenyl | fluoromethyl | |
| 1.2.588 | 3-carbamoyl-5-bromophenyl | fluoromethyl | |
| 1.2.589 | 3-hydroxy-5-bromophenyl | fluoromethyl | |
| 1.2.590 | 3-methoxy-5-bromophenyl | fluoromethyl | |

TABLE 1.2-continued

Inventive compounds of the general formula (I) in which W* is COOH, $R^1$ and $R^2$ are each hydrogen, and aryl is the radical.

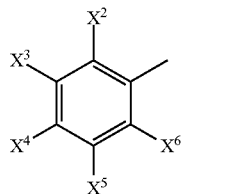

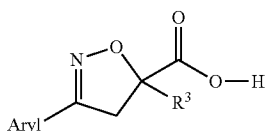

| No. | Aryl | $R^3$ | Physical data |
|---|---|---|---|
| 1.2.591 | 3-ethoxy-5-bromophenyl | fluoromethyl | |
| 1.2.592 | 3-n-propoxy-5-bromophenyl | fluoromethyl | |
| 1.2.593 | 3-isopropoxy-5-bromophenyl | fluoromethyl | |
| 1.2.594 | 3-n-butoxy-5-bromophenyl | fluoromethyl | |
| 1.2.595 | 3-isobutoxy-5-bromophenyl | fluoromethyl | |
| 1.2.596 | 3-tert-butoxy-5-bromophenyl | fluoromethyl | |
| 1.2.597 | 3-difluoromethoxy-5-bromophenyl | fluoromethyl | |
| 1.2.598 | 3-trifluoromethoxy-5-bromophenyl | fluoromethyl | |
| 1.2.599 | 3-(2,2,2-trifluoroethoxy)-5-bromophenyl | fluoromethyl | |
| 1.2.600 | 3-(2-chloroethoxy)-5-bromophenyl | fluoromethyl | |
| 1.2.601 | 3-(2-hydroxyethoxy)-5-bromophenyl | fluoromethyl | |
| 1.2.602 | 3-[(tert-butoxycarbonyl)oxy]-5-bromophenyl | fluoromethyl | |
| 1.2.603 | 3-nitro-5-bromophenyl | fluoromethyl | |
| 1.2.604 | 3-acetoxy-5-bromophenyl | fluoromethyl | |
| 1.2.605 | {3-[(tert-butoxy-carbonyl)amino]-5-bromophenyl} | fluoromethyl | |
| 1.2.606 | 3-methylsulfanyl-5-bromophenyl | fluoromethyl | |
| 1.2.607 | 3,5-diiodophenyl | fluoromethyl | |
| 1.2.608 | 3-methyl-5-iodophenyl | fluoromethyl | |
| 1.2.609 | 3-ethyl-5-iodophenyl | fluoromethyl | |
| 1.2.610 | 3-propyl-5-iodophenyl | fluoromethyl | |
| 1.2.611 | 3-isopropyl-5-iodophenyl | fluoromethyl | |
| 1.2.612 | 3-n-butyl-5-iodophenyl | fluoromethyl | |
| 1.2.613 | 3-isobutyl-5-iodophenyl | fluoromethyl | |
| 1.2.614 | 3-tert-butyl-5-iodophenyl | fluoromethyl | |
| 1.2.615 | 3-cyclopropyl-5-iodophenyl | fluoromethyl | |
| 1.2.616 | 3-vinyl-5-iodophenyl | fluoromethyl | |
| 1.2.617 | 3-ethynyl-5-iodophenyl | fluoromethyl | |
| 1.2.618 | 3-cyano-5-iodophenyl | fluoromethyl | |
| 1.2.619 | 3-trifluoromethyl-5-iodophenyl | fluoromethyl | |
| 1.2.620 | 3-(hydroxycarbonyl)-5-iodophenyl | fluoromethyl | |
| 1.2.621 | 3-(methoxycarbonyl)-5-iodophenyl | fluoromethyl | |
| 1.2.622 | 3-hydroxymethyl-5-iodophenyl | fluoromethyl | |
| 1.2.623 | 3-carbamoyl-5-iodophenyl | fluoromethyl | |
| 1.2.624 | 3-hydroxy-5-iodophenyl | fluoromethyl | |
| 1.2.625 | 3-methoxy-5-iodophenyl | fluoromethyl | |
| 1.2.626 | 3-ethoxy-5-iodophenyl | fluoromethyl | |
| 1.2.627 | 3-n-propoxy-5-iodophenyl | fluoromethyl | |
| 1.2.628 | 3-isopropoxy-5-iodophenyl | fluoromethyl | |
| 1.2.629 | 3-n-butoxy-5-iodophenyl | fluoromethyl | |
| 1.2.630 | 3-isobutoxy-5-iodophenyl | fluoromethyl | |
| 1.2.631 | 3-tert-butoxy-5-iodophenyl | fluoromethyl | |
| 1.2.632 | 3-difluoromethoxy-5-iodophenyl | fluoromethyl | |
| 1.2.633 | 3-trifluoromethoxy-5-iodophenyl | fluoromethyl | |
| 1.2.634 | 3-(2,2,2-trifluoroethoxy)-5-iodophenyl | fluoromethyl | |
| 1.2.635 | 3-(2-chloroethoxy)-5-iodophenyl | fluoromethyl | |
| 1.2.636 | 3-(2-hydroxyethoxy)-5-iodophenyl | fluoromethyl | |
| 1.2.637 | 3-[tert-butoxycarbonyl)oxy]-5-iodophenyl | fluoromethyl | |
| 1.2.638 | 3-nitro-5-iodophenyl | fluoromethyl | |
| 1.2.639 | 3-acetoxy-5-iodophenyl | fluoromethyl | |
| 1.2.640 | (3-[(tert-butoxy-carbonyl)amino]-5-iodophenyl} | fluoromethyl | |
| 1.2.641 | 3-methylsulfanyl-5-iodophenyl | fluoromethyl | |

TABLE 1.2-continued

Inventive compounds of the general formula (I) in which W* is COOH, $R^1$ and $R^2$ are each hydrogen, and aryl is the radical.

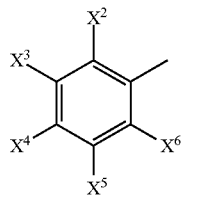

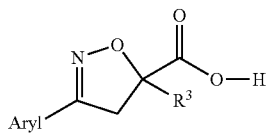

| No. | Aryl | $R^3$ | Physical data |
|---|---|---|---|
| 1.2.642 | 3,5-dimethylphenyl | fluoromethyl | |
| 1.2.643 | 3-ethyl-5-methylphenyl | fluoromethyl | |
| 1.2.644 | 3-propyl-5-methylphenyl | fluoromethyl | |
| 1.2.645 | 3-isopropyl-5-methylphenyl | fluoromethyl | |
| 1.2.646 | 3-n-butyl-5-methylphenyl | fluoromethyl | |
| 1.2.647 | 3-isobutyl-5-methylphenyl | fluoromethyl | |
| 1.2.648 | 3-tert-butyl-5-methylphenyl | fluoromethyl | |
| 1.2.649 | 3-cyclopropyl-5-methylphenyl | fluoromethyl | |
| 1.2.650 | 3-vinyl-5-methylphenyl | fluoromethyl | |
| 1.2.651 | 3-ethynyl-5-methylphenyl | fluoromethyl | |
| 1.2.652 | 3-cyano-5-methylphenyl | fluoromethyl | |
| 1.2.653 | 3-trifluoromethyl-5-methylphenyl | fluoromethyl | |
| 1.2.654 | 3-(hydroxycarbonyl)-5-methylphenyl | fluoromethyl | |
| 1.2.655 | 3-(methoxycarbonyl)-5-methylphenyl | fluoromethyl | |
| 1.2.656 | 3-hydroxymethyl-5-methylphenyl | fluoromethyl | |
| 1.2.657 | 3-carbamoyl-5-methylphenyl | fluoromethyl | |
| 1.2.658 | 3-hydroxy-5-methylphenyl | fluoromethyl | |
| 1.2.659 | 3-methoxy-5-methylphenyl | fluoromethyl | |
| 1.2.660 | 3-ethoxy-5-methylphenyl | fluoromethyl | |
| 1.2.661 | 3-n-propoxy-5-methylphenyl | fluoromethyl | |
| 1.2.662 | 3-n-butoxy-5-methylphenyl | fluoromethyl | |
| 1.2.663 | 3-isobutoxy-5-methylphenyl | fluoromethyl | |
| 1.2.664 | 3-tert-butoxy-5-methylphenyl | fluoromethyl | |
| 1.2.665 | 3-difluoromethoxy-5-methylphenyl | fluoromethyl | |
| 1.2.666 | 3-trifluoromethoxy-5-methylphenyl | fluoromethyl | |
| 1.2.667 | 3-(2,2,2-trifluoroethoxy)-5-methylphenyl | fluoromethyl | |
| 1.2.668 | 3-(2-chloroethoxy)-5-methylphenyl | fluoromethyl | |
| 1.2.669 | 3-(2-hydroxyethoxy)-5-methylphenyl | fluoromethyl | |
| 1.2.670 | 3-[tert-butoxycarbonyl)oxy]-5-methylphenyl | fluoromethyl | |
| 1.2.671 | 3-nitro-5-methylphenyl | fluoromethyl | |
| 1.2.672 | 3-acetoxy-5-methylphenyl | fluoromethyl | |
| 1.2.673 | {3-[(tert-butoxycarbonyl)amino]-5-methylphenyl} | fluoromethyl | |
| 1.2.674 | 3-methylsulfanyl-5-methylphenyl | fluoromethyl | |
| 1.2.675 | 3,5-diethylphenyl | fluoromethyl | |
| 1.2.676 | 3-propyl-5-ethylphenyl | fluoromethyl | |
| 1.2.677 | 3-isopropyl-5-ethylphenyl | fluoromethyl | |
| 1.2.678 | 3-n-butyl-5-ethylphenyl | fluoromethyl | |
| 1.2.679 | 3-isobutyl-5-ethylphenyl | fluoromethyl | |
| 1.2.680 | 3-tert-butyl-5-ethylphenyl | fluoromethyl | |
| 1.2.681 | 3-cyclopropyl-5-ethylphenyl | fluoromethyl | |
| 1.2.682 | 3-vinyl-5-ethylphenyl | fluoromethyl | |
| 1.2.683 | 3-ethynyl-5-ethylphenyl | fluoromethyl | |
| 1.2.684 | 3-cyano-5-ethylphenyl | fluoromethyl | |
| 1.2.685 | 3-trifluoromethyl-5-ethylphenyl | fluoromethyl | |
| 1.2.686 | 3-(hydroxycarbonyl)-5-ethylphenyl | fluoromethyl | |
| 1.2.687 | 3-(methoxycarbonyl)-5-ethylphenyl | fluoromethyl | |
| 1.2.688 | 3-hydroxymethyl-5-ethylphenyl | fluoromethyl | |
| 1.2.689 | 3-carbamoyl-5-ethylphenyl | fluoromethyl | |
| 1.2.690 | 3-hydroxy-5-ethylphenyl | fluoromethyl | |
| 1.2.691 | 3-methoxy-5-ethylphenyl | fluoromethyl | |
| 1.2.692 | 3-ethoxy-5-ethylphenyl | fluoromethyl | |

TABLE 1.2-continued

Inventive compounds of the general formula (I) in which W* is COOH, $R^1$ and $R^2$ are each hydrogen, and aryl is the radical.

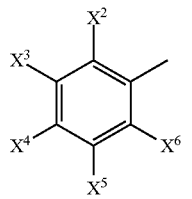

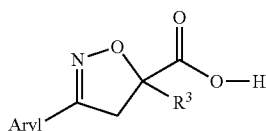

| No. | Aryl | $R^3$ | Physical data |
|---|---|---|---|
| 1.2.693 | 3-n-propoxy-5-ethylphenyl | fluoromethyl | |
| 1.2.694 | 3-n-butoxy-5-ethylphenyl | fluoromethyl | |
| 1.2.695 | 3-isobutoxy-5-ethylphenyl | fluoromethyl | |
| 1.2.696 | 3-tert-butoxy-5-ethylphenyl | fluoromethyl | |
| 1.2.697 | 3-difluoromethoxy-5-ethylphenyl | fluoromethyl | |
| 1.2.698 | 3-trifluoromethoxy-5-ethylphenyl | fluoromethyl | |
| 1.2.699 | 3-(2,2,2-trifluoroethoxy)-5-ethylphenyl | fluoromethyl | |
| 1.2.700 | 3-(2-chloroethoxy)-5-ethylphenyl | fluoromethyl | |
| 1.2.701 | 3-(2-hydroxyethoxy)-5-ethylphenyl | fluoromethyl | |
| 1.2.702 | 3-[tert-butoxycarbonyl)oxy]-5-ethylphenyl | fluoromethyl | |
| 1.2.703 | 3-nitro-5-ethylphenyl | fluoromethyl | |
| 1.2.704 | 3-acetoxy-5-ethylphenyl | fluoromethyl | |
| 1.2.705 | {3-[(tert-butoxy-carbonyl)amino]-5-ethylphenyl} | fluoromethyl | |
| 1.2.706 | 3-methylsulfanyl-5-ethylphenyl | fluoromethyl | |
| 1.2.707 | 3,5-dipropylphenyl | fluoromethyl | |
| 1.2.708 | 3-isopropyl-5-propylphenyl | fluoromethyl | |
| 1.2.709 | 3-n-butyl-5-propylphenyl | fluoromethyl | |
| 1.2.710 | 3-isobutyl-5-propylphenyl | fluoromethyl | |
| 1.2.711 | 3-tert-butyl-5-propylphenyl | fluoromethyl | |
| 1.2.712 | 3-cyclopropyl-5-propylphenyl | fluoromethyl | |
| 1.2.713 | 3-vinyl-5-propylphenyl | fluoromethyl | |
| 1.2.714 | 3-ethynyl-5-propylphenyl | fluoromethyl | |
| 1.2.715 | 3-cyano-5-propylphenyl | fluoromethyl | |
| 1.2.716 | 3-trifluoromethyl-5-propylphenyl | fluoromethyl | |
| 1.2.717 | 3-(hydroxycarbonyl)-5-propylphenyl | fluoromethyl | |
| 1.2.718 | 3-(methoxycarbonyl)-5-propylphenyl | fluoromethyl | |
| 1.2.719 | 3-hydroxymethyl-5-propylphenyl | fluoromethyl | |
| 1.2.720 | 3-carbamoyl-5-propylphenyl | fluoromethyl | |
| 1.2.721 | 3-hydroxy-5-propylphenyl | fluoromethyl | |
| 1.2.722 | 3-methoxy-5-propylphenyl | fluoromethyl | |
| 1.2.723 | 3-ethoxy-5-propylphenyl | fluoromethyl | |
| 1.2.724 | 3-n-propoxy-5-propylphenyl | fluoromethyl | |
| 1.2.725 | 3-n-butoxy-5-propylphenyl | fluoromethyl | |
| 1.2.726 | 3-isobutoxy-5-propylphenyl | fluoromethyl | |
| 1.2.727 | 3-tert-butoxy-5-propylphenyl | fluoromethyl | |
| 1.2.728 | 3-difluoromethoxy-5-propylphenyl | fluoromethyl | |
| 1.2.729 | 3-trifluoromethoxy-5-ethylphenyl | fluoromethyl | |
| 1.2.730 | 3-(2,2,2-trifluoroethoxy)-5-propylphenyl | fluoromethyl | |
| 1.2.731 | 3-(2-chloroethoxy)-5-propylphenyl | fluoromethyl | |
| 1.2.732 | 3-(2-hydroxyethoxy)-5-propylphenyl | fluoromethyl | |
| 1.2.733 | 3-[tert-butoxycarbonyl)oxy]-5-propylphenyl | fluoromethyl | |
| 1.2.734 | 3-nitro-5-propylphenyl | fluoromethyl | |
| 1.2.735 | 3-acetoxy-5-propylphenyl | fluoromethyl | |
| 1.2.736 | {3-[(tert-butoxy-carbonyl)amino]-5-propylphenyl} | fluoromethyl | |
| 1.2.737 | 3-methylsulfanyl-5-propylphenyl | fluoromethyl | |
| 1.2.738 | 3,5-diisopropylphenyl | fluoromethyl | |
| 1.2.739 | 3-n-butyl-5-isopropylphenyl | fluoromethyl | |
| 1.2.740 | 3-isobutyl-5-isopropylphenyl | fluoromethyl | |
| 1.2.741 | 3-tert-butyl-5-isopropylphenyl | fluoromethyl | |
| 1.2.742 | 3-cyclopropyl-5-isopropylphenyl | fluoromethyl | |

TABLE 1.2-continued

Inventive compounds of the general formula (I) in which W* is COOH, $R^1$ and $R^2$ are each hydrogen, and aryl is the radical.

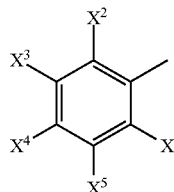

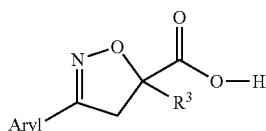

| No. | Aryl | $R^3$ | Physical data |
|---|---|---|---|
| 1.2.743 | 3-vinyl-5-isopropylphenyl | fluoromethyl | |
| 1.2.744 | 3-ethynyl-5-isopropylphenyl | fluoromethyl | |
| 1.2.745 | 3-cyano-5-isopropylphenyl | fluoromethyl | |
| 1.2.746 | 3-trifluoromethyl-5-isopropylphenyl | fluoromethyl | |
| 1.2.747 | 3-(hydroxycarbonyl)-5-isopropylphenyl | fluoromethyl | |
| 1.2.748 | 3-(methoxycarbonyl)-5-isopropylphenyl | fluoromethyl | |
| 1.2.749 | 3-hydroxymethyl-5-isopropylphenyl | fluoromethyl | |
| 1.2.750 | 3-carbamoyl-5-isopropylphenyl | fluoromethyl | |
| 1.2.751 | 3-hydroxy-5-isopropylphenyl | fluoromethyl | |
| 1.2.752 | 3-methoxy-5-isopropylphenyl | fluoromethyl | |
| 1.2.753 | 3-ethoxy-5-isopropylphenyl | fluoromethyl | |
| 1.2.754 | 3-n-propoxy-5-isopropylphenyl | fluoromethyl | |
| 1.2.755 | 3-n-butoxy-5-isopropylphenyl | fluoromethyl | |
| 1.2.756 | 3-isobutoxy-5-isopropylphenyl | fluoromethyl | |
| 1.2.757 | 3-tert-butoxy-5-isopropylphenyl | fluoromethyl | |
| 1.2.758 | 3-difluoromethoxy-5-isopropylphenyl | fluoromethyl | |
| 1.2.759 | 3-trifluoromethoxy-5-isopropylphenyl | fluoromethyl | |
| 1.2.760 | 3-(2,2,2-trifluoroethoxy)-5-isopropylphenyl | fluoromethyl | |
| 1.2.761 | 3-(2-chloroethoxy)-5-isopropylphenyl | fluoromethyl | |
| 1.2.762 | 3-(2-hydroxyethoxy)-5-propylphenyl | fluoromethyl | |
| 1.2.763 | 3-[tert-butoxycarbonyl)oxy]-5-isopropylphenyl | fluoromethyl | |
| 1.2.764 | 3-nitro-5-isopropylphenyl | fluoromethyl | |
| 1.2.765 | 3-acetoxy-5-isopropylphenyl | fluoromethyl | |
| 1.2.766 | {3-[tert-butoxy-carbonyl)amino]-5-isopropylphenyl} | fluoromethyl | |
| 1.2.767 | 3-methylsulfanyl-5-isopropylphenyl | fluoromethyl | |
| 1.2.768 | 3,5-dibutylphenyl | fluoromethyl | |
| 1.2.769 | 3-isobutyl-5-butylphenyl | fluoromethyl | |
| 1.2.770 | 3-tert-butyl-5-butylphenyl | fluoromethyl | |
| 1.2.771 | 3-cyclopropyl-5-butylphenyl | fluoromethyl | |
| 1.2.772 | 3-vinyl-5-butylphenyl | fluoromethyl | |
| 1.2.773 | 3-ethynyl-5-butylphenyl | fluoromethyl | |
| 1.2.774 | 3-cyano-5-butylphenyl | fluoromethyl | |
| 1.2.775 | 3-trifluoromethyl-5-butylphenyl | fluoromethyl | |
| 1.2.776 | 3-(hydroxycarbonyl)-5-butylphenyl | fluoromethyl | |
| 1.2.777 | 3-(methoxycarbonyl)-5-butylphenyl | fluoromethyl | |
| 1.2.778 | 3-hydroxymethyl-5-butylphenyl | fluoromethyl | |
| 1.2.779 | 3-carbamoyl-5-butylphenyl | fluoromethyl | |
| 1.2.780 | 3-hydroxy-5-butylphenyl | fluoromethyl | |
| 1.2.781 | 3-methoxy-5-butylphenyl | fluoromethyl | |
| 1.2.782 | 3-ethoxy-5-butylphenyl | fluoromethyl | |
| 1.2.783 | 3-n-propoxy-5-butylphenyl | fluoromethyl | |
| 1.2.784 | 3-n-butoxy-5-butylphenyl | fluoromethyl | |
| 1.2.785 | 3-isobutoxy-5-butylphenyl | fluoromethyl | |
| 1.2.786 | 3-tert-butoxy-5-butylphenyl | fluoromethyl | |
| 1.2.787 | 3-difluoromethoxy-5-butylphenyl | fluoromethyl | |
| 1.2.788 | 3-trifluoromethoxy-5-butylphenyl | fluoromethyl | |
| 1.2.789 | 3-(2,2,2-trifluoroethoxy)-5-butylphenyl | fluoromethyl | |
| 1.2.790 | 3-(2-chloroethoxy)-5-butylphenyl | fluoromethyl | |

TABLE 1.2-continued

Inventive compounds of the general formula (I) in which W* is COOH, R¹ and R² are each hydrogen, and aryl is the radical.

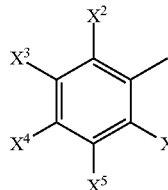

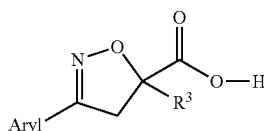

| No. | Aryl | R³ | Physical data |
|---|---|---|---|
| 1.2.791 | 3-(2-hydroxyethoxy)-5-butylphenyl | fluoromethyl | |
| 1.2.792 | 3-[tert-butoxycarbonyl)oxy]-5-butylphenyl | fluoromethyl | |
| 1.2.793 | 3-nitro-5-butylphenyl | fluoromethyl | |
| 1.2.794 | 3-acetoxy-5-butylphenyl | fluoromethyl | |
| 1.2.795 | (3-[(tert-butoxy-carbonyl)amino]-5-butylphenyl} | fluoromethyl | |
| 1.2.796 | 3-methylsulfanyl-5-butylphenyl | fluoromethyl | |
| 1.2.797 | 3,5-diisobutylphenyl | fluoromethyl | |
| 1.2.798 | 3-tert-butyl-5-isobutylphenyl | fluoromethyl | |
| 1.2.799 | 3-cyclopropyl-5-isobutylphenyl | fluoromethyl | |
| 1.2.800 | 3-vinyl-5-isobutylphenyl | fluoromethyl | |
| 1.2.801 | 3-ethynyl-5-isobutylphenyl | fluoromethyl | |
| 1.2.802 | 3-cyano-5-isobutylphenyl | fluoromethyl | |
| 1.2.803 | 3-trifluoromethyl-5-isobutylphenyl | fluoromethyl | |
| 1.2.804 | 3-(hydroxycarbonyl)-5-isobutylphenyl | fluoromethyl | |
| 1.2.805 | 3-(methoxycarbonyl)-5-isobutylphenyl | fluoromethyl | |
| 1.2.806 | 3-hydroxymethyl-5-isobutylphenyl | fluoromethyl | |
| 1.2.807 | 3-carbamoyl-5-isobutylphenyl | fluoromethyl | |
| 1.2.808 | 3-hydroxy-5-isobutylphenyl | fluoromethyl | |
| 1.2.809 | 3-methoxy-5-isobutylphenyl | fluoromethyl | |
| 1.2.810 | 3-ethoxy-5-isobutylphenyl | fluoromethyl | |
| 1.2.811 | 3-n-propoxy-5-isobutylphenyl | fluoromethyl | |
| 1.2.812 | 3-n-butoxy-5-isobutylphenyl | fluoromethyl | |
| 1.2.813 | 3-isobutoxy-5-isobutylphenyl | fluoromethyl | |
| 1.2.814 | 3-tert-butoxy-5-isobutylphenyl | fluoromethyl | |
| 1.2.815 | 3-difluoromethoxy-5-isobutylphenyl | fluoromethyl | |
| 1.2.816 | 3-trifluoromethoxy-5-isobutylphenyl | fluoromethyl | |
| 1.2.817 | 3-(2,2,2-trifluoroethoxy)-5-isobutylphenyl | fluoromethyl | |
| 1.2.818 | 3-(2-chloroethoxy)-5-isobutylphenyl | fluoromethyl | |
| 1.2.819 | 3-(2-hydroxyethoxy)-5-isobutylphenyl | fluoromethyl | |
| 1.2.820 | 3-[(tert-butoxycarbonyl)oxy]-5-isobutylphenyl | fluoromethyl | |
| 1.2.821 | 3-nitro-5-isobutylphenyl | fluoromethyl | |
| 1.2.822 | 3-acetoxy-5-isobutylphenyl | fluoromethyl | |
| 1.2.823 | {3-[tert-butoxycarbonyl)amino]-5-isobutylphenyl} | fluoromethyl | |
| 1.2.824 | 3-methylsulfanyl-5-isobutylphenyl | fluoromethyl | |
| 1.2.825 | 3,5-di(tert-butyl)phenyl | fluoromethyl | |
| 1.2.826 | 3-cyclopropyl-5-tert-butylphenyl | fluoromethyl | |
| 1.2.827 | 3-vinyl-5-tert-butylphenyl | fluoromethyl | |
| 1.2.828 | 3-ethynyl-5-tert-butylphenyl | fluoromethyl | |
| 1.2.829 | 3-cyano-5-tert-butylphenyl | fluoromethyl | |
| 1.2.830 | 3-trifluoromethyl-5-tert-butylphenyl | fluoromethyl | |
| 1.2.831 | 3-(hydroxycarbonyl)-5-tert-butylphenyl | fluoromethyl | |
| 1.2.832 | 3-(methoxycarbonyl)-5-tert-butylphenyl | fluoromethyl | |
| 1.2.833 | 3-hydroxymethyl-5-tert-butylphenyl | fluoromethyl | |
| 1.2.834 | 3-carbamoyl-5-tert-butylphenyl | fluoromethyl | |
| 1.2.835 | 3-hydroxy-5-tert-butylphenyl | fluoromethyl | |
| 1.2.836 | 3-methoxy-5-tert-butylphenyl | fluoromethyl | |
| 1.2.837 | 3-ethoxy-5-tert-butylphenyl | fluoromethyl | |

TABLE 1.2-continued

Inventive compounds of the general formula (I) in which W* is COOH, $R^1$ and $R^2$ are each hydrogen, and aryl is the radical.

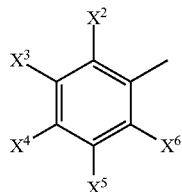

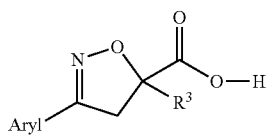

| No. | Aryl | $R^3$ | Physical data |
|---|---|---|---|
| 1.2.838 | 3-n-propoxy-5-tert-butylphenyl | fluoromethyl | |
| 1.2.839 | 3-n-butoxy-5-tert-butylphenyl | fluoromethyl | |
| 1.2.840 | 3-isobutoxy-5-tert-butylphenyl | fluoromethyl | |
| 1.2.841 | 3-tert-butoxy-5-tert-butylphenyl | fluoromethyl | |
| 1.2.842 | 3-difluoromethoxy-5-tert-butylphenyl | fluoromethyl | |
| 1.2.843 | 3-trifluoromethoxy-5-tert-butylphenyl | fluoromethyl | |
| 1.2.844 | 3-(2,2,2-trifluoroethoxy)-5-tert-butylphenyl | fluoromethyl | |
| 1.2.845 | 3-(2-chloroethoxy)-5-tert-butylphenyl | fluoromethyl | |
| 1.2.846 | 3-(2-hydroxyethoxy)-5-tert-butylphenyl | fluoromethyl | |
| 1.2.847 | 3-[tert-butoxycarbonyl)oxy]-5-tert-butylphenyl | fluoromethyl | |
| 1.2.848 | 3-nitro-5-tert-butylphenyl | fluoromethyl | |
| 1.2.849 | 3-acetoxy-5-tert-butylphenyl | fluoromethyl | |
| 1.2.850 | {3-[tert-butoxy-carbonyl)amino]-5-tert-butylphenyl} | fluoromethyl | |
| 1.2.851 | 3-methylsulfanyl-5-tert-butylphenyl | fluoromethyl | |
| 1.2.852 | 3-tert-butyl-5-cyclopropylphenyl | fluoromethyl | |
| 1.2.853 | 3,5-dicyclopropyl-phenyl | fluoromethyl | |
| 1.2.854 | 3-vinyl-5-cyclopropylphenyl | fluoromethyl | |
| 1.2.855 | 3-ethynyl-5-cyclopropylphenyl | fluoromethyl | |
| 1.2.856 | 3-cyano-5-cyclopropylphenyl | fluoromethyl | |
| 1.2.857 | 3-trifluoromethyl-5-cyclopropylphenyl | fluoromethyl | |
| 1.2.858 | 3-(hydroxycarbonyl)-5-cyclopropylphenyl | fluoromethyl | |
| 1.2.859 | 3-(methoxycarbonyl)-5-cyclopropylphenyl | fluoromethyl | |
| 1.2.860 | 3-hydroxymethyl-5-cyclopropylphenyl | fluoromethyl | |
| 1.2.861 | 3-carbamoyl-5-cyclopropylphenyl | fluoromethyl | |
| 1.2.862 | 3-hydroxy-5-cyclopropylphenyl | fluoromethyl | |
| 1.2.863 | 3-methoxy-5-cyclopropylphenyl | fluoromethyl | |
| 1.2.864 | 3-ethoxy-5-cyclopropylphenyl | fluoromethyl | |
| 1.2.865 | 3-n-propoxy-5-cyclopropylphenyl | fluoromethyl | |
| 1.2.866 | 3-n-butoxy-5-cyclopropylphenyl | fluoromethyl | |
| 1.2.867 | 3-isobutoxy-5-cyclopropylphenyl | fluoromethyl | |
| 1.2.868 | 3-tert-butoxy-5-cyclopropylphenyl | fluoromethyl | |
| 1.2.869 | 3-difluoromethoxy-5-cyclopropylphenyl | fluoromethyl | |
| 1.2.870 | 3-trifluoromethoxy-5-cyclopropylphenyl | fluoromethyl | |
| 1.2.871 | 3-(2,2,2-trifluoroethoxy)-5-cyclopropylphenyl | fluoromethyl | |
| 1.2.872 | 3-(2-chloroethoxy)-5-cyclopropylphenyl | fluoromethyl | |
| 1.2.873 | 3-(2-hydroxyethoxy)-5-cyclopropylphenyl | fluoromethyl | |
| 1.2.874 | 3-[tert-butoxycarbonyl)oxy]-5-cyclopropylphenyl | fluoromethyl | |
| 1.2.875 | 3-nitro-5-cyclopropylphenyl | fluoromethyl | |
| 1.2.876 | 3-acetoxy-5-cyclopropylphenyl | fluoromethyl | |

TABLE 1.2-continued

Inventive compounds of the general formula (I) in which W* is COOH, $R^1$ and $R^2$ are each hydrogen, and aryl is the radical.

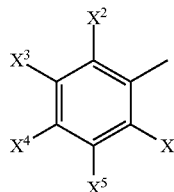

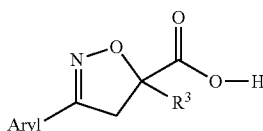

| No. | Aryl | $R^3$ | Physical data |
|---|---|---|---|
| 1.2.877 | {3-[(tert-butoxycarbonyl)amino]-5-cyclopropylphenyl} | fluoromethyl | |
| 1.2.878 | 3-methylsulfanyl-5-cyclopropylphenyl | fluoromethyl | |
| 1.2.879 | 3,5-divinylphenyl | fluoromethyl | |
| 1.2.880 | 3-ethynyl-5-vinylphenyl | fluoromethyl | |
| 1.2.881 | 3-cyano-5-vinylphenyl | fluoromethyl | |
| 1.2.882 | 3-trifluoromethyl-5-vinylphenyl | fluoromethyl | |
| 1.2.883 | 3-(hydroxycarbonyl)-5-vinylphenyl | fluoromethyl | |
| 1.2.884 | 3-(methoxycarbonyl)-5-vinylphenyl | fluoromethyl | |
| 1.2.885 | 3-hydroxymethyl-5-vinylphenyl | fluoromethyl | |
| 1.2.886 | 3-carbamoyl-5-vinylphenyl | fluoromethyl | |
| 1.2.887 | 3-hydroxy-5-vinylphenyl | fluoromethyl | |
| 1.2.888 | 3-methoxy-5-vinylphenyl | fluoromethyl | |
| 1.2.889 | 3-ethoxy-5-vinylphenyl | fluoromethyl | |
| 1.2.890 | 3-n-propoxy-5-vinylphenyl | fluoromethyl | |
| 1.2.891 | 3-n-butoxy-5-vinylphenyl | fluoromethyl | |
| 1.2.892 | 3-isobutoxy-5-vinylphenyl | fluoromethyl | |
| 1.2.893 | 3-tert-butoxy-5-vinylphenyl | fluoromethyl | |
| 1.2.894 | 3-difluoromethoxy-5-vinylphenyl | fluoromethyl | |
| 1.2.895 | 3-trifluoromethoxy-5-vinylphenyl | fluoromethyl | |
| 1.2.896 | 3-(2,2,2-trifluoroethoxy)-5-vinylphenyl | fluoromethyl | |
| 1.2.897 | 3-(2-chloroethoxy)-5-vinylphenyl | fluoromethyl | |
| 1.2.898 | 3-(2-hydroxyethoxy)-5-vinylphenyl | fluoromethyl | |
| 1.2.899 | 3-[tert-butoxycarbonyl)oxy]-5-vinylphenyl | fluoromethyl | |
| 1.2.900 | 3-nitro-5-vinylphenyl | fluoromethyl | |
| 1.2.901 | 3-acetoxy-5-vinylphenyl | fluoromethyl | |
| 1.2.902 | (3-[(tert-butoxy-carbonyl)amino]-5-vinylphenyl} | fluoromethyl | |
| 1.2.903 | 3-methylsulfanyl-5-vinylphenyl | fluoromethyl | |
| 1.2.904 | 3,5-diethynylphenyl | fluoromethyl | |
| 1.2.905 | 3-cyano-5-ethynylphenyl | fluoromethyl | |
| 1.2.906 | 3-trifluoromethyl-5-ethynylphenyl | fluoromethyl | |
| 1.2.907 | 3-(hydroxycarbonyl)-5-ethynylphenyl | fluoromethyl | |
| 1.2.908 | 3-(methoxycarbonyl)-5-ethynylphenyl | fluoromethyl | |
| 1.2.909 | 3-hydroxymethyl-5-ethynylphenyl | fluoromethyl | |
| 1.2.910 | 3-carbamoyl-5-ethynylphenyl | fluoromethyl | |
| 1.2.911 | 3-hydroxy-5-ethynylphenyl | fluoromethyl | |
| 1.2.912 | 3-methoxy-5-ethynylphenyl | fluoromethyl | |
| 1.2.913 | 3-ethoxy-5-ethynylphenyl | fluoromethyl | |
| 1.2.914 | 3-n-propoxy-5-ethynylphenyl | fluoromethyl | |
| 1.2.915 | 3-n-butoxy-5-ethynylphenyl | fluoromethyl | |
| 1.2.916 | 3-isobutoxy-5-ethynylphenyl | fluoromethyl | |
| 1.2.917 | 3-tert-butoxy-5-ethynylphenyl | fluoromethyl | |
| 1.2.918 | 3-difluoromethoxy-5-ethynylphenyl | fluoromethyl | |
| 1.2.919 | 3-trifluoromethoxy-5-ethynylphenyl | fluoromethyl | |
| 1.2.920 | 3-(2,2,2-trifluoroethoxy)-5-ethynylphenyl | fluoromethyl | |
| 1.2.921 | 3-(2-chloroethoxy)-5-ethynylphenyl | fluoromethyl | |
| 1.2.922 | 3-(2-hydroxyethoxy)-5-ethynylphenyl | fluoromethyl | |
| 1.2.923 | 3-[tert-butoxycarbonyl)oxy]-5-ethynylphenyl | fluoromethyl | |
| 1.2.924 | 3-nitro-5-ethynylphenyl | fluoromethyl | |

TABLE 1.2-continued

Inventive compounds of the general formula (I) in which W* is COOH, R¹ and R² are each hydrogen, and aryl is the radical.

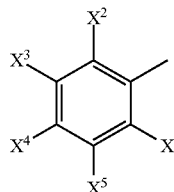

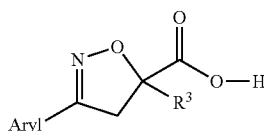

| No. | Aryl | R³ | Physical data |
|---|---|---|---|
| 1.2.925 | 3-acetoxy-5-ethynylphenyl | fluoromethyl | |
| 1.2.926 | (3-[(tert-butoxy-carbonyl)amino]-5-ethynylphenyl} | fluoromethyl | |
| 1.2.927 | 3-methylsulfanyl-5-ethynylphenyl | fluoromethyl | |
| 1.2.928 | 3,5-dicyanophenyl | fluoromethyl | |
| 1.2.929 | 3-trifluoromethyl-5-cyanophenyl | fluoromethyl | |
| 1.2.930 | 3-(hydroxycarbonyl)-5-cyanophenyl | fluoromethyl | |
| 1.2.931 | 3-(methoxycarbonyl)-5-cyanophenyl | fluoromethyl | |
| 1.2.932 | 3-hydroxymethyl-5-cyanophenyl | fluoromethyl | |
| 1.2.933 | 3-carbamoyl-5-cyanophenyl | fluoromethyl | |
| 1.2.934 | 3-hydroxy-5-cyanophenyl | fluoromethyl | |
| 1.2.935 | 3-methoxy-5-cyanophenyl | fluoromethyl | |
| 1.2.936 | 3-ethoxy-5-cyanophenyl | fluoromethyl | |
| 1.2.937 | 3-n-propoxy-5-cyanophenyl | fluoromethyl | |
| 1.2.938 | 3-n-butoxy-5-cyanophenyl | fluoromethyl | |
| 1.2.939 | 3-isobutoxy-5-cyanophenyl | fluoromethyl | |
| 1.2.940 | 3-tert-butoxy-5-cyanophenyl | fluoromethyl | |
| 1.2.941 | 3-difluoromethoxy-5-cyanophenyl | fluoromethyl | |
| 1.2.942 | 3-trifluoromethoxy-5-cyanophenyl | fluoromethyl | |
| 1.2.943 | 3-(2,2,2-trifluoroethoxy)-5-cyanophenyl | fluoromethyl | |
| 1.2.944 | 3-(2-chloroethoxy)-5-cyanophenyl | fluoromethyl | |
| 1.2.945 | 3-(2-hydroxyethoxy)-5-cyanophenyl | fluoromethyl | |
| 1.2.946 | 3-[tert-butoxycarbonyl)oxy]-5-cyanophenyl | fluoromethyl | |
| 1.2.947 | 3-nitro-5-cyanophenyl | fluoromethyl | |
| 1.2.948 | 3-acetoxy-5-cyanophenyl | fluoromethyl | |
| 1.2.949 | (3-[(tert-butoxy-carbonyl)amino]-5-cyanophenyl} | fluoromethyl | |
| 1.2.950 | 3-methylsulfanyl-5-cyanophenyl | fluoromethyl | |
| 1.2.951 | 3,5-di(trifluoromethyl)-phenyl | fluoromethyl | |
| 1.2.952 | 3-(hydroxycarbonyl)-5-trifluoromethyl-phenyl | fluoromethyl | |
| 1.2.953 | 3-(methoxycarbonyl)-5-trifluoromethyl-phenyl | fluoromethyl | |
| 1.2.954 | 3-hydroxymethyl-5-trifluoromethylphenyl | fluoromethyl | |
| 1.2.955 | 3-carbamoyl-5-trifluoromethylphenyl | fluoromethyl | |
| 1.2.956 | 3-hydroxy-5-trifluoromethylphenyl | fluoromethyl | |
| 1.2.957 | 3-methoxy-5-trifluoromethylphenyl | fluoromethyl | |
| 1.2.958 | 3-ethoxy-5-trifluoromethylphenyl | fluoromethyl | |
| 1.2.959 | 3-n-propoxy-5-trifluoromethylphenyl | fluoromethyl | |
| 1.2.960 | 3-n-butoxy-5-trifluoromethylphenyl | fluoromethyl | |
| 1.2.961 | 3-isobutoxy-5-trifluoromethylphenyl | fluoromethyl | |
| 1.2.962 | 3-tert-butoxy-5-trifluoromethylphenyl | fluoromethyl | |
| 1.2.963 | 3-difluoromethoxy-5-trifluoromethylphenyl | fluoromethyl | |
| 1.2.964 | 3-trifluoromethoxy-5-trifluoromethylphenyl | fluoromethyl | |
| 1.2.965 | 3-(2,2,2-trifluoroethoxy)-5-trifluoro-methylphenyl | fluoromethyl | |
| 1.2.966 | 3-(2-chloroethoxy)-5-trifluoromethyl-phenyl | fluoromethyl | |

TABLE 1.2-continued

Inventive compounds of the general formula (I) in which W* is COOH, $R^1$ and $R^2$ are each hydrogen, and aryl is the radical.

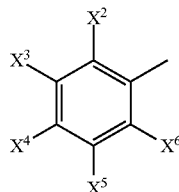

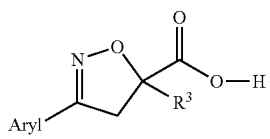

| No. | Aryl | $R^3$ | Physical data |
|---|---|---|---|
| 1.2.967 | 3-(2-hydroxyethoxy)-5-trifluoromethyl-phenyl | fluoromethyl | |
| 1.2.968 | 3-[tert-butoxycarbonyl)oxy]-5-trifluoromethylphenyl | fluoromethyl | |
| 1.2.969 | 3-nitro-5-trifluoromethylphenyl | fluoromethyl | |
| 1.2.970 | 3-acetoxy-5-trifluoromethylphenyl | fluoromethyl | |
| 1.2.971 | (3-[tert-butoxy-carbonyl)amino]-5-trifluoromethylphenyl} | fluoromethyl | |
| 1.2.972 | 3-methylsulfanyl-5-trifluoromethylphenyl | fluoromethyl | |
| 1.2.973 | 3,5-bis(hydroxy-carbonyl)phenyl | fluoromethyl | |
| 1.2.974 | 3-(methoxycarbonyl)-5-(hydroxycarbonyl)phenyl | fluoromethyl | |
| 1.2.975 | 3-hydroxymethyl-5-(hydroxycarbonyl)phenyl | fluoromethyl | |
| 1.2.976 | 3-carbamoyl-5-(hydroxycarbonyl)-phenyl | fluoromethyl | |
| 1.2.977 | 3-hydroxy-5-(hydroxycarbonyl)-phenyl | fluoromethyl | |
| 1.2.978 | 3-methoxy-5-(hydroxycarbonyl)-phenyl | fluoromethyl | |
| 1.2.979 | 3-ethoxy-5-(hydroxycarbonyl)-phenyl | fluoromethyl | |
| 1.2.980 | 3-n-propoxy-5-(hydroxycarbonyl)-phenyl | fluoromethyl | |
| 1.2.981 | 3-n-butoxy-5-(hydroxycarbonyl)-phenyl | fluoromethyl | |
| 1.2.982 | 3-isobutoxy-5-(hydroxycarbonyl)-phenyl | fluoromethyl | |
| 1.2.983 | 3-tert-butoxy-5-(hydroxycarbonyl)-phenyl | fluoromethyl | |
| 1.2.984 | 3-difluoromethoxy-5-(hydroxycarbonyl)phenyl | fluoromethyl | |
| 1.2.985 | 3-trifluoromethoxy-5-(hydroxycarbonyl)phenyl | fluoromethyl | |
| 1.2.986 | 3-(2,2,2-trifluoroethoxy)-5-(hydroxy-carbonyl)phenyl | fluoromethyl | |
| 1.2.987 | 3-(2-chloroethoxy)-5-(hydroxycarbonyl)phenyl | fluoromethyl | |
| 1.2.988 | 3-(2-hydroxyethoxy)-5-(hydroxycarbonyl)phenyl | fluoromethyl | |
| 1.2.989 | 3-[tert-butoxycarbonyl)oxy]-5-(hydroxycarbonyl)phenyl | fluoromethyl | |
| 1.2.990 | 3-nitro-5-(hydroxycarbonyl)phenyl | fluoromethyl | |
| 1.2.991 | 3-acetoxy-5-(hydroxycarbonyl)-phenyl | fluoromethyl | |
| 1.2.992 | (3-[tert-butoxy-carbonyl)amino]-5-(hydroxycarbonyl)phenyl) | fluoromethyl | |
| 1.2.993 | 3-methylsulfanyl-5-(hydroxycarbonyl)phenyl | fluoromethyl | |
| 1.2.994 | 3,5-di(methoxy-carbonyl)phenyl | fluoromethyl | |
| 1.2.995 | 3-hydroxymethyl-5-(methoxycarbonyl)phenyl | fluoromethyl | |
| 1.2.996 | 3-carbamoyl-5-(methoxycarbonyl)-phenyl | fluoromethyl | |
| 1.2.997 | 3-hydroxy-5-(methoxycarbonyl)-phenyl | fluoromethyl | |

TABLE 1.2-continued

Inventive compounds of the general formula (I) in which W* is COOH, $R^1$ and $R^2$ are each hydrogen, and aryl is the radical.

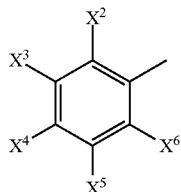

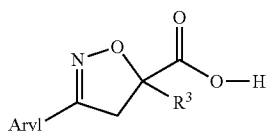

| No. | Aryl | $R^3$ | Physical data |
|---|---|---|---|
| 1.2.998 | 3-methoxy-5-(methoxycarbonyl)-phenyl | fluoromethyl | |
| 1.2.999 | 3-ethoxy-5-(methoxycarbonyl)-phenyl | fluoromethyl | |
| 1.2.1000 | 3-n-propoxy-5-(methoxycarbonyl)-phenyl | fluoromethyl | |
| 1.2.1001 | 3-n-butoxy-5-(methoxycarbonyl)-phenyl | fluoromethyl | |
| 1.2.1002 | 3-isobutoxy-5-(methoxycarbonyl)-phenyl | fluoromethyl | |
| 1.2.1003 | 3-tert-butoxy-5-(methoxycarbonyl)-phenyl | fluoromethyl | |
| 1.2.1004 | 3-difluoromethoxy-5-(methoxycarbonyl)-phenyl | fluoromethyl | |
| 1.2.1005 | 3-trifluoromethoxy-5-(methoxycarbonyl)phenyl | fluoromethyl | |
| 1.2.1006 | 3-(2,2,2-trifluoroethoxy)-5-(methoxy-carbonyl)phenyl | fluoromethyl | |
| 1.2.1007 | 3-(2-chloroethoxy)-5-(methoxycarbonyl)phenyl | fluoromethyl | |
| 1.2.1008 | 3-(2-hydroxyethoxy)-5-(methoxycarbonyl)phenyl | fluoromethyl | |
| 1.2.1009 | 3-[tert-butoxycarbonyl)oxy]-5-(methoxycarbonyl)phenyl | fluoromethyl | |
| 1.2.1010 | 3-nitro-5-(methoxycarbonyl)phenyl | fluoromethyl | |
| 1.2.1011 | 3-acetoxy-5-(methoxycarbonyl)-phenyl | fluoromethyl | |
| 1.2.1012 | {3-[tert-butoxycarbonyl)amino]-5-(methoxycarbonyl)phenyl} | fluoromethyl | |
| 1.2.1013 | 3-methylsulfanyl-5-(methoxycarbonyl)phenyl | fluoromethyl | |
| 1.2.1014 | 3,5-di(hydroxymethyl)phenyl | fluoromethyl | |
| 1.2.1015 | 3-carbamoyl-5-hydroxymethylphenyl | fluoromethyl | |
| 1.2.1016 | 3-hydroxy-5-hydroxymethylphenyl | fluoromethyl | |
| 1.2.1017 | 3-methoxy-5-hydroxymethylphenyl | fluoromethyl | |
| 1.2.1018 | 3-ethoxy-5-hydroxymethylphenyl | fluoromethyl | |
| 1.2.1019 | 3-n-propoxy-5-hydroxymethylphenyl | fluoromethyl | |
| 1.2.1020 | 3-n-butoxy-5-hydroxymethylphenyl | fluoromethyl | |
| 1.2.1021 | 3-isobutoxy-5-hydroxymethylphenyl | fluoromethyl | |
| 1.2.1022 | 3-tert-butoxy-5-hydroxymethylphenyl | fluoromethyl | |
| 1.2.1023 | 3-difluoromethoxy-5-hydroxymethylphenyl | fluoromethyl | |
| 1.2.1024 | 3-trifluoromethoxy-5-hydroxymethylphenyl | fluoromethyl | |
| 1.2.1025 | 3-(2,2,2-trifluoroethoxy)-5-hydroxymethylphenyl | fluoromethyl | |
| 1.2.1026 | 3-(2-chloroethoxy)-5-hydroxymethylphenyl | fluoromethyl | |
| 1.2.1027 | 3-(2-hydroxyethoxy)-5-hydroxymethyl-phenyl | fluoromethyl | |
| 1.2.1028 | 3-[tert-butoxycarbonyl)oxy]-5-hydroxymethylphenyl | fluoromethyl | |
| 1.2.1029 | 3-nitro-5-hydroxymethylphenyl | fluoromethyl | |
| 1.2.1030 | 3-acetoxy-5-hydroxymethylphenyl | fluoromethyl | |

TABLE 1.2-continued

Inventive compounds of the general formula (I) in which W* is COOH, R$^1$ and R$^2$ are each hydrogen, and aryl is the radical.

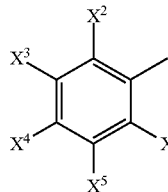

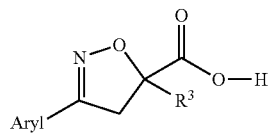

| No. | Aryl | R$^3$ | Physical data |
|---|---|---|---|
| 1.2.1031 | {3-[tert-butoxycarbonyl)amino]-5-hydroxymethyl-phenyl} | fluoromethyl | |
| 1.2.1032 | 3-methylsulfanyl-5-hydroxymethylphenyl | fluoromethyl | |
| 1.2.1033 | 3,5-dicarbamoyl-5-carbamoylphenyl | fluoromethyl | |
| 1.2.1034 | 3-hydroxy-5-carbamoylphenyl | fluoromethyl | |
| 1.2.1035 | 3-methoxy-5-carbamoylphenyl | fluoromethyl | |
| 1.2.1036 | 3-ethoxy-5-carbamoylphenyl | fluoromethyl | |
| 1.2.1037 | 3-n-propoxy-5-carbamoylphenyl | fluoromethyl | |
| 1.2.1038 | 3-n-butoxy-5-carbamoylphenyl | fluoromethyl | |
| 1.2.1039 | 3-isobutoxy-5-carbamoylphenyl | fluoromethyl | |
| 1.2.1040 | 3-tert-butoxy-5-carbamoylphenyl | fluoromethyl | |
| 1.2.1041 | 3-difluoromethoxy-5-carbamoylphenyl | fluoromethyl | |
| 1.2.1042 | 3-trifluoromethoxy-5-carbamoylphenyl | fluoromethyl | |
| 1.2.1043 | 3-(2,2,2-trifluoroethoxy)-5-carbamoylphenyl | fluoromethyl | |
| 1.2.1044 | 3-(2-chloroethoxy)-5-carbamoylphenyl | fluoromethyl | |
| 1.2.1045 | 3-(2-hydroxyethoxy)-5-carbamoylphenyl | fluoromethyl | |
| 1.2.1046 | 3-[tert-butoxycarbonyl)oxy]-5-carbamoylphenyl | fluoromethyl | |
| 1.2.1047 | 3-nitro-5-carbamoylphenyl | fluoromethyl | |
| 1.2.1048 | 3-acetoxy-5-carbamoylphenyl | fluoromethyl | |
| 1.2.1049 | {3-[(tert-butoxycarbonyl)amino]-5-carbamoylphenyl} | fluoromethyl | |
| 1.2.1050 | 3-methylsulfanyl-5-carbamoylphenyl | fluoromethyl | |
| 1.2.1051 | 3,5-dihydroxyphenyl | fluoromethyl | |
| 1.2.1052 | 3-methoxy-5-hydroxyphenyl | fluoromethyl | |
| 1.2.1053 | 3-ethoxy-5-hydroxyphenyl | fluoromethyl | |
| 1.2.1054 | 3-n-propoxy-5-hydroxyphenyl | fluoromethyl | |
| 1.2.1055 | 3-n-butoxy-5-hydroxyphenyl | fluoromethyl | |
| 1.2.1056 | 3-isobutoxy-5-hydroxyphenyl | fluoromethyl | |
| 1.2.1057 | 3-tert-butoxy-5-hydroxyphenyl | fluoromethyl | |
| 1.2.1058 | 3-difluoromethoxy-5-hydroxyphenyl | fluoromethyl | |
| 1.2.1059 | 3-trifluoromethoxy-5-hydroxyphenyl | fluoromethyl | |
| 1.2.1060 | 3-(2,2,2-trifluoroethoxy)-5-hydroxyphenyl | fluoromethyl | |
| 1.2.1061 | 3-(2-chloroethoxy)-5-hydroxyphenyl | fluoromethyl | |
| 1.2.1062 | 3-(2-hydroxyethoxy)-5-hydroxyphenyl | fluoromethyl | |
| 1.2.1063 | 3-[tert-butoxycarbonyl)oxy]-5-hydroxyphenyl | fluoromethyl | |
| 1.2.1064 | 3-nitro-5-hydroxyphenyl | fluoromethyl | |
| 1.2.1065 | 3-acetoxy-5-hydroxyphenyl | fluoromethyl | |
| 1.2.1066 | {3-[(tert-butoxycarbonyl)amino]-5-hydroxyphenyl} | fluoromethyl | |
| 1.2.1067 | 3-methylsulfanyl-5-hydroxyphenyl | fluoromethyl | |
| 1.2.1068 | 3,5-dimethoxyphenyl | fluoromethyl | |
| 1.2.1069 | 3-ethoxy-5-methoxyphenyl | fluoromethyl | |
| 1.2.1070 | 3-n-propoxy-5-methoxyphenyl | fluoromethyl | |
| 1.2.1071 | 3-n-butoxy-5-methoxyphenyl | fluoromethyl | |
| 1.2.1072 | 3-isobutoxy-5-methoxyphenyl | fluoromethyl | |
| 1.2.1073 | 3-tert-butoxy-5-methoxyphenyl | fluoromethyl | |

TABLE 1.2-continued

Inventive compounds of the general formula (I) in which W* is COOH, $R^1$ and $R^2$ are each hydrogen, and aryl is the radical.

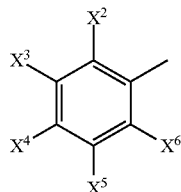

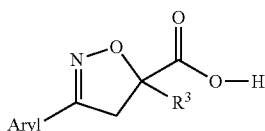

| No. | Aryl | $R^3$ | Physical data |
|---|---|---|---|
| 1.2.1074 | 3-difluoromethoxy-5-methoxyphenyl | fluoromethyl | |
| 1.2.1075 | 3-trifluoromethoxy-5-methoxyphenyl | fluoromethyl | |
| 1.2.1076 | 3-(2,2,2-trifluoroethoxy)-5-methoxyphenyl | fluoromethyl | |
| 1.2.1077 | 3-(2-chloroethoxy)-5-methoxyphenyl | fluoromethyl | |
| 1.2.1078 | 3-(2-hydroxyethoxy)-5-methoxyphenyl | fluoromethyl | |
| 1.2.1079 | 3-[tert-butoxycarbonyl)oxy]-5-methoxyphenyl | fluoromethyl | |
| 1.2.1080 | 3-nitro-5-methoxyphenyl | fluoromethyl | |
| 1.2.1081 | 3-acetoxy-5-methoxyphenyl | fluoromethyl | |
| 1.2.1082 | {3-[(tert-butoxycarbonyl)amino]-5-methoxyphenyl} | fluoromethyl | |
| 1.2.1083 | 3-methylsulfanyl-5-methoxyphenyl | fluoromethyl | |
| 1.2.1084 | 3,5-diethoxyphenyl | fluoromethyl | |
| 1.2.1085 | 3-n-propoxy-5-ethoxyphenyl | fluoromethyl | |
| 1.2.1086 | 3-n-butoxy-5-ethoxyphenyl | fluoromethyl | |
| 1.2.1087 | 3-isobutoxy-5-ethoxyphenyl | fluoromethyl | |
| 1.2.1088 | 3-tert-butoxy-5-ethoxyphenyl | fluoromethyl | |
| 1.2.1089 | 3-difluoromethoxy-5-ethoxyphenyl | fluoromethyl | |
| 1.2.1090 | 3-trifluoromethoxy-5-ethoxyphenyl | fluoromethyl | |
| 1.2.1091 | 3-(2,2,2-trifluoroethoxy)-5-ethoxyphenyl | fluoromethyl | |
| 1.2.1092 | 3-(2-chloroethoxy)-5-ethoxyphenyl | fluoromethyl | |
| 1.2.1093 | 3-(2-hydroxyethoxy)-5-ethoxyphenyl | fluoromethyl | |
| 1.2.1094 | 3-[tert-butoxycarbonyl)oxy]-5-ethoxyphenyl | fluoromethyl | |
| 1.2.1095 | 3-nitro-5-ethoxyphenyl | fluoromethyl | |
| 1.2.1096 | 3-acetoxy-5-ethoxyphenyl | fluoromethyl | |
| 1.2.1097 | {3-[(tert-butoxycarbonyl)amino]-5-ethoxyphenyl} | fluoromethyl | |
| 1.2.1098 | 3-methylsulfanyl-5-ethoxyphenyl | fluoromethyl | |
| 1.2.1099 | 3,5-dipropoxyphenyl | fluoromethyl | |
| 1.2.1100 | 3-n-butoxy-5-propoxyphenyl | fluoromethyl | |
| 1.2.1101 | 3-isobutoxy-5-propoxyphenyl | fluoromethyl | |
| 1.2.1102 | 3-tert-butoxy-5-propoxyphenyl | fluoromethyl | |
| 1.2.1103 | 3-difluoromethoxy-5-propoxyphenyl | fluoromethyl | |
| 1.2.1104 | 3-trifluoromethoxy-5-propoxyphenyl | fluoromethyl | |
| 1.2.1105 | 3-(2,2,2-trifluoroethoxy)-5-propoxyphenyl | fluoromethyl | |
| 1.2.1106 | 3-(2-chloroethoxy)-5-propoxyphenyl | fluoromethyl | |
| 1.2.1107 | 3-(2-hydroxyethoxy)-5-propoxyphenyl | fluoromethyl | |
| 1.2.1108 | 3-[tert-butoxycarbonyl)oxy]-5-propoxyphenyl | fluoromethyl | |
| 1.2.1109 | 3-nitro-5-propoxyphenyl | fluoromethyl | |
| 1.2.1110 | 3-acetoxy-5-propoxyphenyl | fluoromethyl | |
| 1.2.1111 | {3-[(tert-butoxycarbonyl)amino]-5-propoxyphenyl} | fluoromethyl | |
| 1.2.1112 | 3-methylsulfanyl-5-propoxyphenyl | fluoromethyl | |
| 1.2.1113 | 3,5-di(isopropoxy)phenyl | fluoromethyl | |
| 1.2.1114 | 3-n-butoxy-5-isopropoxyphenyl | fluoromethyl | |
| 1.2.1115 | 3-isobutoxy-5-isopropoxyphenyl | fluoromethyl | |
| 1.2.1116 | 3-tert-butoxy-5-isopropoxyphenyl | fluoromethyl | |

TABLE 1.2-continued

Inventive compounds of the general formula (I) in which W* is COOH, R¹ and R² are each hydrogen, and aryl is the radical.

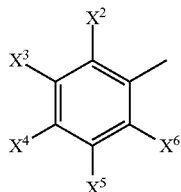

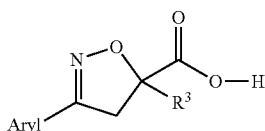

| No. | Aryl | R³ | Physical data |
|---|---|---|---|
| 1.2.1117 | 3-difluoromethoxy-5-isopropoxyphenyl | fluoromethyl | |
| 1.2.1118 | 3-trifluoromethoxy-5-isopropoxyphenyl | fluoromethyl | |
| 1.2.1119 | 3-(2,2,2-trifluoroethoxy)-5-isopropoxyphenyl | fluoromethyl | |
| 1.2.1120 | 3-(2-chloroethoxy)-5-isopropoxyphenyl | fluoromethyl | |
| 1.2.1121 | 3-(2-hydroxyethoxy)-5-isopropoxyphenyl | fluoromethyl | |
| 1.2.1122 | 3-[tert-butoxycarbonyl)oxy]-5-isopropoxyphenyl | fluoromethyl | |
| 1.2.1123 | 3-nitro-5-isopropoxyphenyl | fluoromethyl | |
| 1.2.1124 | 3-acetoxy-5-isopropoxyphenyl | fluoromethyl | |
| 1.2.1125 | {3-[tert-butoxycarbonyl)amino]-5-isopropoxyphenyl} | fluoromethyl | |
| 1.2.1126 | 3-methylsulfanyl-5-isopropoxyphenyl | fluoromethyl | |
| 1.2.1127 | 3,5-di(tert-butoxy)-phenyl | fluoromethyl | |
| 1.2.1128 | 3-difluoromethoxy-5-tert-butoxyphenyl | fluoromethyl | |
| 1.2.1129 | 3-trifluoromethoxy-5-tert-butoxyphenyl | fluoromethyl | |
| 1.2.1130 | 3-(2,2,2-trifluoroethoxy)-5-tert-butoxyphenyl | fluoromethyl | |
| 1.2.1131 | 3-(2-chloroethoxy)-5-tert-butoxylphenyl | fluoromethyl | |
| 1.2.1132 | 3-(2-hydroxyethoxy)-5-tert-butoxyphenyl | fluoromethyl | |
| 1.2.1133 | 3-[tert-butoxycarbonyl)oxy]-5-tert-butoxyphenyl | fluoromethyl | |
| 1.2.1134 | 3-nitro-5-tert-butoxyphenyl | fluoromethyl | |
| 1.2.1135 | 3-acetoxy-5-tert-butoxyphenyl | fluoromethyl | |
| 1.2.1136 | {3-[tert-butoxycarbonyl)amino]-5-tert-butoxyphenyl} | fluoromethyl | |
| 1.2.1137 | 3-methylsulfanyl-5-tert-butoxyphenyl | fluoromethyl | |
| 1.2.1138 | 3,5-di(trifluoromethoxy)phenyl | fluoromethyl | |
| 1.2.1139 | 3-(2,2,2-trifluoroethoxy)-5-trifluoromethoxyphenyl | fluoromethyl | |
| 1.2.1140 | 3-(2-chloroethoxy)-5-trifluoromethoxyphenyl | fluoromethyl | |
| 1.2.1141 | 3-(2-hydroxyethoxy)-5-trifluoromethoxyphenyl | fluoromethyl | |
| 1.2.1142 | 3-[tert-butoxycarbonyl)oxy]-5-trifluoromethoxyphenyl | fluoromethyl | |
| 1.2.1143 | 3-nitro-5-trifluoromethoxyphenyl | fluoromethyl | |
| 1.2.1144 | 3-acetoxy-5-tert-butoxyphenyl | fluoromethyl | |
| 1.2.1145 | {3-[(tert-butoxycarbonyl)amino]-5-trifluoromethoxyphenyl} | fluoromethyl | |
| 1.2.1146 | 3-methylsulfanyl-5-trifluoromethoxy-phenyl | fluoromethyl | |
| 1.2.1147 | 3,5-bis(difluoromethoxy)phenyl | fluoromethyl | |
| 1.2.1148 | 3,5-bis(difluoromethoxy)phenyl | chloromethyl | |
| 1.2.1149 | 3,5-bis(difluoromethoxy)phenyl | bromomethyl | |
| 1.2.1150 | 3,5-bis(difluoromethoxy)phenyl | fluoromethyl | |

TABLE 1.2-continued

Inventive compounds of the general formula (I) in which W* is COOH, R¹ and R² are each hydrogen, and aryl is the radical.

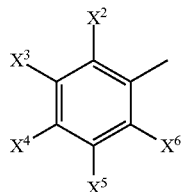

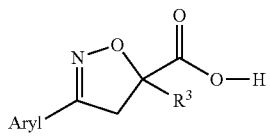

| No. | Aryl | R³ | Physical data |
|---|---|---|---|
| 1.2.1151 | 3-trifluoromethoxy-5-difluoromethoxyphenyl | fluoromethyl | |
| 1.2.1152 | 3-(2,2,2-trifluoroethoxy)-5-difluoro-methoxyphenyl | fluoromethyl | |
| 1.2.1153 | 3-(2-chloroethoxy)-5-difluoromethoxyphenyl | fluoromethyl | |
| 1.2.1154 | 3-(2-hydroxyethoxy)-5-difluoromethoxyphenyl | fluoromethyl | |
| 1.2.1155 | 3-[tert-butoxycarbonyl)oxy]-5-difluoromethoxyphenyl | fluoromethyl | |
| 1.2.1156 | 3-nitro-5-difluoromethoxyphenyl | fluoromethyl | |
| 1.2.1157 | 3-acetoxy-5-difluoromethoxyphenyl | fluoromethyl | |
| 1.2.1158 | {3-[tert-butoxycarbonyl)amino]-5-difluoromethoxyphenyl} | fluoromethyl | |
| 1.2.1159 | 3-methylsulfanyl-5-difluoromethoxyphenyl | fluoromethyl | |
| 1.2.1160 | 3,5-bis(2,2,2-trifluoroethoxy)-phenyl | fluoromethyl | |
| 1.2.1161 | 3-(2-chloroethoxy)-5-(2,2,2-trifluoro-ethoxy)phenyl | fluoromethyl | |
| 1.2.1162 | 3-(2-hydroxyethoxy)-5-(2,2,2-trifluoroethoxy)phenyl | fluoromethyl | |
| 1.2.1163 | 3-[tert-butoxycarbonyl)oxy]-5-(2,2,2-trifluoroethoxy)-phenyl | fluoromethyl | |
| 1.2.1164 | 3-nitro-5-(2,2,2-trifluoroethoxy)-phenyl | fluoromethyl | |
| 1.2.1165 | 3-acetoxy-5-(2,2,2-trifluoroethoxy)-phenyl | fluoromethyl | |
| 1.2.1166 | {3-[tert-butoxycarbonyl)amino]-5-(2,2,2-trifluoroethoxy)phenyl} | fluoromethyl | |
| 1.2.1167 | 3-methylsulfanyl-5-(2,2,2-trifluoro-ethoxy)phenyl | fluoromethyl | |
| 1.2.1168 | 3,5-bis(2-chloroethoxy)phenyl | fluoromethyl | |
| 1.2.1169 | 3-(2-hydroxyethoxy)-5-(2-chloroethoxy)phenyl | fluoromethyl | |
| 1.2.1170 | 3-[tert-butoxycarbonyl)oxy]-5-(2-chloroethoxy)phenyl | fluoromethyl | |
| 1.2.1171 | 3-nitro-5-(2-chloroethoxy)-phenyl | fluoromethyl | |
| 1.2.1172 | 3-acetoxy-5-(2-chloroethoxy)-phenyl | fluoromethyl | |
| 1.2.1173 | {3-[tert-butoxycarbonyl)amino]-5-(2-chloroethoxy)phenyl} | fluoromethyl | |
| 1.2.1174 | 3-methylsulfanyl-5-(2-chloroethoxy)phenyl | fluoromethyl | |
| 1.2.1175 | 3,5-bis(2-hydroxyethoxy)phenyl | fluoromethyl | |
| 1.2.1176 | 3-[tert-butoxycarbonyl)oxy]-5-(2-hydroxyethoxy)phenyl | fluoromethyl | |
| 1.2.1177 | 3-nitro-5-(2-hydroxy-ethoxy)phenyl | fluoromethyl | |
| 1.2.1178 | 3-acetoxy-5-(2-hydroxyethoxy)-phenyl | fluoromethyl | |
| 1.2.1179 | 3-[tert-butoxycarbonyl)amino]-5-(2-hydroxyethoxy)phenyl | fluoromethyl | |
| 1.2.1180 | 3-methylsulfanyl-5-(2-hydroxyethoxy)phenyl | fluoromethyl | |
| 1.2.1181 | 3,5-bis[(tert-butoxy-carbonyl)oxy]phenyl | fluoromethyl | |
| 1.2.1182 | 3-nitro-5-[(tert-butoxy-carbonyl)oxy]phenyl | fluoromethyl | |

TABLE 1.2-continued

Inventive compounds of the general formula (I) in which W* is COOH, $R^1$ and $R^2$ are each hydrogen, and aryl is the radical.

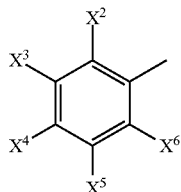

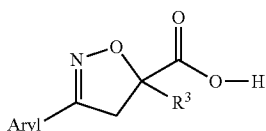

| No. | Aryl | $R^3$ | Physical data |
|---|---|---|---|
| 1.2.1183 | 3-acetoxy-5-[(tert-butoxy-carbonyl)oxy]phenyl | fluoromethyl | |
| 1.2.1184 | {3-[tert-butoxycarbonyl)amino]-5-[(tert-butoxycarbonyl)oxy]phenyl} | fluoromethyl | |
| 1.2.1185 | 3,5-bis(acetoxy)phenyl | fluoromethyl | |
| 1.2.1186 | {3-[tert-butoxycarbonyl)amino]-5-acetoxyphenyl} | fluoromethyl | |
| 1.2.1187 | 3-methylsulfanyl-5-acetoxyphenyl | fluoromethyl | |
| 1.2.1188 | 3,5-dinitrophenyl | fluoromethyl | |
| 1.2.1189 | 3-acetoxy-5-nitrophenyl | fluoromethyl | |
| 1.2.1190 | {3-[tert-butoxycarbonyl)amino]-5-nitrophenyl} | fluoromethyl | |
| 1.2.1191 | 3-methylsulfanyl-5-nitrophenyl | fluoromethyl | |
| 1.2.1192 | 3,5-bis[(tert-butoxycarbonyl)-amino]phenyl | fluoromethyl | |
| 1.2.1193 | 3-methylsulfanyl-5-[(tert-butoxy-carbonyl)amino]phenyl | fluoromethyl | |
| 1.2.1194 | 3,5-di(methylsulfanyl)phenyl | fluoromethyl | |
| 1.2.1195 | 3,4-difluorophenyl | fluoromethyl | |
| 1.2.1196 | 3,4-difluorophenyl | chloromethyl | |
| 1.2.1197 | 3,4-difluorophenyl | bromomethyl | |
| 1.2.1198 | 3,4-difluorophenyl | difluoromethyll | |
| 1.2.1199 | 3,4-difluorophenyl | trifluoromethyl | |
| 1.2.1200 | 3,4-difluorophenyl | cyano | |
| 1.2.1201 | 3-chloro-4-fluorophenyl | fluoromethyl | |
| 1.2.1202 | 3-chloro-4-fluorophenyl | chloromethyl | |
| 1.2.1203 | 3-chloro-4-fluorophenyl | bromomethyl | |
| 1.2.1204 | 3-chloro-4-fluorophenyl | difluoromethyl | |
| 1.2.1205 | 3-chloro-4-fluorophenyl | trifluoromethyl | [CDCl$_3$] 3.81 (d, 1H); 4.00 (d, 1H); 7.22 (m, 1H); 7.58 (m, 1H); 7.74 (m, 1H). |
| 1.2.1206 | 3-chloro-4-fluorophenyl | cyano | |
| 1.2.1207 | 3-bromo-4-fluorophenyl | fluoromethyl | |
| 1.2.1208 | 3-methyl-4-fluorophenyl | fluoromethyl | |
| 1.2.1209 | 3-methyl-4-fluorophenyl | chloromethyl | |
| 1.2.1210 | 3-ethyl-4-fluorophenyl | fluoromethyl | |
| 1.2.1211 | 3-cyclopropyl-4-fluorophenyl | fluoromethyl | |
| 1.2.1212 | 3-cyano-4-fluorophenyl | fluoromethyl | |
| 1.2.1213 | 3-methoxy-4-fluorophenyl | fluoromethyl | |
| 1.2.1214 | 3-ethoxy-4-fluorophenyl | fluoromethyl | |
| 1.2.1215 | 3-trifluoromethoxy-4-fluorophenyl | fluoromethyl | |
| 1.2.1216 | 3-nitro-4-fluorophenyl | fluoromethyl | |
| 1.2.1217 | 3-fluoro-4-chlorophenyl | fluoromethyl | |
| 1.2.1218 | 3,4-dichlorophenyl | fluoromethyl | |
| 1.2.1219 | 3-bromo-4-chlorophenyl | fluoromethyl | |
| 1.2.1220 | 3-methyl-4-chlorophenyl | fluoromethyl | |
| 1.2.1221 | 3-cyclopropyl-4-chlorophenyl | fluoromethyl | |
| 1.2.1222 | 3-cyano-4-chlorophenyl | fluoromethyl | |
| 1.2.1223 | 3-trifluoromethyl-4-chlorophenyl | fluoromethyl | |
| 1.2.1224 | 3-methoxy-4-chlorophenyl | fluoromethyl | |
| 1.2.1225 | 3-ethoxy-4-chlorophenyl | fluoromethyl | |
| 1.2.1226 | 3-trifluoromethoxy-4-chlorophenyl | fluoromethyl | |
| 1.2.1227 | 3-nitro-4-chlorophenyl | fluoromethyl | |
| 1.2.1228 | 3-fluoro-4-bromophenyl | fluoromethyl | |
| 1.2.1229 | 3-chloro-4-bromophenyl | fluoromethyl | |
| 1.2.1230 | 3,4-dibromophenyl | fluoromethyl | |
| 1.2.1231 | 3-methyl-4-bromophenyl | fluoromethyl | |

TABLE 1.2-continued

Inventive compounds of the general formula (I) in which W* is COOH, $R^1$ and $R^2$ are each hydrogen, and aryl is the radical.

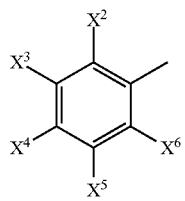

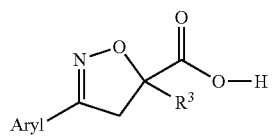

| No. | Aryl | $R^3$ | Physical data |
|---|---|---|---|
| 1.2.1232 | 3-ethyl-4-bromophenyl | fluoromethyl | |
| 1.2.1233 | 3-cyclopropyl-4-bromophenyl | fluoromethyl | |
| 1.2.1234 | 3-cyano-4-bromophenyl | fluoromethyl | |
| 1.2.1235 | 3-trifluoromethyl-4-bromophenyl | fluoromethyl | |
| 1.2.1236 | 3-methoxy-4-phenyl | fluoromethyl | |
| 1.2.1237 | 3-ethoxy-4-bromophenyl | fluoromethyl | |
| 1.2.1238 | 3-trifluoromethoxy-4-bromophenyl | fluoromethyl | |
| 1.2.1239 | 3-nitro-4-bromophenyl | fluoromethyl | |
| 1.2.1240 | 3-fluoro-4-iodophenyl | fluoromethyl | |
| 1.2.1241 | 3-chloro-4-iodophenyl | fluoromethyl | |
| 1.2.1242 | 3-bromo-4-iodophenyl | fluoromethyl | |
| 1.2.1243 | 3-methyl-4-iodophenyl | fluoromethyl | |
| 1.2.1244 | 3-ethyl-4-iodophenyl | fluoromethyl | |
| 1.2.1245 | 3-cyclopropyl-4-iodophenyl | fluoromethyl | |
| 1.2.1246 | 3-cyano-4-iodophenyl | fluoromethyl | |
| 1.2.1247 | 3-trifluoromethyl-4-iodophenyl | fluoromethyl | |
| 1.2.1248 | 3-methoxy-4-iodophenyl | fluoromethyl | |
| 1.2.1249 | 3-ethoxy-4-iodophenyl | fluoromethyl | |
| 1.2.1250 | 3-trifluoromethoxy-4-iodophenyl | fluoromethyl | |
| 1.2.1251 | 3-nitro-4-iodophenyl | fluoromethyl | |
| 1.2.1252 | 3-fluoro-4-methylphenyl | fluoromethyl | |
| 1.2.1253 | 3-chloro-4-methylphenyl | fluoromethyl | |
| 1.2.1254 | 3-bromo-4-methylphenyl | fluoromethyl | |
| 1.2.1255 | 3,4-dimethylphenyl | fluoromethyl | |
| 1.2.1256 | 3,4-dimethylphenyl | chloromethyl | |
| 1.2.1257 | 3,4-dimethylphenyl | bromomethyl | |
| 1.2.1258 | 3,4-dimethylphenyl | difluoromethyl | |
| 1.2.1259 | 3,4-dimethylphenyl | trifluoromethyl | |
| 1.2.1260 | 3,4-dimethylphenyl | cyano | |
| 1.2.1261 | 3-ethyl-4-methylphenyl | fluoromethyl | |
| 1.2.1262 | 3-cyclopropyl-4-methylphenyl | fluoromethyl | |
| 1.2.1263 | 3-cyano-4-methylphenyl | fluoromethyl | |
| 1.2.1264 | 3-trifluoromethyl-4-methylphenyl | fluoromethyl | |
| 1.2.1265 | 3-methoxy-4-methylphenyl | fluoromethyl | |
| 1.2.1266 | 3-ethoxy-4-methylphenyl | fluoromethyl | |
| 1.2.1267 | 3-trifluoromethoxy-4-methylphenyl | fluoromethyl | |
| 1.2.1268 | 3-nitro-4-methylphenyl | fluoromethyl | |
| 1.2.1269 | 3-fluoro-4-ethylphenyl | fluoromethyl | |
| 1.2.1270 | 3-chloro-4-ethylphenyl | fluoromethyl | |
| 1.2.1271 | 3-bromo-4-ethylphenyl | fluoromethyl | |
| 1.2.1272 | 3-methyl-4-ethylphenyl | fluoromethyl | |
| 1.2.1273 | 3,4-diethylphenyl | fluoromethyl | |
| 1.2.1274 | 3-cyclopropyl-4-ethylphenyl | fluoromethyl | |
| 1.2.1275 | 3-cyano-4-ethylphenyl | fluoromethyl | |
| 1.2.1276 | 3-trifluoromethyl-4-ethylphenyl | fluoromethyl | |
| 1.2.1277 | 3-methoxy-4-ethylphenyl | fluoromethyl | |
| 1.2.1278 | 3-ethoxy-4-ethylphenyl | fluoromethyl | |
| 1.2.1279 | 3-trifluoromethoxy-4-ethylphenyl | fluoromethyl | |
| 1.2.1280 | 3-nitro-4-ethylphenyl | fluoromethyl | |
| 1.2.1281 | 3-fluoro-4-propylphenyl | fluoromethyl | |
| 1.2.1282 | 3-chloro-4-propylphenyl | fluoromethyl | |
| 1.2.1283 | 3-bromo-4-propylphenyl | fluoromethyl | |
| 1.2.1284 | 3-methyl-4-propylphenyl | fluoromethyl | |
| 1.2.1285 | 3-cyclopropyl-4-propylphenyl | fluoromethyl | |
| 1.2.1286 | 3-cyano-4-propylphenyl | fluoromethyl | |
| 1.2.1287 | 3-trifluoromethyl-4-propylphenyl | fluoromethyl | |
| 1.2.1288 | 3-methoxy-4-propylphenyl | fluoromethyl | |

TABLE 1.2-continued

Inventive compounds of the general formula (I) in which W* is COOH, $R^1$ and $R^2$ are each hydrogen, and aryl is the radical.

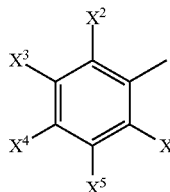

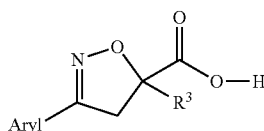

| No. | Aryl | $R^3$ | Physical data |
|---|---|---|---|
| 1.2.1289 | 3-ethoxy-4-propylphenyl | fluoromethyl | |
| 1.2.1290 | 3-trifluoromethoxy-4-propylphenyl | fluoromethyl | |
| 1.2.1291 | 3-nitro-4-propylphenyl | fluoromethyl | |
| 1.2.1292 | 3-fluoro-4-isopropylphenyl | fluoromethyl | |
| 1.2.1293 | 3-chloro-4-isopropylphenyl | fluoromethyl | |
| 1.2.1294 | 3-bromo-4-isopropylphenyl | fluoromethyl | |
| 1.2.1295 | 3-methyl-4-isopropylphenyl | fluoromethyl | |
| 1.2.1296 | 3-ethyl-4-isopropylphenyl | fluoromethyl | |
| 1.2.1297 | 3-cyclopropyl-4-isopropylphenyl | fluoromethyl | |
| 1.2.1298 | 3-cyano-4-isopropylphenyl | fluoromethyl | |
| 1.2.1299 | 3-trifluoromethyl-4-isopropylphenyl | fluoromethyl | |
| 1.2.1300 | 3-methoxy-4-isopropylphenyl | fluoromethyl | |
| 1.2.1301 | 3-ethoxy-4-isopropylphenyl | fluoromethyl | |
| 1.2.1302 | 3-trifluoromethoxy-4-isopropylphenyl | fluoromethyl | |
| 1.2.1303 | 3-nitro-4-isopropylphenyl | fluoromethyl | |
| 1.2.1304 | 3-fluoro-4-tert-butylphenyl | fluoromethyl | |
| 1.2.1305 | 3-chloro-4-tert-butylphenyl | fluoromethyl | |
| 1.2.1306 | 3-bromo-4-tert-butylphenyl | fluoromethyl | |
| 1.2.1307 | 3-methyl-4-tert-butylphenyl | fluoromethyl | |
| 1.2.1308 | 3-cyclopropyl-4-tert-butylphenyl | fluoromethyl | |
| 1.2.1309 | 3-cyano-4-tert-butylphenyl | fluoromethyl | |
| 1.2.1310 | 3-trifluoromethyl-4-tert-butylphenyl | fluoromethyl | |
| 1.2.1311 | 3-trifluoromethyl-4-tert-butylphenyl | chloromethyl | |
| 1.2.1312 | 3-trifluoromethyl-4-tert-butylphenyl | bromomethyl | |
| 1.2.1313 | 3-trifluoromethyl-4-tert-butylphenyl | difluoromethyl | |
| 1.2.1314 | 3-methoxy-4-tert-butylphenyl | fluoromethyl | |
| 1.2.1315 | 3-ethoxy-4-tert-butylphenyl | fluoromethyl | |
| 1.2.1316 | 3-trifluoromethoxy-4-tert-butylphenyl | fluoromethyl | |
| 1.2.1317 | 3-nitro-4-tert-butylphenyl | fluoromethyl | |
| 1.2.1318 | 3-fluoro-4-cyclopropylphenyl | fluoromethyl | |
| 1.2.1319 | 3-chloro-4-cyclopropylphenyl | fluoromethyl | |
| 1.2.1320 | 3-bromo-4-cyclopropylphenyl | fluoromethyl | |
| 1.2.1321 | 3-methyl-4-cyclopropylphenyl | fluoromethyl | |
| 1.2.1322 | 3-ethyl-4-cyclopropylphenyl | fluoromethyl | |
| 1.2.1323 | 3-cyclopropyl-4-cyclopropylphenyl | fluoromethyl | |
| 1.2.1324 | 3-cyano-4-cyclopropylphenyl | fluoromethyl | |
| 1.2.1325 | 3-trifluoromethyl-4-cyclopropylphenyl | fluoromethyl | |
| 1.2.1326 | 3-methoxy-4-cyclopropylphenyl | fluoromethyl | |
| 1.2.1327 | 3-ethoxy-4-cyclopropylphenyl | fluoromethyl | |
| 1.2.1328 | 3-trifluoromethoxy-4-cyclopropylphenyl | fluoromethyl | |
| 1.2.1329 | 3-fluoro-4-methoxycarbonyl-phenyl | fluoromethyl | |
| 1.2.1330 | 3-chloro-4-methoxycarbonylphenyl | fluoromethyl | |
| 1.2.1331 | 3-bromo-4-methoxycarbonylphenyl | fluoromethyl | |
| 1.2.1332 | 3-methyl-4-methoxycarbonylphenyl | fluoromethyl | |
| 1.2.1333 | 3-cyclopropyl-4-methoxycarbonyl-phenyl | fluoromethyl | |
| 1.2.1334 | 3-cyano-4-methoxycarbonylphenyl | fluoromethyl | |
| 1.2.1335 | 3-trifluoromethyl-4-methoxycarbonyl-phenyl | fluoromethyl | |
| 1.2.1336 | 3-methoxy-4-methoxycarbonyl-phenyl | fluoromethyl | |

TABLE 1.2-continued

Inventive compounds of the general formula (I) in which W* is COOH, $R^1$ and $R^2$ are each hydrogen, and aryl is the radical.

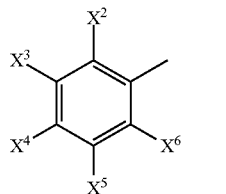

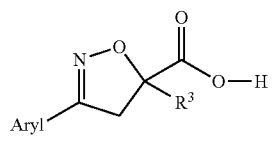

| No. | Aryl | $R^3$ | Physical data |
|---|---|---|---|
| 1.2.1337 | 3-ethoxy-4-methoxycarbonyl-phenyl | fluoromethyl | |
| 1.2.1338 | 3-trifluoromethoxy-4-methoxycarbonyl-phenyl | fluoromethyl | |
| 1.2.1339 | 3-nitro-4-methoxycarbonylphenyl | fluoromethyl | |
| 1.2.1340 | 3-fluoro-4-cyanophenyl | fluoromethyl | |
| 1.2.1341 | 3-chloro-4-cyanophenyl | fluoromethyl | |
| 1.2.1342 | 3-bromo-4-cyanophenyl | fluoromethyl | |
| 1.2.1343 | 3-methyl-4-cyanophenyl | fluoromethyl | |
| 1.2.1344 | 3-cyclopropyl-4-cyanophenyl | fluoromethyl | |
| 1.2.1345 | 3,4-dicyanophenyl | fluoromethyl | |
| 1.2.1346 | 3-trifluoromethyl-4-cyanophenyl | fluoromethyl | |
| 1.2.1347 | 3-trifluoromethyl-4-cyanophenyl | chloromethyl | |
| 1.2.1348 | 3-trifluoromethyl-4-cyanophenyl | bromomethyl | |
| 1.2.1349 | 3-trifluoromethyl-4-cyanophenyl | difluoromethyl | |
| 1.2.1350 | 3-methoxy-4-cyanophenyl | fluoromethyl | |
| 1.2.1351 | 3-ethoxy-4-cyanophenyl | fluoromethyl | |
| 1.2.1352 | 3-trifluoromethoxy-4-cyanophenyl | fluoromethyl | |
| 1.2.1353 | 3-nitro-4-cyanophenyl | fluoromethyl | |
| 1.2.1354 | 3-fluoro-4-methoxyphenyl | fluoromethyl | |
| 1.2.1355 | 3-chloro-4-methoxyphenyl | fluoromethyl | |
| 1.2.1356 | 3-bromo-4-methoxyphenyl | fluoromethyl | |
| 1.2.1357 | 3-methyl-4-methoxyphenyl | fluoromethyl | |
| 1.2.1358 | 3-cyclopropyl-4-methoxyphenyl | fluoromethyl | |
| 1.2.1359 | 3-cyano-4-methoxyphenyl | fluoromethyl | |
| 1.2.1360 | 3-trifluoromethyl-4-methoxyphenyl | fluoromethyl | |
| 1.2.1361 | 3,4-dimethoxyphenyl | fluoromethyl | |
| 1.2.1362 | 3-ethoxy-4-methoxyphenyl | fluoromethyl | |
| 1.2.1363 | 3-trifluoromethoxy-4-methoxyphenyl | fluoromethyl | |
| 1.2.1364 | 3-nitro-4-methoxyphenyl | fluoromethyl | |
| 1.2.1365 | 3-fluoro-4-ethoxyphenyl | fluoromethyl | |
| 1.2.1366 | 3-chloro-4-ethoxyphenyl | fluoromethyl | |
| 1.2.1367 | 3-chloro-4-ethoxyphenyl | chloromethyl | |
| 1.2.1368 | 3-chloro-4-ethoxyphenyl | bromomethyl | |
| 1.2.1369 | 3-chloro-4-ethoxyphenyl | difluoromethyl | |
| 1.2.1370 | 3-bromo-4-ethoxyphenyl | fluoromethyl | |
| 1.2.1371 | 3-methyl-4-ethoxyphenyl | fluoromethyl | |
| 1.2.1372 | 3-ethyl-4-ethoxyphenyl | fluoromethyl | |
| 1.2.1373 | 3-cyclopropyl-4-ethoxyphenyl | fluoromethyl | |
| 1.2.1374 | 3-cyano-4-ethoxyphenyl | fluoromethyl | |
| 1.2.1375 | 3-trifluoromethyl-4-ethoxyphenyl | fluoromethyl | |
| 1.2.1376 | 3-methoxy-4-ethoxyphenyl | fluoromethyl | |
| 1.2.1377 | 2,4-diethoxyphenyl | fluoromethyl | |
| 1.2.1378 | 3-trifluoromethoxy-4-ethoxyphenyl | fluoromethyl | |
| 1.2.1379 | 3-nitro-4-ethoxyphenyl | fluoromethyl | |
| 1.2.1380 | 3-fluoro-4-isopropoxyphenyl | fluoromethyl | |
| 1.2.1381 | 3-chloro-4-isopropoxyphenyl | fluoromethyl | |
| 1.2.1382 | 3-bromo-4-isopropoxyphenyl | fluoromethyl | |
| 1.2.1383 | 3-methyl-4-isopropoxyphenyl | fluoromethyl | |
| 1.2.1384 | 3-cyclopropyl-4-isopropoxyphenyl | fluoromethyl | |
| 1.2.1385 | 3-cyano-4-isopropoxyphenyl | fluoromethyl | |
| 1.2.1386 | 3-trifluoromethyl-4-isopropoxyphenyl | fluoromethyl | |
| 1.2.1387 | 3-methoxy-4-isopropoxyphenyl | fluoromethyl | |
| 1.2.1388 | 3-ethoxy-4-isopropoxyphenyl | fluoromethyl | |
| 1.2.1389 | 3-trifluoromethoxy-4-isopropoxyphenyl | fluoromethyl | |

TABLE 1.2-continued

Inventive compounds of the general formula (I) in which W* is COOH, $R^1$ and $R^2$ are each hydrogen, and aryl is the radical.

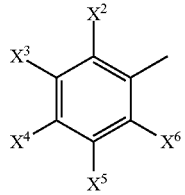

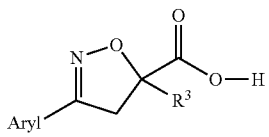

| No. | Aryl | $R^3$ | Physical data |
|---|---|---|---|
| 1.2.1390 | 3-nitro-4-isopropoxyphenyl | fluoromethyl | |
| 1.2.1391 | 3-fluoro-4-trifluoromethoxyphenyl | fluoromethyl | |
| 1.2.1392 | 3-chloro-4-trifluoromethoxyphenyl | fluoromethyl | |
| 1.2.1393 | 3-bromo-4-trifluoromethoxyphenyl | fluoromethyl | |
| 1.2.1394 | 3-methyl-4-trifluoromethoxyphenyl | fluoromethyl | |
| 1.2.1395 | 3-cyclopropyl-4-trifluoromethoxy-phenyl | fluoromethyl | |
| 1.2.1396 | 3-cyano-4-trifluoromethoxyphenyl | fluoromethyl | |
| 1.2.1397 | 3-trifluoromethyl-4-trifluoromethoxy-phenyl | fluoromethyl | |
| 1.2.1398 | 3-methoxy-4-trifluoromethoxy-phenyl | fluoromethyl | |
| 1.2.1399 | 3-ethoxy-4-trifluoromethoxyphenyl | fluoromethyl | |
| 1.2.1400 | 3,4-bis(trifluoromethoxy)phenyl | fluoromethyl | |
| 1.2.1401 | 3-nitro-4-trifluoromethoxyphenyl | fluoromethyl | |
| 1.2.1402 | 3-fluoro-4-difluoromethoxyphenyl | fluoromethyl | |
| 1.2.1403 | 3-chloro-4-difluoromethoxyphenyl | fluoromethyl | |
| 1.2.1404 | 3-bromo-4-difluoromethoxyphenyl | fluoromethyl | |
| 1.2.1405 | 3-methyl-4-difluoromethoxyphenyl | fluoromethyl | |
| 1.2.1406 | 3-cyclopropyl-4-difluoromethoxy-phenyl | fluoromethyl | |
| 1.2.1407 | 3-cyano-4-difluoromethoxyphenyl | fluoromethyl | |
| 1.2.1408 | 3-trifluoromethyl-4-difluoromethoxy-phenyl | fluoromethyl | |
| 1.2.1409 | 3-methoxy-4-difluoromethoxy-phenyl | fluoromethyl | |
| 1.2.1410 | 3-ethoxy-4-difluoromethoxyphenyl | fluoromethyl | |
| 1.2.1411 | 3-trifluoromethoxy-4-difluoromethoxyphenyl | fluoromethyl | |
| 1.2.1412 | 3-nitro-4-difluoromethoxyphenyl | fluoromethyl | |
| 1.2.1413 | 3-fluoro-4-nitrophenyl | fluoromethyl | |
| 1.2.1414 | 3-chloro-4-nitrophenyl | fluoromethyl | |
| 1.2.1415 | 3-bromo-4-nitrophenyl | fluoromethyl | |
| 1.2.1416 | 3-methyl-4-nitrophenyl | fluoromethyl | |
| 1.2.1417 | 3-ethyl-4-nitrophenyl | fluoromethyl | |
| 1.2.1418 | 3-cyclopropyl-4-nitrophenyl | fluoromethyl | |
| 1.2.1419 | 3-cyano-4-nitrophenyl | fluoromethyl | |
| 1.2.1420 | 3-trifluoromethyl-4-nitrophenyl | fluoromethyl | |
| 1.2.1421 | 3-methoxy-4-nitrophenyl | fluoromethyl | |
| 1.2.1422 | 3-ethoxy-4-nitrophenyl | fluoromethyl | |
| 1.2.1423 | 3-trifluoromethoxy-4-nitrophenyl | fluoromethyl | |
| 1.2.1424 | 3-fluoro-4-methylsulfanylphenyl | fluoromethyl | |
| 1.2.1425 | 3-chloro-4-methylsulfanylphenyl | fluoromethyl | |
| 1.2.1426 | 3-bromo-4-methylsulfanylphenyl | fluoromethyl | |
| 1.2.1427 | 3-methyl-4-methylsulfanylphenyl | fluoromethyl | |
| 1.2.1428 | 3-ethyl-4-methylsulfanylphenyl | fluoromethyl | |
| 1.2.1429 | 3-cyclopropyl-4-methylsulfanylphenyl | fluoromethyl | |
| 1.2.1430 | 3-cyano-4-methylsulfanylphenyl | fluoromethyl | |
| 1.2.1431 | 3-trifluoromethyl-4-methylsulfanylphenyl | fluoromethyl | |
| 1.2.1432 | 3-methoxy-4-methylsulfanylphenyl | fluoromethyl | |
| 1.2.1433 | 3-ethoxy-4-methylsulfanylphenyl | fluoromethyl | |
| 1.2.1434 | 3-trifluoromethoxy-4-methylsulfanylphenyl | fluoromethyl | |
| 1.2.1435 | 3-nitro-4-methylsulfanylphenyl | fluoromethyl | |
| 1.2.1436 | 3,6-difluorophenyl | fluoromethyl | |

TABLE 1.2-continued

Inventive compounds of the general formula (I) in which W* is COOH, $R^1$ and $R^2$ are each hydrogen, and aryl is the radical.

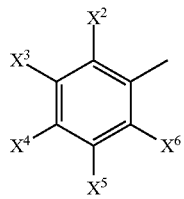

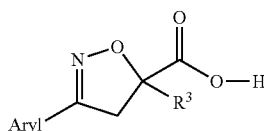

| No. | Aryl | $R^3$ | Physical data |
|---|---|---|---|
| 1.2.1437 | 3,6-difluorophenyl | chloromethyl | |
| 1.2.1438 | 3,6-difluorophenyl | bromomethyl | |
| 1.2.1439 | 3,6-difluorophenyl | difluoromethyl | |
| 1.2.1440 | 3,6-difluorophenyl | trifluoromethyl | |
| 1.2.1441 | 3,6-difluorophenyl | cyano | |
| 1.2.1442 | 3-chloro-6-fluorophenyl | fluoromethyl | |
| 1.2.1443 | 3-bromo-6-fluorophenyl | fluoromethyl | |
| 1.2.1444 | 3-methyl-6-fluorophenyl | fluoromethyl | |
| 1.2.1445 | 3-cyclopropyl-6-fluorophenyl | fluoromethyl | |
| 1.2.1446 | 3-cyano-6-fluorophenyl | fluoromethyl | |
| 1.2.1447 | 3-methoxy-6-fluorophenyl | fluoromethyl | |
| 1.2.1448 | 3-ethoxy-6-fluorophenyl | fluoromethyl | |
| 1.2.1449 | 3-trifluoromethoxy-6-fluorophenyl | fluoromethyl | |
| 1.2.1450 | 3-nitro-6-fluorophenyl | fluoromethyl | |
| 1.2.1451 | 3-fluoro-6-chlorophenyl | fluoromethyl | |
| 1.2.1452 | 3-fluoro-6-chlorophenyl | chloromethyl | |
| 1.2.1453 | 3-fluoro-6-chlorophenyl | bromomethyl | |
| 1.2.1454 | 3-fluoro-6-chlorophenyl | difluoromethyl | |
| 1.2.1455 | 3,6-dichlorophenyl | fluoromethyl | |
| 1.2.1456 | 3,6-dichlorophenyl | chloromethyl | |
| 1.2.1457 | 3,6-dichlorophenyl | bromomethyl | |
| 1.2.1458 | 3,6-dichlorophenyl | difluoromethyl | |
| 1.2.1459 | 3,6-dichlorophenyl | trifluoromethyl | |
| 1.2.1460 | 3,6-dichlorophenyl | cyano | |
| 1.2.1461 | 3-bromo-6-chlorophenyl | fluoromethyl | |
| 1.2.1462 | 3-methyl-6-chlorophenyl | fluoromethyl | |
| 1.2.1463 | 3-cyclopropyl-6-chlorophenyl | fluoromethyl | |
| 1.2.1464 | 3-cyano-6-chlorophenyl | fluoromethyl | |
| 1.2.1465 | 3-trifluoromethyl-6-chlorophenyl | fluoromethyl | |
| 1.2.1466 | 3-methoxy-6-chlorophenyl | fluoromethyl | |
| 1.2.1467 | 3-ethoxy-6-chlorophenyl | fluoromethyl | |
| 1.2.1468 | 3-trifluoromethoxy-6-chlorophenyl | fluoromethyl | |
| 1.2.1469 | 3-nitro-6-chlorophenyl | fluoromethyl | |
| 1.2.1470 | 3-fluoro-6-bromophenyl | fluoromethyl | |
| 1.2.1471 | 3-chloro-6-bromophenyl | fluoromethyl | |
| 1.2.1472 | 3,6-dibromophenyl | fluoromethyl | |
| 1.2.1473 | 3-methyl-6-bromophenyl | fluoromethyl | |
| 1.2.1474 | 3-cyclopropyl-6-bromophenyl | fluoromethyl | |
| 1.2.1475 | 3-cyano-6-bromophenyl | fluoromethyl | |
| 1.2.1476 | 3-trifluoromethyl-6-bromophenyl | fluoromethyl | |
| 1.2.1477 | 3-methoxy-6-phenyl | fluoromethyl | |
| 1.2.1478 | 3-ethoxy-6-bromophenyl | fluoromethyl | |
| 1.2.1479 | 3-trifluoromethoxy-6-bromophenyl | fluoromethyl | |
| 1.2.1480 | 3-nitro-6-bromophenyl | fluoromethyl | |
| 1.2.1481 | 3-fluoro-6-iodophenyl | fluoromethyl | |
| 1.2.1482 | 3-chloro-6-iodophenyl | fluoromethyl | |
| 1.2.1483 | 3-bromo-6-iodophenyl | fluoromethyl | |
| 1.2.1484 | 3-methyl-6-iodophenyl | fluoromethyl | |
| 1.2.1485 | 3-cyclopropyl-6-iodophenyl | fluoromethyl | |
| 1.2.1486 | 3-cyano-6-iodophenyl | fluoromethyl | |
| 1.2.1487 | 3-trifluoromethyl-6-iodophenyl | fluoromethyl | |
| 1.2.1488 | 3-methoxy-6-iodophenyl | fluoromethyl | |
| 1.2.1489 | 3-ethoxy-6-iodophenyl | fluoromethyl | |
| 1.2.1490 | 3-trifluoromethoxy-6-iodophenyl | fluoromethyl | |
| 1.2.1491 | 3-nitro-6-iodophenyl | fluoromethyl | |
| 1.2.1492 | 3-fluoro-6-methylphenyl | fluoromethyl | |
| 1.2.1493 | 3-chloro-6-methylphenyl | fluoromethyl | |

TABLE 1.2-continued

Inventive compounds of the general formula (I) in which W* is COOH, $R^1$ and $R^2$ are each hydrogen, and aryl is the radical.

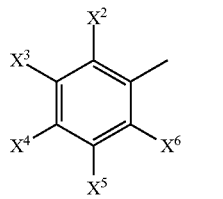

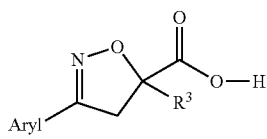

| No. | Aryl | $R^3$ | Physical data |
|---|---|---|---|
| 1.2.1494 | 3-bromo-6-methylphenyl | fluoromethyl | |
| 1.2.1495 | 3,6-dimethylphenyl | fluoromethyl | |
| 1.2.1496 | 3-ethyl-6-methylphenyl | fluoromethyl | |
| 1.2.1497 | 3-cyclopropyl-6-methylphenyl | fluoromethyl | |
| 1.2.1498 | 3-cyano-6-methylphenyl | fluoromethyl | |
| 1.2.1499 | 3-trifluoromethyl-6-methylphenyl | fluoromethyl | |
| 1.2.1500 | 3-methoxy-6-methylphenyl | fluoromethyl | |
| 1.2.1501 | 3-ethoxy-6-methylphenyl | fluoromethyl | |
| 1.2.1502 | 3-trifluoromethoxy-6-methylphenyl | fluoromethyl | |
| 1.2.1503 | 3-nitro-6-methylphenyl | fluoromethyl | |
| 1.2.1504 | 3-fluoro-6-ethylphenyl | fluoromethyl | |
| 1.2.1505 | 3-chloro-6-ethylphenyl | fluoromethyl | |
| 1.2.1506 | 3-bromo-6-ethylphenyl | fluoromethyl | |
| 1.2.1507 | 3-methyl-6-ethylphenyl | fluoromethyl | |
| 1.2.1508 | 3,6-diethylphenyl | fluoromethyl | |
| 1.2.1509 | 3-cyclopropyl-6-ethylphenyl | fluoromethyl | |
| 1.2.1510 | 3-cyano-6-ethylphenyl | fluoromethyl | |
| 1.2.1511 | 3-trifluoromethyl-6-ethylphenyl | fluoromethyl | |
| 1.2.1512 | 3-methoxy-6-ethylphenyl | fluoromethyl | |
| 1.2.1513 | 3-ethoxy-6-ethylphenyl | fluoromethyl | |
| 1.2.1514 | 3-trifluoromethoxy-6-ethylphenyl | fluoromethyl | |
| 1.2.1515 | 3-nitro-6-ethylphenyl | fluoromethyl | |
| 1.2.1516 | 3-fluoro-6-propylphenyl | fluoromethyl | |
| 1.2.1517 | 3-chloro-6-propylphenyl | fluoromethyl | |
| 1.2.1518 | 3-bromo-6-propylphenyl | fluoromethyl | |
| 1.2.1519 | 3-methyl-6-propylphenyl | fluoromethyl | |
| 1.2.1520 | 3-cyclopropyl-6-propylphenyl | fluoromethyl | |
| 1.2.1521 | 3-cyano-6-propylphenyl | fluoromethyl | |
| 1.2.1522 | 3-trifluoromethyl-6-propylphenyl | fluoromethyl | |
| 1.2.1523 | 3-methoxy-6-propylphenyl | fluoromethyl | |
| 1.2.1524 | 3-ethoxy-6-propylphenyl | fluoromethyl | |
| 1.2.1525 | 3-trifluoromethoxy-6-propylphenyl | fluoromethyl | |
| 1.2.1526 | 3-nitro-6-propylphenyl | fluoromethyl | |
| 1.2.1527 | 3-fluoro-6-isopropylphenyl | fluoromethyl | |
| 1.2.1528 | 3-chloro-6-isopropylphenyl | fluoromethyl | |
| 1.2.1529 | 3-bromo-6-isopropylphenyl | fluoromethyl | |
| 1.2.1530 | 3-methyl-6-isopropylphenyl | fluoromethyl | |
| 1.2.1531 | 3-cyclopropyl-6-isopropylphenyl | fluoromethyl | |
| 1.2.1532 | 3-cyano-6-isopropylphenyl | fluoromethyl | |
| 1.2.1533 | 3-trifluoromethyl-6-isopropylphenyl | fluoromethyl | |
| 1.2.1534 | 3-methoxy-6-isopropylphenyl | fluoromethyl | |
| 1.2.1535 | 3-trifluoromethoxy-6-isopropylphenyl | fluoromethyl | |
| 1.2.1536 | 3-nitro-6-isopropylphenyl | fluoromethyl | |
| 1.2.1537 | 3-fluoro-6-tert-butylphenyl | fluoromethyl | |
| 1.2.1538 | 3-chloro-6-tert-butylphenyl | fluoromethyl | |
| 1.2.1539 | 3-bromo-6-tert-butylphenyl | fluoromethyl | |
| 1.2.1540 | 3-methyl-6-tert-butylphenyl | fluoromethyl | |
| 1.2.1541 | 3-cyclopropyl-6-tert-butylphenyl | fluoromethyl | |
| 1.2.1542 | 3-cyano-6-tert-butylphenyl | fluoromethyl | |
| 1.2.1543 | 3-trifluoromethyl-6-tert-butylphenyl | fluoromethyl | |
| 1.2.1544 | 3-methoxy-6-tert-butylphenyl | fluoromethyl | |
| 1.2.1545 | 3-ethoxy-6-tert-butylphenyl | fluoromethyl | |
| 1.2.1546 | 3-trifluoromethoxy-6-tert-butylphenyl | fluoromethyl | |
| 1.2.1547 | 3-nitro-6-tert-butylphenyl | fluoromethyl | |
| 1.2.1548 | 3-fluoro-6-cyclopropylphenyl | fluoromethyl | |

TABLE 1.2-continued

Inventive compounds of the general formula (I) in which W* is COOH, $R^1$ and $R^2$ are each hydrogen, and aryl is the radical.

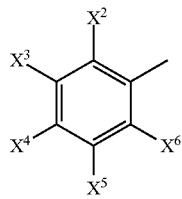

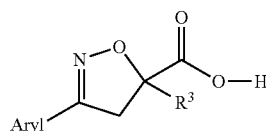

| No. | Aryl | $R^3$ | Physical data |
|---|---|---|---|
| 1.2.1549 | 3-chloro-6-cyclopropylphenyl | fluoromethyl | |
| 1.2.1550 | 3-bromo-6-cyclopropylphenyl | fluoromethyl | |
| 1.2.1551 | 3-methyl-6-cyclopropylphenyl | fluoromethyl | |
| 1.2.1552 | 3-cyclopropyl-6-cyclopropylphenyl | fluoromethyl | |
| 1.2.1553 | 3-cyano-6-cyclopropylphenyl | fluoromethyl | |
| 1.2.1554 | 3-trifluoromethyl-6-cyclopropylphenyl | fluoromethyl | |
| 1.2.1555 | 3-methoxy-6-cyclopropylphenyl | fluoromethyl | |
| 1.2.1556 | 3-ethoxy-6-cyclopropylphenyl | fluoromethyl | |
| 1.2.1557 | 3-trifluoromethoxy-6-cyclopropylphenyl | fluoromethyl | |
| 1.2.1558 | 3-fluoro-6-methoxycarbonyl-phenyl | fluoromethyl | |
| 1.2.1559 | 3-chloro-6-methoxycarbonyl-phenyl | fluoromethyl | |
| 1.2.1560 | 3-bromo-6-methoxycarbonyl-phenyl | fluoromethyl | |
| 1.2.1561 | 3-methyl-6-methoxycarbonyl-phenyl | fluoromethyl | |
| 1.2.1562 | 3-cyclopropyl-6-methoxycarbonyl-phenyl | fluoromethyl | |
| 1.2.1563 | 3-cyano-6-methoxycarbonyl-phenyl | fluoromethyl | |
| 1.2.1564 | 3-trifluoromethyl-6-methoxycarbonyl-phenyl | fluoromethyl | |
| 1.2.1565 | 3-methoxy-6-methoxycarbonyl-phenyl | fluoromethyl | |
| 1.2.1566 | 3-ethoxy-6-methoxycarbonyl-phenyl | fluoromethyl | |
| 1.2.1567 | 3-trifluoromethoxy-6-methoxycarbonyl-phenyl | fluoromethyl | |
| 1.2.1568 | 3-nitro-6-methoxycarbonyl-phenyl | fluoromethyl | |
| 1.2.1569 | 3-fluoro-6-cyanophenyl | fluoromethyl | |
| 1.2.1570 | 3-chloro-6-cyanophenyl | fluoromethyl | |
| 1.2.1571 | 3-bromo-6-cyanophenyl | fluoromethyl | |
| 1.2.1572 | 3-methyl-6-cyanophenyl | fluoromethyl | |
| 1.2.1573 | 3-cyclopropyl-6-cyanophenyl | fluoromethyl | |
| 1.2.1574 | 3-cyano-6-cyanophenyl | fluoromethyl | |
| 1.2.1575 | 3-trifluoromethyl-6-cyanophenyl | fluoromethyl | |
| 1.2.1576 | 3-methoxy-6-cyanophenyl | fluoromethyl | |
| 1.2.1577 | 3-ethoxy-6-cyanophenyl | fluoromethyl | |
| 1.2.1578 | 3-trifluoromethoxy-6-cyanophenyl | fluoromethyl | |
| 1.2.1579 | 3-nitro-6-cyanophenyl | fluoromethyl | |
| 1.2.1580 | 3-fluoro-6-methoxyphenyl | fluoromethyl | |
| 1.2.1581 | 3-chloro-6-methoxyphenyl | fluoromethyl | |
| 1.2.1582 | 3-bromo-6-methoxyphenyl | fluoromethyl | |
| 1.2.1583 | 3-methyl-6-methoxyphenyl | fluoromethyl | |
| 1.2.1584 | 3-cyclopropyl-6-methoxyphenyl | fluoromethyl | |
| 1.2.1585 | 3-cyano-6-methoxyphenyl | fluoromethyl | |
| 1.2.1586 | 3-trifluoromethyl-6-methoxyphenyl | fluoromethyl | |
| 1.2.1587 | 3,6-dimethoxyphenyl | fluoromethyl | |
| 1.2.1588 | 3-ethoxy-6-methoxyphenyl | fluoromethyl | |
| 1.2.1589 | 3-trifluoromethoxy-6-methoxyphenyl | fluoromethyl | |
| 1.2.1590 | 3-nitro-6-methoxyphenyl | fluoromethyl | |
| 1.2.1591 | 3-fluoro-6-ethoxyphenyl | fluoromethyl | |
| 1.2.1592 | 3-chloro-6-ethoxyphenyl | fluoromethyl | |
| 1.2.1593 | 3-bromo-6-ethoxyphenyl | fluoromethyl | |
| 1.2.1594 | 3-methyl-6-ethoxyphenyl | fluoromethyl | |
| 1.2.1595 | 3-ethyl-6-ethoxyphenyl | fluoromethyl | |
| 1.2.1596 | 3-cyclopropyl-6-ethoxyphenyl | fluoromethyl | |
| 1.2.1597 | 3-cyano-6-ethoxyphenyl | fluoromethyl | |
| 1.2.1598 | 3-trifluoromethyl-6-ethoxyphenyl | fluoromethyl | |

TABLE 1.2-continued

Inventive compounds of the general formula (I) in which W* is COOH, $R^1$ and $R^2$ are each hydrogen, and aryl is the radical.

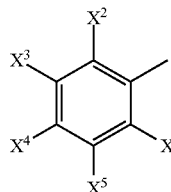

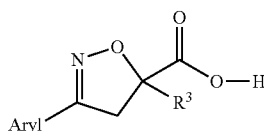

| No. | Aryl | $R^3$ | Physical data |
|---|---|---|---|
| 1.2.1599 | 3-methoxy-6-ethoxyphenyl | fluoromethyl | |
| 1.2.1600 | 2,6-diethoxyphenyl | fluoromethyl | |
| 1.2.1601 | 3-trifluoromethoxy-6-ethoxyphenyl | fluoromethyl | |
| 1.2.1602 | 3-nitro-6-ethoxyphenyl | fluoromethyl | |
| 1.2.1603 | 3-fluoro-6-isopropoxyphenyl | fluoromethyl | |
| 1.2.1604 | 3-chloro-6-isopropoxyphenyl | fluoromethyl | |
| 1.2.1605 | 3-bromo-6-isopropoxyphenyl | fluoromethyl | |
| 1.2.1606 | 3-methyl-6-isopropoxyphenyl | fluoromethyl | |
| 1.2.1607 | 3-cyclopropyl-6-isopropoxyphenyl | fluoromethyl | |
| 1.2.1608 | 3-cyano-6-isopropoxyphenyl | fluoromethyl | |
| 1.2.1609 | 3-trifluoromethyl-6-isopropoxyphenyl | fluoromethyl | |
| 1.2.1610 | 3-methoxy-6-isopropoxyphenyl | fluoromethyl | |
| 1.2.1611 | 3-ethoxy-6-isopropoxyphenyl | fluoromethyl | |
| 1.2.1612 | 3-trifluoromethoxy-6-isopropoxyphenyl | fluoromethyl | |
| 1.2.1613 | 3-nitro-6-isopropoxyphenyl | fluoromethyl | |
| 1.2.1614 | 3-fluoro-6-trifluoromethoxyphenyl | fluoromethyl | |
| 1.2.1615 | 3-chloro-6-trifluoromethoxyphenyl | fluoromethyl | |
| 1.2.1616 | 3-bromo-6-trifluoromethoxyphenyl | fluoromethyl | |
| 1.2.1617 | 3-methyl-6-trifluoromethoxyphenyl | fluoromethyl | |
| 1.2.1618 | 3-cyclopropyl-6-trifluoromethoxyphenyl | fluoromethyl | |
| 1.2.1619 | 3-cyano-6-trifluoromethoxyphenyl | fluoromethyl | |
| 1.2.1620 | 3-trifluoromethyl-6-trifluoromethoxyphenyl | fluoromethyl | |
| 1.2.1621 | 3-methoxy-6-trifluoromethoxyphenyl | fluoromethyl | |
| 1.2.1622 | 3-ethoxy-6-trifluoromethoxyphenyl | fluoromethyl | |
| 1.2.1623 | 3,6-bis(trifluoromethoxy)phenyl | fluoromethyl | |
| 1.2.1624 | 3-nitro-6-trifluoromethoxyphenyl | fluoromethyl | |
| 1.2.1625 | 3-fluoro-6-difluoromethoxyphenyl | fluoromethyl | |
| 1.2.1626 | 3-chloro-6-difluoromethoxyphenyl | fluoromethyl | |
| 1.2.1627 | 3-bromo-6-difluoromethoxyphenyl | fluoromethyl | |
| 1.2.1628 | 3-methyl-6-difluoromethoxyphenyl | fluoromethyl | |
| 1.2.1629 | 3-cyclopropyl-6-difluoromethoxyphenyl | fluoromethyl | |
| 1.2.1630 | 3-cyano-6-difluoromethoxyphenyl | fluoromethyl | |
| 1.2.1631 | 3-trifluoromethyl-6-difluoromethoxyphenyl | fluoromethyl | |
| 1.2.1632 | 3-methoxy-6-difluoromethoxyphenyl | fluoromethyl | |
| 1.2.1633 | 3-ethoxy-6-difluoromethoxyphenyl | fluoromethyl | |
| 1.2.1634 | 3-trifluoromethoxy-6-difluoromethoxyphenyl | fluoromethyl | |
| 1.2.1635 | 3-nitro-6-difluoromethoxyphenyl | fluoromethyl | |
| 1.2.1636 | 3-fluoro-6-nitrophenyl | fluoromethyl | |
| 1.2.1637 | 3-chloro-6-nitrophenyl | fluoromethyl | |
| 1.2.1638 | 3-bromo-6-nitrophenyl | fluoromethyl | |
| 1.2.1639 | 3-methyl-6-nitrophenyl | fluoromethyl | |
| 1.2.1640 | 3-cyclopropyl-6-nitrophenyl | fluoromethyl | |
| 1.2.1641 | 3-cyano-6-nitrophenyl | fluoromethyl | |
| 1.2.1642 | 3-trifluoromethyl-6-nitrophenyl | fluoromethyl | |
| 1.2.1643 | 3-methoxy-6-nitrophenyl | fluoromethyl | |
| 1.2.1644 | 3-ethoxy-6-nitrophenyl | fluoromethyl | |
| 1.2.1645 | 3-trifluoromethoxy-6-nitrophenyl | fluoromethyl | |
| 1.2.1646 | 3-fluoro-6-methylsulfanylphenyl | fluoromethyl | |

TABLE 1.2-continued

Inventive compounds of the general formula (I) in which W* is COOH, $R^1$ and $R^2$ are each hydrogen, and aryl is the radical.

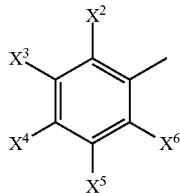

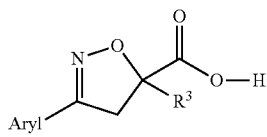

| No. | Aryl | $R^3$ | Physical data |
|---|---|---|---|
| 1.2.1647 | 3-chloro-6-methylsulfanylphenyl | fluoromethyl | |
| 1.2.1648 | 3-bromo-6-methylsulfanylphenyl | fluoromethyl | |
| 1.2.1649 | 3-methyl-6-methylsulfanylphenyl | fluoromethyl | |
| 1.2.1650 | 3-cyclopropyl-6-methylsulfanylphenyl | fluoromethyl | |
| 1.2.1651 | 3-cyano-6-methylsulfanylphenyl | fluoromethyl | |
| 1.2.1652 | 3-trifluoromethyl-6-methylsulfanylphenyl | fluoromethyl | |
| 1.2.1653 | 3-methoxy-6-methylsulfanylphenyl | fluoromethyl | |
| 1.2.1654 | 3-ethoxy-6-methylsulfanylphenyl | fluoromethyl | |
| 1.2.1655 | 3-trifluoromethoxy-6-methylsulfanylphenyl | fluoromethyl | |
| 1.2.1656 | 3-nitro-6-methylsulfanylphenyl | fluoromethyl | |
| 1.2.1657 | 2,3,4-trifluorophenyl | fluoromethyl | |
| 1.2.1658 | 2,3,4-trichlorophenyl | fluoromethyl | |
| 1.2.1659 | 2,3,4-trimethylphenyl | fluoromethyl | |
| 1.2.1660 | 2-fluoro-2-chloro-5-trifluoromethylphenyl | fluoromethyl | |
| 1.2.1661 | 2,3,5-trifluorophenyl | fluoromethyl | |
| 1.2.1662 | 2,3,5-trichlorophenyl | fluoromethyl | |
| 1.2.1663 | 2,3,5-trimethylphenyl | fluoromethyl | |
| 1.2.1664 | 2,3-dichloro-5-methoxyphenyl | fluoromethyl | |
| 1.2.1665 | 2,3,6-trifluorophenyl | fluoromethyl | |
| 1.2.1666 | 2,3,6-trichlorophenyl | fluoromethyl | |
| 1.2.1667 | 2,3,6-trimethylphenyl | fluoromethyl | |
| 1.2.1668 | 3,4,5-trifluorophenyl | fluoromethyl | |
| 1.2.1669 | 3,4,5-trichlorophenyl | fluoromethyl | |
| 1.2.1670 | 3,4,5-trimethylphenyl | fluoromethyl | |
| 1.2.1671 | 3,5-dimethyl-4-fluorophenyl | fluoromethyl | |
| 1.2.1672 | 3,5-dichloro-4-methoxyphenyl | fluoromethyl | |
| 1.2.1673 | 3,5-difluoro-4-chlorophenyl | fluoromethyl | |
| 1.2.1674 | 3,5-dichloro-4-hydroxyphenyl | fluoromethyl | |
| 1.2.1675 | 3,5-trifluoromethyl-4-chlorophenyl | fluoromethyl | |
| 1.2.1676 | 3,4,6-trifluorophenyl | fluoromethyl | |
| 1.2.1677 | 3,4,6-trichlorophenyl | fluoromethyl | |
| 1.2.1678 | 3,4,6-trimethylphenyl | fluoromethyl | |
| 1.2.1679 | pentafluorophenyl | fluoromethyl | |

TABLE 1.3

Inventive compounds of the general formula (I) in which W* is COOH, $R^1$ and $R^2$ are each hydrogen, and aryl is the radical.

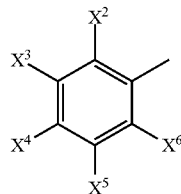

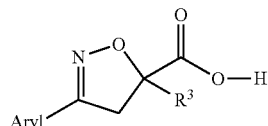

| No. | Aryl | $R^3$ | Physical data |
|---|---|---|---|
| 1.3.1 | 3-fluorophenyl | vinyl | [CDCl$_3$] 3.44 (d, 1H); 3.96 (d, 1H); 5.44 (d, 1H); 5.63 (d, 1H); 6.16 (dd, 1H); 7.10-7.20 (m, 1H); 7.37-7.45 (m, 2H). |
| 1.3.2 | 3-fluorophenyl | 1-methylvinyl | |
| 1.3.3 | 3-fluorophenyl | allyl | |
| 1.3.4 | 3-fluorophenyl | 1-chlorovinyl | [CDCl$_3$] 3.66 (d, 1H); 4.16 (d, 1H); 5.61 (s, 1H); 5.95 (s, 1H); 7.13-7.20 (m, 1H); 7.39-7.45 (m, 2H). |
| 1.3.5 | 3-fluorophenyl | ethynyl | |
| 1.3.6 | 3-chlorophenyl | vinyl | |
| 1.3.7 | 3-chlorophenyl | 1-methylvinyl | |
| 1.3.8 | 3-chlorophenyl | allyl | |
| 1.3.9 | 3-chlorophenyl | 1-chlorovinyl | |
| 1.3.10 | 3-chlorophenyl | ethynyl | |
| 1.3.11 | 3-bromophenyl | vinyl | |
| 1.3.12 | 3-bromophenyl | 1-methylvinyl | |
| 1.3.13 | 3-iodophenyl | vinyl | |
| 1.3.14 | 3-iodophenyl | 1-methylvinyl | |
| 1.3.15 | 3-methylphenyl | vinyl | |
| 1.3.16 | 3-methylphenyl | 1-methylvinyl | |
| 1.3.17 | 3-ethylphenyl | vinyl | |
| 1.3.18 | 3-propylphenyl | vinyl | |
| 1.3.19 | 3-isopropylphenyl | vinyl | |
| 1.3.20 | 3-n-butylphenyl | vinyl | |
| 1.3.21 | 3-i-butylphenyl | vinyl | |
| 1.3.22 | 3-tert-butylphenyl | vinyl | |
| 1.3.23 | 3-cyclopropylphenyl | vinyl | |
| 1.3.24 | 3-cyclobutylphenyl | vinyl | |
| 1.3.25 | 3-cyclopentylphenyl | vinyl | |
| 1.3.26 | 3-vinylphenyl | vinyl | |
| 1.3.27 | 3-ethynylphenyl | vinyl | |
| 1.3.28 | 3-cyanophenyl | vinyl | |
| 1.3.29 | 3-trifluoromethylphenyl | vinyl | |
| 1.3.30 | 3-difluoromethylphenyl | vinyl | |
| 1.3.31 | 3-(hydroxycarbonyl)phenyl | vinyl | |
| 1.3.32 | 3-(methoxycarbonyl)phenyl | vinyl | |
| 1.3.33 | 3-(ethoxycarbonyl)phenyl | vinyl | |
| 1.3.34 | 3-hydroxymethylphenyl | vinyl | |
| 1.3.35 | 3-carbamoylphenyl | vinyl | |
| 1.3.36 | 3-hydroxyphenyl | vinyl | |
| 1.3.37 | 3-methoxyphenyl | vinyl | |
| 1.3.38 | 3-ethoxyphenyl | vinyl | |
| 1.3.39 | 3-propyloxyphenyl | vinyl | |
| 1.3.40 | 3-isopropyloxyphenyl | vinyl | |
| 1.3.41 | 3-n-butyloxyphenyl | vinyl | |
| 1.3.42 | 3-i-butyloxyphenyl | vinyl | |
| 1.3.43 | 3-t-butyloxyphenyl | vinyl | |
| 1.3.44 | 3-difluoromethoxyphenyl | vinyl | |
| 1.3.45 | 3-trifluoromethoxyphenyl | vinyl | |
| 1.3.46 | 3-(2,2,2-trifluoroethoxy)phenyl | vinyl | |
| 1.3.47 | 3-(2-chloroethoxy)phenyl | vinyl | |
| 1.3.48 | 3-(2-hydroxyethoxy)phenyl | vinyl | |

TABLE 1.3-continued

Inventive compounds of the general formula (I) in which W* is COOH, $R^1$ and $R^2$ are each hydrogen, and aryl is the radical.

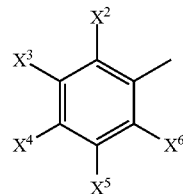

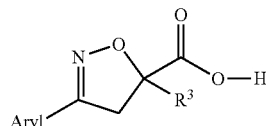

| No. | Aryl | $R^3$ | Physical data |
|---|---|---|---|
| 1.3.49 | 3-(2-methoxyethoxy)phenyl | vinyl | |
| 1.3.50 | 3-[(tert-butoxycarbonyl)oxy]phenyl | vinyl | |
| 1.3.51 | 3-nitrophenyl | vinyl | |
| 1.3.52 | 3-acetoxyphenyl | vinyl | |
| 1.3.53 | {3-[(tert-butoxycarbonyl)amino]phenyl) | vinyl | |
| 1.3.54 | 3-methylsulfanylphenyl | vinyl | |
| 1.3.55 | 3-ethylsulfanylphenyl | vinyl | |
| 1.3.56 | 3-(pentafluoro-lambda$^6$-sulfanyl)phenyl | vinyl | |
| 1.3.57 | 2,3-difluorophenyl | vinyl | |
| 1.3.58 | 2,3-difluorophenyl | 1-methylvinyl | |
| 1.3.59 | 2,3-difluorophenyl | allyl | |
| 1.3.60 | 2,3-difluorophenyl | 1-chlorovinyl | |
| 1.3.61 | 2,3-difluorophenyl | ethynyl | |
| 1.3.62 | 2-chloro-3-fluorophenyl | vinyl | |
| 1.3.63 | 2-bromo-3-fluorophenyl | vinyl | |
| 1.3.64 | 2-methyl-3-fluorophenyl | vinyl | |
| 1.3.65 | 2-ethyl-3-fluorophenyl | vinyl | |
| 1.3.66 | 2-cyclopropyl-3-fluorophenyl | vinyl | |
| 1.3.67 | 2-vinyl-3-fluorophenyl | vinyl | |
| 1.3.68 | 2-ethynyl-3-fluorophenyl | vinyl | |
| 1.3.69 | 2-cyano-3-fluorophenyl | vinyl | |
| 1.3.70 | 2-methoxy-3-fluorophenyl | vinyl | |
| 1.3.71 | 2-ethoxy-3-fluorophenyl | vinyl | |
| 1.3.72 | 2-trifluoromethoxy-3-fluorophenyl | vinyl | |
| 1.3.73 | 2-nitro-3-fluorophenyl | vinyl | |
| 1.3.74 | 2-fluoro-3-chlorophenyl | vinyl | |
| 1.3.75 | 2,3-dichlorophenyl | vinyl | |
| 1.3.76 | 2,3-dichlorophenyl | 1-methylvinyl | |
| 1.3.77 | 2,3-dichlorophenyl | allyl | |
| 1.3.78 | 2,3-dichlorophenyl | 1-chlorovinyl | |
| 1.3.79 | 2,3-dichlorophenyl | ethynyl | |
| 1.3.80 | 2-bromo-3-chlorophenyl | vinyl | |
| 1.3.81 | 2-methyl-3-chlorophenyl | vinyl | |
| 1.3.82 | 2-ethyl-3-chlorophenyl | vinyl | |
| 1.3.83 | 2-cyclopropyl-3-chlorophenyl | vinyl | |
| 1.3.84 | 2-vinyl-3-chlorophenyl | vinyl | |
| 1.3.85 | 2-ethynyl-3-chlorophenyl | vinyl | |
| 1.3.86 | 2-cyano-3-chlorophenyl | vinyl | |
| 1.3.87 | 2-trifluoromethyl-2-chlorophenyl | vinyl | |
| 1.3.88 | 2-methoxy-3-chlorophenyl | vinyl | |
| 1.3.89 | 2-ethoxy-3-chlorophenyl | vinyl | |
| 1.3.90 | 2-trifluoromethoxy-3-chlorophenyl | vinyl | |
| 1.3.91 | 2-nitro-3-chlorophenyl | vinyl | |
| 1.3.92 | 2-fluoro-3-bromophenyl | vinyl | |
| 1.3.93 | 2-chloro-3-bromophenyl | vinyl | |
| 1.3.94 | 2,3-dibromophenyl | vinyl | |
| 1.3.95 | 2-methyl-3-bromophenyl | vinyl | |
| 1.3.96 | 2-ethyl-3-bromophenyl | vinyl | |
| 1.3.97 | 2-cyclopropyl-3-bromophenyl | vinyl | |
| 1.3.98 | 2-vinyl-3-bromophenyl | vinyl | |
| 1.3.99 | 2-ethynyl-3-bromophenyl | vinyl | |
| 1.3.100 | 2-cyano-3-bromophenyl | vinyl | |
| 1.3.101 | 2-trifluoromethyl-3-bromophenyl | vinyl | |
| 1.3.102 | 2-methoxy-3-phenyl | vinyl | |
| 1.3.103 | 2-ethoxy-3-bromophenyl | vinyl | |
| 1.3.104 | 2-trifluoromethoxy-3-bromophenyl | vinyl | |
| 1.3.105 | 2-nitro-3-bromophenyl | vinyl | |

TABLE 1.3-continued

Inventive compounds of the general formula (I) in which W* is COOH, $R^1$ and $R^2$ are each hydrogen, and aryl is the radical.

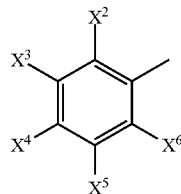

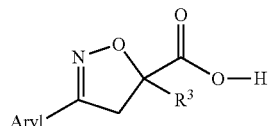

| No. | Aryl | $R^3$ | Physical data |
|---|---|---|---|
| 1.3.106 | 2-fluoro-3-iodophenyl | vinyl | |
| 1.3.107 | 2-chloro-3-iodophenyl | vinyl | |
| 1.3.108 | 2-bromo-3-iodophenyl | vinyl | |
| 1.3.109 | 2-methyl-3-iodophenyl | vinyl | |
| 1.3.110 | 2-ethyl-3-iodophenyl | vinyl | |
| 1.3.111 | 2-cyclopropyl-3-iodophenyl | vinyl | |
| 1.3.112 | 2-vinyl-3-iodophenyl | vinyl | |
| 1.3.113 | 2-ethynyl-3-iodophenyl | vinyl | |
| 1.3.114 | 2-cyano-3-iodophenyl | vinyl | |
| 1.3.115 | 2-trifluoromethyl-3-iodophenyl | vinyl | |
| 1.3.116 | 2-methoxy-3-iodophenyl | vinyl | |
| 1.3.117 | 2-ethoxy-3-iodophenyl | vinyl | |
| 1.3.118 | 2-trifluoromethoxy-3-iodophenyl | vinyl | |
| 1.3.119 | 2-nitro-3-iodophenyl | vinyl | |
| 1.3.120 | 2-fluoro-3-methylphenyl | vinyl | |
| 1.3.121 | 2-fluoro-3-methylphenyl | 1-methylvinyl | |
| 1.3.122 | 2-fluoro-3-methylphenyl | allyl | |
| 1.3.123 | 2-fluoro-3-methylphenyl | 1-chlorovinyl | |
| 1.3.124 | 2-fluoro-3-methylphenyl | ethynyl | |
| 1.3.125 | 2-chloro-3-methylphenyl | vinyl | |
| 1.3.126 | 2-chloro-3-methylphenyl | 1-methylvinyl | |
| 1.3.127 | 2-chloro-3-methylphenyl | allyl | |
| 1.3.128 | 2-chloro-3-methylphenyl | 1-chlorovinyl | |
| 1.3.129 | 2-chloro-3-methylphenyl | ethynyl | |
| 1.3.130 | 2-bromo-3-methylphenyl | vinyl | |
| 1.3.131 | 2,3-dimethylphenyl | vinyl | |
| 1.3.132 | 2,3-dimethylphenyl | 1-methylvinyl | |
| 1.3.133 | 2,3-dimethylphenyl | allyl | |
| 1.3.134 | 2,3-dimethylphenyl | 1-chlorovinyl | |
| 1.3.135 | 2,3-dimethylphenyl | ethynyl | |
| 1.3.136 | 2-ethyl-3-methylphenyl | vinyl | |
| 1.3.137 | 2-cyclopropyl-3-methylphenyl | vinyl | |
| 1.3.138 | 2-vinyl-3-methylphenyl | vinyl | |
| 1.3.139 | 2-ethynyl-3-methylphenyl | vinyl | |
| 1.3.140 | 2-cyano-3-methylphenyl | vinyl | |
| 1.3.141 | 2-trifluoromethyl-3-methylphenyl | vinyl | |
| 1.3.142 | 2-methoxy-3-methylphenyl | vinyl | |
| 1.3.143 | 2-ethoxy-3-methylphenyl | vinyl | |
| 1.3.144 | 2-trifluoromethoxy-3-methylphenyl | vinyl | |
| 1.3.145 | 2-nitro-3-methylphenyl | vinyl | |
| 1.3.146 | 2-fluoro-3-ethylphenyl | vinyl | |
| 1.3.147 | 2-chloro-3-ethylphenyl | vinyl | |
| 1.3.148 | 2-bromo-3-ethylphenyl | vinyl | |
| 1.3.149 | 2-methyl-3-ethylphenyl | vinyl | |
| 1.3.150 | 2,3-diethylphenyl | vinyl | |
| 1.3.151 | 2-cyclopropyl-3-ethylphenyl | vinyl | |
| 1.3.152 | 2-vinyl-3-ethylphenyl | vinyl | |
| 1.3.153 | 2-ethynyl-3-ethylphenyl | vinyl | |
| 1.3.154 | 2-cyano-3-ethylphenyl | vinyl | |
| 1.3.155 | 2-trifluoromethyl-3-ethylphenyl | vinyl | |
| 1.3.156 | 2-methoxy-3-ethylphenyl | vinyl | |
| 1.3.157 | 2-ethoxy-3-ethylphenyl | vinyl | |
| 1.3.158 | 2-trifluoromethoxy-3-ethylphenyl | vinyl | |
| 1.3.159 | 2-nitro-3-ethylphenyl | vinyl | |
| 1.3.160 | 2-fluoro-3-propylphenyl | vinyl | |
| 1.3.161 | 2-chloro-3-propylphenyl | vinyl | |
| 1.3.162 | 2-bromo-3-propylphenyl | vinyl | |

TABLE 1.3-continued

Inventive compounds of the general formula (I) in which W* is COOH, $R^1$ and $R^2$ are each hydrogen, and aryl is the radical.

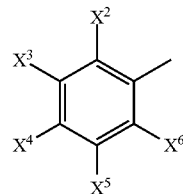

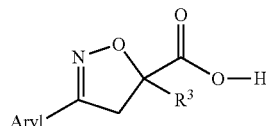

| No. | Aryl | $R^3$ | Physical data |
|---|---|---|---|
| 1.3.163 | 2-methyl-3-propylphenyl | vinyl | |
| 1.3.164 | 2-methyl-3-propylphenyl | vinyl | |
| 1.3.165 | 2-cyclopropyl-3-propylphenyl | vinyl | |
| 1.3.166 | 2-vinyl-3-propylphenyl | vinyl | |
| 1.3.167 | 2-ethynyl-3propylphenyl | vinyl | |
| 1.3.168 | 2-cyano-3-propylphenyl | vinyl | |
| 1.3.169 | 2-trifluoromethyl-3-propylphenyl | vinyl | |
| 1.3.170 | 2- methoxy-3-propylphenyl | vinyl | |
| 1.3.171 | 2-ethoxy-3-propylphenyl | vinyl | |
| 1.3.172 | 2-trifluoromethoxy-3-propyl phenyl | vinyl | |
| 1.3.173 | 2-nitro-3-propylphenyl | vinyl | |
| 1.3.174 | 2-fluoro-3-isopropylphenyl | vinyl | |
| 1.3.175 | 2-chloro-3-isopropylphenyl | vinyl | |
| 1.3.176 | 2-bromo-3- isopropylphenyl | vinyl | |
| 1.3.177 | 2-methyl-3-isopropylphenyl | vinyl | |
| 1.3.178 | 2-ethyl-3-isopropylphenyl | vinyl | |
| 1.3.179 | 2-cyclopropyl-3-isopropylphenyl | vinyl | |
| 1.3.180 | 2-vinyl-3-isopropylphenyl | vinyl | |
| 1.3.181 | 2-ethynyl-3-isopropylphenyl | vinyl | |
| 1.3.182 | 2-cyano-3-isopropylphenyl | vinyl | |
| 1.3.183 | 2-trifluoromethyl-3-isopropylphenyl | vinyl | |
| 1.3.184 | 2-methoxy-3-isopropylphenyl | vinyl | |
| 1.3.185 | 2-ethoxy-3-isopropylphenyl | vinyl | |
| 1.3.186 | 2-trifluoromethoxy-3-isopropylphenyl | vinyl | |
| 1.3.187 | 2-n itro-3-isopropylphenyl | vinyl | |
| 1.3.188 | 2-fluoro-3-tert-butylphenyl | vinyl | |
| 1.3.189 | 2-chloro-3-tert-butylphenyl | vinyl | |
| 1.3.190 | 2-bromo-3-tert-butylphenyl | vinyl | |
| 1.3.191 | 2-methyl-3-tert-butylphenyl | vinyl | |
| 1.3.192 | 2-ethyl-3-tert-butylphenyl | vinyl | |
| 1.3.193 | 2-cyclopropyl-3-tert-butylphenyl | vinyl | |
| 1.3.194 | 2-vinyl-3-tert-butylphenyl | vinyl | |
| 1.3.195 | 2-ethynyl-3-tert-butylphenyl | vinyl | |
| 1.3.196 | 2-cyano-3-tert-butylphenyl | vinyl | |
| 1.3.197 | 2-trifluoromethyl-3-tert-butylphenyl | vinyl | |
| 1.3.198 | 2- methoxy-3-tert-butylphenyl | vinyl | |
| 1.3.199 | 2-ethoxy-3-tert-butylphenyl | vinyl | |
| 1.3.200 | 2-trifluoromethoxy-3-tert-butylphenyl | vinyl | |
| 1.3.201 | 2-nitro-3-tert-butylphenyl | vinyl | |
| 1.3.202 | 2-fluoro-3-hydroxymethylphenyl | vinyl | |
| 1.3.203 | 2-chloro-3-hydroxymethylphenyl | vinyl | |
| 1.3.204 | 2-bromo-3- hydroxymethylphenyl | vinyl | |
| 1.3.205 | 2-methyl-3-hydroxymethylphenyl | vinyl | |
| 1.3.206 | 2-ethyl-3-hydroxymethylphenyl | vinyl | |
| 1.3.207 | 2-cyclopropyl-3-hydroxymethylphenyl | vinyl | |
| 1.3.208 | 2-vinyl-3-hydroxymethylphenyl | vinyl | |
| 1.3.209 | 2-ethynyl-3-hydroxymethylphenyl | vinyl | |
| 1.3.210 | 2-cyano-3-hydroxymethylphenyl | vinyl | |
| 1.3.211 | 2-trifluoromethyl-3-hydroxymethylphenyl | vinyl | |
| 1.3.212 | 2-methoxy-3-hydroxymethylphenyl | vinyl | |
| 1.3.213 | 2-ethoxy-3-hydroxymethylphenyl | vinyl | |
| 1.3.214 | 2-trifluoromethoxy-3-hydroxymethylphenyl | vinyl | |
| 1.3.215 | 2-nitro-3-hydroxymethylphenyl | vinyl | |
| 1.3.216 | 2-fluoro-3-cyclopropylphenyl | vinyl | |
| 1.3.217 | 2-chloro-3-cyclopropylphenyl | vinyl | |
| 1.3.218 | 2-bromo-3-cyclopropylphenyl | vinyl | |
| 1.3.219 | 2-methyl-3-cyclopropylphenyl | vinyl | |

TABLE 1.3-continued

Inventive compounds of the general formula (I) in which W* is COOH, $R^1$ and $R^2$ are each hydrogen, and aryl is the radical.

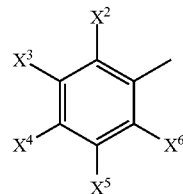

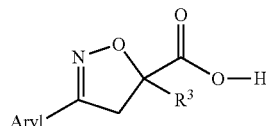

| No. | Aryl | $R^3$ | Physical data |
|---|---|---|---|
| 1.3.220 | 2-ethyl-3-cyclopropylphenyl | vinyl | |
| 1.3.221 | 2-cyclopropyl-3-cyclopropylphenyl | vinyl | |
| 1.3.222 | 2-vinyl-3-cyclopropylphenyl | vinyl | |
| 1.3.223 | 2-ethynyl-3-cyclopropylphenyl | vinyl | |
| 1.3.224 | 2-cyano-3-cyclopropylphenyl | vinyl | |
| 1.3.225 | 2-trifluoromethyl-3-cyclopropylphenyl | vinyl | |
| 1.3.226 | 2-methoxy-3-cyclopropylphenyl | vinyl | |
| 1.3.227 | 2-ethoxy-3-cyclopropylphenyl | vinyl | |
| 1.3.228 | 2-trifluoromethoxy-3-cyclopropylphenyl | vinyl | |
| 1.3.229 | 2-fluoro-3-methoxycarbonylphenyl | vinyl | |
| 1.3.230 | 2-chloro-3-methoxycarbonylphenyl | vinyl | |
| 1.3.231 | 2-bromo-3-methoxycarbonylphenyl | vinyl | |
| 1.3.232 | 2-methyl-3-methoxycarbonylphenyl | vinyl | |
| 1.3.233 | 2-ethyl-3-methoxycarbonylphenyl | vinyl | |
| 1.3.234 | 2-cyclopropyl-3-methoxycarbonylphenyl | vinyl | |
| 1.3.235 | 2-vinyl-3-methoxycarbonylphenyl | vinyl | |
| 1.3.236 | 2-ethynyl-3-methoxycarbonylphenyl | vinyl | |
| 1.3.237 | 2-cyano-3-methoxycarbonylphenyl | vinyl | |
| 1.3.238 | 2-trifluoromethyl-3-methoxycarbonylphenyl | vinyl | |
| 1.3.239 | 2-methoxy-3-methoxycarbonylphenyl | vinyl | |
| 1.3.240 | 2-ethoxy-3-methoxycarbonylphenyl | vinyl | |
| 1.3.241 | 2-trifluoromethoxy-3-methoxycarbonylphenyl | vinyl | |
| 1.3.242 | 2-nitro-3-methoxycarbonylphenyl | vinyl | |
| 1.3.243 | 2-fluoro-3-vinylphenyl | vinyl | |
| 1.3.244 | 2-chloro-3-vinylphenyl | vinyl | |
| 1.3.245 | 2-bromo-3-vinylphenyl | vinyl | |
| 1.3.246 | 2-methyl-3-vinylphenyl | vinyl | |
| 1.3.247 | 2-ethyl-3-vinylphenyl | vinyl | |
| 1.3.248 | 2-cyclopropyl-3-vinylphenyl | vinyl | |
| 1.3.249 | 2-vinyl-3-vinylphenyl | vinyl | |
| 1.3.250 | 2-ethynyl-3-vinylphenyl | vinyl | |
| 1.3.251 | 2-cyano-3-vinylphenyl | vinyl | |
| 1.3.252 | 2-trifluoromethyl-3-vinylphenyl | vinyl | |
| 1.3.253 | 2-methoxy-3-vinylphenyl | vinyl | |
| 1.3.254 | 2-ethoxy-3-vinylphenyl | vinyl | |
| 1.3.255 | 2-trifluoromethoxy-3-vinylphenyl | vinyl | |
| 1.3.256 | 2-nitro-3-vinylphenyl | vinyl | |
| 1.3.257 | 2-fluoro-3-ethynylphenyl | vinyl | |
| 1.3.258 | 2-chloro-3-ethynylphenyl | vinyl | |
| 1.3.259 | 2-bromo-3-ethynylphenyl | vinyl | |
| 1.3.260 | 2-methyl-3-ethynylphenyl | vinyl | |
| 1.3.261 | 2-ethyl-3-ethynylphenyl | vinyl | |
| 1.3.262 | 2-cyclopropyl-3-ethynylphenyl | vinyl | |
| 1.3.263 | 2-vinyl-3-ethynylphenyl | vinyl | |
| 1.3.264 | 2-cyano-3-ethynylphenyl | vinyl | |
| 1.3.265 | 2-trifluoromethyl-3-ethynylphenyl | vinyl | |
| 1.3.266 | 2-methoxy-3-ethynylphenyl | vinyl | |
| 1.3.267 | 2-ethoxy-3-ethynylphenyl | vinyl | |
| 1.3.268 | 2-trifluoromethoxy-3-ethynylphenyl | vinyl | |
| 1.3.269 | 2-nitro-3-ethynylphenyl | vinyl | |
| 1.3.270 | 2-fluoro-3-ethynylphenyl | vinyl | |
| 1.3.271 | 2-fluoro-3-cyanophenyl | vinyl | |
| 1.3.272 | 2-chloro-3-cyanophenyl | vinyl | |
| 1.3.273 | 2-bromo-3-cyanophenyl | vinyl | |
| 1.3.274 | 2-methyl-3-cyanophenyl | vinyl | |

TABLE 1.3-continued

Inventive compounds of the general formula (I) in which W* is COOH, $R^1$ and $R^2$ are each hydrogen, and aryl is the radical.

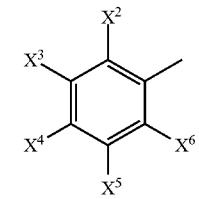

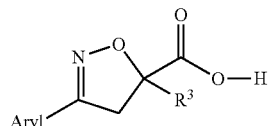

| No. | Aryl | $R^3$ | Physical data |
|---|---|---|---|
| 1.3.275 | 2-ethyl-3-cyanophenyl | vinyl | |
| 1.3.276 | 2-ethyl-3-cyanophenyl | 1-methylvinyl | |
| 1.3.277 | 2-ethyl-3-cyanophenyl | allyl | |
| 1.3.278 | 2-ethyl-3-cyanophenyl | 1-chlorovinyl | |
| 1.3.279 | 2-ethyl-3-cyanophenyl | ethynyl | |
| 1.3.280 | 2-cyclopropyl-3-cyanophenyl | vinyl | |
| 1.3.281 | 2-vinyl-3-cyanophenyl | vinyl | |
| 1.3.282 | 2-ethynyl-3-cyanophenyl | vinyl | |
| 1.3.283 | 2-cyano-3-cyanophenyl | vinyl | |
| 1.3.284 | 2-trifluoromethyl-3-cyanophenyl | vinyl | |
| 1.3.285 | 2- methoxy-3-cyanophenyl | vinyl | |
| 1.3.286 | 2-ethoxy-3-cyanophenyl | vinyl | |
| 1.3.287 | 2-trifluoromethoxy-3-cyanophenyl | vinyl | |
| 1.3.288 | 2-nitro-3-cyanophenyl | vinyl | |
| 1.3.289 | 2-fluoro-3-hydroxyphenyl | vinyl | |
| 1.3.290 | 2-chloro-3-hydroxyphenyl | vinyl | |
| 1.3.291 | 2-bromo-3-hydroxyphenyl | vinyl | |
| 1.3.292 | 2- methyl-3-hydroxyphenyl | vinyl | |
| 1.3.293 | 2-ethyl-3-hydroxyphenyl | vinyl | |
| 1.3.294 | 2-cyclopropyl-3-hydroxyphenyl | vinyl | |
| 1.3.295 | 2-vinyl-3-hydroxyphenyl | vinyl | |
| 1.3.296 | 2-ethynyl-3-hydroxyphenyl | vinyl | |
| 1.3.297 | 2-cyano-3-hydroxyphenyl | vinyl | |
| 1.3.298 | 2-trifluoromethyl-3-hydroxyphenyl | vinyl | |
| 1.3.299 | 2-methoxy-3-hydroxyphenyl | vinyl | |
| 1.3.300 | 2-ethoxy-3-hydroxyphenyl | vinyl | |
| 1.3.301 | 2-trifluoromethoxy-3-hydroxyphenyl | vinyl | |
| 1.3.302 | 2-nitro-3-hydroxyphenyl | vinyl | |
| 1.3.303 | 2-fluoro-3-methoxyphenyl | vinyl | |
| 1.3.304 | 2-chloro-3-methoxyphenyl | vinyl | |
| 1.3.305 | 2-bromo-3-methoxyphenyl | vinyl | |
| 1.3.306 | 2-methyl-3-methoxyphenyl | vinyl | |
| 1.3.307 | 2-ethyl-3-methoxyphenyl | vinyl | |
| 1.3.308 | 2-cyclopropyl-3-methoxyphenyl | vinyl | |
| 1.3.309 | 2-vinyl-3-methoxyphenyl | vinyl | |
| 1.3.310 | 2-ethynyl-3-methoxyphenyl | vinyl | |
| 1.3.311 | 2-cyano-3-methoxyphenyl | vinyl | |
| 1.3.312 | 2-trifluoromethyl-3-methoxyphenyl | vinyl | |
| 1.3.313 | 2,3-dimethoxyphenyl | vinyl | |
| 1.3.314 | 2-ethoxy-3-methoxyphenyl | vinyl | |
| 1.3.315 | 2-trifluoromethoxy-3-methoxyphenyl | vinyl | |
| 1.3.316 | 2-nitro-3-methoxyphenyl | vinyl | |
| 1.3.317 | 2-fluoro-3-ethoxyphenyl | vinyl | |
| 1.3.318 | 2-chloro-3-ethoxyphenyl | vinyl | |
| 1.3.319 | 2-bromo-3-ethoxyphenyl | vinyl | |
| 1.3.320 | 2-methyl-3-ethoxyphenyl | vinyl | |
| 1.3.321 | 2-ethyl-3-ethoxyphenyl | vinyl | |
| 1.3.322 | 2-cyclopropyl-3-ethoxyphenyl | vinyl | |
| 1.3.323 | 2-vinyl-3-ethoxyphenyl | vinyl | |
| 1.3.324 | 2-ethynyl-3-ethoxyphenyl | vinyl | |
| 1.3.325 | 2-cyano-3-ethoxyphenyl | vinyl | |
| 1.3.326 | 2-trifluoromethyl-3-ethoxyphenyl | vinyl | |
| 1.3.327 | 2-methoxy-3-ethoxyphenyl | vinyl | |
| 1.3.328 | 2,3-diethoxy--phenyl | vinyl | |
| 1.3.329 | 2-trifluoromethoxy-3-ethoxyphenyl | vinyl | |
| 1.3.330 | 2-nitro-3-ethoxyphenyl | vinyl | |
| 1.3.331 | 2-fluoro-3-propoxyphenyl | vinyl | |

TABLE 1.3-continued

Inventive compounds of the general formula (I) in which W* is COOH, $R^1$ and $R^2$ are each hydrogen, and aryl is the radical.

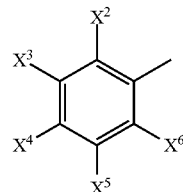

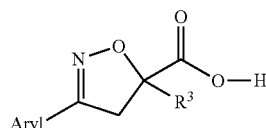

| No. | Aryl | $R^3$ | Physical data |
|---|---|---|---|
| 1.3.332 | 2-chloro-3-propoxyphenyl | vinyl | |
| 1.3.333 | 2-bromo-3-propoxyphenyl | vinyl | |
| 1.3.334 | 2-methyl-3-propoxyphenyl | vinyl | |
| 1.3.335 | 2-ethyl-3-propoxyphenyl | vinyl | |
| 1.3.336 | 2-cyclopropyl-3-propoxyphenyl | vinyl | |
| 1.3.337 | 2-vinyl-3-propoxyphenyl | vinyl | |
| 1.3.338 | 2-ethynyl-3-propoxyphenyl | vinyl | |
| 1.3.339 | 2-cyano-3-propoxyphenyl | vinyl | |
| 1.3.340 | 2-trifluoromethyl-3-propoxyphenyl | vinyl | |
| 1.3.341 | 2-methoxy-3-propoxyphenyl | vinyl | |
| 1.3.342 | 2-ethoxy-3-propoxyphenyl | vinyl | |
| 1.3.343 | 2-trifluoromethoxy-3-propoxyphenyl | vinyl | |
| 1.3.344 | 2-nitro-3-propoxyphenyl | vinyl | |
| 1.3.345 | 2-fluoro-3-isopropoxyphenyl | vinyl | |
| 1.3.346 | 2-chloro-3-isopropoxyphenyl | vinyl | |
| 1.3.347 | 2-bromo-3-isopropoxyphenyl | vinyl | |
| 1.3.348 | 2-methyl-3-isopropoxyphenyl | vinyl | |
| 1.3.349 | 2-ethyl-3-isopropoxyphenyl | vinyl | |
| 1.3.350 | 2-cyclopropyl-3-isopropoxyphenyl | vinyl | |
| 1.3.351 | 2-vinyl-3-isopropoxyphenyl | vinyl | |
| 1.3.352 | 2-ethynyl-3-isopropoxyphenyl | vinyl | |
| 1.3.353 | 2-cyano-3-isopropoxyphenyl | vinyl | |
| 1.3.354 | 2-trifluoromethyl-3-isopropoxyphenyl | vinyl | |
| 1.3.355 | 2-methoxy-3-isopropoxyphenyl | vinyl | |
| 1.3.356 | 2-ethoxy-3-isopropoxyphenyl | vinyl | |
| 1.3.357 | 2-trifluoromethoxy-3-isopropoxyphenyl | vinyl | |
| 1.3.358 | 2-nitro-3-isopropoxyphenyl | vinyl | |
| 1.3.359 | 2-fluoro-3-tert-butoxyphenyl | vinyl | |
| 1.3.360 | 2-chloro-3-tert-butoxyphenyl | vinyl | |
| 1.3.361 | 2-bromo-3-tert-butoxyphenyl | vinyl | |
| 1.3.362 | 2-methyl-3-tert-butoxyphenyl | vinyl | |
| 1.3.363 | 2-ethyl-3-tert-butoxyphenyl | vinyl | |
| 1.3.364 | 2-cyclopropyl-3-tert-butoxyphenyl | vinyl | |
| 1.3.365 | 2-vinyl-3-tert-butoxyphenyl | vinyl | |
| 1.3.366 | 2-ethynyl-3-tert-butoxyphenyl | vinyl | |
| 1.3.367 | 2-cyano-3-tert-butoxyphenyl | vinyl | |
| 1.3.368 | 2-trifluoromethyl-3-tert-butoxyphenyl | vinyl | |
| 1.3.369 | 2-methoxy-3-tert-butoxyphenyl | vinyl | |
| 1.3.370 | 2-ethoxy-3-tert-butoxyphenyl | vinyl | |
| 1.3.371 | 2-trifluoromethoxy-3-tert-butoxyphenyl | vinyl | |
| 1.3.372 | 2-nitro-3-tert-butoxyphenyl | vinyl | |
| 1.3.373 | 2-fluoro-3-trifluoromethoxyphenyl | vinyl | |
| 1.3.374 | 2-chloro-3-trifluoromethoxyphenyl | vinyl | |
| 1.3.375 | 2-bromo-3-trifluoromethoxyphenyl | vinyl | |
| 1.3.376 | 2-methyl-3-trifluoromethoxyphenyl | vinyl | |
| 1.3.377 | 2-ethyl-3-trifluoromethoxyphenyl | vinyl | |
| 1.3.378 | 2-cyclopropyl-3-trifluoromethoxyphenyl | vinyl | |
| 1.3.379 | 2-vinyl-3-trifluoromethoxyphenyl | vinyl | |
| 1.3.380 | 2-ethynyl-3-trifluoromethoxyphenyl | vinyl | |
| 1.3.381 | 2-cyano-3-trifluoromethoxyphenyl | vinyl | |
| 1.3.382 | 2-trifluoromethyl-3-trifluoromethoxy-phenyl | vinyl | |
| 1.3.383 | 2-methoxy-3-trifluoromethoxyphenyl | vinyl | |
| 1.3.384 | 2-ethoxy-3-trifluoromethoxyphenyl | vinyl | |
| 1.3.385 | 2,3-bis(trifluoromethoxy)phenyl | vinyl | |
| 1.3.386 | 2-nitro-3-trifluoromethoxyphenyl | vinyl | |
| 1.3.387 | 2-fluoro-3-(2,2,2-trifluoroethoxy)phenyl | vinyl | |

TABLE 1.3-continued

Inventive compounds of the general formula (I) in which W* is COOH, $R^1$ and $R^2$ are each hydrogen, and aryl is the radical.

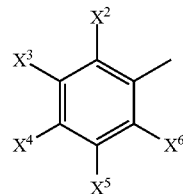

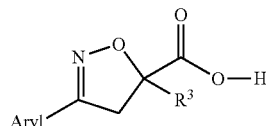

| No. | Aryl | $R^3$ | Physical data |
|---|---|---|---|
| 1.3.388 | 2-chloro-3-(2,2,2-trifluoroethoxy)phenyl | vinyl | |
| 1.3.389 | 2-bromo-3-(2,2,2-trifluoroethoxy)phenyl | vinyl | |
| 1.3.390 | 2-methyl-3-(2,2,2-trifluoroethoxy)phenyl | vinyl | |
| 1.3.391 | 2-ethyl-3-(2,2,2-trifluoroethoxy)phenyl | vinyl | |
| 1.3.392 | 2-cyclopropyl-3-(2,2,2-trifluoro-ethoxy)phenyl | vinyl | |
| 1.3.393 | 2-vinyl-3-(2,2,2-trifluoroethoxy)phenyl | vinyl | |
| 1.3.394 | 2-ethynyl-3-(2,2,2-trifluoroethoxyphenyl | vinyl | |
| 1.3.395 | 2-cyano-3-(2,2,2-trifluoroethoxy)phenyl | vinyl | |
| 1.3.396 | 2-trifluoromethyl-3-(2,2,2-trifluoro-ethoxy)phenyl | vinyl | |
| 1.3.397 | 2-methoxy-3-(2,2,2-trifluoroethoxy)phenyl | vinyl | |
| 1.3.398 | 2-ethoxy-3-(2,2,2-trifluoroethoxy)phenyl | vinyl | |
| 1.3.399 | 2-trifluoromethoxy-3-(2,2,2-trifluoro-ethoxy)phenyl | vinyl | |
| 1.3.400 | 2-nitro-3-(2,2,2-trifluoroethoxy)phenyl | vinyl | |
| 1.3.401 | 2-fluoro-3-difluoromethoxyphenyl | vinyl | |
| 1.3.402 | 2-chloro-3-difluoromethoxyphenyl | vinyl | |
| 1.3.403 | 2-bromo-3-difluoromethoxyphenyl | vinyl | |
| 1.3.404 | 2-methyl-3-difluoromethoxyphenyl | vinyl | |
| 1.3.405 | 2-ethyl-3-difluoromethoxyphenyl | vinyl | |
| 1.3.406 | 2-cyclopropyl-3-difluoromethoxyphenyl | vinyl | |
| 1.3.407 | 2-vinyl-3-difluoromethoxyphenyl | vinyl | |
| 1.3.408 | 2-ethynyl-3-difluoromethoxyphenyl | vinyl | |
| 1.3.409 | 2-cyano-3-difluoromethoxyphenyl | vinyl | |
| 1.3.410 | 2-trifluoromethyl-3-difluoromethoxyphenyl | vinyl | |
| 1.3.411 | 2-methoxy-3-difluoromethoxyphenyl | vinyl | |
| 1.3.412 | 2-ethoxy-3-difluoromethoxyphenyl | vinyl | |
| 1.3.413 | 2-trifluoromethoxy-3-difluoromethoxy-phenyl | vinyl | |
| 1.3.414 | 2-nitro-3-difluoromethoxyphenyl | vinyl | |
| 1.3.415 | 2-fluoro-3-(2-methoxyethoxy)phenyl | vinyl | |
| 1.3.416 | 2-chloro-3-(2-methoxyethoxy)phenyl | vinyl | |
| 1.3.417 | 2-bromo-3-(2-methoxyethoxy)phenyl | vinyl | |
| 1.3.418 | 2-methyl-3-(2-methoxyethoxy)phenyl | vinyl | |
| 1.3.419 | 2-ethyl-3-(2-methoxyethoxy)phenyl | vinyl | |
| 1.3.420 | 2-cyclopropyl-3-(2-methoxyethoxy)phenyl | vinyl | |
| 1.3.421 | 2-vinyl-3-(2-methoxyethoxy)phenyl | vinyl | |
| 1.3.422 | 2-ethynyl-3-(2-methoxyethoxy)phenyl | vinyl | |
| 1.3.423 | 2-cyano-3-(2-methoxyethoxy)phenyl | vinyl | |
| 1.3.424 | 2-trifluoromethyl-3-(2-methoxyethoxy)-phenyl | vinyl | |
| 1.3.425 | 2-methoxy-3-(2-methoxyethoxy)phenyl | vinyl | |
| 1.3.426 | 2-ethoxy-3-(2-methoxyethoxy)phenyl | vinyl | |
| 1.3.427 | 2-trifluoromethoxy-(2-methoxyethoxy)-phenyl | vinyl | |
| 1.3.428 | 2-nitro-3-(2-methoxyethoxy)phenyl | vinyl | |
| 1.3.429 | 2-fluoro-3-(tert-butoxycarbonyloxy)phenyl | vinyl | |
| 1.3.430 | 2-chloro-3-(tert-butoxycarbonyloxy)-phenyl | vinyl | |
| 1.3.431 | 2-bromo-3-(tert-butoxycarbonyl-oxy)phenyl | vinyl | |
| 1.3.432 | 2-methyl-3-(tert-butoxycarbonyl-oxy)phenyl | vinyl | |
| 1.3.433 | 2-ethyl-3-(tert-butoxycarbonyloxy)phenyl | vinyl | |
| 1.3.434 | 2-cyclopropyl-3-(tert-butoxycarbonyl-oxy)phenyl | vinyl | |

TABLE 1.3-continued

Inventive compounds of the general formula (I) in which W* is COOH, $R^1$ and $R^2$ are each hydrogen, and aryl is the radical.

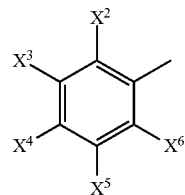

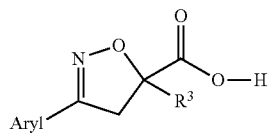

| No. | Aryl | $R^3$ | Physical data |
| --- | --- | --- | --- |
| 1.3.435 | 2-vinyl-3-(tert-butoxycarbonyloxy)phenyl | vinyl | |
| 1.3.436 | 2-ethynyl-3-(tert-butoxycarbonyl-oxy)phenyl | vinyl | |
| 1.3.437 | 2-cyano-3-(tert-butoxycarbonyloxy)-phenyl | vinyl | |
| 1.3.438 | 2-trifluoromethyl-3-(tert-butoxycarbonyl-oxy)phenyl | vinyl | |
| 1.3.439 | 2-methoxy-3-(tert-butoxycarbonyloxy)-phenyl | vinyl | |
| 1.3.440 | 2-ethoxy-3-(tert-butoxycarbonyloxy)-phenyl | vinyl | |
| 1.3.441 | 2-trifluoromethoxy-3-(tert-butoxycarbonyl-oxy)phenyl | vinyl | |
| 1.3.442 | 2-nitro-3-(tert-butoxycarbonyloxy)phenyl | vinyl | |
| 1.3.443 | 2-fluoro-3-nitrophenyl | vinyl | |
| 1.3.444 | 2-chloro-3-nitrophenyl | vinyl | |
| 1.3.445 | 2-bromo-3-nitrophenyl | vinyl | |
| 1.3.446 | 2-methyl-3-nitrophenyl | vinyl | |
| 1.3.447 | 2-ethyl-3-nitrophenyl | vinyl | |
| 1.3.448 | 2-cyclopropyl-3-nitrophenyl | vinyl | |
| 1.3.449 | 2-vinyl-3-nitrophenyl | vinyl | |
| 1.3.450 | 2-ethynyl-3-nitrophenyl | vinyl | |
| 1.3.451 | 2-cyano-3-nitrophenyl | vinyl | |
| 1.3.452 | 2-trifluoromethyl-3-nitrophenyl | vinyl | |
| 1.3.453 | 2-methoxy-3-nitrophenyl | vinyl | |
| 1.3.454 | 2-ethoxy-3-nitrophenyl | vinyl | |
| 1.3.455 | 2-trifluoromethoxy-3-nitrophenyl | vinyl | |
| 1.3.456 | 2-fluoro-3-methylsulfanylphenyl | vinyl | |
| 1.3.457 | 2-chloro-3-methylsulfanylphenyl | vinyl | |
| 1.3.458 | 2-bromo-3-methylsulfanylphenyl | vinyl | |
| 1.3.459 | 2-methyl-3-methylsulfanylphenyl | vinyl | |
| 1.3.460 | 2-ethyl-3-methylsulfanylphenyl | vinyl | |
| 1.3.461 | 2-cyclopropyl-3-methylsulfanylphenyl | vinyl | |
| 1.3.462 | 2-vinyl-3-methylsulfanylphenyl | vinyl | |
| 1.3.463 | 2-ethynyl-3-methylsulfanylphenyl | vinyl | |
| 1.3.464 | 2-cyano-3-methylsulfanylphenyl | vinyl | |
| 1.3.465 | 2-trifluoromethyl-3-methylsulfanylphenyl | vinyl | |
| 1.3.466 | 2-methoxy-3-methylsulfanylphenyl | vinyl | |
| 1.3.467 | 2-ethoxy-3-methylsulfanylphenyl | vinyl | |
| 1.3.468 | (R)- or (S)-3,5-difluorophenyl | vinyl | One unassigned enantiomer [$CDCl_3$] 3.41 (d, 1H); 3.93 (d, 1H); 5.45 (d, 1H); 5.63 (d, 1H); 6.16 (dd, 1H); 6.91 (t, 1H); 7.17 (d, 2H). |
| 1.3.469 | (S)- or (R)-3,5-difluorophenyl | vinyl | One unassigned enantiomer [$CDCl_3$] 3.41 (d, 1H); 3.93 (d, 1H); 5.45 (d, 1H); 5.63 (d, 1H); 6.16 (dd, 1H); 6.91 (t, 1H); 7.17 (d, 2H). |

TABLE 1.3-continued

Inventive compounds of the general formula (I) in which W* is COOH, $R^1$ and $R^2$ are each hydrogen, and aryl is the radical.

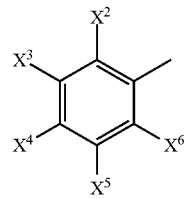

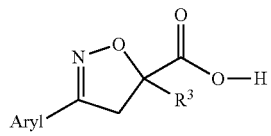

| No. | Aryl | $R^3$ | Physical data |
|---|---|---|---|
| 1.3.470 | 3,5-difluorophenyl | vinyl | [CDCl3] 3.40 (d, 1H); 3.93 (d, 1H); 5.45 (d, 1H); 5.63 (d, 1H); 6.15 (dd, 1H); 6.90 (t, 1H); 7.18 (d, 2H). |
| 1.3.471 | 3,5-difluorophenyl | 1-methylvinyl | |
| 1.3.472 | 3,5-difluorophenyl | 2,2-difluorovinyl | [CDCl3] 3.54 (d, 1H); 4.01 (d, 1H); 4.90 (d, 1H); 6.91 (t, 1H); 7.18 (d, 2H). |
| 1.3.473 | 3,5-difluorophenyl | 1-chlorovinyl | [CDCl$_3$] 3.62 (d, 1H); 4.14 (d, 1H); 5.61 (d, 1H); 5.96 (d, 1H); 6.91 (t, 1H); 7.20 (d, 2H). |
| 1.3.474 | 3,5-difluorophenyl | ethynyl | [CDCl3] 2.1 (s br, 1H); 2.86 (s, 1H), 3.76 (d, 1H); 4.08 (d, 1H); 6.82 (t, 1H); 7.19 (d, 2H). |
| 1.3.475 | 3-chloro-5-fluorophenyl | vinyl | |
| 1.3.476 | 3-chloro-5-fluorophenyl | 1-methylvinyl | [CDCl3] 1.91 (s, 3H); 3.40 (d, 1H); 4.00 (d, 1H); 5.17 (s, 1H); 5.35 (s, 1H); 7.17 (d, 1H); 7.32 (d, 1H); 7.42 (s, 1H), 8.9 (s br, 1H). |
| 1.3.477 | 3-chloro-5-fluorophenyl | allyl | |
| 1.3.478 | 3-chloro-5-fluorophenyl | 1-chlorovinyl | |
| 1.3.479 | 3-chloro-5-fluorophenyl | ethynyl | |
| 1.3.480 | 3-bromo-5-fluorophenyl | vinyl | |
| 1.3.481 | 3-bromo-5-fluorophenyl | 1-methylvinyl | |
| 1.3.482 | 3-bromo-5-fluorophenyl | allyl | |
| 1.3.483 | 3-bromo-5-fluorophenyl | 1-chlorovinyl | |
| 1.3.484 | 3-bromo-5-fluorophenyl | ethynyl | |
| 1.3.485 | 3-iodo-5-fluorophenyl | vinyl | |
| 1.3.486 | 3-methyl-5-fluorophenyl | vinyl | [CDCl3] 2.38 (s, 3H); 3.42 (d, 1H); 3.94 (d, 1H); 5.43 (d, 1H); 5.65 (d, 1H); 6.15 (dd, 1H); 6.98 (d, 1H); 7.18 (d, 1H); 7.22 (s, 1H). |
| 1.3.487 | 3-methyl-5-fluorophenyl | 1-methylvinyl | [CDCl3] 1.91 (s, 3H), 2.38 (s, 3H); 3.42 (d, 1H), 4.00 (d, 1H); 5.15 (s, 1H); 5.35 (s, 1H); 6.3 (s br, 1H), 6.98 (d, 1H); 7.17 (d, 1H); 7.21 (s, 1H). |
| 1.3.488 | 3-methyl-5-fluorophenyl | allyl | |
| 1.3.489 | 3-methyl-5-fluorophenyl | 1-chlorovinyl | |
| 1.3.490 | 3-methyl-5-fluorophenyl | ethynyl | |
| 1.3.491 | 3-ethyl-5-fluorophenyl | vinyl | |
| 1.3.492 | 3-propyl-5-fluorophenyl | vinyl | |
| 1.3.493 | 3-i-propyl-5-fluorophenyl | vinyl | |

TABLE 1.3-continued

Inventive compounds of the general formula (I) in which W* is COOH, $R^1$ and $R^2$ are each hydrogen, and aryl is the radical.

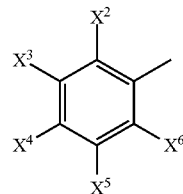

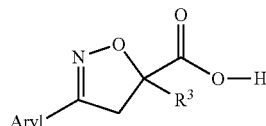

| No. | Aryl | $R^3$ | Physical data |
|---|---|---|---|
| 1.3.494 | 3-n-butyl-5-fluorophenyl | vinyl | |
| 1.3.495 | 3-isobutyl-5-fluorophenyl | vinyl | |
| 1.3.496 | 3-tert-butyl-5-fluorophenyl | vinyl | |
| 1.3.497 | 3-cyclopropyl-5-fluorophenyl | vinyl | |
| 1.3.498 | 3-vinyl-5-fluorophenyl | vinyl | |
| 1.3.499 | 3-ethynyl-5-fluorophenyl | vinyl | |
| 1.3.500 | 3-cyano-5-fluorophenyl | vinyl | |
| 1.3.501 | 3-trifluoromethyl-5-fluorophenyl | vinyl | |
| 1.3.502 | 3-trifluoromethyl-5-fluorophenyl | 1-methylvinyl | |
| 1.3.503 | 3-trifluoromethyl-5-fluorophenyl | allyl | |
| 1.3.504 | 3-trifluoromethyl-5-fluorophenyl | 1-chlorovinyl | |
| 1.3.505 | 3-trifluoromethyl-5-fluorophenyl | ethynyl | |
| 1.3.506 | 3-(methoxycarbonyl)-5-fluorophenyl | vinyl | |
| 1.3.507 | 3-hydroxymethyl-5-fluorophenyl | vinyl | |
| 1.3.508 | 3-carbamoyl-5-fluorophenyl | vinyl | |
| 1.3.509 | 3-hydroxy-5-fluorophenyl | vinyl | |
| 1.3.510 | 3-methoxy-5-fluorophenyl | vinyl | |
| 1.3.511 | 3-ethoxy-5-fluorophenyl | vinyl | |
| 1.3.512 | 3-n-propoxy-5-fluorophenyl | vinyl | |
| 1.3.513 | 3-isopropoxy-5-fluorophenyl | vinyl | |
| 1.3.514 | 3-n-butoxy-5-fluorophenyl | vinyl | |
| 1.3.515 | 3-isobutoxy-5-fluorophenyl | vinyl | |
| 1.3.516 | 3-tert-butoxy-5-fluorophenyl | vinyl | |
| 1.3.517 | 3-difluoromethoxy-5-fluorophenyl | vinyl | |
| 1.3.518 | 3-trifluoromethoxy-5-fluorophenyl | vinyl | |
| 1.3.519 | 3-(2,2,2-trifluoroethoxy)-5-fluorophenyl | vinyl | |
| 1.3.520 | 3-(2-chloroethoxy)-5-fluorophenyl | vinyl | |
| 1.3.521 | 3-(2-hydroxyethoxy)-5-fluorophenyl | vinyl | |
| 1.3.522 | 3-[(tert-butoxycarbonyl)oxy]-5-fluorophenyl | vinyl | |
| 1.3.523 | 3-nitro-5-fluorophenyl | vinyl | |
| 1.3.524 | 3-acetoxy-5-fluorophenyl | vinyl | |
| 1.3.525 | {3-[(tert-butoxycarbonyl)amino]-5-fluorophenyl} | vinyl | |
| 1.3.526 | 3-methylsulfanyl-5-fluorophenyl | vinyl | |
| 1.3.527 | 3,5-dichlorophenyl | vinyl | [CDCl$_3$] 3.41 (d, 1H); 3.93 (d, 1H); 5.45 (d, 1H); 5.62 (d, 1H); 6.15 (dd, 1H); 7.44 (s, 1H); 7.54 (s, 2H). |
| 1.3.528 | 3,5-dichlorophenyl | 1-methylvinyl | [CDCl3] 1.91 (s, 3H); 3.40 (d, 1H); 3.99 (d, 1H); 5.16 (s, 1H), 5.35 (s, 1H); 5.9 (s br, 1H), 7.42 (s, 1H); 7.54 (s, 2H). |
| 1.3.529 | 3,5-dichlorophenyl | allyl | |
| 1.3.530 | 3,5-dichlorophenyl | 1-chlorovinyl | |
| 1.3.531 | 3,5-dichlorophenyl | ethynyl | |
| 1.3.532 | 3-bromo-5-chlorophenyl | vinyl | |
| 1.3.533 | 3-iodo-5-chlorophenyl | vinyl | |
| 1.3.534 | 3-methyl-5-chlorophenyl | vinyl | |
| 1.3.535 | 3-methyl-5-chlorophenyl | 1-methylvinyl | [CDCl$_3$] 1.91 (s, 3H); 2.36 (s, 3H); 3.42 (d, 1H); 4.00 (d, 1H); 5.15 (s, 1H); 5.35 (s, 1H); 6.6 (s br, 1H); |

TABLE 1.3-continued

Inventive compounds of the general formula (I) in which W* is COOH, $R^1$ and $R^2$ are each hydrogen, and aryl is the radical.

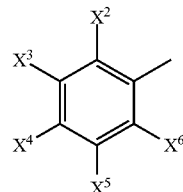

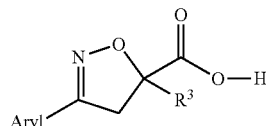

| No. | Aryl | $R^3$ | Physical data |
|---|---|---|---|
| 1.3.536 | 3-ethyl-5-chlorophenyl | vinyl | 7.24 (s, 1H); 7.36 (s, 1H); 7.45 (s, 1H). [CDC$_{13}$] 1.25 (t, 3H); 2.65 (q, 2H); 3.43 (d, 1H); 3.95 (d, 1H); 5.43 (d, 1H); 5.63 (d, 1H); 6.16 (dd, 1H); 7.27 (s, 1H); 7.38 (s, 1H); 7.43 (s, 1H). |
| 1.3.537 | 3-propyl-5-chlorophenyl | vinyl | |
| 1.3.538 | 3-n-butyl-5-chlorophenyl | vinyl | |
| 1.3.539 | 3-isobutyl-5-chlorophenyl | vinyl | |
| 1.3.540 | 3-tert-butyl-5-chlorophenyl | vinyl | |
| 1.3.541 | 3-cyclopropyl-5-chlorophenyl | vinyl | |
| 1.3.542 | 3-vinyl-5-chlorophenyl | vinyl | |
| 1.3.543 | 3-ethynyl-5-chlorophenyl | vinyl | |
| 1.3.544 | 3-cyano-5-chlorophenyl | vinyl | |
| 1.3.545 | 3-trifluoromethyl-5-chlorophenyl | vinyl | |
| 1.3.546 | 3-(hydroxycarbonyl)-5-chlorophenyl | vinyl | |
| 1.3.547 | 3-(methoxycarbonyl)-5-chlorophenyl | vinyl | |
| 1.3.548 | 3-hydroxymethyl-5-chlorophenyl | vinyl | |
| 1.3.549 | 3-carbamoyl-5-chlorophenyl | vinyl | |
| 1.3.550 | 3-hydroxy-5-chlorophenyl | vinyl | |
| 1.3.551 | 3-methoxy-5-chlorophenyl | vinyl | |
| 1.3.552 | 3-ethoxy-5-chlorophenyl | vinyl | |
| 1.3.553 | 3-n-propoxy-5-chlorophenyl | vinyl | |
| 1.3.554 | 3-isopropoxy-5-chlorophenyl | vinyl | |
| 1.3.555 | 3-n-butoxy-5-chlorophenyl | vinyl | |
| 1.3.556 | 3-isobutoxy-5-chlorophenyl | vinyl | |
| 1.3.557 | 3-tert-butoxy-5-chlorophenyl | vinyl | |
| 1.3.558 | 3-difluoromethoxy-5-chlorophenyl | vinyl | |
| 1.3.559 | 3-trifluoromethoxy-5-chlorophenyl | vinyl | |
| 1.3.560 | 3-(2,2,2-trifluoroethoxy)-5-chlorophenyl | vinyl | |
| 1.3.561 | 3-(2-chloroethoxy)-5-chlorophenyl | vinyl | |
| 1.3.562 | 3-(2-hydroxyethoxy)-5-chlorophenyl | vinyl | |
| 1.3.563 | 3-[(tert-butoxycarbonyl)oxy]-5-chlorophenyl | vinyl | |
| 1.3.564 | 3-nitro-5-chlorophenyl | vinyl | |
| 1.3.565 | 3-acetoxy-5-chlorophenyl | vinyl | |
| 1.3.566 | (3-[(tert-butoxycarbonyl)amino]-5-chlorophenyl} | vinyl | |
| 1.3.567 | 3-methylsulfanyl-5-chlorophenyl | vinyl | |
| 1.3.568 | 3,5-dibromophenyl | vinyl | |
| 1.3.569 | 3,5-dibromophenyl | 1-methylvinyl | |
| 1.3.570 | 3-iodo-5-bromophenyl | vinyl | |
| 1.3.571 | 3-methyl-5-bromophenyl | vinyl | [CDCl3] 2.36 (s, 3H); 3.42 (d, 1H); 3.94 (d, 1H); 5.43 (d, 1H); 5.63 (d, 1H); 6.15 (dd, 1H); 7.40 (d, 2H); 7.58 (s, 1H). |
| 1.3.572 | 3-methyl-5-bromophenyl | 1-methylvinyl | |
| 1.3.573 | 3-methyl-5-bromophenyl | allyl | |
| 1.3.574 | 3-methyl-5-bromophenyl | 1-chlorovinyl | |
| 1.3.575 | 3-methyl-5-bromophenyl | ethynyl | |
| 1.3.576 | 3-ethyl-5-bromophenyl | vinyl | |
| 1.3.577 | 3-propyl-5-bromophenyl | vinyl | |

TABLE 1.3-continued

Inventive compounds of the general formula (I) in which W* is COOH, $R^1$ and $R^2$ are each hydrogen, and aryl is the radical.

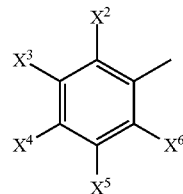

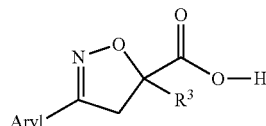

| No. | Aryl | $R^3$ | Physical data |
|---|---|---|---|
| 1.3.578 | 3-isopropyl-5-bromophenyl | vinyl | |
| 1.3.579 | 3-n-butyl-5-bromophenyl | vinyl | |
| 1.3.580 | 3-isobutyl-5-bromophenyl | vinyl | |
| 1.3.581 | 3-tert-butyl-5-bromophenyl | vinyl | |
| 1.3.582 | 3-cyclopropyl-5-bromophenyl | vinyl | |
| 1.3.583 | 3-vinyl-5-bromophenyl | vinyl | |
| 1.3.584 | 3-ethynyl-5-bromophenyl | vinyl | |
| 1.3.585 | 3-cyano-5-bromophenyl | vinyl | |
| 1.3.586 | 3-trifluoromethyl-5-bromophenyl | vinyl | |
| 1.3.587 | 3-(hydroxycarbonyl)-5-bromophenyl | vinyl | |
| 1.3.588 | 3-(methoxycarbonyl)-5-bromophenyl | vinyl | |
| 1.3.589 | 3-hydroxymethyl-5-bromophenyl | vinyl | |
| 1.3.590 | 3-carbamoyl-5-bromophenyl | vinyl | |
| 1.3.591 | 3-hydroxy-5-bromophenyl | vinyl | |
| 1.3.592 | 3-methoxy-5-bromophenyl | vinyl | |
| 1.3.593 | 3-ethoxy-5-bromophenyl | vinyl | |
| 1.3.594 | 3-n-propoxy-5-bromophenyl | vinyl | |
| 1.3.595 | 3-isopropoxy-5-bromophenyl | vinyl | |
| 1.3.596 | 3-n-butoxy-5-bromophenyl | vinyl | |
| 1.3.597 | 3-isobutoxy-5-bromophenyl | vinyl | |
| 1.3.598 | 3-tert-butoxy-5-bromophenyl | vinyl | |
| 1.3.599 | 3-difluoromethoxy-5-bromophenyl | vinyl | |
| 1.3.600 | 3-trifluoromethoxy-5-bromophenyl | vinyl | |
| 1.3.601 | 3-(2,2,2-trifluoroethoxy)-5-bromophenyl | vinyl | |
| 1.3.602 | 3-(2-chloroethoxy)-5-bromophenyl | vinyl | |
| 1.3.603 | 3-(2-hydroxyethoxy)-5-bromophenyl | vinyl | |
| 1.3.604 | 3-[(tert-butoxycarbonyl)oxy]-5-bromophenyl | vinyl | |
| 1.3.605 | 3-nitro-5-bromophenyl | vinyl | |
| 1.3.606 | 3-acetoxy-5-bromophenyl | vinyl | |
| 1.3.607 | (3-[(tert-butoxycarbonyl)amino]-5-bromophenyl} | vinyl | |
| 1.3.608 | 3-methylsulfanyl-5-bromophenyl | vinyl | |
| 1.3.609 | 3,5-diiodophenyl | vinyl | |
| 1.3.610 | 3-methyl-5-iodophenyl | vinyl | |
| 1.3.611 | 3-ethyl-5-iodophenyl | vinyl | |
| 1.3.612 | 3-propyl-5-iodophenyl | vinyl | |
| 1.3.613 | 3-isopropyl-5-iodophenyl | vinyl | |
| 1.3.614 | 3-n-butyl-5-iodophenyl | vinyl | |
| 1.3.615 | 3-isobutyl-5-iodophenyl | vinyl | |
| 1.3.616 | 3-tert-butyl-5-iodophenyl | vinyl | |
| 1.3.617 | 3-cyclopropyl-5-iodophenyl | vinyl | |
| 1.3.618 | 3-vinyl-5-iodophenyl | vinyl | |
| 1.3.619 | 3-ethynyl-5-iodophenyl | vinyl | |
| 1.3.620 | 3-cyano-5-iodophenyl | vinyl | |
| 1.3.621 | 3-trifluoromethyl-5-iodophenyl | vinyl | |
| 1.3.622 | 3-(hydroxycarbonyl)-5-iodophenyl | vinyl | |
| 1.3.623 | 3-(methoxycarbonyl)-5-iodophenyl | vinyl | |
| 1.3.624 | 3-hydroxymethyl-5-iodophenyl | vinyl | |
| 1.3.625 | 3-carbamoyl-5-iodophenyl | vinyl | |
| 1.3.626 | 3-hydroxy-5-iodophenyl | vinyl | |
| 1.3.627 | 3-methoxy-5-iodophenyl | vinyl | |
| 1.3.628 | 3-ethoxy-5-iodophenyl | vinyl | |
| 1.3.629 | 3-n-propoxy-5-iodophenyl | vinyl | |
| 1.3.630 | 3-isopropoxy-5-iodophenyl | vinyl | |
| 1.3.631 | 3-n-butoxy-5-iodophenyl | vinyl | |
| 1.3.632 | 3-isobutoxy-5-iodophenyl | vinyl | |

TABLE 1.3-continued

Inventive compounds of the general formula (I) in which W* is COOH, $R^1$ and $R^2$ are each hydrogen, and aryl is the radical.

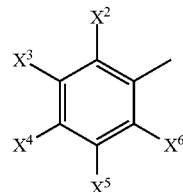

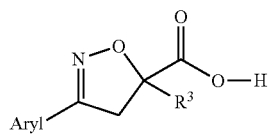

| No. | Aryl | $R^3$ | Physical data |
|---|---|---|---|
| 1.3.633 | 3-tert-butoxy-5-iodophenyl | vinyl | |
| 1.3.634 | 3-difluoromethoxy-5-iodophenyl | vinyl | |
| 1.3.635 | 3-trifluoromethoxy-5-iodophenyl | vinyl | |
| 1.3.636 | 3-(2,2,2-trifluoroethoxy)-5-iodophenyl | vinyl | |
| 1.3.637 | 3-(2-chloroethoxy)-5-iodophenyl | vinyl | |
| 1.3.638 | 3-(2-hydroxyethoxy)-5-iodophenyl | vinyl | |
| 1.3.639 | 3-[(tert-butoxycarbonyl)oxy]-5-iodophenyl | vinyl | |
| 1.3.640 | 3-nitro-5-iodophenyl | vinyl | |
| 1.3.641 | 3-acetoxy-5-iodophenyl | vinyl | |
| 1.3.642 | (3-[(tert-butoxycarbonyl)amino]-5-iodophenyl} | vinyl | |
| 1.3.643 | 3-methylsulfanyl-5-iodophenyl | vinyl | |
| 1.3.644 | 3,5-dimethylphenyl | vinyl | [CDCl$_3$] 2.34 (s, 6H); 3.45 (d, 1H); 3.97 (d, 1H); 5.42 (d, 1H); 5.62 (d, 1H); 6.15 (dd, 1H); 7.09 (s, 1H); 7.26 (s, 2H). |
| 1.3.645 | 3-ethyl-5-methylphenyl | vinyl | |
| 1.3.646 | 3-propyl-5-methylphenyl | vinyl | |
| 1.3.647 | 3-isopropyl-5-methylphenyl | vinyl | |
| 1.3.648 | 3-n-butyl-5-methylphenyl | vinyl | |
| 1.3.649 | 3-isobutyl-5-methylphenyl | vinyl | |
| 1.3.650 | 3-tert-butyl-5-methylphenyl | vinyl | |
| 1.3.651 | 3-cyclopropyl-5-methylphenyl | vinyl | |
| 1.3.652 | 3-cyano-5-methylphenyl | vinyl | |
| 1.3.653 | 3-trifluoromethyl-5-methylphenyl | vinyl | |
| 1.3.654 | 3-(methoxycarbonyl)-5-methylphenyl | vinyl | |
| 1.3.655 | 3-methoxy-5-methylphenyl | vinyl | |
| 1.3.656 | 3-ethoxy-5-methylphenyl | vinyl | |
| 1.3.657 | 3-n-propoxy-5-methylphenyl | vinyl | |
| 1.3.658 | 3-n-butoxy-5-methylphenyl | vinyl | |
| 1.3.659 | 3-isobutoxy-5-methylphenyl | vinyl | |
| 1.3.660 | 3-difluoromethoxy-5-methylphenyl | vinyl | |
| 1.3.661 | 3-trifluoromethoxy-5-methylphenyl | vinyl | |
| 1.3.662 | 3-nitro-5-methylphenyl | vinyl | |
| 1.3.663 | 3-acetoxy-5-methylphenyl | vinyl | |
| 1.3.664 | 3-methylsulfanyl-5-methylphenyl | vinyl | |
| 1.3.665 | 3,5-diethylphenyl | vinyl | |
| 1.3.666 | 3-propyl-5-ethylphenyl | vinyl | |
| 1.3.667 | 3-isopropyl-5-ethylphenyl | vinyl | |
| 1.3.668 | 3-n-butyl-5-ethylphenyl | vinyl | |
| 1.3.669 | 3-isobutyl-5-ethylphenyl | vinyl | |
| 1.3.670 | 3-tert-butyl-5-ethylphenyl | vinyl | |
| 1.3.671 | 3-cyclopropyl-5-ethylphenyl | vinyl | |
| 1.3.672 | 3-cyano-5-ethylphenyl | vinyl | |
| 1.3.673 | 3-trifluoromethyl-5-ethylphenyl | vinyl | |
| 1.3.674 | 3-(methoxycarbonyl)-5-ethylphenyl | vinyl | |
| 1.3.675 | 3-methoxy-5-ethylphenyl | vinyl | |
| 1.3.676 | 3-ethoxy-5-ethylphenyl | vinyl | |
| 1.3.677 | 3-n-propoxy-5-ethylphenyl | vinyl | |
| 1.3.678 | 3-n-butoxy-5-ethylphenyl | vinyl | |
| 1.3.679 | 3-isobutoxy-5-ethylphenyl | vinyl | |
| 1.3.680 | 3-difluoromethoxy-5-ethylphenyl | vinyl | |
| 1.3.681 | 3-trifluoromethoxy-5-ethylphenyl | vinyl | |
| 1.3.682 | 3-nitro-5-ethylphenyl | vinyl | |
| 1.3.683 | 3-acetoxy-5-ethylphenyl | vinyl | |

TABLE 1.3-continued

Inventive compounds of the general formula (I) in which W* is COOH, $R^1$ and $R^2$ are each hydrogen, and aryl is the radical.

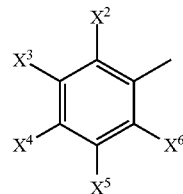

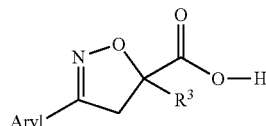

| No. | Aryl | $R^3$ | Physical data |
|---|---|---|---|
| 1.3.684 | 3-methylsulfanyl-5-ethylphenyl | vinyl | |
| 1.3.685 | 3,5-dipropylphenyl | vinyl | |
| 1.3.686 | 3-isopropyl-5-propylphenyl | vinyl | |
| 1.3.687 | 3-n-butyl-5-propylphenyl | vinyl | |
| 1.3.688 | 3-isobutyl-5-propylphenyl | vinyl | |
| 1.3.689 | 3-tert-butyl-5-propylphenyl | vinyl | |
| 1.3.690 | 3-cyclopropyl-5-propylphenyl | vinyl | |
| 1.3.691 | 3-cyano-5-propylphenyl | vinyl | |
| 1.3.692 | 3-trifluoromethyl-5-propylphenyl | vinyl | |
| 1.3.693 | 3-(methoxycarbonyl)-5-propylphenyl | vinyl | |
| 1.3.694 | 3-methoxy-5-propylphenyl | vinyl | |
| 1.3.695 | 3-ethoxy-5-propylphenyl | vinyl | |
| 1.3.696 | 3-n-propoxy-5-propylphenyl | vinyl | |
| 1.3.697 | 3-n-butoxy-5-propylphenyl | vinyl | |
| 1.3.698 | 3-isobutoxy-5-propylphenyl | vinyl | |
| 1.3.699 | 3-tert-butoxy-5-propylphenyl | vinyl | |
| 1.3.700 | 3-difluoromethoxy-5-propylphenyl | vinyl | |
| 1.3.701 | 3-trifluoromethoxy-5-ethylphenyl | vinyl | |
| 1.3.702 | 3-nitro-5-propylphenyl | vinyl | |
| 1.3.703 | 3-acetoxy-5-propylphenyl | vinyl | |
| 1.3.704 | 3-methylsulfanyl-5-propylphenyl | vinyl | |
| 1.3.705 | 3,5-diisopropylphenyl | vinyl | |
| 1.3.706 | 3-n-butyl-5-isopropylphenyl | vinyl | |
| 1.3.707 | 3-isobutyl-5-isopropylphenyl | vinyl | |
| 1.3.708 | 3-tert-butyl-5-isopropylphenyl | vinyl | |
| 1.3.709 | 3-cyclopropyl-5-isopropylphenyl | vinyl | |
| 1.3.710 | 3-cyano-5-isopropylphenyl | vinyl | |
| 1.3.711 | 3-trifluoromethyl-5-isopropylphenyl | vinyl | |
| 1.3.712 | 3-(methoxycarbonyl)-5-isopropylphenyl | vinyl | |
| 1.3.713 | 3-methoxy-5-isopropylphenyl | vinyl | |
| 1.3.714 | 3-ethoxy-5-isopropylphenyl | vinyl | |
| 1.3.715 | 3-n-propoxy-5-isopropylphenyl | vinyl | |
| 1.3.716 | 3-n-butoxy-5-isopropylphenyl | vinyl | |
| 1.3.717 | 3-isobutoxy-5-isopropylphenyl | vinyl | |
| 1.3.718 | 3-difluoromethoxy-5-isopropylphenyl | vinyl | |
| 1.3.719 | 3-trifluoromethoxy-5-isopropylphenyl | vinyl | |
| 1.3.720 | 3-nitro-5-isopropylphenyl | vinyl | |
| 1.3.721 | 3-acetoxy-5-isopropylphenyl | vinyl | |
| 1.3.722 | 3-methylsulfanyl-5-isopropylphenyl | vinyl | |
| 1.3.723 | 3,5-dibutylphenyl | vinyl | |
| 1.3.724 | 3-isobutyl-5-butylphenyl | vinyl | |
| 1.3.725 | 3-tert-butyl-5-butylphenyl | vinyl | |
| 1.3.726 | 3-cyclopropyl-5-butylphenyl | vinyl | |
| 1.3.727 | 3-cyano-5-butylphenyl | vinyl | |
| 1.3.728 | 3-trifluoromethyl-5-butylphenyl | vinyl | |
| 1.3.729 | 3-(methoxycarbonyl)-5-butylphenyl | vinyl | |
| 1.3.730 | 3-methoxy-5-butylphenyl | vinyl | |
| 1.3.731 | 3-ethoxy-5-butylphenyl | vinyl | |
| 1.3.732 | 3-n-propoxy-5-butylphenyl | vinyl | |
| 1.3.733 | 3-n-butoxy-5-butylphenyl | vinyl | |
| 1.3.734 | 3-isobutoxy-5-butylphenyl | vinyl | |
| 1.3.735 | 3-difluoromethoxy-5-butylphenyl | vinyl | |
| 1.3.736 | 3-trifluoromethoxy-5-butylphenyl | vinyl | |
| 1.3.737 | 3-nitro-5-butylphenyl | vinyl | |
| 1.3.738 | 3-acetoxy-5-butylphenyl | vinyl | |
| 1.3.739 | 3-methylsulfanyl-5-butylphenyl | vinyl | |
| 1.3.740 | 3,5-diisobutylphenyl | vinyl | |

TABLE 1.3-continued

Inventive compounds of the general formula (I) in which W* is COOH, $R^1$ and $R^2$ are each hydrogen, and aryl is the radical.

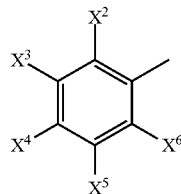

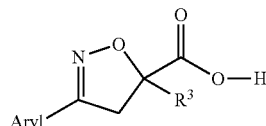

| No. | Aryl | $R^3$ | Physical data |
|---|---|---|---|
| 1.3.741 | 3-tert-butyl-5-isobutylphenyl | vinyl | |
| 1.3.742 | 3-cyclopropyl-5-isobutylphenyl | vinyl | |
| 1.3.743 | 3-cyano-5-isobutylphenyl | vinyl | |
| 1.3.744 | 3-trifluoromethyl-5-isobutylphenyl | vinyl | |
| 1.3.745 | 3-(hydroxycarbonyl)-5-isobutylphenyl | vinyl | |
| 1.3.746 | 3-(methoxycarbonyl)-5-isobutylphenyl | vinyl | |
| 1.3.747 | 3-methoxy-5-isobutylphenyl | vinyl | |
| 1.3.748 | 3-ethoxy-5-isobutylphenyl | vinyl | |
| 1.3.749 | 3-n-propoxy-5-isobutylphenyl | vinyl | |
| 1.3.750 | 3-n-butoxy-5-isobutylphenyl | vinyl | |
| 1.3.751 | 3-isobutoxy-5-isobutylphenyl | vinyl | |
| 1.3.752 | 3-difluoromethoxy-5-isobutylphenyl | vinyl | |
| 1.3.753 | 3-trifluoromethoxy-5-isobutylphenyl | vinyl | |
| 1.3.754 | 3-nitro-5-isobutylphenyl | vinyl | |
| 1.3.755 | 3-acetoxy-5-isobutylphenyl | vinyl | |
| 1.3.756 | 3-methylsulfanyl-5-isobutylphenyl | vinyl | |
| 1.3.757 | 3,5-di(tert-butyl)phenyl | vinyl | |
| 1.3.758 | 3-cyclopropyl-5-tert-butylphenyl | vinyl | |
| 1.3.759 | 3-cyano-5-tert-butylphenyl | vinyl | |
| 1.3.760 | 3-trifluoromethyl-5-tert-butylphenyl | vinyl | |
| 1.3.761 | 3-(methoxycarbonyl)-5-tert-butylphenyl | vinyl | |
| 1.3.762 | 3-methoxy-5-tert-butylphenyl | vinyl | |
| 1.3.763 | 3-ethoxy-5-tert-butylphenyl | vinyl | |
| 1.3.764 | 3-n-propoxy-5-tert-butylphenyl | vinyl | |
| 1.3.765 | 3-n-butoxy-5-tert-butylphenyl | vinyl | |
| 1.3.766 | 3-isobutoxy-5-tert-butylphenyl | vinyl | |
| 1.3.767 | 3-tert-butoxy-5-tert-butylphenyl | vinyl | |
| 1.3.768 | 3-difluoromethoxy-5-tert-butylphenyl | vinyl | |
| 1.3.769 | 3-trifluoromethoxy-5-tert-butylphenyl | vinyl | |
| 1.3.770 | 3-nitro-5-tert-butylphenyl | vinyl | |
| 1.3.771 | 3-acetoxy-5-tert-butylphenyl | vinyl | |
| 1.3.772 | 3-methylsulfanyl-5-tert-butylphenyl | vinyl | |
| 1.3.773 | 3-tert-butyl-5-cyclopropylphenyl | vinyl | |
| 1.3.774 | 3,5-dicyclopropyl-phenyl | vinyl | |
| 1.3.775 | 3-cyano-5-cyclopropylphenyl | vinyl | |
| 1.3.776 | 3-trifluoromethyl-5-cyclopropylphenyl | vinyl | |
| 1.3.777 | 3-(methoxycarbonyl)-5-cyclopropylphenyl | vinyl | |
| 1.3.778 | 3-methoxy-5-cyclopropylphenyl | vinyl | |
| 1.3.779 | 3-ethoxy-5-cyclopropylphenyl | vinyl | |
| 1.3.780 | 3-n-propoxy-5-cyclopropylphenyl | vinyl | |
| 1.3.781 | 3-n-butoxy-5-cyclopropylphenyl | vinyl | |
| 1.3.782 | 3-isobutoxy-5-cyclopropylphenyl | vinyl | |
| 1.3.783 | 3-difluoromethoxy-5-cyclopropylphenyl | vinyl | |
| 1.3.784 | 3-trifluoromethoxy-5-cyclopropylphenyl | vinyl | |
| 1.3.785 | 3-nitro-5-cyclopropylphenyl | vinyl | |
| 1.3.786 | 3-acetoxy-5-cyclopropylphenyl | vinyl | |
| 1.3.787 | 3-methylsulfanyl-5-cyclopropylphenyl | vinyl | |
| 1.3.788 | 3,5-dicyanophenyl | vinyl | |
| 1.3.789 | 3-trifluoromethyl-5-cyanophenyl | vinyl | |
| 1.3.790 | 3-(methoxycarbonyl)-5-cyanophenyl | vinyl | |
| 1.3.791 | 3-methoxy-5-cyanophenyl | vinyl | |
| 1.3.792 | 3-ethoxy-5-cyanophenyl | vinyl | |
| 1.3.793 | 3-n-propoxy-5-cyanophenyl | vinyl | |
| 1.3.794 | 3-n-butoxy-5-cyanophenyl | vinyl | |
| 1.3.795 | 3-isobutoxy-5-cyanophenyl | vinyl | |
| 1.3.796 | 3-difluoromethoxy-5-cyanophenyl | vinyl | |
| 1.3.797 | 3-trifluoromethoxy-5-cyanophenyl | vinyl | |

TABLE 1.3-continued

Inventive compounds of the general formula (I) in which W* is COOH, $R^1$ and $R^2$ are each hydrogen, and aryl is the radical.

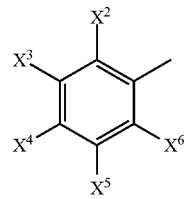

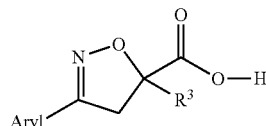

| No. | Aryl | $R^3$ | Physical data |
|---|---|---|---|
| 1.3.798 | 3-nitro-5-cyanophenyl | vinyl | |
| 1.3.799 | 3-acetoxy-5-cyanophenyl | vinyl | |
| 1.3.800 | 3-methylsulfanyl-5-cyanophenyl | vinyl | |
| 1.3.801 | 3,5-di(trifluoromethyl)-phenyl | vinyl | |
| 1.3.802 | 3-(methoxycarbonyl)-5-trifluoromethyl-phenyl | vinyl | |
| 1.3.803 | 3-methoxy-5-trifluoromethylphenyl | vinyl | |
| 1.3.804 | 3-ethoxy-5-trifluoromethylphenyl | vinyl | |
| 1.3.805 | 3-n-propoxy-5-trifluoromethylphenyl | vinyl | |
| 1.3.806 | 3-n-butoxy-5-trifluoromethylphenyl | vinyl | |
| 1.3.807 | 3-isobutoxy-5-trifluoromethylphenyl | vinyl | |
| 1.3.808 | 3-difluoromethoxy-5-trifluoromethylphenyl | vinyl | |
| 1.3.809 | 3-trifluoromethoxy-5-trifluoromethylphenyl | vinyl | |
| 1.3.810 | 3-nitro-5-trifluoromethylphenyl | vinyl | |
| 1.3.811 | 3-acetoxy-5-trifluoromethylphenyl | vinyl | |
| 1.3.812 | 3-methylsulfanyl-5-trifluoromethylphenyl | vinyl | |
| 1.3.813 | 3,5-di(methoxycarbonyl)phenyl | vinyl | |
| 1.3.814 | 3-methoxy-5-(methoxycarbonyl)phenyl | vinyl | |
| 1.3.815 | 3-ethoxy-5-(methoxycarbonyl)phenyl | vinyl | |
| 1.3.816 | 3-n-propoxy-5-(methoxycarbonyl)phenyl | vinyl | |
| 1.3.817 | 3-n-butoxy-5-(methoxycarbonyl)phenyl | vinyl | |
| 1.3.818 | 3-isobutoxy-5-(methoxycarbonyl)phenyl | vinyl | |
| 1.3.819 | 3-difluoromethoxy-5-(methoxycarbonyl)-phenyl | vinyl | |
| 1.3.820 | 3-trifluoromethoxy-5-(methoxycarbonyl)-phenyl | vinyl | |
| 1.3.821 | 3-nitro-5-(methoxycarbonyl)phenyl | vinyl | |
| 1.3.822 | 3-acetoxy-5-(methoxycarbonyl)phenyl | vinyl | |
| 1.3.823 | 3-methylsulfanyl-5-(methoxycarbonyl)-phenyl | vinyl | |
| 1.3.824 | 3,5-dimethoxyphenyl | vinyl | |
| 1.3.825 | 3-ethoxy-5-methoxyphenyl | vinyl | |
| 1.3.826 | 3-n-propoxy-5-methoxyphenyl | vinyl | |
| 1.3.827 | 3-n-butoxy-5-methoxyphenyl | vinyl | |
| 1.3.828 | 3-isobutoxy-5-methoxyphenyl | vinyl | |
| 1.3.829 | 3-difluoromethoxy-5-methoxyphenyl | vinyl | |
| 1.3.830 | 3-trifluoromethoxy-5-methoxyphenyl | vinyl | |
| 1.3.831 | 3-nitro-5-methoxyphenyl | vinyl | |
| 1.3.832 | 3-acetoxy-5-methoxyphenyl | vinyl | |
| 1.3.833 | 3-methylsulfanyl-5-methoxyphenyl | vinyl | |
| 1.3.834 | 3,5-diethoxyphenyl | vinyl | |
| 1.3.835 | 3-n-propoxy-5-ethoxyphenyl | vinyl | |
| 1.3.836 | 3-n-butoxy-5-ethoxyphenyl | vinyl | |
| 1.3.837 | 3-isobutoxy-5-ethoxyphenyl | vinyl | |
| 1.3.838 | 3-difluoromethoxy-5-ethoxyphenyl | vinyl | |
| 1.3.839 | 3-trifluoromethoxy-5-ethoxyphenyl | vinyl | |
| 1.3.840 | 3-nitro-5-ethoxyphenyl | vinyl | |
| 1.3.841 | 3-acetoxy-5-ethoxyphenyl | vinyl | |
| 1.3.842 | 3-methylsulfanyl-5-ethoxyphenyl | vinyl | |
| 1.3.843 | 3,5-di(isopropoxy)phenyl | vinyl | |
| 1.3.844 | 3-n-butoxy-5-isopropoxyphenyl | vinyl | |
| 1.3.845 | 3-isobutoxy-5-isopropoxyphenyl | vinyl | |
| 1.3.846 | 3-difluoromethoxy-5-isopropoxyphenyl | vinyl | |
| 1.3.847 | 3-trifluoromethoxy-5-isopropoxyphenyl | vinyl | |
| 1.3.848 | 3-nitro-5-isopropoxyphenyl | vinyl | |
| 1.3.849 | 3-acetoxy-5-isopropoxyphenyl | vinyl | |
| 1.3.850 | 3-methylsulfanyl-5-isopropoxyphenyl | vinyl | |

TABLE 1.3-continued

Inventive compounds of the general formula (I) in which W* is COOH, $R^1$ and $R^2$ are each hydrogen, and aryl is the radical.

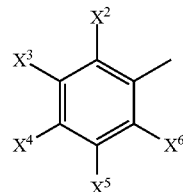

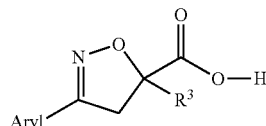

| No. | Aryl | $R^3$ | Physical data |
|---|---|---|---|
| 1.3.851 | 3,5-di(trifluoromethoxy)phenyl | vinyl | |
| 1.3.852 | 3-nitro-5-trifluoromethoxyphenyl | vinyl | |
| 1.3.853 | 3-acetoxy-5-tert-butoxyphenyl | vinyl | |
| 1.3.854 | 3-methylsulfanyl-5-trifluoromethoxyphenyl | vinyl | |
| 1.3.855 | 3,5-bis(difluoromethoxy)phenyl | vinyl | |
| 1.3.856 | 3,5-bis(difluoromethoxy)phenyl | 1-methylvinyl | |
| 1.3.857 | 3,5-bis(difluoromethoxy)phenyl | allyl | |
| 1.3.858 | 3,5-bis(difluoromethoxy)phenyl | 1-chlorovinyl | |
| 1.3.859 | 3-trifluoromethoxy-5-difluoromethoxyphenyl | vinyl | |
| 1.3.860 | 3-nitro-5-difluoromethoxyphenyl | vinyl | |
| 1.3.861 | 3-acetoxy-5-difluoromethoxyphenyl | vinyl | |
| 1.3.862 | 3-methylsulfanyl-5-difluoromethoxyphenyl | vinyl | |
| 1.3.863 | 3,5-bis(acetoxy)phenyl | vinyl | |
| 1.3.864 | 3-methylsulfanyl-5-acetoxyphenyl | vinyl | |
| 1.3.865 | 3-acetoxy-5-nitrophenyl | vinyl | |
| 1.3.866 | 3-methylsulfanyl-5-nitrophenyl | vinyl | |
| 1.3.867 | 3,5-di(methylsulfanyl)phenyl | vinyl | |
| 1.3.868 | 3,4-difluorophenyl | vinyl | |
| 1.3.869 | 3,4-difluorophenyl | 1-methylvinyl | |
| 1.3.870 | 3,4-difluorophenyl | allyl | |
| 1.3.871 | 3,4-difluorophenyl | 1-chlorovinyl | |
| 1.3.872 | 3,4-difluorophenyl | ethynyl | |
| 1.3.873 | 3-chloro-4-fluorophenyl | vinyl | |
| 1.3.874 | 3-chloro-4-fluorophenyl | 1-methylvinyl | |
| 1.3.875 | 3-chloro-4-fluorophenyl | allyl | |
| 1.3.876 | 3-chloro-4-fluorophenyl | 1-chlorovinyl | |
| 1.3.877 | 3-chloro-4-fluorophenyl | ethynyl | |
| 1.3.878 | 3-bromo-4-fluorophenyl | vinyl | |
| 1.3.879 | 3-methyl-4-fluorophenyl | vinyl | |
| 1.3.880 | 3-methyl-4-fluorophenyl | 1-methylvinyl | |
| 1.3.881 | 3-cyclopropyl-4-fluorophenyl | vinyl | |
| 1.3.882 | 3-cyano-4-fluorophenyl | vinyl | |
| 1.3.883 | 3-methoxy-4-fluorophenyl | vinyl | |
| 1.3.884 | 3-ethoxy-4-fluorophenyl | vinyl | |
| 1.3.885 | 3-trifluoromethoxy-4-fluorophenyl | vinyl | |
| 1.3.886 | 3-nitro-4-fluorophenyl | vinyl | |
| 1.3.887 | 3-fluoro-4-chlorophenyl | vinyl | |
| 1.3.888 | 3,4-dichlorophenyl | vinyl | |
| 1.3.889 | 3-bromo-4-chlorophenyl | vinyl | |
| 1.3.890 | 3-methyl-4-chlorophenyl | vinyl | |
| 1.3.891 | 3-ethyl-4-chlorophenyl | vinyl | |
| 1.3.892 | 3-cyclopropyl-4-chlorophenyl | vinyl | |
| 1.3.893 | 3-cyano-4-chlorophenyl | vinyl | |
| 1.3.894 | 3-trifluoromethyl-4-chlorophenyl | vinyl | |
| 1.3.895 | 3-methoxy-4-chlorophenyl | vinyl | |
| 1.3.896 | 3-ethoxy-4-chlorophenyl | vinyl | |
| 1.3.897 | 3-trifluoromethoxy-4-chlorophenyl | vinyl | |
| 1.3.898 | 3-nitro-4-chlorophenyl | vinyl | |
| 1.3.899 | 3-fluoro-4-bromophenyl | vinyl | |
| 1.3.900 | 3-chloro-4-bromophenyl | vinyl | |
| 1.3.901 | 3,4-dibromophenyl | vinyl | |
| 1.3.902 | 3-methyl-4-bromophenyl | vinyl | |
| 1.3.903 | 3-ethyl-4-bromophenyl | vinyl | |
| 1.3.904 | 3-cyclopropyl-4-bromophenyl | vinyl | |

TABLE 1.3-continued

Inventive compounds of the general formula (I) in which W* is COOH, $R^1$ and $R^2$ are each hydrogen, and aryl is the radical.

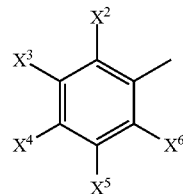

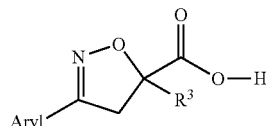

| No. | Aryl | $R^3$ | Physical data |
|---|---|---|---|
| 1.3.905 | 3-cyano-4-bromophenyl | vinyl | |
| 1.3.906 | 3-trifluoromethyl-4-bromophenyl | vinyl | |
| 1.3.907 | 3-methoxy-4-phenyl | vinyl | |
| 1.3.908 | 3-ethoxy-4-bromophenyl | vinyl | |
| 1.3.909 | 3-trifluoromethoxy-4-bromophenyl | vinyl | |
| 1.3.910 | 3-nitro-4-bromophenyl | vinyl | |
| 1.3.911 | 3-fluoro-4-iodophenyl | vinyl | |
| 1.3.912 | 3-chloro-4-iodophenyl | vinyl | |
| 1.3.913 | 3-bromo-4-iodophenyl | vinyl | |
| 1.3.914 | 3-methyl-4-iodophenyl | vinyl | |
| 1.3.915 | 3-cyclopropyl-4-iodophenyl | vinyl | |
| 1.3.916 | 3-cyano-4-iodophenyl | vinyl | |
| 1.3.917 | 3-trifluoromethyl-4-iodophenyl | vinyl | |
| 1.3.918 | 3-methoxy-4-iodophenyl | vinyl | |
| 1.3.919 | 3-ethoxy-4-iodophenyl | vinyl | |
| 1.3.920 | 3-trifluoromethoxy-4-iodophenyl | vinyl | |
| 1.3.921 | 3-nitro-4-iodophenyl | vinyl | |
| 1.3.922 | 3-fluoro-4-methylphenyl | vinyl | |
| 1.3.923 | 3-chloro-4-methylphenyl | vinyl | |
| 1.3.924 | 3-bromo-4-methylphenyl | vinyl | |
| 1.3.925 | 3,4-dimethylphenyl | vinyl | |
| 1.3.926 | 3,4-dimethylphenyl | 1-methylvinyl | |
| 1.3.927 | 3,4-dimethylphenyl | allyl | |
| 1.3.928 | 3,4-dimethylphenyl | 1-chlorovinyl | |
| 1.3.929 | 3,4-dimethylphenyl | ethynyl | |
| 1.3.930 | 3-ethyl-4-methylphenyl | vinyl | |
| 1.3.931 | 3-cyclopropyl-4-methylphenyl | vinyl | |
| 1.3.932 | 3-cyano-4-methylphenyl | vinyl | |
| 1.3.933 | 3-trifluoromethyl-4-methylphenyl | vinyl | |
| 1.3.934 | 3-methoxy-4-methylphenyl | vinyl | |
| 1.3.935 | 3-ethoxy-4-methylphenyl | vinyl | |
| 1.3.936 | 3-trifluoromethoxy-4-methylphenyl | vinyl | |
| 1.3.937 | 3-nitro-4-methylphenyl | vinyl | |
| 1.3.938 | 3-fluoro-4-ethylphenyl | vinyl | |
| 1.3.939 | 3-chloro-4-ethylphenyl | vinyl | |
| 1.3.940 | 3-bromo-4-ethylphenyl | vinyl | |
| 1.3.941 | 3-methyl-4-ethylphenyl | vinyl | |
| 1.3.942 | 3,4-diethylphenyl | vinyl | |
| 1.3.943 | 3-cyclopropyl-4-ethylphenyl | vinyl | |
| 1.3.944 | 3-cyano-4-ethylphenyl | vinyl | |
| 1.3.945 | 3-trifluoromethyl-4-ethylphenyl | vinyl | |
| 1.3.946 | 3-methoxy-4-ethylphenyl | vinyl | |
| 1.3.947 | 3-ethoxy-4-ethylphenyl | vinyl | |
| 1.3.948 | 3-trifluoromethoxy-4-ethylphenyl | vinyl | |
| 1.3.949 | 3-nitro-4-ethylphenyl | vinyl | |
| 1.3.950 | 3-fluoro-4-propylphenyl | vinyl | |
| 1.3.951 | 3-chloro-4-propylphenyl | vinyl | |
| 1.3.952 | 3-bromo-4-propylphenyl | vinyl | |
| 1.3.953 | 3-methyl-4-propylphenyl | vinyl | |
| 1.3.954 | 3-methyl-4-propylphenyl | vinyl | |
| 1.3.955 | 3-cyclopropyl-4-propylphenyl | vinyl | |
| 1.3.956 | 3-cyano-4-propylphenyl | vinyl | |
| 1.3.957 | 3-trifluoromethyl-4-propylphenyl | vinyl | |
| 1.3.958 | 3-methoxy-4-propylphenyl | vinyl | |
| 1.3.959 | 3-ethoxy-4-propylphenyl | vinyl | |
| 1.3.960 | 3-trifluoromethoxy-4-propylphenyl | vinyl | |
| 1.3.961 | 3-nitro-4-propylphenyl | vinyl | |

TABLE 1.3-continued

Inventive compounds of the general formula (I) in which W* is COOH, $R^1$ and $R^2$ are each hydrogen, and aryl is the radical.

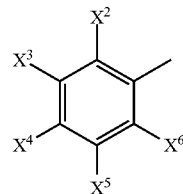

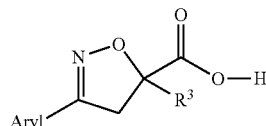

| No. | Aryl | $R^3$ | Physical data |
|---|---|---|---|
| 1.3.962 | 3-fluoro-4-isopropylphenyl | vinyl | |
| 1.3.963 | 3-chloro-4-isopropylphenyl | vinyl | |
| 1.3.964 | 3-bromo-4-isopropylphenyl | vinyl | |
| 1.3.965 | 3-methyl-4-isopropylphenyl | vinyl | |
| 1.3.966 | 3-cyclopropyl-4-isopropylphenyl | vinyl | |
| 1.3.967 | 3-cyano-4-isopropylphenyl | vinyl | |
| 1.3.968 | 3-trifluoromethyl-4-isopropylphenyl | vinyl | |
| 1.3.969 | 3-methoxy-4-isopropylphenyl | vinyl | |
| 1.3.970 | 3-ethoxy-4-isopropylphenyl | vinyl | |
| 1.3.971 | 3-trifluoromethoxy-4-isopropylphenyl | vinyl | |
| 1.3.972 | 3-nitro-4-isopropylphenyl | vinyl | |
| 1.3.973 | 3-fluoro-4-tert-butylphenyl | vinyl | |
| 1.3.974 | 3-chloro-4-tert-butylphenyl | vinyl | |
| 1.3.975 | 3-bromo-4-tert-butylphenyl | vinyl | |
| 1.3.976 | 3-methyl-4-tert-butylphenyl | vinyl | |
| 1.3.977 | 3-cyclopropyl-4-tert-butylphenyl | vinyl | |
| 1.3.978 | 3-cyano-4-tert-butylphenyl | vinyl | |
| 1.3.979 | 3-trifluoromethyl-4-tert-butylphenyl | vinyl | |
| 1.3.980 | 3-trifluoromethyl-4-tert-butylphenyl | 1-methylvinyl | |
| 1.3.981 | 3-trifluoromethyl-4-tert-butylphenyl | allyl | |
| 1.3.982 | 3-trifluoromethyl-4-tert-butylphenyl | 1-chlorovinyl | |
| 1.3.983 | 3-trifluoromethyl-4-tert-butylphenyl | ethynyl | |
| 1.3.984 | 3-methoxy-4-tert-butylphenyl | vinyl | |
| 1.3.985 | 3-ethoxy-4-tert-butylphenyl | vinyl | |
| 1.3.986 | 3-trifluoromethoxy-4-tert-butylphenyl | vinyl | |
| 1.3.987 | 3-nitro-4-tert-butylphenyl | vinyl | |
| 1.3.988 | 3-fluoro-4-cyclopropylphenyl | vinyl | |
| 1.3.989 | 3-chloro-4-cyclopropylphenyl | vinyl | |
| 1.3.990 | 3-bromo-4-cyclopropylphenyl | vinyl | |
| 1.3.991 | 3-methyl-4-cyclopropylphenyl | vinyl | |
| 1.3.992 | 3-cyclopropyl-4-cyclopropylphenyl | vinyl | |
| 1.3.993 | 3-cyano-4-cyclopropylphenyl | vinyl | |
| 1.3.994 | 3-trifluoromethyl-4-cyclopropylphenyl | vinyl | |
| 1.3.995 | 3-methoxy-4-cyclopropylphenyl | vinyl | |
| 1.3.996 | 3-ethoxy-4-cyclopropylphenyl | vinyl | |
| 1.3.997 | 3-trifluoromethoxy-4-cyclopropylphenyl | vinyl | |
| 1.3.998 | 3-fluoro-4-methoxycarbonylphenyl | vinyl | |
| 1.3.999 | 3-chloro-4-methoxycarbonylphenyl | vinyl | |
| 1.3.1000 | 3-bromo-4-methoxycarbonylphenyl | vinyl | |
| 1.3.1001 | 3-methyl-4-methoxycarbonylphenyl | vinyl | |
| 1.3.1002 | 3-cyclopropyl-4-methoxycarbonylphenyl | vinyl | |
| 1.3.1003 | 3-cyano-4-methoxycarbonylphenyl | vinyl | |
| 1.3.1004 | 3-trifluoromethyl-4-methoxycarbonyl-phenyl | vinyl | |
| 1.3.1005 | 3-methoxy-4-methoxycarbonylphenyl | vinyl | |
| 1.3.1006 | 3-ethoxy-4-methoxycarbonylphenyl | vinyl | |
| 1.3.1007 | 3-trifluoromethoxy-4-methoxycarbonyl-phenyl | vinyl | |
| 1.3.1008 | 3-nitro-4-methoxycarbonylphenyl | vinyl | |
| 1.3.1009 | 3-fluoro-4-cyanophenyl | vinyl | |
| 1.3.1010 | 3-chloro-4-cyanophenyl | vinyl | |
| 1.3.1011 | 3-bromo-4-cyanophenyl | vinyl | |
| 1.3.1012 | 3-methyl-4-cyanophenyl | vinyl | |
| 1.3.1013 | 3-cyclopropyl-4-cyanophenyl | vinyl | |
| 1.3.1014 | 3,4-dicyanophenyl | vinyl | |
| 1.3.1015 | 3-trifluoromethyl-4-cyanophenyl | vinyl | |
| 1.3.1016 | 3-trifluoromethyl-4-cyanophenyl | 1-methylvinyl | |

TABLE 1.3-continued

Inventive compounds of the general formula (I) in which W* is COOH, $R^1$ and $R^2$ are each hydrogen, and aryl is the radical.

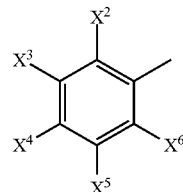

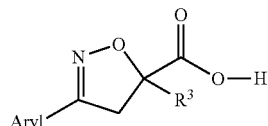

| No. | Aryl | $R^3$ | Physical data |
|---|---|---|---|
| 1.3.1017 | 3-trifluoromethyl-4-cyanophenyl | allyl | |
| 1.3.1018 | 3-trifluoromethyl-4-cyanophenyl | 1-chlorovinyl | |
| 1.3.1019 | 3-trifluoromethyl-4-cyanophenyl | ethynyl | |
| 1.3.1020 | 3-methoxy-4-cyanophenyl | vinyl | |
| 1.3.1021 | 3-ethoxy-4-cyanophenyl | vinyl | |
| 1.3.1022 | 3-trifluoromethoxy-4-cyanophenyl | vinyl | |
| 1.3.1023 | 3-nitro-4-cyanophenyl | vinyl | |
| 1.3.1024 | 3-fluoro-4-methoxyphenyl | vinyl | |
| 1.3.1025 | 3-chloro-4-methoxyphenyl | vinyl | |
| 1.3.1026 | 3-bromo-4-methoxyphenyl | vinyl | |
| 1.3.1027 | 3-methyl-4-methoxyphenyl | vinyl | |
| 1.3.1028 | 3-cyclopropyl-4-methoxyphenyl | vinyl | |
| 1.3.1029 | 3-cyano-4-methoxyphenyl | vinyl | |
| 1.3.1030 | 3-trifluoromethyl-4-methoxyphenyl | vinyl | |
| 1.3.1031 | 3,4-dimethoxyphenyl | vinyl | |
| 1.3.1032 | 3-ethoxy-4-methoxyphenyl | vinyl | |
| 1.3.1033 | 3-trifluoromethoxy-4-methoxyphenyl | vinyl | |
| 1.3.1034 | 3-nitro-4-methoxyphenyl | vinyl | |
| 1.3.1035 | 3-fluoro-4-ethoxyphenyl | vinyl | |
| 1.3.1036 | 3-chloro-4-ethoxyphenyl | vinyl | |
| 1.3.1037 | 3-chloro-4-ethoxyphenyl | 1-methylvinyl | |
| 1.3.1038 | 3-chloro-4-ethoxyphenyl | allyl | |
| 1.3.1039 | 3-chloro-4-ethoxyphenyl | 1-chlorovinyl | |
| 1.3.1040 | 3-chloro-4-ethoxyphenyl | ethynyl | |
| 1.3.1041 | 3-bromo-4-ethoxyphenyl | vinyl | |
| 1.3.1042 | 3-methyl-4-ethoxyphenyl | vinyl | |
| 1.3.1043 | 3-cyclopropyl-4-ethoxyphenyl | vinyl | |
| 1.3.1044 | 3-cyano-4-ethoxyphenyl | vinyl | |
| 1.3.1045 | 3-trifluoromethyl-4-ethoxyphenyl | vinyl | |
| 1.3.1046 | 3-methoxy-4-ethoxyphenyl | vinyl | |
| 1.3.1047 | 2,4-diethoxyphenyl | vinyl | |
| 1.3.1048 | 3-trifluoromethoxy-4-ethoxyphenyl | vinyl | |
| 1.3.1049 | 3-nitro-4-ethoxyphenyl | vinyl | |
| 1.3.1050 | 3-fluoro-4-propoxyphenyl | vinyl | |
| 1.3.1051 | 3-chloro-4-propoxyphenyl | vinyl | |
| 1.3.1052 | 3-bromo-4-propoxyphenyl | vinyl | |
| 1.3.1053 | 3-methyl-4-propoxyphenyl | vinyl | |
| 1.3.1054 | 3-cyclopropyl-4-propoxyphenyl | vinyl | |
| 1.3.1055 | 3-cyano-4-propoxyphenyl | vinyl | |
| 1.3.1056 | 3-trifluoromethyl-4-propoxyphenyl | vinyl | |
| 1.3.1057 | 3-methoxy-4-propoxyphenyl | vinyl | |
| 1.3.1058 | 3-ethoxy-4-propoxyphenyl | vinyl | |
| 1.3.1059 | 3-trifluoromethoxy-4-propoxyphenyl | vinyl | |
| 1.3.1060 | 3-nitro-4-propoxyphenyl | vinyl | |
| 1.3.1061 | 3-fluoro-4-isopropoxyphenyl | vinyl | |
| 1.3.1062 | 3-chloro-4-isopropoxyphenyl | vinyl | |
| 1.3.1063 | 3-bromo-4-isopropoxyphenyl | vinyl | |
| 1.3.1064 | 3-methyl-4-isopropoxyphenyl | vinyl | |
| 1.3.1065 | 3-cyclopropyl-4-isopropoxyphenyl | vinyl | |
| 1.3.1066 | 3-cyano-4-isopropoxyphenyl | vinyl | |
| 1.3.1067 | 3-trifluoromethyl-4-isopropoxyphenyl | vinyl | |
| 1.3.1068 | 3-methoxy-4-isopropoxyphenyl | vinyl | |
| 1.3.1069 | 3-ethoxy-4-isopropoxyphenyl | vinyl | |
| 1.3.1070 | 3-trifluoromethoxy-4-isopropoxyphenyl | vinyl | |
| 1.3.1071 | 3-nitro-4- isopropoxyphenyl | vinyl | |
| 1.3.1072 | 3-fluoro-4-trifluoromethoxyphenyl | vinyl | |
| 1.3.1073 | 3-chloro-4-trifluoromethoxyphenyl | vinyl | |

TABLE 1.3-continued

Inventive compounds of the general formula (I) in which W* is COOH, $R^1$ and $R^2$ are each hydrogen, and aryl is the radical.

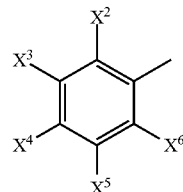

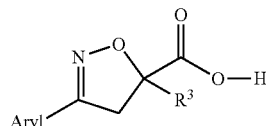

| No. | Aryl | $R^3$ | Physical data |
|---|---|---|---|
| 1.3.1074 | 3-bromo-4-trifluoromethoxyphenyl | vinyl | |
| 1.3.1075 | 3-methyl-4-trifluoromethoxyphenyl | vinyl | |
| 1.3.1076 | 3-cyclopropyl-4-trifluoromethoxyphenyl | vinyl | |
| 1.3.1077 | 3-cyano-4-trifluoromethoxyphenyl | vinyl | |
| 1.3.1078 | 3-trifluoromethyl-4-trifluoromethoxy-phenyl | vinyl | |
| 1.3.1079 | 3-methoxy-4-trifluoromethoxyphenyl | vinyl | |
| 1.3.1080 | 3-ethoxy-4-trifluoromethoxyphenyl | vinyl | |
| 1.3.1081 | 3,4-bis(trifluoromethoxy)phenyl | vinyl | |
| 1.3.1082 | 3-nitro-4-trifluoromethoxyphenyl | vinyl | |
| 1.3.1083 | 3-fluoro-4-difluoromethoxyphenyl | vinyl | |
| 1.3.1084 | 3-chloro-4-difluoromethoxyphenyl | vinyl | |
| 1.3.1085 | 3-bromo-4-difluoromethoxyphenyl | vinyl | |
| 1.3.1086 | 3-methyl-4-difluoromethoxyphenyl | vinyl | |
| 1.3.1087 | 3-cyclopropyl-4-difluoromethoxyphenyl | vinyl | |
| 1.3.1088 | 3-cyano-4-difluoromethoxyphenyl | vinyl | |
| 1.3.1089 | 3-trifluoromethyl-4-difluoromethoxyphenyl | vinyl | |
| 1.3.1090 | 3-methoxy-4-difluoromethoxyphenyl | vinyl | |
| 1.3.1091 | 3-ethoxy-4-difluoromethoxyphenyl | vinyl | |
| 1.3.1092 | 3-trifluoromethoxy-4-difluoromethoxy-phenyl | vinyl | |
| 1.3.1093 | 3-nitro-4-difluoromethoxyphenyl | vinyl | |
| 1.3.1094 | 3-fluoro-4-nitrophenyl | vinyl | |
| 1.3.1095 | 3-chloro-4-nitrophenyl | vinyl | |
| 1.3.1096 | 3-bromo-4-nitrophenyl | vinyl | |
| 1.3.1097 | 3-methyl-4-nitrophenyl | vinyl | |
| 1.3.1098 | 3-cyclopropyl-4-nitrophenyl | vinyl | |
| 1.3.1099 | 3-cyano-4-nitrophenyl | vinyl | |
| 1.3.1100 | 3-trifluoromethyl-4-nitrophenyl | vinyl | |
| 1.3.1101 | 3-methoxy-4-nitrophenyl | vinyl | |
| 1.3.1102 | 3-ethoxy-4-nitrophenyl | vinyl | |
| 1.3.1103 | 3-trifluoromethoxy-4-nitrophenyl | vinyl | |
| 1.3.1104 | 3-fluoro-4-methylsulfanylphenyl | vinyl | |
| 1.3.1105 | 3-chloro-4-methylsulfanylphenyl | vinyl | |
| 1.3.1106 | 3-bromo-4-methylsulfanylphenyl | vinyl | |
| 1.3.1107 | 3-methyl-4-methylsulfanylphenyl | vinyl | |
| 1.3.1108 | 3-cyclopropyl-4-methylsulfanylphenyl | vinyl | |
| 1.3.1109 | 3-cyano-4-methylsulfanylphenyl | vinyl | |
| 1.3.1110 | 3-trifluoromethyl-4-methylsulfanylphenyl | vinyl | |
| 1.3.1111 | 3-methoxy-4-methylsulfanylphenyl | vinyl | |
| 1.3.1112 | 3-ethoxy-4-methylsulfanylphenyl | vinyl | |
| 1.3.1113 | 3-trifluoromethoxy-4-methylsulfanylphenyl | vinyl | |
| 1.3.1114 | 3-nitro-4-methylsulfanylphenyl | vinyl | |
| 1.3.1115 | 3,6-difluorophenyl | vinyl | |
| 1.3.1116 | 3,6-difluorophenyl | 1-methylvinyl | |
| 1.3.1117 | 3,6-difluorophenyl | allyl | |
| 1.3.1118 | 3,6-difluorophenyl | 1-chlorovinyl | |
| 1.3.1119 | 3,6-difluorophenyl | ethynyl | |
| 1.3.1120 | 3-chloro-6-fluorophenyl | vinyl | |
| 1.3.1121 | 3-bromo-6-fluorophenyl | vinyl | |
| 1.3.1122 | 3-methyl-6-fluorophenyl | vinyl | |
| 1.3.1123 | 3-ethyl-6-fluorophenyl | vinyl | |
| 1.3.1124 | 3-cyclopropyl-6-fluorophenyl | vinyl | |
| 1.3.1125 | 3-cyano-6-fluorophenyl | vinyl | |
| 1.3.1126 | 3-methoxy-6-fluorophenyl | vinyl | |
| 1.3.1127 | 3-ethoxy-6-fluorophenyl | vinyl | |
| 1.3.1128 | 3-trifluoromethoxy-6-fluorophenyl | vinyl | |

TABLE 1.3-continued

Inventive compounds of the general formula (I) in which W* is COOH, $R^1$ and $R^2$ are each hydrogen, and aryl is the radical.

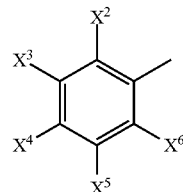

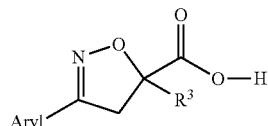

| No. | Aryl | $R^3$ | Physical data |
|---|---|---|---|
| 1.3.1129 | 3-nitro-6-fluorophenyl | vinyl | |
| 1.3.1130 | 3-fluoro-6-chlorophenyl | vinyl | |
| 1.3.1131 | 3-fluoro-6-chlorophenyl | 1-methylvinyl | |
| 1.3.1132 | 3-fluoro-6-chlorophenyl | allyl | |
| 1.3.1133 | 3-fluoro-6-chlorophenyl | 1-chlorovinyl | |
| 1.3.1134 | 3-fluoro-6-chlorophenyl | ethynyl | |
| 1.3.1135 | 3,6-dichlorophenyl | vinyl | |
| 1.3.1136 | 3,6-dichlorophenyl | 1-methylvinyl | |
| 1.3.1137 | 3,6-dichlorophenyl | allyl | |
| 1.3.1138 | 3,6-dichlorophenyl | 1-chlorovinyl | |
| 1.3.1139 | 3,6-dichlorophenyl | ethynyl | |
| 1.3.1140 | 3-bromo-6-chlorophenyl | vinyl | |
| 1.3.1141 | 3-methyl-6-chlorophenyl | vinyl | |
| 1.3.1142 | 3-cyclopropyl-6-chlorophenyl | vinyl | |
| 1.3.1143 | 3-cyano-6-chlorophenyl | vinyl | |
| 1.3.1144 | 3-trifluoromethyl-6-chlorophenyl | vinyl | |
| 1.3.1145 | 3-methoxy-6-chlorophenyl | vinyl | |
| 1.3.1146 | 3-ethoxy-6-chlorophenyl | vinyl | |
| 1.3.1147 | 3-trifluoromethoxy-6-chlorophenyl | vinyl | |
| 1.3.1148 | 3-nitro-6-chlorophenyl | vinyl | |
| 1.3.1149 | 3-fluoro-6-bromophenyl | vinyl | |
| 1.3.1150 | 3-chloro-6-bromophenyl | vinyl | |
| 1.3.1151 | 3,6-dibromophenyl | vinyl | |
| 1.3.1152 | 3-methyl-6-bromophenyl | vinyl | |
| 1.3.1153 | 3-cyclopropyl-6-bromophenyl | vinyl | |
| 1.3.1154 | 3-cyano-6-bromophenyl | vinyl | |
| 1.3.1155 | 3-trifluoromethyl-6-bromophenyl | vinyl | |
| 1.3.1156 | 3-methoxy-6-phenyl | vinyl | |
| 1.3.1157 | 3-ethoxy-6-bromophenyl | vinyl | |
| 1.3.1158 | 3-trifluoromethoxy-6-bromophenyl | vinyl | |
| 1.3.1159 | 3-nitro-6-bromophenyl | vinyl | |
| 1.3.1160 | 3-fluoro-6-iodophenyl | vinyl | |
| 1.3.1161 | 3-chloro-6-iodophenyl | vinyl | |
| 1.3.1162 | 3-bromo-6-iodophenyl | vinyl | |
| 1.3.1163 | 3-methyl-6-iodophenyl | vinyl | |
| 1.3.1164 | 3-cyclopropyl-6-iodophenyl | vinyl | |
| 1.3.1165 | 3-cyano-6-iodophenyl | vinyl | |
| 1.3.1166 | 3-trifluoromethyl-6-iodophenyl | vinyl | |
| 1.3.1167 | 3-methoxy-6-iodophenyl | vinyl | |
| 1.3.1168 | 3-ethoxy-6-iodophenyl | vinyl | |
| 1.3.1169 | 3-trifluoromethoxy-6-iodophenyl | vinyl | |
| 1.3.1170 | 3-nitro-6-iodophenyl | vinyl | |
| 1.3.1171 | 3-fluoro-6-methylphenyl | vinyl | |
| 1.3.1172 | 3-chloro-6-methylphenyl | vinyl | |
| 1.3.1173 | 3-bromo-6-methylphenyl | vinyl | |
| 1.3.1174 | 3,6-dimethylphenyl | vinyl | |
| 1.3.1175 | 3-ethyl-6-methylphenyl | vinyl | |
| 1.3.1176 | 3-cyclopropyl-6-methylphenyl | vinyl | |
| 1.3.1177 | 3-cyano-6-methylphenyl | vinyl | |
| 1.3.1178 | 3-trifluoromethyl-6-methylphenyl | vinyl | |
| 1.3.1179 | 3-methoxy-6-methylphenyl | vinyl | |
| 1.3.1180 | 3-ethoxy-6-methylphenyl | vinyl | |
| 1.3.1181 | 3-trifluoromethoxy-6-methylphenyl | vinyl | |
| 1.3.1182 | 3-nitro-6-methylphenyl | vinyl | |
| 1.3.1183 | 3-fluoro-6-ethylphenyl | vinyl | |
| 1.3.1184 | 3-chloro-6-ethylphenyl | vinyl | |
| 1.3.1185 | 3-bromo-6-ethylphenyl | vinyl | |

TABLE 1.3-continued

Inventive compounds of the general formula (I) in which W* is COOH, $R^1$ and $R^2$ are each hydrogen, and aryl is the radical.

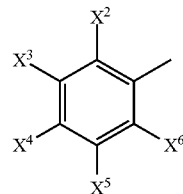

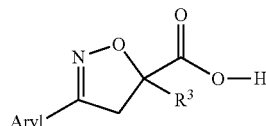

| No. | Aryl | $R^3$ | Physical data |
|---|---|---|---|
| 1.3.1186 | 3-methyl-6-ethylphenyl | vinyl | |
| 1.3.1187 | 3,6-diethylphenyl | vinyl | |
| 1.3.1188 | 3-cyclopropyl-6-ethylphenyl | vinyl | |
| 1.3.1189 | 3-cyano-6-ethylphenyl | vinyl | |
| 1.3.1190 | 3-trifluoromethyl-6-ethylphenyl | vinyl | |
| 1.3.1191 | 3-methoxy-6-ethylphenyl | vinyl | |
| 1.3.1192 | 3-ethoxy-6-ethylphenyl | vinyl | |
| 1.3.1193 | 3-trifluoromethoxy-6-ethylphenyl | vinyl | |
| 1.3.1194 | 3-nitro-6-ethylphenyl | vinyl | |
| 1.3.1195 | 3-fluoro-6-propylphenyl | vinyl | |
| 1.3.1196 | 3-chloro-6-propylphenyl | vinyl | |
| 1.3.1197 | 3-bromo-6-propylphenyl | vinyl | |
| 1.3.1198 | 3-methyl-6-propylphenyl | vinyl | |
| 1.3.1199 | 3-methyl-6-propylphenyl | vinyl | |
| 1.3.1200 | 3-cyclopropyl-6-propylphenyl | vinyl | |
| 1.3.1201 | 3-cyano-6-propylphenyl | vinyl | |
| 1.3.1202 | 3-trifluoromethyl-6-propylphenyl | vinyl | |
| 1.3.1203 | 3-methoxy-6-propylphenyl | vinyl | |
| 1.3.1204 | 3-ethoxy-6-propylphenyl | vinyl | |
| 1.3.1205 | 3-trifluoromethoxy-6-propylphenyl | vinyl | |
| 1.3.1206 | 3-nitro-6-propylphenyl | vinyl | |
| 1.3.1207 | 3-fluoro-6-isopropylphenyl | vinyl | |
| 1.3.1208 | 3-chloro-6-isopropylphenyl | vinyl | |
| 1.3.1209 | 3-bromo-6-isopropylphenyl | vinyl | |
| 1.3.1210 | 3-methyl-6-isopropylphenyl | vinyl | |
| 1.3.1211 | 3-cyclopropyl-6-isopropylphenyl | vinyl | |
| 1.3.1212 | 3-cyano-6-isopropylphenyl | vinyl | |
| 1.3.1213 | 3-trifluoromethyl-6-isopropylphenyl | vinyl | |
| 1.3.1214 | 3-methoxy-6-isopropylphenyl | vinyl | |
| 1.3.1215 | 3-ethoxy-6-isopropylphenyl | vinyl | |
| 1.3.1216 | 3-trifluoromethoxy-6-isopropylphenyl | vinyl | |
| 1.3.1217 | 3-nitro-6-isopropylphenyl | vinyl | |
| 1.3.1218 | 3-fluoro-6-tert-butylphenyl | vinyl | |
| 1.3.1219 | 3-chloro-6-tert-butylphenyl | vinyl | |
| 1.3.1220 | 3-bromo-6-tert-butylphenyl | vinyl | |
| 1.3.1221 | 3-methyl-6-tert-butylphenyl | vinyl | |
| 1.3.1222 | 3-cyclopropyl-6-tert-butylphenyl | vinyl | |
| 1.3.1223 | 3-cyano-6-tert-butylphenyl | vinyl | |
| 1.3.1224 | 3-trifluoromethyl-6-tert-butylphenyl | vinyl | |
| 1.3.1225 | 3-methoxy-6-tert-butylphenyl | vinyl | |
| 1.3.1226 | 3-ethoxy-6-tert-butylphenyl | vinyl | |
| 1.3.1227 | 3-trifluoromethoxy-6-tert-butylphenyl | vinyl | |
| 1.3.1228 | 3-nitro-6-tert-butylphenyl | vinyl | |
| 1.3.1229 | 3-fluoro-6-cyclopropylphenyl | vinyl | |
| 1.3.1230 | 3-chloro-6-cyclopropylphenyl | vinyl | |
| 1.3.1231 | 3-bromo-6-cyclopropylphenyl | vinyl | |
| 1.3.1232 | 3-methyl-6-cyclopropylphenyl | vinyl | |
| 1.3.1233 | 3-cyclopropyl-6-cyclopropylphenyl | vinyl | |
| 1.3.1234 | 3-cyano-6-cyclopropylphenyl | vinyl | |
| 1.3.1235 | 3-trifluoromethyl-6-cyclopropylphenyl | vinyl | |
| 1.3.1236 | 3-methoxy-6-cyclopropylphenyl | vinyl | |
| 1.3.1237 | 3-ethoxy-6-cyclopropylphenyl | vinyl | |
| 1.3.1238 | 3-trifluoromethoxy-6-cyclopropylphenyl | vinyl | |
| 1.3.1239 | 3-fluoro-6-methoxycarbonylphenyl | vinyl | |
| 1.3.1240 | 3-chloro-6-methoxycarbonylphenyl | vinyl | |
| 1.3.1241 | 3-bromo-6-methoxycarbonylphenyl | vinyl | |
| 1.3.1242 | 3-methyl-6-methoxycarbonylphenyl | vinyl | |

TABLE 1.3-continued

Inventive compounds of the general formula (I) in which W* is COOH, $R^1$ and $R^2$ are each hydrogen, and aryl is the radical.

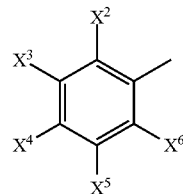

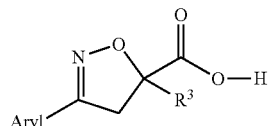

| No. | Aryl | $R^3$ | Physical data |
|---|---|---|---|
| 1.3.1243 | 3-cyclopropyl-6-methoxycarbonylphenyl | vinyl | |
| 1.3.1244 | 3-cyano-6-methoxycarbonylphenyl | vinyl | |
| 1.3.1245 | 3-trifluoromethyl-6-methoxycarbonyl-phenyl | vinyl | |
| 1.3.1246 | 3-methoxy-6-methoxycarbonylphenyl | vinyl | |
| 1.3.1247 | 3-ethoxy-6-methoxycarbonylphenyl | vinyl | |
| 1.3.1248 | 3-trifluoromethoxy-6-methoxycarbonyl-phenyl | vinyl | |
| 1.3.1249 | 3-nitro-6-methoxycarbonylphenyl | vinyl | |
| 1.3.1250 | 3-fluoro-6-cyanophenyl | vinyl | |
| 1.3.1251 | 3-chloro-6-cyanophenyl | vinyl | |
| 1.3.1252 | 3-bromo-6-cyanophenyl | vinyl | |
| 1.3.1253 | 3-methyl-6-cyanophenyl | vinyl | |
| 1.3.1254 | 3-cyclopropyl-6-cyanophenyl | vinyl | |
| 1.3.1255 | 3-cyano-6-cyanophenyl | vinyl | |
| 1.3.1256 | 3-trifluoromethyl-6-cyanophenyl | vinyl | |
| 1.3.1257 | 3-methoxy-6-cyanophenyl | vinyl | |
| 1.3.1258 | 3-ethoxy-6-cyanophenyl | vinyl | |
| 1.3.1259 | 3-trifluoromethoxy-6-cyanophenyl | vinyl | |
| 1.3.1260 | 3-nitro-6-cyanophenyl | vinyl | |
| 1.3.1261 | 3-fluoro-6-methoxyphenyl | vinyl | |
| 1.3.1262 | 3-chloro-6-methoxyphenyl | vinyl | |
| 1.3.1263 | 3-bromo-6-methoxyphenyl | vinyl | |
| 1.3.1264 | 3-methyl-6-methoxyphenyl | vinyl | |
| 1.3.1265 | 3-cyclopropyl-6-methoxyphenyl | vinyl | |
| 1.3.1266 | 3-cyano-6-methoxyphenyl | vinyl | |
| 1.3.1267 | 3-trifluoromethyl-6-methoxyphenyl | vinyl | |
| 1.3.1268 | 3,6-dimethoxyphenyl | vinyl | |
| 1.3.1269 | 3-ethoxy-6-methoxyphenyl | vinyl | |
| 1.3.1270 | 3-trifluoromethoxy-6-methoxyphenyl | vinyl | |
| 1.3.1271 | 3-nitro-6-methoxyphenyl | vinyl | |
| 1.3.1272 | 3-fluoro-6-ethoxyphenyl | vinyl | |
| 1.3.1273 | 3-chloro-6-ethoxyphenyl | vinyl | |
| 1.3.1274 | 3-bromo-6-ethoxyphenyl | vinyl | |
| 1.3.1275 | 3-methyl-6-ethoxyphenyl | vinyl | |
| 1.3.1276 | 3-cyclopropyl-6-ethoxyphenyl | vinyl | |
| 1.3.1277 | 3-cyano-6-ethoxyphenyl | vinyl | |
| 1.3.1278 | 3-trifluoromethyl-6-ethoxyphenyl | vinyl | |
| 1.3.1279 | 3-methoxy-6-ethoxyphenyl | vinyl | |
| 1.3.1280 | 2,6-diethoxyphenyl | vinyl | |
| 1.3.1281 | 3-trifluoromethoxy-6-ethoxyphenyl | vinyl | |
| 1.3.1282 | 3-nitro-6-ethoxyphenyl | vinyl | |
| 1.3.1283 | 3-fluoro-6-isopropoxyphenyl | vinyl | |
| 1.3.1284 | 3-chloro-6-isopropoxyphenyl | vinyl | |
| 1.3.1285 | 3-bromo-6-isopropoxyphenyl | vinyl | |
| 1.3.1286 | 3-methyl-6-isopropoxyphenyl | vinyl | |
| 1.3.1287 | 3-cyclopropyl-6-isopropoxyphenyl | vinyl | |
| 1.3.1288 | 3-cyano-6-isopropoxyphenyl | vinyl | |
| 1.3.1289 | 3-trifluoromethyl-6-isopropoxyphenyl | vinyl | |
| 1.3.1290 | 3-methoxy-6-isopropoxyphenyl | vinyl | |
| 1.3.1291 | 3-ethoxy-6-isopropoxyphenyl | vinyl | |
| 1.3.1292 | 3-trifluoromethoxy-6-isopropoxyphenyl | vinyl | |
| 1.3.1293 | 3-nitro-6-isopropoxyphenyl | vinyl | |
| 1.3.1294 | 3-fluoro-6-trifluoromethoxyphenyl | vinyl | |
| 1.3.1295 | 3-chloro-6-trifluoromethoxyphenyl | vinyl | |
| 1.3.1296 | 3-bromo-6-trifluoromethoxyphenyl | vinyl | |
| 1.3.1297 | 3-methyl-6-trifluoromethoxyphenyl | vinyl | |

TABLE 1.3-continued

Inventive compounds of the general formula (I) in which W* is COOH, $R^1$ and $R^2$ are each hydrogen, and aryl is the radical.

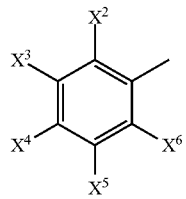

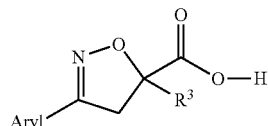

| No. | Aryl | $R^3$ | Physical data |
|---|---|---|---|
| 1.3.1298 | 3-cyclopropyl-6-trifluoromethoxyphenyl | vinyl | |
| 1.3.1299 | 3-cyano-6-trifluoromethoxyphenyl | vinyl | |
| 1.3.1300 | 3-trifluoromethyl-6-trifluoromethoxyphenyl | vinyl | |
| 1.3.1301 | 3-methoxy-6-trifluoromethoxyphenyl | vinyl | |
| 1.3.1302 | 3-ethoxy-6-trifluoromethoxyphenyl | vinyl | |
| 1.3.1303 | 3,6-bis(trifluoromethoxy)phenyl | vinyl | |
| 1.3.1304 | 3-nitro-6-trifluoromethoxyphenyl | vinyl | |
| 1.3.1305 | 3-fluoro-6-difluoromethoxyphenyl | vinyl | |
| 1.3.1306 | 3-chloro-6-difluoromethoxyphenyl | vinyl | |
| 1.3.1307 | 3-bromo-6-difluoromethoxyphenyl | vinyl | |
| 1.3.1308 | 3-methyl-6-difluoromethoxyphenyl | vinyl | |
| 1.3.1309 | 3-cyclopropyl-6-difluoromethoxyphenyl | vinyl | |
| 1.3.1310 | 3-cyano-6-difluoromethoxyphenyl | vinyl | |
| 1.3.1311 | 3-trifluoromethyl-6-difluoromethoxyphenyl | vinyl | |
| 1.3.1312 | 3-methoxy-6-difluoromethoxyphenyl | vinyl | |
| 1.3.1313 | 3-ethoxy-6-difluoromethoxyphenyl | vinyl | |
| 1.3.1314 | 3-trifluoromethoxy-6-difluoromethoxyphenyl | vinyl | |
| 1.3.1315 | 3-nitro-6-difluoromethoxyphenyl | vinyl | |
| 1.3.1316 | 3-fluoro-6-nitrophenyl | vinyl | |
| 1.3.1317 | 3-chloro-6-nitrophenyl | vinyl | |
| 1.3.1318 | 3-bromo-6-nitrophenyl | vinyl | |
| 1.3.1319 | 3-methyl-6-nitrophenyl | vinyl | |
| 1.3.1320 | 3-cyclopropyl-6-nitrophenyl | vinyl | |
| 1.3.1321 | 3-cyano-6-nitrophenyl | vinyl | |
| 1.3.1322 | 3-trifluoromethyl-6-nitrophenyl | vinyl | |
| 1.3.1323 | 3-methoxy-6-nitrophenyl | vinyl | |
| 1.3.1324 | 3-ethoxy-6-nitrophenyl | vinyl | |
| 1.3.1325 | 3-trifluoromethoxy-6-nitrophenyl | vinyl | |
| 1.3.1326 | 3-fluoro-6-methylsulfanylphenyl | vinyl | |
| 1.3.1327 | 3-chloro-6-methylsulfanylphenyl | vinyl | |
| 1.3.1328 | 3-bromo-6-methylsulfanylphenyl | vinyl | |
| 1.3.1329 | 3-methyl-6-methylsulfanylphenyl | vinyl | |
| 1.3.1330 | 3-cyclopropyl-6-methylsulfanylphenyl | vinyl | |
| 1.3.1331 | 3-cyano-6-methylsulfanylphenyl | vinyl | |
| 1.3.1332 | 3-trifluoromethyl-6-methylsulfanylphenyl | vinyl | |
| 1.3.1333 | 3-methoxy-6-methylsulfanylphenyl | vinyl | |
| 1.3.1334 | 3-ethoxy-6-methylsulfanylphenyl | vinyl | |
| 1.3.1335 | 3-trifluoromethoxy-6-methylsulfanylphenyl | vinyl | |
| 1.3.1336 | 3-nitro-6-methylsulfanylphenyl | vinyl | |
| 1.3.1337 | 2,3,4-trifluorophenyl | vinyl | |
| 1.3.1338 | 2,3,4-trichlorophenyl | vinyl | |
| 1.3.1339 | 2,3,4-trimethylphenyl | vinyl | |
| 1.3.1340 | 2-fluoro-2-chloro-5-trifluoromethylphenyl | vinyl | |
| 1.3.1341 | 2,3,5-trifluorophenyl | vinyl | |
| 1.3.1342 | 2,3,5-trichlorophenyl | vinyl | |
| 1.3.1343 | 2,3,5-trimethylphenyl | vinyl | |
| 1.3.1344 | 2,3-dichloro-5-methoxyphenyl | vinyl | |
| 1.3.1345 | 2,3,6-trifluorophenyl | vinyl | |
| 1.3.1346 | 2,3,6-trichlorophenyl | vinyl | |
| 1.3.1347 | 2,3,6-trimethylphenyl | vinyl | |
| 1.3.1348 | 3,4,5-trifluorophenyl | vinyl | |
| 1.3.1349 | 3,4,5-trichlorophenyl | vinyl | |
| 1.3.1350 | 3,4,5-trimethylphenyl | vinyl | |
| 1.3.1351 | 3,5-dimethyl-4-fluorophenyl | vinyl | |
| 1.3.1352 | 3,5-dichloro-4-methoxyphenyl | vinyl | |

TABLE 1.3-continued

Inventive compounds of the general formula (I) in which W* is COOH, $R^1$ and $R^2$ are each hydrogen, and aryl is the radical.

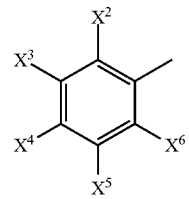

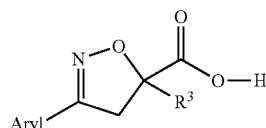

| No. | Aryl | $R^3$ | Physical data |
|---|---|---|---|
| 1.3.1353 | 3,5-difluoro-4-chlorophenyl | vinyl | |
| 1.3.1354 | 3,5-dichloro-4-hydroxyphenyl | vinyl | |
| 1.3.1355 | 3,5-trifluoromethyl-4-chlorophenyl | vinyl | |
| 1.3.1356 | 3,4,6-trifluorophenyl | vinyl | |
| 1.3.1357 | 3,4,6-trichlorophenyl | vinyl | |
| 1.3.1358 | 3,4,6-trimethylphenyl | vinyl | |
| 1.3.1359 | pentafluorophenyl | vinyl | |

TABLE 1.4

Inventive compounds of the general formula (I) in which W* is COOH, $R^1$ and $R^2$ are each hydrogen, and aryl is the radical.

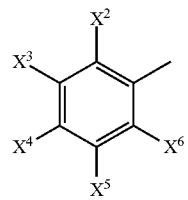

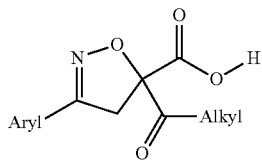

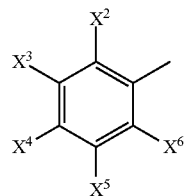

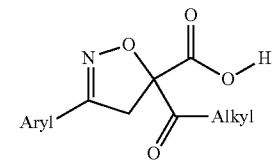

| No. | Aryl | Alkyl | Physical data |
|---|---|---|---|
| 1.4.1 | 3-fluorophenyl | methyl | |
| 1.4.2 | 3-fluorophenyl | ethyl | |
| 1.4.3 | 3-fluorophenyl | propyl | |
| 1.4.4 | 3-fluorophenyl | butyl | |
| 1.4.5 | 3-chlorophenyl | methyl | |
| 1.4.6 | 3-chlorophenyl | ethyl | |
| 1.4.7 | 3-chlorophenyl | propyl | |
| 1.4.8 | 3-chlorophenyl | butyl | |
| 1.4.9 | 3-bromophenyl | methyl | |
| 1.4.10 | 3-bromophenyl | ethyl | |
| 1.4.11 | 3-iodophenyl | methyl | |
| 1.4.12 | 3-iodophenyl | ethyl | |
| 1.4.13 | 3-methylphenyl | methyl | |
| 1.4.14 | 3-methylphenyl | ethyl | |
| 1.4.15 | 3-ethylphenyl | methyl | |
| 1.4.16 | 3-propylphenyl | methyl | |
| 1.4.17 | 3-isopropylphenyl | methyl | |
| 1.4.18 | 3-n-butylphenyl | methyl | |
| 1.4.19 | 3-i-butylphenyl | methyl | |
| 1.4.20 | 3-tert-butylphenyl | methyl | |
| 1.4.21 | 3-cyclopropylphenyl | methyl | |
| 1.4.22 | 3-cyclobutylphenyl | methyl | |
| 1.4.23 | 3-cyclopentylphenyl | methyl | |
| 1.4.24 | 3-vinylphenyl | methyl | |
| 1.4.25 | 3-ethynylphenyl | methyl | |
| 1.4.26 | 3-cyanophenyl | methyl | |
| 1.4.27 | 3-trifluoromethylphenyl | methyl | |
| 1.4.28 | 3-difluoromethylphenyl | methyl | |
| 1.4.29 | 3-(hydroxycarbonyl)phenyl | methyl | |
| 1.4.30 | 3-(methoxycarbonyl)phenyl | methyl | |
| 1.4.31 | 3-(ethoxycarbonyl)phenyl | methyl | |
| 1.4.32 | 3-hydroxymethylphenyl | methyl | |
| 1.4.33 | 3-carbamoylphenyl | methyl | |
| 1.4.34 | 3-hydroxyphenyl | methyl | |
| 1.4.35 | 3-methoxyphenyl | methyl | |
| 1.4.36 | 3-ethoxyphenyl | methyl | |
| 1.4.37 | 3-propyloxyphenyl | methyl | |
| 1.4.38 | 3-isopropyloxyphenyl | methyl | |
| 1.4.39 | 3-n-butyloxyphenyl | methyl | |
| 1.4.40 | 3-i-butyloxyphenyl | methyl | |

TABLE 1.4-continued

Inventive compounds of the general formula (I) in which W* is COOH, $R^1$ and $R^2$ are each hydrogen, and aryl is the radical.

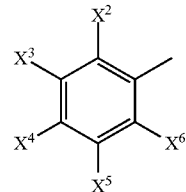

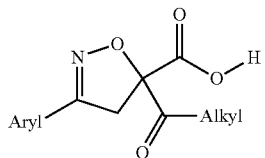

| No. | Aryl | Alkyl | Physical data |
|---|---|---|---|
| 1.4.41 | 3-t-butyloxyphenyl | methyl | |
| 1.4.42 | 3-difluoromethoxyphenyl | methyl | |
| 1.4.43 | 3-trifluoromethoxyphenyl | methyl | |
| 1.4.44 | 3-(2,2,2-trifluoroethoxy)phenyl | methyl | |
| 1.4.45 | 3-(2-chloroethoxy)phenyl | methyl | |
| 1.4.46 | 3-(2-hydroxyethoxy)phenyl | methyl | |
| 1.4.47 | 3-(2-methoxyethoxy)phenyl | methyl | |
| 1.4.48 | 3-[(tert-butoxycarbonyl)oxy]phenyl | methyl | |
| 1.4.49 | 3-nitrophenyl | methyl | |
| 1.4.50 | 3-acetoxyphenyl | methyl | |
| 1.4.51 | {3-[(tert-butoxycarbonyl)amino]phenyl} | methyl | |
| 1.4.52 | 3-methylsulfanylphenyl | methyl | |
| 1.4.53 | 3-(pentafluoro-lambda$^6$-sulfanyl)phenyl | methyl | |
| 1.4.54 | 2,3-difluorophenyl | methyl | |
| 1.4.55 | 2,3-difluorophenyl | ethyl | |
| 1.4.56 | 2,3-difluorophenyl | propyl | |
| 1.4.57 | 2,3-difluorophenyl | butyl | |
| 1.4.58 | 2-chloro-3-fluorophenyl | methyl | |
| 1.4.59 | 2-bromo-3-fluorophenyl | methyl | |
| 1.4.60 | 2-methyl-3-fluorophenyl | methyl | |
| 1.4.61 | 2-cyclopropyl-3-fluorophenyl | methyl | |
| 1.4.62 | 2-cyano-3-fluorophenyl | methyl | |
| 1.4.63 | 2-methoxy-3-fluorophenyl | methyl | |
| 1.4.64 | 2-ethoxy-3-fluorophenyl | methyl | |
| 1.4.65 | 2-trifluoromethoxy-3-fluorophenyl | methyl | |
| 1.4.66 | 2-nitro-3-fluorophenyl | methyl | |
| 1.4.67 | 2-fluoro-3-chlorophenyl | methyl | |
| 1.4.68 | 2,3-dichlorophenyl | methyl | |
| 1.4.69 | 2,3-dichlorophenyl | ethyl | |
| 1.4.70 | 2,3-dichlorophenyl | propyl | |
| 1.4.71 | 2,3-dichlorophenyl | butyl | |
| 1.4.72 | 2-bromo-3-chlorophenyl | methyl | |
| 1.4.73 | 2-methyl-3-chlorophenyl | methyl | |
| 1.4.74 | 2-cyclopropyl-3-chlorophenyl | methyl | |
| 1.4.75 | 2-cyano-3-chlorophenyl | methyl | |
| 1.4.76 | 2-trifluoromethyl-2-chlorophenyl | methyl | |
| 1.4.77 | 2-methoxy-3-chlorophenyl | methyl | |
| 1.4.78 | 2-ethoxy-3-chlorophenyl | methyl | |
| 1.4.79 | 2-trifluoromethoxy-3-chlorophenyl | methyl | |
| 1.4.80 | 2-nitro-3-chlorophenyl | methyl | |
| 1.4.81 | 2-fluoro-3-bromophenyl | methyl | |
| 1.4.82 | 2-chloro-3-bromophenyl | methyl | |
| 1.4.83 | 2,3-dibromophenyl | methyl | |
| 1.4.84 | 2-methyl-3-bromophenyl | methyl | |
| 1.4.85 | 2-ethyl-3-bromophenyl | methyl | |
| 1.4.86 | 2-cyclopropyl-3-bromophenyl | methyl | |
| 1.4.87 | 2-cyano-3-bromophenyl | methyl | |
| 1.4.88 | 2-trifluoromethyl-3-bromophenyl | methyl | |
| 1.4.89 | 2-methoxy-3-phenyl | methyl | |
| 1.4.90 | 2-ethoxy-3-bromophenyl | methyl | |
| 1.4.91 | 2-trifluoromethoxy-3-bromophenyl | methyl | |
| 1.4.92 | 2-nitro-3-bromophenyl | methyl | |
| 1.4.93 | 2-fluoro-3-iodophenyl | methyl | |
| 1.4.94 | 2-chloro-3-iodophenyl | methyl | |
| 1.4.95 | 2-bromo-3-iodophenyl | methyl | |
| 1.4.96 | 2-methyl-3-iodophenyl | methyl | |
| 1.4.97 | 2-cyclopropyl-3-iodophenyl | methyl | |
| 1.4.98 | 2-cyano-3-iodophenyl | methyl | |
| 1.4.99 | 2-trifluoromethyl-3-iodophenyl | methyl | |
| 1.4.100 | 2-methoxy-3-iodophenyl | methyl | |
| 1.4.101 | 2-ethoxy-3-iodophenyl | methyl | |
| 1.4.102 | 2-trifluoromethoxy-3-iodophenyl | methyl | |
| 1.4.103 | 2-fluoro-3-methylphenyl | methyl | |
| 1.4.104 | 2-fluoro-3-methylphenyl | ethyl | |
| 1.4.105 | 2-fluoro-3-methylphenyl | propyl | |
| 1.4.106 | 2-fluoro-3-methylphenyl | butyl | |
| 1.4.107 | 2-chloro-3-methylphenyl | methyl | |
| 1.4.108 | 2-chloro-3-methylphenyl | ethyl | |
| 1.4.109 | 2-chloro-3-methylphenyl | propyl | |
| 1.4.110 | 2-chloro-3-methylphenyl | butyl | |
| 1.4.111 | 2-bromo-3-methylphenyl | methyl | |
| 1.4.112 | 2,3-dimethylphenyl | methyl | |
| 1.4.113 | 2,3-dimethylphenyl | ethyl | |
| 1.4.114 | 2,3-dimethylphenyl | propyl | |
| 1.4.115 | 2,3-dimethylphenyl | butyl | |
| 1.4.116 | 2-cyclopropyl-3-methylphenyl | methyl | |
| 1.4.117 | 2-cyano-3-methylphenyl | methyl | |
| 1.4.118 | 2-trifluoromethyl-3-methylphenyl | methyl | |
| 1.4.119 | 2-methoxy-3-methylphenyl | methyl | |
| 1.4.120 | 2-ethoxy-3-methylphenyl | methyl | |
| 1.4.121 | 2-trifluoromethoxy-3-methylphenyl | methyl | |
| 1.4.122 | 2-nitro-3-methylphenyl | methyl | |
| 1.4.123 | 2-fluoro-3-ethylphenyl | methyl | |
| 1.4.124 | 2-chloro-3-ethylphenyl | methyl | |
| 1.4.125 | 2-bromo-3-ethylphenyl | methyl | |
| 1.4.126 | 2-methyl-3-ethylphenyl | methyl | |
| 1.4.127 | 2,3-diethylphenyl | methyl | |
| 1.4.128 | 2-cyclopropyl-3-ethylphenyl | methyl | |
| 1.4.129 | 2-cyano-3-ethylphenyl | methyl | |
| 1.4.130 | 2-trifluoromethyl-3-ethylphenyl | methyl | |
| 1.4.131 | 2-methoxy-3-ethylphenyl | methyl | |
| 1.4.132 | 2-ethoxy-3-ethylphenyl | methyl | |
| 1.4.133 | 2-trifluoromethoxy-3-ethylphenyl | methyl | |
| 1.4.134 | 2-nitro-3-ethylphenyl | methyl | |
| 1.4.135 | 2-fluoro-3-propylphenyl | methyl | |
| 1.4.136 | 2-chloro-3-propylphenyl | methyl | |
| 1.4.137 | 2-bromo-3-propylphenyl | methyl | |
| 1.4.138 | 2-methyl-3-propylphenyl | methyl | |
| 1.4.139 | 2-cyclopropyl-3-propylphenyl | methyl | |
| 1.4.140 | 2-cyano-3-propylphenyl | methyl | |
| 1.4.141 | 2-trifluoromethyl-3-propylphenyl | methyl | |
| 1.4.142 | 2-methoxy-3-propylphenyl | methyl | |
| 1.4.143 | 2-ethoxy-3-propylphenyl | methyl | |
| 1.4.144 | 2-trifluoromethoxy-3-propylphenyl | methyl | |
| 1.4.145 | 2-nitro-3-propylphenyl | methyl | |
| 1.4.146 | 2-fluoro-3-isopropylphenyl | methyl | |
| 1.4.147 | 2-chloro-3-isopropylphenyl | methyl | |
| 1.4.148 | 2-bromo-3-isopropylphenyl | methyl | |
| 1.4.149 | 2-methyl-3-isopropylphenyl | methyl | |
| 1.4.150 | 2-cyclopropyl-3-isopropylphenyl | methyl | |

TABLE 1.4-continued

Inventive compounds of the general formula (I) in which W* is COOH, R¹ and R² are each hydrogen, and aryl is the radical.

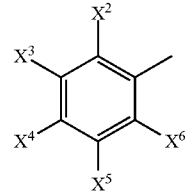

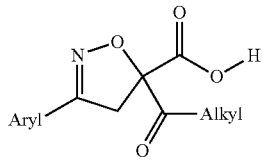

| No. | Aryl | Alkyl | Physical data |
|---|---|---|---|
| 1.4.151 | 2-cyano-3-isopropylphenyl | methyl | |
| 1.4.152 | 2-trifluoromethyl-3-isopropylphenyl | methyl | |
| 1.4.153 | 2-methoxy-3-isopropylphenyl | methyl | |
| 1.4.154 | 2-ethoxy-3-isopropylphenyl | methyl | |
| 1.4.155 | 2-trifluoromethoxy-3-isopropylphenyl | methyl | |
| 1.4.156 | 2-nitro-3-isopropylphenyl | methyl | |
| 1.4.157 | 2-fluoro-3-tert-butylphenyl | methyl | |
| 1.4.158 | 2-chloro-3-tert-butylphenyl | methyl | |
| 1.4.159 | 2-bromo-3-tert-butylphenyl | methyl | |
| 1.4.160 | 2-methyl-3-tert-butylphenyl | methyl | |
| 1.4.161 | 2-cyano-3-tert-butylphenyl | methyl | |
| 1.4.162 | 2-trifluoromethyl-3-tert-butylphenyl | methyl | |
| 1.4.163 | 2-methoxy-3-tert-butylphenyl | methyl | |
| 1.4.164 | 2-ethoxy-3-tert-butylphenyl | methyl | |
| 1.4.165 | 2-nitro-3-tert-butylphenyl | methyl | |
| 1.4.166 | 2-fluoro-3-cyclopropylphenyl | methyl | |
| 1.4.167 | 2-chloro-3-cyclopropylphenyl | methyl | |
| 1.4.168 | 2-bromo-3-cyclopropylphenyl | methyl | |
| 1.4.169 | 2-methyl-3-cyclopropylphenyl | methyl | |
| 1.4.170 | 2-cyano-3-cyclopropylphenyl | methyl | |
| 1.4.171 | 2-trifluoromethyl-3-cyclopropylphenyl | methyl | |
| 1.4.172 | 2-methoxy-3-cyclopropylphenyl | methyl | |
| 1.4.173 | 2-trifluoromethoxy-3-cyclopropylphenyl | methyl | |
| 1.4.174 | 2-fluoro-3-methoxycarbonylphenyl | methyl | |
| 1.4.175 | 2-chloro-3-methoxycarbonylphenyl | methyl | |
| 1.4.176 | 2-bromo-3-methoxycarbonylphenyl | methyl | |
| 1.4.177 | 2-methyl-3-methoxycarbonylphenyl | methyl | |
| 1.4.178 | 2-cyclopropyl-3-methoxycarbonylphenyl | methyl | |
| 1.4.179 | 2-cyano-3-methoxycarbonylphenyl | methyl | |
| 1.4.180 | 2-trifluoromethyl-3-methoxycarbonylphenyl | methyl | |
| 1.4.181 | 2-methoxy-3-methoxycarbonylphenyl | methyl | |
| 1.4.182 | 2-ethoxy-3-methoxycarbonylphenyl | methyl | |
| 1.4.183 | 2-trifluoromethoxy-3-methoxycarbonylphenyl | methyl | |
| 1.4.184 | 2-nitro-3-methoxycarbonylphenyl | methyl | |
| 1.4.185 | 2-fluoro-3-cyanophenyl | methyl | |
| 1.4.186 | 2-chloro-3-cyanophenyl | methyl | |
| 1.4.187 | 2-bromo-3-cyanophenyl | methyl | |
| 1.4.188 | 2-methyl-3-cyanophenyl | methyl | |
| 1.4.189 | 2-ethyl-3-cyanophenyl | methyl | |
| 1.4.190 | 2-ethyl-3-cyanophenyl | ethyl | |
| 1.4.191 | 2-ethyl-3-cyanophenyl | propyl | |
| 1.4.192 | 2-ethyl-3-cyanophenyl | butyl | |
| 1.4.193 | 2-cyclopropyl-3-cyanophenyl | methyl | |
| 1.4.194 | 2-cyano-3-cyanophenyl | methyl | |
| 1.4.195 | 2-trifluoromethyl-3-cyanophenyl | methyl | |
| 1.4.196 | 2-methoxy-3-cyanophenyl | methyl | |
| 1.4.197 | 2-ethoxy-3-cyanophenyl | methyl | |
| 1.4.198 | 2-trifluoromethoxy-3-cyanophenyl | methyl | |
| 1.4.199 | 2-fluoro-3-methoxyphenyl | methyl | |
| 1.4.200 | 2-chloro-3-methoxyphenyl | methyl | |
| 1.4.201 | 2-bromo-3-methoxyphenyl | methyl | |
| 1.4.202 | 2-methyl-3-methoxyphenyl | methyl | |
| 1.4.203 | 2-cyclopropyl-3-methoxyphenyl | methyl | |
| 1.4.204 | 2-cyano-3-methoxyphenyl | methyl | |
| 1.4.205 | 2-trifluoromethyl-3-methoxyphenyl | methyl | |
| 1.4.206 | 2,3-dimethoxyphenyl | methyl | |
| 1.4.207 | 2-ethoxy-3-methoxyphenyl | methyl | |
| 1.4.208 | 2-trifluoromethoxy-3-methoxyphenyl | methyl | |
| 1.4.209 | 2-nitro-3-methoxyphenyl | methyl | |
| 1.4.210 | 2-fluoro-3-ethoxyphenyl | methyl | |
| 1.4.211 | 2-chloro-3-ethoxyphenyl | methyl | |
| 1.4.212 | 2-bromo-3-ethoxyphenyl | methyl | |
| 1.4.213 | 2-methyl-3-ethoxyphenyl | methyl | |
| 1.4.214 | 2-ethyl-3-ethoxyphenyl | methyl | |
| 1.4.215 | 2-cyclopropyl-3-ethoxyphenyl | methyl | |
| 1.4.216 | 2-cyano-3-ethoxyphenyl | methyl | |
| 1.4.217 | 2-trifluoromethyl-3-ethoxyphenyl | methyl | |
| 1.4.218 | 2-methoxy-3-ethoxyphenyl | methyl | |
| 1.4.219 | 2,3-diethoxyphenyl | methyl | |
| 1.4.220 | 2-trifluoromethoxy-3-ethoxyphenyl | methyl | |
| 1.4.221 | 2-nitro-3-ethoxyphenyl | methyl | |
| 1.4.222 | 2-fluoro-3-isopropoxyphenyl | methyl | |
| 1.4.223 | 2-chloro-3-isopropoxyphenyl | methyl | |
| 1.4.224 | 2-bromo-3-isopropoxyphenyl | methyl | |
| 1.4.225 | 2-methyl-3-isopropoxyphenyl | methyl | |
| 1.4.226 | 2-ethyl-3-isopropoxyphenyl | methyl | |
| 1.4.227 | 2-cyclopropyl-3-isopropoxyphenyl | methyl | |
| 1.4.228 | 2-cyano-3-isopropoxyphenyl | methyl | |
| 1.4.229 | 2-trifluoromethyl-3-isopropoxyphenyl | methyl | |
| 1.4.230 | 2-methoxy-3-isopropoxyphenyl | methyl | |
| 1.4.231 | 2-ethoxy-3-isopropoxyphenyl | methyl | |
| 1.4.232 | 2-trifluoromethoxy-3-isopropoxyphenyl | methyl | |
| 1.4.233 | 2-nitro-3-isopropoxyphenyl | methyl | |
| 1.4.234 | 2-fluoro-3-trifluoromethoxyphenyl | methyl | |
| 1.4.235 | 2-chloro-3-trifluoromethoxyphenyl | methyl | |
| 1.4.236 | 2-bromo-3-trifluoromethoxyphenyl | methyl | |
| 1.4.237 | 2-methyl-3-trifluoromethoxyphenyl | methyl | |
| 1.4.238 | 2-cyclopropyl-3-trifluoromethoxyphenyl | methyl | |
| 1.4.239 | 2-cyano-3-trifluoromethoxyphenyl | methyl | |
| 1.4.240 | 2-trifluoromethyl-3-trifluoromethoxyphenyl | methyl | |
| 1.4.241 | 2-methoxy-3-trifluoromethoxyphenyl | methyl | |
| 1.4.242 | 2-ethoxy-3-trifluoromethoxyphenyl | methyl | |
| 1.4.243 | 2,3-bis(trifluoromethoxy)phenyl | methyl | |
| 1.4.244 | 2-nitro-3-trifluoromethoxyphenyl | methyl | |
| 1.4.245 | 2-fluoro-3-difluoromethoxyphenyl | methyl | |
| 1.4.246 | 2-chloro-3-difluoromethoxyphenyl | methyl | |
| 1.4.247 | 2-bromo-3-difluoromethoxyphenyl | methyl | |
| 1.4.248 | 2-methyl-3-difluoromethoxyphenyl | methyl | |
| 1.4.249 | 2-cyclopropyl-3-difluoromethoxyphenyl | methyl | |
| 1.4.250 | 2-cyano-3-difluoromethoxyphenyl | methyl | |
| 1.4.251 | 2-trifluoromethyl-3-difluoromethoxyphenyl | methyl | |
| 1.4.252 | 2-methoxy-3-difluoromethoxyphenyl | methyl | |
| 1.4.253 | 2-ethoxy-3-difluoromethoxyphenyl | methyl | |
| 1.4.254 | 2-trifluoromethoxy-3-difluoromethoxyphenyl | methyl | |
| 1.4.255 | 2-nitro-3-difluoromethoxyphenyl | methyl | |

TABLE 1.4-continued

Inventive compounds of the general formula (I) in which W* is COOH, R¹ and R² are each hydrogen, and aryl is the radical.

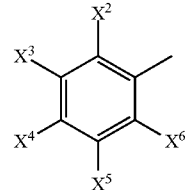

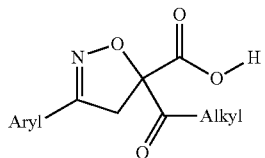

| No. | Aryl | Alkyl | Physical data |
|---|---|---|---|
| 1.4.256 | 2-fluoro-3-nitrophenyl | methyl | |
| 1.4.257 | 2-chloro-3-nitrophenyl | methyl | |
| 1.4.258 | 2-bromo-3-nitrophenyl | methyl | |
| 1.4.259 | 2-methyl-3-nitrophenyl | methyl | |
| 1.4.260 | 2-cyclopropyl-3-nitrophenyl | methyl | |
| 1.4.261 | 2-cyano-3-nitrophenyl | methyl | |
| 1.4.262 | 2-trifluoromethyl-3-nitrophenyl | methyl | |
| 1.4.263 | 2-methoxy-3-nitrophenyl | methyl | |
| 1.4.264 | 2-ethoxy-3-nitrophenyl | methyl | |
| 1.4.265 | 2-trifluoromethoxy-3-nitrophenyl | methyl | |
| 1.4.266 | 2-fluoro-3-methylsulfanylphenyl | methyl | |
| 1.4.267 | 2-chloro-3-methylsulfanylphenyl | methyl | |
| 1.4.268 | 2-bromo-3-methylsulfanylphenyl | methyl | |
| 1.4.269 | 2-methyl-3-methylsulfanylphenyl | methyl | |
| 1.4.270 | 2-ethyl-3-methylsulfanylphenyl | methyl | |
| 1.4.271 | 2-cyclopropyl-3-methylsulfanylphenyl | methyl | |
| 1.4.272 | 2-trifluoromethyl-3-methylsulfanylphenyl | methyl | |
| 1.4.273 | 2-methoxy-3-methylsulfanylphenyl | methyl | |
| 1.4.274 | 3,5-difluorophenyl | methyl | |
| 1.4.275 | 3,5-difluorophenyl | ethyl | |
| 1.4.276 | 3,5-difluorophenyl | propyl | |
| 1.4.277 | 3,5-difluorophenyl | butyl | |
| 1.4.278 | 3-chloro-5-fluorophenyl | methyl | |
| 1.4.279 | 3-chloro-5-fluorophenyl | ethyl | |
| 1.4.280 | 3-chloro-5-fluorophenyl | propyl | |
| 1.4.281 | 3-chloro-5-fluorophenyl | butyl | |
| 1.4.282 | 3-bromo-5-fluorophenyl | methyl | |
| 1.4.283 | 3-bromo-5-fluorophenyl | ethyl | |
| 1.4.284 | 3-bromo-5-fluorophenyl | propyl | |
| 1.4.285 | 3-bromo-5-fluorophenyl | butyl | |
| 1.4.286 | 3-iodo-5-fluorophenyl | methyl | |
| 1.4.287 | 3-methyl-5-fluorophenyl | methyl | |
| 1.4.288 | 3-methyl-5-fluorophenyl | ethyl | |
| 1.4.289 | 3-methyl-5-fluorophenyl | propyl | |
| 1.4.290 | 3-methyl-5-fluorophenyl | butyl | |
| 1.4.291 | 3-propyl-5-fluorophenyl | methyl | |
| 1.4.292 | 3-i-propyl-5-fluorophenyl | methyl | |
| 1.4.293 | 3-n-butyl-5-fluorophenyl | methyl | |
| 1.4.294 | 3-isobutyl-5-fluorophenyl | methyl | |
| 1.4.295 | 3-tert-butyl-5-fluorophenyl | methyl | |
| 1.4.296 | 3-cyclopropyl-5-fluorophenyl | methyl | |
| 1.4.297 | 3-cyano-5-fluorophenyl | methyl | |
| 1.4.298 | 3-trifluoromethyl-5-fluorophenyl | methyl | |
| 1.4.299 | 3-trifluoromethyl-5-fluorophenyl | ethyl | |
| 1.4.300 | 3-trifluoromethyl-5-fluorophenyl | propyl | |
| 1.4.301 | 3-trifluoromethyl-5-fluorophenyl | butyl | |
| 1.4.302 | 3-(methoxycarbonyl)-5-fluorophenyl | methyl | |
| 1.4.303 | 3-methoxy-5-fluorophenyl | methyl | |
| 1.4.304 | 3-ethoxy-5-fluorophenyl | methyl | |
| 1.4.305 | 3-n-propoxy-5-fluorophenyl | methyl | |
| 1.4.306 | 3-isopropoxy-5-fluorophenyl | methyl | |
| 1.4.307 | 3-difluoromethoxy-5-fluorophenyl | methyl | |
| 1.4.308 | 3-trifluoromethoxy-5-fluorophenyl | methyl | |
| 1.4.309 | 3-nitro-5-fluorophenyl | methyl | |
| 1.4.310 | 3-acetoxy-5-fluorophenyl | methyl | |
| 1.4.311 | 3-methylsulfanyl-5-fluorophenyl | methyl | |
| 1.4.312 | 3,5-dichlorophenyl | methyl | |
| 1.4.313 | 3,5-dichlorophenyl | ethyl | |
| 1.4.314 | 3,5-dichlorophenyl | propyl | |
| 1.4.315 | 3,5-dichlorophenyl | butyl | |
| 1.4.316 | 3-bromo-5-chlorophenyl | methyl | |
| 1.4.317 | 3-iodo-5-chlorophenyl | methyl | |
| 1.4.318 | 3-methyl-5-chlorophenyl | methyl | |
| 1.4.319 | 3-ethyl-5-chlorophenyl | methyl | |
| 1.4.320 | 3-propyl-5-chlorophenyl | methyl | |
| 1.4.321 | 3-isopropyl-5-chlorophenyl | methyl | |
| 1.4.322 | 3-n-butyl-5-chlorophenyl | methyl | |
| 1.4.323 | 3-isobutyl-5-chlorophenyl | methyl | |
| 1.4.324 | 3-tert-butyl-5-chlorophenyl | methyl | |
| 1.4.325 | 3-cyclopropyl-5-chlorophenyl | methyl | |
| 1.4.326 | 3-cyano-5-chlorophenyl | methyl | |
| 1.4.327 | 3-trifluoromethyl-5-chlorophenyl | methyl | |
| 1.4.328 | 3-(methoxycarbonyl)-5-chlorophenyl | methyl | |
| 1.4.329 | 3-methoxy-5-chlorophenyl | methyl | |
| 1.4.330 | 3-ethoxy-5-chlorophenyl | methyl | |
| 1.4.331 | 3-n-propoxy-5-chlorophenyl | methyl | |
| 1.4.332 | 3-isopropoxy-5-chlorophenyl | methyl | |
| 1.4.333 | 3-n-butoxy-5-chlorophenyl | methyl | |
| 1.4.334 | 3-isobutoxy-5-chlorophenyl | methyl | |
| 1.4.335 | 3-tert-butoxy-5-chlorophenyl | methyl | |
| 1.4.336 | 3-difluoromethoxy-5-chlorophenyl | methyl | |
| 1.4.337 | 3-trifluoromethoxy-5-chlorophenyl | methyl | |
| 1.4.338 | 3-nitro-5-chlorophenyl | methyl | |
| 1.4.339 | 3-acetoxy-5-chlorophenyl | methyl | |
| 1.4.340 | 3-methylsulfanyl-5-chlorophenyl | methyl | |
| 1.4.341 | 3,5-dibromophenyl | methyl | |
| 1.4.342 | 3,5-dibromophenyl | ethyl | |
| 1.4.343 | 3-iodo-5-bromophenyl | methyl | |
| 1.4.344 | 3-methyl-5-bromophenyl | methyl | |
| 1.4.345 | 3-methyl-5-bromophenyl | ethyl | |
| 1.4.346 | 3-methyl-5-bromophenyl | propyl | |
| 1.4.347 | 3-methyl-5-bromophenyl | butyl | |
| 1.4.348 | 3-ethyl-5-bromophenyl | methyl | |
| 1.4.349 | 3-propyl-5-bromophenyl | methyl | |
| 1.4.350 | 3-isopropyl-5-bromophenyl | methyl | |
| 1.4.351 | 3-n-butyl-5-bromophenyl | methyl | |
| 1.4.352 | 3-isobutyl-5-bromophenyl | methyl | |
| 1.4.353 | 3-tert-butyl-5-bromophenyl | methyl | |
| 1.4.354 | 3-cyclopropyl-5-bromophenyl | methyl | |
| 1.4.355 | 3-cyano-5-bromophenyl | methyl | |
| 1.4.356 | 3-trifluoromethyl-5-bromophenyl | methyl | |
| 1.4.357 | 3-(methoxycarbonyl)-5-bromophenyl | methyl | |
| 1.4.358 | 3-methoxy-5-bromophenyl | methyl | |
| 1.4.359 | 3-ethoxy-5-bromophenyl | methyl | |
| 1.4.360 | 3-n-propoxy-5-bromophenyl | methyl | |
| 1.4.361 | 3-isopropoxy-5-bromophenyl | methyl | |
| 1.4.362 | 3-n-butoxy-5-bromophenyl | methyl | |
| 1.4.363 | 3-isobutoxy-5-bromophenyl | methyl | |
| 1.4.364 | 3-tert-butoxy-5-bromophenyl | methyl | |
| 1.4.365 | 3-difluoromethoxy-5-bromophenyl | methyl | |

TABLE 1.4-continued

Inventive compounds of the general formula (I) in which W* is COOH, R¹ and R² are each hydrogen, and aryl is the radical.

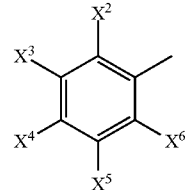

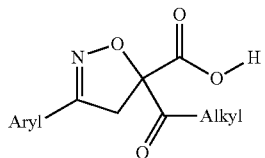

| No. | Aryl | Alkyl | Physical data |
|---|---|---|---|
| 1.4.366 | 3-trifluoromethoxy-5-bromophenyl | methyl | |
| 1.4.367 | 3-nitro-5-bromophenyl | methyl | |
| 1.4.368 | 3-acetoxy-5-bromophenyl | methyl | |
| 1.4.369 | 3-methylsulfanyl-5-bromophenyl | methyl | |
| 1.4.370 | 3,5-diiodophenyl | methyl | |
| 1.4.371 | 3-methyl-5-iodophenyl | methyl | |
| 1.4.372 | 3-ethyl-5-iodophenyl | methyl | |
| 1.4.373 | 3-propyl-5-iodophenyl | methyl | |
| 1.4.374 | 3-isopropyl-5-iodophenyl | methyl | |
| 1.4.375 | 3-n-butyl-5-iodophenyl | methyl | |
| 1.4.376 | 3-isobutyl-5-iodophenyl | methyl | |
| 1.4.377 | 3-tert-butyl-5-iodophenyl | methyl | |
| 1.4.378 | 3-cyclopropyl-5-iodophenyl | methyl | |
| 1.4.379 | 3-cyano-5-iodophenyl | methyl | |
| 1.4.380 | 3-trifluoromethyl-5-iodophenyl | methyl | |
| 1.4.381 | 3-(methoxycarbonyl)-5-iodophenyl | methyl | |
| 1.4.382 | 3-methoxy-5-iodophenyl | methyl | |
| 1.4.383 | 3-ethoxy-5-iodophenyl | methyl | |
| 1.4.384 | 3-n-propoxy-5-iodophenyl | methyl | |
| 1.4.385 | 3-isopropoxy-5-iodophenyl | methyl | |
| 1.4.386 | 3-isobutoxy-5-iodophenyl | methyl | |
| 1.4.387 | 3-difluoromethoxy-5-iodophenyl | methyl | |
| 1.4.388 | 3-trifluoromethoxy-5-iodophenyl | methyl | |
| 1.4.389 | 3-nitro-5-iodophenyl | methyl | |
| 1.4.390 | 3-acetoxy-5-iodophenyl | methyl | |
| 1.4.391 | 3-methylsulfanyl-5-iodophenyl | methyl | |
| 1.4.392 | 3,5-dimethylphenyl | methyl | |
| 1.4.393 | 3-ethyl-5-methylphenyl | methyl | |
| 1.4.394 | 3-propyl-5-methylphenyl | methyl | |
| 1.4.395 | 3-isopropyl-5-methylphenyl | methyl | |
| 1.4.396 | 3-n-butyl-5-methylphenyl | methyl | |
| 1.4.397 | 3-isobutyl-5-methylphenyl | methyl | |
| 1.4.398 | 3-tert-butyl-5-methylphenyl | methyl | |
| 1.4.399 | 3-cyclopropyl-5-methylphenyl | methyl | |
| 1.4.400 | 3-cyano-5-methylphenyl | methyl | |
| 1.4.401 | 3-trifluoromethyl-5-methylphenyl | methyl | |
| 1.4.402 | 3-(methoxycarbonyl)-5-methylphenyl | methyl | |
| 1.4.403 | 3-methoxy-5-methylphenyl | methyl | |
| 1.4.404 | 3-ethoxy-5-methylphenyl | methyl | |
| 1.4.405 | 3-n-propoxy-5-methylphenyl | methyl | |
| 1.4.406 | 3-n-butoxy-5-methylphenyl | methyl | |
| 1.4.407 | 3-isobutoxy-5-methylphenyl | methyl | |
| 1.4.408 | 3-difluoromethoxy-5-methylphenyl | methyl | |
| 1.4.409 | 3-trifluoromethoxy-5-methylphenyl | methyl | |
| 1.4.410 | 3-nitro-5-methylphenyl | methyl | |
| 1.4.411 | 3-acetoxy-5-methylphenyl | methyl | |
| 1.4.412 | 3-methylsulfanyl-5-methylphenyl | methyl | |
| 1.4.413 | 3,5-diethylphenyl | methyl | |
| 1.4.414 | 3-propyl-5-ethylphenyl | methyl | |
| 1.4.415 | 3-isopropyl-5-ethylphenyl | methyl | |
| 1.4.416 | 3-n-butyl-5-ethylphenyl | methyl | |
| 1.4.417 | 3-isobutyl-5-ethylphenyl | methyl | |
| 1.4.418 | 3-tert-butyl-5-ethylphenyl | methyl | |
| 1.4.419 | 3-cyclopropyl-5-ethylphenyl | methyl | |
| 1.4.420 | 3-cyano-5-ethylphenyl | methyl | |
| 1.4.421 | 3-trifluoromethyl-5-ethylphenyl | methyl | |
| 1.4.422 | 3-(methoxycarbonyl)-5-ethylphenyl | methyl | |
| 1.4.423 | 3-methoxy-5-ethylphenyl | methyl | |
| 1.4.424 | 3-ethoxy-5-ethylphenyl | methyl | |
| 1.4.425 | 3-n-propoxy-5-ethylphenyl | methyl | |
| 1.4.426 | 3-n-butoxy-5-ethylphenyl | methyl | |
| 1.4.427 | 3-isobutoxy-5-ethylphenyl | methyl | |
| 1.4.428 | 3-difluoromethoxy-5-ethylphenyl | methyl | |
| 1.4.429 | 3-trifluoromethoxy-5-ethylphenyl | methyl | |
| 1.4.430 | 3-nitro-5-ethylphenyl | methyl | |
| 1.4.431 | 3-acetoxy-5-ethylphenyl | methyl | |
| 1.4.432 | 3-methylsulfanyl-5-ethylphenyl | methyl | |
| 1.4.433 | 3,5-dipropylphenyl | methyl | |
| 1.4.434 | 3-isopropyl-5-propylphenyl | methyl | |
| 1.4.435 | 3-n-butyl-5-propylphenyl | methyl | |
| 1.4.436 | 3-isobutyl-5-propylphenyl | methyl | |
| 1.4.437 | 3-tert-butyl-5-propylphenyl | methyl | |
| 1.4.438 | 3-cyclopropyl-5-propylphenyl | methyl | |
| 1.4.439 | 3-cyano-5-propylphenyl | methyl | |
| 1.4.440 | 3-trifluoromethyl-5-propylphenyl | methyl | |
| 1.4.441 | 3-(methoxycarbonyl)-5-propylphenyl | methyl | |
| 1.4.442 | 3-methoxy-5-propylphenyl | methyl | |
| 1.4.443 | 3-ethoxy-5-propylphenyl | methyl | |
| 1.4.444 | 3-n-propoxy-5-propylphenyl | methyl | |
| 1.4.445 | 3-n-butoxy-5-propylphenyl | methyl | |
| 1.4.446 | 3-isobutoxy-5-propylphenyl | methyl | |
| 1.4.447 | 3-difluoromethoxy-5-propylphenyl | methyl | |
| 1.4.448 | 3-trifluoromethoxy-5-ethylphenyl | methyl | |
| 1.4.449 | 3-nitro-5-propylphenyl | methyl | |
| 1.4.450 | 3-acetoxy-5-propylphenyl | methyl | |
| 1.4.451 | 3-methylsulfanyl-5-propylphenyl | methyl | |
| 1.4.452 | 3,5-diisopropylphenyl | methyl | |
| 1.4.453 | 3-n-butyl-5-isopropylphenyl | methyl | |
| 1.4.454 | 3-tert-butyl-5-isopropylphenyl | methyl | |
| 1.4.455 | 3-cyclopropyl-5-isopropylphenyl | methyl | |
| 1.4.456 | 3-cyano-5-isopropylphenyl | methyl | |
| 1.4.457 | 3-trifluoromethyl-5-isopropylphenyl | methyl | |
| 1.4.458 | 3-(methoxycarbonyl)-5-isopropylphenyl | methyl | |
| 1.4.459 | 3-methoxy-5-isopropylphenyl | methyl | |
| 1.4.460 | 3-ethoxy-5-isopropylphenyl | methyl | |
| 1.4.461 | 3-n-propoxy-5-isopropylphenyl | methyl | |
| 1.4.462 | 3-n-butoxy-5-isopropylphenyl | methyl | |
| 1.4.463 | 3-isobutoxy-5-isopropylphenyl | methyl | |
| 1.4.464 | 3-difluoromethoxy-5-isopropylphenyl | methyl | |
| 1.4.465 | 3-trifluoromethoxy-5-isopropylphenyl | methyl | |
| 1.4.466 | 3-nitro-5-isopropylphenyl | methyl | |
| 1.4.467 | 3-acetoxy-5-isopropylphenyl | methyl | |
| 1.4.468 | 3-methylsulfanyl-5-isopropylphenyl | methyl | |
| 1.4.469 | 3,5-di isobutylphenyl | methyl | |
| 1.4.470 | 3-tert-butyl-5-isobutylphenyl | methyl | |
| 1.4.471 | 3-cyclopropyl-5-isobutylphenyl | methyl | |
| 1.4.472 | 3-cyano-5-isobutylphenyl | methyl | |
| 1.4.473 | 3-trifluoromethyl-5-isobutylphenyl | methyl | |
| 1.4.474 | 3-(methoxycarbonyl)-5-isobutylphenyl | methyl | |
| 1.4.475 | 3-methoxy-5-isobutylphenyl | methyl | |

TABLE 1.4-continued

Inventive compounds of the general formula (I) in which W* is COOH, $R^1$ and $R^2$ are each hydrogen, and aryl is the radical.

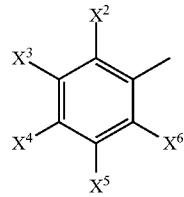

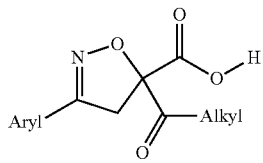

| No. | Aryl | Alkyl | Physical data |
|---|---|---|---|
| 1.4.476 | 3-ethoxy-5-isobutylphenyl | methyl | |
| 1.4.477 | 3-n-propoxy-5-isobutylphenyl | methyl | |
| 1.4.478 | 3-n-butoxy-5-isobutylphenyl | methyl | |
| 1.4.479 | 3-isobutoxy-5-isobutylphenyl | methyl | |
| 1.4.480 | 3-difluoromethoxy-5-isobutylphenyl | methyl | |
| 1.4.481 | 3-trifluoromethoxy-5-isobutylphenyl | methyl | |
| 1.4.482 | 3-nitro-5-isobutylphenyl | methyl | |
| 1.4.483 | 3-acetoxy-5-isobutylphenyl | methyl | |
| 1.4.484 | 3-methylsulfanyl-5-isobutylphenyl | methyl | |
| 1.4.485 | 3,5-di(tert-butyl)phenyl | methyl | |
| 1.4.486 | 3-cyclopropyl-5-tert-butylphenyl | methyl | |
| 1.4.487 | 3-cyano-5-tert-butylphenyl | methyl | |
| 1.4.488 | 3-trifluoromethyl-5-tert-butylphenyl | methyl | |
| 1.4.489 | 3-methoxy-5-tert-butylphenyl | methyl | |
| 1.4.490 | 3-ethoxy-5-tert-butylphenyl | methyl | |
| 1.4.491 | 3-n-propoxy-5-tert-butylphenyl | methyl | |
| 1.4.492 | 3-n-butoxy-5-tert-butylphenyl | methyl | |
| 1.4.493 | 3-isobutoxy-5-tert-butylphenyl | methyl | |
| 1.4.494 | 3-difluoromethoxy-5-tert-butylphenyl | methyl | |
| 1.4.495 | 3-trifluoromethoxy-5-tert-butylphenyl | methyl | |
| 1.4.496 | 3-nitro-5-tert-butylphenyl | methyl | |
| 1.4.497 | 3-acetoxy-5-tert-butylphenyl | methyl | |
| 1.4.498 | 3-methylsulfanyl-5-tert-butylphenyl | methyl | |
| 1.4.499 | 3-tert-butyl-5-cyclopropylphenyl | methyl | |
| 1.4.500 | 3,5-dicyclopropyl-phenyl | methyl | |
| 1.4.501 | 3-cyano-5-cyclopropylphenyl | methyl | |
| 1.4.502 | 3-trifluoromethyl-5-cyclopropylphenyl | methyl | |
| 1.4.503 | 3-(methoxycarbonyl)-5-cyclopropylphenyl | methyl | |
| 1.4.504 | 3-methoxy-5-cyclopropylphenyl | methyl | |
| 1.4.505 | 3-ethoxy-5-cyclopropylphenyl | methyl | |
| 1.4.506 | 3-n-propoxy-5-cyclopropylphenyl | methyl | |
| 1.4.507 | 3-n-butoxy-5-cyclopropylphenyl | methyl | |
| 1.4.508 | 3-isobutoxy-5-cyclopropylphenyl | methyl | |
| 1.4.509 | 3-difluoromethoxy-5-cyclopropylphenyl | methyl | |
| 1.4.510 | 3-trifluoromethoxy-5-cyclopropylphenyl | methyl | |
| 1.4.511 | 3-nitro-5-cyclopropylphenyl | methyl | |
| 1.4.512 | 3-acetoxy-5-cyclopropylphenyl | methyl | |
| 1.4.513 | 3-methylsulfanyl-5-cyclopropylphenyl | methyl | |
| 1.4.514 | 3,5-dicyanophenyl | methyl | |
| 1.4.515 | 3-trifluoromethyl-5-cyanophenyl | methyl | |
| 1.4.516 | 3-(methoxycarbonyl)-5-cyanophenyl | methyl | |
| 1.4.517 | 3-methoxy-5-cyanophenyl | methyl | |
| 1.4.518 | 3-ethoxy-5-cyanophenyl | methyl | |
| 1.4.519 | 3-n-propoxy-5-cyanophenyl | methyl | |
| 1.4.520 | 3-n-butoxy-5-cyanophenyl | methyl | |
| 1.4.521 | 3-isobutoxy-5-cyanophenyl | methyl | |
| 1.4.522 | 3-difluoromethoxy-5-cyanophenyl | methyl | |
| 1.4.523 | 3-trifluoromethoxy-5-cyanophenyl | methyl | |
| 1.4.524 | 3-nitro-5-cyanophenyl | methyl | |
| 1.4.525 | 3-acetoxy-5-cyanophenyl | methyl | |
| 1.4.526 | 3-methylsulfanyl-5-cyanophenyl | methyl | |
| 1.4.527 | 3,5-di(trifluoromethyl)-phenyl | methyl | |
| 1.4.528 | 3-(methoxycarbonyl)-5-trifluoromethyl-phenyl | methyl | |
| 1.4.529 | 3-methoxy-5-trifluoromethylphenyl | methyl | |
| 1.4.530 | 3-ethoxy-5-trifluoromethylphenyl | methyl | |
| 1.4.531 | 3-n-propoxy-5-trifluoromethylphenyl | methyl | |
| 1.4.532 | 3-n-butoxy-5-trifluoromethylphenyl | methyl | |
| 1.4.533 | 3-isobutoxy-5-trifluoromethylphenyl | methyl | |
| 1.4.534 | 3-difluoromethoxy-5-trifluoromethyl-phenyl | methyl | |
| 1.4.535 | 3-trifluoromethoxy-5-trifluoromethyl-phenyl | methyl | |
| 1.4.536 | 3-nitro-5-trifluoromethylphenyl | methyl | |
| 1.4.537 | 3-acetoxy-5-trifluoromethylphenyl | methyl | |
| 1.4.538 | 3-methylsulfanyl-5-trifluoromethylphenyl | methyl | |
| 1.4.539 | 3-methoxy-5-(methoxycarbonyl)phenyl | methyl | |
| 1.4.540 | 3-ethoxy-5-(methoxycarbonyl)phenyl | methyl | |
| 1.4.541 | 3-n-propoxy-5-(methoxycarbonyl)phenyl | methyl | |
| 1.4.542 | 3-n-butoxy-5-(methoxycarbonyl)phenyl | methyl | |
| 1.4.543 | 3-isobutoxy-5-(methoxycarbonyl)phenyl | methyl | |
| 1.4.544 | 3-difluoromethoxy-5-(methoxycarbonyl)-phenyl | methyl | |
| 1.4.545 | 3-trifluoromethoxy-5-(methoxycarbonyl)-phenyl | methyl | |
| 1.4.546 | 3-nitro-5-(methoxycarbonyl)phenyl | methyl | |
| 1.4.547 | 3-acetoxy-5-(methoxycarbonyl)phenyl | methyl | |
| 1.4.548 | 3-methylsulfanyl-5-(methoxycarbonyl)-phenyl | methyl | |
| 1.4.549 | 3,5-dimethoxyphenyl | methyl | |
| 1.4.550 | 3-ethoxy-5-methoxyphenyl | methyl | |
| 1.4.551 | 3-n-propoxy-5-methoxyphenyl | methyl | |
| 1.4.552 | 3-n-butoxy-5-methoxyphenyl | methyl | |
| 1.4.553 | 3-isobutoxy-5-methoxyphenyl | methyl | |
| 1.4.554 | 3-tert-butoxy-5-methoxyphenyl | methyl | |
| 1.4.555 | 3-difluoromethoxy-5-methoxyphenyl | methyl | |
| 1.4.556 | 3-trifluoromethoxy-5-methoxyphenyl | methyl | |
| 1.4.557 | 3-nitro-5-methoxyphenyl | methyl | |
| 1.4.558 | 3-acetoxy-5-methoxyphenyl | methyl | |
| 1.4.559 | 3-methylsulfanyl-5-methoxyphenyl | methyl | |
| 1.4.560 | 3,5-diethoxyphenyl | methyl | |
| 1.4.561 | 3-n-propoxy-5-ethoxyphenyl | methyl | |
| 1.4.562 | 3-n-butoxy-5-ethoxyphenyl | methyl | |
| 1.4.563 | 3-isobutoxy-5-ethoxyphenyl | methyl | |
| 1.4.564 | 3-difluoromethoxy-5-ethoxyphenyl | methyl | |
| 1.4.565 | 3-trifluoromethoxy-5-ethoxyphenyl | methyl | |
| 1.4.566 | 3-nitro-5-ethoxyphenyl | methyl | |
| 1.4.567 | 3-acetoxy-5-ethoxyphenyl | methyl | |
| 1.4.568 | 3-methylsulfanyl-5-ethoxyphenyl | methyl | |
| 1.4.569 | 3,5-di(isopropoxy)phenyl | methyl | |
| 1.4.570 | 3-n-butoxy-5-isopropoxyphenyl | methyl | |
| 1.4.571 | 3-isobutoxy-5-isopropoxyphenyl | methyl | |
| 1.4.572 | 3-difluoromethoxy-5-isopropoxyphenyl | methyl | |
| 1.4.573 | 3-trifluoromethoxy-5-isopropoxyphenyl | methyl | |
| 1.4.574 | 3-nitro-5-isopropoxyphenyl | methyl | |
| 1.4.575 | 3-acetoxy-5-isopropoxyphenyl | methyl | |
| 1.4.576 | 3-methylsulfanyl-5-isopropoxyphenyl | methyl | |
| 1.4.577 | 3,5-di(trifluoromethoxy)phenyl | methyl | |
| 1.4.578 | 3-nitro-5-trifluoromethoxyphenyl | methyl | |

TABLE 1.4-continued

Inventive compounds of the general formula (I) in which W* is COOH, R¹ and R² are each hydrogen, and aryl is the radical.

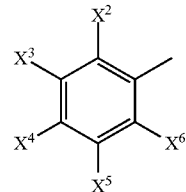

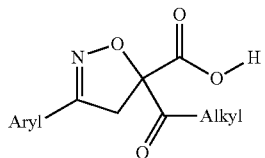

| No. | Aryl | Alkyl | Physical data |
|---|---|---|---|
| 1.4.579 | 3-methylsulfanyl-5-trifluoromethoxy-phenyl | methyl | |
| 1.4.580 | 3,5-bis(difluoromethoxy)phenyl | methyl | |
| 1.4.581 | 3,5-bis(difluoromethoxy)phenyl | ethyl | |
| 1.4.582 | 3,5-bis(difluoromethoxy)phenyl | propyl | |
| 1.4.583 | 3,5-bis(difluoromethoxy)phenyl | butyl | |
| 1.4.584 | 3-trifluoromethoxy-5-difluoromethoxy-phenyl | methyl | |
| 1.4.585 | 3-nitro-5-difluoromethoxyphenyl | methyl | |
| 1.4.586 | 3-acetoxy-5-difluoromethoxyphenyl | methyl | |
| 1.4.587 | 3-methylsulfanyl-5-difluoromethoxy-phenyl | methyl | |
| 1.4.588 | 3-acetoxy-5-nitrophenyl | methyl | |
| 1.4.589 | 3-methylsulfanyl-5-nitrophenyl | methyl | |
| 1.4.590 | 3,4-difluorophenyl | methyl | |
| 1.4.591 | 3,4-difluorophenyl | ethyl | |
| 1.4.592 | 3,4-difluorophenyl | propyl | |
| 1.4.593 | 3,4-difluorophenyl | butyl | |
| 1.4.594 | 3-chloro-4-fluorophenyl | methyl | |
| 1.4.595 | 3-chloro-4-fluorophenyl | ethyl | |
| 1.4.596 | 3-chloro-4-fluorophenyl | propyl | |
| 1.4.597 | 3-chloro-4-fluorophenyl | butyl | |
| 1.4.598 | 3-bromo-4-fluorophenyl | methyl | |
| 1.4.599 | 3-methyl-4-fluorophenyl | methyl | |
| 1.4.600 | 3-methyl-4-fluorophenyl | ethyl | |
| 1.4.601 | 3-cyclopropyl-4-fluorophenyl | methyl | |
| 1.4.602 | 3-cyano-4-fluorophenyl | methyl | |
| 1.4.603 | 3-methoxy-4-fluorophenyl | methyl | |
| 1.4.604 | 3-ethoxy-4-fluorophenyl | methyl | |
| 1.4.605 | 3-trifluoromethoxy-4-fluorophenyl | methyl | |
| 1.4.606 | 3-nitro-4-fluorophenyl | methyl | |
| 1.4.607 | 3-fluoro-4-chlorophenyl | methyl | |
| 1.4.608 | 3,4-dichlorophenyl | methyl | |
| 1.4.609 | 3-bromo-4-chlorophenyl | methyl | |
| 1.4.610 | 3-methyl-4-chlorophenyl | methyl | |
| 1.4.611 | 3-cyclopropyl-4-chlorophenyl | methyl | |
| 1.4.612 | 3-cyano-4-chlorophenyl | methyl | |
| 1.4.613 | 3-trifluoromethyl-4-chlorophenyl | methyl | |
| 1.4.614 | 3-methoxy-4-chlorophenyl | methyl | |
| 1.4.615 | 3-ethoxy-4-chlorophenyl | methyl | |
| 1.4.616 | 3-trifluoromethoxy-4-chlorophenyl | methyl | |
| 1.4.617 | 3-nitro-4-chlorophenyl | methyl | |
| 1.4.618 | 3-fluoro-4-bromophenyl | methyl | |
| 1.4.619 | 3-chloro-4-bromophenyl | methyl | |
| 1.4.620 | 3,4-dibromophenyl | methyl | |
| 1.4.621 | 3-methyl-4-bromophenyl | methyl | |
| 1.4.622 | 3-cyclopropyl-4-bromophenyl | methyl | |
| 1.4.623 | 3-cyano-4-bromophenyl | methyl | |
| 1.4.624 | 3-trifluoromethyl-4-bromophenyl | methyl | |
| 1.4.625 | 3-methoxy-4-phenyl | methyl | |
| 1.4.626 | 3-ethoxy-4-bromophenyl | methyl | |
| 1.4.627 | 3-trifluoromethoxy-4-bromophenyl | methyl | |
| 1.4.628 | 3-nitro-4-bromophenyl | methyl | |
| 1.4.629 | 3-fluoro-4-iodophenyl | methyl | |
| 1.4.630 | 3-chloro-4-iodophenyl | methyl | |
| 1.4.631 | 3-bromo-4-iodophenyl | methyl | |
| 1.4.632 | 3-methyl-4-iodophenyl | methyl | |
| 1.4.633 | 3-cyclopropyl-4-iodophenyl | methyl | |
| 1.4.634 | 3-cyano-4-iodophenyl | methyl | |
| 1.4.635 | 3-trifluoromethyl-4-iodophenyl | methyl | |
| 1.4.636 | 3-methoxy-4-iodophenyl | methyl | |
| 1.4.637 | 3-ethoxy-4-iodophenyl | methyl | |
| 1.4.638 | 3-trifluoromethoxy-4-iodophenyl | methyl | |
| 1.4.639 | 3-nitro-4-iodophenyl | methyl | |
| 1.4.640 | 3-fluoro-4-methylphenyl | methyl | |
| 1.4.641 | 3-chloro-4-methylphenyl | methyl | |
| 1.4.642 | 3-bromo-4-methylphenyl | methyl | |
| 1.4.643 | 3,4-dimethylphenyl | methyl | |
| 1.4.644 | 3,4-dimethylphenyl | ethyl | |
| 1.4.645 | 3,4-dimethylphenyl | propyl | |
| 1.4.646 | 3,4-dimethylphenyl | butyl | |
| 1.4.647 | 3-cyclopropyl-4-methylphenyl | methyl | |
| 1.4.648 | 3-cyano-4-methylphenyl | methyl | |
| 1.4.649 | 3-trifluoromethyl-4-methylphenyl | methyl | |
| 1.4.650 | 3-methoxy-4-methylphenyl | methyl | |
| 1.4.651 | 3-ethoxy-4-methylphenyl | methyl | |
| 1.4.652 | 3-trifluoromethoxy-4-methylphenyl | methyl | |
| 1.4.653 | 3-nitro-4-methylphenyl | methyl | |
| 1.4.654 | 3-fluoro-4-ethylphenyl | methyl | |
| 1.4.655 | 3-chloro-4-ethylphenyl | methyl | |
| 1.4.656 | 3-bromo-4-ethylphenyl | methyl | |
| 1.4.657 | 3-methyl-4-ethylphenyl | methyl | |
| 1.4.658 | 3,4-diethylphenyl | methyl | |
| 1.4.659 | 3-cyclopropyl-4-ethylphenyl | methyl | |
| 1.4.660 | 3-cyano-4-ethylphenyl | methyl | |
| 1.4.661 | 3-trifluoromethyl-4-ethylphenyl | methyl | |
| 1.4.662 | 3-methoxy-4-ethylphenyl | methyl | |
| 1.4.663 | 3-ethoxy-4-ethylphenyl | methyl | |
| 1.4.664 | 3-trifluoromethoxy-4-ethylphenyl | methyl | |
| 1.4.665 | 3-nitro-4-ethylphenyl | methyl | |
| 1.4.666 | 3-fluoro-4-propylphenyl | methyl | |
| 1.4.667 | 3-chloro-4-propylphenyl | methyl | |
| 1.4.668 | 3-bromo-4-propylphenyl | methyl | |
| 1.4.669 | 3-methyl-4-propylphenyl | methyl | |
| 1.4.670 | 3-cyclopropyl-4-propylphenyl | methyl | |
| 1.4.671 | 3-cyano-4-propylphenyl | methyl | |
| 1.4.672 | 3-trifluoromethyl-4-propylphenyl | methyl | |
| 1.4.673 | 3-methoxy-4-propylphenyl | methyl | |
| 1.4.674 | 3-ethoxy-4-propylphenyl | methyl | |
| 1.4.675 | 3-trifluoromethoxy-4-propylphenyl | methyl | |
| 1.4.676 | 3-nitro-4-propylphenyl | methyl | |
| 1.4.677 | 3-fluoro-4-isopropylphenyl | methyl | |
| 1.4.678 | 3-chloro-4-isopropylphenyl | methyl | |
| 1.4.679 | 3-bromo-4-isopropylphenyl | methyl | |
| 1.4.680 | 3-methyl-4-isopropylphenyl | methyl | |
| 1.4.681 | 3-cyclopropyl-4-isopropylphenyl | methyl | |
| 1.4.682 | 3-cyano-4-isopropylphenyl | methyl | |
| 1.4.683 | 3-trifluoromethyl-4-isopropylphenyl | methyl | |
| 1.4.684 | 3-methoxy-4-isopropylphenyl | methyl | |
| 1.4.685 | 3-ethoxy-4-isopropylphenyl | methyl | |

TABLE 1.4-continued

Inventive compounds of the general formula (I) in which W* is COOH, $R^1$ and $R^2$ are each hydrogen, and aryl is the radical.

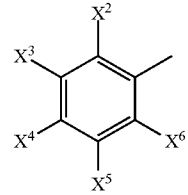

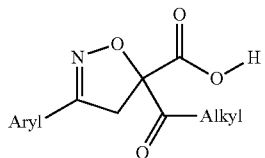

| No. | Aryl | Alkyl | Physical data |
|---|---|---|---|
| 1.4.686 | 3-trifluoromethoxy-4-isopropylphenyl | methyl | |
| 1.4.687 | 3-nitro-4-isopropylphenyl | methyl | |
| 1.4.688 | 3-fluoro-4-tert-butylphenyl | methyl | |
| 1.4.689 | 3-chloro-4-tert-butylphenyl | methyl | |
| 1.4.690 | 3-bromo-4-tert-butylphenyl | methyl | |
| 1.4.691 | 3-methyl-4-tert-butylphenyl | methyl | |
| 1.4.692 | 3-cyclopropyl-4-tert-butylphenyl | methyl | |
| 1.4.693 | 3-cyano-4-tert-butylphenyl | methyl | |
| 1.4.694 | 3-trifluoromethyl-4-tert-butylphenyl | methyl | |
| 1.4.695 | 3-trifluoromethyl-4-tert-butylphenyl | ethyl | |
| 1.4.696 | 3-trifluoromethyl-4-tert-butylphenyl | propyl | |
| 1.4.697 | 3-trifluoromethyl-4-tert-butylphenyl | butyl | |
| 1.4.698 | 3-methoxy-4-tert-butylphenyl | methyl | |
| 1.4.699 | 3-ethoxy-4-tert-butylphenyl | methyl | |
| 1.4.700 | 3-trifluoromethoxy-4-tert-butylphenyl | methyl | |
| 1.4.701 | 3-nitro-4-tert-butylphenyl | methyl | |
| 1.4.702 | 3-fluoro-4-cyclopropylphenyl | methyl | |
| 1.4.703 | 3-chloro-4-cyclopropylphenyl | methyl | |
| 1.4.704 | 3-bromo-4-cyclopropylphenyl | methyl | |
| 1.4.705 | 3-methyl-4-cyclopropylphenyl | methyl | |
| 1.4.706 | 3-trifluoromethyl-4-cyclopropylphenyl | methyl | |
| 1.4.707 | 3-methoxy-4-cyclopropylphenyl | methyl | |
| 1.4.708 | 3-ethoxy-4-cyclopropylphenyl | methyl | |
| 1.4.709 | 3-trifluoromethoxy-4-cyclopropylphenyl | methyl | |
| 1.4.710 | 3-fluoro-4-methoxycarbonylphenyl | methyl | |
| 1.4.711 | 3-chloro-4-methoxycarbonylphenyl | methyl | |
| 1.4.712 | 3-bromo-4-methoxycarbonylphenyl | methyl | |
| 1.4.713 | 3-methyl-4-methoxycarbonylphenyl | methyl | |
| 1.4.714 | 3-cyclopropyl-4-methoxycarbonylphenyl | methyl | |
| 1.4.715 | 3-cyano-4-methoxycarbonylphenyl | methyl | |
| 1.4.716 | 3-trifluoromethyl-4-methoxycarbonyl-phenyl | methyl | |
| 1.4.717 | 3-methoxy-4-methoxycarbonylphenyl | methyl | |
| 1.4.718 | 3-ethoxy-4-methoxycarbonylphenyl | methyl | |
| 1.4.719 | 3-trifluoromethoxy-4-methoxycarbonyl-phenyl | methyl | |
| 1.4.720 | 3-nitro-4-methoxycarbonylphenyl | methyl | |
| 1.4.721 | 3-fluoro-4-cyanophenyl | methyl | |
| 1.4.722 | 3-chloro-4-cyanophenyl | methyl | |
| 1.4.723 | 3-bromo-4-cyanophenyl | methyl | |
| 1.4.724 | 3-methyl-4-cyanophenyl | methyl | |
| 1.4.725 | 3-cyclopropyl-4-cyanophenyl | methyl | |
| 1.4.726 | 3,4-dicyanophenyl | methyl | |
| 1.4.727 | 3-trifluoromethyl-4-cyanophenyl | methyl | |
| 1.4.728 | 3-trifluoromethyl-4-cyanophenyl | ethyl | |
| 1.4.729 | 3-trifluoromethyl-4-cyanophenyl | propyl | |
| 1.4.730 | 3-trifluoromethyl-4-cyanophenyl | butyl | |
| 1.4.731 | 3-methoxy-4-cyanophenyl | methyl | |
| 1.4.732 | 3-ethoxy-4-cyanophenyl | methyl | |
| 1.4.733 | 3-trifluoromethoxy-4-cyanophenyl | methyl | |
| 1.4.734 | 3-nitro-4-cyanophenyl | methyl | |
| 1.4.735 | 3-fluoro-4-methoxyphenyl | methyl | |
| 1.4.736 | 3-chloro-4-methoxyphenyl | methyl | |
| 1.4.737 | 3-bromo-4-methoxyphenyl | methyl | |
| 1.4.738 | 3-methyl-4-methoxyphenyl | methyl | |

TABLE 1.4-continued

Inventive compounds of the general formula (I) in which W* is COOH, $R^1$ and $R^2$ are each hydrogen, and aryl is the radical.

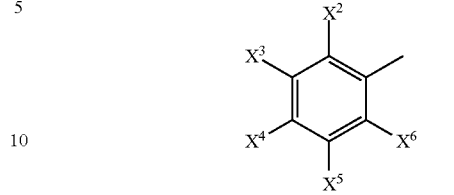

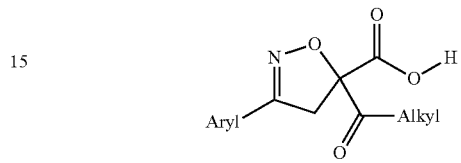

| No. | Aryl | Alkyl | Physical data |
|---|---|---|---|
| 1.4.739 | 3-cyclopropyl-4-methoxyphenyl | methyl | |
| 1.4.740 | 3-cyano-4-methoxyphenyl | methyl | |
| 1.4.741 | 3-trifluoromethyl-4-methoxyphenyl | methyl | |
| 1.4.742 | 3,4-dimethoxyphenyl | methyl | |
| 1.4.743 | 3-ethoxy-4-methoxyphenyl | methyl | |
| 1.4.744 | 3-trifluoromethoxy-4-methoxyphenyl | methyl | |
| 1.4.745 | 3-nitro-4-methoxyphenyl | methyl | |
| 1.4.746 | 3-fluoro-4-ethoxyphenyl | methyl | |
| 1.4.747 | 3-chloro-4-ethoxyphenyl | methyl | |
| 1.4.748 | 3-chloro-4-ethoxyphenyl | ethyl | |
| 1.4.749 | 3-chloro-4-ethoxyphenyl | propyl | |
| 1.4.750 | 3-chloro-4-ethoxyphenyl | butyl | |
| 1.4.751 | 3-bromo-4-ethoxyphenyl | methyl | |
| 1.4.752 | 3-methyl-4-ethoxyphenyl | methyl | |
| 1.4.753 | 3-cyclopropyl-4-ethoxyphenyl | methyl | |
| 1.4.754 | 3-cyano-4-ethoxyphenyl | methyl | |
| 1.4.755 | 3-trifluoromethyl-4-ethoxyphenyl | methyl | |
| 1.4.756 | 3-methoxy-4-ethoxyphenyl | methyl | |
| 1.4.757 | 2,4-diethoxyphenyl | methyl | |
| 1.4.758 | 3-trifluoromethoxy-4-ethoxyphenyl | methyl | |
| 1.4.759 | 3-nitro-4-ethoxyphenyl | methyl | |
| 1.4.760 | 3-fluoro-4-isopropoxyphenyl | methyl | |
| 1.4.761 | 3-chloro-4-isopropoxyphenyl | methyl | |
| 1.4.762 | 3-bromo-4-isopropoxyphenyl | methyl | |
| 1.4.763 | 3-methyl-4-isopropoxyphenyl | methyl | |
| 1.4.764 | 3-cyclopropyl-4-isopropoxyphenyl | methyl | |
| 1.4.765 | 3-cyano-4-isopropoxyphenyl | methyl | |
| 1.4.766 | 3-trifluoromethyl-4-isopropoxyphenyl | methyl | |
| 1.4.767 | 3-methoxy-4-isopropoxyphenyl | methyl | |
| 1.4.768 | 3-ethoxy-4-isopropoxyphenyl | methyl | |
| 1.4.769 | 3-trifluoromethoxy-4-isopropoxyphenyl | methyl | |
| 1.4.770 | 3-nitro-4-isopropoxyphenyl | methyl | |
| 1.4.771 | 3-fluoro-4-trifluoromethoxyphenyl | methyl | |
| 1.4.772 | 3-chloro-4-trifluoromethoxyphenyl | methyl | |
| 1.4.773 | 3-bromo-4-trifluoromethoxyphenyl | methyl | |
| 1.4.774 | 3-methyl-4-trifluoromethoxyphenyl | methyl | |
| 1.4.775 | 3-cyclopropyl-4-trifluoromethoxyphenyl | methyl | |
| 1.4.776 | 3-cyano-4-trifluoromethoxyphenyl | methyl | |
| 1.4.777 | 3-trifluoromethyl-4-trifluoromethoxy-phenyl | methyl | |
| 1.4.778 | 3-methoxy-4-trifluoromethoxyphenyl | methyl | |
| 1.4.779 | 3-ethoxy-4-trifluoromethoxyphenyl | methyl | |
| 1.4.780 | 3,4-bis(trifluoromethoxy)phenyl | methyl | |
| 1.4.781 | 3-nitro-4-trifluoromethoxyphenyl | methyl | |
| 1.4.782 | 3-fluoro-4-difluoromethoxyphenyl | methyl | |
| 1.4.783 | 3-chloro-4-difluoromethoxyphenyl | methyl | |
| 1.4.784 | 3-bromo-4-difluoromethoxyphenyl | methyl | |
| 1.4.785 | 3-methyl-4-difluoromethoxyphenyl | methyl | |
| 1.4.786 | 3-cyclopropyl-4-difluoromethoxyphenyl | methyl | |
| 1.4.787 | 3-cyano-4-difluoromethoxyphenyl | methyl | |
| 1.4.788 | 3-trifluoromethyl-4-difluoromethoxy-phenyl | methyl | |
| 1.4.789 | 3-methoxy-4-difluoromethoxyphenyl | methyl | |
| 1.4.790 | 3-ethoxy-4-difluoromethoxyphenyl | methyl | |
| 1.4.791 | 3-nitro-4-difluoromethoxyphenyl | methyl | |

TABLE 1.4-continued

Inventive compounds of the general formula (I) in which W* is COOH, $R^1$ and $R^2$ are each hydrogen, and aryl is the radical.

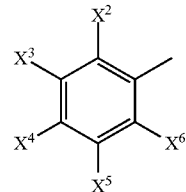

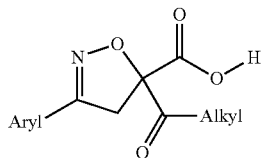

| No. | Aryl | Alkyl | Physical data |
|---|---|---|---|
| 1.4.792 | 3-fluoro-4-nitrophenyl | methyl | |
| 1.4.793 | 3-chloro-4-nitrophenyl | methyl | |
| 1.4.794 | 3-bromo-4-nitrophenyl | methyl | |
| 1.4.795 | 3-methyl-4-nitrophenyl | methyl | |
| 1.4.796 | 3-cyclopropyl-4-nitrophenyl | methyl | |
| 1.4.797 | 3-cyano-4-nitrophenyl | methyl | |
| 1.4.798 | 3-trifluoromethyl-4-nitrophenyl | methyl | |
| 1.4.799 | 3-methoxy-4-nitrophenyl | methyl | |
| 1.4.800 | 3-ethoxy-4-nitrophenyl | methyl | |
| 1.4.801 | 3-trifluoromethoxy-4-nitrophenyl | methyl | |
| 1.4.802 | 3-fluoro-4-methylsulfanylphenyl | methyl | |
| 1.4.803 | 3-chloro-4-methylsulfanylphenyl | methyl | |
| 1.4.804 | 3-bromo-4-methylsulfanylphenyl | methyl | |
| 1.4.805 | 3-methyl-4-methylsulfanylphenyl | methyl | |
| 1.4.806 | 3-cyclopropyl-4-methylsulfanylphenyl | methyl | |
| 1.4.807 | 3-cyano-4-methylsulfanylphenyl | methyl | |
| 1.4.808 | 3-nitro-4-methylsulfanylphenyl | methyl | |
| 1.4.809 | 3,6-difluorophenyl | methyl | |
| 1.4.810 | 3,6-difluorophenyl | ethyl | |
| 1.4.811 | 3,6-difluorophenyl | propyl | |
| 1.4.812 | 3,6-difluorophenyl | butyl | |
| 1.4.813 | 3-chloro-6-fluorophenyl | methyl | |
| 1.4.814 | 3-bromo-6-fluorophenyl | methyl | |
| 1.4.815 | 3-methyl-6-fluorophenyl | methyl | |
| 1.4.816 | 3-cyclopropyl-6-fluorophenyl | methyl | |
| 1.4.817 | 3-cyano-6-fluorophenyl | methyl | |
| 1.4.818 | 3-methoxy-6-fluorophenyl | methyl | |
| 1.4.819 | 3-ethoxy-6-fluorophenyl | methyl | |
| 1.4.820 | 3-trifluoromethoxy-6-fluorophenyl | methyl | |
| 1.4.821 | 3-nitro-6-fluorophenyl | methyl | |
| 1.4.822 | 3-fluoro-6-chlorophenyl | methyl | |
| 1.4.823 | 3-fluoro-6-chlorophenyl | ethyl | |
| 1.4.824 | 3-fluoro-6-chlorophenyl | propyl | |
| 1.4.825 | 3-fluoro-6-chlorophenyl | butyl | |
| 1.4.826 | 3,6-dichlorophenyl | methyl | |
| 1.4.827 | 3,6-dichlorophenyl | ethyl | |
| 1.4.828 | 3,6-dichlorophenyl | propyl | |
| 1.4.829 | 3,6-dichlorophenyl | butyl | |
| 1.4.830 | 3-bromo-6-chlorophenyl | methyl | |
| 1.4.831 | 3-methyl-6-chlorophenyl | methyl | |
| 1.4.832 | 3-ethyl-6-chlorophenyl | methyl | |
| 1.4.833 | 3-cyclopropyl-6-chlorophenyl | methyl | |
| 1.4.834 | 3-cyano-6-chlorophenyl | methyl | |
| 1.4.835 | 3-trifluoromethyl-6-chlorophenyl | methyl | |
| 1.4.836 | 3-methoxy-6-chlorophenyl | methyl | |
| 1.4.837 | 3-ethoxy-6-chlorophenyl | methyl | |
| 1.4.838 | 3-trifluoromethoxy-6-chlorophenyl | methyl | |
| 1.4.839 | 3-nitro-6-chlorophenyl | methyl | |
| 1.4.840 | 3-fluoro-6-bromophenyl | methyl | |
| 1.4.841 | 3-chloro-6-bromophenyl | methyl | |
| 1.4.842 | 3,6-dibromophenyl | methyl | |
| 1.4.843 | 3-methyl-6-bromophenyl | methyl | |
| 1.4.844 | 3-cyclopropyl-6-bromophenyl | methyl | |
| 1.4.845 | 3-cyano-6-bromophenyl | methyl | |
| 1.4.846 | 3-trifluoromethyl-6-bromophenyl | methyl | |
| 1.4.847 | 3-methoxy-6-phenyl | methyl | |
| 1.4.848 | 3-ethoxy-6-bromophenyl | methyl | |
| 1.4.849 | 3-trifluoromethoxy-6-bromophenyl | methyl | |
| 1.4.850 | 3-nitro-6-bromophenyl | methyl | |
| 1.4.851 | 3-fluoro-6-iodophenyl | methyl | |
| 1.4.852 | 3-chloro-6-iodophenyl | methyl | |
| 1.4.853 | 3-bromo-6-iodophenyl | methyl | |
| 1.4.854 | 3-methyl-6-iodophenyl | methyl | |
| 1.4.855 | 3-cyclopropyl-6-iodophenyl | methyl | |
| 1.4.856 | 3-cyano-6-iodophenyl | methyl | |
| 1.4.857 | 3-trifluoromethyl-6-iodophenyl | methyl | |
| 1.4.858 | 3-methoxy-6-iodophenyl | methyl | |
| 1.4.859 | 3-ethoxy-6-iodophenyl | methyl | |
| 1.4.860 | 3-trifluoromethoxy-6-iodophenyl | methyl | |
| 1.4.861 | 3-nitro-6-iodophenyl | methyl | |
| 1.4.862 | 3-fluoro-6-methylphenyl | methyl | |
| 1.4.863 | 3-chloro-6-methylphenyl | methyl | |
| 1.4.864 | 3-bromo-6-methylphenyl | methyl | |
| 1.4.865 | 3,6-dimethylphenyl | methyl | |
| 1.4.866 | 3-cyclopropyl-6-methylphenyl | methyl | |
| 1.4.867 | 3-cyano-6-methylphenyl | methyl | |
| 1.4.868 | 3-trifluoromethyl-6-methylphenyl | methyl | |
| 1.4.869 | 3-methoxy-6-methylphenyl | methyl | |
| 1.4.870 | 3-ethoxy-6-methylphenyl | methyl | |
| 1.4.871 | 3-trifluoromethoxy-6-methylphenyl | methyl | |
| 1.4.872 | 3-nitro-6-methylphenyl | methyl | |
| 1.4.873 | 3-fluoro-6-ethylphenyl | methyl | |
| 1.4.874 | 3-chloro-6-ethylphenyl | methyl | |
| 1.4.875 | 3-bromo-6-ethylphenyl | methyl | |
| 1.4.876 | 3-methyl-6-ethylphenyl | methyl | |
| 1.4.877 | 3,6-diethylphenyl | methyl | |
| 1.4.878 | 3-cyclopropyl-6-ethylphenyl | methyl | |
| 1.4.879 | 3-cyano-6-ethylphenyl | methyl | |
| 1.4.880 | 3-trifluoromethyl-6-ethylphenyl | methyl | |
| 1.4.881 | 3-methoxy-6-ethylphenyl | methyl | |
| 1.4.882 | 3-ethoxy-6-ethylphenyl | methyl | |
| 1.4.883 | 3-trifluoromethoxy-6-ethylphenyl | methyl | |
| 1.4.884 | 3-nitro-6-ethylphenyl | methyl | |
| 1.4.885 | 3-fluoro-6-propylphenyl | methyl | |
| 1.4.886 | 3-chloro-6-propylphenyl | methyl | |
| 1.4.887 | 3-bromo-6-propylphenyl | methyl | |
| 1.4.888 | 3-methyl-6-propylphenyl | methyl | |
| 1.4.889 | 3-cyclopropyl-6-propylphenyl | methyl | |
| 1.4.890 | 3-cyano-6-propylphenyl | methyl | |
| 1.4.891 | 3-trifluoromethyl-6-propylphenyl | methyl | |
| 1.4.892 | 3-methoxy-6-propylphenyl | methyl | |
| 1.4.893 | 3-ethoxy-6-propylphenyl | methyl | |
| 1.4.894 | 3-trifluoromethoxy-6-propylphenyl | methyl | |
| 1.4.895 | 3-nitro-6-propylphenyl | methyl | |
| 1.4.896 | 3-fluoro-6-isopropylphenyl | methyl | |
| 1.4.897 | 3-chloro-6-isopropylphenyl | methyl | |
| 1.4.898 | 3-bromo-6-isopropylphenyl | methyl | |
| 1.4.899 | 3-methyl-6-isopropylphenyl | methyl | |
| 1.4.900 | 3-cyclopropyl-6-isopropylphenyl | methyl | |
| 1.4.901 | 3-cyano-6-isopropylphenyl | methyl | |

TABLE 1.4-continued

Inventive compounds of the general formula (I) in which W* is COOH, R¹ and R² are each hydrogen, and aryl is the radical.

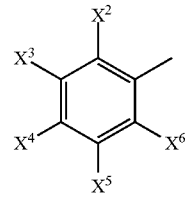

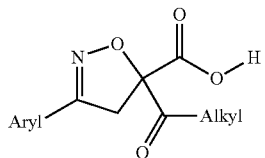

| No. | Aryl | Alkyl | Physical data |
|---|---|---|---|
| 1.4.902 | 3-trifluoromethyl-6-isopropylphenyl | methyl | |
| 1.4.903 | 3-ethoxy-6-isopropylphenyl | methyl | |
| 1.4.904 | 3-trifluoromethoxy-6-isopropylphenyl | methyl | |
| 1.4.905 | 3-nitro-6-isopropylphenyl | methyl | |
| 1.4.906 | 3-fluoro-6-tert-butylphenyl | methyl | |
| 1.4.907 | 3-chloro-6-tert-butylphenyl | methyl | |
| 1.4.908 | 3-bromo-6-tert-butylphenyl | methyl | |
| 1.4.909 | 3-methyl-6-tert-butylphenyl | methyl | |
| 1.4.910 | 3-cyclopropyl-6-tert-butylphenyl | methyl | |
| 1.4.911 | 3-cyano-6-tert-butylphenyl | methyl | |
| 1.4.912 | 3-trifluoromethyl-6-tert-butylphenyl | methyl | |
| 1.4.913 | 3-methoxy-6-tert-butylphenyl | methyl | |
| 1.4.914 | 3-ethoxy-6-tert-butylphenyl | methyl | |
| 1.4.915 | 3-trifluoromethoxy-6-tert-butylphenyl | methyl | |
| 1.4.916 | 3-nitro-6-tert-butylphenyl | methyl | |
| 1.4.917 | 3-fluoro-6-cyclopropylphenyl | methyl | |
| 1.4.918 | 3-chloro-6-cyclopropylphenyl | methyl | |
| 1.4.919 | 3-bromo-6-cyclopropylphenyl | methyl | |
| 1.4.920 | 3-methyl-6-cyclopropylphenyl | methyl | |
| 1.4.921 | 3-cyano-6-cyclopropylphenyl | methyl | |
| 1.4.922 | 3-trifluoromethyl-6-cyclopropylphenyl | methyl | |
| 1.4.923 | 3-methoxy-6-cyclopropylphenyl | methyl | |
| 1.4.924 | 3-ethoxy-6-cyclopropylphenyl | methyl | |
| 1.4.925 | 3-trifluoromethoxy-6-cyclopropylphenyl | methyl | |
| 1.4.926 | 3-fluoro-6-methoxycarbonylphenyl | methyl | |
| 1.4.927 | 3-chloro-6-methoxycarbonylphenyl | methyl | |
| 1.4.928 | 3-bromo-6-methoxycarbonylphenyl | methyl | |
| 1.4.929 | 3-methyl-6-methoxycarbonylphenyl | methyl | |
| 1.4.930 | 3-cyclopropyl-6-methoxycarbonylphenyl | methyl | |
| 1.4.931 | 3-cyano-6-methoxycarbonylphenyl | methyl | |
| 1.4.932 | 3-trifluoromethyl-6-methoxycarbonyl-phenyl | methyl | |
| 1.4.933 | 3-methoxy-6-methoxycarbonylphenyl | methyl | |
| 1.4.934 | 3-ethoxy-6-methoxycarbonylphenyl | methyl | |
| 1.4.935 | 3-trifluoromethoxy-6-methoxycarbonyl-phenyl | methyl | |
| 1.4.936 | 3-nitro-6-methoxycarbonylphenyl | methyl | |
| 1.4.937 | 3-fluoro-6-cyanophenyl | methyl | |
| 1.4.938 | 3-chloro-6-cyanophenyl | methyl | |
| 1.4.939 | 3-bromo-6-cyanophenyl | methyl | |
| 1.4.940 | 3-methyl-6-cyanophenyl | methyl | |
| 1.4.941 | 3-cyclopropyl-6-cyanophenyl | methyl | |
| 1.4.942 | 3-cyano-6-cyanophenyl | methyl | |
| 1.4.943 | 3-trifluoromethyl-6-cyanophenyl | methyl | |
| 1.4.944 | 3-methoxy-6-cyanophenyl | methyl | |
| 1.4.945 | 3-ethoxy-6-cyanophenyl | methyl | |
| 1.4.946 | 3-trifluoromethoxy-6-cyanophenyl | methyl | |
| 1.4.947 | 3-nitro-6-cyanophenyl | methyl | |
| 1.4.948 | 3-fluoro-6-methoxyphenyl | methyl | |
| 1.4.949 | 3-chloro-6-methoxyphenyl | methyl | |
| 1.4.950 | 3-bromo-6-methoxyphenyl | methyl | |
| 1.4.951 | 3-methyl-6-methoxyphenyl | methyl | |
| 1.4.952 | 3-cyclopropyl-6-methoxyphenyl | methyl | |
| 1.4.953 | 3-cyano-6-methoxyphenyl | methyl | |
| 1.4.954 | 3-trifluoromethyl-6-methoxyphenyl | methyl | |
| 1.4.955 | 3,6-dimethoxyphenyl | methyl | |
| 1.4.956 | 3-ethoxy-6-methoxyphenyl | methyl | |
| 1.4.957 | 3-trifluoromethoxy-6-methoxyphenyl | methyl | |
| 1.4.958 | 3-nitro-6-methoxyphenyl | methyl | |
| 1.4.959 | 3-fluoro-6-ethoxyphenyl | methyl | |
| 1.4.960 | 3-chloro-6-ethoxyphenyl | methyl | |
| 1.4.961 | 3-bromo-6-ethoxyphenyl | methyl | |
| 1.4.962 | 3-methyl-6-ethoxyphenyl | methyl | |
| 1.4.963 | 3-cyclopropyl-6-ethoxyphenyl | methyl | |
| 1.4.964 | 3-cyano-6-ethoxyphenyl | methyl | |
| 1.4.965 | 3-trifluoromethyl-6-ethoxyphenyl | methyl | |
| 1.4.966 | 3-methoxy-6-ethoxyphenyl | methyl | |
| 1.4.967 | 2,6-diethoxyphenyl | methyl | |
| 1.4.968 | 3-trifluoromethoxy-6-ethoxyphenyl | methyl | |
| 1.4.969 | 3-nitro-6-ethoxyphenyl | methyl | |
| 1.4.970 | 3-fluoro-6-isopropoxyphenyl | methyl | |
| 1.4.971 | 3-chloro-6-isopropoxyphenyl | methyl | |
| 1.4.972 | 3-bromo-6-isopropoxyphenyl | methyl | |
| 1.4.973 | 3-methyl-6-isopropoxyphenyl | methyl | |
| 1.4.974 | 3-cyclopropyl-6-isopropoxyphenyl | methyl | |
| 1.4.975 | 3-cyano-6-isopropoxyphenyl | methyl | |
| 1.4.976 | 3-trifluoromethyl-6-isopropoxyphenyl | methyl | |
| 1.4.977 | 3-methoxy-6-isopropoxyphenyl | methyl | |
| 1.4.978 | 3-ethoxy-6-isopropoxyphenyl | methyl | |
| 1.4.979 | 3-trifluoromethoxy-6-isopropoxyphenyl | methyl | |
| 1.4.980 | 3-nitro-6-isopropoxyphenyl | methyl | |
| 1.4.981 | 3-fluoro-6-trifluoromethoxyphenyl | methyl | |
| 1.4.982 | 3-chloro-6-trifluoromethoxyphenyl | methyl | |
| 1.4.983 | 3-bromo-6-trifluoromethoxyphenyl | methyl | |
| 1.4.984 | 3-methyl-6-trifluoromethoxyphenyl | methyl | |
| 1.4.985 | 3-cyclopropyl-6-trifluoromethoxyphenyl | methyl | |
| 1.4.986 | 3-cyano-6-trifluoromethoxyphenyl | methyl | |
| 1.4.987 | 3-trifluoromethyl-6-trifluoromethoxy-phenyl | methyl | |
| 1.4.988 | 3-methoxy-6-trifluoromethoxyphenyl | methyl | |
| 1.4.989 | 3-ethoxy-6-trifluoromethoxyphenyl | methyl | |
| 1.4.990 | 3,6-bis(trifluoromethoxy)phenyl | methyl | |
| 1.4.991 | 3-nitro-6-trifluoromethoxyphenyl | methyl | |
| 1.4.992 | 3-fluoro-6-difluoromethoxyphenyl | methyl | |
| 1.4.993 | 3-chloro-6-difluoromethoxyphenyl | methyl | |
| 1.4.994 | 3-bromo-6-difluoromethoxyphenyl | methyl | |
| 1.4.995 | 3-methyl-6-difluoromethoxyphenyl | methyl | |
| 1.4.996 | 3-cyclopropyl-6-difluoromethoxyphenyl | methyl | |
| 1.4.997 | 3-cyano-6-difluoromethoxyphenyl | methyl | |
| 1.4.998 | 3-trifluoromethyl-6-difluoromethoxy-phenyl | methyl | |
| 1.4.999 | 3-methoxy-6-difluoromethoxyphenyl | methyl | |
| 1.4.1000 | 3-ethoxy-6-difluoromethoxyphenyl | methyl | |
| 1.4.1001 | 3-trifluoromethoxy-6-difluoromethoxy-phenyl | methyl | |
| 1.4.1002 | 3-nitro-6-difluoromethoxyphenyl | methyl | |
| 1.4.1003 | 3-fluoro-6-nitrophenyl | methyl | |
| 1.4.1004 | 3-chloro-6-nitrophenyl | methyl | |
| 1.4.1005 | 3-bromo-6-nitrophenyl | methyl | |
| 1.4.1006 | 3-methyl-6-nitrophenyl | methyl | |

TABLE 1.4-continued

Inventive compounds of the general formula (I) in which W* is COOH, R¹ and R² are each hydrogen, and aryl is the radical.

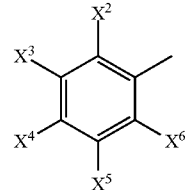

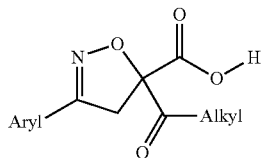

| No. | Aryl | Alkyl | Physical data |
|---|---|---|---|
| 1.4.1007 | 3-cyclopropyl-6-nitrophenyl | methyl | |
| 1.4.1008 | 3-trifluoromethyl-6-nitrophenyl | methyl | |
| 1.4.1009 | 3-methoxy-6-nitrophenyl | methyl | |
| 1.4.1010 | 3-ethoxy-6-nitrophenyl | methyl | |
| 1.4.1011 | 3-trifluoromethoxy-6-nitrophenyl | methyl | |
| 1.4.1012 | 3-fluoro-6-methylsulfanylphenyl | methyl | |
| 1.4.1013 | 3-chloro-6-methylsulfanylphenyl | methyl | |
| 1.4.1014 | 3-bromo-6-methylsulfanylphenyl | methyl | |
| 1.4.1015 | 3-methyl-6-methylsulfanylphenyl | methyl | |
| 1.4.1016 | 3-cyclopropyl-6-methylsulfanylphenyl | methyl | |
| 1.4.1017 | 3-cyano-6-methylsulfanylphenyl | methyl | |
| 1.4.1018 | 3-trifluoromethyl-6-methylsulfanylphenyl | methyl | |
| 1.4.1019 | 2,3,4-trifluorophenyl | methyl | |
| 1.4.1020 | 2,3,4-trichlorophenyl | methyl | |
| 1.4.1021 | 2,3,4-trimethylphenyl | methyl | |
| 1.4.1022 | 2-fluoro-2-chloro-5-trifluoromethylphenyl | methyl | |
| 1.4.1023 | 2,3,5-trifluorophenyl | methyl | |
| 1.4.1024 | 2,3,5-trichlorophenyl | methyl | |

TABLE 1.4-continued

Inventive compounds of the general formula (I) in which W* is COOH, R¹ and R² are each hydrogen, and aryl is the radical.

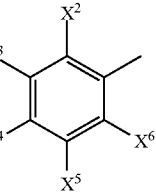

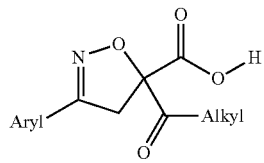

| No. | Aryl | Alkyl | Physical data |
|---|---|---|---|
| 1.4.1025 | 2,3,5-trimethylphenyl | methyl | |
| 1.4.1026 | 2,3-dichloro-5-methoxyphenyl | methyl | |
| 1.4.1027 | 2,3,6-trifluorophenyl | methyl | |
| 1.4.1028 | 2,3,6-trichlorophenyl | methyl | |
| 1.4.1029 | 2,3,6-trimethylphenyl | methyl | |
| 1.4.1030 | 3,4,5-trifluorophenyl | methyl | |
| 1.4.1031 | 3,4,5-trichlorophenyl | methyl | |
| 1.4.1032 | 3,4,5-trimethylphenyl | methyl | |
| 1.4.1033 | 3,5-dimethyl-4-fluorophenyl | methyl | |
| 1.4.1034 | 3,5-dichloro-4-methoxyphenyl | methyl | |
| 1.4.1035 | 3,5-difluoro-4-chlorophenyl | methyl | |
| 1.4.1036 | 3,5-dichloro-4-hydroxyphenyl | methyl | |
| 1.4.1037 | 3,5-trifluoromethyl-4-chlorophenyl | methyl | |
| 1.4.1038 | 3,4,6-trifluorophenyl | methyl | |
| 1.4.1039 | 3,4,6-trichlorophenyl | methyl | |
| 1.4.1040 | 3,4,6-trimethylphenyl | methyl | |
| 1.4.1041 | pentafluorophenyl | methyl | |

TABLE 1.5

Inventive compounds of the general formula (I) in which W* is COOH, R¹ and R² are each hydrogen, and aryl is the radical.

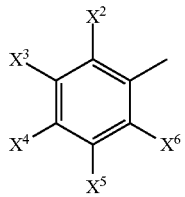

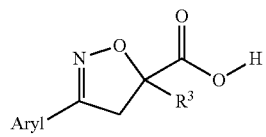

| No. | Aryl | R³ | Physical data |
|---|---|---|---|
| 1.5.1 | 3-fluorophenyl | hydroxymethyl | |
| 1.5.2 | 3-fluorophenyl | 1-hydroxyethyl | |
| 1.5.3 | 3-fluorophenyl | 1-hydroxypropyl | |
| 1.5.4 | 3-fluorophenyl | (1-hydroxy-2-methylpropyl) | |
| 1.5.5 | 3-fluorophenyl | methoxymethyl | |
| 1.5.6 | 3-fluorophenyl | 2-methoxyethyl | |
| 1.5.7 | 3-chlorophenyl | hydroxymethyl | |
| 1.5.8 | 3-chlorophenyl | 1-hydroxyethyl | |
| 1.5.9 | 3-chlorophenyl | 1-hydroxypropyl | |

TABLE 1.5-continued

Inventive compounds of the general formula (I) in which W* is COOH, $R^1$ and $R^2$ are each hydrogen, and aryl is the radical.

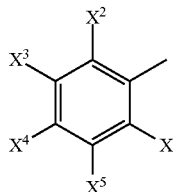

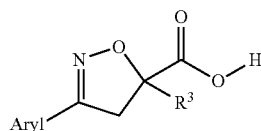

| No. | Aryl | $R^3$ | Physical data |
|---|---|---|---|
| 1.5.10 | 3-chlorophenyl | (1-hydroxy-2-methylpropyl) | |
| 1.5.11 | 3-chlorophenyl | methoxymethyl | |
| 1.5.12 | 3-chlorophenyl | 2-methoxyethyl | |
| 1.5.13 | 3-bromophenyl | hydroxymethyl | |
| 1.5.14 | 3-bromophenyl | 1-hydroxyethyl | |
| 1.5.15 | 3-iodophenyl | hydroxymethyl | |
| 1.5.16 | 3-iodophenyl | 1-hydroxyethyl | |
| 1.5.17 | 3-methylphenyl | hydroxymethyl | |
| 1.5.18 | 3-methylphenyl | 1-hydroxyethyl | |
| 1.5.19 | 3-ethylphenyl | hydroxymethyl | |
| 1.5.20 | 3-propylphenyl | hydroxymethyl | |
| 1.5.21 | 3-isopropylphenyl | hydroxymethyl | |
| 1.5.22 | 3-n-butylphenyl | hydroxymethyl | |
| 1.5.23 | 3-i-butylphenyl | hydroxymethyl | |
| 1.5.24 | 3-tert-butylphenyl | hydroxymethyl | |
| 1.5.25 | 3-cyclopropylphenyl | hydroxymethyl | |
| 1.5.26 | 3-cyclobutylphenyl | hydroxymethyl | |
| 1.5.27 | 3-cyclopentylphenyl | hydroxymethyl | |
| 1.5.28 | 3-vinylphenyl | hydroxymethyl | |
| 1.5.29 | 3-ethynylphenyl | hydroxymethyl | |
| 1.5.30 | 3-cyanophenyl | hydroxymethyl | |
| 1.5.31 | 3-trifluoromethylphenyl | hydroxymethyl | |
| 1.5.32 | 3-difluoromethylphenyl | hydroxymethyl | |
| 1.5.33 | 3-(hydroxycarbonyl)phenyl | hydroxymethyl | |
| 1.5.34 | 3-(methoxycarbonyl)phenyl | hydroxymethyl | |
| 1.5.35 | 3-(ethoxycarbonyl)phenyl | hydroxymethyl | |
| 1.5.36 | 3-hydroxymethylphenyl | hydroxymethyl | |
| 1.5.37 | 3-carbamoylphenyl | hydroxymethyl | |
| 1.5.38 | 3-hydroxyphenyl | hydroxymethyl | |
| 1.5.39 | 3-methoxyphenyl | hydroxymethyl | |
| 1.5.40 | 3-ethoxyphenyl | hydroxymethyl | |
| 1.5.41 | 3-propyloxyphenyl | hydroxymethyl | |
| 1.5.42 | 3-isopropyloxyphenyl | hydroxymethyl | |
| 1.5.43 | 3-n-butyloxyphenyl | hydroxymethyl | |
| 1.5.44 | 3-i-butyloxyphenyl | hydroxymethyl | |
| 1.5.45 | 3-t-butyloxyphenyl | hydroxymethyl | |
| 1.5.46 | 3-difluoromethoxyphenyl | hydroxymethyl | |
| 1.5.47 | 3-trifluoromethoxyphenyl | hydroxymethyl | |
| 1.5.48 | 3-(2,2,2-trifluoroethoxy)phenyl | hydroxymethyl | |
| 1.5.49 | 3-(2-chloroethoxy)phenyl | hydroxymethyl | |
| 1.5.50 | 3-(2-hydroxyethoxy)phenyl | hydroxymethyl | |
| 1.5.51 | 3-(2-methoxyethoxy)phenyl | hydroxymethyl | |
| 1.5.52 | 3-[(tert-butoxycarbonyl)oxy]phenyl | hydroxymethyl | |
| 1.5.53 | 3-nitrophenyl | hydroxymethyl | |
| 1.5.54 | 3-acetoxyphenyl | hydroxymethyl | |
| 1.5.55 | (3-[(tert-butoxycarbonyl)amino]phenyl) | hydroxymethyl | |
| 1.5.56 | 3-methylsulfanylphenyl | hydroxymethyl | |
| 1.5.57 | 3-ethylsulfanylphenyl | hydroxymethyl | |
| 1.5.58 | 3-(pentafluoro-lambda$^6$-sulfanyl)phenyl | hydroxymethyl | |
| 1.5.59 | 2,3-difluorophenyl | hydroxymethyl | |
| 1.5.60 | 2,3-difluorophenyl | 1-hydroxyethyl | |
| 1.5.61 | 2,3-difluorophenyl | 1-hydroxypropyl | |
| 1.5.62 | 2,3-difluorophenyl | (1-hydroxy-2-methylpropyl) | |
| 1.5.63 | 2,3-difluorophenyl | methoxymethyl | |
| 1.5.64 | 2,3-difluorophenyl | 2-methoxyethyl | |

TABLE 1.5-continued

Inventive compounds of the general formula (I) in which W* is COOH, $R^1$ and $R^2$ are each hydrogen, and aryl is the radical.

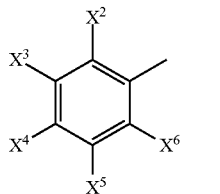

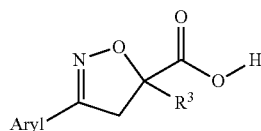

| No. | Aryl | $R^3$ | Physical data |
|---|---|---|---|
| 1.5.65 | 2-chloro-3-fluorophenyl | hydroxymethyl | |
| 1.5.66 | 2-bromo-3-fluorophenyl | hydroxymethyl | |
| 1.5.67 | 2-methyl-3-fluorophenyl | hydroxymethyl | |
| 1.5.68 | 2-ethyl-3-fluorophenyl | hydroxymethyl | |
| 1.5.69 | 2-cyclopropyl-3-fluorophenyl | hydroxymethyl | |
| 1.5.70 | 2-vinyl-3-fluorophenyl | hydroxymethyl | |
| 1.5.71 | 2-ethynyl-3-fluorophenyl | hydroxymethyl | |
| 1.5.72 | 2-cyano-3-fluorophenyl | hydroxymethyl | |
| 1.5.73 | 2-methoxy-3-fluorophenyl | hydroxymethyl | |
| 1.5.74 | 2-ethoxy-3-fluorophenyl | hydroxymethyl | |
| 1.5.75 | 2-trifluoromethoxy-3-fluorophenyl | hydroxymethyl | |
| 1.5.76 | 2-nitro-3-fluorophenyl | hydroxymethyl | |
| 1.5.77 | 2-fluoro-3-chlorophenyl | hydroxymethyl | |
| 1.5.78 | 2,3-dichlorophenyl | hydroxymethyl | |
| 1.5.79 | 2,3-dichlorophenyl | 1-hydroxyethyl | |
| 1.5.80 | 2,3-dichlorophenyl | 1-hydroxypropyl | |
| 1.5.81 | 2,3-dichlorophenyl | (1-hydroxy-2-methylpropyl) | |
| 1.5.82 | 2,3-dichlorophenyl | methoxymethyl | |
| 1.5.83 | 2,3-dichlorophenyl | 2-methoxyethyl | |
| 1.5.84 | 2-bromo-3-chlorophenyl | hydroxymethyl | |
| 1.5.85 | 2-methyl-3-chlorophenyl | hydroxymethyl | |
| 1.5.86 | 2-ethyl-3-chlorophenyl | hydroxymethyl | |
| 1.5.87 | 2-cyclopropyl-3-chlorophenyl | hydroxymethyl | |
| 1.5.88 | 2-vinyl-3-chlorophenyl | hydroxymethyl | |
| 1.5.89 | 2-ethynyl-3-chlorophenyl | hydroxymethyl | |
| 1.5.90 | 2-cyano-3-chlorophenyl | hydroxymethyl | |
| 1.5.91 | 2-trifluoromethyl-2-chlorophenyl | hydroxymethyl | |
| 1.5.92 | 2-methoxy-3-chlorophenyl | hydroxymethyl | |
| 1.5.93 | 2-ethoxy-3-chlorophenyl | hydroxymethyl | |
| 1.5.94 | 2-trifluoromethoxy-3-chlorophenyl | hydroxymethyl | |
| 1.5.95 | 2-nitro-3-chlorophenyl | hydroxymethyl | |
| 1.5.96 | 2-fluoro-3-bromophenyl | hydroxymethyl | |
| 1.5.97 | 2-chloro-3-bromophenyl | hydroxymethyl | |
| 1.5.98 | 2,3-dibromophenyl | hydroxymethyl | |
| 1.5.99 | 2-methyl-3-bromophenyl | hydroxymethyl | |
| 1.5.100 | 2-ethyl-3-bromophenyl | hydroxymethyl | |
| 1.5.101 | 2-cyclopropyl-3-bromophenyl | hydroxymethyl | |
| 1.5.102 | 2-vinyl-3-bromophenyl | hydroxymethyl | |
| 1.5.103 | 2-ethynyl-3-bromophenyl | hydroxymethyl | |
| 1.5.104 | 2-cyano-3-bromophenyl | hydroxymethyl | |
| 1.5.105 | 2-trifluoromethyl-3-bromophenyl | hydroxymethyl | |
| 1.5.106 | 2-methoxy-3-phenyl | hydroxymethyl | |
| 1.5.107 | 2-ethoxy-3-bromophenyl | hydroxymethyl | |
| 1.5.108 | 2-trifluoromethoxy-3-bromophenyl | hydroxymethyl | |
| 1.5.109 | 2-nitro-3-bromophenyl | hydroxymethyl | |
| 1.5.110 | 2-fluoro-3-iodophenyl | hydroxymethyl | |
| 1.5.111 | 2-chloro-3-iodophenyl | hydroxymethyl | |
| 1.5.112 | 2-bromo-3-iodophenyl | hydroxymethyl | |
| 1.5.113 | 2-methyl-3-iodophenyl | hydroxymethyl | |
| 1.5.114 | 2-ethyl-3-iodophenyl | hydroxymethyl | |
| 1.5.115 | 2-cyclopropyl-3-iodophenyl | hydroxymethyl | |
| 1.5.116 | 2-vinyl-3-iodophenyl | hydroxymethyl | |
| 1.5.117 | 2-ethynyl-3-iodophenyl | hydroxymethyl | |
| 1.5.118 | 2-cyano-3-iodophenyl | hydroxymethyl | |
| 1.5.119 | 2-trifluoromethyl-3-iodophenyl | hydroxymethyl | |
| 1.5.120 | 2-methoxy-3-iodophenyl | hydroxymethyl | |

TABLE 1.5-continued

Inventive compounds of the general formula (I) in which W* is COOH, $R^1$ and $R^2$ are each hydrogen, and aryl is the radical.

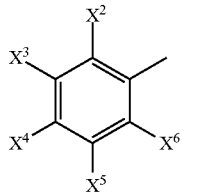

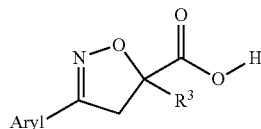

| No. | Aryl | $R^3$ | Physical data |
|---|---|---|---|
| 1.5.121 | 2-ethoxy-3-iodophenyl | hydroxymethyl | |
| 1.5.122 | 2-trifluoromethoxy-3-iodophenyl | hydroxymethyl | |
| 1.5.123 | 2-nitro-3-iodophenyl | hydroxymethyl | |
| 1.5.124 | 2-fluoro-3-methylphenyl | hydroxymethyl | |
| 1.5.125 | 2-fluoro-3-methylphenyl | 1-hydroxyethyl | |
| 1.5.126 | 2-fluoro-3-methylphenyl | 1-hydroxypropyl | |
| 1.5.127 | 2-fluoro-3-methylphenyl | (1-hydroxy-2-methylpropyl) | |
| 1.5.128 | 2-fluoro-3-methylphenyl | methoxymethyl | |
| 1.5.129 | 2-fluoro-3-methylphenyl | 2-methoxyethyl | |
| 1.5.130 | 2-chloro-3-methylphenyl | hydroxymethyl | |
| 1.5.131 | 2-chloro-3-methylphenyl | 1-hydroxyethyl | |
| 1.5.132 | 2-chloro-3-methylphenyl | 1-hydroxypropyl | |
| 1.5.133 | 2-chloro-3-methylphenyl | (1-hydroxy-2-methylpropyl) | |
| 1.5.134 | 2-chloro-3-methylphenyl | methoxymethyl | |
| 1.5.135 | 2-chloro-3-methylphenyl | 2-methoxyethyl | |
| 1.5.136 | 2-bromo-3-methylphenyl | hydroxymethyl | |
| 1.5.137 | 2,3-dimethylphenyl | hydroxymethyl | |
| 1.5.138 | 2,3-dimethylphenyl | 1-hydroxyethyl | |
| 1.5.139 | 2,3-dimethylphenyl | 1-hydroxypropyl | |
| 1.5.140 | 2,3-dimethylphenyl | (1-hydroxy-2-methylpropyl) | |
| 1.5.141 | 2,3-dimethylphenyl | methoxymethyl | |
| 1.5.142 | 2,3-dimethylphenyl | 2-methoxyethyl | |
| 1.5.143 | 2-ethyl-3-methylphenyl | hydroxymethyl | |
| 1.5.144 | 2-cyclopropyl-3-methylphenyl | hydroxymethyl | |
| 1.5.145 | 2-vinyl-3-methylphenyl | hydroxymethyl | |
| 1.5.146 | 2-ethynyl-3-methylphenyl | hydroxymethyl | |
| 1.5.147 | 2-cyano-3-methylphenyl | hydroxymethyl | |
| 1.5.148 | 2-trifluoromethyl-3-methylphenyl | hydroxymethyl | |
| 1.5.149 | 2-methoxy-3-methylphenyl | hydroxymethyl | |
| 1.5.150 | 2-ethoxy-3-methylphenyl | hydroxymethyl | |
| 1.5.151 | 2-trifluoromethoxy-3-methylphenyl | hydroxymethyl | |
| 1.5.152 | 2-nitro-3-methylphenyl | hydroxymethyl | |
| 1.5.153 | 2-fluoro-3-ethylphenyl | hydroxymethyl | |
| 1.5.154 | 2-chloro-3-ethylphenyl | hydroxymethyl | |
| 1.5.155 | 2-bromo-3-ethylphenyl | hydroxymethyl | |
| 1.5.156 | 2-methyl-3-ethylphenyl | hydroxymethyl | |
| 1.5.157 | 2,3-diethylphenyl | hydroxymethyl | |
| 1.5.158 | 2-cyclopropyl-3-ethylphenyl | hydroxymethyl | |
| 1.5.159 | 2-vinyl-3-ethylphenyl | hydroxymethyl | |
| 1.5.160 | 2-ethynyl-3-ethylphenyl | hydroxymethyl | |
| 1.5.161 | 2-cyano-3-ethylphenyl | hydroxymethyl | |
| 1.5.162 | 2-trifluoromethyl-3-ethylphenyl | hydroxymethyl | |
| 1.5.163 | 2-methoxy-3-ethylphenyl | hydroxymethyl | |
| 1.5.164 | 2-ethoxy-3-ethylphenyl | hydroxymethyl | |
| 1.5.165 | 2-trifluoromethoxy-3-ethylphenyl | hydroxymethyl | |
| 1.5.166 | 2-nitro-3-ethylphenyl | hydroxymethyl | |
| 1.5.167 | 2-fluoro-3-propylphenyl | hydroxymethyl | |
| 1.5.168 | 2-chloro-3-propylphenyl | hydroxymethyl | |
| 1.5.169 | 2-bromo-3-propylphenyl | hydroxymethyl | |
| 1.5.170 | 2-methyl-3-propylphenyl | hydroxymethyl | |
| 1.5.171 | 2-methyl-3-propylphenyl | hydroxymethyl | |
| 1.5.172 | 2-cyclopropyl-3-propylphenyl | hydroxymethyl | |
| 1.5.173 | 2-vinyl-3-propylphenyl | hydroxymethyl | |
| 1.5.174 | 2-ethynyl-3propylphenyl | hydroxymethyl | |

TABLE 1.5-continued

Inventive compounds of the general formula (I) in which W* is COOH, $R^1$ and $R^2$ are each hydrogen, and aryl is the radical.

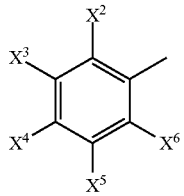

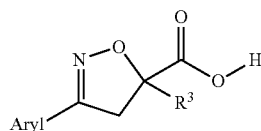

| No. | Aryl | $R^3$ | Physical data |
|---|---|---|---|
| 1.5.175 | 2-cyano-3-propylphenyl | hydroxymethyl | |
| 1.5.176 | 2-trifluoromethyl-3-propylphenyl | hydroxymethyl | |
| 1.5.177 | 2-methoxy-3-propylphenyl | hydroxymethyl | |
| 1.5.178 | 2-ethoxy-3-propylphenyl | hydroxymethyl | |
| 1.5.179 | 2-trifluoromethoxy-3-propylphenyl | hydroxymethyl | |
| 1.5.180 | 2-nitro-3-propylphenyl | hydroxymethyl | |
| 1.5.181 | 2-fluoro-3-isopropylphenyl | hydroxymethyl | |
| 1.5.182 | 2-chloro-3-isopropylphenyl | hydroxymethyl | |
| 1.5.183 | 2-bromo-3-isopropylphenyl | hydroxymethyl | |
| 1.5.184 | 2-methyl-3-isopropylphenyl | hydroxymethyl | |
| 1.5.185 | 2-ethyl-3-isopropylphenyl | hydroxymethyl | |
| 1.5.186 | 2-cyclopropyl-3-isopropylphenyl | hydroxymethyl | |
| 1.5.187 | 2-vinyl-3-isopropylphenyl | hydroxymethyl | |
| 1.5.188 | 2-ethynyl-3-isopropylphenyl | hydroxymethyl | |
| 1.5.189 | 2-cyano-3-isopropylphenyl | hydroxymethyl | |
| 1.5.190 | 2-trifluoromethyl-3-isopropylphenyl | hydroxymethyl | |
| 1.5.191 | 2-methoxy-3-isopropylphenyl | hydroxymethyl | |
| 1.5.192 | 2-ethoxy-3-isopropylphenyl | hydroxymethyl | |
| 1.5.193 | 2-trifluoromethoxy-3-isopropylphenyl | hydroxymethyl | |
| 1.5.194 | 2-nitro-3-isopropylphenyl | hydroxymethyl | |
| 1.5.195 | 2-fluoro-3-tert-butylphenyl | hydroxymethyl | |
| 1.5.196 | 2-chloro-3-tert-butylphenyl | hydroxymethyl | |
| 1.5.197 | 2-bromo-3-tert-butylphenyl | hydroxymethyl | |
| 1.5.198 | 2-methyl-3-tert-butylphenyl | hydroxymethyl | |
| 1.5.199 | 2-ethyl-3-tert-butylphenyl | hydroxymethyl | |
| 1.5.200 | 2-cyclopropyl-3-tert-butylphenyl | hydroxymethyl | |
| 1.5.201 | 2-vinyl-3-tert-butylphenyl | hydroxymethyl | |
| 1.5.202 | 2-ethynyl-3-tert-butylphenyl | hydroxymethyl | |
| 1.5.203 | 2-cyano-3-tert-butylphenyl | hydroxymethyl | |
| 1.5.204 | 2-trifluoromethyl-3-tert-butylphenyl | hydroxymethyl | |
| 1.5.205 | 2-methoxy-3-tert-butylphenyl | hydroxymethyl | |
| 1.5.206 | 2-ethoxy-3-tert-butylphenyl | hydroxymethyl | |
| 1.5.207 | 2-trifluoromethoxy-3-tert-butylphenyl | hydroxymethyl | |
| 1.5.208 | 2-nitro-3-tert-butylphenyl | hydroxymethyl | |
| 1.5.209 | 2-fluoro-3-hydroxymethylphenyl | hydroxymethyl | |
| 1.5.210 | 2-chloro-3-hydroxymethylphenyl | hydroxymethyl | |
| 1.5.211 | 2-bromo-3-hydroxymethylphenyl | hydroxymethyl | |
| 1.5.212 | 2-methyl-3-hydroxymethylphenyl | hydroxymethyl | |
| 1.5.213 | 2-ethyl-3-hydroxymethylphenyl | hydroxymethyl | |
| 1.5.214 | 2-cyclopropyl-3-hydroxymethylphenyl | hydroxymethyl | |
| 1.5.215 | 2-vinyl-3-hydroxymethylphenyl | hydroxymethyl | |
| 1.5.216 | 2-ethynyl-3-hydroxymethylphenyl | hydroxymethyl | |
| 1.5.217 | 2-cyano-3-hydroxymethylphenyl | hydroxymethyl | |
| 1.5.218 | 2-trifluoromethyl-3-hydroxymethylphenyl | hydroxymethyl | |
| 1.5.219 | 2-methoxy-3-hydroxymethylphenyl | hydroxymethyl | |
| 1.5.220 | 2-ethoxy-3-hydroxymethylphenyl | hydroxymethyl | |
| 1.5.221 | 2-trifluoromethoxy-3-hydroxymethylphenyl | hydroxymethyl | |
| 1.5.222 | 2-nitro-3-hydroxymethylphenyl | hydroxymethyl | |
| 1.5.223 | 2-fluoro-3-cyclopropylphenyl | hydroxymethyl | |
| 1.5.224 | 2-chloro-3-cyclopropylphenyl | hydroxymethyl | |
| 1.5.225 | 2-bromo-3-cyclopropylphenyl | hydroxymethyl | |
| 1.5.226 | 2-methyl-3-cyclopropylphenyl | hydroxymethyl | |
| 1.5.227 | 2-ethyl-3-cyclopropylphenyl | hydroxymethyl | |
| 1.5.228 | 2-cyclopropyl-3-cyclopropylphenyl | hydroxymethyl | |
| 1.5.229 | 2-vinyl-3-cyclopropylphenyl | hydroxymethyl | |
| 1.5.230 | 2-ethynyl-3-cyclopropylphenyl | hydroxymethyl | |

TABLE 1.5-continued

Inventive compounds of the general formula (I) in which W* is COOH, $R^1$ and $R^2$ are each hydrogen, and aryl is the radical.

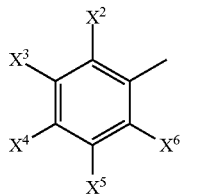

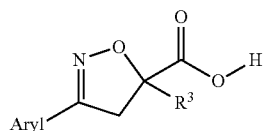

| No. | Aryl | $R^3$ | Physical data |
|---|---|---|---|
| 1.5.231 | 2-cyano-3-cyclopropylphenyl | hydroxymethyl | |
| 1.5.232 | 2-trifluoromethyl-3-cyclopropylphenyl | hydroxymethyl | |
| 1.5.233 | 2-methoxy-3-cyclopropylphenyl | hydroxymethyl | |
| 1.5.234 | 2-ethoxy-3-cyclopropylphenyl | hydroxymethyl | |
| 1.5.235 | 2-trifluoromethoxy-3-cyclopropylphenyl | hydroxymethyl | |
| 1.5.236 | 2-fluoro-3-methoxycarbonylphenyl | hydroxymethyl | |
| 1.5.237 | 2-chloro-3-methoxycarbonylphenyl | hydroxymethyl | |
| 1.5.238 | 2-bromo-3-methoxycarbonylphenyl | hydroxymethyl | |
| 1.5.239 | 2-methyl-3-methoxycarbonylphenyl | hydroxymethyl | |
| 1.5.240 | 2-ethyl-3-methoxycarbonylphenyl | hydroxymethyl | |
| 1.5.241 | 2-cyclopropyl-3-methoxycarbonylphenyl | hydroxymethyl | |
| 1.5.242 | 2-vinyl-3-methoxycarbonylphenyl | hydroxymethyl | |
| 1.5.243 | 2-ethynyl-3-methoxycarbonylphenyl | hydroxymethyl | |
| 1.5.244 | 2-cyano-3-methoxycarbonylphenyl | hydroxymethyl | |
| 1.5.245 | 2-trifluoromethyl-3-methoxycarbonylphenyl | hydroxymethyl | |
| 1.5.246 | 2-methoxy-3-methoxycarbonylphenyl | hydroxymethyl | |
| 1.5.247 | 2-ethoxy-3-methoxycarbonylphenyl | hydroxymethyl | |
| 1.5.248 | 2-trifluoromethoxy-3-methoxycarbonylphenyl | hydroxymethyl | |
| 1.5.249 | 2-nitro-3-methoxycarbonylphenyl | hydroxymethyl | |
| 1.5.250 | 2-fluoro-3-vinylphenyl | hydroxymethyl | |
| 1.5.251 | 2-chloro-3-vinylphenyl | hydroxymethyl | |
| 1.5.252 | 2-bromo-3-vinylphenyl | hydroxymethyl | |
| 1.5.253 | 2-methyl-3-vinylphenyl | hydroxymethyl | |
| 1.5.254 | 2-ethyl-3-vinylphenyl | hydroxymethyl | |
| 1.5.255 | 2-cyclopropyl-3-vinylphenyl | hydroxymethyl | |
| 1.5.256 | 2-vinyl-3-vinylphenyl | hydroxymethyl | |
| 1.5.257 | 2-ethynyl-3-vinylphenyl | hydroxymethyl | |
| 1.5.258 | 2-cyano-3-vinylphenyl | hydroxymethyl | |
| 1.5.259 | 2-trifluoromethyl-3-vinylphenyl | hydroxymethyl | |
| 1.5.260 | 2-methoxy-3-vinylphenyl | hydroxymethyl | |
| 1.5.261 | 2-ethoxy-3-vinylphenyl | hydroxymethyl | |
| 1.5.262 | 2-trifluoromethoxy-3-vinylphenyl | hydroxymethyl | |
| 1.5.263 | 2-nitro-3-vinylphenyl | hydroxymethyl | |
| 1.5.264 | 2-fluoro-3-ethynylphenyl | hydroxymethyl | |
| 1.5.265 | 2-chloro-3-ethynylphenyl | hydroxymethyl | |
| 1.5.266 | 2-bromo-3-ethynylphenyl | hydroxymethyl | |
| 1.5.267 | 2-methyl-3-ethynylphenyl | hydroxymethyl | |
| 1.5.268 | 2-ethyl-3-ethynylphenyl | hydroxymethyl | |
| 1.5.269 | 2-cyclopropyl-3-ethynylphenyl | hydroxymethyl | |
| 1.5.270 | 2-vinyl-3-ethynylphenyl | hydroxymethyl | |
| 1.5.271 | 2-cyano-3-ethynylphenyl | hydroxymethyl | |
| 1.5.272 | 2-trifluoromethyl-3-ethynylphenyl | hydroxymethyl | |
| 1.5.273 | 2-methoxy-3-ethynylphenyl | hydroxymethyl | |
| 1.5.274 | 2-ethoxy-3-ethynylphenyl | hydroxymethyl | |
| 1.5.275 | 2-trifluoromethoxy-3-ethynylphenyl | hydroxymethyl | |
| 1.5.276 | 2-nitro-3-ethynylphenyl | hydroxymethyl | |
| 1.5.277 | 2-fluoro-3-ethynylphenyl | hydroxymethyl | |
| 1.5.278 | 2-fluoro-3-cyanophenyl | hydroxymethyl | |
| 1.5.279 | 2-chloro-3-cyanophenyl | hydroxymethyl | |
| 1.5.280 | 2-bromo-3-cyanophenyl | hydroxymethyl | |
| 1.5.281 | 2-methyl-3-cyanophenyl | hydroxymethyl | |
| 1.5.282 | 2-ethyl-3-cyanophenyl | hydroxymethyl | |
| 1.5.283 | 2-ethyl-3-cyanophenyl | 1-hydroxyethyl | |
| 1.5.284 | 2-ethyl-3-cyanophenyl | 1-hydroxypropyl | |
| 1.5.285 | 2-ethyl-3-cyanophenyl | (1-hydroxy-2- | |

TABLE 1.5-continued

Inventive compounds of the general formula (I) in which W* is COOH, $R^1$ and $R^2$ are each hydrogen, and aryl is the radical.

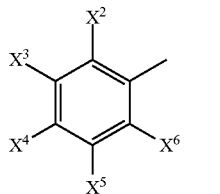

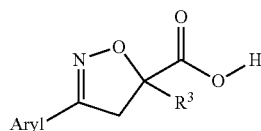

| No. | Aryl | $R^3$ | Physical data |
|---|---|---|---|
| | | methylpropyl) | |
| 1.5.286 | 2-ethyl-3-cyanophenyl | methoxymethyl | |
| 1.5.287 | 2-ethyl-3-cyanophenyl | 2-methoxyethyl | |
| 1.5.288 | 2-cyclopropyl-3-cyanophenyl | hydroxymethyl | |
| 1.5.289 | 2-vinyl-3-cyanophenyl | hydroxymethyl | |
| 1.5.290 | 2-ethynyl-3-cyanophenyl | hydroxymethyl | |
| 1.5.291 | 2-cyano-3-cyanophenyl | hydroxymethyl | |
| 1.5.292 | 2-trifluoromethyl-3-cyanophenyl | hydroxymethyl | |
| 1.5.293 | 2-methoxy-3-cyanophenyl | hydroxymethyl | |
| 1.5.294 | 2-ethoxy-3-cyanophenyl | hydroxymethyl | |
| 1.5.295 | 2-trifluoromethoxy-3-cyanophenyl | hydroxymethyl | |
| 1.5.296 | 2-nitro-3-cyanophenyl | hydroxymethyl | |
| 1.5.297 | 2-fluoro-3-hydroxyphenyl | hydroxymethyl | |
| 1.5.298 | 2-chloro-3-hydroxyphenyl | hydroxymethyl | |
| 1.5.299 | 2-bromo-3-hydroxyphenyl | hydroxymethyl | |
| 1.5.300 | 2-methyl-3-hydroxyphenyl | hydroxymethyl | |
| 1.5.301 | 2-ethyl-3-hydroxyphenyl | hydroxymethyl | |
| 1.5.302 | 2-cyclopropyl-3-hydroxyphenyl | hydroxymethyl | |
| 1.5.303 | 2-vinyl-3-hydroxyphenyl | hydroxymethyl | |
| 1.5.304 | 2-ethynyl-3-hydroxyphenyl | hydroxymethyl | |
| 1.5.305 | 2-cyano-3-hydroxyphenyl | hydroxymethyl | |
| 1.5.306 | 2-trifluoromethyl-3-hydroxyphenyl | hydroxymethyl | |
| 1.5.307 | 2-methoxy-3-hydroxyphenyl | hydroxymethyl | |
| 1.5.308 | 2-ethoxy-3-hydroxyphenyl | hydroxymethyl | |
| 1.5.309 | 2-trifluoromethoxy-3-hydroxyphenyl | hydroxymethyl | |
| 1.5.310 | 2-nitro-3-hydroxyphenyl | hydroxymethyl | |
| 1.5.311 | 2-fluoro-3-methoxyphenyl | hydroxymethyl | |
| 1.5.312 | 2-chloro-3-methoxyphenyl | hydroxymethyl | |
| 1.5.313 | 2-bromo-3-methoxyphenyl | hydroxymethyl | |
| 1.5.314 | 2-methyl-3-methoxyphenyl | hydroxymethyl | |
| 1.5.315 | 2-ethyl-3-methoxyphenyl | hydroxymethyl | |
| 1.5.316 | 2-cyclopropyl-3-methoxyphenyl | hydroxymethyl | |
| 1.5.317 | 2-vinyl-3-methoxyphenyl | hydroxymethyl | |
| 1.5.318 | 2-ethynyl-3-methoxyphenyl | hydroxymethyl | |
| 1.5.319 | 2-cyano-3-methoxyphenyl | hydroxymethyl | |
| 1.5.320 | 2-trifluoromethyl-3-methoxyphenyl | hydroxymethyl | |
| 1.5.321 | 2,3-dimethoxyphenyl | hydroxymethyl | |
| 1.5.322 | 2-ethoxy-3-methoxyphenyl | hydroxymethyl | |
| 1.5.323 | 2-trifluoromethoxy-3-methoxyphenyl | hydroxymethyl | |
| 1.5.324 | 2-nitro-3-methoxyphenyl | hydroxymethyl | |
| 1.5.325 | 2-fluoro-3-ethoxyphenyl | hydroxymethyl | |
| 1.5.326 | 2-chloro-3-ethoxyphenyl | hydroxymethyl | |
| 1.5.327 | 2-bromo-3-ethoxyphenyl | hydroxymethyl | |
| 1.5.328 | 2-methyl-3-ethoxyphenyl | hydroxymethyl | |
| 1.5.329 | 2-ethyl-3-ethoxyphenyl | hydroxymethyl | |
| 1.5.330 | 2-cyclopropyl-3-ethoxyphenyl | hydroxymethyl | |
| 1.5.331 | 2-vinyl-3-ethoxyphenyl | hydroxymethyl | |
| 1.5.332 | 2-ethynyl-3-ethoxyphenyl | hydroxymethyl | |
| 1.5.333 | 2-cyano-3-ethoxyphenyl | hydroxymethyl | |
| 1.5.334 | 2-trifluoromethyl-3-ethoxyphenyl | hydroxymethyl | |
| 1.5.335 | 2-methoxy-3-ethoxyphenyl | hydroxymethyl | |
| 1.5.336 | 2,3-diethoxy--phenyl | hydroxymethyl | |
| 1.5.337 | 2-trifluoromethoxy-3-ethoxyphenyl | hydroxymethyl | |
| 1.5.338 | 2-nitro-3-ethoxyphenyl | hydroxymethyl | |
| 1.5.339 | 2-fluoro-3-propoxyphenyl | hydroxymethyl | |
| 1.5.340 | 2-chloro-3-propoxyphenyl | hydroxymethyl | |
| 1.5.341 | 2-bromo-3-propoxyphenyl | hydroxymethyl | |

TABLE 1.5-continued

Inventive compounds of the general formula (I) in which W* is COOH, R¹ and R² are each hydrogen, and aryl is the radical.

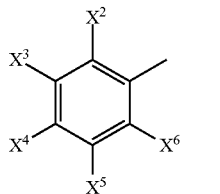

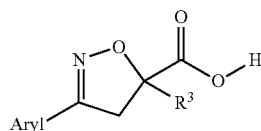

| No. | Aryl | R³ | Physical data |
|---|---|---|---|
| 1.5.342 | 2-methyl-3-propoxyphenyl | hydroxymethyl | |
| 1.5.343 | 2-ethyl-3-propoxyphenyl | hydroxymethyl | |
| 1.5.344 | 2-cyclopropyl-3-propoxyphenyl | hydroxymethyl | |
| 1.5.345 | 2-vinyl-3-propoxyphenyl | hydroxymethyl | |
| 1.5.346 | 2-ethynyl-3-propoxyphenyl | hydroxymethyl | |
| 1.5.347 | 2-cyano-3-propoxyphenyl | hydroxymethyl | |
| 1.5.348 | 2-trifluoromethyl-3-propoxyphenyl | hydroxymethyl | |
| 1.5.349 | 2-methoxy-3-propoxyphenyl | hydroxymethyl | |
| 1.5.350 | 2-ethoxy-3-propoxyphenyl | hydroxymethyl | |
| 1.5.351 | 2-trifluoromethoxy-3-propoxyphenyl | hydroxymethyl | |
| 1.5.352 | 2-nitro-3-propoxyphenyl | hydroxymethyl | |
| 1.5.353 | 2-fluoro-3-isopropoxyphenyl | hydroxymethyl | |
| 1.5.354 | 2-chloro-3-isopropoxyphenyl | hydroxymethyl | |
| 1.5.355 | 2-bromo-3-isopropoxyphenyl | hydroxymethyl | |
| 1.5.356 | 2-methyl-3-isopropoxyphenyl | hydroxymethyl | |
| 1.5.357 | 2-ethyl-3-isopropoxyphenyl | hydroxymethyl | |
| 1.5.358 | 2-cyclopropyl-3-isopropoxyphenyl | hydroxymethyl | |
| 1.5.359 | 2-vinyl-3-isopropoxyphenyl | hydroxymethyl | |
| 1.5.360 | 2-ethynyl-3-isopropoxyphenyl | hydroxymethyl | |
| 1.5.361 | 2-cyano-3-isopropoxyphenyl | hydroxymethyl | |
| 1.5.362 | 2-trifluoromethyl-3-isopropoxyphenyl | hydroxymethyl | |
| 1.5.363 | 2-methoxy-3-isopropoxyphenyl | hydroxymethyl | |
| 1.5.364 | 2-ethoxy-3-isopropoxyphenyl | hydroxymethyl | |
| 1.5.365 | 2-trifluoromethoxy-3-isopropoxyphenyl | hydroxymethyl | |
| 1.5.366 | 2-nitro-3-isopropoxyphenyl | hydroxymethyl | |
| 1.5.367 | 2-fluoro-3-tert-butoxyphenyl | hydroxymethyl | |
| 1.5.368 | 2-chloro-3-tert-butoxyphenyl | hydroxymethyl | |
| 1.5.369 | 2-bromo-3-tert-butoxyphenyl | hydroxymethyl | |
| 1.5.370 | 2-methyl-3-tert-butoxyphenyl | hydroxymethyl | |
| 1.5.371 | 2-ethyl-3-tert-butoxyphenyl | hydroxymethyl | |
| 1.5.372 | 2-cyclopropyl-3-tert-butoxyphenyl | hydroxymethyl | |
| 1.5.373 | 2-vinyl-3-tert-butoxyphenyl | hydroxymethyl | |
| 1.5.374 | 2-ethynyl-3-tert-butoxyphenyl | hydroxymethyl | |
| 1.5.375 | 2-cyano-3-tert-butoxyphenyl | hydroxymethyl | |
| 1.5.376 | 2-trifluoromethyl-3-tert-butoxyphenyl | hydroxymethyl | |
| 1.5.377 | 2-methoxy-3-tert-butoxyphenyl | hydroxymethyl | |
| 1.5.378 | 2-ethoxy-3-tert-butoxyphenyl | hydroxymethyl | |
| 1.5.379 | 2-trifluoromethoxy-3-tert-butoxyphenyl | hydroxymethyl | |
| 1.5.380 | 2-nitro-3-tert-butoxyphenyl | hydroxymethyl | |
| 1.5.381 | 2-fluoro-3-trifluoromethoxyphenyl | hydroxymethyl | |
| 1.5.382 | 2-chloro-3-trifluoromethoxyphenyl | hydroxymethyl | |
| 1.5.383 | 2-bromo-3-trifluoromethoxyphenyl | hydroxymethyl | |
| 1.5.384 | 2-methyl-3-trifluoromethoxyphenyl | hydroxymethyl | |
| 1.5.385 | 2-ethyl-3-trifluoromethoxyphenyl | hydroxymethyl | |
| 1.5.386 | 2-cyclopropyl-3-trifluoromethoxyphenyl | hydroxymethyl | |
| 1.5.387 | 2-vinyl-3-trifluoromethoxyphenyl | hydroxymethyl | |
| 1.5.388 | 2-ethynyl-3-trifluoromethoxyphenyl | hydroxymethyl | |
| 1.5.389 | 2-cyano-3-trifluoromethoxyphenyl | hydroxymethyl | |
| 1.5.390 | 2-trifluoromethyl-3-trifluoromethoxy-phenyl | hydroxymethyl | |
| 1.5.391 | 2-methoxy-3-trifluoromethoxyphenyl | hydroxymethyl | |
| 1.5.392 | 2-ethoxy-3-trifluoromethoxyphenyl | hydroxymethyl | |
| 1.5.393 | 2,3-bis(trifluoromethoxy)phenyl | hydroxymethyl | |
| 1.5.394 | 2-nitro-3-trifluoromethoxyphenyl | hydroxymethyl | |
| 1.5.395 | 2-fluoro-3-(2,2,2-trifluoroethoxy)phenyl | hydroxymethyl | |
| 1.5.396 | 2-chloro-3-(2,2,2-trifluoroethoxy)phenyl | hydroxymethyl | |
| 1.5.397 | 2-bromo-3-(2,2,2-trifluoroethoxy)phenyl | hydroxymethyl | |

TABLE 1.5-continued

Inventive compounds of the general formula (I) in which W* is COOH, $R^1$ and $R^2$ are each hydrogen, and aryl is the radical.

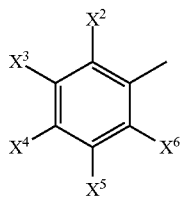

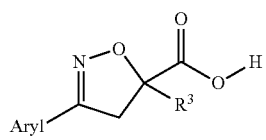

| No. | Aryl | $R^3$ | Physical data |
|---|---|---|---|
| 1.5.398 | 2-methyl-3-(2,2,2-trifluoroethoxy)phenyl | hydroxymethyl | |
| 1.5.399 | 2-ethyl-3-(2,2,2-trifluoroethoxy)phenyl | hydroxymethyl | |
| 1.5.400 | 2-cyclopropyl-3-(2,2,2-trifluoroethoxy)phenyl | hydroxymethyl | |
| 1.5.401 | 2-vinyl-3-(2,2,2-trifluoroethoxy)phenyl | hydroxymethyl | |
| 1.5.402 | 2-ethynyl-3-(2,2,2-trifluoroethoxyphenyl | hydroxymethyl | |
| 1.5.403 | 2-cyano-3-(2,2,2-trifluoroethoxy)phenyl | hydroxymethyl | |
| 1.5.404 | 2-trifluoromethyl-3-(2,2,2-trifluoroethoxy)phenyl | hydroxymethyl | |
| 1.5.405 | 2-methoxy-3-(2,2,2-trifluoroethoxy)phenyl | hydroxymethyl | |
| 1.5.406 | 2-ethoxy-3-(2,2,2-trifluoroethoxy)phenyl | hydroxymethyl | |
| 1.5.407 | 2-trifluoromethoxy-3-(2,2,2-trifluoroethoxy)phenyl | hydroxymethyl | |
| 1.5.408 | 2-nitro-3-(2,2,2-trifluoroethoxy)phenyl | hydroxymethyl | |
| 1.5.409 | 2-fluoro-3-difluoromethoxyphenyl | hydroxymethyl | |
| 1.5.410 | 2-chloro-3-difluoromethoxyphenyl | hydroxymethyl | |
| 1.5.411 | 2-bromo-3-difluoromethoxyphenyl | hydroxymethyl | |
| 1.5.412 | 2-methyl-3-difluoromethoxyphenyl | hydroxymethyl | |
| 1.5.413 | 2-ethyl-3-difluoromethoxyphenyl | hydroxymethyl | |
| 1.5.414 | 2-cyclopropyl-3-difluoromethoxyphenyl | hydroxymethyl | |
| 1.5.415 | 2-vinyl-3-difluoromethoxyphenyl | hydroxymethyl | |
| 1.5.416 | 2-ethynyl-3-difluoromethoxyphenyl | hydroxymethyl | |
| 1.5.417 | 2-cyano-3-difluoromethoxyphenyl | hydroxymethyl | |
| 1.5.418 | 2-trifluoromethyl-3-difluoromethoxyphenyl | hydroxymethyl | |
| 1.5.419 | 2-methoxy-3-difluoromethoxyphenyl | hydroxymethyl | |
| 1.5.420 | 2-ethoxy-3-difluoromethoxyphenyl | hydroxymethyl | |
| 1.5.421 | 2-trifluoromethoxy-3-difluoromethoxyphenyl | hydroxymethyl | |
| 1.5.422 | 2-nitro-3-difluoromethoxyphenyl | hydroxymethyl | |
| 1.5.423 | 2-fluoro-3-(2-methoxyethoxy)phenyl | hydroxymethyl | |
| 1.5.424 | 2-chloro-3-(2-methoxyethoxy)phenyl | hydroxymethyl | |
| 1.5.425 | 2-bromo-3-(2-methoxyethoxy)phenyl | hydroxymethyl | |
| 1.5.426 | 2-methyl-3-(2-methoxyethoxy)phenyl | hydroxymethyl | |
| 1.5.427 | 2-ethyl-3-(2-methoxyethoxy)phenyl | hydroxymethyl | |
| 1.5.428 | 2-cyclopropyl-3-(2-methoxyethoxy)phenyl | hydroxymethyl | |
| 1.5.429 | 2-vinyl-3-(2-methoxyethoxy)phenyl | hydroxymethyl | |
| 1.5.430 | 2-ethynyl-3-(2-methoxyethoxy)phenyl | hydroxymethyl | |
| 1.5.431 | 2-cyano-3-(2-methoxyethoxy)phenyl | hydroxymethyl | |
| 1.5.432 | 2-trifluoromethyl-3-(2-methoxyethoxy)phenyl | hydroxymethyl | |
| 1.5.433 | 2-methoxy-3-(2-methoxyethoxy)phenyl | hydroxymethyl | |
| 1.5.434 | 2-ethoxy-3-(2-methoxyethoxy)phenyl | hydroxymethyl | |
| 1.5.435 | 2-trifluoromethoxy-(2-methoxyethoxy)phenyl | hydroxymethyl | |
| 1.5.436 | 2-nitro-3-(2-methoxyethoxy)phenyl | hydroxymethyl | |
| 1.5.437 | 2-fluoro-3-(tert-butoxycarbonyloxy)phenyl | hydroxymethyl | |
| 1.5.438 | 2-chloro-3-(tert-butoxycarbonyloxy)phenyl | hydroxymethyl | |
| 1.5.439 | 2-bromo-3-(tert-butoxycarbonyloxy)phenyl | hydroxymethyl | |
| 1.5.440 | 2-methyl-3-(tert-butoxycarbonyloxy)phenyl | hydroxymethyl | |

TABLE 1.5-continued

Inventive compounds of the general formula (I) in which W* is COOH, $R^1$ and $R^2$ are each hydrogen, and aryl is the radical.

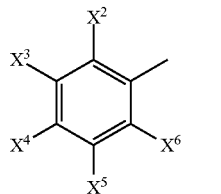

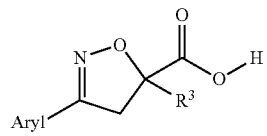

| No. | Aryl | $R^3$ | Physical data |
|---|---|---|---|
| 1.5.441 | 2-ethyl-3-(tert-butoxycarbonyloxy)-phenyl | hydroxymethyl | |
| 1.5.442 | 2-cyclopropyl-3-(tert-butoxycarbonyl-oxy)phenyl | hydroxymethyl | |
| 1.5.443 | 2-vinyl-3-(tert-butoxycarbonyloxy)-phenyl | hydroxymethyl | |
| 1.5.444 | 2-ethynyl-3-(tert-butoxycarbonyl-oxy)phenyl | hydroxymethyl | |
| 1.5.445 | 2-cyano-3-(tert-butoxycarbonyloxy)-phenyl | hydroxymethyl | |
| 1.5.446 | 2-trifluoromethyl-3-(tert-butoxycarbonyl-oxy)phenyl | hydroxymethyl | |
| 1.5.447 | 2-methoxy-3-(tert-butoxycarbonyloxy)-phenyl | hydroxymethyl | |
| 1.5.448 | 2-ethoxy-3-(tert-butoxycarbonyloxy)-phenyl | hydroxymethyl | |
| 1.5.449 | 2-trifluoromethoxy-3-(tert-butoxycarbonyl-oxy)phenyl | hydroxymethyl | |
| 1.5.450 | 2-nitro-3-(tert-butoxycarbonyloxy)-phenyl | hydroxymethyl | |
| 1.5.451 | 2-fluoro-3-nitrophenyl | hydroxymethyl | |
| 1.5.452 | 2-chloro-3-nitrophenyl | hydroxymethyl | |
| 1.5.453 | 2-bromo-3-nitrophenyl | hydroxymethyl | |
| 1.5.454 | 2-methyl-3-nitrophenyl | hydroxymethyl | |
| 1.5.455 | 2-ethyl-3-nitrophenyl | hydroxymethyl | |
| 1.5.456 | 2-cyclopropyl-3-nitrophenyl | hydroxymethyl | |
| 1.5.457 | 2-vinyl-3-nitrophenyl | hydroxymethyl | |
| 1.5.458 | 2-ethynyl-3-nitrophenyl | hydroxymethyl | |
| 1.5.459 | 2-cyano-3-nitrophenyl | hydroxymethyl | |
| 1.5.460 | 2-trifluoromethyl-3-nitrophenyl | hydroxymethyl | |
| 1.5.461 | 2-methoxy-3-nitrophenyl | hydroxymethyl | |
| 1.5.462 | 2-ethoxy-3-nitrophenyl | hydroxymethyl | |
| 1.5.463 | 2-trifluoromethoxy-3-nitrophenyl | hydroxymethyl | |
| 1.5.464 | 2-fluoro-3-methylsulfanylphenyl | hydroxymethyl | |
| 1.5.465 | 2-chloro-3-methylsulfanylphenyl | hydroxymethyl | |
| 1.5.466 | 2-bromo-3-methylsulfanylphenyl | hydroxymethyl | |
| 1.5.467 | 2-methyl-3-methylsulfanylphenyl | hydroxymethyl | |
| 1.5.468 | 2-ethyl-3-methylsulfanylphenyl | hydroxymethyl | |
| 1.5.469 | 2-cyclopropyl-3-methylsulfanylphenyl | hydroxymethyl | |
| 1.5.470 | 2-vinyl-3-methylsulfanylphenyl | hydroxymethyl | |
| 1.5.471 | 2-ethynyl-3-methylsulfanylphenyl | hydroxymethyl | |
| 1.5.472 | 2-cyano-3-methylsulfanylphenyl | hydroxymethyl | |
| 1.5.473 | 2-trifluoromethyl-3-methylsulfanylphenyl | hydroxymethyl | |
| 1.5.474 | 2-methoxy-3-methylsulfanylphenyl | hydroxymethyl | |
| 1.5.475 | 2-ethoxy-3-methylsulfanylphenyl | hydroxymethyl | |
| 1.5.476 | 2-trifluoromethoxy-3-methylsulfanylphenyl | hydroxymethyl | |
| 1.5.477 | 2-nitro-3-methylsulfanylphenyl | hydroxymethyl | |
| 1.5.478 | 3,5-difluorophenyl | hydroxymethyl | [CDCl3] 2.0 (s br, 1H); 3.61 (d, 1H); 3.69 (d, 1H), 3.95 (d, 1H), 4.08 (d, 1H), 6.91 (t, 1H); 7.18 (d, 2H). |
| 1.5.479 | 3,5-difluorophenyl | 1-hydroxyethyl | [CDCl3] D1 1.25 (d, 3H); 1.36 (d, 1H); 3.60 (d, 1H); 3.70 (d, 1H); 4.29 (m, 1H); |

TABLE 1.5-continued

Inventive compounds of the general formula (I) in which W* is COOH, R¹ and R² are each hydrogen, and aryl is the radical.

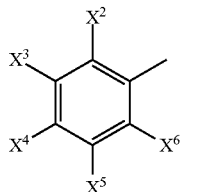

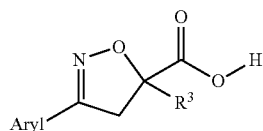

| No. | Aryl | R³ | Physical data |
|---|---|---|---|
| | | | 6.91 (t, 1H); 7.20 (d, 2H). D2 1.29 (d, 3H); 1.42 (d, 1H); 3.60 (d, 1H); 3.69 (d, 1H); 4.22 (m, 1H); 6.91 (t, 1H); 7.20 (d, 2H). |
| 1.5.480 | 3,5-difluorophenyl | 1-hydroxypropyl | |
| 1.5.481 | 3,5-difluorophenyl | (1-hydroxy-2-methylpropyl) | |
| 1.5.482 | 3,5-difluorophenyl | methoxymethyl | [CDCl3] 3.47 (s, 3H); 3.50 (d, 1H); 3.72 (d, 1H); 3.84 (s, 2H); 6.90 (m, 1H); 7.19 (m, 2H). |
| 1.5.483 | 2-ethyl-3-cyanophenyl | 2-methoxyethyl | |
| 1.5.484 | 3-chloro-5-fluorophenyl | hydroxymethyl | |
| 1.5.485 | 3-chloro-5-fluorophenyl | 1-hydroxyethyl | |
| 1.5.486 | 3-chloro-5-fluorophenyl | 1-hydroxypropyl | |
| 1.5.487 | 3-chloro-5-fluorophenyl | (1-hydroxy-2-methylpropyl) | |
| 1.5.488 | 3-chloro-5-fluorophenyl | methoxymethyl | |
| 1.5.489 | 3-chloro-5-fluorophenyl | 2-methoxyethyl | |
| 1.5.490 | 3-bromo-5-fluorophenyl | hydroxymethyl | |
| 1.5.491 | 3-bromo-5-fluorophenyl | 1-hydroxyethyl | |
| 1.5.492 | 3-bromo-5-fluorophenyl | 1-hydroxypropyl | |
| 1.5.493 | 3-bromo-5-fluorophenyl | (1-hydroxy-2-methylpropyl) | |
| 1.5.494 | 3-bromo-5-fluorophenyl | methoxymethyl | |
| 1.5.495 | 3-bromo-5-fluorophenyl | 2-methoxyethyl | |
| 1.5.496 | 3-iodo-5-fluorophenyl | hydroxymethyl | |
| 1.5.497 | 3-methyl-5-fluorophenyl | hydroxymethyl | |
| 1.5.498 | 3-methyl-5-fluorophenyl | 1-hydroxyethyl | |
| 1.5.499 | 3-methyl-5-fluorophenyl | 1-hydroxypropyl | |
| 1.5.500 | 3-methyl-5-fluorophenyl | (1-hydroxy-2-methylpropyl) | |
| 1.5.501 | 3-methyl-5-fluorophenyl | methoxymethyl | |
| 1.5.502 | 3-methyl-5-fluorophenyl | 2-methoxyethyl | |
| 1.5.503 | 3-ethyl-5-fluorophenyl | hydroxymethyl | |
| 1.5.504 | 3-propyl-5-fluorophenyl | hydroxymethyl | |
| 1.5.505 | 3-i-propyl-5-fluorophenyl | hydroxymethyl | |
| 1.5.506 | 3-n-butyl-5-fluorophenyl | hydroxymethyl | |
| 1.5.507 | 3-isobutyl-5-fluorophenyl | hydroxymethyl | |
| 1.5.508 | 3-tert-butyl-5-fluorophenyl | hydroxymethyl | |
| 1.5.509 | 3-cyclopropyl-5-fluorophenyl | hydroxymethyl | |
| 1.5.510 | 3-vinyl-5-fluorophenyl | hydroxymethyl | |
| 1.5.511 | 3-ethynyl-5-fluorophenyl | hydroxymethyl | |
| 1.5.512 | 3-cyano-5-fluorophenyl | hydroxymethyl | |
| 1.5.513 | 3-trifluoromethyl-5-fluorophenyl | hydroxymethyl | |
| 1.5.514 | 3-trifluoromethyl-5-fluorophenyl | 1-hydroxyethyl | |
| 1.5.515 | 3-trifluoromethyl-5-fluorophenyl | 1-hydroxypropyl | |
| 1.5.516 | 3-trifluoromethyl-5-fluorophenyl | (1-hydroxy-2-methylpropyl) | |
| 1.5.517 | 3-trifluoromethyl-5-fluorophenyl | methoxymethyl | |
| 1.5.518 | 3-trifluoromethyl-5-fluorophenyl | 2-methoxyethyl | |
| 1.5.519 | 3-(methoxycarbonyl)-5-fluorophenyl | hydroxymethyl | |
| 1.5.520 | 3-hydroxymethyl-5-fluorophenyl | hydroxymethyl | |
| 1.5.521 | 3-carbamoyl-5-fluorophenyl | hydroxymethyl | |

TABLE 1.5-continued

Inventive compounds of the general formula (I) in which W* is COOH, R¹ and R² are each hydrogen, and aryl is the radical.

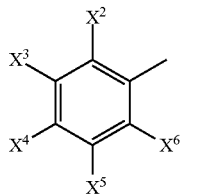

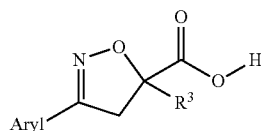

| No. | Aryl | R³ | Physical data |
|---|---|---|---|
| 1.5.522 | 3-hydroxy-5-fluorophenyl | hydroxymethyl | |
| 1.5.523 | 3-methoxy-5-fluorophenyl | hydroxymethyl | |
| 1.5.524 | 3-ethoxy-5-fluorophenyl | hydroxymethyl | |
| 1.5.525 | 3-n-propoxy-5-fluorophenyl | hydroxymethyl | |
| 1.5.526 | 3-isopropoxy-5-fluorophenyl | hydroxymethyl | |
| 1.5.527 | 3-n-butoxy-5-fluorophenyl | hydroxymethyl | |
| 1.5.528 | 3-isobutoxy-5-fluorophenyl | hydroxymethyl | |
| 1.5.529 | 3-tert-butoxy-5-fluorophenyl | hydroxymethyl | |
| 1.5.530 | 3-difluoromethoxy-5-fluorophenyl | hydroxymethyl | |
| 1.5.531 | 3-trifluoromethoxy-5-fluorophenyl | hydroxymethyl | |
| 1.5.532 | 3-(2,2,2-trifluoroethoxy)-5-fluorophenyl | hydroxymethyl | |
| 1.5.533 | 3-(2-chloroethoxy)-5-fluorophenyl | hydroxymethyl | |
| 1.5.534 | 3-(2-hydroxyethoxy)-5-fluorophenyl | hydroxymethyl | |
| 1.5.535 | 3-[(tert-butoxycarbonyl)oxy]-5-fluorophenyl | hydroxymethyl | |
| 1.5.536 | 3-nitro-5-fluorophenyl | hydroxymethyl | |
| 1.5.537 | 3-acetoxy-5-fluorophenyl | hydroxymethyl | |
| 1.5.538 | {3-[(tert-butoxycarbonyl)amino]-5-fluorophenyl} | hydroxymethyl | |
| 1.5.539 | 3-methylsulfanyl-5-fluorophenyl | hydroxymethyl | |
| 1.5.540 | 3,5-dichlorophenyl | hydroxymethyl | [CDCl₃] 3.68 (q, 2H); 3.96 (d, 1H); 4.08 (d, 1H); 7.45 (s, 1H); 7.56 (s, 2H). |
| 1.5.541 | 3,5-dichlorophenyl | 1-hydroxyethyl | |
| 1.5.542 | 3,5-dichlorophenyl | 1-hydroxypropyl | |
| 1.5.543 | 3,5-dichlorophenyl | (1-hydroxy-2-methylpropyl) | |
| 1.5.544 | 3,5-dichlorophenyl | methoxymethyl | [CDCl₃] 3.48 (s, 3H); 3.50 (d, 1H); 3.72 (d, 1H); 3.85 (q, 2H); 7.42 (m, 1H); 7.55 (m, 2H). |
| 1.5.545 | 3,5-dichlorophenyl | 2-methoxyethyl | [CDCl₃] |
| 1.5.546 | 3-bromo-5-chlorophenyl | hydroxymethyl | |
| 1.5.547 | 3-iodo-5-chlorophenyl | hydroxymethyl | |
| 1.5.548 | 3-methyl-5-chlorophenyl | hydroxymethyl | |
| 1.5.549 | 3-propyl-5-chlorophenyl | hydroxymethyl | |
| 1.5.550 | 3-isopropyl-5-chlorophenyl | hydroxymethyl | |
| 1.5.551 | 3-n-butyl-5-chlorophenyl | hydroxymethyl | |
| 1.5.552 | 3-isobutyl-5-chlorophenyl | hydroxymethyl | |
| 1.5.553 | 3-tert-butyl-5-chlorophenyl | hydroxymethyl | |
| 1.5.554 | 3-cyclopropyl-5-chlorophenyl | hydroxymethyl | |
| 1.5.555 | 3-cyano-5-chlorophenyl | hydroxymethyl | |
| 1.5.556 | 3-trifluoromethyl-5-chlorophenyl | hydroxymethyl | |
| 1.5.557 | 3-(methoxycarbonyl)-5-chlorophenyl | hydroxymethyl | |
| 1.5.558 | 3-methoxy-5-chlorophenyl | hydroxymethyl | |
| 1.5.559 | 3-ethoxy-5-chlorophenyl | hydroxymethyl | |
| 1.5.560 | 3-n-propoxy-5-chlorophenyl | hydroxymethyl | |
| 1.5.561 | 3-isopropoxy-5-chlorophenyl | hydroxymethyl | |
| 1.5.562 | 3-n-butoxy-5-chlorophenyl | hydroxymethyl | |
| 1.5.563 | 3-isobutoxy-5-chlorophenyl | hydroxymethyl | |
| 1.5.564 | 3-difluoromethoxy-5-chlorophenyl | hydroxymethyl | |
| 1.5.565 | 3-trifluoromethoxy-5-chlorophenyl | hydroxymethyl | |
| 1.5.566 | 3-nitro-5-chlorophenyl | hydroxymethyl | |
| 1.5.567 | 3-acetoxy-5-chlorophenyl | hydroxymethyl | |
| 1.5.568 | 3,5-dibromophenyl | hydroxymethyl | |
| 1.5.569 | 3,5-dibromophenyl | 1-hydroxyethyl | |

TABLE 1.5-continued

Inventive compounds of the general formula (I) in which W* is COOH, $R^1$ and $R^2$ are each hydrogen, and aryl is the radical.

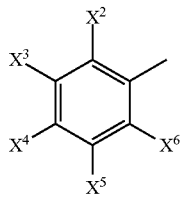

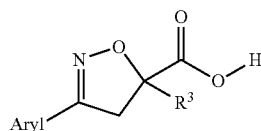

| No. | Aryl | $R^3$ | Physical data |
|---|---|---|---|
| 1.5.570 | 3-iodo-5-bromophenyl | hydroxymethyl | |
| 1.5.571 | 3-methyl-5-bromophenyl | hydroxymethyl | |
| 1.5.572 | 3-methyl-5-bromophenyl | 1-hydroxyethyl | |
| 1.5.573 | 3-methyl-5-bromophenyl | 1-hydroxypropyl | |
| 1.5.574 | 3-methyl-5-bromophenyl | (1-hydroxy-2-methylpropyl) | |
| 1.5.575 | 3-methyl-5-bromophenyl | methoxymethyl | |
| 1.5.576 | 3-methyl-5-bromophenyl | 2-methoxyethyl | |
| 1.5.577 | 3-ethyl-5-bromophenyl | hydroxymethyl | |
| 1.5.578 | 3-propyl-5-bromophenyl | hydroxymethyl | |
| 1.5.579 | 3-isopropyl-5-bromophenyl | hydroxymethyl | |
| 1.5.580 | 3-n-butyl-5-bromophenyl | hydroxymethyl | |
| 1.5.581 | 3-isobutyl-5-bromophenyl | hydroxymethyl | |
| 1.5.582 | 3-tert-butyl-5-bromophenyl | hydroxymethyl | |
| 1.5.583 | 3-cyclopropyl-5-bromophenyl | hydroxymethyl | |
| 1.5.584 | 3-cyano-5-bromophenyl | hydroxymethyl | |
| 1.5.585 | 3-trifluoromethyl-5-bromophenyl | hydroxymethyl | |
| 1.5.586 | 3-(methoxycarbonyl)-5-bromophenyl | hydroxymethyl | |
| 1.5.587 | 3-methoxy-5-bromophenyl | hydroxymethyl | |
| 1.5.588 | 3-ethoxy-5-bromophenyl | hydroxymethyl | |
| 1.5.589 | 3-n-propoxy-5-bromophenyl | hydroxymethyl | |
| 1.5.590 | 3-isopropoxy-5-bromophenyl | hydroxymethyl | |
| 1.5.591 | 3-n-butoxy-5-bromophenyl | hydroxymethyl | |
| 1.5.592 | 3-isobutoxy-5-bromophenyl | hydroxymethyl | |
| 1.5.593 | 3-difluoromethoxy-5-bromophenyl | hydroxymethyl | |
| 1.5.594 | 3-trifluoromethoxy-5-bromophenyl | hydroxymethyl | |
| 1.5.595 | 3-nitro-5-bromophenyl | hydroxymethyl | |
| 1.5.596 | 3-acetoxy-5-bromophenyl | hydroxymethyl | |
| 1.5.597 | 3-methylsulfanyl-5-bromophenyl | hydroxymethyl | |
| 1.5.598 | 3,5-diiodophenyl | hydroxymethyl | |
| 1.5.599 | 3-methyl-5-iodophenyl | hydroxymethyl | |
| 1.5.600 | 3-ethyl-5-iodophenyl | hydroxymethyl | |
| 1.5.601 | 3-propyl-5-iodophenyl | hydroxymethyl | |
| 1.5.602 | 3-isopropyl-5-iodophenyl | hydroxymethyl | |
| 1.5.603 | 3-n-butyl-5-iodophenyl | hydroxymethyl | |
| 1.5.604 | 3-isobutyl-5-iodophenyl | hydroxymethyl | |
| 1.5.605 | 3-tert-butyl-5-iodophenyl | hydroxymethyl | |
| 1.5.606 | 3-cyclopropyl-5-iodophenyl | hydroxymethyl | |
| 1.5.607 | 3-cyano-5-iodophenyl | hydroxymethyl | |
| 1.5.608 | 3-trifluoromethyl-5-iodophenyl | hydroxymethyl | |
| 1.5.609 | 3-(methoxycarbonyl)-5-iodophenyl | hydroxymethyl | |
| 1.5.610 | 3-methoxy-5-iodophenyl | hydroxymethyl | |
| 1.5.611 | 3-ethoxy-5-iodophenyl | hydroxymethyl | |
| 1.5.612 | 3-n-propoxy-5-iodophenyl | hydroxymethyl | |
| 1.5.613 | 3-isopropoxy-5-iodophenyl | hydroxymethyl | |
| 1.5.614 | 3-n-butoxy-5-iodophenyl | hydroxymethyl | |
| 1.5.615 | 3-isobutoxy-5-iodophenyl | hydroxymethyl | |
| 1.5.616 | 3-difluoromethoxy-5-iodophenyl | hydroxymethyl | |
| 1.5.617 | 3-trifluoromethoxy-5-iodophenyl | hydroxymethyl | |
| 1.5.618 | 3-nitro-5-iodophenyl | hydroxymethyl | |
| 1.5.619 | 3-acetoxy-5-iodophenyl | hydroxymethyl | |
| 1.5.620 | 3-methylsulfanyl-5-iodophenyl | hydroxymethyl | |
| 1.5.621 | 3,5-dimethylphenyl | hydroxymethyl | |
| 1.5.622 | 3-ethyl-5-methylphenyl | hydroxymethyl | |
| 1.5.623 | 3-propyl-5-methylphenyl | hydroxymethyl | |
| 1.5.624 | 3-isopropyl-5-methylphenyl | hydroxymethyl | |
| 1.5.625 | 3-n-butyl-5-methylphenyl | hydroxymethyl | |

TABLE 1.5-continued

Inventive compounds of the general formula (I) in which W* is COOH, $R^1$ and $R^2$ are each hydrogen, and aryl is the radical.

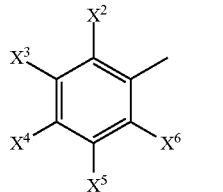

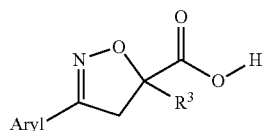

| No. | Aryl | $R^3$ | Physical data |
|---|---|---|---|
| 1.5.626 | 3-isobutyl-5-methylphenyl | hydroxymethyl | |
| 1.5.627 | 3-tert-butyl-5-methylphenyl | hydroxymethyl | |
| 1.5.628 | 3-cyclopropyl-5-methylphenyl | hydroxymethyl | |
| 1.5.629 | 3-cyano-5-methylphenyl | hydroxymethyl | |
| 1.5.630 | 3-trifluoromethyl-5-methylphenyl | hydroxymethyl | |
| 1.5.631 | 3-(methoxycarbonyl)-5-methylphenyl | hydroxymethyl | |
| 1.5.632 | 3-methoxy-5-methylphenyl | hydroxymethyl | |
| 1.5.633 | 3-ethoxy-5-methylphenyl | hydroxymethyl | |
| 1.5.634 | 3-n-propoxy-5-methylphenyl | hydroxymethyl | |
| 1.5.635 | 3-n-butoxy-5-methylphenyl | hydroxymethyl | |
| 1.5.636 | 3-isobutoxy-5-methylphenyl | hydroxymethyl | |
| 1.5.637 | 3-difluoromethoxy-5-methylphenyl | hydroxymethyl | |
| 1.5.638 | 3-trifluoromethoxy-5-methylphenyl | hydroxymethyl | |
| 1.5.639 | 3-nitro-5-methylphenyl | hydroxymethyl | |
| 1.5.640 | 3-acetoxy-5-methylphenyl | hydroxymethyl | |
| 1.5.641 | 3-methylsulfanyl-5-methylphenyl | hydroxymethyl | |
| 1.5.642 | 3,5-diethylphenyl | hydroxymethyl | |
| 1.5.643 | 3-propyl-5-ethylphenyl | hydroxymethyl | |
| 1.5.644 | 3-isopropyl-5-ethylphenyl | hydroxymethyl | |
| 1.5.645 | 3-n-butyl-5-ethylphenyl | hydroxymethyl | |
| 1.5.646 | 3-isobutyl-5-ethylphenyl | hydroxymethyl | |
| 1.5.647 | 3-tert-butyl-5-ethylphenyl | hydroxymethyl | |
| 1.5.648 | 3-cyclopropyl-5-ethylphenyl | hydroxymethyl | |
| 1.5.649 | 3-cyano-5-ethylphenyl | hydroxymethyl | |
| 1.5.650 | 3-trifluoromethyl-5-ethylphenyl | hydroxymethyl | |
| 1.5.651 | 3-(methoxycarbonyl)-5-ethylphenyl | hydroxymethyl | |
| 1.5.652 | 3-methoxy-5-ethylphenyl | hydroxymethyl | |
| 1.5.653 | 3-ethoxy-5-ethylphenyl | hydroxymethyl | |
| 1.5.654 | 3-n-propoxy-5-ethylphenyl | hydroxymethyl | |
| 1.5.655 | 3-n-butoxy-5-ethylphenyl | hydroxymethyl | |
| 1.5.656 | 3-isobutoxy-5-ethylphenyl | hydroxymethyl | |
| 1.5.657 | 3-difluoromethoxy-5-ethylphenyl | hydroxymethyl | |
| 1.5.658 | 3-trifluoromethoxy-5-ethylphenyl | hydroxymethyl | |
| 1.5.659 | 3-nitro-5-ethylphenyl | hydroxymethyl | |
| 1.5.660 | 3-acetoxy-5-ethylphenyl | hydroxymethyl | |
| 1.5.661 | 3-methylsulfanyl-5-ethylphenyl | hydroxymethyl | |
| 1.5.662 | 3,5-dipropylphenyl | hydroxymethyl | |
| 1.5.663 | 3-isopropyl-5-propylphenyl | hydroxymethyl | |
| 1.5.664 | 3-n-butyl-5-propylphenyl | hydroxymethyl | |
| 1.5.665 | 3-isobutyl-5-propylphenyl | hydroxymethyl | |
| 1.5.666 | 3-tert-butyl-5-propylphenyl | hydroxymethyl | |
| 1.5.667 | 3-cyclopropyl-5-propylphenyl | hydroxymethyl | |
| 1.5.668 | 3-cyano-5-propylphenyl | hydroxymethyl | |
| 1.5.669 | 3-trifluoromethyl-5-propylphenyl | hydroxymethyl | |
| 1.5.670 | 3-(methoxycarbonyl)-5-propylphenyl | hydroxymethyl | |
| 1.5.671 | 3-methoxy-5-propylphenyl | hydroxymethyl | |
| 1.5.672 | 3-ethoxy-5-propylphenyl | hydroxymethyl | |
| 1.5.673 | 3-n-propoxy-5-propylphenyl | hydroxymethyl | |
| 1.5.674 | 3-n-butoxy-5-propylphenyl | hydroxymethyl | |
| 1.5.675 | 3-isobutoxy-5-propylphenyl | hydroxymethyl | |
| 1.5.676 | 3-difluoromethoxy-5-propylphenyl | hydroxymethyl | |
| 1.5.677 | 3-trifluoromethoxy-5-ethylphenyl | hydroxymethyl | |
| 1.5.678 | 3-nitro-5-propylphenyl | hydroxymethyl | |
| 1.5.679 | 3-acetoxy-5-propylphenyl | hydroxymethyl | |
| 1.5.680 | 3-methylsulfanyl-5-propylphenyl | hydroxymethyl | |
| 1.5.681 | 3,5-diisopropylphenyl | hydroxymethyl | |
| 1.5.682 | 3-n-butyl-5-isopropylphenyl | hydroxymethyl | |

TABLE 1.5-continued

Inventive compounds of the general formula (I) in which W* is COOH, $R^1$ and $R^2$ are each hydrogen, and aryl is the radical.

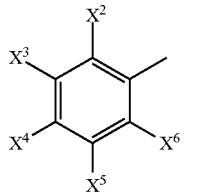

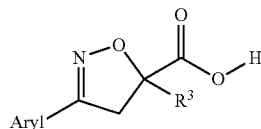

| No. | Aryl | $R^3$ | Physical data |
|---|---|---|---|
| 1.5.683 | 3-isobutyl-5-isopropylphenyl | hydroxymethyl | |
| 1.5.684 | 3-tert-butyl-5-isopropylphenyl | hydroxymethyl | |
| 1.5.685 | 3-cyclopropyl-5-isopropylphenyl | hydroxymethyl | |
| 1.5.686 | 3-cyano-5-isopropylphenyl | hydroxymethyl | |
| 1.5.687 | 3-trifluoromethyl-5-isopropylphenyl | hydroxymethyl | |
| 1.5.688 | 3-(methoxycarbonyl)-5-isopropylphenyl | hydroxymethyl | |
| 1.5.689 | 3-methoxy-5-isopropylphenyl | hydroxymethyl | |
| 1.5.690 | 3-ethoxy-5-isopropylphenyl | hydroxymethyl | |
| 1.5.691 | 3-n-propoxy-5-isopropylphenyl | hydroxymethyl | |
| 1.5.692 | 3-n-butoxy-5-isopropylphenyl | hydroxymethyl | |
| 1.5.693 | 3-isobutoxy-5-isopropylphenyl | hydroxymethyl | |
| 1.5.694 | 3-difluoromethoxy-5-isopropylphenyl | hydroxymethyl | |
| 1.5.695 | 3-trifluoromethoxy-5-isopropylphenyl | hydroxymethyl | |
| 1.5.696 | 3-nitro-5-isopropylphenyl | hydroxymethyl | |
| 1.5.697 | 3-acetoxy-5-isopropylphenyl | hydroxymethyl | |
| 1.5.698 | 3-methylsulfanyl-5-isopropylphenyl | hydroxymethyl | |
| 1.5.699 | 3,5-dibutylphenyl | hydroxymethyl | |
| 1.5.700 | 3-isobutyl-5-butylphenyl | hydroxymethyl | |
| 1.5.701 | 3-tert-butyl-5-butylphenyl | hydroxymethyl | |
| 1.5.702 | 3-cyclopropyl-5-butylphenyl | hydroxymethyl | |
| 1.5.703 | 3-cyano-5-butylphenyl | hydroxymethyl | |
| 1.5.704 | 3-trifluoromethyl-5-butylphenyl | hydroxymethyl | |
| 1.5.705 | 3-(methoxycarbonyl)-5-butylphenyl | hydroxymethyl | |
| 1.5.706 | 3-methoxy-5-butylphenyl | hydroxymethyl | |
| 1.5.707 | 3-ethoxy-5-butylphenyl | hydroxymethyl | |
| 1.5.708 | 3-n-propoxy-5-butylphenyl | hydroxymethyl | |
| 1.5.709 | 3-n-butoxy-5-butylphenyl | hydroxymethyl | |
| 1.5.710 | 3-isobutoxy-5-butylphenyl | hydroxymethyl | |
| 1.5.711 | 3-difluoromethoxy-5-butylphenyl | hydroxymethyl | |
| 1.5.712 | 3-trifluoromethoxy-5-butylphenyl | hydroxymethyl | |
| 1.5.713 | 3-nitro-5-butylphenyl | hydroxymethyl | |
| 1.5.714 | 3-acetoxy-5-butylphenyl | hydroxymethyl | |
| 1.5.715 | 3-methylsulfanyl-5-butylphenyl | hydroxymethyl | |
| 1.5.716 | 3,5-diisobutylphenyl | hydroxymethyl | |
| 1.5.717 | 3-tert-butyl-5-isobutylphenyl | hydroxymethyl | |
| 1.5.718 | 3-cyclopropyl-5-isobutylphenyl | hydroxymethyl | |
| 1.5.719 | 3-cyano-5-isobutylphenyl | hydroxymethyl | |
| 1.5.720 | 3-trifluoromethyl-5-isobutylphenyl | hydroxymethyl | |
| 1.5.721 | 3-(methoxycarbonyl)-5-isobutylphenyl | hydroxymethyl | |
| 1.5.722 | 3-methoxy-5-isobutylphenyl | hydroxymethyl | |
| 1.5.723 | 3-ethoxy-5-isobutylphenyl | hydroxymethyl | |
| 1.5.724 | 3-n-propoxy-5-isobutylphenyl | hydroxymethyl | |
| 1.5.725 | 3-n-butoxy-5-isobutylphenyl | hydroxymethyl | |
| 1.5.726 | 3-isobutoxy-5-isobutylphenyl | hydroxymethyl | |
| 1.5.727 | 3-difluoromethoxy-5-isobutylphenyl | hydroxymethyl | |
| 1.5.728 | 3-trifluoromethoxy-5-isobutylphenyl | hydroxymethyl | |
| 1.5.729 | 3-nitro-5-isobutylphenyl | hydroxymethyl | |
| 1.5.730 | 3-acetoxy-5-isobutylphenyl | hydroxymethyl | |
| 1.5.731 | 3-methylsulfanyl-5-isobutylphenyl | hydroxymethyl | |
| 1.5.732 | 3,5-di(tert-butyl)phenyl | hydroxymethyl | |
| 1.5.733 | 3-cyclopropyl-5-tert-butylphenyl | hydroxymethyl | |
| 1.5.734 | 3-cyano-5-tert-butylphenyl | hydroxymethyl | |
| 1.5.735 | 3-trifluoromethyl-5-tert-butylphenyl | hydroxymethyl | |
| 1.5.736 | 3-(methoxycarbonyl)-5-tert-butylphenyl | hydroxymethyl | |
| 1.5.737 | 3-methoxy-5-tert-butylphenyl | hydroxymethyl | |
| 1.5.738 | 3-ethoxy-5-tert-butylphenyl | hydroxymethyl | |
| 1.5.739 | 3-n-propoxy-5-tert-butylphenyl | hydroxymethyl | |

TABLE 1.5-continued

Inventive compounds of the general formula (I) in which W* is COOH, $R^1$ and $R^2$ are each hydrogen, and aryl is the radical.

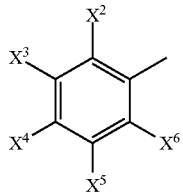

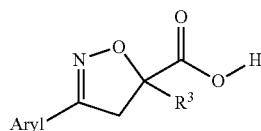

| No. | Aryl | $R^3$ | Physical data |
|---|---|---|---|
| 1.5.740 | 3-n-butoxy-5-tert-butylphenyl | hydroxymethyl | |
| 1.5.741 | 3-isobutoxy-5-tert-butylphenyl | hydroxymethyl | |
| 1.5.742 | 3-difluoromethoxy-5-tert-butylphenyl | hydroxymethyl | |
| 1.5.743 | 3-trifluoromethoxy-5-tert-butylphenyl | hydroxymethyl | |
| 1.5.744 | 3-nitro-5-tert-butylphenyl | hydroxymethyl | |
| 1.5.745 | 3-acetoxy-5-tert-butylphenyl | hydroxymethyl | |
| 1.5.746 | 3-methylsulfanyl-5-tert-butylphenyl | hydroxymethyl | |
| 1.5.747 | 3-tert-butyl-5-cyclopropylphenyl | hydroxymethyl | |
| 1.5.748 | 3,5-dicyclopropyl-phenyl | hydroxymethyl | |
| 1.5.749 | 3-cyano-5-cyclopropylphenyl | hydroxymethyl | |
| 1.5.750 | 3-trifluoromethyl-5-cyclopropylphenyl | hydroxymethyl | |
| 1.5.751 | 3-(hydroxycarbonyl)-5-cyclopropylphenyl | hydroxymethyl | |
| 1.5.752 | 3-(methoxycarbonyl)-5-cyclopropylphenyl | hydroxymethyl | |
| 1.5.753 | 3-methoxy-5-cyclopropylphenyl | hydroxymethyl | |
| 1.5.754 | 3-ethoxy-5-cyclopropylphenyl | hydroxymethyl | |
| 1.5.755 | 3-n-propoxy-5-cyclopropylphenyl | hydroxymethyl | |
| 1.5.756 | 3-n-butoxy-5-cyclopropylphenyl | hydroxymethyl | |
| 1.5.757 | 3-isobutoxy-5-cyclopropylphenyl | hydroxymethyl | |
| 1.5.758 | 3-difluoromethoxy-5-cyclopropylphenyl | hydroxymethyl | |
| 1.5.759 | 3-trifluoromethoxy-5-cyclopropylphenyl | hydroxymethyl | |
| 1.5.760 | 3-nitro-5-cyclopropylphenyl | hydroxymethyl | |
| 1.5.761 | 3-acetoxy-5-cyclopropylphenyl | hydroxymethyl | |
| 1.5.762 | 3-methylsulfanyl-5-cyclopropylphenyl | hydroxymethyl | |
| 1.5.763 | 3,5-dicyanophenyl | hydroxymethyl | |
| 1.5.764 | 3-trifluoromethyl-5-cyanophenyl | hydroxymethyl | |
| 1.5.765 | 3-(methoxycarbonyl)-5-cyanophenyl | hydroxymethyl | |
| 1.5.766 | 3-methoxy-5-cyanophenyl | hydroxymethyl | |
| 1.5.767 | 3-ethoxy-5-cyanophenyl | hydroxymethyl | |
| 1.5.768 | 3-n-propoxy-5-cyanophenyl | hydroxymethyl | |
| 1.5.769 | 3-n-butoxy-5-cyanophenyl | hydroxymethyl | |
| 1.5.770 | 3-isobutoxy-5-cyanophenyl | hydroxymethyl | |
| 1.5.771 | 3-difluoromethoxy-5-cyanophenyl | hydroxymethyl | |
| 1.5.772 | 3-trifluoromethoxy-5-cyanophenyl | hydroxymethyl | |
| 1.5.773 | 3-nitro-5-cyanophenyl | hydroxymethyl | |
| 1.5.774 | 3-acetoxy-5-cyanophenyl | hydroxymethyl | |
| 1.5.775 | 3-methylsulfanyl-5-cyanophenyl | hydroxymethyl | |
| 1.5.776 | 3,5-di(trifluoromethyl)-phenyl | hydroxymethyl | |
| 1.5.777 | 3-(methoxycarbonyl)-5-trifluoromethyl-phenyl | hydroxymethyl | |
| 1.5.778 | 3-methoxy-5-trifluoromethylphenyl | hydroxymethyl | |
| 1.5.779 | 3-ethoxy-5-trifluoromethylphenyl | hydroxymethyl | |
| 1.5.780 | 3-n-propoxy-5-trifluoromethylphenyl | hydroxymethyl | |
| 1.5.781 | 3-isobutoxy-5-trifluoromethylphenyl | hydroxymethyl | |
| 1.5.782 | 3-difluoromethoxy-5-trifluoromethylphenyl | hydroxymethyl | |
| 1.5.783 | 3-trifluoromethoxy-5-trifluoromethylphenyl | hydroxymethyl | |
| 1.5.784 | 3-nitro-5-trifluoromethylphenyl | hydroxymethyl | |
| 1.5.785 | 3-acetoxy-5-trifluoromethylphenyl | hydroxymethyl | |
| 1.5.786 | 3-methylsulfanyl-5-trifluoromethylphenyl | hydroxymethyl | |
| 1.5.787 | 3,5-di(methoxycarbonyl)phenyl | hydroxymethyl | |
| 1.5.788 | 3-methoxy-5-(methoxycarbonyl)phenyl | hydroxymethyl | |
| 1.5.789 | 3-ethoxy-5-(methoxycarbonyl)phenyl | hydroxymethyl | |
| 1.5.790 | 3-n-propoxy-5-(methoxycarbonyl)-phenyl | hydroxymethyl | |
| 1.5.791 | 3-n-butoxy-5-(methoxycarbonyl)phenyl | hydroxymethyl | |

TABLE 1.5-continued

Inventive compounds of the general formula (I) in which W* is COOH, R¹ and R² are each hydrogen, and aryl is the radical.

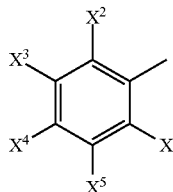

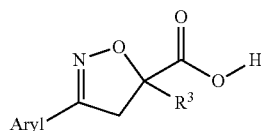

| No. | Aryl | R³ | Physical data |
|---|---|---|---|
| 1.5.792 | 3-isobutoxy-5-(methoxycarbonyl)phenyl | hydroxymethyl | |
| 1.5.793 | 3-difluoromethoxy-5-(methoxycarbonyl)phenyl | hydroxymethyl | |
| 1.5.794 | 3-trifluoromethoxy-5-(methoxycarbonyl)phenyl | hydroxymethyl | |
| 1.5.795 | 3-nitro-5-(methoxycarbonyl)phenyl | hydroxymethyl | |
| 1.5.796 | 3-acetoxy-5-(methoxycarbonyl)phenyl | hydroxymethyl | |
| 1.5.797 | 3-methylsulfanyl-5-(methoxycarbonyl)phenyl | hydroxymethyl | |
| 1.5.798 | 3,5-dimethoxyphenyl | hydroxymethyl | |
| 1.5.799 | 3-ethoxy-5-methoxyphenyl | hydroxymethyl | |
| 1.5.800 | 3-n-propoxy-5-methoxyphenyl | hydroxymethyl | |
| 1.5.801 | 3-isobutoxy-5-methoxyphenyl | hydroxymethyl | |
| 1.5.802 | 3-difluoromethoxy-5-methoxyphenyl | hydroxymethyl | |
| 1.5.803 | 3-trifluoromethoxy-5-methoxyphenyl | hydroxymethyl | |
| 1.5.804 | 3-nitro-5-methoxyphenyl | hydroxymethyl | |
| 1.5.805 | 3-acetoxy-5-methoxyphenyl | hydroxymethyl | |
| 1.5.806 | 3-methylsulfanyl-5-methoxyphenyl | hydroxymethyl | |
| 1.5.807 | 3,5-diethoxyphenyl | hydroxymethyl | |
| 1.5.808 | 3-n-propoxy-5-ethoxyphenyl | hydroxymethyl | |
| 1.5.809 | 3-n-butoxy-5-ethoxyphenyl | hydroxymethyl | |
| 1.5.810 | 3-isobutoxy-5-ethoxyphenyl | hydroxymethyl | |
| 1.5.811 | 3-difluoromethoxy-5-ethoxyphenyl | hydroxymethyl | |
| 1.5.812 | 3-trifluoromethoxy-5-ethoxyphenyl | hydroxymethyl | |
| 1.5.813 | 3-nitro-5-ethoxyphenyl | hydroxymethyl | |
| 1.5.814 | 3-acetoxy-5-ethoxyphenyl | hydroxymethyl | |
| 1.5.815 | 3-methylsulfanyl-5-ethoxyphenyl | hydroxymethyl | |
| 1.5.816 | 3,5-dipropoxyphenyl | hydroxymethyl | |
| 1.5.817 | 3-n-butoxy-5-propoxyphenyl | hydroxymethyl | |
| 1.5.818 | 3-isobutoxy-5-propoxyphenyl | hydroxymethyl | |
| 1.5.819 | 3-difluoromethoxy-5-propoxyphenyl | hydroxymethyl | |
| 1.5.820 | 3-trifluoromethoxy-5-propoxyphenyl | hydroxymethyl | |
| 1.5.821 | 3-nitro-5-propoxyphenyl | hydroxymethyl | |
| 1.5.822 | 3-acetoxy-5-propoxyphenyl | hydroxymethyl | |
| 1.5.823 | 3-methylsulfanyl-5-propoxyphenyl | hydroxymethyl | |
| 1.5.824 | 3,5-di(isopropoxy)phenyl | hydroxymethyl | |
| 1.5.825 | 3-n-butoxy-5-isopropoxyphenyl | hydroxymethyl | |
| 1.5.826 | 3-isobutoxy-5-isopropoxyphenyl | hydroxymethyl | |
| 1.5.827 | 3-difluoromethoxy-5-isopropoxyphenyl | hydroxymethyl | |
| 1.5.828 | 3-trifluoromethoxy-5-isopropoxyphenyl | hydroxymethyl | |
| 1.5.829 | 3-nitro-5-isopropoxyphenyl | hydroxymethyl | |
| 1.5.830 | 3-acetoxy-5-isopropoxyphenyl | hydroxymethyl | |
| 1.5.831 | 3-methylsulfanyl-5-isopropoxyphenyl | hydroxymethyl | |
| 1.5.832 | 3,5-di(trifluoromethoxy)phenyl | hydroxymethyl | |
| 1.5.833 | 3-nitro-5-trifluoromethoxyphenyl | hydroxymethyl | |
| 1.5.834 | 3-methylsulfanyl-5-trifluoromethoxyphenyl | hydroxymethyl | |
| 1.5.835 | 3,5-bis(difluoromethoxy)phenyl | hydroxymethyl | |
| 1.5.836 | 3,5-bis(difluoromethoxy)phenyl | 1-hydroxyethyl | |
| 1.5.837 | 3,5-bis(difluoromethoxy)phenyl | 1-hydroxypropyl | |
| 1.5.838 | 3,5-bis(difluoromethoxy)phenyl | (1-hydroxy-2-methylpropyl) | |
| 1.5.839 | 3-trifluoromethoxy-5-difluoromethoxyphenyl | hydroxymethyl | |
| 1.5.840 | 3-nitro-5-difluoromethoxyphenyl | hydroxymethyl | |
| 1.5.841 | 3-acetoxy-5-difluoromethoxyphenyl | hydroxymethyl | |

TABLE 1.5-continued

Inventive compounds of the general formula (I) in which W* is COOH, $R^1$ and $R^2$ are each hydrogen, and aryl is the radical.

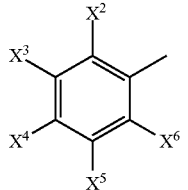

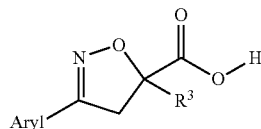

| No. | Aryl | $R^3$ | Physical data |
|---|---|---|---|
| 1.5.842 | 3-methylsulfanyl-5-difluoromethoxy-phenyl | hydroxymethyl | |
| 1.5.843 | 3,5-bis(acetoxy)phenyl | hydroxymethyl | |
| 1.5.844 | 3-methylsulfanyl-5-acetoxyphenyl | hydroxymethyl | |
| 1.5.845 | 3,5-dinitrophenyl | hydroxymethyl | |
| 1.5.846 | 3-acetoxy-5-nitrophenyl | hydroxymethyl | |
| 1.5.847 | 3-methylsulfanyl-5-nitrophenyl | hydroxymethyl | |
| 1.5.848 | 3,5-di(methylsulfanyl)phenyl | hydroxymethyl | |
| 1.5.849 | 3,4-difluorophenyl | hydroxymethyl | |
| 1.5.850 | 3,4-difluorophenyl | 1-hydroxyethyl | |
| 1.5.851 | 3,4-difluorophenyl | 1-hydroxypropyl | |
| 1.5.852 | 3,4-difluorophenyl | (1-hydroxy-2-methylpropyl) | |
| 1.5.853 | 3,4-difluorophenyl | methoxymethyl | |
| 1.5.854 | 3,4-difluorophenyl | 2-methoxyethyl | |
| 1.5.855 | 3-chloro-4-fluorophenyl | hydroxymethyl | |
| 1.5.856 | 3-chloro-4-fluorophenyl | 1-hydroxyethyl | |
| 1.5.857 | 3-chloro-4-fluorophenyl | 1-hydroxypropyl | |
| 1.5.858 | 3-chloro-4-fluorophenyl | (1-hydroxy-2-methylpropyl) | |
| 1.5.859 | 3-chloro-4-fluorophenyl | methoxymethyl | |
| 1.5.860 | 3-chloro-4-fluorophenyl | 2-methoxyethyl | |
| 1.5.861 | 3-bromo-4-fluorophenyl | hydroxymethyl | |
| 1.5.862 | 3-methyl-4-fluorophenyl | hydroxymethyl | |
| 1.5.863 | 3-methyl-4-fluorophenyl | 1-hydroxyethyl | |
| 1.5.864 | 3-ethyl-4-fluorophenyl | hydroxymethyl | |
| 1.5.865 | 3-cyclopropyl-4-fluorophenyl | hydroxymethyl | |
| 1.5.866 | 3-cyano-4-fluorophenyl | hydroxymethyl | |
| 1.5.867 | 3-methoxy-4-fluorophenyl | hydroxymethyl | |
| 1.5.868 | 3-ethoxy-4-fluorophenyl | hydroxymethyl | |
| 1.5.869 | 3-trifluoromethoxy-4-fluorophenyl | hydroxymethyl | |
| 1.5.870 | 3-nitro-4-fluorophenyl | hydroxymethyl | |
| 1.5.871 | 3-fluoro-4-chlorophenyl | hydroxymethyl | |
| 1.5.872 | 3,4-dichlorophenyl | hydroxymethyl | |
| 1.5.873 | 3-bromo-4-chlorophenyl | hydroxymethyl | |
| 1.5.874 | 3-methyl-4-chlorophenyl | hydroxymethyl | |
| 1.5.875 | 3-cyclopropyl-4-chlorophenyl | hydroxymethyl | |
| 1.5.876 | 3-cyano-4-chlorophenyl | hydroxymethyl | |
| 1.5.877 | 3-trifluoromethyl-4-chlorophenyl | hydroxymethyl | |
| 1.5.878 | 3-methoxy-4-chlorophenyl | hydroxymethyl | |
| 1.5.879 | 3-ethoxy-4-chlorophenyl | hydroxymethyl | |
| 1.5.880 | 3-trifluoromethoxy-4-chlorophenyl | hydroxymethyl | |
| 1.5.881 | 3-nitro-4-chlorophenyl | hydroxymethyl | |
| 1.5.882 | 3-fluoro-4-bromophenyl | hydroxymethyl | |
| 1.5.883 | 3-chloro-4-bromophenyl | hydroxymethyl | |
| 1.5.884 | 3,4-dibromophenyl | hydroxymethyl | |
| 1.5.885 | 3-methyl-4-bromophenyl | hydroxymethyl | |
| 1.5.886 | 3-cyclopropyl-4-bromophenyl | hydroxymethyl | |
| 1.5.887 | 3-cyano-4-bromophenyl | hydroxymethyl | |
| 1.5.888 | 3-trifluoromethyl-4-bromophenyl | hydroxymethyl | |
| 1.5.889 | 3-methoxy-4-phenyl | hydroxymethyl | |
| 1.5.890 | 3-ethoxy-4-bromophenyl | hydroxymethyl | |
| 1.5.891 | 3-trifluoromethoxy-4-bromophenyl | hydroxymethyl | |
| 1.5.892 | 3-nitro-4-bromophenyl | hydroxymethyl | |
| 1.5.893 | 3-fluoro-4-iodophenyl | hydroxymethyl | |
| 1.5.894 | 3-chloro-4-iodophenyl | hydroxymethyl | |
| 1.5.895 | 3-bromo-4-iodophenyl | hydroxymethyl | |

TABLE 1.5-continued

Inventive compounds of the general formula (I) in which W* is COOH, $R^1$ and $R^2$ are each hydrogen, and aryl is the radical.

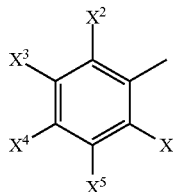

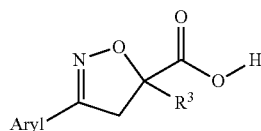

| No. | Aryl | $R^3$ | Physical data |
|---|---|---|---|
| 1.5.896 | 3-methyl-4-iodophenyl | hydroxymethyl | |
| 1.5.897 | 3-cyclopropyl-4-iodophenyl | hydroxymethyl | |
| 1.5.898 | 3-cyano-4-iodophenyl | hydroxymethyl | |
| 1.5.899 | 3-trifluoromethyl-4-iodophenyl | hydroxymethyl | |
| 1.5.900 | 3-methoxy-4-iodophenyl | hydroxymethyl | |
| 1.5.901 | 3-ethoxy-4-iodophenyl | hydroxymethyl | |
| 1.5.902 | 3-trifluoromethoxy-4-iodophenyl | hydroxymethyl | |
| 1.5.903 | 3-nitro-4-iodophenyl | hydroxymethyl | |
| 1.5.904 | 3-fluoro-4-methylphenyl | hydroxymethyl | |
| 1.5.905 | 3-chloro-4-methylphenyl | hydroxymethyl | |
| 1.5.906 | 3-bromo-4-methylphenyl | hydroxymethyl | |
| 1.5.907 | 3,4-dimethylphenyl | hydroxymethyl | |
| 1.5.908 | 3,4-dimethylphenyl | 1-hydroxyethyl | |
| 1.5.909 | 3,4-dimethylphenyl | 1-hydroxypropyl | |
| 1.5.910 | 3,4-dimethylphenyl | (1-hydroxy-2-methylpropyl) | |
| 1.5.911 | 3,4-dimethylphenyl | methoxymethyl | |
| 1.5.912 | 3,4-dimethylphenyl | 2-methoxyethyl | |
| 1.5.913 | 3-ethyl-4-methylphenyl | hydroxymethyl | |
| 1.5.914 | 3-cyclopropyl-4-methylphenyl | hydroxymethyl | |
| 1.5.915 | 3-cyano-4-methylphenyl | hydroxymethyl | |
| 1.5.916 | 3-trifluoromethyl-4-methylphenyl | hydroxymethyl | |
| 1.5.917 | 3-methoxy-4-methylphenyl | hydroxymethyl | |
| 1.5.918 | 3-ethoxy-4-methylphenyl | hydroxymethyl | |
| 1.5.919 | 3-trifluoromethoxy-4-methylphenyl | hydroxymethyl | |
| 1.5.920 | 3-nitro-4-methylphenyl | hydroxymethyl | |
| 1.5.921 | 3-fluoro-4-ethylphenyl | hydroxymethyl | |
| 1.5.922 | 3-chloro-4-ethylphenyl | hydroxymethyl | |
| 1.5.923 | 3-bromo-4-ethylphenyl | hydroxymethyl | |
| 1.5.924 | 3-methyl-4-ethylphenyl | hydroxymethyl | |
| 1.5.925 | 3,4-diethylphenyl | hydroxymethyl | |
| 1.5.926 | 3-cyclopropyl-4-ethylphenyl | hydroxymethyl | |
| 1.5.927 | 3-cyano-4-ethylphenyl | hydroxymethyl | |
| 1.5.928 | 3-trifluoromethyl-4-ethylphenyl | hydroxymethyl | |
| 1.5.929 | 3-methoxy-4-ethylphenyl | hydroxymethyl | |
| 1.5.930 | 3-ethoxy-4-ethylphenyl | hydroxymethyl | |
| 1.5.931 | 3-trifluoromethoxy-4-ethylphenyl | hydroxymethyl | |
| 1.5.932 | 3-nitro-4-ethylphenyl | hydroxymethyl | |
| 1.5.933 | 3-fluoro-4-propylphenyl | hydroxymethyl | |
| 1.5.934 | 3-chloro-4-propylphenyl | hydroxymethyl | |
| 1.5.935 | 3-bromo-4-propylphenyl | hydroxymethyl | |
| 1.5.936 | 3-methyl-4-propylphenyl | hydroxymethyl | |
| 1.5.937 | 3-cyclopropyl-4-propylphenyl | hydroxymethyl | |
| 1.5.938 | 3-cyano-4-propylphenyl | hydroxymethyl | |
| 1.5.939 | 3-trifluoromethyl-4-propylphenyl | hydroxymethyl | |
| 1.5.940 | 3-methoxy-4-propylphenyl | hydroxymethyl | |
| 1.5.941 | 3-ethoxy-4-propylphenyl | hydroxymethyl | |
| 1.5.942 | 3-trifluoromethoxy-4-propylphenyl | hydroxymethyl | |
| 1.5.943 | 3-nitro-4-propylphenyl | hydroxymethyl | |
| 1.5.944 | 3-fluoro-4-isopropylphenyl | hydroxymethyl | |
| 1.5.945 | 3-chloro-4-isopropylphenyl | hydroxymethyl | |
| 1.5.946 | 3-bromo-4-isopropylphenyl | hydroxymethyl | |
| 1.5.947 | 3-methyl-4-isopropylphenyl | hydroxymethyl | |
| 1.5.948 | 3-cyclopropyl-4-isopropylphenyl | hydroxymethyl | |
| 1.5.949 | 3-cyano-4-isopropylphenyl | hydroxymethyl | |
| 1.5.950 | 3-trifluoromethyl-4-isopropylphenyl | hydroxymethyl | |
| 1.5.951 | 3-methoxy-4-isopropylphenyl | hydroxymethyl | |

TABLE 1.5-continued

Inventive compounds of the general formula (I) in which W* is COOH, $R^1$ and $R^2$ are each hydrogen, and aryl is the radical.

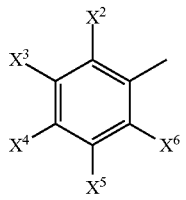

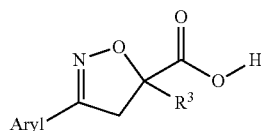

| No. | Aryl | $R^3$ | Physical data |
|---|---|---|---|
| 1.5.952 | 3-ethoxy-4-isopropylphenyl | hydroxymethyl | |
| 1.5.953 | 3-trifluoromethoxy-4-isopropylphenyl | hydroxymethyl | |
| 1.5.954 | 3-nitro-4-isopropylphenyl | hydroxymethyl | |
| 1.5.955 | 3-fluoro-4-tert-butylphenyl | hydroxymethyl | |
| 1.5.956 | 3-chloro-4-tert-butylphenyl | hydroxymethyl | |
| 1.5.957 | 3-bromo-4-tert-butylphenyl | hydroxymethyl | |
| 1.5.958 | 3-methyl-4-tert-butylphenyl | hydroxymethyl | |
| 1.5.959 | 3-cyclopropyl-4-tert-butylphenyl | hydroxymethyl | |
| 1.5.960 | 3-cyano-4-tert-butylphenyl | hydroxymethyl | |
| 1.5.961 | 3-trifluoromethyl-4-tert-butylphenyl | hydroxymethyl | |
| 1.5.962 | 3-trifluoromethyl-4-tert-butylphenyl | 1-hydroxyethyl | |
| 1.5.963 | 3-trifluoromethyl-4-tert-butylphenyl | 1-hydroxypropyl | |
| 1.5.964 | 3-trifluoromethyl-4-tert-butylphenyl | (1-hydroxy-2-methylpropyl) | |
| 1.5.965 | 3-trifluoromethyl-4-tert-butylphenyl | methoxymethyl | |
| 1.5.966 | 3-trifluoromethyl-4-tert-butylphenyl | 2-methoxyethyl | |
| 1.5.967 | 3-methoxy-4-tert-butylphenyl | hydroxymethyl | |
| 1.5.968 | 3-ethoxy-4-tert-butylphenyl | hydroxymethyl | |
| 1.5.969 | 3-trifluoromethoxy-4-tert-butylphenyl | hydroxymethyl | |
| 1.5.970 | 3-nitro-4-tert-butylphenyl | hydroxymethyl | |
| 1.5.971 | 3-fluoro-4-cyclopropylphenyl | hydroxymethyl | |
| 1.5.972 | 3-chloro-4-cyclopropylphenyl | hydroxymethyl | |
| 1.5.973 | 3-bromo-4-cyclopropylphenyl | hydroxymethyl | |
| 1.5.974 | 3-methyl-4-cyclopropylphenyl | hydroxymethyl | |
| 1.5.975 | 3-cyclopropyl-4-cyclopropylphenyl | hydroxymethyl | |
| 1.5.976 | 3-cyano-4-cyclopropylphenyl | hydroxymethyl | |
| 1.5.977 | 3-trifluoromethyl-4-cyclopropylphenyl | hydroxymethyl | |
| 1.5.978 | 3-methoxy-4-cyclopropylphenyl | hydroxymethyl | |
| 1.5.979 | 3-ethoxy-4-cyclopropylphenyl | hydroxymethyl | |
| 1.5.980 | 3-trifluoromethoxy-4-cyclopropylphenyl | hydroxymethyl | |
| 1.5.981 | 3-fluoro-4-methoxycarbonylphenyl | hydroxymethyl | |
| 1.5.982 | 3-chloro-4-methoxycarbonylphenyl | hydroxymethyl | |
| 1.5.983 | 3-bromo-4-methoxycarbonylphenyl | hydroxymethyl | |
| 1.5.984 | 3-methyl-4-methoxycarbonylphenyl | hydroxymethyl | |
| 1.5.985 | 3-cyclopropyl-4-methoxycarbonylphenyl | hydroxymethyl | |
| 1.5.986 | 3-cyano-4-methoxycarbonylphenyl | hydroxymethyl | |
| 1.5.987 | 3-trifluoromethyl-4-methoxycarbonyl-phenyl | hydroxymethyl | |
| 1.5.988 | 3-methoxy-4-methoxycarbonylphenyl | hydroxymethyl | |
| 1.5.989 | 3-ethoxy-4-methoxycarbonylphenyl | hydroxymethyl | |
| 1.5.990 | 3-trifluoromethoxy-4-methoxycarbonyl-phenyl | hydroxymethyl | |
| 1.5.991 | 3-nitro-4-methoxycarbonylphenyl | hydroxymethyl | |
| 1.5.992 | 3-fluoro-4-cyanophenyl | hydroxymethyl | |
| 1.5.993 | 3-chloro-4-cyanophenyl | hydroxymethyl | |
| 1.5.994 | 3-bromo-4-cyanophenyl | hydroxymethyl | |
| 1.5.995 | 3-methyl-4-cyanophenyl | hydroxymethyl | |
| 1.5.996 | 3-cyclopropyl-4-cyanophenyl | hydroxymethyl | |
| 1.5.997 | 3,4-dicyanophenyl | hydroxymethyl | |
| 1.5.998 | 3-trifluoromethyl-4-cyanophenyl | hydroxymethyl | |
| 1.5.999 | 3-trifluoromethyl-4-cyanophenyl | 1-hydroxyethyl | |
| 1.5.1000 | 3-trifluoromethyl-4-cyanophenyl | 1-hydroxypropyl | |
| 1.5.1001 | 3-trifluoromethyl-4-cyanophenyl | (1-hydroxy-2-methylpropyl) | |
| 1.5.1002 | 3-trifluoromethyl-4-cyanophenyl | methoxymethyl | |
| 1.5.1003 | 3-trifluoromethyl-4-cyanophenyl | 2-methoxyethyl | |
| 1.5.1004 | 3-methoxy-4-cyanophenyl | hydroxymethyl | |

TABLE 1.5-continued

Inventive compounds of the general formula (I) in which W* is COOH, $R^1$ and $R^2$ are each hydrogen, and aryl is the radical.

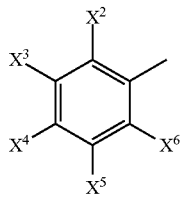

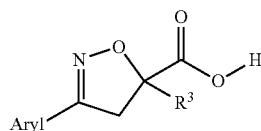

| No. | Aryl | $R^3$ | Physical data |
|---|---|---|---|
| 1.5.1005 | 3-ethoxy-4-cyanophenyl | hydroxymethyl | |
| 1.5.1006 | 3-trifluoromethoxy-4-cyanophenyl | hydroxymethyl | |
| 1.5.1007 | 3-nitro-4-cyanophenyl | hydroxymethyl | |
| 1.5.1008 | 3-fluoro-4-methoxyphenyl | hydroxymethyl | |
| 1.5.1009 | 3-chloro-4-methoxyphenyl | hydroxymethyl | |
| 1.5.1010 | 3-bromo-4-methoxyphenyl | hydroxymethyl | |
| 1.5.1011 | 3-methyl-4-methoxyphenyl | hydroxymethyl | |
| 1.5.1012 | 3-cyclopropyl-4-methoxyphenyl | hydroxymethyl | |
| 1.5.1013 | 3-cyano-4-methoxyphenyl | hydroxymethyl | |
| 1.5.1014 | 3-trifluoromethyl-4-methoxyphenyl | hydroxymethyl | |
| 1.5.1015 | 3,4-dimethoxyphenyl | hydroxymethyl | |
| 1.5.1016 | 3-ethoxy-4-methoxyphenyl | hydroxymethyl | |
| 1.5.1017 | 3-trifluoromethoxy-4-methoxyphenyl | hydroxymethyl | |
| 1.5.1018 | 3-nitro-4-methoxyphenyl | hydroxymethyl | |
| 1.5.1019 | 3-fluoro-4-ethoxyphenyl | hydroxymethyl | |
| 1.5.1020 | 3-chloro-4-ethoxyphenyl | hydroxymethyl | |
| 1.5.1021 | 3-chloro-4-ethoxyphenyl | 1-hydroxyethyl | |
| 1.5.1022 | 3-chloro-4-ethoxyphenyl | 1-hydroxypropyl | |
| 1.5.1023 | 3-chloro-4-ethoxyphenyl | (1-hydroxy-2-methylpropyl) | |
| 1.5.1024 | 3-chloro-4-ethoxyphenyl | methoxymethyl | |
| 1.5.1025 | 3-chloro-4-ethoxyphenyl | 2-methoxyethyl | |
| 1.5.1026 | 3-bromo-4-ethoxyphenyl | hydroxymethyl | |
| 1.5.1027 | 3-methyl-4-ethoxyphenyl | hydroxymethyl | |
| 1.5.1028 | 3-ethyl-4-ethoxyphenyl | hydroxymethyl | |
| 1.5.1029 | 3-cyclopropyl-4-ethoxyphenyl | hydroxymethyl | |
| 1.5.1030 | 3-cyano-4-ethoxyphenyl | hydroxymethyl | |
| 1.5.1031 | 3-trifluoromethyl-4-ethoxyphenyl | hydroxymethyl | |
| 1.5.1032 | 3-methoxy-4-ethoxyphenyl | hydroxymethyl | |
| 1.5.1033 | 2,4-diethoxyphenyl | hydroxymethyl | |
| 1.5.1034 | 3-trifluoromethoxy-4-ethoxyphenyl | hydroxymethyl | |
| 1.5.1035 | 3-nitro-4-ethoxyphenyl | hydroxymethyl | |
| 1.5.1036 | 3-fluoro-4-isopropoxyphenyl | hydroxymethyl | |
| 1.5.1037 | 3-chloro-4-isopropoxyphenyl | hydroxymethyl | |
| 1.5.1038 | 3-bromo-4-isopropoxyphenyl | hydroxymethyl | |
| 1.5.1039 | 3-methyl-4-isopropoxyphenyl | hydroxymethyl | |
| 1.5.1040 | 3-cyclopropyl-4-isopropoxyphenyl | hydroxymethyl | |
| 1.5.1041 | 3-cyano-4-isopropoxyphenyl | hydroxymethyl | |
| 1.5.1042 | 3-trifluoromethyl-4-isopropoxyphenyl | hydroxymethyl | |
| 1.5.1043 | 3-methoxy-4-isopropoxyphenyl | hydroxymethyl | |
| 1.5.1044 | 3-ethoxy-4-isopropoxyphenyl | hydroxymethyl | |
| 1.5.1045 | 3-trifluoromethoxy-4-isopropoxyphenyl | hydroxymethyl | |
| 1.5.1046 | 3-nitro-4-isopropoxyphenyl | hydroxymethyl | |
| 1.5.1047 | 3-fluoro-4-trifluoromethoxyphenyl | hydroxymethyl | |
| 1.5.1048 | 3-chloro-4-trifluoromethoxyphenyl | hydroxymethyl | |
| 1.5.1049 | 3-bromo-4-trifluoromethoxyphenyl | hydroxymethyl | |
| 1.5.1050 | 3-methyl-4-trifluoromethoxyphenyl | hydroxymethyl | |
| 1.5.1051 | 3-cyclopropyl-4-trifluoromethoxyphenyl | hydroxymethyl | |
| 1.5.1052 | 3-cyano-4-trifluoromethoxyphenyl | hydroxymethyl | |
| 1.5.1053 | 3-trifluoromethyl-4-trifluoromethoxy-phenyl | hydroxymethyl | |
| 1.5.1054 | 3-methoxy-4-trifluoromethoxyphenyl | hydroxymethyl | |
| 1.5.1055 | 3-ethoxy-4-trifluoromethoxyphenyl | hydroxymethyl | |
| 1.5.1056 | 3,4-bis(trifluoromethoxy)phenyl | hydroxymethyl | |
| 1.5.1057 | 3-nitro-4-trifluoromethoxyphenyl | hydroxymethyl | |
| 1.5.1058 | 3-fluoro-4-difluoromethoxyphenyl | hydroxymethyl | |
| 1.5.1059 | 3-chloro-4-difluoromethoxyphenyl | hydroxymethyl | |

TABLE 1.5-continued

Inventive compounds of the general formula (I) in which W* is COOH, $R^1$ and $R^2$ are each hydrogen, and aryl is the radical.

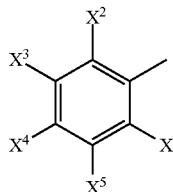

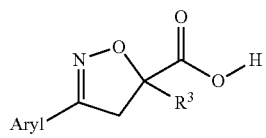

| No. | Aryl | $R^3$ | Physical data |
|---|---|---|---|
| 1.5.1060 | 3-bromo-4-difluoromethoxyphenyl | hydroxymethyl | |
| 1.5.1061 | 3-methyl-4-difluoromethoxyphenyl | hydroxymethyl | |
| 1.5.1062 | 3-cyclopropyl-4-difluoromethoxyphenyl | hydroxymethyl | |
| 1.5.1063 | 3-cyano-4-difluoromethoxyphenyl | hydroxymethyl | |
| 1.5.1064 | 3-trifluoromethyl-4-difluoromethoxyphenyl | hydroxymethyl | |
| 1.5.1065 | 3-methoxy-4-difluoromethoxyphenyl | hydroxymethyl | |
| 1.5.1066 | 3-ethoxy-4-difluoromethoxyphenyl | hydroxymethyl | |
| 1.5.1067 | 3-trifluoromethoxy-4-difluoromethoxyphenyl | hydroxymethyl | |
| 1.5.1068 | 3-nitro-4-difluoromethoxyphenyl | hydroxymethyl | |
| 1.5.1069 | 3-fluoro-4-nitrophenyl | hydroxymethyl | |
| 1.5.1070 | 3-chloro-4-nitrophenyl | hydroxymethyl | |
| 1.5.1071 | 3-bromo-4-nitrophenyl | hydroxymethyl | |
| 1.5.1072 | 3-methyl-4-nitrophenyl | hydroxymethyl | |
| 1.5.1073 | 3-cyclopropyl-4-nitrophenyl | hydroxymethyl | |
| 1.5.1074 | 3-cyano-4-nitrophenyl | hydroxymethyl | |
| 1.5.1075 | 3-trifluoromethyl-4-nitrophenyl | hydroxymethyl | |
| 1.5.1076 | 3-methoxy-4-nitrophenyl | hydroxymethyl | |
| 1.5.1077 | 3-ethoxy-4-nitrophenyl | hydroxymethyl | |
| 1.5.1078 | 3-trifluoromethoxy-4-nitrophenyl | hydroxymethyl | |
| 1.5.1079 | 3-fluoro-4-methylsulfanylphenyl | hydroxymethyl | |
| 1.5.1080 | 3-chloro-4-methylsulfanylphenyl | hydroxymethyl | |
| 1.5.1081 | 3-bromo-4-methylsulfanylphenyl | hydroxymethyl | |
| 1.5.1082 | 3-methyl-4-methylsulfanylphenyl | hydroxymethyl | |
| 1.5.1083 | 3-cyclopropyl-4-methylsulfanylphenyl | hydroxymethyl | |
| 1.5.1084 | 3-cyano-4-methylsulfanylphenyl | hydroxymethyl | |
| 1.5.1085 | 3-trifluoromethyl-4-methylsulfanylphenyl | hydroxymethyl | |
| 1.5.1086 | 3-methoxy-4-methylsulfanylphenyl | hydroxymethyl | |
| 1.5.1087 | 3-ethoxy-4-methylsulfanylphenyl | hydroxymethyl | |
| 1.5.1088 | 3-trifluoromethoxy-4-methylsulfanylphenyl | hydroxymethyl | |
| 1.5.1089 | 3-nitro-4-methylsulfanylphenyl | hydroxymethyl | |
| 1.5.1090 | 3,6-difluorophenyl | hydroxymethyl | |
| 1.5.1091 | 3,6-difluorophenyl | 1-hydroxyethyl | |
| 1.5.1092 | 3,6-difluorophenyl | 1-hydroxypropyl | |
| 1.5.1093 | 3,6-difluorophenyl | (1-hydroxy-2-methylpropyl) | |
| 1.5.1094 | 3,6-difluorophenyl | methoxymethyl | |
| 1.5.1095 | 3,6-difluorophenyl | 2-methoxyethyl | |
| 1.5.1096 | 3-chloro-6-fluorophenyl | hydroxymethyl | |
| 1.5.1097 | 3-bromo-6-fluorophenyl | hydroxymethyl | |
| 1.5.1098 | 3-methyl-6-fluorophenyl | hydroxymethyl | |
| 1.5.1099 | 3-ethyl-6-fluorophenyl | hydroxymethyl | |
| 1.5.1100 | 3-cyclopropyl-6-fluorophenyl | hydroxymethyl | |
| 1.5.1101 | 3-cyano-6-fluorophenyl | hydroxymethyl | |
| 1.5.1102 | 3-methoxy-6-fluorophenyl | hydroxymethyl | |
| 1.5.1103 | 3-ethoxy-6-fluorophenyl | hydroxymethyl | |
| 1.5.1104 | 3-trifluoromethoxy-6-fluorophenyl | hydroxymethyl | |
| 1.5.1105 | 3-nitro-6-fluorophenyl | hydroxymethyl | |
| 1.5.1106 | 3-fluoro-6-chlorophenyl | hydroxymethyl | |
| 1.5.1107 | 3-fluoro-6-chlorophenyl | 1-hydroxyethyl | |
| 1.5.1108 | 3-fluoro-6-chlorophenyl | 1-hydroxypropyl | |
| 1.5.1109 | 3-fluoro-6-chlorophenyl | (1-hydroxy-2-methylpropyl) | |
| 1.5.1110 | 3-fluoro-6-chlorophenyl | methoxymethyl | |
| 1.5.1111 | 3-fluoro-6-chlorophenyl | 2-methoxyethyl | |

TABLE 1.5-continued

Inventive compounds of the general formula (I) in which W* is COOH, $R^1$ and $R^2$ are each hydrogen, and aryl is the radical.

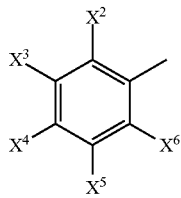

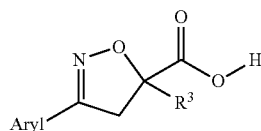

| No. | Aryl | $R^3$ | Physical data |
|---|---|---|---|
| 1.5.1112 | 3,6-dichlorophenyl | hydroxymethyl | |
| 1.5.1113 | 3,6-dichlorophenyl | 1-hydroxyethyl | |
| 1.5.1114 | 3,6-dichlorophenyl | 1-hydroxypropyl | |
| 1.5.1115 | 3,6-dichlorophenyl | (1-hydroxy-2-methylpropyl) | |
| 1.5.1116 | 3,6-dichlorophenyl | methoxymethyl | |
| 1.5.1117 | 3,6-dichlorophenyl | 2-methoxyethyl | |
| 1.5.1118 | 3-bromo-6-chlorophenyl | hydroxymethyl | |
| 1.5.1119 | 3-methyl-6-chlorophenyl | hydroxymethyl | |
| 1.5.1120 | 3-cyclopropyl-6-chlorophenyl | hydroxymethyl | |
| 1.5.1121 | 3-cyano-6-chlorophenyl | hydroxymethyl | |
| 1.5.1122 | 3-trifluoromethyl-6-chlorophenyl | hydroxymethyl | |
| 1.5.1123 | 3-methoxy-6-chlorophenyl | hydroxymethyl | |
| 1.5.1124 | 3-ethoxy-6-chlorophenyl | hydroxymethyl | |
| 1.5.1125 | 3-trifluoromethoxy-6-chlorophenyl | hydroxymethyl | |
| 1.5.1126 | 3-nitro-6-chlorophenyl | hydroxymethyl | |
| 1.5.1127 | 3-fluoro-6-bromophenyl | hydroxymethyl | |
| 1.5.1128 | 3-chloro-6-bromophenyl | hydroxymethyl | |
| 1.5.1129 | 3,6-dibromophenyl | hydroxymethyl | |
| 1.5.1130 | 3-methyl-6-bromophenyl | hydroxymethyl | |
| 1.5.1131 | 3-cyclopropyl-6-bromophenyl | hydroxymethyl | |
| 1.5.1132 | 3-cyano-6-bromophenyl | hydroxymethyl | |
| 1.5.1133 | 3-trifluoromethyl-6-bromophenyl | hydroxymethyl | |
| 1.5.1134 | 3-methoxy-6-phenyl | hydroxymethyl | |
| 1.5.1135 | 3-ethoxy-6-bromophenyl | hydroxymethyl | |
| 1.5.1136 | 3-trifluoromethoxy-6-bromophenyl | hydroxymethyl | |
| 1.5.1137 | 3-nitro-6-bromophenyl | hydroxymethyl | |
| 1.5.1138 | 3-fluoro-6-iodophenyl | hydroxymethyl | |
| 1.5.1139 | 3-chloro-6-iodophenyl | hydroxymethyl | |
| 1.5.1140 | 3-bromo-6-iodophenyl | hydroxymethyl | |
| 1.5.1141 | 3-methyl-6-iodophenyl | hydroxymethyl | |
| 1.5.1142 | 3-cyclopropyl-6-iodophenyl | hydroxymethyl | |
| 1.5.1143 | 3-cyano-6-iodophenyl | hydroxymethyl | |
| 1.5.1144 | 3-trifluoromethyl-6-iodophenyl | hydroxymethyl | |
| 1.5.1145 | 3-methoxy-6-iodophenyl | hydroxymethyl | |
| 1.5.1146 | 3-ethoxy-6-iodophenyl | hydroxymethyl | |
| 1.5.1147 | 3-trifluoromethoxy-6-iodophenyl | hydroxymethyl | |
| 1.5.1148 | 3-nitro-6-iodophenyl | hydroxymethyl | |
| 1.5.1149 | 3-fluoro-6-methylphenyl | hydroxymethyl | |
| 1.5.1150 | 3-chloro-6-methylphenyl | hydroxymethyl | |
| 1.5.1151 | 3-bromo-6-methylphenyl | hydroxymethyl | |
| 1.5.1152 | 3,6-dimethylphenyl | hydroxymethyl | |
| 1.5.1153 | 3-ethyl-6-methylphenyl | hydroxymethyl | |
| 1.5.1154 | 3-cyclopropyl-6-methylphenyl | hydroxymethyl | |
| 1.5.1155 | 3-cyano-6-methylphenyl | hydroxymethyl | |
| 1.5.1156 | 3-trifluoromethyl-6-methylphenyl | hydroxymethyl | |
| 1.5.1157 | 3-methoxy-6-methylphenyl | hydroxymethyl | |
| 1.5.1158 | 3-ethoxy-6-methylphenyl | hydroxymethyl | |
| 1.5.1159 | 3-trifluoromethoxy-6-methylphenyl | hydroxymethyl | |
| 1.5.1160 | 3-nitro-6-methylphenyl | hydroxymethyl | |
| 1.5.1161 | 3-fluoro-6-ethylphenyl | hydroxymethyl | |
| 1.5.1162 | 3-chloro-6-ethylphenyl | hydroxymethyl | |
| 1.5.1163 | 3-bromo-6-ethylphenyl | hydroxymethyl | |
| 1.5.1164 | 3-methyl-6-ethylphenyl | hydroxymethyl | |
| 1.5.1165 | 3,6-diethylphenyl | hydroxymethyl | |
| 1.5.1166 | 3-cyclopropyl-6-ethylphenyl | hydroxymethyl | |
| 1.5.1167 | 3-cyano-6-ethylphenyl | hydroxymethyl | |

TABLE 1.5-continued

Inventive compounds of the general formula (I) in which W* is COOH, $R^1$ and $R^2$ are each hydrogen, and aryl is the radical.

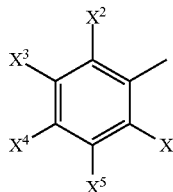

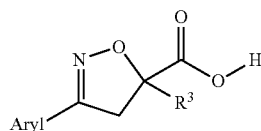

| No. | Aryl | $R^3$ | Physical data |
|---|---|---|---|
| 1.5.1168 | 3-trifluoromethyl-6-ethylphenyl | hydroxymethyl | |
| 1.5.1169 | 3-methoxy-6-ethylphenyl | hydroxymethyl | |
| 1.5.1170 | 3-ethoxy-6-ethylphenyl | hydroxymethyl | |
| 1.5.1171 | 3-trifluoromethoxy-6-ethylphenyl | hydroxymethyl | |
| 1.5.1172 | 3-nitro-6-ethylphenyl | hydroxymethyl | |
| 1.5.1173 | 3-fluoro-6-propylphenyl | hydroxymethyl | |
| 1.5.1174 | 3-chloro-6-propylphenyl | hydroxymethyl | |
| 1.5.1175 | 3-bromo-6-propylphenyl | hydroxymethyl | |
| 1.5.1176 | 3-methyl-6-propylphenyl | hydroxymethyl | |
| 1.5.1177 | 3-methyl-6-propylphenyl | hydroxymethyl | |
| 1.5.1178 | 3-cyclopropyl-6-propylphenyl | hydroxymethyl | |
| 1.5.1179 | 3-cyano-6-propylphenyl | hydroxymethyl | |
| 1.5.1180 | 3-trifluoromethyl-6-propylphenyl | hydroxymethyl | |
| 1.5.1181 | 3-methoxy-6-propylphenyl | hydroxymethyl | |
| 1.5.1182 | 3-ethoxy-6-propylphenyl | hydroxymethyl | |
| 1.5.1183 | 3-trifluoromethoxy-6-propylphenyl | hydroxymethyl | |
| 1.5.1184 | 3-nitro-6-propylphenyl | hydroxymethyl | |
| 1.5.1185 | 3-fluoro-6-isopropylphenyl | hydroxymethyl | |
| 1.5.1186 | 3-chloro-6-isopropylphenyl | hydroxymethyl | |
| 1.5.1187 | 3-bromo-6-isopropylphenyl | hydroxymethyl | |
| 1.5.1188 | 3-methyl-6-isopropylphenyl | hydroxymethyl | |
| 1.5.1189 | 3-cyclopropyl-6-isopropylphenyl | hydroxymethyl | |
| 1.5.1190 | 3-cyano-6-isopropylphenyl | hydroxymethyl | |
| 1.5.1191 | 3-trifluoromethyl-6-isopropylphenyl | hydroxymethyl | |
| 1.5.1192 | 3-ethoxy-6-isopropylphenyl | hydroxymethyl | |
| 1.5.1193 | 3-trifluoromethoxy-6-isopropylphenyl | hydroxymethyl | |
| 1.5.1194 | 3-nitro-6-isopropylphenyl | hydroxymethyl | |
| 1.5.1195 | 3-fluoro-6-tert-butylphenyl | hydroxymethyl | |
| 1.5.1196 | 3-chloro-6-tert-butylphenyl | hydroxymethyl | |
| 1.5.1197 | 3-bromo-6-tert-butylphenyl | hydroxymethyl | |
| 1.5.1198 | 3-methyl-6-tert-butylphenyl | hydroxymethyl | |
| 1.5.1199 | 3-cyclopropyl-6-tert-butylphenyl | hydroxymethyl | |
| 1.5.1200 | 3-cyano-6-tert-butylphenyl | hydroxymethyl | |
| 1.5.1201 | 3-trifluoromethyl-6-tert-butylphenyl | hydroxymethyl | |
| 1.5.1202 | 3-methoxy-6-tert-butylphenyl | hydroxymethyl | |
| 1.5.1203 | 3-ethoxy-6-tert-butylphenyl | hydroxymethyl | |
| 1.5.1204 | 3-trifluoromethoxy-6-tert-butylphenyl | hydroxymethyl | |
| 1.5.1205 | 3-nitro-6-tert-butylphenyl | hydroxymethyl | |
| 1.5.1206 | 3-fluoro-6-cyclopropylphenyl | hydroxymethyl | |
| 1.5.1207 | 3-chloro-6-cyclopropylphenyl | hydroxymethyl | |
| 1.5.1208 | 3-bromo-6-cyclopropylphenyl | hydroxymethyl | |
| 1.5.1209 | 3-methyl-6-cyclopropylphenyl | hydroxymethyl | |
| 1.5.1210 | 3-cyclopropyl-6-cyclopropyl phenyl | hydroxymethyl | |
| 1.5.1211 | 3-cyano-6-cyclopropylphenyl | hydroxymethyl | |
| 1.5.1212 | 3-trifluoromethyl-6-cyclopropylphenyl | hydroxymethyl | |
| 1.5.1213 | 3-methoxy-6-cyclopropylphenyl | hydroxymethyl | |
| 1.5.1214 | 3-ethoxy-6-cyclopropylphenyl | hydroxymethyl | |
| 1.5.1215 | 3-trifluoromethoxy-6-cyclopropylphenyl | hydroxymethyl | |
| 1.5.1216 | 3-fluoro-6-methoxycarbonylphenyl | hydroxymethyl | |
| 1.5.1217 | 3-chloro-6-methoxycarbonylphenyl | hydroxymethyl | |
| 1.5.1218 | 3-bromo-6-methoxycarbonylphenyl | hydroxymethyl | |
| 1.5.1219 | 3-methyl-6-methoxycarbonylphenyl | hydroxymethyl | |
| 1.5.1220 | 3-cyclopropyl-6-methoxycarbonylphenyl | hydroxymethyl | |
| 1.5.1221 | 3-cyano-6-methoxycarbonylphenyl | hydroxymethyl | |
| 1.5.1222 | 3-trifluoromethyl-6-methoxycarbonyl-phenyl | hydroxymethyl | |
| 1.5.1223 | 3-methoxy-6-methoxycarbonylphenyl | hydroxymethyl | |

TABLE 1.5-continued

Inventive compounds of the general formula (I) in which W* is COOH, $R^1$ and $R^2$ are each hydrogen, and aryl is the radical.

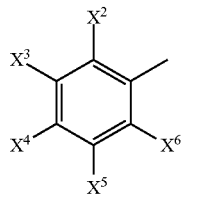

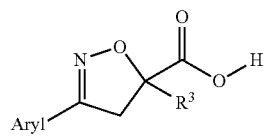

| No. | Aryl | $R^3$ | Physical data |
|---|---|---|---|
| 1.5.1224 | 3-ethoxy-6-methoxycarbonylphenyl | hydroxymethyl | |
| 1.5.1225 | 3-trifluoromethoxy-6-methoxycarbonyl-phenyl | hydroxymethyl | |
| 1.5.1226 | 3-nitro-6-methoxycarbonylphenyl | hydroxymethyl | |
| 1.5.1227 | 3-fluoro-6-cyanophenyl | hydroxymethyl | |
| 1.5.1228 | 3-chloro-6-cyanophenyl | hydroxymethyl | |
| 1.5.1229 | 3-bromo-6-cyanophenyl | hydroxymethyl | |
| 1.5.1230 | 3-methyl-6-cyanophenyl | hydroxymethyl | |
| 1.5.1231 | 3-cyclopropyl-6-cyanophenyl | hydroxymethyl | |
| 1.5.1232 | 3-cyano-6-cyanophenyl | hydroxymethyl | |
| 1.5.1233 | 3-trifluoromethyl-6-cyanophenyl | hydroxymethyl | |
| 1.5.1234 | 3-methoxy-6-cyanophenyl | hydroxymethyl | |
| 1.5.1235 | 3-ethoxy-6-cyanophenyl | hydroxymethyl | |
| 1.5.1236 | 3-trifluoromethoxy-6-cyanophenyl | hydroxymethyl | |
| 1.5.1237 | 3-nitro-6-cyanophenyl | hydroxymethyl | |
| 1.5.1238 | 3-fluoro-6-methoxyphenyl | hydroxymethyl | |
| 1.5.1239 | 3-chloro-6-methoxyphenyl | hydroxymethyl | |
| 1.5.1240 | 3-bromo-6-methoxyphenyl | hydroxymethyl | |
| 1.5.1241 | 3-methyl-6-methoxyphenyl | hydroxymethyl | |
| 1.5.1242 | 3-cyclopropyl-6-methoxyphenyl | hydroxymethyl | |
| 1.5.1243 | 3-cyano-6-methoxyphenyl | hydroxymethyl | |
| 1.5.1244 | 3-trifluoromethyl-6-methoxyphenyl | hydroxymethyl | |
| 1.5.1245 | 3,6-dimethoxyphenyl | hydroxymethyl | |
| 1.5.1246 | 3-ethoxy-6-methoxyphenyl | hydroxymethyl | |
| 1.5.1247 | 3-trifluoromethoxy-6-methoxyphenyl | hydroxymethyl | |
| 1.5.1248 | 3-nitro-6-methoxyphenyl | hydroxymethyl | |
| 1.5.1249 | 3-fluoro-6-ethoxyphenyl | hydroxymethyl | |
| 1.5.1250 | 3-chloro-6-ethoxyphenyl | hydroxymethyl | |
| 1.5.1251 | 3-bromo-6-ethoxyphenyl | hydroxymethyl | |
| 1.5.1252 | 3-methyl-6-ethoxyphenyl | hydroxymethyl | |
| 1.5.1253 | 3-cyclopropyl-6-ethoxyphenyl | hydroxymethyl | |
| 1.5.1254 | 3-cyano-6-ethoxyphenyl | hydroxymethyl | |
| 1.5.1255 | 3-trifluoromethyl-6-ethoxyphenyl | hydroxymethyl | |
| 1.5.1256 | 3-methoxy-6-ethoxyphenyl | hydroxymethyl | |
| 1.5.1257 | 2,6-diethoxyphenyl | hydroxymethyl | |
| 1.5.1258 | 3-trifluoromethoxy-6-ethoxyphenyl | hydroxymethyl | |
| 1.5.1259 | 3-nitro-6-ethoxyphenyl | hydroxymethyl | |
| 1.5.1260 | 3-fluoro-6-isopropoxyphenyl | hydroxymethyl | |
| 1.5.1261 | 3-chloro-6-isopropoxyphenyl | hydroxymethyl | |
| 1.5.1262 | 3-bromo-6-isopropoxyphenyl | hydroxymethyl | |
| 1.5.1263 | 3-methyl-6-isopropoxyphenyl | hydroxymethyl | |
| 1.5.1264 | 3-cyclopropyl-6-isopropoxyphenyl | hydroxymethyl | |
| 1.5.1265 | 3-cyano-6-isopropoxyphenyl | hydroxymethyl | |
| 1.5.1266 | 3-trifluoromethyl-6-isopropoxyphenyl | hydroxymethyl | |
| 1.5.1267 | 3-methoxy-6-isopropoxyphenyl | hydroxymethyl | |
| 1.5.1268 | 3-ethoxy-6-isopropoxyphenyl | hydroxymethyl | |
| 1.5.1269 | 3-trifluoromethoxy-6-isopropoxyphenyl | hydroxymethyl | |
| 1.5.1270 | 3-nitro-6-isopropoxyphenyl | hydroxymethyl | |
| 1.5.1271 | 3-fluoro-6-trifluoromethoxyphenyl | hydroxymethyl | |
| 1.5.1272 | 3-chloro-6-trifluoromethoxyphenyl | hydroxymethyl | |
| 1.5.1273 | 3-bromo-6-trifluoromethoxyphenyl | hydroxymethyl | |
| 1.5.1274 | 3-methyl-6-trifluoromethoxyphenyl | hydroxymethyl | |
| 1.5.1275 | 3-cyclopropyl-6-trifluoromethoxyphenyl | hydroxymethyl | |
| 1.5.1276 | 3-cyano-6-trifluoromethoxyphenyl | hydroxymethyl | |
| 1.5.1277 | 3-trifluoromethyl-6-trifluoromethoxy-phenyl | hydroxymethyl | |
| 1.5.1278 | 3-methoxy-6-trifluoromethoxyphenyl | hydroxymethyl | |

TABLE 1.5-continued

Inventive compounds of the general formula (I) in which W* is COOH, R¹ and R² are each hydrogen, and aryl is the radical.

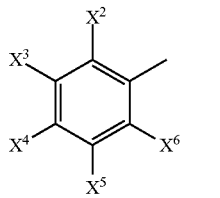

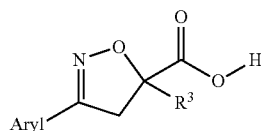

| No. | Aryl | R³ | Physical data |
|---|---|---|---|
| 1.5.1279 | 3-ethoxy-6-trifluoromethoxyphenyl | hydroxymethyl | |
| 1.5.1280 | 3,6-bis(trifluoromethoxy)phenyl | hydroxymethyl | |
| 1.5.1281 | 3-nitro-6-trifluoromethoxyphenyl | hydroxymethyl | |
| 1.5.1282 | 3-fluoro-6-difluoromethoxyphenyl | hydroxymethyl | |
| 1.5.1283 | 3-chloro-6-difluoromethoxyphenyl | hydroxymethyl | |
| 1.5.1284 | 3-bromo-6-difluoromethoxyphenyl | hydroxymethyl | |
| 1.5.1285 | 3-methyl-6-difluoromethoxyphenyl | hydroxymethyl | |
| 1.5.1286 | 3-cyclopropyl-6-difluoromethoxyphenyl | hydroxymethyl | |
| 1.5.1287 | 3-cyano-6-difluoromethoxyphenyl | hydroxymethyl | |
| 1.5.1288 | 3-trifluoromethyl-6-difluoromethoxy-phenyl | hydroxymethyl | |
| 1.5.1289 | 3-methoxy-6-difluoromethoxyphenyl | hydroxymethyl | |
| 1.5.1290 | 3-ethoxy-6-difluoromethoxyphenyl | hydroxymethyl | |
| 1.5.1291 | 3-trifluoromethoxy-6-difluoromethoxy-phenyl | hydroxymethyl | |
| 1.5.1292 | 3-nitro-6-difluoromethoxyphenyl | hydroxymethyl | |
| 1.5.1293 | 3-fluoro-6-nitrophenyl | hydroxymethyl | |
| 1.5.1294 | 3-chloro-6-nitrophenyl | hydroxymethyl | |
| 1.5.1295 | 3-bromo-6-nitrophenyl | hydroxymethyl | |
| 1.5.1296 | 3-methyl-6-nitrophenyl | hydroxymethyl | |
| 1.5.1297 | 3-cyclopropyl-6-nitrophenyl | hydroxymethyl | |
| 1.5.1298 | 3-cyano-6-nitrophenyl | hydroxymethyl | |
| 1.5.1299 | 3-trifluoromethyl-6-nitrophenyl | hydroxymethyl | |
| 1.5.1300 | 3-methoxy-6-nitrophenyl | hydroxymethyl | |
| 1.5.1301 | 3-ethoxy-6-nitrophenyl | hydroxymethyl | |
| 1.5.1302 | 3-trifluoromethoxy-6-nitrophenyl | hydroxymethyl | |
| 1.5.1303 | 3-fluoro-6-methylsulfanylphenyl | hydroxymethyl | |
| 1.5.1304 | 3-chloro-6-methylsulfanylphenyl | hydroxymethyl | |
| 1.5.1305 | 3-bromo-6-methylsulfanylphenyl | hydroxymethyl | |
| 1.5.1306 | 3-methyl-6-methylsulfanylphenyl | hydroxymethyl | |
| 1.5.1307 | 3-cyclopropyl-6-methylsulfanylphenyl | hydroxymethyl | |
| 1.5.1308 | 3-cyano-6-methylsulfanylphenyl | hydroxymethyl | |
| 1.5.1309 | 3-trifluoromethyl-6-methylsulfanylphenyl | hydroxymethyl | |
| 1.5.1310 | 3-methoxy-6-methylsulfanylphenyl | hydroxymethyl | |
| 1.5.1311 | 3-ethoxy-6-methylsulfanylphenyl | hydroxymethyl | |
| 1.5.1312 | 3-trifluoromethoxy-6-methylsulfanylphenyl | hydroxymethyl | |
| 1.5.1313 | 3-nitro-6-methylsulfanylphenyl | hydroxymethyl | |
| 1.5.1314 | 2,3,4-trifluorophenyl | hydroxymethyl | |
| 1.5.1315 | 2,3,4-trichlorophenyl | hydroxymethyl | |
| 1.5.1316 | 2,3,4-trimethylphenyl | hydroxymethyl | |
| 1.5.1317 | 2-fluoro-2-chloro-5-trifluoromethylphenyl | hydroxymethyl | |
| 1.5.1318 | 2,3,5-trifluorophenyl | hydroxymethyl | |
| 1.5.1319 | 2,3,5-trichlorophenyl | hydroxymethyl | |
| 1.5.1320 | 2,3,5-trimethylphenyl | hydroxymethyl | |
| 1.5.1321 | 2,3-dichloro-5-methoxyphenyl | hydroxymethyl | |
| 1.5.1322 | 2,3,6-trifluorophenyl | hydroxymethyl | |
| 1.5.1323 | 2,3,6-trichlorophenyl | hydroxymethyl | |
| 1.5.1324 | 2,3,6-trimethylphenyl | hydroxymethyl | |
| 1.5.1325 | 3,4,5-trifluorophenyl | hydroxymethyl | |
| 1.5.1326 | 3,4,5-trichlorophenyl | hydroxymethyl | |
| 1.5.1327 | 3,4,5-trimethylphenyl | hydroxymethyl | |
| 1.5.1328 | 3,5-dimethyl-4-fluorophenyl | hydroxymethyl | |
| 1.5.1329 | 3,5-dichloro-4-methoxyphenyl | hydroxymethyl | |
| 1.5.1330 | 3,5-difluoro-4-chlorophenyl | hydroxymethyl | |
| 1.5.1331 | 3,5-dichloro-4-hydroxyphenyl | hydroxymethyl | |
| 1.5.1332 | 3,5-trifluoromethyl-4-chlorophenyl | hydroxymethyl | |

TABLE 1.5-continued

Inventive compounds of the general formula (I) in which W* is COOH, R¹ and R² are each hydrogen, and aryl is the radical.

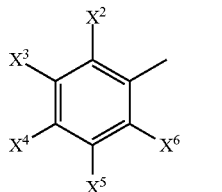

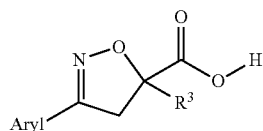

| No. | Aryl | R³ | Physical data |
|---|---|---|---|
| 1.5.1333 | 3,4,6-trifluorophenyl | hydroxymethyl | |
| 1.5.1334 | 3,4,6-trichlorophenyl | hydroxymethyl | |
| 1.5.1335 | 3,4,6-trimethylphenyl | hydroxymethyl | |
| 1.5.1336 | pentafluorophenyl | hydroxymethyl | |

TABLE 2.1

Inventive compounds of the general formula (I) in which W* is COOY, R¹ is hydrogen, and aryl is the radical.

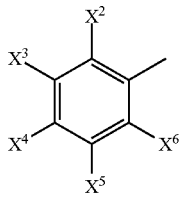

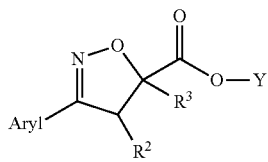

| No. | Aryl | R² | R³ | Y | Physical data |
|---|---|---|---|---|---|
| 2.1.1 | 3-fluorophenyl | H | methyl | ethyl | [CDCl$_3$] 1.31 (t, 3H); 1.71 (s, 3H); 3.6 (d, 1H); 3.85 (d, 1H); 4.25 (m, 2H); 7.10 (m, 1H); 7.40 (m, 2H). |
| 2.1.2 | 3-fluorophenyl | H | ethyl | ethyl | [CDCl$_3$] 1.00 (t, 3H); 1.31 (t, 3H); 2.05 (m, 2H); 3.20 (d, 1H); 3.80 (d, 1H); 4.25 (m, 2H); 7.11 (m, 1H); 7.40 (m, 3H). |
| 2.1.3 | 3-fluorophenyl | H | propyl | ethyl | |
| 2.1.4 | 3-fluorophenyl | H | cyclo-propyl | ethyl | |
| 2.1.5 | 3-chlorophenyl | H | methyl | ethyl | [CDCl$_3$] 1.30 (t, 3H); 1.70 (s, 3H); 3.17 (d, 1H); 3.85 (d, 1H); 4.25 (m, 2H); 7.35 (m, 2H); 7.55 (dd, 1H); 7.65 (s, 1H). |
| 2.1.6 | 3-chlorophenyl | H | ethyl | ethyl | |
| 2.1.7 | 3-chlorophenyl | H | propyl | ethyl | |
| 2.1.8 | 3-chlorophenyl | H | cyclo-propyl | ethyl | |
| 2.1.9 | 3-bromophenyl | H | methyl | methyl | |
| 2.1.10 | 3-bromophenyl | H | ethyl | ethyl | |
| 2.1.11 | 3-iodophenyl | H | methyl | ethyl | [CDCl$_3$] 1.31 (t, 3H); 1.69 (s, 3H); 3.16 (d, 1H); 3.83 (d, 1H); 4.25 (m, 2H); 7.12 (t, 1H); 7.62 (dd, 1H); 7.73 (dd, H); 7.98 d, 1H). |

TABLE 2.1-continued

Inventive compounds of the general formula (I) in which W* is COOY, $R^1$ is hydrogen, and aryl is the radical.

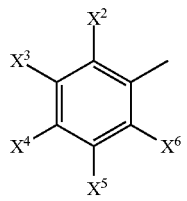

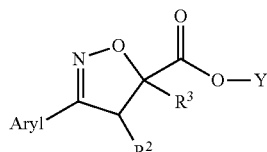

| No. | Aryl | $R^2$ | $R^3$ | Y | Physical data |
| --- | --- | --- | --- | --- | --- |
| 2.1.12 | 3-iodophenyl | H | ethyl | ethyl | |
| 2.1.13 | 3-methylphenyl | H | methyl | ethyl | [CDCl$_3$] 1.30 (t, 3H); 1.70 (s, 3H); 2.36 (s, 3H); 3.20 (d, 1H); 3.88 (d, 1H); 4.25 (m, 2H); 7.25 (mc; 2H); 7.42 (d, 1H); 7.50 (bs, 1H). |
| 2.1.14 | 3-methylphenyl | H | ethyl | ethyl | |
| 2.1.15 | 3-ethylphenyl | H | methyl | ethyl | [CDCl$_3$] 1.22 (t, 3H); 1.31 (t, 3H); 1.70 (s, 3H); 2.65 (q, 2H); 3.20 (d, 1H); 3.90 (d, 1H); 4.25 (m, 2H); 7.25 (m, 1H); 7.31 (t, 1H); 7.42 (d, 1H); 7.58 (bs, 1H). |
| 2.1.16 | 3-propylphenyl | H | methyl | ethyl | |
| 2.1.17 | 3-isopropyl-phenyl | H | methyl | ethyl | [CDCl$_3$] 1.22 (d, 6H); 1.31 (t, 3H); 2.91 (m, 1H); 3.21 (d, 1H); 3.91 (d, 1H); 4.25 (m, 2H); 7.28 (m, 1H); 7.32 t, 1H); 7.41 (d, 1H); 7.58 (bs, 1H). |
| 2.1.18 | 3-n-butylphenyl | H | methyl | ethyl | |
| 2.1.19 | 3-i-butylphenyl | H | methyl | ethyl | |
| 2.1.20 | 3-tert-butylphenyl | H | methyl | ethyl | |
| 2.1.21 | 3-cyclopropyl-phenyl | H | methyl | ethyl | |
| 2.1.22 | 3-cyclobutyl-phenyl | H | methyl | ethyl | |
| 2.1.23 | 3-cyclopentyl-phenyl | H | methyl | ethyl | |
| 2.1.24 | 3-vinylphenyl | H | methyl | ethyl | |
| 2.1.25 | 3-ethynylphenyl | H | methyl | ethyl | |
| 2.1.26 | 3-cyanophenyl | H | methyl | ethyl | [CDCl$_3$] 1.30 (t, 3H); 1.71 (s, 3H); 3.18 (d, 1H); 3.90 (d, 1H); 4.25 (m, 2H); 7.52 (m, 1H); 7.68 (m, 1H); 7.91 (m, 2H). |
| 2.1.27 | 3-trifluoro-methylphenyl | H | methyl | ethyl | [CDCl$_3$] 1.32 (t, 3H); 1.71 (s, 3H); 3.21 (d, 1H); 3.91 (m, 2H); 7.53 (t, 1H); 7.68 (d, 1H); 7.88 (m, 2H). |
| 2.1.28 | 3-difluoro-methylphenyl | H | methyl | ethyl | |
| 2.1.29 | 3-(hydroxy-carbonyl)phenyl | H | methyl | ethyl | |
| 2.1.30 | 3-(methoxy-carbonyl)phenyl | H | methyl | ethyl | [CDCl$_3$] 1.31 (t, 3H); 1.72 (s, 3H); 3.26 (d, 1H); 3.91 (d, 1H); 3.96 (s, 3H); 4.25 (m, 2H); 7.50 (m, 1H); 7.96 (d, 1H); 8.10 (d, 1H); 8.21 (s, 1H). |
| 2.1.31 | 3-(ethoxy-carbonyl)phenyl | H | methyl | ethyl | |
| 2.1.32 | 3-hydroxy-methylphenyl | H | methyl | ethyl | |
| 2.1.33 | 3-acetylphenyl | H | methyl | ethyl | [CDCl$_3$] 1.32 (t, 3H); 1.72 (s, 3H); 2.63 (s, 3H); 3.24 (d, 1H); 3.93 (d, 1H); 4.25 (q, 2H); 7.52 /t, 1H); 7.90 (d, 1H); 8.0 (d, 1H); 8.20 (s, 1H). |

TABLE 2.1-continued

Inventive compounds of the general formula (I) in which W* is COOY, $R^1$ is hydrogen, and aryl is the radical.

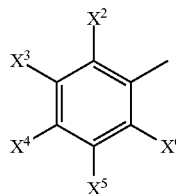

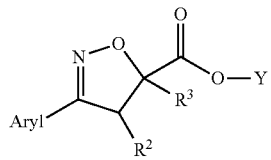

| No. | Aryl | $R^2$ | $R^3$ | Y | Physical data |
|---|---|---|---|---|---|
| 2.1.34 | 3-carbamoyl-phenyl | H | methyl | ethyl | [CDCl$_3$] 1.31 (t, 3H); 1.70 (s, 3H); 3.21 (d, 1H); 3.86 (d, 1h), 4.25 (dq; 2H); 6.52 (bs, 1H); 7.28-7.42 (m, 3H); 7.70 (s, 1H). |
| 2.1.35 | 3-hydroxyphenyl | H | methyl | ethyl | [CDCl$_3$] 1.31 (t, 3H); 1.70 (s, 3H); 3.21 (d, 1H); 3.85 (d, 1H); 4.26 (m, 2H); 5.70 (bs, 1H); 6.92 (dd, 1H); 7.15 (d, 1H); 7.28 (m, 2H). |
| 2.1.36 | 3-methoxy-phenyl | H | methyl | ethyl | [DMSO] 1.21 (t, 3H); 1.59 (s, 3H); 3.25-3.45 (m, 2H); 3.80 (s, 3H); 4.15 (q, 2H); 7.05 (m, 1H); 7.22 (m, 2H); 7.48 (m, 1H). |
| 2.1.37 | 3-ethoxyphenyl | H | methyl | ethyl | [CDCl$_3$] 1.31 (t, 3H); 1.42 (t, 3H); 1.70 (s, 3H); 3.20 (d, 1H); 3.88 (d, 3H); 4.08 (q, 2H); 4.25 (m, 2H); 6.95 (dd, 1H); 7.15 (dd, 1H); 7.31 (mc, 2H). |
| 2.1.38 | 3-propyloxy-phenyl | H | methyl | ethyl | |
| 2.1.39 | 3-isopropyloxy-phenyl | H | methyl | ethyl | [CDCl$_3$] 1.31 (m, 9H); 1.70 (s, 3H); 3.19 (d, 1H); 3.87 (d, 1H); 4.25 (m, 2H); 4.58 (m, 1H); 6.92 (dd, 1H); 7.15 (d, 1H); 7.29 (mc, 2H). |
| 2.1.40 | 3-n-butyloxyphenyl | H | methyl | ethyl | |
| 2.1.41 | 3-i-butyloxyphenyl | H | methyl | ethyl | |
| 2.1.42 | 3-t-butyloxyphenyl | H | methyl | ethyl | |
| 2.1.43 | 3-difluoro-methoxyphenyl | H | methyl | ethyl | [CDCl$_3$] 1.30 (t, 3H); 1.71 (s, 3H); 3.2 (d, 1H); 3.89 (d, 1H); 4.25 (m, 2H); 6.51 (t, 3H); 7.19 (d, 1H); 7.43 (m, 3H). |
| 2.1.44 | 3-trifluoro-methoxyphenyl | H | methyl | ethyl | [CDCl$_3$] 1.31 /t, 3H); 1.71 (s, 3H); 3.20 (d, 1H); 3.91 (d, 1H); 4.25 (m, 2H); 2.25 (d, 1H); 7.42 (t, 1H); 7.55 (mc, 2H). |
| 2.1.45 | 3-(2,2,2-trifluoroethoxy)-phenyl | H | methyl | ethyl | |
| 2.1.46 | 3-(2-chloro-ethoxy)phenyl | H | methyl | ethyl | |
| 2.1.47 | 3-(2-hydroxy-ethoxy)phenyl | H | methyl | ethyl | |
| 2.1.48 | 3-(2-methoxy-ethoxy)phenyl | H | methyl | ethyl | [CDCl$_3$] 1.31 (t, 3H); 1.70 (s, 3H), 3.16 (d, 1H); 3.45 (s, 3H); 3.75 (dd, 2H); 3.85 (d, 1H); 4.13 (dd, 2H); 4.25 (m, 2H); 7.00 (dd, 1H); 7.20 (d, 1H); 7.30 (mc, 2H). |
| 2.1.49 | 3-[(tert-butoxy-carbonyl)oxy]-phenyl | H | methyl | ethyl | [CDCl$_3$] 1.31 (t, 3H); 1.58 (s, 9H); 1.70 (s, 3H); 3.17 (d, 1H); 3.82 (d, 1H); 4.25 (q, 2H); 7.22 (dd, 1H); 7.40 (t, 1H); 7.50 (mc, 2H). |

TABLE 2.1-continued

Inventive compounds of the general formula (I) in which W* is COOY, R¹ is hydrogen, and aryl is the radical.

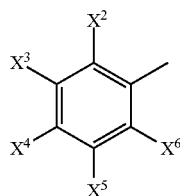

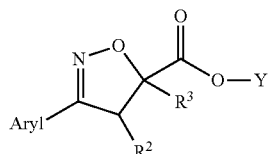

| No. | Aryl | R² | R³ | Y | Physical data |
|---|---|---|---|---|---|
| 2.1.50 | 3-nitrophenyl | H | methyl | ethyl | [CDCl₃] 1.32 (t, 3H); 1.72 (s, 3H); 3.25 (d, 1H); 3.95 (d, 1H); 4.30 (m, 2H); 7.60 (t, 1H); 8.07 (dd, 1H); 8.26 (dd, 1H); 8.41 (d, 1H). |
| 2.1.51 | 3-acetoxyphenyl | H | methyl | ethyl | [CDCl₃] 1.30 (t, 3H); 1.71 (s, 3H); 2.30 (s, 3H); 3.18 (d, 1H); 3.85 (d, 1H); 4.25 (m, 2H); 7.15 (dd, 1H); 7.40 (mc, 2H); 7.51 (dd, 1H). |
| 2.1.52 | {3-[(tert-butoxycarbonyl)amino]phenyl} | H | methyl | ethyl | |
| 2.1.53 | 3-methyl-sulfanylphenyl | H | methyl | ethyl | |
| 2.1.54 | 3-ethyl-sulfanylphenyl | H | methyl | ethyl | |
| 2.1.55 | 3-(pentafluoro-lambda⁶-sulfanyl)phenyl | H | methyl | ethyl | |
| 2.1.56 | 2,3-difluoro-phenyl | H | methyl | ethyl | [CDCl₃] 1.31 (t, 3H); 1.72 (s, 3H); 3.33 (d, 1H); 3.95 (d, 1H); 4.36 (q, 2H); 7.12 (m, 1H); 7.23 (m, 1H); 7.53 (m, 1H). |
| 2.1.57 | 2,3-difluoro-phenyl | H | ethyl | ethyl | |
| 2.1.58 | 2,3-difluoro-phenyl | H | propyl | ethyl | |
| 2.1.59 | 2,3-difluoro-phenyl | H | cyclo-propyl | ethyl | |
| 2.1.60 | 2-chloro-3-fluorophenyl | H | methyl | ethyl | |
| 2.1.61 | 2-bromo-3-fluorophenyl | H | methyl | ethyl | |
| 2.1.62 | 2-methyl-3-fluorophenyl | H | methyl | ethyl | |
| 2.1.63 | 2-ethyl-3-fluorophenyl | H | methyl | ethyl | |
| 2.1.64 | 2-cyclopropyl-3-fluorophenyl | H | methyl | ethyl | |
| 2.1.65 | 2-vinyl-3-fluorophenyl | H | methyl | ethyl | |
| 2.1.66 | 2-ethynyl-3-fluorophenyl | H | methyl | ethyl | |
| 2.1.67 | 2-cyano-3-fluorophenyl | H | methyl | ethyl | |
| 2.1.68 | 2-methoxy-3-fluorophenyl | H | methyl | ethyl | |
| 2.1.69 | 2-ethoxy-3-fluorophenyl | H | methyl | ethyl | |
| 2.1.70 | 2-trifluoro-methoxy-3-fluorophenyl | H | methyl | ethyl | |
| 2.1.71 | 2-nitro-3-fluorophenyl | H | methyl | ethyl | |
| 2.1.72 | 2-fluoro-3-chlorophenyl | H | methyl | ethyl | |

TABLE 2.1-continued

Inventive compounds of the general formula (I) in which W* is COOY, R¹ is hydrogen, and aryl is the radical.

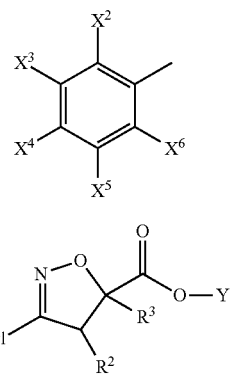

| No. | Aryl | R² | R³ | Y | Physical data |
|---|---|---|---|---|---|
| 2.1.73 | 2,3-dichloro-phenyl | H | methyl | ethyl | [CDCl₃] 1.32 (t, 3H), 1.73 (s, 3H), 3.39 (d, 1H), 3.92 (d, 1H), 4.28 (m, 2H), 7.25 (m, 1H), 7.51 (m, 2H) |
| 2.1.74 | 2,3-dichloro-phenyl | H | ethyl | ethyl | |
| 2.1.75 | 2,3-dichloro-phenyl | H | propyl | ethyl | |
| 2.1.76 | 2,3-dichloro-phenyl | H | cyclo-propyl | ethyl | |
| 2.1.77 | 2-bromo-3-chlorophenyl | H | methyl | ethyl | |
| 2.1.78 | 2-methyl-3-chlorophenyl | H | methyl | ethyl | |
| 2.1.79 | 2-ethyl-3-chlorophenyl | H | methyl | ethyl | |
| 2.1.80 | 2-cyclopropyl-3-chlorophenyl | H | methyl | ethyl | |
| 2.1.81 | 2-vinyl-3-chlorophenyl | H | methyl | ethyl | |
| 2.1.82 | 2-ethynyl-3-chlorophenyl | H | methyl | ethyl | |
| 2.1.83 | 2-cyano-3-chlorophenyl | H | methyl | ethyl | |
| 2.1.84 | 2-trifluoro-methyl-2-chlorophenyl | H | methyl | ethyl | |
| 2.1.85 | 2-methoxy-3-chlorophenyl | H | methyl | ethyl | |
| 2.1.86 | 2-ethoxy-3-chlorophenyl | H | methyl | ethyl | |
| 2.1.87 | 2-trifluoro-methoxy-3-chlorophenyl | H | methyl | ethyl | |
| 2.1.88 | 2-nitro-3-chlorophenyl | H | methyl | ethyl | |
| 2.1.89 | 2-fluoro-3-bromophenyl | H | methyl | ethyl | |
| 2.1.90 | 2-chloro-3-bromophenyl | H | methyl | ethyl | |
| 2.1.91 | 2,3-dibromo-phenyl | H | methyl | ethyl | |
| 2.1.92 | 2-methyl-3-bromophenyl | H | methyl | ethyl | |
| 2.1.93 | 2-ethyl-3-bromophenyl | H | methyl | ethyl | |
| 2.1.94 | 2-cyclopropyl-3-bromophenyl | H | methyl | ethyl | |
| 2.1.95 | 2-vinyl-3-bromophenyl | H | methyl | ethyl | |
| 2.1.96 | 2-ethynyl-3-bromophenyl | H | methyl | ethyl | |
| 2.1.97 | 2-cyano-3-bromophenyl | H | methyl | ethyl | |
| 2.1.98 | 2-trifluoro-methyl-3-bromophenyl | H | methyl | ethyl | |

TABLE 2.1-continued

Inventive compounds of the general formula (I) in which W* is COOY, R¹ is hydrogen, and aryl is the radical.

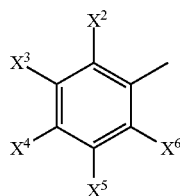

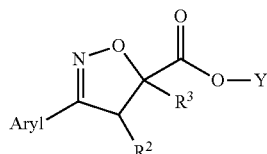

| No. | Aryl | R² | R³ | Y | Physical data |
|---|---|---|---|---|---|
| 2.1.99 | 2-methoxy-3-phenyl | H | methyl | ethyl | |
| 2.1.100 | 2-ethoxy-3-bromophenyl | H | methyl | ethyl | |
| 2.1.101 | 2-trifluoro-methoxy-3-bromophenyl | H | methyl | ethyl | |
| 2.1.102 | 2-nitro-3-bromophenyl | H | methyl | ethyl | |
| 2.1.103 | 2-fluoro-3-iodophenyl | H | methyl | ethyl | |
| 2.1.104 | 2-chloro-3-iodophenyl | H | methyl | ethyl | |
| 2.1.105 | 2-bromo-3-iodophenyl | H | methyl | ethyl | |
| 2.1.106 | 2-methyl-3-iodophenyl | H | methyl | ethyl | |
| 2.1.107 | 2-ethyl-3-iodophenyl | H | methyl | ethyl | |
| 2.1.108 | 2-cyclopropyl-3-iodophenyl | H | methyl | ethyl | |
| 2.1.109 | 2-vinyl-3-iodophenyl | H | methyl | ethyl | |
| 2.1.110 | 2-ethynyl-3-iodophenyl | H | methyl | ethyl | |
| 2.1.111 | 2-cyano-3-iodophenyl | H | methyl | ethyl | |
| 2.1.112 | 2-trifluoro-methyl-3-iodophenyl | H | methyl | ethyl | |
| 2.1.113 | 2-methoxy-3-iodophenyl | H | methyl | ethyl | |
| 2.1.114 | 2-ethoxy-3-iodophenyl | H | methyl | ethyl | |
| 2.1.115 | 2-trifluoro-methoxy-3-iodophenyl | H | methyl | ethyl | |
| 2.1.116 | 2-nitro-3-iodophenyl | H | methyl | ethyl | |
| 2.1.117 | 2-fluoro-3-methylphenyl | H | methyl | ethyl | |
| 2.1.118 | 2-fluoro-3-methylphenyl | H | ethyl | ethyl | |
| 2.1.119 | 2-fluoro-3-methylphenyl | H | propyl | ethyl | |
| 2.1.120 | 2-fluoro-3-methylphenyl | H | cyclo-propyl | ethyl | |
| 2.1.121 | 2-chloro-3-methylphenyl | H | methyl | ethyl | |
| 2.1.122 | 2-chloro-3-methylphenyl | H | ethyl | ethyl | |
| 2.1.123 | 2-chloro-3-methylphenyl | H | propyl | ethyl | |
| 2.1.124 | 2-chloro-3-methylphenyl | H | cyclo-propyl | ethyl | |
| 2.1.125 | 2-bromo-3-methylphenyl | H | methyl | ethyl | |

TABLE 2.1-continued

Inventive compounds of the general formula (I) in which W* is COOY, R¹ is hydrogen, and aryl is the radical.

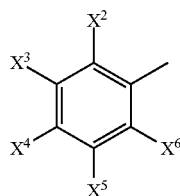

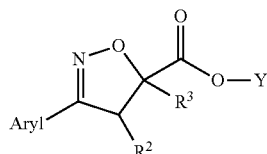

| No. | Aryl | R² | R³ | Y | Physical data |
|---|---|---|---|---|---|
| 2.1.126 | 2,3-dimethyl-phenyl | H | methyl | ethyl | |
| 2.1.127 | 2,3-dimethyl-phenyl | H | ethyl | ethyl | |
| 2.1.128 | 2,3-dimethyl-phenyl | H | propyl | ethyl | |
| 2.1.129 | 2,3-dimethyl-phenyl | H | cyclo-propyl | ethyl | |
| 2.1.130 | 2-ethyl-3-methylphenyl | H | methyl | ethyl | |
| 2.1.131 | 2-cyclopropyl-3-methylphenyl | H | methyl | ethyl | |
| 2.1.132 | 2-vinyl-3-methylphenyl | H | methyl | ethyl | |
| 2.1.133 | 2-ethynyl-3-methylphenyl | H | methyl | ethyl | |
| 2.1.134 | 2-cyano-3-methylphenyl | H | methyl | ethyl | |
| 2.1.135 | 2-trifluoro-methyl-3-methylphenyl | H | methyl | ethyl | |
| 2.1.136 | 2-methoxy-3-methylphenyl | H | methyl | ethyl | |
| 2.1.137 | 2-ethoxy-3-methylphenyl | H | methyl | ethyl | |
| 2.1.138 | 2-trifluoro-methoxy-3-methylphenyl | H | methyl | ethyl | |
| 2.1.139 | 2-nitro-3-methylphenyl | H | methyl | ethyl | |
| 2.1.140 | 2-fluoro-3-ethylphenyl | H | methyl | ethyl | |
| 2.1.141 | 2-chloro-3-ethylphenyl | H | methyl | ethyl | |
| 2.1.142 | 2-bromo-3-ethylphenyl | H | methyl | ethyl | |
| 2.1.143 | 2-methyl-3-ethylphenyl | H | methyl | ethyl | |
| 2.1.144 | 2,3-diethyl-phenyl | H | methyl | ethyl | |
| 2.1.145 | 2-cyclopropyl-3-ethylphenyl | H | methyl | ethyl | |
| 2.1.146 | 2-vinyl-3-ethylphenyl | H | methyl | ethyl | |
| 2.1.147 | 2-ethynyl-3-ethylphenyl | H | methyl | ethyl | |
| 2.1.148 | 2-cyano-3-ethylphenyl | H | methyl | ethyl | |
| 2.1.149 | 2-trifluoro-methyl-3-ethylphenyl | H | methyl | ethyl | |
| 2.1.150 | 2-methoxy-3-ethylphenyl | H | methyl | ethyl | |
| 2.1.151 | 2-ethoxy-3-ethylphenyl | H | methyl | ethyl | |

TABLE 2.1-continued

Inventive compounds of the general formula (I) in which W* is COOY, R¹ is hydrogen, and aryl is the radical.

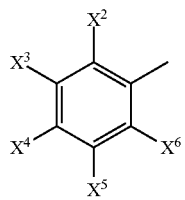

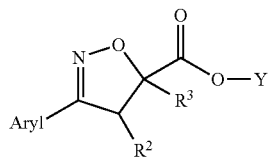

| No. | Aryl | R² | R³ | Y | Physical data |
|---|---|---|---|---|---|
| 2.1.152 | 2-trifluoromethoxy-3-ethylphenyl | H | methyl | ethyl | |
| 2.1.153 | 2-nitro-3-ethylphenyl | H | methyl | ethyl | |
| 2.1.154 | 2-fluoro-3-propylphenyl | H | methyl | ethyl | |
| 2.1.155 | 2-chloro-3-propylphenyl | H | methyl | ethyl | |
| 2.1.156 | 2-bromo-3-propylphenyl | H | methyl | ethyl | |
| 2.1.157 | 2-methyl-3-propylphenyl | H | methyl | ethyl | |
| 2.1.158 | 2-methyl-3-propylphenyl | H | methyl | ethyl | |
| 2.1.159 | 2-cyclopropyl-3-propylphenyl | H | methyl | ethyl | |
| 2.1.160 | 2-vinyl-3-propylphenyl | H | methyl | ethyl | |
| 2.1.161 | 2-ethynyl-3propylphenyl | H | methyl | ethyl | |
| 2.1.162 | 2-cyano-3-propylphenyl | H | methyl | ethyl | |
| 2.1.163 | 2-trifluoromethyl-3-propylphenyl | H | methyl | ethyl | |
| 2.1.164 | 2-methoxy-3-propylphenyl | H | methyl | ethyl | |
| 2.1.165 | 2-ethoxy-3-propylphenyl | H | methyl | ethyl | |
| 2.1.166 | 2-trifluoromethoxy-3-propylphenyl | H | methyl | ethyl | |
| 2.1.167 | 2-nitro-3-propylphenyl | H | methyl | ethyl | |
| 2.1.168 | 2-fluoro-3-isopropylphenyl | H | methyl | ethyl | |
| 2.1.169 | 2-chloro-3-isopropylphenyl | H | methyl | ethyl | |
| 2.1.170 | 2-bomo-3-isopropylphenyl | H | methyl | ethyl | |
| 2.1.171 | 2-methyl-3-isopropylphenyl | H | methyl | ethyl | |
| 2.1.172 | 2-ethyl-3-isopropylphenyl | H | methyl | ethyl | |
| 2.1.173 | 2-cyclopropyl-3-isopropylphenyl | H | methyl | ethyl | |
| 2.1.174 | 2-vinyl-3-isopropylphenyl | H | methyl | ethyl | |
| 2.1.175 | 2-ethynyl-3-isopropylphenyl | H | methyl | ethyl | |
| 2.1.176 | 2-cyano-3-isopropylphenyl | H | methyl | ethyl | |

TABLE 2.1-continued

Inventive compounds of the general formula (I) in which W* is COOY, $R^1$ is hydrogen, and aryl is the radical.

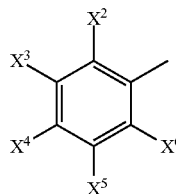

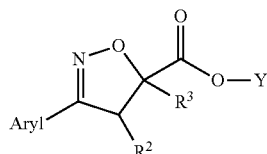

| No. | Aryl | $R^2$ | $R^3$ | Y | Physical data |
|---|---|---|---|---|---|
| 2.1.177 | 2-trifluoro-methyl-3-isopropylphenyl | H | methyl | ethyl | |
| 2.1.178 | 2-methoxy-3-isopropylphenyl | H | methyl | ethyl | |
| 2.1.179 | 2-thoxy-3-isopropylphenyl | H | methyl | ethyl | |
| 2.1.180 | 2-trifluoro-methoxy-3-isopropylphenyl | H | methyl | ethyl | |
| 2.1.181 | 2-nitro-3-isopropylphenyl | H | methyl | ethyl | |
| 2.1.182 | 2-fluoro-3-tert-butylphenyl | H | methyl | ethyl | |
| 2.1.183 | 2-chloro-3-tert-butylphenyl | H | methyl | ethyl | |
| 2.1.184 | 2-bromo-3-tert-butylphenyl | H | methyl | ethyl | |
| 2.1.185 | 2-methyl-3-tert-butylphenyl | H | methyl | ethyl | |
| 2.1.186 | 2-ethyl-3-tert-butylphenyl | H | methyl | ethyl | |
| 2.1.187 | 2-cyclopropyl-3-tert-butylphenyl | H | methyl | ethyl | |
| 2.1.188 | 2-vinyl-3-tert-butylphenyl | H | methyl | ethyl | |
| 2.1.189 | 2-ethynyl-3-tert-butylphenyl | H | methyl | ethyl | |
| 2.1.190 | 2-cyano-3-tert-butylphenyl | H | methyl | ethyl | |
| 2.1.191 | 2-trifluoro-methyl-3-tert-butylphenyl | H | methyl | ethyl | |
| 2.1.192 | 2-methoxy-3-tert-butylphenyl | H | methyl | ethyl | |
| 2.1.193 | 2-ethoxy-3-tert-butylphenyl | H | methyl | ethyl | |
| 2.1.194 | 2-trifluoro-methoxy-3-tert-butylphenyl | H | methyl | ethyl | |
| 2.1.195 | 2-nitro-3-tert-butylphenyl | H | methyl | ethyl | |
| 2.1.196 | 2-fluoro-3-hydroxymethyl-phenyl | H | methyl | ethyl | |
| 2.1.197 | 2-chloro-3-hydroxymethyl-phenyl | H | methyl | ethyl | |
| 2.1.198 | 2-bromo-3-hydroxymethyl-phenyl | H | methyl | ethyl | |
| 2.1.199 | 2-methyl-3-hydroxymethyl-phenyl | H | methyl | ethyl | |
| 2.1.200 | 2-ethyl-3-hydroxymethyl-phenyl | H | methyl | ethyl | |

TABLE 2.1-continued

Inventive compounds of the general formula (I) in which W* is COOY, R¹ is hydrogen, and aryl is the radical.

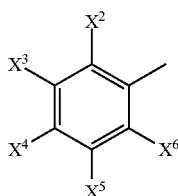

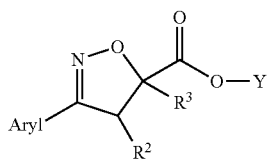

| No. | Aryl | R² | R³ | Y | Physical data |
|---|---|---|---|---|---|
| 2.1.201 | 2-cyclopropyl-3-hydroxymethyl-phenyl | H | methyl | ethyl | |
| 2.1.202 | 2-vinyl-3-hydroxymethyl-phenyl | H | methyl | ethyl | |
| 2.1.203 | 2-ethynyl-3-hydroxymethyl-phenyl | H | methyl | ethyl | |
| 2.1.204 | 2-cyano-3-hydroxymethyl-phenyl | H | methyl | ethyl | |
| 2.1.205 | 2-trifluoro-methyl-3-hydroxymethyl-phenyl | H | methyl | ethyl | |
| 2.1.206 | 2-methoxy-3-hydroxymethyl-phenyl | H | methyl | ethyl | |
| 2.1.207 | 2-ethoxy-3-hydroxymethyl-phenyl | H | methyl | ethyl | |
| 2.1.208 | 2-trifluoro-methoxy-3-hydroxymethyl-phenyl | H | methyl | ethyl | |
| 2.1.209 | 2-nitro-3-hydroxymethyl-phenyl | H | methyl | ethyl | |
| 2.1.210 | 2-fluoro-3-cyclopropyl-phenyl | H | methyl | ethyl | |
| 2.1.211 | 2-chloro-3-cyclopropyl-phenyl | H | methyl | ethyl | |
| 2.1.212 | 2-bromo-3-cyclopropyl-phenyl | H | methyl | ethyl | |
| 2.1.213 | 2-methyl-3-cyclopropyl-phenyl | H | methyl | ethyl | |
| 2.1.214 | 2-ethyl-3-cyclopropyl-phenyl | H | methyl | ethyl | |
| 2.1.215 | 2-cyclopropyl-3-cyclopropyl-phenyl | H | methyl | ethyl | |
| 2.1.216 | 2-vinyl-3-cyclopropyl-phenyl | H | methyl | ethyl | |
| 2.1.217 | 2-ethynyl-3-cyclopropyl-phenyl | H | methyl | ethyl | |

TABLE 2.1-continued

Inventive compounds of the general formula (I) in which W* is COOY, R¹ is hydrogen, and aryl is the radical.

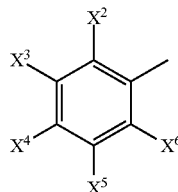

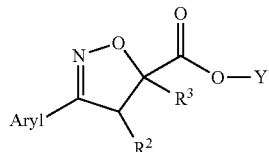

| No. | Aryl | R² | R³ | Y | Physical data |
|---|---|---|---|---|---|
| 2.1.218 | 2-cyano-3-cyclopropyl-phenyl | H | methyl | ethyl | |
| 2.1.219 | 2-trifluoro-methyl-3-cyclopropyl-phenyl | H | methyl | ethyl | |
| 2.1.220 | 2-methoxy-3-cyclopropyl-phenyl | H | methyl | ethyl | |
| 2.1.221 | 2-ethoxy-3-cyclopropyl-phenyl | H | methyl | ethyl | |
| 2.1.222 | 2-trifluoro-methoxy-3-cyclopropyl-phenyl | H | methyl | ethyl | |
| 2.1.223 | 2-fluoro-3-methoxy-carbonylphenyl | H | methyl | ethyl | |
| 2.1.224 | 2-chloro-3-methoxy-carbonylphenyl | H | methyl | ethyl | |
| 2.1.225 | 2-bromo-3-methoxy-carbonylphenyl | H | methyl | ethyl | |
| 2.1.226 | 2-methyl-3-methoxy-carbonylphenyl | H | methyl | ethyl | |
| 2.1.227 | 2-ethyl-3-methoxy-carbonylphenyl | H | methyl | ethyl | |
| 2.1.228 | 2-cyclopropyl-3-methoxy-carbonylphenyl | H | methyl | ethyl | |
| 2.1.229 | 2-vinyl-3-methoxy-carbonylphenyl | H | methyl | ethyl | |
| 2.1.230 | 2-ethynyl-3-methoxycarbonyl-phenyl | H | methyl | ethyl | |
| 2.1.231 | 2-cyano-3-methoxy-carbonylphenyl | H | methyl | ethyl | |
| 2.1.232 | 2-trifluoro-methyl-3-methoxy-carbonylphenyl | H | methyl | ethyl | |
| 2.1.233 | 2-methoxy-3-methoxy-carbonylphenyl | H | methyl | ethyl | |
| 2.1.234 | 2-ethoxy-3-methoxy-carbonylphenyl | H | methyl | ethyl | |

TABLE 2.1-continued

Inventive compounds of the general formula (I) in which W* is COOY, R¹ is hydrogen, and aryl is the radical.

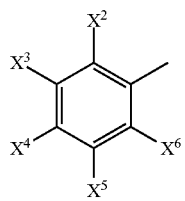

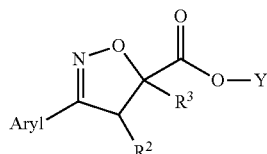

| No. | Aryl | R² | R³ | Y | Physical data |
|---|---|---|---|---|---|
| 2.1.235 | 2-trifluoromethoxy-3-methoxycarbonylphenyl | H | methyl | ethyl | |
| 2.1.236 | 2-nitro-3-methoxycarbonylphenyl | H | methyl | ethyl | |
| 2.1.237 | 2-fluoro-3-vinylphenyl | H | methyl | ethyl | |
| 2.1.238 | 2-chloro-3-vinylphenyl | H | methyl | ethyl | |
| 2.1.239 | 2-bromo-3-vinylphenyl | H | methyl | ethyl | |
| 2.1.240 | 2-methyl-3-vinylphenyl | H | methyl | ethyl | |
| 2.1.241 | 2-ethyl-3-vinylphenyl | H | methyl | ethyl | |
| 2.1.242 | 2-cyclopropyl-3-vinylphenyl | H | methyl | ethyl | |
| 2.1.243 | 2-vinyl-3-vinylphenyl | H | methyl | ethyl | |
| 2.1.244 | 2-ethynyl-3-vinylphenyl | H | methyl | ethyl | |
| 2.1.245 | 2-cyano-3-vinylphenyl | H | methyl | ethyl | |
| 2.1.246 | 2-trifluoromethyl-3-vinylphenyl | H | methyl | ethyl | |
| 2.1.247 | 2-methoxy-3-vinylphenyl | H | methyl | ethyl | |
| 2.1.248 | 2-ethoxy-3-vinylphenyl | H | methyl | ethyl | |
| 2.1.249 | 2-trifluoromethoxy-3-vinylphenyl | H | methyl | ethyl | |
| 2.1.250 | 2-nitro-3-vinylphenyl | H | methyl | ethyl | |
| 2.1.251 | 2-fluoro-3-ethynylphenyl | H | methyl | ethyl | |
| 2.1.252 | 2-chloro-3-ethynylphenyl | H | methyl | ethyl | |
| 2.1.253 | 2-bromo-3-ethynylphenyl | H | methyl | ethyl | |
| 2.1.254 | 2-methyl-3-ethynylphenyl | H | methyl | ethyl | |
| 2.1.255 | 2-ethyl-3-ethynylphenyl | H | methyl | ethyl | |
| 2.1.256 | 2-cyclopropyl-3-ethynylphenyl | H | methyl | ethyl | |
| 2.1.257 | 2-vinyl-3-ethynylphenyl | H | methyl | ethyl | |
| 2.1.258 | 2-cyano-3-ethynylphenyl | H | methyl | ethyl | |
| 2.1.259 | 2-trifluoromethyl-3-ethynylphenyl | H | methyl | ethyl | |
| 2.1.260 | 2-methoxy-3-ethynylphenyl | H | methyl | ethyl | |
| 2.1.261 | 2-ethoxy-3-ethynylphenyl | H | methyl | ethyl | |

TABLE 2.1-continued

Inventive compounds of the general formula (I) in which W* is COOY, R¹ is hydrogen, and aryl is the radical.

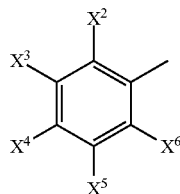

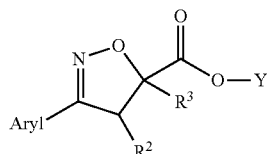

| No. | Aryl | R² | R³ | Y | Physical data |
|---|---|---|---|---|---|
| 2.1.262 | 2-trifluoromethoxy-3-ethynylphenyl | H | methyl | ethyl | |
| 2.1.263 | 2-nitro-3-ethynylphenyl | H | methyl | ethyl | |
| 2.1.264 | 2-fluoro-3-ethynylphenyl | H | methyl | ethyl | |
| 2.1.265 | 2-fluoro-3-cyanophenyl | H | methyl | ethyl | |
| 2.1.266 | 2-chloro-3-cyanophenyl | H | methyl | ethyl | |
| 2.1.267 | 2-bromo-3-cyanophenyl | H | methyl | ethyl | |
| 2.1.268 | 2-methyl-3-cyanophenyl | H | methyl | ethyl | |
| 2.1.269 | 2-ethyl-3-cyanophenyl | H | methyl | ethyl | |
| 2.1.270 | 2-ethyl-3-cyanophenyl | H | ethyl | ethyl | |
| 2.1.271 | 2-ethyl-3-cyanophenyl | H | propyl | ethyl | |
| 2.1.272 | 2-ethyl-3-cyanophenyl | H | cyclo-propyl | ethyl | |
| 2.1.273 | 2-cyclopropyl-3-cyanophenyl | H | methyl | ethyl | |
| 2.1.274 | 2-vinyl-3-cyanophenyl | H | methyl | ethyl | |
| 2.1.275 | 2-ethynyl-3-cyanophenyl | H | methyl | ethyl | |
| 2.1.276 | 2-cyano-3-cyanophenyl | H | methyl | ethyl | |
| 2.1.277 | 2-trifluoromethyl-3-cyanophenyl | H | methyl | ethyl | |
| 2.1.278 | 2-methoxy-3-cyanophenyl | H | methyl | ethyl | |
| 2.1.279 | 2-ethoxy-3-cyanophenyl | H | methyl | ethyl | |
| 2.1.280 | 2-trifluoro-methoxy-3-cyanophenyl | H | methyl | ethyl | |
| 2.1.281 | 2-nitro-3-cyanophenyl | H | methyl | ethyl | |
| 2.1.282 | 2-fluoro-3-hydroxyphenyl | H | methyl | ethyl | |
| 2.1.283 | 2-chloro-3-hydroxyphenyl | H | methyl | ethyl | |
| 2.1.284 | 2-bromo-3-hydroxyphenyl | H | methyl | ethyl | |
| 2.1.285 | 2-methyl-3-hydroxyphenyl | H | methyl | ethyl | |
| 2.1.286 | 2-ethyl-3-hydroxyphenyl | H | methyl | ethyl | |
| 2.1.287 | 2-cyclopropyl-3-hydroxyphenyl | H | methyl | ethyl | |
| 2.1.288 | 2-vinyl-3-hydroxyphenyl | H | methyl | ethyl | |
| 2.1.289 | 2-ethynyl-3-hydroxyphenyl | H | methyl | ethyl | |

TABLE 2.1-continued

Inventive compounds of the general formula (I) in which W* is COOY, R¹ is hydrogen, and aryl is the radical.

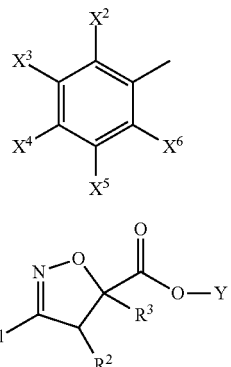

| No. | Aryl | R² | R³ | Y | Physical data |
|---|---|---|---|---|---|
| 2.1.290 | 2-cyano-3-hydroxyphenyl | H | methyl | ethyl | |
| 2.1.291 | 2-trifluoromethyl-3-hydroxyphenyl | H | methyl | ethyl | |
| 2.1.292 | 2-methoxy-3-hydroxyphenyl | H | methyl | ethyl | |
| 2.1.293 | 2-ethoxy-3-hydroxyphenyl | H | methyl | ethyl | |
| 2.1.294 | 2-trifluoromethoxy-3-hydroxyphenyl | H | methyl | ethyl | |
| 2.1.295 | 2-nitro-3-hydroxyphenyl | H | methyl | ethyl | |
| 2.1.296 | 2-fluoro-3-methoxyphenyl | H | methyl | ethyl | |
| 2.1.297 | 2-chloro-3-methoxyphenyl | H | methyl | ethyl | |
| 2.1.298 | 2-bromo-3-methoxyphenyl | H | methyl | ethyl | |
| 2.1.299 | 2-methyl-3-methoxyphenyl | H | methyl | ethyl | |
| 2.1.300 | 2-ethyl-3-methoxyphenyl | H | methyl | ethyl | |
| 2.1.301 | 2-cyclopropyl-3-methoxyphenyl | H | methyl | ethyl | |
| 2.1.302 | 2-vinyl-3-methoxyphenyl | H | methyl | ethyl | |
| 2.1.303 | 2-ethynyl-3-methoxyphenyl | H | methyl | ethyl | |
| 2.1.304 | 2-cyano-3-methoxyphenyl | H | methyl | ethyl | |
| 2.1.305 | 2-trifluoromethyl-3-methoxyphenyl | H | methyl | ethyl | |
| 2.1.306 | 2,3-dimethoxy-phenyl | H | methyl | ethyl | |
| 2.1.307 | 2-ethoxy-3-methoxyphenyl | H | methyl | ethyl | |
| 2.1.308 | 2-trifluoromethoxy-3-methoxyphenyl | H | methyl | ethyl | |
| 2.1.309 | 2-nitro-3-methoxyphenyl | H | methyl | ethyl | |
| 2.1.310 | 2-fluoro-3-ethoxyphenyl | H | methyl | ethyl | |
| 2.1.311 | 2-chloro-3-ethoxyphenyl | H | methyl | ethyl | |
| 2.1.312 | 2-bromo-3-ethoxyphenyl | H | methyl | ethyl | |
| 2.1.313 | 2-methyl-3-ethoxyphenyl | H | methyl | ethyl | |
| 2.1.314 | 2-ethyl-3-ethoxyphenyl | H | methyl | ethyl | |
| 2.1.315 | 2-cyclopropyl-3-ethoxyphenyl | H | methyl | ethyl | |

TABLE 2.1-continued

Inventive compounds of the general formula (I) in which W* is COOY, R¹ is hydrogen, and aryl is the radical.

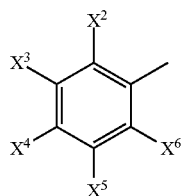

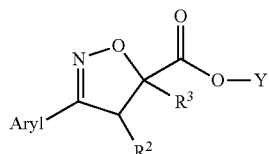

| No. | Aryl | R² | R³ | Y | Physical data |
|---|---|---|---|---|---|
| 2.1.316 | 2-vinyl-3-ethoxyphenyl | H | methyl | ethyl | |
| 2.1.317 | 2-ethynyl-3-ethoxyphenyl | H | methyl | ethyl | |
| 2.1.318 | 2-cyano-3-ethoxyphenyl | H | methyl | ethyl | |
| 2.1.319 | 2-trifluoromethyl-3-ethoxyphenyl | H | methyl | ethyl | |
| 2.1.320 | 2-methoxy-3-ethoxyphenyl | H | methyl | ethyl | |
| 2.1.321 | 2,3-diethoxy-phenyl | H | methyl | ethyl | |
| 2.1.322 | 2-trifluoromethoxy-3-ethoxyphenyl | H | methyl | ethyl | |
| 2.1.323 | 2-nitro-3-ethoxyphenyl | H | methyl | ethyl | |
| 2.1.324 | 2-fluoro-3-propoxyphenyl | H | methyl | ethyl | |
| 2.1.325 | 2-chloro-3-propoxyphenyl | H | methyl | ethyl | |
| 2.1.326 | 2-bromo-3-propoxyphenyl | H | methyl | ethyl | |
| 2.1.327 | 2-methyl-3-propoxyphenyl | H | methyl | ethyl | |
| 2.1.328 | 2-ethyl-3-propoxyphenyl | H | methyl | ethyl | |
| 2.1.329 | 2-cyclopropyl-3-propoxyphenyl | H | methyl | ethyl | |
| 2.1.330 | 2-vinyl-3-propoxyphenyl | H | methyl | ethyl | |
| 2.1.331 | 2-ethynyl-3-propoxyphenyl | H | methyl | ethyl | |
| 2.1.332 | 2-cyano-3-propoxyphenyl | H | methyl | ethyl | |
| 2.1.333 | 2-trifluoromethyl-3-propoxyphenyl | H | methyl | ethyl | |
| 2.1.334 | 2-methoxy-3-propoxyphenyl | H | methyl | ethyl | |
| 2.1.335 | 2-ethoxy-3-propoxyphenyl | H | methyl | ethyl | |
| 2.1.336 | 2-trifluoromethoxy-3-propoxyphenyl | H | methyl | ethyl | |
| 2.1.337 | 2-nitro-3-propoxyphenyl | H | methyl | ethyl | |
| 2.1.338 | 2-fluoro-3-isopropoxy-phenyl | H | methyl | ethyl | |
| 2.1.339 | 2-chloro-3-isopropoxy-phenyl | H | methyl | ethyl | |
| 2.1.340 | 2-bromo-3-isopropoxy-phenyl | H | methyl | ethyl | |

TABLE 2.1-continued

Inventive compounds of the general formula (I) in which W* is COOY, R¹ is hydrogen, and aryl is the radical.

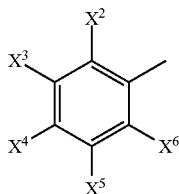

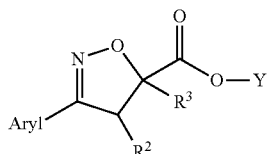

| No. | Aryl | R² | R³ | Y | Physical data |
|---|---|---|---|---|---|
| 2.1.341 | 2-methyl-3-isopropoxy-phenyl | H | methyl | ethyl | |
| 2.1.342 | 2-ethyl-3-isopropoxy-phenyl | H | methyl | ethyl | |
| 2.1.343 | 2-cyclopropyl-3-isopropoxy-phenyl | H | methyl | ethyl | |
| 2.1.344 | 2-vinyl-3-isopropoxy-phenyl | H | methyl | ethyl | |
| 2.1.345 | 2-ethynyl-3-isopropoxy-phenyl | H | methyl | ethyl | |
| 2.1.346 | 2-cyano-3-isopropoxy-phenyl | H | methyl | ethyl | |
| 2.1.347 | 2-trifluoro-methyl-3-isopropoxy-phenyl | H | methyl | ethyl | |
| 2.1.348 | 2-methoxy-3-isopropoxy-phenyl | H | methyl | ethyl | |
| 2.1.349 | 2-ethoxy-3-isopropoxy-phenyl | H | methyl | ethyl | |
| 2.1.350 | 2-trifluoro-methoxy-3-isopropoxy-phenyl | H | methyl | ethyl | |
| 2.1.351 | 2-nitro-3-isopropoxy-phenyl | H | methyl | ethyl | |
| 2.1.352 | 2-fluoro-3-tert-butoxyphenyl | H | methyl | ethyl | |
| 2.1.353 | 2-chloro-3-tert-butoxyphenyl | H | methyl | ethyl | |
| 2.1.354 | 2-bromo-3-tert-butoxyphenyl | H | methyl | ethyl | |
| 2.1.355 | 2-methyl-3-tert-butoxyphenyl | H | methyl | ethyl | |
| 2.1.356 | 2-ethyl-3-tert-butoxyphenyl | H | methyl | ethyl | |
| 2.1.357 | 2-cyclopropyl-3-tert-butoxy-phenyl | H | methyl | ethyl | |
| 2.1.358 | 2-vinyl-3-tert-butoxyphenyl | H | methyl | ethyl | |
| 2.1.359 | 2-ethynyl-3-tert-butoxyphenyl | H | methyl | ethyl | |
| 2.1.360 | 2-cyano-3-tert-butoxyphenyl | H | methyl | ethyl | |
| 2.1.361 | 2-trifluoro-methyl-3-tert-butoxyphenyl | H | methyl | ethyl | |

TABLE 2.1-continued

Inventive compounds of the general formula (I) in which W* is COOY, R¹ is hydrogen, and aryl is the radical.

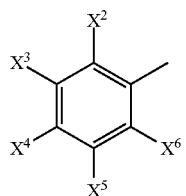

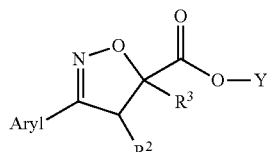

| No. | Aryl | R² | R³ | Y | Physical data |
|---|---|---|---|---|---|
| 2.1.362 | 2-methoxy-3-tert-butoxy-phenyl | H | methyl | ethyl | |
| 2.1.363 | 2-ethoxy-3-tert-butoxyphenyl | H | methyl | ethyl | |
| 2.1.364 | 2-trifluoro-methoxy-3-tert-butoxyphenyl | H | methyl | ethyl | |
| 2.1.365 | 2-nitro-3-tert-butoxyphenyl | H | methyl | ethyl | |
| 2.1.366 | 2-fluoro-3-trifluoromethoxy-phenyl | H | methyl | ethyl | |
| 2.1.367 | 2-chloro-3-trifluoromethoxy-phenyl | H | methyl | ethyl | |
| 2.1.368 | 2-bromo-3-trifluoromethoxy-phenyl | H | methyl | ethyl | |
| 2.1.369 | 2-methyl-3-trifluoromethoxy-phenyl | H | methyl | ethyl | |
| 2.1.370 | 2-ethyl-3-trifluoromethoxy-phenyl | H | methyl | ethyl | |
| 2.1.371 | 2-cyclopropyl-3-trifluoromethoxy-phenyl | H | methyl | ethyl | |
| 2.1.372 | 2-vinyl-3-trifluoromethoxy-phenyl | H | methyl | ethyl | |
| 2.1.373 | 2-ethynyl-3-trifluoromethoxy-phenyl | H | methyl | ethyl | |
| 2.1.374 | 2-cyano-3-trifluoromethoxy-phenyl | H | methyl | ethyl | |
| 2.1.375 | 2-trifluoro-methyl-3-trifluoro-methoxyphenyl | H | methyl | ethyl | |
| 2.1.376 | 2-methoxy-3-trifluoro-methoxyphenyl | H | methyl | ethyl | |
| 2.1.377 | 2-ethoxy-3-trifluoro-methoxyphenyl | H | methyl | ethyl | |
| 2.1.378 | 2,3-bis(trifluoro-methoxy)phenyl | H | methyl | ethyl | |
| 2.1.379 | 2-nitro-3-trifluoromethoxy-phenyl | H | methyl | ethyl | |
| 2.1.380 | 2-fluoro-3-(2,2,2-trifluoro-ethoxy)phenyl | H | methyl | ethyl | |

TABLE 2.1-continued

Inventive compounds of the general formula (I) in which W* is COOY, R¹ is hydrogen, and aryl is the radical.

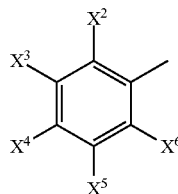

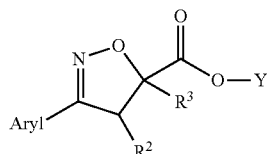

| No. | Aryl | R² | R³ | Y | Physical data |
|---|---|---|---|---|---|
| 2.1.381 | 2-chloro-3-(2,2,2-trifluoro-ethoxy)phenyl | H | methyl | ethyl | |
| 2.1.382 | 2-bromo-3-(2,2,2-trifluoro-ethoxy)phenyl | H | methyl | ethyl | |
| 2.1.383 | 2-methyl-3-(2,2,2-trifluoro-ethoxy)phenyl | H | methyl | ethyl | |
| 2.1.384 | 2-ethyl-3-(2,2,2-trifluoroethoxy)-phenyl | H | methyl | ethyl | |
| 2.1.385 | 2-cyclopropyl-3-(2,2,2-trifluoro-ethoxy)phenyl | H | methyl | ethyl | |
| 2.1.386 | 2-vinyl-3-(2,2,2-trifluoroethoxy)-phenyl | H | methyl | ethyl | |
| 2.1.387 | 2-ethynyl-3-(2,2,2-trifluoro-ethoxyphenyl | H | methyl | ethyl | |
| 2.1.388 | 2-cyano-3-(2,2,2-trifluoro-ethoxy)phenyl | H | methyl | ethyl | |
| 2.1.389 | 2-trifluoro-methyl-3-(2,2,2-trifluoroethoxy)-phenyl | H | methyl | ethyl | |
| 2.1.390 | 2-methoxy-3-(2,2,2-trifluoro-ethoxy)phenyl | H | methyl | ethyl | |
| 2.1.391 | 2-ethoxy-3-(2,2,2-trifluoroethoxy)-phenyl | H | methyl | ethyl | |
| 2.1.392 | 2-trifluoro-methoxy-3-(2,2,2-trifluoro-ethoxy)phenyl | H | methyl | ethyl | |
| 2.1.393 | 2-nitro-3-(2,2,2-trifluoroethoxy)-phenyl | H | methyl | ethyl | |
| 2.1.394 | 2-fluoro-3-difluoromethoxy-phenyl | H | methyl | ethyl | |
| 2.1.395 | 2-chloro-3-difluoromethoxy-phenyl | H | methyl | ethyl | |
| 2.1.396 | 2-bromo-3-difluoromethoxy-phenyl | H | methyl | ethyl | |
| 2.1.397 | 2-methyl-3-difluoromethoxy-phenyl | H | methyl | ethyl | |
| 2.1.398 | 2-ethyl-3-difluoromethoxy-phenyl | H | methyl | ethyl | |

TABLE 2.1-continued

Inventive compounds of the general formula (I) in which W* is COOY, $R^1$ is hydrogen, and aryl is the radical.

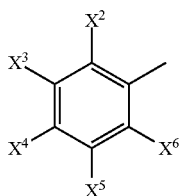

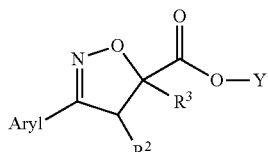

| No. | Aryl | $R^2$ | $R^3$ | Y | Physical data |
|---|---|---|---|---|---|
| 2.1.399 | 2-cyclopropyl-3-difluoromethoxy-phenyl | H | methyl | ethyl | |
| 2.1.400 | 2-vinyl-3-difluoromethoxy-phenyl | H | methyl | ethyl | |
| 2.1.401 | 2-ethynyl-3-difluoromethoxy-phenyl | H | methyl | ethyl | |
| 2.1.402 | 2-cyano-3-difluoro-methoxyphenyl | H | methyl | ethyl | |
| 2.1.403 | 2-trifluoromethyl-3-difluoro-methoxyphenyl | H | methyl | ethyl | |
| 2.1.404 | 2-methoxy-3-difluoro-methoxyphenyl | H | methyl | ethyl | |
| 2.1.405 | 2-ethoxy-3-difluoromethoxy phenyl | H | methyl | ethyl | |
| 2.1.406 | 2-trifluoro-methoxy-3-difluoromethoxy-phenyl | H | methyl | ethyl | |
| 2.1.407 | 2-nitro-3-difluoromethoxy phenyl | H | methyl | ethyl | |
| 2.1.408 | 2-fluoro-3-(2-methoxyethoxy)-phenyl | H | methyl | ethyl | |
| 2.1.409 | 2-chloro-3-(2-methoxyethoxy)-phenyl | H | methyl | ethyl | |
| 2.1.410 | 2-bromo-3-(2-methoxyethoxy)-phenyl | H | methyl | ethyl | |
| 2.1.411 | 2-methyl-3-(2-methoxyethoxy)-phenyl | H | methyl | ethyl | |
| 2.1.412 | 2-ethyl-3-(2-methoxyethoxy) phenyl | H | methyl | ethyl | |
| 2.1.413 | 2-cyclopropyl-3-(2-methoxy-ethoxy)phenyl | H | methyl | ethyl | |
| 2.1.414 | 2-vinyl-3-(2-methoxyethoxy) phenyl | H | methyl | ethyl | |
| 2.1.415 | 2-ethynyl-3-(2-methoxyethoxy)-phenyl | H | methyl | ethyl | |
| 2.1.416 | 2-cyano-3-(2-methoxyethoxy)-phenyl | H | methyl | ethyl | |

TABLE 2.1-continued

Inventive compounds of the general formula (I) in which W* is COOY, R¹ is hydrogen, and aryl is the radical.

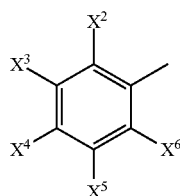

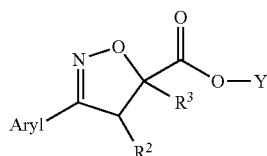

| No. | Aryl | R² | R³ | Y | Physical data |
|---|---|---|---|---|---|
| 2.1.417 | 2-trifluoro-methyl-3-(2-methoxyethoxy)-phenyl | H | methyl | ethyl | |
| 2.1.418 | 2-methoxy-3-(2-methoxyethoxy)-phenyl | H | methyl | ethyl | |
| 2.1.419 | 2-ethoxy-3-(2-methoxyethoxy)-phenyl | H | methyl | ethyl | |
| 2.1.420 | 2-trifluoro-methoxy-(2-methoxyethoxy)-phenyl | H | methyl | ethyl | |
| 2.1.421 | 2-nitro-3-(2-methoxyethoxy)phenyl | H | methyl | ethyl | |
| 2.1.422 | 2-fluoro-3-(tert-butoxycarbonyl-oxy)phenyl | H | methyl | ethyl | |
| 2.1.423 | 2-chloro-3-(tert-butoxycarbonyl-oxy)phenyl | H | methyl | ethyl | |
| 2.1.424 | 2-bromo-3-(tert-butoxycarbonyl-oxy)phenyl | H | methyl | ethyl | |
| 2.1.425 | 2-methyl-3-(tert-butoxycarbonyl-oxy)phenyl | H | methyl | ethyl | |
| 2.1.426 | 2-ethyl-3-(tert-butoxycarbonyl-oxy)phenyl | H | methyl | ethyl | |
| 2.1.427 | 2-cyclopropyl-3-(tert-butoxy-carbonyloxy)-phenyl | H | methyl | ethyl | |
| 2.1.428 | 2-vinyl-3-(tert-butoxycarbonyl-oxy)phenyl | H | methyl | ethyl | |
| 2.1.429 | 2-ethynyl-3-(tert-butoxycarbonyl-oxy)phenyl | H | methyl | ethyl | |
| 2.1.430 | 2-cyano-3-(tert-butoxycarbonyl-oxy)phenyl | H | methyl | ethyl | |
| 2.1.431 | 2-trifluoro-methyl-3-(tert-butoxycarbonyl-oxy)phenyl | H | methyl | ethyl | |
| 2.1.432 | 2-methoxy-3-(tert-butoxy-carbonyloxy)-phenyl | H | methyl | ethyl | |

TABLE 2.1-continued

Inventive compounds of the general formula (I) in which W* is COOY, R¹ is hydrogen, and aryl is the radical.

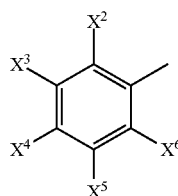

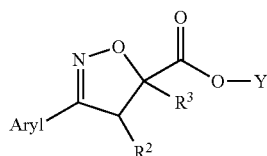

| No. | Aryl | R² | R³ | Y | Physical data |
|---|---|---|---|---|---|
| 2.1.433 | 2-ethoxy-3-(tert-butoxycarbonyl-oxy)phenyl | H | methyl | ethyl | |
| 2.1.434 | 2-trifluoro-methoxy-3-(tert-butoxycarbonyl-oxy)phenyl | H | methyl | ethyl | |
| 2.1.435 | 2-nitro-3-(tert-butoxycarbonyl-oxy)phenyl | H | methyl | ethyl | |
| 2.1.436 | 2-fluoro-3-nitrophenyl | H | methyl | ethyl | |
| 2.1.437 | 2-chloro-3-nitrophenyl | H | methyl | ethyl | |
| 2.1.438 | 2-bromo-3-nitrophenyl | H | methyl | ethyl | |
| 2.1.439 | 2-methyl-3-nitrophenyl | H | methyl | ethyl | |
| 2.1.440 | 2-ethyl-3-nitrophenyl | H | methyl | ethyl | |
| 2.1.441 | 2-cyclopropyl-3-nitrophenyl | H | methyl | ethyl | |
| 2.1.442 | 2-vinyl-3-nitrophenyl | H | methyl | ethyl | |
| 2.1.443 | 2-ethynyl-3-nitrophenyl | H | methyl | ethyl | |
| 2.1.444 | 2-cyano-3-nitrophenyl | H | methyl | ethyl | |
| 2.1.445 | 2-trifluoro-methyl-3-nitrophenyl | H | methyl | ethyl | |
| 2.1.446 | 2-methoxy-3-nitrophenyl | H | methyl | ethyl | |
| 2.1.447 | 2-ethoxy-3-nitrophenyl | H | methyl | ethyl | |
| 2.1.448 | 2-trifluoro-methoxy-3-nitrophenyl | H | methyl | ethyl | |
| 2.1.449 | 2-fluoro-3-methylsulfanyl-phenyl | H | methyl | ethyl | |
| 2.1.450 | 2-chloro-3-methylsulfanyl-phenyl | H | methyl | ethyl | |
| 2.1.451 | 2-bromo-3-methylsulfanyl-phenyl | H | methyl | ethyl | |
| 2.1.452 | 2-methyl-3-methylsulfanyl-phenyl | H | methyl | ethyl | |
| 2.1.453 | 2-ethyl-3-methylsulfanyl-phenyl | H | methyl | ethyl | |

TABLE 2.1-continued

Inventive compounds of the general formula (I) in which W* is COOY, R¹ is hydrogen, and aryl is the radical.

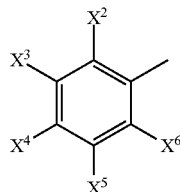

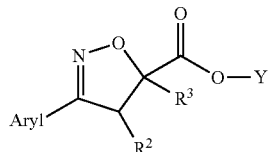

| No. | Aryl | R² | R³ | Y | Physical data |
|---|---|---|---|---|---|
| 2.1.454 | 2-cyclopropyl-3-methylsulfanyl-phenyl | H | methyl | ethyl | |
| 2.1.455 | 2-vinyl-3-methylsulfanyl-phenyl | H | methyl | ethyl | |
| 2.1.456 | 2-ethynyl-3-methylsulfanyl-phenyl | H | methyl | ethyl | |
| 2.1.457 | 2-cyano-3-methylsulfanyl-phenyl | H | methyl | ethyl | |
| 2.1.458 | 2-trifluoro-methyl-3-methylsulfanyl-phenyl | H | methyl | ethyl | |
| 2.1.459 | 2-methoxy-3-methylsulfanyl-phenyl | H | methyl | ethyl | |
| 2.1.460 | 2-ethoxy-3-methylsulfanyl-phenyl | H | methyl | ethyl | |
| 2.1.461 | 2-trifluoro-methoxy-3-methylsulfanyl-phenyl | H | methyl | ethyl | |
| 2.1.462 | 2-nitro-3-methylsulfanyl-phenyl | H | methyl | ethyl | |
| 2.1.463 | 3,5-difluoro-phenyl | H | methyl | methyl | |
| 2.1.464 | (S)-3,5-difluorophenyl | H | methyl | methyl | |
| 2.1.465 | (R)-3,5-difluoro-phenyl | H | methyl | methyl | |
| 2.1.466 | 3,5-difluoro-phenyl | H | methyl | ethyl | [CDCl₃] 1.30 (t, 3H); 1.71 (s, 3H); 3.15 (d, 1H); 3.85 (d, 1H); 4.25 (m, 2H); 6.85 (m, 1H); 7.18 (m, 2H). |
| 2.1.467 | rel-(4R,5R)-3,5-difluorophenyl | Me | Me | methyl | [CDCl₃] 1.22 (d, 3H); 1.65 (s, 3H); 3.76 (s, 3H); 3.92 (q, 1H); 6.89 (m, 1H); 7.21 (m, 2H). |
| 2.1.468 | rel-(4R,5R)-3,5-difluorophenyl | ethyl | Me | ethyl | [CDCl₃] 0.92 (t, 3H); 1.28 (t, 3H); 1.69 (s, 3H); 1.74 (m, 2H); 3.80 (dd, 1H); 4.21 (m, 2H); 6.86 (m, 1H); 7.20 (m, 2H). |
| 2.1.469 | rel-(4R,5R)-3,5-difluorophenyl | trifluoromethyl | Me | ethyl | [CDCl₃] 1.32 (t, 3H); 1.86 ("t", 3H); 4.30 (m, 2H); 4.72 (q, 1H); 6.91 (m, 1H); 7.25 (m, 2H). |
| 2.1.470 | 3,5-difluorophenyl | Cl | Me | methyl | |
| 2.1.471 | 3,5-difluorophenyl | H | Et | ethyl | [CDCl₃] 1.00 (t, 3H); 1.32 (t, 3H); 2.06 (q, 2H); 3.18 (d, 1H); 3.88 (d, 1H); 4.27 (M, 2H); 6.85 (m, 1H); 7.18 (m, 2H). |

TABLE 2.1-continued

Inventive compounds of the general formula (I) in which W* is COOY, R¹ is hydrogen, and aryl is the radical.

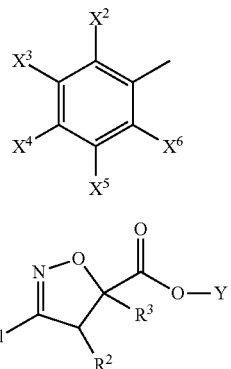

| No. | Aryl | R² | R³ | Y | Physical data |
|---|---|---|---|---|---|
| 2.1.472 | 3,5-difluorophenyl | H | isopropyl | ethyl | [CDCl₃] 0.95-1.00 (m, 6H); 1.32 (t, 3H); 2.45 (m, 1H); 3.19 (d, 1H); 3.74 (d, 1H); 4.22-4.33 (m, 2H); 6.85 (m, 1H); 7.19 (m, 2H). |
| 2.1.473 | 3,5-difluorophenyl | H | cyclo-propyl | ethyl | |
| 2.1.474 | 3-chloro-5-fluorophenyl | H | methyl | ethyl | [CDCl₃] 1.3 (t, 3H); 1.72 (s, 3H); 3.14 (d, 1H); 3.82 (d, 1H); 4.28 (mc, 2H); 7.15 (mc, 1H); 7.30 (mc, 1H); 7.410 (s, 1H). |
| 2.1.475 | 3-chloro-5-fluorophenyl | H | ethyl | ethyl | [CDCl₃] 1.00 (t, 3H); 1.35 (t, 3H); 2.08 (q, 2H); 3.19 (d, 1H); 3.75 (d, 1H); 4.29 (m, 2H); 7.15 (m, 1H); 7.30 (m, 1H); 7.41 (s, 1H). |
| 2.1.476 | 3-chloro-5-fluorophenyl | H | isopropyl | ethyl | |
| 2.1.477 | 3-chloro-5-fluorophenyl | H | cyclo-propyl | ethyl | |
| 2.1.478 | 3-bromo-5-fluorophenyl | H | methyl | ethyl | [CDCl₃] 1.31 (t, 3H); 1.72 (s, 3H); 3.15 (d, 1H); 3.85 (d, 1H); 4.28 (m, 2H); 7.31 (mc; 2H); 7.55 (m, 1H). |
| 2.1.479 | 3-bromo-5-fluorophenyl | H | ethyl | ethyl | |
| 2.1.480 | 3-bromo-5-fluorophenyl | H | isopropyl | ethyl | |
| 2.1.481 | 3-bromo-5-fluorophenyl | H | cyclo-propyl | ethyl | |
| 2.1.482 | 3-iodo-5-fluorophenyl | H | methyl | ethyl | |
| 2.1.483 | 3-methyl-5-fluorophenyl | H | methyl | ethyl | [CDCl₃] 1.32 (t, 3H); 1.70 (s, 3H); 2.38 (s, 3H); 3.18 (d, 1H); 3.83 (d, 1H); 4.25 (m, 2H); 6.92 (d, 1H); 7.15 (dd, 1H); 7.24 (d, 1H). |
| 2.1.484 | 3-methyl-5-fluorophenyl | H | ethyl | ethyl | |
| 2.1.485 | 3-methyl-5-fluorophenyl | H | isopropyl | ethyl | |
| 2.1.486 | 3-methyl-5-fluorophenyl | H | cyclo-propyl | ethyl | |
| 2.1.487 | 3-ethyl-5-fluorophenyl | H | methyl | ethyl | [CDCl₃] 1.25 (t, 3H); 1.35 (t, 3H); 1.72 (s, 3H); 2.68 (q, 2H); 3.18 (d, 1H); 3.82 (d, 1H); 4.25 (m, 2H); 6.95 (d, 1H); 7.18 (dd, 1H); 7.25 (d, 1H). |
| 2.1.488 | 3-propyl-5-fluorophenyl | H | methyl | ethyl | |
| 2.1.489 | 3-i-propyl-5-fluorophenyl | H | methyl | ethyl | |
| 2.1.490 | 3-n-butyl-5-fluorophenyl | H | methyl | ethyl | |
| 2.1.491 | 3-isobutyl-5-fluorophenyl | H | methyl | ethyl | |
| 2.1.492 | 3-tert-butyl-5-fluorophenyl | H | methyl | ethyl | |

TABLE 2.1-continued

Inventive compounds of the general formula (I) in which W* is COOY, R¹ is hydrogen, and aryl is the radical.

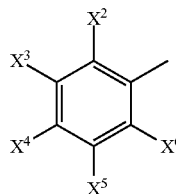

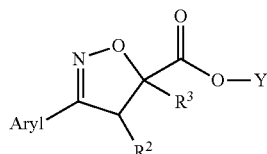

| No. | Aryl | R² | R³ | Y | Physical data |
|---|---|---|---|---|---|
| 2.1.493 | 3-cyclopropyl-5-fluorophenyl | H | methyl | ethyl | [CDCl₃] 0.7 (m, 2H); 1.1 (m, 2H); 1.32 (t, 3H); 1.70 (s, 3H); 1.90 (m, 1H); 3.15 (d, 1H); 3.82 (d, 1H); 4.25 (m, 2H); 6.78 (dd, 1H); 7.11 (dd, 1H); 7.20 (s, 1H). |
| 2.1.494 | 3-vinyl-5-fluorophenyl | H | methyl | ethyl | |
| 2.1.495 | 3-ethynyl-5-fluorophenyl | H | methyl | ethyl | |
| 2.1.496 | 3-cyano-5-fluorophenyl | H | methyl | ethyl | |
| 2.1.497 | 3-trifluoromethyl-5-fluorophenyl | H | methyl | ethyl | [CDCl₃] 1.31 (t, 3H); 1.72 (s, 3H); 3.18 (d, 1H); 3.89 (d, 1H); 4.25 (m, 2H); 7.35 (d, 1H); 7.58 (d, 1H); 7.65 (bs, 1H). |
| 2.1.498 | 3-trifluoromethyl-5-fluorophenyl | H | ethyl | ethyl | |
| 2.1.499 | 3-trifluoromethyl-5-fluorophenyl | H | isopropyl | ethyl | |
| 2.1.500 | 3-trifluoromethyl-5-fluorophenyl | H | cyclopropyl | ethyl | |
| 2.1.501 | 3-(methoxycarbonyl)-5-fluorophenyl | H | methyl | ethyl | |
| 2.1.502 | 3-hydroxymethyl-5-fluorophenyl | H | methyl | ethyl | |
| 2.1.503 | 3-carbamoyl-5-fluorophenyl | H | methyl | ethyl | |
| 2.1.504 | 3-hydroxy-5-fluorophenyl | H | methyl | ethyl | |
| 2.1.505 | 3-methoxy-5-fluorophenyl | H | methyl | ethyl | [CDCl₃] 1.31 (t, 3H); 1.71 (s, 3H); 3.16 (d, 1H); 3.80 (s, 3H); 3.85 (d, 1H); 4.25 (m, 2H); 6.65 (dd, 1H); 6.91 (dd, 1H); 7.02 (s, 1H). |
| 2.1.506 | 3-ethoxy-5-fluorophenyl | H | methyl | ethyl | |
| 2.1.507 | 3-n-propoxy-5-fluorophenyl | H | methyl | ethyl | |
| 2.1.508 | 3-isopropoxy-5-fluorophenyl | H | methyl | ethyl | |
| 2.1.509 | 3-n-butoxy-5-fluorophenyl | H | methyl | ethyl | |
| 2.1.510 | 3-isobutoxy-5-fluorophenyl | H | methyl | ethyl | |
| 2.1.511 | 3-tert-butoxy-5-fluorophenyl | H | methyl | ethyl | |
| 2.1.512 | 3-difluoromethoxy-5-fluorophenyl | H | methyl | ethyl | |
| 2.1.513 | 3-trifluoromethoxy-5-fluorophenyl | H | methyl | ethyl | |

TABLE 2.1-continued

Inventive compounds of the general formula (I) in which W* is COOY, R¹ is hydrogen, and aryl is the radical.

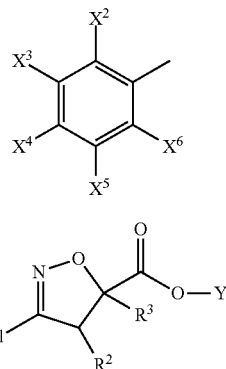

| No. | Aryl | R² | R³ | Y | Physical data |
|---|---|---|---|---|---|
| 2.1.514 | 3-(2,2,2-trifluoroethoxy)-5-fluorophenyl | H | methyl | ethyl | |
| 2.1.515 | 3-(2-chloro-ethoxy)-5-fluorophenyl | H | methyl | ethyl | |
| 2.1.516 | 3-(2-hydroxy-ethoxy)-5-fluorophenyl | H | methyl | ethyl | |
| 2.1.517 | 3-[(tert-butoxy-carbonyl)oxy]-5-fluorophenyl | H | methyl | ethyl | |
| 2.1.518 | 3-nitro-5-fluorophenyl | H | methyl | ethyl | |
| 2.1.519 | 3-acetoxy-5-fluorophenyl | H | methyl | ethyl | |
| 2.1.520 | {3-[(tert-butoxy-carbonyl)amino]-5-fluorophenyl} | H | methyl | ethyl | |
| 2.1.521 | 3-methyl-sulfanyl-5-fluorophenyl | H | methyl | ethyl | [CDCl₃] 1.32 (t, 3H); 1.70 (s, 3H); 2.5 (s, 3H); 3.15 (d, 1H); 3.82 (d, 1H); 6.95 (dd, 1H); 7.10 (dd, 1H); 7.25 (d, 1H). |
| 2.1.522 | 3,5-dichloro-phenyl | H | methyl | ethyl | [CDCl₃] 1.31 (3, 3H); 1.70 (s, 3H); 3.15 (d, 1H); 3.82 (d, 1H); 4.25 (m, 2H); 7.40 (s, 1H); 7.52 (s, 2H). |
| 2.1.523 | 3,5-dichloro-phenyl | H | methyl | methyl | [CDCl₃] 1.72 (s, 3H); 3.15 (d, 1H); 3.81 (s, 3H); 3.87 (d, 1H); 7.40 (m, 1H); 7.5 (m, 2H). |
| 2.1.524 | 3,5-dichloro-phenyl | H | methyl | isopropyl | [CDCl₃] 1.30 (d, 6H); 1.70 (s, 3H); 3.12 (d, 1H); 3.82 (d, 1H); 5.10 (m, 1H); 7.40 (s, 1H); 7.52 (s, 2H). |
| 2.1.525 | (S)-3,5-dichlorophenyl | H | methyl | methyl | [CDCl₃] 1.72 (s, 3H); 3.16 (d,1H), 3.82 (s, 3H), 3.84 (d, 1H); 7.40 (s, 1H); 7.53 (s, 2H). |
| 2.1.526 | (R)-3,5-dichlorophenyl | H | methyl | methyl | [CDCl₃] 1.72 (s, 3H); 3.15 (d, 1H); 3.82 (s, 3H); 3.84 (d, 1H); 7.41 (s, 1H); 7.54 (s, 2H). |
| 2.1.527 | 3,5-dichlorophenyl | H | ethyl | ethyl | [CDCl₃] 1.00 (t, 3H); 1.38 (t, 3H); 2.07 (q, 2H); 2.18 (q, 2H); 3.16 (d, 1H); 3.76 (d, 1H); 7.37 (s, 1H); 7.55 (s, 2H). |
| 2.1.528 | 3,5-dichloro-phenyl | H | propyl | ethyl | |
| 2.1.529 | 3,5-dichloro-phenyl | H | iPr | ethyl | [CDCl₃] 0.92 (dd; mc, 6H); 1.32 (t, 3H); 2.45 (MC, 1H); 3.18 (d, 1H); 3.74 (d, 1H); 4.25 (mc, 2H); 7.41 (s, 1H); 7.55 (s, 2H). |
| 2.1.530 | 3,5-dichloro-phenyl | H | cyclo-propyl | ethyl | [CDCl₃] 0.45-0.75 (m, 4H); 1.32 (t, 3H); 1.42 (m, 1H); 3.23 (d, 1H); 3.78 (d, 1H); 4.29 (mc, 2H); 7.38 (s, 1H); 7.51 (s, 2H). |
| 2.1.531 | 3-bromo-5-chlorophenyl | H | methyl | methyl | [CDCl₃] 1.72 (s, 3H); 3.15 (d, 1H); 3.81 (s, 3H); 3.85 (d, 1H); 7.55 (m, 2H); 7.70 (m, 1H). |

TABLE 2.1-continued

Inventive compounds of the general formula (I) in which W* is COOY, R¹ is hydrogen, and aryl is the radical.

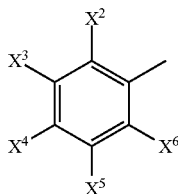

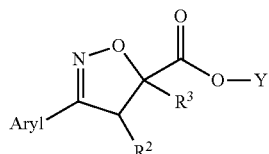

| No. | Aryl | R² | R³ | Y | Physical data |
|---|---|---|---|---|---|
| 2.1.532 | 3-bromo-5-chlorophenyl | H | methyl | ethyl | [CDCl₃] 1.32 (t, 3H); 1.70 (s, 3H); 3.13 (d, 1H); 3.82 (d, 1H); 4.28 (m, 2H); 7.58 (m, 2H); 7.69 (m, 1H). |
| 2.1.533 | rel-(4R,5R)-3,5-dichlorophenyl | methyl | methyl | methyl | [CDCl₃] 1.20 (d, 3H); 1.61 (s, 3H); 3.78 (s, 3H); 3.82 (q, 1H); 7.41 (s, 1H); 7.58 (s, 2H). |
| 2.1.534 | Rel-(4R,5S)-3,5-dichlorophenyl | methyl | methyl | methyl | [CDCl₃] 1.15 (d, 3H); 1.62 (s, 3H); 3.48 (q, 1H); 3.83 (s, 3H); 7.40 (s, 1H); 7.55 (s, 2H). |
| 2.1.535 | 3-methyl-5-chlorophenyl | H | methyl | ethyl | [CDCl₃] 1.31 (t, 3H); 1.70 (s, 3H); 2.35 (s, 3H); 3.15 (d, 1H); 3.85 (d, 1H); 4.25 (m, 2H); 7.21 (s, 1H); 7.37 (s, 1H); 7.42 (s, 1H). |
| 2.1.536 | 3-propyl-5-chlorophenyl | H | methyl | ethyl | |
| 2.1.537 | 3-isopropyl-5-chlorophenyl | H | methyl | ethyl | |
| 2.1.538 | 3-n-butyl-5-chlorophenyl | H | methyl | ethyl | |
| 2.1.539 | 3-isobutyl-5-chlorophenyl | H | methyl | ethyl | |
| 2.1.540 | 3-tert-butyl-5-chlorophenyl | H | methyl | ethyl | |
| 2.1.541 | 3-cyclopropyl-5-chlorophenyl | H | methyl | ethyl | |
| 2.1.542 | 3-vinyl-5-chlorophenyl | H | methyl | ethyl | |
| 2.1.543 | 3-ethynyl-5-chlorophenyl | H | methyl | ethyl | |
| 2.1.544 | 3-cyano-5-chlorophenyl | H | methyl | ethyl | |
| 2.1.545 | 3-trifluoromethyl-5-chlorophenyl | H | methyl | ethyl | [CDCl₃] 1.31 (t, 3H); 1.72 (s, 3H); 3.20 (d, 1H); 3.90 (d, 1H); 4.25 (m, 2H); 7.65 (s, 1H); 7.76 (s, 1H); 7.84 (s, 1H). |
| 2.1.546 | 3-trifluoromethyl-5-chlorophenyl | H | methyl | isopropyl | [CDCl₃] 1.30 (d, 6H); 1.71 (s, 3H); 3.15 (d, 1H); 3.85 (d, 1H); 5.10 (m, 1H); 7.65 (s, 1H); 7.77 (s, 1H); 7.85 (s, 1H). |
| 2.1.547 | 3-(hydroxycarbonyl)-5-chlorophenyl | H | methyl | ethyl | [CDCl₃] 1.31 (t, 3H); 3.18 (d, 1H); 3.85 (d, 1H); 4.25 (q, 2H); 6.15 (bs, 1H); 6.92 (d, 1H); 7.10 (s, 1H); 7.20 (s, 1H). |
| 2.1.548 | 3-(methoxycarbonyl)-5-chlorophenyl | H | methyl | ethyl | |
| 2.1.549 | 3-hydroxymethyl-5-chlorophenyl | H | methyl | ethyl | [CDCl₃] 1.31 (t, 3H); 1.71 (s, 3H); 3.17 (d, 1H); 3.85 (d, 1H); 4.25 (m, 2H); 4.70 (s, 2H); 7.41 (s, 1H); 7.60 (mc, 2H). |
| 2.1.550 | 3-carbamoyl-5-chlorophenyl | H | methyl | ethyl | |
| 2.1.551 | 3-hydroxy-5-chlorophenyl | H | methyl | ethyl | |

TABLE 2.1-continued

Inventive compounds of the general formula (I) in which W* is COOY, R¹ is hydrogen, and aryl is the radical.

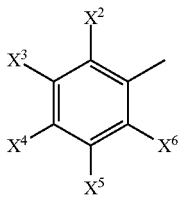

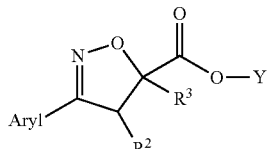

| No. | Aryl | R² | R³ | Y | Physical data |
|---|---|---|---|---|---|
| 2.1.552 | 3-methoxy-5-chlorophenyl | H | methyl | ethyl | [CDCl₃] 1.32 (t, 3H); 1.71 (s, 3H); 3.16 (d, 1H); 3.82 (s, 3H); 3.86 (d, 1H); 4.25 (mc, 2H); 6.95 (m, 1H); 7.16 (m, 2H). |
| 2.1.553 | 3-ethoxy-5-chlorophenyl | H | methyl | ethyl | |
| 2.1.554 | 3-n-propoxy-5-chlorophenyl | H | methyl | ethyl | |
| 2.1.555 | 3-isopropoxy-5-chlorophenyl | H | methyl | ethyl | |
| 2.1.556 | 3-n-butoxy-5-chlorophenyl | H | methyl | ethyl | |
| 2.1.557 | 3-isobutoxy-5-chlorophenyl | H | methyl | ethyl | |
| 2.1.558 | 3-tert-butoxy-5-chlorophenyl | H | methyl | ethyl | |
| 2.1.559 | 3-difluoro-methoxy-5-chlorophenyl | H | methyl | ethyl | |
| 2.1.560 | 3-trifluoro-methoxy-5-chlorophenyl | H | methyl | ethyl | |
| 2.1.561 | 3-(2,2,2-trifluoroethoxy)-5-chlorophenyl | H | methyl | ethyl | |
| 2.1.562 | 3-(2-chloro-ethoxy)-5-chlorophenyl | H | methyl | ethyl | |
| 2.1.563 | 3-(2-hydroxyethoxy)-5-chlorophenyl | H | methyl | ethyl | |
| 2.1.564 | 3-[(tert-butoxy-carbonyl)oxy]-5-chlorophenyl | H | methyl | ethyl | [CDCl₃] 1.30 (t, 3H); 1.55 (s, 9H); 1.70 (s, 3H); 3.15 (d, 1H); 3.82 (d, 1H); 4.25 (m, 2H); 7.25 (s, 1H); 7.38 (d, 1H); 7.51 (s, 1H). |
| 2.1.565 | 3-nitro-5-chlorophenyl | H | methyl | ethyl | |
| 2.1.566 | 3-acetoxy-5-chlorophenyl | H | methyl | ethyl | |
| 2.1.567 | {3-[(tert-butoxy-carbonyl)amino]-5-chlorophenyl} | H | methyl | ethyl | |
| 2.1.568 | 3-methyl-sulfanyl-5-chlorophenyl | H | methyl | ethyl | |
| 2.1.569 | 3,5-dibromo-phenyl | H | methyl | ethyl | [CDCl₃] 1.31 (t, 3H); 1.71 (s, H); 3.15 (d, 1H); 3.82 (d, 1H); 4.28 (m, 2H); 7.70 (s, 1H); 7.75 (s, 2H). |
| 2.1.570 | 3,5-dibromo-phenyl | H | ethyl | ethyl | [CDCl₃] 1.00 (t, 3H); 1.31 (t, 3H); 2.05 (q, 2H); 3.15 (d, 1H); 3.75 (d, 1H); 4.30 (m, 2H); 7.70 (s, 1H); 7.78 (s, 2H). |

TABLE 2.1-continued

Inventive compounds of the general formula (I) in which W* is COOY, R¹ is hydrogen, and aryl is the radical.

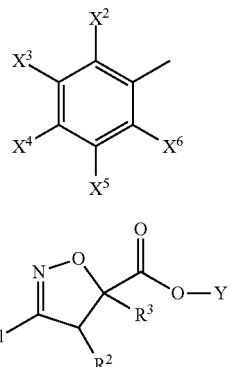

| No. | Aryl | R² | R³ | Y | Physical data |
|---|---|---|---|---|---|
| 2.1.571 | 3,5-dibromo-phenyl | H | isopropyl | ethyl | |
| 2.1.572 | 3,5-dibromo-phenyl | H | cyclo-propyl | ethyl | |
| 2.1.573 | 3-iodo-5-bromophenyl | H | methyl | ethyl | |
| 2.1.574 | 3-methyl-5-bromophenyl | H | methyl | ethyl | [CDCl₃] 1.31 (t, 3H); 1.70 (s, 3H); 2.35 (s, 3H); 3.15 (d, 1H); 3.85 (d, 1H); 4.26 (m, 2H); 7.38 (s, 1H); 7.43 (s, 1H); 7.58 (s, 1H). |
| 2.1.575 | 3-methyl-5-bromophenyl | H | ethyl | ethyl | |
| 2.1.576 | 3-methyl-5-bromophenyl | H | isopropyl | ethyl | |
| 2.1.577 | 3-methyl-5-bromophenyl | H | cyclo-propyl | ethyl | |
| 2.1.578 | 3-ethyl-5-bromophenyl | H | methyl | ethyl | |
| 2.1.579 | 3-propyl-5-bromophenyl | H | methyl | ethyl | |
| 2.1.580 | 3-isopropyl-5-bromophenyl | H | methyl | ethyl | |
| 2.1.581 | 3-n-butyl-5-bromophenyl | H | methyl | ethyl | |
| 2.1.582 | 3-isobutyl-5-bromophenyl | H | methyl | ethyl | |
| 2.1.583 | 3-tert-butyl-5-bromophenyl | H | methyl | ethyl | |
| 2.1.584 | 3-cyclopropyl-5-bromophenyl | H | methyl | ethyl | |
| 2.1.585 | 3-vinyl-5-bromophenyl | H | methyl | ethyl | |
| 2.1.586 | 3-ethynyl-5-bromophenyl | H | methyl | ethyl | |
| 2.1.587 | 3-cyano-5-bromophenyl | H | methyl | ethyl | |
| 2.1.588 | 3-trifluoro-methyl-5-bromophenyl | H | methyl | ethyl | [CDCl₃] 1.31 (t, 3H); 1.75 (s, 3H); 3.2 (d, 1H); 3.89 (d, 1H); 7.81 (d, 2H); 8.0 (m, 1H). |
| 2.1.589 | 3-(hydroxy-carbonyl)-5-bromophenyl | H | methyl | ethyl | |
| 2.1.590 | 3-(methoxy-carbonyl)-5-bromophenyl | H | methyl | ethyl | |
| 2.1.591 | 3-hydroxy-methyl-5-bromophenyl | H | methyl | ethyl | |
| 2.1.592 | 3-carbamoyl-5-bromophenyl | H | methyl | ethyl | |
| 2.1.593 | 3-hydroxy-5-bromophenyl | H | methyl | ethyl | |
| 2.1.594 | 3-methoxy-5-bromophenyl | H | methyl | ethyl | |
| 2.1.595 | 3-ethoxy-5-bromophenyl | H | methyl | ethyl | |

TABLE 2.1-continued

Inventive compounds of the general formula (I) in which W* is COOY, R¹ is hydrogen, and aryl is the radical.

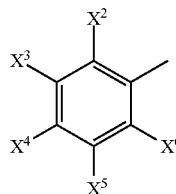

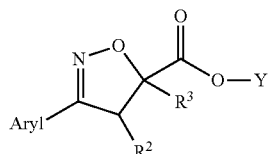

| No. | Aryl | R² | R³ | Y | Physical data |
|---|---|---|---|---|---|
| 2.1.596 | 3-n-propoxy-5-bromophenyl | H | methyl | ethyl | |
| 2.1.597 | 3-isopropoxy-5-bromophenyl | H | methyl | ethyl | |
| 2.1.598 | 3-n-butoxy-5-bromophenyl | H | methyl | ethyl | |
| 2.1.599 | 3-isobutoxy-5-bromophenyl | H | methyl | ethyl | |
| 2.1.600 | 3-tert-butoxy-5-bromophenyl | H | methyl | ethyl | |
| 2.1.601 | 3-difluoro-methoxy-5-bromophenyl | H | methyl | ethyl | |
| 2.1.602 | 3-trifluoro-methoxy-5-bromophenyl | H | methyl | ethyl | |
| 2.1.603 | 3-(2,2,2-trifluoroethoxy)-5-bromophenyl | H | methyl | ethyl | |
| 2.1.604 | 3-(2-chloro-ethoxy)-5-bromophenyl | H | methyl | ethyl | |
| 2.1.605 | 3-(2-hydroxy-ethoxy)-5-bromophenyl | H | methyl | ethyl | |
| 2.1.606 | 3-[(tert-butoxy-carbonyl)oxy]-5-bromophenyl | H | methyl | ethyl | |
| 2.1.607 | 3-nitro-5-bromophenyl | H | methyl | ethyl | |
| 2.1.608 | 3-acetoxy-5-bromophenyl | H | methyl | ethyl | |
| 2.1.609 | {3-[(tert-butoxy-carbonyl)amino]-5-bromophenyl} | H | methyl | ethyl | |
| 2.1.610 | 3-methyl-sulfanyl-5-bromophenyl | H | methyl | ethyl | |
| 2.1.611 | 3,5-diiodophenyl | H | methyl | ethyl | [CDCl$_3$] 1.32 (st, 3H); 1.70 (s, 3H); 3.12 (d, 1H); 3.81 (d, 1H); 7.93 (s, 2H); 8.09 (s, 1H). |
| 2.1.612 | 3-methyl-5-iodophenyl | H | methyl | ethyl | |
| 2.1.613 | 3-ethyl-5-iodophenyl | H | methyl | ethyl | |
| 2.1.614 | 3-propyl-5-iodophenyl | H | methyl | ethyl | |
| 2.1.615 | 3-isopropyl-5-iodophenyl | H | methyl | ethyl | |
| 2.1.616 | 3-n-butyl-5-iodophenyl | H | methyl | ethyl | |
| 2.1.617 | 3-isobutyl-5-iodophenyl | H | methyl | ethyl | |
| 2.1.618 | 3-tert-butyl-5-iodophenyl | H | methyl | ethyl | |
| 2.1.619 | 3-cyclopropyl-5-iodophenyl | H | methyl | ethyl | |

TABLE 2.1-continued

Inventive compounds of the general formula (I) in which W* is COOY, R¹ is hydrogen, and aryl is the radical.

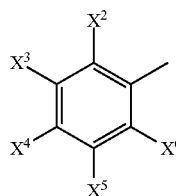

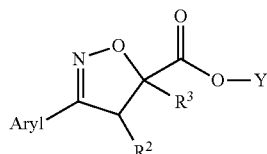

| No. | Aryl | R² | R³ | Y | Physical data |
|---|---|---|---|---|---|
| 2.1.620 | 3-vinyl-5-iodophenyl | H | methyl | ethyl | |
| 2.1.621 | 3-ethynyl-5-iodophenyl | H | methyl | ethyl | |
| 2.1.622 | 3-cyano-5-iodophenyl | H | methyl | ethyl | |
| 2.1.623 | 3-trifluoromethyl-5-iodophenyl | H | methyl | ethyl | |
| 2.1.624 | 3-(hydroxycarbonyl)-5-iodophenyl | H | methyl | ethyl | |
| 2.1.625 | 3-(methoxycarbonyl)-5-iodophenyl | H | methyl | ethyl | |
| 2.1.626 | 3-hydroxymethyl-5-iodophenyl | H | methyl | ethyl | |
| 2.1.627 | 3-carbamoyl-5-iodophenyl | H | methyl | ethyl | |
| 2.1.628 | 3-hydroxy-5-iodophenyl | H | methyl | ethyl | |
| 2.1.629 | 3-methoxy-5-iodophenyl | H | methyl | ethyl | |
| 2.1.630 | 3-ethoxy-5-iodophenyl | H | methyl | ethyl | |
| 2.1.631 | 3-n-propoxy-5-iodophenyl | H | methyl | ethyl | |
| 2.1.632 | 3-isopropoxy-5-iodophenyl | H | methyl | ethyl | |
| 2.1.633 | 3-n-butoxy-5-iodophenyl | H | methyl | ethyl | |
| 2.1.634 | 3-isobutoxy-5-iodophenyl | H | methyl | ethyl | |
| 2.1.635 | 3-tert-butoxy-5-iodophenyl | H | methyl | ethyl | |
| 2.1.636 | 3-difluoromethoxy-5-iodophenyl | H | methyl | ethyl | |
| 2.1.637 | 3-trifluoromethoxy-5-iodophenyl | H | methyl | ethyl | |
| 2.1.638 | 3-(2,2,2-trifluoroethoxy)-5-iodophenyl | H | methyl | ethyl | |
| 2.1.639 | 3-(2-chloroethoxy)-5-iodophenyl | H | methyl | ethyl | |
| 2.1.640 | 3-(2-hydroxyethoxy)-5-iodophenyl | H | methyl | ethyl | |
| 2.1.641 | 3-[(tert-butoxycarbonyl)oxy]-5-iodophenyl | H | methyl | ethyl | |
| 2.1.642 | 3-nitro-5-iodophenyl | H | methyl | ethyl | |
| 2.1.643 | 3-acetoxy-5-iodophenyl | H | methyl | ethyl | |

TABLE 2.1-continued

Inventive compounds of the general formula (I) in which W* is COOY, R¹ is hydrogen, and aryl is the radical.

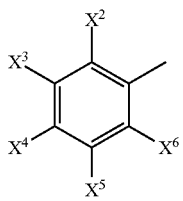

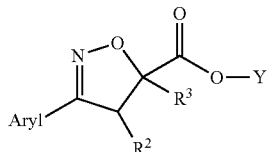

| No. | Aryl | R² | R³ | Y | Physical data |
|---|---|---|---|---|---|
| 2.1.644 | {3-[(tert-butoxy-carbonyl)amino]-5-iodophenyl} | H | methyl | ethyl | |
| 2.1.645 | 3-methyl-sulfanyl-5-iodophenyl | H | methyl | ethyl | |
| 2.1.646 | 3,5-dimethyl-phenyl | H | methyl | ethyl | [CDCl₃] 1.30 (t, 3H); 1.69 (s, 3H); 2.31 (s, 6H); 3.19 (d, 1H); 3.85 (d, 1H); 4.25 (mc, 2H); 7.05 (s, 1H); 7.25 (s, 2H). |
| 2.1.647 | 3-ethyl-5-methylphenyl | H | methyl | ethyl | |
| 2.1.648 | 3-propyl-5-methylphenyl | H | methyl | ethyl | |
| 2.1.649 | 3-isopropyl-5-methylphenyl | H | methyl | ethyl | |
| 2.1.650 | 3-n-butyl-5-methylphenyl | H | methyl | ethyl | |
| 2.1.651 | 3-isobutyl-5-methylphenyl | H | methyl | ethyl | |
| 2.1.652 | 3-tert-butyl-5-methylphenyl | H | methyl | ethyl | |
| 2.1.653 | 3-cyclopropyl-5-methylphenyl | H | methyl | ethyl | |
| 2.1.654 | 3-vinyl-5-methylphenyl | H | methyl | ethyl | |
| 2.1.655 | 3-ethynyl-5-methylphenyl | H | methyl | ethyl | |
| 2.1.656 | 3-cyano-5-methylphenyl | H | methyl | ethyl | |
| 2.1.657 | 3-trifluoro-methyl-5-methylphenyl | H | methyl | ethyl | |
| 2.1.658 | 3-(hydroxy-carbonyl)-5-methylphenyl | H | methyl | ethyl | |
| 2.1.659 | 3-(methoxy-carbonyl)-5-methylphenyl | H | methyl | ethyl | |
| 2.1.660 | 3-hydroxy-methyl-5-methylphenyl | H | methyl | ethyl | |
| 2.1.661 | 3-carbamoyl-5-methylphenyl | H | methyl | ethyl | |
| 2.1.662 | 3-hydroxy-5-methylphenyl | H | methyl | ethyl | |
| 2.1.663 | 3-methoxy-5-methylphenyl | H | methyl | ethyl | |
| 2.1.664 | 3-ethoxy-5-methylphenyl | H | methyl | ethyl | |
| 2.1.665 | 3-n-propoxy-5-methylphenyl | H | methyl | ethyl | |
| 2.1.666 | 3-n-butoxy-5-methylphenyl | H | methyl | ethyl | |

TABLE 2.1-continued

Inventive compounds of the general formula (I) in which W* is COOY, $R^1$ is hydrogen, and aryl is the radical.

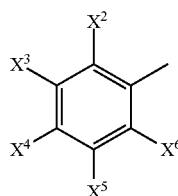

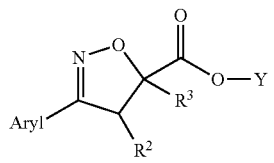

| No. | Aryl | $R^2$ | $R^3$ | Y | Physical data |
|---|---|---|---|---|---|
| 2.1.667 | 3-isobutoxy-5-methylphenyl | H | methyl | ethyl | |
| 2.1.668 | 3-tert-butoxy-5-methylphenyl | H | methyl | ethyl | |
| 2.1.669 | 3-difluoro-methoxy-5-methylphenyl | H | methyl | ethyl | |
| 2.1.670 | 3-trifluoro-methoxy-5-methylphenyl | H | methyl | ethyl | [CDCl$_3$] 1.30 (t, 3H); 1.72 (s, 3H); 2.40 (s, 3H); 3.18 (d, 1H); 3.86 (d, 1H); 4.25 (m, 2H); 7.08 (s, 1H); 7.31 (s, 1H); 7.41 (s, 1H). |
| 2.1.671 | 3-(2,2,2-trifluoroethoxy)-5-methylphenyl | H | methyl | ethyl | |
| 2.1.672 | 3-(2-chloro-ethoxy)-5-methylphenyl | H | methyl | ethyl | |
| 2.1.673 | 3-(2-hydroxy-ethoxy)-5-methylphenyl | H | methyl | ethyl | |
| 2.1.674 | 3-[(tert-butoxy-carbonyl)oxy]-5-methylphenyl | H | methyl | ethyl | |
| 2.1.675 | 3-nitro-5-methylphenyl | H | methyl | ethyl | |
| 2.1.676 | 3-acetoxy-5-methylphenyl | H | methyl | ethyl | |
| 2.1.677 | {3-[(tert-butoxy-carbonyl)amino]-5-methyl-phenyl} | H | methyl | ethyl | |
| 2.1.678 | 3-methyl-sulfanyl-5-methylphenyl | H | methyl | ethyl | |
| 2.1.679 | 3,5-diethyl-phenyl | H | methyl | ethyl | |
| 2.1.680 | 3-propyl-5-ethylphenyl | H | methyl | ethyl | |
| 2.1.681 | 3-isopropyl-5-ethylphenyl | H | methyl | ethyl | |
| 2.1.682 | 3-n-butyl-5-ethylphenyl | H | methyl | ethyl | |
| 2.1.683 | 3-isobutyl-5-ethylphenyl | H | methyl | ethyl | |
| 2.1.684 | 3-tert-butyl-5-ethylphenyl | H | methyl | ethyl | |
| 2.1.685 | 3-cyclopropyl-5-ethylphenyl | H | methyl | ethyl | |
| 2.1.686 | 3-vinyl-5-ethylphenyl | H | methyl | ethyl | |
| 2.1.687 | 3-ethynyl-5-ethylphenyl | H | methyl | ethyl | |

TABLE 2.1-continued

Inventive compounds of the general formula (I) in which W* is COOY, R¹ is hydrogen, and aryl is the radical.

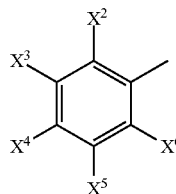

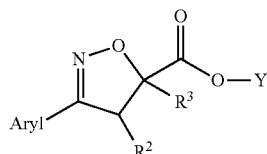

| No. | Aryl | R² | R³ | Y | Physical data |
|---|---|---|---|---|---|
| 2.1.688 | 3-cyano-5-ethylphenyl | H | methyl | ethyl | |
| 2.1.689 | 3-trifluoromethyl-5-ethylphenyl | H | methyl | ethyl | |
| 2.1.690 | 3-(hydroxycarbonyl)-5-ethylphenyl | H | methyl | ethyl | |
| 2.1.691 | 3-(methoxycarbonyl)-5-ethylphenyl | H | methyl | ethyl | |
| 2.1.692 | 3-hydroxymethyl-5-ethylphenyl | H | methyl | ethyl | |
| 2.1.693 | 3-carbamoyl-5-ethylphenyl | H | methyl | ethyl | |
| 2.1.694 | 3-hydroxy-5-ethylphenyl | H | methyl | ethyl | |
| 2.1.695 | 3-methoxy-5-ethylphenyl | H | methyl | ethyl | |
| 2.1.696 | 3-ethoxy-5-ethylphenyl | H | methyl | ethyl | |
| 2.1.697 | 3-n-propoxy-5-ethylphenyl | H | methyl | ethyl | |
| 2.1.698 | 3-n-butoxy-5-ethylphenyl | H | methyl | ethyl | |
| 2.1.699 | 3-isobutoxy-5-ethylphenyl | H | methyl | ethyl | |
| 2.1.700 | 3-tert-butoxy-5-ethylphenyl | H | methyl | ethyl | |
| 2.1.701 | 3-difluoromethoxy-5-ethylphenyl | H | methyl | ethyl | |
| 2.1.702 | 3-trifluoromethoxy-5-ethylphenyl | H | methyl | ethyl | |
| 2.1.703 | 3-(2,2,2-trifluoroethoxy)-5-ethylphenyl | H | methyl | ethyl | |
| 2.1.704 | 3-(2-chloroethoxy)-5-ethylphenyl | H | methyl | ethyl | |
| 2.1.705 | 3-(2-hydroxyethoxy)-5-ethylphenyl | H | methyl | ethyl | |
| 2.1.706 | 3-[(tert-butoxycarbonyl)oxy]-5-ethylphenyl | H | methyl | ethyl | |
| 2.1.707 | 3-nitro-5-ethylphenyl | H | methyl | ethyl | |
| 2.1.708 | 3-acetoxy-5-ethylphenyl | H | methyl | ethyl | |
| 2.1.709 | {3-[(tert-butoxycarbonyl)amino]-5-ethylphenyl} | H | methyl | ethyl | |

TABLE 2.1-continued

Inventive compounds of the general formula (I) in which W* is COOY, R¹ is hydrogen, and aryl is the radical.

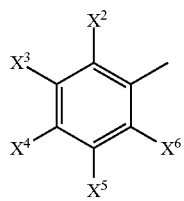

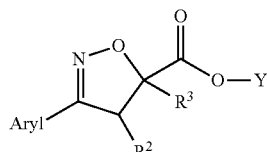

| No. | Aryl | R² | R³ | Y | Physical data |
|---|---|---|---|---|---|
| 2.1.710 | 3-methyl-sulfanyl-5-ethylphenyl | H | methyl | ethyl | |
| 2.1.711 | 3,5-dipropyl-phenyl | H | methyl | ethyl | |
| 2.1.712 | 3-isopropyl-5-propylphenyl | H | methyl | ethyl | |
| 2.1.713 | 3-n-butyl-5-propylphenyl | H | methyl | ethyl | |
| 2.1.714 | 3-isobutyl-5-propylphenyl | H | methyl | ethyl | |
| 2.1.715 | 3-tert-butyl-5-propylphenyl | H | methyl | ethyl | |
| 2.1.716 | 3-cyclopropyl-5-propylphenyl | H | methyl | ethyl | |
| 2.1.717 | 3-vinyl-5-propylphenyl | H | methyl | ethyl | |
| 2.1.718 | 3-ethynyl-5-propylphenyl | H | methyl | ethyl | |
| 2.1.719 | 3-cyano-5-propylphenyl | H | methyl | ethyl | |
| 2.1.720 | 3-trifluoro-methyl-5-propylphenyl | H | methyl | ethyl | |
| 2.1.721 | 3-(hydroxy-carbonyl)-5-propylphenyl | H | methyl | ethyl | |
| 2.1.722 | 3-(methoxy-carbonyl)-5-propylphenyl | H | methyl | ethyl | |
| 2.1.723 | 3-hydroxy-methyl-5-propylphenyl | H | methyl | ethyl | |
| 2.1.724 | 3-carbamoyl-5-propylphenyl | H | methyl | ethyl | |
| 2.1.725 | 3-hydroxy-5-propylphenyl | H | methyl | ethyl | |
| 2.1.726 | 3-methoxy-5-propylphenyl | H | methyl | ethyl | |
| 2.1.727 | 3-ethoxy-5-propylphenyl | H | methyl | ethyl | |
| 2.1.728 | 3-n-propoxy-5-propylphenyl | H | methyl | ethyl | |
| 2.1.729 | 3-n-butoxy-5-propylphenyl | H | methyl | ethyl | |
| 2.1.730 | 3-isobutoxy-5-propylphenyl | H | methyl | ethyl | |
| 2.1.731 | 3-tert-butoxy-5-propylphenyl | H | methyl | ethyl | |
| 2.1.732 | 3-difluoro-methoxy-5-propylphenyl | H | methyl | ethyl | |
| 2.1.733 | 3-trifluoro-methoxy-5-ethylphenyl | H | methyl | ethyl | |

TABLE 2.1-continued

Inventive compounds of the general formula (I) in which W* is COOY, R¹ is hydrogen, and aryl is the radical.

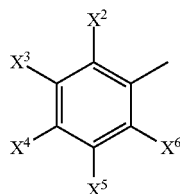

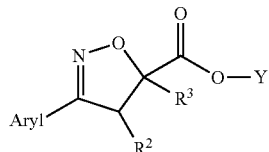

| No. | Aryl | R² | R³ | Y | Physical data |
|---|---|---|---|---|---|
| 2.1.734 | 3-(2,2,2-trifluoroethoxy)-5-propylphenyl | H | methyl | ethyl | |
| 2.1.735 | 3-(2-chloro-ethoxy)-5-propylphenyl | H | methyl | ethyl | |
| 2.1.736 | 3-(2-hydroxy-ethoxy)-5-propylphenyl | H | methyl | ethyl | |
| 2.1.737 | 3-[(tert-butoxy-carbonyl)oxy]-5-propylphenyl | H | methyl | ethyl | |
| 2.1.738 | 3-nitro-5-propylphenyl | H | methyl | ethyl | |
| 2.1.739 | 3-acetoxy-5-propylphenyl | H | methyl | ethyl | |
| 2.1.740 | {3-[(tert-butoxy-carbonyl)amino]-5-propylphenyl} | H | methyl | ethyl | |
| 2.1.741 | 3-methyl-sulfanyl-5-propylphenyl | H | methyl | ethyl | |
| 2.1.742 | 3,5-diisopropyl-phenyl | H | methyl | ethyl | |
| 2.1.743 | 3-n-butyl-5-isopropylphenyl | H | methyl | ethyl | |
| 2.1.744 | 3-isobutyl-5-isopropylphenyl | H | methyl | ethyl | |
| 2.1.745 | 3-tert-butyl-5-isopropylphenyl | H | methyl | ethyl | |
| 2.1.746 | 3-cyclopropyl-5-isopropylphenyl | H | methyl | ethyl | |
| 2.1.747 | 3-vinyl-5-isopropylphenyl | H | methyl | ethyl | |
| 2.1.748 | 3-ethynyl-5-isopropylphenyl | H | methyl | ethyl | |
| 2.1.749 | 3-cyano-5-isopropylphenyl | H | methyl | ethyl | |
| 2.1.750 | 3-trifluoro-methyl-5-isopropylphenyl | H | methyl | ethyl | |
| 2.1.751 | 3-(hydroxy-carbonyl)-5-isopropylphenyl | H | methyl | ethyl | |
| 2.1.752 | 3-(methoxy-carbonyl)-5-isopropylphenyl | H | methyl | ethyl | |
| 2.1.753 | 3-hydroxy-methyl-5-isopropylphenyl | H | methyl | ethyl | |
| 2.1.754 | 3-carbamoyl-5-isopropylphenyl | H | methyl | ethyl | |
| 2.1.755 | 3-hydroxy-5-isopropylphenyl | H | methyl | ethyl | |

TABLE 2.1-continued

Inventive compounds of the general formula (I) in which W* is COOY, R¹ is hydrogen, and aryl is the radical.

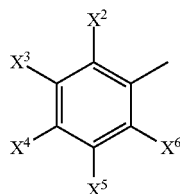

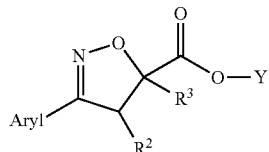

| No. | Aryl | R² | R³ | Y | Physical data |
|---|---|---|---|---|---|
| 2.1.756 | 3-methoxy-5-isopropylphenyl | H | methyl | ethyl | |
| 2.1.757 | 3-ethoxy-5-isopropylphenyl | H | methyl | ethyl | |
| 2.1.758 | 3-n-propoxy-5-isopropylphenyl | H | methyl | ethyl | |
| 2.1.759 | 3-n-butoxy-5-isopropylphenyl | H | methyl | ethyl | |
| 2.1.760 | 3-isobutoxy-5-isopropylphenyl | H | methyl | ethyl | |
| 2.1.761 | 3-tert-butoxy-5-isopropylphenyl | H | methyl | ethyl | |
| 2.1.762 | 3-difluoro-methoxy-5-isopropylphenyl | H | methyl | ethyl | |
| 2.1.763 | 3-trifluoro-methoxy-5-isopropylphenyl | H | methyl | ethyl | |
| 2.1.764 | 3-(2,2,2-trifluoroethoxy)-5-isopropyl-phenyl | H | methyl | ethyl | |
| 2.1.765 | 3-(2-chloro-ethoxy)-5-isopropylphenyl | H | methyl | ethyl | |
| 2.1.766 | 3-(2-hydroxy-ethoxy)-5-propylphenyl | H | methyl | ethyl | |
| 2.1.767 | 3-[(tert-butoxy-carbonyl)oxy]-5-isopropylphenyl | H | methyl | ethyl | |
| 2.1.768 | 3-nitro-5-isopropylphenyl | H | methyl | ethyl | |
| 2.1.769 | 3-acetoxy-5-isopropylphenyl | H | methyl | ethyl | |
| 2.1.770 | {3-[(tert-butoxy-carbonyl)amino]-5-isopropyl-phenyl} | H | methyl | ethyl | |
| 2.1.771 | 3-methyl-sulfanyl-5-isopropyl-phenyl | H | methyl | ethyl | |
| 2.1.772 | 3,5-dibutyl-phenyl | H | methyl | ethyl | |
| 2.1.773 | 3-isobutyl-5-butylphenyl | H | methyl | ethyl | |
| 2.1.774 | 3-tert-butyl-5-butylphenyl | H | methyl | ethyl | |
| 2.1.775 | 3-cyclopropyl-5-butylphenyl | H | methyl | ethyl | |
| 2.1.776 | 3-vinyl-5-butylphenyl | H | methyl | ethyl | |
| 2.1.777 | 3-ethynyl-5-butylphenyl | H | methyl | ethyl | |

TABLE 2.1-continued

Inventive compounds of the general formula (I) in which W* is COOY, R¹ is hydrogen, and aryl is the radical.

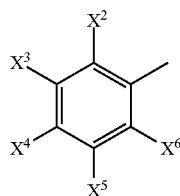

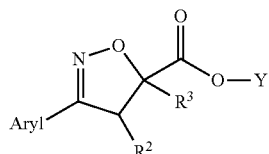

| No. | Aryl | $R^2$ | $R^3$ | Y | Physical data |
|---|---|---|---|---|---|
| 2.1.778 | 3-cyano-5-butylphenyl | H | methyl | ethyl | |
| 2.1.779 | 3-trifluoro-methyl-5-butylphenyl | H | methyl | ethyl | |
| 2.1.780 | 3-(hydroxy-carbonyl)-5-butylphenyl | H | methyl | ethyl | |
| 2.1.781 | 3-(methoxy-carbonyl)-5-butylphenyl | H | methyl | ethyl | |
| 2.1.782 | 3-hydroxy-methyl-5-butylphenyl | H | methyl | ethyl | |
| 2.1.783 | 3-carbamoyl-5-butylphenyl | H | methyl | ethyl | |
| 2.1.784 | 3-hydroxy-5-butylphenyl | H | methyl | ethyl | |
| 2.1.785 | 3-methoxy-5-butylphenyl | H | methyl | ethyl | |
| 2.1.786 | 3-ethoxy-5-butylphenyl | H | methyl | ethyl | |
| 2.1.787 | 3-n-propoxy-5-butylphenyl | H | methyl | ethyl | |
| 2.1.788 | 3-n-butoxy-5-butylphenyl | H | methyl | ethyl | |
| 2.1.789 | 3-isobutoxy-5-butylphenyl | H | methyl | ethyl | |
| 2.1.790 | 3-tert-butoxy-5-butylphenyl | H | methyl | ethyl | |
| 2.1.791 | 3-difluoro-methoxy-5-butylphenyl | H | methyl | ethyl | |
| 2.1.792 | 3-trifluoro-methoxy-5-butylphenyl | H | methyl | ethyl | |
| 2.1.793 | 3-(2,2,2-trifluoroethoxy)-5-butylphenyl | H | methyl | ethyl | |
| 2.1.794 | 3-(2-chloro-ethoxy)-5-butylphenyl | H | methyl | ethyl | |
| 2.1.795 | 3-(2-hydroxy-ethoxy)-5-butylphenyl | H | methyl | ethyl | |
| 2.1.796 | 3-[(tert-butoxy-carbonyl)oxy]-5-butylphenyl | H | methyl | ethyl | |
| 2.1.797 | 3-nitro-5-butylphenyl | H | methyl | ethyl | |
| 2.1.798 | 3-acetoxy-5-butylphenyl | H | methyl | ethyl | |
| 2.1.799 | {3-[(tert-butoxy-carbonyl)amino]-5-butylphenyl} | H | methyl | ethyl | |

TABLE 2.1-continued

Inventive compounds of the general formula (I) in which W* is COOY, R¹ is hydrogen, and aryl is the radical.

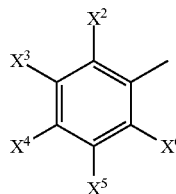

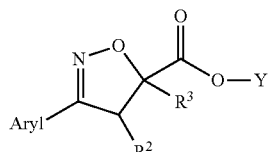

| No. | Aryl | R² | R³ | Y | Physical data |
|---|---|---|---|---|---|
| 2.1.800 | 3-methyl-sulfanyl-5-butylphenyl | H | methyl | ethyl | |
| 2.1.801 | 3,5-diisobutyl-phenyl | H | methyl | ethyl | |
| 2.1.802 | 3-tert-butyl-5-isobutylphenyl | H | methyl | ethyl | |
| 2.1.803 | 3-cyclopropyl-5-isobutylphenyl | H | methyl | ethyl | |
| 2.1.804 | 3-vinyl-5-isobutylphenyl | H | methyl | ethyl | |
| 2.1.805 | 3-ethynyl-5-isobutylphenyl | H | methyl | ethyl | |
| 2.1.806 | 3-cyano-5-isobutylphenyl | H | methyl | ethyl | |
| 2.1.807 | 3-trifluoro-methyl-5-isobutylphenyl | H | methyl | ethyl | |
| 2.1.808 | 3-(hydroxy-carbonyl)-5-isobutylphenyl | H | methyl | ethyl | |
| 2.1.809 | 3-(methoxy-carbonyl)-5-isobutylphenyl | H | methyl | ethyl | |
| 2.1.810 | 3-hydroxy-methyl-5-isobutylphenyl | H | methyl | ethyl | |
| 2.1.811 | 3-carbamoyl-5-isobutylphenyl | H | methyl | ethyl | |
| 2.1.812 | 3-hydroxy-5-isobutylphenyl | H | methyl | ethyl | |
| 2.1.813 | 3-methoxy-5-isobutylphenyl | H | methyl | ethyl | |
| 2.1.814 | 3-ethoxy-5-isobutylphenyl | H | methyl | ethyl | |
| 2.1.815 | 3-n-propoxy-5-isobutylphenyl | H | methyl | ethyl | |
| 2.1.816 | 3-n-butoxy-5-isobutylphenyl | H | methyl | ethyl | |
| 2.1.817 | 3-isobutoxy-5-isobutylphenyl | H | methyl | ethyl | |
| 2.1.818 | 3-tert-butoxy-5-isobutylphenyl | H | methyl | ethyl | |
| 2.1.819 | 3-difluoro-methoxy-5-isobutylphenyl | H | methyl | ethyl | |
| 2.1.820 | 3-trifluoro-methoxy-5-isobutylphenyl | H | methyl | ethyl | |
| 2.1.821 | 3-(2,2,2-trifluoroethoxy)-5-isobutylphenyl | H | methyl | ethyl | |
| 2.1.822 | 3-(2-chloro-ethoxy)-5-isobutylphenyl | H | methyl | ethyl | |

TABLE 2.1-continued

Inventive compounds of the general formula (I) in which W* is COOY, R¹ is hydrogen, and aryl is the radical.

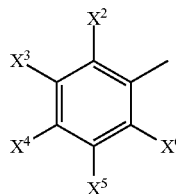

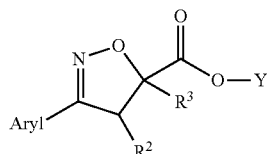

| No. | Aryl | R² | R³ | Y | Physical data |
|---|---|---|---|---|---|
| 2.1.823 | 3-(2-hydroxy-ethoxy)-5-isobutylphenyl | H | methyl | ethyl | |
| 2.1.824 | 3-[(tert-butoxy-carbonyl)oxy]-5-isobutylphenyl | H | methyl | ethyl | |
| 2.1.825 | 3-nitro-5-isobutylphenyl | H | methyl | ethyl | |
| 2.1.826 | 3-acetoxy-5-isobutylphenyl | H | methyl | ethyl | |
| 2.1.827 | {3-[(tert-butoxy-carbonyl)amino]-5-isobutyl-phenyl} | H | methyl | ethyl | |
| 2.1.828 | 3-methyl-sulfanyl-5-isobutylphenyl | H | methyl | ethyl | |
| 2.1.829 | 3,5-di-tert-butylphenyl | H | methyl | ethyl | |
| 2.1.830 | 3-cyclopropyl-5-tert-butylphenyl | H | methyl | ethyl | |
| 2.1.831 | 3-vinyl-5-tert-butylphenyl | H | methyl | ethyl | |
| 2.1.832 | 3-ethynyl-5-tert-butylphenyl | H | methyl | ethyl | |
| 2.1.833 | 3-cyano-5-tert-butylphenyl | H | methyl | ethyl | |
| 2.1.834 | 3-trifluoro-methyl-5-tert-butylphenyl | H | methyl | ethyl | |
| 2.1.835 | 3-(hydroxy-carbonyl)-5-tert-butylphenyl | H | methyl | ethyl | |
| 2.1.836 | 3-(methoxy-carbonyl)-5-tert-butylphenyl | H | methyl | ethyl | |
| 2.1.837 | 3-hydroxy-methyl-5-tert-butylphenyl | H | methyl | ethyl | |
| 2.1.838 | 3-carbamoyl-5-tert-butylphenyl | H | methyl | ethyl | |
| 2.1.839 | 3-hydroxy-5-tert-butylphenyl | H | methyl | ethyl | |
| 2.1.840 | 3-methoxy-5-tert-butylphenyl | H | methyl | ethyl | |
| 2.1.841 | 3-ethoxy-5-tert-butylphenyl | H | methyl | ethyl | |
| 2.1.842 | 3-n-propoxy-5-tert-butylphenyl | H | methyl | ethyl | |
| 2.1.843 | 3-n-butoxy-5-tert-butylphenyl | H | methyl | ethyl | |
| 2.1.844 | 3-isobutoxy-5-tert-butylphenyl | H | methyl | ethyl | |
| 2.1.845 | 3-tert-butoxy-5-tert-butylphenyl | H | methyl | ethyl | |

TABLE 2.1-continued

Inventive compounds of the general formula (I) in which W* is COOY, R¹ is hydrogen, and aryl is the radical.

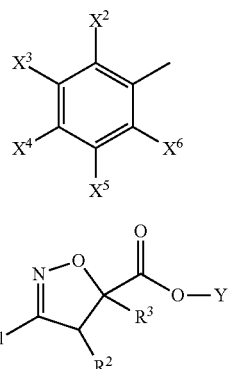

| No. | Aryl | R² | R³ | Y | Physical data |
|---|---|---|---|---|---|
| 2.1.846 | 3-difluoro-methoxy-5-tert-butylphenyl | H | methyl | ethyl | |
| 2.1.847 | 3-trifluoro-methoxy-5-tert-butylphenyl | H | methyl | ethyl | |
| 2.1.848 | 3-(2,2,2-trifluoroethoxy)-5-tert-butyl-phenyl | H | methyl | ethyl | |
| 2.1.849 | 3-(2-chloro-ethoxy)-5-tert-butylphenyl | H | methyl | ethyl | |
| 2.1.850 | 3-(2-hydroxy-ethoxy)-5-tert-butylphenyl | H | methyl | ethyl | |
| 2.1.851 | 3-[(tert-butoxy-carbonyl)oxy]-5-tert-butylphenyl | H | methyl | ethyl | |
| 2.1.852 | 3-nitro-5-tert-butylphenyl | H | methyl | ethyl | |
| 2.1.853 | 3-acetoxy-5-tert-butylphenyl | H | methyl | ethyl | |
| 2.1.854 | {3-[(tert-butoxy-carbonyl)amino]-5-tert-butyl-phenyl} | H | methyl | ethyl | |
| 2.1.855 | 3-methyl-sulfanyl-5-tert-butylphenyl | H | methyl | ethyl | |
| 2.1.856 | 3-tert-butyl-5-cyclopropyl-phenyl | H | methyl | ethyl | |
| 2.1.857 | 3,5-dicyclo-propylphenyl | H | methyl | ethyl | |
| 2.1.858 | 3-vinyl-5-cyclo-propylphenyl | H | methyl | ethyl | |
| 2.1.859 | 3-ethynyl-5-cyclopropyl-phenyl | H | methyl | ethyl | |
| 2.1.860 | 3-cyano-5-cyclopropyl-phenyl | H | methyl | ethyl | |
| 2.1.861 | 3-trifluoro-methyl-5-cyclopropyl-phenyl | H | methyl | ethyl | |
| 2.1.862 | 3-(hydroxy-carbonyl)-5-cyclopropyl-phenyl | H | methyl | ethyl | |
| 2.1.863 | 3-(methoxy-carbonyl)-5-cyclopropyl-phenyl | H | methyl | ethyl | |

TABLE 2.1-continued

Inventive compounds of the general formula (I) in which W* is COOY, R¹ is hydrogen, and aryl is the radical.

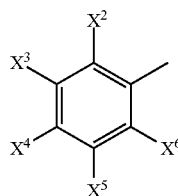

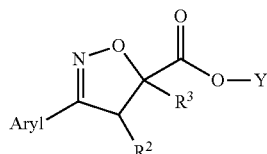

| No. | Aryl | R² | R³ | Y | Physical data |
|---|---|---|---|---|---|
| 2.1.864 | 3-hydroxy-methyl-5-cyclopropyl-phenyl | H | methyl | ethyl | |
| 2.1.865 | 3-carbamoyl-5-cyclopropyl-phenyl | H | methyl | ethyl | |
| 2.1.866 | 3-hydroxy-5-cyclopropyl-phenyl | H | methyl | ethyl | |
| 2.1.867 | 3-methoxy-5-cyclopropyl-phenyl | H | methyl | ethyl | |
| 2.1.868 | 3-ethoxy-5-cyclopropyl-phenyl | H | methyl | ethyl | |
| 2.1.869 | 3-n-propoxy-5-cyclopropyl-phenyl | H | methyl | ethyl | |
| 2.1.870 | 3-n-butoxy-5-cyclopropyl-phenyl | H | methyl | ethyl | |
| 2.1.871 | 3-isobutoxy-5-cyclopropyl-phenyl | H | methyl | ethyl | |
| 2.1.872 | 3-tert-butoxy-5-cyclopropyl-phenyl | H | methyl | ethyl | |
| 2.1.873 | 3-difluoro-methoxy-5-cyclopropyl-phenyl | H | methyl | ethyl | |
| 2.1.874 | 3-trifluoro-methoxy-5-cyclopropyl-phenyl | H | methyl | ethyl | |
| 2.1.875 | 3-(2,2,2-trifluoroethoxy)-5-cyclopropyl-phenyl | H | methyl | ethyl | |
| 2.1.876 | 3-(2-chloro-ethoxy)-5-cyclopropyl-phenyl | H | methyl | ethyl | |
| 2.1.877 | 3-(2-hydroxy-ethoxy)-5-cyclopropyl-phenyl | H | methyl | ethyl | |
| 2.1.878 | 3-[(tert-butoxy-carbonyl)oxy]-5-cyclopropyl-phenyl | H | methyl | ethyl | |
| 2.1.879 | 3-nitro-5-cyclopropyl-phenyl | H | methyl | ethyl | |

TABLE 2.1-continued

Inventive compounds of the general formula (I) in which W* is COOY, $R^1$ is hydrogen, and aryl is the radical.

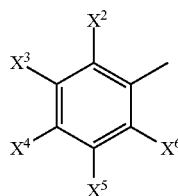

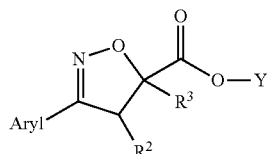

| No. | Aryl | $R^2$ | $R^3$ | Y | Physical data |
|---|---|---|---|---|---|
| 2.1.880 | 3-acetoxy-5-cyclopropyl-phenyl | H | methyl | ethyl | |
| 2.1.881 | {3-[(tert-butoxy-carbonyl)amino]-5-cyclopropyl-phenyl} | H | methyl | ethyl | |
| 2.1.882 | 3-methyl-sulfanyl-5-cyclopropyl-phenyl | H | methyl | ethyl | |
| 2.1.883 | 3,5-divinyl-phenyl | H | methyl | ethyl | |
| 2.1.884 | 3-ethynyl-5-vinylphenyl | H | methyl | ethyl | |
| 2.1.885 | 3-cyano-5-vinylphenyl | H | methyl | ethyl | |
| 2.1.886 | 3-trifluoro-methyl-5-vinylphenyl | H | methyl | ethyl | |
| 2.1.887 | 3-(hydroxy-carbonyl)-5-vinylphenyl | H | methyl | ethyl | |
| 2.1.888 | 3-(methoxy-carbonyl)-5-vinylphenyl | H | methyl | ethyl | |
| 2.1.889 | 3-hydroxy-methyl-5-vinylphenyl | H | methyl | ethyl | |
| 2.1.890 | 3-carbamoyl-5-vinylphenyl | H | methyl | ethyl | |
| 2.1.891 | 3-hydroxy-5-vinylphenyl | H | methyl | ethyl | |
| 2.1.892 | 3-methoxy-5-vinylphenyl | H | methyl | ethyl | |
| 2.1.893 | 3-ethoxy-5-vinylphenyl | H | methyl | ethyl | |
| 2.1.894 | 3-n-propoxy-5-vinylphenyl | H | methyl | ethyl | |
| 2.1.895 | 3-n-butoxy-5-vinylphenyl | H | methyl | ethyl | |
| 2.1.896 | 3-isobutoxy-5-vinylphenyl | H | methyl | ethyl | |
| 2.1.897 | 3-tert-butoxy-5-vinylphenyl | H | methyl | ethyl | |
| 2.1.898 | 3-difluoro-methoxy-5-vinylphenyl | H | methyl | ethyl | |
| 2.1.899 | 3-trifluoro-methoxy-5-vinylphenyl | H | methyl | ethyl | |
| 2.1.900 | 3-(2,2,2-trifluoroethoxy)-5-vinylphenyl | H | methyl | ethyl | |
| 2.1.901 | 3-(2-chloro-ethoxy)-5-vinylphenyl | H | methyl | ethyl | |

TABLE 2.1-continued

Inventive compounds of the general formula (I) in which W* is COOY, R¹ is hydrogen, and aryl is the radical.

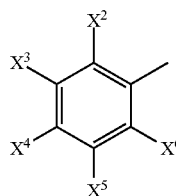

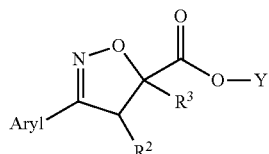

| No. | Aryl | R² | R³ | Y | Physical data |
|---|---|---|---|---|---|
| 2.1.902 | 3-(2-hydroxy-ethoxy)-5-vinylphenyl | H | methyl | ethyl | |
| 2.1.903 | 3-[(tert-butoxy-carbonyl)oxy]-5-vinylphenyl | H | methyl | ethyl | |
| 2.1.904 | 3-nitro-5-vinylphenyl | H | methyl | ethyl | |
| 2.1.905 | 3-acetoxy-5-vinylphenyl | H | methyl | ethyl | |
| 2.1.906 | {3-[(tert-butoxy-carbonyl)amino]-5-vinylphenyl} | H | methyl | ethyl | |
| 2.1.907 | 3-methyl-sulfanyl-5-vinylphenyl | H | methyl | ethyl | |
| 2.1.908 | 3,5-diethynyl-phenyl | H | methyl | ethyl | |
| 2.1.909 | 3-cyano-5-ethynylphenyl | H | methyl | ethyl | |
| 2.1.910 | 3-trifluoro-methyl-5-ethynylphenyl | H | methyl | ethyl | |
| 2.1.911 | 3-(hydroxy-carbonyl)-5-ethynylphenyl | H | methyl | ethyl | |
| 2.1.912 | 3-(methoxy-carbonyl)-5-ethynylphenyl | H | methyl | ethyl | |
| 2.1.913 | 3-hydroxy-methyl-5-ethynylphenyl | H | methyl | ethyl | |
| 2.1.914 | 3-carbamoyl-5-ethynylphenyl | H | methyl | ethyl | |
| 2.1.915 | 3-hydroxy-5-ethynylphenyl | H | methyl | ethyl | |
| 2.1.916 | 3-methoxy-5-ethynylphenyl | H | methyl | ethyl | |
| 2.1.917 | 3-ethoxy-5-ethynylphenyl | H | methyl | ethyl | |
| 2.1.918 | 3-n-propoxy-5-ethynylphenyl | H | methyl | ethyl | |
| 2.1.919 | 3-n-butoxy-5-ethynylphenyl | H | methyl | ethyl | |
| 2.1.920 | 3-isobutoxy-5-ethynylphenyl | H | methyl | ethyl | |
| 2.1.921 | 3-tert-butoxy-5-ethynylphenyl | H | methyl | ethyl | |
| 2.1.922 | 3-difluoro-methoxy-5-ethynylphenyl | H | methyl | ethyl | |
| 2.1.923 | 3-trifluoro-methoxy-5-ethynylphenyl | H | methyl | ethyl | |
| 2.1.924 | 3-(2,2,2-trifluoroethoxy)-5-ethynylphenyl | H | methyl | ethyl | |

TABLE 2.1-continued

Inventive compounds of the general formula (I) in which W* is COOY, R¹ is hydrogen, and aryl is the radical.

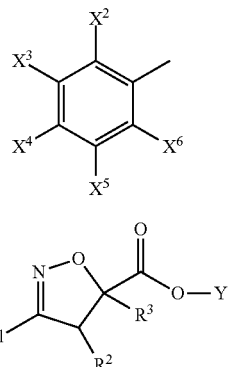

| No. | Aryl | R² | R³ | Y | Physical data |
|---|---|---|---|---|---|
| 2.1.925 | 3-(2-chloro-ethoxy)-5-ethynylphenyl | H | methyl | ethyl | |
| 2.1.926 | 3-(2-hydroxy-ethoxy)-5-ethynylphenyl | H | methyl | ethyl | |
| 2.1.927 | 3-[(tert-butoxy-carbonyl)oxy]-5-ethynylphenyl | H | methyl | ethyl | |
| 2.1.928 | 3-nitro-5-ethynylphenyl | H | methyl | ethyl | |
| 2.1.929 | 3-acetoxy-5-ethynylphenyl | H | methyl | ethyl | |
| 2.1.930 | {3-[(tert-butoxy-carbonyl)amino]-5-ethynyl-phenyl} | H | methyl | ethyl | |
| 2.1.931 | 3-methyl-sulfanyl-5-ethynylphenyl | H | methyl | ethyl | |
| 2.1.932 | 3,5-dicyano-phenyl | H | methyl | ethyl | |
| 2.1.933 | 3-trifluoro-methyl-5-cyanophenyl | H | methyl | ethyl | |
| 2.1.934 | 3-(hydroxy-carbonyl)-5-cyanophenyl | H | methyl | ethyl | |
| 2.1.935 | 3-(methoxy-carbonyl)-5-cyanophenyl | H | methyl | ethyl | |
| 2.1.936 | 3-hydroxy-methyl-5-cyanophenyl | H | methyl | ethyl | |
| 2.1.937 | 3-carbamoyl-5-cyanophenyl | H | methyl | ethyl | |
| 2.1.938 | 3-hydroxy-5-cyanophenyl | H | methyl | ethyl | |
| 2.1.939 | 3-methoxy-5-cyanophenyl | H | methyl | ethyl | |
| 2.1.940 | 3-ethoxy-5-cyanophenyl | H | methyl | ethyl | |
| 2.1.941 | 3-n-propoxy-5-cyanophenyl | H | methyl | ethyl | |
| 2.1.942 | 3-n-butoxy-5-cyanophenyl | H | methyl | ethyl | |
| 2.1.943 | 3-isobutoxy-5-cyanophenyl | H | methyl | ethyl | |
| 2.1.944 | 3-tert-butoxy-5-cyanophenyl | H | methyl | ethyl | |
| 2.1.945 | 3-difluoro-methoxy-5-cyanophenyl | H | methyl | ethyl | |
| 2.1.946 | 3-trifluoro-methoxy-5-cyanophenyl | H | methyl | ethyl | |

TABLE 2.1-continued

Inventive compounds of the general formula (I) in which W* is COOY, R¹ is hydrogen, and aryl is the radical.

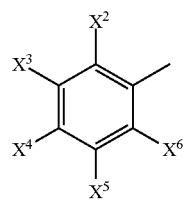

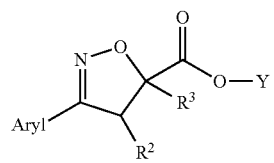

| No. | Aryl | R² | R³ | Y | Physical data |
|---|---|---|---|---|---|
| 2.1.947 | 3-(2,2,2-tri-fluoroethoxy)-5-cyanophenyl | H | methyl | ethyl | |
| 2.1.948 | 3-(2-chloro-ethoxy)-5-cyanophenyl | H | methyl | ethyl | |
| 2.1.949 | 3-(2-hydroxy-ethoxy)-5-cyanophenyl | H | methyl | ethyl | |
| 2.1.950 | 3-[(tert-butoxy-carbonyl)oxy]-5-cyanophenyl | H | methyl | ethyl | |
| 2.1.951 | 3-nitro-5-cyanophenyl | H | methyl | ethyl | |
| 2.1.952 | 3-acetoxy-5-cyanophenyl | H | methyl | ethyl | |
| 2.1.953 | {3-[(tert-butoxy-carbonyl)amino]-5-cyanophenyl} | H | methyl | ethyl | |
| 2.1.954 | 3-methyl-sulfanyl-5-cyanophenyl | H | methyl | ethyl | |
| 2.1.955 | 3,5-di(trifluoro-methyl)-phenyl | H | methyl | ethyl | [CDCl₃] 1.30 (t, 3H); 1.75 (s, 3H); 3.25 (d, 1H); 3.95 (d, 1H), 4.39 (m, 2H); 7.91 (bs, 1H); 8.10 (bs, 2H). |
| 2.1.956 | 3-(hydroxy-carbonyl)-5-trifluoromethyl-phenyl | H | methyl | ethyl | |
| 2.1.957 | 3-(methoxy-carbonyl)-5-trifluoromethyl-phenyl | H | methyl | ethyl | |
| 2.1.958 | 3-hydroxy-methyl-5-trifluoromethyl-phenyl | H | methyl | ethyl | |
| 2.1.959 | 3-carbamoyl-5-trifluoromethyl-phenyl | H | methyl | ethyl | |
| 2.1.960 | 3-hydroxy-5-trifluoromethyl-phenyl | H | methyl | ethyl | |
| 2.1.961 | 3-methoxy-5-trifluoromethyl-phenyl | H | methyl | ethyl | |
| 2.1.962 | 3-ethoxy-5-trifluoromethyl-phenyl | H | methyl | ethyl | |
| 2.1.963 | 3-n-propoxy-5-trifluoromethyl-phenyl | H | methyl | ethyl | |

TABLE 2.1-continued

Inventive compounds of the general formula (I) in which W* is COOY, R¹ is hydrogen, and aryl is the radical.

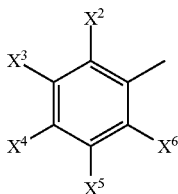

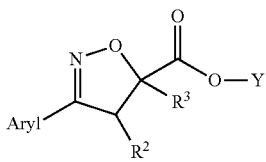

| No. | Aryl | R² | R³ | Y | Physical data |
|---|---|---|---|---|---|
| 2.1.964 | 3-n-butoxy-5-trifluoromethyl-phenyl | H | methyl | ethyl | |
| 2.1.965 | 3-isobutoxy-5-trifluoromethyl-phenyl | H | methyl | ethyl | |
| 2.1.966 | 3-tert-butoxy-5-trifluoromethyl-phenyl | H | methyl | ethyl | |
| 2.1.967 | 3-difluoro-methoxy-5-trifluoromethyl-phenyl | H | methyl | ethyl | |
| 2.1.968 | 3-trifluoro-methoxy-5-trifluoromethyl-phenyl | H | methyl | ethyl | |
| 2.1.969 | 3-(2,2,2-trifluoroethoxy)-5-trifluoro-methylphenyl | H | methyl | ethyl | |
| 2.1.970 | 3-(2-chloro-ethoxy)-5-trifluoromethyl-phenyl | H | methyl | ethyl | |
| 2.1.971 | 3-(2-hydroxy-ethoxy)-5-trifluoromethyl-phenyl | H | methyl | ethyl | |
| 2.1.972 | 3-[(tert-butoxy-carbonyl)oxy]-5-trifluoromethyl-phenyl | H | methyl | ethyl | |
| 2.1.973 | 3-nitro-5-trifluoromethyl-phenyl | H | methyl | ethyl | |
| 2.1.974 | 3-acetoxy-5-trifluoromethyl-phenyl | H | methyl | ethyl | |
| 2.1.975 | {3-[(tert-butoxy-carbonyl)amino]-5-trifluoro-methylphenyl} | H | methyl | ethyl | |
| 2.1.976 | 3-methyl-sulfanyl-5-trifluoromethyl-phenyl | H | methyl | ethyl | |
| 2.1.977 | 3,5-bis(hydroxy-carbonyl)phenyl | H | methyl | ethyl | |
| 2.1.978 | 3-(methoxy-carbonyl)-5-(hydroxy-carbonyl)phenyl | H | methyl | ethyl | |
| 2.1.979 | 3-hydroxy-methyl-5-(hydroxy-carbonyl)phenyl | H | methyl | ethyl | |

TABLE 2.1-continued

Inventive compounds of the general formula (I) in which W* is COOY, R¹ is hydrogen, and aryl is the radical.

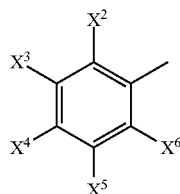

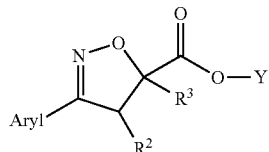

| No. | Aryl | R² | R³ | Y | Physical data |
|---|---|---|---|---|---|
| 2.1.980 | 3-carbamoyl-5-(hydroxy-carbonyl)phenyl | H | methyl | ethyl | |
| 2.1.981 | 3-hydroxy-5-(hydroxy-carbonyl)phenyl | H | methyl | ethyl | |
| 2.1.982 | 3-methoxy-5-(hydroxy-carbonyl)phenyl | H | methyl | ethyl | |
| 2.1.983 | 3-ethoxy-5-(hydroxy-carbonyl)phenyl | H | methyl | ethyl | |
| 2.1.984 | 3-n-propoxy-5-(hydroxy-carbonyl)phenyl | H | methyl | ethyl | |
| 2.1.985 | 3-n-butoxy-5-(hydroxy-carbonyl)phenyl | H | methyl | ethyl | |
| 2.1.986 | 3-isobutoxy-5-(hydroxy-carbonyl)phenyl | H | methyl | ethyl | |
| 2.1.987 | 3-tert-butoxy-5-(hydroxy-carbonyl)phenyl | H | methyl | ethyl | |
| 2.1.988 | 3-difluoro-methoxy-5-(hydroxy-carbonyl)phenyl | H | methyl | ethyl | |
| 2.1.989 | 3-trifluoro-methoxy-5-(hydroxy-carbonyl)phenyl | H | methyl | ethyl | |
| 2.1.990 | 3-(2,2,2-trifluoroethoxy)-5-(hydroxy-carbonyl)phenyl | H | methyl | ethyl | |
| 2.1.991 | 3-(2-chloro-ethoxy)-5-(hydroxy-carbonyl)phenyl | H | methyl | ethyl | |
| 2.1.992 | 3-(2-hydroxy-ethoxy)-5-(hydroxy-carbonyl)phenyl | H | methyl | ethyl | |
| 2.1.993 | 3-[(tert-butoxy-carbonyl)oxy]-5-(hydroxy-carbonyl)phenyl | H | methyl | ethyl | |
| 2.1.994 | 3-nitro-5-(hydroxy-carbonyl)phenyl | H | methyl | ethyl | |
| 2.1.995 | 3-acetoxy-5-(hydroxy-carbonyl)phenyl | H | methyl | ethyl | |

TABLE 2.1-continued

Inventive compounds of the general formula (I) in which W* is COOY, R¹ is hydrogen, and aryl is the radical.

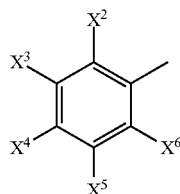

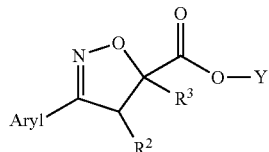

| No. | Aryl | R² | R³ | Y | Physical data |
|---|---|---|---|---|---|
| 2.1.996 | {3-[(tert-butoxy-carbonyl)amino]-5-(hydroxy-carbonyl)phenyl} | H | methyl | ethyl | |
| 2.1.997 | 3-methyl-sulfanyl-5-(hydroxy-carbonyl)phenyl | H | methyl | ethyl | |
| 2.1.998 | 3,5-di(methoxy-carbonyl)phenyl | H | methyl | ethyl | |
| 2.1.999 | 3-hydroxy-methyl-5-(methoxy-carbonyl)phenyl | H | methyl | ethyl | |
| 2.1.1000 | 3-carbamoyl-5-(methoxy-carbonyl)phenyl | H | methyl | ethyl | |
| 2.1.1001 | 3-hydroxy-5-(methoxy-carbonyl)phenyl | H | methyl | ethyl | |
| 2.1.1002 | 3-methoxy-5-(methoxy-carbonyl)phenyl | H | methyl | ethyl | |
| 2.1.1003 | 3-ethoxy-5-(methoxy-carbonyl)phenyl | H | methyl | ethyl | |
| 2.1.1004 | 3-n-propoxy-5-(methoxy-carbonyl)phenyl | H | methyl | ethyl | |
| 2.1.1005 | 3-n-butoxy-5-(methoxy-carbonyl)phenyl | H | methyl | ethyl | |
| 2.1.1006 | 3-isobutoxy-5-(methoxy-carbonyl)phenyl | H | methyl | ethyl | |
| 2.1.1007 | 3-tert-butoxy-5-(methoxy-carbonyl)phenyl | H | methyl | ethyl | |
| 2.1.1008 | 3-difluoro-methoxy-5-(methoxy-carbonyl)phenyl | H | methyl | ethyl | |
| 2.1.1009 | 3-trifluoro-methoxy-5-(methoxy-carbonyl)phenyl | H | methyl | ethyl | |
| 2.1.1010 | 3-(2,2,2-trifluoro-ethoxy)-5-(methoxy-carbonyl)phenyl | H | methyl | ethyl | |
| 2.1.1011 | 3-(2-chloro-ethoxy)-(methoxy-carbonyl)phenyl | H | methyl | ethyl | |

TABLE 2.1-continued

Inventive compounds of the general formula (I) in which W* is COOY, $R^1$ is hydrogen, and aryl is the radical.

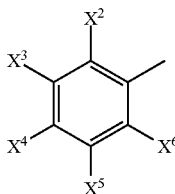

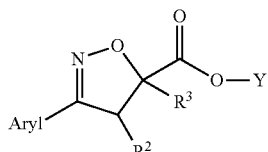

| No. | Aryl | $R^2$ | $R^3$ | Y | Physical data |
|---|---|---|---|---|---|
| 2.1.1012 | 3-(2-hydroxy-ethoxy)-(methoxy-carbonyl)phenyl | H | methyl | ethyl | |
| 2.1.1013 | 3-[(tert-butoxy-carbonyl)oxy]-5-(methoxy-carbonyl)phenyl | H | methyl | ethyl | |
| 2.1.1014 | 3-nitro-5-(methoxy-carbonyl)phenyl | H | methyl | ethyl | |
| 2.1.1015 | 3-acetoxy-5-(methoxy-carbonyl)phenyl | H | methyl | ethyl | |
| 2.1.1016 | {3-[(tert-butoxy-carbonyl)amino]-5-(methoxy-carbonyl)phenyl} | H | methyl | ethyl | |
| 2.1.1017 | 3-methyl-sulfanyl-5-(methoxy-carbonyl)phenyl | H | methyl | ethyl | |
| 2.1.1018 | 3,5-di(hydroxy-methyl)phenyl | H | methyl | ethyl | |
| 2.1.1019 | 3-carbamoyl-5-hydroxymethyl-phenyl | H | methyl | ethyl | |
| 2.1.1020 | 3-hydroxy-5-hydroxymethyl-phenyl | H | methyl | ethyl | |
| 2.1.1021 | 3-methoxy-5-hydroxymethyl-phenyl | H | methyl | ethyl | |
| 2.1.1022 | 3-ethoxy-5-hydroxymethyl-phenyl | H | methyl | ethyl | |
| 2.1.1023 | 3-n-propoxy-5-hydroxymethyl-phenyl | H | methyl | ethyl | |
| 2.1.1024 | 3-n-butoxy-5-hydroxymethyl-phenyl | H | methyl | ethyl | |
| 2.1.1025 | 3-isobutoxy-5-hydroxymethyl-phenyl | H | methyl | ethyl | |
| 2.1.1026 | 3-tert-butoxy-5-hydroxymethyl-phenyl | H | methyl | ethyl | |
| 2.1.1027 | 3-difluoro-methoxy-5-hydroxymethyl-phenyl | H | methyl | ethyl | |
| 2.1.1028 | 3-trifluoro-methoxy-5-hydroxymethyl-phenyl | H | methyl | ethyl | |

TABLE 2.1-continued

Inventive compounds of the general formula (I) in which W* is COOY, $R^1$ is hydrogen, and aryl is the radical.

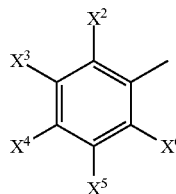

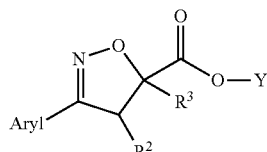

| No. | Aryl | $R^2$ | $R^3$ | Y | Physical data |
|---|---|---|---|---|---|
| 2.1.1029 | 3-(2,2,2-trifluoroethoxy)-5-hydroxy-methylphenyl | H | methyl | ethyl | |
| 2.1.1030 | 3-(2-chloro-ethoxy)-5-hydroxymethyl-phenyl | H | methyl | ethyl | |
| 2.1.1031 | 3-(2-hydroxy-ethoxy)-5-hydroxymethyl-phenyl | H | methyl | ethyl | |
| 2.1.1032 | 3-[(tert-butoxy-carbonyl)oxy]-5-hydroxymethyl-phenyl | H | methyl | ethyl | |
| 2.1.1033 | 3-nitro-5-hydroxymethyl-phenyl | H | methyl | ethyl | |
| 2.1.1034 | 3-acetoxy-5-hydroxymethyl-phenyl | H | methyl | ethyl | |
| 2.1.1035 | {3-[(tert-butoxy-carbonyl)amino]-5-hydroxy-methylphenyl) | H | methyl | ethyl | |
| 2.1.1036 | 3-methyl-sulfanyl-5-hydroxymethyl-phenyl | H | methyl | ethyl | |
| 2.1.1037 | 3,5-dicarbamoyl-5-carbamoyl-phenyl | H | methyl | ethyl | |
| 2.1.1038 | 3-hydroxy-5-carbamoyl-phenyl | H | methyl | ethyl | |
| 2.1.1039 | 3-methoxy-5-carbamoyl-phenyl | H | methyl | ethyl | |
| 2.1.1040 | 3-ethoxy-5-carbamoyl-phenyl | H | methyl | ethyl | |
| 2.1.1041 | 3-n-propoxy-5-carbamoyl-phenyl | H | methyl | ethyl | |
| 2.1.1042 | 3-n-butoxy-5-carbamoyl-phenyl | H | methyl | ethyl | |
| 2.1.1043 | 3-isobutoxy-5-carbamoyl-phenyl | H | methyl | ethyl | |
| 2.1.1044 | 3-tert-butoxy-5-carbamoyl-phenyl | H | methyl | ethyl | |

TABLE 2.1-continued

Inventive compounds of the general formula (I) in which W* is COOY, R¹ is hydrogen, and aryl is the radical.

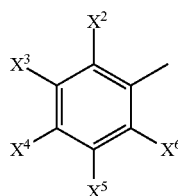

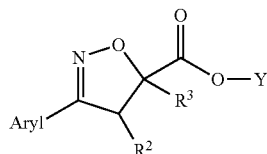

| No. | Aryl | R² | R³ | Y | Physical data |
|---|---|---|---|---|---|
| 2.1.1045 | 3-difluoro-methoxy-5-carbamoyl-phenyl | H | methyl | ethyl | |
| 2.1.1046 | 3-trifluoro-methoxy-5-carbamoyl-phenyl | H | methyl | ethyl | |
| 2.1.1047 | 3-(2,2,2-trifluoroethoxy)-5-carbamoyl-phenyl | H | methyl | ethyl | |
| 2.1.1048 | 3-(2-chloro-ethoxy)-5-carbamoyl-phenyl | H | methyl | ethyl | |
| 2.1.1049 | 3-(2-hydroxy-ethoxy)-5-carbamoyl-phenyl | H | methyl | ethyl | |
| 2.1.1050 | 3-[(tert-butoxy-carbonyl)oxy]-5-carbamoyl-phenyl | H | methyl | ethyl | |
| 2.1.1051 | 3-nitro-5-carbamoyl-phenyl | H | methyl | ethyl | |
| 2.1.1052 | 3-acetoxy-5-carbamoyl-phenyl | H | methyl | ethyl | |
| 2.1.1053 | {3-[(tert-butoxy-carbonyl)-amino]-5-carbamoyl-phenyl} | H | methyl | ethyl | |
| 2.1.1054 | 3-methyl-sulfanyl-5-carbamoyl-phenyl | H | methyl | ethyl | |
| 2.1.1055 | 3,5-dihydroxy-phenyl | H | methyl | ethyl | |
| 2.1.1056 | 3-methoxy-5-hydroxyphenyl | H | methyl | ethyl | |
| 2.1.1057 | 3-ethoxy-5-hydroxyphenyl | H | methyl | ethyl | |
| 2.1.1058 | 3-n-propoxy-5-hydroxyphenyl | H | methyl | ethyl | |
| 2.1.1059 | 3-n-butoxy-5-hydroxyphenyl | H | methyl | ethyl | |
| 2.1.1060 | 3-isobutoxy-5-hydroxyphenyl | H | methyl | ethyl | |
| 2.1.1061 | 3-tert-butoxy-5-hydroxyphenyl | H | methyl | ethyl | |

TABLE 2.1-continued

Inventive compounds of the general formula (I) in which W* is COOY, R¹ is hydrogen, and aryl is the radical.

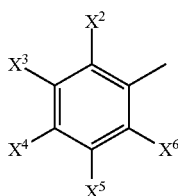

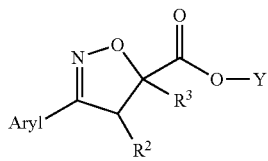

| No. | Aryl | R² | R³ | Y | Physical data |
|---|---|---|---|---|---|
| 2.1.1062 | 3-difluoro-methoxy-5-hydroxyphenyl | H | methyl | ethyl | |
| 2.1.1063 | 3-trifluoro-methoxy-5-hydroxyphenyl | H | methyl | ethyl | |
| 2.1.1064 | 3-(2,2,2-trifluoroethoxy)-5-hydroxyphenyl | H | methyl | ethyl | |
| 2.1.1065 | 3-(2-chloro-ethoxy)-5-hydroxyphenyl | H | methyl | ethyl | |
| 2.1.1066 | 3-(2-hydroxy-ethoxy)-5-hydroxyphenyl | H | methyl | ethyl | |
| 2.1.1067 | 3-[(tert-butoxy-carbonyl)oxy]-5-hydroxyphenyl | H | methyl | ethyl | |
| 2.1.1068 | 3-nitro-5-hydroxyphenyl | H | methyl | ethyl | |
| 2.1.1069 | 3-acetoxy-5-hydroxyphenyl | H | methyl | ethyl | |
| 2.1.1070 | {3-[(tert-butoxy-carbonyl)amino]-5-hydroxy-phenyl} | H | methyl | ethyl | |
| 2.1.1071 | 3-methyl-sulfanyl-5-hydroxyphenyl | H | methyl | ethyl | |
| 2.1.1072 | 3,5-dimethoxy-phenyl | H | methyl | ethyl | [CDCl₃] 1.30 (t, 3H); 1.71 (s, 3H); 3.15 (d, 1H); 3.80 (s, 6H); 3.85 (d, 1H); 4.25 (m, 2H); 6.51 (d, 1H); 6.80 (d, 1H). |
| 2.1.1073 | 3-ethoxy-5-methoxyphenyl | H | methyl | ethyl | |
| 2.1.1074 | 3-n-propoxy-5-methoxyphenyl | H | methyl | ethyl | |
| 2.1.1075 | 3-n-butoxy-5-methoxyphenyl | H | methyl | ethyl | |
| 2.1.1076 | 3-isobutoxy-5-methoxyphenyl | H | methyl | ethyl | |
| 2.1.1077 | 3-tert-butoxy-5-methoxyphenyl | H | methyl | ethyl | |
| 2.1.1078 | 3-difluoro-methoxy-5-methoxyphenyl | H | methyl | ethyl | |
| 2.1.1079 | 3-trifluoro-methoxy-5-methoxyphenyl | H | methyl | ethyl | |
| 2.1.1080 | 3-(2,2,2-trifluoroethoxy)-5-methoxy-phenyl | H | methyl | ethyl | |

TABLE 2.1-continued

Inventive compounds of the general formula (I) in which W* is COOY, R¹ is hydrogen, and aryl is the radical.

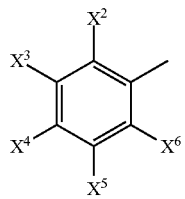

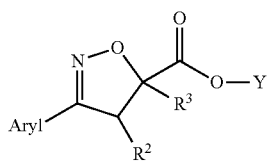

| No. | Aryl | R² | R³ | Y | Physical data |
|---|---|---|---|---|---|
| 2.1.1081 | 3-(2-chloro-ethoxy)-5-methoxyphenyl | H | methyl | ethyl | |
| 2.1.1082 | 3-(2-hydroxy-ethoxy)-5-methoxyphenyl | H | methyl | ethyl | |
| 2.1.1083 | 3-[(tert-butoxy-carbonyl)oxy]-5-methoxyphenyl | H | methyl | ethyl | |
| 2.1.1084 | 3-nitro-5-methoxyphenyl | H | methyl | ethyl | |
| 2.1.1085 | 3-acetoxy-5-methoxyphenyl | H | methyl | ethyl | |
| 2.1.1086 | {3-[(tert-butoxy-carbonyl)amino]-5-methoxy-phenyl} | H | methyl | ethyl | |
| 2.1.1087 | 3-methyl-sulfanyl-5-methoxyphenyl | H | methyl | ethyl | |
| 2.1.1088 | 3,5-diethoxy-phenyl | H | methyl | ethyl | |
| 2.1.1089 | 3-n-propoxy-5-ethoxyphenyl | H | methyl | ethyl | |
| 2.1.1090 | 3-n-butoxy-5-ethoxyphenyl | H | methyl | ethyl | |
| 2.1.1091 | 3-isobutoxy-5-ethoxyphenyl | H | methyl | ethyl | |
| 2.1.1092 | 3-tert-butoxy-5-ethoxyphenyl | H | methyl | ethyl | |
| 2.1.1093 | 3-difluoro-methoxy-5-ethoxyphenyl | H | methyl | ethyl | |
| 2.1.1094 | 3-trifluoro-methoxy-5-ethoxyphenyl | H | methyl | ethyl | |
| 2.1.1095 | 3-(2,2,2-trifluoroethoxy)-5-ethoxyphenyl | H | methyl | ethyl | |
| 2.1.1096 | 3-(2-chloro-ethoxy)-5-ethoxyphenyl | H | methyl | ethyl | |
| 2.1.1097 | 3-(2-hydroxy-ethoxy)-5-ethoxyphenyl | H | methyl | ethyl | |
| 2.1.1098 | 3-[(tert-butoxy-carbonyl)oxy]-5-ethoxyphenyl | H | methyl | ethyl | |
| 2.1.1099 | 3-nitro-5-ethoxyphenyl | H | methyl | ethyl | |
| 2.1.1100 | 3-acetoxy-5-ethoxyphenyl | H | methyl | ethyl | |
| 2.1.1101 | {3-[(tert-butoxy-carbonyl)amino]-5-ethoxy-phenyl} | H | methyl | ethyl | |

TABLE 2.1-continued

Inventive compounds of the general formula (I) in which W* is COOY, $R^1$ is hydrogen, and aryl is the radical.

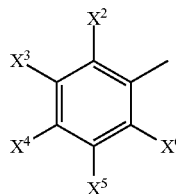

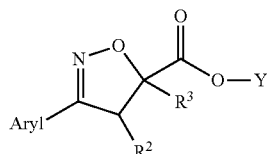

| No. | Aryl | $R^2$ | $R^3$ | Y | Physical data |
|---|---|---|---|---|---|
| 2.1.1102 | 3-methyl-sulfanyl-5-ethoxyphenyl | H | methyl | ethyl | |
| 2.1.1103 | 3,5-dipropoxy-phenyl | H | methyl | ethyl | |
| 2.1.1104 | 3-n-butoxy-5-propoxyphenyl | H | methyl | ethyl | |
| 2.1.1105 | 3-isobutoxy-5-propoxyphenyl | H | methyl | ethyl | |
| 2.1.1106 | 3-tert-butoxy-5-propoxyphenyl | H | methyl | ethyl | |
| 2.1.1107 | 3-difluoro-methoxy-5-propoxyphenyl | H | methyl | ethyl | |
| 2.1.1108 | 3-trifluoro-methoxy-5-propoxyphenyl | H | methyl | ethyl | |
| 2.1.1109 | 3-(2,2,2-trifluoroethoxy)-5-propoxyphenyl | H | methyl | ethyl | |
| 2.1.1110 | 3-(2-chloro-ethoxy)-5-propoxyphenyl | H | methyl | ethyl | |
| 2.1.1111 | 3-(2-hydroxy-ethoxy)-5-propoxyphenyl | H | methyl | ethyl | |
| 2.1.1112 | 3-[(tert-butoxy-carbonyl)oxy]-5-propoxyphenyl | H | methyl | ethyl | |
| 2.1.1113 | 3-nitro-5-propoxyphenyl | H | methyl | ethyl | |
| 2.1.1114 | 3-acetoxy-5-propoxyphenyl | H | methyl | ethyl | |
| 2.1.1115 | {3-[(tert-butoxy-carbonyl)amino]-5-propoxy-phenyl} | H | methyl | ethyl | |
| 2.1.1116 | 3-methyl-sulfanyl-5-propoxyphenyl | H | methyl | ethyl | |
| 2.1.1117 | 3,5-di(isopropoxy)-phenyl | H | methyl | ethyl | |
| 2.1.1118 | 3-n-butoxy-5-isopropoxy-phenyl | H | methyl | ethyl | |
| 2.1.1119 | 3-isobutoxy-5-isopropoxy-phenyl | H | methyl | ethyl | |
| 2.1.1120 | 3-tert-butoxy-5-isopropoxy-phenyl | H | methyl | ethyl | |
| 2.1.1121 | 3-difluoro-methoxy-5-isopropoxy-phenyl | H | methyl | ethyl | |

TABLE 2.1-continued

Inventive compounds of the general formula (I) in which W* is COOY, $R^1$ is hydrogen, and aryl is the radical.

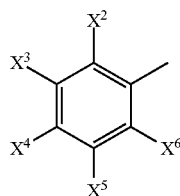

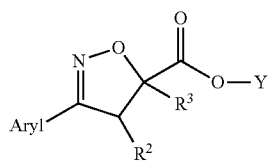

| No. | Aryl | $R^2$ | $R^3$ | Y | Physical data |
|---|---|---|---|---|---|
| 2.1.1122 | 3-trifluoro-methoxy-5-isopropoxy-phenyl | H | methyl | ethyl | |
| 2.1.1123 | 3-(2,2,2-trifluoroethoxy)-5-isopropoxy-phenyl | H | methyl | ethyl | |
| 2.1.1124 | 3-(2-chloro-ethoxy)-5-isopropoxy-phenyl | H | methyl | ethyl | |
| 2.1.1125 | 3-(2-hydroxy-ethoxy)-5-isopropoxy-phenyl | H | methyl | ethyl | |
| 2.1.1126 | 3-[(tert-butoxy-carbonyl)oxy]-5-isopropoxy-phenyl | H | methyl | ethyl | |
| 2.1.1127 | 3-nitro-5-isopropoxy-phenyl | H | methyl | ethyl | |
| 2.1.1128 | 3-acetoxy-5-isopropoxy-phenyl | H | methyl | ethyl | |
| 2.1.1129 | {3-[(tert-butoxy-carbonyl)amino]-5-isopropoxy-phenyl} | H | methyl | ethyl | |
| 2.1.1130 | 3-methyl-sulfanyl-5-isopropoxy-phenyl | H | methyl | ethyl | |
| 2.1.1131 | 3,5-di(tert-butoxy)phenyl | H | methyl | ethyl | |
| 2.1.1132 | 3-difluoro-methoxy-5-tert-butoxyphenyl | H | methyl | ethyl | |
| 2.1.1133 | 3-trifluoro-methoxy-5-tert-butoxyphenyl | H | methyl | ethyl | |
| 2.1.1134 | 3-(2,2,2-trifluoroethoxy)-5-tert-butoxy-phenyl | H | methyl | ethyl | |
| 2.1.1135 | 3-(2-chloro-ethoxy)-5-tert-butoxylphenyl | H | methyl | ethyl | |
| 2.1.1136 | 3-(2-hydroxy-ethoxy)-5-tert-butoxyphenyl | H | methyl | ethyl | |
| 2.1.1137 | 3-[(tert-butoxy-carbonyl)oxy]-5-tert-butoxy-phenyl | H | methyl | ethyl | |

TABLE 2.1-continued

Inventive compounds of the general formula (I) in which W* is COOY, R¹ is hydrogen, and aryl is the radical.

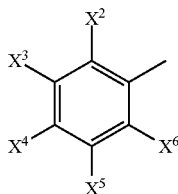

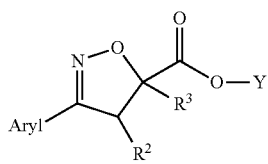

| No. | Aryl | R² | R³ | Y | Physical data |
|---|---|---|---|---|---|
| 2.1.1138 | 3-nitro-5-tert-butoxyphenyl | H | methyl | ethyl | |
| 2.1.1139 | 3-acetoxy-5-tert-butoxyphenyl | H | methyl | ethyl | |
| 2.1.1140 | {3-[(tert-butoxy-carbonyl)amino]-5-tert-butoxy-phenyl} | H | methyl | ethyl | |
| 2.1.1141 | 3-methyl-sulfanyl-5-tert-butoxyphenyl | H | methyl | ethyl | |
| 2.1.1142 | 3,5-di(trifluoro-methoxy)phenyl | H | methyl | ethyl | |
| 2.1.1143 | 3-(2,2,2-trifluoroethoxy)-5-trifluoro-methoxyphenyl | H | methyl | ethyl | |
| 2.1.1144 | 3-(2-chloro-ethoxy)-5-trifluoromethoxy-phenyl | H | methyl | ethyl | |
| 2.1.1145 | 3-(2-hydroxy-ethoxy)-5-trifluoro-methoxyphenyl | H | methyl | ethyl | |
| 2.1.1146 | 3-[(tert-butoxy-carbonyl)oxy]-5-trifluoro-methoxyphenyl | H | methyl | ethyl | |
| 2.1.1147 | 3-nitro-5-trifluoro-methoxyphenyl | H | methyl | ethyl | |
| 2.1.1148 | 3-acetoxy-5-tert-butoxyphenyl | H | methyl | ethyl | |
| 2.1.1149 | {3-[(tert-butoxy-carbonyl)amino]-5-trifluoro-methoxyphenyl} | H | methyl | ethyl | |
| 2.1.1150 | 3-methyl-sulfanyl-5-trifluoro-methoxyphenyl | H | methyl | ethyl | |
| 2.1.1151 | 3,5-bis(difluoro-methoxy)phenyl | H | methyl | ethyl | |
| 2.1.1152 | 3-trifluoro-methoxy-5-difluoromethoxy-phenyl | H | methyl | ethyl | |
| 2.1.1153 | 3-(2,2,2-trifluoroethoxy)-5-difluoro-methoxyphenyl | H | methyl | ethyl | |
| 2.1.1154 | 3-(2-chloro-ethoxy)-5-difluoromethoxy-phenyl | H | methyl | ethyl | |

TABLE 2.1-continued

Inventive compounds of the general formula (I) in which W* is COOY, $R^1$ is hydrogen, and aryl is the radical.

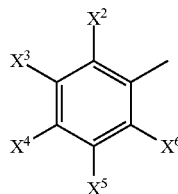

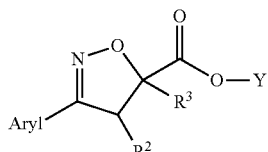

| No. | Aryl | $R^2$ | $R^3$ | Y | Physical data |
|---|---|---|---|---|---|
| 2.1.1155 | 3-(2-hydroxy-ethoxy)-5-difluoromethoxy-phenyl | H | methyl | ethyl | |
| 2.1.1156 | 3-[(tert-butoxy-carbonyl)oxy]-5-difluoromethoxy-phenyl | H | methyl | ethyl | |
| 2.1.1157 | 3-nitro-5-difluoro-methoxyphenyl | H | methyl | ethyl | |
| 2.1.1158 | 3-acetoxy-5-difluoro-methoxyphenyl | H | methyl | ethyl | |
| 2.1.1159 | {3-[(tert-butoxy-carbonyl)amino]-5-difluoro-methoxyphenyl} | H | methyl | ethyl | |
| 2.1.1160 | 3-methyl-sulfanyl-5-difluoromethoxy-phenyl | H | methyl | ethyl | |
| 2.1.1161 | 3,5-bis(2,2,2-trifluoroethoxy)-phenyl | H | methyl | ethyl | |
| 2.1.1162 | 3-(2-chloro-ethoxy)-5-(2,2,2-trifluoro-ethoxy)phenyl | H | methyl | ethyl | |
| 2.1.1163 | 3-(2-hydroxy-ethoxy)-5-(2,2,2-trifluoro-ethoxy)phenyl | H | methyl | ethyl | |
| 2.1.1164 | 3-[(tert-butoxy-carbonyl)oxy]-5-(2,2,2-trifluoro-ethoxy)phenyl | H | methyl | ethyl | |
| 2.1.1165 | 3-nitro-5--(2,2,2-trifluoroethoxy)-phenyl | H | methyl | ethyl | |
| 2.1.1166 | 3-acetoxy-5-(2,2,2-trifluoro-ethoxy)phenyl | H | methyl | ethyl | |
| 2.1.1167 | {3-[(tert-butoxy-carbonyl)amino]-5-(2,2,2-trifluoroethoxy)-phenyl} | H | methyl | ethyl | |
| 2.1.1168 | 3-methyl-sulfanyl-5-(2,2,2-trifluoro-ethoxy)phenyl | H | methyl | ethyl | |
| 2.1.1169 | 3,5-bis(2-chloroethoxy)-phenyl | H | methyl | ethyl | |

TABLE 2.1-continued

Inventive compounds of the general formula (I) in which W* is COOY, R¹ is hydrogen, and aryl is the radical.

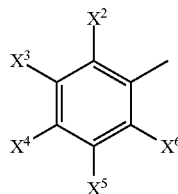

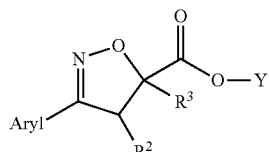

| No. | Aryl | R² | R³ | Y | Physical data |
|---|---|---|---|---|---|
| 2.1.1170 | 3-(2-hydroxy-ethoxy)-5-(2-chloroethoxy)-phenyl | H | methyl | ethyl | |
| 2.1.1171 | 3-[(tert-butoxy-carbonyl)oxy]-5-(2-chloro-ethoxy)phenyl | H | methyl | ethyl | |
| 2.1.1172 | 3-nitro-5-(2-chloroethoxy)-phenyl | H | methyl | ethyl | |
| 2.1.1173 | 3-acetoxy-5-(2-chloroethoxy)-phenyl | H | methyl | ethyl | |
| 2.1.1174 | {3-[(tert-butoxy-carbonyl)amino]-5-(2-chloro-ethoxy)phenyl} | H | methyl | ethyl | |
| 2.1.1175 | 3-methyl-sulfanyl-5-(2-chloroethoxy)-phenyl | H | methyl | ethyl | |
| 2.1.1176 | 3,5-bis(2-hydroxy-ethoxy)phenyl | H | methyl | ethyl | |
| 2.1.1177 | 3-[(tert-butoxy-carbonyl)oxy]-5-(2-hydroxy-ethoxy)phenyl | H | methyl | ethyl | |
| 2.1.1178 | 3-nitro-5-(2-hydroxy-ethoxy)phenyl | H | methyl | ethyl | |
| 2.1.1179 | 3-acetoxy-5-(2-hydroxyethoxy)-phenyl | H | methyl | ethyl | |
| 2.1.1180 | 3-[(tert-butoxy-carbonyl)amino]-5-(2-hydroxy-ethoxy)-phenyl | H | methyl | ethyl | |
| 2.1.1181 | 3-methyl-sulfanyl-5-(2-hydroxyethoxy)-phenyl | H | methyl | ethyl | |
| 2.1.1182 | 3,5-bis[(tert-butoxy-carbonyl)oxy]-phenyl | H | methyl | ethyl | |
| 2.1.1183 | 3-nitro-5-[(tert-butoxy-carbonyl)oxy]-phenyl | H | methyl | ethyl | |
| 2.1.1184 | 3-acetoxy-5-[(tert-butoxy-carbonyl)oxy]-phenyl | H | methyl | ethyl | |
| 2.1.1185 | {3-[(tert-butoxy-carbonyl)amino]- | H | methyl | ethyl | |

TABLE 2.1-continued

Inventive compounds of the general formula (I) in which W* is COOY, R¹ is hydrogen, and aryl is the radical.

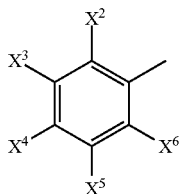

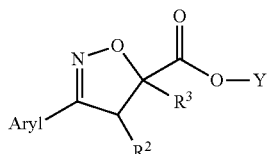

| No. | Aryl | R² | R³ | Y | Physical data |
|---|---|---|---|---|---|
| 2.1.1186 | 5[(tert-butoxy-carbonyl)oxy]-phenyl) 3,5-bis(acetoxy)-phenyl | H | methyl | ethyl | |
| 2.1.1187 | {3-[(tert-butoxy-carbonyl)amino]-5-acetoxy-phenyl} | H | methyl | ethyl | |
| 2.1.1188 | 3-methyl-sulfanyl-5-acetoxyphenyl | H | methyl | ethyl | |
| 2.1.1189 | 3,5-dinitrophenyl | H | methyl | ethyl | |
| 2.1.1190 | 3-acetoxy-5-nitrophenyl | H | methyl | ethyl | |
| 2.1.1191 | {3-[(tert-butoxy-carbonyl)amino]-5-nitrophenyl} | H | methyl | ethyl | |
| 2.1.1192 | 3-methyl-sulfanyl-5-nitrophenyl | H | methyl | ethyl | |
| 2.1.1193 | 3,5-bis[(tert-butoxycarbonyl)-amino]phenyl | H | methyl | ethyl | |
| 2.1.1194 | 3-methyl-sulfanyl-5-[(tert-butoxy-carbonyl)amino]phenyl | H | methyl | ethyl | |
| 2.1.1195 | 3,5-di(methyl-sulfanyl)phenyl | H | methyl | ethyl | |
| 2.1.1196 | 3,4-difluoro-phenyl | H | methyl | ethyl | [CDCl₃] 1.35 (t, 3H); 1.72 (s, 3H); 3.15 (d, 1H); 3.86 (d, 1H); 4.25 (m, 2H); 7.20 (m, 1H); 7.35 (m, 1H); 7.52 (m, 1H). |
| 2.1.1197 | 3,4-difluoro-phenyl | H | ethyl | ethyl | [CDCl₃] 1.0 (t, 3H); 1.32 (t, 3H); 2.08 (q, 2H); 3.18 (d, 1H); 3.80 (d, 1H); 4.25 (m, 2H); 7.22 (m, 1H); 7.38 (m, 1H); 7.52 (m, 1H). |
| 2.1.1198 | 3,4-difluoro-phenyl | H | isopropyl | ethyl | |
| 2.1.1199 | 3,4-difluoro-phenyl | H | cyclo-propyl | ethyl | |
| 2.1.1200 | 3-chloro-4-fluorophenyl | H | methyl | ethyl | [CDCl₃] 1.31 (t, 3H); 1.71 (s, 3H); 3.15 (d, 1H); 3.82 (d, 1H); 4.25 (m, 2H); 7.18 (t, 1H); 7.55 (m, 1H); 7.70 (m, 1H). |
| 2.1.1201 | 3-chloro-4-fluorophenyl | H | ethyl | ethyl | |
| 2.1.1202 | 3-chloro-4-fluorophenyl | H | isopropyl | ethyl | |
| 2.1.1203 | 3-chloro-4-fluorophenyl | H | cyclo-propyl | ethyl | |
| 2.1.1204 | 3-bromo-4-fluorophenyl | H | methyl | ethyl | |

TABLE 2.1-continued

Inventive compounds of the general formula (I) in which W* is COOY, R¹ is hydrogen, and aryl is the radical.

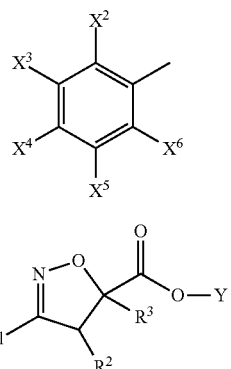

| No. | Aryl | R² | R³ | Y | Physical data |
|---|---|---|---|---|---|
| 2.1.1205 | 3-methyl-4-fluorophenyl | H | methyl | ethyl | |
| 2.1.1206 | 3-ethyl-4-fluorophenyl | H | methyl | ethyl | |
| 2.1.1207 | 3-cyclopropyl-4-fluorophenyl | H | methyl | ethyl | |
| 2.1.1208 | 3-vinyl-4-fluorophenyl | H | methyl | ethyl | |
| 2.1.1209 | 3-ethynyl-4-fluorophenyl | H | methyl | ethyl | |
| 2.1.1210 | 3-cyano-4-fluorophenyl | H | methyl | ethyl | |
| 2.1.1211 | 3-methoxy-4-fluorophenyl | H | methyl | ethyl | |
| 2.1.1212 | 3-ethoxy-4-fluorophenyl | H | methyl | ethyl | |
| 2.1.1213 | 3-trifluoromethoxy-4-fluorophenyl | H | methyl | ethyl | |
| 2.1.1214 | 3-nitro-4-fluorophenyl | H | methyl | ethyl | |
| 2.1.1215 | 3-fluoro-4-chlorophenyl | H | methyl | ethyl | [$CDCl_3$] 1.31 (t, 3H); 1.71 (s, 3H); 3.15 (d, 1H); 3.85 (d, 1H); 4.25 (m, 2H); 7.40-7.50 (m, 3H). |
| 2.1.1216 | 3,4-dichlorophenyl | H | methyl | ethyl | [$CDCl_3$] 1.31 (t, 3H); 1.72 (s, 3H); 3.15 (d, 1H); 3.84 (d, 1H); 4.25 (mc, 2H); 7.5 (mc, 2H); 7.71 (s, 1H) |
| 2.1.1217 | 3-bromo-4-chlorophenyl | H | methyl | ethyl | |
| 2.1.1218 | 3-methyl-4-chlorophenyl | H | methyl | ethyl | |
| 2.1.1219 | 3-ethyl-4-chlorophenyl | H | methyl | ethyl | |
| 2.1.1220 | 3-cyclopropyl-4-chlorophenyl | H | methyl | ethyl | |
| 2.1.1221 | 3-vinyl-4-chlorophenyl | H | methyl | ethyl | |
| 2.1.1222 | 3-ethynyl-4-chlorophenyl | H | methyl | ethyl | |
| 2.1.1223 | 3-cyano-4-chlorophenyl | H | methyl | ethyl | |
| 2.1.1224 | 3-trifluoromethyl-4-chlorophenyl | H | methyl | ethyl | |
| 2.1.1225 | 3-methoxy-4-chlorophenyl | H | methyl | ethyl | |
| 2.1.1226 | 3-ethoxy-4-chlorophenyl | H | methyl | ethyl | |
| 2.1.1227 | 3-trifluoromethoxy-4-chlorophenyl | H | methyl | ethyl | |
| 2.1.1228 | 3-nitro-4-chlorophenyl | H | methyl | ethyl | |
| 2.1.1229 | 3-fluoro-4-bromophenyl | H | methyl | ethyl | |

TABLE 2.1-continued

Inventive compounds of the general formula (I) in which W* is COOY, R¹ is hydrogen, and aryl is the radical.

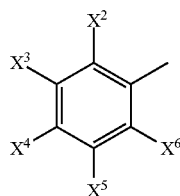

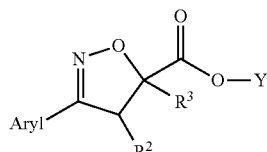

| No. | Aryl | R² | R³ | Y | Physical data |
|---|---|---|---|---|---|
| 2.1.1230 | 3-chloro-4-bromophenyl | H | methyl | ethyl | |
| 2.1.1231 | 3,4-dibromo-phenyl | H | methyl | ethyl | |
| 2.1.1232 | 3-methyl-4-bromophenyl | H | methyl | ethyl | |
| 2.1.1233 | 3-ethyl-4-bromophenyl | H | methyl | ethyl | |
| 2.1.1234 | 3-cyclopropyl-4-bromophenyl | H | methyl | ethyl | |
| 2.1.1235 | 3-vinyl-4-bromophenyl | H | methyl | ethyl | |
| 2.1.1236 | 3-ethynyl-4-bromophenyl | H | methyl | ethyl | |
| 2.1.1237 | 3-cyano-4-bromophenyl | H | methyl | ethyl | |
| 2.1.1238 | 3-trifluoro-methyl-4-bromophenyl | H | methyl | ethyl | |
| 2.1.1239 | 3-methoxy-4-phenyl | H | methyl | ethyl | |
| 2.1.1240 | 3-ethoxy-4-bromophenyl | H | methyl | ethyl | |
| 2.1.1241 | 3-trifluoro-methoxy-4-bromophenyl | H | methyl | ethyl | |
| 2.1.1242 | 3-nitro-4-bromophenyl | H | methyl | ethyl | |
| 2.1.1243 | 3-fluoro-4-iodophenyl | H | methyl | ethyl | |
| 2.1.1244 | 3-chloro-4-iodophenyl | H | methyl | ethyl | |
| 2.1.1245 | 3-bromo-4-iodophenyl | H | methyl | ethyl | |
| 2.1.1246 | 3-methyl-4-iodophenyl | H | methyl | ethyl | |
| 2.1.1247 | 3-ethyl-4-iodophenyl | H | methyl | ethyl | |
| 2.1.1248 | 3-cyclopropyl-4-iodophenyl | H | methyl | ethyl | |
| 2.1.1249 | 3-vinyl-4-iodophenyl | H | methyl | ethyl | |
| 2.1.1250 | 3-ethynyl-4-iodophenyl | H | methyl | ethyl | |
| 2.1.1251 | 3-cyano-4-iodophenyl | H | methyl | ethyl | |
| 2.1.1252 | 3-trifluoro-methyl-4-iodophenyl | H | methyl | ethyl | |
| 2.1.1253 | 3-methoxy-4-iodophenyl | H | methyl | ethyl | |
| 2.1.1254 | 3-ethoxy-4-iodophenyl | H | methyl | ethyl | |
| 2.1.1255 | 3-trifluoro-methoxy-4-iodophenyl | H | methyl | ethyl | |

TABLE 2.1-continued

Inventive compounds of the general formula (I) in which W* is COOY, R¹ is hydrogen, and aryl is the radical.

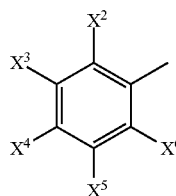

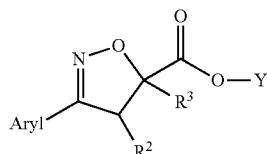

| No. | Aryl | R² | R³ | Y | Physical data |
|---|---|---|---|---|---|
| 2.1.1256 | 3-nitro-4-iodophenyl | H | methyl | ethyl | |
| 2.1.1257 | 3-fluoro-4-methylphenyl | H | methyl | ethyl | |
| 2.1.1258 | 3-chloro-4-methylphenyl | H | methyl | ethyl | [CDCl$_3$] 1.32 t, 3H); 1.70 (s, 3H); 2.41 (s, 3H); 3.15 (d, 1H); 3.85 (d, 1H); 4.25 (m, 2H); 7.24 (m, 1H); 7.45 (m, 1H); 7.61 (s, 1H). |
| 2.1.1259 | 3-bromo-4-methylphenyl | H | methyl | ethyl | |
| 2.1.1260 | 3,4-dimethyl-phenyl | H | methyl | ethyl | |
| 2.1.1261 | 3,4-dimethyl-phenyl | H | ethyl | ethyl | |
| 2.1.1262 | 3,4-dimethyl-phenyl | H | isopropyl | ethyl | |
| 2.1.1263 | 3,4-dimethyl-phenyl | H | cyclopropyl | ethyl | |
| 2.1.1264 | 3-ethyl-4-methylphenyl | H | methyl | ethyl | |
| 2.1.1265 | 3-cyclopropyl-4-methylphenyl | H | methyl | ethyl | |
| 2.1.1266 | 3-vinyl-4-methylphenyl | H | methyl | ethyl | |
| 2.1.1267 | 3-ethynyl-4-methylphenyl | H | methyl | ethyl | |
| 2.1.1268 | 3-cyano-4-methylphenyl | H | methyl | ethyl | |
| 2.1.1269 | 3-trifluoro-methyl-4-methylphenyl | H | methyl | ethyl | |
| 2.1.1270 | 3-methoxy-4-methylphenyl | H | methyl | ethyl | |
| 2.1.1271 | 3-ethoxy-4-methylphenyl | H | methyl | ethyl | |
| 2.1.1272 | 3-trifluoro-methoxy-4-methylphenyl | H | methyl | ethyl | |
| 2.1.1273 | 3-nitro-4-methylphenyl | H | methyl | ethyl | |
| 2.1.1274 | 3-fluoro-4-ethylphenyl | H | methyl | ethyl | |
| 2.1.1275 | 3-chloro-4-ethylphenyl | H | methyl | ethyl | |
| 2.1.1276 | 3-bromo-4-ethylphenyl | H | methyl | ethyl | |
| 2.1.1277 | 3-methyl-4-ethylphenyl | H | methyl | ethyl | |
| 2.1.1278 | 3,4-diethyl-phenyl | H | methyl | ethyl | |
| 2.1.1279 | 3-cyclopropyl-4-ethylphenyl | H | methyl | ethyl | |
| 2.1.1280 | 3-vinyl-4-ethylphenyl | H | methyl | ethyl | |
| 2.1.1281 | 3-ethynyl-4-ethylphenyl | H | methyl | ethyl | |

TABLE 2.1-continued

Inventive compounds of the general formula (I) in which W* is COOY, R¹ is hydrogen, and aryl is the radical.

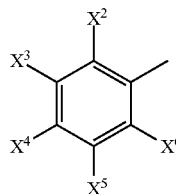

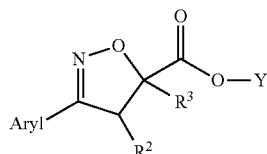

| No. | Aryl | R² | R³ | Y | Physical data |
|---|---|---|---|---|---|
| 2.1.1282 | 3-cyano-4-ethylphenyl | H | methyl | ethyl | |
| 2.1.1283 | 3-trifluoromethyl-4-ethylphenyl | H | methyl | ethyl | |
| 2.1.1284 | 3-methoxy-4-ethylphenyl | H | methyl | ethyl | |
| 2.1.1285 | 3-ethoxy-4-ethylphenyl | H | methyl | ethyl | |
| 2.1.1286 | 3-trifluoromethoxy-4-ethylphenyl | H | methyl | ethyl | |
| 2.1.1287 | 3-nitro-4-ethylphenyl | H | methyl | ethyl | |
| 2.1.1288 | 3-fluoro-4-propylphenyl | H | methyl | ethyl | |
| 2.1.1289 | 3-chloro-4-propylphenyl | H | methyl | ethyl | |
| 2.1.1290 | 3-bromo-4-propylphenyl | H | methyl | ethyl | |
| 2.1.1291 | 3-methyl-4-propylphenyl | H | methyl | ethyl | |
| 2.1.1292 | 3-methyl-4-propylphenyl | H | methyl | ethyl | |
| 2.1.1293 | 3-cyclopropyl-4-propylphenyl | H | methyl | ethyl | |
| 2.1.1294 | 3-vinyl-4-propylphenyl | H | methyl | ethyl | |
| 2.1.1295 | 3-ethynyl-4-propylphenyl | H | methyl | ethyl | |
| 2.1.1296 | 3-cyano-4-propylphenyl | H | methyl | ethyl | |
| 2.1.1297 | 3-trifluoromethyl-4-propylphenyl | H | methyl | ethyl | |
| 2.1.1298 | 3-methoxy-4-propylphenyl | H | methyl | ethyl | |
| 2.1.1299 | 3-ethoxy-4-propylphenyl | H | methyl | ethyl | |
| 2.1.1300 | 3-trifluoromethoxy-4-propylphenyl | H | methyl | ethyl | |
| 2.1.1301 | 3-nitro-4-propylphenyl | H | methyl | ethyl | |
| 2.1.1302 | 3-fluoro-4-isopropylphenyl | H | methyl | ethyl | |
| 2.1.1303 | 3-chloro-4-isopropylphenyl | H | methyl | ethyl | |
| 2.1.1304 | 3-bromo-4-isopropylphenyl | H | methyl | ethyl | |
| 2.1.1305 | 3-methyl-4-isopropylphenyl | H | methyl | ethyl | |
| 2.1.1306 | 3-ethyl-4-isopropylphenyl | H | methyl | ethyl | |
| 2.1.1307 | 3-cyclopropyl-4-isopropylphenyl | H | methyl | ethyl | |

TABLE 2.1-continued

Inventive compounds of the general formula (I) in which W* is COOY, $R^1$ is hydrogen, and aryl is the radical.

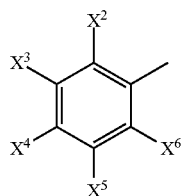

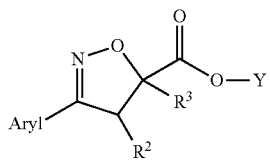

| No. | Aryl | $R^2$ | $R^3$ | Y | Physical data |
|---|---|---|---|---|---|
| 2.1.1308 | 3-vinyl-4-isopropylphenyl | H | methyl | ethyl | |
| 2.1.1309 | 3-ethynyl-4-isopropylphenyl | H | methyl | ethyl | |
| 2.1.1310 | 3-cyano-4-isopropylphenyl | H | methyl | ethyl | |
| 2.1.1311 | 3-trifluoromethyl-4-isopropyl-phenyl | H | methyl | ethyl | |
| 2.1.1312 | 3-methoxy-4-isopropylphenyl | H | methyl | ethyl | |
| 2.1.1313 | 3-thoxy-4-isopropylphenyl | H | methyl | ethyl | |
| 2.1.1314 | 3-trifluoromethoxy-4-isopropyl-phenyl | H | methyl | ethyl | |
| 2.1.1315 | 3-nitro-4-isopropylphenyl | H | methyl | ethyl | |
| 2.1.1316 | 3-fluoro-4-tert-butylphenyl | H | methyl | ethyl | |
| 2.1.1317 | 3-chloro-4-tert-butylphenyl | H | methyl | ethyl | |
| 2.1.1318 | 3-bromo-4-tert-butylphenyl | H | methyl | ethyl | |
| 2.1.1319 | 3-methyl-4-tert-butylphenyl | H | methyl | ethyl | |
| 2.1.1320 | 3-ethyl-4-tert-butylphenyl | H | methyl | ethyl | |
| 2.1.1321 | 3-cyclopropyl-4-tert-butylphenyl | H | methyl | ethyl | |
| 2.1.1322 | 3-vinyl-4-tert-butylphenyl | H | methyl | ethyl | |
| 2.1.1323 | 3-ethynyl-4-tert-butylphenyl | H | methyl | ethyl | |
| 2.1.1324 | 3-cyano-4-tert-butylphenyl | H | methyl | ethyl | |
| 2.1.1325 | 3-trifluoromethyl-4-tert-butylphenyl | H | methyl | ethyl | |
| 2.1.1326 | 3-methoxy-4-tert-butylphenyl | H | methyl | ethyl | |
| 2.1.1327 | 3-ethoxy-4-tert-butylphenyl | H | methyl | ethyl | |
| 2.1.1328 | 3-trifluoromethoxy-4-tert-butylphenyl | H | methyl | ethyl | |
| 2.1.1329 | 3-nitro-4-tert-butylphenyl | H | methyl | ethyl | |
| 2.1.1330 | 3-fluoro-4-hydroxymethyl-phenyl | H | methyl | ethyl | |
| 2.1.1331 | 3-chloro-4-hydroxymethyl-phenyl | H | methyl | ethyl | |
| 2.1.1332 | 3-bromo-4-hydroxymethyl-phenyl | H | methyl | ethyl | |

TABLE 2.1-continued

Inventive compounds of the general formula (I) in which W* is COOY, R¹ is hydrogen, and aryl is the radical.

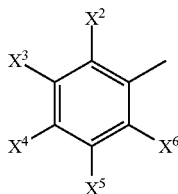

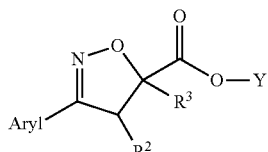

| No. | Aryl | R² | R³ | Y | Physical data |
|---|---|---|---|---|---|
| 2.1.1333 | 3-methyl-4-hydroxymethyl-phenyl | H | methyl | ethyl | |
| 2.1.1334 | 3-ethyl-4-hydroxymethyl-phenyl | H | methyl | ethyl | |
| 2.1.1335 | 3-cyclopropyl-4-hydroxymethyl-phenyl | H | methyl | ethyl | |
| 2.1.1336 | 3-vinyl-4-hydroxymethyl-phenyl | H | methyl | ethyl | |
| 2.1.1337 | 3-ethynyl-4-hydroxymethyl-phenyl | H | methyl | ethyl | |
| 2.1.1338 | 3-cyano-4-hydroxymethyl-phenyl | H | methyl | ethyl | |
| 2.1.1339 | 3-trifluoromethyl-4-hydroxymethyl-phenyl | H | methyl | ethyl | |
| 2.1.1340 | 3-methoxy-4-hydroxymethyl-phenyl | H | methyl | ethyl | |
| 2.1.1341 | 3-ethoxy-4-hydroxymethyl-phenyl | H | methyl | ethyl | |
| 2.1.1342 | 3-trifluoromethoxy-4-hydroxymethyl-phenyl | H | methyl | ethyl | |
| 2.1.1343 | 3-nitro-4-hydroxymethyl-phenyl | H | methyl | ethyl | |
| 2.1.1344 | 3-fluoro-4-cyclopropyl-phenyl | H | methyl | ethyl | |
| 2.1.1345 | 3-chloro-4-cyclopropyl-phenyl | H | methyl | ethyl | |
| 2.1.1346 | 3-bromo-4-cyclopropyl-phenyl | H | methyl | ethyl | |
| 2.1.1347 | 3-methyl-4-cyclopropyl-phenyl | H | methyl | ethyl | |
| 2.1.1348 | 3-ethyl-4-cyclopropyl-phenyl | H | methyl | ethyl | |
| 2.1.1349 | 3-cyclopropyl-4-cyclopropyl-phenyl | H | methyl | ethyl | |
| 2.1.1350 | 3-vinyl-4-cyclopropyl-phenyl | H | methyl | ethyl | |

TABLE 2.1-continued

Inventive compounds of the general formula (I) in which W* is COOY, R¹ is hydrogen, and aryl is the radical.

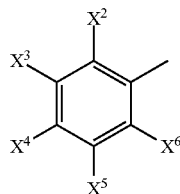

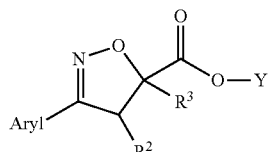

| No. | Aryl | R² | R³ | Y | Physical data |
|---|---|---|---|---|---|
| 2.1.1351 | 3-ethynyl-4-cyclopropyl-phenyl | H | methyl | ethyl | |
| 2.1.1352 | 3-cyano-4-cyclopropyl-phenyl | H | methyl | ethyl | |
| 2.1.1353 | 3-trifluoro-methyl-4-cyclopropyl-phenyl | H | methyl | ethyl | |
| 2.1.1354 | 3-methoxy-4-cyclopropyl-phenyl | H | methyl | ethyl | |
| 2.1.1355 | 3-ethoxy-4-cyclopropyl-phenyl | H | methyl | ethyl | |
| 2.1.1356 | 3-trifluoro-methoxy-4-cyclopropyl-phenyl | H | methyl | ethyl | |
| 2.1.1357 | 3-fluoro-4-methoxy-carbonylphenyl | H | methyl | ethyl | |
| 2.1.1358 | 3-chloro-4-methoxy-carbonylphenyl | H | methyl | ethyl | |
| 2.1.1359 | 3-bromo-4-methoxy-carbonylphenyl | H | methyl | ethyl | |
| 2.1.1360 | 3-methyl-4-methoxy-carbonylphenyl | H | methyl | ethyl | |
| 2.1.1361 | 3-ethyl-4-methoxy-carbonylphenyl | H | methyl | ethyl | |
| 2.1.1362 | 3-cyclopropyl-4-methoxy-carbonylphenyl | H | methyl | ethyl | |
| 2.1.1363 | 3-vinyl-4-methoxy-carbonylphenyl | H | methyl | ethyl | |
| 2.1.1364 | 3-ethynyl-4-methoxy-carbonylphenyl | H | methyl | ethyl | |
| 2.1.1365 | 3-cyano-4-methoxy-carbonylphenyl | H | methyl | ethyl | |
| 2.1.1366 | 3-trifluoro-methyl-4-methoxy-carbonylphenyl | H | methyl | ethyl | |
| 2.1.1367 | 3-methoxy-4-methoxy-carbonylphenyl | H | methyl | ethyl | |
| 2.1.1368 | 3-ethoxy-4-methoxy-carbonylphenyl | H | methyl | ethyl | |

TABLE 2.1-continued

Inventive compounds of the general formula (I) in which W* is COOY, R¹ is hydrogen, and aryl is the radical.

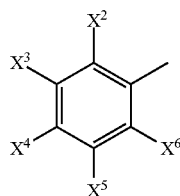

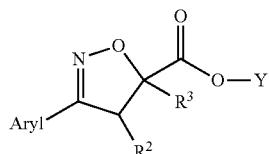

| No. | Aryl | R² | R³ | Y | Physical data |
|---|---|---|---|---|---|
| 2.1.1369 | 3-trifluoro-methoxy-4-methoxy-carbonylphenyl | H | methyl | ethyl | |
| 2.1.1370 | 3-nitro-4-methoxy-carbonylphenyl | H | methyl | ethyl | |
| 2.1.1371 | 3-fluoro-4-vinylphenyl | H | methyl | ethyl | |
| 2.1.1372 | 3-chloro-4-vinylphenyl | H | methyl | ethyl | |
| 2.1.1373 | 3-bromo-4-vinylphenyl | H | methyl | ethyl | |
| 2.1.1374 | 3-methyl-4-vinylphenyl | H | methyl | ethyl | |
| 2.1.1375 | 3-ethyl-4-vinylphenyl | H | methyl | ethyl | |
| 2.1.1376 | 3-cyclopropyl-4-vinylphenyl | H | methyl | ethyl | |
| 2.1.1377 | 3-vinyl-4-vinylphenyl | H | methyl | ethyl | |
| 2.1.1378 | 3-ethynyl-4-vinylphenyl | H | methyl | ethyl | |
| 2.1.1379 | 3-cyano-4-vinylphenyl | H | methyl | ethyl | |
| 2.1.1380 | 3-trifluoro-methyl-4-vinylphenyl | H | methyl | ethyl | |
| 2.1.1381 | 3-methoxy-4-vinylphenyl | H | methyl | ethyl | |
| 2.1.1382 | 3-ethoxy-4-vinylphenyl | H | methyl | ethyl | |
| 2.1.1383 | 3-trifluoro-methoxy-4-vinylphenyl | H | methyl | ethyl | |
| 2.1.1384 | 3-nitro-4-vinylphenyl | H | methyl | ethyl | |
| 2.1.1385 | 3-fluoro-4-ethynylphenyl | H | methyl | ethyl | |
| 2.1.1386 | 3-chloro-4-ethynylphenyl | H | methyl | ethyl | |
| 2.1.1387 | 3-bromo-4-ethynylphenyl | H | methyl | ethyl | |
| 2.1.1388 | 3-methyl-4-ethynylphenyl | H | methyl | ethyl | |
| 2.1.1389 | 3-ethyl-4-ethynylphenyl | H | methyl | ethyl | |
| 2.1.1390 | 3-cyclopropyl-4-ethynylphenyl | H | methyl | ethyl | |
| 2.1.1391 | 3-vinyl-4-ethynylphenyl | H | methyl | ethyl | |
| 2.1.1392 | 3-cyano-4-ethynylphenyl | H | methyl | ethyl | |
| 2.1.1393 | 3-trifluoro-methyl-4-ethynylphenyl | H | methyl | ethyl | |

TABLE 2.1-continued

Inventive compounds of the general formula (I) in which W* is COOY, R¹ is hydrogen, and aryl is the radical.

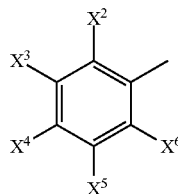

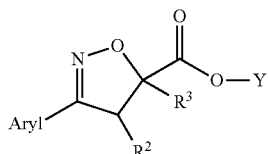

| No. | Aryl | R² | R³ | Y | Physical data |
|---|---|---|---|---|---|
| 2.1.1394 | 3-methoxy-4-ethynylphenyl | H | methyl | ethyl | |
| 2.1.1395 | 3-ethoxy-4-ethynylphenyl | H | methyl | ethyl | |
| 2.1.1396 | 3-trifluoro-methoxy-4-ethynylphenyl | H | methyl | ethyl | |
| 2.1.1397 | 3-nitro-4-ethynylphenyl | H | methyl | ethyl | |
| 2.1.1398 | 3-fluoro-4-ethynylphenyl | H | methyl | ethyl | |
| 2.1.1399 | 3-fluoro-4-cyanophenyl | H | methyl | ethyl | |
| 2.1.1400 | 3-chloro-4-cyanophenyl | H | methyl | ethyl | |
| 2.1.1401 | 3-bromo-4-cyanophenyl | H | methyl | ethyl | |
| 2.1.1402 | 3-methyl-4-cyanophenyl | H | methyl | ethyl | |
| 2.1.1403 | 3-ethyl-4-cyanophenyl | H | methyl | ethyl | |
| 2.1.1404 | 3-cyclopropyl-4-cyanophenyl | H | methyl | ethyl | |
| 2.1.1405 | 3-vinyl-4-cyanophenyl | H | methyl | ethyl | |
| 2.1.1406 | 3-ethynyl-4-cyanophenyl | H | methyl | ethyl | |
| 2.1.1407 | 3-cyano-4-cyanophenyl | H | methyl | ethyl | |
| 2.1.1408 | 3-trifluoro-methyl-4-cyanophenyl | H | methyl | ethyl | |
| 2.1.1409 | 3-trifluoro-methyl-4-cyanophenyl | H | ethyl | ethyl | |
| 2.1.1410 | 3-trifluoro-methyl-4-cyanophenyl | H | isopropyl | ethyl | |
| 2.1.1411 | 3-trifluoro-methyl-4-cyanophenyl | H | cyclo-propyl | ethyl | |
| 2.1.1412 | 3-methoxy-4-cyanophenyl | H | methyl | ethyl | |
| 2.1.1413 | 3-ethoxy-4-cyanophenyl | H | methyl | ethyl | |
| 2.1.1414 | 3-trifluoro-methoxy-4-cyanophenyl | H | methyl | ethyl | |
| 2.1.1415 | 3-nitro-4-cyanophenyl | H | methyl | ethyl | |
| 2.1.1416 | 3-fluoro-4-hydroxyphenyl | H | methyl | ethyl | |
| 2.1.1417 | 3-chloro-4-hydroxyphenyl | H | methyl | ethyl | |
| 2.1.1418 | 3-bromo-4-hydroxyphenyl | H | methyl | ethyl | |

TABLE 2.1-continued

Inventive compounds of the general formula (I) in which W* is COOY, R¹ is hydrogen, and aryl is the radical.

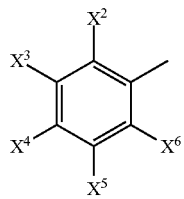

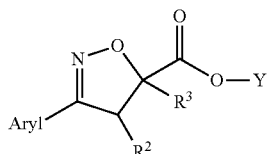

| No. | Aryl | R² | R³ | Y | Physical data |
|---|---|---|---|---|---|
| 2.1.1419 | 3-methyl-4-hydroxyphenyl | H | methyl | ethyl | |
| 2.1.1420 | 3-ethyl-4-hydroxyphenyl | H | methyl | ethyl | |
| 2.1.1421 | 3-cyclopropyl-4-hydroxyphenyl | H | methyl | ethyl | |
| 2.1.1422 | 3-vinyl-4-hydroxyphenyl | H | methyl | ethyl | |
| 2.1.1423 | 3-ethynyl-4-hydroxyphenyl | H | methyl | ethyl | |
| 2.1.1424 | 3-cyano-4-hydroxyphenyl | H | methyl | ethyl | |
| 2.1.1425 | 3-trifluoro-methyl-4-hydroxyphenyl | H | methyl | ethyl | |
| 2.1.1426 | 3-methoxy-4-hydroxyphenyl | H | methyl | ethyl | |
| 2.1.1427 | 3-ethoxy-4-hydroxyphenyl | H | methyl | ethyl | |
| 2.1.1428 | 3-trifluoro-methoxy-4-hydroxyphenyl | H | methyl | ethyl | |
| 2.1.1429 | 3-nitro-4-hydroxyphenyl | H | methyl | ethyl | |
| 2.1.1430 | 3-fluoro-4-methoxyphenyl | H | methyl | ethyl | |
| 2.1.1431 | 3-chloro-4-methoxyphenyl | H | methyl | ethyl | |
| 2.1.1432 | 3-bromo-4-methoxyphenyl | H | methyl | ethyl | |
| 2.1.1433 | 3-methyl-4-methoxyphenyl | H | methyl | ethyl | |
| 2.1.1434 | 3-ethyl-4-methoxyphenyl | H | methyl | ethyl | |
| 2.1.1435 | 3-cyclopropyl-4-methoxyphenyl | H | methyl | ethyl | |
| 2.1.1436 | 3-vinyl-4-methoxyphenyl | H | methyl | ethyl | |
| 2.1.1437 | 3-ethynyl-4-methoxyphenyl | H | methyl | ethyl | |
| 2.1.1438 | 3-cyano-4-methoxyphenyl | H | methyl | ethyl | |
| 2.1.1439 | 3-trifluoro-methyl-4-methoxyphenyl | H | methyl | ethyl | |
| 2.1.1440 | 3,4-dimethoxy-phenyl | H | methyl | ethyl | |
| 2.1.1441 | 3-ethoxy-4-methoxyphenyl | H | methyl | ethyl | |
| 2.1.1442 | 3-trifluoro-methoxy-4-methoxyphenyl | H | methyl | ethyl | |
| 2.1.1443 | 3-nitro-4-methoxyphenyl | H | methyl | ethyl | |
| 2.1.1444 | 3-fluoro-4-ethoxyphenyl | H | methyl | ethyl | |

TABLE 2.1-continued

Inventive compounds of the general formula (I) in which W* is COOY, R¹ is hydrogen, and aryl is the radical.

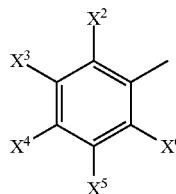

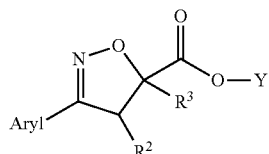

| No. | Aryl | R² | R³ | Y | Physical data |
|---|---|---|---|---|---|
| 2.1.1445 | 3-chloro-4-ethoxyphenyl | H | methyl | ethyl | |
| 2.1.1446 | 3-bromo-4-ethoxyphenyl | H | methyl | ethyl | |
| 2.1.1447 | 3-methyl-4-ethoxyphenyl | H | methyl | ethyl | |
| 2.1.1448 | 3-ethyl-4-ethoxyphenyl | H | methyl | ethyl | |
| 2.1.1449 | 3-cyclopropyl-4-ethoxyphenyl | H | methyl | ethyl | |
| 2.1.1450 | 3-vinyl-4-ethoxyphenyl | H | methyl | ethyl | |
| 2.1.1451 | 3-ethynyl-4-ethoxyphenyl | H | methyl | ethyl | |
| 2.1.1452 | 3-cyano-4-ethoxyphenyl | H | methyl | ethyl | |
| 2.1.1453 | 3-trifluoro-methyl-4-ethoxyphenyl | H | methyl | ethyl | |
| 2.1.1454 | 3-methoxy-4-ethoxyphenyl | H | methyl | ethyl | |
| 2.1.1455 | 2,4-diethoxy-phenyl | H | methyl | ethyl | |
| 2.1.1456 | 3-trifluoro-methoxy-4-ethoxyphenyl | H | methyl | ethyl | |
| 2.1.1457 | 3-nitro-4-ethoxyphenyl | H | methyl | ethyl | |
| 2.1.1458 | 3-fluoro-4-propoxyphenyl | H | methyl | ethyl | |
| 2.1.1459 | 3-chloro-4-propoxyphenyl | H | methyl | ethyl | |
| 2.1.1460 | 3-bromo-4-propoxyphenyl | H | methyl | ethyl | |
| 2.1.1461 | 3-methyl-4-propoxyphenyl | H | methyl | ethyl | |
| 2.1.1462 | 3-ethyl-4-propoxyphenyl | H | methyl | ethyl | |
| 2.1.1463 | 3-cyclopropyl-4-propoxyphenyl | H | methyl | ethyl | |
| 2.1.1464 | 3-vinyl-4-propoxyphenyl | H | methyl | ethyl | |
| 2.1.1465 | 3-ethynyl-4-propoxyphenyl | H | methyl | ethyl | |
| 2.1.1466 | 3-cyano-4-propoxyphenyl | H | methyl | ethyl | |
| 2.1.1467 | 3-trifluoro-methyl-4-propoxyphenyl | H | methyl | ethyl | |
| 2.1.1468 | 3-methoxy-4-propoxyphenyl | H | methyl | ethyl | |
| 2.1.1469 | 3-ethoxy-4-propoxyphenyl | H | methyl | ethyl | |
| 2.1.1470 | 3-trifluoro-methoxy-4-propoxyphenyl | H | methyl | ethyl | |

TABLE 2.1-continued

Inventive compounds of the general formula (I) in which W* is COOY, R¹ is hydrogen, and aryl is the radical.

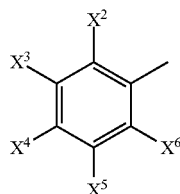

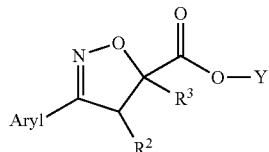

| No. | Aryl | R² | R³ | Y | Physical data |
|---|---|---|---|---|---|
| 2.1.1471 | 3-nitro-4-propoxyphenyl | H | methyl | ethyl | |
| 2.1.1472 | 3-fluoro-4-isopropoxy-phenyl | H | methyl | ethyl | |
| 2.1.1473 | 3-chloro-4-isopropoxy-phenyl | H | methyl | ethyl | |
| 2.1.1474 | 3-bromo-4-isopropoxy-phenyl | H | methyl | ethyl | |
| 2.1.1475 | 3-methyl-4-isopropoxy-phenyl | H | methyl | ethyl | |
| 2.1.1476 | 3-ethyl-4-isopropoxy-phenyl | H | methyl | ethyl | |
| 2.1.1477 | 3-cyclopropyl-4-isopropoxy-phenyl | H | methyl | ethyl | |
| 2.1.1478 | 3-vinyl-4-isopropoxy-phenyl | H | methyl | ethyl | |
| 2.1.1479 | 3-ethynyl-4-isopropoxy-phenyl | H | methyl | ethyl | |
| 2.1.1480 | 3-cyano-4-isopropoxy-phenyl | H | methyl | ethyl | |
| 2.1.1481 | 3-trifluoro-methyl-4-isopropoxy-phenyl | H | methyl | ethyl | |
| 2.1.1482 | 3-methoxy-4-isopropoxy-phenyl | H | methyl | ethyl | |
| 2.1.1483 | 3-ethoxy-4-isopropoxy-phenyl | H | methyl | ethyl | |
| 2.1.1484 | 3-trifluoro-methoxy-4-isopropoxy-phenyl | H | methyl | ethyl | |
| 2.1.1485 | 3-nitro-4-isopropoxy-phenyl | H | methyl | ethyl | |
| 2.1.1486 | 3-fluoro-4-tert-butoxyphenyl | H | methyl | ethyl | |
| 2.1.1487 | 3-chloro-4-tert-butoxyphenyl | H | methyl | ethyl | |
| 2.1.1488 | 3-bromo-4-tert-butoxyphenyl | H | methyl | ethyl | |
| 2.1.1489 | 3-methyl-4-tert-butoxyphenyl | H | methyl | ethyl | |

TABLE 2.1-continued

Inventive compounds of the general formula (I) in which W* is COOY, R¹ is hydrogen, and aryl is the radical.

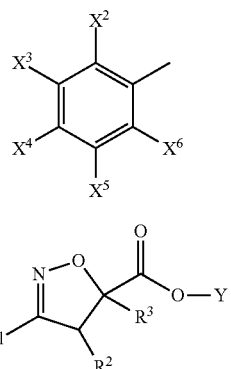

| No. | Aryl | R² | R³ | Y | Physical data |
|---|---|---|---|---|---|
| 2.1.1490 | 3-ethyl-4-tert-butoxyphenyl | H | methyl | ethyl | |
| 2.1.1491 | 3-cyclopropyl-4-tert-butoxyphenyl | H | methyl | ethyl | |
| 2.1.1492 | 3-vinyl-4-tert-butoxyphenyl | H | methyl | ethyl | |
| 2.1.1493 | 3-ethynyl-4-tert-butoxyphenyl | H | methyl | ethyl | |
| 2.1.1494 | 3-cyano-4-tert-butoxyphenyl | H | methyl | ethyl | |
| 2.1.1495 | 3-trifluoromethyl-4-tert-butoxyphenyl | H | methyl | ethyl | |
| 2.1.1496 | 3-methoxy-4-tert-butoxyphenyl | H | methyl | ethyl | |
| 2.1.1497 | 3-ethoxy-4-tert-butoxyphenyl | H | methyl | ethyl | |
| 2.1.1498 | 3-trifluoromethoxy-4-tert-butoxyphenyl | H | methyl | ethyl | |
| 2.1.1499 | 3-nitro-4-tert-butoxyphenyl | H | methyl | ethyl | |
| 2.1.1500 | 3-fluoro-4-trifluoromethoxyphenyl | H | methyl | ethyl | |
| 2.1.1501 | 3-chloro-4-trifluoromethoxyphenyl | H | methyl | ethyl | |
| 2.1.1502 | 3-bromo-4-trifluoromethoxyphenyl | H | methyl | ethyl | |
| 2.1.1503 | 3-methyl-4-trifluoromethoxyphenyl | H | methyl | ethyl | |
| 2.1.1504 | 3-ethyl-4-trifluoromethoxyphenyl | H | methyl | ethyl | |
| 2.1.1505 | 3-cyclopropyl-4-trifluoromethoxyphenyl | H | methyl | ethyl | |
| 2.1.1506 | 3-vinyl-4-trifluoromethoxyphenyl | H | methyl | ethyl | |
| 2.1.1507 | 3-ethynyl-4-trifluoromethoxyphenyl | H | methyl | ethyl | |
| 2.1.1508 | 3-cyano-4-trifluoromethoxyphenyl | H | methyl | ethyl | |
| 2.1.1509 | 3-trifluoromethyl-4-trifluoromethoxyphenyl | H | methyl | ethyl | |

TABLE 2.1-continued

Inventive compounds of the general formula (I) in which W* is COOY, R¹ is hydrogen, and aryl is the radical.

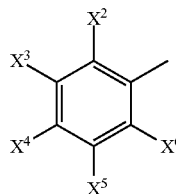

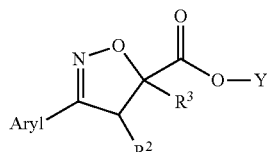

| No. | Aryl | R² | R³ | Y | Physical data |
|---|---|---|---|---|---|
| 2.1.1510 | 3-methoxy-4-trifluoro-methoxyphenyl | H | methyl | ethyl | |
| 2.1.1511 | 3-ethoxy-4-trifluoro-methoxyphenyl | H | methyl | ethyl | |
| 2.1.1512 | 3,4-bis(trifluoro-methoxy)phenyl | H | methyl | ethyl | |
| 2.1.1513 | 3-nitro-4-trifluoro-methoxyphenyl | H | methyl | ethyl | |
| 2.1.1514 | 3-fluoro-4-(2,2,2-trifluoro-ethoxy)phenyl | H | methyl | ethyl | |
| 2.1.1515 | 3-chloro-4-(2,2,2-trifluoro-ethoxy)phenyl | H | methyl | ethyl | |
| 2.1.1516 | 3-bromo-4-(2,2,2-trifluoro-ethoxy)phenyl | H | methyl | ethyl | |
| 2.1.1517 | 3-methyl-4-(2,2,2-trifluoro-ethoxy)phenyl | H | methyl | ethyl | |
| 2.1.1518 | 3-ethyl-4-(2,2,2-trifluoroethoxy)-phenyl | H | methyl | ethyl | |
| 2.1.1519 | 3-cyclopropyl-4-(2,2,2-trifluoro-ethoxy)phenyl | H | methyl | ethyl | |
| 2.1.1520 | 3-vinyl-4-(2,2,2-trifluoroethoxy)-phenyl | H | methyl | ethyl | |
| 2.1.1521 | 3-ethynyl-4-(2,2,2-trifluoro-ethoxyphenyl | H | methyl | ethyl | |
| 2.1.1522 | 3-cyano-4-(2,2,2-trifluoro-ethoxy)phenyl | H | methyl | ethyl | |
| 2.1.1523 | 3-trifluoro-methyl-4-(2,2,2-trifluoroethoxy)-phenyl | H | methyl | ethyl | |
| 2.1.1524 | 3-methoxy-4-(2,2,2-trifluoro-ethoxy)phenyl | H | methyl | ethyl | |
| 2.1.1525 | 3-ethoxy-4-(2,2,2-trifluoro-ethoxy)phenyl | H | methyl | ethyl | |
| 2.1.1526 | 3-trifluoro-methoxy-4-(2,2,2-trifluoro-ethoxy)phenyl | H | methyl | ethyl | |
| 2.1.1527 | 3-nitro-4-(2,2,2-trifluoroethoxy)-phenyl | H | methyl | ethyl | |

TABLE 2.1-continued

Inventive compounds of the general formula (I) in which W* is COOY, R¹ is hydrogen, and aryl is the radical.

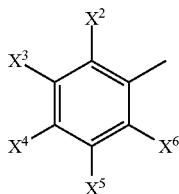

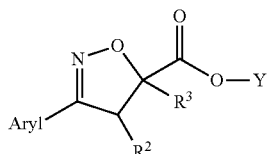

| No. | Aryl | R² | R³ | Y | Physical data |
|---|---|---|---|---|---|
| 2.1.1528 | 3-fluoro-4-difluoromethoxy-phenyl | H | methyl | ethyl | |
| 2.1.1529 | 3-chloro-4-difluoromethoxy-phenyl | H | methyl | ethyl | |
| 2.1.1530 | 3-bromo-4-difluoromethoxy-phenyl | H | methyl | ethyl | |
| 2.1.1531 | 3-methyl-4-difluoromethoxy-phenyl | H | methyl | ethyl | |
| 2.1.1532 | 3-ethyl-4-difluoromethoxy-phenyl | H | methyl | ethyl | |
| 2.1.1533 | 3-cyclopropyl-4-difluoromethoxy-phenyl | H | methyl | ethyl | |
| 2.1.1534 | 3-vinyl-4-difluoromethoxy-phenyl | H | methyl | ethyl | |
| 2.1.1535 | 3-ethynyl-4-difluoromethoxy-phenyl | H | methyl | ethyl | |
| 2.1.1536 | 3-cyano-4-difluoromethoxyphenyl | H | methyl | ethyl | |
| 2.1.1537 | 3-trifluoro-methyl-4-difluoromethoxyphenyl | H | methyl | ethyl | |
| 2.1.1538 | 3-methoxy-4-difluoromethoxyphenyl | H | methyl | ethyl | |
| 2.1.1539 | 3-ethoxy-4-difluoromethoxy-phenyl | H | methyl | ethyl | |
| 2.1.1540 | 3-trifluoro-methoxy-4-difluoromethoxy-phenyl | H | methyl | ethyl | |
| 2.1.1541 | 3-nitro-4-difluoromethoxy-phenyl | H | methyl | ethyl | |
| 2.1.1542 | 3-fluoro-4-(2-methoxyethoxy)-phenyl | H | methyl | ethyl | |
| 2.1.1543 | 3-chloro-4-(2-methoxyethoxy)-phenyl | H | methyl | ethyl | |
| 2.1.1544 | 3-bromo-4-(2-methoxyethoxy)-phenyl | H | methyl | ethyl | |
| 2.1.1545 | 3-methyl-4-(2-methoxyethoxy)-phenyl | H | methyl | ethyl | |

TABLE 2.1-continued

Inventive compounds of the general formula (I) in which W* is COOY, $R^1$ is hydrogen, and aryl is the radical.

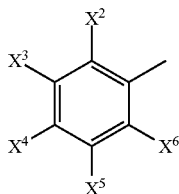

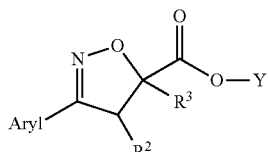

| No. | Aryl | $R^2$ | $R^3$ | Y | Physical data |
|---|---|---|---|---|---|
| 2.1.1546 | 3-ethyl-4-(2-methoxyethoxy)-phenyl | H | methyl | ethyl | |
| 2.1.1547 | 3-cyclopropyl-4-(2-methoxy-ethoxy)phenyl | H | methyl | ethyl | |
| 2.1.1548 | 3-vinyl-4-(2-methoxyethoxy)-phenyl | H | methyl | ethyl | |
| 2.1.1549 | 3-ethynyl-4-(2-methoxyethoxy)-phenyl | H | methyl | ethyl | |
| 2.1.1550 | 3-cyano-4-(2-methoxyethoxy)-phenyl | H | methyl | ethyl | |
| 2.1.1551 | 3-trifluoro-methyl-4-(2-methoxyethoxy)-phenyl | H | methyl | ethyl | |
| 2.1.1552 | 3-methoxy-4-(2-methoxyethoxy)-phenyl | H | methyl | ethyl | |
| 2.1.1553 | 3-ethoxy-4-(2-methoxyethoxy)-phenyl | H | methyl | ethyl | |
| 2.1.1554 | 3-trifluoro-methoxy-(2-methoxyethoxy)-phenyl | H | methyl | ethyl | |
| 2.1.1555 | 3-nitro-4-(2-methoxy-ethoxy)phenyl | H | methyl | ethyl | |
| 2.1.1556 | 3-fluoro-4-(tert-butoxycarbonyl-oxy)phenyl | H | methyl | ethyl | |
| 2.1.1557 | 3-chloro-4-(tert-butoxycarbonyl-oxy)phenyl | H | methyl | ethyl | |
| 2.1.1558 | 3-bromo-4-(tert-butoxycarbonyl-oxy)phenyl | H | methyl | ethyl | |
| 2.1.1559 | 3-methyl-4-(tert-butoxycarbonyl-oxy)phenyl | H | methyl | ethyl | |
| 2.1.1560 | 3-ethyl-4-(tert-butoxycarbonyl-oxy)phenyl | H | methyl | ethyl | |
| 2.1.1561 | 3-cyclopropyl-4-(tert-butoxy-carbonyloxy)-phenyl | H | methyl | ethyl | |
| 2.1.1562 | 3-vinyl-4-(tert-butoxycarbonyl-oxy)phenyl | H | methyl | ethyl | |
| 2.1.1563 | 3-ethynyl-4-(tert-butoxycarbonyl-oxy)phenyl | H | methyl | ethyl | |

TABLE 2.1-continued

Inventive compounds of the general formula (I) in which W* is COOY, R¹ is hydrogen, and aryl is the radical.

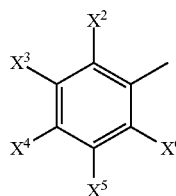

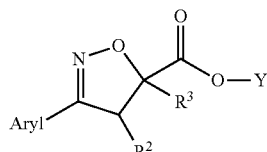

| No. | Aryl | R² | R³ | Y | Physical data |
|---|---|---|---|---|---|
| 2.1.1564 | 3-cyano-4-(tert-butoxycarbonyl-oxy)phenyl | H | methyl | ethyl | |
| 2.1.1565 | 3-trifluoro-methyl-4-(tert-butoxycarbonyl-oxy)phenyl | H | methyl | ethyl | |
| 2.1.1566 | 3-methoxy-4-(tert-butoxy-carbonyloxy)-phenyl | H | methyl | ethyl | |
| 2.1.1567 | 3-ethoxy-4-(tert-butoxycarbonyl-oxy)phenyl | H | methyl | ethyl | |
| 2.1.1568 | 3-trifluoro-methoxy-4-(tert-butoxycarbonyl-oxy)phenyl | H | methyl | ethyl | |
| 2.1.1569 | 2-nitro-4-(tert-butoxycarbonyl-oxy)phenyl | H | methyl | ethyl | |
| 2.1.1570 | 3-fluoro-4-nitrophenyl | H | methyl | ethyl | |
| 2.1.1571 | 3-chloro-4-nitrophenyl | H | methyl | ethyl | |
| 2.1.1572 | 3-bromo-4-nitrophenyl | H | methyl | ethyl | |
| 2.1.1573 | 3-methyl-4-nitrophenyl | H | methyl | ethyl | |
| 2.1.1574 | 3-ethyl-4-nitrophenyl | H | methyl | ethyl | |
| 2.1.1575 | 3-cyclopropyl-4-nitrophenyl | H | methyl | ethyl | |
| 2.1.1576 | 3-vinyl-4-nitrophenyl | H | methyl | ethyl | |
| 2.1.1577 | 3-ethynyl-4-nitrophenyl | H | methyl | ethyl | |
| 2.1.1578 | 3-cyano-4-nitrophenyl | H | methyl | ethyl | |
| 2.1.1579 | 3-trifluoro-methyl-4-nitrophenyl | H | methyl | ethyl | |
| 2.1.1580 | 3-methoxy-4-nitrophenyl | H | methyl | ethyl | |
| 2.1.1581 | 3-ethoxy-4-nitrophenyl | H | methyl | ethyl | |
| 2.1.1582 | 3-trifluoro-methoxy-4-nitrophenyl | H | methyl | ethyl | |
| 2.1.1583 | 3-fluoro-4-methylsulfanyl-phenyl | H | methyl | ethyl | |
| 2.1.1584 | 3-chloro-4-methylsulfanyl-phenyl | H | methyl | ethyl | |

TABLE 2.1-continued

Inventive compounds of the general formula (I) in which W* is COOY, R¹ is hydrogen, and aryl is the radical.

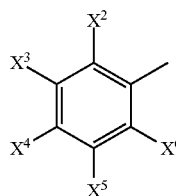

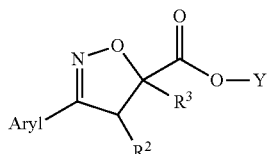

| No. | Aryl | R² | R³ | Y | Physical data |
|---|---|---|---|---|---|
| 2.1.1585 | 3-bromo-4-methylsulfanyl-phenyl | H | methyl | ethyl | |
| 2.1.1586 | 3-methyl-4-methylsulfanyl-phenyl | H | methyl | ethyl | |
| 2.1.1587 | 3-ethyl-4-methylsulfanyl-phenyl | H | methyl | ethyl | |
| 2.1.1588 | 3-cyclopropyl-4-methylsulfanyl-phenyl | H | methyl | ethyl | |
| 2.1.1589 | 3-vinyl-4-methylsulfanyl-phenyl | H | methyl | ethyl | |
| 2.1.1590 | 3-ethynyl-4-methylsulfanyl-phenyl | H | methyl | ethyl | |
| 2.1.1591 | 3-cyano-4-methylsulfanyl-phenyl | H | methyl | ethyl | |
| 2.1.1592 | 3-trifluoromethyl-4-methylsulfanyl-phenyl | H | methyl | ethyl | |
| 2.1.1593 | 3-methoxy-4-methylsulfanyl-phenyl | H | methyl | ethyl | |
| 2.1.1594 | 3-ethoxy-4-methylsulfanyl-phenyl | H | methyl | ethyl | |
| 2.1.1595 | 3-trifluoromethoxy-4-methylsulfanyl-phenyl | H | methyl | ethyl | |
| 2.1.1596 | 3-nitro-4-methyl-sulfanylphenyl | H | methyl | ethyl | |
| 2.1.1597 | 3,6-difluoro-phenyl | H | methyl | ethyl | [CDCl$_3$] 1.31 (t, 3H); 1.70 (s, 3H); 3.29 (dd, 1H); 3.92 (dd, 1H); 4.25 (q, 2H); 7.10 (m, 2H); 7.59 (m, 1H). |
| 2.1.1598 | 3,6-difluoro-phenyl | H | ethyl | ethyl | |
| 2.1.1599 | 3,6-difluoro-phenyl | H | isopropyl | ethyl | |
| 2.1.1600 | 3,6-difluoro-phenyl | H | cyclo-propyl | ethyl | |
| 2.1.1601 | 3-chloro-6-fluorophenyl | H | methyl | ethyl | |
| 2.1.1602 | 3-bromo-6-fluorophenyl | H | methyl | ethyl | [CDCl$_3$] 1.30 (t, 3H); 1.71 (s, 3H); 3.29 (d, 1H); 3.91 (d, 1H); 4.25 (m, 2H); 7.00 (d, 1H); 7.50 (m, 1H); 8.01 (m, 1H). |
| 2.1.1603 | 3-methyl-6-fluorophenyl | H | methyl | ethyl | |
| 2.1.1604 | 3-ethyl-6-fluorophenyl | H | methyl | ethyl | |

TABLE 2.1-continued

Inventive compounds of the general formula (I) in which W* is COOY, R¹ is hydrogen, and aryl is the radical.

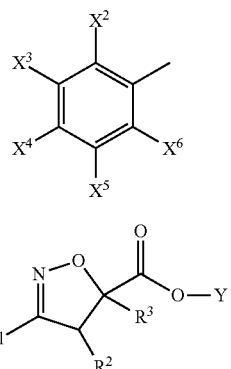

| No. | Aryl | R² | R³ | Y | Physical data |
|---|---|---|---|---|---|
| 2.1.1605 | 3-cyclopropyl-6-fluorophenyl | H | methyl | ethyl | |
| 2.1.1606 | 3-vinyl-6-fluorophenyl | H | methyl | ethyl | |
| 2.1.1607 | 3-ethynyl-6-fluorophenyl | H | methyl | ethyl | |
| 2.1.1608 | 3-cyano-6-fluorophenyl | H | methyl | ethyl | |
| 2.1.1609 | 3-methoxy-6-fluorophenyl | H | methyl | ethyl | [CDCl₃] 1.31 (t, 3H); 1.71 (s, 3H); 3.31 (dd, 1H); 3.80 (s, 3H); 3.90 (dd, 1H); 4.25 (m, 2H); 6.91 (m, 1H); 7.2 (t, 1H); 7.35 (m, 1H). |
| 2.1.1610 | 3-ethoxy-6-fluorophenyl | H | methyl | ethyl | |
| 2.1.1611 | 3-trifluoromethoxy-6-fluorophenyl | H | methyl | ethyl | |
| 2.1.1612 | 3-nitro-6-fluorophenyl | H | methyl | ethyl | |
| 2.1.1613 | 3-fluoro-6-chlorophenyl | H | methyl | ethyl | [CDCl₃] 1.35 (t, 3H); 1.75, (s, 3H); 3.40 (d, 1H); 3.98 (d, 1H); 4.28 (q, 2H); 7.08 (m, 1H); 7.40 (m; 2H). |
| 2.1.1614 | 3-fluoro-6-chlorophenyl | H | ethyl | ethyl | |
| 2.1.1615 | 3-fluoro-6-chlorophenyl | H | propyl | ethyl | |
| 2.1.1616 | 3-fluoro-6-chlorophenyl | H | cyclopropyl | ethyl | |
| 2.1.1617 | 3,6-dichlorophenyl | H | methyl | ethyl | [CDCl₃] 1.33 (t, 3H); 1.72 (s, 3H); 3.38 (d, 1H); 3.98 (d, 1H); 4.39 (m, 2H); 7.32 (m, 2H); 7.68 (m, 1H). |
| 2.1.1618 | 3-bromo-6-chlorophenyl | H | methyl | ethyl | |
| 2.1.1619 | 3-methyl-6-chlorophenyl | H | methyl | ethyl | |
| 2.1.1620 | 3-ethyl-6-chlorophenyl | H | methyl | ethyl | |
| 2.1.1621 | 3-cyclopropyl-6-chlorophenyl | H | methyl | ethyl | |
| 2.1.1622 | 3-vinyl-6-chlorophenyl | H | methyl | ethyl | |
| 2.1.1623 | 3-ethynyl-6-chlorophenyl | H | methyl | ethyl | |
| 2.1.1624 | 3-cyano-6-chlorophenyl | H | methyl | ethyl | |
| 2.1.1625 | 3-trifluoromethyl-6-chlorophenyl | H | methyl | ethyl | |
| 2.1.1626 | 3-hydroxy-6-chlorophenyl | H | methyl | ethyl | [CDCl₃] 1.31 (t, 3H); 1.72 (s, 3H); 3.45 (d, 1H); 3.95 (d, 1H); 4.28 (q, 2H); 6.85 (dd, 1H); 7.20 (dd, 1H); 7.28 (m, 1H). |
| 2.1.1627 | 3-methoxy-6-chlorophenyl | H | methyl | ethyl | |

TABLE 2.1-continued

Inventive compounds of the general formula (I) in which W* is COOY, R¹ is hydrogen, and aryl is the radical.

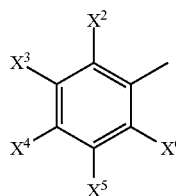

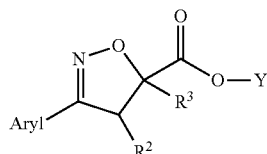

| No. | Aryl | R² | R³ | Y | Physical data |
|---|---|---|---|---|---|
| 2.1.1628 | 3-ethoxy-6-chlorophenyl | H | methyl | ethyl | |
| 2.1.1629 | 3-trifluoromethoxy-6-chlorophenyl | H | methyl | ethyl | |
| 2.1.1630 | 3-nitro-6-chlorophenyl | H | methyl | ethyl | |
| 2.1.1631 | 3-fluoro-6-bromophenyl | H | methyl | ethyl | |
| 2.1.1632 | 3-chloro-6-bromophenyl | H | methyl | ethyl | |
| 2.1.1633 | 3,6-dibromophenyl | H | methyl | ethyl | |
| 2.1.1634 | 3-methyl-6-bromophenyl | H | methyl | ethyl | |
| 2.1.1635 | 3-ethyl-6-bromophenyl | H | methyl | ethyl | |
| 2.1.1636 | 3-cyclopropyl-6-bromophenyl | H | methyl | ethyl | |
| 2.1.1637 | 3-vinyl-6-bromophenyl | H | methyl | ethyl | |
| 2.1.1638 | 3-ethynyl-6-bromophenyl | H | methyl | ethyl | |
| 2.1.1639 | 3-cyano-6-bromophenyl | H | methyl | ethyl | |
| 2.1.1640 | 3-trifluoromethyl-6-bromophenyl | H | methyl | ethyl | |
| 2.1.1641 | 3-methoxy-6-phenyl | H | methyl | ethyl | |
| 2.1.1642 | 3-ethoxy-6-bromophenyl | H | methyl | ethyl | |
| 2.1.1643 | 3-trifluoromethoxy-6-bromophenyl | H | methyl | ethyl | |
| 2.1.1644 | 3-nitro-6-bromophenyl | H | methyl | ethyl | |
| 2.1.1645 | 3-fluoro-6-iodophenyl | H | methyl | ethyl | |
| 2.1.1646 | 3-chloro-6-iodophenyl | H | methyl | ethyl | |
| 2.1.1647 | 3-bromo-6-iodophenyl | H | methyl | ethyl | |
| 2.1.1648 | 3-methyl-6-iodophenyl | H | methyl | ethyl | |
| 2.1.1649 | 3-ethyl-6-iodophenyl | H | methyl | ethyl | |
| 2.1.1650 | 3-cyclopropyl-6-iodophenyl | H | methyl | ethyl | |
| 2.1.1651 | 3-vinyl-6-iodophenyl | H | methyl | ethyl | |
| 2.1.1652 | 3-ethynyl-6-iodophenyl | H | methyl | ethyl | |
| 2.1.1653 | 3-cyano-6-iodophenyl | H | methyl | ethyl | |

TABLE 2.1-continued

Inventive compounds of the general formula (I) in which W* is COOY, R¹ is hydrogen, and aryl is the radical.

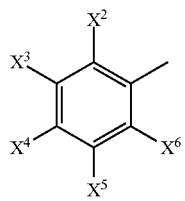

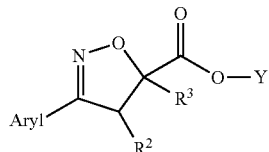

| No. | Aryl | R² | R³ | Y | Physical data |
|---|---|---|---|---|---|
| 2.1.1654 | 3-trifluoro-methyl-6-iodophenyl | H | methyl | ethyl | |
| 2.1.1655 | 3-methoxy-6-iodophenyl | H | methyl | ethyl | |
| 2.1.1656 | 3-ethoxy-6-iodophenyl | H | methyl | ethyl | |
| 2.1.1657 | 3-trifluoro-methoxy-6-iodophenyl | H | methyl | ethyl | |
| 2.1.1658 | 3-nitro-6-iodophenyl | H | methyl | ethyl | |
| 2.1.1659 | 3-fluoro-6-methylphenyl | H | methyl | ethyl | [CDCl₃] 1.31 (t, 3H); 1.72 (s, 3H); 2.50 (s, 3H); 3.22 (d, 1H); 3.87 (d, 1H); 4.28 (m, 2H); 7.00 (m, 2H); 7.21 (m, 1H). |
| 2.1.1660 | 3-chloro-6-methylphenyl | H | methyl | ethyl | |
| 2.1.1661 | 3-bromo-6-methylphenyl | H | methyl | ethyl | |
| 2.1.1662 | 3,6-dimethylphenyl | H | methyl | ethyl | |
| 2.1.1663 | 3-ethyl-6-methylphenyl | H | methyl | ethyl | |
| 2.1.1664 | 3-cyclopropyl-6-methylphenyl | H | methyl | ethyl | |
| 2.1.1665 | 3-vinyl-6-methylphenyl | H | methyl | ethyl | |
| 2.1.1666 | 3-ethynyl-6-methylphenyl | H | methyl | ethyl | |
| 2.1.1667 | 3-cyano-6-methylphenyl | H | methyl | ethyl | |
| 2.1.1668 | 3-trifluoro-methyl-6-methylphenyl | H | methyl | ethyl | |
| 2.1.1669 | 3-methoxy-6-methylphenyl | H | methyl | ethyl | |
| 2.1.1670 | 3-ethoxy-6-methylphenyl | H | methyl | ethyl | |
| 2.1.1671 | 3-trifluoro-methoxy-6-methylphenyl | H | methyl | ethyl | |
| 2.1.1672 | 3-nitro-6-methylphenyl | H | methyl | ethyl | |
| 2.1.1673 | 3-fluoro-6-ethylphenyl | H | methyl | ethyl | |
| 2.1.1674 | 3-chloro-6-ethylphenyl | H | methyl | ethyl | |
| 2.1.1675 | 3-bromo-6-ethylphenyl | H | methyl | ethyl | |
| 2.1.1676 | 3-methyl-6-ethylphenyl | H | methyl | ethyl | |
| 2.1.1677 | 3,6-diethyl-phenyl | H | methyl | ethyl | |

TABLE 2.1-continued

Inventive compounds of the general formula (I) in which W* is COOY, R¹ is hydrogen, and aryl is the radical.

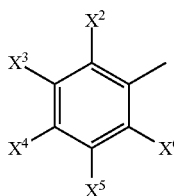

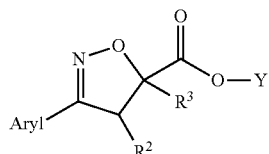

| No. | Aryl | R² | R³ | Y | Physical data |
|---|---|---|---|---|---|
| 2.1.1678 | 3-cyclopropyl-6-ethylphenyl | H | methyl | ethyl | |
| 2.1.1679 | 3-vinyl-6-ethylphenyl | H | methyl | ethyl | |
| 2.1.1680 | 3-ethynyl-6-ethylphenyl | H | methyl | ethyl | |
| 2.1.1681 | 3-cyano-6-ethylphenyl | H | methyl | ethyl | |
| 2.1.1682 | 3-trifluoromethyl-6-ethylphenyl | H | methyl | ethyl | |
| 2.1.1683 | 3-methoxy-6-ethylphenyl | H | methyl | ethyl | |
| 2.1.1684 | 3-ethoxy-6-ethylphenyl | H | methyl | ethyl | |
| 2.1.1685 | 3-trifluoromethoxy-6-ethylphenyl | H | methyl | ethyl | |
| 2.1.1686 | 3-nitro-6-ethylphenyl | H | methyl | ethyl | |
| 2.1.1687 | 3-fluoro-6-propylphenyl | H | methyl | ethyl | |
| 2.1.1688 | 3-chloro-6-propylphenyl | H | methyl | ethyl | |
| 2.1.1689 | 3-bromo-6-propylphenyl | H | methyl | ethyl | |
| 2.1.1690 | 3-methyl-6-propylphenyl | H | methyl | ethyl | |
| 2.1.1691 | 3-methyl-6-propylphenyl | H | methyl | ethyl | |
| 2.1.1692 | 3-cyclopropyl-6-propylphenyl | H | methyl | ethyl | |
| 2.1.1693 | 3-vinyl-6-propylphenyl | H | methyl | ethyl | |
| 2.1.1694 | 3-ethynyl-6-propylphenyl | H | methyl | ethyl | |
| 2.1.1695 | 3-cyano-6-propylphenyl | H | methyl | ethyl | |
| 2.1.1696 | 3-trifluoromethyl-6-propylphenyl | H | methyl | ethyl | |
| 2.1.1697 | 3-methoxy-6-propylphenyl | H | methyl | ethyl | |
| 2.1.1698 | 3-ethoxy-6-propylphenyl | H | methyl | ethyl | |
| 2.1.1699 | 3-trifluoromethoxy-6-propylphenyl | H | methyl | ethyl | |
| 2.1.1700 | 3-nitro-6-propylphenyl | H | methyl | ethyl | |
| 2.1.1701 | 3-fluoro-6-isopropylphenyl | H | methyl | ethyl | |
| 2.1.1702 | 3-chloro-6-isopropylphenyl | H | methyl | ethyl | |
| 2.1.1703 | 3-bromo-6-isopropylphenyl | H | methyl | ethyl | |

TABLE 2.1-continued

Inventive compounds of the general formula (I) in which W* is COOY, R$^1$ is hydrogen, and aryl is the radical.

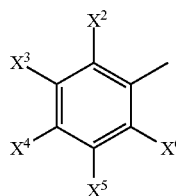

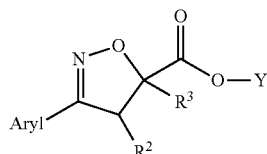

| No. | Aryl | R$^2$ | R$^3$ | Y | Physical data |
|---|---|---|---|---|---|
| 2.1.1704 | 3-methyl-6-isopropylphenyl | H | methyl | ethyl | |
| 2.1.1705 | 3-ethyl-6-isopropylphenyl | H | methyl | ethyl | |
| 2.1.1706 | 3-cyclopropyl-6-isopropylphenyl | H | methyl | ethyl | |
| 2.1.1707 | 3-vinyl-6-isopropylphenyl | H | methyl | ethyl | |
| 2.1.1708 | 3-ethynyl-6-isopropylphenyl | H | methyl | ethyl | |
| 2.1.1709 | 3-cyano-6-isopropylphenyl | H | methyl | ethyl | |
| 2.1.1710 | 3-trifluoromethyl-6-isopropylphenyl | H | methyl | ethyl | |
| 2.1.1711 | 3-methoxy-6-isopropylphenyl | H | methyl | ethyl | |
| 2.1.1712 | 3-ethoxy-6-isopropylphenyl | H | methyl | ethyl | |
| 2.1.1713 | 3-trifluoromethoxy-6-isopropylphenyl | H | methyl | ethyl | |
| 2.1.1714 | 3-nitro-6-isopropylphenyl | H | methyl | ethyl | |
| 2.1.1715 | 3-fluoro-6-tert-butylphenyl | H | methyl | ethyl | |
| 2.1.1716 | 3-chloro-6-tert-butylphenyl | H | methyl | ethyl | |
| 2.1.1717 | 3-bromo-6-tert-butylphenyl | H | methyl | ethyl | |
| 2.1.1718 | 3-methyl-6-tert-butylphenyl | H | methyl | ethyl | |
| 2.1.1719 | 3-ethyl-6-tert-butylphenyl | H | methyl | ethyl | |
| 2.1.1720 | 3-cyclopropyl-6-tert-butylphenyl | H | methyl | ethyl | |
| 2.1.1721 | 3-vinyl-6-tert-butylphenyl | H | methyl | ethyl | |
| 2.1.1722 | 3-ethynyl-6-tert-butylphenyl | H | methyl | ethyl | |
| 2.1.1723 | 3-cyano-6-tert-butylphenyl | H | methyl | ethyl | |
| 2.1.1724 | 3-trifluoromethyl-6-tert-butylphenyl | H | methyl | ethyl | |
| 2.1.1725 | 3-methoxy-6-tert-butylphenyl | H | methyl | ethyl | |
| 2.1.1726 | 3-ethoxy-6-tert-butylphenyl | H | methyl | ethyl | |
| 2.1.1727 | 3-trifluoromethoxy-6-tert-butylphenyl | H | methyl | ethyl | |
| 2.1.1728 | 3-nitro-6-tert-butylphenyl | H | methyl | ethyl | |
| 2.1.1729 | 3-fluoro-6-hydroxymethyl-phenyl | H | methyl | ethyl | |

TABLE 2.1-continued

Inventive compounds of the general formula (I) in which W* is COOY, R¹ is hydrogen, and aryl is the radical.

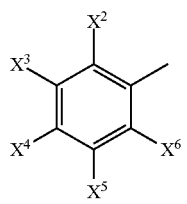

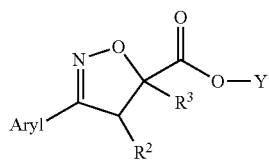

| No. | Aryl | R² | R³ | Y | Physical data |
|---|---|---|---|---|---|
| 2.1.1730 | 3-chloro-6-hydroxymethyl-phenyl | H | methyl | ethyl | |
| 2.1.1731 | 3-bromo-6-hydroxymethyl-phenyl | H | methyl | ethyl | |
| 2.1.1732 | 3-methyl-6-hydroxymethyl-phenyl | H | methyl | ethyl | |
| 2.1.1733 | 3-ethyl-6-hydroxymethyl-phenyl | H | methyl | ethyl | |
| 2.1.1734 | 3-cyclopropyl-6-hydroxymethyl-phenyl | H | methyl | ethyl | |
| 2.1.1735 | 3-vinyl-6-hydroxymethyl-phenyl | H | methyl | ethyl | |
| 2.1.1736 | 3-ethynyl-6-hydroxymethyl-phenyl | H | methyl | ethyl | |
| 2.1.1737 | 3-cyano-6-hydroxymethyl-phenyl | H | methyl | ethyl | |
| 2.1.1738 | 3-trifluoro-methyl-6-hydroxymethyl-phenyl | H | methyl | ethyl | |
| 2.1.1739 | 3-methoxy-6-hydroxymethyl-phenyl | H | methyl | ethyl | |
| 2.1.1740 | 3-ethoxy-6-hydroxymethyl-phenyl | H | methyl | ethyl | |
| 2.1.1741 | 3-trifluoro-methoxy-6-hydroxymethyl-phenyl | H | methyl | ethyl | |
| 2.1.1742 | 3-nitro-6-hydroxymethyl-phenyl | H | methyl | ethyl | |
| 2.1.1743 | 3-fluoro-6-cyclopropyl-phenyl | H | methyl | ethyl | |
| 2.1.1744 | 3-chloro-6-cyclopropyl-phenyl | H | methyl | ethyl | |
| 2.1.1745 | 3-bromo-6-cyclopropyl-phenyl | H | methyl | ethyl | |
| 2.1.1746 | 3-methyl-6-cyclopropyl-phenyl | H | methyl | ethyl | |

TABLE 2.1-continued

Inventive compounds of the general formula (I) in which W* is COOY, R¹ is hydrogen, and aryl is the radical.

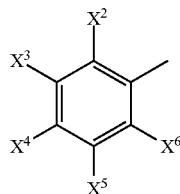

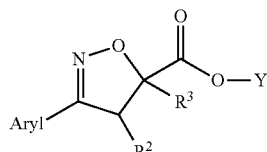

| No. | Aryl | R² | R³ | Y | Physical data |
|---|---|---|---|---|---|
| 2.1.1747 | 3-ethyl-6-cyclopropyl-phenyl | H | methyl | ethyl | |
| 2.1.1748 | 3-cyclopropyl-6-cyclopropyl-phenyl | H | methyl | ethyl | |
| 2.1.1749 | 3-vinyl-6-cyclopropyl-phenyl | H | methyl | ethyl | |
| 2.1.1750 | 3-ethynyl-6-cyclopropyl-phenyl | H | methyl | ethyl | |
| 2.1.1751 | 3-cyano-6-cyclopropyl-phenyl | H | methyl | ethyl | |
| 2.1.1752 | 3-trifluoromethyl-6-cyclopropyl-phenyl | H | methyl | ethyl | |
| 2.1.1753 | 3-methoxy-6-cyclopropyl-phenyl | H | methyl | ethyl | |
| 2.1.1754 | 3-ethoxy-6-cyclopropyl-phenyl | H | methyl | ethyl | |
| 2.1.1755 | 3-trifluoromethoxy-6-cyclopropyl-phenyl | H | methyl | ethyl | |
| 2.1.1756 | 3-fluoro-6-methoxy-carbonylphenyl | H | methyl | ethyl | |
| 2.1.1757 | 3-chloro-6-methoxy-carbonylphenyl | H | methyl | ethyl | |
| 2.1.1758 | 3-bromo-6-methoxy-carbonylphenyl | H | methyl | ethyl | |
| 2.1.1759 | 3-methyl-6-methoxy-carbonylphenyl | H | methyl | ethyl | |
| 2.1.1760 | 3-ethyl-6-methoxy-carbonylphenyl | H | methyl | ethyl | |
| 2.1.1761 | 3-cyclopropyl-6-methoxy-carbonylphenyl | H | methyl | ethyl | |
| 2.1.1762 | 3-vinyl-6-methoxy-carbonylphenyl | H | methyl | ethyl | |
| 2.1.1763 | 3-ethynyl-6-methoxy-carbonylphenyl | H | methyl | ethyl | |
| 2.1.1764 | 3-cyano-6-methoxy-carbonylphenyl | H | methyl | ethyl | |

TABLE 2.1-continued

Inventive compounds of the general formula (I) in which W* is COOY, R¹ is hydrogen, and aryl is the radical.

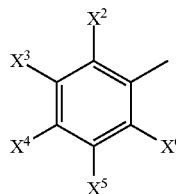

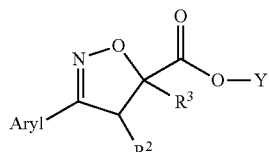

| No. | Aryl | R² | R³ | Y | Physical data |
|---|---|---|---|---|---|
| 2.1.1765 | 3-trifluoro-methyl-6-methoxy-carbonylphenyl | H | methyl | ethyl | |
| 2.1.1766 | 3-methoxy-6-methoxy-carbonylphenyl | H | methyl | ethyl | |
| 2.1.1767 | 3-ethoxy-6-methoxy-carbonylphenyl | H | methyl | ethyl | |
| 2.1.1768 | 3-trifluoro-methoxy-6-methoxy-carbonylphenyl | H | methyl | ethyl | |
| 2.1.1769 | 3-nitro-6-methoxy-carbonylphenyl | H | methyl | ethyl | |
| 2.1.1770 | 3-fluoro-6-vinylphenyl | H | methyl | ethyl | |
| 2.1.1771 | 3-chloro-6-vinylphenyl | H | methyl | ethyl | |
| 2.1.1772 | 3-bromo-6-vinylphenyl | H | methyl | ethyl | |
| 2.1.1773 | 3-methyl-6-vinylphenyl | H | methyl | ethyl | |
| 2.1.1774 | 3-ethyl-6-vinylphenyl | H | methyl | ethyl | |
| 2.1.1775 | 3-cyclopropyl-6-vinylphenyl | H | methyl | ethyl | |
| 2.1.1776 | 3,6-divinyl-phenyl | H | methyl | ethyl | |
| 2.1.1777 | 3-ethynyl-6-vinylphenyl | H | methyl | ethyl | |
| 2.1.1778 | 3-cyano-6-vinylphenyl | H | methyl | ethyl | |
| 2.1.1779 | 3-trifluoro-methyl-6-vinylphenyl | H | methyl | ethyl | |
| 2.1.1780 | 3-methoxy-6-vinylphenyl | H | methyl | ethyl | |
| 2.1.1781 | 3-ethoxy-6-vinylphenyl | H | methyl | ethyl | |
| 2.1.1782 | 3-trifluoro-methoxy-6-vinylphenyl | H | methyl | ethyl | |
| 2.1.1783 | 3-nitro-6-vinylphenyl | H | methyl | ethyl | |
| 2.1.1784 | 3-fluoro-6-ethynylphenyl | H | methyl | ethyl | |
| 2.1.1785 | 3-chloro-6-ethynylphenyl | H | methyl | ethyl | |
| 2.1.1786 | 3-bromo-6-ethynylphenyl | H | methyl | ethyl | |
| 2.1.1787 | 3-methyl-6-ethynylphenyl | H | methyl | ethyl | |
| 2.1.1788 | 3-ethyl-6-ethynylphenyl | H | methyl | ethyl | |

TABLE 2.1-continued

Inventive compounds of the general formula (I) in which W* is COOY, R¹ is hydrogen, and aryl is the radical.

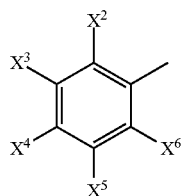

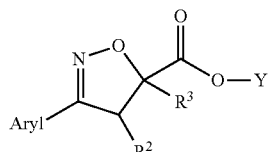

| No. | Aryl | R² | R³ | Y | Physical data |
|---|---|---|---|---|---|
| 2.1.1789 | 3-cyclopropyl-6-ethynylphenyl | H | methyl | ethyl | |
| 2.1.1790 | 3-vinyl-6-ethynylphenyl | H | methyl | ethyl | |
| 2.1.1791 | 3-cyano-6-ethynylphenyl | H | methyl | ethyl | |
| 2.1.1792 | 3-trifluoromethyl-6-ethynylphenyl | H | methyl | ethyl | |
| 2.1.1793 | 3-methoxy-6-ethynylphenyl | H | methyl | ethyl | |
| 2.1.1794 | 3-ethoxy-6-ethynylphenyl | H | methyl | ethyl | |
| 2.1.1795 | 3-trifluoromethoxy-6-ethynylphenyl | H | methyl | ethyl | |
| 2.1.1796 | 3-nitro-6-ethynylphenyl | H | methyl | ethyl | |
| 2.1.1797 | 3-fluoro-6-ethynylphenyl | H | methyl | ethyl | |
| 2.1.1798 | 3-fluoro-6-cyanophenyl | H | methyl | ethyl | |
| 2.1.1799 | 3-chloro-6-cyanophenyl | H | methyl | ethyl | |
| 2.1.1800 | 3-bromo-6-cyanophenyl | H | methyl | ethyl | |
| 2.1.1801 | 3-methyl-6-cyanophenyl | H | methyl | ethyl | |
| 2.1.1802 | 3-ethyl-6-cyanophenyl | H | methyl | ethyl | |
| 2.1.1803 | 3-cyclopropyl-6-cyanophenyl | H | methyl | ethyl | |
| 2.1.1804 | 3-vinyl-6-cyanophenyl | H | methyl | ethyl | |
| 2.1.1805 | 3-ethynyl-6-cyanophenyl | H | methyl | ethyl | |
| 2.1.1806 | 3-cyano-6-cyanophenyl | H | methyl | ethyl | |
| 2.1.1807 | 3-trifluoromethyl-6-cyanophenyl | H | methyl | ethyl | |
| 2.1.1808 | 3-methoxy-6-cyanophenyl | H | methyl | ethyl | |
| 2.1.1809 | 3-ethoxy-6-cyanophenyl | H | methyl | ethyl | |
| 2.1.1810 | 3-trifluoromethoxy-6-cyanophenyl | H | methyl | ethyl | |
| 2.1.1811 | 3-nitro-6-cyanophenyl | H | methyl | ethyl | |
| 2.1.1812 | 3-fluoro-6-hydroxyphenyl | H | methyl | ethyl | |
| 2.1.1813 | 3-chloro-6-hydroxyphenyl | H | methyl | ethyl | |
| 2.1.1814 | 3-bromo-6-hydroxyphenyl | H | methyl | ethyl | |

TABLE 2.1-continued

Inventive compounds of the general formula (I) in which W* is COOY, R¹ is hydrogen, and aryl is the radical.

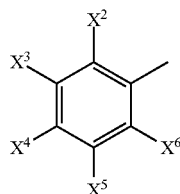

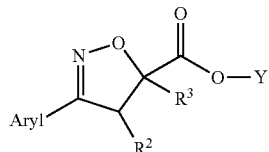

| No. | Aryl | R² | R³ | Y | Physical data |
|---|---|---|---|---|---|
| 2.1.1815 | 3-methyl-6-hydroxyphenyl | H | methyl | ethyl | |
| 2.1.1816 | 3-ethyl-6-hydroxyphenyl | H | methyl | ethyl | |
| 2.1.1817 | 3-cyclopropyl-6-hydroxyphenyl | H | methyl | ethyl | |
| 2.1.1818 | 3-vinyl-6-hydroxyphenyl | H | methyl | ethyl | |
| 2.1.1819 | 3-ethynyl-6-hydroxyphenyl | H | methyl | ethyl | |
| 2.1.1820 | 3-cyano-6-hydroxyphenyl | H | methyl | ethyl | |
| 2.1.1821 | 3-trifluoromethyl-6-hydroxyphenyl | H | methyl | ethyl | |
| 2.1.1822 | 3-methoxy-6-hydroxyphenyl | H | methyl | ethyl | |
| 2.1.1823 | 3-ethoxy-6-hydroxyphenyl | H | methyl | ethyl | |
| 2.1.1824 | 3-trifluoromethoxy-6-hydroxyphenyl | H | methyl | ethyl | |
| 2.1.1825 | 3-nitro-6-hydroxyphenyl | H | methyl | ethyl | |
| 2.1.1826 | 3-fluoro-6-methoxyphenyl | H | methyl | ethyl | |
| 2.1.1827 | 3-chloro-6-methoxyphenyl | H | methyl | ethyl | |
| 2.1.1828 | 3-bromo-6-methoxyphenyl | H | methyl | ethyl | |
| 2.1.1829 | 3-methyl-6-methoxyphenyl | H | methyl | ethyl | |
| 2.1.1830 | 3-ethyl-6-methoxyphenyl | H | methyl | ethyl | |
| 2.1.1831 | 3-cyclopropyl-6-methoxyphenyl | H | methyl | ethyl | |
| 2.1.1832 | 3-vinyl-6-methoxyphenyl | H | methyl | ethyl | |
| 2.1.1833 | 3-ethynyl-6-methoxyphenyl | H | methyl | ethyl | |
| 2.1.1834 | 3-cyano-6-methoxyphenyl | H | methyl | ethyl | |
| 2.1.1835 | 3-trifluoromethyl-6-methoxyphenyl | H | methyl | ethyl | |
| 2.1.1836 | 3,6-dimethoxy-phenyl | H | methyl | ethyl | |
| 2.1.1837 | 3-ethoxy-6-methoxyphenyl | H | methyl | ethyl | |
| 2.1.1838 | 3-trifluoromethoxy-6-methoxyphenyl | H | methyl | ethyl | |
| 2.1.1839 | 3-nitro-6-methoxyphenyl | H | methyl | ethyl | |

TABLE 2.1-continued

Inventive compounds of the general formula (I) in which W* is COOY, $R^1$ is hydrogen, and aryl is the radical.

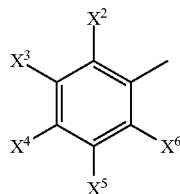

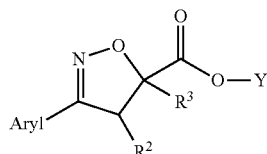

| No. | Aryl | $R^2$ | $R^3$ | Y | Physical data |
|---|---|---|---|---|---|
| 2.1.1840 | 3-fluoro-6-ethoxyphenyl | H | methyl | ethyl | |
| 2.1.1841 | 3-chloro-6-ethoxyphenyl | H | methyl | ethyl | |
| 2.1.1842 | 3-bromo-6-ethoxyphenyl | H | methyl | ethyl | |
| 2.1.1843 | 3-methyl-6-ethoxyphenyl | H | methyl | ethyl | |
| 2.1.1844 | 3-ethyl-6-ethoxyphenyl | H | methyl | ethyl | |
| 2.1.1845 | 3-cyclopropyl-6-ethoxyphenyl | H | methyl | ethyl | |
| 2.1.1846 | 3-vinyl-6-ethoxyphenyl | H | methyl | ethyl | |
| 2.1.1847 | 3-ethynyl-6-ethoxyphenyl | H | methyl | ethyl | |
| 2.1.1848 | 3-cyano-6-ethoxyphenyl | H | methyl | ethyl | |
| 2.1.1849 | 3-trifluoromethyl-6-ethoxyphenyl | H | methyl | ethyl | |
| 2.1.1850 | 3-methoxy-6-ethoxyphenyl | H | methyl | ethyl | |
| 2.1.1851 | 2,6-diethoxyphenyl | H | methyl | ethyl | |
| 2.1.1852 | 3-trifluoromethoxy-6-ethoxyphenyl | H | methyl | ethyl | |
| 2.1.1853 | 3-nitro-6-ethoxyphenyl | H | methyl | ethyl | |
| 2.1.1854 | 3-fluoro-6-propoxyphenyl | H | methyl | ethyl | |
| 2.1.1855 | 3-chloro-6-propoxyphenyl | H | methyl | ethyl | |
| 2.1.1856 | 3-bromo-6-propoxyphenyl | H | methyl | ethyl | |
| 2.1.1857 | 3-methyl-6-propoxyphenyl | H | methyl | ethyl | |
| 2.1.1858 | 3-ethyl-6-propoxyphenyl | H | methyl | ethyl | |
| 2.1.1859 | 3-cyclopropyl-6-propoxyphenyl | H | methyl | ethyl | |
| 2.1.1860 | 3-vinyl-6-propoxyphenyl | H | methyl | ethyl | |
| 2.1.1861 | 3-ethynyl-6-propoxyphenyl | H | methyl | ethyl | |
| 2.1.1862 | 3-cyano-6-propoxyphenyl | H | methyl | ethyl | |
| 2.1.1863 | 3-trifluoromethyl-6-propoxyphenyl | H | methyl | ethyl | |
| 2.1.1864 | 3-methoxy-6-propoxy-phenyl | H | methyl | ethyl | |
| 2.1.1865 | 3-ethoxy-6-propoxyphenyl | H | methyl | ethyl | |

TABLE 2.1-continued

Inventive compounds of the general formula (I) in which W* is COOY, R¹ is hydrogen, and aryl is the radical.

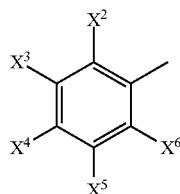

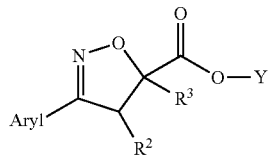

| No. | Aryl | R² | R³ | Y | Physical data |
|---|---|---|---|---|---|
| 2.1.1866 | 3-trifluoro-methoxy-6-propoxyphenyl | H | methyl | ethyl | |
| 2.1.1867 | 3-nitro-6-propoxyphenyl | H | methyl | ethyl | |
| 2.1.1868 | 3-fluoro-6-isopropoxy-phenyl | H | methyl | ethyl | |
| 2.1.1869 | 3-chloro-6-iso-propoxyphenyl | H | methyl | ethyl | |
| 2.1.1870 | 3-bromo-6-iso-propoxyphenyl | H | methyl | ethyl | |
| 2.1.1871 | 3-methyl-6-iso-propoxyphenyl | H | methyl | ethyl | |
| 2.1.1872 | 3-ethyl-6-iso-propoxyphenyl | H | methyl | ethyl | |
| 2.1.1873 | 3-cyclopropyl-6-isopropoxy-phenyl | H | methyl | ethyl | |
| 2.1.1874 | 3-vinyl-6-iso-propoxyphenyl | H | methyl | ethyl | |
| 2.1.1875 | 3-ethynyl-6-iso-propoxyphenyl | H | methyl | ethyl | |
| 2.1.1876 | 3-cyano-6-iso-propoxyphenyl | H | methyl | ethyl | |
| 2.1.1877 | 3-trifluoro-methyl-6-iso-propoxyphenyl | H | methyl | ethyl | |
| 2.1.1878 | 3-methoxy-6-isopropoxy-phenyl | H | methyl | ethyl | |
| 2.1.1879 | 3-ethoxy-6-isopropoxy-phenyl | H | methyl | ethyl | |
| 2.1.1880 | 3-trifluoro-methoxy-6-iso-propoxyphenyl | H | methyl | ethyl | |
| 2.1.1881 | 3-nitro-6-iso-propoxyphenyl | H | methyl | ethyl | |
| 2.1.1882 | 3-fluoro-6-tert-butoxyphenyl | H | methyl | ethyl | |
| 2.1.1883 | 3-chloro-6-tert-butoxyphenyl | H | methyl | ethyl | |
| 2.1.1884 | 3-bromo-6-tert-butoxyphenyl | H | methyl | ethyl | |
| 2.1.1885 | 3-methyl-6-tert-butoxyphenyl | H | methyl | ethyl | |
| 2.1.1886 | 3-ethyl-6-tert-butoxyphenyl | H | methyl | ethyl | |
| 2.1.1887 | 3-cyclopropyl-6-tert-butoxy-phenyl | H | methyl | ethyl | |
| 2.1.1888 | 3-vinyl-6-tert-butoxyphenyl | H | methyl | ethyl | |

TABLE 2.1-continued

Inventive compounds of the general formula (I) in which W* is COOY, R¹ is hydrogen, and aryl is the radical.

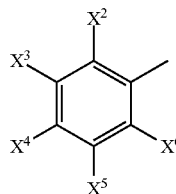

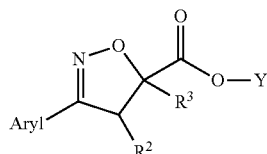

| No. | Aryl | R² | R³ | Y | Physical data |
|---|---|---|---|---|---|
| 2.1.1889 | 3-ethynyl-6-tert-butoxyphenyl | H | methyl | ethyl | |
| 2.1.1890 | 3-cyano-6-tert-butoxyphenyl | H | methyl | ethyl | |
| 2.1.1891 | 3-trifluoro-methyl-6-tert-butoxyphenyl | H | methyl | ethyl | |
| 2.1.1892 | 3-methoxy-6-tert-butoxy-phenyl | H | methyl | ethyl | |
| 2.1.1893 | 3-ethoxy-6-tert-butoxyphenyl | H | methyl | ethyl | |
| 2.1.1894 | 3-trifluoro-methoxy-6-tert-butoxyphenyl | H | methyl | ethyl | |
| 2.1.1895 | 3-nitro-6-tert-butoxyphenyl | H | methyl | ethyl | |
| 2.1.1896 | 3-fluoro-6-tri-fluoromethoxy-phenyl | H | methyl | ethyl | |
| 2.1.1897 | 3-chloro-6-tri-fluoromethoxy-phenyl | H | methyl | ethyl | |
| 2.1.1898 | 3-bromo-6-tri-fluoromethoxy-phenyl | H | methyl | ethyl | |
| 2.1.1899 | 3-methyl-6-tri-fluoromethoxy-phenyl | H | methyl | ethyl | |
| 2.1.1900 | 3-ethyl-6-tri-fluoromethoxy-phenyl | H | methyl | ethyl | |
| 2.1.1901 | 3-cyclopropyl-6-trifluorometh-oxyphenyl | H | methyl | ethyl | |
| 2.1.1902 | 3-vinyl-6-tri-fluoromethoxy-phenyl | H | methyl | ethyl | |
| 2.1.1903 | 3-ethynyl-6-tri-fluoromethoxy-phenyl | H | methyl | ethyl | |
| 2.1.1904 | 3-cyano-6-tri-fluoromethoxy-phenyl | H | methyl | ethyl | |
| 2.1.1905 | 3-trifluoro-methyl-6-tri-fluoromethoxy-phenyl | H | methyl | ethyl | |
| 2.1.1906 | 3-methoxy-6-trifluoro-methoxyphenyl | H | methyl | ethyl | |
| 2.1.1907 | 3-ethoxy-6-trifluoro-methoxyphenyl | H | methyl | ethyl | |
| 2.1.1908 | 3,6-bis(trifluoro-methoxy)phenyl | H | methyl | ethyl | |

TABLE 2.1-continued

Inventive compounds of the general formula (I) in which W* is COOY, R¹ is hydrogen, and aryl is the radical.

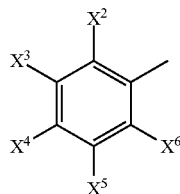

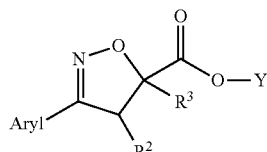

| No. | Aryl | R² | R³ | Y | Physical data |
|---|---|---|---|---|---|
| 2.1.1909 | 3-nitro-6-tri-fluoromethoxy-phenyl | H | methyl | ethyl | |
| 2.1.1910 | 3-fluoro-6-(2,2,2-trifluoro-ethoxy)phenyl | H | methyl | ethyl | |
| 2.1.1911 | 3-chloro-6-(2,2,2-trifluoro-ethoxy)phenyl | H | methyl | ethyl | |
| 2.1.1912 | 3-bromo-6-(2,2,2-trifluoroethoxy)-phenyl | H | methyl | ethyl | |
| 2.1.1913 | 3-methyl-6-(2,2,2-trifluoro-ethoxy)phenyl | H | methyl | ethyl | |
| 2.1.1914 | 3-ethyl-6-(2,2,2-trifluoroethoxy)-phenyl | H | methyl | ethyl | |
| 2.1.1915 | 3-cyclopropyl-6-(2,2,2-trifluoro-ethoxy)phenyl | H | methyl | ethyl | |
| 2.1.1916 | 3-vinyl-6-(2,2,2-trifluoroethoxy)-phenyl | H | methyl | ethyl | |
| 2.1.1917 | 3-ethynyl-6-(2,2,2-trifluoro-ethoxyphenyl | H | methyl | ethyl | |
| 2.1.1918 | 3-cyano-6-(2,2,2-trifluoro-ethoxy)phenyl | H | methyl | ethyl | |
| 2.1.1919 | 3-trifluoro-methyl-6-(2,2,2-trifluoroethoxy)-phenyl | H | methyl | ethyl | |
| 2.1.1920 | 3-methoxy-6-(2,2,2-trifluoro-ethoxy)phenyl | H | methyl | ethyl | |
| 2.1.1921 | 3-ethoxy-6-(2,2,2-trifluoroethoxy)-phenyl | H | methyl | ethyl | |
| 2.1.1922 | 3-trifluoro-methoxy-6-(2,2,2-trifluoro-ethoxy)phenyl | H | methyl | ethyl | |
| 2.1.1923 | 3-nitro-6-(2,2,2-trifluoroethoxy)-phenyl | H | methyl | ethyl | |
| 2.1.1924 | 3-fluoro-6-difluoromethoxy-phenyl | H | methyl | ethyl | |
| 2.1.1925 | 3-chloro-6-difluoromethoxy-phenyl | H | methyl | ethyl | |

TABLE 2.1-continued

Inventive compounds of the general formula (I) in which W* is COOY, R¹ is hydrogen, and aryl is the radical.

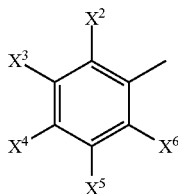

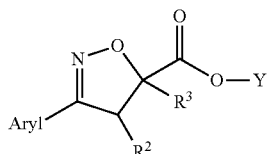

| No. | Aryl | R² | R³ | Y | Physical data |
|---|---|---|---|---|---|
| 2.1.1926 | 3-bromo-6-difluoromethoxy-phenyl | H | methyl | ethyl | |
| 2.1.1927 | 3-methyl-6-difluoromethoxy-phenyl | H | methyl | ethyl | |
| 2.1.1928 | 3-ethyl-6-difluoromethoxy-phenyl | H | methyl | ethyl | |
| 2.1.1929 | 3-cyclopropyl-6-difluoromethoxy-phenyl | H | methyl | ethyl | |
| 2.1.1930 | 3-vinyl-6-difluoromethoxy-phenyl | H | methyl | ethyl | |
| 2.1.1931 | 3-ethynyl-6-difluoromethoxy-phenyl | H | methyl | ethyl | |
| 2.1.1932 | 3-cyano-6-difluoromethoxy phenyl | H | methyl | ethyl | |
| 2.1.1933 | 3-trifluoro-methyl-6-di-fluoromethoxy-phenyl | H | methyl | ethyl | |
| 2.1.1934 | 3-methoxy-6-difluoromethoxy phenyl | H | methyl | ethyl | |
| 2.1.1935 | 3-ethoxy-6-difluoromethoxy-phenyl | H | methyl | ethyl | |
| 2.1.1936 | 3-trifluoro-methoxy-6-di-fluoromethoxy-phenyl | H | methyl | ethyl | |
| 2.1.1937 | 3-nitro-6-difluoromethoxy-phenyl | H | methyl | ethyl | |
| 2.1.1938 | 3-fluoro-6-(2-methoxyethoxy)-phenyl | H | methyl | ethyl | |
| 2.1.1939 | 3-chloro-6-(2-methoxyethoxy)-phenyl | H | methyl | ethyl | |
| 2.1.1940 | 3-bromo-6-(2-methoxyethoxy)-phenyl | H | methyl | ethyl | |
| 2.1.1941 | 3-methyl-6-(2-methoxyethoxy)-phenyl | H | methyl | ethyl | |
| 2.1.1942 | 3-ethyl-6-(2-methoxyethoxy)-phenyl | H | methyl | ethyl | |
| 2.1.1943 | 3-cyclopropyl-6-(2-methoxy-ethoxy)phenyl | H | methyl | ethyl | |

TABLE 2.1-continued

Inventive compounds of the general formula (I) in which W* is COOY, R¹ is hydrogen, and aryl is the radical.

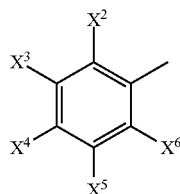

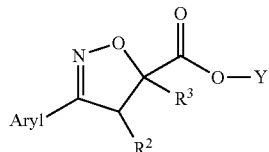

| No. | Aryl | R² | R³ | Y | Physical data |
|---|---|---|---|---|---|
| 2.1.1944 | 3-vinyl-6-(2-methoxyethoxy)-phenyl | H | methyl | ethyl | |
| 2.1.1945 | 3-ethynyl-6-(2-methoxyethoxy)-phenyl | H | methyl | ethyl | |
| 2.1.1946 | 3-cyano-6-(2-methoxyethoxy)-phenyl | H | methyl | ethyl | |
| 2.1.1947 | 3-trifluoromethyl-6-(2-methoxyethoxy)-phenyl | H | methyl | ethyl | |
| 2.1.1948 | 3-methoxy-6-(2-methoxyethoxy)-phenyl | H | methyl | ethyl | |
| 2.1.1949 | 3-ethoxy-6-(2-methoxyethoxy)-phenyl | H | methyl | ethyl | |
| 2.1.1950 | 3-trifluoromethoxy-(2-methoxyethoxy)-phenyl | H | methyl | ethyl | |
| 2.1.1951 | 3-nitro-6-(2-methoxyethoxy)-phenyl | H | methyl | ethyl | |
| 2.1.1952 | 3-fluoro-6-(tert-butoxycarbonyloxy)phenyl | H | methyl | ethyl | |
| 2.1.1953 | 3-chloro-6-(tert-butoxycarbonyloxy)phenyl | H | methyl | ethyl | |
| 2.1.1954 | 3-bromo-6-(tert-butoxycarbonyloxy)phenyl | H | methyl | ethyl | |
| 2.1.1955 | 3-methyl-6-(tert-butoxycarbonyloxy)phenyl | H | methyl | ethyl | |
| 2.1.1956 | 3-ethyl-6-(tert-butoxycarbonyloxy)phenyl | H | methyl | ethyl | |
| 2.1.1957 | 3-cyclopropyl-6-(tert-butoxycarbonyloxy)-phenyl | H | methyl | ethyl | |
| 2.1.1958 | 3-vinyl-6-(tert-butoxycarbonyloxy)phenyl | H | methyl | ethyl | |
| 2.1.1959 | 3-ethynyl-6-(tert-butoxycarbonyloxy)phenyl | H | methyl | ethyl | |
| 2.1.1960 | 3-cyano-6-(tert-butoxycarbonyloxy)phenyl | H | methyl | ethyl | |

TABLE 2.1-continued

Inventive compounds of the general formula (I) in which W* is COOY, R¹ is hydrogen, and aryl is the radical.

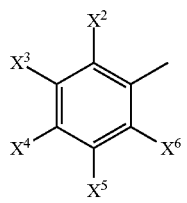

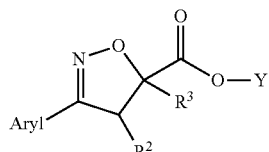

| No. | Aryl | R² | R³ | Y | Physical data |
|---|---|---|---|---|---|
| 2.1.1961 | 3-trifluoro-methyl-6-(tert-butoxycarbonyl-oxy)phenyl | H | methyl | ethyl | |
| 2.1.1962 | 3-methoxy-6-(tert-butoxy-carbonyloxy)-phenyl | H | methyl | ethyl | |
| 2.1.1963 | 3-ethoxy-6-(tert-butoxycarbonyl-oxy)phenyl | H | methyl | ethyl | |
| 2.1.1964 | 3-trifluoro-methoxy-6-(tert-butoxycarbonyl-oxy)phenyl | H | methyl | ethyl | |
| 2.1.1965 | 2-nitro-6-(tert-butoxycarbonyl-oxy)phenyl | H | methyl | ethyl | |
| 2.1.1966 | 3-fluoro-6-nitrophenyl | H | methyl | ethyl | |
| 2.1.1967 | 3-chloro-6-nitrophenyl | H | methyl | ethyl | |
| 2.1.1968 | 3-bromo-6-nitrophenyl | H | methyl | ethyl | |
| 2.1.1969 | 3-methyl-6-nitrophenyl | H | methyl | ethyl | |
| 2.1.1970 | 3-ethyl-6-nitrophenyl | H | methyl | ethyl | |
| 2.1.1971 | 3-cyclopropyl-6-nitrophenyl | H | methyl | ethyl | |
| 2.1.1972 | 3-vinyl-6-nitrophenyl | H | methyl | ethyl | |
| 2.1.1973 | 3-ethynyl-6-nitrophenyl | H | methyl | ethyl | |
| 2.1.1974 | 3-cyano-6-nitrophenyl | H | methyl | ethyl | |
| 2.1.1975 | 3-trifluoro-methyl-6-nitrophenyl | H | methyl | ethyl | |
| 2.1.1976 | 3-methoxy-6-nitrophenyl | H | methyl | ethyl | |
| 2.1.1977 | 3-ethoxy-6-nitrophenyl | H | methyl | ethyl | |
| 2.1.1978 | 3-trifluoro-methoxy-6-nitrophenyl | H | methyl | ethyl | |
| 2.1.1979 | 3-fluoro-6-methylsulfanyl-phenyl | H | methyl | ethyl | |
| 2.1.1980 | 3-chloro-6-methylsulfanyl-phenyl | H | methyl | ethyl | |
| 2.1.1981 | 3-bromo-6-methylsulfanyl-phenyl | H | methyl | ethyl | |

TABLE 2.1-continued

Inventive compounds of the general formula (I) in which W* is COOY, R¹ is hydrogen, and aryl is the radical.

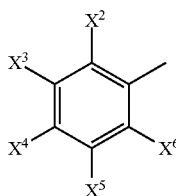

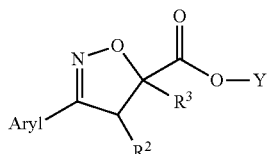

| No. | Aryl | R² | R³ | Y | Physical data |
|---|---|---|---|---|---|
| 2.1.1982 | 3-methyl-6-methylsulfanyl-phenyl | H | methyl | ethyl | |
| 2.1.1983 | 3-ethyl-6-methylsulfanyl-phenyl | H | methyl | ethyl | |
| 2.1.1984 | 3-cyclopropyl-6-methylsulfanyl-phenyl | H | methyl | ethyl | |
| 2.1.1985 | 3-vinyl-6-methylsulfanyl-phenyl | H | methyl | ethyl | |
| 2.1.1986 | 3-ethynyl-6-methylsulfanyl-phenyl | H | methyl | ethyl | |
| 2.1.1987 | 3-cyano-6-methylsulfanyl-phenyl | H | methyl | ethyl | |
| 2.1.1988 | 3-trifluoro-methyl-6-methylsulfanyl-phenyl | H | methyl | ethyl | |
| 2.1.1989 | 3-methoxy-6-methylsulfanyl-phenyl | H | methyl | ethyl | |
| 2.1.1990 | 3-ethoxy-6-methylsulfanyl-phenyl | H | methyl | ethyl | |
| 2.1.1991 | 3-trifluoro-methoxy-6-methylsulfanyl-phenyl | H | methyl | ethyl | |
| 2.1.1992 | 3-nitro-6-methylsulfanyl-phenyl | H | methyl | ethyl | |
| 2.1.1993 | 2,3,4-trifluoro-phenyl | H | methyl | ethyl | [CDCl₃] 1.31 (t, 3H); 1.71 (s, 3H); 3.25 (dd, 1H); 3.92 (dd, 1H); 4.25 (q, 2H); 7.00 (m, 1H); 7.61 (m, 1H). |
| 2.1.1994 | 2,3,4-trichloro-phenyl | H | methyl | ethyl | |
| 2.1.1995 | 2,3,4-trimethyl-phenyl | H | methyl | ethyl | |
| 2.1.1996 | 2-fluoro-2-chloro-5-tri-fluoromethyl-phenyl | H | methyl | ethyl | |
| 2.1.1997 | 2,3,5-trifluorophenyl | H | methyl | ethyl | [CDCl₃] 1.30 (t, 3H); 1.72 (s, 3H); 3.28 (dd, 1H); 3.92 (dd, 1H); 4.25 (q, 2H); 6.97 (m, 1H); 7.39 (m, 1H). |
| 2.1.1998 | 2,3,5-trichloro-phenyl | H | methyl | ethyl | |
| 2.1.1999 | 2,3,5-trimethyl-phenyl | H | methyl | ethyl | |

TABLE 2.1-continued

Inventive compounds of the general formula (I) in which W* is COOY, $R^1$ is hydrogen, and aryl is the radical.

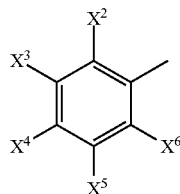

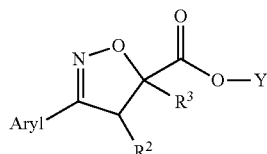

| No. | Aryl | $R^2$ | $R^3$ | Y | Physical data |
|---|---|---|---|---|---|
| 2.1.2000 | 2,3-dichloro-5-methoxyphenyl | H | methyl | ethyl | [CDCl$_3$] 1.32 (t, 3H); 1.72 (s, 3H); 3.40 (d, 1H); 3.81 (s, 3H); 3.92 (d, 1H): 4.30 (mc, 2H); 7.11 (mc, 2H). |
| 2.1.2001 | 2,3,6-trifluorophenyl | H | methyl | ethyl | |
| 2.1.2002 | 2,3,6-trichlorophenyl | H | methyl | ethyl | [CDCl$_3$] 1.34 (t, 3H); 1.75 (s, 3H); 3.13 (d, 1H); 3.79 (d, 1H); 4.30 (q, 2H); 7.3 (d, 1H); 7.48 (d, 1H). |
| 2.1.2003 | 2,3,6-trimethylphenyl | H | methyl | ethyl | |
| 2.1.2004 | 3,4,5-trifluorophenyl | H | methyl | ethyl | [CDCl$_3$] 1.32 (t, 3H); 1.70 (s, 3H); 3.10 (d, 1H); 3.81 (d, 1H); 4.25 (m, 1H); 7.32 (m, 2H). |
| 2.1.2005 | 3,4,5-trichlorophenyl | H | methyl | ethyl | [CDCl$_3$] 1.32 (t, 3H); 1.71 (s, 3H); 3.12 (d, 1H); 3.81 (d, 1H); 4.25 (m, 2H); 7.66 (s, 2H). |
| 2.1.2006 | 3,4,5-trimethylphenyl | H | methyl | ethyl | |
| 2.1.2007 | 3,5-dimethyl-4-fluorophenyl | H | methyl | ethyl | [CDCl$_3$] 1.31 (t, 3H); 1.70 (s, 3H); 2.25 (s, 6H); 3.17 (d, 1H); 3.85 (d, 1H); 4.25 (m, 2H); 7.32 (d, 2H). |
| 2.1.2008 | 3,5-dichloro-4-methoxyphenyl | H | methyl | ethyl | [CDCl$_3$] 1.30 (t, 3H); 1.70 (s, 3H); 3.14 (d, 1H); 3.82 (d, 1H); 3.91 (s, 3H); 4.28 (q, 2H); 7.60 (s, 2H). |
| 2.1.2009 | 3,5-difluoro-4-chlorophenyl | H | methyl | ethyl | [CDCl$_3$] 1.30 (t, 3H); 1.71 (s, 3H); 3.12 (d, 1H); 3.82 (d, 1H); 4.25 (m, 2H); 7.32 (m, 2H). |
| 2.1.2010 | 3,5-dichloro-4-hydroxyphenyl | H | methyl | ethyl | [CDCl$_3$] 1.31 (t, 3H); 1.71 (s, 3H); 3.12 (d, 1H); 3.82 (d, 1H); 4.25 (m, 2H); 7.58 (s, 2H). |
| 2.1.2011 | 3,5-trifluoromethyl-4-chlorophenyl | H | methyl | ethyl | |
| 2.1.2012 | 3,4,6-trifluorophenyl | H | methyl | ethyl | |
| 2.1.2013 | 3,4,6-trichlorophenyl | H | methyl | ethyl | |
| 2.1.2014 | 3,4,6-trimethylphenyl | H | methyl | ethyl | |
| 2.1.2015 | 2,3,4,5-pentafluorophenyl | H | methyl | ethyl | [CDCl$_3$] 1.31 (t, 3H); 1.72 (s, 3H); 3.25 (dd, 1H); 3.90 (d, 1H); 4.25 (m, 2H). |
| 2.1.2016 | 3,5-difluorophenyl | Br | methyl | ethyl | One unassigned diastereomer [CDCl3] 1.32 (t, 3H); 1.93 (s, 3H); 4.27 (m , 2H); 5.80 (s, 1H); 6.93 (dt, 1H); 7.35 (m, 2H). |
| 2.1.2017 | 3,5-difluorophenyl | Br | methyl | ethyl | The other unassigned diastereomer [CDCl3] 1.32 (t, 3H); 1.62 (s, 3H), 4.30 (q, 2H); 5.08 (s, 1H); 6.85 (t, 1H); 7.24 (d, 2H). |

TABLE 2.1-continued

Inventive compounds of the general formula (I) in which W* is COOY, R¹ is hydrogen, and aryl is the radical.

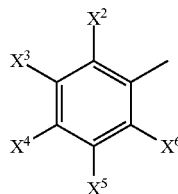

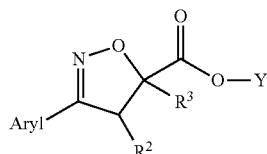

| No. | Aryl | R² | R³ | Y | Physical data |
|---|---|---|---|---|---|
| 2.1.2018 | 3,5-dichloro-phenyl | Br | methyl | ethyl | One unassigned diastereomer [CDCl3] 1.25 (t, 3H); 1.85 (s, 3H); 4.17 (m, 2H); 5.71 (s, 1H); 7.37 (s, 1H); 7.61 (s, 2H). |
| 2.1.2019 | 3,5-dichloro-phenyl | Br | methyl | ethyl | The other unassigned diastereomer [CDCl3] 1.39 (t, 3H); 1.68 (s, 3H); 4.37 (q, 2H); 5.15 (s, 1H); 7.45 (s, 1H); 7.67 (s, 2H). |

TABLE 2.2

Inventive compounds of the general formula (I) in which W* is CODY, R¹ and R² are each hydrogen, and aryl is the radical.

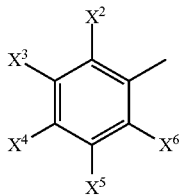

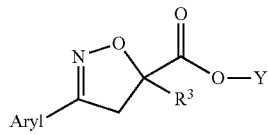

| No. | Aryl | R³ | Y | Physical data |
|---|---|---|---|---|
| 2.2.1 | 3-fluorophenyl | fluoromethyl | ethyl | [CDCl$_3$] 1.33 (t, 3H); 3.53 (d, 1H); 3.84 (d, 1H); 4.31 (q, 2H); 4.68 (d, 1H); 4.78 (d, 1H); 7.14 (t, 1H); 7.41 (m, 3H). |
| 2.2.2 | 3-fluorophenyl | chloromethyl | ethyl | [CDCl$_3$] 1.35 (t, 3H); 3.55 (d, 1H); 3.79 (d, 1H); 4.01 (dd, 2H); 4.32 (m, 2H); 7.15 (t, 1H); 7.41 (m, 3H). |
| 2.2.3 | 3-fluorophenyl | bromomethyl | ethyl | [CDCl$_3$] 1.35 (t, 3H); 3.50 (d, 1H); 3.62 (d, 1H); 3.90 (d, 1H); 4.05 (d, 1H); 4.33 (m, 2H); 7.15 (t, 1H); 7.43 (m, 3H). |
| 2.2.4 | 3-fluorophenyl | difluoromethyl | ethyl | |
| 2.2.5 | 3-fluorophenyl | 1,1-dichloroethyl | methyl | [CDCl$_3$] 2.40 (s, 3H); 3.88 (s, 3H); 4.07 (AB, 2H); 7.16 (t, 1H); 7.39-7.46 (m, 3H). |
| 2.2.6 | 3-fluorophenyl | cyano | ethyl | |
| 2.2.7 | 3-chlorophenyl | fluoromethyl | ethyl | |

TABLE 2.2-continued

Inventive compounds of the general formula (I) in which W* is CODY, R¹ and R² are each hydrogen, and aryl is the radical.

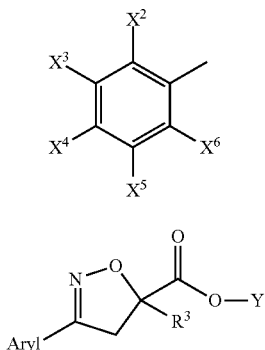

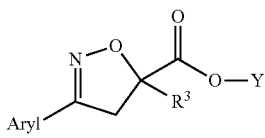

| No. | Aryl | R³ | Y | Physical data |
|---|---|---|---|---|
| 2.2.8 | 3-chlorophenyl | chloromethyl | ethyl | |
| 2.2.9 | 3-chlorophenyl | bromomethyl | ethyl | |
| 2.2.10 | 3-chlorophenyl | difluoromethyl | ethyl | |
| 2.2.11 | 3-chlorophenyl | trifluoromethyl | ethyl | |
| 2.2.12 | 3-chlorophenyl | cyano | ethyl | |
| 2.2.13 | 3-bromophenyl | fluoromethyl | ethyl | |
| 2.2.14 | 3-bromophenyl | chloromethyl | ethyl | |
| 2.2.15 | 3-iodophenyl | fluoromethyl | ethyl | |
| 2.2.16 | 3-iodophenyl | chloromethyl | ethyl | |
| 2.2.17 | 3-methylphenyl | fluoromethyl | ethyl | |
| 2.2.18 | 3-methylphenyl | chloromethyl | ethyl | |
| 2.2.19 | 3-ethylphenyl | fluoromethyl | ethyl | |
| 2.2.20 | 3-propylphenyl | fluoromethyl | ethyl | |
| 2.2.21 | 3-isopropylphenyl | fluoromethyl | ethyl | |
| 2.2.22 | 3-n-butylphenyl | fluoromethyl | ethyl | |
| 2.2.23 | 3-i-butylphenyl | fluoromethyl | ethyl | |
| 2.2.24 | 3-tert-butylphenyl | fluoromethyl | ethyl | |
| 2.2.25 | 3-cyclopropylphenyl | fluoromethyl | ethyl | |
| 2.2.26 | 3-cyclobutylphenyl | fluoromethyl | ethyl | |
| 2.2.27 | 3-cyclopentylphenyl | fluoromethyl | ethyl | |
| 2.2.28 | 3-vinylphenyl | fluoromethyl | ethyl | |
| 2.2.29 | 3-ethynylphenyl | fluoromethyl | ethyl | |
| 2.2.30 | 3-cyanophenyl | fluoromethyl | ethyl | |
| 2.2.31 | 3-trifluoromethylphenyl | fluoromethyl | ethyl | |
| 2.2.32 | 3-difluoromethylphenyl | fluoromethyl | ethyl | |
| 2.2.33 | 3-(hydroxycarbonyl)-phenyl | fluoromethyl | ethyl | |
| 2.2.34 | 3-(methoxycarbonyl)-phenyl | fluoromethyl | ethyl | |
| 2.2.35 | 3-(ethoxycarbonyl)phenyl | fluoromethyl | ethyl | |
| 2.2.36 | 3-hydroxymethylphenyl | fluoromethyl | ethyl | |
| 2.2.37 | 3-carbamoylphenyl | fluoromethyl | ethyl | |
| 2.2.38 | 3-hydroxyphenyl | fluoromethyl | ethyl | |
| 2.2.39 | 3-methoxyphenyl | fluoromethyl | ethyl | |
| 2.2.40 | 3-ethoxyphenyl | fluoromethyl | ethyl | |
| 2.2.41 | 3-propyloxyphenyl | fluoromethyl | ethyl | |
| 2.2.42 | 3-isopropyloxyphenyl | fluoromethyl | ethyl | |
| 2.2.43 | 3-n-butyloxyphenyl | fluoromethyl | ethyl | |
| 2.2.44 | 3-i-butyloxyphenyl | fluoromethyl | ethyl | |
| 2.2.45 | 3-t-butyloxyphenyl | fluoromethyl | ethyl | |
| 2.2.46 | 3-difluoromethoxyphenyl | fluoromethyl | ethyl | |
| 2.2.47 | 3-trifluoromethoxyphenyl | fluoromethyl | ethyl | |
| 2.2.48 | 3-(2,2,2-trifluoroethoxy)-phenyl | fluoromethyl | ethyl | |
| 2.2.49 | 3-(2-chloroethoxy)phenyl | fluoromethyl | ethyl | |
| 2.2.50 | 3-(2-hydroxyethoxy)-phenyl | fluoromethyl | ethyl | |
| 2.2.51 | 3-(2-methoxyethoxy)-phenyl | fluoromethyl | ethyl | |
| 2.2.52 | 3-[(tert-butoxycarbonyl)-oxy]phenyl | fluoromethyl | ethyl | |
| 2.2.53 | 3-nitrophenyl | fluoromethyl | ethyl | |
| 2.2.54 | 3-acetoxyphenyl | fluoromethyl | ethyl | |
| 2.2.55 | {3-[(tert-butoxycarbonyl)-amino]phenyl} | fluoromethyl | ethyl | |
| 2.2.56 | 3-methylsulfanylphenyl | fluoromethyl | ethyl | |
| 2.2.57 | 3-ethylsulfanylphenyl | fluoromethyl | ethyl | |

TABLE 2.2-continued

Inventive compounds of the general formula (I) in which W* is CODY, R¹ and R² are each hydrogen, and aryl is the radical.

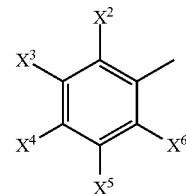

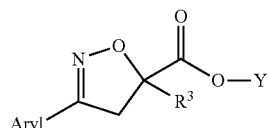

| No. | Aryl | R³ | Y | Physical data |
|---|---|---|---|---|
| 2.2.58 | 3-(pentafluoro-lambda⁶-sulfanyl)phenyl | fluoromethyl | ethyl | |
| 2.2.59 | 2,3-difluorophenyl | fluoromethyl | ethyl | |
| 2.2.60 | 2,3-difluorophenyl | chloromethyl | ethyl | |
| 2.2.61 | 2,3-difluorophenyl | bromomethyl | ethyl | |
| 2.2.62 | 2,3-difluorophenyl | difluoromethyl | ethyl | |
| 2.2.63 | 2,3-difluorophenyl | trifluoromethyl | ethyl | |
| 2.2.64 | 2,3-difluorophenyl | cyano | ethyl | |
| 2.2.65 | 2-chloro-3-fluorophenyl | fluoromethyl | ethyl | |
| 2.2.66 | 2-bromo-3-fluorophenyl | fluoromethyl | ethyl | |
| 2.2.67 | 2-methyl-3-fluorophenyl | fluoromethyl | ethyl | |
| 2.2.68 | 2-ethyl-3-fluorophenyl | fluoromethyl | ethyl | |
| 2.2.69 | 2-cyclopropyl-3-fluorophenyl | fluoromethyl | ethyl | |
| 2.2.70 | 2-vinyl-3-fluorophenyl | fluoromethyl | ethyl | |
| 2.2.71 | 2-ethynyl-3-fluorophenyl | fluoromethyl | ethyl | |
| 2.2.72 | 2-cyano-3-fluorophenyl | fluoromethyl | ethyl | |
| 2.2.73 | 2-methoxy-3-fluorophenyl | fluoromethyl | ethyl | |
| 2.2.74 | 2-ethoxy-3-fluorophenyl | fluoromethyl | ethyl | |
| 2.2.75 | 2-trifluoromethoxy-3-fluorophenyl | fluoromethyl | ethyl | |
| 2.2.76 | 2-nitro-3-fluorophenyl | fluoromethyl | ethyl | |
| 2.2.77 | 2-fluoro-3-chlorophenyl | fluoromethyl | ethyl | |
| 2.2.78 | 2,3-dichlorophenyl | fluoromethyl | ethyl | |
| 2.2.79 | 2,3-dichlorophenyl | chloromethyl | ethyl | |
| 2.2.80 | 2,3-dichlorophenyl | bromomethyl | ethyl | |
| 2.2.81 | 2,3-dichlorophenyl | difluoromethyl | ethyl | |
| 2.2.82 | 2-bromo-3-chlorophenyl | fluoromethyl | ethyl | |
| 2.2.83 | 2-methyl-3-chlorophenyl | fluoromethyl | ethyl | |
| 2.2.84 | 2-ethyl-3-chlorophenyl | fluoromethyl | ethyl | |
| 2.2.85 | 2-cyclopropyl-3-chlorophenyl | fluoromethyl | ethyl | |
| 2.2.86 | 2-vinyl-3-chlorophenyl | fluoromethyl | ethyl | |
| 2.2.87 | 2-ethynyl-3-chlorophenyl | fluoromethyl | ethyl | |
| 2.2.88 | 2-cyano-3-chlorophenyl | fluoromethyl | ethyl | |
| 2.2.89 | 2-trifluoromethyl-2-chlorophenyl | fluoromethyl | ethyl | |
| 2.2.90 | 2-methoxy-3-chlorophenyl | fluoromethyl | ethyl | |
| 2.2.91 | 2-ethoxy-3-chlorophenyl | fluoromethyl | ethyl | |
| 2.2.92 | 2-trifluoromethoxy-3-chlorophenyl | fluoromethyl | ethyl | |
| 2.2.93 | 2-nitro-3-chlorophenyl | fluoromethyl | ethyl | |
| 2.2.94 | 2-fluoro-3-bromophenyl | fluoromethyl | ethyl | |
| 2.2.95 | 2-chloro-3-bromophenyl | fluoromethyl | ethyl | |
| 2.2.96 | 2,3-dibromophenyl | fluoromethyl | ethyl | |
| 2.2.97 | 2-methyl-3-bromophenyl | fluoromethyl | ethyl | |
| 2.2.98 | 2-ethyl-3-bromophenyl | fluoromethyl | ethyl | |
| 2.2.99 | 2-cyclopropyl-3-bromophenyl | fluoromethyl | ethyl | |
| 2.2.100 | 2-vinyl-3-bromophenyl | fluoromethyl | ethyl | |
| 2.2.101 | 2-ethynyl-3-bromophenyl | fluoromethyl | ethyl | |
| 2.2.102 | 2-cyano-3-bromophenyl | fluoromethyl | ethyl | |
| 2.2.103 | 2-trifluoromethyl-3-bromophenyl | fluoromethyl | ethyl | |
| 2.2.104 | 2-methoxy-3-phenyl | fluoromethyl | ethyl | |
| 2.2.105 | 2-ethoxy-3-bromophenyl | fluoromethyl | ethyl | |

TABLE 2.2-continued

Inventive compounds of the general formula (I) in which W* is CODY, $R^1$ and $R^2$ are each hydrogen, and aryl is the radical.

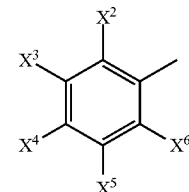

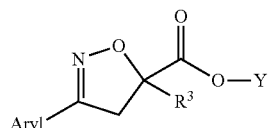

| No. | Aryl | $R^3$ | Y | Physical data |
|---|---|---|---|---|
| 2.2.106 | 2-trifluoromethoxy-3-bromophenyl | fluoromethyl | ethyl | |
| 2.2.107 | 2-nitro-3-bromophenyl | fluoromethyl | ethyl | |
| 2.2.108 | 2-fluoro-3-iodophenyl | fluoromethyl | ethyl | |
| 2.2.109 | 2-chloro-3-iodophenyl | fluoromethyl | ethyl | |
| 2.2.110 | 2-bromo-3-iodophenyl | fluoromethyl | ethyl | |
| 2.2.111 | 2-methyl-3-iodophenyl | fluoromethyl | ethyl | |
| 2.2.112 | 2-ethyl-3-iodophenyl | fluoromethyl | ethyl | |
| 2.2.113 | 2-cyclopropyl-3-iodophenyl | fluoromethyl | ethyl | |
| 2.2.114 | 2-vinyl-3-iodophenyl | fluoromethyl | ethyl | |
| 2.2.115 | 2-ethynyl-3-iodophenyl | fluoromethyl | ethyl | |
| 2.2.116 | 2-cyano-3-iodophenyl | fluoromethyl | ethyl | |
| 2.2.117 | 2-trifluoromethyl-3-iodophenyl | fluoromethyl | ethyl | |
| 2.2.118 | 2-methoxy-3-iodophenyl | fluoromethyl | ethyl | |
| 2.2.119 | 2-ethoxy-3-iodophenyl | fluoromethyl | ethyl | |
| 2.2.120 | 2-trifluoromethoxy-3-iodophenyl | fluoromethyl | ethyl | |
| 2.2.121 | 2-nitro-3-iodophenyl | fluoromethyl | ethyl | |
| 2.2.122 | 2-fluoro-3-methylphenyl | fluoromethyl | ethyl | |
| 2.2.123 | 2-fluoro-3-methylphenyl | chloromethyl | ethyl | |
| 2.2.124 | 2-fluoro-3-methylphenyl | bromomethyl | ethyl | |
| 2.2.125 | 2-fluoro-3-methylphenyl | difluoromethyl | ethyl | |
| 2.2.126 | 2-chloro-3-methylphenyl | fluoromethyl | ethyl | |
| 2.2.127 | 2-chloro-3-methylphenyl | chloromethyl | ethyl | |
| 2.2.128 | 2-chloro-3-methylphenyl | bromomethyl | ethyl | |
| 2.2.129 | 2-chloro-3-methylphenyl | difluoromethyl | ethyl | |
| 2.2.130 | 2-bromo-3-methylphenyl | fluoromethyl | ethyl | |
| 2.2.131 | 2,3-dimethylphenyl | fluoromethyl | ethyl | |
| 2.2.132 | 2,3-dimethylphenyl | chloromethyl | ethyl | |
| 2.2.133 | 2,3-dimethylphenyl | bromomethyl | ethyl | |
| 2.2.134 | 2,3-dimethylphenyl | difluoromethyl | ethyl | |
| 2.2.135 | 2-ethyl-3-methylphenyl | fluoromethyl | ethyl | |
| 2.2.136 | 2-cyclopropyl-3-methylphenyl | fluoromethyl | ethyl | |
| 2.2.137 | 2-vinyl-3-methylphenyl | fluoromethyl | ethyl | |
| 2.2.138 | 2-ethynyl-3-methylphenyl | fluoromethyl | ethyl | |
| 2.2.139 | 2-cyano-3-methylphenyl | fluoromethyl | ethyl | |
| 2.2.140 | 2-trifluoromethyl-3-methylphenyl | fluoromethyl | ethyl | |
| 2.2.141 | 2-methoxy-3-methylphenyl | fluoromethyl | ethyl | |
| 2.2.142 | 2-ethoxy-3-methylphenyl | fluoromethyl | ethyl | |
| 2.2.143 | 2-trifluoromethoxy-3-methylphenyl | fluoromethyl | ethyl | |
| 2.2.144 | 2-nitro-3-methylphenyl | fluoromethyl | ethyl | |
| 2.2.145 | 2-fluoro-3-ethylphenyl | fluoromethyl | ethyl | |
| 2.2.146 | 2-chloro-3-ethylphenyl | fluoromethyl | ethyl | |
| 2.2.147 | 2-bromo-3-ethylphenyl | fluoromethyl | ethyl | |
| 2.2.148 | 2-methyl-3-ethylphenyl | fluoromethyl | ethyl | |
| 2.2.149 | 2,3-diethylphenyl | fluoromethyl | ethyl | |
| 2.2.150 | 2-cyclopropyl-3-ethylphenyl | fluoromethyl | ethyl | |
| 2.2.151 | 2-vinyl-3-ethylphenyl | fluoromethyl | ethyl | |
| 2.2.152 | 2-ethynyl-3-ethylphenyl | fluoromethyl | ethyl | |
| 2.2.153 | 2-cyano-3-ethylphenyl | fluoromethyl | ethyl | |

TABLE 2.2-continued

Inventive compounds of the general formula (I) in which W* is CODY, R¹ and R² are each hydrogen, and aryl is the radical.

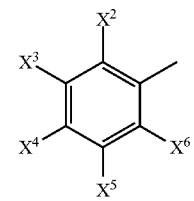

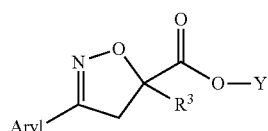

| No. | Aryl | R³ | Y | Physical data |
|---|---|---|---|---|
| 2.2.154 | 2-trifluoromethyl-3-ethylphenyl | fluoromethyl | ethyl | |
| 2.2.155 | 2-methoxy-3-ethylphenyl | fluoromethyl | ethyl | |
| 2.2.156 | 2-ethoxy-3-ethylphenyl | fluoromethyl | ethyl | |
| 2.2.157 | 2-trifluoromethoxy-3-ethylphenyl | fluoromethyl | ethyl | |
| 2.2.158 | 2-nitro-3-ethylphenyl | fluoromethyl | ethyl | |
| 2.2.159 | 2-fluoro-3-propylphenyl | fluoromethyl | ethyl | |
| 2.2.160 | 2-chloro-3-propylphenyl | fluoromethyl | ethyl | |
| 2.2.161 | 2-bromo-3-propylphenyl | fluoromethyl | ethyl | |
| 2.2.162 | 2-methyl-3-propylphenyl | fluoromethyl | ethyl | |
| 2.2.163 | 2-methyl-3-propylphenyl | fluoromethyl | ethyl | |
| 2.2.164 | 2-cyclopropyl-3-propylphenyl | fluoromethyl | ethyl | |
| 2.2.165 | 2-vinyl-3-propylphenyl | fluoromethyl | ethyl | |
| 2.2.166 | 2-ethynyl-3propylphenyl | fluoromethyl | ethyl | |
| 2.2.167 | 2-cyano-3-propylphenyl | fluoromethyl | ethyl | |
| 2.2.168 | 2-trifluoromethyl-3-propylphenyl | fluoromethyl | ethyl | |
| 2.2.169 | 2-methoxy-3-propylphenyl | fluoromethyl | ethyl | |
| 2.2.170 | 2-ethoxy-3-propylphenyl | fluoromethyl | ethyl | |
| 2.2.171 | 2-trifluoromethoxy-3-propylphenyl | fluoromethyl | ethyl | |
| 2.2.172 | 2-nitro-3-propylphenyl | fluoromethyl | ethyl | |
| 2.2.173 | 2-fluoro-3-isopropylphenyl | fluoromethyl | ethyl | |
| 2.2.174 | 2-chloro-3-isopropyl-phenyl | fluoromethyl | ethyl | |
| 2.2.175 | 2-bromo-3-isopropyl-phenyl | fluoromethyl | ethyl | |
| 2.2.176 | 2-methyl-3-isopropyl-phenyl | fluoromethyl | ethyl | |
| 2.2.177 | 2-ethyl-3-isopropylphenyl | fluoromethyl | ethyl | |
| 2.2.178 | 2-cyclopropyl-3-isopropyl-phenyl | fluoromethyl | ethyl | |
| 2.2.179 | 2-vinyl-3-isopropylphenyl | fluoromethyl | ethyl | |
| 2.2.180 | 2-ethynyl-3-isopropyl-phenyl | fluoromethyl | ethyl | |
| 2.2.181 | 2-cyano-3-isopropyl-phenyl | fluoromethyl | ethyl | |
| 2.2.182 | 2-trifluoromethyl-3-isopropylphenyl | fluoromethyl | ethyl | |
| 2.2.183 | 2-methoxy-3-isopropyl-phenyl | fluoromethyl | ethyl | |
| 2.2.184 | 2-ethoxy-3-isopropyl-phenyl | fluoromethyl | ethyl | |
| 2.2.185 | 2-trifluoromethoxy-3-isopropylphenyl | fluoromethyl | ethyl | |
| 2.2.186 | 2-nitro-3-isopropylphenyl | fluoromethyl | ethyl | |
| 2.2.187 | 2-fluoro-3-tert-butylphenyl | fluoromethyl | ethyl | |
| 2.2.188 | 2-chloro-3-tert-butylphenyl | fluoromethyl | ethyl | |
| 2.2.189 | 2-bromo-3-tert-butyl-phenyl | fluoromethyl | ethyl | |
| 2.2.190 | 2-methyl-3-tert-butyl-phenyl | fluoromethyl | ethyl | |
| 2.2.191 | 2-ethyl-3-tert-butylphenyl | fluoromethyl | ethyl | |
| 2.2.192 | 2-cyclopropyl-3-tert-butyl-phenyl | fluoromethyl | ethyl | |

TABLE 2.2-continued

Inventive compounds of the general formula (I) in which W* is CODY, $R^1$ and $R^2$ are each hydrogen, and aryl is the radical.

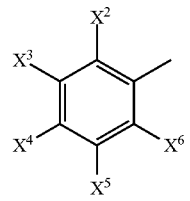

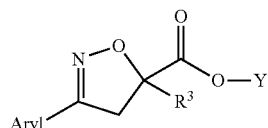

| No. | Aryl | $R^3$ | Y | Physical data |
|---|---|---|---|---|
| 2.2.193 | 2-vinyl-3-tert-butylphenyl | fluoromethyl | ethyl | |
| 2.2.194 | 2-ethynyl-3-tert-butyl-phenyl | fluoromethyl | ethyl | |
| 2.2.195 | 2-cyano-3-tert-butylphenyl | fluoromethyl | ethyl | |
| 2.2.196 | 2-trifluoromethyl-3-tert-butylphenyl | fluoromethyl | ethyl | |
| 2.2.197 | 2-methoxy-3-tert-butyl-phenyl | fluoromethyl | ethyl | |
| 2.2.198 | 2-ethoxy-3-tert-butyl-phenyl | fluoromethyl | ethyl | |
| 2.2.199 | 2-trifluoromethoxy-3-tert-butylphenyl | fluoromethyl | ethyl | |
| 2.2.200 | 2-nitro-3-tert-butylphenyl | fluoromethyl | ethyl | |
| 2.2.201 | 2-fluoro-3-hydroxymethyl-phenyl | fluoromethyl | ethyl | |
| 2.2.202 | 2-chloro-3-hydroxymethyl-phenyl | fluoromethyl | ethyl | |
| 2.2.203 | 2-bromo-3-hydroxy-methylphenyl | fluoromethyl | ethyl | |
| 2.2.204 | 2-methyl-3-hydroxy-methylphenyl | fluoromethyl | ethyl | |
| 2.2.205 | 2-ethyl-3-hydroxymethyl-phenyl | fluoromethyl | ethyl | |
| 2.2.206 | 2-cyclopropyl-3-hydroxy-methylphenyl | fluoromethyl | ethyl | |
| 2.2.207 | 2-vinyl-3-hydroxymethyl-phenyl | fluoromethyl | ethyl | |
| 2.2.208 | 2-ethynyl-3-hydroxy-methylphenyl | fluoromethyl | ethyl | |
| 2.2.209 | 2-cyano-3-hydroxymethyl-phenyl | fluoromethyl | ethyl | |
| 2.2.210 | 2-trifluoromethyl-3-hydroxymethylphenyl | fluoromethyl | ethyl | |
| 2.2.211 | 2-methoxy-3-hydroxymethylphenyl | fluoromethyl | ethyl | |
| 2.2.212 | 2-ethoxy-3-hydroxy-methylphenyl | fluoromethyl | ethyl | |
| 2.2.213 | 2-trifluoromethoxy-3-hydroxymethylphenyl | fluoromethyl | ethyl | |
| 2.2.214 | 2-nitro-3-hydroxymethyl-phenyl | fluoromethyl | ethyl | |
| 2.2.215 | 2-fluoro-3-cyclopropyl-phenyl | fluoromethyl | ethyl | |
| 2.2.216 | 2-chloro-3-cyclopropyl-phenyl | fluoromethyl | ethyl | |
| 2.2.217 | 2-bromo-3-cyclopropyl-phenyl | fluoromethyl | ethyl | |
| 2.2.218 | 2-methyl-3-cyclopropyl-phenyl | fluoromethyl | ethyl | |
| 2.2.219 | 2-ethyl-3-cyclopropyl-phenyl | fluoromethyl | ethyl | |
| 2.2.220 | 2-cyclopropyl-3-cyclopropylphenyl | fluoromethyl | ethyl | |
| 2.2.221 | 2-vinyl-3-cyclopropyl-phenyl | fluoromethyl | ethyl | |
| 2.2.222 | 2-ethynyl-3-cyclopropyl-phenyl | fluoromethyl | ethyl | |

TABLE 2.2-continued

Inventive compounds of the general formula (I) in which W* is CODY, $R^1$ and $R^2$ are each hydrogen, and aryl is the radical.

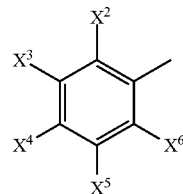

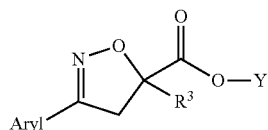

| No. | Aryl | $R^3$ | Y | Physical data |
|---|---|---|---|---|
| 2.2.223 | 2-cyano-3-cyclopropyl-phenyl | fluoromethyl | ethyl | |
| 2.2.224 | 2-trifluoromethyl-3-cyclopropylphenyl | fluoromethyl | ethyl | |
| 2.2.225 | 2-methoxy-3-cyclopropyl-phenyl | fluoromethyl | ethyl | |
| 2.2.226 | 2-ethoxy-3-cyclopropyl-phenyl | fluoromethyl | ethyl | |
| 2.2.227 | 2-trifluoromethoxy-3-cyclopropylphenyl | fluoromethyl | ethyl | |
| 2.2.228 | 2-fluoro-3-methoxy-carbonylphenyl | fluoromethyl | ethyl | |
| 2.2.229 | 2-chloro-3-methoxy-carbonylphenyl | fluoromethyl | ethyl | |
| 2.2.230 | 2-bromo-3-methoxy-carbonylphenyl | fluoromethyl | ethyl | |
| 2.2.231 | 2-methyl-3-methoxy-carbonylphenyl | fluoromethyl | ethyl | |
| 2.2.232 | 2-ethyl-3-methoxy-carbonylphenyl | fluoromethyl | ethyl | |
| 2.2.233 | 2-cyclopropyl-3-methoxy-carbonylphenyl | fluoromethyl | ethyl | |
| 2.2.234 | 2-vinyl-3-methoxy-carbonylphenyl | fluoromethyl | ethyl | |
| 2.2.235 | 2-ethynyl-3-methoxy-carbonylphenyl | fluoromethyl | ethyl | |
| 2.2.236 | 2-cyano-3-methoxy-carbonylphenyl | fluoromethyl | ethyl | |
| 2.2.237 | 2-trifluoromethyl-3-methoxycarbonylphenyl | fluoromethyl | ethyl | |
| 2.2.238 | 2-methoxy-3-methoxy-carbonylphenyl | fluoromethyl | ethyl | |
| 2.2.239 | 2-ethoxy-3-methoxy-carbonylphenyl | fluoromethyl | ethyl | |
| 2.2.240 | 2-trifluoromethoxy-3-methoxycarbonylphenyl | fluoromethyl | ethyl | |
| 2.2.241 | 2-nitro-3-methoxy-carbonylphenyl | fluoromethyl | ethyl | |
| 2.2.242 | 2-fluoro-3-vinylphenyl | fluoromethyl | ethyl | |
| 2.2.243 | 2-chloro-3-vinylphenyl | fluoromethyl | ethyl | |
| 2.2.244 | 2-bromo-3-vinylphenyl | fluoromethyl | ethyl | |
| 2.2.245 | 2-methyl-3-vinylphenyl | fluoromethyl | ethyl | |
| 2.2.246 | 2-ethyl-3-vinylphenyl | fluoromethyl | ethyl | |
| 2.2.247 | 2-cyclopropyl-3-vinylphenyl | fluoromethyl | ethyl | |
| 2.2.248 | 2-vinyl-3-vinylphenyl | fluoromethyl | ethyl | |
| 2.2.249 | 2-ethynyl-3-vinylphenyl | fluoromethyl | ethyl | |
| 2.2.250 | 2-cyano-3-vinylphenyl | fluoromethyl | ethyl | |
| 2.2.251 | 2-trifluoromethyl-3-vinylphenyl | fluoromethyl | ethyl | |
| 2.2.252 | 2-methoxy-3-vinylphenyl | fluoromethyl | ethyl | |
| 2.2.253 | 2-ethoxy-3-vinylphenyl | fluoromethyl | ethyl | |
| 2.2.254 | 2-trifluoromethoxy-3-vinylphenyl | fluoromethyl | ethyl | |
| 2.2.255 | 2-nitro-3-vinylphenyl | fluoromethyl | ethyl | |
| 2.2.256 | 2-fluoro-3-ethynylphenyl | fluoromethyl | ethyl | |
| 2.2.257 | 2-chloro-3-ethynylphenyl | fluoromethyl | ethyl | |

TABLE 2.2-continued

Inventive compounds of the general formula (I) in which W* is CODY, $R^1$ and $R^2$ are each hydrogen, and aryl is the radical.

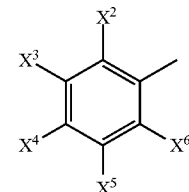

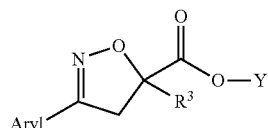

| No. | Aryl | $R^3$ | Y | Physical data |
|---|---|---|---|---|
| 2.2.258 | 2-bromo-3-ethynylphenyl | fluoromethyl | ethyl | |
| 2.2.259 | 2-methyl-3-ethynylphenyl | fluoromethyl | ethyl | |
| 2.2.260 | 2-ethyl-3-ethynylphenyl | fluoromethyl | ethyl | |
| 2.2.261 | 2-cyclopropyl-3-ethynylphenyl | fluoromethyl | ethyl | |
| 2.2.262 | 2-vinyl-3-ethynylphenyl | fluoromethyl | ethyl | |
| 2.2.263 | 2-cyano-3-ethynylphenyl | fluoromethyl | ethyl | |
| 2.2.264 | 2-trifluoromethyl-3-ethynylphenyl | fluoromethyl | ethyl | |
| 2.2.265 | 2-methoxy-3-ethynylphenyl | fluoromethyl | ethyl | |
| 2.2.266 | 2-ethoxy-3-ethynylphenyl | fluoromethyl | ethyl | |
| 2.2.267 | 2-trifluoromethoxy-3-ethynylphenyl | fluoromethyl | ethyl | |
| 2.2.268 | 2-nitro-3-ethynylphenyl | fluoromethyl | ethyl | |
| 2.2.269 | 2-fluoro-3-ethynylphenyl | fluoromethyl | ethyl | |
| 2.2.270 | 2-fluoro-3-cyanophenyl | fluoromethyl | ethyl | |
| 2.2.271 | 2-chloro-3-cyanophenyl | fluoromethyl | ethyl | |
| 2.2.272 | 2-bromo-3-cyanophenyl | fluoromethyl | ethyl | |
| 2.2.273 | 2-methyl-3-cyanophenyl | fluoromethyl | ethyl | |
| 2.2.274 | 2-ethyl-3-cyanophenyl | fluoromethyl | ethyl | |
| 2.2.275 | 2-ethyl-3-cyanophenyl | chloromethyl | ethyl | |
| 2.2.276 | 2-ethyl-3-cyanophenyl | bromomethyl | ethyl | |
| 2.2.277 | 2-ethyl-3-cyanophenyl | difluoromethyl | ethyl | |
| 2.2.278 | 2-cyclopropyl-3-cyanophenyl | fluoromethyl | ethyl | |
| 2.2.279 | 2-vinyl-3-cyanophenyl | fluoromethyl | ethyl | |
| 2.2.280 | 2-ethynyl-3-cyanophenyl | fluoromethyl | ethyl | |
| 2.2.281 | 2-cyano-3-cyanophenyl | fluoromethyl | ethyl | |
| 2.2.282 | 2-trifluoromethyl-3-cyanophenyl | fluoromethyl | ethyl | |
| 2.2.283 | 2-methoxy-3-cyanophenyl | fluoromethyl | ethyl | |
| 2.2.284 | 2-ethoxy-3-cyanophenyl | fluoromethyl | ethyl | |
| 2.2.285 | 2-trifluoromethoxy-3-cyanophenyl | fluoromethyl | ethyl | |
| 2.2.286 | 2-nitro-3-cyanophenyl | fluoromethyl | ethyl | |
| 2.2.287 | 2-fluoro-3-hydroxyphenyl | fluoromethyl | ethyl | |
| 2.2.288 | 2-chloro-3-hydroxyphenyl | fluoromethyl | ethyl | |
| 2.2.289 | 2-bromo-3-hydroxyphenyl | fluoromethyl | ethyl | |
| 2.2.290 | 2-methyl-3-hydroxyphenyl | fluoromethyl | ethyl | |
| 2.2.291 | 2-ethyl-3-hydroxyphenyl | fluoromethyl | ethyl | |
| 2.2.292 | 2-cyclopropyl-3-hydroxyphenyl | fluoromethyl | ethyl | |
| 2.2.293 | 2-vinyl-3-hydroxyphenyl | fluoromethyl | ethyl | |
| 2.2.294 | 2-ethynyl-3-hydroxyphenyl | fluoromethyl | ethyl | |
| 2.2.295 | 2-cyano-3-hydroxyphenyl | fluoromethyl | ethyl | |
| 2.2.296 | 2-trifluoromethyl-3-hydroxyphenyl | fluoromethyl | ethyl | |
| 2.2.297 | 2-methoxy-3-hydroxyphenyl | fluoromethyl | ethyl | |
| 2.2.298 | 2-ethoxy-3-hydroxyphenyl | fluoromethyl | ethyl | |
| 2.2.299 | 2-trifluoromethoxy-3-hydroxyphenyl | fluoromethyl | ethyl | |
| 2.2.300 | 2-nitro-3-hydroxyphenyl | fluoromethyl | ethyl | |
| 2.2.301 | 2-fluoro-3-methoxyphenyl | fluoromethyl | ethyl | |
| 2.2.302 | 2-chloro-3-methoxyphenyl | fluoromethyl | ethyl | |

TABLE 2.2-continued

Inventive compounds of the general formula (I) in which W* is CODY, R¹ and R² are each hydrogen, and aryl is the radical.

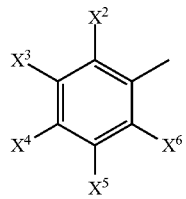

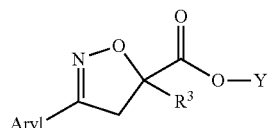

| No. | Aryl | R³ | Y | Physical data |
|---|---|---|---|---|
| 2.2.303 | 2-bromo-3-methoxyphenyl | fluoromethyl | ethyl | |
| 2.2.304 | 2-methyl-3-methoxyphenyl | fluoromethyl | ethyl | |
| 2.2.305 | 2-ethyl-3-methoxyphenyl | fluoromethyl | ethyl | |
| 2.2.306 | 2-cyclopropyl-3-methoxyphenyl | fluoromethyl | ethyl | |
| 2.2.307 | 2-vinyl-3-methoxyphenyl | fluoromethyl | ethyl | |
| 2.2.308 | 2-ethynyl-3-methoxyphenyl | fluoromethyl | ethyl | |
| 2.2.309 | 2-cyano-3-methoxyphenyl | fluoromethyl | ethyl | |
| 2.2.310 | 2-trifluoromethyl-3-methoxyphenyl | fluoromethyl | ethyl | |
| 2.2.311 | 2,3-dimethoxy--phenyl | fluoromethyl | ethyl | |
| 2.2.312 | 2-ethoxy-3-methoxyphenyl | fluoromethyl | ethyl | |
| 2.2.313 | 2-trifluoromethoxy-3-methoxyphenyl | fluoromethyl | ethyl | |
| 2.2.314 | 2-nitro-3-methoxyphenyl | fluoromethyl | ethyl | |
| 2.2.315 | 2-fluoro-3-ethoxyphenyl | fluoromethyl | ethyl | |
| 2.2.316 | 2-chloro-3-ethoxyphenyl | fluoromethyl | ethyl | |
| 2.2.317 | 2-bromo-3-ethoxyphenyl | fluoromethyl | ethyl | |
| 2.2.318 | 2-methyl-3-ethoxyphenyl | fluoromethyl | ethyl | |
| 2.2.319 | 2-ethyl-3-ethoxyphenyl | fluoromethyl | ethyl | |
| 2.2.320 | 2-cyclopropyl-3-ethoxyphenyl | fluoromethyl | ethyl | |
| 2.2.321 | 2-vinyl-3-ethoxyphenyl | fluoromethyl | ethyl | |
| 2.2.322 | 2-ethynyl-3-ethoxyphenyl | fluoromethyl | ethyl | |
| 2.2.323 | 2-cyano-3-ethoxyphenyl | fluoromethyl | ethyl | |
| 2.2.324 | 2-trifluoromethyl-3-ethoxyphenyl | fluoromethyl | ethyl | |
| 2.2.325 | 2-methoxy-3-ethoxyphenyl | fluoromethyl | ethyl | |
| 2.2.326 | 2,3-diethoxy--phenyl | fluoromethyl | ethyl | |
| 2.2.327 | 2-trifluoromethoxy-3-ethoxyphenyl | fluoromethyl | ethyl | |
| 2.2.328 | 2-nitro-3-ethoxyphenyl | fluoromethyl | ethyl | |
| 2.2.329 | 2-fluoro-3-propoxyphenyl | fluoromethyl | ethyl | |
| 2.2.330 | 2-chloro-3-propoxyphenyl | fluoromethyl | ethyl | |
| 2.2.331 | 2-bromo-3-propoxyphenyl | fluoromethyl | ethyl | |
| 2.2.332 | 2-methyl-3-propoxyphenyl | fluoromethyl | ethyl | |
| 2.2.333 | 2-ethyl-3-propoxyphenyl | fluoromethyl | ethyl | |
| 2.2.334 | 2-cyclopropyl-3-propoxyphenyl | fluoromethyl | ethyl | |
| 2.2.335 | 2-vinyl-3-propoxyphenyl | fluoromethyl | ethyl | |
| 2.2.336 | 2-ethynyl-3-propoxyphenyl | fluoromethyl | ethyl | |
| 2.2.337 | 2-cyano-3-propoxyphenyl | fluoromethyl | ethyl | |
| 2.2.338 | 2-trifluoromethyl-3-propoxyphenyl | fluoromethyl | ethyl | |
| 2.2.339 | 2-methoxy-3-propoxyphenyl | fluoromethyl | ethyl | |
| 2.2.340 | 2-ethoxy-3-propoxyphenyl | fluoromethyl | ethyl | |
| 2.2.341 | 2-trifluoromethoxy-3-propoxyphenyl | fluoromethyl | ethyl | |
| 2.2.342 | 2-nitro-3-propoxyphenyl | fluoromethyl | ethyl | |
| 2.2.343 | 2-fluoro-3-isopropoxyphenyl | fluoromethyl | ethyl | |

TABLE 2.2-continued

Inventive compounds of the general formula (I) in which W* is CODY, $R^1$ and $R^2$ are each hydrogen, and aryl is the radical.

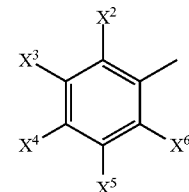

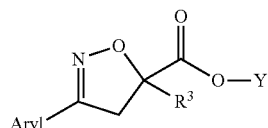

| No. | Aryl | $R^3$ | Y | Physical data |
|---|---|---|---|---|
| 2.2.344 | 2-chloro-3-isopropoxyphenyl | fluoromethyl | ethyl | |
| 2.2.345 | 2-bromo-3-isopropoxyphenyl | fluoromethyl | ethyl | |
| 2.2.346 | 2-methyl-3-isopropoxyphenyl | fluoromethyl | ethyl | |
| 2.2.347 | 2-ethyl-3-isopropoxyphenyl | fluoromethyl | ethyl | |
| 2.2.348 | 2-cyclopropyl-3-isopropoxyphenyl | fluoromethyl | ethyl | |
| 2.2.349 | 2-vinyl-3-isopropoxyphenyl | fluoromethyl | ethyl | |
| 2.2.350 | 2-ethynyl-3-isopropoxyphenyl | fluoromethyl | ethyl | |
| 2.2.351 | 2-cyano-3-isopropoxyphenyl | fluoromethyl | ethyl | |
| 2.2.352 | 2-trifluoromethyl-3-isopropoxyphenyl | fluoromethyl | ethyl | |
| 2.2.353 | 2-methoxy-3-isopropoxyphenyl | fluoromethyl | ethyl | |
| 2.2.354 | 2-ethoxy-3-isopropoxyphenyl | fluoromethyl | ethyl | |
| 2.2.355 | 2-trifluoromethoxy-3-isopropoxyphenyl | fluoromethyl | ethyl | |
| 2.2.356 | 2-nitro-3-isopropoxyphenyl | fluoromethyl | ethyl | |
| 2.2.357 | 2-fluoro-3-tert-butoxyphenyl | fluoromethyl | ethyl | |
| 2.2.358 | 2-chloro-3-tert-butoxyphenyl | fluoromethyl | ethyl | |
| 2.2.359 | 2-bromo-3-tert-butoxyphenyl | fluoromethyl | ethyl | |
| 2.2.360 | 2-methyl-3-tert-butoxyphenyl | fluoromethyl | ethyl | |
| 2.2.361 | 2-ethyl-3-tert-butoxyphenyl | fluoromethyl | ethyl | |
| 2.2.362 | 2-cyclopropyl-3-tert-butoxyphenyl | fluoromethyl | ethyl | |
| 2.2.363 | 2-vinyl-3-tert-butoxyphenyl | fluoromethyl | ethyl | |
| 2.2.364 | 2-ethynyl-3-tert-butoxyphenyl | fluoromethyl | ethyl | |
| 2.2.365 | 2-cyano-3-tert-butoxyphenyl | fluoromethyl | ethyl | |
| 2.2.366 | 2-trifluoromethyl-3-tert-butoxyphenyl | fluoromethyl | ethyl | |
| 2.2.367 | 2-methoxy-3-tert-butoxyphenyl | fluoromethyl | ethyl | |
| 2.2.368 | 2-ethoxy-3-tert-butoxyphenyl | fluoromethyl | ethyl | |
| 2.2.369 | 2-trifluoromethoxy-3-tert-butoxyphenyl | fluoromethyl | ethyl | |
| 2.2.370 | 2-nitro-3-tert-butoxyphenyl | fluoromethyl | ethyl | |
| 2.2.371 | 2-fluoro-3-trifluoromethoxy-phenyl | fluoromethyl | ethyl | |

TABLE 2.2-continued

Inventive compounds of the general formula (I) in which W* is CODY, R¹ and R² are each hydrogen, and aryl is the radical.

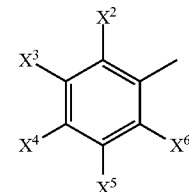

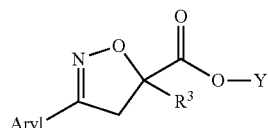

| No. | Aryl | R³ | Y | Physical data |
|---|---|---|---|---|
| 2.2.372 | 2-chloro-3-trifluoromethoxy-phenyl | fluoromethyl | ethyl | |
| 2.2.373 | 2-bromo-3-trifluoromethoxy-phenyl | fluoromethyl | ethyl | |
| 2.2.374 | 2-methyl-3-trifluoromethoxy-phenyl | fluoromethyl | ethyl | |
| 2.2.375 | 2-ethyl-3-trifluoromethoxy-phenyl | fluoromethyl | ethyl | |
| 2.2.376 | 2-cyclopropyl-3-trifluoromethoxy-phenyl | fluoromethyl | ethyl | |
| 2.2.377 | 2-vinyl-3-trifluoromethoxy-phenyl | fluoromethyl | ethyl | |
| 2.2.378 | 2-ethynyl-3-trifluoromethoxy-phenyl | fluoromethyl | ethyl | |
| 2.2.379 | 2-cyano-3-trifluoromethoxy-phenyl | fluoromethyl | ethyl | |
| 2.2.380 | 2-trifluoromethyl-3-trifluoromethoxy-phenyl | fluoromethyl | ethyl | |
| 2.2.381 | 2-methoxy-3-trifluoromethoxy-phenyl | fluoromethyl | ethyl | |
| 2.2.382 | 2-ethoxy-3-trifluoromethoxy-phenyl | fluoromethyl | ethyl | |
| 2.2.383 | 2,3-bis(trifluoromethoxy)phenyl | fluoromethyl | ethyl | |
| 2.2.384 | 2-nitro-3-trifluoromethoxy-phenyl | fluoromethyl | ethyl | |
| 2.2.385 | 2-fluoro-3-(2,2,2-trifluoroethoxy)-phenyl | fluoromethyl | ethyl | |
| 2.2.386 | 2-chloro-3-(2,2,2-trifluoroethoxy)-phenyl | fluoromethyl | ethyl | |
| 2.2.387 | 2-bromo-3-(2,2,2-trifluoroethoxy)-phenyl | fluoromethyl | ethyl | |
| 2.2.388 | 2-methyl-3-(2,2,2-trifluoroethoxy)-phenyl | fluoromethyl | ethyl | |
| 2.2.389 | 2-ethyl-3-(2,2,2-trifluoroethoxy)-phenyl | fluoromethyl | ethyl | |
| 2.2.390 | 2-cyclopropyl-3-(2,2,2-trifluoro-ethoxy)phenyl | fluoromethyl | ethyl | |
| 2.2.391 | 2-vinyl-3-(2,2,2-trifluoroethoxy)-phenyl | fluoromethyl | ethyl | |
| 2.2.392 | 2-ethynyl-3-(2,2,2-trifluoroethoxyphenyl | fluoromethyl | ethyl | |
| 2.2.393 | 2-cyano-3-(2,2,2-trifluoroethoxy)-phenyl | fluoromethyl | ethyl | |
| 2.2.394 | 2-trifluoromethyl-3-(2,2,2-trifluoro-ethoxy)phenyl | fluoromethyl | ethyl | |
| 2.2.395 | 2-methoxy-3-(2,2,2-trifluoroethoxy)-phenyl | fluoromethyl | ethyl | |
| 2.2.396 | 2-ethoxy-3-(2,2,2-trifluoroethoxy)-phenyl | fluoromethyl | ethyl | |
| 2.2.397 | 2-trifluoromethoxy-3-(2,2,2-trifluoroethoxy)-phenyl | fluoromethyl | ethyl | |
| 2.2.398 | 2-nitro-3-(2,2,2-trifluoro-ethoxy)phenyl | fluoromethyl | ethyl | |
| 2.2.399 | 2-fluoro-3-difluoro-methoxyphenyl | fluoromethyl | ethyl | |

TABLE 2.2-continued

Inventive compounds of the general formula (I) in which W* is CODY, $R^1$ and $R^2$ are each hydrogen, and aryl is the radical.

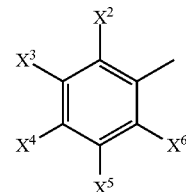

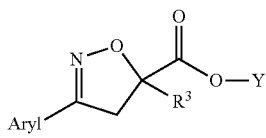

| No. | Aryl | $R^3$ | Y | Physical data |
|---|---|---|---|---|
| 2.2.400 | 2-chloro-3-difluoro-methoxyphenyl | fluoromethyl | ethyl | |
| 2.2.401 | 2-bromo-3-difluoro-methoxyphenyl | fluoromethyl | ethyl | |
| 2.2.402 | 2-methyl-3-difluoro-methoxyphenyl | fluoromethyl | ethyl | |
| 2.2.403 | 2-ethyl-3-difluoromethoxy-phenyl | fluoromethyl | ethyl | |
| 2.2.404 | 2-cyclopropyl-3-difluoromethoxy-phenyl | fluoromethyl | ethyl | |
| 2.2.405 | 2-vinyl-3-difluoromethoxy-phenyl | fluoromethyl | ethyl | |
| 2.2.406 | 2-ethynyl-3-difluoro-methoxyphenyl | fluoromethyl | ethyl | |
| 2.2.407 | 2-cyano-3-difluoro-methoxyphenyl | fluoromethyl | ethyl | |
| 2.2.408 | 2-trifluoromethyl-3-difluoromethoxy-phenyl | fluoromethyl | ethyl | |
| 2.2.409 | 2-methoxy-3-difluoro-methoxyphenyl | fluoromethyl | ethyl | |
| 2.2.410 | 2-ethoxy-3-difluoro-methoxyphenyl | fluoromethyl | ethyl | |
| 2.2.411 | 2-trifluoromethoxy-3-difluoromethoxyphenyl | fluoromethyl | ethyl | |
| 2.2.412 | 2-nitro-3-difluoromethoxy-phenyl | fluoromethyl | ethyl | |
| 2.2.413 | 2-fluoro-3-(2-methoxy-ethoxy)phenyl | fluoromethyl | ethyl | |
| 2.2.414 | 2-chloro-3-(2-methoxy-ethoxy)phenyl | fluoromethyl | ethyl | |
| 2.2.415 | 2-bromo-3-(2-methoxy-ethoxy)phenyl | fluoromethyl | ethyl | |
| 2.2.416 | 2-methyl-3-(2-methoxy-ethoxy)phenyl | fluoromethyl | ethyl | |
| 2.2.417 | 2-ethyl-3-(2-methoxyethoxy)phenyl | fluoromethyl | ethyl | |
| 2.2.418 | 2-cyclopropyl-3-(2-methoxyethoxy)-phenyl | fluoromethyl | ethyl | |
| 2.2.419 | 2-vinyl-3-(2-methoxy-ethoxy)phenyl | fluoromethyl | ethyl | |
| 2.2.420 | 2-ethynyl-3-(2-methoxy-ethoxy)phenyl | fluoromethyl | ethyl | |
| 2.2.421 | 2-cyano-3-(2-methoxy-ethoxy)phenyl | fluoromethyl | ethyl | |
| 2.2.422 | 2-trifluoromethyl-3-(2-methoxyethoxy)-phenyl | fluoromethyl | ethyl | |
| 2.2.423 | 2-methoxy-3-(2-methoxy-ethoxy)phenyl | fluoromethyl | ethyl | |
| 2.2.424 | 2-ethoxy-3-(2-methoxy-ethoxy)phenyl | fluoromethyl | ethyl | |
| 2.2.425 | 2-trifluoromethoxy-(2-methoxyethoxy)-phenyl | fluoromethyl | ethyl | |
| 2.2.426 | 2-nitro-3-(2-methoxy-ethoxy)phenyl | fluoromethyl | ethyl | |

TABLE 2.2-continued

Inventive compounds of the general formula (I) in which W* is CODY, $R^1$ and $R^2$ are each hydrogen, and aryl is the radical.

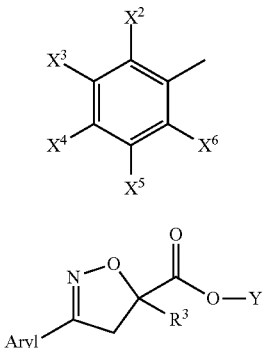

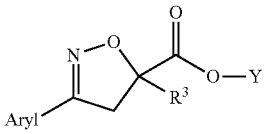

| No. | Aryl | $R^3$ | Y | Physical data |
|---|---|---|---|---|
| 2.2.427 | 2-fluoro-3-(tert-butoxy-carbonyloxy)phenyl | fluoromethyl | ethyl | |
| 2.2.428 | 2-chloro-3-(tert-butoxy-carbonyloxy)phenyl | fluoromethyl | ethyl | |
| 2.2.429 | 2-bromo-3-(tert-butoxy-carbonyloxy)phenyl | fluoromethyl | ethyl | |
| 2.2.430 | 2-methyl-3-(tert-butoxy-carbonyloxy)phenyl | fluoromethyl | ethyl | |
| 2.2.431 | 2-ethyl-3-(tert-butoxy-carbonyloxy)phenyl | fluoromethyl | ethyl | |
| 2.2.432 | 2-cyclopropyl-3-(tert-butoxycarbonyloxy)phenyl | fluoromethyl | ethyl | |
| 2.2.433 | 2-vinyl-3-(tert-butoxy-carbonyloxy)phenyl | fluoromethyl | ethyl | |
| 2.2.434 | 2-ethynyl-3-(tert-butoxy-carbonyloxy)phenyl | fluoromethyl | ethyl | |
| 2.2.435 | 2-cyano-3-(tert-butoxy-carbonyloxy)phenyl | fluoromethyl | ethyl | |
| 2.2.436 | 2-trifluoromethyl-3-(tert-butoxycarbonyloxy)phenyl | fluoromethyl | ethyl | |
| 2.2.437 | 2-methoxy-3-(tert-butoxy-carbonyloxy)phenyl | fluoromethyl | ethyl | |
| 2.2.438 | 2-ethoxy-3-(tert-butoxy-carbonyloxy)phenyl | fluoromethyl | ethyl | |
| 2.2.439 | 2-trifluoromethoxy-3-(tert-butoxycarbonyloxy)phenyl | fluoromethyl | ethyl | |
| 2.2.440 | 2-nitro-3-(tert-butoxy-carbonyloxy)phenyl | fluoromethyl | ethyl | |
| 2.2.441 | 2-fluoro-3-nitrophenyl | fluoromethyl | ethyl | |
| 2.2.442 | 2-chloro-3-nitrophenyl | fluoromethyl | ethyl | |
| 2.2.443 | 2-bromo-3-nitrophenyl | fluoromethyl | ethyl | |
| 2.2.444 | 2-methyl-3-nitrophenyl | fluoromethyl | ethyl | |
| 2.2.445 | 2-ethyl-3-nitrophenyl | fluoromethyl | ethyl | |
| 2.2.446 | 2-cyclopropyl-3-nitrophenyl | fluoromethyl | ethyl | |
| 2.2.447 | 2-vinyl-3-nitrophenyl | fluoromethyl | ethyl | |
| 2.2.448 | 2-ethynyl-3-nitrophenyl | fluoromethyl | ethyl | |
| 2.2.449 | 2-cyano-3-nitrophenyl | fluoromethyl | ethyl | |
| 2.2.450 | 2-trifluoromethy1-3-nitrophenyl | fluoromethyl | ethyl | |
| 2.2.451 | 2-methoxy-3-nitrophenyl | fluoromethyl | ethyl | |
| 2.2.452 | 2-ethoxy-3-nitrophenyl | fluoromethyl | ethyl | |
| 2.2.453 | 2-trifluoromethoxy-3-nitrophenyl | fluoromethyl | ethyl | |
| 2.2.454 | 2-fluoro-3-methylsulfanylphenyl | fluoromethyl | ethyl | |
| 2.2.455 | 2-chloro-3-methylsulfanylphenyl | fluoromethyl | ethyl | |
| 2.2.456 | 2-bromo-3-methylsulfanylphenyl | fluoromethyl | ethyl | |
| 2.2.457 | 2-methy1-3-methylsulfanylphenyl | fluoromethyl | ethyl | |
| 2.2.458 | 2-ethyl-3-methylsulfanylphenyl | fluoromethyl | ethyl | |
| 2.2.459 | 2-cyclopropy1-3-methylsulfanylphenyl | fluoromethyl | ethyl | |

TABLE 2.2-continued

Inventive compounds of the general formula (I) in which W* is CODY, $R^1$ and $R^2$ are each hydrogen, and aryl is the radical.

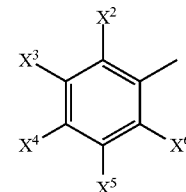

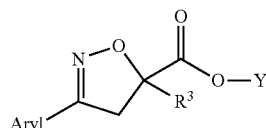

| No. | Aryl | $R^3$ | Y | Physical data |
|---|---|---|---|---|
| 2.2.460 | 2-vinyl-3-methylsulfanylphenyl | fluoromethyl | ethyl | |
| 2.2.461 | 2-ethynyl-3-methylsulfanylphenyl | fluoromethyl | ethyl | |
| 2.2.462 | 2-cyano-3-methylsulfanylphenyl | fluoromethyl | ethyl | |
| 2.2.463 | 2-trifluoromethyl-3-methylsulfanylphenyl | fluoromethyl | ethyl | |
| 2.2.464 | 2-methoxy-3-methylsulfanylphenyl | fluoromethyl | ethyl | |
| 2.2.465 | 2-ethoxy-3-methylsulfanylphenyl | fluoromethyl | ethyl | |
| 2.2.466 | 2-trifluoromethoxy-3-methylsulfanylphenyl | fluoromethyl | ethyl | |
| 2.2467 | 2-nitro-3-methylsulfanylphenyl | fluoromethyl | ethyl | |
| 2.2.468 | 3,5-difluorophenyl | F | methyl | [CDCl3] 3.65 (dd, 1H); 3.96 (s, 3H); 4.12 (dd, 1H); 6.96 (t, 1H); 7.22 (d, 2H). |
| 2.2469 | 3,5-difluorophenyl | fluoromethyl | ethyl | [CDCl$_3$] 1.33 (t, 3H); 3.50 (d, 1H); 3.80 (d, 1H); 4.30 (q, 2H); 4.67 (s, 1H); 4.79 (s, 1H); 6.89 (t, 1H); 7.20 (d, 2H). |
| 2.2.470 | 3,5-difluorophenyl | chloromethyl | ethyl | [CDCl$_3$] 1.34 (t, 3H); 3.50 (d, 1H); 3.80 (d, 1H); 4.00 (dd, 2H); 4.32 (m, 2H); 6.89 (t, 1H); 7.20 (d, 2H). |
| 2.2.471 | 3,5-difluorophenyl | bromomethyl | ethyl | [CDCl$_3$] 1.36 (t, 3H); 3.48 (1H) und 3.55 (d, 1H); 3.89 (d, 1H) und 4.01 (d, 1H); 4.32 (m, 2H); 6.89 (m, 1H); 7.23 (m, 2H). |
| 2.2.472 | 3,5-difluorophenyl | difluoromethyl | ethyl | [CDCl$_3$] 1.36 (t, 3H); 3.63 (d, 1H); 3.91 (d, 1H); 4.35 (q, 2H); 6.25 (tt, 1H); 6.91 (t, 1H); 7.21 (d, 2H). |
| 2.2.473 | 3,5-difluorophenyl | trifluoromethyl | ethyl | |
| 2.2.474 | 3,5-difluorophenyl | 1,1-dichloroethyl | methyl | [CDCl$_3$] 2.40 (s, 3H); 3.88 (s, 3H); 3.98 (d, 1H); 4.10 (d, 1H); 6.91 (t, 1H); 7.21 (d, 2H). |
| 2.2.475 | 3,5-difluorophenyl | CN | ethyl | [DMSO] 1.30 (t, 3H); 4.11 (d, 1H); 4.32 (q, 2H); 4.48 (d, 1H); 7.48 (m, 3H). |
| 2.2.476 | 3,5-difluorophenyl | CN | isopropyl | [CDCl$_3$] 1.40 (m, 6H); 3.91 (d, 1H); 4.12 (d, 1H); 5.20 (m, 1H); 6.96 (m, 1H); 7.19 (m, 2H). |
| 2.2.477 | 3-chloro-5-fluorophenyl | fluoromethyl | ethyl | |
| 2.2.478 | 3-chloro-5-fluorophenyl | chloromethyl | ethyl | |
| 2.2.479 | 3-chloro-5-fluorophenyl | bromomethyl | ethyl | |
| 2.2.480 | 3-chloro-5-fluorophenyl | difluoromethyl | ethyl | |
| 2.2.481 | 3-chloro-5-fluorophenyl | cyano | ethyl | [CDCl$_3$] 1.45 (t, 3H); 3.91 (d, 1H); 4.15 (d, 1H); 4.42 (q, 2H); 7.25 (m, 1H); 7.32 (d, 1H); 7.40 (s, 1H). |

TABLE 2.2-continued

Inventive compounds of the general formula (I) in which W* is CODY, $R^1$ and $R^2$ are each hydrogen, and aryl is the radical.

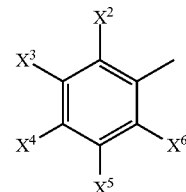

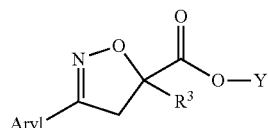

| No. | Aryl | $R^3$ | Y | Physical data |
|---|---|---|---|---|
| 2.2.482 | 3-bromo-5-fluorophenyl | fluoromethyl | ethyl | |
| 2.2.483 | 3-bromo-5-fluorophenyl | chloromethyl | ethyl | |
| 2.2.484 | 3-bromo-5-fluorophenyl | bromomethyl | ethyl | |
| 2.2.485 | 3-bromo-5-fluorophenyl | difluoromethyl | ethyl | |
| 2.2.486 | 3-iodo-5-fluorophenyl | fluoromethyl | ethyl | |
| 2.2.487 | 3-methyl-5-fluorophenyl | fluoromethyl | ethyl | |
| 2.2.488 | 3-methyl-5-fluorophenyl | chloromethyl | ethyl | |
| 2.2.489 | 3-methyl-5-fluorophenyl | bromomethyl | ethyl | |
| 2.2.490 | 3-methyl-5-fluorophenyl | difluoromethyl | ethyl | |
| 2.2.491 | 3-ethyl-5-fluorophenyl | fluoromethyl | ethyl | |
| 2.2.492 | 3-propyl-5-fluorophenyl | fluoromethyl | ethyl | |
| 2.2.493 | 3-i-propyl-5-fluorophenyl | fluoromethyl | ethyl | |
| 2.2.494 | 3-n-butyl-5-fluorophenyl | fluoromethyl | ethyl | |
| 2.2.495 | 3-isobutyl-5-fluorophenyl | fluoromethyl | ethyl | |
| 2.2.496 | 3-tert-butyl-5-fluorophenyl | fluoromethyl | ethyl | |
| 2.2.497 | 3-cyclopropyl-5-fluorophenyl | fluoromethyl | ethyl | |
| 2.2.498 | 3-vinyl-5-fluorophenyl | fluoromethyl | ethyl | |
| 2.2.499 | 3-ethynyl-5-fluorophenyl | fluoromethyl | ethyl | |
| 2.2.500 | 3-cyano-5-fluorophenyl | fluoromethyl | ethyl | |
| 2.2.501 | 3-trifluoromethyl-5-fluorophenyl | fluoromethyl | ethyl | |
| 2.2.502 | 3-trifluoromethyl-5-fluorophenyl | chloromethyl | ethyl | |
| 2.2.503 | 3-trifluoromethyl-5-fluorophenyl | bromomethyl | ethyl | |
| 2.2.504 | 3-trifluoromethyl-5-fluorophenyl | difluoromethyl | ethyl | |
| 2.2.505 | 3-(methoxycarbonyl)-5-fluorophenyl | fluoromethyl | ethyl | |
| 2.2.506 | 3-hydroxymethyl-5-fluorophenyl | fluoromethyl | ethyl | |
| 2.2.507 | 3-carbamoyl-5-fluorophenyl | fluoromethyl | ethyl | |
| 2.2.508 | 3-hydroxy-5-fluorophenyl | fluoromethyl | ethyl | |
| 2.2.509 | 3-methoxy-5-fluorophenyl | fluoromethyl | ethyl | |
| 2.2.510 | 3-ethoxy-5-fluorophenyl | fluoromethyl | ethyl | |
| 2.2.511 | 3-n-propoxy-5-fluorophenyl | fluoromethyl | ethyl | |
| 2.2.512 | 3-isopropoxy-5-fluorophenyl | fluoromethyl | ethyl | |
| 2.2.513 | 3-n-butoxy-5-fluorophenyl | fluoromethyl | ethyl | |
| 2.2.514 | 3-isobutoxy-5-fluorophenyl | fluoromethyl | ethyl | |
| 2.2.515 | 3-tert-butoxy-5-fluorophenyl | fluoromethyl | ethyl | |
| 2.2.516 | 3-difluoromethoxy-5-fluorophenyl | fluoromethyl | ethyl | |
| 2.2.517 | 3-trifluoromethoxy-5-fluorophenyl | fluoromethyl | ethyl | |
| 2.2.518 | 3-(2,2,2-trifluoroethoxy)-5-fluorophenyl | fluoromethyl | ethyl | |
| 2.2.519 | 3-(2-chloroethoxy)-5-fluorophenyl | fluoromethyl | ethyl | |
| 2.2.520 | 3-(2-hydroxyethoxy)-5-fluorophenyl | fluoromethyl | ethyl | |

TABLE 2.2-continued

Inventive compounds of the general formula (I) in which W* is CODY, R¹ and R² are each hydrogen, and aryl is the radical.

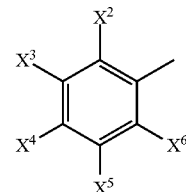

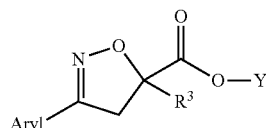

| No. | Aryl | R³ | Y | Physical data |
|---|---|---|---|---|
| 2.2.521 | 3-[(tert-butoxycarbonyl)-oxy]-5-fluorophenyl | fluoromethyl | ethyl | |
| 2.2.522 | 3-nitro-5-fluorophenyl | fluoromethyl | ethyl | |
| 2.2.523 | 3-acetoxy-5-fluorophenyl | fluoromethyl | ethyl | |
| 2.2.524 | {3-[(tert-butoxy-carbonyl)-amino]-5-fluorophenyl} | fluoromethyl | ethyl | |
| 2.2.525 | 3-methylsulfanyl-5-fluorophenyl | fluoromethyl | ethyl | |
| 2.2.526 | 3,5-dichlorophenyl | fluoromethyl | ethyl | |
| 2.2.527 | 3,5-dichlorophenyl | chloromethyl | ethyl | [CDCl$_3$] 1.35 (t, 3H); 3.51 (d, 1H); 3.80 (d, 1H); 3.96 (d, 1H); 4.03 (d, 1H); 4.33 (m, 2H); 7.43 (s, 1H); 7.58 (s, 1H). |
| 2.2.528 | 3,5-dichlorophenyl | bromomethyl | ethyl | [CDCl$_3$] 1.35 (t, 3H); 3.47 (d, 1H); 3.62 (d, 1H); 3.90 (d, 1H); 4.32 (m, 2H); 7.40 (s, 1H); 7.55 (s, 2H). |
| 2.2.529 | 3,5-dichlorophenyl | difluoromethyl | ethyl | |
| 2.2.530 | 3,5-dichlorophenyl | trifluoromethyl | methyl | [CDCl$_3$] 3.75 (d, 1H); 3.92 (s, 3H); 4.00 (d, 1H); 7.45 (s, 1H); 7.58 (s, 2H). |
| 2.2.531 | 3,5-dichlorophenyl | cyano | ethyl | [CDCl$_3$] 1.41 (t, 3H); 3.90 (d, 1H); 4.15 (d, 1H); 4.42 (q, 2H); 7.49 (d, 1H); 7.55 (d, 2H). |
| 2.2.532 | 3-bromo-5-chlorophenyl | fluoromethyl | ethyl | |
| 2.2.533 | 3-iodo-5-chlorophenyl | fluoromethyl | ethyl | |
| 2.2.534 | 3-methyl-5-chlorophenyl | fluoromethyl | ethyl | |
| 2.2.535 | 3-ethyl-5-chlorophenyl | fluoromethyl | ethyl | |
| 2.2.536 | 3-propyl-5-chlorophenyl | fluoromethyl | ethyl | |
| 2.2.537 | 3-isopropyl-5-chlorophenyl | fluoromethyl | ethyl | |
| 2.2.538 | 3-n-butyl-5-chlorophenyl | fluoromethyl | ethyl | |
| 2.2.539 | 3-isobutyl-5-chlorophenyl | fluoromethyl | ethyl | |
| 2.2.540 | 3-tert-butyl-5-chlorophenyl | fluoromethyl | ethyl | |
| 2.2.541 | 3-cyclopropyl-5-chlorophenyl | fluoromethyl | ethyl | |
| 2.2.542 | 3-vinyl-5-chlorophenyl | fluoromethyl | ethyl | |
| 2.2.543 | 3-ethynyl-5-chlorophenyl | fluoromethyl | ethyl | |
| 2.2.544 | 3-cyano-5-chlorophenyl | fluoromethyl | ethyl | |
| 2.2.545 | 3-trifluoromethyl-5-chlorophenyl | fluoromethyl | ethyl | |
| 2.2.546 | 3-(hydroxycarbonyl)-5-chlorophenyl | fluoromethyl | ethyl | |
| 2.2.547 | 3-(methoxycarbonyl)-5-chlorophenyl | fluoromethyl | ethyl | |
| 2.2.548 | 3-hydroxymethyl-5-chlorophenyl | fluoromethyl | ethyl | |
| 2.2.549 | 3-carbamoyl-5-chlorophenyl | fluoromethyl | ethyl | |
| 2.2.550 | 3-hydroxy-5-chlorophenyl | fluoromethyl | ethyl | |
| 2.2.551 | 3-methoxy-5-chlorophenyl | fluoromethyl | ethyl | |
| 2.2.552 | 3-ethoxy-5-chlorophenyl | fluoromethyl | ethyl | |
| 2.2.553 | 3-n-propoxy-5-chlorophenyl | fluoromethyl | ethyl | |

TABLE 2.2-continued

Inventive compounds of the general formula (I) in which W* is CODY, $R^1$ and $R^2$ are each hydrogen, and aryl is the radical.

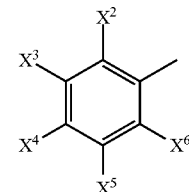

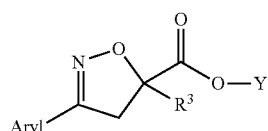

| No. | Aryl | $R^3$ | Y | Physical data |
|---|---|---|---|---|
| 2.2.554 | 3-isopropoxy-5-chlorophenyl | fluoromethyl | ethyl | |
| 2.2.555 | 3-n-butoxy-5-chlorophenyl | fluoromethyl | ethyl | |
| 2.2.556 | 3-isobutoxy-5-chlorophenyl | fluoromethyl | ethyl | |
| 2.2.557 | 3-tert-butoxy-5-chlorophenyl | fluoromethyl | ethyl | |
| 2.2.558 | 3-difluoromethoxy-5-chlorophenyl | fluoromethyl | ethyl | |
| 2.2.559 | 3-trifluoromethoxy-5-chlorophenyl | fluoromethyl | ethyl | |
| 2.2.560 | 3-(2,2,2-trifluoroethoxy)-5-chlorophenyl | fluoromethyl | ethyl | |
| 2.2.561 | 3-(2-chloroethoxy)-5-chlorophenyl | fluoromethyl | ethyl | |
| 2.2.562 | 3-(2-hydroxyethoxy)-5-chlorophenyl | fluoromethyl | ethyl | |
| 2.2.563 | 3-[(tert-butoxy-carbonyl)oxy]-5-chlorophenyl | fluoromethyl | ethyl | |
| 2.2.564 | 3-nitro-5-chlorophenyl | fluoromethyl | ethyl | |
| 2.2.565 | 3-acetoxy-5-chlorophenyl | fluoromethyl | ethyl | |
| 2.2.566 | {3-[(tert-butoxy-cabonyl)-amino]-5-chlorophenyl} | fluoromethyl | ethyl | |
| 2.2.567 | 3-methylsulfanyl-5-chlorophenyl | fluoromethyl | ethyl | |
| 2.2.568 | 3,5-dibromophenyl | fluoromethyl | ethyl | |
| 2.2.569 | 3,5-dibromophenyl | chloromethyl | ethyl | |
| 2.2.570 | 3-iodo-5-bromophenyl | fluoromethyl | ethyl | |
| 2.2.571 | 3-methyl-5-bromophenyl | fluoromethyl | ethyl | |
| 2.2.572 | 3-methyl-5-bromophenyl | chloromethyl | ethyl | |
| 2.2.573 | 3-methyl-5-bromophenyl | bromomethyl | ethyl | |
| 2.2.574 | 3-methyl-5-bromophenyl | difluoromethyl | ethyl | |
| 2.2.575 | 3-methyl-5-bromophenyl | trifluoromethyl | ethyl | |
| 2.2.576 | 3-methyl-5-bromophenyl | cyano | ethyl | |
| 2.2.577 | 3-ethyl-5-bromophenyl | fluoromethyl | ethyl | |
| 2.2.578 | 3-propyl-5-bromophenyl | fluoromethyl | ethyl | |
| 2.2.579 | 3-isopropyl-5-bromophenyl | fluoromethyl | ethyl | |
| 2.2.580 | 3-n-butyl-5-bromophenyl | fluoromethyl | ethyl | |
| 2.2.581 | 3-isobutyl-5-bromophenyl | fluoromethyl | ethyl | |
| 2.2.582 | 3-tert-butyl-5-bromophenyl | fluoromethyl | ethyl | |
| 2.2.583 | 3-cyclopropyl-5-bromophenyl | fluoromethyl | ethyl | |
| 2.2.584 | 3-vinyl-5-bromophenyl | fluoromethyl | ethyl | |
| 2.2.585 | 3-ethynyl-5-bromophenyl | fluoromethyl | ethyl | |
| 2.2.586 | 3-cyano-5-bromophenyl | fluoromethyl | ethyl | |
| 2.2.587 | 3-trifluoromethyl-5-bromophenyl | fluoromethyl | ethyl | |
| 2.2.588 | 3-(hydroxycarbonyl)-5-bromophenyl | fluoromethyl | ethyl | |
| 2.2.589 | 3-(methoxycarbonyl)-5-bromophenyl | fluoromethyl | ethyl | |

TABLE 2.2-continued

Inventive compounds of the general formula (I) in which W* is CODY, R¹ and R² are each hydrogen, and aryl is the radical.

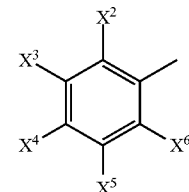

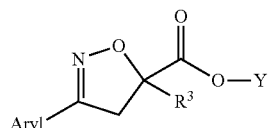

| No. | Aryl | R³ | Y | Physical data |
|---|---|---|---|---|
| 2.2.590 | 3-hydroxymethyl-5-bromophenyl | fluoromethyl | ethyl | |
| 2.2.591 | 3-carbamoyl-5-bromophenyl | fluoromethyl | ethyl | |
| 2.2.592 | 3-hydroxy-5-bromophenyl | fluoromethyl | ethyl | |
| 2.2.593 | 3-methoxy-5-bromophenyl | fluoromethyl | ethyl | |
| 2.2.594 | 3-ethoxy-5-bromophenyl | fluoromethyl | ethyl | |
| 2.2.595 | 3-n-propoxy-5-bromophenyl | fluoromethyl | ethyl | |
| 2.2.596 | 3-isopropoxy-5-bromophenyl | fluoromethyl | ethyl | |
| 2.2.597 | 3-n-butoxy-5-bromophenyl | fluoromethyl | ethyl | |
| 2.2.598 | 3-isobutoxy-5-bromophenyl | fluoromethyl | ethyl | |
| 2.2.599 | 3-tert-butoxy-5-bromophenyl | fluoromethyl | ethyl | |
| 2.2.600 | 3-difluoromethoxy-5-bromophenyl | fluoromethyl | ethyl | |
| 2.2.601 | 3-trifluoromethoxy-5-bromophenyl | fluoromethyl | ethyl | |
| 2.2.602 | 3-(2,2,2-trifluoroethoxy)-5-bromophenyl | fluoromethyl | ethyl | |
| 2.2.603 | 3-(2-chloroethoxy)-5-bromophenyl | fluoromethyl | ethyl | |
| 2.2.604 | 3-(2-hydroxyethoxy)-5-bromophenyl | fluoromethyl | ethyl | |
| 2.2.605 | 3-[(tert-butoxycarbonyl)-oxy]-5-bromophenyl | fluoromethyl | ethyl | |
| 2.2.606 | 3-nitro-5-bromophenyl | fluoromethyl | ethyl | |
| 2.2.607 | 3-acetoxy-5-bromophenyl | fluoromethyl | ethyl | |
| 2.2.608 | {3-[(tert-butoxy-carbonyl)-amino]-5-bromophenyl} | fluoromethyl | ethyl | |
| 2.2.609 | 3-methylsulfanyl-5-bromophenyl | fluoromethyl | ethyl | |
| 2.2.610 | 3,5-diiodophenyl | fluoromethyl | ethyl | |
| 2.2.611 | 3-methyl-5-iodophenyl | fluoromethyl | ethyl | |
| 2.2.612 | 3-ethyl-5-iodophenyl | fluoromethyl | ethyl | |
| 2.2.613 | 3-propyl-5-iodophenyl | fluoromethyl | ethyl | |
| 2.2.614 | 3-isopropyl-5-iodophenyl | fluoromethyl | ethyl | |
| 2.2.615 | 3-n-butyl-5-iodophenyl | fluoromethyl | ethyl | |
| 2.2.616 | 3-isobutyl-5-iodophenyl | fluoromethyl | ethyl | |
| 2.2.617 | 3-tert-butyl-5-iodophenyl | fluoromethyl | ethyl | |
| 2.2.618 | 3-cyclopropyl-5-iodophenyl | fluoromethyl | ethyl | |
| 2.2.619 | 3-vinyl-5-iodophenyl | fluoromethyl | ethyl | |
| 2.2.620 | 3-ethynyl-5-iodophenyl | fluoromethyl | ethyl | |
| 2.2.621 | 3-cyano-5-iodophenyl | fluoromethyl | ethyl | |
| 2.2.622 | 3-trifluoromethyl-5-iodophenyl | fluoromethyl | ethyl | |
| 2.2.623 | 3-(hydroxycarbonyl)-5-iodophenyl | fluoromethyl | ethyl | |
| 2.2.624 | 3-(methoxycarbonyl)-5-iodophenyl | fluoromethyl | ethyl | |

TABLE 2.2-continued

Inventive compounds of the general formula (I) in which W* is CODY, R¹ and R² are each hydrogen, and aryl is the radical.

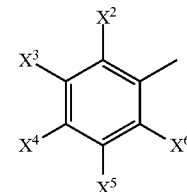

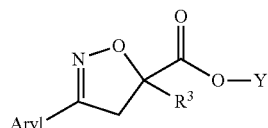

| No. | Aryl | R³ | Y | Physical data |
|---|---|---|---|---|
| 2.2.625 | 3-hydroxymethyl-5-iodophenyl | fluoromethyl | ethyl | |
| 2.2.626 | 3-carbamoyl-5-iodophenyl | fluoromethyl | ethyl | |
| 2.2.627 | 3-hydroxy-5-iodophenyl | fluoromethyl | ethyl | |
| 2.2.628 | 3-methoxy-5-iodophenyl | fluoromethyl | ethyl | |
| 2.2.629 | 3-ethoxy-5-iodophenyl | fluoromethyl | ethyl | |
| 2.2.630 | 3-n-propoxy-5-iodophenyl | fluoromethyl | ethyl | |
| 2.2.631 | 3-isopropoxy-5-iodophenyl | fluoromethyl | ethyl | |
| 2.2.632 | 3-n-butoxy-5-iodophenyl | fluoromethyl | ethyl | |
| 2.2.633 | 3-isobutoxy-5-iodophenyl | fluoromethyl | ethyl | |
| 2.2.634 | 3-tert-butoxy-5-iodophenyl | fluoromethyl | ethyl | |
| 2.2.635 | 3-difluoromethoxy-5-iodophenyl | fluoromethyl | ethyl | |
| 2.2.636 | 3-trifluoromethoxy-5-iodophenyl | fluoromethyl | ethyl | |
| 2.2.637 | 3-(2,2,2-trifluoroethoxy)-5-iodophenyl | fluoromethyl | ethyl | |
| 2.2.638 | 3-(2-chloroethoxy)-5-iodophenyl | fluoromethyl | ethyl | |
| 2.2.639 | 3-(2-hydroxyethoxy)-5-iodophenyl | fluoromethyl | ethyl | |
| 2.2.640 | 3-[(tert-butoxycarbonyl)-oxy]-5-iodophenyl | fluoromethyl | ethyl | |
| 2.2.641 | 3-nitro-5-iodophenyl | fluoromethyl | ethyl | |
| 2.2.642 | 3-acetoxy-5-iodophenyl | fluoromethyl | ethyl | |
| 2.2.643 | {3-[(tert-butoxy-carbonyl)-amino]-5-iodophenyl} | fluoromethyl | ethyl | |
| 2.2.644 | 3-methylsulfanyl-5-iodophenyl | fluoromethyl | ethyl | |
| 2.2.645 | 3,5-dimethylphenyl | fluoromethyl | ethyl | |
| 2.2.646 | 3-ethyl-5-methylphenyl | fluoromethyl | ethyl | |
| 2.2.647 | 3-propyl-5-methylphenyl | fluoromethyl | ethyl | |
| 2.2.648 | 3-isopropyl-5-methylphenyl | fluoromethyl | ethyl | |
| 2.2.649 | 3-n-butyl-5-methylphenyl | fluoromethyl | ethyl | |
| 2.2.650 | 3-isobutyl-5-methylphenyl | fluoromethyl | ethyl | |
| 2.2.651 | 3-tert-butyl-5-methylphenyl | fluoromethyl | ethyl | |
| 2.2.652 | 3-cyclopropyl-5-methylphenyl | fluoromethyl | ethyl | |
| 2.2.653 | 3-vinyl-5-methylphenyl | fluoromethyl | ethyl | |
| 2.2.654 | 3-ethynyl-5-methylphenyl | fluoromethyl | ethyl | |
| 2.2.655 | 3-cyano-5-methylphenyl | fluoromethyl | ethyl | |
| 2.2.656 | 3-trifluoromethyl-5-methylphenyl | fluoromethyl | ethyl | |
| 2.2.657 | 3-(hydroxycarbonyl)-5-methylphenyl | fluoromethyl | ethyl | |
| 2.2.658 | 3-(methoxycarbonyl)-5-methylphenyl | fluoromethyl | ethyl | |
| 2.2.659 | 3-hydroxymethyl-5-methylphenyl | fluoromethyl | ethyl | |
| 2.2.660 | 3-carbamoyl-5-methylphenyl | fluoromethyl | ethyl | |
| 2.2.661 | 3-hydroxy-5-methylphenyl | fluoromethyl | ethyl | |
| 2.2.662 | 3-methoxy-5-methylphenyl | fluoromethyl | ethyl | |

TABLE 2.2-continued

Inventive compounds of the general formula (I) in which W* is CODY, $R^1$ and $R^2$ are each hydrogen, and aryl is the radical.

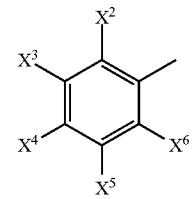

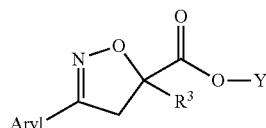

| No. | Aryl | $R^3$ | Y | Physical data |
|---|---|---|---|---|
| 2.2.663 | 3-ethoxy-5-methylphenyl | fluoromethyl | ethyl | |
| 2.2.664 | 3-n-propoxy-5-methylphenyl | fluoromethyl | ethyl | |
| 2.2.665 | 3-n-butoxy-5-methylphenyl | fluoromethyl | ethyl | |
| 2.2.666 | 3-isobutoxy-5-methylphenyl | fluoromethyl | ethyl | |
| 2.2.667 | 3-tert-butoxy-5-methylphenyl | fluoromethyl | ethyl | |
| 2.2.668 | 3-difluoromethoxy-5-methylphenyl | fluoromethyl | ethyl | |
| 2.2.669 | 3-trifluoromethoxy-5-methylphenyl | fluoromethyl | ethyl | |
| 2.2.670 | 3-(2,2,2-trifluoroethoxy)-5-methylphenyl | fluoromethyl | ethyl | |
| 2.2.671 | 3-(2-chloroethoxy)-5-methylphenyl | fluoromethyl | ethyl | |
| 2.2.672 | 3-(2-hydroxyethoxy)-5-methylphenyl | fluoromethyl | ethyl | |
| 2.2.673 | 3-[(tert-butoxy-carbonyl)oxy]-5-methylphenyl | fluoromethyl | ethyl | |
| 2.2.674 | 3-nitro-5-methylphenyl | fluoromethyl | ethyl | |
| 2.2.675 | 3-acetoxy-5-methylphenyl | fluoromethyl | ethyl | |
| 2.2.676 | {3-[(tert-butoxy-carbonyl)-amino]-5-methylphenyl} | fluoromethyl | ethyl | |
| 2.2.677 | 3-methylsulfanyl-5-methylphenyl | fluoromethyl | ethyl | |
| 2.2.678 | 3,5-diethylphenyl | fluoromethyl | ethyl | |
| 2.2.679 | 3-propyl-5-ethylphenyl | fluoromethyl | ethyl | |
| 2.2.680 | 3-isopropyl-5-ethylphenyl | fluoromethyl | ethyl | |
| 2.2.681 | 3-n-butyl-5-ethylphenyl | fluoromethyl | ethyl | |
| 2.2.682 | 3-isobutyl-5-ethylphenyl | fluoromethyl | ethyl | |
| 2.2.683 | 3-tert-butyl-5-ethylphenyl | fluoromethyl | ethyl | |
| 2.2.684 | 3-cyclopropyl-5-ethylphenyl | fluoromethyl | ethyl | |
| 2.2.685 | 3-vinyl-5-ethylphenyl | fluoromethyl | ethyl | |
| 2.2.686 | 3-ethynyl-5-ethylphenyl | fluoromethyl | ethyl | |
| 2.2.687 | 3-cyano-5-ethylphenyl | fluoromethyl | ethyl | |
| 2.2.688 | 3-trifluoromethyl-5-ethylphenyl | fluoromethyl | ethyl | |
| 2.2.689 | 3-(hydroxycarbonyl)-5-ethylphenyl | fluoromethyl | ethyl | |
| 2.2.690 | 3-(methoxycarbonyl)-5-ethylphenyl | fluoromethyl | ethyl | |
| 2.2.691 | 3-hydroxymethyl-5-ethylphenyl | fluoromethyl | ethyl | |
| 2.2.692 | 3-carbamoyl-5-ethylphenyl | fluoromethyl | ethyl | |
| 2.2.693 | 3-hydroxy-5-ethylphenyl | fluoromethyl | ethyl | |
| 2.2.694 | 3-methoxy-5-ethylphenyl | fluoromethyl | ethyl | |
| 2.2.695 | 3-ethoxy-5-ethylphenyl | fluoromethyl | ethyl | |
| 2.2.696 | 3-n-propoxy-5-ethylphenyl | fluoromethyl | ethyl | |
| 2.2.697 | 3-n-butoxy-5-ethylphenyl | fluoromethyl | ethyl | |
| 2.2.698 | 3-isobutoxy-5-ethylphenyl | fluoromethyl | ethyl | |
| 2.2.699 | 3-tert-butoxy-5-ethylphenyl | fluoromethyl | ethyl | |

TABLE 2.2-continued

Inventive compounds of the general formula (I) in which W* is CODY, R¹ and R² are each hydrogen, and aryl is the radical.

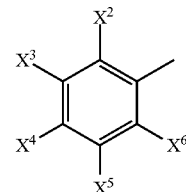

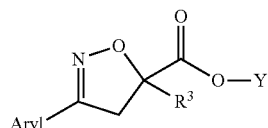

| No. | Aryl | R³ | Y | Physical data |
|---|---|---|---|---|
| 2.2.700 | 3-difluoromethoxy-5-ethylphenyl | fluoromethyl | ethyl | |
| 2.2.701 | 3-trifluoromethoxy-5-ethylphenyl | fluoromethyl | ethyl | |
| 2.2.702 | 3-(2,2,2-trifluoroethoxy)-5-ethylphenyl | fluoromethyl | ethyl | |
| 2.2.703 | 3-(2-chloroethoxy)-5-ethylphenyl | fluoromethyl | ethyl | |
| 2.2.704 | 3-(2-hydroxyethoxy)-5-ethylphenyl | fluoromethyl | ethyl | |
| 2.2.705 | 3-[(tert-butoxy-carbonyl)oxy]-5-ethylphenyl | fluoromethyl | ethyl | |
| 2.2.706 | 3-nitro-5-ethylphenyl | fluoromethyl | ethyl | |
| 2.2.707 | 3-acetoxy-5-ethylphenyl | fluoromethyl | ethyl | |
| 2.2.708 | {3-[(tert-butoxy-carbonyl)-amino]-5-ethylphenyl} | fluoromethyl | ethyl | |
| 2.2.709 | 3-methylsulfanyl-5-ethylphenyl | fluoromethyl | ethyl | |
| 2.2.710 | 3,5-dipropylphenyl | fluoromethyl | ethyl | |
| 2.2.711 | 3-isopropyl-5-propylphenyl | fluoromethyl | ethyl | |
| 2.2.712 | 3-n-butyl-5-propylphenyl | fluoromethyl | ethyl | |
| 2.2.713 | 3-isobutyl-5-propylphenyl | fluoromethyl | ethyl | |
| 2.2.714 | 3-tert-butyl-5-propylphenyl | fluoromethyl | ethyl | |
| 2.2.715 | 3-cyclopropyl-5-propylphenyl | fluoromethyl | ethyl | |
| 2.2.716 | 3-vinyl-5-propylphenyl | fluoromethyl | ethyl | |
| 2.2.717 | 3-ethynyl-5-propylphenyl | fluoromethyl | ethyl | |
| 2.2.718 | 3-cyano-5-propylphenyl | fluoromethyl | ethyl | |
| 2.2.719 | 3-trifluoromethyl-5-propylphenyl | fluoromethyl | ethyl | |
| 2.2.720 | 3-(hydroxycarbonyl)-5-propylphenyl | fluoromethyl | ethyl | |
| 2.2.721 | 3-(methoxycarbonyl)-5-propylphenyl | fluoromethyl | ethyl | |
| 2.2.722 | 3-hydroxymethyl-5-propylphenyl | fluoromethyl | ethyl | |
| 2.2.723 | 3-carbamoyl-5-propylphenyl | fluoromethyl | ethyl | |
| 2.2.724 | 3-hydroxy-5-propylphenyl | fluoromethyl | ethyl | |
| 2.2.725 | 3-methoxy-5-propylphenyl | fluoromethyl | ethyl | |
| 2.2.726 | 3-ethoxy-5-propylphenyl | fluoromethyl | ethyl | |
| 2.2.727 | 3-n-propoxy-5-propylphenyl | fluoromethyl | ethyl | |
| 2.2.728 | 3-n-butoxy-5-propylphenyl | fluoromethyl | ethyl | |
| 2.2.729 | 3-isobutoxy-5-propylphenyl | fluoromethyl | ethyl | |
| 2.2.730 | 3-tert-butoxy-5-propylphenyl | fluoromethyl | ethyl | |
| 2.2.731 | 3-difluoromethoxy-5-propylphenyl | fluoromethyl | ethyl | |
| 2.2.732 | 3-trifluoromethoxy-5-ethylphenyl | fluoromethyl | ethyl | |

TABLE 2.2-continued

Inventive compounds of the general formula (I) in which W* is CODY, $R^1$ and $R^2$ are each hydrogen, and aryl is the radical.

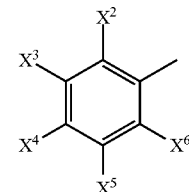

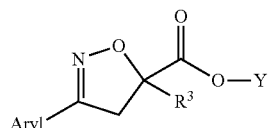

| No. | Aryl | $R^3$ | Y | Physical data |
|---|---|---|---|---|
| 2.2.733 | 3-(2,2,2-trifluoroethoxy)-5-propylphenyl | fluoromethyl | ethyl | |
| 2.2.734 | 3-(2-chloroethoxy)-5-propylphenyl | fluoromethyl | ethyl | |
| 2.2.735 | 3-(2-hydroxyethoxy)-5-propylphenyl | fluoromethyl | ethyl | |
| 2.2.736 | 3-[(tert-butoxy-carbonyl)oxy]-5-propylphenyl | fluoromethyl | ethyl | |
| 2.2.737 | 3-nitro-5-propylphenyl | fluoromethyl | ethyl | |
| 2.2.738 | 3-acetoxy-5-propylphenyl | fluoromethyl | ethyl | |
| 2.2.739 | {3-[(tert-butoxy-carbonyl)-amino]-5-propylphenyl} | fluoromethyl | ethyl | |
| 2.2.740 | 3-methylsulfanyl-5-propylphenyl | fluoromethyl | ethyl | |
| 2.2.741 | 3,5-diisopropylphenyl | fluoromethyl | ethyl | |
| 2.2.742 | 3-n-butyl-5-isopropylphenyl | fluoromethyl | ethyl | |
| 2.2.743 | 3-isobutyl-5-isopropylphenyl | fluoromethyl | ethyl | |
| 2.2.744 | 3-tert-butyl-5-isopropylphenyl | fluoromethyl | ethyl | |
| 2.2.745 | 3-cyclopropyl-5-isopropylphenyl | fluoromethyl | ethyl | |
| 2.2.746 | 3-vinyl-5-isopropylphenyl | fluoromethyl | ethyl | |
| 2.2.747 | 3-ethynyl-5-isopropylphenyl | fluoromethyl | ethyl | |
| 2.2.748 | 3-cyano-5-isopropylphenyl | fluoromethyl | ethyl | |
| 2.2.749 | 3-trifluoromethyl-5-isopropylphenyl | fluoromethyl | ethyl | |
| 2.2.750 | 3-(hydroxycarbonyl)-5-isopropylphenyl | fluoromethyl | ethyl | |
| 2.2.751 | 3-(methoxycarbonyl)-5-isopropylphenyl | fluoromethyl | ethyl | |
| 2.2.752 | 3-hydroxymethyl-5-isopropylphenyl | fluoromethyl | ethyl | |
| 2.2.753 | 3-carbamoyl-5-isopropylphenyl | fluoromethyl | ethyl | |
| 2.2.754 | 3-hydroxy-5-isopropylphenyl | fluoromethyl | ethyl | |
| 2.2.755 | 3-methoxy-5-isopropylphenyl | fluoromethyl | ethyl | |
| 2.2.756 | 3-ethoxy-5-isoperopylphenyl | fluoromethyl | ethyl | |
| 2.2.757 | 3-n-propoxy-5-isopropylphenyl | fluoromethyl | ethyl | |
| 2.2.758 | 3-n-butoxy-5-isopropylphenyl | fluoromethyl | ethyl | |
| 2.2.759 | 3-isobutoxy-5-isopropylphenyl | fluoromethyl | ethyl | |
| 2.2.760 | 3-tert-butoxy-5-isopropylphenyl | fluoromethyl | ethyl | |
| 2.2.761 | 3-difluoromethoxy-5-isopropylphenyl | fluoromethyl | ethyl | |
| 2.2.762 | 3-trifluoromethoxy-5-isopropylphenyl | fluoromethyl | ethyl | |

TABLE 2.2-continued

Inventive compounds of the general formula (I) in which W* is CODY, $R^1$ and $R^2$ are each hydrogen, and aryl is the radical.

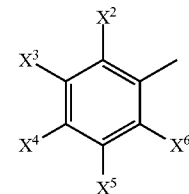

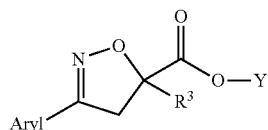

| No. | Aryl | $R^3$ | Y | Physical data |
|---|---|---|---|---|
| 2.2.763 | 3-(2,2,2-trifluoroethoxy)-5-isopropylphenyl | fluoromethyl | ethyl | |
| 2.2.764 | 3-(2-chloroethoxy)-5-isopropylphenyl | fluoromethyl | ethyl | |
| 2.2.765 | 3-(2-hydroxyethoxy)-5-propylphenyl | fluoromethyl | ethyl | |
| 2.2.766 | 3-[(tert-butoxycarbonyl)-oxy]-5-isopropylphenyl | fluoromethyl | ethyl | |
| 2.2.767 | 3-nitro-5-isopropylphenyl | fluoromethyl | ethyl | |
| 2.2.768 | 3-acetoxy-5-isopropylphenyl | fluoromethyl | ethyl | |
| 2.2.769 | {3-[(tert-butoxycarbonyl)-amino]-5-isopropylphenyl} | fluoromethyl | ethyl | |
| 2.2.770 | 3-methylsulfanyl-5-isopropylphenyl | fluoromethyl | ethyl | |
| 2.2.771 | 3,5-dibutylphenyl | fluoromethyl | ethyl | |
| 2.2.772 | 3-isobutyl-5-butylphenyl | fluoromethyl | ethyl | |
| 2.2.773 | 3-tert-butyl-5-butylphenyl | fluoromethyl | ethyl | |
| 2.2.774 | 3-cyclopropyl-5-butylphenyl | fluoromethyl | ethyl | |
| 2.2.775 | 3-vinyl-5-butylphenyl | fluoromethyl | ethyl | |
| 2.2.776 | 3-ethynyl-5-butylphenyl | fluoromethyl | ethyl | |
| 2.2.777 | 3-cyano-5-butylphenyl | fluoromethyl | ethyl | |
| 2.2.778 | 3-trifluoromethyl-5-butylphenyl | fluoromethyl | ethyl | |
| 2.2.779 | 3-(hydroxycarbonyl)-5-butylphenyl | fluoromethyl | ethyl | |
| 2.2.780 | 3-(methoxycarbonyl)-5-butylphenyl | fluoromethyl | ethyl | |
| 2.2.781 | 3-hydroxymethyl-5-butylphenyl | fluoromethyl | ethyl | |
| 2.2.782 | 3-carbamoyl-5-butylphenyl | fluoromethyl | ethyl | |
| 2.2.783 | 3-hydroxy-5-butylphenyl | fluoromethyl | ethyl | |
| 2.2.784 | 3-methoxy-5-butylphenyl | fluoromethyl | ethyl | |
| 2.2.785 | 3-ethoxy-5-butylphenyl | fluoromethyl | ethyl | |
| 2.2.786 | 3-n-propoxy-5-butylphenyl | fluoromethyl | ethyl | |
| 2.2.787 | 3-n-butoxy-5-butylphenyl | fluoromethyl | ethyl | |
| 2.2.788 | 3-isobutoxy-5-butylphenyl | fluoromethyl | ethyl | |
| 2.2.789 | 3-tert-butoxy-5-butylphenyl | fluoromethyl | ethyl | |
| 2.2.790 | 3-difluoromethoxy-5-butylphenyl | fluoromethyl | ethyl | |
| 2.2.791 | 3-trifluoromethoxy-5-butylphenyl | fluoromethyl | ethyl | |
| 2.2.792 | 3-(2,2,2-trifluoroethoxy)-5-butylphenyl | fluoromethyl | ethyl | |
| 2.2.793 | 3-(2-chloroethoxy)-5-butylphenyl | fluoromethyl | ethyl | |
| 2.2.794 | 3-(2-hydroxyethoxy)-5-butylphenyl | fluoromethyl | ethyl | |
| 2.2.795 | 3-[(tert-butoxycarbonyl)-oxy]-5-butylphenyl | fluoromethyl | ethyl | |
| 2.2.796 | 3-nitro-5-butylphenyl | fluoromethyl | ethyl | |
| 2.2.797 | 3-acetoxy-5-butylphenyl | fluoromethyl | ethyl | |
| 2.2.798 | {3-[(tert-butoxy-carbonyl)-amino]-5-butylphenyl} | fluoromethyl | ethyl | |

TABLE 2.2-continued

Inventive compounds of the general formula (I) in which W* is CODY, $R^1$ and $R^2$ are each hydrogen, and aryl is the radical.

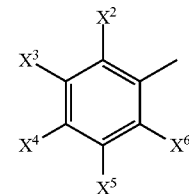

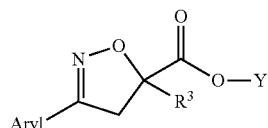

| No. | Aryl | $R^3$ | Y | Physical data |
|---|---|---|---|---|
| 2.2.799 | 3-methylsulfanyl-5-butylphenyl | fluoromethyl | ethyl | |
| 2.2.800 | 3,5-diisobutylphenyl | fluoromethyl | ethyl | |
| 2.2.801 | 3-tert-butyl-5-isobutylphenyl | fluoromethyl | ethyl | |
| 2.2.802 | 3-cyclopropyl-5-isobutylphenyl | fluoromethyl | ethyl | |
| 2.2.803 | 3-vinyl-5-isobutylphenyl | fluoromethyl | ethyl | |
| 2.2.804 | 3-ethynyl-5-isobutylphenyl | fluoromethyl | ethyl | |
| 2.2.805 | 3-cyano-5-isobutylphenyl | fluoromethyl | ethyl | |
| 2.2.806 | 3-trifluoromethyl-5-isobutylphenyl | fluoromethyl | ethyl | |
| 2.2.807 | 3-(hydroxycarbonyl)-5-isobutylphenyl | fluoromethyl | ethyl | |
| 2.2.808 | 3-(methoxycarbonyl)-5-isobutylphenyl | fluoromethyl | ethyl | |
| 2.2.809 | 3-hydroxymethyl-5-isobutylphenyl | fluoromethyl | ethyl | |
| 2.2.810 | 3-carbamoyl-5-isobutylphenyl | fluoromethyl | ethyl | |
| 2.2.811 | 3-hydroxy-5-isobutylphenyl | fluoromethyl | ethyl | |
| 2.2.812 | 3-methoxy-5-isobutylphenyl | fluoromethyl | ethyl | |
| 2.2.813 | 3-ethoxy-5-isobutylphenyl | fluoromethyl | ethyl | |
| 2.2.814 | 3-n-propoxy-5-isobutylphenyl | fluoromethyl | ethyl | |
| 2.2.815 | 3-n-butoxy-5-isobutylphenyl | fluoromethyl | ethyl | |
| 2.2.816 | 3-isobutoxy-5-isobutylphenyl | fluoromethyl | ethyl | |
| 2.2.817 | 3-tert-butoxy-5-isobutylphenyl | fluoromethyl | ethyl | |
| 2.2.818 | 3-difluoromethoxy-5-isobutylphenyl | fluoromethyl | ethyl | |
| 2.2.819 | 3-trifluoromethoxy-5-isobutylphenyl | fluoromethyl | ethyl | |
| 2.2.820 | 3-(2,2,2-trifluoroethoxy)-5-isobutylphenyl | fluoromethyl | ethyl | |
| 2.2.821 | 3-(2-chloroethoxy)-5-isobutylphenyl | fluoromethyl | ethyl | |
| 2.2.822 | 3-(2-hydroxyethoxy)-5-isobutylphenyl | fluoromethyl | ethyl | |
| 2.2.823 | 3-[(tert-butoxy-carbonyl)oxy]-5-isobutylphenyl | fluoromethyl | ethyl | |
| 2.2.824 | 3-nitro-5-isobutylphenyl | fluoromethyl | ethyl | |
| 2.2.825 | 3-acetoxy-5-isobutylphenyl | fluoromethyl | ethyl | |
| 2.2.826 | {3-[(tert-butoxy-carbonyl)-amino]-5-isobutylphenyl} | fluoromethyl | ethyl | |
| 2.2.827 | 3-methylsulfanyl-5-isobutylphenyl | fluoromethyl | ethyl | |
| 2.2.828 | 3,5-di(tert-butyl)phenyl | fluoromethyl | ethyl | |
| 2.2.829 | 3-cyclopropyl-5-tert-butylphenyl | fluoromethyl | ethyl | |

TABLE 2.2-continued

Inventive compounds of the general formula (I) in which W* is CODY, $R^1$ and $R^2$ are each hydrogen, and aryl is the radical.

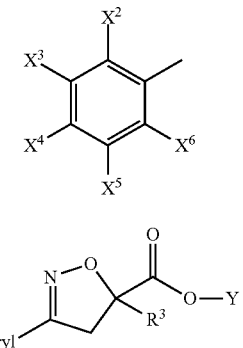

| No. | Aryl | $R^3$ | Y | Physical data |
|---|---|---|---|---|
| 2.2.830 | 3-vinyl-5-tert-butylphenyl | fluoromethyl | ethyl | |
| 2.2.831 | 3-ethynyl-5-tert-butylphenyl | fluoromethyl | ethyl | |
| 2.2.832 | 3-cyano-5-tert-butylphenyl | fluoromethyl | ethyl | |
| 2.2.833 | 3-trifluoromethyl-5-tert-butylphenyl | fluoromethyl | ethyl | |
| 2.2.834 | 3-(hydroxycarbonyl)-5-tert-butylphenyl | fluoromethyl | ethyl | |
| 2.2.835 | 3-(methoxycarbonyl)-5-tert-butylphenyl | fluoromethyl | ethyl | |
| 2.2.836 | 3-hydroxymethyl-5-tert-butylphenyl | fluoromethyl | ethyl | |
| 2.2.837 | 3-carbamoyl-5-tert-butylphenyl | fluoromethyl | ethyl | |
| 2.2.838 | 3-hydroxy-5-tert-butylphenyl | fluoromethyl | ethyl | |
| 2.2.839 | 3-methoxy-5-tert-butylphenyl | fluoromethyl | ethyl | |
| 2.2.840 | 3-ethoxy-5-tert-butylphenyl | fluoromethyl | ethyl | |
| 2.2.841 | 3-n-propoxy-5-tert-butylphenyl | fluoromethyl | ethyl | |
| 2.2.842 | 3-n-butoxy-5-tert-butylphenyl | fluoromethyl | ethyl | |
| 2.2.843 | 3-isobutoxy-5-tert-butylphenyl | fluoromethyl | ethyl | |
| 2.2.844 | 3-tert-butoxy-5-tert-butylphenyl | fluoromethyl | ethyl | |
| 2.2.845 | 3-difluoromethoxy-5-tert-butylphenyl | fluoromethyl | ethyl | |
| 2.2.846 | 3-trifluoromethoxy-5-tert-butylphenyl | fluoromethyl | ethyl | |
| 2.2.847 | 3-(2,2,2-trifluoroethoxy)-5-tert-butylphenyl | fluoromethyl | ethyl | |
| 2.2.848 | 3-(2-chloroethoxy)-5-tert-butylphenyl | fluoromethyl | ethyl | |
| 2.2.849 | 3-(2-hydroxyethoxy)-5-tert-butylphenyl | fluoromethyl | ethyl | |
| 2.2.850 | 3-[(tert-butoxycarbonyl)-oxy]-5-tert-butylphenyl | fluoromethyl | ethyl | |
| 2.2.851 | 3-nitro-5-tert-butylphenyl | fluoromethyl | ethyl | |
| 2.2.852 | 3-acetoxy-5-tert-butylphenyl | fluoromethyl | ethyl | |
| 2.2.853 | {3-[(tert-butoxy-carbonyl)-amino]-5-tert-butylphenyl} | fluoromethyl | ethyl | |
| 2.2.854 | 3-methylsulfanyl-5-tert-butylphenyl | fluoromethyl | ethyl | |
| 2.2.855 | 3-tert-butyl-5-cyclopropylphenyl | fluoromethyl | ethyl | |
| 2.2.856 | 3,5-dicyclopropylphenyl | fluoromethyl | ethyl | |
| 2.2.857 | 3-vinyl-5-cyclopropylphenyl | fluoromethyl | ethyl | |
| 2.2.858 | 3-ethynyl-5-cyclopropylphenyl | fluoromethyl | ethyl | |
| 2.2.859 | 3-cyano-5-cyclopropylphenyl | fluoromethyl | ethyl | |

TABLE 2.2-continued

Inventive compounds of the general formula (I) in which W* is CODY, $R^1$ and $R^2$ are each hydrogen, and aryl is the radical.

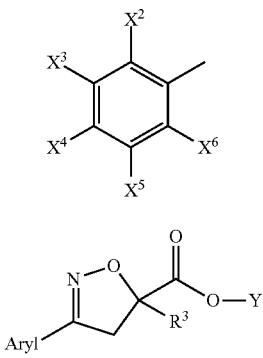

| No. | Aryl | $R^3$ | Y | Physical data |
|---|---|---|---|---|
| 2.2.860 | 3-trifluoromethyl-5-cyclopropylphenyl | fluoromethyl | ethyl | |
| 2.2.861 | 3-(hydroxycarbonyl)-5-cyclopropylphenyl | fluoromethyl | ethyl | |
| 2.2.862 | 3-(methoxycarbonyl)-5-cyclopropylphenyl | fluoromethyl | ethyl | |
| 2.2.863 | 3-hydroxymethyl-5-cyclopropylphenyl | fluoromethyl | ethyl | |
| 2.2.864 | 3-carbamoyl-5-cyclopropylphenyl | fluoromethyl | ethyl | |
| 2.2.865 | 3-hydroxy-5-cyclopropylphenyl | fluoromethyl | ethyl | |
| 2.2.866 | 3-methoxy-5-cyclopropylphenyl | fluoromethyl | ethyl | |
| 2.2.867 | 3-ethoxy-5-cyclopropylphenyl | fluoromethyl | ethyl | |
| 2.2.868 | 3-n-propoxy-5-cyclopropylphenyl | fluoromethyl | ethyl | |
| 2.2.869 | 3-n-butoxy-5-cyclopropylphenyl | fluoromethyl | ethyl | |
| 2.2.870 | 3-isobutoxy-5-cyclopropylphenyl | fluoromethyl | ethyl | |
| 2.2.871 | 3-tert-butoxy-5-cyclopropylphenyl | fluoromethyl | ethyl | |
| 2.2.872 | 3-difluoromethoxy-5-cyclopropylphenyl | fluoromethyl | ethyl | |
| 2.2.873 | 3-trifluoromethoxy-5-cyclopropylphenyl | fluoromethyl | ethyl | |
| 2.2.874 | 3-(2,2,2-trifluoroethoxy)-5-cyclopropylphenyl | fluoromethyl | ethyl | |
| 2.2.875 | 3-(2-chloroethoxy)-5-cyclopropylphenyl | fluoromethyl | ethyl | |
| 2.2.876 | 3-(2-hydroxyethoxy)-5-cyclopropylphenyl | fluoromethyl | ethyl | |
| 2.2.877 | 3-[(tert-butoxycarbonyl)oxy]-5-cyclopropylphenyl | fluoromethyl | ethyl | |
| 2.2.878 | 3-nitro-5-cyclopropylphenyl | fluoromethyl | ethyl | |
| 2.2.879 | 3-acetoxy-5-cyclopropylphenyl | fluoromethyl | ethyl | |
| 2.2.880 | {3-[(tert-butoxycarbonyl)-amino]-5-cyclopropyl-phenyl} | fluoromethyl | ethyl | |
| 2.2.881 | 3-methylsulfanyl-5-cyclopropylphenyl | fluoromethyl | ethyl | |
| 2.2.882 | 3,5-divinylphenyl | fluoromethyl | ethyl | |
| 2.2.883 | 3-ethynyl-5-vinylphenyl | fluoromethyl | ethyl | |
| 2.2.884 | 3-cyano-5-vinylphenyl | fluoromethyl | ethyl | |
| 2.2.885 | 3-trifluoromethyl-5-vinylphenyl | fluoromethyl | ethyl | |
| 2.2.886 | 3-(hydroxycarbonyl)-5-vinylphenyl | fluoromethyl | ethyl | |
| 2.2.887 | 3-(methoxycarbonyl)-5-vinylphenyl | fluoromethyl | ethyl | |
| 2.2.888 | 3-hydroxymethyl-5-vinylphenyl | fluoromethyl | ethyl | |

TABLE 2.2-continued

Inventive compounds of the general formula (I) in which W* is CODY, R¹ and R² are each hydrogen, and aryl is the radical.

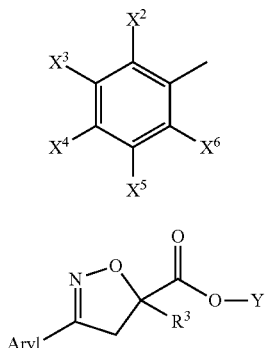

| No. | Aryl | R³ | Y | Physical data |
|---|---|---|---|---|
| 2.2.889 | 3-carbamoyl-5-vinylphenyl | fluoromethyl | ethyl | |
| 2.2.890 | 3-hydroxy-5-vinylphenyl | fluoromethyl | ethyl | |
| 2.2.891 | 3-methoxy-5-vinylphenyl | fluoromethyl | ethyl | |
| 2.2.892 | 3-ethoxy-5-vinylphenyl | fluoromethyl | ethyl | |
| 2.2.893 | 3-n-propoxy-5-vinylphenyl | fluoromethyl | ethyl | |
| 2.2.894 | 3-n-butoxy-5-vinylphenyl | fluoromethyl | ethyl | |
| 2.2.895 | 3-isobutoxy-5-vinylphenyl | fluoromethyl | ethyl | |
| 2.2.896 | 3-tert-butoxy-5-vinylphenyl | fluoromethyl | ethyl | |
| 2.2.897 | 3-difluoromethoxy-5-vinylphenyl | fluoromethyl | ethyl | |
| 2.2.898 | 3-trifluoromethoxy-5-vinylphenyl | fluoromethyl | ethyl | |
| 2.2.899 | 3-(2,2,2-trifluoroethoxy)-5-vinylphenyl | fluoromethyl | ethyl | |
| 2.2.900 | 3-(2-chloroethoxy)-5-vinylphenyl | fluoromethyl | ethyl | |
| 2.2.901 | 3-(2-hydroxyethoxy)-5-vinylphenyl | fluoromethyl | ethyl | |
| 2.2.902 | 3-[(tert-butoxycarbonyl)-oxy]-5-vinylphenyl | fluoromethyl | ethyl | |
| 2.2.903 | 3-nitro-5-vinylphenyl | fluoromethyl | ethyl | |
| 2.2.904 | 3-acetoxy-5-vinylphenyl | fluoromethyl | ethyl | |
| 2.2.905 | {3-[(tert-butoxy-carbonyl)-amino]-5-vinylphenyl} | fluoromethyl | ethyl | |
| 2.2.906 | 3-methylsulfanyl-5-vinylphenyl | fluoromethyl | ethyl | |
| 2.2.907 | 3,5-diethynylphenyl | fluoromethyl | ethyl | |
| 2.2.908 | 3-cyano-5-ethynylphenyl | fluoromethyl | ethyl | |
| 2.2.909 | 3-trifluoromethyl-5-ethynylphenyl | fluoromethyl | ethyl | |
| 2.2.910 | 3-(hydroxycarbonyl)-5-ethynylphenyl | fluoromethyl | ethyl | |
| 2.2.911 | 3-(methoxycarbonyl)-5-ethynylphenyl | fluoromethyl | ethyl | |
| 2.2.912 | 3-hydroxymethyl-5-ethynylphenyl | fluoromethyl | ethyl | |
| 2.2.913 | 3-carbamoyl-5-ethynylphenyl | fluoromethyl | ethyl | |
| 2.2.914 | 3-hydroxy-5-ethynylphenyl | fluoromethyl | ethyl | |
| 2.2.915 | 3-methoxy-5-ethynylphenyl | fluoromethyl | ethyl | |
| 2.2.916 | 3-ethoxy-5-ethynylphenyl | fluoromethyl | ethyl | |
| 2.2.917 | 3-n-propoxy-5-ethynylphenyl | fluoromethyl | ethyl | |
| 2.2.918 | 3-n-butoxy-5-ethynylphenyl | fluoromethyl | ethyl | |
| 2.2.919 | 3-isobutoxy-5-ethynylphenyl | fluoromethyl | ethyl | |
| 2.2.920 | 3-tert-butoxy-5-ethynylphenyl | fluoromethyl | ethyl | |
| 2.2.921 | 3-difluoromethoxy-5-ethynylphenyl | fluoromethyl | ethyl | |

TABLE 2.2-continued

Inventive compounds of the general formula (I) in which W* is CODY, R¹ and R² are each hydrogen, and aryl is the radical.

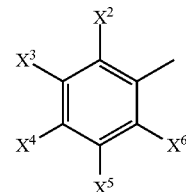

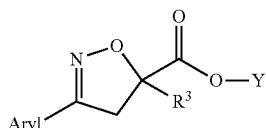

| No. | Aryl | R³ | Y | Physical data |
|---|---|---|---|---|
| 2.2.922 | 3-trifluoromethoxy-5-ethynylphenyl | fluoromethyl | ethyl | |
| 2.2.923 | 3-(2,2,2-trifluoroethoxy)-5-ethynylphenyl | fluoromethyl | ethyl | |
| 2.2.924 | 3-(2-chloroethoxy)-5-ethynylphenyl | fluoromethyl | ethyl | |
| 2.2.925 | 3-(2-hydroxyethoxy)-5-ethynylphenyl | fluoromethyl | ethyl | |
| 2.2.926 | 3-[(tert-butoxycarbonyl)-oxy]-5-ethynylphenyl | fluoromethyl | ethyl | |
| 2.2.927 | 3-nitro-5-ethynylphenyl | fluoromethyl | ethyl | |
| 2.2.928 | 3-acetoxy-5-ethynylphenyl | fluoromethyl | ethyl | |
| 2.2.929 | {3-[(tert-butoxy-carbonyl)-amino]-5-ethynylphenyl} | fluoromethyl | ethyl | |
| 2.2.930 | 3-methylsulfanyl-5-ethynylphenyl | fluoromethyl | ethyl | |
| 2.2.931 | 3,5-dicyanophenyl | fluoromethyl | ethyl | |
| 2.2.932 | 3-trifluoromethyl-5-cyanophenyl | fluoromethyl | ethyl | |
| 2.2.933 | 3-(hydroxycarbonyl)-5-cyanophenyl | fluoromethyl | ethyl | |
| 2.2.934 | 3-(methoxycarbonyl)-5-cyanophenyl | fluoromethyl | ethyl | |
| 2.2.935 | 3-hydroxymethyl-5-cyanophenyl | fluoromethyl | ethyl | |
| 2.2.936 | 3-carbamoyl-5-cyanophenyl | fluoromethyl | ethyl | |
| 2.2.937 | 3-hydroxy-5-cyanophenyl | fluoromethyl | ethyl | |
| 2.2.938 | 3-methoxy-5-cyanophenyl | fluoromethyl | ethyl | |
| 2.2.939 | 3-ethoxy-5-cyanophenyl | fluoromethyl | ethyl | |
| 2.2.940 | 3-n-propoxy-5-cyanophenyl | fluoromethyl | ethyl | |
| 2.2.941 | 3-n-butoxy-5-cyanophenyl | fluoromethyl | ethyl | |
| 2.2.942 | 3-isobutoxy-5-cyanophenyl | fluoromethyl | ethyl | |
| 2.2.943 | 3-tert-butoxy-5-cyanophenyl | fluoromethyl | ethyl | |
| 2.2.944 | 3-difluoromethoxy-5-cyanophenyl | fluoromethyl | ethyl | |
| 2.2.945 | 3-trifluoromethoxy-5-cyanophenyl | fluoromethyl | ethyl | |
| 2.2.946 | 3-(2,2,2-trifluoroethoxy)-5-cyanophenyl | fluoromethyl | ethyl | |
| 2.2.947 | 3-(2-chloroethoxy)-5-cyanophenyl | fluoromethyl | ethyl | |
| 2.2.948 | 3-(2-hydroxyethoxy)-5-cyanophenyl | fluoromethyl | ethyl | |
| 2.2.949 | 3-[(tert-butoxycarbonyl)-oxy]-5-cyanophenyl | fluoromethyl | ethyl | |
| 2.2.950 | 3-nitro-5-cyanophenyl | fluoromethyl | ethyl | |
| 2.2.951 | 3-acetoxy-5-cyanophenyl | fluoromethyl | ethyl | |
| 2.2.952 | {3-[(tert-butoxycarbonyl)-amino-5-cyanophenyl} | fluoromethyl | ethyl | |
| 2.2.953 | 3-methylsulfanyl-5-cyanophenyl | fluoromethyl | ethyl | |
| 2.2.954 | 3,5-di(trifluoromethyl)-phenyl | fluoromethyl | ethyl | |

TABLE 2.2-continued

Inventive compounds of the general formula (I) in which W* is CODY, $R^1$ and $R^2$ are each hydrogen, and aryl is the radical.

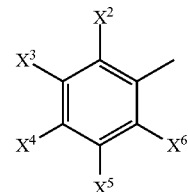

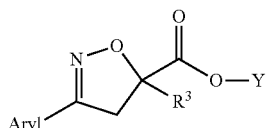

| No. | Aryl | $R^3$ | Y | Physical data |
|---|---|---|---|---|
| 2.2.955 | 3-(hydroxycarbonyl)-5-trifluoromethylphenyl | fluoromethyl | ethyl | |
| 2.2.956 | 3-(methoxycarbonyl)-5-trifluoromethylphenyl | fluoromethyl | ethyl | |
| 2.2.957 | 3-hydroxymethyl-5-trifluoromethylphenyl | fluoromethyl | ethyl | |
| 2.2.958 | 3-carbamoyl-5-trifluoromethylphenyl | fluoromethyl | ethyl | |
| 2.2.959 | 3-hydroxy-5-trifluoromethylphenyl | fluoromethyl | ethyl | |
| 2.2.960 | 3-methoxy-5-trifluoromethylphenyl | fluoromethyl | ethyl | |
| 2.2.961 | 3-ethoxy-5-trifluoromethylphenyl | fluoromethyl | ethyl | |
| 2.2.962 | 3-n-propoxy-5-trifluoromethylphenyl | fluoromethyl | ethyl | |
| 2.2.963 | 3-n-butoxy-5-trifluoromethylphenyl | fluoromethyl | ethyl | |
| 2.2.964 | 3-isobutoxy-5-trifluoromethylphenyl | fluoromethyl | ethyl | |
| 2.2.965 | 3-tert-butoxy-5-trifluoromethylphenyl | fluoromethyl | ethyl | |
| 2.2.966 | 3-difluoromethoxy-5-trifluoromethylphenyl | fluoromethyl | ethyl | |
| 2.2.967 | 3-trifluoromethoxy-5-trifluoromethylphenyl | fluoromethyl | ethyl | |
| 2.2.968 | 3-(2,2,2-trifluoro-ethoxy)-5-trifluoro-methylphenyl | fluoromethyl | ethyl | |
| 2.2.969 | 3-(2-chloroethoxy)-5-trifluoromethyl-phenyl | fluoromethyl | ethyl | |
| 2.2.970 | 3-(2-hydroxyethoxy)-5-trifluoromethyl-phenyl | fluoromethyl | ethyl | |
| 2.2.971 | 3-[(tert-butoxycarbonyl)-oxy]-5-trifluoromethyl-phenyl | fluoromethyl | ethyl | |
| 2.2.972 | 3-nitro-5-trifluoromethyl-phenyl | fluoromethyl | ethyl | |
| 2.2.973 | 3-acetoxy-5-trifluoro-methylphenyl | fluoromethyl | ethyl | |
| 2.2.974 | {3-[(tert-butoxy-carbonyl)-amino]-5-trifluoromethyl-phenyl} | fluoromethyl | ethyl | |
| 2.2.975 | 3-methylsulfanyl-5-trifluoromethylphenyl | fluoromethyl | ethyl | |
| 2.2.976 | 3,5-bis(hydroxy-carbonyl)phenyl | fluoromethyl | ethyl | |
| 2.2.977 | 3-(methoxycarbonyl)-5-(hydroxycarbonyl)phenyl | fluoromethyl | ethyl | |
| 2.2.978 | 3-hydroxymethyl-5-(hydroxycarbonyl)phenyl | fluoromethyl | ethyl | |
| 2.2.979 | 3-carbamoyl-5-(hydroxycarbonyl)phenyl | fluoromethyl | ethyl | |
| 2.2.980 | 3-hydroxy-5-(hydroxycarbonyl)phenyl | fluoromethyl | ethyl | |
| 2.2.981 | 3-methoxy-5-(hydroxycarbonyl)phenyl | fluoromethyl | ethyl | |

TABLE 2.2-continued

Inventive compounds of the general formula (I) in which W* is CODY, $R^1$ and $R^2$ are each hydrogen, and aryl is the radical.

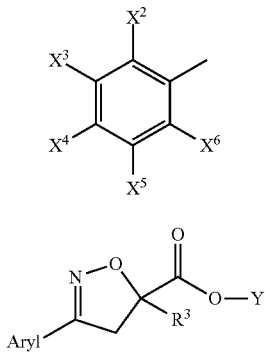

| No. | Aryl | $R^3$ | Y | Physical data |
|---|---|---|---|---|
| 2.2.982 | 3-ethoxy-5-(hydroxycarbonyl)phenyl | fluoromethyl | ethyl | |
| 2.2.983 | 3-n-propoxy-5-(hydroxycarbonyl)phenyl | fluoromethyl | ethyl | |
| 2.2.984 | 3-n-butoxy-5-(hydroxycarbonyl)phenyl | fluoromethyl | ethyl | |
| 2.2.985 | 3-isobutoxy-5-(hydroxycarbonyl)phenyl | fluoromethyl | ethyl | |
| 2.2.986 | 3-tert-butoxy-5-(hydroxycarbonyl)phenyl | fluoromethyl | ethyl | |
| 2.2.987 | 3-difluoromethoxy-5-(hydroxycarbonyl)phenyl | fluoromethyl | ethyl | |
| 2.2.988 | 3-trifluoromethoxy-5-(hydroxycarbonyl)phenyl | fluoromethyl | ethyl | |
| 2.2.989 | 3-(2,2,2-trifluoroethoxy)-5-(hydroxycarbonyl)phenyl | fluoromethyl | ethyl | |
| 2.2.990 | 3-(2-chloroethoxy)-5-(hydroxycarbonyl)phenyl | fluoromethyl | ethyl | |
| 2.2.991 | 3-(2-hydroxyethoxy)-5-(hydroxycarbonyl)phenyl | fluoromethyl | ethyl | |
| 2.2.992 | 3-[(tert-butoxycarbonyl)-oxy]-5-(hydroxycarbonyl)-phenyl | fluoromethyl | ethyl | |
| 2.2.993 | 3-nitro-5-(hydroxy-carbonyl)phenyl | fluoromethyl | ethyl | |
| 2.2.994 | 3-acetoxy-5-(hydroxy-carbonyl)phenyl | fluoromethyl | ethyl | |
| 2.2.995 | {3-[(tert-butoxycarbonyl)-amino]-5-(hydroxy-carbonyl)phenyl} | fluoromethyl | ethyl | |
| 2.2.996 | 3-methylsulfanyl-5-(hydroxycarbonyl)phenyl | fluoromethyl | ethyl | |
| 2.2.997 | 3,5-di(methoxy-carbonyl)phenyl | fluoromethyl | ethyl | |
| 2.2.998 | 3-hydroxymethyl-5-(methoxycarbonyl)phenyl | fluoromethyl | ethyl | |
| 2.2.999 | 3-carbamoyl-5-(methoxy carbonyl)phenyl | fluoromethyl | lethyl | |
| 2.2.1000 | 3-hydroxy-5-(methoxy-carbonyl)phenyl | fluoromethyl | ethyl | |
| 2.2.1001 | 3-methoxy-5-(methoxy-carbonyl)phenyl | fluoromethyl | ethyl | |
| 2.2.1002 | 3-ethoxy-5-(methoxy-carbonyl)phenyl | fluoromethyl | ethyl | |
| 2.2.1003 | 3-n-propoxy-5-(methoxy-carbonyl)phenyl | fluoromethyl | ethyl | |
| 2.2.1004 | 3-n-butoxy-5-(methoxy-carbonyl)phenyl | fluoromethyl | ethyl | |
| 2.2.1005 | 3-isobutoxy-5-(methoxy-carbonyl)phenyl | fluoromethyl | ethyl | |
| 2.2.1006 | 3-tert-butoxy-5-(methoxy-carbonyl)phenyl | fluoromethyl | ethyl | |
| 2.2.1007 | 3-difluoromethoxy-5-(methoxycarbonyl)phenyl | fluoromethyl | ethyl | |
| 2.2.1008 | 3-trifluoromethoxy-5-(methoxycarbonyl)phenyl | fluoromethyl | ethyl | |

TABLE 2.2-continued

Inventive compounds of the general formula (I) in which W* is CODY, $R^1$ and $R^2$ are each hydrogen, and aryl is the radical.

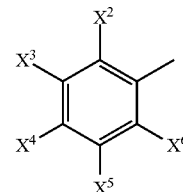

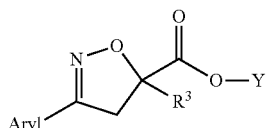

| No. | Aryl | $R^3$ | Y | Physical data |
|---|---|---|---|---|
| 2.2.1009 | 3-(2,2,2-trifluoroethoxy)-5-(methoxycarbonyl)phenyl | fluoromethyl | ethyl | |
| 2.2.1010 | 3-(2-chloroethoxy)-5-(methoxycarbonyl)phenyl | fluoromethyl | ethyl | |
| 2.2.1011 | 3-(2-hydroxyethoxy)-5-(methoxycarbonyl)-phenyl | fluoromethyl | ethyl | |
| 2.2.1012 | 3-[(tert-butoxycarbonyl)-oxy]-5-(methoxycarbonyl)-phenyl | fluoromethyl | ethyl | |
| 2.2.1013 | 3-nitro-5-(methoxy-carbonyl)phenyl | fluoromethyl | ethyl | |
| 2.2.1014 | 3-acetoxy-5-(methoxy-carbonyl)phenyl | fluoromethyl | ethyl | |
| 2.2.1015 | {3-[(tert-butoxycarbonyl)-amino]-5-(methoxy-carbonyl)phenyl} | fluoromethyl | ethyl | |
| 2.2.1016 | 3-methylsulfany1-5-(methoxycarbonyl)phenyl | fluoromethyl | ethyl | |
| 2.2.1017 | 3,5-di(hydroxymethyl)-phenyl | fluoromethyl | ethyl | |
| 2.2.1018 | 3-carbamoyl-5-hydroxy-methylphenyl | fluoromethyl | ethyl | |
| 2.2.1019 | 3-hydroxy-5-hydroxy-methylphenyl | fluoromethyl | ethyl | |
| 2.2.1020 | 3-methoxy-5-hydroxy-methylphenyl | fluoromethyl | ethyl | |
| 2.2.1021 | 3-ethoxy-5-hydroxy-methylphenyl | fluoromethyl | ethyl | |
| 2.2.1022 | 3-n-propoxy-5-hydroxy-methylphenyl | fluoromethyl | ethyl | |
| 2.2.1023 | 3-n-butoxy-5- hydroxy -methylphenyl | fluoromethyl | ethyl | |
| 2.2.1024 | 3-isobutoxy-5-hydroxy -methylphenyl | fluoromethyl | ethyl | |
| 2.2.1025 | 3-tert-butoxy-5-hydroxy-methylphenyl | fluoromethyl | ethyl | |
| 2.2.1026 | 3-difluoromethoxy-5-hydroxymethylphenyl | fluoromethyl | ethyl | |
| 2.2.1027 | 3-trifluoromethoxy-5-hydroxymethylphenyl | fluoromethyl | ethyl | |
| 2.2.1028 | 3-(2,2,2-trifluoroethoxy)-5-hydroxymethylphenyl | fluoromethyl | ethyl | |
| 2.2.1029 | 3-(2-chloroethoxy)-5-hydroxymethylphenyl | fluoromethyl | ethyl | |
| 2.2.1030 | 3-(2-hydroxyethoxy)-5-hydroxymethyl-phenyl | fluoromethyl | ethyl | |
| 2.2.1031 | 3-[(tert-butoxycarbonyl)-oxy]-5-hydroxymethyl-phenyl | fluoromethyl | ethyl | |
| 2.2.1032 | 3-nitro-5- hydroxymethyl-phenyl | fluoromethyl | ethyl | |
| 2.2.1033 | 3-acetoxy-5- hydroxy -methylphenyl | fluoromethyl | ethyl | |
| 2.2.1034 | {3-[(tert-butoxycarbonyl)-amino]-5-hydroxymethyl-phenyl} | fluoromethyl | ethyl | |

TABLE 2.2-continued

Inventive compounds of the general formula (I) in which W* is CODY, $R^1$ and $R^2$ are each hydrogen, and aryl is the radical.

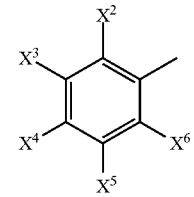

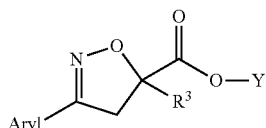

| No. | Aryl | $R^3$ | Y | Physical data |
|---|---|---|---|---|
| 2.2.1035 | 3-methylsulfanyl-5-hydroxymethylphenyl | fluoromethyl | ethyl | |
| 2.2.1036 | 3,5-dicarbamoyl-5-carbamoylphenyl | fluoromethyl | ethyl | |
| 2.2.1037 | 3-hydroxy-5-carbamoylphenyl | fluoromethyl | ethyl | |
| 2.2.1038 | 3-methoxy-5-carbamoylphenyl | fluoromethyl | ethyl | |
| 2.2.1039 | 3-ethoxy-5-carbamoylphenyl | fluoromethyl | ethyl | |
| 2.2.1040 | 3-n-propoxy-5-carbamoylphenyl | fluoromethyl | ethyl | |
| 2.2.1041 | 3-n-butoxy-5-carbamoylphenyl | fluoromethyl | ethyl | |
| 2.2.1042 | 3-isobutoxy-5-carbamoylphenyl | fluoromethyl | ethyl | |
| 2.2.1043 | 3-tert-butoxy-5-carbamoylphenyl | fluoromethyl | ethyl | |
| 2.2.1044 | 3-difluoromethoxy-5-carbamoylphenyl | fluoromethyl | ethyl | |
| 2.2.1045 | 3-trifluoromethoxy-5-carbamoylphenyl | fluoromethyl | ethyl | |
| 2.2.1046 | 3-(2,2,2-trifluoroethoxy)-5-carbamoylphenyl | fluoromethyl | ethyl | |
| 2.2.1047 | 3-(2-chloroethoxy)-5-carbamoylphenyl | fluoromethyl | ethyl | |
| 2.2.1048 | 3-(2-hydroxyethoxy)-5-carbamoylphenyl | fluoromethyl | ethyl | |
| 2.2.1049 | 3-{(tert-butoxy-carbonyl)oxy]-5-carbamoylphenyl | fluoromethyl | ethyl | |
| 2.2.1050 | 3-nitro-5-carbamoylphenyl | fluoromethyl | ethyl | |
| 2.2.1051 | 3-acetoxy-5-carbamoylphenyl | fluoromethyl | ethyl | |
| 2.2.1052 | {3-[(tert-butoxy-carbonyl)amino]-5-carbamoylphenyl} | fluoromethyl | ethyl | |
| 2.2.1053 | 3-methylsulfanyl-5-carbamoylphenyl | fluoromethyl | ethyl | |
| 2.2.1054 | 3,5-dihydroxyphenyl | fluoromethyl | ethyl | |
| 2.2.1055 | 3-methoxy-5-hydroxyphenyl | fluoromethyl | ethyl | |
| 2.2.1056 | 3-ethoxy-5-hydroxyphenyl | fluoromethyl | ethyl | |
| 2.2.1057 | 3-n-propoxy-5-hydroxyphenyl | fluoromethyl | ethyl | |
| 2.2.1058 | 3-n-butoxy-5-hydroxyphenyl | fluoromethyl | ethyl | |
| 2.2.1059 | 3-isobutoxy-5-hydroxyphenyl | fluoromethyl | ethyl | |
| 2.2.1060 | 3-tert-butoxy-5-hydroxyphenyl | fluoromethyl | ethyl | |
| 2.2.1061 | 3-difluoromethoxy-5-hydroxyphenyl | fluoromethyl | ethyl | |
| 2.2.1062 | 3-trifluoromethoxy-5-hydroxyphenyl | fluoromethyl | ethyl | |
| 2.2.1063 | 3-(2,2,2-trifluoroethoxy)-5-hydroxyphenyl | fluoromethyl | ethyl | |

TABLE 2.2-continued

Inventive compounds of the general formula (I) in which W* is CODY, $R^1$ and $R^2$ are each hydrogen, and aryl is the radical.

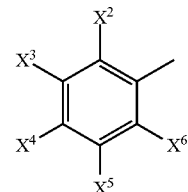

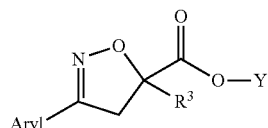

| No. | Aryl | $R^3$ | Y | Physical data |
|---|---|---|---|---|
| 2.2.1064 | 3-(2-chloroethoxy)-5-hydroxyphenyl | fluoromethyl | ethyl | |
| 2.2.1065 | 3-(2-hydroxyethoxy)-5-hydroxyphenyl | fluoromethyl | ethyl | |
| 2.2.1066 | 3-[(tert-butoxycarbonyl)-oxy]-5-hydroxyphenyl | fluoromethyl | ethyl | |
| 2.2.1067 | 3-nitro-5-hydroxyphenyl | fluoromethyl | ethyl | |
| 2.2.1068 | 3-acetoxy-5-hydroxyphenyl | fluoromethyl | ethyl | |
| 2.2.1069 | {3-[(tert-butoxycarbonyl)-amino]-5-hydroxyphenyl} | fluoromethyl | ethyl | |
| 2.2.1070 | 3-methylsulfanyl-5-hydroxyphenyl | fluoromethyl | ethyl | |
| 2.2.1071 | 3,5-dimethoxyphenyl | fluoromethyl | ethyl | |
| 2.2.1072 | 3-ethoxy-5-methoxyphenyl | fluoromethyl | ethyl | |
| 2.2.1073 | 3-n-propoxy-5-methoxyphenyl | fluoromethyl | ethyl | |
| 2.2.1074 | 3-n-butoxy-5-methoxyphenyl | fluoromethyl | ethyl | |
| 2.2.1075 | 3-isobutoxy-5-methoxyphenyl | fluoromethyl | ethyl | |
| 2.2.1076 | 3-tert-butoxy-5-methoxyphenyl | fluoromethyl | ethyl | |
| 2.2.1077 | 3-difluoromethoxy-5-methoxyphenyl | fluoromethyl | ethyl | |
| 2.2.1078 | 3-trifluoromethoxy-5-methoxyphenyl | fluoromethyl | ethyl | |
| 2.2.1079 | 3-(2,2,2-trifluoroethoxy)-5-methoxyphenyl | fluoromethyl | ethyl | |
| 2.2.1080 | 3-(2-chloroethoxy)-5-methoxyphenyl | fluoromethyl | ethyl | |
| 2.2.1081 | 3-(2-hydroxyethoxy)-5-methoxyphenyl | fluoromethyl | ethyl | |
| 2.2.1082 | 3-[(tert-butoxycarbonyl)-oxy]-5-methoxyphenyl | fluoromethyl | ethyl | |
| 2.2.1083 | 3-nitro-5-methoxyphenyl | fluoromethyl | ethyl | |
| 2.2.1084 | 3-acetoxy-5-methoxyphenyl | fluoromethyl | ethyl | |
| 2.2.1085 | {3-[(tert-butoxycarbonyl)-amino]-5-methoxyphenyl} | fluoromethyl | ethyl | |
| 2.2.1086 | 3-methylsulfanyl-5-methoxyphenyl | fluoromethyl | ethyl | |
| 2.2.1087 | 3,5-diethoxyphenyl | fluoromethyl | ethyl | |
| 2.2.1088 | 3-n-propoxy-5-ethoxyphenyl | fluoromethyl | ethyl | |
| 2.2.1089 | 3-n-butoxy-5-ethoxyphenyl | fluoromethyl | ethyl | |
| 2.2.1090 | 3-isobutoxy-5-ethoxyphenyl | fluoromethyl | ethyl | |
| 2.2.1091 | 3-tert-butoxy-5-ethoxyphenyl | fluoromethyl | ethyl | |
| 2.2.1092 | 3-difluoromethoxy-5-ethoxyphenyl | fluoromethyl | ethyl | |
| 2.2.1093 | 3-trifluoromethoxy-5-ethoxyphenyl | fluoromethyl | ethyl | |

TABLE 2.2-continued

Inventive compounds of the general formula (I) in which W* is CODY, $R^1$ and $R^2$ are each hydrogen, and aryl is the radical.

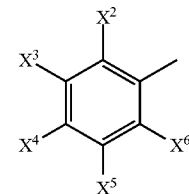

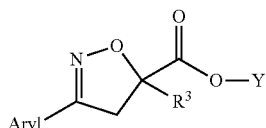

| No. | Aryl | $R^3$ | Y | Physical data |
|---|---|---|---|---|
| 2.2.1094 | 3-(2,2,2-trifluoroethoxy)-5-ethoxyphenyl | fluoromethyl | ethyl | |
| 2.2.1095 | 3-(2-chloroethoxy)-5-ethoxyphenyl | fluoromethyl | ethyl | |
| 2.2.1096 | 3-(2-hydroxyethoxy)-5-ethoxyphenyl | fluoromethyl | ethyl | |
| 2.2.1097 | 3-[(tert-butoxy-carbonyl)oxy]-5-ethoxyphenyl | fluoromethyl | ethyl | |
| 2.2.1098 | 3-nitro-5-ethoxyphenyl | fluoromethyl | ethyl | |
| 2.2.1099 | 3-acetoxy-5-ethoxyphenyl | fluoromethyl | ethyl | |
| 2.2.1100 | {3-[(tert-butoxycarbonyl)-amino]-5-ethoxyphenyl} | fluoromethyl | ethyl | |
| 2.2.1101 | 3-methylsulfanyl-5-ethoxyphenyl | fluoromethyl | ethyl | |
| 2.2.1102 | 3,5-dipropoxyphenyl | fluoromethyl | ethyl | |
| 2.2.1103 | 3-n-butoxy-5-propoxyphenyl | fluoromethyl | ethyl | |
| 2.2.1104 | 3-isobutoxy-5-propoxyphenyl | fluoromethyl | ethyl | |
| 2.2.1105 | 3-tert-butoxy-5-propoxyphenyl | fluoromethyl | ethyl | |
| 2.2.1106 | 3-difluoromethoxy-5-propoxyphenyl | fluoromethyl | ethyl | |
| 2.2.1107 | 3-trifluoromethoxy-5-propoxyphenyl | fluoromethyl | ethyl | |
| 2.2.1108 | 3-(2,2,2-trifluoroethoxy)-5-propoxyphenyl | fluoromethyl | ethyl | |
| 2.2.1109 | 3-(2-chloroethoxy)-5-propoxyphenyl | fluoromethyl | ethyl | |
| 2.2.1110 | 3-(2-hydroxyethoxy)-5-propoxyphenyl | fluoromethyl | ethyl | |
| 2.2.1111 | 3-[(tert-butoxy-carbonyl)oxy]-5-propoxyphenyl | fluoromethyl | ethyl | |
| 2.2.1112 | 3-nitro-5-propoxyphenyl | fluoromethyl | ethyl | |
| 2.2.1113 | 3-acetoxy-5-propoxy-phenyl | fluoromethyl | ethyl | |
| 2.2.1114 | {3-[(tert-butoxycarbonyl)-amino]-5-propoxyphenyl} | fluoromethyl | ethyl | |
| 2.2.1115 | 3-methylsulfanyl-5-propoxyphenyl | fluoromethyl | ethyl | |
| 2.2.1116 | 3,5-di(isopropoxy)phenyl | fluoromethyl | ethyl | |
| 2.2.1117 | 3-n-butoxy-5-isopropoxyphenyl | fluoromethyl | ethyl | |
| 2.2.1118 | 3-isobutoxy-5-isopropoxyphenyl | fluoromethyl | ethyl | |
| 2.2.1119 | 3-tert-butoxy-5-isopropoxyphenyl | fluoromethyl | ethyl | |
| 2.2.1120 | 3-difluoromethoxy-5-isopropoxyphenyl | fluoromethyl | ethyl | |
| 2.2.1121 | 3-trifluoromethoxy-5-isopropoxyphenyl | fluoromethyl | ethyl | |
| 2.2.1122 | 3-(2,2,2-trifluoroethoxy)-5-isopropoxyphenyl | fluoromethyl | ethyl | |
| 2.2.1123 | 3-(2-chloroethoxy)-5-isopropoxyphenyl | fluoromethyl | ethyl | |

TABLE 2.2-continued

Inventive compounds of the general formula (I) in which W* is CODY, R¹ and R² are each hydrogen, and aryl is the radical.

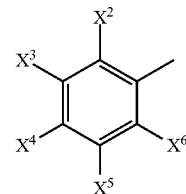

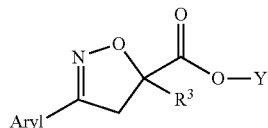

| No. | Aryl | R³ | Y | Physical data |
|---|---|---|---|---|
| 2.2.1124 | 3-(2-hydroxyethoxy)-5-isopropoxyphenyl | fluoromethyl | ethyl | |
| 2.2.1125 | 3-[(tert-butoxycarbonyl)-oxy]-5-isopropoxyphenyl | fluoromethyl | ethyl | |
| 2.2.1126 | 3-nitro-5-isopropoxy-phenyl | fluoromethyl | ethyl | |
| 2.2.1127 | 3-acetoxy-5-isopropoxy-phenyl | fluoromethyl | ethyl | |
| 2.2.1128 | {3-[(tert-butoxycarbonyl)-amino]-5-isopropoxy-phenyl} | fluoromethyl | ethyl | |
| 2.2.1129 | 3-methylsulfanyl-5-isopropoxyphenyl | fluoromethyl | ethyl | |
| 2.2.1130 | 3,5-di(tert-butoxy)phenyl | fluoromethyl | ethyl | |
| 2.2.1131 | 3-difluoromethoxy-5-tert-butoxyphenyl | fluoromethyl | ethyl | |
| 2.2.1132 | 3-trifluoromethoxy-5-tert-butoxyphenyl | fluoromethyl | ethyl | |
| 2.2.1133 | 3-(2,2,2-trifluoroethoxy)-5-tert-butoxyphenyl | fluoromethyl | ethyl | |
| 2.2.1134 | 3-(2-chloroethoxy)-5-tert-butoxylphenyl | fluoromethyl | ethyl | |
| 2.2.1135 | 3-(2-hydroxyethoxy)-5-tert-butoxyphenyl | fluoromethyl | ethyl | |
| 2.2.1136 | 3-[(tert-butoxycarbonyl)-oxy]-5-tert-butoxyphenyl | fluoromethyl | ethyl | |
| 2.2.1137 | 3-nitro-5-tert-butoxyphenyl | fluoromethyl | ethyl | |
| 2.2.1138 | 3-acetoxy-5-tert-butoxyphenyl | fluoromethyl | ethyl | |
| 2.2.1139 | {3-[(tert-butoxycarbonyl)-amino]-5-tert-butoxy-phenyl} | fluoromethyl | ethyl | |
| 2.2.1140 | 3-methylsulfanyl-5-tert-butoxyphenyl | fluoromethyl | ethyl | |
| 2.2.1141 | 3,5-di(trifluoro-methoxy)phenyl | fluoromethyl | ethyl | |
| 2.2.1142 | 3-(2,2,2-trifluoroethoxy)-5-trifluoro-methoxyphenyl | fluoromethyl | ethyl | |
| 2.2.1143 | 3-(2-chloroethoxy)-5-trifluoromethoxy-phenyl | fluoromethyl | ethyl | |
| 2.2.1144 | 3-(2-hydroxyethoxy)-5-trifluoromethoxy-phenyl | fluoromethyl | ethyl | |
| 2.2.1145 | 3-[(tert-butoxycarbonyl)-oxy]-5-trifluoromethoxy-phenyl | fluoromethyl | ethyl | |
| 2.2.1146 | 3-nitro-5-trifluoro-methoxyphenyl | fluoromethyl | ethyl | |
| 2.2.1147 | 3-acetoxy-5-tert-butoxyphenyl | fluoromethyl | ethyl | |
| 2.2.1148 | {3-[(tert-butoxycarbonyl)-amino]-5-trifluoromethoxy-phenyl} | fluoromethyl | ethyl | |
| 2.2.1149 | 3-methylsulfaonyl-5-trifluoromethoxy-phenyl | fluoromethyl | ethyl | |
| 2.2.1150 | 3,5-bis(difluoro-methoxy)phenyl | fluoromethyl | ethyl | |

TABLE 2.2-continued

Inventive compounds of the general formula (I) in which W* is CODY, $R^1$ and $R^2$ are each hydrogen, and aryl is the radical.

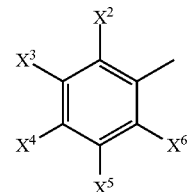

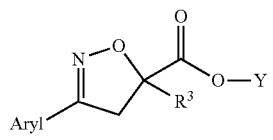

| No. | Aryl | $R^3$ | Y | Physical data |
|---|---|---|---|---|
| 2.2.1151 | 3,5-bis(difluoro-methoxy)phenyl | chloromethyl | ethyl | |
| 2.2.1152 | 3,5-bis(difluoro-methoxy)phenyl | bromomethyl | ethyl | |
| 2.2.1153 | 3,5-bis(difluoro-methoxy)phenyl | fluoromethyl | ethyl | |
| 2.2.1154 | 3-trifluoromethoxy-5-difluoromethoxy-phenyl | fluoromethyl | ethyl | |
| 2.2.1155 | 3-(2,2,2-trifluoroethoxy)-5-difluoro-methoxyphenyl | fluoromethyl | ethyl | |
| 2.2.1156 | 3-(2-chloroethoxy)-5-difluoromethoxy-phenyl | fluoromethyl | ethyl | |
| 2.2.1157 | 3-(2-hydroxyethoxy)-5-difluoromethoxy-phenyl | fluoromethyl | ethyl | |
| 2.2.1158 | 3-[(tert-butoxycarbonyl)-oxy]-5-difluoromethoxy-phenyl | fluoromethyl | ethyl | |
| 2.2.1159 | 3-nitro-5-difluoro-methoxyphenyl | fluoromethyl | ethyl | |
| 2.2.1160 | 3-acetoxy-5-difluoro-methoxyphenyl | fluoromethyl | ethyl | |
| 2.2.1161 | {3-[(tert-butoxycarbonyl)-amino]-5-difluoromethoxy-phenyl} | fluoromethyl | ethyl | |
| 2.2.1162 | 3-methylsulfanyl-5-difluoromethoxy-phenyl | fluoromethyl | ethyl | |
| 2.2.1163 | 3,5-bis(2,2,2-trifluoro-ethoxy)phenyl | fluoromethyl | ethyl | |
| 2.2.1164 | 3-(2-chloroethoxy)-5-(2,2,2-trifluoroethoxy)-phenyl | fluoromethyl | ethyl | |
| 2.2.1165 | 3-(2-hydroxyethoxy)-5-(2,2,2-trifluoro-ethoxy)phenyl | fluoromethyl | ethyl | |
| 2.2.1166 | 3-[(tert-butoxycarbonyl)-oxy]-5-(2,2,2-trifluoro-ethoxy)phenyl | fluoromethyl | ethyl | |
| 2.2.1167 | 3-nitro-5-(2,2,2-trifluoroethoxy)-phenyl | fluoromethyl | ethyl | |
| 2.2.1168 | 3-acetoxy-5-(2,2,2-trifluoroethoxy)-phenyl | fluoromethyl | ethyl | |
| 2.2.1169 | {3-[(tert-butoxycarbonyl)-amino]-5-(2,2,2-trifluoro-ethoxy)-phenyl} | fluoromethyl | ethyl | |
| 2.2.1170 | 3-methylsulfanyl-5-(2,2,2-trifluoroethoxy)-phenyl | fluoromethyl | ethyl | |
| 2.2.1171 | 3,5-bis(2-chloro-ethoxy)phenyl | fluoromethyl | ethyl | |
| 2.2.1172 | 3-(2-hydroxyethoxy)-5-(2-chloroethoxy)phenyl | fluoromethyl | ethyl | |
| 2.2.1173 | 3-{(tert-butoxycarbonyl)-oxy]-5-(2-chloro-ethoxy)phenyl | fluoromethyl | ethyl | |
| 2.2.1174 | 3-nitro-5-(2-chloroethoxy)-phenyl | fluoromethyl | ethyl | |
| 2.2.1175 | 3-acetoxy-5-(2-chloro-ethoxy)phenyl | fluoromethyl | ethyl | |

TABLE 2.2-continued

Inventive compounds of the general formula (I) in which W* is CODY, $R^1$ and $R^2$ are each hydrogen, and aryl is the radical.

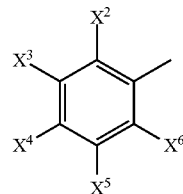

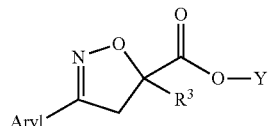

| No. | Aryl | $R^3$ | Y | Physical data |
|---|---|---|---|---|
| 2.2.1176 | {3-[(tert-butoxy-carbonyl)-amino]-5-(2-chloro-ethoxy)phenyl} | fluoromethyl | ethyl | |
| 2.2.1177 | 3-methylsulfanyl-5-(2-chloroethoxy)-phenyl | fluoromethyl | ethyl | |
| 2.2.1178 | 3,5-bis(2-hydroxy-ethoxy)phenyl | fluoromethyl | ethyl | |
| 2.2.1179 | 3-[(tert-butoxycarbonyl)-oxy]-5-(2-hydroxyethoxy)-phenyl | fluoromethyl | ethyl | |
| 2.2.1180 | 3-nitro-5-(2-hydroxy-ethoxy)phenyl | fluoromethyl | ethyl | |
| 2.2.1181 | 3-acetoxy-5-(2-hydroxyethoxy)-phenyl | fluoromethyl | ethyl | |
| 2.2.1182 | 3-[(tert-butoxycarbonyl)-amino]-5-(2-hydroxy-ethoxy)phenyl | fluoromethyl | ethyl | |
| 2.2.1183 | 3-methylsulfanyl-5-(2-hydroxyethoxy)-phenyl | fluoromethyl | ethyl | |
| 2.2.1184 | 3,5-bis[(tert-butoxy-carbonyl)oxy]phenyl | fluoromethyl | ethyl | |
| 2.2.1185 | 3-nitro-5-[(tert-butoxy-carbonyl)oxy]phenyl | fluoromethyl | ethyl | |
| 2.2.1186 | 3-acetoxy-5-[(tert-butoxy-carbonyl)oxy]phenyl | fluoromethyl | ethyl | |
| 2.2.1187 | {3-[(tert-butoxy-carbonyl)-amino]-5(tert-butoxy-carbonyl)oxy]phenyl} | fluoromethyl | ethyl | |
| 2.2.1188 | 3,5-bis(acetoxy)phenyl | fluoromethyl | ethyl | |
| 2.2.1189 | {3-[(tert-butoxycarbonyl)-amino]-5-acetoxyphenyl} | fluoromethyl | ethyl | |
| 2.2.1190 | 3-methylsulfaonyl-5-acetoxyphenyl | fluoromethyl | ethyl | |
| 2.2.1191 | 3,5-dinitrophenyl | fluoromethyl | ethyl | |
| 2.2.1192 | 3-acetoxy-5-nitrophenyl | fluoromethyl | ethyl | |
| 2.2.1193 | {3-[(tert-butoxy-carbonyl)-amino]-5-nitrophenyl} | fluoromethyl | ethyl | |
| 2.2.1194 | 3-methylsulfanyl-5-nitrophenyl | fluoromethyl | ethyl | |
| 2.2.1195 | 3,5-bis[(tert-butoxy-carbonyl)amino]phenyl | fluoromethyl | ethyl | |
| 2.2.1196 | 3-methylsulfanyl-5-[(tert-butoxycarbonyl)-amino]phenyl | fluoromethyl | ethyl | |
| 2.2.1197 | 3,5-di(methylsulfanyl)-phenyl | fluoromethyl | ethyl | |
| 2.2.1198 | 3,4-difluorophenyl | fluoromethyl | ethyl | |
| 2.2.1199 | 3,4-difluorophenyl | chloromethyl | ethyl | |
| 2.2.1200 | 3,4-difluorophenyl | bromomethyl | ethyl | |
| 2.2.1201 | 3,4-difluorophenyl | difluoromethyl | ethyl | |
| 2.2.1202 | 3,4-difluorophenyl | trifluoromethyl | ethyl | |
| 2.2.1203 | 3,4-difluorophenyl | cyano | ethyl | |
| 2.2.1204 | 3-chloro-4-fluorophenyl | fluoromethyl | ethyl | |
| 2.2.1205 | 3-chloro-4-fluorophenyl | chloromethyl | ethyl | |
| 2.2.1206 | 3-chloro-4-fluorophenyl | bromomethyl | ethyl | |
| 2.2.1207 | 3-chloro-4-fluorophenyl | difluoromethyl | ethyl | |

TABLE 2.2-continued

Inventive compounds of the general formula (I) in which W* is CODY, $R^1$ and $R^2$ are each hydrogen, and aryl is the radical.

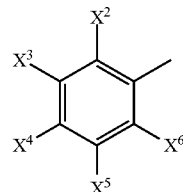

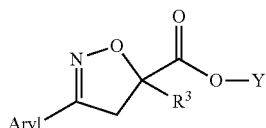

| No. | Aryl | $R^3$ | Y | Physical data |
|---|---|---|---|---|
| 2.2.1208 | 3-chloro-4-fluorophenyl | trifluoromethyl | methyl | [CDCl$_3$] 1.52 (s, 3H); 3.74 (d, 1H); 3.94 (s, 3H); 4.03 (d, 1H); 7.22 (m, 1H); 7.58 (m, 1H); 7.72 (m, 1H). |
| 2.2.1209 | 3-chloro-4-fluorophenyl | cyano | ethyl | |
| 2.2.1210 | 3-bromo-4-fluorophenyl | fluoromethyl | ethyl | |
| 2.2.1211 | 3-methyl-4-fluorophenyl | fluoromethyl | ethyl | |
| 2.2.1212 | 3-methyl-4-fluorophenyl | chloromethyl | ethyl | |
| 2.2.1213 | 3-cyclopropyl-4-fluorophenyl | fluoromethyl | ethyl | |
| 2.2.1214 | 3-cyano-4-fluorophenyl | fluoromethyl | ethyl | |
| 2.2.1215 | 3-methoxy-4-fluorophenyl | fluoromethyl | ethyl | |
| 2.2.1216 | 3-ethoxy-4-fluorophenyl | fluoromethyl | ethyl | |
| 2.2.1217 | 3-trifluoromethoxy-4-fluorophenyl | fluoromethyl | ethyl | |
| 2.2.1218 | 3-nitro-4-fluorophenyl | fluoromethyl | ethyl | |
| 2.2.1219 | 3-fluoro-4-chlorophenyl | fluoromethyl | ethyl | |
| 2.2.1220 | 3,4-dichlorophenyl | fluoromethyl | ethyl | |
| 2.2.1221 | 3-bromo-4-chlorophenyl | fluoromethyl | ethyl | |
| 2.2.1222 | 3-methyl-4-chlorophenyl | fluoromethyl | ethyl | |
| 2.2.1223 | 3-cyclopropyl-4-chlorophenyl | fluoromethyl | ethyl | |
| 2.2.1224 | 3-cyano-4-chlorophenyl | fluoromethyl | ethyl | |
| 2.2.1225 | 3-trifluoromethyl-4-chlorophenyl | fluoromethyl | ethyl | |
| 2.2.1226 | 3-methoxy-4-chlorophenyl | fluoromethyl | ethyl | |
| 2.2.1227 | 3-ethoxy-4-chlorophenyl | fluoromethyl | ethyl | |
| 2.2.1228 | 3-trifluoromethoxy-4-chlorophenyl | fluoromethyl | ethyl | |
| 2.2.1229 | 3-nitro-4-chlorophenyl | fluoromethyl | ethyl | |
| 2.2.1230 | 3-fluoro-4-bromophenyl | fluoromethyl | ethyl | |
| 2.2.1231 | 3-chloro-4-bromophenyl | fluoromethyl | ethyl | |
| 2.2.1232 | 3,4-dibromophenyl | fluoromethyl | ethyl | |
| 2.2.1233 | 3-methyl-4-bromophenyl | fluoromethyl | ethyl | |
| 2.2.1234 | 3-ethyl-4-bromophenyl | fluoromethyl | ethyl | |
| 2.2.1235 | 3-cyclopropyl-4-bromophenyl | fluoromethyl | ethyl | |
| 2.2.1236 | 3-cyano-4-bromophenyl | fluoromethyl | ethyl | |
| 2.2.1237 | 3-trifluoromethyl-4-bromophenyl | fluoromethyl | ethyl | |
| 2.2.1238 | 3-methoxy-4-phenyl | fluoromethyl | ethyl | |
| 2.2.1239 | 3-ethoxy-4-bromophenyl | fluoromethyl | ethyl | |
| 2.2.1240 | 3-trifluoromethoxy-4-bromophenyl | fluoromethyl | ethyl | |
| 2.2.1241 | 3-nitro-4-bromophenyl | fluoromethyl | ethyl | |
| 2.2.1242 | 3-fluoro-4-iodophenyl | fluoromethyl | ethyl | |
| 2.2.1243 | 3-chloro-4-iodophenyl | fluoromethyl | ethyl | |
| 2.2.1244 | 3-bromo-4-iodophenyl | fluoromethyl | ethyl | |
| 2.2.1245 | 3-methyl-4-iodophenyl | fluoromethyl | ethyl | |
| 2.2.1246 | 3-cyclopropyl-4-iodophenyl | fluoromethyl | ethyl | |
| 2.2.1247 | 3-cyano-4-iodophenyl | fluoromethyl | ethyl | |
| 2.2.1248 | 3-trifluoromethyl-4-iodophenyl | fluoromethyl | ethyl | |

TABLE 2.2-continued

Inventive compounds of the general formula (I) in which W* is CODY, R¹ and R² are each hydrogen, and aryl is the radical.

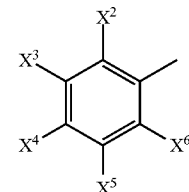

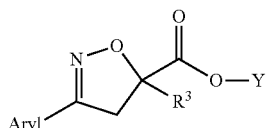

| No. | Aryl | R³ | Y | Physical data |
|---|---|---|---|---|
| 2.2.1249 | 3-methoxy-4-iodophenyl | fluoromethyl | ethyl | |
| 2.2.1250 | 3-ethoxy-4-iodophenyl | fluoromethyl | ethyl | |
| 2.2.1251 | 3-trifluoromethoxy-4-iodophenyl | fluoromethyl | ethyl | |
| 2.2.1252 | 3-nitro-4-iodophenyl | fluoromethyl | ethyl | |
| 2.2.1253 | 3-fluoro-4-methylphenyl | fluoromethyl | ethyl | |
| 2.2.1254 | 3-chloro-4-methylphenyl | fluoromethyl | ethyl | |
| 2.2.1255 | 3-bromo-4-methylphenyl | fluoromethyl | ethyl | |
| 2.2.1256 | 3,4-dimethylphenyl | fluoromethyl | ethyl | |
| 2.2.1257 | 3,4-dimethylphenyl | chloromethyl | ethyl | |
| 2.2.1258 | 3,4-dimethylphenyl | bromomethyl | ethyl | |
| 2.2.1259 | 3,4-dimethylphenyl | difluoromethyl | ethyl | |
| 2.2.1260 | 3,4-dimethylphenyl | trifluoromethyl | ethyl | |
| 2.2.1261 | 3,4-dimethylphenyl | cyano | ethyl | |
| 2.2.1262 | 3-ethyl-4-methylphenyl | fluoromethyl | ethyl | |
| 2.2.1263 | 3-cyclopropyl-4-methylphenyl | fluoromethyl | ethyl | |
| 2.2.1264 | 3-cyano-4-methylphenyl | fluoromethyl | ethyl | |
| 2.2.1265 | 3-trifluoromethyl-4-methylphenyl | fluoromethyl | ethyl | |
| 2.2.1266 | 3-methoxy-4-methylphenyl | fluoromethyl | ethyl | |
| 2.2.1267 | 3-ethoxy-4-methylphenyl | fluoromethyl | ethyl | |
| 2.2.1268 | 3-trifluoromethoxy-4-methylphenyl | fluoromethyl | ethyl | |
| 2.2.1269 | 3-nitro-4-methylphenyl | fluoromethyl | ethyl | |
| 2.2.1270 | 3-fluoro-4-ethylphenyl | fluoromethyl | ethyl | |
| 2.2.1271 | 3-chloro-4-ethylphenyl | fluoromethyl | ethyl | |
| 2.2.1272 | 3-bromo-4-ethylphenyl | fluoromethyl | ethyl | |
| 2.2.1273 | 3-methyl-4-ethylphenyl | fluoromethyl | ethyl | |
| 2.2.1274 | 3,4-diethylphenyl | fluoromethyl | ethyl | |
| 2.2.1275 | 3-cyclopropyl-4-ethylphenyl | fluoromethyl | ethyl | |
| 2.2.1276 | 3-cyano-4-ethylphenyl | fluoromethyl | ethyl | |
| 2.2.1277 | 3-trifluoromethyl-4-ethylphenyl | fluoromethyl | ethyl | |
| 2.2.1278 | 3-methoxy-4-ethylphenyl | fluoromethyl | ethyl | |
| 2.2.1279 | 3-ethoxy-4-ethylphenyl | fluoromethyl | ethyl | |
| 2.2.1280 | 3-trifluoromethoxy-4-ethylphenyl | fluoromethyl | ethyl | |
| 2.2.1281 | 3-nitro-4-ethylphenyl | fluoromethyl | ethyl | |
| 2.2.1282 | 3-fluoro-4-propylphenyl | fluoromethyl | ethyl | |
| 2.2.1283 | 3-chloro-4-propylphenyl | fluoromethyl | ethyl | |
| 2.2.1284 | 3-bromo-4-propylphenyl | fluoromethyl | ethyl | |
| 2.2.1285 | 3-methyl-4-propylphenyl | fluoromethyl | ethyl | |
| 2.2.1286 | 3-cyclopropyl-4-propylphenyl | fluoromethyl | ethyl | |
| 2.2.1287 | 3-cyano-4-propylphenyl | fluoromethyl | ethyl | |
| 2.2.1288 | 3-trifluoromethyl-4-propylphenyl | fluoromethyl | ethyl | |
| 2.2.1289 | 3-methoxy-4-propylphenyl | fluoromethyl | ethyl | |
| 2.2.1290 | 3-ethoxy-4-propylphenyl | fluoromethyl | ethyl | |
| 2.2.1291 | 3-trifluoromethoxy-4-propylphenyl | fluoromethyl | ethyl | |

TABLE 2.2-continued

Inventive compounds of the general formula (I) in which W* is CODY, R¹ and R² are each hydrogen, and aryl is the radical.

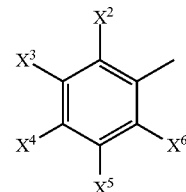

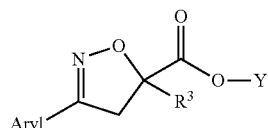

| No. | Aryl | R³ | Y | Physical data |
|---|---|---|---|---|
| 2.2.1292 | 3-nitro-4-propylphenyl | fluoromethyl | ethyl | |
| 2.2.1293 | 3-fluoro-4-isopropylphenyl | fluoromethyl | ethyl | |
| 2.2.1294 | 3-chloro-4-isopropylphenyl | fluoromethyl | ethyl | |
| 2.2.1295 | 3-bromo-4-isopropylphenyl | fluoromethyl | ethyl | |
| 2.2.1296 | 3-methyl-4-isopropylphenyl | fluoromethyl | ethyl | |
| 2.2.1297 | 3-cyclopropyl-4-isopropylphenyl | fluoromethyl | ethyl | |
| 2.2.1298 | 3-cyano-4-isopropylphenyl | fluoromethyl | ethyl | |
| 2.2.1299 | 3-trifluoromethyl-4-isopropylphenyl | fluoromethyl | ethyl | |
| 2.2.1300 | 3-methoxy-4-isopropylphenyl | fluoromethyl | ethyl | |
| 2.2.1301 | 3-ethoxy-4-isopropylphenyl | fluoromethyl | ethyl | |
| 2.2.1302 | 3-trifluoromethoxy-4-isopropylphenyl | fluoromethyl | ethyl | |
| 2.2.1303 | 3-nitro-4-isopropylphenyl | fluoromethyl | ethyl | |
| 2.2.1304 | 3-fluoro-4-tert-butylphenyl | fluoromethyl | ethyl | |
| 2.2.1305 | 3-chloro-4-tert-butylphenyl | fluoromethyl | ethyl | |
| 2.2.1306 | 3-bromo-4-tert-butylphenyl | fluoromethyl | ethyl | |
| 2.2.1307 | 3-methyl-4-tert-butylphenyl | fluoromethyl | ethyl | |
| 2.2.1308 | 3-ethyl-4-tert-butylphenyl | fluoromethyl | ethyl | |
| 2.2.1309 | 3-cyclopropyl-4-tert-butylphenyl | fluoromethyl | ethyl | |
| 2.2.1310 | 3-cyano-4-tert-butylphenyl | fluoromethyl | ethyl | |
| 2.2.1311 | 3-trifluoromethyl-4-tert-butylphenyl | fluoromethyl | ethyl | |
| 2.2.1312 | 3-trifluoromethyl-4-tert-butylphenyl | chloromethyl | ethyl | |
| 2.2.1313 | 3-trifluoromethyl-4-tert-butylphenyl | bromomethyl | ethyl | |
| 2.2.1314 | 3-trifluoromethyl-4-tert-butylphenyl | difluoromethyl | ethyl | |
| 2.2.1315 | 3-methoxy-4-tert-butylphenyl | fluoromethyl | ethyl | |
| 2.2.1316 | 3-ethoxy-4-tert-butylphenyl | fluoromethyl | ethyl | |
| 2.2.1317 | 3-trifluoromethoxy-4-tert-butylphenyl | fluoromethyl | ethyl | |
| 2.2.1318 | 3-nitro-4-tert-butylphenyl | fluoromethyl | ethyl | |
| 2.2.1319 | 3-fluoro-4-cyclopropylphenyl | fluoromethyl | ethyl | |
| 2.2.1320 | 3-chloro-4-cyclopropylphenyl | fluoromethyl | ethyl | |
| 2.2.1321 | 3-bromo-4-cyclopropylphenyl | fluoromethyl | ethyl | |
| 2.2.1322 | 3-methyl-4-cyclopropylphenyl | fluoromethyl | ethyl | |

TABLE 2.2-continued

Inventive compounds of the general formula (I) in which W* is CODY, $R^1$ and $R^2$ are each hydrogen, and aryl is the radical.

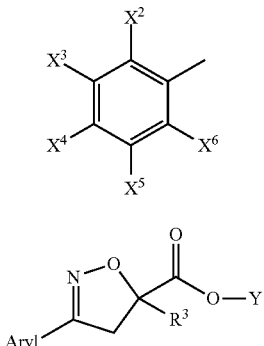

| No. | Aryl | $R^3$ | Y | Physical data |
|---|---|---|---|---|
| 2.2.1323 | 3-cyclopropyl-4-cyclopropylphenyl | fluoromethyl | ethyl | |
| 2.2.1324 | 3-cyano-4-cyclopropylphenyl | fluoromethyl | ethyl | |
| 2.2.1325 | 3-trifluoromethyl-4-cyclopropylphenyl | fluoromethyl | ethyl | |
| 2.2.1326 | 3-methoxy-4-cyclopropylphenyl | fluoromethyl | ethyl | |
| 2.2.1327 | 3-ethoxy-4-cyclopropylphenyl | fluoromethyl | ethyl | |
| 2.2.1328 | 3-trifluoromethoxy-4-cyclopropylphenyl | fluoromethyl | ethyl | |
| 2.2.1329 | 3-fluoro-4-methoxycarbonylphenyl | fluoromethyl | ethyl | |
| 2.2.1330 | 3-chloro-4-methoxycarbonylphenyl | fluoromethyl | ethyl | |
| 2.2.1331 | 3-bromo-4-methoxycarbonylphenyl | fluoromethyl | ethyl | |
| 2.2.1332 | 3-methyl-4-methoxycarbonylphenyl | fluoromethyl | ethyl | |
| 2.2.1333 | 3-ethyl-4-methoxycarbonylphenyl | fluoromethyl | ethyl | |
| 2.2.1334 | 3-cyclopropyl-4-methoxycarbonylphenyl | fluoromethyl | ethyl | |
| 2.2.1335 | 3-cyano-4-methoxycarbonylphenyl | fluoromethyl | ethyl | |
| 2.2.1336 | 3-trifluoromethyl-4-methoxycarbonylphenyl | fluoromethyl | ethyl | |
| 2.2.1337 | 3-methoxy-4-methoxycarbonylphenyl | fluoromethyl | ethyl | |
| 2.2.1338 | 3-ethoxy-4-methoxycarbonylphenyl | fluoromethyl | ethyl | |
| 2.2.1339 | 3-trifluoromethoxy-4-methoxycarbonylphenyl | fluoromethyl | ethyl | |
| 2.2.1340 | 3-nitro-4-methoxycarbonylphenyl | fluoromethyl | ethyl | |
| 2.2.1341 | 3-fluoro-4-cyanophenyl | fluoromethyl | ethyl | |
| 2.2.1342 | 3-chloro-4-cyanophenyl | fluoromethyl | ethyl | |
| 2.2.1343 | 3-bromo-4-cyanophenyl | fluoromethyl | ethyl | |
| 2.2.1344 | 3-methyl-4-cyanophenyl | fluoromethyl | ethyl | |
| 2.2.1345 | 3-cyclopropyl-4-cyanophenyl | fluoromethyl | ethyl | |
| 2.2.1346 | 3,4-dicyanophenyl | fluoromethyl | ethyl | |
| 2.2.1347 | 3-trifluoromethyl-4-cyanophenyl | fluoromethyl | ethyl | |
| 2.2.1348 | 3-trifluoromethyl-4-cyanophenyl | chloromethyl | ethyl | |
| 2.2.1349 | 3-trifluoromethyl-4-cyanophenyl | bromomethyl | ethyl | |
| 2.2.1350 | 3-trifluoromethyl-4-cyanophenyl | difluoromethyl | ethyl | |
| 2.2.1351 | 3-methoxy-4-cyanophenyl | fluoromethyl | ethyl | |
| 2.2.1352 | 3-ethoxy-4-cyanophenyl | fluoromethyl | ethyl | |
| 2.2.1353 | 3-trifluoromethoxy-4-cyanophenyl | fluoromethyl | ethyl | |
| 2.2.1354 | 3-nitro-4-cyanophenyl | fluoromethyl | ethyl | |
| 2.2.1355 | 3-fluoro-4-methoxyphenyl | fluoromethyl | ethyl | |

TABLE 2.2-continued

Inventive compounds of the general formula (I) in which W* is CODY, $R^1$ and $R^2$ are each hydrogen, and aryl is the radical.

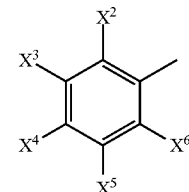

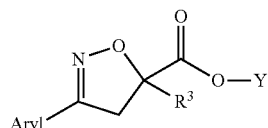

| No. | Aryl | $R^3$ | Y | Physical data |
|---|---|---|---|---|
| 2.2.1356 | 3-chloro-4-methoxyphenyl | fluoromethyl | ethyl | |
| 2.2.1357 | 3-bromo-4-methoxyphenyl | fluoromethyl | ethyl | |
| 2.2.1358 | 3-methyl-4-methoxyphenyl | fluoromethyl | ethyl | |
| 2.2.1359 | 3-cyclopropyl-4-methoxyphenyl | fluoromethyl | ethyl | |
| 2.2.1360 | 3-cyano-4-methoxyphenyl | fluoromethyl | ethyl | |
| 2.2.1361 | 3-trifluoromethyl-4-methoxyphenyl | fluoromethyl | ethyl | |
| 2.2.1362 | 3,4-dimethoxyphenyl | fluoromethyl | ethyl | |
| 2.2.1363 | 3-ethoxy-4-methoxyphenyl | fluoromethyl | ethyl | |
| 2.2.1364 | 3-trifluoromethoxy-4-methoxyphenyl | fluoromethyl | ethyl | |
| 2.2.1365 | 3-nitro-4-methoxyphenyl | fluoromethyl | ethyl | |
| 2.2.1366 | 3-fluoro-4-ethoxyphenyl | fluoormethyl | ethyl | |
| 2.2.1367 | 3-chloro-4-ethoxyphenyl | fluoromethyl | ethyl | |
| 2.2.1368 | 3-chloro-4-ethoxyphenyl | chloromethyl | ethyl | |
| 2.2.1369 | 3-chloro-4-ethoxyphenyl | bromomethyl | ethyl | |
| 2.2.1370 | 3-chloro-4-ethoxyphenyl | difluoromethyl | ethyl | |
| 2.2.1371 | 3-bromo-4-ethoxyphenyl | fluoromethyl | ethyl | |
| 2.2.1372 | 3-methyl-4-ethoxyphenyl | fluoromethyl | ethyl | |
| 2.2.1373 | 3-cyclopropy1-4-ethoxyphenyl | fluoromethyl | ethyl | |
| 2.2.1374 | 3-cyano-4-ethoxyphenyl | fluoromethyl | ethyl | |
| 2.2.1375 | 3-trifluoromethy1-4-ethoxyphenyl | fluoromethyl | ethyl | |
| 2.2.1376 | 3-methoxy-4-ethoxyphenyl | fluoromethyl | ethyl | |
| 2.2.1377 | 2,4-diethoxyphenyl | fluoromethyl | ethyl | |
| 2.2.1378 | 3-trifluoromethoxy-4-ethoxyphenyl | fluoromethyl | ethyl | |
| 2.2.1379 | 3-nitro-4-ethoxyphenyl | fluoromethyl | ethyl | |
| 2.2.1380 | 3-fluoro-4-propoxyphenyl | fluoromethyl | ethyl | |
| 2.2.1381 | 3-chloro-4-propoxyphenyl | fluoromethyl | ethyl | |
| 2.2.1382 | 3-bromo-4-propoxyphenyl | fluoromethyl | ethyl | |
| 2.2.1383 | 3-methyl-4-propoxyphenyl | fluoromethyl | ethyl | |
| 2.2.1384 | 3-cyclopropy1-4-propoxyphenyl | fluoromethyl | ethyl | |
| 2.2.1385 | 3-cyano-4-propoxyphenyl | fluoromethyl | ethyl | |
| 2.2.1386 | 3-trifluoromethy1-4-propoxyphenyl | fluoromethyl | ethyl | |
| 2.2.1387 | 3-methoxy-4-propoxyphenyl | fluoromethyl | ethyl | |
| 2.2.1388 | 3-ethoxy-4-propoxyphenyl | fluoromethyl | ethyl | |
| 2.2.1389 | 3-trifluoromethoxy-4-propoxyphenyl | fluoromethyl | ethyl | |
| 2.2.1390 | 3-nitro-4-propoxyphenyl | fluoromethyl | ethyl | |
| 2.2.1391 | 3-fluoro-4-isopropoxyphenyl | fluoromethyl | ethyl | |
| 2.2.1392 | 3-chloro-4-isopropoxyphenyl | fluoromethyl | ethyl | |
| 2.2.1393 | 3-bromo-4-isopropoxyphenyl | fluoromethyl | ethyl | |

TABLE 2.2-continued

Inventive compounds of the general formula (I) in which W* is CODY, $R^1$ and $R^2$ are each hydrogen, and aryl is the radical.

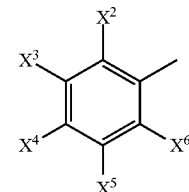

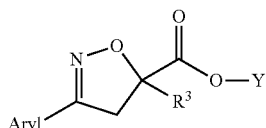

| No. | Aryl | $R^3$ | Y | Physical data |
|---|---|---|---|---|
| 2.2.1394 | 3-methyl-4-isopropoxyphenyl | fluoromethyl | ethyl | |
| 2.2.1395 | 3-cyclopropyl-4-isopropoxyphenyl | fluoromethyl | ethyl | |
| 2.2.1396 | 3-cyano-4-isopropoxyphenyl | fluoromethyl | ethyl | |
| 2.2.1397 | 3-trifluoromethy1-4-isopropoxyphenyl | fluoromethyl | ethyl | |
| 2.2.1398 | 3-methoxy-4-isopropoxyphenyl | fluoromethyl | ethyl | |
| 2.2.1399 | 3-ethoxy-4-isopropoxyphenyl | fluoromethyl | ethyl | |
| 2.2.1400 | 3-trifluoromethoxy-4-isopropoxyphenyl | fluoromethyl | ethyl | |
| 2.2.1401 | 3-nitro-4-isopropoxyphenyl | fluoromethyl | ethyl | |
| 2.2.1402 | 3-fluoro-4-trifluoro-methoxyphenyl | fluoromethyl | ethyl | |
| 2.2.1403 | 3-chloro-4-trifluoro-methoxyphenyl | fluoromethyl | ethyl | |
| 2.2.1404 | 3-bromo-4-trifluoro-methoxyphenyl | fluoromethyl | ethyl | |
| 2.2.1405 | 3-methy1-4-trifluoro-methoxyphenyl | fluoromethyl | ethyl | |
| 2.2.1406 | 3-cyclopropy1-4-trifluoromethoxy-phenyl | fluoromethyl | ethyl | |
| 2.2.1407 | 3-cyano-4-trifluoro-methoxyphenyl | fluoromethyl | ethyl | |
| 2.2.1408 | 3-trifluoromethy1-4-trifluoromethoxy-phenyl | fluoromethyl | ethyl | |
| 2.2.1409 | 3-methoxy-4-trifluoromethoxy-phenyl | fluoromethyl | ethyl | |
| 2.2.1410 | 3-ethoxy-4-trifluoro-methoxyphenyl | fluoromethyl | ethyl | |
| 2.2.1411 | 3,4-bis(trifluoro-methoxy)phenyl | fluoromethyl | ethyl | |
| 2.2.1412 | 3-nitro-4-trifluoro-methoxyphenyl | fluoromethyl | ethyl | |
| 2.2.1413 | 3-fluoro-4-difluoromethoxy-phenyl | fluoromethyl | ethyl | |
| 2.2.1414 | 3-chloro-4-difluoromethoxy-phenyl | fluoromethyl | ethyl | |
| 2.2.1415 | 3-bromo-4-difluoromethoxy-phenyl | fluoromethyl | ethyl | |
| 2.2.1416 | 3-methyl-4-difluoromethoxy-phenyl | fluoromethyl | ethyl | |
| 2.2.1417 | 3-cyclopropyl-4-difluoromethoxy-phenyl | fluoromethyl | ethyl | |
| 2.2.1418 | 3-cyano-4-difluoromethoxy-phenyl | fluoromethyl | ethyl | |
| 2.2.1419 | 3-trifluoromethy1-4-difluoromethoxy-phenyl | fluoromethyl | ethyl | |
| 2.2.1420 | 3-methoxy-4-difluoromethoxy-phenyl | fluoromethyl | ethyl | |
| 2.2.1421 | 3-ethoxy-4-difluoromethoxy-phenyl | fluoromethyl | ethyl | |

TABLE 2.2-continued

Inventive compounds of the general formula (I) in which W* is CODY, $R^1$ and $R^2$ are each hydrogen, and aryl is the radical.

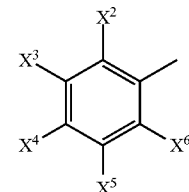

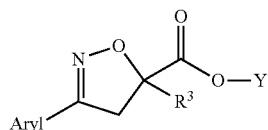

| No. | Aryl | $R^3$ | Y | Physical data |
|---|---|---|---|---|
| 2.2.1422 | 3-trifluoromethoxy-4-difluoromethoxy-phenyl | fluoromethyl | ethyl | |
| 2.2.1423 | 3-nitro-4-difluoromethoxy-phenyl | fluoromethyl | ethyl | |
| 2.2.1424 | 3-fluoro-4-nitrophenyl | fluoromethyl | ethyl | |
| 2.2.1425 | 3-chloro-4-nitrophenyl | fluoromethyl | ethyl | |
| 2.2.1426 | 3-bromo-4-nitrophenyl | fluoromethyl | ethyl | |
| 2.2.1427 | 3-methyl-4-nitrophenyl | fluoromethyl | ethyl | |
| 2.2.1428 | 3-cyclopropyl-4-nitrophenyl | fluoromethyl | ethyl | |
| 2.2.1429 | 3-cyano-4-nitrophenyl | fluoromethyl | ethyl | |
| 2.2.1430 | 3-trifluoromethyl-4-nitrophenyl | fluoromethyl | ethyl | |
| 2.2.1431 | 3-methoxy-4-nitrophenyl | fluoromethyl | ethyl | |
| 2.2.1432 | 3-ethoxy-4-nitrophenyl | fluoromethyl | ethyl | |
| 2.2.1433 | 3-trifluoromethoxy-4-nitrophenyl | fluoromethyl | ethyl | |
| 2.2.1434 | 3-fluoro-4-methylsulfanylphenyl | fluoromethyl | ethyl | |
| 2.2.1435 | 3-chloro-4-methylsulfanylphenyl | fluoromethyl | ethyl | |
| 2.2.1436 | 3-bromo-4-methylsulfanylphenyl | fluoromethyl | ethyl | |
| 2.2.1437 | 3-methyl-4-methylsulfanylphenyl | fluoromethyl | ethyl | |
| 2.2.1438 | 3-cyclopropyl-4-methylsulfanylphenyl | fluoromethyl | ethyl | |
| 2.2.1439 | 3-cyano-4-methylsulfanylphenyl | fluoromethyl | ethyl | |
| 2.2.1440 | 3-trifluoromethyl-4-methylsulfanylphenyl | fluoromethyl | ethyl | |
| 2.2.1441 | 3-methoxy-4-methylsulfanylphenyl | fluoromethyl | ethyl | |
| 2.2.1442 | 3-ethoxy-4-methylsulfanylphenyl | fluoromethyl | ethyl | |
| 2.2.1443 | 3-trifluoromethoxy-4-methylsulfanylphenyl | fluoromethyl | ethyl | |
| 2.2.1444 | 3-nitro-4-methylsulfanylphenyl | fluoromethyl | ethyl | |
| 2.2.1445 | 3,6-difluorophenyl | fluoromethyl | ethyl | |
| 2.2.1446 | 3,6-difluorophenyl | chloromethyl | ethyl | |
| 2.2.1447 | 3,6-difluorophenyl | bromomethyl | ethyl | |
| 2.2.1448 | 3,6-difluorophenyl | difluoromethyl | ethyl | |
| 2.2.1449 | 3,6-difluorophenyl | trifluoromethyl | ethyl | |
| 2.2.1450 | 3,6-difluorophenyl | cyano | ethyl | |
| 2.2.1451 | 3-chloro-6-fluorophenyl | fluoromethyl | ethyl | |
| 2.2.1452 | 3-bromo-6-fluorophenyl | fluoromethyl | ethyl | |
| 2.2.1453 | 3-methyl-6-fluorophenyl | fluoromethyl | ethyl | |
| 2.2.1454 | 3-ethyl-6-fluorophenyl | fluoromethyl | ethyl | |
| 2.2.1455 | 3-cyclopropyl-6-fluorophenyl | fluoromethyl | ethyl | |
| 2.2.1456 | 3-cyano-6-fluorophenyl | fluoromethyl | ethyl | |
| 2.2.1457 | 3-methoxy-6-fluorophenyl | fluoromethyl | ethyl | |
| 2.2.1458 | 3-ethoxy-6-fluorophenyl | fluoromethyl | ethyl | |
| 2.2.1459 | 3-trifluoromethoxy-6-fluorophenyl | fluoromethyl | ethyl | |

TABLE 2.2-continued

Inventive compounds of the general formula (I) in which W* is CODY, $R^1$ and $R^2$ are each hydrogen, and aryl is the radical.

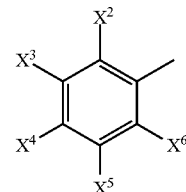

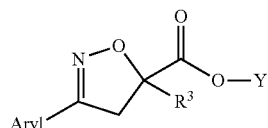

| No. | Aryl | $R^3$ | Y | Physical data |
| --- | --- | --- | --- | --- |
| 2.2.1460 | 3-nitro-6-fluorophenyl | fluoromethyl | ethyl | |
| 2.2.1461 | 3-fluoro-6-chlorophenyl | fluoromethyl | ethyl | |
| 2.2.1462 | 3-fluoro-6-chlorophenyl | chloromethyl | ethyl | |
| 2.2.1463 | 3-fluoro-6-chlorophenyl | bromomethyl | ethyl | |
| 2.2.1464 | 3-fluoro-6-chlorophenyl | difluoromethyl | ethyl | |
| 2.2.1465 | 3,6-dichlorophenyl | fluoromethyl | ethyl | |
| 2.2.1466 | 3,6-dichlorophenyl | chloromethyl | ethyl | |
| 2.2.1467 | 3,6-dichlorophenyl | bromomethyl | ethyl | |
| 2.2.1468 | 3,6-dichlorophenyl | difluoromethyl | ethyl | |
| 2.2.1469 | 3,6-dichlorophenyl | trifluoromethyl | ethyl | |
| 2.2.1470 | 3,6-dichlorophenyl | cyano | ethyl | |
| 2.2.1471 | 3-bromo-6-chlorophenyl | fluoromethyl | ethyl | |
| 2.2.1472 | 3-methyl-6-chlorophenyl | fluoromethyl | ethyl | |
| 2.2.1473 | 3-cyclopropy1-6-chlorophenyl | fluoromethyl | ethyl | |
| 2.2.1474 | 3-cyano-6-chlorophenyl | fluoromethyl | ethyl | |
| 2.2.1475 | 3-trifluoromethy1-6-chlorophenyl | fluoromethyl | ethyl | |
| 2.2.1476 | 3-methoxy-6-chlorophenyl | fluoromethyl | ethyl | |
| 2.2.1477 | 3-ethoxy-6-chlorophenyl | fluoromethyl | ethyl | |
| 2.2.1478 | 3-trifluoromethoxy-6-chlorophenyl | fluoromethyl | ethyl | |
| 2.2.1479 | 3-nitro-6-chlorophenyl | fluoromethyl | ethyl | |
| 2.2.1480 | 3-fluoro-6-bromophenyl | fluoromethyl | ethyl | |
| 2.2.1481 | 3-chloro-6-bromophenyl | fluoromethyl | ethyl | |
| 2.2.1482 | 3,6-dibromophenyl | fluoromethyl | ethyl | |
| 2.2.1483 | 3-methyl-6-bromophenyl | fluoromethyl | ethyl | |
| 2.2.1484 | 3-cyclopropyl-6-bromophenyl | fluoromethyl | ethyl | |
| 2.2.1485 | 3-cyano-6-bromophenyl | fluoromethyl | ethyl | |
| 2.2.1486 | 3-trifluoromethy1-6-bromophenyl | fluoromethyl | ethyl | |
| 2.2.1487 | 3-methoxy-6-phenyl | fluoromethyl | ethyl | |
| 2.2.1488 | 3-ethoxy-6-bromophenyl | fluoromethyl | ethyl | |
| 2.2.1489 | 3-trifluoromethoxy-6-bromophenyl | fluoromethyl | ethyl | |
| 2.2.1490 | 3-nitro-6-bromophenyl | fluoromethyl | ethyl | |
| 2.2.1491 | 3-fluoro-6-iodophenyl | fluoromethyl | ethyl | |
| 2.2.1492 | 3-chloro-6-iodophenyl | fluoromethyl | ethyl | |
| 2.2.1493 | 3-bromo-6-iodophenyl | fluoromethyl | ethyl | |
| 2.2.1494 | 3-methyl-6-iodophenyl | fluoromethyl | ethyl | |
| 2.2.1495 | 3-cyclopropy1-6-iodophenyl | fluoromethyl | ethyl | |
| 2.2.1496 | 3-cyano-6-iodophenyl | fluoromethyl | ethyl | |
| 2.2.1497 | 3-trifluoromethyl-6-iodophenyl | fluoromethyl | ethyl | |
| 2.2.1498 | 3-methoxy-6-iodophenyl | fluoromethyl | ethyl | |
| 2.2.1499 | 3-ethoxy-6-iodophenyl | fluoromethyl | ethyl | |
| 2.2.1500 | 3-trifluoromethoxy-6-iodophenyl | fluoromethyl | ethyl | |
| 2.2.1501 | 3-nitro-6-iodophenyl | fluoromethyl | ethyl | |
| 2.2.1502 | 3-fluoro-6-methylphenyl | fluoromethyl | ethyl | |
| 2.2.1503 | 3-chloro-6-methylphenyl | fluoromethyl | ethyl | |
| 2.2.1504 | 3-bromo-6-methylphenyl | fluoromethyl | ethyl | |
| 2.2.1505 | 3,6-dimethylphenyl | fluoromethyl | ethyl | |

TABLE 2.2-continued

Inventive compounds of the general formula (I) in which W* is CODY, $R^1$ and $R^2$ are each hydrogen, and aryl is the radical.

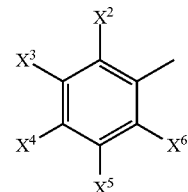

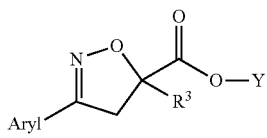

| No. | Aryl | $R^3$ | Y | Physical data |
|---|---|---|---|---|
| 2.2.1506 | 3-ethyl-6-methylphenyl | fluoromethyl | ethyl | |
| 2.2.1507 | 3-cyclopropyl-6-methylphenyl | fluoromethyl | ethyl | |
| 2.2.1508 | 3-cyano-6-methylphenyl | fluoromethyl | ethyl | |
| 2.2.1509 | 3-trifluoromethyl-6-methylphenyl | fluoromethyl | ethyl | |
| 2.2.1510 | 3-methoxy-6-methylphenyl | fluoromethyl | ethyl | |
| 2.2.1511 | 3-ethoxy-6-methylphenyl | fluoromethyl | ethyl | |
| 2.2.1512 | 3-trifluoromethoxy-6-methylphenyl | fluoromethyl | ethyl | |
| 2.2.1513 | 3-nitro-6-methylphenyl | fluoromethyl | ethyl | |
| 2.2.1514 | 3-fluoro-6-ethylphenyl | fluoromethyl | ethyl | |
| 2.2.1515 | 3-chloro-6-ethylphenyl | fluoromethyl | ethyl | |
| 2.2.1516 | 3-bromo-6-ethylphenyl | fluoromethyl | ethyl | |
| 2.2.1517 | 3-methyl-6-ethylphenyl | fluoromethyl | ethyl | |
| 2.2.1518 | 3,6-diethylphenyl | fluoromethyl | ethyl | |
| 2.2.1519 | 3-cyclopropyl-6-ethylphenyl | fluoromethyl | ethyl | |
| 2.2.1520 | 3-cyano-6-ethylphenyl | fluoromethyl | ethyl | |
| 2.2.1521 | 3-trifluoromethyl-6-ethylphenyl | fluoromethyl | ethyl | |
| 2.2.1522 | 3-methoxy-6-ethylphenyl | fluoromethyl | ethyl | |
| 2.2.1523 | 3-ethoxy-6-ethylphenyl | fluoromethyl | ethyl | |
| 2.2.1524 | 3-trifluoromethoxy-6-ethylphenyl | fluoromethyl | ethyl | |
| 2.2.1525 | 3-nitro-6-ethylphenyl | fluoromethyl | ethyl | |
| 2.2.1526 | 3-fluoro-6-propylphenyl | fluoromethyl | ethyl | |
| 2.2.1527 | 3-chloro-6-propylphenyl | fluoromethyl | ethyl | |
| 2.2.1528 | 3-bromo-6-propylphenyl | fluoromethyl | ethyl | |
| 2.2.1529 | 3-methyl-6-propylphenyl | fluoromethyl | ethyl | |
| 2.2.1530 | 3-cyclopropyl-6-propylphenyl | fluoromethyl | ethyl | |
| 2.2.1531 | 3-cyano-6-propylphenyl | fluoromethyl | ethyl | |
| 2.2.1532 | 3-trifluoromethyl-6-propylphenyl | fluoromethyl | ethyl | |
| 2.2.1533 | 3-methoxy-6-propylphenyl | fluoromethyl | ethyl | |
| 2.2.1534 | 3-ethoxy-6-propylphenyl | fluoromethyl | ethyl | |
| 2.2.1535 | 3-trifluoromethoxy-6-propylphenyl | fluoromethyl | ethyl | |
| 2.2.1536 | 3-nitro-6-propylphenyl | fluoromethyl | ethyl | |
| 2.2.1537 | 3-fluoro-6-isopropylphenyl | fluoromethyl | ethyl | |
| 2.2.1538 | 3-chloro-6-isopropylphenyl | fluoromethyl | ethyl | |
| 2.2.1539 | 3-bromo-6-isopropylphenyl | fluoromethyl | ethyl | |
| 2.2.1540 | 3-methyl-6-isopropylphenyl | lfuoromethyl | ethyl | |
| 2.2.1541 | 3-cyclopropyl-6-isopropylphenyl | fluoromethyl | ethyl | |
| 2.2.1542 | 3-cyano-6-isopropylphenyl | fluoromethyl | ethyl | |
| 2.2.1543 | 3-trifluoromethyl-6-isopropylphenyl | fluoromethyl | ethyl | |

TABLE 2.2-continued

Inventive compounds of the general formula (I) in which W* is CODY, R¹ and R² are each hydrogen, and aryl is the radical.

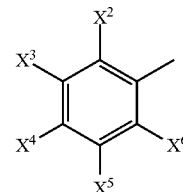

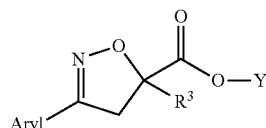

| No. | Aryl | R³ | Y | Physical data |
|---|---|---|---|---|
| 2.2.1544 | 3-methoxy-6-isopropylphenyl | fluoromethyl | ethyl | |
| 2.2.1545 | 3-ethoxy-6-isopropylphenyl | fluoromethyl | ethyl | |
| 2.2.1546 | 3-trifluoromethoxy-6-isopropylphenyl | fluoromethyl | ethyl | |
| 2.2.1547 | 3-nitro-6-isopropylphenyl | fluoromethyl | ethyl | |
| 2.2.1548 | 3-fluoro-6-tert-butylphenyl | fluoromethyl | ethyl | |
| 2.2.1549 | 3-chloro-6-tert-butylphenyl | fluoromethyl | ethyl | |
| 2.2.1550 | 3-bromo-6-tert-butylphenyl | fluoromethyl | ethyl | |
| 2.2.1551 | 3-methyl-6-tert-butylphenyl | fluoromethyl | ethyl | |
| 2.2.1552 | 3-cyclopropyl-6-tert-butylphenyl | fluoromethyl | ethyl | |
| 2.2.1553 | 3-cyano-6-tert-butylphenyl | fluoromethyl | ethyl | |
| 2.2.1554 | 3-trifluoromethyl-6-tert-butylphenyl | fluoromethyl | ethyl | |
| 2.2.1555 | 3-methoxy-6-tert-butylphenyl | fluoromethyl | ethyl | |
| 2.2.1556 | 3-ethxoy-6-tert-butylphenyl | fluoromethyl | ethyl | |
| 2.2.1557 | 3-trifluoromethoxy-6-tert-butylphenyl | fluoromethyl | ethyl | |
| 2.2.1558 | 3-nitro-6-tert-butylphenyl | fluoromethyl | ethyl | |
| 2.2.1559 | 3-fluoro-6-cyclopropylphenyl | fluoromethyl | ethyl | |
| 2.2.1560 | 3-chloro-6-cyclopropylphenyl | fluoromethyl | ethyl | |
| 2.2.1561 | 3-bromo-6-cyclopropylphenyl | fluoromethyl | ethyl | |
| 2.2.1562 | 3-methyl-6-cyclopropylphenyl | fluoromethyl | ethyl | |
| 2.2.1563 | 3-cyclopropyl-6-cyclopropylphenyl | fluoromethyl | ethyl | |
| 2.2.1564 | 3-cyano-6-cyclopropylphenyl | fluoromethyl | ethyl | |
| 2.2.1565 | 3-trifluoromethyl-6-cyclopropylphenyl | fluoromethyl | ethyl | |
| 2.2.1566 | 3-methoxy-6-cyclopropylphenyl | fluoromethyl | ethyl | |
| 2.2.1567 | 3-ethoxy-6-cyclopropylphenyl | fluoromethyl | ethyl | |
| 2.2.1568 | 3-trifluoromethoxy-6-cyclopropylphenyl | fluoromethyl | ethyl | |
| 2.2.1569 | 3-fluoro-6-methoxy-carbonylphenyl | fluoromethyl | ethyl | |
| 2.2.1570 | 3-chloro-6-methoxy-carbonylphenyl | fluoromethyl | ethyl | |
| 2.2.1571 | 3-bromo-6-methoxy-carbonylphenyl | fluoromethyl | ethyl | |
| 2.2.1572 | 3-methyl-6-methoxy-carbonylphenyl | fluoromethyl | ethyl | |
| 2.2.1573 | 3-cyclopropyl-6-methoxy-carbonylphenyl | fluoromethyl | ethyl | |
| 2.2.1574 | 3-cyano-6-methoxy-carbonylphenyl | fluoromethyl | ethyl | |

TABLE 2.2-continued

Inventive compounds of the general formula (I) in which W* is CODY, $R^1$ and $R^2$ are each hydrogen, and aryl is the radical.

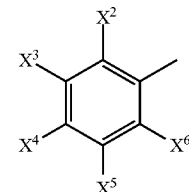

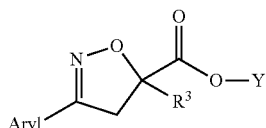

| No. | Aryl | $R^3$ | Y | Physical data |
|---|---|---|---|---|
| 2.2.1575 | 3-trifluoromethyl-6-methoxycarbonylphenyl | fluoromethyl | ethyl | |
| 2.2.1576 | 3-methoxy-6-methoxycarbonylphenyl | fluoromethyl | ethyl | |
| 2.2.1577 | 3-ethoxy-6-methoxycarbonylphenyl | fluoromethyl | ethyl | |
| 2.2.1578 | 3-trifluoromethoxy-6-methoxycarbonyl-phenyl | fluoromethyl | ethyl | |
| 2.2.1579 | 3-nitro-6-methoxycarbonylphenyl | fluoromethyl | ethyl | |
| 2.2.1580 | 3-fluoro-6-cyanophenyl | fluoromethyl | ethyl | |
| 2.2.1581 | 3-chloro-6-cyanophenyl | fluoromethyl | ethyl | |
| 2.2.1582 | 3-bromo-6-cyanophenyl | fluoromethyl | ethyl | |
| 2.2.1583 | 3-methyl-6-cyanophenyl | fluoromethyl | ethyl | |
| 2.2.1584 | 3-cyclopropyl-6-cyanophenyl | fluoromethyl | ethyl | |
| 2.2.1585 | 3-cyano-6-cyanophenyl | fluoromethyl | ethyl | |
| 2.2.1586 | 3-trifluoromethyl-6-cyanophenyl | fluoromethyl | ethyl | |
| 2.2.1587 | 3-methoxy-6-cyanophenyl | fluoromethyl | ethyl | |
| 2.2.1588 | 3-ethoxy-6-cyanophenyl | fluoromethyl | ethyl | |
| 2.2.1589 | 3-trifluoromethoxy-6-cyanophenyl | fluoromethyl | ethyl | |
| 2.2.1590 | 3-nitro-6-cyanophenyl | fluoromethyl | ethyl | |
| 2.2.1591 | 3-fluoro-6-methoxyphenyl | fluoromethyl | ethyl | |
| 2.2.1592 | 3-chloro-6-methoxyphenyl | fluoromethyl | ethyl | |
| 2.2.1593 | 3-bromo-6-methoxyphenyl | fluoromethyl | ethyl | |
| 2.2.1594 | 3-methyl-6-methoxyphenyl | fluoromethyl | ethyl | |
| 2.2.1595 | 3-cyclopropyl-6-methoxyphenyl | fluoromethyl | ethyl | |
| 2.2.1596 | 3-cyano-6-methoxyphenyl | fluoromethyl | ethyl | |
| 2.2.1597 | 3-trifluoromethyl-6-methoxyphenyl | fluoromethyl | ethyl | |
| 2.2.1598 | 3,6-dimethoxyphenyl | fluoromethyl | ethyl | |
| 2.2.1599 | 3-ethoxy-6-methoxyphenyl | fluoromethyl | ethyl | |
| 2.2.1600 | 3-trifluoromethoxy-6-methoxyphenyl | fluoromethyl | ethyl | |
| 2.2.1601 | 3-nitro-6-methoxyphenyl | fluoromethyl | ethyl | |
| 2.2.1602 | 3-fluoro-6-ethoxyphenyl | fluoromethyl | ethyl | |
| 2.2.1603 | 3-chloro-6-ethoxyphenyl | fluoromethyl | ethyl | |
| 2.2.1604 | 3-bromo-6-ethoxyphenyl | fluoromethyl | ethyl | |
| 2.2.1605 | 3-methyl-6-ethoxyphenyl | fluoromethyl | ethyl | |
| 2.2.1606 | 3-cyclopropyl-6-ethoxyphenyl | fluoromethyl | ethyl | |
| 2.2.1607 | 3-cyano-6-ethoxyphenyl | fluoromethyl | ethyl | |
| 2.2.1608 | 3-trifluoromethyl-6-ethoxyphenyl | fluoromethyl | ethyl | |
| 2.2.1609 | 3-methoxy-6-ethoxyphenyl | fluoromethyl | ethyl | |
| 2.2.1610 | 2,6-diethoxyphenyl | fluoromethyl | ethyl | |
| 2.2.1611 | 3-trifluoromethoxy-6-ethoxyphenyl | fluoromethyl | ethyl | |
| 2.2.1612 | 3-nitro-6-ethoxyphenyl | fluoromethyl | ethyl | |
| 2.2.1613 | 3-fluoro-6-propoxyphenyl | fluoromethyl | ethyl | |
| 2.2.1614 | 3-chloro-6-propoxyphenyl | fluoromethyl | ethyl | |

TABLE 2.2-continued

Inventive compounds of the general formula (I) in which W* is CODY, $R^1$ and $R^2$ are each hydrogen, and aryl is the radical.

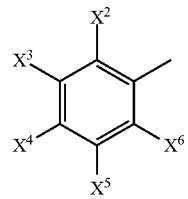

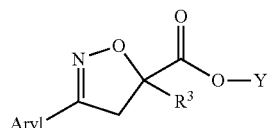

| No. | Aryl | $R^3$ | Y | Physical data |
|---|---|---|---|---|
| 2.2.1615 | 3-bromo-6-propoxyphenyl | fluoromethyl | ethyl | |
| 2.2.1616 | 3-methyl-6-propoxyphenyl | fluoromethyl | ethyl | |
| 2.2.1617 | 3-cyclopropyl-6-propoxyphenyl | fluoromethyl | ethyl | |
| 2.2.1618 | 3-cyano-6-propoxyphenyl | fluoromethyl | ethyl | |
| 2.2.1619 | 3-trifluoromethyl-6-propoxyphenyl | fluoromethyl | ethyl | |
| 2.2.1620 | 3-methoxy-6-propoxyphenyl | fluoromethyl | ethyl | |
| 2.2.1621 | 3-ethoxy-6-propoxyphenyl | fluoromethyl | ethyl | |
| 2.2.1622 | 3-trifluoromethoxy-6-propoxyphenyl | fluoromethyl | ethyl | |
| 2.2.1623 | 3-nitro-6-propoxyphenyl | fluoromethyl | ethyl | |
| 2.2.1624 | 3-fluoro-6-isopropoxyphenyl | fluoromethyl | ethyl | |
| 2.2.1625 | 3-chloro-6-isopropoxyphenyl | fluoromethyl | ethyl | |
| 2.2.1626 | 3-bromo-6-isopropoxyphenyl | fluoromethyl | ethyl | |
| 2.2.1627 | 3-methyl-6-isopropoxyphenyl | fluoromethyl | ethyl | |
| 2.2.1628 | 3-cyclopropyl-6-isopropoxyphenyl | fluoromethyl | ethyl | |
| 2.2.1629 | 3-cyano-6-isopropoxyphenyl | fluoromethyl | ethyl | |
| 2.2.1630 | 3-trifluoromethyl-6-isopropoxyphenyl | fluoromethyl | ethyl | |
| 2.2.1631 | 3-methoxy-6-isopropoxyphenyl | fluoromethyl | ethyl | |
| 2.2.1632 | 3-ethoxy-6-isopropoxyphenyl | fluoromethyl | ethyl | |
| 2.2.1633 | 3-trifluoromethoxy-6-isopropoxyphenyl | fluoromethyl | ethyl | |
| 2.2.1634 | 3-nitro-6-isopropoxyphenyl | fluoromethyl | ethyl | |
| 2.2.1635 | 3-fluoro-6-trifluoromethoxyphenyl | fluoromethyl | ethyl | |
| 2.2.1636 | 3-chloro-6-trifluoromethoxyphenyl | fluoromethyl | ethyl | |
| 2.2.1637 | 3-bromo-6-trifluoromethoxyphenyl | fluoromethyl | ethyl | |
| 2.2.1638 | 3-methyl-6-trifluoromethoxyphenyl | fluoromethyl | ethyl | |
| 2.2.1639 | 3-cyclopropyl-6-trifluoromethoxyphenyl | fluoromethyl | ethyl | |
| 2.2.1640 | 3-cyano-6-trifluoromethoxyphenyl | fluoromethyl | ethyl | |
| 2.2.1641 | 3-trifluoromethyl-6-trifluoromethoxyphenyl | fluoromethyl | ethyl | |
| 2.2.1642 | 3-methoxy-6-trifluoromethoxyphenyl | fluoromethyl | ethyl | |
| 2.2.1643 | 3-ethoxy-6-trifluoromethoxyphenyl | fluoromethyl | ethyl | |
| 2.2.1644 | 3,6-bis(trifluoromethoxy)phenyl | fluoromethyl | ethyl | |
| 2.2.1645 | 3-nitro-6-trifluoromethoxyphenyl | fluoromethyl | ethyl | |

TABLE 2.2-continued

Inventive compounds of the general formula (I) in which W* is CODY, $R^1$ and $R^2$ are each hydrogen, and aryl is the radical.

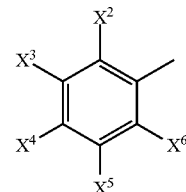

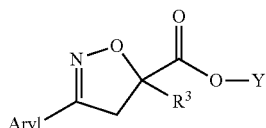

| No. | Aryl | $R^3$ | Y | Physical data |
|---|---|---|---|---|
| 2.2.1646 | 3-fluoro-6-difluoro-methoxyphenyl | fluoromethyl | ethyl | |
| 2.2.1647 | 3-chloro-6-difluoro-methoxyphenyl | fluoromethyl | ethyl | |
| 2.2.1648 | 3-bromo-6-difluoro-methoxyphenyl | fluoromethyl | ethyl | |
| 2.2.1649 | 3-methyl-6-difluoro-methoxyphenyl | fluoromethyl | ethyl | |
| 2.2.1650 | 3-cyclopropyl-6-difluoro-methoxyphenyl | fluoromethyl | ethyl | |
| 2.2.1651 | 3-cyano-6-difluoro-methoxyphenyl | fluoromethyl | ethyl | |
| 2.2.1652 | 3-trifluoromethyl-6-difluoromethoxyphenyl | fluoromethyl | ethyl | |
| 2.2.1653 | 3-methoxy-6-difluoro-methoxyphenyl | fluoromethyl | ethyl | |
| 2.2.1654 | 3-ethoxy-6-difluoro-methoxyphenyl | fluoromethyl | ethyl | |
| 2.2.1655 | 3-trifluoromethoxy-6-difluoromethoxyphenyl | fluoromethyl | ethyl | |
| 2.2.1656 | 3-nitro-6-difluoromethoxy-phenyl | fluoromethyl | ethyl | |
| 2.2.1657 | 3-fluoro-6-nitrophenyl | fluoromethyl | ethyl | |
| 2.2.1658 | 3-chloro-6-nitrophenyl | fluoromethyl | ethyl | |
| 2.2.1659 | 3-bromo-6-nitrophenyl | fluoromethyl | ethyl | |
| 2.2.1660 | 3-methyl-6-nitrophenyl | fluoromethyl | ethyl | |
| 2.2.1661 | 3-cyclopropyl-6-nitrophenyl | fluoromethyl | ethyl | |
| 2.2.1662 | 3-cyano-6-nitrophenyl | fluoromethyl | ethyl | |
| 2.2.1663 | 3-trifluoromethyl-6-nitrophenyl | fluoromethyl | ethyl | |
| 2.2.1664 | 3-methoxy-6-nitrophenyl | fluoromethyl | ethyl | |
| 2.2.1665 | 3-ethoxy-6-nitrophenyl | fluoromethyl | ethyl | |
| 2.2.1666 | 3-trifluoromethoxy-6-nitrophenyl | fluoromethyl | ethyl | |
| 2.2.1667 | 3-fluoro-6-methylsulfanylphenyl | fluoromethyl | ethyl | |
| 2.2.1668 | 3-chloro-6-methylsulfanylphenyl | fluoromethyl | ethyl | |
| 2.2.1669 | 3-bromo-6-methylsulfanylphenyl | fluoromethyl | ethyl | |
| 2.2.1670 | 3-methyl-6-methylsulfanylphenyl | fluoromethyl | ethyl | |
| 2.2.1671 | 3-cyclopropyl-6-methylsulfanylphenyl | fluoromethyl | ethyl | |
| 2.2.1672 | 3-cyano-6-methylsulfanylphenyl | fluoromethyl | ethyl | |
| 2.2.1673 | 3-trifluoromethyl-6-methylsulfanylphenyl | fluoromethyl | ethyl | |
| 2.2.1674 | 3-methoxy-6-methylsulfanylphenyl | fluoromethyl | ethyl | |
| 2.2.1675 | 3-ethoxy-6-methylsulfanylphenyl | fluoromethyl | ethyl | |
| 2.2.1676 | 3-trifluoromethoxy-6-methylsulfanylphenyl | fluoromethyl | ethyl | |
| 2.2.1677 | 3-nitro-6-methylsulfanylphenyl | fluoromethyl | ethyl | |

TABLE 2.2-continued

Inventive compounds of the general formula (I) in which W* is CODY, $R^1$ and $R^2$ are each hydrogen, and aryl is the radical.

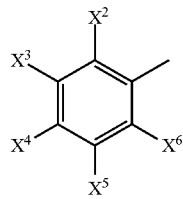

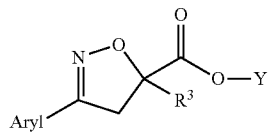

| No. | Aryl | $R^3$ | Y | Physical data |
|---|---|---|---|---|
| 2.2.1678 | 2,3,4-trifluorophenyl | fluoromethyl | ethyl | |
| 2.2.1679 | 2,3,4-trichlorophenyl | fluoromethyl | ethyl | |
| 2.2.1680 | 2,3,4-trimethylphenyl | fluoromethyl | ethyl | |
| 2.2.1681 | 2-fluoro-2-chloro-5-trifluoromethylphenyl | fluoromethyl | ethyl | |
| 2.2.1682 | 2,3,5-trifluorophenyl | fluoromethyl | ethyl | |
| 2.2.1683 | 2,3,5-trichlorophenyl | fluoromethyl | ethyl | |
| 2.2.1684 | 2,3,5-trimethylphenyl | fluoromethyl | ethyl | |
| 2.2.1685 | 2,3-dichloro-5-methoxyphenyl | fluoromethyl | ethyl | |
| 2.2.1686 | 2,3,6-trifluorophenyl | fluoromethyl | ethyl | |
| 2.2.1687 | 2,3,6-trichlorophenyl | fluoromethyl | ethyl | |
| 2.2.1688 | 2,3,6-trimethylphenyl | fluoromethyl | ethyl | |
| 2.2.1689 | 3,4,5-trifluorophenyl | fluoromethyl | ethyl | |
| 2.2.1690 | 3,4,5-trichlorophenyl | fluoromethyl | ethyl | |
| 2.2.1691 | 3,4,5-trimethylphenyl | fluoromethyl | ethyl | |
| 2.2.1692 | 3,5-dimethyl-4-fluorophenyl | fluoromethyl | ethyl | |
| 2.2.1693 | 3,5-dichloro-4-methoxyphenyl | fluoromethyl | ethyl | |
| 2.2.1694 | 3,5-difluoro-4-chlorophenyl | fluoromethyl | ethyl | |
| 2.2.1695 | 3,5-dichloro-4-hydroxyphenyl | fluoromethyl | ethyl | |
| 2.2.1696 | 3,5-trifluoromethyl-4-chlorophenyl | fluoromethyl | ethyl | |
| 2.2.1697 | 3,4,6-trifluorophenyl | fluoromethyl | ethyl | |
| 2.2.1698 | 3,4,6-trichlorophenyl | fluoromethyl | ethyl | |
| 2.2.1699 | 3,4,6-trimethylphenyl | fluoromethyl | ethyl | |
| 2.2.1700 | pentafluorophenyl | fluoromethyl | ethyl | |

TABLE 2.3

Inventive compounds of the general formula (I) in which W* is COOY, R¹ R² are each hydrogen, and aryl is the radical.

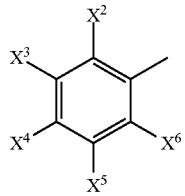

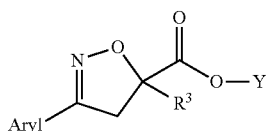

| No. | Aryl | R³ | Y | Physical data |
|---|---|---|---|---|
| 2.3.1 | 3-fluorophenyl | vinyl | methyl | [CDCl₃] 3.37 (d, 1H); 3.84 (s, 3H); 3.96 (d, 1H); 5.37 (d,1H); 5.56 (d, 1H); 6.15 (dd, 1H); 7.13 (t, 1H); 7.37-7.42 (m, 3H). |
| 2.3.2 | 3-fluorophenyl | 1-methylvinyl | ethyl | |
| 2.3.3 | 3-fluorophenyl | allyl | ethyl | |
| 2.3.4 | 3-fluorophenyl | 1-chlorovinyl | methyl | [CDCl₃] 3.57 (d, 1H); 3.88 (s, 3H); 4.25 (d, 1H); 5.55 (s, 1H); 5.94 (s, 1H); 7.15 (t, 1H); 7.39-7.43 (m, 3H). |
| 2.3.5 | 3-fluorophenyl | ethynyl | ethyl | |
| 2.3.6 | 3-chlorophenyl | vinyl | ethyl | |
| 2.3.7 | 3-chlorophenyl | 1-methylvinyl | ethyl | |
| 2.3.8 | 3-chlorophenyl | allyl | ethyl | |
| 2.3.9 | 3-chlorophenyl | 1-chlorovinyl | ethyl | |
| 2.3.10 | 3-chlorophenyl | ethynyl | ethyl | |
| 2.3.11 | 3-bromophenyl | vinyl | ethyl | |
| 2.3.12 | 3-bromophenyl | 1-methylvinyl | ethyl | |
| 2.3.13 | 3-iodophenyl | vinyl | ethyl | |
| 2.3.14 | 3-iodophenyl | 1-methylvinyl | ethyl | |
| 2.3.15 | 3-methylphenyl | vinyl | ethyl | |
| 2.3.16 | 3-methylphenyl | 1-methylvinyl | ethyl | |
| 2.3.17 | 3-ethylphenyl | vinyl | ethyl | |
| 2.3.18 | 3-propylphenyl | vinyl | ethyl | |
| 2.3.19 | 3-isopropylphenyl | vinyl | ethyl | |
| 2.3.20 | 3-n-butylphenyl | vinyl | ethyl | |
| 2.3.21 | 3-i-butylphenyl | vinyl | ethyl | |
| 2.3.22 | 3-tert-butylphenyl | vinyl | ethyl | |
| 2.3.23 | 3-cyclopropylphenyl | vinyl | ethyl | |
| 2.3.24 | 3-cyclobutylphenyl | vinyl | ethyl | |
| 2.3.25 | 3-cyclopentylphenyl | vinyl | ethyl | |
| 2.3.26 | 3-vinylphenyl | vinyl | ethyl | |
| 2.3.27 | 3-ethynylphenyl | vinyl | ethyl | |
| 2.3.28 | 3-cyanophenyl | vinyl | ethyl | |
| 2.3.29 | 3-trifluoromethylphenyl | vinyl | ethyl | |
| 2.3.30 | 3-difluoromethylphenyl | vinyl | ethyl | |
| 2.3.31 | 3-(hydroxycarbonyl)-phenyl | vinyl | ethyl | |
| 2.3.32 | 3-(methoxycarbonyl)-phenyl | vinyl | ethyl | |
| 2.3.33 | 3-(ethoxycarbonyl)-phenyl | vinyl | ethyl | |
| 2.3.34 | 3-hydroxymethylphenyl | vinyl | ethyl | |
| 2.3.35 | 3-carbamoylphenyl | vinyl | ethyl | |
| 2.3.36 | 3-hydroxyphenyl | vinyl | ethyl | |
| 2.3.37 | 3-methoxyphenyl | vinyl | ethyl | |
| 2.3.38 | 3-ethoxyphenyl | vinyl | ethyl | |
| 2.3.39 | 3-propyloxyphenyl | vinyl | ethyl | |
| 2.3.40 | 3-isopropyloxyphenyl | vinyl | ethyl | |
| 2.3.41 | 3-n-butyloxyphenyl | vinyl | ethyl | |
| 2.3.42 | 3-i-butyloxyphenyl | vinyl | ethyl | |
| 2.3.43 | 3-t-butyloxyphenyl | vinyl | ethyl | |
| 2.3.44 | 3-difluoromethoxy-phenyl | vinyl | ethyl | |
| 2.3.45 | 3-trifluoromethoxy-phenyl | vinyl | ethyl | |
| 2.3.46 | 3-(2,2,2-trifluoroethoxy)-phenyl | vinyl | ethyl | |
| 2.3.47 | 3-(2-chloroethoxy)-phenyl | vinyl | ethyl | |

TABLE 2.3-continued

Inventive compounds of the general formula (I) in which W* is COOY, $R^1$ $R^2$ are each hydrogen, and aryl is the radical.

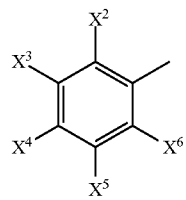

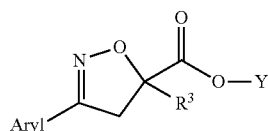

| No. | Aryl | $R^3$ | Y | Physical data |
|---|---|---|---|---|
| 2.3.48 | 3-(2-hydroxyethoxy)-phenyl | vinyl | ethyl | |
| 2.3.49 | 3-(2-methoxyethoxy)-phenyl | vinyl | ethyl | |
| 2.3.50 | 3-[(tert-butoxy-carbonyl)oxy]phenyl | vinyl | ethyl | |
| 2.3.51 | 3-nitrophenyl | vinyl | ethyl | |
| 2.3.52 | 3-acetoxyphenyl | vinyl | ethyl | |
| 2.3.53 | {3-[(tert-butoxycarbonyl)amino]phenyl} | vinyl | ethyl | |
| 2.3.54 | 3-methylsulfanylphenyl | vinyl | ethyl | |
| 2.3.55 | 3-ethylsulfanylphenyl | vinyl | ethyl | |
| 2.3.56 | 3-(pentafluoro-lambda$^6$-sulfanyl)phenyl | vinyl | ethyl | |
| 2.3.57 | 2,3-difluorophenyl | vinyl | ethyl | |
| 2.3.58 | 2,3-difluorophenyl | 1-methylvinyl | ethyl | |
| 2.3.59 | 2,3-difluorophenyl | allyl | ethyl | |
| 2.3.60 | 2,3-difluorophenyl | 1-chlorovinyl | ethyl | |
| 2.3.61 | 2,3-difluorophenyl | ethynyl | ethyl | |
| 2.3.62 | 2-chloro-3-fluorophenyl | vinyl | ethyl | |
| 2.3.63 | 2-bromo-3-fluorophenyl | vinyl | ethyl | |
| 2.3.64 | 2-methyl-3-fluorophenyl | vinyl | ethyl | |
| 2.3.65 | 2-ethyl-3-fluorophenyl | vinyl | ethyl | |
| 2.3.66 | 2-cyclopropyl-3-fluorophenyl | vinyl | ethyl | |
| 2.3.67 | 2-vinyl-3-fluorophenyl | vinyl | ethyl | |
| 2.3.68 | 2-ethynyl-3-fluorophenyl | vinyl | ethyl | |
| 2.3.69 | 2-cyano-3-fluorophenyl | vinyl | ethyl | |
| 2.3.70 | 2-methoxy-3-fluorophenyl | vinyl | ethyl | |
| 2.3.71 | 2-ethoxy-3-fluorophenyl | vinyl | ethyl | |
| 2.3.72 | 2-trifluoromethoxy-3-fluorophenyl | vinyl | ethyl | |
| 2.3.73 | 2-nitro-3-fluorophenyl | vinyl | ethyl | |
| 2.3.74 | 2-fluoro-3-chlorophenyl | vinyl | ethyl | |
| 2.3.75 | 2,3-dichlorophenyl | vinyl | ethyl | |
| 2.3.76 | 2,3-dichlorophenyl | 1-methylvinyl | ethyl | |
| 2.3.77 | 2,3-dichlorophenyl | allyl | ethyl | |
| 2.3.78 | 2,3-dichlorophenyl | 1-chlorovinyl | ethyl | |
| 2.3.79 | 2,3-dichlorophenyl | ethynyl | ethyl | |
| 2.3.80 | 2-bromo-3-chlorophenyl | vinyl | ethyl | |
| 2.3.81 | 2-methyl-3-chlorophenyl | vinyl | ethyl | |
| 2.3.82 | 2-ethyl-3-chlorophenyl | vinyl | ethyl | |
| 2.3.83 | 2-cyclopropyl-3-chlorophenyl | vinyl | ethyl | |
| 2.3.84 | 2-vinyl-3-chlorophenyl | vinyl | ethyl | |
| 2.3.85 | 2-ethynyl-3-chlorophenyl | vinyl | ethyl | |
| 2.3.86 | 2-cyano-3-chlorophenyl | vinyl | ethyl | |
| 2.3.87 | 2-trifluoromethyl-2-chlorophenyl | vinyl | ethyl | |
| 2.3.88 | 2-methoxy-3-chlorophenyl | vinyl | ethyl | |
| 2.3.89 | 2-ethoxy-3-chlorophenyl | vinyl | ethyl | |
| 2.3.90 | 2-trifluoromethoxy-3-chlorophenyl | vinyl | ethyl | |
| 2.3.91 | 2-nitro-3-chlorophenyl | vinyl | ethyl | |
| 2.3.92 | 2-fluoro-3-bromophenyl | vinyl | ethyl | |
| 2.3.93 | 2-chloro-3-bromophenyl | vinyl | ethyl | |
| 2.3.94 | 2,3-dibromophenyl | vinyl | ethyl | |
| 2.3.95 | 2-methyl-3-bromophenyl | vinyl | ethyl | |
| 2.3.96 | 2-ethyl-3-bromophenyl | vinyl | ethyl | |
| 2.3.97 | 2-cyclopropyl-3-bromophenyl | vinyl | ethyl | |
| 2.3.98 | 2-vinyl-3-bromophenyl | vinyl | ethyl | |
| 2.3.99 | 2-ethynyl-3-bromophenyl | vinyl | ethyl | |

TABLE 2.3-continued

Inventive compounds of the general formula (I) in which W* is COOY, R¹ R² are each hydrogen, and aryl is the radical.

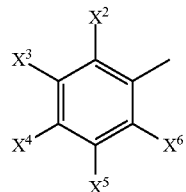

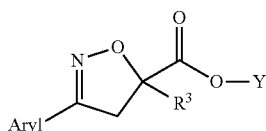

| No. | Aryl | R³ | Y | Physical data |
|---|---|---|---|---|
| 2.3.100 | 2-cyano-3-bromophenyl | vinyl | ethyl | |
| 2.3.101 | 2-trifluoromethyl-3-bromophenyl | vinyl | ethyl | |
| 2.3.102 | 2-methoxy-3-phenyl | vinyl | ethyl | |
| 2.3.103 | 2-ethoxy-3-bromophenyl | vinyl | ethyl | |
| 2.3.104 | 2-trifluoromethoxy-3-bromophenyl | vinyl | ethyl | |
| 2.3.105 | 2-nitro-3-bromophenyl | vinyl | ethyl | |
| 2.3.106 | 2-fluoro-3-iodophenyl | vinyl | ethyl | |
| 2.3.107 | 2-chloro-3-iodophenyl | vinyl | ethyl | |
| 2.3.108 | 2-bromo-3-iodophenyl | vinyl | ethyl | |
| 2.3.109 | 2-methyl-3-iodophenyl | vinyl | ethyl | |
| 2.3.110 | 2-ethyl-3-iodophenyl | vinyl | ethyl | |
| 2.3.111 | 2-cyclopropyl-3-iodophenyl | vinyl | ethyl | |
| 2.3.112 | 2-vinyl-3-iodophenyl | vinyl | ethyl | |
| 2.3.113 | 2-ethynyl-3-iodophenyl | vinyl | ethyl | |
| 2.3.114 | 2-cyano-3-iodophenyl | vinyl | ethyl | |
| 2.3.115 | 2-trifluoromethyl-3-iodophenyl | vinyl | ethyl | |
| 2.3.116 | 2-methoxy-3-iodophenyl | vinyl | ethyl | |
| 2.3.117 | 2-ethoxy-3-iodophenyl | vinyl | ethyl | |
| 2.3.118 | 2-trifluoromethoxy-3-iodophenyl | vinyl | ethyl | |
| 2.3.119 | 2-nitro-3-iodophenyl | vinyl | ethyl | |
| 2.3.120 | 2-fluoro-3-methylphenyl | vinyl | ethyl | |
| 2.3.121 | 2-fluoro-3-methylphenyl | 1-methylvinyl | ethyl | |
| 2.3.122 | 2-fluoro-3-methylphenyl | allyl | ethyl | |
| 2.3.123 | 2-fluoro-3-methylphenyl | 1-chlorovinyl | ethyl | |
| 2.3.124 | 2-fluoro-3-methylphenyl | ethynyl | ethyl | |
| 2.3.125 | 2-chloro-3-methylphenyl | vinyl | ethyl | |
| 2.3.126 | 2-chloro-3-methylphenyl | 1-methylvinyl | ethyl | |
| 2.3.127 | 2-chloro-3-methylphenyl | allyl | ethyl | |
| 2.3.128 | 2-chloro-3-methylphenyl | 1-chlorovinyl | ethyl | |
| 2.3.129 | 2-chloro-3-methylphenyl | ethynyl | ethyl | |
| 2.3.130 | 2-bromo-3-methylphenyl | vinyl | ethyl | |
| 2.3.131 | 2,3-dimethylphenyl | vinyl | ethyl | |
| 2.3.132 | 2,3-dimethylphenyl | 1-methylvinyl | ethyl | |
| 2.3.133 | 2,3-dimethylphenyl | allyl | ethyl | |
| 2.3.134 | 2,3-dimethylphenyl | 1-chlorovinyl | ethyl | |
| 2.3.135 | 2,3-dimethylphenyl | ethynyl | ethyl | |
| 2.3.136 | 2-ethyl-3-methylphenyl | vinyl | ethyl | |
| 2.3.137 | 2-cyclopropyl-3-methylphenyl | vinyl | ethyl | |
| 2.3.138 | 2-vinyl-3-methylphenyl | vinyl | ethyl | |
| 2.3.139 | 2-ethynyl-3-methylphenyl | vinyl | ethyl | |
| 2.3.140 | 2-cyano-3-methylphenyl | vinyl | ethyl | |
| 2.3.141 | 2-trifluoromethyl-3-methylphenyl | vinyl | ethyl | |
| 2.3.142 | 2-methoxy-3-methylphenyl | vinyl | ethyl | |
| 2.3.143 | 2-ethoxy-3-methylphenyl | vinyl | ethyl | |
| 2.3.144 | 2-trifluoromethoxy-3-methylphenyl | vinyl | ethyl | |
| 2.3.145 | 2-nitro-3-methylphenyl | vinyl | ethyl | |
| 2.3.146 | 2-fluoro-3-ethylphenyl | vinyl | ethyl | |
| 2.3.147 | 2-chloro-3-ethylphenyl | vinyl | ethyl | |
| 2.3.148 | 2-bromo-3-ethylphenyl | vinyl | ethyl | |
| 2.3.149 | 2-methyl-3-ethylphenyl | vinyl | ethyl | |
| 2.3.150 | 2,3-diethylphenyl | vinyl | ethyl | |
| 2.3.151 | 2-cyclopropyl-3-ethylphenyl | vinyl | ethyl | |
| 2.3.152 | 2-vinyl-3-ethylphenyl | vinyl | ethyl | |
| 2.3.153 | 2-ethynyl-3-ethylphenyl | vinyl | ethyl | |

TABLE 2.3-continued

Inventive compounds of the general formula (I) in which W* is COOY, R¹ R² are each hydrogen, and aryl is the radical.

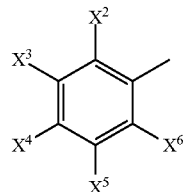

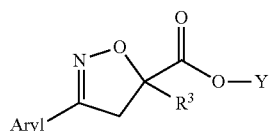

| No. | Aryl | R³ | Y | Physical data |
|---|---|---|---|---|
| 2.3.154 | 2-cyano-3-ethylphenyl | vinyl | ethyl | |
| 2.3.155 | 2-trifluoromethyl-3-ethylphenyl | vinyl | ethyl | |
| 2.3.156 | 2-methoxy-3-ethylphenyl | vinyl | ethyl | |
| 2.3.157 | 2-ethoxy-3-ethylphenyl | vinyl | ethyl | |
| 2.3.158 | 2-trifluoromethoxy-3-ethylphenyl | vinyl | ethyl | |
| 2.3.159 | 2-nitro-3-ethylphenyl | vinyl | ethyl | |
| 2.3.160 | 2-fluoro-3-propylphenyl | vinyl | ethyl | |
| 2.3.161 | 2-chloro-3-propylphenyl | vinyl | ethyl | |
| 2.3.162 | 2-bromo-3-propylphenyl | vinyl | ethyl | |
| 2.3.163 | 2-methyl-3-propylphenyl | vinyl | ethyl | |
| 2.3.164 | 2-methyl-3-propylphenyl | vinyl | ethyl | |
| 2.3.165 | 2-cyclopropyl-3-propylphenyl | vinyl | ethyl | |
| 2.3.166 | 2-vinyl-3-propylphenyl | vinyl | ethyl | |
| 2.3.167 | 2-ethynyl-3-propylphenyl | vinyl | ethyl | |
| 2.3.168 | 2-cyano-3-propylphenyl | vinyl | ethyl | |
| 2.3.169 | 2-trifluoromethyl-3-propylphenyl | vinyl | ethyl | |
| 2.3.170 | 2-methoxy-3-propylphenyl | vinyl | ethyl | |
| 2.3.171 | 2-ethoxy-3-propylphenyl | vinyl | ethyl | |
| 2.3.172 | 2-trifluoromethoxy-3-propylphenyl | vinyl | ethyl | |
| 2.3.173 | 2-nitro-3-propylphenyl | vinyl | ethyl | |
| 2.3.174 | 2-fluoro-3-isopropylphenyl | vinyl | ethyl | |
| 2.3.175 | 2-chloro-3-isopropylphenyl | vinyl | ethyl | |
| 2.3.176 | 2-bromo-3-isopropylphenyl | vinyl | ethyl | |
| 2.3.177 | 2-methyl-3-isopropylphenyl | vinyl | ethyl | |
| 2.3.178 | 2-ethyl-3-isopropylphenyl | vinyl | ethyl | |
| 2.3.179 | 2-cyclopropyl-3-isopropylphenyl | vinyl | ethyl | |
| 2.3.180 | 2-vinyl-3-isopropylphenyl | vinyl | ethyl | |
| 2.3.181 | 2-ethynyl-3-isopropylphenyl | vinyl | ethyl | |
| 2.3.182 | 2-cyano-3-isopropylphenyl | vinyl | ethyl | |
| 2.3.183 | 2-trifluoromethyl-3-isopropylphenyl | vinyl | ethyl | |
| 2.3.184 | 2-methoxy-3-isopropylphenyl | vinyl | ethyl | |
| 2.3.185 | 2-ethoxy-3-isopropylphenyl | vinyl | ethyl | |
| 2.3.186 | 2-trifluoromethoxy-3-isopropylphenyl | vinyl | ethyl | |
| 2.3.187 | 2-nitro-3-isopropylphenyl | vinyl | ethyl | |
| 2.3.188 | 2-fluoro-3-tert-butylphenyl | vinyl | ethyl | |
| 2.3.189 | 2-chloro-3-tert-butylphenyl | vinyl | ethyl | |
| 2.3.190 | 2-bromo-3-tert-butylphenyl | vinyl | ethyl | |
| 2.3.191 | 2-methyl-3-tert-butylphenyl | vinyl | ethyl | |
| 2.3.192 | 2-ethyl-3-tert-butylphenyl | vinyl | ethyl | |
| 2.3.193 | 2-cyclopropyl-3-tert-butylphenyl | vinyl | ethyl | |
| 2.3.194 | 2-vinyl-3-tert-butylphenyl | vinyl | ethyl | |
| 2.3.195 | 2-ethynyl-3-tert-butylphenyl | vinyl | ethyl | |
| 2.3.196 | 2-cyano-3-tert-butylphenyl | vinyl | ethyl | |
| 2.3.197 | 2-trifluoromethyl-3-tert-butylphenyl | vinyl | ethyl | |
| 2.3.198 | 2-methoxy-3-tert-butylphenyl | vinyl | ethyl | |
| 2.3.199 | 2-ethoxy-3-tert-butylphenyl | vinyl | ethyl | |
| 2.3.200 | 2-trifluoromethoxy-3-tert-butylphenyl | vinyl | ethyl | |
| 2.3.201 | 2-nitro-3-tert-butylphenyl | vinyl | ethyl | |
| 2.3.202 | 2-fluoro-3-hydroxymethylphenyl | vinyl | ethyl | |
| 2.3.203 | 2-chloro-3-hydroxymethylphenyl | vinyl | ethyl | |
| 2.3.204 | 2-bromo-3-hydroxymethylphenyl | vinyl | ethyl | |
| 2.3.205 | 2-methyl-3-hydroxymethylphenyl | vinyl | ethyl | |

TABLE 2.3-continued

Inventive compounds of the general formula (I) in which W* is COOY, R¹ R² are each hydrogen, and aryl is the radical.

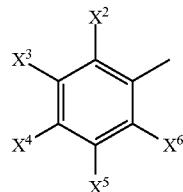

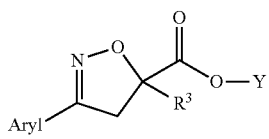

| No. | Aryl | R³ | Y | Physical data |
|---|---|---|---|---|
| 2.3.206 | 2-ethyl-3-hydroxymethylphenyl | vinyl | ethyl | |
| 2.3.207 | 2-cyclopropyl-3-hydroxymethylphenyl | vinyl | ethyl | |
| 2.3.208 | 2-vinyl-3-hydroxymethylphenyl | vinyl | ethyl | |
| 2.3.209 | 2-ethynyl-3-hydroxymethylphenyl | vinyl | ethyl | |
| 2.3.210 | 2-cyano-3-hydroxymethylphenyl | vinyl | ethyl | |
| 2.3.211 | 2-trifluoromethyl-3-hydroxymethylphenyl | vinyl | ethyl | |
| 2.3.212 | 2-methoxy-3-hydroxymethylphenyl | vinyl | ethyl | |
| 2.3.213 | 2-ethoxy-3-hydroxymethylphenyl | vinyl | ethyl | |
| 2.3.214 | 2-trifluoromethoxy-3-hydroxymethylphenyl | vinyl | ethyl | |
| 2.3.215 | 2-nitro-3-hydroxymethylphenyl | vinyl | ethyl | |
| 2.3.216 | 2-fluoro-3-cyclopropylphenyl | vinyl | ethyl | |
| 2.3.217 | 2-chloro-3-cyclopropylphenyl | vinyl | ethyl | |
| 2.3.218 | 2-bromo-3-cyclopropylphenyl | vinyl | ethyl | |
| 2.3.219 | 2-methyl-3-cyclopropylphenyl | vinyl | ethyl | |
| 2.3.220 | 2-ethyl-3-cyclopropylphenyl | vinyl | ethyl | |
| 2.3.221 | 2-cyclopropyl-3-cyclopropylphenyl | vinyl | ethyl | |
| 2.3.222 | 2-vinyl-3-cyclopropylphenyl | vinyl | ethyl | |
| 2.3.223 | 2-ethynyl-3-cyclopropylphenyl | vinyl | ethyl | |
| 2.3.224 | 2-cyano-3-cyclopropylphenyl | vinyl | ethyl | |
| 2.3.225 | 2-trifluoromethyl-3-cyclopropylphenyl | vinyl | ethyl | |
| 2.3.226 | 2-methoxy-3-cyclopropylphenyl | vinyl | ethyl | |
| 2.3.227 | 2-ethoxy-3-cyclopropylphenyl | vinyl | ethyl | |
| 2.3.228 | 2-trifluoromethoxy-3-cyclopropylphenyl | vinyl | ethyl | |
| 2.3.229 | 2-fluoro-3-methoxycarbonylphenyl | vinyl | ethyl | |
| 2.3.230 | 2-chloro-3-methoxycarbonylphenyl | vinyl | ethyl | |
| 2.3.231 | 2-bromo-3-methoxycarbonylphenyl | vinyl | ethyl | |
| 2.3.232 | 2-methyl-3-methoxycarbonylphenyl | vinyl | ethyl | |
| 2.3.233 | 2-ethyl-3-methoxycarbonylphenyl | vinyl | ethyl | |
| 2.3.234 | 2-cyclopropyl-3-methoxycarbonyl-phenyl | vinyl | ethyl | |
| 2.3.235 | 2-vinyl-3-methoxycarbonylphenyl | vinyl | ethyl | |
| 2.3.236 | 2-ethynyl-3-methoxycarbonyl-phenyl | vinyl | ethyl | |
| 2.3.237 | 2-cyano-3-methoxycarbonylphenyl | vinyl | ethyl | |
| 2.3.238 | 2-trifluoromethyl-3-methoxycarbonylphenyl | vinyl | ethyl | |
| 2.3.239 | 2-methoxy-3-methoxycarbonyl-phenyl | vinyl | ethyl | |
| 2.3.240 | 2-ethoxy-3-methoxycarbonylphenyl | vinyl | ethyl | |
| 2.3.241 | 2-trifluoromethoxy-3-methoxycarbonylphenyl | vinyl | ethyl | |

TABLE 2.3-continued

Inventive compounds of the general formula (I) in which W* is COOY, R¹ R² are each hydrogen, and aryl is the radical.

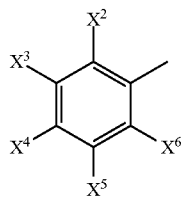

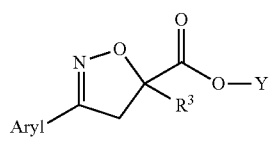

| No. | Aryl | R³ | Y | Physical data |
|---|---|---|---|---|
| 2.3.242 | 2-nitro-3-methoxycarbonylphenyl | vinyl | ethyl | |
| 2.3.243 | 2-fluoro-3-vinylphenyl | vinyl | ethyl | |
| 2.3.244 | 2-chloro-3-vinylphenyl | vinyl | ethyl | |
| 2.3.245 | 2-bromo-3-vinylphenyl | vinyl | ethyl | |
| 2.3.246 | 2-methyl-3-vinylphenyl | vinyl | ethyl | |
| 2.3.247 | 2-ethyl-3-vinylphenyl | vinyl | ethyl | |
| 2.3.248 | 2-cyclopropyl-3-vinylphenyl | vinyl | ethyl | |
| 2.3.249 | 2-vinyl-3-vinylphenyl | vinyl | ethyl | |
| 2.3.250 | 2-ethynyl-3-vinylphenyl | vinyl | ethyl | |
| 2.3.251 | 2-cyano-3-vinylphenyl | vinyl | ethyl | |
| 2.3.252 | 2-trifluoromethyl-3-vinylphenyl | vinyl | ethyl | |
| 2.3.253 | 2-methoxy-3-vinylphenyl | vinyl | ethyl | |
| 2.3.254 | 2-ethoxy-3-vinylphenyl | vinyl | ethyl | |
| 2.3.255 | 2-trifluoromethoxy-3-vinylphenyl | vinyl | ethyl | |
| 2.3.256 | 2-nitro-3-vinylphenyl | vinyl | ethyl | |
| 2.3.257 | 2-fluoro-3-ethynylphenyl | vinyl | ethyl | |
| 2.3.258 | 2-chloro-3-ethynylphenyl | vinyl | ethyl | |
| 2.3.259 | 2-bromo-3-ethynylphenyl | vinyl | ethyl | |
| 2.3.260 | 2-methyl-3-ethynylphenyl | vinyl | ethyl | |
| 2.3.261 | 2-ethyl-3-ethynylphenyl | vinyl | ethyl | |
| 2.3.262 | 2-cyclopropyl-3-ethynylphenyl | vinyl | ethyl | |
| 2.3.263 | 2-vinyl-3-ethynylphenyl | vinyl | ethyl | |
| 2.3.264 | 2-cyano-3-ethynylphenyl | vinyl | ethyl | |
| 2.3.265 | 2-trifluoromethyl-3-ethynylphenyl | vinyl | ethyl | |
| 2.3.266 | 2-methoxy-3-ethynylphenyl | vinyl | ethyl | |
| 2.3.267 | 2-ethoxy-3-ethynylphenyl | vinyl | ethyl | |
| 2.3.268 | 2-trifluoromethoxy-3-ethynylphenyl | vinyl | ethyl | |
| 2.3.269 | 2-nitro-3-ethynylphenyl | vinyl | ethyl | |
| 2.3.270 | 2-fluoro-3-ethynylphenyl | vinyl | ethyl | |
| 2.3.271 | 2-fluoro-3-cyanophenyl | vinyl | ethyl | |
| 2.3.272 | 2-chloro-3-cyanophenyl | vinyl | ethyl | |
| 2.3.273 | 2-bromo-3-cyanophenyl | vinyl | ethyl | |
| 2.3.274 | 2-methyl-3-cyanophenyl | vinyl | ethyl | |
| 2.3.275 | 2-ethyl-3-cyanophenyl | vinyl | ethyl | |
| 2.3.276 | 2-ethyl-3-cyanophenyl | 1-methylvinyl | ethyl | |
| 2.3.277 | 2-ethyl-3-cyanophenyl | allyl | ethyl | |
| 2.3.278 | 2-ethyl-3-cyanophenyl | 1-chlorovinyl | ethyl | |
| 2.3.279 | 2-ethyl-3-cyanophenyl | ethynyl | ethyl | |
| 2.3.280 | 2-cyclopropyl-3-cyanophenyl | vinyl | ethyl | |
| 2.3.281 | 2-vinyl-3-cyanophenyl | vinyl | ethyl | |
| 2.3.282 | 2-ethynyl-3-cyanophenyl | vinyl | ethyl | |
| 2.3.283 | 2-cyano-3-cyanophenyl | vinyl | ethyl | |
| 2.3.284 | 2-trifluoromethyl-3-cyanophenyl | vinyl | ethyl | |
| 2.3.285 | 2-methoxy-3-cyanophenyl | vinyl | ethyl | |
| 2.3.286 | 2-ethoxy-3-cyanophenyl | vinyl | ethyl | |
| 2.3.287 | 2-trifluoromethoxy-3-cyanophenyl | vinyl | ethyl | |
| 2.3.288 | 2-nitro-3-cyanophenyl | vinyl | ethyl | |
| 2.3.289 | 2-fluoro-3-hydroxyphenyl | vinyl | ethyl | |
| 2.3.290 | 2-chloro-3-hydroxyphenyl | vinyl | ethyl | |
| 2.3.291 | 2-bromo-3-hydroxyphenyl | vinyl | ethyl | |
| 2.3.292 | 2-methyl-3-hydroxyphenyl | vinyl | ethyl | |
| 2.3.293 | 2-ethyl-3-hydroxyphenyl | vinyl | ethyl | |
| 2.3.294 | 2-cyclopropyl-3-hydroxyphenyl | vinyl | ethyl | |
| 2.3.295 | 2-vinyl-3-hydroxyphenyl | vinyl | ethyl | |

TABLE 2.3-continued

Inventive compounds of the general formula (I) in which W* is COOY, R¹ R² are each hydrogen, and aryl is the radical.

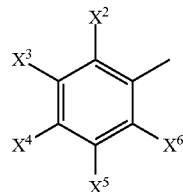

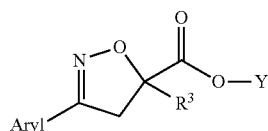

| No. | Aryl | R³ | Y | Physical data |
|---|---|---|---|---|
| 2.3.296 | 2-ethynyl-3-hydroxyphenyl | vinyl | ethyl | |
| 2.3.297 | 2-cyano-3-hydroxyphenyl | vinyl | ethyl | |
| 2.3.298 | 2-trifluoromethyl-3-hydroxyphenyl | vinyl | ethyl | |
| 2.3.299 | 2-methoxy-3-hydroxyphenyl | vinyl | ethyl | |
| 2.3.300 | 2-ethoxy-3-hydroxyphenyl | vinyl | ethyl | |
| 2.3.301 | 2-trifluoromethoxy-3-hydroxyphenyl | vinyl | ethyl | |
| 2.3.302 | 2-nitro-3-hydroxyphenyl | vinyl | ethyl | |
| 2.3.303 | 2-fluoro-3-methoxyphenyl | vinyl | ethyl | |
| 2.3.304 | 2-chloro-3-methoxyphenyl | vinyl | ethyl | |
| 2.3.305 | 2-bromo-3-methoxyphenyl | vinyl | ethyl | |
| 2.3.306 | 2-methyl-3-methoxyphenyl | vinyl | ethyl | |
| 2.3.307 | 2-ethyl-3-methoxyphenyl | vinyl | ethyl | |
| 2.3.308 | 2-cyclopropyl-3-methoxyphenyl | vinyl | ethyl | |
| 2.3.309 | 2-vinyl-3-methoxyphenyl | vinyl | ethyl | |
| 2.3.310 | 2-ethynyl-3-methoxyphenyl | vinyl | ethyl | |
| 2.3.311 | 2-cyano-3-methoxyphenyl | vinyl | ethyl | |
| 2.3.312 | 2-trifluoromethyl-3-methoxyphenyl | vinyl | ethyl | |
| 2.3.313 | 2,3-dimethoxyphenyl | vinyl | ethyl | |
| 2.3.314 | 2-ethoxy-3-methoxyphenyl | vinyl | ethyl | |
| 2.3.315 | 2-trifluoromethoxy-3-methoxyphenyl | vinyl | ethyl | |
| 2.3.316 | 2-nitro-3-methoxyphenyl | vinyl | ethyl | |
| 2.3.317 | 2-fluoro-3-ethoxyphenyl | vinyl | ethyl | |
| 2.3.318 | 2-chloro-3-ethoxyphenyl | vinyl | ethyl | |
| 2.3.319 | 2-bromo-3-ethoxyphenyl | vinyl | ethyl | |
| 2.3.320 | 2-methyl-3-ethoxyphenyl | vinyl | ethyl | |
| 2.3.321 | 2-ethyl-3-ethoxyphenyl | vinyl | ethyl | |
| 2.3.322 | 2-cyclopropyl-3-ethoxyphenyl | vinyl | ethyl | |
| 2.3.323 | 2-vinyl-3-ethoxyphenyl | vinyl | ethyl | |
| 2.3.324 | 2-ethynyl-3-ethoxyphenyl | vinyl | ethyl | |
| 2.3.325 | 2-cyano-3-ethoxyphenyl | vinyl | ethyl | |
| 2.3.326 | 2-trifluoromethyl-3-ethoxyphenyl | vinyl | ethyl | |
| 2.3.327 | 2-methoxy-3-ethoxyphenyl | vinyl | ethyl | |
| 2.3.328 | 2,3-diethoxyphenyl | vinyl | ethyl | |
| 2.3.329 | 2-trifluoromethoxy-3-ethoxyphenyl | vinyl | ethyl | |
| 2.3.330 | 2-nitro-3-ethoxyphenyl | vinyl | ethyl | |
| 2.3.331 | 2-fluoro-3-propoxyphenyl | vinyl | ethyl | |
| 2.3.332 | 2-chloro-3-propoxyphenyl | vinyl | ethyl | |
| 2.3.333 | 2-bromo-3-propoxyphenyl | vinyl | ethyl | |
| 2.3.334 | 2-methyl-3-propoxyphenyl | vinyl | ethyl | |
| 2.3.335 | 2-ethyl-3-propoxyphenyl | vinyl | ethyl | |
| 2.3.336 | 2-cyclopropyl-3-propoxyphenyl | vinyl | ethyl | |
| 2.3.337 | 2-vinyl-3-propoxyphenyl | vinyl | ethyl | |
| 2.3.338 | 2-ethynyl-3-propoxyphenyl | vinyl | ethyl | |
| 2.3.339 | 2-cyano-3-propoxyphenyl | vinyl | ethyl | |
| 2.3.340 | 2-trifluoromethyl-3-propoxyphenyl | vinyl | ethyl | |
| 2.3.341 | 2-methoxy-3-propoxyphenyl | vinyl | ethyl | |
| 2.3.342 | 2-ethoxy-3-propoxyphenyl | vinyl | ethyl | |
| 2.3.343 | 2-trifluoromethoxy-3-propoxyphenyl | vinyl | ethyl | |
| 2.3.344 | 2-nitro-3-propoxyphenyl | vinyl | ethyl | |
| 2.3.345 | 2-fluoro-3-isopropoxyphenyl | vinyl | ethyl | |

TABLE 2.3-continued

Inventive compounds of the general formula (I) in which W* is COOY, R¹ R² are each hydrogen, and aryl is the radical.

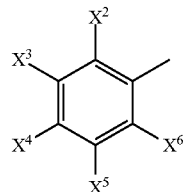

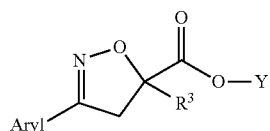

| No. | Aryl | R³ | Y | Physical data |
|---|---|---|---|---|
| 2.3.346 | 2-chloro-3-isopropoxyphenyl | vinyl | ethyl | |
| 2.3.347 | 2-bromo-3-isopropoxyphenyl | vinyl | ethyl | |
| 2.3.348 | 2-methyl-3-isopropoxyphenyl | vinyl | ethyl | |
| 2.3.349 | 2-ethyl-3-isopropoxyphenyl | vinyl | ethyl | |
| 2.3.350 | 2-cyclopropyl-3-isopropoxyphenyl | vinyl | ethyl | |
| 2.3.351 | 2-vinyl-3-isopropoxyphenyl | vinyl | ethyl | |
| 2.3.352 | 2-ethynyl-3-isopropoxyphenyl | vinyl | ethyl | |
| 2.3.353 | 2-cyano-3-isopropoxyphenyl | vinyl | ethyl | |
| 2.3.354 | 2-trifluoromethyl-3-isopropoxyphenyl | vinyl | ethyl | |
| 2.3.355 | 2-methoxy-3-isopropoxyphenyl | vinyl | ethyl | |
| 2.3.356 | 2-ethoxy-3-isopropoxyphenyl | vinyl | ethyl | |
| 2.3.357 | 2-trifluoromethoxy-3-isopropoxyphenyl | vinyl | ethyl | |
| 2.3.358 | 2-nitro-3-isopropoxyphenyl | vinyl | ethyl | |
| 2.3.359 | 2-fluoro-3-tert-butoxyphenyl | vinyl | ethyl | |
| 2.3.360 | 2-chloro-3-tert-butoxyphenyl | vinyl | ethyl | |
| 2.3.361 | 2-bromo-3-tert-butoxyphenyl | vinyl | ethyl | |
| 2.3.362 | 2-methyl-3-tert-butoxyphenyl | vinyl | ethyl | |
| 2.3.363 | 2-ethyl-3-tert-butoxyphenyl | vinyl | ethyl | |
| 2.3.364 | 2-cyclopropyl-3-tert-butoxyphenyl | vinyl | ethyl | |
| 2.3.365 | 2-vinyl-3-tert-butoxyphenyl | vinyl | ethyl | |
| 2.3.366 | 2-ethynyl-3-tert-butoxyphenyl | vinyl | ethyl | |
| 2.3.367 | 2-cyano-3-tert-butoxyphenyl | vinyl | ethyl | |
| 2.3.368 | 2-trifluoromethyl-3-tert-butoxyphenyl | vinyl | ethyl | |
| 2.3.369 | 2-methoxy-3-tert-butoxyphenyl | vinyl | ethyl | |
| 2.3.370 | 2-ethoxy-3-tert-butoxyphenyl | vinyl | ethyl | |
| 2.3.371 | 2-trifluoromethoxy-3-tert-butoxyphenyl | vinyl | ethyl | |
| 2.3.372 | 2-nitro-3-tert-butoxyphenyl | vinyl | ethyl | |
| 2.3.373 | 2-fluoro-3-trifluoromethoxy-phenyl | vinyl | ethyl | |
| 2.3.374 | 2-chloro-3-trifluoromethoxy-phenyl | vinyl | ethyl | |
| 2.3.375 | 2-bromo-3-trifluoromethoxy-phenyl | vinyl | ethyl | |
| 2.3.376 | 2-methyl-3-trifluoromethoxy-phenyl | vinyl | ethyl | |
| 2.3.377 | 2-ethyl-3-trifluoromethoxy-phenyl | vinyl | ethyl | |
| 2.3.378 | 2-cyclopropyl-3-trifluoromethoxyphenyl | vinyl | ethyl | |
| 2.3.379 | 2-vinyl-3-trifluoromethoxyphenyl | vinyl | ethyl | |
| 2.3.380 | 2-ethynyl-3-trifluoromethoxy-phenyl | vinyl | ethyl | |
| 2.3.381 | 2-cyano-3-trifluoromethoxy-phenyl | vinyl | ethyl | |
| 2.3.382 | 2-trifluoromethyl-3-trifluoromethoxyphenyl | vinyl | ethyl | |
| 2.3.383 | 2-methoxy-3-trifluoromethoxy-phenyl | vinyl | ethyl | |
| 2.3.384 | 2-ethoxy-3-trifluoromethoxy-phenyl | vinyl | ethyl | |

TABLE 2.3-continued

Inventive compounds of the general formula (I) in which W* is COOY, R¹ R² are each hydrogen, and aryl is the radical.

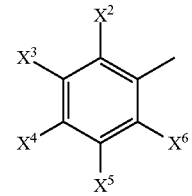

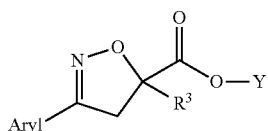

| No. | Aryl | R³ | Y | Physical data |
|---|---|---|---|---|
| 2.3.385 | 2,3-bis(trifluoromethoxy)phenyl | vinyl | ethyl | |
| 2.3.386 | 2-nitro-3-trifluoromethoxyphenyl | vinyl | ethyl | |
| 2.3.387 | 2-fluoro-3-(2,2,2-trifluoroethoxy)-phenyl | vinyl | ethyl | |
| 2.3.388 | 2-chloro-3-(2,2,2-trifluoroethoxy)phenyl | vinyl | ethyl | |
| 2.3.389 | 2-bromo-3-(2,2,2-trifluoroethoxy)phenyl | vinyl | ethyl | |
| 2.3.390 | 2-methyl-3-(2,2,2-trifluoroethoxy)phenyl | vinyl | ethyl | |
| 2.3.391 | 2-ethyl-3-(2,2,2-trifluoroethoxy)-phenyl | vinyl | ethyl | |
| 2.3.392 | 2-cyclopropyl-3-(2,2,2-trifluoro-ethoxy)phenyl | vinyl | ethyl | |
| 2.3.393 | 2-vinyl-3-(2,2,2-trifluoroethoxy)-phenyl | vinyl | ethyl | |
| 2.3.394 | 2-ethynyl-3-(2,2,2-trifluoroethoxyphenyl | vinyl | ethyl | |
| 2.3.395 | 2-cyano-3-(2,2,2-trifluoroethoxy)phenyl | vinyl | ethyl | |
| 2.3.396 | 2-trifluoromethyl-3-(2,2,2-trifluoro-ethoxy)phenyl | vinyl | ethyl | |
| 2.3.397 | 2-methoxy-3-(2,2,2-trifluoroethoxy)phenyl | vinyl | ethyl | |
| 2.3.398 | 2-ethoxy-3-(2,2,2-trifluoroethoxy)phenyl | vinyl | ethyl | |
| 2.3.399 | 2-trifluoromethoxy-3-(2,2,2-trifluoro-ethoxy)phenyl | vinyl | ethyl | |
| 2.3.400 | 2-nitro-3-(2,2,2-trifluoroethoxy)-phenyl | vinyl | ethyl | |
| 2.3.401 | 2-fluoro-3-difluoromethoxy-phenyl | vinyl | ethyl | |
| 2.3.402 | 2-chloro-3-difluoromethoxy-phenyl | vinyl | ethyl | |
| 2.3.403 | 2-bromo-3-difluoromethoxy-phenyl | vinyl | ethyl | |
| 2.3.404 | 2-methyl-3-difluoromethoxy-phenyl | vinyl | ethyl | |
| 2.3.405 | 2-ethyl-3-difluoromethoxy-phenyl | vinyl | ethyl | |
| 2.3.406 | 2-cyclopropyl-3-difluoromethoxy-phenyl | vinyl | ethyl | |
| 2.3.407 | 2-vinyl-3-difluoromethoxyphenyl | vinyl | ethyl | |
| 2.3.408 | 2-ethynyl-3-difluoromethoxy-phenyl | vinyl | ethyl | |
| 2.3.409 | 2-cyano-3-difluoromethoxy-phenyl | vinyl | ethyl | |
| 2.3.410 | 2-trifluoromethyl-3-difluoromethoxyphenyl | vinyl | ethyl | |
| 2.3.411 | 2-methoxy-3-difluoromethoxy-phenyl | vinyl | ethyl | |
| 2.3.412 | 2-ethoxy-3-difluoromethoxyphenyl | vinyl | ethyl | |
| 2.3.413 | 2-trifluoromethoxy-3-difluoromethoxyphenyl | vinyl | ethyl | |

TABLE 2.3-continued

Inventive compounds of the general formula (I) in which W* is COOY, $R^1$ $R^2$ are each hydrogen, and aryl is the radical.

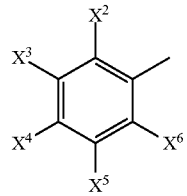

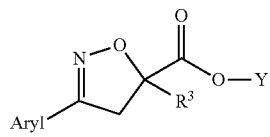

| No. | Aryl | $R^3$ | Y | Physical data |
|---|---|---|---|---|
| 2.3.414 | 2-nitro-3-difluoromethoxyphenyl | vinyl | ethyl | |
| 2.3.415 | 2-fluoro-3-(2-methoxyethoxy)-phenyl | vinyl | ethyl | |
| 2.3.416 | 2-chloro-3-(2-methoxyethoxy)-phenyl | vinyl | ethyl | |
| 2.3.417 | 2-bromo-3-(2-methoxyethoxy)-phenyl | vinyl | ethyl | |
| 2.3.418 | 2-methyl-3-(2-methoxyethoxy)-phenyl | vinyl | ethyl | |
| 2.3.419 | 2-ethyl-3-(2-methoxyethoxy)phenyl | vinyl | ethyl | |
| 2.3.420 | 2-cyclopropyl-3-(2-methoxyethoxy)phenyl | vinyl | ethyl | |
| 2.3.421 | 2-vinyl-3-(2-methoxyethoxy)phenyl | vinyl | ethyl | |
| 2.3.422 | 2-ethynyl-3-(2-methoxyethoxy)-phenyl | vinyl | ethyl | |
| 2.3.423 | 2-cyano-3-(2-methoxyethoxy)-phenyl | vinyl | ethyl | |
| 2.3.424 | 2-trifluoromethyl-3-(2-methoxyethoxy)phenyl | vinyl | ethyl | |
| 2.3.425 | 2-methoxy-3-(2-methoxyethoxy)-phenyl | vinyl | ethyl | |
| 2.3.426 | 2-ethoxy-3-(2-methoxyethoxy)-phenyl | vinyl | ethyl | |
| 2.3.427 | 2-trifluoromethoxy-(2-methoxyethoxy)phenyl | vinyl | ethyl | |
| 2.3.428 | 2-nitro-3-(2-methoxyethoxy)phenyl | vinyl | ethyl | |
| 2.3.429 | 2-fluoro-3-(tert-butoxycarbonyloxy)phenyl | vinyl | ethyl | |
| 2.3.430 | 2-chloro-3-(tert-butoxycarbonyloxy)phenyl | vinyl | ethyl | |
| 2.3.431 | 2-bromo-3-(tert-butoxycarbonyl-oxy)phenyl | vinyl | ethyl | |
| 2.3.432 | 2-methyl-3-(tert-butoxycarbonyl-oxy)phenyl | vinyl | ethyl | |
| 2.3.433 | 2-ethyl-3-(tert-butoxycarbonyloxy)phenyl | vinyl | ethyl | |
| 2.3.434 | 2-cyclopropyl-3-(tert-butoxycarbonyl-oxy)phenyl | vinyl | ethyl | |
| 2.3.435 | 2-vinyl-3-(tert-butoxycarbonyloxy)phenyl | vinyl | ethyl | |
| 2.3.436 | 2-ethynyl-3-(tert-butoxycarbonyl-oxy)phenyl | vinyl | ethyl | |
| 2.3.437 | 2-cyano-3-(tert-butoxycarbonyloxy)phenyl | vinyl | ethyl | |
| 2.3.438 | 2-trifluoromethyl-3-(tert-butoxycarbonyl-oxy)phenyl | vinyl | ethyl | |
| 2.3.439 | 2-methoxy-3-(tert-butoxycarbonyloxy)phenyl | vinyl | ethyl | |
| 2.3.440 | 2-ethoxy-3-(tert-butoxycarbonyloxy)phenyl | vinyl | ethyl | |
| 2.3.441 | 2-trifluoromethoxy-3-(tert-butoxycarbonyl-oxy)phenyl | vinyl | ethyl | |
| 2.3.442 | 2-nitro-3-(tert-butoxycarbonyloxy)phenyl | vinyl | ethyl | |

TABLE 2.3-continued

Inventive compounds of the general formula (I) in which W* is COOY, R¹ R² are each hydrogen, and aryl is the radical.

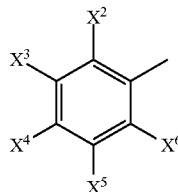

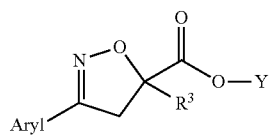

| No. | Aryl | R³ | Y | Physical data |
|---|---|---|---|---|
| 2.3.443 | 2-fluoro-3-nitrophenyl | vinyl | ethyl | |
| 2.3.444 | 2-chloro-3-nitrophenyl | vinyl | ethyl | |
| 2.3.445 | 2-bromo-3-nitrophenyl | vinyl | ethyl | |
| 2.3.446 | 2-methyl-3-nitrophenyl | vinyl | ethyl | |
| 2.3.447 | 2-ethyl-3-nitrophenyl | vinyl | ethyl | |
| 2.3.448 | 2-cyclopropyl-3-nitrophenyl | vinyl | ethyl | |
| 2.3.449 | 2-vinyl-3-nitrophenyl | vinyl | ethyl | |
| 2.3.450 | 2-ethynyl-3-nitrophenyl | vinyl | ethyl | |
| 2.3.451 | 2-cyano-3-nitrophenyl | vinyl | ethyl | |
| 2.3.452 | 2-trifluoromethyl-3-nitrophenyl | vinyl | ethyl | |
| 2.3.453 | 2-methoxy-3-nitrophenyl | vinyl | ethyl | |
| 2.3.454 | 2-ethoxy-3-nitrophenyl | vinyl | ethyl | |
| 2.3.455 | 2-trifluoromethoxy-3-nitrophenyl | vinyl | ethyl | |
| 2.3.456 | 2-fluoro-3-methylsulfanylphenyl | vinyl | ethyl | |
| 2.3.457 | 2-chloro-3-methylsulfanylphenyl | vinyl | ethyl | |
| 2.3.458 | 2-bromo-3-methylsulfanylphenyl | vinyl | ethyl | |
| 2.3.459 | 2-methyl-3-methylsulfanylphenyl | vinyl | ethyl | |
| 2.3.460 | 2-ethyl-3-methylsulfanylphenyl | vinyl | ethyl | |
| 2.3.461 | 2-cyclopropyl-3-methylsulfanylphenyl | vinyl | ethyl | |
| 2.3.462 | 2-vinyl-3-methylsulfanylphenyl | vinyl | ethyl | |
| 2.3.463 | 2-ethynyl-3-methylsulfanylphenyl | vinyl | ethyl | |
| 2.3.464 | 2-cyano-3-methylsulfanylphenyl | vinyl | ethyl | |
| 2.3.465 | 2-trifluoromethyl-3-methylsulfanylphenyl | vinyl | ethyl | |
| 2.3.466 | 2-methoxy-3-methylsulfanylphenyl | vinyl | ethyl | |
| 2.3.467 | 3,5-difluorophenyl | vinyl | methyl | One unassigned enantiomer [CDCl₃] 3.34 (d, 1H); 3.84 (s, 3H); 3.94 (d, 1H); 5.38 (d, 1H); 5.55 (d, 1H); 6.14 (dd, 1H); 8.88 t, 1H); 7.18 (d, 2H). |
| 2.3.468 | 3,5-difluorophenyl | vinyl | methyl | The other unassigned enantiomer [CDCl₃] 3.34 (d, 1H); 3.84 (s, 3H); 3.94 (d, 1H); 5.38 (d, 1H); 5.55 (d, 1H); 6.14 (dd, 1H); 8.88 t, 1H); 7.18 (d, 2H). |
| 2.3.469 | 3,5-difluorophenyl | 2,2-difluoro-vinyl | ethyl | [CDCl₃] 1.33 (t, 3H); 3.46 (d, 1H); 4.02 (d, 1H); 4.23-4.37 (m, 2H); 4.91 (dd, 1H); 6.91 (t, 1H); 7.19 (d, 2H). |
| 2.3.470 | 3,5-difluorophenyl | vinyl | ethyl | [CDCl₃] 1.33 (t, 3H); 3.32 (d, 1H); 3.92 (d, 1H); 4.29 (m, 2H); 5.38 (d, 1H); 5.57 (d, 1H); 6.13 (dd, 1H); 6.89 (m, 1H); 7.19 (m, 2H). |

TABLE 2.3-continued

Inventive compounds of the general formula (I) in which W* is COOY, R¹ R² are each hydrogen, and aryl is the radical.

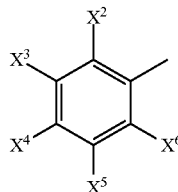

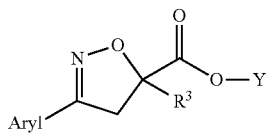

| No. | Aryl | R³ | Y | Physical data |
|---|---|---|---|---|
| 2.3.471 | 3,5-difluorophenyl | 1-methylvinyl | methyl | [CDCl₃] 1.85 (s, 3H); 3.30 (d, 1H); 3.83 (s, 3H); 4.06 (d, 1H); 5.10 (s, 1H); 5.28 (s, 1H); 6.87 (m, 1H); 7.19 (d, 2H). |
| 2.3.472 | 3,5-difluorophenyl | allyl | ethyl | |
| 2.3.473 | 3,5-difluorophenyl | 1-chlorovinyl | methyl | [CDCl₃] 3.53 (d, 1H); 3.88 (s, 3H); 4.22 (d, 1H); 5.55 (s, 1H); 5.93 (s, 1H); 6.90 (m, 1H); 7.20 (d, 2H). |
| 2.3.474 | 3,5-difluorophenyl | ethynyl | ethyl | |
| 2.3.475 | 3-chloro-5-fluorophenyl | vinyl | methyl | [CDCl₃] 3.34 (d, 1H); 3.84 (s, 3H); 3.93 (d, 1H); 5.39 (d, 1H); 5.55 (d, 1H), 6.14 (dd, 1H); 7.14 (d, 1H); 7.30 (d, 1H); 7.41 (s, 1H). |
| 2.3.476 | 3-chloro-5-fluorophenyl | 1-methylvinyl | methyl | [CDCl₃] 1.84 (s, 3H); 3.30 (d, 1H); 3.83 (s, 3H); 4.07 (d, 1H); 5.10 (s, 1H); 5.28 (s, 1H); 7.14 (d, 1H); 7.32 (d, 1H); 7.43 (s, 1H). |
| 2.3.477 | 3-chloro-5-fluorophenyl | allyl | ethyl | |
| 2.3.478 | 3-chloro-5-fluorophenyl | 1-chlorovinyl | ethyl | |
| 2.3.479 | 3-chloro-5-fluorophenyl | ethynyl | ethyl | |
| 2.3.480 | 3-bromo-5-fluorophenyl | vinyl | ethyl | |
| 2.3.481 | 3-bromo-5-fluorophenyl | 1-methylvinyl | ethyl | |
| 2.3.482 | 3-bromo-5-fluorophenyl | allyl | ethyl | |
| 2.3.483 | 3-bromo-5-fluorophenyl | 1-chlorovinyl | ethyl | |
| 2.3.484 | 3-bromo-5-fluorophenyl | ethynyl | ethyl | |
| 2.3.485 | 3-iodo-5-fluorophenyl | vinyl | ethyl | |
| 2.3.486 | 3-methyl-5-fluorophenyl | vinyl | methyl | [CDCl₃] 2.37 (s, 3H); 3.36 (d, 1H); 3.83 (s, 3H); 3.94 (d, 1H); 5.37 (d, 1H); 5.55 (d, 1H); 6.13 (dd, 1H); 6.94 (d, 1H); 7.18 (d, 1H); 7.24 (s, 1H). |
| 2.3.487 | 3-methyl-5-fluorophenyl | 1-methylvinyl | ethyl | |
| 2.3.488 | 3-methyl-5-fluorophenyl | allyl | ethyl | |
| 2.3.489 | 3-methyl-5-fluorophenyl | 1-chlorovinyl | ethyl | |
| 2.3.490 | 3-methyl-5-fluorophenyl | ethynyl | ethyl | |
| 2.3.491 | 3-ethyl-5-fluorophenyl | vinyl | ethyl | |
| 2.3.492 | 3-propyl-5-fluorophenyl | vinyl | ethyl | |
| 2.3.493 | 3-i-propyl-5-fluorophenyl | vinyl | ethyl | |
| 2.3.494 | 3-n-butyl-5-fluorophenyl | vinyl | ethyl | |
| 2.3.495 | 3-isobutyl-5-fluorophenyl | vinyl | ethyl | |
| 2.3.496 | 3-tert-butyl-5-fluorophenyl | vinyl | ethyl | |
| 2.3.497 | 3-cyclopropyl-5-fluorophenyl | vinyl | ethyl | |
| 2.3.498 | 3-vinyl-5-fluorophenyl | vinyl | ethyl | |
| 2.3.499 | 3-ethynyl-5-fluorophenyl | vinyl | ethyl | |
| 2.3.500 | 3-cyano-5-fluorophenyl | vinyl | ethyl | |

TABLE 2.3-continued

Inventive compounds of the general formula (I) in which W* is COOY, $R^1$ $R^2$ are each hydrogen, and aryl is the radical.

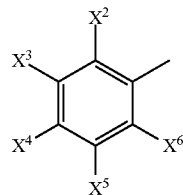

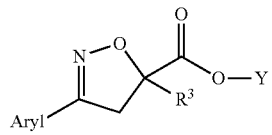

| No. | Aryl | $R^3$ | Y | Physical data |
|---|---|---|---|---|
| 2.3.501 | 3-trifluoromethyl-5-fluorophenyl | vinyl | ethyl | |
| 2.3.502 | 3-trifluoromethyl-5-fluorophenyl | 1-methylvinyl | ethyl | |
| 2.3.503 | 3-trifluoromethyl-5-fluorophenyl | allyl | ethyl | |
| 2.3.504 | 3-trifluoromethyl-5-fluorophenyl | 1-chlorovinyl | ethyl | |
| 2.3.505 | 3-trifluoromethyl-5-fluorophenyl | ethynyl | ethyl | |
| 2.3.506 | 3-(methoxycarbonyl)-5-fluorophenyl | vinyl | ethyl | |
| 2.3.507 | 3-hydroxymethyl-5-fluorophenyl | vinyl | ethyl | |
| 2.3.508 | 3-carbamoyl-5-fluorophenyl | vinyl | ethyl | |
| 2.3.509 | 3-hydroxy-5-fluorophenyl | vinyl | ethyl | |
| 2.3.510 | 3-methoxy-5-fluorophenyl | vinyl | ethyl | |
| 2.3.511 | 3-ethoxy-5-fluorophenyl | vinyl | ethyl | |
| 2.3.512 | 3-n-propoxy-5-fluorophenyl | vinyl | ethyl | |
| 2.3.513 | 3-isopropoxy-5-fluorophenyl | vinyl | ethyl | |
| 2.3.514 | 3-n-butoxy-5-fluorophenyl | vinyl | ethyl | |
| 2.3.515 | 3-isobutoxy-5-fluorophenyl | vinyl | ethyl | |
| 2.3.516 | 3-tert-butoxy-5-fluorophenyl | vinyl | ethyl | |
| 2.3.517 | 3-difluoromethoxy-5-fluorophenyl | vinyl | ethyl | |
| 2.3.518 | 3-trifluoromethoxy-5-fluorophenyl | vinyl | ethyl | |
| 2.3.519 | 3-(2,2,2-trifluoroethoxy)-5-fluorophenyl | vinyl | ethyl | |
| 2.3.520 | 3-(2-chloroethoxy)-5-fluorophenyl | vinyl | ethyl | |
| 2.3.521 | 3-(2-hydroxyethoxy)-5-fluorophenyl | vinyl | ethyl | |
| 2.3.522 | 3-[(tert-butoxycarbonyl)oxy]-5-fluorophenyl | vinyl | ethyl | |
| 2.3.523 | 3-nitro-5-fluorophenyl | vinyl | ethyl | |
| 2.3.524 | 3-acetoxy-5-fluorophenyl | vinyl | ethyl | |
| 2.3.525 | {3-[(tert-butoxy-carbonyl)amino]-5-fluorophenyl} | vinyl | ethyl | |
| 2.3.526 | 3-methylsulfanyl-5-fluorophenyl | vinyl | ethyl | |
| 2.3.527 | 3,5-dichlorophenyl | vinyl | methyl | [CDCl$_3$] 3.34 (d, 1H); 3.84 (s, 3H); 3.93 (d, 1H), 5.39 (d, 1H); 5.55 (d, 1H); 6.14 (dd, 1H); 7.40 (s, 1H); 7.54 (s, 2H). |
| 2.3.528 | 3,5-dichlorophenyl | 1-methylvinyl | methyl | [CDCl$_3$] 1.84 (s, 3H); 3.30 (d, 1H); 3.83 (s, 3H); 4.06 (d, 1H); 5.10 (s, 1H); 5.28 (s, 1H); 7.41 (s, 1H); 7.55 (s, 2H). |
| 2.3.529 | 3,5-dichlorophenyl | allyl | ethyl | |
| 2.3.530 | 3,5-dichlorophenyl | 1-chlorovinyl | ethyl | |
| 2.3.531 | 3,5-dichlorophenyl | ethynyl | ethyl | |
| 2.3.532 | 3-bromo-5-chlorophenyl | vinyl | ethyl | |
| 2.3.533 | 3-iodo-5-chlorophenyl | vinyl | ethyl | |

TABLE 2.3-continued

Inventive compounds of the general formula (I) in which W* is COOY, $R^1$ $R^2$ are each hydrogen, and aryl is the radical.

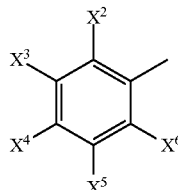

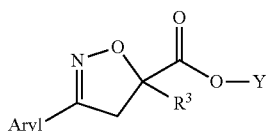

| No. | Aryl | $R^3$ | Y | Physical data |
|---|---|---|---|---|
| 2.3.534 | 3-methyl-5-chlorophenyl | vinyl | methyl | [CDCl$_3$] 2.36 (s, 3H); 3.35 (d, 1H); 3.83 (s, 3H); 3.94 (d, 1H); 5.37 (d, 1H); 5.55 (d, 1H); 6.13 (dd, 1H); 7.22 (s, 1H); 7.38 (s, 1H); 7.43 (s, 1H). |
| 2.3.535 | 3-methyl-5-chlorophenyl | 1-methylvinyl | methyl | [CDCl$_3$] 1.85 (s, 3H); 2.36 (s, 3H); 3.32 (d, 1H); 3.82 (s, 3H); 4.07 (d, 1H); 5.08 (s, 1H); 5.28 (s, 1H); 7.21 (s, 1H); 7.38 (s, 1H); 7.45 (s, 1H). |
| 2.3.536 | 3-ethyl-5-chlorophenyl | vinyl | methyl | [CDCl$_3$] 1.24 (t, 1H); 2.65 (q, 2H); 3.37 (d, 1H); 3.83 (s, 3H); 3.95 (d, 2H); 5.37 (d, 1H); 5.55 (d, 1H); 6.14 (dd, 1H); 7.24 (s, 1H); 7.40 (s, 1H); 7.43 (s, 1H). |
| 2.3.537 | 3-propyl-5-chlorophenyl | vinyl | ethyl | |
| 2.3.538 | 3-isopropyl-5-chlorophenyl | vinyl | ethyl | |
| 2.3.539 | 3-n-butyl-5-chlorophenyl | vinyl | ethyl | |
| 2.3.540 | 3-isobutyl-5-chlorophenyl | vinyl | ethyl | |
| 2.3.541 | 3-tert-butyl-5-chlorophenyl | vinyl | ethyl | |
| 2.3.542 | 3-cyclopropyl-5-chlorophenyl | vinyl | ethyl | |
| 2.3.543 | 3-vinyl-5-chlorophenyl | vinyl | ethyl | |
| 2.3.544 | 3-ethynyl-5-chlorophenyl | vinyl | ethyl | |
| 2.3.545 | 3-cyano-5-chlorophenyl | vinyl | ethyl | |
| 2.3.546 | 3-trifluoromethyl-5-chlorophenyl | vinyl | ethyl | |
| 2.3.547 | 3-(hydroxycarbonyl)-5-chlorophenyl | vinyl | ethyl | |
| 2.3.548 | 3-(methoxycarbonyl)-5-chlorophenyl | vinyl | ethyl | |
| 2.3.549 | 3-hydroxymethyl-5-chlorophenyl | vinyl | ethyl | |
| 2.3.550 | 3-carbamoyl-5-chlorophenyl | vinyl | ethyl | |
| 2.3.551 | 3-hydroxy-5-chlorophenyl | vinyl | ethyl | |
| 2.3.552 | 3-methoxy-5-chlorophenyl | vinyl | ethyl | |
| 2.3.553 | 3-ethoxy-5-chlorophenyl | vinyl | ethyl | |
| 2.3.554 | 3-n-propoxy-5-chlorophenyl | vinyl | ethyl | |
| 2.3.555 | 3-isopropoxy-5-chlorophenyl | vinyl | ethyl | |
| 2.3.556 | 3-n-butoxy-5-chlorophenyl | vinyl | ethyl | |
| 2.3.557 | 3-isobutoxy-5-chlorophenyl | vinyl | ethyl | |
| 2.3.558 | 3-tert-butoxy-5-chlorophenyl | vinyl | ethyl | |
| 2.3.559 | 3-difluoromethoxy-5-chlorophenyl | vinyl | ethyl | |
| 2.3.560 | 3-trifluoromethoxy-5-chlorophenyl | vinyl | ethyl | |
| 2.3.561 | 3-(2,2,2-trifluoroethoxy)-5-chlorophenyl | vinyl | ethyl | |
| 2.3.562 | 3-(2-chloroethoxy)-5-chlorophenyl | vinyl | ethyl | |
| 2.3.563 | 3-(2-hydroxyethoxy)-5-chlorophenyl | vinyl | ethyl | |

TABLE 2.3-continued

Inventive compounds of the general formula (I) in which W* is COOY, R¹
R² are each hydrogen, and aryl is the radical.

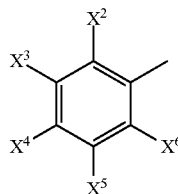

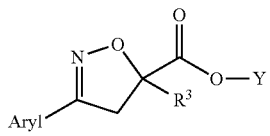

| No. | Aryl | R³ | Y | Physical data |
|---|---|---|---|---|
| 2.3.564 | 3-[(tert-butoxycarbonyl)oxy]-5-chlorophenyl | vinyl | ethyl | |
| 2.3.565 | 3-nitro-5-chlorophenyl | vinyl | ethyl | |
| 2.3.566 | 3-acetoxy-5-chlorophenyl | vinyl | ethyl | |
| 2.3.567 | {3-[(tert-butoxy-carbonyl)amino]-5-chlorophenyl} | vinyl | ethyl | |
| 2.3.568 | 3-methylsulfanyl-5-chlorophenyl | vinyl | ethyl | |
| 2.3.569 | 3,5-dibromophenyl | vinyl | ethyl | |
| 2.3.570 | 3,5-dibromophenyl | 1-methylvinyl | ethyl | |
| 2.3.571 | 3-iodo-5-bromophenyl | vinyl | ethyl | |
| 2.3.572 | 3-methyl-5-bromophenyl | vinyl | methyl | [CDCl₃] 2.35 (s, 3H), 3.35 (d, 1H); 3.83 (s, 3H); 3.93 (d, 1H); 5.35 (d, 1H), 5.55 (d, 1H); 6.13 (dd, 1H); 7.38 (s, 1H), 7.42 (s, 1H); 7.58 (s, 1H). |
| 2.3.573 | 3-methyl-5-bromophenyl | 1-methylvinyl | methyl | [CDCl₃] 1.84 (s, 3H); 2.35 (s, 3H); 3.31 (d, 1H); 3.82 (s, 3H); 4.07 (d, 1H); 5.08 (s, 1H); 5.28 (s, 1H); 7.38 (s, 1H), 7.43 (s, 1H); 7.59 (s, 1H). |
| 2.3.574 | 3-methyl-5-bromophenyl | allyl | ethyl | |
| 2.3.575 | 3-methyl-5-bromophenyl | 1-chlorovinyl | ethyl | |
| 2.3.576 | 3-methyl-5-bromophenyl | ethynyl | ethyl | |
| 2.3.577 | 3-ethyl-5-bromophenyl | vinyl | ethyl | |
| 2.3.578 | 3-propyl-5-bromophenyl | vinyl | ethyl | |
| 2.3.579 | 3-isopropyl-5-bromophenyl | vinyl | ethyl | |
| 2.3.580 | 3-n-butyl-5-bromophenyl | vinyl | ethyl | |
| 2.3.581 | 3-isobutyl-5-bromophenyl | vinyl | ethyl | |
| 2.3.582 | 3-tert-butyl-5-bromophenyl | vinyl | ethyl | |
| 2.3.583 | 3-cyclopropyl-5-bromophenyl | vinyl | ethyl | |
| 2.3.584 | 3-vinyl-5-bromophenyl | vinyl | ethyl | |
| 2.3.585 | 3-ethynyl-5-bromophenyl | vinyl | ethyl | |
| 2.3.586 | 3-cyano-5-bromophenyl | vinyl | ethyl | |
| 2.3.587 | 3-trifluoromethyl-5-bromophenyl | vinyl | ethyl | |
| 2.3.588 | 3-(hydroxycarbonyl)-5-bromophenyl | vinyl | ethyl | |
| 2.3.589 | 3-(methoxycarbonyl)-5-bromophenyl | vinyl | ethyl | |
| 2.3.590 | 3-hydroxymethyl-5-bromophenyl | vinyl | ethyl | |
| 2.3.591 | 3-carbamoyl-5-bromophenyl | vinyl | ethyl | |
| 2.3.592 | 3-hydroxy-5-bromophenyl | vinyl | ethyl | |
| 2.3.593 | 3-methoxy-5-bromophenyl | vinyl | ethyl | |
| 2.3.594 | 3-ethoxy-5-bromophenyl | vinyl | ethyl | |
| 2.3.595 | 3-n-propoxy-5-bromophenyl | vinyl | ethyl | |
| 2.3.596 | 3-isopropoxy-5-bromophenyl | vinyl | ethyl | |
| 2.3.597 | 3-n-butoxy-5-bromophenyl | vinyl | ethyl | |
| 2.3.598 | 3-isobutoxy-5-bromophenyl | vinyl | ethyl | |
| 2.3.599 | 3-tert-butoxy-5-bromophenyl | vinyl | ethyl | |
| 2.3.600 | 3-difluoromethoxy-5-bromophenyl | vinyl | ethyl | |

TABLE 2.3-continued

Inventive compounds of the general formula (I) in which W* is COOY, $R^1$ $R^2$ are each hydrogen, and aryl is the radical.

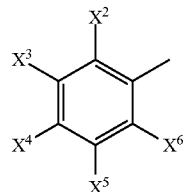

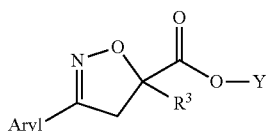

| No. | Aryl | $R^3$ | Y | Physical data |
|---|---|---|---|---|
| 2.3.601 | 3-trifluoromethoxy-5-bromophenyl | vinyl | ethyl | |
| 2.3.602 | 3-(2,2,2-trifluoroethoxy)-5-bromophenyl | vinyl | ethyl | |
| 2.3.603 | 3-(2-chloroethoxy)-5-bromophenyl | vinyl | ethyl | |
| 2.3.604 | 3-(2-hydroxyethoxy)-5-bromophenyl | vinyl | ethyl | |
| 2.3.605 | 3-[(tert-butoxycarbonyl)oxy]-5-bromophenyl | vinyl | ethyl | |
| 2.3.606 | 3-nitro-5-bromophenyl | vinyl | ethyl | |
| 2.3.607 | 3-acetoxy-5-bromophenyl | vinyl | ethyl | |
| 2.3.608 | {3-[(tert-butoxy-carbonyl)amino]-5-bromophenyl} | vinyl | ethyl | |
| 2.3.609 | 3-methylsulfanyl-5-bromophenyl | vinyl | ethyl | |
| 2.3.610 | 3,5-diiodophenyl | vinyl | ethyl | |
| 2.3.611 | 3-methyl-5-iodophenyl | vinyl | ethyl | |
| 2.3.612 | 3-ethyl-5-iodophenyl | vinyl | ethyl | |
| 2.3.613 | 3-propyl-5-iodophenyl | vinyl | ethyl | |
| 2.3.614 | 3-isopropyl-5-iodophenyl | vinyl | ethyl | |
| 2.3.615 | 3-n-butyl-5-iodophenyl | vinyl | ethyl | |
| 2.3.616 | 3-isobutyl-5-iodophenyl | vinyl | ethyl | |
| 2.3.617 | 3-tert-butyl-5-iodophenyl | vinyl | ethyl | |
| 2.3.618 | 3-cyclopropyl-5-iodophenyl | vinyl | ethyl | |
| 2.3.619 | 3-vinyl-5-iodophenyl | vinyl | ethyl | |
| 2.3.620 | 3-ethynyl-5-iodophenyl | vinyl | ethyl | |
| 2.3.621 | 3-cyano-5-iodophenyl | vinyl | ethyl | |
| 2.3.622 | 3-trifluoromethyl-5-iodophenyl | vinyl | ethyl | |
| 2.3.623 | 3-(hydroxycarbonyl)-5-iodophenyl | vinyl | ethyl | |
| 2.3.624 | 3-(methoxycarbonyl)-5-iodophenyl | vinyl | ethyl | |
| 2.3.625 | 3-hydroxymethyl-5-iodophenyl | vinyl | ethyl | |
| 2.3.626 | 3-carbamoyl-5-iodophenyl | vinyl | ethyl | |
| 2.3.627 | 3-hydroxy-5-iodophenyl | vinyl | ethyl | |
| 2.3.628 | 3-methoxy-5-iodophenyl | vinyl | ethyl | |
| 2.3.629 | 3-ethoxy-5-iodophenyl | vinyl | ethyl | |
| 2.3.630 | 3-n-propoxy-5-iodophenyl | vinyl | ethyl | |
| 2.3.631 | 3-isopropoxy-5-iodophenyl | vinyl | ethyl | |
| 2.3.632 | 3-n-butoxy-5-iodophenyl | vinyl | ethyl | |
| 2.3.633 | 3-isobutoxy-5-iodophenyl | vinyl | ethyl | |
| 2.3.634 | 3-tert-butoxy-5-iodophenyl | vinyl | ethyl | |
| 2.3.635 | 3-difluoromethoxy-5-iodophenyl | vinyl | ethyl | |
| 2.3.636 | 3-trifluoromethoxy-5-iodophenyl | vinyl | ethyl | |
| 2.3.637 | 3-(2,2,2-trifluoroethoxy)-5-iodophenyl | vinyl | ethyl | |
| 2.3.638 | 3-(2-chloroethoxy)-5-iodophenyl | vinyl | ethyl | |
| 2.3.639 | 3-(2-hydroxyethoxy)-5-iodophenyl | vinyl | ethyl | |
| 2.3.640 | 3-[(tert-butoxycarbonyl)oxy]-5-iodophenyl | vinyl | ethyl | |
| 2.3.641 | 3-nitro-5-iodophenyl | vinyl | ethyl | |
| 2.3.642 | 3-acetoxy-5-iodophenyl | vinyl | ethyl | |
| 2.3.643 | {3-[(tert-butoxy-carbonyl)amino]-5-iodophenyl} | vinyl | ethyl | |

TABLE 2.3-continued

Inventive compounds of the general formula (I) in which W* is COOY, R¹ R² are each hydrogen, and aryl is the radical.

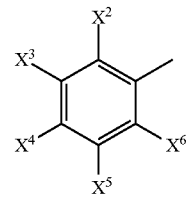

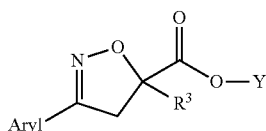

| No. | Aryl | R³ | Y | Physical data |
|---|---|---|---|---|
| 2.3.644 | 3-methylsulfanyl-5-iodophenyl | vinyl | ethyl | |
| 2.3.645 | 3,5-dimethylphenyl | vinyl | methyl | [CDCl₃] 2.33 (s, 6H); 3.38 (d, 1H); 3.83 (s, 3H); 3.96 (d, 1H); 5.35 (d, 1H); 5.55 (d, 1H); 6.15 (dd, 1H); 7.06 (s, 1H); 7.28 (s, 2H). |
| 2.3.646 | 3-ethyl-5-methylphenyl | vinyl | ethyl | |
| 2.3.647 | 3-propyl-5-methylphenyl | vinyl | ethyl | |
| 2.3.648 | 3-isopropyl-5-methylphenyl | vinyl | ethyl | |
| 2.3.649 | 3-n-butyl-5-methylphenyl | vinyl | ethyl | |
| 2.3.650 | 3-isobutyl-5-methylphenyl | vinyl | ethyl | |
| 2.3.651 | 3-tert-butyl-5-methylphenyl | vinyl | ethyl | |
| 2.3.652 | 3-cyclopropyl-5-methylphenyl | vinyl | ethyl | |
| 2.3.653 | 3-cyano-5-methylphenyl | vinyl | ethyl | |
| 2.3.654 | 3-trifluoromethyl-5-methylphenyl | vinyl | ethyl | |
| 2.3.655 | 3-(methoxycarbonyl)-5-methylphenyl | vinyl | ethyl | |
| 2.3.656 | 3-methoxy-5-methylphenyl | vinyl | ethyl | |
| 2.3.657 | 3-ethoxy-5-methylphenyl | vinyl | ethyl | |
| 2.3.658 | 3-n-propoxy-5-methylphenyl | vinyl | ethyl | |
| 2.3.659 | 3-n-butoxy-5-methylphenyl | vinyl | ethyl | |
| 2.3.660 | 3-isobutoxy-5-methylphenyl | vinyl | ethyl | |
| 2.3.661 | 3-difluoromethoxy-5-methylphenyl | vinyl | ethyl | |
| 2.3.662 | 3-trifluoromethoxy-5-methylphenyl | vinyl | ethyl | |
| 2.3.663 | 3-nitro-5-methylphenyl | vinyl | ethyl | |
| 2.3.664 | 3-acetoxy-5-methylphenyl | vinyl | ethyl | |
| 2.3.665 | 3-methylsulfanyl-5-methylphenyl | vinyl | ethyl | |
| 2.3.666 | 3,5-diethylphenyl | vinyl | ethyl | |
| 2.3.667 | 3-propyl-5-ethylphenyl | vinyl | ethyl | |
| 2.3.668 | 3-isopropyl-5-ethylphenyl | vinyl | ethyl | |
| 2.3.669 | 3-n-butyl-5-ethylphenyl | vinyl | ethyl | |
| 2.3.670 | 3-isobutyl-5-ethylphenyl | vinyl | ethyl | |
| 2.3.671 | 3-tert-butyl-5-ethylphenyl | vinyl | ethyl | |
| 2.3.672 | 3-cyclopropyl-5-ethylphenyl | vinyl | ethyl | |
| 2.3.673 | 3-cyano-5-ethylphenyl | vinyl | ethyl | |
| 2.3.674 | 3-trifluoromethyl-5-ethylphenyl | vinyl | ethyl | |
| 2.3.675 | 3-(methoxycarbonyl)-5-ethylphenyl | vinyl | ethyl | |
| 2.3.676 | 3-methoxy-5-ethylphenyl | vinyl | ethyl | |
| 2.3.677 | 3-ethoxy-5-ethylphenyl | vinyl | ethyl | |
| 2.3.678 | 3-n-propoxy-5-ethylphenyl | vinyl | ethyl | |
| 2.3.679 | 3-n-butoxy-5-ethylphenyl | vinyl | ethyl | |
| 2.3.680 | 3-isobutoxy-5-ethylphenyl | vinyl | ethyl | |
| 2.3.681 | 3-difluoromethoxy-5-ethylphenyl | vinyl | ethyl | |
| 2.3.682 | 3-trifluoromethoxy-5-ethylphenyl | vinyl | ethyl | |
| 2.3.683 | 3-nitro-5-ethylphenyl | vinyl | ethyl | |
| 2.3.684 | 3-acetoxy-5-ethylphenyl | vinyl | ethyl | |
| 2.3.685 | 3-methylsulfanyl-5-ethylphenyl | vinyl | ethyl | |
| 2.3.686 | 3,5-dipropylphenyl | vinyl | ethyl | |
| 2.3.687 | 3-isopropyl-5-propylphenyl | vinyl | ethyl | |
| 2.3.688 | 3-n-butyl-5-propylphenyl | vinyl | ethyl | |
| 2.3.689 | 3-isobutyl-5-propylphenyl | vinyl | ethyl | |
| 2.3.690 | 3-tert-butyl-5-propylphenyl | vinyl | ethyl | |

TABLE 2.3-continued

Inventive compounds of the general formula (I) in which W* is COOY, R¹ R² are each hydrogen, and aryl is the radical.

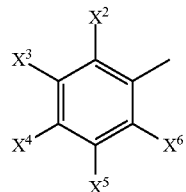

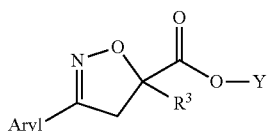

| No. | Aryl | R³ | Y | Physical data |
|---|---|---|---|---|
| 2.3.691 | 3-cyclopropyl-5-propylphenyl | vinyl | ethyl | |
| 2.3.692 | 3-cyano-5-propylphenyl | vinyl | ethyl | |
| 2.3.693 | 3-trifluoromethyl-5-propylphenyl | vinyl | ethyl | |
| 2.3.694 | 3-(methoxycarbonyl)-5-propylphenyl | vinyl | ethyl | |
| 2.3.695 | 3-methoxy-5-propylphenyl | vinyl | ethyl | |
| 2.3.696 | 3-ethoxy-5-propylphenyl | vinyl | ethyl | |
| 2.3.697 | 3-n-propoxy-5-propylphenyl | vinyl | ethyl | |
| 2.3.698 | 3-n-butoxy-5-propylphenyl | vinyl | ethyl | |
| 2.3.699 | 3-isobutoxy-5-propylphenyl | vinyl | ethyl | |
| 2.3.700 | 3-difluoromethoxy-5-propylphenyl | vinyl | ethyl | |
| 2.3.701 | 3-trifluoromethoxy-5-ethylphenyl | vinyl | ethyl | |
| 2.3.702 | 3-nitro-5-propylphenyl | vinyl | ethyl | |
| 2.3.703 | 3-acetoxy-5-propylphenyl | vinyl | ethyl | |
| 2.3.704 | 3-methylsulfanyl-5-propylphenyl | vinyl | ethyl | |
| 2.3.705 | 3,5-diisopropylphenyl | vinyl | ethyl | |
| 2.3.706 | 3-n-butyl-5-isopropylphenyl | vinyl | ethyl | |
| 2.3.707 | 3-isobutyl-5-isopropylphenyl | vinyl | ethyl | |
| 2.3.708 | 3-tert-butyl-5-isopropylphenyl | vinyl | ethyl | |
| 2.3.709 | 3-cyclopropyl-5-isopropylphenyl | vinyl | ethyl | |
| 2.3.710 | 3-cyano-5-isopropylphenyl | vinyl | ethyl | |
| 2.3.711 | 3-trifluoromethyl-5-isopropylphenyl | vinyl | ethyl | |
| 2.3.712 | 3-(methoxycarbonyl)-5-isopropylphenyl | vinyl | ethyl | |
| 2.3.713 | 3-methoxy-5-isopropylphenyl | vinyl | ethyl | |
| 2.3.714 | 3-ethoxy-5-isopropylphenyl | vinyl | ethyl | |
| 2.3.715 | 3-n-propoxy-5-isopropylphenyl | vinyl | ethyl | |
| 2.3.716 | 3-n-butoxy-5-isopropylphenyl | vinyl | ethyl | |
| 2.3.717 | 3-isobutoxy-5-isopropylphenyl | vinyl | ethyl | |
| 2.3.718 | 3-difluoromethoxy-5-isopropylphenyl | vinyl | ethyl | |
| 2.3.719 | 3-trifluoromethoxy-5-isopropylphenyl | vinyl | ethyl | |
| 2.3.720 | 3-nitro-5-isopropylphenyl | vinyl | ethyl | |
| 2.3.721 | 3-acetoxy-5-isopropylphenyl | vinyl | ethyl | |
| 2.3.722 | 3-methylsulfanyl-5-isopropylphenyl | vinyl | ethyl | |
| 2.3.723 | 3,5-dibutylphenyl | vinyl | ethyl | |
| 2.3.724 | 3-isobutyl-5-butylphenyl | vinyl | ethyl | |
| 2.3.725 | 3-tert-butyl-5-butylphenyl | vinyl | ethyl | |
| 2.3.726 | 3-cyclopropyl-5-butylphenyl | vinyl | ethyl | |
| 2.3.727 | 3-cyano-5-butylphenyl | vinyl | ethyl | |
| 2.3.728 | 3-trifluoromethyl-5-butylphenyl | vinyl | ethyl | |
| 2.3.729 | 3-(methoxycarbonyl)-5-butylphenyl | vinyl | ethyl | |
| 2.3.730 | 3-methoxy-5-butylphenyl | vinyl | ethyl | |
| 2.3.731 | 3-ethoxy-5-butylphenyl | vinyl | ethyl | |
| 2.3.732 | 3-n-propoxy-5-butylphenyl | vinyl | ethyl | |
| 2.3.733 | 3-n-butoxy-5-butylphenyl | vinyl | ethyl | |
| 2.3.734 | 3-isobutoxy-5-butylphenyl | vinyl | ethyl | |
| 2.3.735 | 3-difluoromethoxy-5-butylphenyl | vinyl | ethyl | |
| 2.3.736 | 3-trifluoromethoxy-5-butylphenyl | vinyl | ethyl | |
| 2.3.737 | 3-nitro-5-butylphenyl | vinyl | ethyl | |
| 2.3.738 | 3-acetoxy-5-butylphenyl | vinyl | ethyl | |
| 2.3.739 | 3-methylsulfanyl-5-butylphenyl | vinyl | ethyl | |

TABLE 2.3-continued

Inventive compounds of the general formula (I) in which W* is COOY, R¹ R² are each hydrogen, and aryl is the radical.

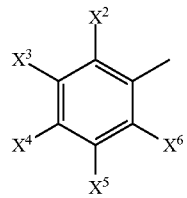

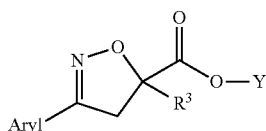

| No. | Aryl | R³ | Y | Physical data |
|---|---|---|---|---|
| 2.3.740 | 3,5-diisobutylphenyl | vinyl | ethyl | |
| 2.3.741 | 3-tert-butyl-5-isobutylphenyl | vinyl | ethyl | |
| 2.3.742 | 3-cyclopropyl-5-isobutylphenyl | vinyl | ethyl | |
| 2.3.743 | 3-cyano-5-isobutylphenyl | vinyl | ethyl | |
| 2.3.744 | 3-trifluoromethyl-5-isobutylphenyl | vinyl | ethyl | |
| 2.3.745 | 3-(methoxycarbonyl)-5-isobutylphenyl | vinyl | ethyl | |
| 2.3.746 | 3-methoxy-5-isobutylphenyl | vinyl | ethyl | |
| 2.3.747 | 3-ethoxy-5-isobutylphenyl | vinyl | ethyl | |
| 2.3.748 | 3-n-propoxy-5-isobutylphenyl | vinyl | ethyl | |
| 2.3.749 | 3-n-butoxy-5-isobutylphenyl | vinyl | ethyl | |
| 2.3.750 | 3-isobutoxy-5-isobutylphenyl | vinyl | ethyl | |
| 2.3.751 | 3-difluoromethoxy-5-isobutylphenyl | vinyl | ethyl | |
| 2.3.752 | 3-trifluoromethoxy-5-isobutylphenyl | vinyl | ethyl | |
| 2.3.753 | 3-nitro-5-isobutylphenyl | vinyl | ethyl | |
| 2.3.754 | 3-acetoxy-5-isobutylphenyl | vinyl | ethyl | |
| 2.3.755 | 3-methylsulfanyl-5-isobutylphenyl | vinyl | ethyl | |
| 2.3.756 | 3,5-di(tert-butyl)phenyl | vinyl | ethyl | |
| 2.3.757 | 3-cyclopropyl-5-tert-butylphenyl | vinyl | ethyl | |
| 2.3.758 | 3-cyano-5-tert-butylphenyl | vinyl | ethyl | |
| 2.3.759 | 3-trifluoromethyl-5-tert-butylphenyl | vinyl | ethyl | |
| 2.3.760 | 3-(methoxycarbonyl)-5-tert-butylphenyl | vinyl | ethyl | |
| 2.3.761 | 3-methoxy-5-tert-butylphenyl | vinyl | ethyl | |
| 2.3.762 | 3-ethoxy-5-tert-butylphenyl | vinyl | ethyl | |
| 2.3.763 | 3-n-propoxy-5-tert-butylphenyl | vinyl | ethyl | |
| 2.3.764 | 3-n-butoxy-5-tert-butylphenyl | vinyl | ethyl | |
| 2.3.765 | 3-isobutoxy-5-tert-butylphenyl | vinyl | ethyl | |
| 2.3.766 | 3-difluoromethoxy-5-tert-butylphenyl | vinyl | ethyl | |
| 2.3.767 | 3-trifluoromethoxy-5-tert-butylphenyl | vinyl | ethyl | |
| 2.3.768 | 3-nitro-5-tert-butylphenyl | vinyl | ethyl | |
| 2.3.769 | 3-acetoxy-5-tert-butylphenyl | vinyl | ethyl | |
| 2.3.770 | 3-methylsulfanyl-5-tert-butylphenyl | vinyl | ethyl | |
| 2.3.771 | 3-tert-butyl-5-cyclopropylphenyl | vinyl | ethyl | |
| 2.3.772 | 3,5-dicyclopropyl-phenyl | vinyl | ethyl | |
| 2.3.773 | 3-cyano-5-cyclopropylphenyl | vinyl | ethyl | |
| 2.3.774 | 3-trifluoromethyl-5-cyclopropylphenyl | vinyl | ethyl | |
| 2.3.775 | 3-(methoxycarbonyl)-5-cyclopropylphenyl | vinyl | ethyl | |
| 2.3.776 | 3-methoxy-5-cyclopropylphenyl | vinyl | ethyl | |
| 2.3.777 | 3-ethoxy-5-cyclopropylphenyl | vinyl | ethyl | |
| 2.3.778 | 3-n-propoxy-5-cyclopropylphenyl | vinyl | ethyl | |
| 2.3.779 | 3-n-butoxy-5-cyclopropylphenyl | vinyl | ethyl | |
| 2.3.780 | 3-isobutoxy-5-cyclopropylphenyl | vinyl | ethyl | |
| 2.3.781 | 3-difluoromethoxy-5-cyclopropylphenyl | vinyl | ethyl | |
| 2.3.782 | 3-trifluoromethoxy-5-cyclopropylphenyl | vinyl | ethyl | |

TABLE 2.3-continued

Inventive compounds of the general formula (I) in which W* is COOY, R¹ R² are each hydrogen, and aryl is the radical.

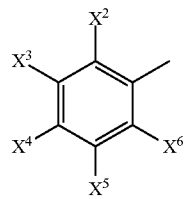

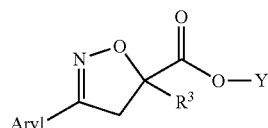

| No. | Aryl | R³ | Y | Physical data |
|---|---|---|---|---|
| 2.3.783 | 3-nitro-5-cyclopropylphenyl | vinyl | ethyl | |
| 2.3.784 | 3-acetoxy-5-cyclopropylphenyl | vinyl | ethyl | |
| 2.3.785 | 3-methylsulfanyl-5-cyclopropylphenyl | vinyl | ethyl | |
| 2.3.786 | 3,5-dicyanophenyl | vinyl | ethyl | |
| 2.3.787 | 3-trifluoromethyl-5-cyanophenyl | vinyl | ethyl | |
| 2.3.788 | 3-(methoxycarbonyl)-5-cyanophenyl | vinyl | ethyl | |
| 2.3.789 | 3-methoxy-5-cyanophenyl | vinyl | ethyl | |
| 2.3.790 | 3-ethoxy-5-cyanophenyl | vinyl | ethyl | |
| 2.3.791 | 3-n-propoxy-5-cyanophenyl | vinyl | ethyl | |
| 2.3.792 | 3-n-butoxy-5-cyanophenyl | vinyl | ethyl | |
| 2.3.793 | 3-isobutoxy-5-cyanophenyl | vinyl | ethyl | |
| 2.3.794 | 3-difluoromethoxy-5-cyanophenyl | vinyl | ethyl | |
| 2.3.795 | 3-trifluoromethoxy-5-cyanophenyl | vinyl | ethyl | |
| 2.3.796 | 3-nitro-5-cyanophenyl | vinyl | ethyl | |
| 2.3.797 | 3-acetoxy-5-cyanophenyl | vinyl | ethyl | |
| 2.3.798 | 3-methylsulfanyl-5-cyanophenyl | vinyl | ethyl | |
| 2.3.799 | 3,5-di(trifluoromethyl)-phenyl | vinyl | ethyl | |
| 2.3.800 | 3-(methoxycarbonyl)-5-trifluoromethyl-phenyl | vinyl | ethyl | |
| 2.3.801 | 3-methoxy-5-trifluoromethylphenyl | vinyl | ethyl | |
| 2.3.802 | 3-ethoxy-5-trifluoromethylphenyl | vinyl | ethyl | |
| 2.3.803 | 3-n-propoxy-5-trifluoromethylphenyl | vinyl | ethyl | |
| 2.3.804 | 3-isobutoxy-5-trifluoromethylphenyl | vinyl | ethyl | |
| 2.3.805 | 3-difluoromethoxy-5-trifluoromethylphenyl | vinyl | ethyl | |
| 2.3.806 | 3-trifluoromethoxy-5-trifluoromethylphenyl | vinyl | ethyl | |
| 2.3.807 | 3-nitro-5-trifluoromethylphenyl | vinyl | ethyl | |
| 2.3.808 | 3-acetoxy-5-trifluoromethylphenyl | vinyl | ethyl | |
| 2.3.809 | 3-methylsulfanyl-5-trifluoromethylphenyl | vinyl | ethyl | |
| 2.3.810 | 3,5-di(methoxycarbonyl)phenyl | vinyl | ethyl | |
| 2.3.811 | 3-methoxy-5-(methoxycarbonyl)-phenyl | vinyl | ethyl | |
| 2.3.812 | 3-ethoxy-5-(methoxycarbonyl)-phenyl | vinyl | ethyl | |
| 2.3.813 | 3-n-propoxy-5-(methoxycarbonyl)-phenyl | vinyl | ethyl | |
| 2.3.814 | 3-n-butoxy-5-(methoxycarbonyl)-phenyl | vinyl | ethyl | |
| 2.3.815 | 3-isobutoxy-5-(methoxycarbonyl)-phenyl | vinyl | ethyl | |
| 2.3.816 | 3-difluoromethoxy-5-(methoxycarbonyl)-phenyl | vinyl | ethyl | |
| 2.3.817 | 3-trifluoromethoxy-5-(methoxycarbonyl)-phenyl | vinyl | ethyl | |

TABLE 2.3-continued

Inventive compounds of the general formula (I) in which W* is COOY, R¹ R² are each hydrogen, and aryl is the radical.

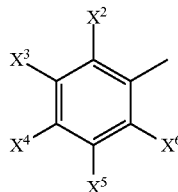

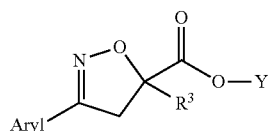

| No. | Aryl | R³ | Y | Physical data |
|---|---|---|---|---|
| 2.3.818 | 3-nitro-5-(methoxy-carbonyl)phenyl | vinyl | ethyl | |
| 2.3.819 | 3-acetoxy-5-(methoxycarbonyl)-phenyl | vinyl | ethyl | |
| 2.3.820 | 3-methylsulfanyl-5-(methoxycarbonyl)-phenyl | vinyl | ethyl | |
| 2.3.821 | 3,5-dimethoxyphenyl | vinyl | ethyl | |
| 2.3.822 | 3-ethoxy-5-methoxyphenyl | vinyl | ethyl | |
| 2.3.823 | 3-n-propoxy-5-methoxyphenyl | vinyl | ethyl | |
| 2.3.824 | 3-n-butoxy-5-methoxyphenyl | vinyl | ethyl | |
| 2.3.825 | 3-isobutoxy-5-methoxyphenyl | vinyl | ethyl | |
| 2.3.826 | 3-difluoromethoxy-5-methoxyphenyl | vinyl | ethyl | |
| 2.3.827 | 3-trifluoromethoxy-5-methoxyphenyl | vinyl | ethyl | |
| 2.3.828 | 3-nitro-5-methoxyphenyl | vinyl | ethyl | |
| 2.3.829 | 3-acetoxy-5-methoxyphenyl | vinyl | ethyl | |
| 2.3.830 | 3-methylsulfanyl-5-methoxyphenyl | vinyl | ethyl | |
| 2.3.831 | 3,5-diethoxyphenyl | vinyl | ethyl | |
| 2.3.832 | 3-n-propoxy-5-ethoxyphenyl | vinyl | ethyl | |
| 2.3.833 | 3-n-butoxy-5-ethoxyphenyl | vinyl | ethyl | |
| 2.3.834 | 3-isobutoxy-5-ethoxyphenyl | vinyl | ethyl | |
| 2.3.835 | 3-difluoromethoxy-5-ethoxyphenyl | vinyl | ethyl | |
| 2.3.836 | 3-trifluoromethoxy-5-ethoxyphenyl | vinyl | ethyl | |
| 2.3.837 | 3-nitro-5-ethoxyphenyl | vinyl | ethyl | |
| 2.3.838 | 3-acetoxy-5-ethoxyphenyl | vinyl | ethyl | |
| 2.3.839 | 3-methylsulfanyl-5-ethoxyphenyl | vinyl | ethyl | |
| 2.3.840 | 3,5-di(isopropoxy)phenyl | vinyl | ethyl | |
| 2.3.841 | 3-n-butoxy-5-isopropoxyphenyl | vinyl | ethyl | |
| 2.3.842 | 3-isobutoxy-5-isopropoxyphenyl | vinyl | ethyl | |
| 2.3.843 | 3-difluoromethoxy-5-isopropoxyphenyl | vinyl | ethyl | |
| 2.3.844 | 3-trifluoromethoxy-5-isopropoxyphenyl | vinyl | ethyl | |
| 2.3.845 | 3-nitro-5-isopropoxyphenyl | vinyl | ethyl | |
| 2.3.846 | 3-acetoxy-5-isopropoxyphenyl | vinyl | ethyl | |
| 2.3.847 | 3-methylsulfanyl-5-isopropoxyphenyl | vinyl | ethyl | |
| 2.3.848 | 3,5-di(trifluoro-methoxy)phenyl | vinyl | ethyl | |
| 2.3.849 | 3-nitro-5-trifluoro-methoxyphenyl | vinyl | ethyl | |
| 2.3.850 | 3-methylsulfanyl-5-trifluoromethoxy-phenyl | vinyl | ethyl | |
| 2.3.851 | 3,5-bis(difluoro-methoxy)phenyl | vinyl | ethyl | |
| 2.3.852 | 3,5-bis(difluoro-methoxy)phenyl | 1-methylvinyl | ethyl | |
| 2.3.853 | 3,5-bis(difluoro-methoxy)phenyl | allyl | ethyl | |
| 2.3.854 | 3,5-bis(difluoro-methoxy)phenyl | 1-chlorovinyl | ethyl | |
| 2.3.855 | 3-trifluoromethoxy-5-difluoromethoxy-phenyl | vinyl | ethyl | |
| 2.3.856 | 3-nitro-5-difluoro-methoxyphenyl | vinyl | ethyl | |
| 2.3.857 | 3-acetoxy-5-difluoromethoxy-phenyl | vinyl | ethyl | |
| 2.3.858 | 3-methylsulfanyl-5-difluoromethoxy-phenyl | vinyl | ethyl | |
| 2.3.859 | 3,5-bis(acetoxy)phenyl | vinyl | ethyl | |

TABLE 2.3-continued

Inventive compounds of the general formula (I) in which W* is COOY, $R^1$ $R^2$ are each hydrogen, and aryl is the radical.

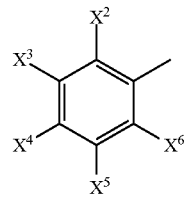

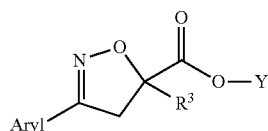

| No. | Aryl | $R^3$ | Y | Physical data |
|---|---|---|---|---|
| 2.3.860 | 3-methylsulfanyl-5-acetoxyphenyl | vinyl | ethyl | |
| 2.3.861 | 3,5-dinitrophenyl | vinyl | ethyl | |
| 2.3.862 | 3-acetoxy-5-nitrophenyl | vinyl | ethyl | |
| 2.3.863 | 3-methylsulfanyl-5-nitrophenyl | vinyl | ethyl | |
| 2.3.864 | 3,5-di(methylsulfanyl)phenyl | vinyl | ethyl | |
| 2.3.865 | 3,4-difluorophenyl | vinyl | ethyl | |
| 2.3.866 | 3,4-difluorophenyl | 1-methylvinyl | ethyl | |
| 2.3.867 | 3,4-difluorophenyl | allyl | ethyl | |
| 2.3.868 | 3,4-difluorophenyl | 1-chlorovinyl | ethyl | |
| 2.3.869 | 3,4-difluorophenyl | ethynyl | ethyl | |
| 2.3.870 | 3-chloro-4-fluorophenyl | vinyl | ethyl | |
| 2.3.871 | 3-chloro-4-fluorophenyl | 1-methylvinyl | ethyl | |
| 2.3.872 | 3-chloro-4-fluorophenyl | allyl | ethyl | |
| 2.3.873 | 3-chloro-4-fluorophenyl | 1-chlorovinyl | ethyl | |
| 2.3.874 | 3-chloro-4-fluorophenyl | ethynyl | ethyl | |
| 2.3.875 | 3-bromo-4-fluorophenyl | vinyl | ethyl | |
| 2.3.876 | 3-methyl-4-fluorophenyl | vinyl | ethyl | |
| 2.3.877 | 3-methyl-4-fluorophenyl | 1-methylvinyl | ethyl | |
| 2.3.878 | 3-ethyl-4-fluorophenyl | vinyl | ethyl | |
| 2.3.879 | 3-cyclopropyl-4-fluorophenyl | vinyl | ethyl | |
| 2.3.880 | 3-cyano-4-fluorophenyl | vinyl | ethyl | |
| 2.3.881 | 3-methoxy-4-fluorophenyl | vinyl | ethyl | |
| 2.3.882 | 3-ethoxy-4-fluorophenyl | vinyl | ethyl | |
| 2.3.883 | 3-trifluoromethoxy-4-fluorophenyl | vinyl | ethyl | |
| 2.3.884 | 3-nitro-4-fluorophenyl | vinyl | ethyl | |
| 2.3.885 | 3-fluoro-4-chlorophenyl | vinyl | ethyl | |
| 2.3.886 | 3,4-dichlorophenyl | vinyl | ethyl | |
| 2.3.887 | 3-bromo-4-chlorophenyl | vinyl | ethyl | |
| 2.3.888 | 3-methyl-4-chlorophenyl | vinyl | ethyl | |
| 2.3.889 | 3-cyclopropyl-4-chlorophenyl | vinyl | ethyl | |
| 2.3.890 | 3-cyano-4-chlorophenyl | vinyl | ethyl | |
| 2.3.891 | 3-trifluoromethyl-4-chlorophenyl | vinyl | ethyl | |
| 2.3.892 | 3-methoxy-4-chlorophenyl | vinyl | ethyl | |
| 2.3.893 | 3-ethoxy-4-chlorophenyl | vinyl | ethyl | |
| 2.3.894 | 3-trifluoromethoxy-4-chlorophenyl | vinyl | ethyl | |
| 2.3.895 | 3-nitro-4-chlorophenyl | vinyl | ethyl | |
| 2.3.896 | 3-fluoro-4-bromophenyl | vinyl | ethyl | |
| 2.3.897 | 3-chloro-4-bromophenyl | vinyl | ethyl | |
| 2.3.898 | 3,4-dibromophenyl | vinyl | ethyl | |
| 2.3.899 | 3-methyl-4-bromophenyl | vinyl | ethyl | |
| 2.3.900 | 3-ethyl-4-bromophenyl | vinyl | ethyl | |
| 2.3.901 | 3-cyclopropyl-4-bromophenyl | vinyl | ethyl | |
| 2.3.902 | 3-cyano-4-bromophenyl | vinyl | ethyl | |
| 2.3.903 | 3-trifluoromethyl-4-bromophenyl | vinyl | ethyl | |
| 2.3.904 | 3-methoxy-4-phenyl | vinyl | ethyl | |
| 2.3.905 | 3-ethoxy-4-bromophenyl | vinyl | ethyl | |
| 2.3.906 | 3-trifluoromethoxy-4-bromophenyl | vinyl | ethyl | |
| 2.3.907 | 3-nitro-4-bromophenyl | vinyl | ethyl | |
| 2.3.908 | 3-fluoro-4-iodophenyl | vinyl | ethyl | |
| 2.3.909 | 3-chloro-4-iodophenyl | vinyl | ethyl | |
| 2.3.910 | 3-bromo-4-iodophenyl | vinyl | ethyl | |
| 2.3.911 | 3-methyl-4-iodophenyl | vinyl | ethyl | |
| 2.3.912 | 3-cyclopropyl-4-iodophenyl | vinyl | ethyl | |

TABLE 2.3-continued

Inventive compounds of the general formula (I) in which W* is COOY, R¹
R² are each hydrogen, and aryl is the radical.

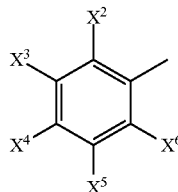

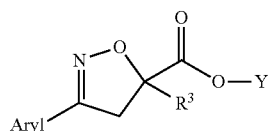

| No. | Aryl | R³ | Y | Physical data |
|---|---|---|---|---|
| 2.3.913 | 3-cyano-4-iodophenyl | vinyl | ethyl | |
| 2.3.914 | 3-trifluoromethyl-4-iodophenyl | vinyl | ethyl | |
| 2.3.915 | 3-methoxy-4-iodophenyl | vinyl | ethyl | |
| 2.3.916 | 3-ethoxy-4-iodophenyl | vinyl | ethyl | |
| 2.3.917 | 3-trifluoromethoxy-4-iodophenyl | vinyl | ethyl | |
| 2.3.918 | 3-nitro-4-iodophenyl | vinyl | ethyl | |
| 2.3.919 | 3-fluoro-4-methylphenyl | vinyl | ethyl | |
| 2.3.920 | 3-chloro-4-methylphenyl | vinyl | ethyl | |
| 2.3.921 | 3-bromo-4-methylphenyl | vinyl | ethyl | |
| 2.3.922 | 3,4-dimethylphenyl | vinyl | ethyl | |
| 2.3.923 | 3,4-dimethylphenyl | 1-methylvinyl | ethyl | |
| 2.3.924 | 3,4-dimethylphenyl | allyl | ethyl | |
| 2.3.925 | 3,4-dimethylphenyl | 1-chlorovinyl | ethyl | |
| 2.3.926 | 3,4-dimethylphenyl | ethynyl | ethyl | |
| 2.3.927 | 3-ethyl-4-methylphenyl | vinyl | ethyl | |
| 2.3.928 | 3-cyclopropyl-4-methylphenyl | vinyl | ethyl | |
| 2.3.929 | 3-cyano-4-methylphenyl | vinyl | ethyl | |
| 2.3.930 | 3-trifluoromethyl-4-methylphenyl | vinyl | ethyl | |
| 2.3.931 | 3-methoxy-4-methylphenyl | vinyl | ethyl | |
| 2.3.932 | 3-ethoxy-4-methylphenyl | vinyl | ethyl | |
| 2.3.933 | 3-trifluoromethoxy-4-methylphenyl | vinyl | ethyl | |
| 2.3.934 | 3-nitro-4-methylphenyl | vinyl | ethyl | |
| 2.3.935 | 3-fluoro-4-ethylphenyl | vinyl | ethyl | |
| 2.3.936 | 3-chloro-4-ethylphenyl | vinyl | ethyl | |
| 2.3.937 | 3-bromo-4-ethylphenyl | vinyl | ethyl | |
| 2.3.938 | 3-methyl-4-ethylphenyl | vinyl | ethyl | |
| 2.3.939 | 3,4-diethylphenyl | vinyl | ethyl | |
| 2.3.940 | 3-cyclopropyl-4-ethylphenyl | vinyl | ethyl | |
| 2.3.941 | 3-cyano-4-ethylphenyl | vinyl | ethyl | |
| 2.3.942 | 3-trifluoromethyl-4-ethylphenyl | vinyl | ethyl | |
| 2.3.943 | 3-methoxy-4-ethylphenyl | vinyl | ethyl | |
| 2.3.944 | 3-ethoxy-4-ethylphenyl | vinyl | ethyl | |
| 2.3.945 | 3-trifluoromethoxy-4-ethylphenyl | vinyl | ethyl | |
| 2.3.946 | 3-nitro-4-ethylphenyl | vinyl | ethyl | |
| 2.3.947 | 3-fluoro-4-propylphenyl | vinyl | ethyl | |
| 2.3.948 | 3-chloro-4-propylphenyl | vinyl | ethyl | |
| 2.3.949 | 3-bromo-4-propylphenyl | vinyl | ethyl | |
| 2.3.950 | 3-methyl-4-propylphenyl | vinyl | ethyl | |
| 2.3.951 | 3-cyclopropyl-4-propylphenyl | vinyl | ethyl | |
| 2.3.952 | 3-cyano-4-propylphenyl | vinyl | ethyl | |
| 2.3.953 | 3-trifluoromethyl-4-propylphenyl | vinyl | ethyl | |
| 2.3.954 | 3-methoxy-4-propylphenyl | vinyl | ethyl | |
| 2.3.955 | 3-ethoxy-4-propylphenyl | vinyl | ethyl | |
| 2.3.956 | 3-trifluoromethoxy-4-propylphenyl | vinyl | ethyl | |
| 2.3.957 | 3-nitro-4-propylphenyl | vinyl | ethyl | |
| 2.3.958 | 3-fluoro-4-isopropylphenyl | vinyl | ethyl | |
| 2.3.959 | 3-chloro-4-isopropylphenyl | vinyl | ethyl | |
| 2.3.960 | 3-bromo-4-isopropylphenyl | vinyl | ethyl | |
| 2.3.961 | 3-methyl-4-isopropylphenyl | vinyl | ethyl | |
| 2.3.962 | 3-cyclopropyl-4-isopropylphenyl | vinyl | ethyl | |
| 2.3.963 | 3-cyano-4-isopropylphenyl | vinyl | ethyl | |
| 2.3.964 | 3-trifluoromethyl-4-isopropylphenyl | vinyl | ethyl | |
| 2.3.965 | 3-methoxy-4-isopropylphenyl | vinyl | ethyl | |
| 2.3.966 | 3-ethoxy-4-isopropylphenyl | vinyl | ethyl | |

TABLE 2.3-continued

Inventive compounds of the general formula (I) in which W* is COOY, R¹ R² are each hydrogen, and aryl is the radical.

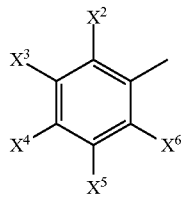

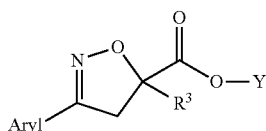

| No. | Aryl | R³ | Y | Physical data |
|---|---|---|---|---|
| 2.3.967 | 3-trifluoromethoxy-4-isopropylphenyl | vinyl | ethyl | |
| 2.3.968 | 3-nitro-4-isopropylphenyl | vinyl | ethyl | |
| 2.3.969 | 3-fluoro-4-tert-butylphenyl | vinyl | ethyl | |
| 2.3.970 | 3-chloro-4-tert-butylphenyl | vinyl | ethyl | |
| 2.3.971 | 3-bromo-4-tert-butylphenyl | vinyl | ethyl | |
| 2.3.972 | 3-methyl-4-tert-butylphenyl | vinyl | ethyl | |
| 2.3.973 | 3-cyclopropyl-4-tert-butylphenyl | vinyl | ethyl | |
| 2.3.974 | 3-cyano-4-tert-butylphenyl | vinyl | ethyl | |
| 2.3.975 | 3-trifluoromethyl-4-tert-butylphenyl | vinyl | ethyl | |
| 2.3.976 | 3-trifluoromethyl-4-tert-butylphenyl | 1-methylvinyl | ethyl | |
| 2.3.977 | 3-trifluoromethyl-4-tert-butylphenyl | allyl | ethyl | |
| 2.3.978 | 3-trifluoromethyl-4-tert-butylphenyl | 1-chlorovinyl | ethyl | |
| 2.3.979 | 3-trifluoromethyl-4-tert-butylphenyl | ethynyl | ethyl | |
| 2.3.980 | 3-methoxy-4-tert-butylphenyl | vinyl | ethyl | |
| 2.3.981 | 3-ethoxy-4-tert-butylphenyl | vinyl | ethyl | |
| 2.3.982 | 3-trifluoromethoxy-4-tert-butylphenyl | vinyl | ethyl | |
| 2.3.983 | 3-nitro-4-tert-butylphenyl | vinyl | ethyl | |
| 2.3.984 | 3-fluoro-4-cyclopropylphenyl | vinyl | ethyl | |
| 2.3.985 | 3-chloro-4-cyclopropylphenyl | vinyl | ethyl | |
| 2.3.986 | 3-bromo-4-cyclopropylphenyl | vinyl | ethyl | |
| 2.3.987 | 3-methyl-4-cyclopropylphenyl | vinyl | ethyl | |
| 2.3.988 | 3-cyclopropyl-4-cyclopropylphenyl | vinyl | ethyl | |
| 2.3.989 | 3-cyano-4-cyclopropylphenyl | vinyl | ethyl | |
| 2.3.990 | 3-trifluoromethyl-4-cyclopropylphenyl | vinyl | ethyl | |
| 2.3.991 | 3-methoxy-4-cyclopropylphenyl | vinyl | ethyl | |
| 2.3.992 | 3-ethoxy-4-cyclopropylphenyl | vinyl | ethyl | |
| 2.3.993 | 3-trifluoromethoxy-4-cyclopropylphenyl | vinyl | ethyl | |
| 2.3.994 | 3-fluoro-4-methoxycarbonyl-phenyl | vinyl | ethyl | |
| 2.3.995 | 3-chloro-4-methoxy-carbonylphenyl | vinyl | ethyl | |
| 2.3.996 | 3-bromo-4-methoxy-carbonylphenyl | vinyl | ethyl | |
| 2.3.997 | 3-methyl-4-methoxy-carbonylphenyl | vinyl | ethyl | |
| 2.3.998 | 3-cyclopropyl-4-methoxycarbonyl-phenyl | vinyl | ethyl | |
| 2.3.999 | 3-cyano-4-methoxycarbonylphenyl | vinyl | ethyl | |
| 2.3.1000 | 3-trifluoromethyl-4-methoxycarbonyl-phenyl | vinyl | ethyl | |
| 2.3.1001 | 3-methoxy-4-methoxycarbonyl-phenyl | vinyl | ethyl | |
| 2.3.1002 | 3-ethoxy-4-methoxycarbonyl-phenyl | vinyl | ethyl | |
| 2.3.1003 | 3-trifluoromethoxy-4-methoxycarbonyl-phenyl | vinyl | ethyl | |

TABLE 2.3-continued

Inventive compounds of the general formula (I) in which W* is COOY, R¹ R² are each hydrogen, and aryl is the radical.

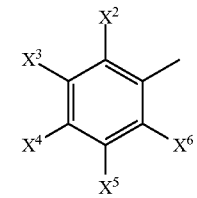

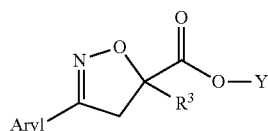

| No. | Aryl | R³ | Y | Physical data |
|---|---|---|---|---|
| 2.3.1004 | 3-nitro-4-methoxy-carbonylphenyl | vinyl | ethyl | |
| 2.3.1005 | 3-fluoro-4-cyanophenyl | vinyl | ethyl | |
| 2.3.1006 | 3-chloro-4-cyanophenyl | vinyl | ethyl | |
| 2.3.1007 | 3-bromo-4-cyanophenyl | vinyl | ethyl | |
| 2.3.1008 | 3-methyl-4-cyanophenyl | vinyl | ethyl | |
| 2.3.1009 | 3-cyclopropyl-4-cyanophenyl | vinyl | ethyl | |
| 2.3.1010 | 3,4-dicyanophenyl | vinyl | ethyl | |
| 2.3.1011 | 3-trifluoromethyl-4-cyanophenyl | vinyl | ethyl | |
| 2.3.1012 | 3-trifluoromethyl-4-cyanophenyl | 1-methylvinyl | ethyl | |
| 2.3.1013 | 3-trifluoromethyl-4-cyanophenyl | allyl | ethyl | |
| 2.3.1014 | 3-trifluoromethyl-4-cyanophenyl | 1-chlorovinyl | ethyl | |
| 2.3.1015 | 3-trifluoromethyl-4-cyanophenyl | ethynyl | ethyl | |
| 2.3.1016 | 3-methoxy-4-cyanophenyl | vinyl | ethyl | |
| 2.3.1017 | 3-ethoxy-4-cyanophenyl | vinyl | ethyl | |
| 2.3.1018 | 3-trifluoromethoxy-4-cyanophenyl | vinyl | ethyl | |
| 2.3.1019 | 3-nitro-4-cyanophenyl | vinyl | ethyl | |
| 2.3.1020 | 3-fluoro-4-methoxyphenyl | vinyl | ethyl | |
| 2.3.1021 | 3-chloro-4-methoxyphenyl | vinyl | ethyl | |
| 2.3.1022 | 3-bromo-4-methoxyphenyl | vinyl | ethyl | |
| 2.3.1023 | 3-methyl-4-methoxyphenyl | vinyl | ethyl | |
| 2.3.1024 | 3-cyclopropyl-4-methoxyphenyl | vinyl | ethyl | |
| 2.3.1025 | 3-cyano-4-methoxyphenyl | vinyl | ethyl | |
| 2.3.1026 | 3-trifluoromethyl-4-methoxyphenyl | vinyl | ethyl | |
| 2.3.1027 | 3,4-dimethoxyphenyl | vinyl | ethyl | |
| 2.3.1028 | 3-ethoxy-4-methoxyphenyl | vinyl | ethyl | |
| 2.3.1029 | 3-trifluoromethoxy-4-methoxyphenyl | vinyl | ethyl | |
| 2.3.1030 | 3-nitro-4-methoxyphenyl | vinyl | ethyl | |
| 2.3.1031 | 3-fluoro-4-ethoxyphenyl | vinyl | ethyl | |
| 2.3.1032 | 3-chloro-4-ethoxyphenyl | vinyl | ethyl | |
| 2.3.1033 | 3-chloro-4-ethoxyphenyl | 1-methylvinyl | ethyl | |
| 2.3.1034 | 3-chloro-4-ethoxyphenyl | allyl | ethyl | |
| 2.3.1035 | 3-chloro-4-ethoxyphenyl | 1-chlorovinyl | ethyl | |
| 2.3.1036 | 3-chloro-4-ethoxyphenyl | ethynyl | ethyl | |
| 2.3.1037 | 3-bromo-4-ethoxyphenyl | vinyl | ethyl | |
| 2.3.1038 | 3-methyl-4-ethoxyphenyl | vinyl | ethyl | |
| 2.3.1039 | 3-cyclopropyl-4-ethoxyphenyl | vinyl | ethyl | |
| 2.3.1040 | 3-cyano-4-ethoxyphenyl | vinyl | ethyl | |
| 2.3.1041 | 3-trifluoromethyl-4-ethoxyphenyl | vinyl | ethyl | |
| 2.3.1042 | 3-methoxy-4-ethoxyphenyl | vinyl | ethyl | |
| 2.3.1043 | 2,4-diethoxyphenyl | vinyl | ethyl | |
| 2.3.1044 | 3-trifluoromethoxy-4-ethoxyphenyl | vinyl | ethyl | |
| 2.3.1045 | 3-nitro-4-ethoxyphenyl | vinyl | ethyl | |
| 2.3.1046 | 3-fluoro-4-isopropoxyphenyl | vinyl | ethyl | |
| 2.3.1047 | 3-chloro-4-isopropoxyphenyl | vinyl | ethyl | |
| 2.3.1048 | 3-bromo-4-isopropoxyphenyl | vinyl | ethyl | |
| 2.3.1049 | 3-methyl-4-isopropoxyphenyl | vinyl | ethyl | |
| 2.3.1050 | 3-cyclopropyl-4-isopropoxyphenyl | vinyl | ethyl | |
| 2.3.1051 | 3-cyano-4-isopropoxyphenyl | vinyl | ethyl | |
| 2.3.1052 | 3-trifluoromethyl-4-isopropoxyphenyl | vinyl | ethyl | |
| 2.3.1053 | 3-methoxy-4-isopropoxyphenyl | vinyl | ethyl | |

TABLE 2.3-continued

Inventive compounds of the general formula (I) in which W* is COOY, R¹ R² are each hydrogen, and aryl is the radical.

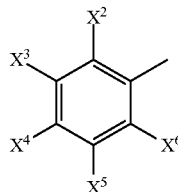

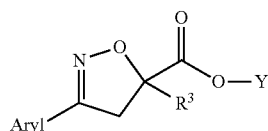

| No. | Aryl | R³ | Y | Physical data |
|---|---|---|---|---|
| 2.3.1054 | 3-ethoxy-4-isopropoxyphenyl | vinyl | ethyl | |
| 2.3.1055 | 3-trifluoromethoxy-4-isopropoxyphenyl | vinyl | ethyl | |
| 2.3.1056 | 3-nitro-4-isopropoxyphenyl | vinyl | ethyl | |
| 2.3.1057 | 3-fluoro-4-trifluoromethoxyphenyl | vinyl | ethyl | |
| 2.3.1058 | 3-chloro-4-trifluoromethoxyphenyl | vinyl | ethyl | |
| 2.3.1059 | 3-bromo-4-trifluoromethoxyphenyl | vinyl | ethyl | |
| 2.3.1060 | 3-methyl-4-trifluoromethoxyphenyl | vinyl | ethyl | |
| 2.3.1061 | 3-cyclopropyl-4-trifluoromethoxyphenyl | vinyl | ethyl | |
| 2.3.1062 | 3-cyano-4-trifluoromethoxyphenyl | vinyl | ethyl | |
| 2.3.1063 | 3-trifluoromethyl-4-trifluoromethoxyphenyl | vinyl | ethyl | |
| 2.3.1064 | 3-methoxy-4-trifluoromethoxyphenyl | vinyl | ethyl | |
| 2.3.1065 | 3-ethoxy-4-trifluoromethoxyphenyl | vinyl | ethyl | |
| 2.3.1066 | 3,4-bis(trifluoromethoxy)phenyl | vinyl | ethyl | |
| 2.3.1067 | 3-nitro-4-trifluoromethoxyphenyl | vinyl | ethyl | |
| 2.3.1068 | 3-fluoro-4-difluoromethoxyphenyl | vinyl | ethyl | |
| 2.3.1069 | 3-chloro-4-difluoromethoxyphenyl | vinyl | ethyl | |
| 2.3.1070 | 3-bromo-4-difluoromethoxyphenyl | vinyl | ethyl | |
| 2.3.1071 | 3-methyl-4-difluoromethoxyphenyl | vinyl | ethyl | |
| 2.3.1072 | 3-cyclopropyl-4-difluoromethoxyphenyl | vinyl | ethyl | |
| 2.3.1073 | 3-cyano-4-difluoromethoxyphenyl | vinyl | ethyl | |
| 2.3.1074 | 3-trifluoromethyl-4-difluoromethoxyphenyl | vinyl | ethyl | |
| 2.3.1075 | 3-methoxy-4-difluoromethoxyphenyl | vinyl | ethyl | |
| 2.3.1076 | 3-ethoxy-4-difluoromethoxyphenyl | vinyl | ethyl | |
| 2.3.1077 | 3-trifluoromethoxy-4-difluoromethoxyphenyl | vinyl | ethyl | |
| 2.3.1078 | 3-nitro-4-difluoromethoxyphenyl | vinyl | ethyl | |
| 2.3.1079 | 3-fluoro-4-nitrophenyl | vinyl | ethyl | |
| 2.3.1080 | 3-chloro-4-nitrophenyl | vinyl | ethyl | |
| 2.3.1081 | 3-bromo-4-nitrophenyl | vinyl | ethyl | |
| 2.3.1082 | 3-methyl-4-nitrophenyl | vinyl | ethyl | |
| 2.3.1083 | 3-cyclopropyl-4-nitrophenyl | vinyl | ethyl | |
| 2.3.1084 | 3-cyano-4-nitrophenyl | vinyl | ethyl | |
| 2.3.1085 | 3-trifluoromethyl-4-nitrophenyl | vinyl | ethyl | |
| 2.3.1086 | 3-methoxy-4-nitrophenyl | vinyl | ethyl | |
| 2.3.1087 | 3-ethoxy-4-nitrophenyl | vinyl | ethyl | |
| 2.3.1088 | 3-trifluoromethoxy-4-nitrophenyl | vinyl | ethyl | |
| 2.3.1089 | 3-fluoro-4-methylsulfanylphenyl | vinyl | ethyl | |
| 2.3.1090 | 3-chloro-4-methylsulfanylphenyl | vinyl | ethyl | |

TABLE 2.3-continued

Inventive compounds of the general formula (I) in which W* is COOY, R¹ R² are each hydrogen, and aryl is the radical.

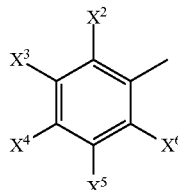

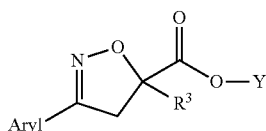

| No. | Aryl | R³ | Y | Physical data |
|---|---|---|---|---|
| 2.3.1091 | 3-bromo-4-methylsulfanylphenyl | vinyl | ethyl | |
| 2.3.1092 | 3-methyl-4-methylsulfanylphenyl | vinyl | ethyl | |
| 2.3.1093 | 3-cyclopropyl-4-methylsulfanylphenyl | vinyl | ethyl | |
| 2.3.1094 | 3-cyano-4-methylsulfanylphenyl | vinyl | ethyl | |
| 2.3.1095 | 3-trifluoromethyl-4-methylsulfanylphenyl | vinyl | ethyl | |
| 2.3.1096 | 3-methoxy-4-methylsulfanylphenyl | vinyl | ethyl | |
| 2.3.1097 | 3-ethoxy-4-methylsulfanylphenyl | vinyl | ethyl | |
| 2.3.1098 | 3-trifluoromethoxy-4-methylsulfanylphenyl | vinyl | ethyl | |
| 2.3.1099 | 3-nitro-4-methylsulfanylphenyl | vinyl | ethyl | |
| 2.3.1100 | 3,6-difluorophenyl | vinyl | ethyl | |
| 2.3.1101 | 3,6-difluorophenyl | 1-methylvinyl | ethyl | |
| 2.3.1102 | 3,6-difluorophenyl | allyl | ethyl | |
| 2.3.1103 | 3,6-difluorophenyl | 1-chlorovinyl | ethyl | |
| 2.3.1104 | 3,6-difluorophenyl | ethynyl | ethyl | |
| 2.3.1105 | 3-chloro-6-fluorophenyl | vinyl | ethyl | |
| 2.3.1106 | 3-bromo-6-fluorophenyl | vinyl | ethyl | |
| 2.3.1107 | 3-methyl-6-fluorophenyl | vinyl | ethyl | |
| 2.3.1108 | 3-cyclopropyl-6-fluorophenyl | vinyl | ethyl | |
| 2.3.1109 | 3-cyano-6-fluorophenyl | vinyl | ethyl | |
| 2.3.1110 | 3-methoxy-6-fluorophenyl | vinyl | ethyl | |
| 2.3.1111 | 3-ethoxy-6-fluorophenyl | vinyl | ethyl | |
| 2.3.1112 | 3-trifluoromethoxy-6-fluorophenyl | vinyl | ethyl | |
| 2.3.1113 | 3-nitro-6-fluorophenyl | vinyl | ethyl | |
| 2.3.1114 | 3-fluoro-6-chlorophenyl | vinyl | ethyl | |
| 2.3.1115 | 3-fluoro-6-chlorophenyl | 1-methylvinyl | ethyl | |
| 2.3.1116 | 3-fluoro-6-chlorophenyl | allyl | ethyl | |
| 2.3.1117 | 3-fluoro-6-chlorophenyl | 1-chlorovinyl | ethyl | |
| 2.3.1118 | 3-fluoro-6-chlorophenyl | ethynyl | ethyl | |
| 2.3.1119 | 3,6-dichlorophenyl | vinyl | ethyl | |
| 2.3.1120 | 3,6-dichlorophenyl | 1-methylvinyl | ethyl | |
| 2.3.1121 | 3,6-dichlorophenyl | allyl | ethyl | |
| 2.3.1122 | 3,6-dichlorophenyl | 1-chlorovinyl | ethyl | |
| 2.3.1123 | 3,6-dichlorophenyl | ethynyl | ethyl | |
| 2.3.1124 | 3-bromo-6-chlorophenyl | vinyl | ethyl | |
| 2.3.1125 | 3-methyl-6-chlorophenyl | vinyl | ethyl | |
| 2.3.1126 | 3-cyclopropyl-6-chlorophenyl | vinyl | ethyl | |
| 2.3.1127 | 3-cyano-6-chlorophenyl | vinyl | ethyl | |
| 2.3.1128 | 3-trifluoromethyl-6-chlorophenyl | vinyl | ethyl | |
| 2.3.1129 | 3-methoxy-6-chlorophenyl | vinyl | ethyl | |
| 2.3.1130 | 3-ethoxy-6-chlorophenyl | vinyl | ethyl | |
| 2.3.1131 | 3-trifluoromethoxy-6-chlorophenyl | vinyl | ethyl | |
| 2.3.1132 | 3-nitro-6-chlorophenyl | vinyl | ethyl | |
| 2.3.1133 | 3-fluoro-6-bromophenyl | vinyl | ethyl | |
| 2.3.1134 | 3-chloro-6-bromophenyl | vinyl | ethyl | |
| 2.3.1135 | 3,6-dibromophenyl | vinyl | ethyl | |
| 2.3.1136 | 3-methyl-6-bromophenyl | vinyl | ethyl | |
| 2.3.1137 | 3-cyclopropyl-6-bromophenyl | vinyl | ethyl | |
| 2.3.1138 | 3-cyano-6-bromophenyl | vinyl | ethyl | |
| 2.3.1139 | 3-trifluoromethyl-6-bromophenyl | vinyl | ethyl | |
| 2.3.1140 | 3-methoxy-6-phenyl | vinyl | ethyl | |
| 2.3.1141 | 3-ethoxy-6-bromophenyl | vinyl | ethyl | |

TABLE 2.3-continued

Inventive compounds of the general formula (I) in which W* is COOY, R¹ R² are each hydrogen, and aryl is the radical.

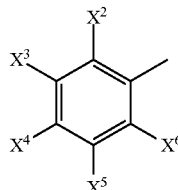

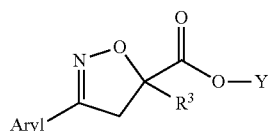

| No. | Aryl | R³ | Y | Physical data |
|---|---|---|---|---|
| 2.3.1142 | 3-trifluoromethoxy-6-bromophenyl | vinyl | ethyl | |
| 2.3.1143 | 3-nitro-6-bromophenyl | vinyl | ethyl | |
| 2.3.1144 | 3-fluoro-6-iodophenyl | vinyl | ethyl | |
| 2.3.1145 | 3-chloro-6-iodophenyl | vinyl | ethyl | |
| 2.3.1146 | 3-bromo-6-iodophenyl | vinyl | ethyl | |
| 2.3.1147 | 3-methyl-6-iodophenyl | vinyl | ethyl | |
| 2.3.1148 | 3-cyclopropyl-6-iodophenyl | vinyl | ethyl | |
| 2.3.1149 | 3-cyano-6-iodophenyl | vinyl | ethyl | |
| 2.3.1150 | 3-trifluoromethyl-6-iodophenyl | vinyl | ethyl | |
| 2.3.1151 | 3-methoxy-6-iodophenyl | vinyl | ethyl | |
| 2.3.1152 | 3-ethoxy-6-iodophenyl | vinyl | ethyl | |
| 2.3.1153 | 3-trifluoromethoxy-6-iodophenyl | vinyl | ethyl | |
| 2.3.1154 | 3-nitro-6-iodophenyl | vinyl | ethyl | |
| 2.3.1155 | 3-fluoro-6-methylphenyl | vinyl | ethyl | |
| 2.3.1156 | 3-chloro-6-methylphenyl | vinyl | ethyl | |
| 2.3.1157 | 3-bromo-6-methylphenyl | vinyl | ethyl | |
| 2.3.1158 | 3,6-dimethylphenyl | vinyl | ethyl | |
| 2.3.1159 | 3-ethyl-6-methylphenyl | vinyl | ethyl | |
| 2.3.1160 | 3-cyclopropyl-6-methylphenyl | vinyl | ethyl | |
| 2.3.1161 | 3-cyano-6-methylphenyl | vinyl | ethyl | |
| 2.3.1162 | 3-trifluoromethyl-6-methylphenyl | vinyl | ethyl | |
| 2.3.1163 | 3-methoxy-6-methylphenyl | vinyl | ethyl | |
| 2.3.1164 | 3-ethoxy-6-methylphenyl | vinyl | ethyl | |
| 2.3.1165 | 3-trifluoromethoxy-6-methylphenyl | vinyl | ethyl | |
| 2.3.1166 | 3-nitro-6-methylphenyl | vinyl | ethyl | |
| 2.3.1167 | 3-fluoro-6-ethylphenyl | vinyl | ethyl | |
| 2.3.1168 | 3-chloro-6-ethylphenyl | vinyl | ethyl | |
| 2.3.1169 | 3-bromo-6-ethylphenyl | vinyl | ethyl | |
| 2.3.1170 | 3-methyl-6-ethylphenyl | vinyl | ethyl | |
| 2.3.1171 | 3,6-diethylphenyl | vinyl | ethyl | |
| 2.3.1172 | 3-cyclopropyl-6-ethylphenyl | vinyl | ethyl | |
| 2.3.1173 | 3-cyano-6-ethylphenyl | vinyl | ethyl | |
| 2.3.1174 | 3-trifluoromethyl-6-ethylphenyl | vinyl | ethyl | |
| 2.3.1175 | 3-methoxy-6-ethylphenyl | vinyl | ethyl | |
| 2.3.1176 | 3-ethoxy-6-ethylphenyl | vinyl | ethyl | |
| 2.3.1177 | 3-trifluoromethoxy-6-ethylphenyl | vinyl | ethyl | |
| 2.3.1178 | 3-nitro-6-ethylphenyl | vinyl | ethyl | |
| 2.3.1179 | 3-fluoro-6-propylphenyl | vinyl | ethyl | |
| 2.3.1180 | 3-chloro-6-propylphenyl | vinyl | ethyl | |
| 2.3.1181 | 3-bromo-6-propylphenyl | vinyl | ethyl | |
| 2.3.1182 | 3-methyl-6-propylphenyl | vinyl | ethyl | |
| 2.3.1183 | 3-cyclopropyl-6-propylphenyl | vinyl | ethyl | |
| 2.3.1184 | 3-cyano-6-propylphenyl | vinyl | ethyl | |
| 2.3.1185 | 3-trifluoromethyl-6-propylphenyl | vinyl | ethyl | |
| 2.3.1186 | 3-methoxy-6-propylphenyl | vinyl | ethyl | |
| 2.3.1187 | 3-ethoxy-6-propylphenyl | vinyl | ethyl | |
| 2.3.1188 | 3-trifluoromethoxy-6-propylphenyl | vinyl | ethyl | |
| 2.3.1189 | 3-nitro-6-propylphenyl | vinyl | ethyl | |
| 2.3.1190 | 3-fluoro-6-isopropylphenyl | vinyl | ethyl | |
| 2.3.1191 | 3-chloro-6-isopropylphenyl | vinyl | ethyl | |
| 2.3.1192 | 3-bromo-6-isopropylphenyl | vinyl | ethyl | |
| 2.3.1193 | 3-methyl-6-isopropylphenyl | vinyl | ethyl | |
| 2.3.1194 | 3-cyclopropyl-6-isopropylphenyl | vinyl | ethyl | |
| 2.3.1195 | 3-cyano-6-isopropylphenyl | vinyl | ethyl | |

TABLE 2.3-continued

Inventive compounds of the general formula (I) in which W* is COOY, R¹ R² are each hydrogen, and aryl is the radical.

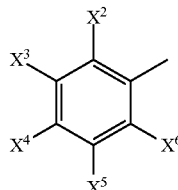

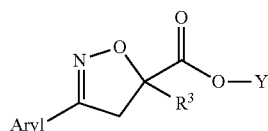

| No. | Aryl | R³ | Y | Physical data |
|---|---|---|---|---|
| 2.3.1196 | 3-trifluoromethyl-6-isopropylphenyl | vinyl | ethyl | |
| 2.3.1197 | 3-methoxy-6-isopropylphenyl | vinyl | ethyl | |
| 2.3.1198 | 3-ethoxy-6-isopropylphenyl | vinyl | ethyl | |
| 2.3.1199 | 3-trifluoromethoxy-6-isopropylphenyl | vinyl | ethyl | |
| 2.3.1200 | 3-nitro-6-isopropylphenyl | vinyl | ethyl | |
| 2.3.1201 | 3-fluoro-6-tert-butylphenyl | vinyl | ethyl | |
| 2.3.1202 | 3-chloro-6-tert-butylphenyl | vinyl | ethyl | |
| 2.3.1203 | 3-bromo-6-tert-butylphenyl | vinyl | ethyl | |
| 2.3.1204 | 3-methyl-6-tert-butylphenyl | vinyl | ethyl | |
| 2.3.1205 | 3-ethyl-6-tert-butylphenyl | vinyl | ethyl | |
| 2.3.1206 | 3-cyclopropyl-6-tert-butylphenyl | vinyl | ethyl | |
| 2.3.1207 | 3-cyano-6-tert-butylphenyl | vinyl | ethyl | |
| 2.3.1208 | 3-trifluoromethyl-6-tert-butylphenyl | vinyl | ethyl | |
| 2.3.1209 | 3-methoxy-6-tert-butylphenyl | vinyl | ethyl | |
| 2.3.1210 | 3-ethoxy-6-tert-butylphenyl | vinyl | ethyl | |
| 2.3.1211 | 3-trifluoromethoxy-6-tert-butylphenyl | vinyl | ethyl | |
| 2.3.1212 | 3-nitro-6-tert-butylphenyl | vinyl | ethyl | |
| 2.3.1213 | 3-fluoro-6-cyclopropylphenyl | vinyl | ethyl | |
| 2.3.1214 | 3-chloro-6-cyclopropylphenyl | vinyl | ethyl | |
| 2.3.1215 | 3-bromo-6-cyclopropylphenyl | vinyl | ethyl | |
| 2.3.1216 | 3-methyl-6-cyclopropylphenyl | vinyl | ethyl | |
| 2.3.1217 | 3-cyclopropyl-6-cyclopropylphenyl | vinyl | ethyl | |
| 2.3.1218 | 3-cyano-6-cyclopropylphenyl | vinyl | ethyl | |
| 2.3.1219 | 3-trifluoromethyl-6-cyclopropylphenyl | vinyl | ethyl | |
| 2.3.1220 | 3-methoxy-6-cyclopropylphenyl | vinyl | ethyl | |
| 2.3.1221 | 3-ethoxy-6-cyclopropylphenyl | vinyl | ethyl | |
| 2.3.1222 | 3-trifluoromethoxy-6-cyclopropylphenyl | vinyl | ethyl | |
| 2.3.1223 | 3-fluoro-6-methoxycarbonyl-phenyl | vinyl | ethyl | |
| 2.3.1224 | 3-chloro-6-methoxycarbonyl-phenyl | vinyl | ethyl | |
| 2.3.1225 | 3-bromo-6-methoxycarbonyl-phenyl | vinyl | ethyl | |
| 2.3.1226 | 3-methyl-6-methoxycarbonyl-phenyl | vinyl | ethyl | |
| 2.3.1227 | 3-cyclopropyl-6-methoxycarbonyl-phenyl | vinyl | ethyl | |
| 2.3.1228 | 3-cyano-6-methoxycarbonyl-phenyl | vinyl | ethyl | |
| 2.3.1229 | 3-trifluoromethyl-6-methoxycarbonyl-phenyl | vinyl | ethyl | |
| 2.3.1230 | 3-methoxy-6-methoxycarbonyl-phenyl | vinyl | ethyl | |
| 2.3.1231 | 3-ethoxy-6-methoxycarbonyl-phenyl | vinyl | ethyl | |
| 2.3.1232 | 3-trifluoromethoxy-6-methoxycarbonyl-phenyl | vinyl | ethyl | |
| 2.3.1233 | 3-nitro-6-methoxycarbonyl-phenyl | vinyl | ethyl | |
| 2.3.1234 | 3-fluoro-6-cyanophenyl | vinyl | ethyl | |

TABLE 2.3-continued

Inventive compounds of the general formula (I) in which W* is COOY, R¹ R² are each hydrogen, and aryl is the radical.

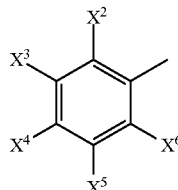

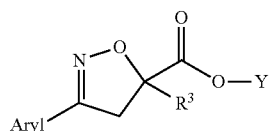

| No. | Aryl | R³ | Y | Physical data |
|---|---|---|---|---|
| 2.3.1235 | 3-chloro-6-cyanophenyl | vinyl | ethyl | |
| 2.3.1236 | 3-bromo-6-cyanophenyl | vinyl | ethyl | |
| 2.3.1237 | 3-methyl-6-cyanophenyl | vinyl | ethyl | |
| 2.3.1238 | 3-cyclopropyl-6-cyanophenyl | vinyl | ethyl | |
| 2.3.1239 | 3-cyano-6-cyanophenyl | vinyl | ethyl | |
| 2.3.1240 | 3-trifluoromethyl-6-cyanophenyl | vinyl | ethyl | |
| 2.3.1241 | 3-methoxy-6-cyanophenyl | vinyl | ethyl | |
| 2.3.1242 | 3-ethoxy-6-cyanophenyl | vinyl | ethyl | |
| 2.3.1243 | 3-trifluoromethoxy-6-cyanophenyl | vinyl | ethyl | |
| 2.3.1244 | 3-nitro-6-cyanophenyl | vinyl | ethyl | |
| 2.3.1245 | 3-fluoro-6-methoxyphenyl | vinyl | ethyl | |
| 2.3.1246 | 3-chloro-6-methoxyphenyl | vinyl | ethyl | |
| 2.3.1247 | 3-bromo-6-methoxyphenyl | vinyl | ethyl | |
| 2.3.1248 | 3-methyl-6-methoxyphenyl | vinyl | ethyl | |
| 2.3.1249 | 3-cyclopropyl-6-methoxyphenyl | vinyl | ethyl | |
| 2.3.1250 | 3-cyano-6-methoxyphenyl | vinyl | ethyl | |
| 2.3.1251 | 3-trifluoromethyl-6-methoxyphenyl | vinyl | ethyl | |
| 2.3.1252 | 3,6-dimethoxyphenyl | vinyl | ethyl | |
| 2.3.1253 | 3-ethoxy-6-methoxyphenyl | vinyl | ethyl | |
| 2.3.1254 | 3-trifluoromethoxy-6-methoxyphenyl | vinyl | ethyl | |
| 2.3.1255 | 3-nitro-6-methoxyphenyl | vinyl | ethyl | |
| 2.3.1256 | 3-fluoro-6-ethoxyphenyl | vinyl | ethyl | |
| 2.3.1257 | 3-chloro-6-ethoxyphenyl | vinyl | ethyl | |
| 2.3.1258 | 3-bromo-6-ethoxyphenyl | vinyl | ethyl | |
| 2.3.1259 | 3-methyl-6-ethoxyphenyl | vinyl | ethyl | |
| 2.3.1260 | 3-cyclopropyl-6-ethoxyphenyl | vinyl | ethyl | |
| 2.3.1261 | 3-cyano-6-ethoxyphenyl | vinyl | ethyl | |
| 2.3.1262 | 3-trifluoromethyl-6-ethoxyphenyl | vinyl | ethyl | |
| 2.3.1263 | 3-methoxy-6-ethoxyphenyl | vinyl | ethyl | |
| 2.3.1264 | 2,6-diethoxyphenyl | vinyl | ethyl | |
| 2.3.1265 | 3-trifluoromethoxy-6-ethoxyphenyl | vinyl | ethyl | |
| 2.3.1266 | 3-nitro-6-ethoxyphenyl | vinyl | ethyl | |
| 2.3.1267 | 3-fluoro-6-isopropoxyphenyl | vinyl | ethyl | |
| 2.3.1268 | 3-chloro-6-isopropoxyphenyl | vinyl | ethyl | |
| 2.3.1269 | 3-bromo-6-isopropoxyphenyl | vinyl | ethyl | |
| 2.3.1270 | 3-methyl-6-isopropoxyphenyl | vinyl | ethyl | |
| 2.3.1271 | 3-cyclopropyl-6-isopropoxyphenyl | vinyl | ethyl | |
| 2.3.1272 | 3-cyano-6-isopropoxyphenyl | vinyl | ethyl | |
| 2.3.1273 | 3-trifluoromethyl-6-isopropoxyphenyl | vinyl | ethyl | |
| 2.3.1274 | 3-methoxy-6-isopropoxyphenyl | vinyl | ethyl | |
| 2.3.1275 | 3-ethoxy-6-isopropoxyphenyl | vinyl | ethyl | |
| 2.3.1276 | 3-trifluoromethoxy-6-isopropoxyphenyl | vinyl | ethyl | |
| 2.3.1277 | 3-nitro-6-isopropoxyphenyl | vinyl | ethyl | |
| 2.3.1278 | 3-fluoro-6-trifluoromethoxy-phenyl | vinyl | ethyl | |
| 2.3.1279 | 3-chloro-6-trifluoromethoxy-phenyl | vinyl | ethyl | |
| 2.3.1280 | 3-bromo-6-trifluoromethoxy-phenyl | vinyl | ethyl | |

TABLE 2.3-continued

Inventive compounds of the general formula (I) in which W* is COOY, R¹ R² are each hydrogen, and aryl is the radical.

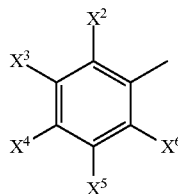

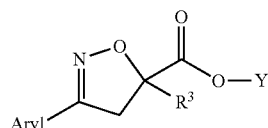

| No. | Aryl | R³ | Y | Physical data |
|---|---|---|---|---|
| 2.3.1281 | 3-methyl-6-trifluoromethoxy-phenyl | vinyl | ethyl | |
| 2.3.1282 | 3-cyclopropyl-6-trifluoromethoxyphenyl | vinyl | ethyl | |
| 2.3.1283 | 3-cyano-6-trifluoromethoxy-phenyl | vinyl | ethyl | |
| 2.3.1284 | 3-trifluoromethyl-6-trifluoromethoxyphenyl | vinyl | ethyl | |
| 2.3.1285 | 3-methoxy-6-trifluoromethoxy-phenyl | vinyl | ethyl | |
| 2.3.1286 | 3-ethoxy-6-trifluoromethoxy-phenyl | vinyl | ethyl | |
| 2.3.1287 | 3,6-bis(trifluoro-methoxy)phenyl | vinyl | ethyl | |
| 2.3.1288 | 3-nitro-6-trifluoromethoxyphenyl | vinyl | ethyl | |
| 2.3.1289 | 3-fluoro-6-difluoromethoxy-phenyl | vinyl | ethyl | |
| 2.3.1290 | 3-chloro-6-difluoromethoxy-phenyl | vinyl | ethyl | |
| 2.3.1291 | 3-bromo-6-difluoromethoxy-phenyl | vinyl | ethyl | |
| 2.3.1292 | 3-methyl-6-difluoromethoxy-phenyl | vinyl | ethyl | |
| 2.3.1293 | 3-cyclopropyl-6-difluoromethoxy-phenyl | vinyl | ethyl | |
| 2.3.1294 | 3-cyano-6-difluoromethoxy-phenyl | vinyl | ethyl | |
| 2.3.1295 | 3-trifluoromethyl-6-difluoromethoxyphenyl | vinyl | ethyl | |
| 2.3.1296 | 3-methoxy-6-difluoromethoxy-phenyl | vinyl | ethyl | |
| 2.3.1297 | 3-ethoxy-6-difluoromethoxy-phenyl | vinyl | ethyl | |
| 2.3.1298 | 3-trifluoromethoxy-6-difluoromethoxyphenyl | vinyl | ethyl | |
| 2.3.1299 | 3-nitro-6-difluoromethoxyphenyl | vinyl | ethyl | |
| 2.3.1300 | 3-fluoro-6-nitrophenyl | vinyl | ethyl | |
| 2.3.1301 | 3-chloro-6-nitrophenyl | vinyl | ethyl | |
| 2.3.1302 | 3-bromo-6-nitrophenyl | vinyl | ethyl | |
| 2.3.1303 | 3-methyl-6-nitrophenyl | vinyl | ethyl | |
| 2.3.1304 | 3-cyclopropyl-6-nitrophenyl | vinyl | ethyl | |
| 2.3.1305 | 3-cyano-6-nitrophenyl | vinyl | ethyl | |
| 2.3.1306 | 3-trifluoromethyl-6-nitrophenyl | vinyl | ethyl | |
| 2.3.1307 | 3-methoxy-6-nitrophenyl | vinyl | ethyl | |
| 2.3.1308 | 3-ethoxy-6-nitrophenyl | vinyl | ethyl | |
| 2.3.1309 | 3-trifluoromethoxy-6-nitrophenyl | vinyl | ethyl | |
| 2.3.1310 | 3-fluoro-6-methylsulfanylphenyl | vinyl | ethyl | |
| 2.3.1311 | 3-chloro-6-methylsulfanylphenyl | vinyl | ethyl | |
| 2.3.1312 | 3-bromo-6-methylsulfanylphenyl | vinyl | ethyl | |
| 2.3.1313 | 3-methyl-6-methylsulfanylphenyl | vinyl | ethyl | |
| 2.3.1314 | 3-cyclopropyl-6-methylsulfanylphenyl | vinyl | ethyl | |
| 2.3.1315 | 3-cyano-6-methylsulfanylphenyl | vinyl | ethyl | |
| 2.3.1316 | 3-trifluoromethyl-6-methylsulfanylphenyl | vinyl | ethyl | |

TABLE 2.3-continued

Inventive compounds of the general formula (I) in which W* is COOY, $R^1$ $R^2$ are each hydrogen, and aryl is the radical.

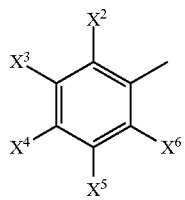

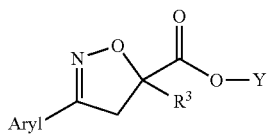

| No. | Aryl | $R^3$ | Y | Physical data |
|---|---|---|---|---|
| 2.3.1317 | 3-methoxy-6-methylsulfanylphenyl | vinyl | ethyl | |
| 2.3.1318 | 3-ethoxy-6-methylsulfanylphenyl | vinyl | ethyl | |
| 2.3.1319 | 3-trifluoromethoxy-6-methylsulfanylphenyl | vinyl | ethyl | |
| 2.3.1320 | 3-nitro-6-methylsulfanylphenyl | vinyl | ethyl | |
| 2.3.1321 | 2,3,4-trifluorophenyl | vinyl | ethyl | |
| 2.3.1322 | 2,3,4-trichlorophenyl | vinyl | ethyl | |
| 2.3.1323 | 2,3,4-trimethylphenyl | vinyl | ethyl | |
| 2.3.1324 | 2-fluoro-2-chloro-5-trifluoromethylphenyl | vinyl | ethyl | |
| 2.3.1325 | 2,3,5-trifluorophenyl | vinyl | ethyl | |
| 2.3.1326 | 2,3,5-trichlorophenyl | vinyl | ethyl | |
| 2.3.1327 | 2,3,5-trimethylphenyl | vinyl | ethyl | |
| 2.3.1328 | 2,3-dichloro-5-methoxyphenyl | vinyl | ethyl | |
| 2.3.1329 | 2,3,6-trifluorophenyl | vinyl | ethyl | |
| 2.3.1330 | 2,3,6-trichlorophenyl | vinyl | ethyl | |
| 2.3.1331 | 2,3,6-trimethylphenyl | vinyl | ethyl | |
| 2.3.1332 | 3,4,5-trifluorophenyl | vinyl | ethyl | |
| 2.3.1333 | 3,4,5-trichlorophenyl | vinyl | ethyl | |
| 2.3.1334 | 3,4,5-trimethylphenyl | vinyl | ethyl | |
| 2.3.1335 | 3,5-dimethyl-4-fluorophenyl | vinyl | ethyl | |
| 2.3.1336 | 3,5-dichloro-4-methoxyphenyl | vinyl | ethyl | |
| 2.3.1337 | 3,5-difluoro-4-chlorophenyl | vinyl | ethyl | |
| 2.3.1338 | 3,5-dichloro-4-hydroxyphenyl | vinyl | ethyl | |
| 2.3.1339 | 3,5-trifluoromethyl-4-chlorophenyl | vinyl | ethyl | |
| 2.3.1340 | 3,4,6-trifluorophenyl | vinyl | ethyl | |
| 2.3.1341 | 3,4,6-trichlorophenyl | vinyl | ethyl | |
| 2.3.1342 | 3,4,6-trimethylphenyl | vinyl | ethyl | |
| 2.3.1343 | pentafluorophenyl | vinyl | ethyl | |

TABLE 2.4

Inventive compounds of the general formula (I) in which W* is COOY, $R^1$ and $R^2$ are each hydrogen, and aryl is the radical.

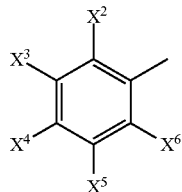

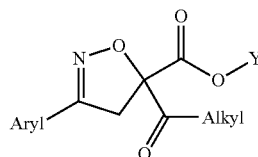

| No. | Aryl | Alkyl | Y | Physical data |
|---|---|---|---|---|
| 2.4.1 | 3-fluorophenyl | methyl | methyl | [CDCl3] 2.44 (s, 3H); 3.87 (s, 3H); 3.87 (AB, 2H); 7.12-7.20 (m, 1H); 7.38-7.43 (m, 3H). |
| 2.4.2 | 3-fluorophenyl | ethyl | ethyl | |
| 2.4.3 | 3-fluorophenyl | propyl | ethyl | |
| 2.4.4 | 3-fluorophenyl | butyl | ethyl | |
| 2.4.5 | 3-chlorophenyl | methyl | ethyl | |
| 2.4.6 | 3-chlorophenyl | ethyl | ethyl | |
| 2.4.7 | 3-chlorophenyl | propyl | ethyl | |
| 2.4.8 | 3-chlorophenyl | butyl | ethyl | |
| 2.4.9 | 3-bromophenyl | methyl | ethyl | |
| 2.4.10 | 3-bromophenyl | ethyl | ethyl | |
| 2.4.11 | 3-iodophenyl | methyl | ethyl | |
| 2.4.12 | 3-iodophenyl | ethyl | ethyl | |
| 2.4.13 | 3-methylphenyl | methyl | ethyl | |
| 2.4.14 | 3-methylphenyl | ethyl | ethyl | |
| 2.4.15 | 3-ethylphenyl | methyl | ethyl | |
| 2.4.16 | 3-propylphenyl | methyl | ethyl | |
| 2.4.17 | 3-isopropylphenyl | methyl | ethyl | |
| 2.4.18 | 3-n-butylphenyl | methyl | ethyl | |
| 2.4.19 | 3-i-butylphenyl | methyl | ethyl | |
| 2.4.20 | 3-tert-butylphenyl | methyl | ethyl | |
| 2.4.21 | 3-cyclopropylphenyl | methyl | ethyl | |
| 2.4.22 | 3-cyclobutylphenyl | methyl | ethyl | |
| 2.4.23 | 3-cyclopentylphenyl | methyl | ethyl | |
| 2.4.24 | 3-vinylphenyl | methyl | ethyl | |
| 2.4.25 | 3-ethynylphenyl | methyl | ethyl | |
| 2.4.26 | 3-cyanophenyl | methyl | ethyl | |
| 2.4.27 | 3-trifluoromethylphenyl | methyl | ethyl | |
| 2.4.28 | 3-difluoromethylphenyl | methyl | ethyl | |
| 2.4.29 | 3-(hydroxycarbonyl)-phenyl | methyl | ethyl | |
| 2.4.30 | 3-(methoxycarbonyl)-phenyl | methyl | ethyl | |
| 2.4.31 | 3-(ethoxycarbonyl)-phenyl | methyl | ethyl | |
| 2.4.32 | 3-hydroxymethylphenyl | methyl | ethyl | |
| 2.4.33 | 3-carbamoylphenyl | methyl | ethyl | |
| 2.4.34 | 3-hydroxyphenyl | methyl | ethyl | |
| 2.4.35 | 3-methoxyphenyl | methyl | ethyl | |
| 2.4.36 | 3-ethoxyphenyl | methyl | ethyl | |
| 2.4.37 | 3-propyloxyphenyl | methyl | ethyl | |
| 2.4.38 | 3-isopropyloxyphenyl | methyl | ethyl | |
| 2.4.39 | 3-n-butyloxyphenyl | methyl | ethyl | |
| 2.4.40 | 3-i-butyloxyphenyl | methyl | ethyl | |
| 2.4.41 | 3-t-butyloxyphenyl | methyl | ethyl | |
| 2.4.42 | 3-difluoromethoxyphenyl | methyl | ethyl | |
| 2.4.43 | 3-trifluoromethoxyphenyl | methyl | ethyl | |
| 2.4.44 | 3-(2,2,2-trifluoroethoxy)phenyl | methyl | ethyl | |
| 2.4.45 | 3-(2-chloroethoxy)phenyl | methyl | ethyl | |
| 2.4.46 | 3-(2-hydroxyethoxy)phenyl | methyl | ethyl | |
| 2.4.47 | 3-(2-methoxyethoxy)phenyl | methyl | ethyl | |
| 2.4.48 | 3-[(tert-butoxycarbonyl)oxy]phenyl | methyl | ethyl | |
| 2.4.49 | 3-nitrophenyl | methyl | ethyl | |
| 2.4.50 | 3-acetoxyphenyl | methyl | ethyl | |
| 2.4.51 | {3-[(tert-butoxycarbonyl)amino]-phenyl} | methyl | ethyl | |
| 2.4.52 | 3-methylsulfanylphenyl | methyl | ethyl | |

TABLE 2.4-continued

Inventive compounds of the general formula (I) in which W* is COOY, $R^1$ and $R^2$ are each hydrogen, and aryl is the radical.

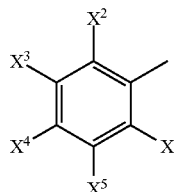

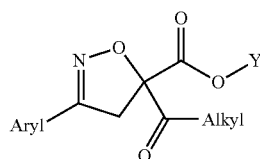

| No. | Aryl | Alkyl | Y | Physical data |
|---|---|---|---|---|
| 2.4.53 | 3-ethylsulfanylphenyl | methyl | ethyl | |
| 2.4.54 | 3-(pentafluoro-lambda$^6$-sulfanyl)-phenyl | methyl | ethyl | |
| 2.4.55 | 2,3-difluorophenyl | methyl | ethyl | |
| 2.4.56 | 2,3-difluorophenyl | ethyl | ethyl | |
| 2.4.57 | 2,3-difluorophenyl | propyl | ethyl | |
| 2.4.58 | 2,3-difluorophenyl | butyl | ethyl | |
| 2.4.59 | 2-chloro-3-fluorophenyl | methyl | ethyl | |
| 2.4.60 | 2-bromo-3-fluorophenyl | methyl | ethyl | |
| 2.4.61 | 2-methyl-3-fluorophenyl | methyl | ethyl | |
| 2.4.62 | 2-ethyl-3-fluorophenyl | methyl | ethyl | |
| 2.4.63 | 2-cyclopropyl-3-fluorophenyl | methyl | ethyl | |
| 2.4.64 | 2-vinyl-3-fluorophenyl | methyl | ethyl | |
| 2.4.65 | 2-ethynyl-3-fluorophenyl | methyl | ethyl | |
| 2.4.66 | 2-cyano-3-fluorophenyl | methyl | ethyl | |
| 2.4.67 | 2-methoxy-3-fluorophenyl | methyl | ethyl | |
| 2.4.68 | 2-ethoxy-3-fluorophenyl | methyl | ethyl | |
| 2.4.69 | 2-trifluoromethoxy-3-fluorophenyl | methyl | ethyl | |
| 2.4.70 | 2-nitro-3-fluorophenyl | methyl | ethyl | |
| 2.4.71 | 2-fluoro-3-chlorophenyl | methyl | ethyl | |
| 2.4.72 | 2,3-dichlorophenyl | methyl | ethyl | |
| 2.4.73 | 2,3-dichlorophenyl | ethyl | ethyl | |
| 2.4.74 | 2,3-dichlorophenyl | propyl | ethyl | |
| 2.4.75 | 2,3-dichlorophenyl | butyl | ethyl | |
| 2.4.76 | 2-bromo-3-chlorophenyl | methyl | ethyl | |
| 2.4.77 | 2-methyl-3-chlorophenyl | methyl | ethyl | |
| 2.4.78 | 2-ethyl-3-chlorophenyl | methyl | ethyl | |
| 2.4.79 | 2-cyclopropyl-3-chlorophenyl | methyl | ethyl | |
| 2.4.80 | 2-vinyl-3-chlorophenyl | methyl | ethyl | |
| 2.4.81 | 2-ethynyl-3-chlorophenyl | methyl | ethyl | |
| 2.4.82 | 2-cyano-3-chlorophenyl | methyl | ethyl | |
| 2.4.83 | 2-trifluoromethyl-2-chlorophenyl | methyl | ethyl | |
| 2.4.84 | 2-methoxy-3-chlorophenyl | methyl | ethyl | |
| 2.4.85 | 2-ethoxy-3-chlorophenyl | methyl | ethyl | |
| 2.4.86 | 2-trifluoromethoxy-3-chlorophenyl | methyl | ethyl | |
| 2.4.87 | 2-nitro-3-chlorophenyl | methyl | ethyl | |
| 2.4.88 | 2-fluoro-3-bromophenyl | methyl | ethyl | |
| 2.4.89 | 2-chloro-3-bromophenyl | methyl | ethyl | |
| 2.4.90 | 2,3-dibromophenyl | methyl | ethyl | |
| 2.4.91 | 2-methyl-3-bromophenyl | methyl | ethyl | |
| 2.4.92 | 2-ethyl-3-bromophenyl | methyl | ethyl | |
| 2.4.93 | 2-cyclopropyl-3-bromophenyl | methyl | ethyl | |
| 2.4.94 | 2-vinyl-3-bromophenyl | methyl | ethyl | |
| 2.4.95 | 2-ethynyl-3-bromophenyl | methyl | ethyl | |
| 2.4.96 | 2-cyano-3-bromophenyl | methyl | ethyl | |
| 2.4.97 | 2-trifluoromethyl-3-bromophenyl | methyl | ethyl | |
| 2.4.98 | 2-methoxy-3-phenyl | methyl | ethyl | |
| 2.4.99 | 2-ethoxy-3-bromophenyl | methyl | ethyl | |
| 2.4.100 | 2-trifluoromethoxy-3-bromophenyl | methyl | ethyl | |
| 2.4.101 | 2-nitro-3-bromophenyl | methyl | ethyl | |
| 2.4.102 | 2-fluoro-3-iodophenyl | methyl | ethyl | |
| 2.4.103 | 2-chloro-3-iodophenyl | methyl | ethyl | |
| 2.4.104 | 2-bromo-3-iodophenyl | methyl | ethyl | |
| 2.4.105 | 2-methyl-3-iodophenyl | methyl | ethyl | |
| 2.4.106 | 2-ethyl-3-iodophenyl | methyl | ethyl | |
| 2.4.107 | 2-cyclopropyl-3-iodophenyl | methyl | ethyl | |

TABLE 2.4-continued

Inventive compounds of the general formula (I) in which W* is COOY, R¹ and R² are each hydrogen, and aryl is the radical.

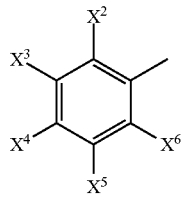

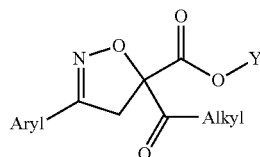

| No. | Aryl | Alkyl | Y | Physical data |
|---|---|---|---|---|
| 2.4.108 | 2-vinyl-3-iodophenyl | methyl | ethyl | |
| 2.4.109 | 2-ethynyl-3-iodophenyl | methyl | ethyl | |
| 2.4.110 | 2-cyano-3-iodophenyl | methyl | ethyl | |
| 2.4.111 | 2-trifluoromethyl-3-iodophenyl | methyl | ethyl | |
| 2.4.112 | 2-methoxy-3-iodophenyl | methyl | ethyl | |
| 2.4.113 | 2-ethoxy-3-iodophenyl | methyl | ethyl | |
| 2.4.114 | 2-trifluoromethoxy-3-iodophenyl | methyl | ethyl | |
| 2.4.115 | 2-nitro-3- iodophenyl | methyl | ethyl | |
| 2.4.116 | 2-fluoro-3-methylphenyl | methyl | ethyl | |
| 2.4.117 | 2-fluoro-3-methylphenyl | ethyl | ethyl | |
| 2.4.118 | 2-fluoro-3-methylphenyl | propyl | ethyl | |
| 2.4.119 | 2-fluoro-3-methylphenyl | butyl | ethyl | |
| 2.4.120 | 2-chloro-3-methylphenyl | methyl | ethyl | |
| 2.4.121 | 2-chloro-3-methylphenyl | ethyl | ethyl | |
| 2.4.122 | 2-chloro-3-methylphenyl | propyl | ethyl | |
| 2.4.123 | 2-chloro-3-methylphenyl | butyl | ethyl | |
| 2.4.124 | 2-bromo-3-methylphenyl | methyl | ethyl | |
| 2.4.125 | 2,3-dimethylphenyl | methyl | ethyl | |
| 2.4.126 | 2,3-dimethylphenyl | ethyl | ethyl | |
| 2.4.127 | 2,3-dimethylphenyl | propyl | ethyl | |
| 2.4.128 | 2,3-dimethylphenyl | butyl | ethyl | |
| 2.4.129 | 2-ethyl-3-methylphenyl | methyl | ethyl | |
| 2.4.130 | 2-cyclopropyl-3-methylphenyl | methyl | ethyl | |
| 2.4.131 | 2-vinyl-3-methylphenyl | methyl | ethyl | |
| 2.4.132 | 2-ethynyl-3-methylphenyl | methyl | ethyl | |
| 2.4.133 | 2-cyano-3-methylphenyl | methyl | ethyl | |
| 2.4.134 | 2-trifluoromethyl-3-methylphenyl | methyl | ethyl | |
| 2.4.135 | 2-methoxy-3-methylphenyl | methyl | ethyl | |
| 2.4.136 | 2-ethoxy-3-methylphenyl | methyl | ethyl | |
| 2.4.137 | 2-trifluoromethoxy-3-methylphenyl | methyl | ethyl | |
| 2.4.138 | 2-nitro-3-methylphenyl | methyl | ethyl | |
| 2.4.139 | 2-fluoro-3-ethylphenyl | methyl | ethyl | |
| 2.4.140 | 2-chloro-3-ethylphenyl | methyl | ethyl | |
| 2.4.141 | 2-bromo-3-ethylphenyl | methyl | ethyl | |
| 2.4.142 | 2-methyl-3-ethylphenyl | methyl | ethyl | |
| 2.4.143 | 2,3-diethylphenyl | methyl | ethyl | |
| 2.4.144 | 2-cyclopropyl-3-ethylphenyl | methyl | ethyl | |
| 2.4.145 | 2-vinyl-3-ethylphenyl | methyl | ethyl | |
| 2.4.146 | 2-ethynyl-3-ethylphenyl | methyl | ethyl | |
| 2.4.147 | 2-cyano-3-ethylphenyl | methyl | ethyl | |
| 2.4.148 | 2-trifluoromethyl-3-ethylphenyl | methyl | ethyl | |
| 2.4.149 | 2-methoxy-3-ethylphenyl | methyl | ethyl | |
| 2.4.150 | 2-ethoxy-3-ethylphenyl | methyl | ethyl | |
| 2.4.151 | 2-trifluoromethoxy-3-ethylphenyl | methyl | ethyl | |
| 2.4.152 | 2-nitro-3-ethylphenyl | methyl | ethyl | |
| 2.4.153 | 2-fluoro-3-propylphenyl | methyl | ethyl | |
| 2.4.154 | 2-chloro-3-propylphenyl | methyl | ethyl | |
| 2.4.155 | 2-bromo-3-propylphenyl | methyl | ethyl | |
| 2.4.156 | 2-methyl-3-propylphenyl | methyl | ethyl | |
| 2.4.157 | 2-methyl-3-propylphenyl | methyl | ethyl | |
| 2.4.158 | 2-cyclopropyl-3-propylphenyl | methyl | ethyl | |
| 2.4.159 | 2-vinyl-3-propylphenyl | methyl | ethyl | |
| 2.4.160 | 2-ethynyl-3propylphenyl | methyl | ethyl | |
| 2.4.161 | 2-cyano-3-propylphenyl | methyl | ethyl | |
| 2.4.162 | 2-trifluoromethyl-3-propylphenyl | methyl | ethyl | |
| 2.4.163 | 2-methoxy-3-propylphenyl | methyl | ethyl | |

TABLE 2.4-continued

Inventive compounds of the general formula (I) in which W* is COOY, $R^1$ and $R^2$ are each hydrogen, and aryl is the radical.

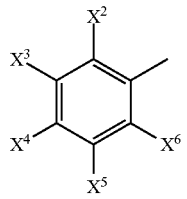

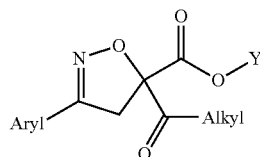

| No. | Aryl | Alkyl | Y | Physical data |
|---|---|---|---|---|
| 2.4.164 | 2-ethoxy-3-propylphenyl | methyl | ethyl | |
| 2.4.165 | 2-trifluoromethoxy-3-propylphenyl | methyl | ethyl | |
| 2.4.166 | 2-nitro-3-propylphenyl | methyl | ethyl | |
| 2.4.167 | 2-fluoro-3-isopropylphenyl | methyl | ethyl | |
| 2.4.168 | 2-chloro-3-isopropylphenyl | methyl | ethyl | |
| 2.4.169 | 2-bromo-3-isopropylphenyl | methyl | ethyl | |
| 2.4.170 | 2-methyl-3-isopropylphenyl | methyl | ethyl | |
| 2.4.171 | 2-ethyl-3-isopropylphenyl | methyl | ethyl | |
| 2.4.172 | 2-cyclopropyl-3-isopropylphenyl | methyl | ethyl | |
| 2.4.173 | 2-vinyl-3-isopropylphenyl | methyl | ethyl | |
| 2.4.174 | 2-ethynyl-3-isopropylphenyl | methyl | ethyl | |
| 2.4.175 | 2-cyano-3-isopropylphenyl | methyl | ethyl | |
| 2.4.176 | 2-trifluoromethyl-3-isopropylphenyl | methyl | ethyl | |
| 2.4.177 | 2-methoxy-3-isopropylphenyl | methyl | ethyl | |
| 2.4.178 | 2-ethoxy-3-isopropylphenyl | methyl | ethyl | |
| 2.4.179 | 2-trifluoromethoxy-3-isopropylphenyl | methyl | ethyl | |
| 2.4.180 | 2-nitro-3-isopropylphenyl | methyl | ethyl | |
| 2.4.181 | 2-fluoro-3-tert-butylphenyl | methyl | ethyl | |
| 2.4.182 | 2-chloro-3-tert-butylphenyl | methyl | ethyl | |
| 2.4.183 | 2-bromo-3-tert-butylphenyl | methyl | ethyl | |
| 2.4.184 | 2-methyl-3-tert-butylphenyl | methyl | ethyl | |
| 2.4.185 | 2-ethyl-3-tert-butylphenyl | methyl | ethyl | |
| 2.4.186 | 2-cyclopropyl-3-tert-butylphenyl | methyl | ethyl | |
| 2.4.187 | 2-vinyl-3-tert-butylphenyl | methyl | ethyl | |
| 2.4.188 | 2-ethynyl-3-tert-butylphenyl | methyl | ethyl | |
| 2.4.189 | 2-cyano-3-tert-butylphenyl | methyl | ethyl | |
| 2.4.190 | 2-trifluoromethyl-3-tert-butylphenyl | methyl | ethyl | |
| 2.4.191 | 2-methoxy-3-tert-butylphenyl | methyl | ethyl | |
| 2.4.192 | 2-ethoxy-3-tert-butylphenyl | methyl | ethyl | |
| 2.4.193 | 2-trifluoromethoxy-3-tert-butylphenyl | methyl | ethyl | |
| 2.4.194 | 2-nitro-3-tert-butylphenyl | methyl | ethyl | |
| 2.4.195 | 2-fluoro-3-hydroxymethylphenyl | methyl | ethyl | |
| 2.4.196 | 2-chloro-3-hydroxymethylphenyl | methyl | ethyl | |
| 2.4.197 | 2-bromo-3-hydroxymethylphenyl | methyl | ethyl | |
| 2.4.198 | 2-methyl-3-hydroxymethylphenyl | methyl | ethyl | |
| 2.4.199 | 2-ethyl-3-hydroxymethylphenyl | methyl | ethyl | |
| 2.4.200 | 2-cyclopropyl-3-hydroxymethylphenyl | methyl | ethyl | |
| 2.4.201 | 2-vinyl-3-hydroxymethylphenyl | methyl | ethyl | |
| 2.4.202 | 2-ethynyl-3-hydroxymethylphenyl | methyl | ethyl | |
| 2.4.203 | 2-cyano-3-hydroxymethylphenyl | methyl | ethyl | |
| 2.4.204 | 2-trifluoromethyl-3-hydroxymethylphenyl | methyl | ethyl | |
| 2.4.205 | 2-methoxy-3-hydroxymethylphenyl | methyl | ethyl | |
| 2.4.206 | 2-ethoxy-3-hydroxymethylphenyl | methyl | ethyl | |
| 2.4.207 | 2-trifluoromethoxy-3-hydroxymethylphenyl | methyl | ethyl | |
| 2.4.208 | 2-nitro-3-hydroxymethylphenyl | methyl | ethyl | |
| 2.4.209 | 2-fluoro-3-cyclopropylphenyl | methyl | ethyl | |
| 2.4.210 | 2-chloro-3-cyclopropylphenyl | methyl | ethyl | |
| 2.4.211 | 2-bromo-3-cyclopropylphenyl | methyl | ethyl | |
| 2.4.212 | 2-methyl-3-cyclopropylphenyl | methyl | ethyl | |
| 2.4.213 | 2-ethyl-3-cyclopropylphenyl | methyl | ethyl | |
| 2.4.214 | 2-cyclopropyl-3-cyclopropylphenyl | methyl | ethyl | |

TABLE 2.4-continued

Inventive compounds of the general formula (I) in which W* is COOY, $R^1$ and $R^2$ are each hydrogen, and aryl is the radical.

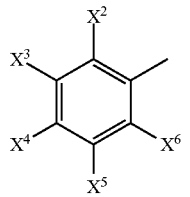

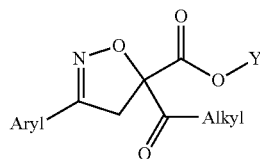

| No. | Aryl | Alkyl | Y | Physical data |
|---|---|---|---|---|
| 2.4.215 | 2-vinyl-3-cyclopropylphenyl | methyl | ethyl | |
| 2.4.216 | 2-ethynyl-3-cyclopropylphenyl | methyl | ethyl | |
| 2.4.217 | 2-cyano-3-cyclopropylphenyl | methyl | ethyl | |
| 2.4.218 | 2-trifluoromethyl-3-cyclopropylphenyl | methyl | ethyl | |
| 2.4.219 | 2-methoxy-3-cyclopropylphenyl | methyl | ethyl | |
| 2.4.220 | 2-ethoxy-3-cyclopropylphenyl | methyl | ethyl | |
| 2.4.221 | 2-trifluoromethoxy-3-cyclopropylphenyl | methyl | ethyl | |
| 2.4.222 | 2-fluoro-3-methoxycarbonylphenyl | methyl | ethyl | |
| 2.4.223 | 2-chloro-3-methoxycarbonylphenyl | methyl | ethyl | |
| 2.4.224 | 2-bromo-3-methoxycarbonylphenyl | methyl | ethyl | |
| 2.4.225 | 2-methyl-3-methoxycarbonylphenyl | methyl | ethyl | |
| 2.4.226 | 2-ethyl-3-methoxycarbonylphenyl | methyl | ethyl | |
| 2.4.227 | 2-cyclopropyl-3-methoxycarbonyl-phenyl | methyl | ethyl | |
| 2.4.228 | 2-vinyl-3-methoxycarbonylphenyl | methyl | ethyl | |
| 2.4.229 | 2-ethynyl-3-methoxycarbonyl-phenyl | methyl | ethyl | |
| 2.4.230 | 2-cyano-3-methoxycarbonylphenyl | methyl | ethyl | |
| 2.4.231 | 2-trifluoromethyl-3-methoxycarbonylphenyl | methyl | ethyl | |
| 2.4.232 | 2-methoxy-3-methoxycarbonyl-phenyl | methyl | ethyl | |
| 2.4.233 | 2-ethoxy-3-methoxycarbonylphenyl | methyl | ethyl | |
| 2.4.234 | 2-trifluoromethoxy-3-methoxycarbonylphenyl | methyl | ethyl | |
| 2.4.235 | 2-nitro-3-methoxycarbonylphenyl | methyl | ethyl | |
| 2.4.236 | 2-fluoro-3-vinylphenyl | methyl | ethyl | |
| 2.4.237 | 2-chloro-3-vinylphenyl | methyl | ethyl | |
| 2.4.238 | 2-bromo-3-vinylphenyl | methyl | ethyl | |
| 2.4.239 | 2-methyl-3-vinylphenyl | methyl | ethyl | |
| 2.4.240 | 2-ethyl-3-vinylphenyl | methyl | ethyl | |
| 2.4.241 | 2-cyclopropyl-3-vinylphenyl | methyl | ethyl | |
| 2.4.242 | 2-vinyl-3-vinylphenyl | methyl | ethyl | |
| 2.4.243 | 2-ethynyl-3-vinylphenyl | methyl | ethyl | |
| 2.4.244 | 2-cyano-3-vinylphenyl | methyl | ethyl | |
| 2.4.245 | 2-trifluoromethyl-3-vinylphenyl | methyl | ethyl | |
| 2.4.246 | 2-methoxy-3-vinylphenyl | methyl | ethyl | |
| 2.4.247 | 2-ethoxy-3-vinylphenyl | methyl | ethyl | |
| 2.4.248 | 2-trifluoromethoxy-3-vinylphenyl | methyl | ethyl | |
| 2.4.249 | 2-nitro-3-vinylphenyl | methyl | ethyl | |
| 2.4.250 | 2-fluoro-3-ethynylphenyl | methyl | ethyl | |
| 2.4.251 | 2-chloro-3-ethynylphenyl | methyl | ethyl | |
| 2.4.252 | 2-bromo-3-ethynylphenyl | methyl | ethyl | |
| 2.4.253 | 2-methyl-3-ethynylphenyl | methyl | ethyl | |
| 2.4.254 | 2-ethyl-3-ethynylphenyl | methyl | ethyl | |
| 2.4.255 | 2-cyclopropyl-3-ethynylphenyl | methyl | ethyl | |
| 2.4.256 | 2-vinyl-3-ethynylphenyl | methyl | ethyl | |
| 2.4.257 | 2-cyano-3-ethynylphenyl | methyl | ethyl | |
| 2.4.258 | 2-trifluoromethyl-3-ethynylphenyl | methyl | ethyl | |
| 2.4.259 | 2-methoxy-3-ethynylphenyl | methyl | ethyl | |
| 2.4.260 | 2-ethoxy-3-ethynylphenyl | methyl | ethyl | |
| 2.4.261 | 2-trifluoromethoxy-3-ethynylphenyl | methyl | ethyl | |
| 2.4.262 | 2-nitro-3-ethynylphenyl | methyl | ethyl | |
| 2.4.263 | 2-fluoro-3-ethynylphenyl | methyl | ethyl | |

TABLE 2.4-continued

Inventive compounds of the general formula (I) in which W* is COOY, $R^1$ and $R^2$ are each hydrogen, and aryl is the radical.

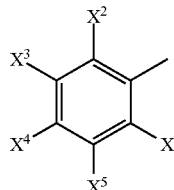

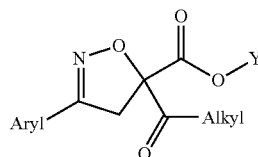

| No. | Aryl | Alkyl | Y | Physical data |
|---|---|---|---|---|
| 2.4.264 | 2-fluoro-3-cyanophenyl | methyl | ethyl | |
| 2.4.265 | 2-chloro-3-cyanophenyl | methyl | ethyl | |
| 2.4.266 | 2-bromo-3-cyanophenyl | methyl | ethyl | |
| 2.4.267 | 2-methyl-3-cyanophenyl | methyl | ethyl | |
| 2.4.268 | 2-ethyl-3-cyanophenyl | methyl | ethyl | |
| 2.4.269 | 2-ethyl-3-cyanophenyl | ethyl | ethyl | |
| 2.4.270 | 2-ethyl-3-cyanophenyl | propyl | ethyl | |
| 2.4.271 | 2-ethyl-3-cyanophenyl | butyl | ethyl | |
| 2.4.272 | 2-cyclopropyl-3-cyanophenyl | methyl | ethyl | |
| 2.4.273 | 2-vinyl-3-cyanophenyl | methyl | ethyl | |
| 2.4.274 | 2-ethynyl-3-cyanophenyl | methyl | ethyl | |
| 2.4.275 | 2-cyano-3-cyanophenyl | methyl | ethyl | |
| 2.4.276 | 2-trifluoromethyl-3-cyanophenyl | methyl | ethyl | |
| 2.4.277 | 2-methoxy-3-cyanophenyl | methyl | ethyl | |
| 2.4.278 | 2-ethoxy-3-cyanophenyl | methyl | ethyl | |
| 2.4.279 | 2-trifluoromethoxy-3-cyanophenyl | methyl | ethyl | |
| 2.4.280 | 2-nitro-3-cyanophenyl | methyl | ethyl | |
| 2.4.281 | 2-fluoro-3-hydroxyphenyl | methyl | ethyl | |
| 2.4.282 | 2-chloro-3-hydroxyphenyl | methyl | ethyl | |
| 2.4.283 | 2-bromo-3-hydroxyphenyl | methyl | ethyl | |
| 2.4.284 | 2-methyl-3-hydroxyphenyl | methyl | ethyl | |
| 2.4.285 | 2-ethyl-3-hydroxyphenyl | methyl | ethyl | |
| 2.4.286 | 2-cyclopropyl-3-hydroxyphenyl | methyl | ethyl | |
| 2.4.287 | 2-vinyl-3-hydroxyphenyl | methyl | ethyl | |
| 2.4.288 | 2-ethynyl-3-hydroxyphenyl | methyl | ethyl | |
| 2.4.289 | 2-cyano-3-hydroxyphenyl | methyl | ethyl | |
| 2.4.290 | 2-trifluoromethyl-3-hydroxyphenyl | methyl | ethyl | |
| 2.4.291 | 2-methoxy-3-hydroxyphenyl | methyl | ethyl | |
| 2.4.292 | 2-ethoxy-3-hydroxyphenyl | methyl | ethyl | |
| 2.4.293 | 2-trifluoromethoxy-3-hydroxyphenyl | methyl | ethyl | |
| 2.4.294 | 2-nitro-3-hydroxyphenyl | methyl | ethyl | |
| 2.4.295 | 2-fluoro-3-methoxyphenyl | methyl | ethyl | |
| 2.4.296 | 2-chloro-3-methoxyphenyl | methyl | ethyl | |
| 2.4.297 | 2-bromo-3-methoxyphenyl | methyl | ethyl | |
| 2.4.298 | 2-methyl-3-methoxyphenyl | methyl | ethyl | |
| 2.4.299 | 2-ethyl-3-methoxyphenyl | methyl | ethyl | |
| 2.4.300 | 2-cyclopropyl-3-methoxyphenyl | methyl | ethyl | |
| 2.4.301 | 2-vinyl-3-methoxyphenyl | methyl | ethyl | |
| 2.4.302 | 2-ethynyl-3-methoxyphenyl | methyl | ethyl | |
| 2.4.303 | 2-cyano-3-methoxyphenyl | methyl | ethyl | |
| 2.4.304 | 2-trifluoromethyl-3-methoxyphenyl | methyl | ethyl | |
| 2.4.305 | 2,3-dimethoxyphenyl | methyl | ethyl | |
| 2.4.306 | 2-ethoxy-3-methoxyphenyl | methyl | ethyl | |
| 2.4.307 | 2-trifluoromethoxy-3-methoxyphenyl | methyl | ethyl | |
| 2.4.308 | 2-nitro-3-methoxyphenyl | methyl | ethyl | |
| 2.4.309 | 2-fluoro-3-ethoxyphenyl | methyl | ethyl | |
| 2.4.310 | 2-chloro-3-ethoxyphenyl | methyl | ethyl | |
| 2.4.311 | 2-bromo-3-ethoxyphenyl | methyl | ethyl | |
| 2.4.312 | 2-methyl-3-ethoxyphenyl | methyl | ethyl | |
| 2.4.313 | 2-ethyl-3-ethoxyphenyl | methyl | ethyl | |
| 2.4.314 | 2-cyclopropyl-3-ethoxyphenyl | methyl | ethyl | |
| 2.4.315 | 2-vinyl-3-ethoxyphenyl | methyl | ethyl | |
| 2.4.316 | 2-ethynyl-3-ethoxyphenyl | methyl | ethyl | |
| 2.4.317 | 2-cyano-3-ethoxyphenyl | methyl | ethyl | |
| 2.4.318 | 2-trifluoromethyl-3-ethoxyphenyl | methyl | ethyl | |

TABLE 2.4-continued

Inventive compounds of the general formula (I) in which W* is COOY, R¹ and R² are each hydrogen, and aryl is the radical.

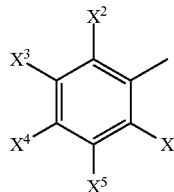

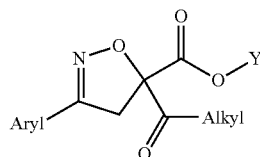

| No. | Aryl | Alkyl | Y | Physical data |
|---|---|---|---|---|
| 2.4.319 | 2-methoxy-3-ethoxyphenyl | methyl | ethyl | |
| 2.4.320 | 2,3-diethoxy--phenyl | methyl | ethyl | |
| 2.4.321 | 2-trifluoromethoxy-3-ethoxyphenyl | methyl | ethyl | |
| 2.4.322 | 2-nitro-3-ethoxyphenyl | methyl | ethyl | |
| 2.4.323 | 2-fluoro-3-propoxyphenyl | methyl | ethyl | |
| 2.4.324 | 2-chloro-3-propoxyphenyl | methyl | ethyl | |
| 2.4.325 | 2-bromo-3-propoxyphenyl | methyl | ethyl | |
| 2.4.326 | 2-methyl-3-propoxyphenyl | methyl | ethyl | |
| 2.4.327 | 2-ethyl-3-propoxyphenyl | methyl | ethyl | |
| 2.4.328 | 2-cyclopropyl-3-propoxyphenyl | methyl | ethyl | |
| 2.4.329 | 2-vinyl-3-propoxyphenyl | methyl | ethyl | |
| 2.4.330 | 2-ethynyl-3-propoxyphenyl | methyl | ethyl | |
| 2.4.331 | 2-cyano-3-propoxyphenyl | methyl | ethyl | |
| 2.4.332 | 2-trifluoromethyl-3-propoxyphenyl | methyl | ethyl | |
| 2.4.333 | 2-methoxy-3-propoxyphenyl | methyl | ethyl | |
| 2.4.334 | 2-ethoxy-3-propoxyphenyl | methyl | ethyl | |
| 2.4.335 | 2-trifluoromethoxy-3-propoxyphenyl | methyl | ethyl | |
| 2.4.336 | 2-nitro-3-propoxyphenyl | methyl | ethyl | |
| 2.4.337 | 2-fluoro-3-isopropoxyphenyl | methyl | ethyl | |
| 2.4.338 | 2-chloro-3-isopropoxyphenyl | methyl | ethyl | |
| 2.4.339 | 2-bromo-3-isopropoxyphenyl | methyl | ethyl | |
| 2.4.340 | 2-methyl-3-isopropoxyphenyl | methyl | ethyl | |
| 2.4.341 | 2-ethyl-3-isopropoxyphenyl | methyl | ethyl | |
| 2.4.342 | 2-cyclopropyl-3-isopropoxyphenyl | methyl | ethyl | |
| 2.4.343 | 2-vinyl-3-isopropoxyphenyl | methyl | ethyl | |
| 2.4.344 | 2-ethynyl-3-isopropoxyphenyl | methyl | ethyl | |
| 2.4.345 | 2-cyano-3-isopropoxyphenyl | methyl | ethyl | |
| 2.4.346 | 2-trifluoromethyl-3-isopropoxyphenyl | methyl | ethyl | |
| 2.4.347 | 2-methoxy-3-isopropoxyphenyl | methyl | ethyl | |
| 2.4.348 | 2-ethoxy-3-isopropoxyphenyl | methyl | ethyl | |
| 2.4.349 | 2-trifluoromethoxy-3-isopropoxyphenyl | methyl | ethyl | |
| 2.4.350 | 2-nitro-3-isopropoxyphenyl | methyl | ethyl | |
| 2.4.351 | 2-fluoro-3-tert-butoxyphenyl | methyl | ethyl | |
| 2.4.352 | 2-chloro-3-tert-butoxyphenyl | methyl | ethyl | |
| 2.4.353 | 2-bromo-3-tert-butoxyphenyl | methyl | ethyl | |
| 2.4.354 | 2-methyl-3-tert-butoxyphenyl | methyl | ethyl | |
| 2.4.355 | 2-ethyl-3-tert-butoxyphenyl | methyl | ethyl | |
| 2.4.356 | 2-cyclopropyl-3-tert-butoxyphenyl | methyl | ethyl | |
| 2.4.357 | 2-vinyl-3-tert-butoxyphenyl | methyl | ethyl | |
| 2.4.358 | 2-ethynyl-3-tert-butoxyphenyl | methyl | ethyl | |
| 2.4.359 | 2-cyano-3-tert-butoxyphenyl | methyl | ethyl | |
| 2.4.360 | 2-trifluoromethyl-3-tert-butoxyphenyl | methyl | ethyl | |
| 2.4.361 | 2-methoxy-3-tert-butoxyphenyl | methyl | ethyl | |
| 2.4.362 | 2-ethoxy-3-tert-butoxyphenyl | methyl | ethyl | |
| 2.4.363 | 2-trifluoromethoxy-3-tert-butoxyphenyl | methyl | ethyl | |
| 2.4.364 | 2-nitro-3-tert-butoxyphenyl | methyl | ethyl | |
| 2.4.365 | 2-fluoro-3-trifluoromethoxyphenyl | methyl | ethyl | |
| 2.4.366 | 2-chloro-3-trifluoromethoxyphenyl | methyl | ethyl | |
| 2.4.367 | 2-bromo-3-trifluoromethoxyphenyl | methyl | ethyl | |
| 2.4.368 | 2-methyl-3-trifluoromethoxyphenyl | methyl | ethyl | |
| 2.4.369 | 2-ethyl-3-trifluoromethoxyphenyl | methyl | ethyl | |

TABLE 2.4-continued

Inventive compounds of the general formula (I) in which W* is COOY, $R^1$ and $R^2$ are each hydrogen, and aryl is the radical.

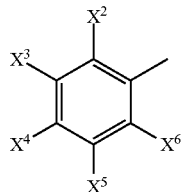

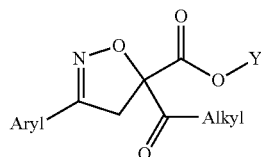

| No. | Aryl | Alkyl | Y | Physical data |
|---|---|---|---|---|
| 2.4.370 | 2-cyclopropyl-3-trifluoromethoxy-phenyl | methyl | ethyl | |
| 2.4.371 | 2-vinyl-3-trifluoromethoxyphenyl | methyl | ethyl | |
| 2.4.372 | 2-ethynyl-3-trifluoromethoxyphenyl | methyl | ethyl | |
| 2.4.373 | 2-cyano-3-trifluoromethoxyphenyl | methyl | ethyl | |
| 2.4.374 | 2-trifluoromethyl-3-trifluoromethoxy-phenyl | methyl | ethyl | |
| 2.4.375 | 2-methoxy-3-trifluoromethoxy-phenyl | methyl | ethyl | |
| 2.4.376 | 2-ethoxy-3-trifluoromethoxyphenyl | methyl | ethyl | |
| 2.4.377 | 2,3-bis(trifluoromethoxy)phenyl | methyl | ethyl | |
| 2.4.378 | 2-nitro-3-trifluoromethoxyphenyl | methyl | ethyl | |
| 2.4.379 | 2-fluoro-3-(2,2,2-trifluoroethoxy)-phenyl | methyl | ethyl | |
| 2.4.380 | 2-chloro-3-(2,2,2-trifluoroethoxy)-phenyl | methyl | ethyl | |
| 2.4.381 | 2-bromo-3-(2,2,2-trifluoroethoxy)-phenyl | methyl | ethyl | |
| 2.4.382 | 2-methyl-3-(2,2,2-trifluoroethoxy)-phenyl | methyl | ethyl | |
| 2.4.383 | 2-ethyl-3-(2,2,2-trifluoroethoxy)-phenyl | methyl | ethyl | |
| 2.4.384 | 2-cyclopropyl-3-(2,2,2-trifluoro-ethoxy)phenyl | methyl | ethyl | |
| 2.4.385 | 2-vinyl-3-(2,2,2-trifluoroethoxy)-phenyl | methyl | ethyl | |
| 2.4.386 | 2-ethynyl-3-(2,2,2-trifluoroethoxyphenyl | methyl | ethyl | |
| 2.4.387 | 2-cyano-3-(2,2,2-trifluoroethoxy)-phenyl | methyl | ethyl | |
| 2.4.388 | 2-trifluoromethyl-3-(2,2,2-trifluoro-ethoxy)phenyl | methyl | ethyl | |
| 2.4.389 | 2-methoxy-3-(2,2,2-trifluoroethoxy)-phenyl | methyl | ethyl | |
| 2.4.390 | 2-ethoxy-3-(2,2,2-trifluoroethoxy)-phenyl | methyl | ethyl | |
| 2.4.391 | 2-trifluoromethoxy-3-(2,2,2-trifluoro-ethoxy)phenyl | methyl | ethyl | |
| 2.4.392 | 2-nitro-3-(2,2,2-trifluoroethoxy)-phenyl | methyl | ethyl | |
| 2.4.393 | 2-fluoro-3-difluoromethoxyphenyl | methyl | ethyl | |
| 2.4.394 | 2-chloro-3-difluoromethoxyphenyl | methyl | ethyl | |
| 2.4.395 | 2-bromo-3-difluoromethoxyphenyl | methyl | ethyl | |
| 2.4.396 | 2-methyl-3-difluoromethox-phenyl | methyl | ethyl | |
| 2.4.397 | 2-ethyl-3-difluoromethoxyphenyl | methyl | ethyl | |
| 2.4.398 | 2-cyclopropyl-3-difluoromethoxy-phenyl | methyl | ethyl | |
| 2.4.399 | 2-vinyl-3-difluoromethoxyphenyl | methyl | ethyl | |
| 2.4.400 | 2-ethynyl-3-difluoromethoxyphenyl | methyl | ethyl | |
| 2.4.401 | 2-cyano-3-difluoro-methoxyphenyl | methyl | ethyl | |
| 2.4.402 | 2-trifluoromethyl-3-difluoromethoxy-phenyl | methyl | ethyl | |
| 2.4.403 | 2-methoxy-3-difluoro-methoxyphenyl | methyl | ethyl | |

TABLE 2.4-continued

Inventive compounds of the general formula (I) in which W* is COOY, $R^1$ and $R^2$ are each hydrogen, and aryl is the radical.

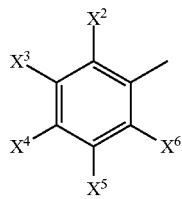

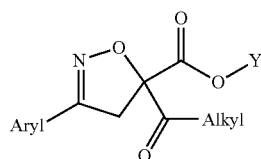

| No. | Aryl | Alkyl | Y | Physical data |
|---|---|---|---|---|
| 2.4.404 | 2-ethoxy-3-difluoromethoxyphenyl | methyl | ethyl | |
| 2.4.405 | 2-trifluoromethoxy-3-difluoromethoxyphenyl | methyl | ethyl | |
| 2.4.406 | 2-nitro-3-difluoromethoxyphenyl | methyl | ethyl | |
| 2.4.407 | 2-fluoro-3-(2-methoxyethoxy)-phenyl | methyl | ethyl | |
| 2.4.408 | 2-chloro-3-(2-methoxyethoxy)-phenyl | methyl | ethyl | |
| 2.4.409 | 2-bromo-3-(2-methoxyethoxy)-phenyl | methyl | ethyl | |
| 2.4.410 | 2-methyl-3-(2-methoxyethoxy)-phenyl | methyl | ethyl | |
| 2.4.411 | 2-ethyl-3-(2-methoxyethoxy)phenyl | methyl | ethyl | |
| 2.4.412 | 2-cyclopropyl-3-(2-methoxyethoxy)-phenyl | methyl | ethyl | |
| 2.4.413 | 2-vinyl-3-(2-methoxyethoxy)phenyl | methyl | ethyl | |
| 2.4.414 | 2-ethynyl-3-(2-methoxyethoxy)-phenyl | methyl | ethyl | |
| 2.4.415 | 2-cyano-3-(2-methoxyethoxy)-phenyl | methyl | ethyl | |
| 2.4.416 | 2-trifluoromethyl-3-(2-methoxyethoxy)phenyl | methyl | ethyl | |
| 2.4.417 | 2-methoxy-3-(2-methoxyethoxy)-phenyl | methyl | ethyl | |
| 2.4.418 | 2-ethoxy-3-(2-methoxyethoxy)-phenyl | methyl | ethyl | |
| 2.4.419 | 2-trifluoromethoxy-(2-methoxyethoxy)phenyl | methyl | ethyl | |
| 2.4.420 | 2-nitro-3-(2-methoxyethoxy)phenyl | methyl | ethyl | |
| 2.4.421 | 2-fluoro-3-(tert-butoxycarbonyloxy)-phenyl | methyl | ethyl | |
| 2.4.422 | 2-chloro-3-(tert-butoxycarbonyloxy)-phenyl | methyl | ethyl | |
| 2.4.423 | 2-bromo-3-(tert-butoxycarbonyl-oxy)phenyl | methyl | ethyl | |
| 2.4.424 | 2-methyl-3-(tert-butoxycarbonyl-oxy)phenyl | methyl | ethyl | |
| 2.4.425 | 2-ethyl-3-(tert-butoxycarbonyloxy)-phenyl | methyl | ethyl | |
| 2.4.426 | 2-cyclopropyl-3-(tert-butoxycarbonyl-oxy)phenyl | methyl | ethyl | |
| 2.4.427 | 2-vinyl-3-(tert-butoxycarbonyloxy)-phenyl | methyl | ethyl | |
| 2.4.428 | 2-ethynyl-3-(tert-butoxycarbonyl-oxy)phenyl | methyl | ethyl | |
| 2.4.429 | 2-cyano-3-(tert-butoxycarbonyloxy)-phenyl | methyl | ethyl | |
| 2.4.430 | 2-trifluoromethyl-3-(tert-butoxycarbonyl-oxy)phenyl | methyl | ethyl | |
| 2.4.431 | 2-methoxy-3-(tert-butoxycarbonyloxy)phenyl | methyl | ethyl | |
| 2.4.432 | 2-ethoxy-3-(tert-butoxycarbonyloxy)phenyl | methyl | ethyl | |
| 2.4.433 | 2-trifluoromethoxy-3-(tert-butoxycarbonyl-oxy)phenyl | methyl | ethyl | |

TABLE 2.4-continued

Inventive compounds of the general formula (I) in which W* is COOY, R¹ and R² are each hydrogen, and aryl is the radical.

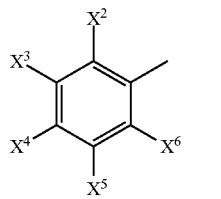

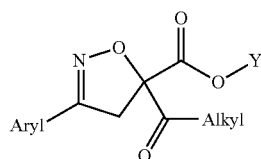

| No. | Aryl | Alkyl | Y | Physical data |
|---|---|---|---|---|
| 2.4.434 | 2-nitro-3-(tert-butoxycarbonyloxy)-phenyl | methyl | ethyl | |
| 2.4.435 | 2-fluoro-3-nitrophenyl | methyl | ethyl | |
| 2.4.436 | 2-chloro-3-nitrophenyl | methyl | ethyl | |
| 2.4.437 | 2-bromo-3-nitrophenyl | methyl | ethyl | |
| 2.4.438 | 2-methyl-3-nitrophenyl | methyl | ethyl | |
| 2.4.439 | 2-ethyl-3-nitrophenyl | methyl | ethyl | |
| 2.4.440 | 2-cyclopropyl-3-nitrophenyl | methyl | ethyl | |
| 2.4.441 | 2-vinyl-3-nitrophenyl | methyl | ethyl | |
| 2.4.442 | 2-ethynyl-3-nitrophenyl | methyl | ethyl | |
| 2.4.443 | 2-cyano-3-nitrophenyl | methyl | ethyl | |
| 2.4.444 | 2-trifluoromethyl-3-nitrophenyl | methyl | ethyl | |
| 2.4.445 | 2-methoxy-3-nitrophenyl | methyl | ethyl | |
| 2.4.446 | 2-ethoxy-3-nitrophenyl | methyl | ethyl | |
| 2.4.447 | 2-trifluoromethoxy-3-nitrophenyl | methyl | ethyl | |
| 2.4.448 | 2-fluoro-3-methylsulfanylphenyl | methyl | ethyl | |
| 2.4.449 | 2-chloro-3-methylsulfanylphenyl | methyl | ethyl | |
| 2.4.450 | 2-bromo-3-methylsulfanylphenyl | methyl | ethyl | |
| 2.4.451 | 2-methyl-3-methylsulfanylphenyl | methyl | ethyl | |
| 2.4.452 | 2-ethyl-3-methylsulfanylphenyl | methyl | ethyl | |
| 2.4.453 | 2-cyclopropyl-3-methylsulfanylphenyl | methyl | ethyl | |
| 2.4.454 | 2-vinyl-3-methylsulfanylphenyl | methyl | ethyl | |
| 2.4.455 | 2-ethynyl-3-methylsulfanylphenyl | methyl | ethyl | |
| 2.4.456 | 2-cyano-3-methylsulfanylphenyl | methyl | ethyl | |
| 2.4.457 | 2-trifluoromethyl-3-methylsulfanylphenyl | methyl | ethyl | |
| 2.4.458 | 2-methoxy-3-methylsulfanylphenyl | methyl | ethyl | |
| 2.4.459 | 2-ethoxy-3-methylsulfanylphenyl | methyl | methyl | |
| 2.4.460 | 2-trifluoromethoxy-3-methylsulfanylphenyl | methyl | ethyl | |
| 2.4.61 | 2-nitro-3-methylsulfanylphenyl | methyl | ethyl | |
| 2.4.62 | 3,5-difluorophenyl | methyl | methyl | [CDCl3] 2.44 (s, 3H); 3.80 (d, 1H); 3.86 (s, 3H); 3.89 (d, 1H); 6.90 (m, 1H); 7.19 (d, 2H). |
| 2.4.463 | 3,5-difluorophenyl | ethyl | methyl | [CDCl3] 1.12 (t, 3H); 2.83 (q, 2H); 3.81 (d, 1H); 3.86 (s, 4H); 6.90 (m, 1H); 7.20 (d, 2H). |
| 2.4.464 | 3,5-difluorophenyl | propyl | ethyl | |
| 2.4.465 | 3,5-difluorophenyl | butyl | ethyl | |
| 2.4.466 | 3-chloro-5-fluorophenyl | methyl | methyl | [CDCl3] 2.43 (s, 3H); 3.80 (d, 1H); 3.87 (s, 3H); 3.90 (d, 1H); 7.18 (d, 1H), 7.30 (d, 1H), 7.43 (s, 1H). |
| 2.4.467 | 3-chloro-5-fluorophenyl | ethyl | ethyl | |
| 2.4.468 | 3-chloro-5-fluorophenyl | propyl | ethyl | |
| 2.4.469 | 3-chloro-5-fluorophenyl | butyl | ethyl | |
| 2.4.470 | 3-bromo-5-fluorophenyl | methyl | ethyl | |
| 2.4.471 | 3-bromo-5-fluorophenyl | ethyl | ethyl | |
| 2.4.472 | 3-bromo-5-fluorophenyl | propyl | ethyl | |
| 2.4.473 | 3-bromo-5-fluorophenyl | butyl | ethyl | |
| 2.4.474 | 3-iodo-5-fluorophenyl | methyl | ethyl | |
| 2.4.475 | 3-methyl-5-fluorophenyl | methyl | ethyl | |
| 2.4.476 | 3-methyl-5-fluorophenyl | ethyl | ethyl | |

TABLE 2.4-continued

Inventive compounds of the general formula (I) in which W* is COOY, R¹ and R² are each hydrogen, and aryl is the radical.

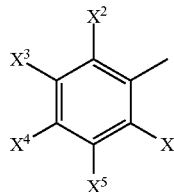

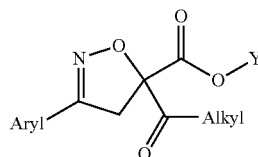

| No. | Aryl | Alkyl | Y | Physical data |
|---|---|---|---|---|
| 2.4.477 | 3-methyl-5-fluorophenyl | propyl | ethyl | |
| 2.4.478 | 3-methyl-5-fluorophenyl | butyl | ethyl | |
| 2.4.479 | 3-ethyl-5-fluorophenyl | methyl | ethyl | |
| 2.4.480 | 3-propyl-5-fluorophenyl | methyl | ethyl | |
| 2.4.481 | 3-i-propyl-5-fluorophenyl | methyl | ethyl | |
| 2.4.482 | 3-n-butyl-5-fluorophenyl | methyl | ethyl | |
| 2.4.483 | 3-isobutyl-5-fluorophenyl | methyl | ethyl | |
| 2.4.484 | 3-tert-butyl-5-fluorophenyl | methyl | ethyl | |
| 2.4.485 | 3-cyclopropyl-5-fluorophenyl | methyl | ethyl | |
| 2.4.486 | 3-vinyl-5-fluorophenyl | methyl | ethyl | |
| 2.4.487 | 3-ethynyl-5-fluorophenyl | methyl | ethyl | |
| 2.4.488 | 3-cyano-5-fluorophenyl | methyl | ethyl | |
| 2.4.489 | 3-trifluoromethyl-5-fluorophenyl | methyl | ethyl | |
| 2.4.490 | 3-trifluoromethyl-5-fluorophenyl | ethyl | ethyl | |
| 2.4.491 | 3-trifluoromethyl-5-fluorophenyl | propyl | ethyl | |
| 2.4.492 | 3-trifluoromethyl-5-fluorophenyl | butyl | ethyl | |
| 2.4.493 | 3-(methoxycarbonyl)-5-fluorophenyl | methyl | ethyl | |
| 2.4.494 | 3-hydroxymethyl-5-fluorophenyl | methyl | ethyl | |
| 2.4.495 | 3-carbamoyl-5-fluorophenyl | methyl | ethyl | |
| 2.4.496 | 3-hydroxy-5-fluorophenyl | methyl | ethyl | |
| 2.4.497 | 3-methoxy-5-fluorophenyl | methyl | ethyl | |
| 2.4.498 | 3-ethoxy-5-fluorophenyl | methyl | ethyl | |
| 2.4.499 | 3-n-propoxy-5-fluorophenyl | methyl | ethyl | |
| 2.4.500 | 3-isopropoxy-5-fluorophenyl | methyl | ethyl | |
| 2.4.501 | 3-n-butoxy-5-fluorophenyl | methyl | ethyl | |
| 2.4.502 | 3-isobutoxy-5-fluorophenyl | methyl | ethyl | |
| 2.4.503 | 3-tert-butoxy-5-fluorophenyl | methyl | ethyl | |
| 2.4.504 | 3-difluoromethoxy-5-fluorophenyl | methyl | ethyl | |
| 2.4.505 | 3-trifluoromethoxy-5-fluorophenyl | methyl | ethyl | |
| 2.4.506 | 3-(2,2,2-trifluoroethoxy)-5-fluorophenyl | methyl | ethyl | |
| 2.4.507 | 3-(2-chloroethoxy)-5-fluorophenyl | methyl | ethyl | |
| 2.4.508 | 3-(2-hydroxyethoxy)-5-fluorophenyl | methyl | ethyl | |
| 2.4.509 | 3-[(tert-butoxycarbonyl)oxy]-5-fluorophenyl | methyl | ethyl | |
| 2.4.510 | 3-nitro-5-fluorophenyl | methyl | ethyl | |
| 2.4.511 | 3-acetoxy-5-fluorophenyl | methyl | ethyl | |
| 2.4.512 | {3-[(tert-butoxy-carbonyl)amino]-5-fluorophenyl} | methyl | ethyl | |
| 2.4.513 | 3-methylsulfanyl-5-fluorophenyl | methyl | ethyl | |
| 2.4.514 | 3,5-difluorophenyl | methyl | methyl | [CDCl3] 2.43 (s, 3H); 3.79 (d, 1H); 3.86 (s, 3H); 3.90 (d, 1H), 7.43 (s, 1H); 7.55 (s, 2H). |
| 2.4.515 | 3,5-dichlorophenyl | ethyl | methyl | [CDCl3] 1.12 (t, 3H); 2.82 (q, 2H); 3.81 (d, 1H); 3.85 (s, 3H); 7.43 (s, 1H); 7.54 (s, 2H). |
| 2.4.516 | 3,5-dichlorophenyl | propyl | ethyl | |
| 2.4.517 | 3,5-dichlorophenyl | butyl | ethyl | |
| 2.4.518 | 3-bromo-5-chlorophenyl | methyl | ethyl | |
| 2.4.519 | 3-iodo-5-chlorophenyl | methyl | ethyl | |
| 2.4.520 | 3-methyl-5-chlorophenyl | methyl | methyl | [CDCl3] 2.36 (s, 3H), 2.43 (s, 3H); 3.82 (d, 1H); 3.86 (s, 4H); 7.24 (s, 1H); 7.36 (s, 1H); 7.46 (s, 1H). |

TABLE 2.4-continued

Inventive compounds of the general formula (I) in which W* is COOY, R¹ and R² are each hydrogen, and aryl is the radical.

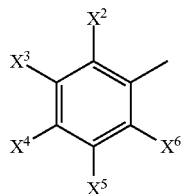

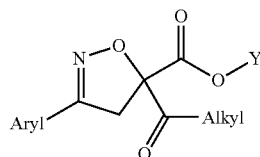

| No. | Aryl | Alkyl | Y | Physical data |
|---|---|---|---|---|
| 2.4.521 | 3-ethyl-5-chlorophenyl | methyl | ethyl | |
| 2.4.522 | 3-propyl-5-chlorophenyl | methyl | ethyl | |
| 2.4.523 | 3-isopropyl-5-chlorophenyl | methyl | ethyl | |
| 2.4.524 | 3-n-butyl-5-chlorophenyl | methyl | ethyl | |
| 2.4.525 | 3-isobutyl-5-chlorophenyl | methyl | ethyl | |
| 2.4.526 | 3-tert-butyl-5-chlorophenyl | methyl | ethyl | |
| 2.4.527 | 3-cyclopropyl-5-chlorophenyl | methyl | ethyl | |
| 2.4.528 | 3-vinyl-5-chlorophenyl | methyl | ethyl | |
| 2.4.529 | 3-ethynyl-5-chlorophenyl | methyl | ethyl | |
| 2.4.530 | 3-cyano-5-chlorophenyl | methyl | ethyl | |
| 2.4.531 | 3-trifluoromethyl-5-chlorophenyl | methyl | ethyl | |
| 2.4.532 | 3-(hydroxycarbonyl)-5-chlorophenyl | methyl | ethyl | |
| 2.4.533 | 3-(methoxycarbonyl)-5-chlorophenyl | methyl | ethyl | |
| 2.4.534 | 3-hydroxymethyl-5-chlorophenyl | methyl | ethyl | |
| 2.4.535 | 3-carbamoyl-5-chlorophenyl | methyl | ethyl | |
| 2.4.536 | 3-hydroxy-5-chlorophenyl | methyl | ethyl | |
| 2.4.537 | 3-methoxy-5-chlorophenyl | methyl | ethyl | |
| 2.4.538 | 3-ethoxy-5-chlorophenyl | methyl | ethyl | |
| 2.4.539 | 3-n-propoxy-5-chlorophenyl | methyl | ethyl | |
| 2.4.540 | 3-isopropoxy-5-chlorophenyl | methyl | ethyl | |
| 2.4.541 | 3-n-butoxy-5-chlorophenyl | methyl | ethyl | |
| 2.4.542 | 3-isobutoxy-5-chlorophenyl | methyl | ethyl | |
| 2.4.543 | 3-tert-butoxy-5-chlorophenyl | methyl | ethyl | |
| 2.4.544 | 3-difluoromethoxy-5-chlorophenyl | methyl | ethyl | |
| 2.4.545 | 3-trifluoromethoxy-5-chlorophenyl | methyl | ethyl | |
| 2.4.546 | 3-(2,2,2-trifluoroethoxy)-5-chlorophenyl | methyl | ethyl | |
| 2.4.547 | 3-(2-chloroethoxy)-5-chlorophenyl | methyl | ethyl | |
| 2.4.548 | 3-(2-hydroxyethoxy)-5-chlorophenyl | methyl | ethyl | |
| 2.4.549 | 3-[(tert-butoxycarbonyl)oxy]-5-chlorophenyl | methyl | ethyl | |
| 2.4.550 | 3-nitro-5-chlorophenyl | methyl | ethyl | |
| 2.4.551 | 3-acetoxy-5-chlorophenyl | methyl | ethyl | |
| 2.4.552 | {3-[(tert-butoxy-carbonyl)amino]-5-chlorophenyl} | methyl | ethyl | |
| 2.4.553 | 3-methylsulfanyl-5-chlorophenyl | methyl | ethyl | |
| 2.4.554 | 3,5-dibromophenyl | methyl | ethyl | |
| 2.4.555 | 3,5-dibromophenyl | ethyl | ethyl | |
| 2.4.556 | 3-iodo-5-bromophenyl | methyl | ethyl | |
| 2.4.557 | 3-methyl-5-bromophenyl | methyl | methyl | [CDCl₃] 2.36 (s, 3H); 2.43 (s, 3H); 3.81 (d, 1H); 3.86 (s, 3H); 3.89 (d, 1H); 7.41 (s, 2H); 7.61 (s, 1H). |
| 2.4.558 | 3-methyl-5-bromophenyl | ethyl | ethyl | |
| 2.4.559 | 3-methyl-5-bromophenyl | propyl | ethyl | |
| 2.4.560 | 3-methyl-5-bromophenyl | butyl | ethyl | |
| 2.4.561 | 3-ethyl-5-bromophenyl | methyl | ethyl | |
| 2.4.562 | 3-propyl-5-bromophenyl | methyl | ethyl | |
| 2.4.563 | 3-isopropyl-5-bromophenyl | methyl | ethyl | |
| 2.4.564 | 3-n-butyl-5-bromophenyl | methyl | ethyl | |
| 2.4.565 | 3-isobutyl-5-bromophenyl | methyl | ethyl | |
| 2.4.566 | 3-tert-butyl-5-bromophenyl | methyl | ethyl | |
| 2.4.567 | 3-cyclopropyl-5-bromophenyl | methyl | ethyl | |
| 2.4.568 | 3-cyano-5-bromophenyl | methyl | ethyl | |
| 2.4.569 | 3-trifluoromethyl-5-bromophenyl | methyl | ethyl | |

TABLE 2.4-continued

Inventive compounds of the general formula (I) in which W* is COOY, $R^1$ and $R^2$ are each hydrogen, and aryl is the radical.

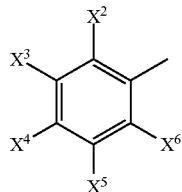

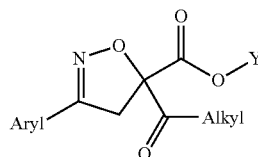

| No. | Aryl | Alkyl | Y | Physical data |
|---|---|---|---|---|
| 2.4.570 | 3-(methoxycarbonyl)-5-bromophenyl | methyl | ethyl | |
| 2.4.571 | 3-methoxy-5-bromophenyl | methyl | ethyl | |
| 2.4.572 | 3-ethoxy-5-bromophenyl | methyl | ethyl | |
| 2.4.573 | 3-n-propoxy-5-bromophenyl | methyl | ethyl | |
| 2.4.574 | 3-isopropoxy-5-bromophenyl | methyl | ethyl | |
| 2.4.575 | 3-n-butoxy-5-bromophenyl | methyl | ethyl | |
| 2.4.576 | 3-isobutoxy-5-bromophenyl | methyl | ethyl | |
| 2.4.577 | 3-difluoromethoxy-5-bromophenyl | methyl | ethyl | |
| 2.4.578 | 3-trifluoromethoxy-5-bromophenyl | methyl | ethyl | |
| 2.4.579 | 3-nitro-5-bromophenyl | methyl | ethyl | |
| 2.4.580 | 3-acetoxy-5-bromophenyl | methyl | ethyl | |
| 2.4.581 | 3-methylsulfanyl-5-bromophenyl | methyl | ethyl | |
| 2.4.582 | 3,5-diiodophenyl | methyl | ethyl | |
| 2.4.583 | 3-methyl-5-iodophenyl | methyl | ethyl | |
| 2.4.584 | 3-ethyl-5-iodophenyl | methyl | ethyl | |
| 2.4.585 | 3-propyl-5-iodophenyl | methyl | ethyl | |
| 2.4.586 | 3-isopropyl-5-iodophenyl | methyl | ethyl | |
| 2.4.587 | 3-n-butyl-5-iodophenyl | methyl | ethyl | |
| 2.4.588 | 3-isobutyl-5-iodophenyl | methyl | ethyl | |
| 2.4.589 | 3-tert-butyl-5-iodophenyl | methyl | ethyl | |
| 2.4.590 | 3-cyclopropyl-5-iodophenyl | methyl | ethyl | |
| 2.4.591 | 3-cyano-5-iodophenyl | methyl | ethyl | |
| 2.4.592 | 3-trifluoromethyl-5-iodophenyl | methyl | ethyl | |
| 2.4.593 | 3-(methoxycarbonyl)-5-iodophenyl | methyl | ethyl | |
| 2.4.594 | 3-methoxy-5-iodophenyl | methyl | ethyl | |
| 2.4.595 | 3-ethoxy-5-iodophenyl | methyl | ethyl | |
| 2.4.596 | 3-n-propoxy-5-iodophenyl | methyl | ethyl | |
| 2.4.597 | 3-isopropoxy-5-iodophenyl | methyl | ethyl | |
| 2.4.598 | 3-n-butoxy-5-iodophenyl | methyl | ethyl | |
| 2.4.599 | 3-isobutoxy-5-iodophenyl | methyl | ethyl | |
| 2.4.600 | 3-difluoromethoxy-5-iodophenyl | methyl | ethyl | |
| 2.4.601 | 3-trifluoromethoxy-5-iodophenyl | methyl | ethyl | |
| 2.4.602 | 3-nitro-5-iodophenyl | methyl | ethyl | |
| 2.4.603 | 3-acetoxy-5-iodophenyl | methyl | ethyl | |
| 2.4.604 | 3-methylsulfanyl-5-iodophenyl | methyl | ethyl | |
| 2.4.605 | 3,5-dimethylphenyl | methyl | ethyl | |
| 2.4.606 | 3-ethyl-5-methylphenyl | methyl | ethyl | |
| 2.4.607 | 3-propyl-5-methylphenyl | methyl | ethyl | |
| 2.4.608 | 3-isopropyl-5-methylphenyl | methyl | ethyl | |
| 2.4.609 | 3-n-butyl-5-methylphenyl | methyl | ethyl | |
| 2.4.610 | 3-isobutyl-5-methylphenyl | methyl | ethyl | |
| 2.4.611 | 3-tert-butyl-5-methylphenyl | methyl | ethyl | |
| 2.4.612 | 3-cyclopropyl-5-methylphenyl | methyl | ethyl | |
| 2.4.613 | 3-cyano-5-methylphenyl | methyl | ethyl | |
| 2.4.614 | 3-trifluoromethyl-5-methylphenyl | methyl | ethyl | |
| 2.4.615 | 3-(methoxycarbonyl)-5-methylphenyl | methyl | ethyl | |
| 2.4.616 | 3-methoxy-5-methylphenyl | methyl | ethyl | |
| 2.4.617 | 3-ethoxy-5-methylphenyl | methyl | ethyl | |
| 2.4.618 | 3-n-propoxy-5-methylphenyl | methyl | ethyl | |
| 2.4.619 | 3-n-butoxy-5-methylphenyl | methyl | ethyl | |
| 2.4.620 | 3-isobutoxy-5-methylphenyl | methyl | ethyl | |
| 2.4.621 | 3-difluoromethoxy-5-methylphenyl | methyl | ethyl | |
| 2.4.622 | 3-trifluoromethoxy-5-methylphenyl | methyl | ethyl | |
| 2.4.623 | 3-nitro-5-methylphenyl | methyl | ethyl | |

TABLE 2.4-continued

Inventive compounds of the general formula (I) in which W* is COOY, $R^1$ and $R^2$ are each hydrogen, and aryl is the radical.

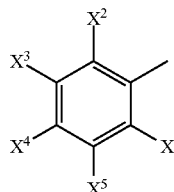

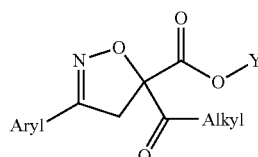

| No. | Aryl | Alkyl | Y | Physical data |
|---|---|---|---|---|
| 2.4.624 | 3-acetoxy-5-methylphenyl | methyl | ethyl | |
| 2.4.625 | 3-methylsulfanyl-5-methylphenyl | methyl | ethyl | |
| 2.4.626 | 3,5-diethylphenyl | methyl | ethyl | |
| 2.4.627 | 3-propyl-5-ethylphenyl | methyl | ethyl | |
| 2.4.628 | 3-isopropyl-5-ethylphenyl | methyl | ethyl | |
| 2.4.629 | 3-n-butyl-5-ethylphenyl | methyl | ethyl | |
| 2.4.630 | 3-isobutyl-5-ethylphenyl | methyl | ethyl | |
| 2.4.631 | 3-tert-butyl-5-ethylphenyl | methyl | ethyl | |
| 2.4.632 | 3-cyclopropyl-5-ethylphenyl | methyl | ethyl | |
| 2.4.633 | 3-cyano-5-ethylphenyl | methyl | ethyl | |
| 2.4.634 | 3-trifluoromethyl-5-ethylphenyl | methyl | ethyl | |
| 2.4.635 | 3-(methoxycarbonyl)-5-ethylphenyl | methyl | ethyl | |
| 2.4.636 | 3-methoxy-5-ethylphenyl | methyl | ethyl | |
| 2.4.637 | 3-ethoxy-5-ethylphenyl | methyl | ethyl | |
| 2.4.638 | 3-n-propoxy-5-ethylphenyl | methyl | ethyl | |
| 2.4.639 | 3-n-butoxy-5-ethylphenyl | methyl | ethyl | |
| 2.4.640 | 3-isobutoxy-5-ethylphenyl | methyl | ethyl | |
| 2.4.641 | 3-difluoromethoxy-5-ethylphenyl | methyl | ethyl | |
| 2.4.642 | 3-trifluoromethoxy-5-ethylphenyl | methyl | ethyl | |
| 2.4.643 | 3-nitro-5-ethylphenyl | methyl | ethyl | |
| 2.4.644 | 3-acetoxy-5-ethylphenyl | methyl | ethyl | |
| 2.4.645 | 3-methylsulfanyl-5-ethylphenyl | methyl | ethyl | |
| 2.4.646 | 3,5-dipropylphenyl | methyl | ethyl | |
| 2.4.647 | 3-isopropyl-5-propylphenyl | methyl | ethyl | |
| 2.4.648 | 3-n-butyl-5-propylphenyl | methyl | ethyl | |
| 2.4.649 | 3-isobutyl-5-propylphenyl | methyl | ethyl | |
| 2.4.650 | 3-tert-butyl-5-propylphenyl | methyl | ethyl | |
| 2.4.651 | 3-cyclopropyl-5-propylphenyl | methyl | ethyl | |
| 2.4.652 | 3-cyano-5-propylphenyl | methyl | ethyl | |
| 2.4.653 | 3-trifluoromethyl-5-propylphenyl | methyl | ethyl | |
| 2.4.654 | 3-(hydroxycarbonyl)-5-propylphenyl | methyl | ethyl | |
| 2.4.655 | 3-(methoxycarbonyl)-5-propylphenyl | methyl | ethyl | |
| 2.4.656 | 3-methoxy-5-propylphenyl | methyl | ethyl | |
| 2.4.657 | 3-ethoxy-5-propylphenyl | methyl | ethyl | |
| 2.4.658 | 3-n-propoxy-5-propylphenyl | methyl | ethyl | |
| 2.4.659 | 3-n-butoxy-5-propylphenyl | methyl | ethyl | |
| 2.4.660 | 3-isobutoxy-5-propylphenyl | methyl | ethyl | |
| 2.4.661 | 3-difluoromethoxy-5-propylphenyl | methyl | ethyl | |
| 2.4.662 | 3-trifluoromethoxy-5-ethylphenyl | methyl | ethyl | |
| 2.4.663 | 3-nitro-5-propylphenyl | methyl | ethyl | |
| 2.4.664 | 3-acetoxy-5-propylphenyl | methyl | ethyl | |
| 2.4.665 | 3-methylsulfanyl-5-propylphenyl | methyl | ethyl | |
| 2.4.666 | 3,5-diisopropylphenyl | methyl | ethyl | |
| 2.4.667 | 3-n-butyl-5-isopropylphenyl | methyl | ethyl | |
| 2.4.668 | 3-isobutyl-5-isopropylphenyl | methyl | ethyl | |
| 2.4.669 | 3-tert-butyl-5-isopropylphenyl | methyl | ethyl | |
| 2.4.670 | 3-cyclopropyl-5-isopropylphenyl | methyl | ethyl | |
| 2.4.671 | 3-cyano-5-isopropylphenyl | methyl | ethyl | |
| 2.4.672 | 3-trifluoromethyl-5-isopropylphenyl | methyl | ethyl | |
| 2.4.673 | 3-(methoxycarbonyl)-5-isopropylphenyl | methyl | ethyl | |
| 2.4.674 | 3-methoxy-5-isopropylphenyl | methyl | ethyl | |
| 2.4.675 | 3-ethoxy-5-isopropylphenyl | methyl | ethyl | |
| 2.4.676 | 3-n-propoxy-5-isopropylphenyl | methyl | ethyl | |
| 2.4.677 | 3-n-butoxy-5-isopropylphenyl | methyl | ethyl | |

TABLE 2.4-continued

Inventive compounds of the general formula (I) in which W* is COOY, R¹ and R² are each hydrogen, and aryl is the radical.

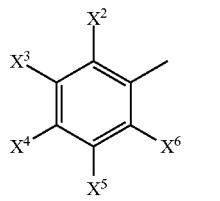

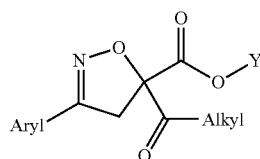

| No. | Aryl | Alkyl | Y | Physical data |
|---|---|---|---|---|
| 2.4.678 | 3-isobutoxy-5-isopropylphenyl | methyl | ethyl | |
| 2.4.679 | 3-difluoromethoxy-5-isopropylphenyl | methyl | ethyl | |
| 2.4.680 | 3-trifluoromethoxy-5-isopropylphenyl | methyl | ethyl | |
| 2.4.681 | 3-nitro-5-isopropylphenyl | methyl | ethyl | |
| 2.4.682 | 3-acetoxy-5-isopropylphenyl | methyl | ethyl | |
| 2.4.683 | 3-methylsulfanyl-5-isopropylphenyl | methyl | ethyl | |
| 2.4.684 | 3,5-dibutylphenyl | methyl | ethyl | |
| 2.4.685 | 3-isobutyl-5-butylphenyl | methyl | ethyl | |
| 2.4.686 | 3-tert-butyl-5-butylphenyl | methyl | ethyl | |
| 2.4.687 | 3-cyclopropyl-5-butylphenyl | methyl | ethyl | |
| 2.4.688 | 3-cyano-5-butylphenyl | methyl | ethyl | |
| 2.4.689 | 3-trifluoromethyl-5-butylphenyl | methyl | ethyl | |
| 2.4.690 | 3-(methoxycarbonyl)-5-butylphenyl | methyl | ethyl | |
| 2.4.691 | 3-methoxy-5-butylphenyl | methyl | ethyl | |
| 2.4.692 | 3-ethoxy-5-butylphenyl | methyl | ethyl | |
| 2.4.693 | 3-n-propoxy-5-butylphenyl | methyl | ethyl | |
| 2.4.694 | 3-n-butoxy-5-butylphenyl | methyl | ethyl | |
| 2.4.695 | 3-isobutoxy-5-butylphenyl | methyl | ethyl | |
| 2.4.696 | 3-difluoromethoxy-5-butylphenyl | methyl | ethyl | |
| 2.4.697 | 3-trifluoromethoxy-5-butylphenyl | methyl | ethyl | |
| 2.4.698 | 3-nitro-5-butylphenyl | methyl | ethyl | |
| 2.4.699 | 3-acetoxy-5-butylphenyl | methyl | ethyl | |
| 2.4.700 | 3-methylsulfanyl-5-butylphenyl | methyl | ethyl | |
| 2.4.701 | 3,5-diisobutylphenyl | methyl | ethyl | |
| 2.4.702 | 3-tert-butyl-5-isobutylphenyl | methyl | ethyl | |
| 2.4.703 | 3-cyclopropyl-5-isobutylphenyl | methyl | ethyl | |
| 2.4.704 | 3-cyano-5-isobutylphenyl | methyl | ethyl | |
| 2.4.705 | 3-trifluoromethyl-5-isobutylphenyl | methyl | ethyl | |
| 2.4.706 | 3-(methoxycarbonyl)-5-isobutylphenyl | methyl | ethyl | |
| 2.4.707 | 3-methoxy-5-isobutylphenyl | methyl | ethyl | |
| 2.4.708 | 3-ethoxy-5-isobutylphenyl | methyl | ethyl | |
| 2.4.709 | 3-n-propoxy-5-isobutylphenyl | methyl | ethyl | |
| 2.4.710 | 3-n-butoxy-5-isobutylphenyl | methyl | ethyl | |
| 2.4.711 | 3-isobutoxy-5-isobutylphenyl | methyl | ethyl | |
| 2.4.712 | 3-difluoromethoxy-5-isobutylphenyl | methyl | ethyl | |
| 2.4.713 | 3-trifluoromethoxy-5-isobutylphenyl | methyl | ethyl | |
| 2.4.714 | 3-nitro-5-isobutylphenyl | methyl | ethyl | |
| 2.4.715 | 3-acetoxy-5-isobutylphenyl | methyl | ethyl | |
| 2.4.716 | 3-methylsulfanyl-5-isobutylphenyl | methyl | ethyl | |
| 2.4.717 | 3,5-di(tert-butyl)phenyl | methyl | ethyl | |
| 2.4.718 | 3-cyclopropyl-5-tert-butylphenyl | methyl | ethyl | |
| 2.4.719 | 3-cyano-5-tert-butylphenyl | methyl | ethyl | |
| 2.4.720 | 3-trifluoromethyl-5-tert-butylphenyl | methyl | ethyl | |
| 2.4.721 | 3-(methoxycarbonyl)-5-tert-butylphenyl | methyl | ethyl | |
| 2.4.722 | 3-methoxy-5-tert-butylphenyl | methyl | ethyl | |
| 2.4.723 | 3-ethoxy-5-tert-butylphenyl | methyl | ethyl | |
| 2.4.724 | 3-n-propoxy-5-tert-butylphenyl | methyl | ethyl | |
| 2.4.725 | 3-n-butoxy-5-tert-butylphenyl | methyl | ethyl | |
| 2.4.726 | 3-isobutoxy-5-tert-butylphenyl | methyl | ethyl | |
| 2.4.727 | 3-difluoromethoxy-5-tert-butylphenyl | methyl | ethyl | |

TABLE 2.4-continued

Inventive compounds of the general formula (I) in which W* is COOY, $R^1$ and $R^2$ are each hydrogen, and aryl is the radical.

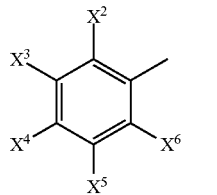

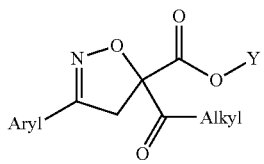

| No. | Aryl | Alkyl | Y | Physical data |
|---|---|---|---|---|
| 2.4.728 | 3-trifluoromethoxy-5-tert-butylphenyl | methyl | ethyl | |
| 2.4.729 | 3-nitro-5-tert-butylphenyl | methyl | ethyl | |
| 2.4.730 | 3-acetoxy-5-tert-butylphenyl | methyl | ethyl | |
| 2.4.731 | 3-methylsulfanyl-5-tert-butylphenyl | methyl | ethyl | |
| 2.4.732 | 3-tert-butyl-5-cyclopropylphenyl | methyl | ethyl | |
| 2.4.733 | 3,5-dicyclopropyl-phenyl | methyl | ethyl | |
| 2.4.734 | 3-cyano-5-cyclopropylphenyl | methyl | ethyl | |
| 2.4.735 | 3-trifluoromethyl-5-cyclopropylphenyl | methyl | ethyl | |
| 2.4.736 | 3-(methoxycarbonyl)-5-cyclopropylphenyl | methyl | ethyl | |
| 2.4.737 | 3-methoxy-5-cyclopropylphenyl | methyl | ethyl | |
| 2.4.738 | 3-ethoxy-5-cyclopropylphenyl | methyl | ethyl | |
| 2.4.739 | 3-n-propoxy-5-cyclopropylphenyl | methyl | ethyl | |
| 2.4.740 | 3-n-butoxy-5-cyclopropylphenyl | methyl | ethyl | |
| 2.4.741 | 3-isobutoxy-5-cyclopropylphenyl | methyl | ethyl | |
| 2.4.742 | 3-difluoromethoxy-5-cyclopropylphenyl | methyl | ethyl | |
| 2.4.743 | 3-trifluoromethoxy-5-cyclopropylphenyl | methyl | ethyl | |
| 2.4.744 | 3-nitro-5-cyclopropylphenyl | methyl | ethyl | |
| 2.4.745 | 3-acetoxy-5-cyclopropylphenyl | methyl | ethyl | |
| 2.4.746 | 3-methylsulfanyl-5-cyclopropylphenyl | methyl | ethyl | |
| 2.4.747 | 3,5-dicyanophenyl | methyl | ethyl | |
| 2.4.748 | 3-trifluoromethyl-5-cyanophenyl | methyl | ethyl | |
| 2.4.749 | 3-(methoxycarbonyl)-5-cyanophenyl | methyl | ethyl | |
| 2.4.750 | 3-methoxy-5-cyanophenyl | methyl | ethyl | |
| 2.4.751 | 3-ethoxy-5-cyanophenyl | methyl | ethyl | |
| 2.4.752 | 3-n-propoxy-5-cyanophenyl | methyl | ethyl | |
| 2.4.753 | 3-n-butoxy-5-cyanophenyl | methyl | ethyl | |
| 2.4.754 | 3-isobutoxy-5-cyanophenyl | methyl | ethyl | |
| 2.4.755 | 3-difluoromethoxy-5-cyanophenyl | methyl | ethyl | |
| 2.4.756 | 3-trifluoromethoxy-5-cyanophenyl | methyl | ethyl | |
| 2.4.757 | 3-nitro-5-cyanophenyl | methyl | ethyl | |
| 2.4.758 | 3-acetoxy-5-cyanophenyl | methyl | ethyl | |
| 2.4.759 | 3-methylsulfanyl-5-cyanophenyl | methyl | ethyl | |
| 2.4.760 | 3,5-di(trifluoromethyl)-phenyl | methyl | ethyl | |
| 2.4.761 | 3-(methoxycarbonyl)-5-trifluoromethyl-phenyl | methyl | ethyl | |
| 2.4.762 | 3-methoxy-5-trifluoromethylphenyl | methyl | ethyl | |
| 2.4.763 | 3-ethoxy-5-trifluoromethylphenyl | methyl | ethyl | |
| 2.4.764 | 3-n-propoxy-5-trifluoromethylphenyl | methyl | ethyl | |
| 2.4.765 | 3-n-butoxy-5-trifluoromethylphenyl | methyl | ethyl | |
| 2.4.766 | 3-isobutoxy-5-trifluoromethylphenyl | methyl | ethyl | |
| 2.4.767 | 3-difluoromethoxy-5-trifluoromethylphenyl | methyl | ethyl | |
| 2.4.768 | 3-trifluoromethoxy-5-trifluoromethylphenyl | methyl | ethyl | |
| 2.4.769 | 3-nitro-5-trifluoromethylphenyl | methyl | ethyl | |
| 2.4.770 | 3-acetoxy-5-trifluoromethylphenyl | methyl | ethyl | |
| 2.4.771 | 3-methylsulfanyl-5-trifluoromethylphenyl | methyl | ethyl | |
| 2.4.772 | 3,5-di(methoxy-carbonyl)phenyl | methyl | ethyl | |

TABLE 2.4-continued

Inventive compounds of the general formula (I) in which W* is COOY, $R^1$ and $R^2$ are each hydrogen, and aryl is the radical.

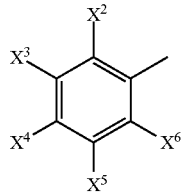

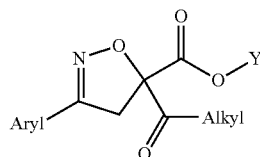

| No. | Aryl | Alkyl | Y | Physical data |
|---|---|---|---|---|
| 2.4.773 | 3-methoxy-5-(methoxycarbonyl)-phenyl | methyl | ethyl | |
| 2.4.774 | 3-ethoxy-5-(methoxycarbonyl)-phenyl | methyl | ethyl | |
| 2.4.775 | 3-n-propoxy-5-(methoxycarbonyl)-phenyl | methyl | ethyl | |
| 2.4.776 | 3-isobutoxy-5-(methoxycarbonyl)-phenyl | methyl | ethyl | |
| 2.4.777 | 3-difluoromethoxy-5-(methoxycarbonyl)phenyl | methyl | ethyl | |
| 2.4.778 | 3-trifluoromethoxy-5-(methoxycarbonyl)phenyl | methyl | ethyl | |
| 2.4.779 | 3-nitro-5-(methoxy-carbonyl)phenyl | methyl | ethyl | |
| 2.4.780 | 3-acetoxy-5-(methoxycarbonyl)-phenyl | methyl | ethyl | |
| 2.4.781 | 3-methylsulfanyl-5-(methoxycarbonyl)phenyl | methyl | ethyl | |
| 2.4.782 | 3,5-dimethoxyphenyl | methyl | ethyl | |
| 2.4.783 | 3-ethoxy-5-methoxyphenyl | methyl | ethyl | |
| 2.4.784 | 3-n-propoxy-5-methoxyphenyl | methyl | ethyl | |
| 2.4.785 | 3-n-butoxy-5-methoxyphenyl | methyl | ethyl | |
| 2.4.786 | 3-isobutoxy-5-methoxyphenyl | methyl | ethyl | |
| 2.4.787 | 3-difluoromethoxy-5-methoxyphenyl | methyl | ethyl | |
| 2.4.788 | 3-trifluoromethoxy-5-methoxyphenyl | methyl | ethyl | |
| 2.4.789 | 3-nitro-5-methoxyphenyl | methyl | ethyl | |
| 2.4.790 | 3-acetoxy-5-methoxyphenyl | methyl | ethyl | |
| 2.4.791 | 3-methylsulfanyl-5-methoxyphenyl | methyl | ethyl | |
| 2.4.792 | 3,5-diethoxyphenyl | methyl | ethyl | |
| 2.4.793 | 3-n-propoxy-5-ethoxyphenyl | methyl | ethyl | |
| 2.4.794 | 3-n-butoxy-5-ethoxyphenyl | methyl | ethyl | |
| 2.4.795 | 3-isobutoxy-5-ethoxyphenyl | methyl | ethyl | |
| 2.4.796 | 3-difluoromethoxy-5-ethoxyphenyl | methyl | ethyl | |
| 2.4.797 | 3-trifluoromethoxy-5-ethoxyphenyl | methyl | ethyl | |
| 2.4.798 | 3-nitro-5-ethoxyphenyl | methyl | ethyl | |
| 2.4.799 | 3-acetoxy-5-ethoxyphenyl | methyl | ethyl | |
| 2.4.800 | 3-methylsulfanyl-5-ethoxyphenyl | methyl | ethyl | |
| 2.4.801 | 3,5-dipropoxyphenyl | methyl | ethyl | |
| 2.4.802 | 3-n-butoxy-5-propoxyphenyl | methyl | ethyl | |
| 2.4.803 | 3-isobutoxy-5-propoxyphenyl | methyl | ethyl | |
| 2.4.804 | 3-difluoromethoxy-5-propoxyphenyl | methyl | ethyl | |
| 2.4.805 | 3-trifluoromethoxy-5-propoxyphenyl | methyl | ethyl | |
| 2.4.806 | 3-nitro-5-propoxyphenyl | methyl | ethyl | |
| 2.4.807 | 3-acetoxy-5-propoxyphenyl | methyl | ethyl | |
| 2.4.808 | 3-methylsulfanyl-5-propoxyphenyl | methyl | ethyl | |
| 2.4.809 | 3,5-di(isopropoxy)phenyl | methyl | ethyl | |
| 2.4.810 | 3-n-butoxy-5-isopropoxyphenyl | methyl | ethyl | |
| 2.4.811 | 3-isobutoxy-5-isopropoxyphenyl | methyl | ethyl | |
| 2.4.812 | 3-difluoromethoxy-5-isopropoxyphenyl | methyl | ethyl | |
| 2.4.813 | 3-trifluoromethoxy-5-isopropoxyphenyl | methyl | ethyl | |
| 2.4.814 | 3-nitro-5-isopropoxyphenyl | methyl | ethyl | |
| 2.4.815 | 3-acetoxy-5-isopropoxyphenyl | methyl | ethyl | |
| 2.4.816 | 3-methylsulfanyl-5-isopropoxyphenyl | methyl | ethyl | |

TABLE 2.4-continued

Inventive compounds of the general formula (I) in which W* is COOY, R¹ and R² are each hydrogen, and aryl is the radical.

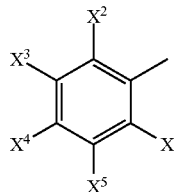

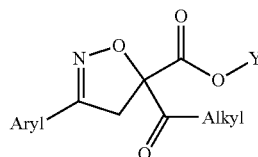

| No. | Aryl | Alkyl | Y | Physical data |
|---|---|---|---|---|
| 2.4.817 | 3,5-di(trifluoro-methoxy)phenyl | methyl | ethyl | |
| 2.4.818 | 3-nitro-5-trifluoro-methoxyphenyl | methyl | ethyl | |
| 2.4.819 | 3-acetoxy-5-tert-butoxyphenyl | methyl | ethyl | |
| 2.4.820 | 3-methylsulfanyl-5-trifluoromethoxy-phenyl | methyl | ethyl | |
| 2.4.821 | 3,5-bis(difluoromethoxy)phenyl | methyl | ethyl | |
| 2.4.822 | 3,5-bis(difluoromethoxy)phenyl | ethyl | ethyl | |
| 2.4.823 | 3,5-bis(difluoromethoxy)phenyl | propyl | ethyl | |
| 2.4.824 | 3,5-bis(difluoromethoxy)phenyl | butyl | ethyl | |
| 2.4.825 | 3-trifluoromethoxy-5-difluoromethoxyphenyl | methyl | ethyl | |
| 2.4.826 | 3-nitro-5-difluoromethoxyphenyl | methyl | ethyl | |
| 2.4.827 | 3-acetoxy-5-difluoro-methoxyphenyl | methyl | ethyl | |
| 2.4.828 | 3-methylsulfanyl-5-difluoromethoxy-phenyl | methyl | ethyl | |
| 2.4.829 | 3,5-bis(acetoxy)phenyl | methyl | ethyl | |
| 2.4.830 | 3-methylsulfanyl-5-acetoxyphenyl | methyl | ethyl | |
| 2.4.831 | 3-acetoxy-5-nitrophenyl | methyl | ethyl | |
| 2.4.832 | 3-methylsulfanyl-5-nitrophenyl | methyl | ethyl | |
| 2.4.833 | 3,5-di(methylsulfanyl)phenyl | methyl | ethyl | |
| 2.4.834 | 3,4-difluorophenyl | methyl | ethyl | |
| 2.4.835 | 3,4-difluorophenyl | ethyl | ethyl | |
| 2.4.836 | 3,4-difluorophenyl | propyl | ethyl | |
| 2.4.837 | 3,4-difluorophenyl | butyl | ethyl | |
| 2.4.838 | 3-chloro-4-fluorophenyl | methyl | ethyl | |
| 2.4.839 | 3-chloro-4-fluorophenyl | ethyl | ethyl | |
| 2.4.840 | 3-chloro-4-fluorophenyl | propyl | ethyl | |
| 2.4.841 | 3-chloro-4-fluorophenyl | butyl | ethyl | |
| 2.4.842 | 3-bromo-4-fluorophenyl | methyl | ethyl | |
| 2.4.843 | 3-methyl-4-fluorophenyl | methyl | ethyl | |
| 2.4.844 | 3-methyl-4-fluorophenyl | ethyl | ethyl | |
| 2.4.845 | 3-ethyl-4-fluorophenyl | methyl | ethyl | |
| 2.4.846 | 3-cyclopropyl-4-fluorophenyl | methyl | ethyl | |
| 2.4.847 | 3-cyano-4-fluorophenyl | methyl | ethyl | |
| 2.4.848 | 3-methoxy-4-fluorophenyl | methyl | ethyl | |
| 2.4.849 | 3-ethoxy-4-fluorophenyl | methyl | ethyl | |
| 2.4.850 | 3-trifluoromethoxy-4-fluorophenyl | methyl | ethyl | |
| 2.4.851 | 3-nitro-4-fluorophenyl | methyl | ethyl | |
| 2.4.852 | 3-fluoro-4-chlorophenyl | methyl | ethyl | |
| 2.4.853 | 3,4-dichlorophenyl | methyl | ethyl | |
| 2.4.854 | 3-bromo-4-chlorophenyl | methyl | ethyl | |
| 2.4.855 | 3-methyl-4-chlorophenyl | methyl | ethyl | |
| 2.4.856 | 3-cyclopropyl-4-chlorophenyl | methyl | ethyl | |
| 2.4.857 | 3-cyano-4-chlorophenyl | methyl | ethyl | |
| 2.4.858 | 3-trifluoromethyl-4-chlorophenyl | methyl | ethyl | |
| 2.4.859 | 3-methoxy-4-chlorophenyl | methyl | ethyl | |
| 2.4.860 | 3-ethoxy-4-chlorophenyl | methyl | ethyl | |
| 2.4.861 | 3-trifluoromethoxy-4-chlorophenyl | methyl | ethyl | |
| 2.4.862 | 3-nitro-4-chlorophenyl | methyl | ethyl | |
| 2.4.863 | 3-fluoro-4-bromophenyl | methyl | ethyl | |
| 2.4.864 | 3-chloro-4-bromophenyl | methyl | ethyl | |
| 2.4.865 | 3,4-dibromophenyl | methyl | ethyl | |
| 2.4.866 | 3-methyl-4-bromophenyl | methyl | ethyl | |
| 2.4.867 | 3-cyclopropyl-4-bromophenyl | methyl | ethyl | |
| 2.4.868 | 3-cyano-4-bromophenyl | methyl | ethyl | |
| 2.4.869 | 3-trifluoromethyl-4-bromophenyl | methyl | ethyl | |

TABLE 2.4-continued

Inventive compounds of the general formula (I) in which W* is COOY, $R^1$ and $R^2$ are each hydrogen, and aryl is the radical.

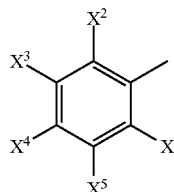

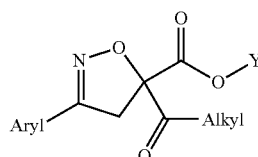

| No. | Aryl | Alkyl | Y | Physical data |
|---|---|---|---|---|
| 2.4.870 | 3-methoxy-4-phenyl | methyl | ethyl | |
| 2.4.871 | 3-ethoxy-4-bromophenyl | methyl | ethyl | |
| 2.4.872 | 3-trifluoromethoxy-4-bromophenyl | methyl | ethyl | |
| 2.4.873 | 3-nitro-4-bromophenyl | methyl | ethyl | |
| 2.4.874 | 3-fluoro-4-iodophenyl | methyl | ethyl | |
| 2.4.875 | 3-chloro-4-iodophenyl | methyl | ethyl | |
| 2.4.876 | 3-bromo-4-iodophenyl | methyl | ethyl | |
| 2.4.877 | 3-methyl-4-iodophenyl | methyl | ethyl | |
| 2.4.878 | 3-cyclopropyl-4-iodophenyl | methyl | ethyl | |
| 2.4.879 | 3-cyano-4-iodophenyl | methyl | ethyl | |
| 2.4.880 | 3-trifluoromethyl-4-iodophenyl | methyl | ethyl | |
| 2.4.881 | 3-methoxy-4-iodophenyl | methyl | ethyl | |
| 2.4.882 | 3-ethoxy-4-iodophenyl | methyl | ethyl | |
| 2.4.883 | 3-trifluoromethoxy-4-iodophenyl | methyl | ethyl | |
| 2.4.884 | 3-nitro-4-iodophenyl | methyl | ethyl | |
| 2.4.885 | 3-fluoro-4-methylphenyl | methyl | ethyl | |
| 2.4.886 | 3-chloro-4-methylphenyl | methyl | ethyl | |
| 2.4.887 | 3-bromo-4-methylphenyl | methyl | ethyl | |
| 2.4.888 | 3,4-dimethylphenyl | methyl | ethyl | |
| 2.4.889 | 3,4-dimethylphenyl | ethyl | ethyl | |
| 2.4.890 | 3,4-dimethylphenyl | propyl | ethyl | |
| 2.4.891 | 3,4-dimethylphenyl | butyl | ethyl | |
| 2.4.892 | 3-cyclopropyl-4-methylphenyl | methyl | ethyl | |
| 2.4.893 | 3-cyano-4-methylphenyl | methyl | ethyl | |
| 2.4.894 | 3-trifluoromethyl-4-methylphenyl | methyl | ethyl | |
| 2.4.895 | 3-methoxy-4-methylphenyl | methyl | ethyl | |
| 2.4.896 | 3-ethoxy-4-methylphenyl | methyl | ethyl | |
| 2.4.897 | 3-trifluoromethoxy-4-methylphenyl | methyl | ethyl | |
| 2.4.898 | 3-nitro-4-methylphenyl | methyl | ethyl | |
| 2.4.899 | 3-fluoro-4-ethylphenyl | methyl | ethyl | |
| 2.4.900 | 3-chloro-4-ethylphenyl | methyl | ethyl | |
| 2.4.901 | 3-bromo-4-ethylphenyl | methyl | ethyl | |
| 2.4.902 | 3-methyl-4-ethylphenyl | methyl | ethyl | |
| 2.4.903 | 3,4-diethylphenyl | methyl | ethyl | |
| 2.4.904 | 3-cyclopropyl-4-ethylphenyl | methyl | ethyl | |
| 2.4.905 | 3-cyano-4-ethylphenyl | methyl | ethyl | |
| 2.4.906 | 3-trifluoromethyl-4-ethylphenyl | methyl | ethyl | |
| 2.4.907 | 3-methoxy-4-ethylphenyl | methyl | ethyl | |
| 2.4.908 | 3-ethoxy-4-ethylphenyl | methyl | ethyl | |
| 2.4.909 | 3-trifluoromethoxy-4-ethylphenyl | methyl | ethyl | |
| 2.4.910 | 3-nitro-4-ethylphenyl | methyl | ethyl | |
| 2.4.911 | 3-fluoro-4-isopropylphenyl | methyl | ethyl | |
| 2.4.912 | 3-chloro-4-isopropylphenyl | methyl | ethyl | |
| 2.4.913 | 3-bromo-4-isopropylphenyl | methyl | ethyl | |
| 2.4.914 | 3-methyl-4-isopropylphenyl | methyl | ethyl | |
| 2.4.915 | 3-cyclopropyl-4-isopropylphenyl | methyl | ethyl | |
| 2.4.916 | 3-cyano-4-isopropylphenyl | methyl | ethyl | |
| 2.4.917 | 3-trifluoromethyl-4-isopropylphenyl | methyl | ethyl | |
| 2.4.918 | 3-methoxy-4-isopropylphenyl | methyl | ethyl | |
| 2.4.919 | 3-ethoxy-4-isopropylphenyl | methyl | ethyl | |
| 2.4.920 | 3-trifluoromethoxy-4-isopropylphenyl | methyl | ethyl | |
| 2.4.921 | 3-nitro-4-isopropylphenyl | methyl | ethyl | |
| 2.4.922 | 3-fluoro-4-tert-butylphenyl | methyl | ethyl | |
| 2.4.923 | 3-chloro-4-tert-butylphenyl | methyl | ethyl | |
| 2.4.924 | 3-bromo-4-tert-butylphenyl | methyl | ethyl | |

TABLE 2.4-continued

Inventive compounds of the general formula (I) in which W* is COOY, $R^1$ and $R^2$ are each hydrogen, and aryl is the radical.

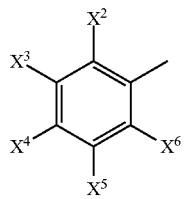

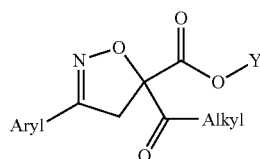

| No. | Aryl | Alkyl | Y | Physical data |
|---|---|---|---|---|
| 2.4.925 | 3-methyl-4-tert-butylphenyl | methyl | ethyl | |
| 2.4.926 | 3-ethyl-4-tert-butylphenyl | methyl | ethyl | |
| 2.4.927 | 3-cyclopropyl-4-tert-butylphenyl | methyl | ethyl | |
| 2.4.928 | 3-cyano-4-tert-butylphenyl | methyl | ethyl | |
| 2.4.929 | 3-trifluoromethyl-4-tert-butylphenyl | methyl | ethyl | |
| 2.4.930 | 3-trifluoromethyl-4-tert-butylphenyl | ethyl | ethyl | |
| 2.4.931 | 3-trifluoromethyl-4-tert-butylphenyl | propyl | ethyl | |
| 2.4.932 | 3-trifluoromethyl-4-tert-butylphenyl | butyl | ethyl | |
| 2.4.933 | 3-methoxy-4-tert-butylphenyl | methyl | ethyl | |
| 2.4.934 | 3-ethoxy-4-tert-butylphenyl | methyl | ethyl | |
| 2.4.935 | 3-trifluoromethoxy-4-tert-butylphenyl | methyl | ethyl | |
| 2.4.936 | 3-nitro-4-tert-butylphenyl | methyl | ethyl | |
| 2.4.937 | 3-fluoro-4-cyclopropylphenyl | methyl | ethyl | |
| 2.4.938 | 3-chloro-4-cyclopropylphenyl | methyl | ethyl | |
| 2.4.939 | 3-bromo-4-cyclopropylphenyl | methyl | ethyl | |
| 2.4.940 | 3-methyl-4-cyclopropylphenyl | methyl | ethyl | |
| 2.4.941 | 3-cyclopropyl-4-cyclopropylphenyl | methyl | ethyl | |
| 2.4.942 | 3-cyano-4-cyclopropylphenyl | methyl | ethyl | |
| 2.4.943 | 3-trifluoromethyl-4-cyclopropylphenyl | methyl | ethyl | |
| 2.4.944 | 3-methoxy-4-cyclopropylphenyl | methyl | ethyl | |
| 2.4.945 | 3-ethoxy-4-cyclopropylphenyl | methyl | ethyl | |
| 2.4.946 | 3-trifluoromethoxy-4-cyclopropylphenyl | methyl | ethyl | |
| 2.4.947 | 3-fluoro-4-methoxycarbonylphenyl | methyl | ethyl | |
| 2.4.948 | 3-chloro-4-methoxy-carbonylphenyl | methyl | ethyl | |
| 2.4.949 | 3-bromo-4-methoxy-carbonylphenyl | methyl | ethyl | |
| 2.4.950 | 3-methyl-4-methoxy-carbonylphenyl | methyl | ethyl | |
| 2.4.951 | 3-cyclopropyl-4-methoxycarbonyl-phenyl | methyl | ethyl | |
| 2.4.952 | 3-cyano-4-methoxycarbonylphenyl | methyl | ethyl | |
| 2.4.953 | 3-trifluoromethyl-4-methoxycarbonylphenyl | methyl | ethyl | |
| 2.4.954 | 3-methoxy-4-methoxycarbonyl-phenyl | methyl | ethyl | |
| 2.4.955 | 3-ethoxy-4-methoxycarbonylphenyl | methyl | ethyl | |
| 2.4.956 | 3-trifluoromethoxy-4-methoxycarbonylphenyl | methyl | ethyl | |
| 2.4.957 | 3-nitro-4-methoxy-carbonylphenyl | methyl | ethyl | |
| 2.4.958 | 3-fluoro-4-cyanophenyl | methyl | ethyl | |
| 2.4.959 | 3-chloro-4-cyanophenyl | methyl | ethyl | |
| 2.4.960 | 3-bromo-4-cyanophenyl | methyl | ethyl | |
| 2.4.961 | 3-methyl-4-cyanophenyl | methyl | ethyl | |
| 2.4.962 | 3-cyclopropyl-4-cyanophenyl | methyl | ethyl | |
| 2.4.963 | 3,4-dicyanophenyl | methyl | ethyl | |
| 2.4.964 | 3-trifluoromethyl-4-cyanophenyl | methyl | ethyl | |
| 2.4.965 | 3-trifluoromethyl-4-cyanophenyl | ethyl | ethyl | |
| 2.4.966 | 3-trifluoromethyl-4-cyanophenyl | propyl | ethyl | |
| 2.4.967 | 3-trifluoromethyl-4-cyanophenyl | butyl | ethyl | |
| 2.4.968 | 3-methoxy-4-cyanophenyl | methyl | ethyl | |
| 2.4.969 | 3-ethoxy-4-cyanophenyl | methyl | ethyl | |
| 2.4.970 | 3-trifluoromethoxy-4-cyanophenyl | methyl | ethyl | |
| 2.4.971 | 3-nitro-4-cyanophenyl | methyl | ethyl | |
| 2.4.972 | 3-fluoro-4-methoxyphenyl | methyl | ethyl | |
| 2.4.973 | 3-chloro-4-methoxyphenyl | methyl | ethyl | |

TABLE 2.4-continued

Inventive compounds of the general formula (I) in which W* is COOY, $R^1$ and $R^2$ are each hydrogen, and aryl is the radical.

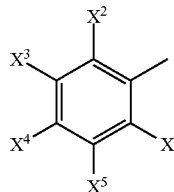

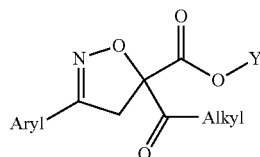

| No. | Aryl | Alkyl | Y | Physical data |
|---|---|---|---|---|
| 2.4.974 | 3-bromo-4-methoxyphenyl | methyl | ethyl | |
| 2.4.975 | 3-methyl-4-methoxyphenyl | methyl | ethyl | |
| 2.4.976 | 3-ethyl-4-methoxyphenyl | methyl | ethyl | |
| 2.4.977 | 3-cyclopropyl-4-methoxyphenyl | methyl | ethyl | |
| 2.4.978 | 3-cyano-4-methoxyphenyl | methyl | ethyl | |
| 2.4.979 | 3-trifluoromethyl-4-methoxyphenyl | methyl | ethyl | |
| 2.4.980 | 3,4-dimethoxyphenyl | methyl | ethyl | |
| 2.4.981 | 3-ethoxy-4-methoxyphenyl | methyl | ethyl | |
| 2.4.982 | 3-trifluoromethoxy-4-methoxyphenyl | methyl | ethyl | |
| 2.4.983 | 3-nitro-4-methoxyphenyl | methyl | ethyl | |
| 2.4.984 | 3-fluoro-4-ethoxyphenyl | methyl | ethyl | |
| 2.4.985 | 3-chloro-4-ethoxyphenyl | methyl | ethyl | |
| 2.4.986 | 3-chloro-4-ethoxyphenyl | ethyl | ethyl | |
| 2.4.987 | 3-chloro-4-ethoxyphenyl | propyl | ethyl | |
| 2.4.988 | 3-chloro-4-ethoxyphenyl | butyl | ethyl | |
| 2.4.989 | 3-bromo-4-ethoxyphenyl | methyl | ethyl | |
| 2.4.990 | 3-methyl-4-ethoxyphenyl | methyl | ethyl | |
| 2.4.991 | 3-cyclopropyl-4-ethoxyphenyl | methyl | ethyl | |
| 2.4.992 | 3-cyano-4-ethoxyphenyl | methyl | ethyl | |
| 2.4.993 | 3-trifluoromethyl-4-ethoxyphenyl | methyl | ethyl | |
| 2.4.994 | 3-methoxy-4-ethoxyphenyl | methyl | ethyl | |
| 2.4.995 | 2,4-diethoxyphenyl | methyl | ethyl | |
| 2.4.996 | 3-trifluoromethoxy-4-ethoxyphenyl | methyl | ethyl | |
| 2.4.997 | 3-nitro-4-ethoxyphenyl | methyl | ethyl | |
| 2.4.998 | 3-fluoro-4-propoxyphenyl | methyl | ethyl | |
| 2.4.999 | 3-chloro-4-propoxyphenyl | methyl | ethyl | |
| 2.4.1000 | 3-bromo-4-propoxyphenyl | methyl | ethyl | |
| 2.4.1001 | 3-methyl-4-propoxyphenyl | methyl | ethyl | |
| 2.4.1002 | 3-cyclopropyl-4-propoxyphenyl | methyl | ethyl | |
| 2.4.1003 | 3-cyano-4-propoxyphenyl | methyl | ethyl | |
| 2.4.1004 | 3-trifluoromethyl-4-propoxyphenyl | methyl | ethyl | |
| 2.4.1005 | 3-methoxy-4-propoxyphenyl | methyl | ethyl | |
| 2.4.1006 | 3-ethoxy-4-propoxyphenyl | methyl | ethyl | |
| 2.4.1007 | 3-trifluoromethoxy-4-propoxyphenyl | methyl | ethyl | |
| 2.4.1008 | 3-nitro-4-propoxyphenyl | methyl | ethyl | |
| 2.4.1009 | 3-fluoro-4-isopropoxyphenyl | methyl | ethyl | |
| 2.4.1010 | 3-chloro-4-isopropoxyphenyl | methyl | ethyl | |
| 2.4.1011 | 3-bromo-4-isopropoxyphenyl | methyl | ethyl | |
| 2.4.1012 | 3-methyl-4-isopropoxyphenyl | methyl | ethyl | |
| 2.4.1013 | 3-cyclopropyl-4-isopropoxyphenyl | methyl | ethyl | |
| 2.4.1014 | 3-cyano-4-isopropoxyphenyl | methyl | ethyl | |
| 2.4.1015 | 3-trifluoromethyl-4-isopropoxyphenyl | methyl | ethyl | |
| 2.4.1016 | 3-methoxy-4-isopropoxyphenyl | methyl | ethyl | |
| 2.4.1017 | 3-ethoxy-4-isopropoxyphenyl | methyl | ethyl | |
| 2.4.1018 | 3-trifluoromethoxy-4-isopropoxyphenyl | methyl | ethyl | |
| 2.4.1019 | 3-nitro-4-isopropoxyphenyl | methyl | ethyl | |
| 2.4.1020 | 3-fluoro-4-trifluoromethoxyphenyl | methyl | ethyl | |
| 2.4.1021 | 3-chloro-4-trifluoromethoxyphenyl | methyl | ethyl | |
| 2.4.1022 | 3-bromo-4-trifluoromethoxyphenyl | methyl | ethyl | |
| 2.4.1023 | 3-methyl-4-trifluoromethoxyphenyl | methyl | ethyl | |
| 2.4.1024 | 3-cyclopropyl-4-trifluoromethoxyphenyl | methyl | ethyl | |
| 2.4.1025 | 3-cyano-4-trifluoromethoxyphenyl | methyl | ethyl | |

TABLE 2.4-continued

Inventive compounds of the general formula (I) in which W* is COOY, $R^1$ and $R^2$ are each hydrogen, and aryl is the radical.

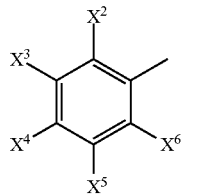

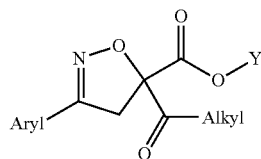

| No. | Aryl | Alkyl | Y | Physical data |
|---|---|---|---|---|
| 2.4.1026 | 3-trifluoromethyl-4-trifluoromethoxy-phenyl | methyl | ethyl | |
| 2.4.1027 | 3-methoxy-4-trifluoromethoxy-phenyl | methyl | ethyl | |
| 2.4.1028 | 3-ethoxy-4-trifluoromethoxyphenyl | methyl | ethyl | |
| 2.4.1029 | 3,4-bis(trifluoromethoxy)phenyl | methyl | ethyl | |
| 2.4.1030 | 3-nitro-4-trifluoromethoxyphenyl | methyl | ethyl | |
| 2.4.1031 | 3-fluoro-4-difluoromethoxyphenyl | methyl | ethyl | |
| 2.4.1032 | 3-chloro-4-difluoromethoxyphenyl | methyl | ethyl | |
| 2.4.1033 | 3-bromo-4-difluoromethoxyphenyl | methyl | ethyl | |
| 2.4.1034 | 3-methyl-4-difluoromethoxy-henyl | methyl | ethyl | |
| 2.4.1035 | 3-cyclopropyl-4-difluoromethoxy-phenyl | methyl | ethyl | |
| 2.4.1036 | 3-cyano-4-difluoromethoxyphenyl | methyl | ethyl | |
| 2.4.1037 | 3-trifluoromethyl-4-difluoromethoxy-phenyl | methyl | ethyl | |
| 2.4.1038 | 3-methoxy-4-difluoromethoxy-phenyl | methyl | ethyl | |
| 2.4.1039 | 3-ethoxy-4-difluoromethoxyphenyl | methyl | ethyl | |
| 2.4.1040 | 3-trifluoromethoxy-4-difluoromethoxyphenyl | methyl | ethyl | |
| 2.4.1041 | 3-nitro-4-difluoromethoxyphenyl | methyl | ethyl | |
| 2.4.1042 | 3-fluoro-4-nitrophenyl | methyl | ethyl | |
| 2.4.1043 | 3-chloro-4-nitrophenyl | methyl | ethyl | |
| 2.4.1044 | 3-bromo-4-nitrophenyl | methyl | ethyl | |
| 2.4.1045 | 3-methyl-4-nitrophenyl | methyl | ethyl | |
| 2.4.1046 | 3-cyclopropyl-4-nitrophenyl | methyl | ethyl | |
| 2.4.1047 | 3-cyano-4-nitrophenyl | methyl | ethyl | |
| 2.4.1048 | 3-trifluoromethyl-4-nitrophenyl | methyl | ethyl | |
| 2.4.1049 | 3-methoxy-4-nitrophenyl | methyl | ethyl | |
| 2.4.1050 | 3-ethoxy-4-nitrophenyl | methyl | ethyl | |
| 2.4.1051 | 3-trifluoromethoxy-4-nitrophenyl | methyl | ethyl | |
| 2.4.1052 | 3-fluoro-4-methylsulfanylphenyl | methyl | ethyl | |
| 2.4.1053 | 3-chloro-4-methylsulfanylphenyl | methyl | ethyl | |
| 2.4.1054 | 3-bromo-4-methylsulfanylphenyl | methyl | ethyl | |
| 2.4.1055 | 3-methyl-4-methylsulfanylphenyl | methyl | ethyl | |
| 2.4.1056 | 3-cyclopropyl-4-methylsulfanylphenyl | methyl | ethyl | |
| 2.4.1057 | 3-cyano-4-methylsulfanylphenyl | methyl | ethyl | |
| 2.4.1058 | 3-trifluoromethyl-4-methylsulfanylphenyl | methyl | ethyl | |
| 2.4.1059 | 3-methoxy-4-methylsulfanylphenyl | methyl | ethyl | |
| 2.4.1060 | 3-ethoxy-4-methylsulfanylphenyl | methyl | ethyl | |
| 2.4.1061 | 3-trifluoromethoxy-4-methylsulfanylphenyl | methyl | ethyl | |
| 2.4.1062 | 3-nitro-4-methylsulfanylphenyl | methyl | ethyl | |
| 2.4.1063 | 3,6-difluorophenyl | methyl | ethyl | |
| 2.4.1064 | 3,6-difluorophenyl | ethyl | ethyl | |
| 2.4.1065 | 3,6-difluorophenyl | propyl | ethyl | |
| 2.4.1066 | 3,6-difluorophenyl | butyl | ethyl | |
| 2.4.1067 | 3-chloro-6-fluorophenyl | methyl | ethyl | |
| 2.4.1068 | 3-bromo-6-fluorophenyl | methyl | ethyl | |
| 2.4.1069 | 3-methyl-6-fluorophenyl | methyl | ethyl | |
| 2.4.1070 | 3-ethyl-6-fluorophenyl | methyl | ethyl | |
| 2.4.1071 | 3-cyclopropyl-6-fluorophenyl | methyl | ethyl | |
| 2.4.1072 | 3-cyano-6-fluorophenyl | methyl | ethyl | |

TABLE 2.4-continued

Inventive compounds of the general formula (I) in which W* is COOY, $R^1$ and $R^2$ are each hydrogen, and aryl is the radical.

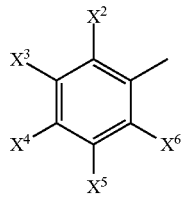

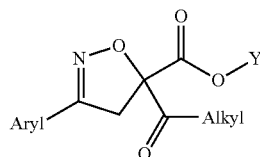

| No. | Aryl | Alkyl | Y | Physical data |
|---|---|---|---|---|
| 2.4.1073 | 3-methoxy-6-fluorophenyl | methyl | ethyl | |
| 2.4.1074 | 3-ethoxy-6-fluorophenyl | methyl | ethyl | |
| 2.4.1075 | 3-trifluoromethoxy-6-fluorophenyl | methyl | ethyl | |
| 2.4.1076 | 3-nitro-6-fluorophenyl | methyl | ethyl | |
| 2.4.1077 | 3-fluoro-6-chlorophenyl | methyl | ethyl | |
| 2.4.1078 | 3-fluoro-6-chlorophenyl | ethyl | ethyl | |
| 2.4.1079 | 3-fluoro-6-chlorophenyl | propyl | ethyl | |
| 2.4.1080 | 3-fluoro-6-chlorophenyl | butyl | ethyl | |
| 2.4.1081 | 3,6-dichlorophenyl | methyl | ethyl | |
| 2.4.1082 | 3,6-dichlorophenyl | ethyl | ethyl | |
| 2.4.1083 | 3,6-dichlorophenyl | propyl | ethyl | |
| 2.4.1084 | 3,6-dichlorophenyl | butyl | ethyl | |
| 2.4.1085 | 3-bromo-6-chlorophenyl | methyl | ethyl | |
| 2.4.1086 | 3-methyl-6-chlorophenyl | methyl | ethyl | |
| 2.4.1087 | 3-ethyl-6-chlorophenyl | methyl | ethyl | |
| 2.4.1088 | 3-cyclopropyl-6-chlorophenyl | methyl | ethyl | |
| 2.4.1089 | 3-cyano-6-chlorophenyl | methyl | ethyl | |
| 2.4.1090 | 3-trifluoromethyl-6-chlorophenyl | methyl | ethyl | |
| 2.4.1091 | 3-methoxy-6-chlorophenyl | methyl | ethyl | |
| 2.4.1092 | 3-ethoxy-6-chlorophenyl | methyl | ethyl | |
| 2.4.1093 | 3-trifluoromethoxy-6-chlorophenyl | methyl | ethyl | |
| 2.4.1094 | 3-nitro-6-chlorophenyl | methyl | ethyl | |
| 2.4.1095 | 3-fluoro-6-bromophenyl | methyl | ethyl | |
| 2.4.1096 | 3-chloro-6-bromophenyl | methyl | ethyl | |
| 2.4.1097 | 3,6-dibromophenyl | methyl | ethyl | |
| 2.4.1098 | 3-methyl-6-bromophenyl | methyl | ethyl | |
| 2.4.1099 | 3-ethyl-6-bromophenyl | methyl | ethyl | |
| 2.4.1100 | 3-cyclopropyl-6-bromophenyl | methyl | ethyl | |
| 2.4.1101 | 3-cyano-6-bromophenyl | methyl | ethyl | |
| 2.4.1102 | 3-trifluoromethyl-6-bromophenyl | methyl | ethyl | |
| 2.4.1103 | 3-methoxy-6-phenyl | methyl | ethyl | |
| 2.4.1104 | 3-ethoxy-6-bromophenyl | methyl | ethyl | |
| 2.4.1105 | 3-trifluoromethoxy-6-bromophenyl | methyl | ethyl | |
| 2.4.1106 | 3-nitro-6-bromophenyl | methyl | ethyl | |
| 2.4.1107 | 3-fluoro-6-iodophenyl | methyl | ethyl | |
| 2.4.1108 | 3-chloro-6-iodophenyl | methyl | ethyl | |
| 2.4.1109 | 3-bromo-6-iodophenyl | methyl | ethyl | |
| 2.4.1110 | 3-methyl-6-iodophenyl | methyl | ethyl | |
| 2.4.1111 | 3-ethyl-6-iodophenyl | methyl | ethyl | |
| 2.4.1112 | 3-cyclopropyl-6-iodophenyl | methyl | ethyl | |
| 2.4.1113 | 3-cyano-6-iodophenyl | methyl | ethyl | |
| 2.4.1114 | 3-trifluoromethyl-6-iodophenyl | methyl | ethyl | |
| 2.4.1115 | 3-methoxy-6-iodophenyl | methyl | ethyl | |
| 2.4.1116 | 3-ethoxy-6-iodophenyl | methyl | ethyl | |
| 2.4.1117 | 3-trifluoromethoxy-6-iodophenyl | methyl | ethyl | |
| 2.4.1118 | 3-nitro-6-iodophenyl | methyl | ethyl | |
| 2.4.1119 | 3-fluoro-6-methylphenyl | methyl | ethyl | |
| 2.4.1120 | 3-chloro-6-methylphenyl | methyl | ethyl | |
| 2.4.1121 | 3-bromo-6-methylphenyl | methyl | ethyl | |
| 2.4.1122 | 3,6-dimethylphenyl | methyl | ethyl | |
| 2.4.1123 | 3-ethyl-6-methylphenyl | methyl | ethyl | |
| 2.4.1124 | 3-cyclopropyl-6-methylphenyl | methyl | ethyl | |
| 2.4.1125 | 3-cyano-6-methylphenyl | methyl | ethyl | |
| 2.4.1126 | 3-trifluoromethyl-6-methylphenyl | methyl | ethyl | |
| 2.4.1127 | 3-methoxy-6-methylphenyl | methyl | ethyl | |
| 2.4.1128 | 3-ethoxy-6-methylphenyl | methyl | ethyl | |

TABLE 2.4-continued

Inventive compounds of the general formula (I) in which W* is COOY, $R^1$ and $R^2$ are each hydrogen, and aryl is the radical.

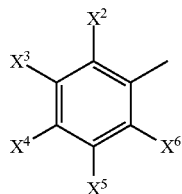

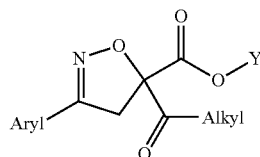

| No. | Aryl | Alkyl | Y | Physical data |
|---|---|---|---|---|
| 2.4.1129 | 3-trifluoromethoxy-6-methylphenyl | methyl | ethyl | |
| 2.4.1130 | 3-nitro-6-methylphenyl | methyl | ethyl | |
| 2.4.1131 | 3-fluoro-6-ethylphenyl | methyl | ethyl | |
| 2.4.1132 | 3-chloro-6-ethylphenyl | methyl | ethyl | |
| 2.4.1133 | 3-bromo-6-ethylphenyl | methyl | ethyl | |
| 2.4.1134 | 3-methyl-6-ethylphenyl | methyl | ethyl | |
| 2.4.1135 | 3,6-diethylphenyl | methyl | ethyl | |
| 2.4.1136 | 3-cyclopropyl-6-ethylphenyl | methyl | ethyl | |
| 2.4.1137 | 3-cyano-6-ethylphenyl | methyl | ethyl | |
| 2.4.1138 | 3-trifluoromethyl-6-ethylphenyl | methyl | ethyl | |
| 2.4.1139 | 3-methoxy-6-ethylphenyl | methyl | ethyl | |
| 2.4.1140 | 3-ethoxy-6-ethylphenyl | methyl | ethyl | |
| 2.4.1141 | 3-trifluoromethoxy-6-ethylphenyl | methyl | ethyl | |
| 2.4.1142 | 3-nitro-6-ethylphenyl | methyl | ethyl | |
| 2.4.1143 | 3-fluoro-6-propylphenyl | methyl | ethyl | |
| 2.4.1144 | 3-chloro-6-propylphenyl | methyl | ethyl | |
| 2.4.1145 | 3-bromo-6-propylphenyl | methyl | ethyl | |
| 2.4.1146 | 3-methyl-6-propylphenyl | methyl | ethyl | |
| 2.4.1147 | 3-methyl-6-propylphenyl | methyl | ethyl | |
| 2.4.1148 | 3-cyclopropyl-6-propylphenyl | methyl | ethyl | |
| 2.4.1149 | 3-cyano-6-propylphenyl | methyl | ethyl | |
| 2.4.1150 | 3-trifluoromethyl-6-propylphenyl | methyl | ethyl | |
| 2.4.1151 | 3-methoxy-6-propylphenyl | methyl | ethyl | |
| 2.4.1152 | 3-ethoxy-6-propylphenyl | methyl | ethyl | |
| 2.4.1153 | 3-trifluoromethoxy-6-propylphenyl | methyl | ethyl | |
| 2.4.1154 | 3-nitro-6-propylphenyl | methyl | ethyl | |
| 2.4.1155 | 3-fluoro-6-isopropylphenyl | methyl | ethyl | |
| 2.4.1156 | 3-chloro-6-isopropylphenyl | methyl | ethyl | |
| 2.4.1157 | 3-bromo-6-isopropylphenyl | methyl | ethyl | |
| 2.4.1158 | 3-methyl-6-isopropylphenyl | methyl | ethyl | |
| 2.4.1159 | 3-cyclopropyl-6-isopropylphenyl | methyl | ethyl | |
| 2.4.1160 | 3-cyano-6-isopropylphenyl | methyl | ethyl | |
| 2.4.1161 | 3-trifluoromethyl-6-isopropylphenyl | methyl | ethyl | |
| 2.4.1162 | 3-methoxy-6-isopropylphenyl | methyl | ethyl | |
| 2.4.1163 | 3-ethoxy-6-isopropylphenyl | methyl | ethyl | |
| 2.4.1164 | 3-trifluoromethoxy-6-isopropylphenyl | methyl | ethyl | |
| 2.4.1165 | 3-nitro-6-isopropylphenyl | methyl | ethyl | |
| 2.4.1166 | 3-fluoro-6-tert-butylphenyl | methyl | ethyl | |
| 2.4.1167 | 3-chloro-6-tert-butylphenyl | methyl | ethyl | |
| 2.4.1168 | 3-bromo-6-tert-butylphenyl | methyl | ethyl | |
| 2.4.1169 | 3-methyl-6-tert-butylphenyl | methyl | ethyl | |
| 2.4.1170 | 3-cyclopropyl-6-tert-butylphenyl | methyl | ethyl | |
| 2.4.1171 | 3-cyano-6-tert-butylphenyl | methyl | ethyl | |
| 2.4.1172 | 3-trifluoromethyl-6-tert-butylphenyl | methyl | ethyl | |
| 2.4.1173 | 3-methoxy-6-tert-butylphenyl | methyl | ethyl | |
| 2.4.1174 | 3-ethoxy-6-tert-butylphenyl | methyl | ethyl | |
| 2.4.1175 | 3-trifluoromethoxy-6-tert-butylphenyl | methyl | ethyl | |
| 2.4.1176 | 3-nitro-6-tert-butylphenyl | methyl | ethyl | |
| 2.4.1177 | 3-fluoro-6-cyclopropylphenyl | methyl | ethyl | |
| 2.4.1178 | 3-chloro-6-cyclopropylphenyl | methyl | ethyl | |
| 2.4.1179 | 3-bromo-6-cyclopropylphenyl | methyl | ethyl | |
| 2.4.1180 | 3-methyl-6-cyclopropylphenyl | methyl | ethyl | |
| 2.4.1181 | 3-cyclopropyl-6-cyclopropylphenyl | methyl | ethyl | |
| 2.4.1182 | 3-cyano-6-cyclopropylphenyl | methyl | ethyl | |

TABLE 2.4-continued

Inventive compounds of the general formula (I) in which W* is COOY, $R^1$ and $R^2$ are each hydrogen, and aryl is the radical.

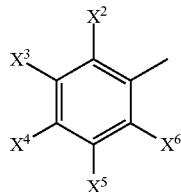

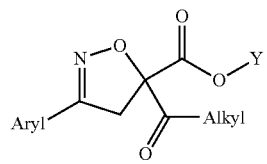

| No. | Aryl | Alkyl | Y | Physical data |
|---|---|---|---|---|
| 2.4.1183 | 3-trifluoromethyl-6-cyclopropylphenyl | methyl | ethyl | |
| 2.4.1184 | 3-methoxy-6-cyclopropylphenyl | methyl | ethyl | |
| 2.4.1185 | 3-ethoxy-6-cyclopropylphenyl | methyl | ethyl | |
| 2.4.1186 | 3-trifluoromethoxy-6-cyclopropylphenyl | methyl | ethyl | |
| 2.4.1187 | 3-fluoro-6-methoxycarbonylphenyl | methyl | ethyl | |
| 2.4.1188 | 3-chloro-6-methoxycarbonylphenyl | methyl | ethyl | |
| 2.4.1189 | 3-bromo-6-methoxycarbonylphenyl | methyl | ethyl | |
| 2.4.1190 | 3-methyl-6-methoxycarbonylphenyl | methyl | ethyl | |
| 2.4.1191 | 3-cyclopropyl-6-methoxycarbonylphenyl | methyl | ethyl | |
| 2.4.1192 | 3-cyano-6-methoxycarbonylphenyl | methyl | ethyl | |
| 2.4.1193 | 3-trifluoromethyl-6-methoxycarbonylphenyl | methyl | ethyl | |
| 2.4.1194 | 3-methoxy-6-methoxycarbonylphenyl | methyl | ethyl | |
| 2.4.1195 | 3-ethoxy-6-methoxycarbonylphenyl | methyl | ethyl | |
| 2.4.1196 | 3-trifluoromethoxy-6-methoxycarbonyl-phenyl | methyl | ethyl | |
| 2.4.1197 | 3-nitro-6-methoxycarbonylphenyl | methyl | ethyl | |
| 2.4.1198 | 3-fluoro-6-cyanophenyl | methyl | ethyl | |
| 2.4.1199 | 3-chloro-6-cyanophenyl | methyl | ethyl | |
| 2.4.1200 | 3-bromo-6-cyanophenyl | methyl | ethyl | |
| 2.4.1201 | 3-methyl-6-cyanophenyl | methyl | ethyl | |
| 2.4.1202 | 3-cyclopropyl-6-cyanophenyl | methyl | ethyl | |
| 2.4.1203 | 3-cyano-6-cyanophenyl | methyl | ethyl | |
| 2.4.1204 | 3-trifluoromethyl-6-cyanophenyl | methyl | ethyl | |
| 2.4.1205 | 3-methoxy-6-cyanophenyl | methyl | ethyl | |
| 2.4.1206 | 3-ethoxy-6-cyanophenyl | methyl | ethyl | |
| 2.4.1207 | 3-trifluoromethoxy-6-cyanophenyl | methyl | ethyl | |
| 2.4.1208 | 3-nitro-6-cyanophenyl | methyl | ethyl | |
| 2.4.1209 | 3-fluoro-6-methoxyphenyl | methyl | ethyl | |
| 2.4.1210 | 3-chloro-6-methoxyphenyl | methyl | ethyl | |
| 2.4.1211 | 3-bromo-6-methoxyphenyl | methyl | ethyl | |
| 2.4.1212 | 3-methyl-6-methoxyphenyl | methyl | ethyl | |
| 2.4.1213 | 3-cyclopropyl-6-methoxyphenyl | methyl | ethyl | |
| 2.4.1214 | 3-cyano-6-methoxyphenyl | methyl | ethyl | |
| 2.4.1215 | 3-trifluoromethyl-6-methoxyphenyl | methyl | ethyl | |
| 2.4.1216 | 3,6-dimethoxyphenyl | methyl | ethyl | |
| 2.4.1217 | 3-ethoxy-6-methoxyphenyl | methyl | ethyl | |
| 2.4.1218 | 3-trifluoromethoxy-6-methoxyphenyl | methyl | ethyl | |
| 2.4.1219 | 3-nitro-6-methoxyphenyl | methyl | ethyl | |
| 2.4.1220 | 3-fluoro-6-ethoxyphenyl | methyl | ethyl | |
| 2.4.1221 | 3-chloro-6-ethoxyphenyl | methyl | ethyl | |
| 2.4.1222 | 3-bromo-6-ethoxyphenyl | methyl | ethyl | |
| 2.4.1223 | 3-methyl-6-ethoxyphenyl | methyl | ethyl | |
| 2.4.1224 | 3-cyclopropyl-6-ethoxyphenyl | methyl | ethyl | |
| 2.4.1225 | 3-cyano-6-ethoxyphenyl | methyl | ethyl | |
| 2.4.1226 | 3-trifluoromethyl-6-ethoxyphenyl | methyl | ethyl | |
| 2.4.1227 | 3-methoxy-6-ethoxyphenyl | methyl | ethyl | |
| 2.4.1228 | 2,6-diethoxyphenyl | methyl | ethyl | |
| 2.4.1229 | 3-trifluoromethoxy-6-ethoxyphenyl | methyl | ethyl | |
| 2.4.1230 | 3-nitro-6-ethoxyphenyl | methyl | ethyl | |
| 2.4.1231 | 3-fluoro-6-propoxyphenyl | methyl | ethyl | |
| 2.4.1232 | 3-chloro-6-propoxyphenyl | methyl | ethyl | |
| 2.4.1233 | 3-bromo-6-propoxyphenyl | methyl | ethyl | |
| 2.4.1234 | 3-methyl-6-propoxyphenyl | methyl | ethyl | |
| 2.4.1235 | 3-cyclopropyl-6-propoxyphenyl | methyl | ethyl | |

TABLE 2.4-continued

Inventive compounds of the general formula (I) in which W* is COOY, $R^1$ and $R^2$ are each hydrogen, and aryl is the radical.

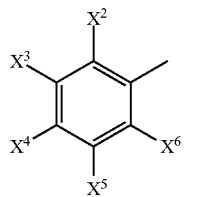

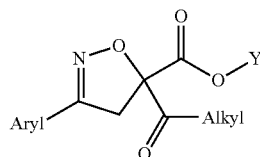

| No. | Aryl | Alkyl | Y | Physical data |
|---|---|---|---|---|
| 2.4.1236 | 3-cyano-6-propoxyphenyl | methyl | ethyl | |
| 2.4.1237 | 3-trifluoromethyl-6-propoxyphenyl | methyl | ethyl | |
| 2.4.1238 | 3-methoxy-6-propoxyphenyl | methyl | ethyl | |
| 2.4.1239 | 3-ethoxy-6-propoxyphenyl | methyl | ethyl | |
| 2.4.1240 | 3-trifluoromethoxy-6-propoxyphenyl | methyl | ethyl | |
| 2.4.1241 | 3-nitro-6-propoxyphenyl | methyl | ethyl | |
| 2.4.1242 | 3-fluoro-6-isopropoxyphenyl | methyl | ethyl | |
| 2.4.1243 | 3-chloro-6-isopropoxyphenyl | methyl | ethyl | |
| 2.4.1244 | 3-bromo-6-isopropoxyphenyl | methyl | ethyl | |
| 2.4.1245 | 3-methyl-6-isopropoxyphenyl | methyl | ethyl | |
| 2.4.1246 | 3-cyclopropyl-6-isopropoxyphenyl | methyl | ethyl | |
| 2.4.1247 | 3-cyano-6-isopropoxyphenyl | methyl | ethyl | |
| 2.4.1248 | 3-trifluoromethyl-6-isopropoxyphenyl | methyl | ethyl | |
| 2.4.1249 | 3-methoxy-6-isopropoxyphenyl | methyl | ethyl | |
| 2.4.1250 | 3-ethoxy-6-isopropoxyphenyl | methyl | ethyl | |
| 2.4.1251 | 3-trifluoromethoxy-6-isopropoxyphenyl | methyl | ethyl | |
| 2.4.1252 | 3-nitro-6-isopropoxyphenyl | methyl | ethyl | |
| 2.4.1253 | 3-fluoro-6-trifluoromethoxyphenyl | methyl | ethyl | |
| 2.4.1254 | 3-chloro-6-trifluoromethoxyphenyl | methyl | ethyl | |
| 2.4.1255 | 3-bromo-6-trifluoromethoxyphenyl | methyl | ethyl | |
| 2.4.1256 | 3-methyl-6-trifluoromethoxyphenyl | methyl | ethyl | |
| 2.4.1257 | 3-cyclopropyl-6-trifluoromethoxy-phenyl | methyl | ethyl | |
| 2.4.1258 | 3-cyano-6-trifluoromethoxyphenyl | methyl | ethyl | |
| 2.4.1259 | 3-trifluoromethyl-6-trifluoromethoxy-phenyl | methyl | ethyl | |
| 2.4.1260 | 3-methoxy-6-trifluoromethoxy-phenyl | methyl | ethyl | |
| 2.4.1261 | 3-ethoxy-6-trifluoromethoxyphenyl | methyl | ethyl | |
| 2.4.1262 | 3,6-bis(trifluoro-methoxy)phenyl | methyl | ethyl | |
| 2.4.1263 | 3-nitro-6-trifluoromethoxyphenyl | methyl | ethyl | |
| 2.4.1264 | 3-fluoro-6-difluoromethoxyphenyl | methyl | ethyl | |
| 2.4.1265 | 3-chloro-6-difluoromethoxyphenyl | methyl | ethyl | |
| 2.4.1266 | 3-bromo-6-difluoromethoxyphenyl | methyl | ethyl | |
| 2.4.1267 | 3-methyl-6-difluoromethoxyphenyl | methyl | ethyl | |
| 2.4.1268 | 3-cyclopropyl-6-difluoromethoxy-phenyl | methyl | ethyl | |
| 2.4.1269 | 3-cyano-6-difluoromethoxyphenyl | methyl | ethyl | |
| 2.4.1270 | 3-trifluoromethyl-6-difluoromethoxyphenyl | methyl | ethyl | |
| 2.4.1271 | 3-methoxy-6-difluoromethoxy-phenyl | methyl | ethyl | |
| 2.4.1272 | 3-ethoxy-6-difluoromethoxyphenyl | methyl | ethyl | |
| 2.4.1273 | 3-trifluoromethoxy-6-difluoromethoxyphenyl | methyl | ethyl | |
| 2.4.1274 | 3-nitro-6-difluoromethoxyphenyl | methyl | ethyl | |
| 2.4.1275 | 3-fluoro-6-nitrophenyl | methyl | ethyl | |
| 2.4.1276 | 3-chloro-6-nitrophenyl | methyl | ethyl | |
| 2.4.1277 | 3-bromo-6-nitrophenyl | methyl | ethyl | |
| 2.4.1278 | 3-methyl-6-nitrophenyl | methyl | ethyl | |
| 2.4.1279 | 3-cyclopropyl-6-nitrophenyl | methyl | ethyl | |
| 2.4.1280 | 3-cyano-6-nitrophenyl | methyl | ethyl | |
| 2.4.1281 | 3-trifluoromethyl-6-nitrophenyl | methyl | ethyl | |
| 2.4.1282 | 3-methoxy-6-nitrophenyl | methyl | ethyl | |

TABLE 2.4-continued

Inventive compounds of the general formula (I) in which W* is COOY, $R^1$ and $R^2$ are each hydrogen, and aryl is the radical.

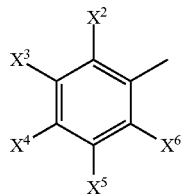

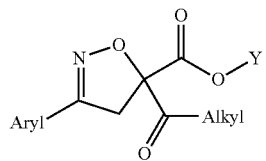

| No. | Aryl | Alkyl | Y | Physical data |
|---|---|---|---|---|
| 2.4.1283 | 3-ethoxy-6-nitrophenyl | methyl | ethyl | |
| 2.4.1284 | 3-trifluoromethoxy-6-nitrophenyl | methyl | ethyl | |
| 2.4.1285 | 3-fluoro-6-methylsulfanylphenyl | methyl | ethyl | |
| 2.4.1286 | 3-chloro-6-methylsulfanylphenyl | methyl | ethyl | |
| 2.4.1287 | 3-bromo-6-methylsulfanylphenyl | methyl | ethyl | |
| 2.4.1288 | 3-methyl-6-methylsulfanylphenyl | methyl | ethyl | |
| 2.4.1289 | 3-cyclopropyl-6-methylsulfanylphenyl | methyl | ethyl | |
| 2.4.1290 | 3-cyano-6-methylsulfanylphenyl | methyl | ethyl | |
| 2.4.1291 | 3-trifluoromethyl-6-methylsulfanylphenyl | methyl | ethyl | |
| 2.4.1292 | 3-methoxy-6-methylsulfanylphenyl | methyl | ethyl | |
| 2.4.1293 | 3-ethoxy-6-methylsulfanylphenyl | methyl | ethyl | |
| 2.4.1294 | 3-trifluoromethoxy-6-methylsulfanylphenyl | methyl | ethyl | |
| 2.4.1295 | 3-nitro-6-methylsulfanylphenyl | methyl | ethyl | |
| 2.4.1296 | 2,3,4-trifluorophenyl | methyl | ethyl | |
| 2.4.1297 | 2,3,4-trichlorophenyl | methyl | ethyl | |
| 2.4.1298 | 2,3,4-trimethylphenyl | methyl | ethyl | |
| 2.4.1299 | 2-fluoro-2-chloro-5-trifluoromethyl-phenyl | methyl | ethyl | |
| 2.4.1300 | 2,3,5-trifluorophenyl | methyl | ethyl | |
| 2.4.1301 | 2,3,5-trichlorophenyl | methyl | ethyl | |
| 2.4.1302 | 2,3,5-trimethylphenyl | methyl | ethyl | |
| 2.4.1303 | 2,3-dichloro-5-methoxyphenyl | methyl | ethyl | |
| 2.4.1304 | 2,3,6-trifluorophenyl | methyl | ethyl | |
| 2.4.1305 | 2,3,6-trichlorophenyl | methyl | ethyl | |
| 2.4.1306 | 2,3,6-trimethylphenyl | methyl | ethyl | |
| 2.4.1307 | 3,4,5-trifluorophenyl | methyl | ethyl | |
| 2.4.1308 | 3,4,5-trichlorophenyl | methyl | ethyl | |
| 2.4.1309 | 3,4,5-trimethylphenyl | methyl | ethyl | |
| 2.4.1310 | 3,5-dimethyl-4-fluorophenyl | methyl | ethyl | |
| 2.4.1311 | 3,5-dichloro-4-methoxyphenyl | methyl | ethyl | |
| 2.4.1312 | 3,5-difluoro-4-chlorophenyl | methyl | ethyl | |
| 2.4.1313 | 3,5-dichloro-4-hydroxyphenyl | methyl | ethyl | |
| 2.4.1314 | 3,5-trifluoromethyl-4-chlorophenyl | methyl | ethyl | |
| 2.4.1315 | 3,4,6-trifluorophenyl | methyl | ethyl | |
| 2.4.1316 | 3,4,6-trichlorophenyl | methyl | ethyl | |
| 2.4.1317 | 3,4,6-trimethylphenyl | methyl | ethyl | |
| 2.4.1318 | pentafluorophenyl | methyl | ethyl | |

TABLE 2.5

Inventive compounds of the general formula (I) in which W* is COOY, $R^1$ and $R^2$ are each hydrogen, and aryl is the radical.

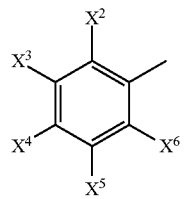

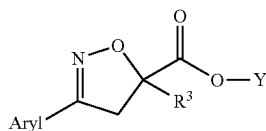

| No. | Aryl | $R^3$ | Y | Physical data |
|---|---|---|---|---|
| 2.5.1 | 3-fluorophenyl | hydroxymethyl | ethyl | |
| 2.5.2 | 3-fluorophenyl | 1-hydroxyethyl | methyl | [CDCl3] D1 1.20 (d, 3H); 2.39 (d br, 1H); 3.60 (d, 1H); 3.71 (d, 1H); 3.83 (s, 3H); 4.30-4.37 (m, 1H); 7.13 (t, 1H); 7.34-7.45 (m, 2H). D2 1.28 (d, 3H); 2.1 7(d br, 1H); 3.56 (d, 1H); 3.76 (d, 1H); 3.84 (s, 3H); 4.20-4.28 (m, 1H); 7.13 (t, 1H); 7.34-7.45 (m, 3H). |
| 2.5.3 | 3-fluorophenyl | 1-hydroxypropyl | ethyl | |
| 2.5.4 | 3-fluorophenyl | (1-hydroxy-2-methylpropyl) | ethyl | |
| 2.5.5 | 3-fluorophenyl | methoxymethyl | ethyl | |
| 2.5.6 | 3-fluorophenyl | 2-methoxyethyl | ethyl | |
| 2.5.7 | 3-chlorophenyl | hydroxymethyl | ethyl | |
| 2.5.8 | 3-chlorophenyl | 1-hydroxyethyl | ethyl | |
| 2.5.9 | 3-chlorophenyl | 1-hydroxypropyl | ethyl | |
| 2.5.10 | 3-chlorophenyl | (1-hydroxy-2-methylpropyl) | ethyl | |
| 2.5.11 | 3-chlorophenyl | methoxymethyl | ethyl | |
| 2.5.12 | 3-chlorophenyl | 2-methoxyethyl | ethyl | |
| 2.5.13 | 3-bromophenyl | hydroxymethyl | ethyl | |
| 2.5.14 | 3-bromophenyl | 1-hydroxyethyl | ethyl | |
| 2.5.15 | 3-iodophenyl | hydroxymethyl | ethyl | |
| 2.5.16 | 3-iodophenyl | 1-hydroxyethyl | ethyl | |
| 2.5.17 | 3-methylphenyl | hydroxymethyl | ethyl | |
| 2.5.18 | 3-methylphenyl | 1-hydroxyethyl | ethyl | |
| 2.5.19 | 3-ethylphenyl | hydroxymethyl | ethyl | |
| 2.5.20 | 3-propylphenyl | hydroxymethyl | ethyl | |
| 2.5.21 | 3-isopropylphenyl | hydroxymethyl | ethyl | |
| 2.5.22 | 3-n-butylphenyl | hydroxymethyl | ethyl | |
| 2.5.23 | 3-i-butylphenyl | hydroxymethyl | ethyl | |
| 2.5.24 | 3-tert-butylphenyl | hydroxymethyl | ethyl | |
| 2.5.25 | 3-cyclopropylphenyl | hydroxymethyl | ethyl | |
| 2.5.26 | 3-cyclobutylphenyl | hydroxymethyl | ethyl | |
| 2.5.27 | 3-cyclopentylphenyl | hydroxymethyl | ethyl | |
| 2.5.28 | 3-vinylphenyl | hydroxymethyl | ethyl | |
| 2.5.29 | 3-ethynylphenyl | hydroxymethyl | ethyl | |
| 2.5.30 | 3-cyanophenyl | hydroxymethyl | ethyl | |
| 2.5.31 | 3-trifluoromethylphenyl | hydroxymethyl | ethyl | |
| 2.5.32 | 3-difluoromethylphenyl | hydroxymethyl | ethyl | |
| 2.5.33 | 3-(hydroxycarbonyl)phenyl | hydroxymethyl | ethyl | |
| 2.5.34 | 3-(methoxycarbonyl)phenyl | hydroxymethyl | ethyl | |
| 2.5.35 | 3-(ethoxycarbonyl)phenyl | hydroxymethyl | ethyl | |
| 2.5.36 | 3-hydroxymethylphenyl | hydroxymethyl | ethyl | |
| 2.5.37 | 3-carbamoylphenyl | hydroxymethyl | ethyl | |
| 2.5.38 | 3-hydroxyphenyl | hydroxymethyl | ethyl | |
| 2.5.39 | 3-methoxyphenyl | hydroxymethyl | ethyl | |
| 2.5.40 | 3-ethoxyphenyl | hydroxymethyl | ethyl | |
| 2.5.41 | 3-propyloxyphenyl | hydroxymethyl | ethyl | |
| 2.5.42 | 3-isopropyloxyphenyl | hydroxymethyl | ethyl | |
| 2.5.43 | 3-n-butyloxyphenyl | hydroxymethyl | ethyl | |
| 2.5.44 | 3-i-butyloxyphenyl | hydroxymethyl | ethyl | |

TABLE 2.5-continued

Inventive compounds of the general formula (I) in which W* is COOY, R¹ and R² are each hydrogen, and aryl is the radical.

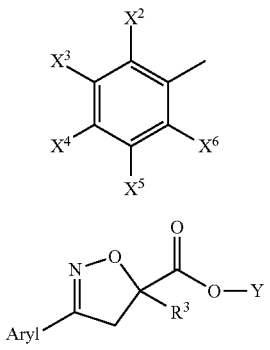

| No. | Aryl | R³ | Y | Physical data |
|---|---|---|---|---|
| 2.5.45 | 3-t-butyloxyphenyl | hydroxymethyl | ethyl | |
| 2.5.46 | 3-difluoromethoxyphenyl | hydroxymethyl | ethyl | |
| 2.5.47 | 3-trifluoromethoxyphenyl | hydroxymethyl | ethyl | |
| 2.5.48 | 3-(2,2,2-trifluoroethoxy)phenyl | hydroxymethyl | ethyl | |
| 2.5.49 | 3-(2-chloroethoxy)phenyl | hydroxymethyl | ethyl | |
| 2.5.50 | 3-(2-hydroxyethoxy)phenyl | hydroxymethyl | ethyl | |
| 2.5.51 | 3-(2-methoxyethoxy)phenyl | hydroxymethyl | ethyl | |
| 2.5.52 | 3-[(tert-butoxycarbonyl)oxy]-phenyl | hydroxymethyl | ethyl | |
| 2.5.53 | 3-nitrophenyl | hydroxymethyl | ethyl | |
| 2.5.54 | 3-acetoxyphenyl | hydroxymethyl | ethyl | |
| 2.5.55 | {3-[(tert-butoxycarbonyl)amino]-phenyl} | hydroxymethyl | ethyl | |
| 2.5.56 | 3-methylsulfanylphenyl | hydroxymethyl | ethyl | |
| 2.5.57 | 3-ethylsulfanylphenyl | hydroxymethyl | ethyl | |
| 2.5.58 | 3-(pentafluoro-lambda⁶-sulfanyl)phenyl | hydroxymethyl | ethyl | |
| 2.5.59 | 2,3-difluorophenyl | hydroxymethyl | ethyl | |
| 2.5.60 | 2,3-difluorophenyl | 1-hydroxyethyl | ethyl | |
| 2.5.61 | 2,3-difluorophenyl | 1-hydroxypropyl | ethyl | |
| 2.5.62 | 2,3-difluorophenyl | (1-hydroxy-2-methylpropyl) | ethyl | |
| 2.5.63 | 2,3-difluorophenyl | methoxymethyl | ethyl | |
| 2.5.64 | 2,3-difluorophenyl | 2-methoxyethyl | ethyl | |
| 2.5.65 | 2-chloro-3-fluorophenyl | hydroxymethyl | ethyl | |
| 2.5.66 | 2-bromo-3-fluorophenyl | hydroxymethyl | ethyl | |
| 2.5.67 | 2-methyl-3-fluorophenyl | hydroxymethyl | ethyl | |
| 2.5.68 | 2-ethyl-3-fluorophenyl | hydroxymethyl | ethyl | |
| 2.5.69 | 2-cyclopropyl-3-fluorophenyl | hydroxymethyl | ethyl | |
| 2.5.70 | 2-vinyl-3-fluorophenyl | hydroxymethyl | ethyl | |
| 2.5.71 | 2-ethynyl-3-fluorophenyl | hydroxymethyl | ethyl | |
| 2.5.72 | 2-cyano-3-fluorophenyl | hydroxymethyl | ethyl | |
| 2.5.73 | 2-methoxy-3-fluorophenyl | hydroxymethyl | ethyl | |
| 2.5.74 | 2-ethoxy-3-fluorophenyl | hydroxymethyl | ethyl | |
| 2.5.75 | 2-trifluoromethoxy-3-fluorophenyl | hydroxymethyl | ethyl | |
| 2.5.76 | 2-nitro-3-fluorophenyl | hydroxymethyl | ethyl | |
| 2.5.77 | 2-fluoro-3-chlorophenyl | hydroxymethyl | ethyl | |
| 2.5.78 | 2,3-dichlorophenyl | hydroxymethyl | ethyl | |
| 2.5.79 | 2,3-dichlorophenyl | 1-hydroxyethyl | ethyl | |
| 2.5.80 | 2,3-dichlorophenyl | 1-hydroxypropyl | ethyl | |
| 2.5.81 | 2,3-dichlorophenyl | (1-hydroxy-2-methylpropyl) | ethyl | |
| 2.5.82 | 2,3-dichlorophenyl | methoxymethyl | ethyl | |
| 2.5.83 | 2,3-dichlorophenyl | 2-methoxyethyl | ethyl | |
| 2.5.84 | 2-bromo-3-chlorophenyl | hydroxymethyl | ethyl | |
| 2.5.85 | 2-methyl-3-chlorophenyl | hydroxymethyl | ethyl | |
| 2.5.86 | 2-ethyl-3-chlorophenyl | hydroxymethyl | ethyl | |
| 2.5.87 | 2-cyclopropyl-3-chlorophenyl | hydroxymethyl | ethyl | |
| 2.5.88 | 2-vinyl-3-chlorophenyl | hydroxymethyl | ethyl | |
| 2.5.89 | 2-ethynyl-3-chlorophenyl | hydroxymethyl | ethyl | |
| 2.5.90 | 2-cyano-3-chlorophenyl | hydroxymethyl | ethyl | |
| 2.5.91 | 2-trifluoromethyl-2-chlorophenyl | hydroxymethyl | ethyl | |
| 2.5.92 | 2-methoxy-3-chlorophenyl | hydroxymethyl | ethyl | |
| 2.5.93 | 2-ethoxy-3-chlorophenyl | hydroxymethyl | ethyl | |
| 2.5.94 | 2-trifluoromethoxy-3-chlorophenyl | hydroxymethyl | ethyl | |
| 2.5.95 | 2-nitro-3-chlorophenyl | hydroxymethyl | ethyl | |
| 2.5.96 | 2-fluoro-3-bromophenyl | hydroxymethyl | ethyl | |
| 2.5.97 | 2-chloro-3-bromophenyl | hydroxymethyl | ethyl | |
| 2.5.98 | 2,3-dibromophenyl | hydroxymethyl | ethyl | |
| 2.5.99 | 2-methyl-3-bromophenyl | hydroxymethyl | ethyl | |

TABLE 2.5-continued

Inventive compounds of the general formula (I) in which W* is COOY,
R¹ and R² are each hydrogen, and aryl is the radical.

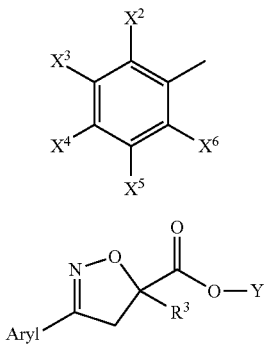

| No. | Aryl | R³ | Y | Physical data |
|---|---|---|---|---|
| 2.5.100 | 2-ethyl-3-bromophenyl | hydroxymethyl | ethyl | |
| 2.5.101 | 2-cyclopropyl-3-bromophenyl | hydroxymethyl | ethyl | |
| 2.5.102 | 2-vinyl-3-bromophenyl | hydroxymethyl | ethyl | |
| 2.5.103 | 2-ethynyl-3-bromophenyl | hydroxymethyl | ethyl | |
| 2.5.104 | 2-cyano-3-bromophenyl | hydroxymethyl | ethyl | |
| 2.5.105 | 2-trifluoromethyl-3-bromophenyl | hydroxymethyl | ethyl | |
| 2.5.106 | 2-methoxy-3-phenyl | hydroxymethyl | ethyl | |
| 2.5.107 | 2-ethoxy-3-bromophenyl | hydroxymethyl | ethyl | |
| 2.5.108 | 2-trifluoromethoxy-3-bromophenyl | hydroxymethyl | ethyl | |
| 2.5.109 | 2-nitro-3-bromophenyl | hydroxymethyl | ethyl | |
| 2.5.110 | 2-fluoro-3-iodophenyl | hydroxymethyl | ethyl | |
| 2.5.111 | 2-chloro-3-iodophenyl | hydroxymethyl | ethyl | |
| 2.5.112 | 2-bromo-3-iodophenyl | hydroxymethyl | ethyl | |
| 2.5.113 | 2-methyl-3-iodophenyl | hydroxymethyl | ethyl | |
| 2.5.114 | 2-ethyl-3-iodophenyl | hydroxymethyl | ethyl | |
| 2.5.115 | 2-cyclopropyl-3-iodophenyl | hydroxymethyl | ethyl | |
| 2.5.116 | 2-vinyl-3-iodophenyl | hydroxymethyl | ethyl | |
| 2.5.117 | 2-ethynyl-3-iodophenyl | hydroxymethyl | ethyl | |
| 2.5.118 | 2-cyano-3-iodophenyl | hydroxymethyl | ethyl | |
| 2.5.119 | 2-trifluoromethyl-3-iodophenyl | hydroxymethyl | ethyl | |
| 2.5.120 | 2-methoxy-3-iodophenyl | hydroxymethyl | ethyl | |
| 2.5.121 | 2-ethoxy-3-iodophenyl | hydroxymethyl | ethyl | |
| 2.5.122 | 2-trifluoromethoxy-3-iodophenyl | hydroxymethyl | ethyl | |
| 2.5.123 | 2-nitro-3-iodophenyl | hydroxymethyl | ethyl | |
| 2.5.124 | 2-fluoro-3-methylphenyl | hydroxymethyl | ethyl | |
| 2.5.125 | 2-fluoro-3-methylphenyl | 1-hydroxyethyl | ethyl | |
| 2.5.126 | 2-fluoro-3-methylphenyl | 1-hydroxypropyl | ethyl | |
| 2.5.127 | 2-fluoro-3-methylphenyl | (1-hydroxy-2-methylpropyl) | ethyl | |
| 2.5.128 | 2-fluoro-3-methylphenyl | methoxymethyl | ethyl | |
| 2.5.129 | 2-fluoro-3-methylphenyl | 2-methoxyethyl | ethyl | |
| 2.5.130 | 2-chloro-3-methylphenyl | hydroxymethyl | ethyl | |
| 2.5.131 | 2-chloro-3-methylphenyl | 1-hydroxyethyl | ethyl | |
| 2.5.132 | 2-chloro-3-methylphenyl | 1-hydroxypropyl | ethyl | |
| 2.5.133 | 2-chloro-3-methylphenyl | (1-hydroxy-2-methylpropyl) | ethyl | |
| 2.5.134 | 2-chloro-3-methylphenyl | methoxymethyl | ethyl | |
| 2.5.135 | 2-chloro-3-methylphenyl | 2-methoxyethyl | ethyl | |
| 2.5.136 | 2-bromo-3-methylphenyl | hydroxymethyl | ethyl | |
| 2.5.137 | 2,3-dimethylphenyl | hydroxymethyl | ethyl | |
| 2.5.138 | 2,3-dimethylphenyl | 1-hydroxyethyl | ethyl | |
| 2.5.139 | 2,3-dimethylphenyl | 1-hydroxypropyl | ethyl | |
| 2.5.140 | 2,3-dimethylphenyl | (1-hydroxy-2-methylpropyl) | ethyl | |
| 2.5.141 | 2,3-dimethylphenyl | methoxymethyl | ethyl | |
| 2.5.142 | 2,3-dimethylphenyl | 2-methoxyethyl | ethyl | |
| 2.5.143 | 2-ethyl-3-methylphenyl | hydroxymethyl | ethyl | |
| 2.5.144 | 2-cyclopropyl-3-methylphenyl | hydroxymethyl | ethyl | |
| 2.5.145 | 2-vinyl-3-methylphenyl | hydroxymethyl | ethyl | |
| 2.5.146 | 2-ethynyl-3-methylphenyl | hydroxymethyl | ethyl | |
| 2.5.147 | 2-cyano-3-methylphenyl | hydroxymethyl | ethyl | |
| 2.5.148 | 2-trifluoromethyl-3-methylphenyl | hydroxymethyl | ethyl | |
| 2.5.149 | 2-methoxy-3-methylphenyl | hydroxymethyl | ethyl | |
| 2.5.150 | 2-ethoxy-3-methylphenyl | hydroxymethyl | ethyl | |
| 2.5.151 | 2-trifluoromethoxy-3-methylphenyl | hydroxymethyl | ethyl | |
| 2.5.152 | 2-nitro-3-methylphenyl | hydroxymethyl | ethyl | |
| 2.5.153 | 2-fluoro-3-ethylphenyl | hydroxymethyl | ethyl | |
| 2.5.154 | 2-chloro-3-ethylphenyl | hydroxymethyl | ethyl | |

TABLE 2.5-continued

Inventive compounds of the general formula (I) in which W* is COOY,
R¹ and R² are each hydrogen, and aryl is the radical.

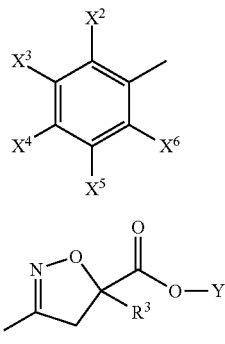

| No. | Aryl | R³ | Y | Physical data |
|---|---|---|---|---|
| 2.5.155 | 2-bromo-3-ethylphenyl | hydroxymethyl | ethyl | |
| 2.5.156 | 2-methyl-3-ethylphenyl | hydroxymethyl | ethyl | |
| 2.5.157 | 2,3-diethylphenyl | hydroxymethyl | ethyl | |
| 2.5.158 | 2-cyclopropyl-3-ethylphenyl | hydroxymethyl | ethyl | |
| 2.5.159 | 2-vinyl-3-ethylphenyl | hydroxymethyl | ethyl | |
| 2.5.160 | 2-ethynyl-3-ethylphenyl | hydroxymethyl | ethyl | |
| 2.5.161 | 2-cyano-3-ethylphenyl | hydroxymethyl | ethyl | |
| 2.5.162 | 2-trifluoromethyl-3-ethylphenyl | hydroxymethyl | ethyl | |
| 2.5.163 | 2-methoxy-3-ethylphenyl | hydroxymethyl | ethyl | |
| 2.5.164 | 2-ethoxy-3-ethylphenyl | hydroxymethyl | ethyl | |
| 2.5.165 | 2-trifluoromethoxy-3-ethylphenyl | hydroxymethyl | ethyl | |
| 2.5.166 | 2-nitro-3-ethylphenyl | hydroxymethyl | ethyl | |
| 2.5.167 | 2-fluoro-3-propylphenyl | hydroxymethyl | ethyl | |
| 2.5.168 | 2-chloro-3-propylphenyl | hydroxymethyl | ethyl | |
| 2.5.169 | 2-bromo-3-propylphenyl | hydroxymethyl | ethyl | |
| 2.5.170 | 2-methyl-3-propylphenyl | hydroxymethyl | ethyl | |
| 2.5.171 | 2-methyl-3-propylphenyl | hydroxymethyl | ethyl | |
| 2.5.172 | 2-cyclopropyl-3-propylphenyl | hydroxymethyl | ethyl | |
| 2.5.173 | 2-vinyl-3-propylphenyl | hydroxymethyl | ethyl | |
| 2.5.174 | 2-ethynyl-3propylphenyl | hydroxymethyl | ethyl | |
| 2.5.175 | 2-cyano-3-propylphenyl | hydroxymethyl | ethyl | |
| 2.5.176 | 2-trifluoromethyl-3-propylphenyl | hydroxymethyl | ethyl | |
| 2.5.177 | 2-methoxy-3-propylphenyl | hydroxymethyl | ethyl | |
| 2.5.178 | 2-ethoxy-3-propylphenyl | hydroxymethyl | ethyl | |
| 2.5.179 | 2-trifluoromethoxy-3-propylphenyl | hydroxymethyl | ethyl | |
| 2.5.180 | 2-nitro-3-propylphenyl | hydroxymethyl | ethyl | |
| 2.5.181 | 2-fluoro-3-isopropylphenyl | hydroxymethyl | ethyl | |
| 2.5.182 | 2-chloro-3-isopropylphenyl | hydroxymethyl | ethyl | |
| 2.5.183 | 2-bromo-3-isopropylphenyl | hydroxymethyl | ethyl | |
| 2.5.184 | 2-methyl-3-isopropylphenyl | hydroxymethyl | ethyl | |
| 2.5.185 | 2-ethyl-3-isopropylphenyl | hydroxymethyl | ethyl | |
| 2.5.186 | 2-cyclopropyl-3-isopropylphenyl | hydroxymethyl | ethyl | |
| 2.5.187 | 2-vinyl-3-isopropylphenyl | hydroxymethyl | ethyl | |
| 2.5.188 | 2-ethynyl-3-isopropylphenyl | hydroxymethyl | ethyl | |
| 2.5.189 | 2-cyano-3-isopropylphenyl | hydroxymethyl | ethyl | |
| 2.5.190 | 2-trifluoromethyl-3-isopropylphenyl | hydroxymethyl | ethyl | |
| 2.5.191 | 2-methoxy-3-isopropylphenyl | hydroxymethyl | ethyl | |
| 2.5.192 | 2-ethoxy-3-isopropylphenyl | hydroxymethyl | ethyl | |
| 2.5.193 | 2-trifluoromethoxy-3-isopropylphenyl | hydroxymethyl | ethyl | |
| 2.5.194 | 2-nitro-3-isopropylphenyl | hydroxymethyl | ethyl | |
| 2.5.195 | 2-fluoro-3-tert-butylphenyl | hydroxymethyl | ethyl | |
| 2.5.196 | 2-chloro-3-tert-butylphenyl | hydroxymethyl | ethyl | |
| 2.5.197 | 2-bromo-3-tert-butylphenyl | hydroxymethyl | ethyl | |
| 2.5.198 | 2-methyl-3-tert-butylphenyl | hydroxymethyl | ethyl | |
| 2.5.199 | 2-ethyl-3-tert-butylphenyl | hydroxymethyl | ethyl | |
| 2.5.200 | 2-cyclopropyl-3-tert-butylphenyl | hydroxymethyl | ethyl | |
| 2.5.201 | 2-vinyl-3-tert-butylphenyl | hydroxymethyl | ethyl | |
| 2.5.202 | 2-ethynyl-3-tert-butylphenyl | hydroxymethyl | ethyl | |
| 2.5.203 | 2-cyano-3-tert-butylphenyl | hydroxymethyl | ethyl | |
| 2.5.204 | 2-trifluoromethyl-3-tert-butylphenyl | hydroxymethyl | ethyl | |
| 2.5.205 | 2-methoxy-3-tert-butylphenyl | hydroxymethyl | ethyl | |
| 2.5.206 | 2-ethoxy-3-tert-butylphenyl | hydroxymethyl | ethyl | |
| 2.5.207 | 2-trifluoromethoxy-3-tert-butylphenyl | hydroxymethyl | ethyl | |
| 2.5.208 | 2-nitro-3-tert-butylphenyl | hydroxymethyl | ethyl | |
| 2.5.209 | 2-fluoro-3-hydroxymethylphenyl | hydroxymethyl | ethyl | |
| 2.5.210 | 2-chloro-3-hydroxymethylphenyl | hydroxymethyl | ethyl | |
| 2.5.211 | 2-bromo-3-hydroxymethylphenyl | hydroxymethyl | ethyl | |
| 2.5.212 | 2-methyl-3-hydroxymethylphenyl | hydroxymethyl | ethyl | |

TABLE 2.5-continued

Inventive compounds of the general formula (I) in which W* is COOY,
R¹ and R² are each hydrogen, and aryl is the radical.

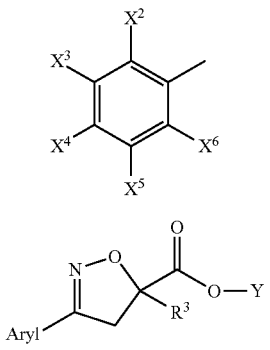

| No. | Aryl | R³ | Y | Physical data |
|---|---|---|---|---|
| 2.5.213 | 2-ethyl-3-hydroxymethylphenyl | hydroxymethyl | ethyl | |
| 2.5.214 | 2-cyclopropyl-3-hydroxymethylphenyl | hydroxymethyl | ethyl | |
| 2.5.215 | 2-vinyl-3-hydroxymethylphenyl | hydroxymethyl | ethyl | |
| 2.5.216 | 2-ethynyl-3-hydroxymethylphenyl | hydroxymethyl | ethyl | |
| 2.5.217 | 2-cyano-3-hydroxymethylphenyl | hydroxymethyl | ethyl | |
| 2.5.218 | 2-trifluoromethyl-3-hydroxymethylphenyl | hydroxymethyl | ethyl | |
| 2.5.219 | 2-methoxy-3-hydroxymethylphenyl | hydroxymethyl | ethyl | |
| 2.5.220 | 2-ethoxy-3-hydroxymethylphenyl | hydroxymethyl | ethyl | |
| 2.5.221 | 2-trifluoromethoxy-3-hydroxymethylphenyl | hydroxymethyl | ethyl | |
| 2.5.222 | 2-nitro-3-hydroxymethylphenyl | hydroxymethyl | ethyl | |
| 2.5.223 | 2-fluoro-3-cyclopropylphenyl | hydroxymethyl | ethyl | |
| 2.5.224 | 2-chloro-3-cyclopropylphenyl | hydroxymethyl | ethyl | |
| 2.5.225 | 2-bromo-3-cyclopropylphenyl | hydroxymethyl | ethyl | |
| 2.5.226 | 2-methyl-3-cyclopropylphenyl | hydroxymethyl | ethyl | |
| 2.5.227 | 2-ethyl-3-cyclopropylphenyl | hydroxymethyl | ethyl | |
| 2.5.228 | 2-cyclopropyl-3-cyclopropylphenyl | hydroxymethyl | ethyl | |
| 2.5.229 | 2-vinyl-3-cyclopropylphenyl | hydroxymethyl | ethyl | |
| 2.5.230 | 2-ethynyl-3-cyclopropylphenyl | hydroxymethyl | ethyl | |
| 2.5.231 | 2-cyano-3-cyclopropylphenyl | hydroxymethyl | ethyl | |
| 2.5.232 | 2-trifluoromethyl-3-cyclopropylphenyl | hydroxymethyl | ethyl | |
| 2.5.233 | 2-methoxy-3-cyclopropylphenyl | hydroxymethyl | ethyl | |
| 2.5.234 | 2-ethoxy-3-cyclopropylphenyl | hydroxymethyl | ethyl | |
| 2.5.235 | 2-trifluoromethoxy-3-cyclopropylphenyl | hydroxymethyl | ethyl | |
| 2.5.236 | 2-fluoro-3-methoxycarbonylphenyl | hydroxymethyl | ethyl | |
| 2.5.237 | 2-chloro-3-methoxycarbonylphenyl | hydroxymethyl | ethyl | |
| 2.5.238 | 2-bromo-3-methoxycarbonylphenyl | hydroxymethyl | ethyl | |
| 2.5.239 | 2-methyl-3-methoxycarbonylphenyl | hydroxymethyl | ethyl | |
| 2.5.240 | 2-ethyl-3-methoxycarbonylphenyl | hydroxymethyl | ethyl | |
| 2.5.241 | 2-cyclopropyl-3-methoxycarbonyl-phenyl | hydroxymethyl | ethyl | |
| 2.5.242 | 2-vinyl-3-methoxycarbonylphenyl | hydroxymethyl | ethyl | |
| 2.5.243 | 2-ethynyl-3-methoxycarbonyl-phenyl | hydroxymethyl | ethyl | |
| 2.5.244 | 2-cyano-3-methoxycarbonylphenyl | hydroxymethyl | ethyl | |
| 2.5.245 | 2-trifluoromethyl-3-methoxycarbonylphenyl | hydroxymethyl | ethyl | |
| 2.5.246 | 2-methoxy-3-methoxycarbonyl-phenyl | hydroxymethyl | ethyl | |
| 2.5.247 | 2-ethoxy-3-methoxycarbonylphenyl | hydroxymethyl | ethyl | |
| 2.5.248 | 2-trifluoromethoxy-3-methoxycarbonylphenyl | hydroxymethyl | ethyl | |
| 2.5.249 | 2-nitro-3-methoxycarbonylphenyl | hydroxymethyl | ethyl | |
| 2.5.250 | 2-fluoro-3-vinylphenyl | hydroxymethyl | ethyl | |
| 2.5.251 | 2-chloro-3-vinylphenyl | hydroxymethyl | ethyl | |
| 2.5.252 | 2-bromo-3-vinylphenyl | hydroxymethyl | ethyl | |
| 2.5.253 | 2-methyl-3-vinylphenyl | hydroxymethyl | ethyl | |
| 2.5.254 | 2-ethyl-3-vinylphenyl | hydroxymethyl | ethyl | |
| 2.5.255 | 2-cyclopropyl-3-vinylphenyl | hydroxymethyl | ethyl | |
| 2.5.256 | 2-vinyl-3-vinylphenyl | hydroxymethyl | ethyl | |
| 2.5.257 | 2-ethynyl-3-vinylphenyl | hydroxymethyl | ethyl | |
| 2.5.258 | 2-cyano-3-vinylphenyl | hydroxymethyl | ethyl | |
| 2.5.259 | 2-trifluoromethyl-3-vinylphenyl | hydroxymethyl | ethyl | |
| 2.5.260 | 2-methoxy-3-vinylphenyl | hydroxymethyl | ethyl | |
| 2.5.261 | 2-ethoxy-3-vinylphenyl | hydroxymethyl | ethyl | |
| 2.5.262 | 2-trifluoromethoxy-3-vinylphenyl | hydroxymethyl | ethyl | |
| 2.5.263 | 2-nitro-3-vinylphenyl | hydroxymethyl | ethyl | |
| 2.5.264 | 2-fluoro-3-ethynylphenyl | hydroxymethyl | ethyl | |

TABLE 2.5-continued

Inventive compounds of the general formula (I) in which W* is COOY,
R¹ and R² are each hydrogen, and aryl is the radical.

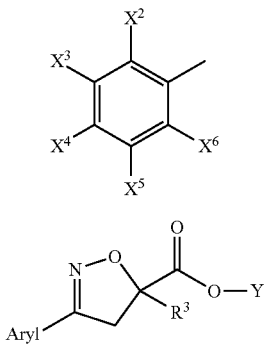

| No. | Aryl | R³ | Y | Physical data |
|---|---|---|---|---|
| 2.5.265 | 2-chloro-3-ethynylphenyl | hydroxymethyl | ethyl | |
| 2.5.266 | 2-bromo-3-ethynylphenyl | hydroxymethyl | ethyl | |
| 2.5.267 | 2-methyl-3-ethynylphenyl | hydroxymethyl | ethyl | |
| 2.5.268 | 2-ethyl-3-ethynylphenyl | hydroxymethyl | ethyl | |
| 2.5.269 | 2-cyclopropyl-3-ethynylphenyl | hydroxymethyl | ethyl | |
| 2.5.270 | 2-vinyl-3-ethynylphenyl | hydroxymethyl | ethyl | |
| 2.5.271 | 2-cyano-3-ethynylphenyl | hydroxymethyl | ethyl | |
| 2.5.272 | 2-trifluoromethyl-3-ethynylphenyl | hydroxymethyl | ethyl | |
| 2.5.273 | 2-methoxy-3-ethynylphenyl | hydroxymethyl | ethyl | |
| 2.5.274 | 2-ethoxy-3-ethynylphenyl | hydroxymethyl | ethyl | |
| 2.5.275 | 2-trifluoromethoxy-3-ethynylphenyl | hydroxymethyl | ethyl | |
| 2.5.276 | 2-nitro-3-ethynylphenyl | hydroxymethyl | ethyl | |
| 2.5.277 | 2-fluoro-3-ethynylphenyl | hydroxymethyl | ethyl | |
| 2.5.278 | 2-fluoro-3-cyanophenyl | hydroxymethyl | ethyl | |
| 2.5.279 | 2-chloro-3-cyanophenyl | hydroxymethyl | ethyl | |
| 2.5.280 | 2-bromo-3-cyanophenyl | hydroxymethyl | ethyl | |
| 2.5.281 | 2-methyl-3-cyanophenyl | hydroxymethyl | ethyl | |
| 2.5.282 | 2-ethyl-3-cyanophenyl | hydroxymethyl | ethyl | |
| 2.5.283 | 2-ethyl-3-cyanophenyl | 1-hydroxyethyl | ethyl | |
| 2.5.284 | 2-ethyl-3-cyanophenyl | 1-hydroxypropyl | ethyl | |
| 2.5.285 | 2-ethyl-3-cyanophenyl | (1-hydroxy-2-methylpropyl) | ethyl | |
| 2.5.286 | 2-ethyl-3-cyanophenyl | methoxymethyl | ethyl | |
| 2.5.287 | 2-ethyl-3-cyanophenyl | 2-methoxyethyl | ethyl | |
| 2.5.288 | 2-cyclopropyl-3-cyanophenyl | hydroxymethyl | ethyl | |
| 2.5.289 | 2-vinyl-3-cyanophenyl | hydroxymethyl | ethyl | |
| 2.5.290 | 2-ethynyl-3-cyanophenyl | hydroxymethyl | ethyl | |
| 2.5.291 | 2-cyano-3-cyanophenyl | hydroxymethyl | ethyl | |
| 2.5.292 | 2-trifluoromethyl-3-cyanophenyl | hydroxymethyl | ethyl | |
| 2.5.293 | 2-methoxy-3-cyanophenyl | hydroxymethyl | ethyl | |
| 2.5.294 | 2-ethoxy-3-cyanophenyl | hydroxymethyl | ethyl | |
| 2.5.295 | 2-trifluoromethoxy-3-cyanophenyl | hydroxymethyl | ethyl | |
| 2.5.296 | 2-nitro-3-cyanophenyl | hydroxymethyl | ethyl | |
| 2.5.297 | 2-fluoro-3-hydroxyphenyl | hydroxymethyl | ethyl | |
| 2.5.298 | 2-chloro-3-hydroxyphenyl | hydroxymethyl | ethyl | |
| 2.5.299 | 2-bromo-3-hydroxyphenyl | hydroxymethyl | ethyl | |
| 2.5.300 | 2-methyl-3-hydroxyphenyl | hydroxymethyl | ethyl | |
| 2.5.301 | 2-ethyl-3-hydroxyphenyl | hydroxymethyl | ethyl | |
| 2.5.302 | 2-cyclopropyl-3-hydroxyphenyl | hydroxymethyl | ethyl | |
| 2.5.303 | 2-vinyl-3-hydroxyphenyl | hydroxymethyl | ethyl | |
| 2.5.304 | 2-ethynyl-3-hydroxyphenyl | hydroxymethyl | ethyl | |
| 2.5.305 | 2-cyano-3-hydroxyphenyl | hydroxymethyl | ethyl | |
| 2.5.306 | 2-trifluoromethyl-3-hydroxyphenyl | hydroxymethyl | ethyl | |
| 2.5.307 | 2-methoxy-3-hydroxyphenyl | hydroxymethyl | ethyl | |
| 2.5.308 | 2-ethoxy-3-hydroxyphenyl | hydroxymethyl | ethyl | |
| 2.5.309 | 2-trifluoromethoxy-3-hydroxyphenyl | hydroxymethyl | ethyl | |
| 2.5.310 | 2-nitro-3-hydroxyphenyl | hydroxymethyl | ethyl | |
| 2.5.311 | 2-fluoro-3-methoxyphenyl | hydroxymethyl | ethyl | |
| 2.5.312 | 2-chloro-3-methoxyphenyl | hydroxymethyl | ethyl | |
| 2.5.313 | 2-bromo-3-methoxyphenyl | hydroxymethyl | ethyl | |
| 2.5.314 | 2-methyl-3-methoxyphenyl | hydroxymethyl | ethyl | |
| 2.5.315 | 2-ethyl-3-methoxyphenyl | hydroxymethyl | ethyl | |
| 2.5.316 | 2-cyclopropyl-3-methoxyphenyl | hydroxymethyl | ethyl | |
| 2.5.317 | 2-vinyl-3-methoxyphenyl | hydroxymethyl | ethyl | |
| 2.5.318 | 2-ethynyl-3-methoxyphenyl | hydroxymethyl | ethyl | |
| 2.5.319 | 2-cyano-3-methoxyphenyl | hydroxymethyl | ethyl | |
| 2.5.320 | 2-trifluoromethyl-3-methoxyphenyl | hydroxymethyl | ethyl | |
| 2.5.321 | 2,3-dimethoxyphenyl | hydroxymethyl | ethyl | |

TABLE 2.5-continued

Inventive compounds of the general formula (I) in which W* is COOY, R¹ and R² are each hydrogen, and aryl is the radical.

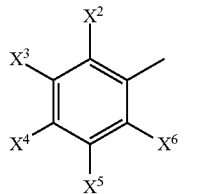

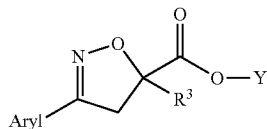

| No. | Aryl | R³ | Y | Physical data |
|---|---|---|---|---|
| 2.5.322 | 2-ethoxy-3-methoxyphenyl | hydroxymethyl | ethyl | |
| 2.5.323 | 2-trifluoromethoxy-3-methoxyphenyl | hydroxymethyl | ethyl | |
| 2.5.324 | 2-nitro-3-methoxyphenyl | hydroxymethyl | ethyl | |
| 2.5.325 | 2-fluoro-3-ethoxyphenyl | hydroxymethyl | ethyl | |
| 2.5.326 | 2-chloro-3-ethoxyphenyl | hydroxymethyl | ethyl | |
| 2.5.327 | 2-bromo-3-ethoxyphenyl | hydroxymethyl | ethyl | |
| 2.5.328 | 2-methyl-3-ethoxyphenyl | hydroxymethyl | ethyl | |
| 2.5.329 | 2-ethyl-3-ethoxyphenyl | hydroxymethyl | ethyl | |
| 2.5.330 | 2-cyclopropyl-3-ethoxyphenyl | hydroxymethyl | ethyl | |
| 2.5.331 | 2-vinyl-3-ethoxyphenyl | hydroxymethyl | ethyl | |
| 2.5.332 | 2-ethynyl-3-ethoxyphenyl | hydroxymethyl | ethyl | |
| 2.5.333 | 2-cyano-3-ethoxyphenyl | hydroxymethyl | ethyl | |
| 2.5.334 | 2-trifluoromethyl-3-ethoxyphenyl | hydroxymethyl | ethyl | |
| 2.5.335 | 2-methoxy-3-ethoxyphenyl | hydroxymethyl | ethyl | |
| 2.5.336 | 2,3-diethoxy--phenyl | hydroxymethyl | ethyl | |
| 2.5.337 | 2-trifluoromethoxy-3-ethoxyphenyl | hydroxymethyl | ethyl | |
| 2.5.338 | 2-nitro-3-ethoxyphenyl | hydroxymethyl | ethyl | |
| 2.5.339 | 2-fluoro-3-propoxyphenyl | hydroxymethyl | ethyl | |
| 2.5.340 | 2-chloro-3-propoxyphenyl | hydroxymethyl | ethyl | |
| 2.5.341 | 2-bromo-3-propoxyphenyl | hydroxymethyl | ethyl | |
| 2.5.342 | 2-methyl-3-propoxyphenyl | hydroxymethyl | ethyl | |
| 2.5.343 | 2-ethyl-3-propoxyphenyl | hydroxymethyl | ethyl | |
| 2.5.344 | 2-cyclopropyl-3-propoxyphenyl | hydroxymethyl | ethyl | |
| 2.5.345 | 2-vinyl-3-propoxyphenyl | hydroxymethyl | ethyl | |
| 2.5.346 | 2-ethynyl-3-propoxyphenyl | hydroxymethyl | ethyl | |
| 2.5.347 | 2-cyano-3-propoxyphenyl | hydroxymethyl | ethyl | |
| 2.5.348 | 2-trifluoromethyl-3-propoxyphenyl | hydroxymethyl | ethyl | |
| 2.5.349 | 2-methoxy-3-propoxyphenyl | hydroxymethyl | ethyl | |
| 2.5.350 | 2-ethoxy-3-propoxyphenyl | hydroxymethyl | ethyl | |
| 2.5.351 | 2-trifluoromethoxy-3-propoxyphenyl | hydroxymethyl | ethyl | |
| 2.5.352 | 2-nitro-3-propoxyphenyl | hydroxymethyl | ethyl | |
| 2.5.353 | 2-fluoro-3-isopropoxyphenyl | hydroxymethyl | ethyl | |
| 2.5.354 | 2-chloro-3-isopropoxyphenyl | hydroxymethyl | ethyl | |
| 2.5.355 | 2-bromo-3-isopropoxyphenyl | hydroxymethyl | ethyl | |
| 2.5.356 | 2-methyl-3-isopropoxyphenyl | hydroxymethyl | ethyl | |
| 2.5.357 | 2-ethyl-3-isopropoxyphenyl | hydroxymethyl | ethyl | |
| 2.5.358 | 2-cyclopropyl-3-isopropoxyphenyl | hydroxymethyl | ethyl | |
| 2.5.359 | 2-vinyl-3-isopropoxyphenyl | hydroxymethyl | ethyl | |
| 2.5.360 | 2-ethynyl-3-isopropoxyphenyl | hydroxymethyl | ethyl | |
| 2.5.361 | 2-cyano-3-isopropoxyphenyl | hydroxymethyl | ethyl | |
| 2.5.362 | 2-trifluoromethyl-3-isopropoxyphenyl | hydroxymethyl | ethyl | |
| 2.5.363 | 2-methoxy-3-isopropoxyphenyl | hydroxymethyl | ethyl | |
| 2.5.364 | 2-ethoxy-3-isopropoxyphenyl | hydroxymethyl | ethyl | |
| 2.5.365 | 2-trifluoromethoxy-3-isopropoxyphenyl | hydroxymethyl | ethyl | |
| 2.5.366 | 2-nitro-3-isopropoxyphenyl | hydroxymethyl | ethyl | |
| 2.5.367 | 2-fluoro-3-tert-butoxyphenyl | hydroxymethyl | ethyl | |
| 2.5.368 | 2-chloro-3-tert-butoxyphenyl | hydroxymethyl | ethyl | |
| 2.5.369 | 2-bromo-3-tert-butoxyphenyl | hydroxymethyl | ethyl | |
| 2.5.370 | 2-methyl-3-tert-butoxyphenyl | hydroxymethyl | ethyl | |
| 2.5.371 | 2-ethyl-3-tert-butoxyphenyl | hydroxymethyl | ethyl | |
| 2.5.372 | 2-cyclopropyl-3-tert-butoxyphenyl | hydroxymethyl | ethyl | |
| 2.5.373 | 2-vinyl-3-tert-butoxyphenyl | hydroxymethyl | ethyl | |
| 2.5.374 | 2-ethynyl-3-tert-butoxyphenyl | hydroxymethyl | ethyl | |
| 2.5.375 | 2-cyano-3-tert-butoxyphenyl | hydroxymethyl | ethyl | |
| 2.5.376 | 2-trifluoromethyl-3-tert-butoxyphenyl | hydroxymethyl | ethyl | |
| 2.5.377 | 2-methoxy-3-tert-butoxyphenyl | hydroxymethyl | ethyl | |
| 2.5.378 | 2-ethoxy-3-tert-butoxyphenyl | hydroxymethyl | ethyl | |
| 2.5.379 | 2-trifluoromethoxy-3-tert-butoxyphenyl | hydroxymethyl | ethyl | |

TABLE 2.5-continued

Inventive compounds of the general formula (I) in which W* is COOY, R¹ and R² are each hydrogen, and aryl is the radical.

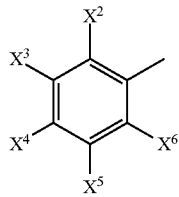

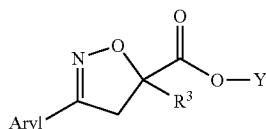

| No. | Aryl | R³ | Y | Physical data |
|---|---|---|---|---|
| 2.5.380 | 2-nitro-3-tert-butoxyphenyl | hydroxymethyl | ethyl | |
| 2.5.381 | 2-fluoro-3-trifluoromethoxy-phenyl | hydroxymethyl | ethyl | |
| 2.5.382 | 2-chloro-3-trifluoromethoxy-phenyl | hydroxymethyl | ethyl | |
| 2.5.383 | 2-bromo-3-trifluoromethoxy-phenyl | hydroxymethyl | ethyl | |
| 2.5.384 | 2-methyl-3-trifluoromethoxy-phenyl | hydroxymethyl | ethyl | |
| 2.5.385 | 2-ethyl-3-trifluoromethoxy-phenyl | hydroxymethyl | ethyl | |
| 2.5.386 | 2-cyclopropyl-3-trifluoromethoxyphenyl | hydroxymethyl | ethyl | |
| 2.5.387 | 2-vinyl-3-trifluoromethoxyphenyl | hydroxymethyl | ethyl | |
| 2.5.388 | 2-ethynyl-3-trifluoromethoxy-phenyl | hydroxymethyl | ethyl | |
| 2.5.389 | 2-cyano-3-trifluoromethoxy-phenyl | hydroxymethyl | ethyl | |
| 2.5.390 | 2-trifluoromethyl-3-trifluoromethoxyphenyl | hydroxymethyl | ethyl | |
| 2.5.391 | 2-methoxy-3-trifluoromethoxy-phenyl | hydroxymethyl | ethyl | |
| 2.5.392 | 2-ethoxy-3-trifluoromethoxy-phenyl | hydroxymethyl | ethyl | |
| 2.5.393 | 2,3-bis(trifluoromethoxy)phenyl | hydroxymethyl | ethyl | |
| 2.5.394 | 2-nitro-3-trifluoromethoxyphenyl | hydroxymethyl | ethyl | |
| 2.5.395 | 2-fluoro-3-(2,2,2-trifluoroethoxy)-phenyl | hydroxymethyl | ethyl | |
| 2.5.396 | 2-chloro-3-(2,2,2-trifluoroethoxy)phenyl | hydroxymethyl | ethyl | |
| 2.5.397 | 2-bromo-3-(2,2,2-trifluoroethoxy)phenyl | hydroxymethyl | ethyl | |
| 2.5.398 | 2-methyl-3-(2,2,2-trifluoroethoxy)phenyl | hydroxymethyl | ethyl | |
| 2.5.399 | 2-ethyl-3-(2,2,2-trifluoroethoxy)-phenyl | hydroxymethyl | ethyl | |
| 2.5.400 | 2-cyclopropyl-3-(2,2,2-trifluoro-ethoxy)phenyl | hydroxymethyl | ethyl | |
| 2.5.401 | 2-vinyl-3-(2,2,2-trifluoroethoxy)-phenyl | hydroxymethyl | ethyl | |
| 2.5.402 | 2-ethynyl-3-(2,2,2-trifluoroethoxyphenyl | hydroxymethyl | ethyl | |
| 2.5.403 | 2-cyano-3-(2,2,2-trifluoroethoxy)phenyl | hydroxymethyl | ethyl | |
| 2.5.404 | 2-trifluoromethyl-3-(2,2,2-trifluoro-ethoxy)phenyl | hydroxymethyl | ethyl | |
| 2.5.405 | 2-methoxy-3-(2,2,2-trifluoroethoxy)phenyl | hydroxymethyl | ethyl | |
| 2.5.406 | 2-ethoxy-3-(2,2,2-trifluoroethoxy)phenyl | hydroxymethyl | ethyl | |
| 2.5.407 | 2-trifluoromethoxy-3-(2,2,2-trifluoro-ethoxy)phenyl | hydroxymethyl | ethyl | |
| 2.5.408 | 2-nitro-3-(2,2,2-trifluoroethoxy)-phenyl | hydroxymethyl | ethyl | |
| 2.5.409 | 2-fluoro-3-difluoromethoxy-phenyl | hydroxymethyl | ethyl | |
| 2.5.410 | 2-chloro-3-difluoromethoxy-phenyl | hydroxymethyl | ethyl | |
| 2.5.411 | 2-bromo-3-difluoromethoxy-phenyl | hydroxymethyl | ethyl | |
| 2.5.412 | 2-methyl-3-difluoromethoxy-phenyl | hydroxymethyl | ethyl | |
| 2.5.413 | 2-ethyl-3-difluoromethoxy-phenyl | hydroxymethyl | ethyl | |
| 2.5.414 | 2-cyclopropyl-3-difluoromethoxy-phenyl | hydroxymethyl | ethyl | |
| 2.5.415 | 2-vinyl-3-difluoromethoxyphenyl | hydroxymethyl | ethyl | |
| 2.5.416 | 2-ethynyl-3-difluoromethoxy-phenyl | hydroxymethyl | ethyl | |
| 2.5.417 | 2-cyano-3-difluoro-methoxyphenyl | hydroxymethyl | ethyl | |
| 2.5.418 | 2-trifluoromethyl-3-difluoromethoxyphenyl | hydroxymethyl | ethyl | |
| 2.5.419 | 2-methoxy-3-difluoro-methoxyphenyl | hydroxymethyl | ethyl | |
| 2.5.420 | 2-ethoxy-3-difluoromethoxyphenyl | hydroxymethyl | ethyl | |
| 2.5.421 | 2-trifluoromethoxy-3-difluoromethoxyphenyl | hydroxymethyl | ethyl | |
| 2.5.422 | 2-nitro-3-difluoromethoxyphenyl | hydroxymethyl | ethyl | |
| 2.5.423 | 2-fluoro-3-(2-methoxyethoxy)-phenyl | hydroxymethyl | ethyl | |
| 2.5.424 | 2-chloro-3-(2-methoxyethoxy)-phenyl | hydroxymethyl | ethyl | |
| 2.5.425 | 2-bromo-3-(2-methoxyethoxy)-phenyl | hydroxymethyl | ethyl | |
| 2.5.426 | 2-methyl-3-(2-methoxyethoxy)-phenyl | hydroxymethyl | ethyl | |
| 2.5.427 | 2-ethyl-3-(2-methoxyethoxy)phenyl | hydroxymethyl | ethyl | |
| 2.5.428 | 2-cyclopropyl-3-(2-methoxyethoxy)phenyl | hydroxymethyl | ethyl | |
| 2.5.429 | 2-vinyl-3-(2-methoxyethoxy)phenyl | hydroxymethyl | ethyl | |

TABLE 2.5-continued

Inventive compounds of the general formula (I) in which W* is COOY, R¹ and R² are each hydrogen, and aryl is the radical.

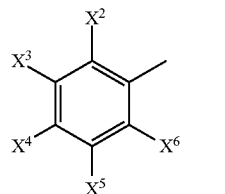

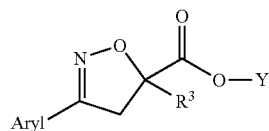

| No. | Aryl | R³ | Y | Physical data |
|---|---|---|---|---|
| 2.5.430 | 2-ethynyl-3-(2-methoxyethoxy)-phenyl | hydroxymethyl | ethyl | |
| 2.5.431 | 2-cyano-3-(2-methoxyethoxy)-phenyl | hydroxymethyl | ethyl | |
| 2.5.432 | 2-trifluoromethyl-3-(2-methoxyethoxy)phenyl | hydroxymethyl | ethyl | |
| 2.5.433 | 2-methoxy-3-(2-methoxyethoxy)-phenyl | hydroxymethyl | ethyl | |
| 2.5.434 | 2-ethoxy-3-(2-methoxyethoxy)-phenyl | hydroxymethyl | ethyl | |
| 2.5.435 | 2-trifluoromethoxy-(2-methoxyethoxy)phenyl | hydroxymethyl | ethyl | |
| 2.5.436 | 2-nitro-3-(2-methoxyethoxy)phenyl | hydroxymethyl | ethyl | |
| 2.5.437 | 2-fluoro-3-(tert-butoxycarbonyloxy)phenyl | hydroxymethyl | ethyl | |
| 2.5.438 | 2-chloro-3-(tert-butoxycarbonyloxy)phenyl | hydroxymethyl | ethyl | |
| 2.5.439 | 2-bromo-3-(tert-butoxycarbonyl-oxy)phenyl | hydroxymethyl | ethyl | |
| 2.5.440 | 2-methyl-3-(tert-butoxycarbonyl-oxy)phenyl | hydroxymethyl | ethyl | |
| 2.5.441 | 2-ethyl-3-(tert-butoxycarbonyloxy)phenyl | hydroxymethyl | ethyl | |
| 2.5.442 | 2-cyclopropyl-3-(tert-butoxycarbonyl-oxy)phenyl | hydroxymethyl | ethyl | |
| 2.5.443 | 2-vinyl-3-(tert-butoxycarbonyloxy)phenyl | hydroxymethyl | ethyl | |
| 2.5.444 | 2-ethynyl-3-(tert-butoxycarbonyl-oxy)phenyl | hydroxymethyl | ethyl | |
| 2.5.445 | 2-cyano-3-(tert-butoxycarbonyloxy)phenyl | hydroxymethyl | ethyl | |
| 2.5.446 | 2-trifluoromethyl-3-(tert-butoxycarbonyl-oxy)phenyl | hydroxymethyl | ethyl | |
| 2.5.447 | 2-methoxy-3-(tert-butoxycarbonyloxy)phenyl | hydroxymethyl | ethyl | |
| 2.5.448 | 2-ethoxy-3-(tert-butoxycarbonyloxy)phenyl | hydroxymethyl | ethyl | |
| 2.5.449 | 2-trifluoromethoxy-3-(tert-butoxycarbonyl-oxy)phenyl | hydroxymethyl | ethyl | |
| 2.5.450 | 2-nitro-3-(tert-butoxycarbonyloxy)phenyl | hydroxymethyl | ethyl | |
| 2.5.451 | 2-fluoro-3-nitrophenyl | hydroxymethyl | ethyl | |
| 2.5.452 | 2-chloro-3-nitrophenyl | hydroxymethyl | ethyl | |
| 2.5.453 | 2-bromo-3-nitrophenyl | hydroxymethyl | ethyl | |
| 2.5.454 | 2-methyl-3-nitrophenyl | hydroxymethyl | ethyl | |
| 2.5.455 | 2-ethyl-3-nitrophenyl | hydroxymethyl | ethyl | |
| 2.5.456 | 2-cyclopropyl-3-nitrophenyl | hydroxymethyl | ethyl | |
| 2.5.457 | 2-vinyl-3-nitrophenyl | hydroxymethyl | ethyl | |
| 2.5.458 | 2-ethynyl-3-nitrophenyl | hydroxymethyl | ethyl | |
| 2.5.459 | 2-cyano-3-nitrophenyl | hydroxymethyl | ethyl | |
| 2.5.460 | 2-trifluoromethyl-3-nitrophenyl | hydroxymethyl | ethyl | |
| 2.5.461 | 2-methoxy-3-nitrophenyl | hydroxymethyl | ethyl | |
| 2.5.462 | 2-ethoxy-3-nitrophenyl | hydroxymethyl | ethyl | |
| 2.5.463 | 2-trifluoromethoxy-3-nitrophenyl | hydroxymethyl | ethyl | |
| 2.5.464 | 2-fluoro-3-methylsulfanylphenyl | hydroxymethyl | ethyl | |
| 2.5.465 | 2-chloro-3-methylsulfanylphenyl | hydroxymethyl | ethyl | |
| 2.5.466 | 2-bromo-3-methylsulfanylphenyl | hydroxymethyl | ethyl | |
| 2.5.467 | 2-methyl-3-methylsulfanylphenyl | hydroxymethyl | ethyl | |
| 2.5.468 | 2-ethyl-3-methylsulfanylphenyl | hydroxymethyl | ethyl | |
| 2.5.469 | 2-cyclopropyl-3-methylsulfanylphenyl | hydroxymethyl | ethyl | |
| 2.5.470 | 2-vinyl-3-methylsulfanylphenyl | hydroxymethyl | ethyl | |
| 2.5.471 | 2-ethynyl-3-methylsulfanylphenyl | hydroxymethyl | ethyl | |

TABLE 2.5-continued

Inventive compounds of the general formula (I) in which W* is COOY,
R¹ and R² are each hydrogen, and aryl is the radical.

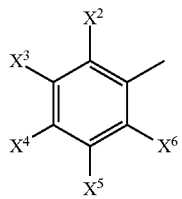

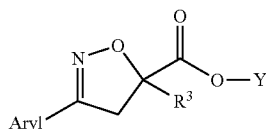

| No. | Aryl | $R^3$ | Y | Physical data |
|---|---|---|---|---|
| 2.5.472 | 2-cyano-3-methylsulfanylphenyl | hydroxymethyl | ethyl | |
| 2.5.473 | 2-trifluoromethyl-3-methylsulfanylphenyl | hydroxymethyl | ethyl | |
| 2.5.474 | 2-methoxy-3-methylsulfanylphenyl | hydroxymethyl | ethyl | |
| 2.5.475 | 2-ethoxy-3-methylsulfanylphenyl | hydroxymethyl | ethyl | |
| 2.5.476 | 2-trifluoromethoxy-3-methylsulfanylphenyl | hydroxymethyl | ethyl | |
| 2.5.477 | 2-nitro-3-methylsulfanylphenyl | hydroxymethyl | ethyl | |
| 2.5.478 | 3,5-difluorophenyl | hydroxymethyl | ethyl | [CDCl3] 1.32 (t, 3H); 2.23 (m, 1H); 3.56-3.69 (m, 2H); 3.90 (m, 1H); 4.02 (m, 1H); 4.29 (m, 2H); 6.88 (m, 1H); 7.19 (m, 2H). |
| 2.5.479 | 3,5-difluorophenyl | 1-hydroxyethyl | methyl | [CDCl3] D1 1.06 (t, 3H); 1.30-1.49 (m, 2H); 2.27 (d, 1H); 3.52 (d, 1H); 3.73 (d, 1H); 3.83 (s, 3H); 4.05 (m, 1H); 6.88 (t, 1H); 7.20 (d, 2H). [CDCl3] D2 1.06 (t, 3H); 1.55 (m, 2H); 1.97 (d, 1H); 3.58 (d, 1H); 3.70 (d, 1H); 3.83 (s, 3H); 3.94 (t, 1H); 6.88 (t, 1H); 7.18 (d, 2H). |
| 2.5.480 | 3,5-difluorophenyl | 1-hydroxypropyl | ethyl | |
| 2.5.481 | 3,5-difluorophenyl | (1-hydroxy-2-methylpropyl) | ethyl | |
| 2.5.482 | 3,5-difluorophenyl | methoxymethyl | ethyl | [CDCl3] 1.33 (t, 3H); 3.44 (s, 3H); 3.47-3.51 (d, 1H); 3.72-3.83 (m, 3H); 4.29 (m, 2H): 6.88 (m, 1H); 7.20 (m, 2H). |
| 2.5.483 | 2-ethyl-3-cyanophenyl | 2-methoxyethyl | ethyl | |
| 2.5.484 | 3-chloro-5-fluorophenyl | hydroxymethyl | ethyl | |
| 2.5.485 | 3-chloro-5-fluorophenyl | 1-hydroxyethyl | methyl | [CDCl3] D1 1.19 (d, 3H); 2.42 (s br, 1H); 3.53 (d, 1H); 3.68 (d, 1H); 3.83 (s, 3H); 4.34 (m, 1H); 7.14 (d, 1H); 7.31 (d, 1H); 7.44 (s, 1H). D2 1.29 (d, 3H); 2.18 (s br, 1H); 3.58 (d, 1H); 3.73 (d, 1H); 3.73 (s, 3H); 4.22 (m, 1H); 7.14 (d, 1H); 7.31 (d, 1H); 7.42 (s, 1H). |
| 2.5.486 | 3-chloro-5-fluorophenyl | 1-hydroxypropyl | ethyl | |
| 2.5.487 | 3-chloro-5-fluorophenyl | (1-hydroxy-2-methylpropyl) | ethyl | |
| 2.5.488 | 3-chloro-5-fluorophenyl | methoxymethyl | ethyl | |
| 2.5.489 | 3-chloro-5-fluorophenyl | 2-methoxyethyl | ethyl | |
| 2.5.490 | 3-bromo-5-fluorophenyl | hydroxymethyl | ethyl | |

TABLE 2.5-continued

Inventive compounds of the general formula (I) in which W* is COOY,
R¹ and R² are each hydrogen, and aryl is the radical.

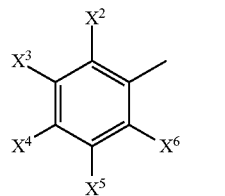

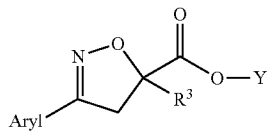

| No. | Aryl | R³ | Y | Physical data |
|---|---|---|---|---|
| 2.5.491 | 3-bromo-5-fluorophenyl | 1-hydroxyethyl | ethyl | |
| 2.5.492 | 3-bromo-5-fluorophenyl | 1-hydroxypropyl | ethyl | |
| 2.5.493 | 3-bromo-5-fluorophenyl | (1-hydroxy-2-methylpropyl) | ethyl | |
| 2.5.494 | 3-bromo-5-fluorophenyl | methoxymethyl | ethyl | |
| 2.5.495 | 3-bromo-5-fluorophenyl | 2-methoxyethyl | ethyl | |
| 2.5.496 | 3-iodo-5-fluorophenyl | hydroxymethyl | ethyl | |
| 2.5.497 | 3-methyl-5-fluorophenyl | hydroxymethyl | ethyl | |
| 2.5.498 | 3-methyl-5-fluorophenyl | 1-hydroxyethyl | methyl | [CDCl3] D1 1.20 (d, 3H); 2.37 (d, 1H); 2.38 (s, 3H); 3.54 (d, 1H), 3.69 (d, 1H); 3.83 (s, 3H); 4.33 (m, 1H); 6.96 (s, 1H); 7.23 (s, 1H); 7.25 (s, 1H). D2 1.26 (d, 3H); 2.18 (d, 1H); 2.38 (s, 3H); 3.60 (d, 1H); 3.72 (d, 1H); 3.83 (s, 3H); 4.22 (m, 1H); 6.93 (s, 1H); 7.21 (s, 1H); 7.25 (s, 1H) |
| 2.5.499 | 3-methyl-5-fluorophenyl | 1-hydroxypropyl | ethyl | |
| 2.5.500 | 3-methyl-5-fluorophenyl | (1-hydroxy-2-methylpropyl) | ethyl | |
| 2.5.501 | 3-methyl-5-fluorophenyl | methoxymethyl | ethyl | |
| 2.5.502 | 3-methyl-5-fluorophenyl | 2-methoxyethyl | ethyl | |
| 2.5.503 | 3-ethyl-5-fluorophenyl | hydroxymethyl | ethyl | |
| 2.5.504 | 3-propyl-5-fluorophenyl | hydroxymethyl | ethyl | |
| 2.5.505 | 3-i-propyl-5-fluorophenyl | hydroxymethyl | ethyl | |
| 2.5.506 | 3-n-butyl-5-fluorophenyl | hydroxymethyl | ethyl | |
| 2.5.507 | 3-isobutyl-5-fluorophenyl | hydroxymethyl | ethyl | |
| 2.5.508 | 3-tert-butyl-5-fluorophenyl | hydroxymethyl | ethyl | |
| 2.5.509 | 3-cyclopropyl-5-fluorophenyl | hydroxymethyl | ethyl | |
| 2.5.510 | 3-vinyl-5-fluorophenyl | hydroxymethyl | ethyl | |
| 2.5.511 | 3-ethynyl-5-fluorophenyl | hydroxymethyl | ethyl | |
| 2.5.512 | 3-cyano-5-fluorophenyl | hydroxymethyl | ethyl | |
| 2.5.513 | 3-trifluoromethyl-5-fluorophenyl | hydroxymethyl | ethyl | |
| 2.5.514 | 3-trifluoromethyl-5-fluorophenyl | 1-hydroxyethyl | ethyl | |
| 2.5.515 | 3-trifluoromethyl-5-fluorophenyl | 1-hydroxypropyl | ethyl | |
| 2.5.516 | 3-trifluoromethyl-5-fluorophenyl | (1-hydroxy-2-methylpropyl) | ethyl | |
| 2.5.517 | 3-trifluoromethyl-5-fluorophenyl | methoxymethyl | ethyl | |
| 2.5.518 | 3-trifluoromethyl-5-fluorophenyl | 2-methoxyethyl | ethyl | |
| 2.5.519 | 3-(methoxycarbonyl)-5-fluorophenyl | hydroxymethyl | ethyl | |
| 2.5.520 | 3-hydroxymethyl-5-fluorophenyl | hydroxymethyl | ethyl | |
| 2.5.521 | 3-carbamoyl-5-fluorophenyl | hydroxymethyl | ethyl | |
| 2.5.522 | 3-hydroxy-5-fluorophenyl | hydroxymethyl | ethyl | |
| 2.5.523 | 3-methoxy-5-fluorophenyl | hydroxymethyl | ethyl | |
| 2.5.524 | 3-ethoxy-5-fluorophenyl | hydroxymethyl | ethyl | |
| 2.5.525 | 3-n-propoxy-5-fluorophenyl | hydroxymethyl | ethyl | |
| 2.5.526 | 3-isopropoxy-5-fluorophenyl | hydroxymethyl | ethyl | |
| 2.5.527 | 3-n-butoxy-5-fluorophenyl | hydroxymethyl | ethyl | |
| 2.5.528 | 3-isobutoxy-5-fluorophenyl | hydroxymethyl | ethyl | |
| 2.5.529 | 3-tert-butoxy-5-fluorophenyl | hydroxymethyl | ethyl | |
| 2.5.530 | 3-difluoromethoxy-5-fluorophenyl | hydroxymethyl | ethyl | |
| 2.5.531 | 3-trifluoromethoxy-5-fluorophenyl | hydroxymethyl | ethyl | |
| 2.5.532 | 3-(2,2,2-trifluoroethoxy)-5-fluorophenyl | hydroxymethyl | ethyl | |

TABLE 2.5-continued

Inventive compounds of the general formula (I) in which W* is COOY,
R¹ and R² are each hydrogen, and aryl is the radical.

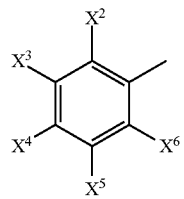

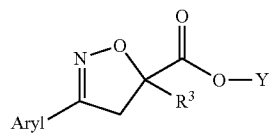

| No. | Aryl | R³ | Y | Physical data |
|---|---|---|---|---|
| 2.5.533 | 3-(2-chloroethoxy)-5-fluorophenyl | hydroxymethyl | ethyl | |
| 2.5.534 | 3-(2-hydroxyethoxy)-5-fluorophenyl | hydroxymethyl | ethyl | |
| 2.5.535 | 3-[(tert-butoxycarbonyl)oxy]-5-fluorophenyl | hydroxymethyl | ethyl | |
| 2.5.536 | 3-nitro-5-fluorophenyl | hydroxymethyl | ethyl | |
| 2.5.537 | 3-acetoxy-5-fluorophenyl | hydroxymethyl | ethyl | |
| 2.5.538 | {3-[(tert-butoxycarbonyl)amino]-5-fluorophenyl} | hydroxymethyl | ethyl | |
| 2.5.539 | 3-methylsulfanyl-5-fluorophenyl | hydroxymethyl | ethyl | |
| 2.5.540 | 3,5-dichlorophenyl | hydroxymethyl | ethyl | [CDCl3] 1.31 (t, 3H); 2.05 (m, 1H, OH) 3.65 (q, 2H); 3.90 (m, 1H); 4.01 (m, 1H): 4.29 (q, 2H); 7.40 (s, 1H): 7.55 (s, 2H). |
| 2.5.541 | 3,5-dichlorophenyl | 1-hydroxyethyl | methyl | [CDCl3] D1 1.08 (t, 3H); 1.36-1.51 (m, 2H); 2.27 (s, 1H); 3.53 (d, 1H); 3.73 (d, 1H); 3.84 (s, 3H); 4.06 (m, 1H); 7.42 (s, 1H) 7.55 (s, 2H). D2 1.08 (t, 3H); 1.36-1.51 (m, 2H); 1.96 (s, 1H); 3.53 (d, 1H); 3.73 (d, 1H); 3.84 (s, 3H); 3.95 (m, 1H); 7.42 (s, 1H) 7.55 (s, 2H). |
| 2.5.542 | 3,5-dichlorophenyl | 1-hydroxypropyl | ethyl | |
| 2.5.543 | 3,5-dichlorophenyl | (1-hydroxy-2-methylpropyl) | ethyl | |
| 2.5.544 | 3,5-dichlorophenyl | methoxymethyl | methyl | [CDCl3] 3.43 (s, 3H); 3.50 (d, 1H); 3.72 (d, 1H); 3.80 (mc, 2H); 3.82 (s, 3H); 7.41 (m, 1H); 7.55 (s, 2H). |
| 2.5.545 | 3,5-dichlorophenyl | 2-methoxyethyl | methyl | [CDCl3] 1.55 (s, 3H); 2.30 (m, 2H), 3.22 (s, 3H); 3.42 (d, 1H); 3.55 (m, 2H); 3.75 (d, 1H); 3.82 (s, 3H), 7.40 (s, 1H); 7.55 (s, 2H). |
| 2.5.546 | 3-bromo-5-chlorophenyl | 1-hydroxyethyl | methyl | [CDCl3] D1 1.19 (d, 3H); 2.35 (d br, 1H); 3.53 (d, 1H); 3.73 (d, 1H); 3.83 (s, 3H); 4.30-4.37 (m, 1H); 7.56-7.61 (m, 2H); 7.68-7.72 (m, 1H). D2 1.28 (d, 3H); 2.10 (d br, 1H); 3.58 (d, 1H); 3.68 (d, 1H); 3.83 (s, 3H); |
| 2.5.547 | 3-iodo-5-chlorophenyl | hydroxymethyl | ethyl | |
| 2.5.548 | 3-methyl-5-chlorophenyl | hydroxymethyl | ethyl | |
| 2.5.549 | 3-methyl-5-chlorophenyl | 1-hydroxyethyl | methyl | [CDCl3] D1 1.20 (d, 3H); 2.33 (d, 1H); 2.36 (s, 3H); 3.54 |

TABLE 2.5-continued

Inventive compounds of the general formula (I) in which W* is COOY, $R^1$ and $R^2$ are each hydrogen, and aryl is the radical.

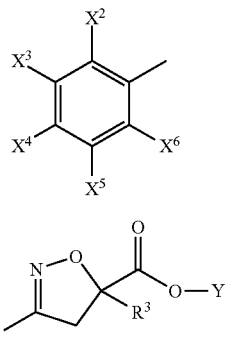

| No. | Aryl | $R^3$ | Y | Physical data |
|---|---|---|---|---|
| | | | | (d, 1H); 3.69 (d, 1H); 3.83 (s, 3H); 4.33 (m, 1H); 7.23 (s, 1H); 7.38 (s, 1H); 7.46 (s, 1H). D2 1.29 (d, 3H) 2.14 (d, 1H); 2.36 (s, 3H); 3.59 (d, 1H); 3.74 (d, 1H); 3.83 (s, 3H); 4.23 (m, 1H); 7.23 (s, 1H); 7.37 (s, 1H); 7.44 (s, 1H). |
| 2.5.550 | 3-ethyl-5-chlorophenyl | 1-hydroxyethyl | methyl | One unassigned diastereomer [CDCl$_3$] 1.24 (t, 3H); 1.28 (d, 3H); 2.14 (d, 1H); 2.65 (q, 2H); 3.64 (AB, 2H); 4.20-4.28 (m,1H); 7.24 (s, 1H); 7.40 (s, 1H); 7.45 (1H). |
| 2.5.551 | 3-ethyl-5-chlorophenyl | 1-hydroxyethyl | methyl | One unassigned diastereomer [CDCl$_3$] 1.20 (d, 3H); 1.25 (t, 3H); 2.33 (d, 1H); 2.65 (q, 2H); 3.55 (d, 1H); 3.74 (d, 1H); 3.83 (s, 3H); 4.30-4.36 (m, 1H); 7.24 (s, 1H); 7.41 (s, 1H); 7.47 (s,1H) |
| 2.5.552 | 3-ethyl-5-chlorophenyl | 1-hydroxyethyl | ethyl | [CDCl3] D1 1.20 (d, 3H); 1.25 (t, 3H); 2.33 (d, 1H); 2.65 (q, 2H); 3.55 (d, 1H); 3.74 (d, 1H); 3.83 (s, 3H); 4.30-4.36 (m, 1H); 7.24 (s, 1H); 7.41 (s, 1H); 7.47 (s, 1H). D2 1.24 (t, 3H); 1.28 (d, 3H); 2.14 (d, 1H); 2.65 (q, 2H); 3.64 (AB, 2H); 4.20-4.28 (m, 1H); 7.24 (s, 1H); 7.40 s, 1H); 7.45 (1H). |
| 2.5.553 | 3-n-butyl-5-chlorophenyl | hydroxymethyl | ethyl | |
| 2.5.554 | 3-isobutyl-5-chlorophenyl | hydroxymethyl | ethyl | |
| 2.5.555 | 3-tert-butyl-5-chlorophenyl | hydroxymethyl | ethyl | |
| 2.5.556 | 3-cyclopropyl-5-chlorophenyl | hydroxymethyl | ethyl | |
| 2.5.557 | 3-vinyl-5-chlorophenyl | hydroxymethyl | ethyl | |
| 2.5.558 | 3-ethynyl-5-chlorophenyl | hydroxymethyl | ethyl | |
| 2.5.559 | 3-cyano-5-chlorophenyl | hydroxymethyl | ethyl | |
| 2.5.560 | 3-trifluoromethyl-5-chlorophenyl | hydroxymethyl | ethyl | |
| 2.5.561 | 3-(hydroxycarbonyl)-5-chlorophenyl | hydroxymethyl | ethyl | |
| 2.5.562 | 3-(methoxycarbonyl)-5-chlorophenyl | hydroxymethyl | ethyl | |
| 2.5.563 | 3-hydroxymethyl-5-chlorophenyl | hydroxymethyl | ethyl | |
| 2.5.564 | 3-carbamoyl-5-chlorophenyl | hydroxymethyl | ethyl | |
| 2.5.565 | 3-hydroxy-5-chlorophenyl | hydroxymethyl | ethyl | |

TABLE 2.5-continued

Inventive compounds of the general formula (I) in which W* is COOY, R¹ and R² are each hydrogen, and aryl is the radical.

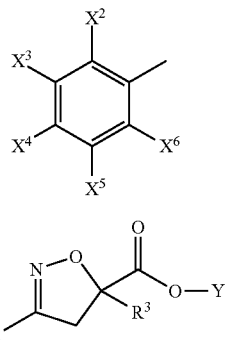

| No. | Aryl | R³ | Y | Physical data |
|---|---|---|---|---|
| 2.5.566 | 3-methoxy-5-chlorophenyl | hydroxymethyl | ethyl | |
| 2.5.567 | 3-ethoxy-5-chlorophenyl | hydroxymethyl | ethyl | |
| 2.5.568 | 3-n-propoxy-5-chlorophenyl | hydroxymethyl | ethyl | |
| 2.5.569 | 3-isopropoxy-5-chlorophenyl | hydroxymethyl | ethyl | |
| 2.5.570 | 3-n-butoxy-5-chlorophenyl | hydroxymethyl | ethyl | |
| 2.5.571 | 3-isobutoxy-5-chlorophenyl | hydroxymethyl | ethyl | |
| 2.5.572 | 3-tert-butoxy-5-chlorophenyl | hydroxymethyl | ethyl | |
| 2.5.573 | 3-difluoromethoxy-5-chlorophenyl | hydroxymethyl | ethyl | |
| 2.5.574 | 3-trifluoromethoxy-5-chlorophenyl | hydroxymethyl | ethyl | |
| 2.5.575 | 3-(2,2,2-trifluoroethoxy)-5-chlorophenyl | hydroxymethyl | ethyl | |
| 2.5.576 | 3-(2-chloroethoxy)-5-chlorophenyl | hydroxymethyl | ethyl | |
| 2.5.577 | 3-(2-hydroxyethoxy)-5-chlorophenyl | hydroxymethyl | ethyl | |
| 2.5.578 | 3-[(tert-butoxycarbonyl)oxy]-5-chlorophenyl | hydroxymethyl | ethyl | |
| 2.5.579 | 3-nitro-5-chlorophenyl | hydroxymethyl | ethyl | |
| 2.5.580 | 3-acetoxy-5-chlorophenyl | hydroxymethyl | ethyl | |
| 2.5.581 | {3-[(tert-butoxycarbonyl)amino]-5-chlorophenyl} | hydroxymethyl | ethyl | |
| 2.5.582 | 3-methylsulfanyl-5-chlorophenyl | hydroxymethyl | ethyl | |
| 2.5.583 | 3,5-dibromophenyl | hydroxymethyl | ethyl | |
| 2.5.584 | 3,5-dibromophenyl | 1-hydroxyethyl | ethyl | |
| 2.5.585 | 3-iodo-5-bromophenyl | hydroxymethyl | ethyl | |
| 2.5.586 | 3-methyl-5-bromophenyl | hydroxymethyl | ethyl | |
| 2.5.587 | 3-methyl-5-bromophenyl | 1-hydroxyethyl | methyl | [CDCl3] D1 1.20 (d, 3H); 1.55 (s br, 1H); 2.36 (s, 3H); 3.53 (d, 1H); 3.68 (d, 1H); 3.83 (s, 3H); 4.32 (m, 1H); 7.38 (s, 1H); 7.43 (s, 1H); 7.62 (s, 1H). D2 1.28 (d, 3H); 2.14 (d, 1H); 2.36 (s, 3H); 3.58 (d, 1H); 3.73 (d, 1H); 3.83 (s, 3H); 4.25 (m, 1H); 7.39 (s, 1H); 7.41 (s, 1H); 7.60 (s, 1H). |
| 2.5.588 | 3-methyl-5-bromophenyl | 1-hydroxypropyl | ethyl | |
| 2.5.589 | 3-methyl-5-bromophenyl | (1-hydroxy-2-methylpropyl) | ethyl | |
| 2.5.590 | 3-methyl-5-bromophenyl | methoxymethyl | ethyl | |
| 2.5.591 | 3-methyl-5-bromophenyl | 2-methoxyethyl | ethyl | |
| 2.5.592 | 3-ethyl-5-bromophenyl | hydroxymethyl | ethyl | |
| 2.5.593 | 3-propyl-5-bromophenyl | hydroxymethyl | ethyl | |
| 2.5.594 | 3-isopropyl-5-bromophenyl | hydroxymethyl | ethyl | |
| 2.5.595 | 3-n-butyl-5-bromophenyl | hydroxymethyl | ethyl | |
| 2.5.596 | 3-isobutyl-5-bromophenyl | hydroxymethyl | ethyl | |
| 2.5.597 | 3-tert-butyl-5-bromophenyl | hydroxymethyl | ethyl | |
| 2.5.598 | 3-cyclopropyl-5-bromophenyl | hydroxymethyl | ethyl | |
| 2.5.599 | 3-vinyl-5-bromophenyl | hydroxymethyl | ethyl | |
| 2.5.600 | 3-ethynyl-5-bromophenyl | hydroxymethyl | ethyl | |
| 2.5.601 | 3-cyano-5-bromophenyl | hydroxymethyl | ethyl | |
| 2.5.602 | 3-trifluoromethyl-5-bromophenyl | hydroxymethyl | ethyl | |
| 2.5.603 | 3-(hydroxycarbonyl)-5-bromophenyl | hydroxymethyl | ethyl | |
| 2.5.604 | 3-(methoxycarbonyl)-5-bromophenyl | hydroxymethyl | ethyl | |
| 2.5.605 | 3-hydroxymethyl-5-bromophenyl | hydroxymethyl | ethyl | |
| 2.5.606 | 3-carbamoyl-5-bromophenyl | hydroxymethyl | ethyl | |
| 2.5.607 | 3-hydroxy-5-bromophenyl | hydroxymethyl | ethyl | |

TABLE 2.5-continued

Inventive compounds of the general formula (I) in which W* is COOY,
R¹ and R² are each hydrogen, and aryl is the radical.

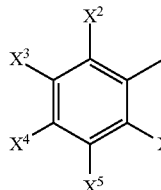

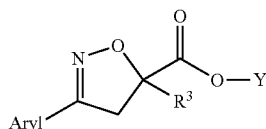

| No. | Aryl | R³ | Y | Physical data |
|---|---|---|---|---|
| 2.5.608 | 3-methoxy-5-bromophenyl | hydroxymethyl | ethyl | |
| 2.5.609 | 3-ethoxy-5-bromophenyl | hydroxymethyl | ethyl | |
| 2.5.610 | 3-n-propoxy-5-bromophenyl | hydroxymethyl | ethyl | |
| 2.5.611 | 3-isopropoxy-5-bromophenyl | hydroxymethyl | ethyl | |
| 2.5.612 | 3-n-butoxy-5-bromophenyl | hydroxymethyl | ethyl | |
| 2.5.613 | 3-isobutoxy-5-bromophenyl | hydroxymethyl | ethyl | |
| 2.5.614 | 3-tert-butoxy-5-bromophenyl | hydroxymethyl | ethyl | |
| 2.5.615 | 3-difluoromethoxy-5-bromophenyl | hydroxymethyl | ethyl | |
| 2.5.616 | 3-trifluoromethoxy-5-bromophenyl | hydroxymethyl | ethyl | |
| 2.5.617 | 3-(2,2,2-trifluoroethoxy)-5-bromophenyl | hydroxymethyl | ethyl | |
| 2.5.618 | 3-(2-chloroethoxy)-5-bromophenyl | hydroxymethyl | ethyl | |
| 2.5.619 | 3-(2-hydroxyethoxy)-5-bromophenyl | hydroxymethyl | ethyl | |
| 2.5.620 | 3-[(tert-butoxycarbonyl)oxy]-5-bromophenyl | hydroxymethyl | ethyl | |
| 2.5.621 | 3-nitro-5-bromophenyl | hydroxymethyl | ethyl | |
| 2.5.622 | 3-acetoxy-5-bromophenyl | hydroxymethyl | ethyl | |
| 2.5.623 | {3-[(tert-butoxy-carbonyl)amino]-5-bromophenyl} | hydroxymethyl | ethyl | |
| 2.5.624 | 3-methylsulfanyl-5-bromophenyl | hydroxymethyl | ethyl | |
| 2.5.625 | 3,5-diiodophenyl | hydroxymethyl | ethyl | |
| 2.5.626 | 3-methyl-5-iodophenyl | hydroxymethyl | ethyl | |
| 2.5.627 | 3-ethyl-5-iodophenyl | hydroxymethyl | ethyl | |
| 2.5.628 | 3-propyl-5-iodophenyl | hydroxymethyl | ethyl | |
| 2.5.629 | 3-isopropyl-5-iodophenyl | hydroxymethyl | ethyl | |
| 2.5.630 | 3-n-butyl-5-iodophenyl | hydroxymethyl | ethyl | |
| 2.5.631 | 3-isobutyl-5-iodophenyl | hydroxymethyl | ethyl | |
| 2.5.632 | 3-tert-butyl-5-iodophenyl | hydroxymethyl | ethyl | |
| 2.5.633 | 3-cyclopropyl-5-iodophenyl | hydroxymethyl | ethyl | |
| 2.5.634 | 3-vinyl-5-iodophenyl | hydroxymethyl | ethyl | |
| 2.5.635 | 3-ethynyl-5-iodophenyl | hydroxymethyl | ethyl | |
| 2.5.636 | 3-cyano-5-iodophenyl | hydroxymethyl | ethyl | |
| 2.5.637 | 3-trifluoromethyl-5-iodophenyl | hydroxymethyl | ethyl | |
| 2.5.638 | 3-(hydroxycarbonyl)-5-iodophenyl | hydroxymethyl | ethyl | |
| 2.5.639 | 3-(methoxycarbonyl)-5-iodophenyl | hydroxymethyl | ethyl | |
| 2.5.640 | 3-hydroxymethyl-5-iodophenyl | hydroxymethyl | ethyl | |
| 2.5.641 | 3-carbamoyl-5-iodophenyl | hydroxymethyl | ethyl | |
| 2.5.642 | 3-hydroxy-5-iodophenyl | hydroxymethyl | ethyl | |
| 2.5.643 | 3-methoxy-5-iodophenyl | hydroxymethyl | ethyl | |
| 2.5.644 | 3-ethoxy-5-iodophenyl | hydroxymethyl | ethyl | |
| 2.5.645 | 3-n-propoxy-5-iodophenyl | hydroxymethyl | ethyl | |
| 2.5.646 | 3-isopropoxy-5-iodophenyl | hydroxymethyl | ethyl | |
| 2.5.647 | 3-n-butoxy-5-iodophenyl | hydroxymethyl | ethyl | |
| 2.5.648 | 3-isobutoxy-5-iodophenyl | hydroxymethyl | ethyl | |
| 2.5.649 | 3-tert-butoxy-5-iodophenyl | hydroxymethyl | ethyl | |
| 2.5.650 | 3-difluoromethoxy-5-iodophenyl | hydroxymethyl | ethyl | |
| 2.5.651 | 3-trifluoromethoxy-5-iodophenyl | hydroxymethyl | ethyl | |
| 2.5.652 | 3-(2,2,2-trifluoroethoxy)-5-iodophenyl | hydroxymethyl | ethyl | |
| 2.5.653 | 3-(2-chloroethoxy)-5-iodophenyl | hydroxymethyl | ethyl | |
| 2.5.654 | 3-(2-hydroxyethoxy)-5-iodophenyl | hydroxymethyl | ethyl | |
| 2.5.655 | 3-[(tert-butoxycarbonyl)oxy]-5-iodophenyl | hydroxymethyl | ethyl | |
| 2.5.656 | 3-nitro-5-iodophenyl | hydroxymethyl | ethyl | |
| 2.5.657 | 3-acetoxy-5-iodophenyl | hydroxymethyl | ethyl | |
| 2.5.658 | {3-[(tert-butoxycarbonyl)amino]-5-iodophenyl} | hydroxymethyl | ethyl | |
| 2.5.659 | 3-methylsulfanyl-5-iodophenyl | hydroxymethyl | ethyl | |
| 2.5.660 | 3,5-dimethylphenyl | hydroxymethyl | ethyl | |

TABLE 2.5-continued

Inventive compounds of the general formula (I) in which W* is COOY,
R¹ and R² are each hydrogen, and aryl is the radical.

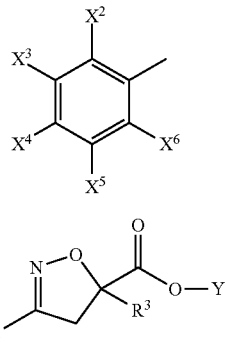

| No. | Aryl | R³ | Y | Physical data |
|---|---|---|---|---|
| 2.5.661 | 3,5-dimethylphenyl | 1-hydroxyethyl | methyl | [CDCl3] D1 1.29 (d, 3H), 2.19 (d, 1H); 2.35 (s, 6H); 3.56 (d, 1H); 3.75 (d, 1H); 3.82 (s, 3H); 4.31 (m, 1H); 7.07 (s, 1H); 7.29 (s, 2H). D2 1.20 (d, 3H); 1.40 (d, 1H); 2.35 (s, 6H); 3.62 (d, 1H); 3.78 (d, 1H); 3.83 (s, 3H); 4.22 (m, 1H); 7.07 (s, 1H); 7.29 (s, 2H). |
| 2.5.662 | 3-ethyl-5-methylphenyl | hydroxymethyl | ethyl | |
| 2.5.663 | 3-propyl-5-methylphenyl | hydroxymethyl | ethyl | |
| 2.5.664 | 3-isopropyl-5-methylphenyl | hydroxymethyl | ethyl | |
| 2.5.665 | 3-n-butyl-5-methylphenyl | hydroxymethyl | ethyl | |
| 2.5.666 | 3-isobutyl-5-methylphenyl | hydroxymethyl | ethyl | |
| 2.5.667 | 3-tert-butyl-5-methylphenyl | hydroxymethyl | ethyl | |
| 2.5.668 | 3-cyclopropyl-5-methylphenyl | hydroxymethyl | ethyl | |
| 2.5.669 | 3-cyano-5-methylphenyl | hydroxymethyl | ethyl | |
| 2.5.670 | 3-trifluoromethyl-5-methylphenyl | hydroxymethyl | ethyl | |
| 2.5.671 | 3-(methoxycarbonyl)-5-methylphenyl | hydroxymethyl | ethyl | |
| 2.5.672 | 3-methoxy-5-methylphenyl | hydroxymethyl | ethyl | |
| 2.5.673 | 3-ethoxy-5-methylphenyl | hydroxymethyl | ethyl | |
| 2.5.674 | 3-n-propoxy-5-methylphenyl | hydroxymethyl | ethyl | |
| 2.5.675 | 3-isobutoxy-5-methylphenyl | hydroxymethyl | ethyl | |
| 2.5.676 | 3-difluoromethoxy-5-methylphenyl | hydroxymethyl | ethyl | |
| 2.5.677 | 3-trifluoromethoxy-5-methylphenyl | hydroxymethyl | ethyl | |
| 2.5.678 | 3-nitro-5-methylphenyl | hydroxymethyl | ethyl | |
| 2.5.679 | 3-acetoxy-5-methylphenyl | hydroxymethyl | ethyl | |
| 2.5.680 | 3-methylsulfanyl-5-methylphenyl | hydroxymethyl | ethyl | |
| 2.5.681 | 3,5-diethylphenyl | hydroxymethyl | ethyl | |
| 2.5.682 | 3-propyl-5-ethylphenyl | hydroxymethyl | ethyl | |
| 2.5.683 | 3-isopropyl-5-ethylphenyl | hydroxymethyl | ethyl | |
| 2.5.684 | 3-n-butyl-5-ethylphenyl | hydroxymethyl | ethyl | |
| 2.5.685 | 3-isobutyl-5-ethylphenyl | hydroxymethyl | ethyl | |
| 2.5.686 | 3-tert-butyl-5-ethylphenyl | hydroxymethyl | ethyl | |
| 2.5.687 | 3-cyclopropyl-5-ethylphenyl | hydroxymethyl | ethyl | |
| 2.5.688 | 3-cyano-5-ethylphenyl | hydroxymethyl | ethyl | |
| 2.5.689 | 3-trifluoromethyl-5-ethylphenyl | hydroxymethyl | ethyl | |
| 2.5.690 | 3-(methoxycarbonyl)-5-ethylphenyl | hydroxymethyl | ethyl | |
| 2.5.691 | 3-methoxy-5-ethylphenyl | hydroxymethyl | ethyl | |
| 2.5.692 | 3-ethoxy-5-ethylphenyl | hydroxymethyl | ethyl | |
| 2.5.693 | 3-n-propoxy-5-ethylphenyl | hydroxymethyl | ethyl | |
| 2.5.694 | 3-isobutoxy-5-ethylphenyl | hydroxymethyl | ethyl | |
| 2.5.695 | 3-difluoromethoxy-5-ethylphenyl | hydroxymethyl | ethyl | |
| 2.5.696 | 3-trifluoromethoxy-5-ethylphenyl | hydroxymethyl | ethyl | |
| 2.5.697 | 3-nitro-5-ethylphenyl | hydroxymethyl | ethyl | |
| 2.5.698 | 3-acetoxy-5-ethylphenyl | hydroxymethyl | ethyl | |
| 2.5.699 | 3-methylsulfanyl-5-ethylphenyl | hydroxymethyl | ethyl | |
| 2.5.700 | 3,5-dipropylphenyl | hydroxymethyl | ethyl | |
| 2.5.701 | 3-isopropyl-5-propylphenyl | hydroxymethyl | ethyl | |
| 2.5.702 | 3-n-butyl-5-propylphenyl | hydroxymethyl | ethyl | |
| 2.5.703 | 3-isobutyl-5-propylphenyl | hydroxymethyl | ethyl | |
| 2.5.704 | 3-tert-butyl-5-propylphenyl | hydroxymethyl | ethyl | |
| 2.5.705 | 3-cyclopropyl-5-propylphenyl | hydroxymethyl | ethyl | |
| 2.5.706 | 3-cyano-5-propylphenyl | hydroxymethyl | ethyl | |

TABLE 2.5-continued

Inventive compounds of the general formula (I) in which W* is COOY, R¹ and R² are each hydrogen, and aryl is the radical.

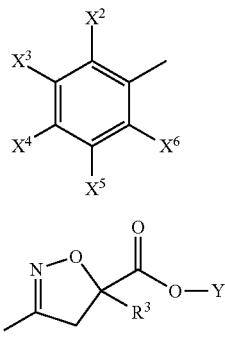

| No. | Aryl | R³ | Y | Physical data |
|---|---|---|---|---|
| 2.5.707 | 3-trifluoromethyl-5-propylphenyl | hydroxymethyl | ethyl | |
| 2.5.708 | 3-(methoxycarbonyl)-5-propylphenyl | hydroxymethyl | ethyl | |
| 2.5.709 | 3-methoxy-5-propylphenyl | hydroxymethyl | ethyl | |
| 2.5.710 | 3-ethoxy-5-propylphenyl | hydroxymethyl | ethyl | |
| 2.5.711 | 3-n-propoxy-5-propylphenyl | hydroxymethyl | ethyl | |
| 2.5.712 | 3-isobutoxy-5-propylphenyl | hydroxymethyl | ethyl | |
| 2.5.713 | 3-difluoromethoxy-5-propylphenyl | hydroxymethyl | ethyl | |
| 2.5.714 | 3-trifluoromethoxy-5-ethylphenyl | hydroxymethyl | ethyl | |
| 2.5.715 | 3-nitro-5-propylphenyl | hydroxymethyl | ethyl | |
| 2.5.716 | 3-acetoxy-5-propylphenyl | hydroxymethyl | ethyl | |
| 2.5.717 | 3-methylsulfanyl-5-propylphenyl | hydroxymethyl | ethyl | |
| 2.5.718 | 3,5-diisopropylphenyl | hydroxymethyl | ethyl | |
| 2.5.719 | 3-n-butyl-5-isopropylphenyl | hydroxymethyl | ethyl | |
| 2.5.720 | 3-isobutyl-5-isopropylphenyl | hydroxymethyl | ethyl | |
| 2.5.721 | 3-tert-butyl-5-isopropylphenyl | hydroxymethyl | ethyl | |
| 2.5.722 | 3-cyclopropyl-5-isopropylphenyl | hydroxymethyl | ethyl | |
| 2.5.723 | 3-cyano-5-isopropylphenyl | hydroxymethyl | ethyl | |
| 2.5.724 | 3-trifluoromethyl-5-isopropylphenyl | hydroxymethyl | ethyl | |
| 2.5.725 | 3-(methoxycarbonyl)-5-isopropylphenyl | hydroxymethyl | ethyl | |
| 2.5.726 | 3-methoxy-5-isopropylphenyl | hydroxymethyl | ethyl | |
| 2.5.727 | 3-ethoxy-5-isopropylphenyl | hydroxymethyl | ethyl | |
| 2.5.728 | 3-n-propoxy-5-isopropylphenyl | hydroxymethyl | ethyl | |
| 2.5.729 | 3-isobutoxy-5-isopropylphenyl | hydroxymethyl | ethyl | |
| 2.5.730 | 3-difluoromethoxy-5-isopropylphenyl | hydroxymethyl | ethyl | |
| 2.5.731 | 3-trifluoromethoxy-5-isopropylphenyl | hydroxymethyl | ethyl | |
| 2.5.732 | 3-nitro-5-isopropylphenyl | hydroxymethyl | ethyl | |
| 2.5.733 | 3-acetoxy-5-isopropylphenyl | hydroxymethyl | ethyl | |
| 2.5.734 | 3-methylsulfanyl-5-isopropylphenyl | hydroxymethyl | ethyl | |
| 2.5.735 | 3,5-dibutylphenyl | hydroxymethyl | ethyl | |
| 2.5.736 | 3-isobutyl-5-butylphenyl | hydroxymethyl | ethyl | |
| 2.5.737 | 3-tert-butyl-5-butylphenyl | hydroxymethyl | ethyl | |
| 2.5.738 | 3-cyclopropyl-5-butylphenyl | hydroxymethyl | ethyl | |
| 2.5.739 | 3-cyano-5-butylphenyl | hydroxymethyl | ethyl | |
| 2.5.740 | 3-trifluoromethyl-5-butylphenyl | hydroxymethyl | ethyl | |
| 2.5.741 | 3-(methoxycarbonyl)-5-butylphenyl | hydroxymethyl | ethyl | |
| 2.5.742 | 3-methoxy-5-butylphenyl | hydroxymethyl | ethyl | |
| 2.5.743 | 3-ethoxy-5-butylphenyl | hydroxymethyl | ethyl | |
| 2.5.744 | 3-n-propoxy-5-butylphenyl | hydroxymethyl | ethyl | |
| 2.5.745 | 3-isobutoxy-5-butylphenyl | hydroxymethyl | ethyl | |
| 2.5.746 | 3-difluoromethoxy-5-butylphenyl | hydroxymethyl | ethyl | |
| 2.5.747 | 3-trifluoromethoxy-5-butylphenyl | hydroxymethyl | ethyl | |
| 2.5.748 | 3-nitro-5-butylphenyl | hydroxymethyl | ethyl | |
| 2.5.749 | 3-acetoxy-5-butylphenyl | hydroxymethyl | ethyl | |
| 2.5.750 | 3-methylsulfanyl-5-butylphenyl | hydroxymethyl | ethyl | |
| 2.5.751 | 3,5-diisobutylphenyl | hydroxymethyl | ethyl | |
| 2.5.752 | 3-tert-butyl-5-isobutylphenyl | hydroxymethyl | ethyl | |
| 2.5.753 | 3-cyclopropyl-5-isobutylphenyl | hydroxymethyl | ethyl | |
| 2.5.754 | 3-cyano-5-isobutylphenyl | hydroxymethyl | ethyl | |
| 2.5.755 | 3-trifluoromethyl-5-isobutylphenyl | hydroxymethyl | ethyl | |
| 2.5.756 | 3-(methoxycarbonyl)-5-isobutylphenyl | hydroxymethyl | ethyl | |
| 2.5.757 | 3-methoxy-5-isobutylphenyl | hydroxymethyl | ethyl | |
| 2.5.758 | 3-ethoxy-5-isobutylphenyl | hydroxymethyl | ethyl | |
| 2.5.759 | 3-n-propoxy-5-isobutylphenyl | hydroxymethyl | ethyl | |
| 2.5.760 | 3-isobutoxy-5-isobutylphenyl | hydroxymethyl | ethyl | |
| 2.5.761 | 3-difluoromethoxy-5-isobutylphenyl | hydroxymethyl | ethyl | |
| 2.5.762 | 3-trifluoromethoxy-5-isobutylphenyl | hydroxymethyl | ethyl | |
| 2.5.763 | 3-nitro-5-isobutylphenyl | hydroxymethyl | ethyl | |
| 2.5.764 | 3-acetoxy-5-isobutylphenyl | hydroxymethyl | ethyl | |

TABLE 2.5-continued

Inventive compounds of the general formula (I) in which W* is COOY, R¹ and R² are each hydrogen, and aryl is the radical.

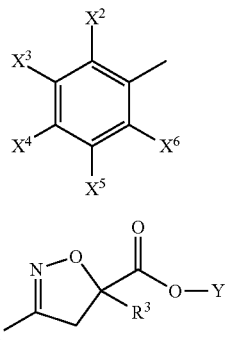

| No. | Aryl | R³ | Y | Physical data |
|---|---|---|---|---|
| 2.5.765 | 3-methylsulfanyl-5-isobutylphenyl | hydroxymethyl | ethyl | |
| 2.5.766 | 3,5-(di-tert-butyl)phenyl | hydroxymethyl | ethyl | |
| 2.5.767 | 3-cyclopropyl-5-tert-butylphenyl | hydroxymethyl | ethyl | |
| 2.5.768 | 3-cyano-5-tert-butylphenyl | hydroxymethyl | ethyl | |
| 2.5.769 | 3-trifluoromethyl-5-tert-butylphenyl | hydroxymethyl | ethyl | |
| 2.5.770 | 3-(methoxycarbonyl)-5-tert-butylphenyl | hydroxymethyl | ethyl | |
| 2.5.771 | 3-methoxy-5-tert-butylphenyl | hydroxymethyl | ethyl | |
| 2.5.772 | 3-ethoxy-5-tert-butylphenyl | hydroxymethyl | ethyl | |
| 2.5.773 | 3-n-propoxy-5-tert-butylphenyl | hydroxymethyl | ethyl | |
| 2.5.774 | 3-isobutoxy-5-tert-butylphenyl | hydroxymethyl | ethyl | |
| 2.5.775 | 3-difluoromethoxy-5-tert-butylphenyl | hydroxymethyl | ethyl | |
| 2.5.776 | 3-trifluoromethoxy-5-tert-butylphenyl | hydroxymethyl | ethyl | |
| 2.5.777 | 3-nitro-5-tert-butylphenyl | hydroxymethyl | ethyl | |
| 2.5.778 | 3-acetoxy-5-tert-butylphenyl | hydroxymethyl | ethyl | |
| 2.5.779 | 3-methylsulfanyl-5-tert-butylphenyl | hydroxymethyl | ethyl | |
| 2.5.780 | 3-tert-butyl-5-cyclopropylphenyl | hydroxymethyl | ethyl | |
| 2.5.781 | 3,5-dicyclopropyl-phenyl | hydroxymethyl | ethyl | |
| 2.5.782 | 3-cyano-5-cyclopropylphenyl | hydroxymethyl | ethyl | |
| 2.5.783 | 3-trifluoromethyl-5-cyclopropylphenyl | hydroxymethyl | ethyl | |
| 2.5.784 | 3-(methoxycarbonyl)-5-cyclopropylphenyl | hydroxymethyl | ethyl | |
| 2.5.785 | 3-methoxy-5-cyclopropylphenyl | hydroxymethyl | ethyl | |
| 2.5.786 | 3-ethoxy-5-cyclopropylphenyl | hydroxymethyl | ethyl | |
| 2.5.787 | 3-n-propoxy-5-cyclopropylphenyl | hydroxymethyl | ethyl | |
| 2.5.788 | 3-isobutoxy-5-cyclopropylphenyl | hydroxymethyl | ethyl | |
| 2.5.789 | 3-difluoromethoxy-5-cyclopropylphenyl | hydroxymethyl | ethyl | |
| 2.5.790 | 3-trifluoromethoxy-5-cyclopropylphenyl | hydroxymethyl | ethyl | |
| 2.5.791 | 3-nitro-5-cyclopropylphenyl | hydroxymethyl | ethyl | |
| 2.5.792 | 3-acetoxy-5-cyclopropylphenyl | hydroxymethyl | ethyl | |
| 2.5.793 | 3-methylsulfanyl-5-cyclopropylphenyl | hydroxymethyl | ethyl | |
| 2.5.794 | 3,5-dicyanophenyl | hydroxymethyl | ethyl | |
| 2.5.795 | 3-trifluoromethyl-5-cyanophenyl | hydroxymethyl | ethyl | |
| 2.5.796 | 3-(methoxycarbonyl)-5-cyanophenyl | hydroxymethyl | ethyl | |
| 2.5.797 | 3-methoxy-5-cyanophenyl | hydroxymethyl | ethyl | |
| 2.5.798 | 3-ethoxy-5-cyanophenyl | hydroxymethyl | ethyl | |
| 2.5.799 | 3-n-propoxy-5-cyanophenyl | hydroxymethyl | ethyl | |
| 2.5.800 | 3-isobutoxy-5-cyanophenyl | hydroxymethyl | ethyl | |
| 2.5.801 | 3-difluoromethoxy-5-cyanophenyl | hydroxymethyl | ethyl | |
| 2.5.802 | 3-trifluoromethoxy-5-cyanophenyl | hydroxymethyl | ethyl | |
| 2.5.803 | 3-nitro-5-cyanophenyl | hydroxymethyl | ethyl | |
| 2.5.804 | 3-acetoxy-5-cyanophenyl | hydroxymethyl | ethyl | |
| 2.5.805 | 3-methylsulfanyl-5-cyanophenyl | hydroxymethyl | ethyl | |
| 2.5.806 | 3,5-di(trifluoromethyl)phenyl | hydroxymethyl | ethyl | |
| 2.5.807 | 3-(methoxycarbonyl)-5-trifluoromethylphenyl | hydroxymethyl | ethyl | |
| 2.5.808 | 3-methoxy-5-trifluoromethylphenyl | hydroxymethyl | ethyl | |
| 2.5.809 | 3-ethoxy-5-trifluoromethylphenyl | hydroxymethyl | ethyl | |
| 2.5.810 | 3-n-propoxy-5-trifluoromethylphenyl | hydroxymethyl | ethyl | |
| 2.5.811 | 3-isobutoxy-5-trifluoromethylphenyl | hydroxymethyl | ethyl | |
| 2.5.812 | 3-difluoromethoxy-5-trifluoromethylphenyl | hydroxymethyl | ethyl | |
| 2.5.813 | 3-trifluoromethoxy-5-trifluoromethylphenyl | hydroxymethyl | ethyl | |
| 2.5.814 | 3-nitro-5-trifluoromethylphenyl | hydroxymethyl | ethyl | |
| 2.5.815 | 3-acetoxy-5-trifluoromethylphenyl | hydroxymethyl | ethyl | |
| 2.5.816 | 3-methylsulfanyl-5-trifluoromethylphenyl | hydroxymethyl | ethyl | |
| 2.5.817 | 3,5-di(methoxycarbonyl)phenyl | hydroxymethyl | ethyl | |

TABLE 2.5-continued

Inventive compounds of the general formula (I) in which W* is COOY,
R¹ and R² are each hydrogen, and aryl is the radical.

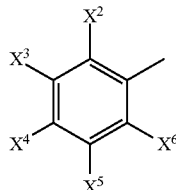

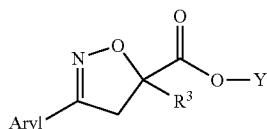

| No. | Aryl | R³ | Y | Physical data |
|---|---|---|---|---|
| 2.5.818 | 3-methoxy-5-(methoxycarbonyl)-phenyl | hydroxymethyl | ethyl | |
| 2.5.819 | 3-ethoxy-5-(methoxycarbonyl)-phenyl | hydroxymethyl | ethyl | |
| 2.5.820 | 3-n-propoxy-5-(methoxycarbonyl)-phenyl | hydroxymethyl | ethyl | |
| 2.5.821 | 3-isobutoxy-5-(methoxycarbonyl)-phenyl | hydroxymethyl | ethyl | |
| 2.5.822 | 3-difluoromethoxy-5-(methoxycarbonyl)-phenyl | hydroxymethyl | ethyl | |
| 2.5.823 | 3-trifluoromethoxy-5-(methoxycarbonyl)-phenyl | hydroxymethyl | ethyl | |
| 2.5.824 | 3-nitro-5-(methoxy-carbonyl)phenyl | hydroxymethyl | ethyl | |
| 2.5.825 | 3-acetoxy-5-(methoxycarbonyl)-phenyl | hydroxymethyl | ethyl | |
| 2.5.826 | 3-methylsulfanyl-5-(methoxycarbonyl)-phenyl | hydroxymethyl | ethyl | |
| 2.5.827 | 3,5-dimethoxyphenyl | hydroxymethyl | ethyl | |
| 2.5.828 | 3-ethoxy-5-methoxyphenyl | hydroxymethyl | ethyl | |
| 2.5.829 | 3-n-propoxy-5-methoxyphenyl | hydroxymethyl | ethyl | |
| 2.5.830 | 3-isobutoxy-5-methoxyphenyl | hydroxymethyl | ethyl | |
| 2.5.831 | 3-difluoromethoxy-5-methoxyphenyl | hydroxymethyl | ethyl | |
| 2.5.832 | 3-trifluoromethoxy-5-methoxyphenyl | hydroxymethyl | ethyl | |
| 2.5.833 | 3-nitro-5-methoxyphenyl | hydroxymethyl | ethyl | |
| 2.5.834 | 3-acetoxy-5-methoxyphenyl | hydroxymethyl | ethyl | |
| 2.5.835 | 3-methylsulfanyl-5-methoxyphenyl | hydroxymethyl | ethyl | |
| 2.5.836 | 3,5-diethoxyphenyl | hydroxymethyl | ethyl | |
| 2.5.837 | 3-n-propoxy-5-ethoxyphenyl | hydroxymethyl | ethyl | |
| 2.5.838 | 3-isobutoxy-5-ethoxyphenyl | hydroxymethyl | ethyl | |
| 2.5.839 | 3-difluoromethoxy-5-ethoxyphenyl | hydroxymethyl | ethyl | |
| 2.5.840 | 3-trifluoromethoxy-5-ethoxyphenyl | hydroxymethyl | ethyl | |
| 2.5.841 | 3-nitro-5-ethoxyphenyl | hydroxymethyl | ethyl | |
| 2.5.842 | 3-acetoxy-5-ethoxyphenyl | hydroxymethyl | ethyl | |
| 2.5.843 | 3-methylsulfanyl-5-ethoxyphenyl | hydroxymethyl | ethyl | |
| 2.5.844 | 3,5-di(isopropoxy)phenyl | hydroxymethyl | ethyl | |
| 2.5.845 | 3-isobutoxy-5-isopropoxyphenyl | hydroxymethyl | ethyl | |
| 2.5.846 | 3-difluoromethoxy-5-isopropoxyphenyl | hydroxymethyl | ethyl | |
| 2.5.847 | 3-trifluoromethoxy-5-isopropoxyphenyl | hydroxymethyl | ethyl | |
| 2.5.848 | 3-nitro-5-isopropoxyphenyl | hydroxymethyl | ethyl | |
| 2.5.849 | 3-acetoxy-5-isopropoxyphenyl | hydroxymethyl | ethyl | |
| 2.5.850 | 3-methylsulfanyl-5-isopropoxyphenyl | hydroxymethyl | ethyl | |
| 2.5.851 | 3,5-di(trifluoro-methoxy)phenyl | hydroxymethyl | ethyl | |
| 2.5.852 | 3-nitro-5-trifluoro-methoxyphenyl | hydroxymethyl | ethyl | |
| 2.5.853 | 3-methylsulfanyl-5-trifluoromethoxyphenyl | hydroxymethyl | ethyl | |
| 2.5.854 | 3,5-bis(difluoromethoxy)phenyl | hydroxymethyl | ethyl | |
| 2.5.855 | 3,5-bis(difluoromethoxy)phenyl | 1-hydroxyethyl | ethyl | |
| 2.5.856 | 3,5-bis(difluoromethoxy)phenyl | 1-hydroxypropyl | ethyl | |
| 2.5.857 | 3,5-bis(difluoromethoxy)phenyl | (1-hydroxy-2-methylpropyl) | ethyl | |
| 2.5.858 | 3-trifluoromethoxy-5-difluoromethoxyphenyl | hydroxymethyl | ethyl | |
| 2.5.859 | 3-nitro-5-difluoromethoxyphenyl | hydroxymethyl | ethyl | |
| 2.5.860 | 3-acetoxy-5-difluoromethoxy-phenyl | hydroxymethyl | ethyl | |
| 2.5.861 | 3-methylsulfanyl-5-difluoromethoxyphenyl | hydroxymethyl | ethyl | |
| 2.5.862 | 3,5-bis(acetoxy)phenyl | hydroxymethyl | ethyl | |
| 2.5.863 | 3-methylsulfanyl-5-acetoxyphenyl | hydroxymethyl | ethyl | |
| 2.5.864 | 3-acetoxy-5-nitrophenyl | hydroxymethyl | ethyl | |
| 2.5.865 | 3-methylsulfanyl-5-nitrophenyl | hydroxymethyl | ethyl | |
| 2.5.866 | 3,4-difluorophenyl | hydroxymethyl | ethyl | |

TABLE 2.5-continued

Inventive compounds of the general formula (I) in which W* is COOY, $R^1$ and $R^2$ are each hydrogen, and aryl is the radical.

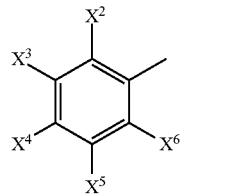

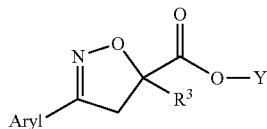

| No. | Aryl | $R^3$ | Y | Physical data |
|---|---|---|---|---|
| 2.5.867 | 3,4-difluorophenyl | 1-hydroxyethyl | ethyl | |
| 2.5.868 | 3,4-difluorophenyl | 1-hydroxypropyl | ethyl | |
| 2.5.869 | 3,4-difluorophenyl | (1-hydroxy-2-methylpropyl) | ethyl | |
| 2.5.870 | 3,4-difluorophenyl | methoxymethyl | ethyl | |
| 2.5.871 | 3,4-difluorophenyl | 2-methoxyethyl | ethyl | |
| 2.5.872 | 3-chloro-4-fluorophenyl | hydroxymethyl | ethyl | |
| 2.5.873 | 3-chloro-4-fluorophenyl | 1-hydroxyethyl | ethyl | |
| 2.5.874 | 3-chloro-4-fluorophenyl | 1-hydroxypropyl | ethyl | |
| 2.5.875 | 3-chloro-4-fluorophenyl | (1-hydroxy-2-methylpropyl) | ethyl | |
| 2.5.876 | 3-chloro-4-fluorophenyl | methoxymethyl | ethyl | |
| 2.5.877 | 3-chloro-4-fluorophenyl | 2-methoxyethyl | ethyl | |
| 2.5.878 | 3-bromo-4-fluorophenyl | hydroxymethyl | ethyl | |
| 2.5.879 | 3-methyl-4-fluorophenyl | hydroxymethyl | ethyl | |
| 2.5.880 | 3-methyl-4-fluorophenyl | 1-hydroxyethyl | ethyl | |
| 2.5.881 | 3-cyclopropyl-4-fluorophenyl | hydroxymethyl | ethyl | |
| 2.5.882 | 3-cyano-4-fluorophenyl | hydroxymethyl | ethyl | |
| 2.5.883 | 3-methoxy-4-fluorophenyl | hydroxymethyl | ethyl | |
| 2.5.884 | 3-ethoxy-4-fluorophenyl | hydroxymethyl | ethyl | |
| 2.5.885 | 3-trifluoromethoxy-4-fluorophenyl | hydroxymethyl | ethyl | |
| 2.5.886 | 3-nitro-4-fluorophenyl | hydroxymethyl | ethyl | |
| 2.5.887 | 3-fluoro-4-chlorophenyl | hydroxymethyl | ethyl | |
| 2.5.888 | 3,4-dichlorophenyl | hydroxymethyl | ethyl | |
| 2.5.889 | 3-bromo-4-chlorophenyl | hydroxymethyl | ethyl | |
| 2.5.890 | 3-methyl-4-chlorophenyl | hydroxymethyl | ethyl | |
| 2.5.891 | 3-cyclopropyl-4-chlorophenyl | hydroxymethyl | ethyl | |
| 2.5.892 | 3-cyano-4-chlorophenyl | hydroxymethyl | ethyl | |
| 2.5.893 | 3-trifluoromethyl-4-chlorophenyl | hydroxymethyl | ethyl | |
| 2.5.894 | 3-methoxy-4-chlorophenyl | hydroxymethyl | ethyl | |
| 2.5.895 | 3-ethoxy-4-chlorophenyl | hydroxymethyl | ethyl | |
| 2.5.896 | 3-trifluoromethoxy-4-chlorophenyl | hydroxymethyl | ethyl | |
| 2.5.897 | 3-nitro-4-chlorophenyl | hydroxymethyl | ethyl | |
| 2.5.898 | 3-fluoro-4-bromophenyl | hydroxymethyl | ethyl | |
| 2.5.899 | 3-chloro-4-bromophenyl | hydroxymethyl | ethyl | |
| 2.5.900 | 3,4-dibromophenyl | hydroxymethyl | ethyl | |
| 2.5.901 | 3-methyl-4-bromophenyl | hydroxymethyl | ethyl | |
| 2.5.902 | 3-cyclopropyl-4-bromophenyl | hydroxymethyl | ethyl | |
| 2.5.903 | 3-cyano-4-bromophenyl | hydroxymethyl | ethyl | |
| 2.5.904 | 3-trifluoromethyl-4-bromophenyl | hydroxymethyl | ethyl | |
| 2.5.905 | 3-methoxy-4-phenyl | hydroxymethyl | ethyl | |
| 2.5.906 | 3-ethoxy-4-bromophenyl | hydroxymethyl | ethyl | |
| 2.5.907 | 3-trifluoromethoxy-4-bromophenyl | hydroxymethyl | ethyl | |
| 2.5.908 | 3-nitro-4-bromophenyl | hydroxymethyl | ethyl | |
| 2.5.909 | 3-fluoro-4-iodophenyl | hydroxymethyl | ethyl | |
| 2.5.910 | 3-chloro-4-iodophenyl | hydroxymethyl | ethyl | |
| 2.5.911 | 3-bromo-4-iodophenyl | hydroxymethyl | ethyl | |
| 2.5.912 | 3-methyl-4-iodophenyl | hydroxymethyl | ethyl | |
| 2.5.913 | 3-cyclopropyl-4-iodophenyl | hydroxymethyl | ethyl | |
| 2.5.914 | 3-cyano-4-iodophenyl | hydroxymethyl | ethyl | |
| 2.5.915 | 3-trifluoromethyl-4-iodophenyl | hydroxymethyl | ethyl | |
| 2.5.916 | 3-methoxy-4-iodophenyl | hydroxymethyl | ethyl | |
| 2.5.917 | 3-ethoxy-4-iodophenyl | hydroxymethyl | ethyl | |
| 2.5.918 | 3-trifluoromethoxy-4-iodophenyl | hydroxymethyl | ethyl | |
| 2.5.919 | 3-nitro-4-iodophenyl | hydroxymethyl | ethyl | |
| 2.5.920 | 3-fluoro-4-methylphenyl | hydroxymethyl | ethyl | |
| 2.5.921 | 3-chloro-4-methylphenyl | hydroxymethyl | ethyl | |
| 2.5.922 | 3-bromo-4-methylphenyl | hydroxymethyl | ethyl | |

TABLE 2.5-continued

Inventive compounds of the general formula (I) in which W* is COOY,
R¹ and R² are each hydrogen, and aryl is the radical.

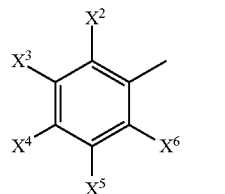

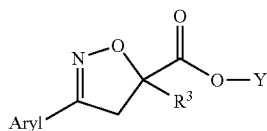

| No. | Aryl | R³ | Y | Physical data |
|---|---|---|---|---|
| 2.5.923 | 3,4-dimethylphenyl | hydroxymethyl | ethyl | |
| 2.5.924 | 3,4-dimethylphenyl | 1-hydroxyethyl | ethyl | |
| 2.5.925 | 3,4-dimethylphenyl | 1-hydroxypropyl | ethyl | |
| 2.5.926 | 3,4-dimethylphenyl | (1-hydroxy-2-methylpropyl) | ethyl | |
| 2.5.927 | 3,4-dimethylphenyl | methoxymethyl | ethyl | |
| 2.5.928 | 3,4-dimethylphenyl | 2-methoxyethyl | ethyl | |
| 2.5.929 | 3-cyclopropyl-4-methylphenyl | hydroxymethyl | ethyl | |
| 2.5.930 | 3-cyano-4-methylphenyl | hydroxymethyl | ethyl | |
| 2.5.931 | 3-trifluoromethyl-4-methylphenyl | hydroxymethyl | ethyl | |
| 2.5.932 | 3-methoxy-4-methylphenyl | hydroxymethyl | ethyl | |
| 2.5.933 | 3-ethoxy-4-methylphenyl | hydroxymethyl | ethyl | |
| 2.5.934 | 3-trifluoromethoxy-4-methylphenyl | hydroxymethyl | ethyl | |
| 2.5.935 | 3-nitro-4-methylphenyl | hydroxymethyl | ethyl | |
| 2.5.936 | 3-fluoro-4-ethylphenyl | hydroxymethyl | ethyl | |
| 2.5.937 | 3-chloro-4-ethylphenyl | hydroxymethyl | ethyl | |
| 2.5.938 | 3-bromo-4-ethylphenyl | hydroxymethyl | ethyl | |
| 2.5.939 | 3-methyl-4-ethylphenyl | hydroxymethyl | ethyl | |
| 2.5.940 | 3,4-diethylphenyl | hydroxymethyl | ethyl | |
| 2.5.941 | 3-cyclopropyl-4-ethylphenyl | hydroxymethyl | ethyl | |
| 2.5.942 | 3-cyano-4-ethylphenyl | hydroxymethyl | ethyl | |
| 2.5.943 | 3-trifluoromethyl-4-ethylphenyl | hydroxymethyl | ethyl | |
| 2.5.944 | 3-methoxy-4-ethylphenyl | hydroxymethyl | ethyl | |
| 2.5.945 | 3-ethoxy-4-ethylphenyl | hydroxymethyl | ethyl | |
| 2.5.946 | 3-trifluoromethoxy-4-ethylphenyl | hydroxymethyl | ethyl | |
| 2.5.947 | 3-nitro-4-ethylphenyl | hydroxymethyl | ethyl | |
| 2.5.948 | 3-fluoro-4-propylphenyl | hydroxymethyl | ethyl | |
| 2.5.949 | 3-chloro-4-propylphenyl | hydroxymethyl | ethyl | |
| 2.5.950 | 3-bromo-4-propylphenyl | hydroxymethyl | ethyl | |
| 2.5.951 | 3-methyl-4-propylphenyl | hydroxymethyl | ethyl | |
| 2.5.952 | 3-cyclopropyl-4-propylphenyl | hydroxymethyl | ethyl | |
| 2.5.953 | 3-cyano-4-propylphenyl | hydroxymethyl | ethyl | |
| 2.5.954 | 3-trifluoromethyl-4-propylphenyl | hydroxymethyl | ethyl | |
| 2.5.955 | 3-methoxy-4-propylphenyl | hydroxymethyl | ethyl | |
| 2.5.956 | 3-ethoxy-4-propylphenyl | hydroxymethyl | ethyl | |
| 2.5.957 | 3-trifluoromethoxy-4-propylphenyl | hydroxymethyl | ethyl | |
| 2.5.958 | 3-nitro-4-propylphenyl | hydroxymethyl | ethyl | |
| 2.5.959 | 3-fluoro-4-isopropylphenyl | hydroxymethyl | ethyl | |
| 2.5.960 | 3-chloro-4-isopropylphenyl | hydroxymethyl | ethyl | |
| 2.5.961 | 3-bromo-4-isopropylphenyl | hydroxymethyl | ethyl | |
| 2.5.962 | 3-methyl-4-isopropylphenyl | hydroxymethyl | ethyl | |
| 2.5.963 | 3-cyclopropyl-4-isopropylphenyl | hydroxymethyl | ethyl | |
| 2.5.964 | 3-cyano-4-isopropylphenyl | hydroxymethyl | ethyl | |
| 2.5.965 | 3-trifluoromethyl-4-isopropylphenyl | hydroxymethyl | ethyl | |
| 2.5.966 | 3-methoxy-4-isopropylphenyl | hydroxymethyl | ethyl | |
| 2.5.967 | 3-ethoxy-4-isopropylphenyl | hydroxymethyl | ethyl | |
| 2.5.968 | 3-trifluoromethoxy-4-isopropylphenyl | hydroxymethyl | ethyl | |
| 2.5.969 | 3-nitro-4-isopropylphenyl | hydroxymethyl | ethyl | |
| 2.5.970 | 3-fluoro-4-tert-butylphenyl | hydroxymethyl | ethyl | |
| 2.5.971 | 3-chloro-4-tert-butylphenyl | hydroxymethyl | ethyl | |
| 2.5.972 | 3-bromo-4-tert-butylphenyl | hydroxymethyl | ethyl | |
| 2.5.973 | 3-methyl-4-tert-butylphenyl | hydroxymethyl | ethyl | |
| 2.5.974 | 3-cyclopropyl-4-tert-butylphenyl | hydroxymethyl | ethyl | |
| 2.5.975 | 3-cyano-4-tert-butylphenyl | hydroxymethyl | ethyl | |
| 2.5.976 | 3-trifluoromethyl-4-tert-butylphenyl | hydroxymethyl | ethyl | |
| 2.5.977 | 3-trifluoromethyl-4-tert-butylphenyl | 1-hydroxyethyl | ethyl | |
| 2.5.978 | 3-trifluoromethyl-4-tert-butylphenyl | 1-hydroxypropyl | ethyl | |

TABLE 2.5-continued

Inventive compounds of the general formula (I) in which W* is COOY, R¹ and R² are each hydrogen, and aryl is the radical.

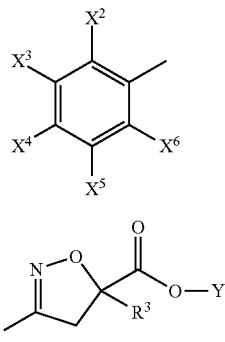

| No. | Aryl | R³ | Y | Physical data |
|---|---|---|---|---|
| 2.5.979 | 3-trifluoromethyl-4-tert-butylphenyl | (1-hydroxy-2-methylpropyl) | ethyl | |
| 2.5.980 | 3-trifluoromethyl-4-tert-butylphenyl | methoxymethyl | ethyl | |
| 2.5.981 | 3-trifluoromethyl-4-tert-butylphenyl | 2-methoxyethyl | ethyl | |
| 2.5.982 | 3-methoxy-4-tert-butylphenyl | hydroxymethyl | ethyl | |
| 2.5.983 | 3-ethoxy-4-tert-butylphenyl | hydroxymethyl | ethyl | |
| 2.5.984 | 3-trifluoromethoxy-4-tert-butylphenyl | hydroxymethyl | ethyl | |
| 2.5.985 | 3-nitro-4-tert-butylphenyl | hydroxymethyl | ethyl | |
| 2.5.986 | 3-fluoro-4-cyclopropylphenyl | hydroxymethyl | ethyl | |
| 2.5.987 | 3-chloro-4-cyclopropylphenyl | hydroxymethyl | ethyl | |
| 2.5.988 | 3-bromo-4-cyclopropylphenyl | hydroxymethyl | ethyl | |
| 2.5.989 | 3-methyl-4-cyclopropylphenyl | hydroxymethyl | ethyl | |
| 2.5.990 | 3-cyano-4-cyclopropylphenyl | hydroxymethyl | ethyl | |
| 2.5.991 | 3-trifluoromethyl-cyclopropylphenyl | hydroxymethyl | ethyl | |
| 2.5.992 | 3-methoxy-4-cyclopropylphenyl | hydroxymethyl | ethyl | |
| 2.5.993 | 3-ethoxy-4-cyclopropylphenyl | hydroxymethyl | ethyl | |
| 2.5.994 | 3-trifluoromethoxy-4-cyclopropylphenyl | hydroxymethyl | ethyl | |
| 2.5.995 | 3-fluoro-4-methoxycarbonyl-phenyl | hydroxymethyl | ethyl | |
| 2.5.996 | 3-chloro-4-methoxy-carbonylphenyl | hydroxymethyl | ethyl | |
| 2.5.997 | 3-bromo-4-methoxy-carbonylphenyl | hydroxymethyl | ethyl | |
| 2.5.998 | 3-methyl-4-methoxy-carbonylphenyl | hydroxymethyl | ethyl | |
| 2.5.999 | 3-cyclopropyl-4-methoxycarbonyl-phenyl | hydroxymethyl | ethyl | |
| 2.5.1000 | 3-cyano-4-methoxycarbonylphenyl | hydroxymethyl | ethyl | |
| 2.5.1001 | 3-trifluoromethyl-4-methoxycarbonyl-phenyl | hydroxymethyl | ethyl | |
| 2.5.1002 | 3-methoxy-4-methoxycarbonyl-phenyl | hydroxymethyl | ethyl | |
| 2.5.1003 | 3-ethoxy-4-methoxycarbonyl-phenyl | hydroxymethyl | ethyl | |
| 2.5.1004 | 3-trifluoromethoxy-4-methoxycarbonyl-phenyl | hydroxymethyl | ethyl | |
| 2.5.1005 | 3-nitro-4-methoxy-carbonylphenyl | hydroxymethyl | ethyl | |
| 2.5.1006 | 3-fluoro-4-cyanophenyl | hydroxymethyl | ethyl | |
| 2.5.1007 | 3-chloro-4-cyanophenyl | hydroxymethyl | ethyl | |
| 2.5.1008 | 3-bromo-4-cyanophenyl | hydroxymethyl | ethyl | |
| 2.5.1009 | 3-methyl-4-cyanophenyl | hydroxymethyl | ethyl | |
| 2.5.1010 | 3-cyclopropyl-4-cyanophenyl | hydroxymethyl | ethyl | |
| 2.5.1011 | 3,4-dicyanophenyl | hydroxymethyl | ethyl | |
| 2.5.1012 | 3-trifluoromethyl-4-cyanophenyl | hydroxymethyl | ethyl | |
| 2.5.1013 | 3-trifluoromethyl-4-cyanophenyl | 1-hydroxyethyl | ethyl | |
| 2.5.1014 | 3-trifluoromethyl-4-cyanophenyl | 1-hydroxypropyl | ethyl | |
| 2.5.1015 | 3-trifluoromethyl-4-cyanophenyl | (1-hydroxy-2-methylpropyl) | ethyl | |
| 2.5.1016 | 3-trifluoromethyl-4-cyanophenyl | methoxymethyl | ethyl | |
| 2.5.1017 | 3-trifluoromethyl-4-cyanophenyl | 2-methoxyethyl | ethyl | |
| 2.5.1018 | 3-methoxy-4-cyanophenyl | hydroxymethyl | ethyl | |
| 2.5.1019 | 3-ethoxy-4-cyanophenyl | hydroxymethyl | ethyl | |
| 2.5.1020 | 3-trifluoromethoxy-4-cyanophenyl | hydroxymethyl | ethyl | |
| 2.5.1021 | 3-nitro-4-cyanophenyl | hydroxymethyl | ethyl | |
| 2.5.1022 | 3-fluoro-4-methoxyphenyl | hydroxymethyl | ethyl | |
| 2.5.1023 | 3-chloro-4-methoxyphenyl | hydroxymethyl | ethyl | |
| 2.5.1024 | 3-bromo-4-methoxyphenyl | hydroxymethyl | ethyl | |
| 2.5.1025 | 3-methyl-4-methoxyphenyl | hydroxymethyl | ethyl | |
| 2.5.1026 | 3-cyclopropyl-4-methoxyphenyl | hydroxymethyl | ethyl | |
| 2.5.1027 | 3-cyano-4-methoxyphenyl | hydroxymethyl | ethyl | |
| 2.5.1028 | 3-trifluoromethyl-4-methoxyphenyl | hydroxymethyl | ethyl | |
| 2.5.1029 | 3,4-dimethoxyphenyl | hydroxymethyl | ethyl | |
| 2.5.1030 | 3-ethoxy-4-methoxyphenyl | hydroxymethyl | ethyl | |
| 2.5.1031 | 3-trifluoromethoxy-4-methoxyphenyl | hydroxymethyl | ethyl | |

TABLE 2.5-continued

Inventive compounds of the general formula (I) in which W* is COOY, $R^1$ and $R^2$ are each hydrogen, and aryl is the radical.

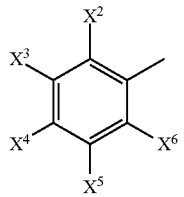

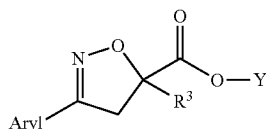

| No. | Aryl | $R^3$ | Y | Physical data |
|---|---|---|---|---|
| 2.5.1032 | 3-nitro-4-methoxyphenyl | hydroxymethyl | ethyl | |
| 2.5.1033 | 3-fluoro-4-ethoxyphenyl | hydroxymethyl | ethyl | |
| 2.5.1034 | 3-chloro-4-ethoxyphenyl | hydroxymethyl | ethyl | |
| 2.5.1035 | 3-chloro-4-ethoxyphenyl | 1-hydroxyethyl | ethyl | |
| 2.5.1036 | 3-chloro-4-ethoxyphenyl | 1-hydroxypropyl | ethyl | |
| 2.5.1037 | 3-chloro-4-ethoxyphenyl | (1-hydroxy-2-methylpropyl) | ethyl | |
| 2.5.1038 | 3-chloro-4-ethoxyphenyl | methoxymethyl | ethyl | |
| 2.5.1039 | 3-chloro-4-ethoxyphenyl | 2-methoxyethyl | ethyl | |
| 2.5.1040 | 3-bromo-4-ethoxyphenyl | hydroxymethyl | ethyl | |
| 2.5.1041 | 3-methyl-4-ethoxyphenyl | hydroxymethyl | ethyl | |
| 2.5.1042 | 3-cyclopropyl-4-ethoxyphenyl | hydroxymethyl | ethyl | |
| 2.5.1043 | 3-cyano-4-ethoxyphenyl | hydroxymethyl | ethyl | |
| 2.5.1044 | 3-trifluoromethyl-4-ethoxyphenyl | hydroxymethyl | ethyl | |
| 2.5.1045 | 3-methoxy-4-ethoxyphenyl | hydroxymethyl | ethyl | |
| 2.5.1046 | 2,4-diethoxyphenyl | hydroxymethyl | ethyl | |
| 2.5.1047 | 3-trifluoromethoxy-4-ethoxyphenyl | hydroxymethyl | ethyl | |
| 2.5.1048 | 3-nitro-4-ethoxyphenyl | hydroxymethyl | ethyl | |
| 2.5.1049 | 3-fluoro-4-isopropoxyphenyl | hydroxymethyl | ethyl | |
| 2.5.1050 | 3-chloro-4-isopropoxyphenyl | hydroxymethyl | ethyl | |
| 2.5.1051 | 3-bromo-4-isopropoxyphenyl | hydroxymethyl | ethyl | |
| 2.5.1052 | 3-methyl-4-isopropoxyphenyl | hydroxymethyl | ethyl | |
| 2.5.1053 | 3-cyclopropyl-4-isopropoxyphenyl | hydroxymethyl | ethyl | |
| 2.5.1054 | 3-cyano-4-isopropoxyphenyl | hydroxymethyl | ethyl | |
| 2.5.1055 | 3-trifluoromethyl-4-isopropoxyphenyl | hydroxymethyl | ethyl | |
| 2.5.1056 | 3-methoxy-4-isopropoxyphenyl | hydroxymethyl | ethyl | |
| 2.5.1057 | 3-ethoxy-4-isopropoxyphenyl | hydroxymethyl | ethyl | |
| 2.5.1058 | 3-trifluoromethoxy-4-isopropoxyphenyl | hydroxymethyl | ethyl | |
| 2.5.1059 | 3-nitro-4-isopropoxyphenyl | hydroxymethyl | ethyl | |
| 2.5.1060 | 3-fluoro-4-trifluoro-methoxyphenyl | hydroxymethyl | ethyl | |
| 2.5.1061 | 3-chloro-4-trifluoro-methoxyphenyl | hydroxymethyl | ethyl | |
| 2.5.1062 | 3-bromo-4-trifluoro-methoxyphenyl | hydroxymethyl | ethyl | |
| 2.5.1063 | 3-methyl-4-trifluoro-methoxyphenyl | hydroxymethyl | ethyl | |
| 2.5.1064 | 3-cyclopropyl-4-trifluoromethoxyphenyl | hydroxymethyl | ethyl | |
| 2.5.1065 | 3-cyano-4-trifluoro-methoxyphenyl | hydroxymethyl | ethyl | |
| 2.5.1066 | 3-trifluoromethyl-4-trifluoromethoxyphenyl | hydroxymethyl | ethyl | |
| 2.5.1067 | 3-methoxy-4-trifluoromethoxy-phenyl | hydroxymethyl | ethyl | |
| 2.5.1068 | 3-ethoxy-4-trifluoro-methoxyphenyl | hydroxymethyl | ethyl | |
| 2.5.1069 | 3,4-bis(trifluoromethoxy)phenyl | hydroxymethyl | ethyl | |
| 2.5.1070 | 3-nitro-4-trifluoromethoxyphenyl | hydroxymethyl | ethyl | |
| 2.5.1071 | 3-fluoro-4-difluoromethoxy-phenyl | hydroxymethyl | ethyl | |
| 2.5.1072 | 3-chloro-4-difluoromethoxy-phenyl | hydroxymethyl | ethyl | |
| 2.5.1073 | 3-bromo-4-difluoromethoxy-phenyl | hydroxymethyl | ethyl | |
| 2.5.1074 | 3-methyl-4-difluoromethoxy-phenyl | hydroxymethyl | ethyl | |
| 2.5.1075 | 3-cyclopropyl-4-difluoromethoxy-phenyl | hydroxymethyl | ethyl | |
| 2.5.1076 | 3-cyano-4-difluoromethoxy-phenyl | hydroxymethyl | ethyl | |
| 2.5.1077 | 3-trifluoromethyl-4-difluoromethoxyphenyl | hydroxymethyl | ethyl | |
| 2.5.1078 | 3-methoxy-4-difluoromethoxy-phenyl | hydroxymethyl | ethyl | |
| 2.5.1079 | 3-ethoxy-4-difluoromethoxy-phenyl | hydroxymethyl | ethyl | |
| 2.5.1080 | 3-trifluoromethoxy-4-difluoromethoxyphenyl | hydroxymethyl | ethyl | |
| 2.5.1081 | 3-nitro-4-difluoromethoxyphenyl | hydroxymethyl | ethyl | |
| 2.5.1082 | 3-fluoro-4-nitrophenyl | hydroxymethyl | ethyl | |
| 2.5.1083 | 3-chloro-4-nitrophenyl | hydroxymethyl | ethyl | |
| 2.5.1084 | 3-bromo-4-nitrophenyl | hydroxymethyl | ethyl | |
| 2.5.1085 | 3-methyl-4-nitrophenyl | hydroxymethyl | ethyl | |

TABLE 2.5-continued

Inventive compounds of the general formula (I) in which W* is COOY,
R¹ and R² are each hydrogen, and aryl is the radical.

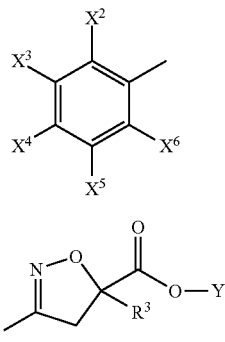

| No. | Aryl | R³ | Y | Physical data |
|---|---|---|---|---|
| 2.5.1086 | 3-cyclopropyl-4-nitrophenyl | hydroxymethyl | ethyl | |
| 2.5.1087 | 3-cyano-4-nitrophenyl | hydroxymethyl | ethyl | |
| 2.5.1088 | 3-trifluoromethyl-4-nitrophenyl | hydroxymethyl | ethyl | |
| 2.5.1089 | 3-methoxy-4-nitrophenyl | hydroxymethyl | ethyl | |
| 2.5.1090 | 3-ethoxy-4-nitrophenyl | hydroxymethyl | ethyl | |
| 2.5.1091 | 3-trifluoromethoxy-4-nitrophenyl | hydroxymethyl | ethyl | |
| 2.5.1092 | 3-fluoro-4-methylsulfanylphenyl | hydroxymethyl | ethyl | |
| 2.5.1093 | 3-chloro-4-methylsulfanylphenyl | hydroxymethyl | ethyl | |
| 2.5.1094 | 3-bromo-4-methylsulfanylphenyl | hydroxymethyl | ethyl | |
| 2.5.1095 | 3-methyl-4-methylsulfanylphenyl | hydroxymethyl | ethyl | |
| 2.5.1096 | 3-cyclopropyl-4-methylsulfanylphenyl | hydroxymethyl | ethyl | |
| 2.5.1097 | 3-cyano-4-methylsulfanylphenyl | hydroxymethyl | ethyl | |
| 2.5.1098 | 3-trifluoromethyl-4-methylsulfanylphenyl | hydroxymethyl | ethyl | |
| 2.5.1099 | 3-methoxy-4-methylsulfanylphenyl | hydroxymethyl | ethyl | |
| 2.5.1100 | 3-ethoxy-4-methylsulfanylphenyl | hydroxymethyl | ethyl | |
| 2.5.1101 | 3-trifluoromethoxy-4-methylsulfanylphenyl | hydroxymethyl | ethyl | |
| 2.5.1102 | 3-nitro-4-methylsulfanylphenyl | hydroxymethyl | ethyl | |
| 2.5.1103 | 3,6-difluorophenyl | hydroxymethyl | ethyl | |
| 2.5.1104 | 3,6-difluorophenyl | 1-hydroxyethyl | ethyl | |
| 2.5.1105 | 3,6-difluorophenyl | 1-hydroxypropyl | ethyl | |
| 2.5.1106 | 3,6-difluorophenyl | (1-hydroxy-2-methylpropyl) | ethyl | |
| 2.5.1107 | 3,6-difluorophenyl | methoxymethyl | ethyl | |
| 2.5.1108 | 3,6-difluorophenyl | 2-methoxyethyl | ethyl | |
| 2.5.1109 | 3-chloro-6-fluorophenyl | hydroxymethyl | ethyl | |
| 2.5.1110 | 3-bromo-6-fluorophenyl | hydroxymethyl | ethyl | |
| 2.5.1111 | 3-methyl-6-fluorophenyl | hydroxymethyl | ethyl | |
| 2.5.1112 | 3-cyclopropyl-6-fluorophenyl | hydroxymethyl | ethyl | |
| 2.5.1113 | 3-cyano-6-fluorophenyl | hydroxymethyl | ethyl | |
| 2.5.1114 | 3-methoxy-6-fluorophenyl | hydroxymethyl | ethyl | |
| 2.5.1115 | 3-ethoxy-6-fluorophenyl | hydroxymethyl | ethyl | |
| 2.5.1116 | 3-trifluoromethoxy-6-fluorophenyl | hydroxymethyl | ethyl | |
| 2.5.1117 | 3-nitro-6-fluorophenyl | hydroxymethyl | ethyl | |
| 2.5.1118 | 3-fluoro-6-chlorophenyl | hydroxymethyl | ethyl | |
| 2.5.1119 | 3-fluoro-6-chlorophenyl | 1-hydroxyethyl | ethyl | |
| 2.5.1120 | 3-fluoro-6-chlorophenyl | 1-hydroxypropyl | ethyl | |
| 2.5.1121 | 3-fluoro-6-chlorophenyl | (1-hydroxy-2-methylpropyl) | ethyl | |
| 2.5.1122 | 3-fluoro-6-chlorophenyl | methoxymethyl | ethyl | |
| 2.5.1123 | 3-fluoro-6-chlorophenyl | 2-methoxyethyl | ethyl | |
| 2.5.1124 | 3,6-dichlorophenyl | hydroxymethyl | ethyl | |
| 2.5.1125 | 3,6-dichlorophenyl | 1-hydroxyethyl | ethyl | |
| 2.5.1126 | 3,6-dichlorophenyl | 1-hydroxypropyl | ethyl | |
| 2.5.1127 | 3,6-dichlorophenyl | (1-hydroxy-2-methylpropyl) | ethyl | |
| 2.5.1128 | 3,6-dichlorophenyl | methoxymethyl | ethyl | |
| 2.5.1129 | 3,6-dichlorophenyl | 2-methoxyethyl | ethyl | |
| 2.5.1130 | 3-bromo-6-chlorophenyl | hydroxymethyl | ethyl | |
| 2.5.1131 | 3-methyl-6-chlorophenyl | hydroxymethyl | ethyl | |
| 2.5.1132 | 3-ethyl-6-chlorophenyl | hydroxymethyl | ethyl | |
| 2.5.1133 | 3-cyclopropyl-6-chlorophenyl | hydroxymethyl | ethyl | |
| 2.5.1134 | 3-cyano-6-chlorophenyl | hydroxymethyl | ethyl | |
| 2.5.1135 | 3-trifluoromethyl-6-chlorophenyl | hydroxymethyl | ethyl | |
| 2.5.1136 | 3-methoxy-6-chlorophenyl | hydroxymethyl | ethyl | |
| 2.5.1137 | 3-ethoxy-6-chlorophenyl | hydroxymethyl | ethyl | |
| 2.5.1138 | 3-trifluoromethoxy-6-chlorophenyl | hydroxymethyl | ethyl | |

TABLE 2.5-continued

Inventive compounds of the general formula (I) in which W* is COOY,
R¹ and R² are each hydrogen, and aryl is the radical.

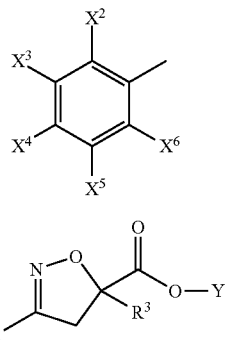

| No. | Aryl | R³ | Y | Physical data |
|---|---|---|---|---|
| 2.5.1139 | 3-nitro-6-chlorophenyl | hydroxymethyl | ethyl | |
| 2.5.1140 | 3-fluoro-6-bromophenyl | hydroxymethyl | ethyl | |
| 2.5.1141 | 3-chloro-6-bromophenyl | hydroxymethyl | ethyl | |
| 2.5.1142 | 3,6-dibromophenyl | hydroxymethyl | ethyl | |
| 2.5.1143 | 3-methyl-6-bromophenyl | hydroxymethyl | ethyl | |
| 2.5.1144 | 3-cyclopropyl-6-bromophenyl | hydroxymethyl | ethyl | |
| 2.5.1145 | 3-cyano-6-bromophenyl | hydroxymethyl | ethyl | |
| 2.5.1146 | 3-trifluoromethyl-6-bromophenyl | hydroxymethyl | ethyl | |
| 2.5.1147 | 3-methoxy-6-phenyl | hydroxymethyl | ethyl | |
| 2.5.1148 | 3-ethoxy-6-bromophenyl | hydroxymethyl | ethyl | |
| 2.5.1149 | 3-trifluoromethoxy-6-bromophenyl | hydroxymethyl | ethyl | |
| 2.5.1150 | 3-nitro-6-bromophenyl | hydroxymethyl | ethyl | |
| 2.5.1151 | 3-fluoro-6-iodophenyl | hydroxymethyl | ethyl | |
| 2.5.1152 | 3-chloro-6-iodophenyl | hydroxymethyl | ethyl | |
| 2.5.1153 | 3-bromo-6-iodophenyl | hydroxymethyl | ethyl | |
| 2.5.1154 | 3-methyl-6-iodophenyl | hydroxymethyl | ethyl | |
| 2.5.1155 | 3-cyclopropyl-6-iodophenyl | hydroxymethyl | ethyl | |
| 2.5.1156 | 3-cyano-6-iodophenyl | hydroxymethyl | ethyl | |
| 2.5.1157 | 3-trifluoromethyl-6-iodophenyl | hydroxymethyl | ethyl | |
| 2.5.1158 | 3-methoxy-6-iodophenyl | hydroxymethyl | ethyl | |
| 2.5.1159 | 3-ethoxy-6-iodophenyl | hydroxymethyl | ethyl | |
| 2.5.1160 | 3-trifluoromethoxy-6-iodophenyl | hydroxymethyl | ethyl | |
| 2.5.1161 | 3-nitro-6-iodophenyl | hydroxymethyl | ethyl | |
| 2.5.1162 | 3-fluoro-6-methylphenyl | hydroxymethyl | ethyl | |
| 2.5.1163 | 3-chloro-6-methylphenyl | hydroxymethyl | ethyl | |
| 2.5.1164 | 3-bromo-6-methylphenyl | hydroxymethyl | ethyl | |
| 2.5.1165 | 3,6-dimethylphenyl | hydroxymethyl | ethyl | |
| 2.5.1166 | 3-cyclopropyl-6-methylphenyl | hydroxymethyl | ethyl | |
| 2.5.1167 | 3-cyano-6-methylphenyl | hydroxymethyl | ethyl | |
| 2.5.1168 | 3-trifluoromethyl-6-methylphenyl | hydroxymethyl | ethyl | |
| 2.5.1169 | 3-methoxy-6-methylphenyl | hydroxymethyl | ethyl | |
| 2.5.1170 | 3-ethoxy-6-methylphenyl | hydroxymethyl | ethyl | |
| 2.5.1171 | 3-trifluoromethoxy-6-methylphenyl | hydroxymethyl | ethyl | |
| 2.5.1172 | 3-nitro-6-methylphenyl | hydroxymethyl | ethyl | |
| 2.5.1173 | 3-fluoro-6-ethylphenyl | hydroxymethyl | ethyl | |
| 2.5.1174 | 3-chloro-6-ethylphenyl | hydroxymethyl | ethyl | |
| 2.5.1175 | 3-bromo-6-ethylphenyl | hydroxymethyl | ethyl | |
| 2.5.1176 | 3-methyl-6-ethylphenyl | hydroxymethyl | ethyl | |
| 2.5.1177 | 3,6-diethylphenyl | hydroxymethyl | ethyl | |
| 2.5.1178 | 3-cyclopropyl-6-ethylphenyl | hydroxymethyl | ethyl | |
| 2.5.1179 | 3-cyano-6-ethylphenyl | hydroxymethyl | ethyl | |
| 2.5.1180 | 3-trifluoromethyl-6-ethylphenyl | hydroxymethyl | ethyl | |
| 2.5.1181 | 3-methoxy-6-ethylphenyl | hydroxymethyl | ethyl | |
| 2.5.1182 | 3-ethoxy-6-ethylphenyl | hydroxymethyl | ethyl | |
| 2.5.1183 | 3-trifluoromethoxy-6-ethylphenyl | hydroxymethyl | ethyl | |
| 2.5.1184 | 3-nitro-6-ethylphenyl | hydroxymethyl | ethyl | |
| 2.5.1185 | 3-fluoro-6-isopropylphenyl | hydroxymethyl | ethyl | |
| 2.5.1186 | 3-chloro-6-isopropylphenyl | hydroxymethyl | ethyl | |
| 2.5.1187 | 3-bromo-6-isopropylphenyl | hydroxymethyl | ethyl | |
| 2.5.1188 | 3-methyl-6-isopropylphenyl | hydroxymethyl | ethyl | |
| 2.5.1189 | 3-ethyl-6-isopropylphenyl | hydroxymethyl | ethyl | |
| 2.5.1190 | 3-cyclopropyl-6-isopropylphenyl | hydroxymethyl | ethyl | |
| 2.5.1191 | 3-cyano-6-isopropylphenyl | hydroxymethyl | ethyl | |
| 2.5.1192 | 3-trifluoromethyl-6-isopropylphenyl | hydroxymethyl | ethyl | |
| 2.5.1193 | 3-methoxy-6-isopropylphenyl | hydroxymethyl | ethyl | |
| 2.5.1194 | 3-ethoxy-6-isopropylphenyl | hydroxymethyl | ethyl | |
| 2.5.1195 | 3-trifluoromethoxy-6-isopropylphenyl | hydroxymethyl | ethyl | |
| 2.5.1196 | 3-nitro-6-isopropylphenyl | hydroxymethyl | ethyl | |

TABLE 2.5-continued

Inventive compounds of the general formula (I) in which W* is COOY,
R¹ and R² are each hydrogen, and aryl is the radical.

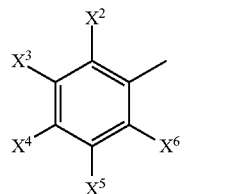

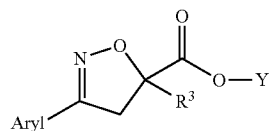

| No. | Aryl | R³ | Y | Physical data |
|---|---|---|---|---|
| 2.5.1197 | 3-fluoro-6-tert-butylphenyl | hydroxymethyl | ethyl | |
| 2.5.1198 | 3-chloro-6-tert-butylphenyl | hydroxymethyl | ethyl | |
| 2.5.1199 | 3-bromo-6-tert-butylphenyl | hydroxymethyl | ethyl | |
| 2.5.1200 | 3-methyl-6-tert-butylphenyl | hydroxymethyl | ethyl | |
| 2.5.1201 | 3-cyclopropyl-6-tert-butylphenyl | hydroxymethyl | ethyl | |
| 2.5.1202 | 3-cyano-6-tert-butylphenyl | hydroxymethyl | ethyl | |
| 2.5.1203 | 3-trifluoromethyl-6-tert-butylphenyl | hydroxymethyl | ethyl | |
| 2.5.1204 | 3-methoxy-6-tert-butylphenyl | hydroxymethyl | ethyl | |
| 2.5.1205 | 3-ethoxy-6-tert-butylphenyl | hydroxymethyl | ethyl | |
| 2.5.1206 | 3-trifluoromethoxy-6-tert-butylphenyl | hydroxymethyl | ethyl | |
| 2.5.1207 | 3-nitro-6-tert-butylphenyl | hydroxymethyl | ethyl | |
| 2.5.1208 | 3-fluoro-6-cyclopropylphenyl | hydroxymethyl | ethyl | |
| 2.5.1209 | 3-chloro-6-cyclopropylphenyl | hydroxymethyl | ethyl | |
| 2.5.1210 | 3-bromo-6-cyclopropylphenyl | hydroxymethyl | ethyl | |
| 2.5.1211 | 3-methyl-6-cyclopropylphenyl | hydroxymethyl | ethyl | |
| 2.5.1212 | 3,6-dicyclopropylphenyl | hydroxymethyl | ethyl | |
| 2.5.1213 | 3-cyano-6-cyclopropylphenyl | hydroxymethyl | ethyl | |
| 2.5.1214 | 3-trifluoromethyl-6-cyclopropylphenyl | hydroxymethyl | ethyl | |
| 2.5.1215 | 3-methoxy-6-cyclopropylphenyl | hydroxymethyl | ethyl | |
| 2.5.1216 | 3-ethoxy-6-cyclopropylphenyl | hydroxymethyl | ethyl | |
| 2.5.1217 | 3-trifluoromethoxy-6-cyclopropylphenyl | hydroxymethyl | ethyl | |
| 2.5.1218 | 3-fluoro-6-methoxycarbonyl-phenyl | hydroxymethyl | ethyl | |
| 2.5.1219 | 3-chloro-6-methoxycarbonyl-phenyl | hydroxymethyl | ethyl | |
| 2.5.1220 | 3-bromo-6-methoxycarbonyl-phenyl | hydroxymethyl | ethyl | |
| 2.5.1221 | 3-methyl-6-methoxycarbonyl-phenyl | hydroxymethyl | ethyl | |
| 2.5.1222 | 3-cyclopropyl-6-methoxycarbonyl-phenyl | hydroxymethyl | ethyl | |
| 2.5.1223 | 3-cyano-6-methoxycarbonyl-phenyl | hydroxymethyl | ethyl | |
| 2.5.1224 | 3-trifluoromethyl-6-methoxycarbonyl-phenyl | hydroxymethyl | ethyl | |
| 2.5.1225 | 3-methoxy-6-methoxycarbonyl-phenyl | hydroxymethyl | ethyl | |
| 2.5.1226 | 3-ethoxy-6-methoxycarbonyl-phenyl | hydroxymethyl | ethyl | |
| 2.5.1227 | 3-trifluoromethoxy-6-methoxycarbonyl-phenyl | hydroxymethyl | ethyl | |
| 2.5.1228 | 3-nitro-6-methoxycarbonyl-phenyl | hydroxymethyl | ethyl | |
| 2.5.1229 | 3-fluoro-6-cyanophenyl | hydroxymethyl | ethyl | |
| 2.5.1230 | 3-chloro-6-cyanophenyl | hydroxymethyl | ethyl | |
| 2.5.1231 | 3-bromo-6-cyanophenyl | hydroxymethyl | ethyl | |
| 2.5.1232 | 3-methyl-6-cyanophenyl | hydroxymethyl | ethyl | |
| 2.5.1233 | 3-cyclopropyl-6-cyanophenyl | hydroxymethyl | ethyl | |
| 2.5.1234 | 3,6-dicyanophenyl | hydroxymethyl | ethyl | |
| 2.5.1235 | 3-trifluoromethyl-6-cyanophenyl | hydroxymethyl | ethyl | |
| 2.5.1236 | 3-methoxy-6-cyanophenyl | hydroxymethyl | ethyl | |
| 2.5.1237 | 3-ethoxy-6-cyanophenyl | hydroxymethyl | ethyl | |
| 2.5.1238 | 3-trifluoromethoxy-6-cyanophenyl | hydroxymethyl | ethyl | |
| 2.5.1239 | 3-nitro-6-cyanophenyl | hydroxymethyl | ethyl | |
| 2.5.1240 | 3-fluoro-6-methoxyphenyl | hydroxymethyl | ethyl | |
| 2.5.1241 | 3-chloro-6-methoxyphenyl | hydroxymethyl | ethyl | |
| 2.5.1242 | 3-bromo-6-methoxyphenyl | hydroxymethyl | ethyl | |
| 2.5.1243 | 3-methyl-6-methoxyphenyl | hydroxymethyl | ethyl | |
| 2.5.1244 | 3-cyclopropyl-6-methoxyphenyl | hydroxymethyl | ethyl | |
| 2.5.1245 | 3-cyano-6-methoxyphenyl | hydroxymethyl | ethyl | |
| 2.5.1246 | 3-trifluoromethyl-6-methoxyphenyl | hydroxymethyl | ethyl | |
| 2.5.1247 | 3,6-dimethoxyphenyl | hydroxymethyl | ethyl | |
| 2.5.1248 | 3-ethoxy-6-methoxyphenyl | hydroxymethyl | ethyl | |
| 2.5.1249 | 3-trifluoromethoxy-6-methoxyphenyl | hydroxymethyl | ethyl | |
| 2.5.1250 | 3-nitro-6-methoxyphenyl | hydroxymethyl | ethyl | |
| 2.5.1251 | 3-fluoro-6-ethoxyphenyl | hydroxymethyl | ethyl | |

TABLE 2.5-continued

Inventive compounds of the general formula (I) in which W* is COOY,
$R^1$ and $R^2$ are each hydrogen, and aryl is the radical.

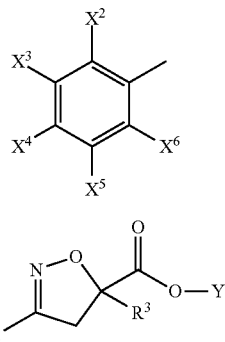

| No. | Aryl | $R^3$ | Y | Physical data |
|---|---|---|---|---|
| 2.5.1252 | 3-chloro-6-ethoxyphenyl | hydroxymethyl | ethyl | |
| 2.5.1253 | 3-bromo-6-ethoxyphenyl | hydroxymethyl | ethyl | |
| 2.5.1254 | 3-methyl-6-ethoxyphenyl | hydroxymethyl | ethyl | |
| 2.5.1255 | 3-cyclopropyl-6-ethoxyphenyl | hydroxymethyl | ethyl | |
| 2.5.1256 | 3-cyano-6-ethoxyphenyl | hydroxymethyl | ethyl | |
| 2.5.1257 | 3-trifluoromethyl-6-ethoxyphenyl | hydroxymethyl | ethyl | |
| 2.5.1258 | 3-methoxy-6-ethoxyphenyl | hydroxymethyl | ethyl | |
| 2.5.1259 | 2,6-diethoxyphenyl | hydroxymethyl | ethyl | |
| 2.5.1260 | 3-trifluoromethoxy-6-ethoxyphenyl | hydroxymethyl | ethyl | |
| 2.5.1261 | 3-nitro-6-ethoxyphenyl | hydroxymethyl | ethyl | |
| 2.5.1262 | 3-fluoro-6-isopropoxyphenyl | hydroxymethyl | ethyl | |
| 2.5.1263 | 3-chloro-6-isopropoxyphenyl | hydroxymethyl | ethyl | |
| 2.5.1264 | 3-bromo-6-isopropoxyphenyl | hydroxymethyl | ethyl | |
| 2.5.1265 | 3-methyl-6-isopropoxyphenyl | hydroxymethyl | ethyl | |
| 2.5.1266 | 3-cyclopropyl-6-isopropoxyphenyl | hydroxymethyl | ethyl | |
| 2.5.1267 | 3-cyano-6-isopropoxyphenyl | hydroxymethyl | ethyl | |
| 2.5.1268 | 3-trifluoromethyl-6-isopropoxyphenyl | hydroxymethyl | ethyl | |
| 2.5.1269 | 3-methoxy-6-isopropoxyphenyl | hydroxymethyl | ethyl | |
| 2.5.1270 | 3-trifluoromethoxy-6-isopropoxyphenyl | hydroxymethyl | ethyl | |
| 2.5.1271 | 3-nitro-6-isopropoxyphenyl | hydroxymethyl | ethyl | |
| 2.5.1272 | 3-fluoro-6-trifluoromethoxy-phenyl | hydroxymethyl | ethyl | |
| 2.5.1273 | 3-chloro-6-trifluoromethoxy-phenyl | hydroxymethyl | ethyl | |
| 2.5.1274 | 3-bromo-6-trifluoromethoxy-phenyl | hydroxymethyl | ethyl | |
| 2.5.1275 | 3-methyl-6-trifluoromethoxy-phenyl | hydroxymethyl | ethyl | |
| 2.5.1276 | 3-cyclopropyl-6-trifluoromethoxyphenyl | hydroxymethyl | ethyl | |
| 2.5.1277 | 3-cyano-6-trifluoromethoxy-phenyl | hydroxymethyl | ethyl | |
| 2.5.1278 | 3-trifluoromethyl-6-trifluoromethoxyphenyl | hydroxymethyl | ethyl | |
| 2.5.1279 | 3-methoxy-6-trifluoromethoxy-phenyl | hydroxymethyl | ethyl | |
| 2.5.1280 | 3-ethoxy-6-trifluoromethoxy-phenyl | hydroxymethyl | ethyl | |
| 2.5.1281 | 3,6-bis(trifluoromethoxy)phenyl | hydroxymethyl | ethyl | |
| 2.5.1282 | 3-nitro-6-trifluoromethoxyphenyl | hydroxymethyl | ethyl | |
| 2.5.1283 | 3-fluoro-6-difluoromethoxy-phenyl | hydroxymethyl | ethyl | |
| 2.5.1284 | 3-chloro-6-difluoromethoxy-phenyl | hydroxymethyl | ethyl | |
| 2.5.1285 | 3-bromo-6-difluoromethoxy-phenyl | hydroxymethyl | ethyl | |
| 2.5.1286 | 3-methyl-6-difluoromethoxy-phenyl | hydroxymethyl | ethyl | |
| 2.5.1287 | 3-ethyl-6-difluoromethoxy-phenyl | hydroxymethyl | ethyl | |
| 2.5.1288 | 3-cyclopropyl-6-difluoromethoxy-phenyl | hydroxymethyl | ethyl | |
| 2.5.1289 | 3-cyano-6-difluoromethoxy-phenyl | hydroxymethyl | ethyl | |
| 2.5.1290 | 3-trifluoromethyl-6-difluoromethoxyphenyl | hydroxymethyl | ethyl | |
| 2.5.1291 | 3-methoxy-6-difluoromethoxy-phenyl | hydroxymethyl | ethyl | |
| 2.5.1292 | 3-nitro-6-difluoromethoxyphenyl | hydroxymethyl | ethyl | |
| 2.5.1293 | 3-fluoro-6-nitrophenyl | hydroxymethyl | ethyl | |
| 2.5.1294 | 3-chloro-6-nitrophenyl | hydroxymethyl | ethyl | |
| 2.5.1295 | 3-bromo-6-nitrophenyl | hydroxymethyl | ethyl | |
| 2.5.1296 | 3-methyl-6-nitrophenyl | hydroxymethyl | ethyl | |
| 2.5.1297 | 3-cyclopropyl-6-nitrophenyl | hydroxymethyl | ethyl | |
| 2.5.1298 | 3-cyano-6-nitrophenyl | hydroxymethyl | ethyl | |
| 2.5.1299 | 3-trifluoromethyl-6-nitrophenyl | hydroxymethyl | ethyl | |

TABLE 2.5-continued

Inventive compounds of the general formula (I) in which W* is COOY, $R^1$ and $R^2$ are each hydrogen, and aryl is the radical.

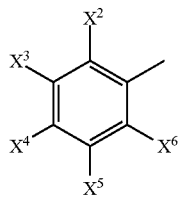

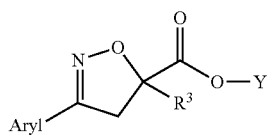

| No. | Aryl | $R^3$ | Y | Physical data |
|---|---|---|---|---|
| 2.5.1300 | 3-methoxy-6-nitrophenyl | hydroxymethyl | ethyl | |
| 2.5.1301 | 3-trifluoromethoxy-6-nitrophenyl | hydroxymethyl | ethyl | |
| 2.5.1302 | 3-fluoro-6-methylsulfanylphenyl | hydroxymethyl | ethyl | |
| 2.5.1303 | 3-chloro-6-methylsulfanylphenyl | hydroxymethyl | ethyl | |
| 2.5.1304 | 3-bromo-6-methylsulfanylphenyl | hydroxymethyl | ethyl | |
| 2.5.1305 | 3-methyl-6-methylsulfanylphenyl | hydroxymethyl | ethyl | |
| 2.5.1306 | 3-cyclopropyl-6-methylsulfanylphenyl | hydroxymethyl | ethyl | |
| 2.5.1307 | 3-cyano-6-methylsulfanylphenyl | hydroxymethyl | ethyl | |
| 2.5.1308 | 3-trifluoromethyl-6-methylsulfanylphenyl | hydroxymethyl | ethyl | |
| 2.5.1309 | 3-methoxy-6-methylsulfanylphenyl | hydroxymethyl | ethyl | |
| 2.5.1310 | 3-trifluoromethoxy-6-methylsulfanylphenyl | hydroxymethyl | ethyl | |
| 2.5.1311 | 3-nitro-6-methylsulfanylphenyl | hydroxymethyl | ethyl | |
| 2.5.1312 | 2,3,4-trifluorophenyl | hydroxymethyl | ethyl | |
| 2.5.1313 | 2,3,4-trichlorophenyl | hydroxymethyl | ethyl | |
| 2.5.1314 | 2,3,4-trimethylphenyl | hydroxymethyl | ethyl | |
| 2.5.1315 | 2-fluoro-2-chloro-5-trifluoromethylphenyl | hydroxymethyl | ethyl | |
| 2.5.1316 | 2,3,5-trifluorophenyl | hydroxymethyl | ethyl | |
| 2.5.1317 | 2,3,5-trichlorophenyl | hydroxymethyl | ethyl | |
| 2.5.1318 | 2,3,5-trimethylphenyl | hydroxymethyl | ethyl | |
| 2.5.1319 | 2,3-dichloro-5-methoxyphenyl | hydroxymethyl | ethyl | |
| 2.5.1320 | 2,3,6-trifluorophenyl | hydroxymethyl | ethyl | |
| 2.5.1321 | 2,3,6-trichlorophenyl | hydroxymethyl | ethyl | |
| 2.5.1322 | 2,3,6-trimethylphenyl | hydroxymethyl | ethyl | |
| 2.5.1323 | 3,4,5-trifluorophenyl | hydroxymethyl | ethyl | |
| 2.5.1324 | 3,4,5-trichlorophenyl | hydroxymethyl | ethyl | |
| 2.5.1325 | 3,4,5-trimethylphenyl | hydroxymethyl | ethyl | |
| 2.5.1326 | 3,5-dimethyl-4-fluorophenyl | hydroxymethyl | ethyl | |
| 2.5.1327 | 3,5-dichloro-4-methoxyphenyl | hydroxymethyl | ethyl | |
| 2.5.1328 | 3,5-difluoro-4-chlorophenyl | hydroxymethyl | ethyl | |
| 2.5.1329 | 3,5-dichloro-4-hydroxyphenyl | hydroxymethyl | ethyl | |
| 2.5.1330 | 3,5-trifluoromethyl-4-chlorophenyl | hydroxymethyl | ethyl | |
| 2.5.1331 | 3,4,6-trifluorophenyl | hydroxymethyl | ethyl | |
| 2.5.1332 | 3,4,6-trichlorophenyl | hydroxymethyl | ethyl | |
| 2.5.1333 | 3,4,6-trimethylphenyl | hydroxymethyl | ethyl | |
| 2.5.1334 | pentafluorophenyl | hydroxymethyl | ethyl | |

TABLE 2.6

Inventive compounds of the general formula (I) in which W* is COOY, R¹ and R² are each hydrogen, and aryl is the radical.

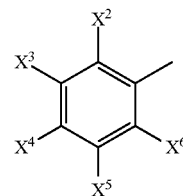

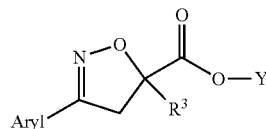

| No. | Aryl | R³ | Y | Physical data |
|---|---|---|---|---|
| 2.6.1 | 3-fluorophenyl | methyl | (cyclohex-2-en-1-one)-3-yl | |
| 2.6.2 | 3-fluorophenyl | methyl | (propan-1-ol)-3-yl | |
| 2.6.3 | 3-fluorophenyl | methyl | (2,2-dimethylpropan-1-ol)-3-yl | |
| 2.6.4 | 3-fluorophenyl | methyl | (methyl 2,2-dimethyl propanoate)-3-yl | |
| 2.6.5 | 3-fluorophenyl | methyl | (methyl propanoate)-3-yl | |
| 2.6.6 | 3-fluorophenyl | methyl | (ethyl propanoate)-3-yl | |
| 2.6.7 | 3-fluorophenyl | methyl | 4-ethoxy-4-oxobutan-2-yl | |
| 2.6.8 | 3-fluorophenyl | methyl | (ethyl (3R)-4,4,4-trifluorobutanoate)-3-yl | |
| 2.6.9 | 3-fluorophenyl | methyl | (butan-1-ol)-4-yl | [CDCl₃] 1.55 (bs , 1H); 1.65 (mc, 2H); 1.75 (s, 3H); 1.80 (mc, 2H); 3.18 (d, 1H); 3.68 (t, 2H); 3.85 (d, 1H); 4.25 (t, 2H); 7.11 (m, 1H); 7.40 (m, 3H). |
| 2.6.10 | 3-fluorophenyl | methyl | (3-methylbutan-2-one)-4-yl | |
| 2.6.11 | 3-fluorophenyl | methyl | (pent-3-en-2-one)-4-yl | |
| 2.6.12 | 3-fluorophenyl | methyl | ((2S)-dimethyl butanedioate)-2-yl | |
| 2.6.13 | 3-fluorophenyl | methyl | (dimethyl pentanedioate)-3-yl | |
| 2.6.14 | 3-fluorophenyl | ethyl | (dimethyl pentanedioate)-3-yl | [CDCl₃] D1 0.98 (t, 3H); 1.24 (t, 3H); 1.35 (d, 3H); 1.95-2.12 (m, 2H); 2.50-2.75 (m, 2H); 3.18 (d, 1H); 3.81 (d, 1H); 3.98-4.09 (m, 2H); 5.33-5.42 (m, 1H); 7.12 (t, 1H); 7.33-7.43 (m 3H). D2 1.02 (t, 3H); 1.19 (t, 3H); 1.36 (d, 3H); 1.95-2.12 (m, 2H); 2.50-2.75 (m, 2H); 3.20 (d, 1H); 3.76 (d, 1H); 4.09-4.17 (m, 2H); 5.33-5.42 (m, 1H); 7.12 (t, 1H); 7.33-7.43 (m 3H). |
| 2.6.15 | 3-fluorophenyl | methyl | (methyl (2R)-2-methyl propanoate)-3-yl | |
| 2.6.16 | 3-fluorophenyl | methyl | 4-methoxycarbonylbenzyl | |
| 2.6.17 | 3-fluorophenyl | methyl | 3,5-difluorobenzyl | |
| 2.6.18 | 3-fluorophenyl | methyl | 3,4-difluorobenzyl | |
| 2.6.19 | 3-fluorophenyl | methyl | 2,6-difluorobenzyl | |
| 2.6.20 | 3-fluorophenyl | methyl | (5-methylpyridin-3-yl)methyl | [CDCl₃] 1.73 (s, 3H); 2.36 (s, 3H); 3.20 (d, 1H); 3.85 (d, 1H); 5.22 (s, 2H); 7.13 (m, 1H); 7.39 (m, 3H); 7.51 (s, 1H); 8.42 (d, 2H). |
| 2.6.21 | 3-fluorophenyl | methyl | (tetrahydrofuran)-3-yl | |
| 2.6.22 | 3-fluorophenyl | ethyl | 4-ethoxy-4-oxobutan-2-yl | |
| 2.6.23 | 3-chlorophenyl | methyl | (ethyl butanoate)-3-yl | |
| 2.6.24 | 3-iodophenyl | methyl | (ethyl butanoate)-3-yl | |
| 2.6.25 | 3-iodophenyl | ethyl | (ethyl butanoate)-3-yl | |
| 2.6.26 | 3-methylphenyl | methyl | (ethyl butanoate)-3-yl | |
| 2.6.27 | 3-methylphenyl | ethyl | (ethyl butanoate)-3-yl | |
| 2.6.28 | 3-ethylphenyl | methyl | (ethyl butanoate)-3-yl | |
| 2.6.29 | 3-propylphenyl | methyl | (ethyl butanoate)-3-yl | |
| 2.6.30 | 3-isopropylphenyl | methyl | (ethyl butanoate)-3-yl | |
| 2.6.31 | 3-n-butylphenyl | methyl | (ethyl butanoate)-3-yl | |
| 2.6.32 | 3-i-butylphenyl | methyl | (ethyl butanoate)-3-yl | |
| 2.6.33 | 3-tert-butylphenyl | methyl | (ethyl butanoate)-3-yl | |
| 2.6.34 | 3-cyclopropyl-phenyl | methyl | (ethyl butanoate)-3-yl | |
| 2.6.35 | 3-cyclobutyl-phenyl | methyl | (ethyl butanoate)-3-yl | |
| 2.6.36 | 3-cyclopentyl-phenyl | methyl | (ethyl butanoate)-3-yl | |
| 2.6.37 | 3-vinylphenyl | methyl | (ethyl butanoate)-3-yl | |
| 2.6.38 | 3-ethynylphenyl | methyl | (ethyl butanoate)-3-yl | |
| 2.6.39 | 3-cyanophenyl | methyl | (ethyl butanoate)-3-yl | |
| 2.6.40 | 3-trifluoromethyl-phenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

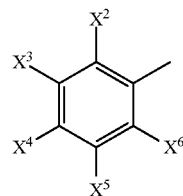

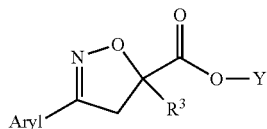

| No. | Aryl | $R^3$ | Y | Physical data |
|---|---|---|---|---|
| 2.6.41 | 3-difluoromethyl-phenyl | methyl | (ethyl butanoate)-3-yl | |
| 2.6.42 | 3-(hydroxy-carbonyl)phenyl | methyl | (ethyl butanoate)-3-yl | |
| 2.6.43 | 3-(methoxy-carbonyl)phenyl | methyl | (ethyl butanoate)-3-yl | |
| 2.6.44 | 3-(ethoxy-carbonyl)phenyl | methyl | (ethyl butanoate)-3-yl | |
| 2.6.45 | 3-hydroxymethyl-phenyl | methyl | (ethyl butanoate)-3-yl | |
| 2.6.46 | 3-acetylphenyl | methyl | (ethyl butanoate)-3-yl | |
| 2.6.47 | 3-carbamoyl-phenyl | methyl | (ethyl butanoate)-3-yl | |
| 2.6.48 | 3-hydroxyphenyl | methyl | (ethyl butanoate)-3-yl | |
| 2.6.49 | 3-methoxyphenyl | methyl | (ethyl butanoate)-3-yl | |
| 2.6.50 | 3-ethoxyphenyl | methyl | (ethyl butanoate)-3-yl | |
| 2.6.51 | 3-propyloxyphenyl | methyl | (ethyl butanoate)-3-yl | |
| 2.6.52 | 3-isopropyloxy-phenyl | methyl | (ethyl butanoate)-3-yl | |
| 2.6.53 | 3-n-butyloxy-phenyl | methyl | (ethyl butanoate)-3-yl | |
| 2.6.54 | 3-i-butyloxyphenyl | methyl | (ethyl butanoate)-3-yl | |
| 2.6.55 | 3-t-butyloxyphenyl | methyl | (ethyl butanoate)-3-yl | |
| 2.6.56 | 3-difluoro-methoxyphenyl | methyl | (ethyl butanoate)-3-yl | |
| 2.6.57 | 3-trifluoro-methoxyphenyl | methyl | (ethyl butanoate)-3-yl | |
| 2.6.58 | 3-(2,2,2-trifluoro-ethoxy)phenyl | methyl | (ethyl butanoate)-3-yl | |
| 2.6.59 | 3-(2-chloro-ethoxy)phenyl | methyl | (ethyl butanoate)-3-yl | |
| 2.6.60 | 3-(2-hydroxy-ethoxy)phenyl | methyl | (ethyl butanoate)-3-yl | |
| 2.6.61 | 3-(2-methoxy-ethoxy)phenyl | methyl | (ethyl butanoate)-3-yl | |
| 2.6.62 | 3-[(tert-butoxy-carbonyl)oxy]-phenyl | methyl | (ethyl butanoate)-3-yl | |
| 2.6.63 | 3-nitrophenyl | methyl | (ethyl butanoate)-3-yl | |
| 2.6.64 | 3-acetoxyphenyl | methyl | (ethyl butanoate)-3-yl | |
| 2.6.65 | {3-[(tert-butoxy-carbonyl)amino]-phenyl} | methyl | (ethyl butanoate)-3-yl | |
| 2.6.66 | 3-methylsulfanyl-phenyl | methyl | (ethyl butanoate)-3-yl | |
| 2.6.67 | 3-ethylsulfanyl-phenyl | methyl | (ethyl butanoate)-3-yl | |
| 2.6.68 | 3-(pentafluoro-lambda$^6$-sulfanyl)-phenyl | methyl | (ethyl butanoate)-3-yl | |
| 2.6.69 | 2,3-difluorophenyl | methyl | (ethyl butanoate)-3-yl | |
| 2.6.70 | 2-chloro-3-fluorophenyl | methyl | (ethyl butanoate)-3-yl | |
| 2.6.71 | 2-bromo-3-fluorophenyl | methyl | (ethyl butanoate)-3-yl | |
| 2.6.72 | 2-methyl-3-fluorophenyl | methyl | (ethyl butanoate)-3-yl | |
| 2.6.73 | 2-ethyl-3-fluorophenyl | methyl | (ethyl butanoate)-3-yl | |
| 2.6.74 | 2-cyclopropyl-3-fluorophenyl | methyl | (ethyl butanoate)-3-yl | |
| 2.6.75 | 2-vinyl-3-fluorophenyl | methyl | (ethyl butanoate)-3-yl | |
| 2.6.76 | 2-ethynyl-3-fluorophenyl | methyl | (ethyl butanoate)-3-yl | |

TABLE 2.6-continued

Inventive compounds of the general formula (I) in which W* is COOY, R¹ and R² are each hydrogen, and aryl is the radical.

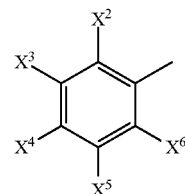

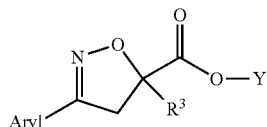

| No. | Aryl | R³ | Y | Physical data |
|---|---|---|---|---|
| 2.6.77 | 2-cyano-3-fluorophenyl | methyl | (ethyl butanoate)-3-yl | |
| 2.6.78 | 2-methoxy-3-fluorophenyl | methyl | (ethyl butanoate)-3-yl | |
| 2.6.79 | 2-ethoxy-3-fluorophenyl | methyl | (ethyl butanoate)-3-yl | |
| 2.6.80 | 2-trifluoro-methoxy-3-fluorophenyl | methyl | (ethyl butanoate)-3-yl | |
| 2.6.81 | 2-nitro-3-fluorophenyl | methyl | (ethyl butanoate)-3-yl | |
| 2.6.82 | 2-fluoro-3-chlorophenyl | methyl | (ethyl butanoate)-3-yl | |
| 2.6.83 | 2,3-dichloro-phenyl | methyl | (ethyl butanoate)-3-yl | |
| 2.6.84 | 2-bromo-3-chlorophenyl | methyl | (ethyl butanoate)-3-yl | |
| 2.6.85 | 2-methyl-3-chlorophenyl | methyl | (ethyl butanoate)-3-yl | |
| 2.6.86 | 2-ethyl-3-chlorophenyl | methyl | (ethyl butanoate)-3-yl | |
| 2.6.87 | 2-cyclopropyl-3-chlorophenyl | methyl | (ethyl butanoate)-3-yl | |
| 2.6.88 | 2-vinyl-3-chlorophenyl | methyl | (ethyl butanoate)-3-yl | |
| 2.6.89 | 2-ethynyl-3-chlorophenyl | methyl | (ethyl butanoate)-3-yl | |
| 2.6.90 | 2-cyano-3-chlorophenyl | methyl | (ethyl butanoate)-3-yl | |
| 2.6.91 | 2-trifluoromethyl-2-chlorophenyl | methyl | (ethyl butanoate)-3-yl | |
| 2.6.92 | 2-methoxy-3-chlorophenyl | methyl | (ethyl butanoate)-3-yl | |
| 2.6.93 | 2-ethoxy-3-chlorophenyl | methyl | (ethyl butanoate)-3-yl | |
| 2.6.94 | 2-trifluoro-methoxy-3-chlorophenyl | methyl | (ethyl butanoate)-3-yl | |
| 2.6.95 | 2-nitro-3-chlorophenyl | methyl | (ethyl butanoate)-3-yl | |
| 2.6.96 | 2-fluoro-3-bromophenyl | methyl | (ethyl butanoate)-3-yl | |
| 2.6.97 | 2-chloro-3-bromophenyl | methyl | (ethyl butanoate)-3-yl | |
| 2.6.98 | 2,3-dibromo-phenyl | methyl | (ethyl butanoate)-3-yl | |
| 2.6.99 | 2-methyl-3-bromophenyl | methyl | (ethyl butanoate)-3-yl | |
| 2.6.100 | 2-ethyl-3-bromophenyl | methyl | (ethyl butanoate)-3-yl | |
| 2.6.101 | 2-cyclopropyl-3-bromophenyl | methyl | (ethyl butanoate)-3-yl | |
| 2.6.102 | 2-vinyl-3-bromophenyl | methyl | (ethyl butanoate)-3-yl | |
| 2.6.103 | 2-ethynyl-3-bromophenyl | methyl | (ethyl butanoate)-3-yl | |
| 2.6.104 | 2-cyano-3-bromophenyl | methyl | (ethyl butanoate)-3-yl | |
| 2.6.105 | 2-trifluoromethyl-3-bromophenyl | methyl | (ethyl butanoate)-3-yl | |
| 2.6.106 | 2-methoxy-3-phenyl | methyl | (ethyl butanoate)-3-yl | |
| 2.6.107 | 2-ethoxy-3-bromophenyl | methyl | (ethyl butanoate)-3-yl | |
| 2.6.108 | 2-trifluoro-methoxy-3-bromophenyl | methyl | (ethyl butanoate)-3-yl | |
| 2.6.109 | 2-nitro-3-bromophenyl | methyl | (ethyl butanoate)-3-yl | |
| 2.6.110 | 2-fluoro-3-iodophenyl | methyl | (ethyl butanoate)-3-yl | |
| 2.6.111 | 2-chloro-3-iodophenyl | methyl | (ethyl butanoate)-3-yl | |
| 2.6.112 | 2-bromo-3-iodophenyl | methyl | (ethyl butanoate)-3-yl | |

TABLE 2.6-continued

Inventive compounds of the general formula (I) in which W* is COOY, R¹ and R² are each hydrogen, and aryl is the radical.

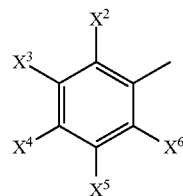

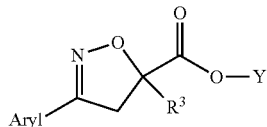

| No. | Aryl | R³ | Y | Physical data |
|---|---|---|---|---|
| 2.6.113 | 2-methyl-3-iodophenyl | methyl | (ethyl butanoate)-3-yl | |
| 2.6.114 | 2-ethyl-3-iodophenyl | methyl | (ethyl butanoate)-3-yl | |
| 2.6.115 | 2-cyclopropyl-3-iodophenyl | methyl | (ethyl butanoate)-3-yl | |
| 2.6.116 | 2-vinyl-3-iodophenyl | methyl | (ethyl butanoate)-3-yl | |
| 2.6.117 | 2-ethynyl-3-iodophenyl | methyl | (ethyl butanoate)-3-yl | |
| 2.6.118 | 2-cyano-3-iodophenyl | methyl | (ethyl butanoate)-3-yl | |
| 2.6.119 | 2-trifluoromethyl-3-iodophenyl | methyl | (ethyl butanoate)-3-yl | |
| 2.6.120 | 2-methoxy-3-iodophenyl | methyl | (ethyl butanoate)-3-yl | |
| 2.6.121 | 2-ethoxy-3-iodophenyl | methyl | (ethyl butanoate)-3-yl | |
| 2.6.122 | 2-trifluoro-methoxy-3-iodophenyl | methyl | (ethyl butanoate)-3-yl | |
| 2.6.123 | 2-nitro-3-iodophenyl | methyl | (ethyl butanoate)-3-yl | |
| 2.6.124 | 2-fluoro-3-methylphenyl | methyl | (ethyl butanoate)-3-yl | |
| 2.6.125 | 2-chloro-3-methylphenyl | methyl | (ethyl butanoate)-3-yl | |
| 2.6.126 | 2-bromo-3-methylphenyl | methyl | (ethyl butanoate)-3-yl | |
| 2.6.127 | 2,3-dimethyl-phenyl | methyl | (ethyl butanoate)-3-yl | |
| 2.6.128 | 2-ethyl-3-methylphenyl | methyl | (ethyl butanoate)-3-yl | |
| 2.6.129 | 2-cyclopropyl-3-methylphenyl | methyl | (ethyl butanoate)-3-yl | |
| 2.6.130 | 2-vinyl-3-methylphenyl | methyl | (ethyl butanoate)-3-yl | |
| 2.6.131 | 2-ethynyl-3-methylphenyl | methyl | (ethyl butanoate)-3-yl | |
| 2.6.132 | 2-cyano-3-methylphenyl | methyl | (ethyl butanoate)-3-yl | |
| 2.6.133 | 2-trifluoromethyl-3-methylphenyl | methyl | (ethyl butanoate)-3-yl | |
| 2.6.134 | 2-methoxy-3-methylphenyl | methyl | (ethyl butanoate)-3-yl | |
| 2.6.135 | 2-ethoxy-3-methylphenyl | methyl | (ethyl butanoate)-3-yl | |
| 2.6.136 | 2-trifluoro-methoxy-3-methylphenyl | methyl | (ethyl butanoate)-3-yl | |
| 2.6.137 | 2-nitro-3-methylphenyl | methyl | (ethyl butanoate)-3-yl | |
| 2.6.138 | 2-fluoro-3-ethylphenyl | methyl | (ethyl butanoate)-3-yl | |
| 2.6.139 | 2-chloro-3-ethylphenyl | methyl | (ethyl butanoate)-3-yl | |
| 2.6.140 | 2-bromo-3-ethylphenyl | methyl | (ethyl butanoate)-3-yl | |
| 2.6.141 | 2-methyl-3-ethylphenyl | methyl | (ethyl butanoate)-3-yl | |
| 2.6.142 | 2,3-diethylphenyl | methyl | (ethyl butanoate)-3-yl | |
| 2.6.143 | 2-cyclopropyl-3-ethylphenyl | methyl | (ethyl butanoate)-3-yl | |
| 2.6.144 | 2-vinyl-3-ethylphenyl | methyl | (ethyl butanoate)-3-yl | |
| 2.6.145 | 2-ethynyl-3-ethylphenyl | methyl | (ethyl butanoate)-3-yl | |
| 2.6.146 | 2-cyano-3-ethylphenyl | methyl | (ethyl butanoate)-3-yl | |
| 2.6.147 | 2-trifluoromethyl-3-ethylphenyl | methyl | (ethyl butanoate)-3-yl | |
| 2.6.148 | 2-methoxy-3-ethylphenyl | methyl | (ethyl butanoate)-3-yl | |
| 2.6.149 | 2-ethoxy-3-ethylphenyl | methyl | (ethyl butanoate)-3-yl | |

TABLE 2.6-continued

Inventive compounds of the general formula (I) in which W* is COOY, R¹ and R² are each hydrogen, and aryl is the radical.

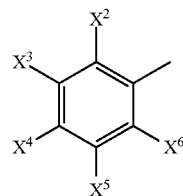

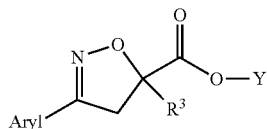

| No. | Aryl | R³ | Y | Physical data |
|---|---|---|---|---|
| 2.6.150 | 2-trifluoro-methoxy-3-ethylphenyl | methyl | (ethyl butanoate)-3-yl | |
| 2.6.151 | 2-nitro-3-ethylphenyl | methyl | (ethyl butanoate)-3-yl | |
| 2.6.152 | 2-fluoro-3-propylphenyl | methyl | (ethyl butanoate)-3-yl | |
| 2.6.153 | 2-chloro-3-propylphenyl | methyl | (ethyl butanoate)-3-yl | |
| 2.6.154 | 2-bromo-3-propylphenyl | methyl | (ethyl butanoate)-3-yl | |
| 2.6.155 | 2-methyl-3-propylphenyl | methyl | (ethyl butanoate)-3-yl | |
| 2.6.156 | 2-methyl-3-propylphenyl | methyl | (ethyl butanoate)-3-yl | |
| 2.6.157 | 2-cyclopropyl-3-propylphenyl | methyl | (ethyl butanoate)-3-yl | |
| 2.6.158 | 2-vinyl-3-propylphenyl | methyl | (ethyl butanoate)-3-yl | |
| 2.6.159 | 2-ethynyl-3propylphenyl | methyl | (ethyl butanoate)-3-yl | |
| 2.6.160 | 2-cyano-3-propylphenyl | methyl | (ethyl butanoate)-3-yl | |
| 2.6.161 | 2-trifluoromethyl-3-propylphenyl | methyl | (ethyl butanoate)-3-yl | |
| 2.6.162 | 2-methoxy-3-propylphenyl | methyl | (ethyl butanoate)-3-yl | |
| 2.6.163 | 2-ethoxy-3-propylphenyl | methyl | (ethyl butanoate)-3-yl | |
| 2.6.164 | 2-trifluoro-methoxy-3-propylphenyl | methyl | (ethyl butanoate)-3-yl | |
| 2.6.165 | 2-nitro-3-propylphenyl | methyl | (ethyl butanoate)-3-yl | |
| 2.6.166 | 2-fluoro-3-isopropylphenyl | methyl | (ethyl butanoate)-3-yl | |
| 2.6.167 | 2-chloro-3-isopropylphenyl | methyl | (ethyl butanoate)-3-yl | |
| 2.6.168 | 2-bromo-3-isopropylphenyl | methyl | (ethyl butanoate)-3-yl | |
| 2.6.169 | 2-methyl-3-isopropylphenyl | methyl | (ethyl butanoate)-3-yl | |
| 2.6.170 | 2-ethyl-3-isopropylphenyl | methyl | (ethyl butanoate)-3-yl | |
| 2.6.171 | 2-cyclopropyl-3-isopropylphenyl | methyl | (ethyl butanoate)-3-yl | |
| 2.6.172 | 2-vinyl-3-isopropylphenyl | methyl | (ethyl butanoate)-3-yl | |
| 2.6.173 | 2-ethynyl-3-isopropylphenyl | methyl | (ethyl butanoate)-3-yl | |
| 2.6.174 | 2-cyano-3-isopropylphenyl | methyl | (ethyl butanoate)-3-yl | |
| 2.6.175 | 2-trifluoromethyl-3-isopropylphenyl | methyl | (ethyl butanoate)-3-yl | |
| 2.6.176 | 2-methoxy-3-isopropylphenyl | methyl | (ethyl butanoate)-3-yl | |
| 2.6.177 | 2-ethoxy-3-isopropylphenyl | methyl | (ethyl butanoate)-3-yl | |
| 2.6.178 | 2-trifluoro-methoxy-3-isopropylphenyl | methyl | (ethyl butanoate)-3-yl | |
| 2.6.179 | 2-nitro-3-isopropylphenyl | methyl | (ethyl butanoate)-3-yl | |
| 2.6.180 | 2-fluoro-3-tert-butylphenyl | methyl | (ethyl butanoate)-3-yl | |

TABLE 2.6-continued

Inventive compounds of the general formula (I) in which W* is COOY, R¹ and R² are each hydrogen, and aryl is the radical.

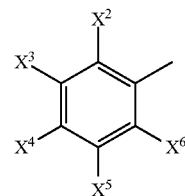

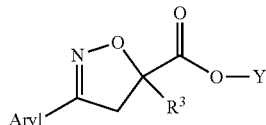

| No. | Aryl | R³ | Y | Physical data |
|---|---|---|---|---|
| 2.6.181 | 2-chloro-3-tert-butylphenyl | methyl | (ethyl butanoate)-3-yl | |
| 2.6.182 | 2-bromo-3-tert-butylphenyl | methyl | (ethyl butanoate)-3-yl | |
| 2.6.183 | 2-methyl-3-tert-butylphenyl | methyl | (ethyl butanoate)-3-yl | |
| 2.6.184 | 2-ethyl-3-tert-butylphenyl | methyl | (ethyl butanoate)-3-yl | |
| 2.6.185 | 2-cyclopropyl-3-tert-butylphenyl | methyl | (ethyl butanoate)-3-yl | |
| 2.6.186 | 2-vinyl-3-tert-butylphenyl | methyl | (ethyl butanoate)-3-yl | |
| 2.6.187 | 2-ethynyl-3-tert-butylphenyl | methyl | (ethyl butanoate)-3-yl | |
| 2.6.188 | 2-cyano-3-tert-butylphenyl | methyl | (ethyl butanoate)-3-yl | |
| 2.6.189 | 2-trifluoromethyl-3-tert-butylphenyl | methyl | (ethyl butanoate)-3-yl | |
| 2.6.190 | 2-methoxy-3-tert-butylphenyl | methyl | (ethyl butanoate)-3-yl | |
| 2.6.191 | 2-ethoxy-3-tert-butylphenyl | methyl | (ethyl butanoate)-3-yl | |
| 2.6.192 | 2-trifluoro-methoxy-3-tert-butylphenyl | methyl | (ethyl butanoate)-3-yl | |
| 2.6.193 | 2-nitro-3-tert-butylphenyl | methyl | (ethyl butanoate)-3-yl | |
| 2.6.194 | 2-fluoro-3-hydroxy-methylphenyl | methyl | (ethyl butanoate)-3-yl | |
| 2.6.195 | 2-chloro-3-hydroxy-methylphenyl | methyl | (ethyl butanoate)-3-yl | |
| 2.6.196 | 2-bromo-3-hydroxy-methylphenyl | methyl | (ethyl butanoate)-3-yl | |
| 2.6.197 | 2-methyl-3-hydroxy-methylphenyl | methyl | (ethyl butanoate)-3-yl | |
| 2.6.198 | 2-ethyl-3-hydroxy-methylphenyl | methyl | (ethyl butanoate)-3-yl | |
| 2.6.199 | 2-cyclopropyl-3-hydroxymethylphenyl | methyl | (ethyl butanoate)-3-yl | |
| 2.6.200 | 2-vinyl-3-hydroxy-methylphenyl | methyl | (ethyl butanoate)-3-yl | |
| 2.6.201 | 2-ethynyl-3-hydroxy-methylphenyl | methyl | (ethyl butanoate)-3-yl | |
| 2.6.202 | 2-cyano-3-hydroxy-methylphenyl | methyl | (ethyl butanoate)-3-yl | |
| 2.6.203 | 2-trifluoromethyl-3-hydroxy-methylphenyl | methyl | (ethyl butanoate)-3-yl | |
| 2.6.204 | 2-methoxy-3-hydroxy-methylphenyl | methyl | (ethyl butanoate)-3-yl | |
| 2.6.205 | 2-ethoxy-3-hydroxy-methylphenyl | methyl | (ethyl butanoate)-3-yl | |
| 2.6.206 | 2-trifluoro-methoxy-3-hydroxymethyl-phenyl | methyl | (ethyl butanoate)-3-yl | |
| 2.6.207 | 2-nitro-3-hydroxy-methylphenyl | methyl | (ethyl butanoate)-3-yl | |
| 2.6.208 | 2-fluoro-3-cyclopropylphenyl | methyl | (ethyl butanoate)-3-yl | |
| 2.6.209 | 2-chloro-3-cyclopropylphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

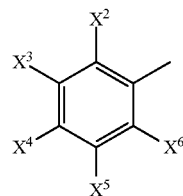

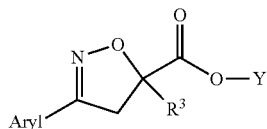

| No. | Aryl | $R^3$ | Y | Physical data |
|---|---|---|---|---|
| 2.6.210 | 2-bromo-3-cyclopropylphenyl | methyl | (ethyl butanoate)-3-yl | |
| 2.6.211 | 2-methyl-3-cyclopropylphenyl | methyl | (ethyl butanoate)-3-yl | |
| 2.6.212 | 2-ethyl-3-cyclopropylphenyl | methyl | (ethyl butanoate)-3-yl | |
| 2.6.213 | 2-cyclopropyl-3-cyclopropylphenyl | methyl | (ethyl butanoate)-3-yl | |
| 2.6.214 | 2-vinyl-3-cyclopropylphenyl | methyl | (ethyl butanoate)-3-yl | |
| 2.6.215 | 2-ethynyl-3-cyclopropylphenyl | methyl | (ethyl butanoate)-3-yl | |
| 2.6.216 | 2-cyano-3-cyclopropylphenyl | methyl | (ethyl butanoate)-3-yl | |
| 2.6.217 | 2-trifluoromethyl-3-cyclopropyl-phenyl | methyl | (ethyl butanoate)-3-yl | |
| 2.6.218 | 2-methoxy-3-cyclopropylphenyl | methyl | (ethyl butanoate)-3-yl | |
| 2.6.219 | 2-ethoxy-3-cyclopropylphenyl | methyl | (ethyl butanoate)-3-yl | |
| 2.6.220 | 2-trifluoro-methoxy-3-cyclopropylphenyl | methyl | (ethyl butanoate)-3-yl | |
| 2.6.221 | 2-fluoro-3-methoxy-carbonylphenyl | methyl | (ethyl butanoate)-3-yl | |
| 2.6.222 | 2-chloro-3-methoxy-carbonylphenyl | methyl | (ethyl butanoate)-3-yl | |
| 2.6.223 | 2-bromo-3-methoxy-carbonylphenyl | methyl | (ethyl butanoate)-3-yl | |
| 2.6.224 | 2-methyl-3-methoxy-carbonylphenyl | methyl | (ethyl butanoate)-3-yl | |
| 2.6.225 | 2-ethyl-3-methoxy-carbonylphenyl | methyl | (ethyl butanoate)-3-yl | |
| 2.6.226 | 2-cyclopropyl-3-methoxycarbonyl-phenyl | methyl | (ethyl butanoate)-3-yl | |
| 2.6.227 | 2-vinyl-3-methoxy-carbonylphenyl | methyl | (ethyl butanoate)-3-yl | |
| 2.6.228 | 2-ethynyl-3-methoxycarbonyl-phenyl | methyl | (ethyl butanoate)-3-yl | |
| 2.6.229 | 2-cyano-3-methoxy-carbonylphenyl | methyl | (ethyl butanoate)-3-yl | |
| 2.6.230 | 2-trifluoromethyl-3-methoxy-carbonylphenyl | methyl | (ethyl butanoate)-3-yl | |
| 2.6.231 | 2-methoxy-3-methoxycarbonyl-phenyl | methyl | (ethyl butanoate)-3-yl | |
| 2.6.232 | 2-ethoxy-3-methoxy-carbonylphenyl | methyl | (ethyl butanoate)-3-yl | |
| 2.6.233 | 2-trifluoro-methoxy-3-methoxy-carbonylphenyl | methyl | (ethyl butanoate)-3-yl | |
| 2.6.234 | 2-nitro-3-methoxy-carbonylphenyl | methyl | (ethyl butanoate)-3-yl | |
| 2.6.235 | 2-fluoro-3-vinylphenyl | methyl | (ethyl butanoate)-3-yl | |
| 2.6.236 | 2-chloro-3-vinylphenyl | methyl | (ethyl butanoate)-3-yl | |
| 2.6.237 | 2-bromo-3-vinylphenyl | methyl | (ethyl butanoate)-3-yl | |

TABLE 2.6-continued

Inventive compounds of the general formula (I) in which W* is COOY, R¹ and R² are each hydrogen, and aryl is the radical.

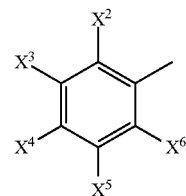

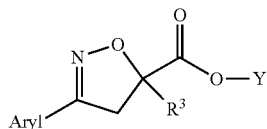

| No. | Aryl | R³ | Y | Physical data |
|---|---|---|---|---|
| 2.6.238 | 2-methyl-3-vinylphenyl | methyl | (ethyl butanoate)-3-yl | |
| 2.6.239 | 2-ethyl-3-vinylphenyl | methyl | (ethyl butanoate)-3-yl | |
| 2.6.240 | 2-cyclopropyl-3-vinylphenyl | methyl | (ethyl butanoate)-3-yl | |
| 2.6.241 | 2-vinyl-3-vinylphenyl | methyl | (ethyl butanoate)-3-yl | |
| 2.6.242 | 2-ethynyl-3-vinylphenyl | methyl | (ethyl butanoate)-3-yl | |
| 2.6.243 | 2-cyano-3-vinylphenyl | methyl | (ethyl butanoate)-3-yl | |
| 2.6.244 | 2-trifluoromethyl-3-vinylphenyl | methyl | (ethyl butanoate)-3-yl | |
| 2.6.245 | 2-methoxy-3-vinylphenyl | methyl | (ethyl butanoate)-3-yl | |
| 2.6.246 | 2-ethoxy-3-vinylphenyl | methyl | (ethyl butanoate)-3-yl | |
| 2.6.247 | 2-trifluoro-methoxy-3-vinylphenyl | methyl | (ethyl butanoate)-3-yl | |
| 2.6.248 | 2-nitro-3-vinylphenyl | methyl | (ethyl butanoate)-3-yl | |
| 2.6.249 | 2-fluoro-3-ethynylphenyl | methyl | (ethyl butanoate)-3-yl | |
| 2.6.250 | 2-chloro-3-ethynylphenyl | methyl | (ethyl butanoate)-3-yl | |
| 2.6.251 | 2-bromo-3-ethynylphenyl | methyl | (ethyl butanoate)-3-yl | |
| 2.6.252 | 2-methyl-3-ethynylphenyl | methyl | (ethyl butanoate)-3-yl | |
| 2.6.253 | 2-ethyl-3-ethynylphenyl | methyl | (ethyl butanoate)-3-yl | |
| 2.6.254 | 2-cyclopropyl-3-ethynylphenyl | methyl | (ethyl butanoate)-3-yl | |
| 2.6.255 | 2-vinyl-3-ethynylphenyl | methyl | (ethyl butanoate)-3-yl | |
| 2.6.256 | 2-cyano-3-ethynylphenyl | methyl | (ethyl butanoate)-3-yl | |
| 2.6.257 | 2-trifluoromethyl-3-ethynylphenyl | methyl | (ethyl butanoate)-3-yl | |
| 2.6.258 | 2-methoxy-3-ethynylphenyl | methyl | (ethyl butanoate)-3-yl | |
| 2.6.259 | 2-ethoxy-3-ethynylphenyl | methyl | (ethyl butanoate)-3-yl | |
| 2.6.260 | 2-trifluoro-methoxy-3-ethynylphenyl | methyl | (ethyl butanoate)-3-yl | |
| 2.6.261 | 2-nitro-3-ethynylphenyl | methyl | (ethyl butanoate)-3-yl | |
| 2.6.262 | 2-fluoro-3-ethynylphenyl | methyl | (ethyl butanoate)-3-yl | |
| 2.6.263 | 2-fluoro-3-cyanophenyl | methyl | (ethyl butanoate)-3-yl | |
| 2.6.264 | 2-chloro-3-cyanophenyl | methyl | (ethyl butanoate)-3-yl | |
| 2.6.265 | 2-bromo-3-cyanophenyl | methyl | (ethyl butanoate)-3-yl | |
| 2.6.266 | 2-methyl-3-cyanophenyl | methyl | (ethyl butanoate)-3-yl | |
| 2.6.267 | 2-ethyl-3-cyanophenyl | methyl | (ethyl butanoate)-3-yl | |
| 2.6.268 | 2-ethyl-3-cyanophenyl | ethyl | (ethyl butanoate)-3-yl | |
| 2.6.269 | 2-ethyl-3-cyanophenyl | propyl | (ethyl butanoate)-3-yl | |

TABLE 2.6-continued

Inventive compounds of the general formula (I) in which W* is COOY, R¹ and R² are each hydrogen, and aryl is the radical.

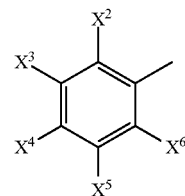

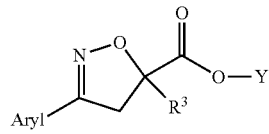

| No. | Aryl | R³ | Y | Physical data |
|---|---|---|---|---|
| 2.6.270 | 2-ethyl-3-cyanophenyl | cyclopropyl | (ethyl butanoate)-3-yl | |
| 2.6.271 | 2-cyclopropyl-3-cyanophenyl | methyl | (ethyl butanoate)-3-yl | |
| 2.6.272 | 2-vinyl-3-cyanophenyl | methyl | (ethyl butanoate)-3-yl | |
| 2.6.273 | 2-ethynyl-3-cyanophenyl | methyl | (ethyl butanoate)-3-yl | |
| 2.6.274 | 2-cyano-3-cyanophenyl | methyl | (ethyl butanoate)-3-yl | |
| 2.6.275 | 2-trifluoromethyl-3-cyanophenyl | methyl | (ethyl butanoate)-3-yl | |
| 2.6.276 | 2-methoxy-3-cyanophenyl | methyl | (ethyl butanoate)-3-yl | |
| 2.6.277 | 2-ethoxy-3-cyanophenyl | methyl | (ethyl butanoate)-3-yl | |
| 2.6.278 | 2-trifluoro-methoxy-3-cyanophenyl | methyl | (ethyl butanoate)-3-yl | |
| 2.6.279 | 2-nitro-3-cyanophenyl | methyl | (ethyl butanoate)-3-yl | |
| 2.6.280 | 2-fluoro-3-hydroxyphenyl | methyl | (ethyl butanoate)-3-yl | |
| 2.6.281 | 2-chloro-3-hydroxyphenyl | methyl | (ethyl butanoate)-3-yl | |
| 2.6.282 | 2-bromo-3-hydroxyphenyl | methyl | (ethyl butanoate)-3-yl | |
| 2.6.283 | 2-methyl-3-hydroxyphenyl | methyl | (ethyl butanoate)-3-yl | |
| 2.6.284 | 2-ethyl-3-hydroxyphenyl | methyl | (ethyl butanoate)-3-yl | |
| 2.6.285 | 2-cyclopropyl-3-hydroxyphenyl | methyl | (ethyl butanoate)-3-yl | |
| 2.6.286 | 2-vinyl-3-hydroxyphenyl | methyl | (ethyl butanoate)-3-yl | |
| 2.6.287 | 2-ethynyl-3-hydroxyphenyl | methyl | (ethyl butanoate)-3-yl | |
| 2.6.288 | 2-cyano-3-hydroxyphenyl | methyl | (ethyl butanoate)-3-yl | |
| 2.6.289 | 2-trifluoromethyl-3-hydroxyphenyl | methyl | (ethyl butanoate)-3-yl | |
| 2.6.290 | 2-methoxy-3-hydroxyphenyl | methyl | (ethyl butanoate)-3-yl | |
| 2.6.291 | 2-ethoxy-3-hydroxyphenyl | methyl | (ethyl butanoate)-3-yl | |
| 2.6.292 | 2-trifluoro-methoxy-3-hydroxyphenyl | methyl | (ethyl butanoate)-3-yl | |
| 2.6.293 | 2-nitro-3-hydroxyphenyl | methyl | (ethyl butanoate)-3-yl | |
| 2.6.294 | 2-fluoro-3-methoxyphenyl | methyl | (ethyl butanoate)-3-yl | |
| 2.6.295 | 2-chloro-3-methoxyphenyl | methyl | (ethyl butanoate)-3-yl | |
| 2.6.296 | 2-bromo-3-methoxyphenyl | methyl | (ethyl butanoate)-3-yl | |
| 2.6.297 | 2-methyl-3-methoxyphenyl | methyl | (ethyl butanoate)-3-yl | |
| 2.6.298 | 2-ethyl-3-methoxyphenyl | methyl | (ethyl butanoate)-3-yl | |
| 2.6.299 | 2-cyclopropyl-3-methoxyphenyl | methyl | (ethyl butanoate)-3-yl | |
| 2.6.300 | 2-vinyl-3-methoxyphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

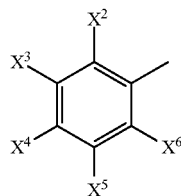

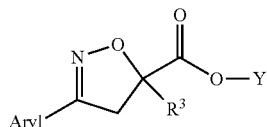

| No. | Aryl | $R^3$ | Y | Physical data |
|---|---|---|---|---|
| 2.6.301 | 2-ethynyl-3-methoxyphenyl | methyl | (ethyl butanoate)-3-yl | |
| 2.6.302 | 2-cyano-3-methoxyphenyl | methyl | (ethyl butanoate)-3-yl | |
| 2.6.303 | 2-trifluoromethyl-3-methoxyphenyl | methyl | (ethyl butanoate)-3-yl | |
| 2.6.304 | 2,3-dimethoxyphenyl | methyl | (ethyl butanoate)-3-yl | |
| 2.6.305 | 2-ethoxy-3-methoxyphenyl | methyl | (ethyl butanoate)-3-yl | |
| 2.6.306 | 2-trifluoro-methoxy-3-methoxyphenyl | methyl | (ethyl butanoate)-3-yl | |
| 2.6.307 | 2-nitro-3-methoxyphenyl | methyl | (ethyl butanoate)-3-yl | |
| 2.6.308 | 2-fluoro-3-ethoxyphenyl | methyl | (ethyl butanoate)-3-yl | |
| 2.6.309 | 2-chloro-3-ethoxyphenyl | methyl | (ethyl butanoate)-3-yl | |
| 2.6.310 | 2-bromo-3-ethoxyphenyl | methyl | (ethyl butanoate)-3-yl | |
| 2.6.311 | 2-methyl-3-ethoxyphenyl | methyl | (ethyl butanoate)-3-yl | |
| 2.6.312 | 2-ethyl-3-ethoxyphenyl | methyl | (ethyl butanoate)-3-yl | |
| 2.6.313 | 2-cyclopropyl-3-ethoxyphenyl | methyl | (ethyl butanoate)-3-yl | |
| 2.6.314 | 2-vinyl-3-ethoxyphenyl | methyl | (ethyl butanoate)-3-yl | |
| 2.6.315 | 2-ethynyl-3-ethoxyphenyl | methyl | (ethyl butanoate)-3-yl | |
| 2.6.316 | 2-cyano-3-ethoxyphenyl | methyl | (ethyl butanoate)-3-yl | |
| 2.6.317 | 2-trifluoromethyl-3-ethoxyphenyl | methyl | (ethyl butanoate)-3-yl | |
| 2.6.318 | 2-methoxy-3-ethoxyphenyl | methyl | (ethyl butanoate)-3-yl | |
| 2.6.319 | 2,3-diethoxy--phenyl | methyl | (ethyl butanoate)-3-yl | |
| 2.6.320 | 2-trifluoro-methoxy-3-ethoxyphenyl | methyl | (ethyl butanoate)-3-yl | |
| 2.6.321 | 2-nitro-3-ethoxyphenyl | methyl | (ethyl butanoate)-3-yl | |
| 2.6.322 | 2-fluoro-3-propoxyphenyl | methyl | (ethyl butanoate)-3-yl | |
| 2.6.323 | 2-chloro-3-propoxyphenyl | methyl | (ethyl butanoate)-3-yl | |
| 2.6.324 | 2-bromo-3-propoxyphenyl | methyl | (ethyl butanoate)-3-yl | |
| 2.6.325 | 2-methyl-3-propoxyphenyl | methyl | (ethyl butanoate)-3-yl | |
| 2.6.326 | 2-ethyl-3-propoxyphenyl | methyl | (ethyl butanoate)-3-yl | |
| 2.6.327 | 2-cyclopropyl-3-propoxyphenyl | methyl | (ethyl butanoate)-3-yl | |
| 2.6.328 | 2-vinyl-3-propoxyphenyl | methyl | (ethyl butanoate)-3-yl | |
| 2.6.329 | 2-ethynyl-3-propoxyphenyl | methyl | (ethyl butanoate)-3-yl | |
| 2.6.330 | 2-cyano-3-propoxyphenyl | methyl | (ethyl butanoate)-3-yl | |
| 2.6.331 | 2-trifluoromethyl-3-propoxyphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

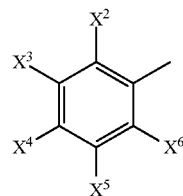

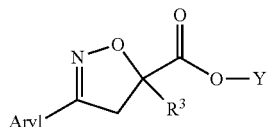

| No. | Aryl | $R^3$ | Y | Physical data |
|---|---|---|---|---|
| 2.6.332 | 2-methoxy-3-propoxyphenyl | methyl | (ethyl butanoate)-3-yl | |
| 2.6.333 | 2-ethoxy-3-propoxyphenyl | methyl | (ethyl butanoate)-3-yl | |
| 2.6.334 | 2-trifluoro-methoxy-3-propoxyphenyl | methyl | (ethyl butanoate)-3-yl | |
| 2.6.335 | 2-nitro-3-propoxyphenyl | methyl | (ethyl butanoate)-3-yl | |
| 2.6.336 | 2-fluoro-3-isopropoxyphenyl | methyl | (ethyl butanoate)-3-yl | |
| 2.6.337 | 2-chloro-3-isopropoxyphenyl | methyl | (ethyl butanoate)-3-yl | |
| 2.6.338 | 2-bromo-3-isopropoxyphenyl | methyl | (ethyl butanoate)-3-yl | |
| 2.6.339 | 2-methyl-3-isopropoxyphenyl | methyl | (ethyl butanoate)-3-yl | |
| 2.6.340 | 2-ethyl-3-isopropoxyphenyl | methyl | (ethyl butanoate)-3-yl | |
| 2.6.341 | 2-cyclopropyl-3-isopropoxyphenyl | methyl | (ethyl butanoate)-3-yl | |
| 2.6.342 | 2-vinyl-3-isopropoxyphenyl | methyl | (ethyl butanoate)-3-yl | |
| 2.6.343 | 2-ethynyl-3-isopropoxyphenyl | methyl | (ethyl butanoate)-3-yl | |
| 2.6.344 | 2-cyano-3-isopropoxyphenyl | methyl | (ethyl butanoate)-3-yl | |
| 2.6.345 | 2-trifluoromethyl-3-isopropoxy-phenyl | methyl | (ethyl butanoate)-3-yl | |
| 2.6.346 | 2-methoxy-3-isopropoxyphenyl | methyl | (ethyl butanoate)-3-yl | |
| 2.6.347 | 2-ethoxy-3-isopropoxyphenyl | methyl | (ethyl butanoate)-3-yl | |
| 2.6.348 | 2-trifluoro-methoxy-3-isopropoxyphenyl | methyl | (ethyl butanoate)-3-yl | |
| 2.6.349 | 2-nitro-3-isopropoxyphenyl | methyl | (ethyl butanoate)-3-yl | |
| 2.6.350 | 2-fluoro-3-tert-butoxyphenyl | methyl | (ethyl butanoate)-3-yl | |
| 2.6.351 | 2-chloro-3-tert-butoxyphenyl | methyl | (ethyl butanoate)-3-yl | |
| 2.6.352 | 2-bromo-3-tert-butoxyphenyl | methyl | (ethyl butanoate)-3-yl | |
| 2.6.353 | 2-methyl-3-tert-butoxyphenyl | methyl | (ethyl butanoate)-3-yl | |
| 2.6.354 | 2-ethyl-3-tert-butoxyphenyl | methyl | (ethyl butanoate)-3-yl | |
| 2.6.355 | 2-cyclopropyl-3-tert-butoxyphenyl | methyl | (ethyl butanoate)-3-yl | |
| 2.6.356 | 2-vinyl-3-tert-butoxyphenyl | methyl | (ethyl butanoate)-3-yl | |
| 2.6.357 | 2-ethynyl-3-tert-butoxyphenyl | methyl | (ethyl butanoate)-3-yl | |
| 2.6.358 | 2-cyano-3-tert-butoxyphenyl | methyl | (ethyl butanoate)-3-yl | |
| 2.6.359 | 2-trifluoromethyl-3-tert-butoxy-phenyl | methyl | (ethyl butanoate)-3-yl | |
| 2.6.360 | 2-methoxy-3-tert-butoxyphenyl | methyl | (ethyl butanoate)-3-yl | |

TABLE 2.6-continued

Inventive compounds of the general formula (I) in which W* is COOY, R¹ and R² are each hydrogen, and aryl is the radical.

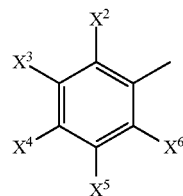

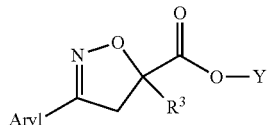

| No. | Aryl | R³ | Y | Physical data |
|---|---|---|---|---|
| 2.6.361 | 2-ethoxy-3-tert-butoxyphenyl | methyl | (ethyl butanoate)-3-yl | |
| 2.6.362 | 2-trifluoro-methoxy-3-tert-butoxyphenyl | methyl | (ethyl butanoate)-3-yl | |
| 2.6.363 | 2-nitro-3-tert-butoxyphenyl | methyl | (ethyl butanoate)-3-yl | |
| 2.6.364 | 2-fluoro-3-trifluoromethoxy-phenyl | methyl | (ethyl butanoate)-3-yl | |
| 2.6.365 | 2-chloro-3-trifluoromethoxy-phenyl | methyl | (ethyl butanoate)-3-yl | |
| 2.6.366 | 2-bromo-3-trifluoromethoxy-phenyl | methyl | (ethyl butanoate)-3-yl | |
| 2.6.367 | 2-methyl-3-trifluoromethoxy-phenyl | methyl | (ethyl butanoate)-3-yl | |
| 2.6.368 | 2-ethyl-3-trifluoromethoxy-phenyl | methyl | (ethyl butanoate)-3-yl | |
| 2.6.369 | 2-cyclopropyl-3-trifluoromethoxy-phenyl | methyl | (ethyl butanoate)-3-yl | |
| 2.6.370 | 2-vinyl-3-trifluoromethoxy-phenyl | methyl | (ethyl butanoate)-3-yl | |
| 2.6.371 | 2-ethynyl-3-trifluoromethoxy-phenyl | methyl | (ethyl butanoate)-3-yl | |
| 2.6.372 | 2-cyano-3-trifluoromethoxy-phenyl | methyl | (ethyl butanoate)-3-yl | |
| 2.6.373 | 2-trifluoromethyl-3-trifluoro-methoxy-phenyl | methyl | (ethyl butanoate)-3-yl | |
| 2.6.374 | 2-methoxy-3-trifluoromethoxy-phenyl | methyl | (ethyl butanoate)-3-yl | |
| 2.6.375 | 2-ethoxy-3-trifluoromethoxy-phenyl | methyl | (ethyl butanoate)-3-yl | |
| 2.6.376 | 2,3-bis(trifluoro-methoxy)phenyl | methyl | (ethyl butanoate)-3-yl | |
| 2.6.377 | 2-nitro-3-trifluoro-methoxyphenyl | methyl | (ethyl butanoate)-3-yl | |
| 2.6.378 | 2-fluoro-3-(2,2,2-trifluoroethoxy)-phenyl | methyl | (ethyl butanoate)-3-yl | |
| 2.6.379 | 2-chloro-3-(2,2,2-trifluoroethoxy)-phenyl | methyl | (ethyl butanoate)-3-yl | |
| 2.6.380 | 2-bromo-3-(2,2,2-trifluoroethoxy)-phenyl | methyl | (ethyl butanoate)-3-yl | |
| 2.6.381 | 2-methyl-3-(2,2,2-trifluoroethoxy)-phenyl | methyl | (ethyl butanoate)-3-yl | |
| 2.6.382 | 2-ethyl-3-(2,2,2-trifluoroethoxy)-phenyl | methyl | (ethyl butanoate)-3-yl | |
| 2.6.383 | 2-cyclopropyl-3-(2,2,2-trifluoro-ethoxy)phenyl | methyl | (ethyl butanoate)-3-yl | |

TABLE 2.6-continued

Inventive compounds of the general formula (I) in which W* is COOY, R¹ and R² are each hydrogen, and aryl is the radical.

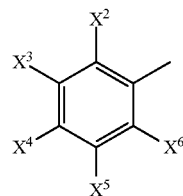

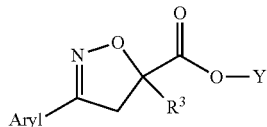

| No. | Aryl | R³ | Y | Physical data |
|---|---|---|---|---|
| 2.6.384 | 2-vinyl-3-(2,2,2-trifluoroethoxy)-phenyl | methyl | (ethyl butanoate)-3-yl | |
| 2.6.385 | 2-ethynyl-3-(2,2,2-trifluoro-ethoxyphenyl | methyl | (ethyl butanoate)-3-yl | |
| 2.6.386 | 2-cyano-3-(2,2,2-trifluoroethoxy)-phenyl | methyl | (ethyl butanoate)-3-yl | |
| 2.6.387 | 2-trifluoromethyl-3-(2,2,2-trifluoro-ethoxy)phenyl | methyl | (ethyl butanoate)-3-yl | |
| 2.6.388 | 2-methoxy-3-(2,2,2-trifluoro-ethoxy)phenyl | methyl | (ethyl butanoate)-3-yl | |
| 2.6.389 | 2-ethoxy-3-(2,2,2-trifluoroethoxy)-phenyl | methyl | (ethyl butanoate)-3-yl | |
| 2.6.390 | 2-trifluoro-methoxy-3-(2,2,2-trifluoroethoxy)-phenyl | methyl | (ethyl butanoate)-3-yl | |
| 2.6.391 | 2-nitro-3-(2,2,2-trifluoroethoxy)-phenyl | methyl | (ethyl butanoate)-3-yl | |
| 2.6.392 | 2-fluoro-3-difluoromethoxy-phenyl | methyl | (ethyl butanoate)-3-yl | |
| 2.6.393 | 2-chloro-3-difluoromethoxy-phenyl | methyl | (ethyl butanoate)-3-yl | |
| 2.6.394 | 2-bromo-3-difluoromethoxy-phenyl | methyl | (ethyl butanoate)-3-yl | |
| 2.6.395 | 2-methyl-3-difluoromethoxy-phenyl | methyl | (ethyl butanoate)-3-yl | |
| 2.6.396 | 2-ethyl-3-difluoromethoxy-phenyl | methyl | (ethyl butanoate)-3-yl | |
| 2.6.397 | 2-cyclopropyl-3-difluoromethoxy-phenyl | methyl | (ethyl butanoate)-3-yl | |
| 2.6.398 | 2-vinyl-3-difluoromethoxy-phenyl | methyl | (ethyl butanoate)-3-yl | |
| 2.6.399 | 2-ethynyl-3-difluoromethoxy-phenyl | methyl | (ethyl butanoate)-3-yl | |
| 2.6.400 | 2-cyano-3-difluoro-methoxyphenyl | methyl | (ethyl butanoate)-3-yl | |
| 2.6.401 | 2-trifluoromethyl-3-difluoro-methoxyphenyl | methyl | (ethyl butanoate)-3-yl | |
| 2.6.402 | 2-methoxy-3-difluoro-methoxyphenyl | methyl | (ethyl butanoate)-3-yl | |
| 2.6.403 | 2-ethoxy-3-difluoromethoxyphenyl | methyl | (ethyl butanoate)-3-yl | |
| 2.6.404 | 2-trifluoro-methoxy-3-difluoromethoxy-phenyl | methyl | (ethyl butanoate)-3-yl | |
| 2.6.405 | 2-nitro-3-difluoro-methoxyphenyl | methyl | (ethyl butanoate)-3-yl | |
| 2.6.406 | 2-fluoro-3-(2-methoxyethoxy)-phenyl | methyl | (ethyl butanoate)-3-yl | |

TABLE 2.6-continued

Inventive compounds of the general formula (I) in which W* is COOY, R¹ and R² are each hydrogen, and aryl is the radical.

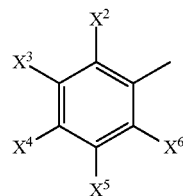

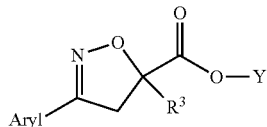

| No. | Aryl | R³ | Y | Physical data |
|---|---|---|---|---|
| 2.6.407 | 2-chloro-3-(2-methoxyethoxy)-phenyl | methyl | (ethyl butanoate)-3-yl | |
| 2.6.408 | 2-bromo-3-(2-methoxyethoxy)-phenyl | methyl | (ethyl butanoate)-3-yl | |
| 2.6.409 | 2-methyl-3-(2-methoxyethoxy)-phenyl | methyl | (ethyl butanoate)-3-yl | |
| 2.6.410 | 2-ethyl-3-(2-methoxyethoxy)phenyl | methyl | (ethyl butanoate)-3-yl | |
| 2.6.411 | 2-cyclopropyl-3-(2-methoxy-ethoxy)phenyl | methyl | (ethyl butanoate)-3-yl | |
| 2.6.412 | 2-vinyl-3-(2-methoxyethoxy)phenyl | methyl | (ethyl butanoate)-3-yl | |
| 2.6.413 | 2-ethynyl-3-(2-methoxyethoxy)-phenyl | methyl | (ethyl butanoate)-3-yl | |
| 2.6.414 | 2-cyano-3-(2-methoxyethoxy)-phenyl | methyl | (ethyl butanoate)-3-yl | |
| 2.6.415 | 2-trifluoromethyl-3-(2-methoxy-ethoxy)phenyl | methyl | (ethyl butanoate)-3-yl | |
| 2.6.416 | 2-methoxy-3-(2-methoxyethoxy)-phenyl | methyl | (ethyl butanoate)-3-yl | |
| 2.6.417 | 2-ethoxy-3-(2-methoxyethoxy)-phenyl | methyl | (ethyl butanoate)-3-yl | |
| 2.6.418 | 2-trifluoro-methoxy-(2-methoxyethoxy)-phenyl | methyl | (ethyl butanoate)-3-yl | |
| 2.6.419 | 2-nitro-3-(2-methoxyethoxy)phenyl | methyl | (ethyl butanoate)-3-yl | |
| 2.6.420 | 2-fluoro-3-(tert-butoxycarbonyloxy)-phenyl | methyl | (ethyl butanoate)-3-yl | |
| 2.6.421 | 2-chloro-3-(tert-butoxycarbonyloxy)-phenyl | methyl | (ethyl butanoate)-3-yl | |
| 2.6.422 | 2-bromo-3-(tert-butoxycarbonyl-oxy)phenyl | methyl | (ethyl butanoate)-3-yl | |
| 2.6.423 | 2-methyl-3-(tert-butoxycarbonyl-oxy)phenyl | methyl | (ethyl butanoate)-3-yl | |
| 2.6.424 | 2-ethyl-3-(tert-butoxycarbonyloxy)-phenyl | methyl | (ethyl butanoate)-3-yl | |
| 2.6.425 | 2-cyclopropyl-3-(tert-butoxy-carbonyloxy)-phenyl | methyl | (ethyl butanoate)-3-yl | |
| 2.6.426 | 2-vinyl-3-(tert-butoxycarbonyl-oxy)-phenyl | methyl | (ethyl butanoate)-3-yl | |

TABLE 2.6-continued

Inventive compounds of the general formula (I) in which W* is COOY, R¹ and R² are each hydrogen, and aryl is the radical.

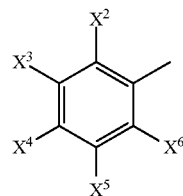

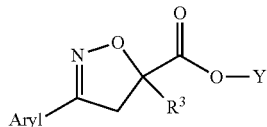

| No. | Aryl | R³ | Y | Physical data |
|---|---|---|---|---|
| 2.6.427 | 2-ethynyl-3-(tert-butoxycarbonyl-oxy)phenyl | methyl | (ethyl butanoate)-3-yl | |
| 2.6.428 | 2-cyano-3-(tert-butoxycarbonyl-oxy)-phenyl | methyl | (ethyl butanoate)-3-yl | |
| 2.6.429 | 2-trifluoromethyl-3-(tert-butoxy-carbonyloxy)-phenyl | methyl | (ethyl butanoate)-3-yl | |
| 2.6.430 | 2-methoxy-3-(tert-butoxycarbonyl-oxy)-phenyl | methyl | (ethyl butanoate)-3-yl | |
| 2.6.431 | 2-ethoxy-3-(tert-butoxycarbonyl-oxy)-phenyl | methyl | (ethyl butanoate)-3-yl | |
| 2.6.432 | 2-trifluoro-methoxy-3-(tert-butoxycarbonyl-oxy)phenyl | methyl | (ethyl butanoate)-3-yl | |
| 2.6.433 | 2-nitro-3-(tert-butoxycarbonyl-oxy)-phenyl | methyl | (ethyl butanoate)-3-yl | |
| 2.6.434 | 2-fluoro-3-nitrophenyl | methyl | (ethyl butanoate)-3-yl | |
| 2.6.435 | 2-chloro-3-nitrophenyl | methyl | (ethyl butanoate)-3-yl | |
| 2.6.436 | 2-bromo-3-nitrophenyl | methyl | (ethyl butanoate)-3-yl | |
| 2.6.437 | 2-methyl-3-nitrophenyl | methyl | (ethyl butanoate)-3-yl | |
| 2.6.438 | 2-ethyl-3-nitrophenyl | methyl | (ethyl butanoate)-3-yl | |
| 2.6.439 | 2-cyclopropyl-3-nitrophenyl | methyl | (ethyl butanoate)-3-yl | |
| 2.6.440 | 2-vinyl-3-nitrophenyl | methyl | (ethyl butanoate)-3-yl | |
| 2.6.441 | 2-ethynyl-3-nitrophenyl | methyl | (ethyl butanoate)-3-yl | |
| 2.6.442 | 2-cyano-3-nitrophenyl | methyl | (ethyl butanoate)-3-yl | |
| 2.6.443 | 2-trifluoromethyl-3-nitrophenyl | methyl | (ethyl butanoate)-3-yl | |
| 2.6.444 | 2-methoxy-3-nitrophenyl | methyl | (ethyl butanoate)-3-yl | |
| 2.6.445 | 2-ethoxy-3-nitrophenyl | methyl | (ethyl butanoate)-3-yl | |
| 2.6.446 | 2-trifluoro-methoxy-3-nitrophenyl | methyl | (ethyl butanoate)-3-yl | |
| 2.6.447 | 2-fluoro-3-methyl-sulfanylphenyl | methyl | (ethyl butanoate)-3-yl | |
| 2.6.448 | 2-chloro-3-methyl-sulfanylphenyl | methyl | (ethyl butanoate)-3-yl | |
| 2.6.449 | 2-bromo-3-methylsulfanyl-phenyl | methyl | (ethyl butanoate)-3-yl | |
| 2.6.450 | 2-methyl-3-methylsulfanyl-phenyl | methyl | (ethyl butanoate)-3-yl | |
| 2.6.451 | 2-ethyl-3-methylsulfanyl-phenyl | methyl | (ethyl butanoate)-3-yl | |
| 2.6.452 | 2-cyclopropyl-3-methylsulfanyl-phenyl | methyl | (ethyl butanoate)-3-yl | |
| 2.6.453 | 2-vinyl-3-methylsulfanyl-phenyl | methyl | (ethyl butanoate)-3-yl | |
| 2.6.454 | 2-ethynyl-3-methylsulfanyl-phenyl | methyl | (ethyl butanoate)-3-yl | |
| 2.6.455 | 2-cyano-3-methylsulfanyl-phenyl | methyl | (ethyl butanoate)-3-yl | |
| 2.6.456 | 2-trifluoromethyl-3-methylsulfanyl-phenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

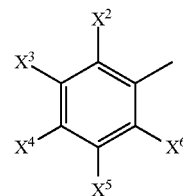

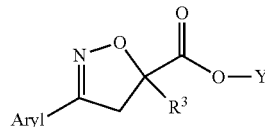

| No. | Aryl | $R^3$ | Y | Physical data |
|---|---|---|---|---|
| 2.6.457 | 2-methoxy-3-methylsulfanyl-phenyl | methyl | (ethyl butanoate)-3-yl | |
| 2.6.458 | 2-ethoxy-3-methylsulfanyl-phenyl | methyl | (ethyl butanoate)-3-yl | |
| 2.6.459 | 2-trifluoro-methoxy-3-methylsulfanyl-phenyl | methyl | (ethyl butanoate)-3-yl | |
| 2.6.460 | 2-nitro-3-methylsulfanyl-phenyl | methyl | (ethyl butanoate)-3-yl | |
| 2.6.461 | 3,5-difluorophenyl | methyl | (cyclohex-2-en-1-one)-3-yl | |
| 2.6.462 | 3,5-difluorophenyl | methyl | (propan-1-ol)-3-yl | [CDCl$_3$] 1.73 (s, 3H); 1.94 (quin, 2H); 3.15 (d, 1H); 3.73 (t, 2H); 3.85 (d, 1H); 4.38 (t, 2H); 6.88 (t, 1H); 7.17 (d, 2H). |
| 2.6.463 | 3,5-difluorophenyl | methyl | (2,2-dimethylpropan-1-ol)-3-yl | [CDCl$_3$] 0.89 (d, 6H); 1.74 (s, 3H), 3.16 (d, 1H); 3.33 (s, 2H); 3.84 (d, 1H); 4.07 (s, 2H), 6.88 (t, 1H); 7.18 (d, 2H). |
| 2.6.464 | 3,5-difluorophenyl | methyl | (methyl 2,2-dimethyl propanoate)-3-yl | [CDCl$_3$] 1.24 (d, 6H); 1.71 (s, 3H); 3.14 (d, 1H); 3.65 (s, 3H); 3.81 (d, 1H); 4.22 (s, 2H); 6.87 (t, 1H); 7.18 (d, 2H). |
| 2.6.465 | 3,5-difluorophenyl | methyl | (methyl propanoate)-3-yl | [CDCl$_3$] 1.71 (s, 3H), 2.72 (t, 2H); 3.14 (d, 1H); 3.68 (s, 3H); 3.82 (d, 1H); 4.47 (m, 2H); 6.86 (t, 1H); 7.18 (d, 2H). |
| 2.6.466 | 3,5-difluorophenyl | methyl | (ethyl propanoate)-3-yl | |
| 2.6.467 | 3,5-difluorophenyl | methyl | (ethyl butanoate)-3-yl | [CDCl$_3$] 1.17-1.26 (m, 3H); 1.36 (d, 3H); 1.69 (d, 3H); 2.55 (m, 1H); 2.69 (m, 1H); 3.11 (dd, 1H); 3.81 (dd, 1H); 4.03-4.15 (m, 2H); 5.35 (m, 1H); 6.87 (t, 1H); 7.17 (m, 2H). |
| 2.6.468 | 3,5-difluorophenyl | methyl | (ethyl (3R)-4,4,4-trifluorobutanoate)-3-yl one diastereomer | [CDCl$_3$] 1.20 (t, 3H); 1.75 (s, 3H); 2.85 (t, 2H); 3.19 (d, 1H); 3.85 (d, 1H); 4.09 (m, 2H); 5.82 (m, 1H); 6.88 (t, 1H); 7.17 (d, 2H). |
| 2.6.469 | 3,5-difluorophenyl | methyl | (ethyl (3R)-4,4,4-trifluorobutanoate)-3-yl the other diastereomer | [CDCl$_3$] 1.25 (t, 3H); 1.74 (s, 3H); 2.86 (t, 2H); 3.20 (d, 1H); 3.80 (d, 1H); 4.15 (q, 2H); 5.80 (m, 1H); 6.88 (t, 1H); 7.18 (d, 2H). |
| 2.6.470 | 3,5-difluorophenyl | methyl | (butan-2-one)-4-yl | [CDCl$_3$] 1.70 (s, 3H), 2.18 (s, 3H); 2.83 (q, 2H); 3.15 (d, 1H), 3.83 (d, 1H); 4.44 (m, 2H); 6.87 (t, 1H); 7.18 (d, 2H). |
| 2.6.471 | 3,5-difluorophenyl | methyl | (3-methylbutan-2-one)-4-yl | [CDCl$_3$] 1.16 (t, 3H), 1.70 (d, 3H), 2.19 (d, 3H); 2.95 (quin, 1H), 3.11 (dd, 1H); 3.81 (d, 1H); 4.21 (dd, 1H); 4.37 (dd, 1H); 6.87 (t, 1H); 7.18 (m, 2H). |
| 2.6.472 | 3,5-difluorophenyl | methyl | (pent-3-en-2-one)-4-yl | |
| 2.6.473 | 3,5-difluorophenyl | methyl | ((2S)-dimethyl butanedioate)-2-yl | [CDCl$_3$] 1.75 (d, 3H); 2.95 (m, 2H); 3.18 (dd, 1H); 3.68 (d, 3H); 3.76 (d, 3H); 3.88 (dd, 1H); 5.55 (t, 1H); 6.87 (t, 1H); 7.18 (d, 2H). |
| 2.6.474 | 3,5-difluorophenyl | methyl | (dimethyl pentanedioate)-3-yl | [CDCl$_3$] 1.69 (s, 3H); 2.75 (t, 4H); 3.13 (d, 1H); 3.62 (s, 3H); 3.69 (s, 3H); 3.83 (d, 1H); 5.58 (quin, 1H); 6.87 (t, 1H); 7.18 (d, 2H). |
| 2.6.475 | 3,5-difluorophenyl | methyl | (methyl (2R)-2-methyl propanoate)-3-yl | [CDCl$_3$] D1: 1.22 (t, 3H), 1.71 (s, 3H); 2.88 (m, 1H), 3.15 (d, 1H), 3.66 (s, 3H); 3.81 (d, 1H), 4.29 (m, 1H); 4.37 (m, 1H), 6.87 (t, 1H); 7.17 (d, 2H). D2: 1.22 (t, 3H), 1.71 (s, 3H); 2.88 (m, 1H), 3.15 (d, 1H), 3.67 (s, 3H); 3.83 (d, 1H), 4.29 (m, 1H); 4.37 (m, 1H), 6.87 (t, 1H); 7.17 (d, 2H). |
| 2.6.476 | 3,5-difluorophenyl | methyl | 4-methoxycarbonylbenzyl | [CDCl$_3$] 1.75 (s, 3H); 3.17 (d, 1H); 3.84 (d, 1H); 3.92 (s, 3H); 5.28 (d, 2H); 6.88 (t, 1H); 7.17 (d, 2H); 7.42 (d, 2H); 8.04 (d, 2H). |

TABLE 2.6-continued

Inventive compounds of the general formula (I) in which W* is COOY, $R^1$ and $R^2$ are each hydrogen, and aryl is the radical.

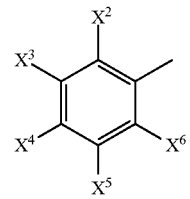

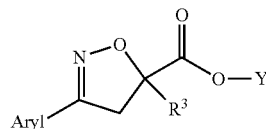

| No. | Aryl | $R^3$ | Y | Physical data |
|---|---|---|---|---|
| 2.6.477 | 3,5-difluorophenyl | methyl | 3,5-difluorobenzyl | [CDCl$_3$] 1.76 (s, 3H); 3.19 (d, 1H); 3.84 (d, 1H); 5.19 (d, 2H); 6.76 (t, 1H); 6.88 (m, 3H); 7.17 (d, 2H). |
| 2.6.478 | 3,5-difluorophenyl | methyl | 3,4-difluorobenzyl | [CDCl$_3$] 1.73 (s, 3H); 3.17 (d, 1H); 3.82 (d, 1H); 5.18 (d, 2H); 6.87 (t, 1H); 7.10 (m, 1H); 7.15 (m, 4H). |
| 2.6.479 | 3,5-diluorophenyl | methyl | 2,6-difluorobenzyl | [CDCl$_3$] 1.72 (s, 3H); 3.15 (d, 1H); 3.82 (d, 1H); 3.33 (d, 2H); 6.86 (t, 1H); 6.94 (t, 2H); 7.16 (d, 2H); 7.35 (m, 1H). |
| 2.6.480 | 3,5-diluorophenyl | methyl | (5-methylpyridin-3-yl)methyl | [CDCl$_3$] 1.73 (s, 3H), 2.34 (s, 3H); 3.17 (d, 1H); 3.82 (d, 1H); 5.22 (d, 2H); 6.88 (t, 1H); 7.17 (d, 2H), 7.51 (s, 1H); 8.43 (s, 2H). |
| 2.6.481 | 3,5-diluorophenyl | methyl | (tetrahydrofuran)-3yl | [CDCl$_3$] 1.72 (s, 3H); 2.06 (m, 1H); 2.22 (m, 1H); 3.17 (dd, 1H); 3.81-3.99 (m, 5H); 5.38 (m, 1H); 6.89 (t, 1H); 7.17 (d, 2H). |
| 2.6.482 | 3,5-diluorophenyl | ethyl | (cyclohex-2-en-1-one)-3-yl | |
| 2.6.483 | 3,5-diluorophenyl | ethyl | (propan-1-ol)-3-yl | |
| 2.6.484 | 3,5-diluorophenyl | ethyl | (2,2-dimethylpropan-1-ol)-3-yl | |
| 2.6.485 | 3,5-diluorophenyl | ethyl | (methyl 2,2-dimethyl propanoate)-3-yl | |
| 2.6.486 | 3,5-diluorophenyl | ethyl | (methyl propanoate)-3-yl | [CDCl$_3$] 0.99 (t, 3H); 2.01-2.07 (m, 2H); 2.72 (t, 2H); 3.17 (d, 1H); 3.68 (s, 3H); 3.75 (d, 1H); 4.41-4.53 (m, 2H); 6.86 (t, 1H); 7.18 (d, 2H). |
| 2.6.487 | 3,5-diluorophenyl | ethyl | (ethyl propanoate)-3-yl | |
| 2.6.488 | 3,5-diluorophenyl | ethyl | (ethyl butanoate)-3-yl | [CDCl$_3$] D1 0.98 (t, 3H); 1.27 (t, 3H); 1.36 (d, 3H); 1.95-2.12 (m, 2H); 2.51-2.73 (m, 2H); 3.14 (d, 1H); 3.78 (d, 1H); 4.07-4.18 (m, 2H); 5.32-5.43 (m, 1H); 6.86 (t, 1H); 7.13-7.22 (m, 2H). D2 1.00 (t, 3H); 1.22 (t, 3H); 1.35 (d, 3H); 1.95-2.12 (m, 2H); 2.51-2.73 (m, 2H); 3.17 (d, 1H); 3.72 (d, 1H); 4.00-4.07(m, 2H); 5.32-5.43 (m, 1H); 6.86 (t, 1H); 7.13-7.22 (m, 2H). |
| 2.6.489 | 3,5-difluorophenyl | ethyl | (ethyl (3R)-4,4,4-trifluorobutanoate)-3-yl one diastereomer | [CDCl$_3$] D1 1.01 (t, 3H); 1.19 (t, 3H); 2.05-2.11 (m, 2H); 2.81-2.91 (m, 2H); 3.21 (d, 1H); 3.77 (d, 1H); 4.04-4.11 (m, 2H); 5.84 (m, 1H); 6.87 (t, 1H); 7.17 (d, 2H). |
| 2.6.490 | 3,5-difluorophenyl | ethyl | (ethyl (3R)-4,4,4-trifluorobutanoate)-3-yl the other diastereomer | [CDCl$_3$] 1.01 (t, 3H); 1.24 (t, 3H); 2.01-2.13 (m, 2H); 2.85 (d, 2H); 3.23 (d, 1H); 3.72 (d, 1H); 4.13 (q, 2H); 5.83 (m, 1H); 6.87 (t, 1H); 7.16 (d, 2H). |
| 2.6.491 | 3,5-difluorophenyl | ethyl | (butan-2-one)-4-yl | |
| 2.6.492 | 3,5-difluorophenyl | ethyl | (3-methylbutan-2-one)-4-yl | |
| 2.6.493 | 3,5-difluorophenyl | ethyl | (pent-3-en-2-one)-4-yl | |
| 2.6.494 | 3,5-difluorophenyl | ethyl | ((2S)-dimethyl butanedioate)-2-yl | [CDCl$_3$] D1 1.02-1.07 (m, 3H), 2.02-2.15 (m, 2H); 2.95 (m, 2H); 3.21 (d, 1H); 3.69 (s, 3H), 3.75 (s, 3H); 3.79 (d, 1H); 5.58 (t, 1H); 6.87 (t, 1H); 7.19 (d, 2H). D2 1.02-1.07 (m, 3H); 2.02-2.15 (m, 2H); 2.95 (m, 2H); 3.22 (d, 1H); 3.68 (s, 3H); 3.77 (s, 3H); 3.81 (d, 1H); 5.58 (t, 1H); 6.87 (t, 1H); 7.19 (d, 2H). |
| 2.6.495 | 3,5-difluorophenyl | ethyl | (dimethyl pentanedioate)-3-yl | [CDCl$_3$] 0.99 (t, 3H); 1.97-2.06 (m, 2H); 2.75 (m, 4H); 3.16 (d, 1H); 3.62 (s, 3H); 3.67 (s, 3H); 3.75 (d, 1H); 5.60 (quin, 1H); 6.86 (t, 1H); 7.19 (d, 2H). |
| 2.6.496 | 3,5-difluorophenyl | ethyl | (methyl (2R)-2-methyl propanoate)-3-yl | |
| 2.6.497 | 3,5-difluorophenyl | ethyl | 4-methoxycarbonylbenzyl | |

TABLE 2.6-continued

Inventive compounds of the general formula (I) in which W* is COOY, R¹ and R² are each hydrogen, and aryl is the radical.

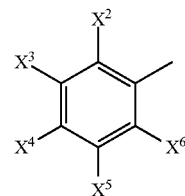

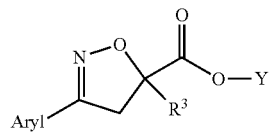

| No. | Aryl | R³ | Y | Physical data |
|---|---|---|---|---|
| 2.6.498 | 3,5-difluorophenyl | ethyl | 3,5-difluorobenzyl | |
| 2.6.499 | 3,5-difluorophenyl | ethyl | 3,4-difluorobenzyl | |
| 2.6.500 | 3,5-difluorophenyl | ethyl | 2,6-difluorobenzyl | |
| 2.6.501 | 3,5-difluorophenyl | ethyl | (5-methylpyridin-3-yl)-methyl | |
| 2.6.502 | 3,5-difluorophenyl | ethyl | (tetrahydrofuran)-3-yl | |
| 2.6.503 | (S)-3,5-difluorophenyl | methyl | (ethyl butanoate)-3-yl | |
| 2.6.504 | (R)-3,5-difluorophenyl | methyl | (ethyl butanoate)-3-yl | |
| 2.6.505 | 3-chloro-5-fluorophenyl | methyl | (ethyl butanoate)-3-yl | |
| 2.6.506 | 3-bromo-5-fluorophenyl | methyl | (ethyl butanoate)-3-yl | |
| 2.6.507 | 3-iodo-5-fluorophenyl | methyl | (ethyl butanoate)-3-yl | |
| 2.6.508 | 3-methyl-5-fluorophenyl | methyl | (ethyl butanoate)-3-yl | |
| 2.6.509 | 3-ethyl-5-fluorophenyl | methyl | (ethyl butanoate)-3-yl | |
| 2.6.510 | 3-propyl-5-fluorophenyl | methyl | (ethyl butanoate)-3-yl | |
| 2.6.511 | 3-i-propyl-5-fluorophenyl | methyl | (ethyl butanoate)-3-yl | |
| 2.6.512 | 3-n-butyl-5-fluorophenyl | methyl | (ethyl butanoate)-3-yl | |
| 2.6.513 | 3-isobutyl-5-fluorophenyl | methyl | (ethyl butanoate)-3-yl | |
| 2.6.514 | 3-tert-butyl-5-fluorophenyl | methyl | (ethyl butanoate)-3-yl | |
| 2.6.515 | 3-cyclopropyl-5-fluorophenyl | methyl | (ethyl butanoate)-3-yl | |
| 2.6.516 | 3-vinyl-5-fluorophenyl | methyl | (ethyl butanoate)-3-yl | |
| 2.6.517 | 3-ethynyl-5-fluorophenyl | methyl | (ethyl butanoate)-3-yl | |
| 2.6.518 | 3-cyano-5-fluorophenyl | methyl | (ethyl butanoate)-3-yl | |
| 2.6.519 | 3-trifluoromethyl-5-fluorophenyl | methyl | (ethyl butanoate)-3-yl | |
| 2.6.520 | 3-(methoxy-carbonyl)-5-fluorophenyl | methyl | (ethyl butanoate)-3-yl | |
| 2.6.521 | 3-hydroxymethyl-5-fluorophenyl | methyl | (ethyl butanoate)-3-yl | |
| 2.6.522 | 3-carbamoyl-5-fluorophenyl | methyl | (ethyl butanoate)-3-yl | |
| 2.6.523 | 3-hydroxy-5-fluorophenyl | methyl | (ethyl butanoate)-3-yl | |
| 2.6.524 | 3-methoxy-5-fluorophenyl | methyl | (ethyl butanoate)-3-yl | |
| 2.6.525 | 3-ethoxy-5-fluorophenyl | methyl | (ethyl butanoate)-3-yl | |
| 2.6.526 | 3-n-propoxy-5-fluorophenyl | methyl | (ethyl butanoate)-3-yl | |
| 2.6.527 | 3-isopropoxy-5-fluorophenyl | methyl | (ethyl butanoate)-3-yl | |
| 2.6.528 | 3-n-butoxy-5-fluorophenyl | methyl | (ethyl butanoate)-3-yl | |
| 2.6.529 | 3-isobutoxy-5-fluorophenyl | methyl | (ethyl butanoate)-3-yl | |
| 2.6.530 | 3-tert-butoxy-5-fluorophenyl | methyl | (ethyl butanoate)-3-yl | |
| 2.6.531 | 3-difluoro-methoxy-5-fluorophenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

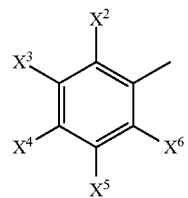

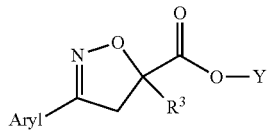

| No. | Aryl | $R^3$ | Y | Physical data |
|---|---|---|---|---|
| 2.6.532 | 3-trifluoro-methoxy-5-fluorophenyl | methyl | (ethyl butanoate)-3-yl | |
| 2.6.533 | 3-(2,2,2-trifluoro-ethoxy)-5-fluorophenyl | methyl | (ethyl butanoate)-3-yl | |
| 2.6.534 | 3-(2-chloro-ethoxy)-5-fluorophenyl | methyl | (ethyl butanoate)-3-yl | |
| 2.6.535 | 3-(2-hydroxy-ethoxy)-5-fluorophenyl | methyl | (ethyl butanoate)-3-yl | |
| 2.6.536 | 3-[(tert-butoxy-carbonyl)oxy]-5-fluorophenyl | methyl | (ethyl butanoate)-3-yl | |
| 2.6.537 | 3-nitro-5-fluorophenyl | methyl | (ethyl butanoate)-3-yl | |
| 2.6.538 | 3-acetoxy-5-fluorophenyl | methyl | (ethyl butanoate)-3-yl | |
| 2.6.539 | {3-[(tert-butoxy-carbonyl)amino]-5-fluorophenyl} | methyl | (ethyl butanoate)-3-yl | |
| 2.6.540 | 3-methylsulfanyl-5-fluorophenyl | methyl | (ethyl butanoate)-3-yl | |
| 2.6.541 | 3,5-dichlorophenyl | methyl | (cyclohex-2-en-1-one)-3-yl | [CDCl$_3$] 1.79 (s, 3H); 2.08 (quin, 2H); 2.43 (t, 2H); 2.58 (t, 2H); 3.22 (d, 1H); 3.88 (d, 1H); 5.97 (s, 1H); 7.42 (s, 1H); 7.53 (s, 2H). |
| 2.6.542 | 3,5-dichlorophenyl | methyl | (propan-1-ol)-3-yl | |
| 2.6.543 | 3,5-dichlorophenyl | methyl | (2,2-dimethylpropan-1-ol)-3-yl | |
| 2.6.544 | 3,5-dichlorophenyl | methyl | (methyl 2,2-dimethyl propanoate)-3-yl | |
| 2.6.545 | 3,5-dichlorophenyl | methyl | (methyl propanoate)-3-yl | [CDCl$_3$] 1.71 (s, 3H); 2.72 (t, 2H); 3.15 (d, 1H); 3.68 (s, 3H); 3.83 (d, 1H); 4.46 (t, 2H); 7.40 (s, 1H); 7.53 (s, 2H). |
| 2.6.546 | 3,5-dichlorophenyl | methyl | (ethyl propanoate)-3-yl | [CDCl$_3$] 1.23 (t, 3H), 1.70 (s, 3H); 2.70 (t, 2H); 3.15 (d, 1H); 3.82 (d, 1H); 4.12 (q, 2H), 4.47 (t, 2H); 7.40 (s, 1H); 7.52 (s, 2H). |
| 2.6.547 | 3,5-dichlorophenyl | methyl | (ethyl butanoate)-3-yl | [CDCl$_3$] 1.18-1.27 (m, 3H); 1.36 (d, 3H); 1.68 (d, 3H); 2.55 (m, 1H); 2.67 (m, 1H); 3.12 (dd, 1H); 3.81 (dd, 1H), 4.03-4.16 (m, 2H); 5.36 (m, 1H); 7.39 (s, 1H); 7.53 (s, 2H). |
| 2.6.548 | 3,5-dichlorophenyl | methyl | (ethyl (3R)-4,4,4-trifluorobutanoate)-3-yl (1 diastereomer) | [CDCl$_3$] (t, 3H); 1.75 (s, 3H); 2.85 (m, 2H); 3.19 (d, 1H); 3.84 (d, 1H); 4.09 (m, 2H); 5.81 (m, 1H); 7.41 (s, 1H); 7.52 (s, 2H). 6-1-1 |
| 2.6.549 | 3,5-dichlorophenyl | methyl | (ethyl (3R)-4,4,4-trifluorobutanoate)-3-yl (the other diastereomer) | [CDCl$_3$] 1.25 (t, 3H); 1.74 (s, 3H); 2.86 (d, 2H); 3.20 (d, 1H); 3.80 (d, 1H); 4.16 (q, 2H); 5.81 (m, 1H); 7.41 (s, 1H); 7.53 (s, 2H). |
| 2.6.550 | 3,5-dichlorophenyl | methyl | (butan-1-ol)-4-yl | [CDCl$_3$] 1.58 (bs, 1H); 1.65 (m, 2H); 1.72 (s, 3H); 1.80 (mc, 2H); 3.13 (d, 1H); 3.68 (t, 2H); 3.82 (d, 1H); 4.25 (t, 2H); 7.40 (d, 1H); 7.52 (s, 2d). |
| 2.6.551 | 3,5-dichlorophenyl | methyl | (3-methylbutan-2-one)-4-yl | |
| 2.6.552 | 3,5-dichlorophenyl | methyl | (pent-3-en-2-one)-4-yl (E or Z) | [CDCl$_3$] 1.79 (s, 3H); 2.21 (s, 3H); 2.33 (s, 3H); 3.21 (d, 1H); 3.89 (d, 1H); 6.11 (s, 1H); 7.41 (s, 1H); 7.55 (s, 2H). |
| 2.6.553 | 3,5-dichlorophenyl | methyl | (pent-3-en-2-one)-4-yl (Z or E) | [CDCl$_3$] 1.80 (s, 3H); 2.10 (s, 6H); 3.22 (d, 1H); 4.20 (d, 1H); 5.96 (s, 1H); 7.40 (s, 1H); 7.58 (s, 2H). |
| 2.6.554 | 3,5-dichlorophenyl | methyl | ((2S)-dimethyl butanedioate)-2-yl | [CDCl$_3$] 1.75 (d, 3H); 2.96 (m, 2H); 3.20 (dd, 1H); 3.68 (s, 3H); 3.77 (s, 3H); 3.90 (dd, 1H); 5.57 (t, 1H); 7.41 (s, 1H); 7.53 (s, 2H). |
| 2.6.555 | 3,5-dichlorophenyl | methyl | (dimethyl pentanedioate)-3-yl | [CDCl$_3$] 1.68 (s, 3H); 2.75 (t, 4H); 3.11 (d, 1H); 3.62 (s, 3H); 3.69 (s, 3H); 3.81 (d, 1H); 5.58 (quin, 1H); 7.41 (s, 1H); 7.53 (s, 2H). |

TABLE 2.6-continued

Inventive compounds of the general formula (I) in which W* is COOY, R¹ and R² are each hydrogen, and aryl is the radical.

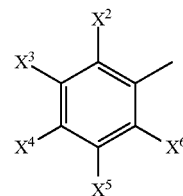

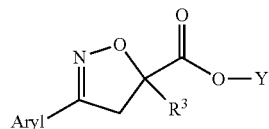

| No. | Aryl | R³ | Y | Physical data |
|---|---|---|---|---|
| 2.6.556 | 3,5-dichlorophenyl | methyl | (methyl (2R)-2-methyl propanoate)-3-yl | |
| 2.6.557 | 3,5-dichlorophenyl | methyl | 4-methoxycarbonylbenzyl | |
| 2.6.558 | 3,5-dichlorophenyl | methyl | 3,5-difluorobenzyl | |
| 2.6.559 | 3,5-dichlorophenyl | methyl | 3,4-difluorobenzyl | |
| 2.6.560 | 3,5-dichlorophenyl | methyl | 2,6-difluorobenzyl | |
| 2.6.561 | 3,5-dichlorophenyl | methyl | (5-methylpyridin-3-yl)methyl | [CDCl$_3$] 1.72 (s, 3H); 2.34 (s, 3H); 3.17 (d, 1H); 3.82 (d, 1H); 5.22 (d, 2H); 7.41 (s, 1H); 7.51 (m, 3H); 8.43 (s, 2H). |
| 2.6.562 | 3,5-dichlorophenyl | methyl | (tetrahydrofuran)-3-yl | |
| 2.6.563 | 3,5-dichlorophenyl | ethyl | (cyclohex-2-en-1-one)-3-yl | |
| 2.6.564 | 3,5-dichlorophenyl | ethyl | (propan-1-ol)-3-yl | |
| 2.6.565 | 3,5-dichlorophenyl | ethyl | (2,2-dimethylpropan-1-ol)-3-yl | |
| 2.6.566 | 3,5-dichlorophenyl | ethyl | (methyl 2,2-dimethyl propanoate)-3-yl | |
| 2.6.567 | 3,5-dichlorophenyl | ethyl | (methyl propanoate)-3-yl | |
| 2.6.568 | 3,5-dichlorophenyl | ethyl | (ethyl propanoate)-3-yl | |
| 2.6.569 | 3,5-dichlorophenyl | ethyl | (ethyl butanoate)-3-yl | |
| 2.6.570 | 3,5-dichlorophenyl | ethyl | (ethyl (3R)-4,4,4-trifluorobutanoate)-3-yl | |
| 2.6.571 | 3,5-dichlorophenyl | ethyl | (butan-2-one)-4-yl | |
| 2.6.572 | 3,5-dichlorophenyl | ethyl | (3-methylbutan-2-one)-4-yl | |
| 2.6.573 | 3,5-dichlorophenyl | ethyl | (pent-3-en-2-one)-4-yl | |
| 2.6.574 | 3,5-dichlorophenyl | ethyl | ((2S)-dimethyl butanedioate)-2-yl | |
| 2.6.575 | 3,5-dichlorophenyl | ethyl | (dimethyl pentanedioate)-3-yl | |
| 2.6.576 | 3,5-dichlorophenyl | ethyl | (methyl (2R)-2-methyl propanoate)-3-yl | |
| 2.6.577 | 3,5-dichlorophenyl | ethyl | 4-methoxycarbonylbenzyl | |
| 2.6.578 | 3,5-dichlorophenyl | ethyl | 3,5-difluorobenzyl | |
| 2.6.579 | 3,5-dichlorophenyl | ethyl | 3,4-difluorobenzyl | |
| 2.6.580 | 3,5-dichlorophenyl | ethyl | 2,6-difluorobenzyl | |
| 2.6.581 | 3,5-dichlorophenyl | ethyl | (5-methylpyridin-3-yl)methyl | |
| 2.6.582 | 3,5-dichlorophenyl | ethyl | (tetrahydrofuran)-3-yl | |
| 2.6.583 | (S)-3,5-dichlorophenyl | methyl | (ethyl butanoate)-3-yl | |
| 2.6.584 | (R)-3,5-dichlorophenyl | methyl | (ethyl butanoate)-3-yl | |
| 2.6.585 | 3-bromo-5-chlorophenyl | methyl | (ethyl butanoate)-3-yl | |
| 2.6.586 | 3-iodo-5-chlorophenyl | methyl | (ethyl butanoate)-3-yl | |
| 2.6.587 | 3-methyl-5-chlorophenyl | methyl | (ethyl butanoate)-3-yl | |
| 2.6.588 | 3-ethyl-5-chlorophenyl | methyl | (ethyl butanoate)-3-yl | |
| 2.6.589 | 3-propyl-5-chlorophenyl | methyl | (ethyl butanoate)-3-yl | |
| 2.6.590 | 3-isopropyl-5-chlorophenyl | methyl | (ethyl butanoate)-3-yl | |
| 2.6.591 | 3-n-butyl-5-chlorophenyl | methyl | (ethyl butanoate)-3-yl | |
| 2.6.592 | 3-isobutyl-5-chlorophenyl | methyl | (ethyl butanoate)-3-yl | |
| 2.6.593 | 3-tert-butyl-5-chlorophenyl | methyl | (ethyl butanoate)-3-yl | |
| 2.6.594 | 3-cyclopropyl-5-chlorophenyl | methyl | (ethyl butanoate)-3-yl | |
| 2.6.595 | 3-cyano-5-chlorophenyl | methyl | (ethyl butanoate)-3-yl | |
| 2.6.596 | 3-trifluoromethyl-5-chlorophenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

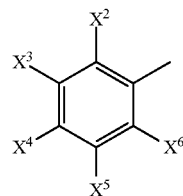

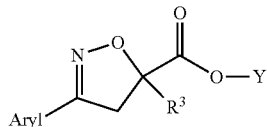

| No. | Aryl | $R^3$ | Y | Physical data |
|---|---|---|---|---|
| 2.6.597 | 3-trifluoromethyl-5-chlorophenyl | methyl | (ethyl butanoate)-3-yl | |
| 2.6.598 | 3-(hydroxy-carbonyl)-5-chlorophenyl | methyl | (ethyl butanoate)-3-yl | |
| 2.6.599 | 3-(methoxy-carbonyl)-5-chlorophenyl | methyl | (ethyl butanoate)-3-yl | |
| 2.6.600 | 3-methoxy-5-chlorophenyl | methyl | (ethyl butanoate)-3-yl | |
| 2.6.601 | 3-ethoxy-5-chlorophenyl | methyl | (ethyl butanoate)-3-yl | |
| 2.6.602 | 3-n-propoxy-5-chlorophenyl | methyl | (ethyl butanoate)-3-yl | |
| 2.6.603 | 3-isopropoxy-5-chlorophenyl | methyl | (ethyl butanoate)-3-yl | |
| 2.6.604 | 3-n-butoxy-5-chlorophenyl | methyl | (ethyl butanoate)-3-yl | |
| 2.6.605 | 3-isobutoxy-5-chlorophenyl | methyl | (ethyl butanoate)-3-yl | |
| 2.6.606 | 3-difluoro-methoxy-5-chlorophenyl | methyl | (ethyl butanoate)-3-yl | |
| 2.6.607 | 3-trifluoro-methoxy-5-chlorophenyl | methyl | (ethyl butanoate)-3-yl | |
| 2.6.608 | 3-nitro-5-chlorophenyl | methyl | (ethyl butanoate)-3-yl | |
| 2.6.609 | 3-acetoxy-5-chlorophenyl | methyl | (ethyl butanoate)-3-yl | |
| 2.6.610 | 3-methylsulfanyl-5-chlorophenyl | methyl | (ethyl butanoate)-3-yl | |
| 2.6.611 | 3,5-dibromophenyl | methyl | (ethyl butanoate)-3-yl | |
| 2.6.612 | 3-iodo-5-bromophenyl | methyl | (ethyl butanoate)-3-yl | |
| 2.6.613 | 3-methyl-5-bromophenyl | methyl | (ethyl butanoate)-3-yl | |
| 2.6.614 | 3-ethyl-5-bromophenyl | methyl | (ethyl butanoate)-3-yl | |
| 2.6.615 | 3-propyl-5-bromophenyl | methyl | (ethyl butanoate)-3-yl | |
| 2.6.616 | 3-isopropyl-5-bromophenyl | methyl | (ethyl butanoate)-3-yl | |
| 2.6.617 | 3-n-butyl-5-bromophenyl | methyl | (ethyl butanoate)-3-yl | |
| 2.6.618 | 3-isobutyl-5-bromophenyl | methyl | (ethyl butanoate)-3-yl | |
| 2.6.619 | 3-tert-butyl-5-bromophenyl | methyl | (ethyl butanoate)-3-yl | |
| 2.6.620 | 3-cyclopropyl-5-bromophenyl | methyl | (ethyl butanoate)-3-yl | |
| 2.6.621 | 3-cyano-5-bromophenyl | methyl | (ethyl butanoate)-3-yl | |
| 2.6.622 | 3-trifluoromethyl-5-bromophenyl | methyl | (ethyl butanoate)-3-yl | |
| 2.6.623 | 3-(hydroxy-carbonyl)-5-bromophenyl | methyl | (ethyl butanoate)-3-yl | |
| 2.6.624 | 3-(methoxy-carbonyl)-5-bromophenyl | methyl | (ethyl butanoate)-3-yl | |
| 2.6.625 | 3-methoxy-5-bromophenyl | methyl | (ethyl butanoate)-3-yl | |
| 2.6.626 | 3-ethoxy-5-bromophenyl | methyl | (ethyl butanoate)-3-yl | |
| 2.6.627 | 3-n-propoxy-5-bromophenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

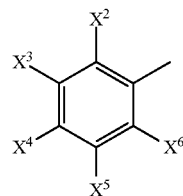

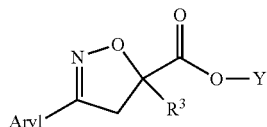

| No. | Aryl | $R^3$ | Y | Physical data |
|---|---|---|---|---|
| 2.6.628 | 3-isopropoxy-5-bromophenyl | methyl | (ethyl butanoate)-3-yl | |
| 2.6.629 | 3-n-butoxy-5-bromophenyl | methyl | (ethyl butanoate)-3-yl | |
| 2.6.630 | 3-isobutoxy-5-bromophenyl | methyl | (ethyl butanoate)-3-yl | |
| 2.6.631 | 3-difluoro-methoxy-5-bromophenyl | methyl | (ethyl butanoate)-3-yl | |
| 2.6.632 | 3-trifluoro-methoxy-5-bromophenyl | methyl | (ethyl butanoate)-3-yl | |
| 2.6.633 | 3-nitro-5-bromophenyl | methyl | (ethyl butanoate)-3-yl | |
| 2.6.634 | 3-acetoxy-5-bromophenyl | methyl | (ethyl butanoate)-3-yl | |
| 2.6.635 | 3-methylsulfanyl-5-bromophenyl | methyl | (ethyl butanoate)-3-yl | |
| 2.6.636 | 3,5-diiodophenyl | methyl | (ethyl butanoate)-3-yl | |
| 2.6.637 | 3-methyl-5-iodophenyl | methyl | (ethyl butanoate)-3-yl | |
| 2.6.638 | 3-ethyl-5-iodophenyl | methyl | (ethyl butanoate)-3-yl | |
| 2.6.639 | 3-propyl-5-iodophenyl | methyl | (ethyl butanoate)-3-yl | |
| 2.6.640 | 3-isopropyl-5-iodophenyl | methyl | (ethyl butanoate)-3-yl | |
| 2.6.641 | 3-n-butyl-5-iodophenyl | methyl | (ethyl butanoate)-3-yl | |
| 2.6.642 | 3-isobutyl-5-iodophenyl | methyl | (ethyl butanoate)-3-yl | |
| 2.6.643 | 3-tert-butyl-5-iodophenyl | methyl | (ethyl butanoate)-3-yl | |
| 2.6.644 | 3-cyclopropyl-5-iodophenyl | methyl | (ethyl butanoate)-3-yl | |
| 2.6.645 | 3-cyano-5-iodophenyl | methyl | (ethyl butanoate)-3-yl | |
| 2.6.646 | 3-trifluoromethyl-5-iodophenyl | methyl | (ethyl butanoate)-3-yl | |
| 2.6.647 | 3-(hydroxy-carbonyl)-5-iodophenyl | methyl | (ethyl butanoate)-3-yl | |
| 2.6.648 | 3-(methoxy-carbonyl)-5-iodophenyl | methyl | (ethyl butanoate)-3-yl | |
| 2.6.649 | 3-methoxy-5-iodophenyl | methyl | (ethyl butanoate)-3-yl | |
| 2.6.650 | 3-ethoxy-5-iodophenyl | methyl | (ethyl butanoate)-3-yl | |
| 2.6.651 | 3-n-propoxy-5-iodophenyl | methyl | (ethyl butanoate)-3-yl | |
| 2.6.652 | 3-isopropoxy-5-iodophenyl | methyl | (ethyl butanoate)-3-yl | |
| 2.6.653 | 3-n-butoxy-5-iodophenyl | methyl | (ethyl butanoate)-3-yl | |
| 2.6.654 | 3-isobutoxy-5-iodophenyl | methyl | (ethyl butanoate)-3-yl | |
| 2.6.655 | 3-difluoro-methoxy-5-iodophenyl | methyl | (ethyl butanoate)-3-yl | |
| 2.6.656 | 3-trifluoro-methoxy-5-iodophenyl | methyl | (ethyl butanoate)-3-yl | |
| 2.6.657 | 3-nitro-5-iodophenyl | methyl | (ethyl butanoate)-3-yl | |
| 2.6.658 | 3-acetoxy-5-iodophenyl | methyl | (ethyl butanoate)-3-yl | |
| 2.6.659 | 3-methylsulfanyl-5-iodophenyl | methyl | (ethyl butanoate)-3-yl | |
| 2.6.660 | 3,5-dimethylphenyl | methyl | (ethyl butanoate)-3-yl | |
| 2.6.661 | 3-ethyl-5-methylphenyl | methyl | (ethyl butanoate)-3-yl | |

TABLE 2.6-continued

Inventive compounds of the general formula (I) in which W* is COOY, R¹ and R² are each hydrogen, and aryl is the radical.

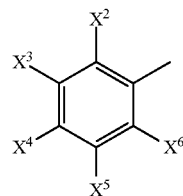

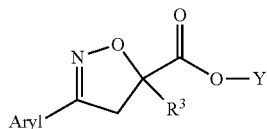

| No. | Aryl | R³ | Y | Physical data |
|---|---|---|---|---|
| 2.6.662 | 3-propyl-5-methylphenyl | methyl | (ethyl butanoate)-3-yl | |
| 2.6.663 | 3-isopropyl-5-methylphenyl | methyl | (ethyl butanoate)-3-yl | |
| 2.6.664 | 3-n-butyl-5-methylphenyl | methyl | (ethyl butanoate)-3-yl | |
| 2.6.665 | 3-isobutyl-5-methylphenyl | methyl | (ethyl butanoate)-3-yl | |
| 2.6.666 | 3-tert-butyl-5-methylphenyl | methyl | (ethyl butanoate)-3-yl | |
| 2.6.667 | 3-cyclopropyl-5-methylphenyl | methyl | (ethyl butanoate)-3-yl | |
| 2.6.668 | 3-cyano-5-methylphenyl | methyl | (ethyl butanoate)-3-yl | |
| 2.6.669 | 3-trifluoromethyl-5-methylphenyl | methyl | (ethyl butanoate)-3-yl | |
| 2.6.670 | 3-(hydroxy-carbonyl)-5-methylphenyl | methyl | (ethyl butanoate)-3-yl | |
| 2.6.671 | 3-(methoxy-carbonyl)-5-methylphenyl | methyl | (ethyl butanoate)-3-yl | |
| 2.6.672 | 3-methoxy-5-methylphenyl | methyl | (ethyl butanoate)-3-yl | |
| 2.6.673 | 3-ethoxy-5-methylphenyl | methyl | (ethyl butanoate)-3-yl | |
| 2.6.674 | 3-propoxy-5-methylphenyl | methyl | (ethyl butanoate)-3-yl | |
| 2.6.675 | 3-butoxy-5-methylphenyl | methyl | (ethyl butanoate)-3-yl | |
| 2.6.676 | 3-isobutoxy-5-methylphenyl | methyl | (ethyl butanoate)-3-yl | |
| 2.6.677 | 3-difluoro-methoxy-5-methylphenyl | methyl | (ethyl butanoate)-3-yl | |
| 2.6.678 | 3-trifluoro-methoxy-5-methylphenyl | methyl | (ethyl butanoate)-3-yl | |
| 2.6.679 | 3-nitro-5-methylphenyl | methyl | (ethyl butanoate)-3-yl | |
| 2.6.680 | 3-acetoxy-5-methylphenyl | methyl | (ethyl butanoate)-3-yl | |
| 2.6.681 | 3-methylsulfanyl-5-methylphenyl | methyl | (ethyl butanoate)-3-yl | |
| 2.6.682 | 3,5-diethylphenyl | methyl | (ethyl butanoate)-3-yl | |
| 2.6.683 | 3-propyl-5-ethylphenyl | methyl | (ethyl butanoate)-3-yl | |
| 2.6.684 | 3-isopropyl-5-ethylphenyl | methyl | (ethyl butanoate)-3-yl | |
| 2.6.685 | 3-n-butyl-5-ethylphenyl | methyl | (ethyl butanoate)-3-yl | |
| 2.6.686 | 3-isobutyl-5-ethylphenyl | methyl | (ethyl butanoate)-3-yl | |
| 2.6.687 | 3-tert-butyl-5-ethylphenyl | methyl | (ethyl butanoate)-3-yl | |
| 2.6.688 | 3-cyclopropyl-5-ethylphenyl | methyl | (ethyl butanoate)-3-yl | |
| 2.6.689 | 3-cyano-5-ethylphenyl | methyl | (ethyl butanoate)-3-yl | |
| 2.6.690 | 3-trifluoromethyl-5-ethylphenyl | methyl | (ethyl butanoate)-3-yl | |
| 2.6.691 | 3-(hydroxy-carbonyl)-5-ethylphenyl | methyl | (ethyl butanoate)-3-yl | |
| 2.6.692 | 3-(methoxy-carbonyl)-5-ethylphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

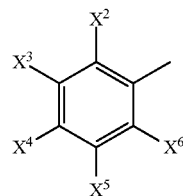

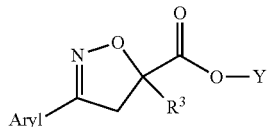

| No. | Aryl | $R^3$ | Y | Physical data |
|---|---|---|---|---|
| 2.6.693 | 3-methoxy-5-ethylphenyl | methyl | (ethyl butanoate)-3-yl | |
| 2.6.694 | 3-ethoxy-5-ethylphenyl | methyl | (ethyl butanoate)-3-yl | |
| 2.6.695 | 3-n-propoxy-5-ethylphenyl | methyl | (ethyl butanoate)-3-yl | |
| 2.6.696 | 3-n-butoxy-5-ethylphenyl | methyl | (ethyl butanoate)-3-yl | |
| 2.6.697 | 3-isobutoxy-5-ethylphenyl | methyl | (ethyl butanoate)-3-yl | |
| 2.6.698 | 3-difluoro-methoxy-5-ethylphenyl | methyl | (ethyl butanoate)-3-yl | |
| 2.6.699 | 3-trifluoro-methoxy-5-ethylphenyl | methyl | (ethyl butanoate)-3-yl | |
| 2.6.700 | 3-nitro-5-ethylphenyl | methyl | (ethyl butanoate)-3-yl | |
| 2.6.701 | 3-acetoxy-5-ethylphenyl | methyl | (ethyl butanoate)-3-yl | |
| 2.6.702 | 3-methylsulfanyl-5-ethylphenyl | methyl | (ethyl butanoate)-3-yl | |
| 2.6.703 | 3,5-dipropylphenyl | methyl | (ethyl butanoate)-3-yl | |
| 2.6.704 | 3-isopropyl-5-propylphenyl | methyl | (ethyl butanoate)-3-yl | |
| 2.6.705 | 3-n-butyl-5-propylphenyl | methyl | (ethyl butanoate)-3-yl | |
| 2.6.706 | 3-isobutyl-5-propylphenyl | methyl | (ethyl butanoate)-3-yl | |
| 2.6.707 | 3-tert-butyl-5-propylphenyl | methyl | (ethyl butanoate)-3-yl | |
| 2.6.708 | 3-cyclopropyl-5-propylphenyl | methyl | (ethyl butanoate)-3-yl | |
| 2.6.709 | 3-cyano-5-propylphenyl | methyl | (ethyl butanoate)-3-yl | |
| 2.6.710 | 3-trifluoromethyl-5-propylphenyl | methyl | (ethyl butanoate)-3-yl | |
| 2.6.711 | 3-(hydroxy-carbonyl)-5-propylphenyl | methyl | (ethyl butanoate)-3-yl | |
| 2.6.712 | 3-(methoxy-carbonyl)-5-propylphenyl | methyl | (ethyl butanoate)-3-yl | |
| 2.6.713 | 3-methoxy-5-propylphenyl | methyl | (ethyl butanoate)-3-yl | |
| 2.6.714 | 3-ethoxy-5-propylphenyl | methyl | (ethyl butanoate)-3-yl | |
| 2.6.715 | 3-n-propoxy-5-propylphenyl | methyl | (ethyl butanoate)-3-yl | |
| 2.6.716 | 3-isobutoxy-5-propylphenyl | methyl | (ethyl butanoate)-3-yl | |
| 2.6.717 | 3-difluoro-methoxy-5-propylphenyl | methyl | (ethyl butanoate)-3-yl | |
| 2.6.718 | 3-trifluoro-methoxy-5-ethylphenyl | methyl | (ethyl butanoate)-3-yl | |
| 2.6.719 | 3-nitro-5-propylphenyl | methyl | (ethyl butanoate)-3-yl | |
| 2.6.720 | 3-acetoxy-5-propylphenyl | methyl | (ethyl butanoate)-3-yl | |
| 2.6.721 | 3-methylsulfanyl-5-propylphenyl | methyl | (ethyl butanoate)-3-yl | |
| 2.6.722 | 3,5-diisopropylphenyl | methyl | (ethyl butanoate)-3-yl | |
| 2.6.723 | 3-n-butyl-5-isopropylphenyl | methyl | (ethyl butanoate)-3-yl | |
| 2.6.724 | 3-isobutyl-5-isopropylphenyl | methyl | (ethyl butanoate)-3-yl | |

TABLE 2.6-continued

Inventive compounds of the general formula (I) in which W* is COOY, R¹ and R² are each hydrogen, and aryl is the radical.

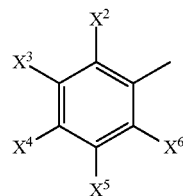

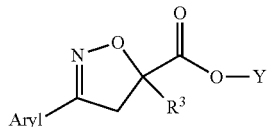

| No. | Aryl | R³ | Y | Physical data |
|---|---|---|---|---|
| 2.6.725 | 3-tert-butyl-5-isopropylphenyl | methyl | (ethyl butanoate)-3-yl | |
| 2.6.726 | 3-cyclopropyl-5-isopropylphenyl | methyl | (ethyl butanoate)-3-yl | |
| 2.6.727 | 3-cyano-5-isopropylphenyl | methyl | (ethyl butanoate)-3-yl | |
| 2.6.728 | 3-trifluoromethyl-5-isopropylphenyl | methyl | (ethyl butanoate)-3-yl | |
| 2.6.729 | 3-(hydroxy-carbonyl)-5-isopropylphenyl | methyl | (ethyl butanoate)-3-yl | |
| 2.6.730 | 3-(methoxy-carbonyl)-5-isopropylphenyl | methyl | (ethyl butanoate)-3-yl | |
| 2.6.731 | 3-methoxy-5-isopropylphenyl | methyl | (ethyl butanoate)-3-yl | |
| 2.6.732 | 3-ethoxy-5-isopropylphenyl | methyl | (ethyl butanoate)-3-yl | |
| 2.6.733 | 3-n-propoxy-5-isopropylphenyl | methyl | (ethyl butanoate)-3-yl | |
| 2.6.734 | 3-isobutoxy-5-isopropylphenyl | methyl | (ethyl butanoate)-3-yl | |
| 2.6.735 | 3-difluoro-methoxy-5-isopropylphenyl | methyl | (ethyl butanoate)-3-yl | |
| 2.6.736 | 3-trifluoro-methoxy-5-isopropylphenyl | methyl | (ethyl butanoate)-3-yl | |
| 2.6.737 | 3-nitro-5-isopropylphenyl | methyl | (ethyl butanoate)-3-yl | |
| 2.6.738 | 3-acetoxy-5-isopropylphenyl | methyl | (ethyl butanoate)-3-yl | |
| 2.6.739 | 3-methylsulfanyl-5-isopropylphenyl | methyl | (ethyl butanoate)-3-yl | |
| 2.6.740 | 3,5-diisobutylphenyl | methyl | (ethyl butanoate)-3-yl | |
| 2.6.741 | 3-tert-butyl-5-isobutylphenyl | methyl | (ethyl butanoate)-3-yl | |
| 2.6.742 | 3-cyclopropyl-5-isobutylphenyl | methyl | (ethyl butanoate)-3-yl | |
| 2.6.743 | 3-cyano-5-isobutylphenyl | methyl | (ethyl butanoate)-3-yl | |
| 2.6.744 | 3-trifluoromethyl-5-isobutylphenyl | methyl | (ethyl butanoate)-3-yl | |
| 2.6.745 | 3-(methoxy-carbonyl)-5-isobutylphenyl | methyl | (ethyl butanoate)-3-yl | |
| 2.6.746 | 3-methoxy-5-isobutylphenyl | methyl | (ethyl butanoate)-3-yl | |
| 2.6.747 | 3-ethoxy-5-isobutylphenyl | methyl | (ethyl butanoate)-3-yl | |
| 2.6.748 | 3-n-propoxy-5-isobutylphenyl | methyl | (ethyl butanoate)-3-yl | |
| 2.6.749 | 3-isobutoxy-5-isobutylphenyl | methyl | (ethyl butanoate)-3-yl | |
| 2.6.750 | 3-difluoro-methoxy-5-isobutylphenyl | methyl | (ethyl butanoate)-3-yl | |
| 2.6.751 | 3-trifluoro-methoxy-5-isobutylphenyl | methyl | (ethyl butanoate)-3-yl | |
| 2.6.752 | 3-nitro-5-isobutylphenyl | methyl | (ethyl butanoate)-3-yl | |
| 2.6.753 | 3-acetoxy-5-isobutylphenyl | methyl | (ethyl butanoate)-3-yl | |
| 2.6.754 | 3-methylsulfanyl-5-isobutylphenyl | methyl | (ethyl butanoate)-3-yl | |

TABLE 2.6-continued

Inventive compounds of the general formula (I) in which W* is COOY, R¹ and R² are each hydrogen, and aryl is the radical.

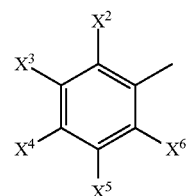

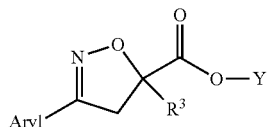

| No. | Aryl | R³ | Y | Physical data |
|---|---|---|---|---|
| 2.6.755 | 3,5-di-tert-butylphenyl | methyl | (ethyl butanoate)-3-yl | |
| 2.6.756 | 3-cyclopropyl-5-tert-butylphenyl | methyl | (ethyl butanoate)-3-yl | |
| 2.6.757 | 3-cyano-5-tert-butylphenyl | methyl | (ethyl butanoate)-3-yl | |
| 2.6.758 | 3-trifluoromethyl-5-tert-butylphenyl | methyl | (ethyl butanoate)-3-yl | |
| 2.6.759 | 3-(hydroxy-carbonyl)-5-tert-butylphenyl | methyl | (ethyl butanoate)-3-yl | |
| 2.6.760 | 3-(methoxy-carbonyl)-5-tert-butylphenyl | methyl | (ethyl butanoate)-3-yl | |
| 2.6.761 | 3-methoxy-5-tert-butylphenyl | methyl | (ethyl butanoate)-3-yl | |
| 2.6.762 | 3-ethoxy-5-tert-butylphenyl | methyl | (ethyl butanoate)-3-yl | |
| 2.6.763 | 3-n-propoxy-5-tert-butylphenyl | methyl | (ethyl butanoate)-3-yl | |
| 2.6.764 | 3-isobutoxy-5-tert-butylphenyl | methyl | (ethyl butanoate)-3-yl | |
| 2.6.765 | 3-difluoro-methoxy-5-tert-butylphenyl | methyl | (ethyl butanoate)-3-yl | |
| 2.6.766 | 3-trifluoro-methoxy-5-tert-butylphenyl | methyl | (ethyl butanoate)-3-yl | |
| 2.6.767 | 3-nitro-5-tert-butylphenyl | methyl | (ethyl butanoate)-3-yl | |
| 2.6.768 | 3-acetoxy-5-tert-butylphenyl | methyl | (ethyl butanoate)-3-yl | |
| 2.6.769 | 3-methylsulfanyl-5-tert-butylphenyl | methyl | (ethyl butanoate)-3-yl | |
| 2.6.770 | 3-tert-butyl-5-cyclopropylphenyl | methyl | (ethyl butanoate)-3-yl | |
| 2.6.771 | 3,5-dicyclopropyl-phenyl | methyl | (ethyl butanoate)-3-yl | |
| 2.6.772 | 3-cyano-5-cyclopropylphenyl | methyl | (ethyl butanoate)-3-yl | |
| 2.6.773 | 3-trifluoromethyl-5-cyclopropyl-phenyl | methyl | (ethyl butanoate)-3-yl | |
| 2.6.774 | 3-(hydroxy-carbonyl)-5-cyclopropylphenyl | methyl | (ethyl butanoate)-3-yl | |
| 2.6.775 | 3-(methoxy-carbonyl)-5-cyclopropylphenyl | methyl | (ethyl butanoate)-3-yl | |
| 2.6.776 | 3-methoxy-5-cyclopropylphenyl | methyl | (ethyl butanoate)-3-yl | |
| 2.6.777 | 3-ethoxy-5-cyclopropylphenyl | methyl | (ethyl butanoate)-3-yl | |
| 2.6.778 | 3-n-propoxy-5-cyclopropylphenyl | methyl | (ethyl butanoate)-3-yl | |
| 2.6.779 | 3-isobutoxy-5-cyclopropylphenyl | methyl | (ethyl butanoate)-3-yl | |
| 2.6.780 | 3-difluoro-methoxy-5-cyclopropylphenyl | methyl | (ethyl butanoate)-3-yl | |
| 2.6.781 | 3-trifluoro-methoxy-5-cyclopropylphenyl | methyl | (ethyl butanoate)-3-yl | |
| 2.6.782 | 3-nitro-5-cyclopropylphenyl | methyl | (ethyl butanoate)-3-yl | |
| 2.6.783 | 3-acetoxy-5-cyclopropylphenyl | methyl | (ethyl butanoate)-3-yl | |
| 2.6.784 | 3-methylsulfanyl-5-cyclopropyl-phenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

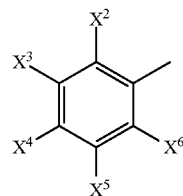

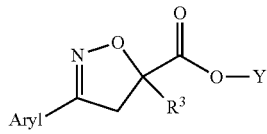

| No. | Aryl | $R^3$ | Y | Physical data |
|---|---|---|---|---|
| 2.6.785 | 3,5-dicyanophenyl | methyl | (ethyl butanoate)-3-yl | |
| 2.6.786 | 3-trifluoromethyl-5-cyanophenyl | methyl | (ethyl butanoate)-3-yl | |
| 2.6.787 | 3-(methoxy-carbonyl)-5-cyanophenyl | methyl | (ethyl butanoate)-3-yl | |
| 2.6.788 | 3-methoxy-5-cyanophenyl | methyl | (ethyl butanoate)-3-yl | |
| 2.6.789 | 3-ethoxy-5-cyanophenyl | methyl | (ethyl butanoate)-3-yl | |
| 2.6.790 | 3-n-propoxy-5-cyanophenyl | methyl | (ethyl butanoate)-3-yl | |
| 2.6.791 | 3-n-butoxy-5-cyanophenyl | methyl | (ethyl butanoate)-3-yl | |
| 2.6.792 | 3-isobutoxy-5-cyanophenyl | methyl | (ethyl butanoate)-3-yl | |
| 2.6.793 | 3-difluoro-methoxy-5-cyanophenyl | methyl | (ethyl butanoate)-3-yl | |
| 2.6.794 | 3-trifluoro-methoxy-5-cyanophenyl | methyl | (ethyl butanoate)-3-yl | |
| 2.6.795 | 3-nitro-5-cyanophenyl | methyl | (ethyl butanoate)-3-yl | |
| 2.6.796 | 3-acetoxy-5-cyanophenyl | methyl | (ethyl butanoate)-3-yl | |
| 2.6.797 | 3-methylsulfanyl-5-cyanophenyl | methyl | (ethyl butanoate)-3-yl | |
| 2.6.798 | 3,5-di(trifluoro-methyl)-phenyl | methyl | (ethyl butanoate)-3-yl | |
| 2.6.799 | 3-(hydroxy-carbonyl)-5-trifluoromethyl-phenyl | methyl | (ethyl butanoate)-3-yl | |
| 2.6.800 | 3-(methoxy-carbonyl)-5-trifluoromethyl-phenyl | methyl | (ethyl butanoate)-3-yl | |
| 2.6.801 | 3-methoxy-5-trifluoromethyl-phenyl | methyl | (ethyl butanoate)-3-yl | |
| 2.6.802 | 3-ethoxy-5-trifluoromethyl-phenyl | methyl | (ethyl butanoate)-3-yl | |
| 2.6.803 | 3-n-propoxy-5-trifluoromethyl-phenyl | methyl | (ethyl butanoate)-3-yl | |
| 2.6.804 | 3-isobutoxy-5-trifluoromethyl-phenyl | methyl | (ethyl butanoate)-3-yl | |
| 2.6.805 | 3-difluoro-methoxy-5-trifluoromethyl-phenyl | methyl | (ethyl butanoate)-3-yl | |
| 2.6.806 | 3-trifluoro-methoxy-5-trifluoromethyl-phenyl | methyl | (ethyl butanoate)-3-yl | |
| 2.6.807 | 3-nitro-5-trifluoromethyl-phenyl | methyl | (ethyl butanoate)-3-yl | |
| 2.6.808 | 3-acetoxy-5-trifluoromethyl-phenyl | methyl | (ethyl butanoate)-3-yl | |
| 2.6.809 | 3-methylsulfanyl-5-trifluoromethyl-phenyl | methyl | (ethyl butanoate)-3-yl | |
| 2.6.810 | 3,5-di(methoxy-carbonyl)phenyl | methyl | (ethyl butanoate)-3-yl | |
| 2.6.811 | 3-methoxy-5-(methoxycarbonyl)-phenyl | methyl | (ethyl butanoate)-3-yl | |
| 2.6.812 | 3-ethoxy-5-(methoxycarbonyl)-phenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

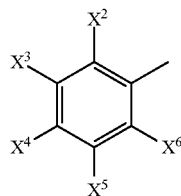

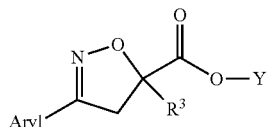

| No. | Aryl | $R^3$ | Y | Physical data |
|---|---|---|---|---|
| 2.6.813 | 3-n-propoxy-5-(methoxycarbonyl)-phenyl | methyl | (ethyl butanoate)-3-yl | |
| 2.6.814 | 3-isobutoxy-5-(methoxycarbonyl)-phenyl | methyl | (ethyl butanoate)-3-yl | |
| 2.6.815 | 3-difluoro-methoxy-5-(methoxy-carbonyl)phenyl | methyl | (ethyl butanoate)-3-yl | |
| 2.6.816 | 3-trifluoro-methoxy-5-(methoxy-carbonyl)phenyl | methyl | (ethyl butanoate)-3-yl | |
| 2.6.817 | 3-nitro-5-(methoxy-carbonyl)phenyl | methyl | (ethyl butanoate)-3-yl | |
| 2.6.818 | 3-acetoxy-5-(methoxy-carbonyl)phenyl | methyl | (ethyl butanoate)-3-yl | |
| 2.6.819 | 3-methylsulfanyl-5-(methoxy-carbonyl)phenyl | methyl | (ethyl butanoate)-3-yl | |
| 2.6.820 | 3,5-dimethoxyphenyl | methyl | (ethyl butanoate)-3-yl | |
| 2.6.821 | 3-ethoxy-5-methoxyphenyl | methyl | (ethyl butanoate)-3-yl | |
| 2.6.822 | 3-n-propoxy-5-methoxyphenyl | methyl | (ethyl butanoate)-3-yl | |
| 2.6.823 | 3-isobutoxy-5-methoxyphenyl | methyl | (ethyl butanoate)-3-yl | |
| 2.6.824 | 3-difluoro-methoxy-5-methoxyphenyl | methyl | (ethyl butanoate)-3-yl | |
| 2.6.825 | 3-trifluoro-methoxy-5-methoxyphenyl | methyl | (ethyl butanoate)-3-yl | |
| 2.6.826 | 3-nitro-5-methoxyphenyl | methyl | (ethyl butanoate)-3-yl | |
| 2.6.827 | 3-acetoxy-5-methoxyphenyl | methyl | (ethyl butanoate)-3-yl | |
| 2.6.828 | 3-methylsulfanyl-5-methoxyphenyl | methyl | (ethyl butanoate)-3-yl | |
| 2.6.829 | 3,5-diethoxyphenyl | methyl | (ethyl butanoate)-3-yl | |
| 2.6.830 | 3-n-propoxy-5-ethoxyphenyl | methyl | (ethyl butanoate)-3-yl | |
| 2.6.831 | 3-isobutoxy-5-ethoxyphenyl | methyl | (ethyl butanoate)-3-yl | |
| 2.6.832 | 3-difluoro-methoxy-5-ethoxyphenyl | methyl | (ethyl butanoate)-3-yl | |
| 2.6.833 | 3-trifluoro-methoxy-5-ethoxyphenyl | methyl | (ethyl butanoate)-3-yl | |
| 2.6.834 | 3-nitro-5-ethoxyphenyl | methyl | (ethyl butanoate)-3-yl | |
| 2.6.835 | 3-acetoxy-5-ethoxyphenyl | methyl | (ethyl butanoate)-3-yl | |
| 2.6.836 | 3-methylsulfanyl-5-ethoxyphenyl | methyl | (ethyl butanoate)-3-yl | |
| 2.6.837 | 3,5-di(isopropoxy)-phenyl | methyl | (ethyl butanoate)-3-yl | |
| 2.6.838 | 3-n-butoxy-5-isopropoxyphenyl | methyl | (ethyl butanoate)-3-yl | |
| 2.6.839 | 3-isobutoxy-5-isopropoxyphenyl | methyl | (ethyl butanoate)-3-yl | |
| 2.6.840 | 3-difluoro-methoxy-5-isopropoxyphenyl | methyl | (ethyl butanoate)-3-yl | |

TABLE 2.6-continued

Inventive compounds of the general formula (I) in which W* is COOY, R¹ and R² are each hydrogen, and aryl is the radical.

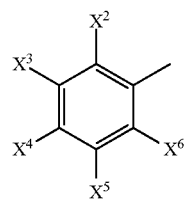

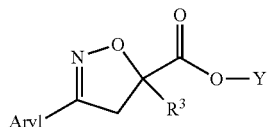

| No. | Aryl | R³ | Y | Physical data |
|---|---|---|---|---|
| 2.6.841 | 3-trifluoro-methoxy-5-isopropoxyphenyl | methyl | (ethyl butanoate)-3-yl | |
| 2.6.842 | 3-nitro-5-isopropoxyphenyl | methyl | (ethyl butanoate)-3-yl | |
| 2.6.843 | 3-acetoxy-5-isopropoxyphenyl | methyl | (ethyl butanoate)-3-yl | |
| 2.6.844 | 3-methylsulfanyl-5-isopropoxy-phenyl | methyl | (ethyl butanoate)-3-yl | |
| 2.6.845 | 3,5-di(trifluoro-methoxy)phenyl | methyl | (ethyl butanoate)-3-yl | |
| 2.6.846 | 3-nitro-5-trifluoro-methoxyphenyl | methyl | (ethyl butanoate)-3-yl | |
| 2.6.847 | 3-methylsulfanyl-5-trifluoro-methoxy-phenyl | methyl | (ethyl butanoate)-3-yl | |
| 2.6.848 | 3,5-bis(difluoro-methoxy)phenyl | methyl | (ethyl butanoate)-3-yl | |
| 2.6.849 | 3-trifluoro-methoxy-5-difluoromethoxy-phenyl | methyl | (ethyl butanoate)-3-yl | |
| 2.6.850 | 3-nitro-5-difluoro-methoxyphenyl | methyl | (ethyl butanoate)-3-yl | |
| 2.6.851 | 3-acetoxy-5-difluoromethoxy-phenyl | methyl | (ethyl butanoate)-3-yl | |
| 2.6.852 | 3-methylsulfanyl-5-difluoro-methoxyphenyl | methyl | (ethyl butanoate)-3-yl | |
| 2.6.853 | 3,5-bis(acetoxy)-phenyl | methyl | (ethyl butanoate)-3-yl | |
| 2.6.854 | 3-methylsulfanyl-5-acetoxyphenyl | methyl | (ethyl butanoate)-3-yl | |
| 2.6.855 | 3,5-dinitrophenyl | methyl | (ethyl butanoate)-3-yl | |
| 2.6.856 | 3-acetoxy-5-nitrophenyl | methyl | (ethyl butanoate)-3-yl | |
| 2.6.857 | 3-methylsulfanyl-5-nitrophenyl | methyl | (ethyl butanoate)-3-yl | |
| 2.6.858 | 3,5-di(methyl-sulfanyl)phenyl | methyl | (ethyl butanoate)-3-yl | |
| 2.6.859 | 3,4-difluorophenyl | methyl | (ethyl butanoate)-3-yl | |
| 2.6.860 | 3-chloro-4-fluorophenyl | methyl | (ethyl butanoate)-3-yl | |
| 2.6.861 | 3-bromo-4-fluorophenyl | methyl | (ethyl butanoate)-3-yl | |
| 2.6.862 | 3-methyl-4-fluorophenyl | methyl | (ethyl butanoate)-3-yl | |
| 2.6.863 | 3-ethyl-4-fluorophenyl | methyl | (ethyl butanoate)-3-yl | |
| 2.6.864 | 3-cyclopropyl-4-fluorophenyl | methyl | (ethyl butanoate)-3-yl | |
| 2.6.865 | 3-cyano-4-fluorophenyl | methyl | (ethyl butanoate)-3-yl | |
| 2.6.866 | 3-methoxy-4-fluorophenyl | methyl | (ethyl butanoate)-3-yl | |
| 2.6.867 | 3-ethoxy-4-fluorophenyl | methyl | (ethyl butanoate)-3-yl | |
| 2.6.868 | 3-trifluoro-methoxy-4-fluorophenyl | methyl | (ethyl butanoate)-3-yl | |

TABLE 2.6-continued

Inventive compounds of the general formula (I) in which W* is COOY, R¹ and R² are each hydrogen, and aryl is the radical.

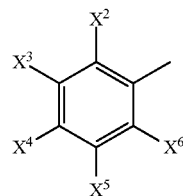

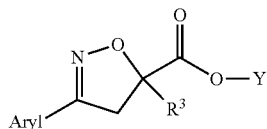

| No. | Aryl | R³ | Y | Physical data |
|---|---|---|---|---|
| 2.6.869 | 3-nitro-4-fluorophenyl | methyl | (ethyl butanoate)-3-yl | |
| 2.6.870 | 3-fluoro-4-chlorophenyl | methyl | (ethyl butanoate)-3-yl | |
| 2.6.871 | 3,4-dichlorophenyl | methyl | (ethyl butanoate)-3-yl | |
| 2.6.872 | 3-bromo-4-chlorophenyl | methyl | (ethyl butanoate)-3-yl | |
| 2.6.873 | 3-methyl-4-chlorophenyl | methyl | (ethyl butanoate)-3-yl | |
| 2.6.874 | 3-cyclopropyl-4-chlorophenyl | methyl | (ethyl butanoate)-3-yl | |
| 2.6.875 | 3-cyano-4-chlorophenyl | methyl | (ethyl butanoate)-3-yl | |
| 2.6.876 | 3-trifluoromethyl-4-chlorophenyl | methyl | (ethyl butanoate)-3-yl | |
| 2.6.877 | 3-methoxy-4-chlorophenyl | methyl | (ethyl butanoate)-3-yl | |
| 2.6.878 | 3-ethoxy-4-chlorophenyl | methyl | (ethyl butanoate)-3-yl | |
| 2.6.879 | 3-trifluoro-methoxy-4-chlorophenyl | methyl | (ethyl butanoate)-3-yl | |
| 2.6.880 | 3-nitro-4-chlorophenyl | methyl | (ethyl butanoate)-3-yl | |
| 2.6.881 | 3-fluoro-4-bromophenyl | methyl | (ethyl butanoate)-3-yl | |
| 2.6.882 | 3-chloro-4-bromophenyl | methyl | (ethyl butanoate)-3-yl | |
| 2.6.883 | 3,4-dibromophenyl | methyl | (ethyl butanoate)-3-yl | |
| 2.6.884 | 3-methyl-4-bromophenyl | methyl | (ethyl butanoate)-3-yl | |
| 2.6.885 | 3-ethyl-4-bromophenyl | methyl | (ethyl butanoate)-3-yl | |
| 2.6.886 | 3-cyclopropyl-4-bromophenyl | methyl | (ethyl butanoate)-3-yl | |
| 2.6.887 | 3-cyano-4-bromophenyl | methyl | (ethyl butanoate)-3-yl | |
| 2.6.888 | 3-trifluoromethyl-4-bromophenyl | methyl | (ethyl butanoate)-3-yl | |
| 2.6.889 | 3-methoxy-4-phenyl | methyl | (ethyl butanoate)-3-yl | |
| 2.6.890 | 3-ethoxy-4-bromophenyl | methyl | (ethyl butanoate)-3-yl | |
| 2.6.891 | 3-trifluoro-methoxy-4-bromophenyl | methyl | (ethyl butanoate)-3-yl | |
| 2.6.892 | 3-nitro-4-bromophenyl | methyl | (ethyl butanoate)-3-yl | |
| 2.6.893 | 3-fluoro-4-iodophenyl | methyl | (ethyl butanoate)-3-yl | |
| 2.6.894 | 3-chloro-4-iodophenyl | methyl | (ethyl butanoate)-3-yl | |
| 2.6.895 | 3-bromo-4-iodophenyl | methyl | (ethyl butanoate)-3-yl | |
| 2.6.896 | 3-methyl-4-iodophenyl | methyl | (ethyl butanoate)-3-yl | |
| 2.6.897 | 3-cyclopropyl-4-iodophenyl | methyl | (ethyl butanoate)-3-yl | |
| 2.6.898 | 3-cyano-4-iodophenyl | methyl | (ethyl butanoate)-3-yl | |
| 2.6.899 | 3-trifluoromethyl-4-iodophenyl | methyl | (ethyl butanoate)-3-yl | |
| 2.6.900 | 3-methoxy-4-iodophenyl | methyl | (ethyl butanoate)-3-yl | |
| 2.6.901 | 3-ethoxy-4-iodophenyl | methyl | (ethyl butanoate)-3-yl | |
| 2.6.902 | 3-trifluoro-methoxy-4-iodophenyl | methyl | (ethyl butanoate)-3-yl | |
| 2.6.903 | 3-nitro-4-iodophenyl | methyl | (ethyl butanoate)-3-yl | |
| 2.6.904 | 3-fluoro-4-methylphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

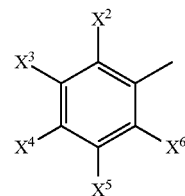

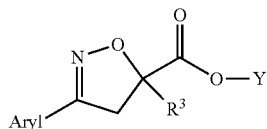

| No. | Aryl | $R^3$ | Y | Physical data |
|---|---|---|---|---|
| 2.6.905 | 3-chloro-4-methylphenyl | methyl | (ethyl butanoate)-3-yl | |
| 2.6.906 | 3-bromo-4-methylphenyl | methyl | (ethyl butanoate)-3-yl | |
| 2.6.907 | 3,4-dimethylphenyl | methyl | (ethyl butanoate)-3-yl | |
| 2.6.908 | 3,4-dimethylphenyl | ethyl | (ethyl butanoate)-3-yl | |
| 2.6.909 | 3,4-dimethylphenyl | isopropyl | (ethyl butanoate)-3-yl | |
| 2.6.910 | 3,4-dimethylphenyl | cyclo-propyl | (ethyl butanoate)-3-yl | |
| 2.6.911 | 3-ethyl-4-methylphenyl | methyl | (ethyl butanoate)-3-yl | |
| 2.6.912 | 3-cyclopropyl-4-methylphenyl | methyl | (ethyl butanoate)-3-yl | |
| 2.6.913 | 3-cyano-4-methylphenyl | methyl | (ethyl butanoate)-3-yl | |
| 2.6.914 | 3-trifluoromethyl-4-methylphenyl | methyl | (ethyl butanoate)-3-yl | |
| 2.6.915 | 3-methoxy-4-methylphenyl | methyl | (ethyl butanoate)-3-yl | |
| 2.6.916 | 3-ethoxy-4-methylphenyl | methyl | (ethyl butanoate)-3-yl | |
| 2.6.917 | 3-trifluoro-methoxy-4-methylphenyl | methyl | (ethyl butanoate)-3-yl | |
| 2.6.918 | 3-nitro-4-methylphenyl | methyl | (ethyl butanoate)-3-yl | |
| 2.6.919 | 3-fluoro-4-ethylphenyl | methyl | (ethyl butanoate)-3-yl | |
| 2.6.920 | 3-chloro-4-ethylphenyl | methyl | (ethyl butanoate)-3-yl | |
| 2.6.921 | 3-bromo-4-ethylphenyl | methyl | (ethyl butanoate)-3-yl | |
| 2.6.922 | 3-methyl-4-ethylphenyl | methyl | (ethyl butanoate)-3-yl | |
| 2.6.923 | 3,4-diethylphenyl | methyl | (ethyl butanoate)-3-yl | |
| 2.6.924 | 3-cyclopropyl-4-ethylphenyl | methyl | (ethyl butanoate)-3-yl | |
| 2.6.925 | 3-cyano-4-ethylphenyl | methyl | (ethyl butanoate)-3-yl | |
| 2.6.926 | 3-trifluoromethyl-4-ethylphenyl | methyl | (ethyl butanoate)-3-yl | |
| 2.6.927 | 3-methoxy-4-ethylphenyl | methyl | (ethyl butanoate)-3-yl | |
| 2.6.928 | 3-ethoxy-4-ethylphenyl | methyl | (ethyl butanoate)-3-yl | |
| 2.6.929 | 3-trifluoro-methoxy-4-ethylphenyl | methyl | (ethyl butanoate)-3-yl | |
| 2.6.930 | 3-nitro-4-ethylphenyl | methyl | (ethyl butanoate)-3-yl | |
| 2.6.931 | 3-fluoro-4-propylphenyl | methyl | (ethyl butanoate)-3-yl | |
| 2.6.932 | 3-chloro-4-propylphenyl | methyl | (ethyl butanoate)-3-yl | |
| 2.6.933 | 3-bromo-4-propylphenyl | methyl | (ethyl butanoate)-3-yl | |
| 2.6.934 | 3-methyl-4-propylphenyl | methyl | (ethyl butanoate)-3-yl | |
| 2.6.935 | 3-methyl-4-propylphenyl | methyl | (ethyl butanoate)-3-yl | |
| 2.6.936 | 3-cyclopropyl-4-propylphenyl | methyl | (ethyl butanoate)-3-yl | |
| 2.6.937 | 3-cyano-4-propylphenyl | methyl | (ethyl butanoate)-3-yl | |
| 2.6.938 | 3-trifluoromethyl-4-propylphenyl | methyl | (ethyl butanoate)-3-yl | |
| 2.6.939 | 3-methoxy-4-propylphenyl | methyl | (ethyl butanoate)-3-yl | |

TABLE 2.6-continued

Inventive compounds of the general formula (I) in which W* is COOY, R¹ and R² are each hydrogen, and aryl is the radical.

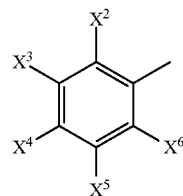

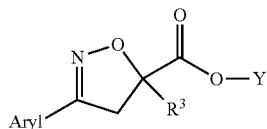

| No. | Aryl | R³ | Y | Physical data |
|---|---|---|---|---|
| 2.6.940 | 3-ethoxy-4-propylphenyl | methyl | (ethyl butanoate)-3-yl | |
| 2.6.941 | 3-trifluoro-methoxy-4-propylphenyl | methyl | (ethyl butanoate)-3-yl | |
| 2.6.942 | 3-nitro-4-propylphenyl | methyl | (ethyl butanoate)-3-yl | |
| 2.6.943 | 3-fluoro-4-isopropylphenyl | methyl | (ethyl butanoate)-3-yl | |
| 2.6.944 | 3-chloro-4-isopropylphenyl | methyl | (ethyl butanoate)-3-yl | |
| 2.6.945 | 3-bromo-4-isopropylphenyl | methyl | (ethyl butanoate)-3-yl | |
| 2.6.946 | 3-methyl-4-isopropylphenyl | methyl | (ethyl butanoate)-3-yl | |
| 2.6.947 | 3-cyclopropyl-4-isopropylphenyl | methyl | (ethyl butanoate)-3-yl | |
| 2.6.948 | 3-cyano-4-isopropylphenyl | methyl | (ethyl butanoate)-3-yl | |
| 2.6.949 | 3-trifluoromethyl-4-isopropylphenyl | methyl | (ethyl butanoate)-3-yl | |
| 2.6.950 | 3-methoxy-4-isopropylphenyl | methyl | (ethyl butanoate)-3-yl | |
| 2.6.951 | 3-thoxy-4-isopropylphenyl | methyl | (ethyl butanoate)-3-yl | |
| 2.6.952 | 3-trifluoro-methoxy-4-isopropylphenyl | methyl | (ethyl butanoate)-3-yl | |
| 2.6.953 | 3-nitro-4-isopropylphenyl | methyl | (ethyl butanoate)-3-yl | |
| 2.6.954 | 3-fluoro-4-tert-butylphenyl | methyl | (ethyl butanoate)-3-yl | |
| 2.6.955 | 3-chloro-4-tert-butylphenyl | methyl | (ethyl butanoate)-3-yl | |
| 2.6.956 | 3-bromo-4-tert-butylphenyl | methyl | (ethyl butanoate)-3-yl | |
| 2.6.957 | 3-methyl-4-tert-butylphenyl | methyl | (ethyl butanoate)-3-yl | |
| 2.6.958 | 3-cyclopropyl-4-tert-butylphenyl | methyl | (ethyl butanoate)-3-yl | |
| 2.6.959 | 3-cyano-4-tert-butylphenyl | methyl | (ethyl butanoate)-3-yl | |
| 2.6.960 | 3-trifluoromethyl-4-tert-butylphenyl | methyl | (ethyl butanoate)-3-yl | |
| 2.6.961 | 3-methoxy-4-tert-butylphenyl | methyl | (ethyl butanoate)-3-yl | |
| 2.6.962 | 3-ethoxy-4-tert-butylphenyl | methyl | (ethyl butanoate)-3-yl | |
| 2.6.963 | 3-trifluoro-methoxy-4-tert-butylphenyl | methyl | (ethyl butanoate)-3-yl | |
| 2.6.964 | 3-nitro-4-tert-butylphenyl | methyl | (ethyl butanoate)-3-yl | |
| 2.6.965 | 3-fluoro-4-cyclopropylphenyl | methyl | (ethyl butanoate)-3-yl | |
| 2.6.966 | 3-chloro-4-cyclopropylphenyl | methyl | (ethyl butanoate)-3-yl | |
| 2.6.967 | 3-bromo-4-cyclopropylphenyl | methyl | (ethyl butanoate)-3-yl | |
| 2.6.968 | 3-methyl-4-cyclopropylphenyl | methyl | (ethyl butanoate)-3-yl | |
| 2.6.969 | 3,4-dicyclopropyl-phenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

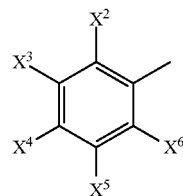

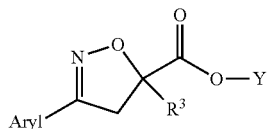

| No. | Aryl | $R^3$ | Y | Physical data |
|---|---|---|---|---|
| 2.6.970 | 3-cyano-4-cyclopropylphenyl | methyl | (ethyl butanoate)-3-yl | |
| 2.6.971 | 3-trifluoromethyl-4-cyclopropyl-phenyl | methyl | (ethyl butanoate)-3-yl | |
| 2.6.972 | 3-methoxy-4-cyclopropylphenyl | methyl | (ethyl butanoate)-3-yl | |
| 2.6.973 | 3-ethoxy-4-cyclopropylphenyl | methyl | (ethyl butanoate)-3-yl | |
| 2.6.974 | 3-trifluoro-methoxy-4-cyclopropylphenyl | methyl | (ethyl butanoate)-3-yl | |
| 2.6.975 | 3-fluoro-4-methoxycarbonyl-phenyl | methyl | (ethyl butanoate)-3-yl | |
| 2.6.976 | 3-chloro-4-methoxy-carbonylphenyl | methyl | (ethyl butanoate)-3-yl | |
| 2.6.977 | 3-bromo-4-methoxy-carbonylphenyl | methyl | (ethyl butanoate)-3-yl | |
| 2.6.978 | 3-methyl-4-methoxy-carbonylphenyl | methyl | (ethyl butanoate)-3-yl | |
| 2.6.979 | 3-cyclopropyl-4-methoxycarbonyl-phenyl | methyl | (ethyl butanoate)-3-yl | |
| 2.6.980 | 3-cyano-4-methoxy-carbonylphenyl | methyl | (ethyl butanoate)-3-yl | |
| 2.6.981 | 3-trifluoromethyl-4-methoxy-carbonylphenyl | methyl | (ethyl butanoate)-3-yl | |
| 2.6.982 | 3-methoxy-4-methoxycarbonyl-phenyl | methyl | (ethyl butanoate)-3-yl | |
| 2.6.983 | 3-ethoxy-4-methoxycarbonyl-phenyl | methyl | (ethyl butanoate)-3-yl | |
| 2.6.984 | 3-trifluoro-methoxycarbonyl-phenyl | methyl | (ethyl butanoate)-3-yl | |
| 2.6.985 | 3-nitro-4-methoxy-carbonylphenyl | methyl | (ethyl butanoate)-3-yl | |
| 2.6.986 | 3-fluoro-4-cyanophenyl | methyl | (ethyl butanoate)-3-yl | |
| 2.6.987 | 3-chloro-4-cyanophenyl | methyl | (ethyl butanoate)-3-yl | |
| 2.6.988 | 3-bromo-4-cyanophenyl | methyl | (ethyl butanoate)-3-yl | |
| 2.6.989 | 3-methyl-4-cyanophenyl | methyl | (ethyl butanoate)-3-yl | |
| 2.6.990 | 3-cyclopropyl-4-cyanophenyl | methyl | (ethyl butanoate)-3-yl | |
| 2.6.991 | 3-cyano-4-cyanophenyl | methyl | (ethyl butanoate)-3-yl | |
| 2.6.992 | 3-trifluoromethyl-4-cyanophenyl | methyl | (ethyl butanoate)-3-yl | |
| 2.6.993 | 3-methoxy-4-cyanophenyl | methyl | (ethyl butanoate)-3-yl | |
| 2.6.994 | 3-ethoxy-4-cyanophenyl | methyl | (ethyl butanoate)-3-yl | |
| 2.6.995 | 3-trifluoro-methoxy-4-cyanophenyl | methyl | (ethyl butanoate)-3-yl | |
| 2.6.996 | 3-nitro-4-cyanophenyl | methyl | (ethyl butanoate)-3-yl | |

TABLE 2.6-continued

Inventive compounds of the general formula (I) in which W* is COOY, R¹ and R² are each hydrogen, and aryl is the radical.

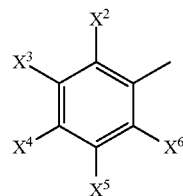

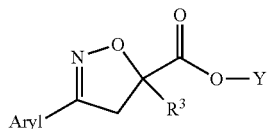

| No. | Aryl | R³ | Y | Physical data |
|---|---|---|---|---|
| 2.6.997 | 3-fluoro-4-methoxyphenyl | methyl | (ethyl butanoate)-3-yl | |
| 2.6.998 | 3-chloro-4-methoxyphenyl | methyl | (ethyl butanoate)-3-yl | |
| 2.6.999 | 3-bromo-4-methoxyphenyl | methyl | (ethyl butanoate)-3-yl | |
| 2.6.1000 | 3-methyl-4-methoxyphenyl | methyl | (ethyl butanoate)-3-yl | |
| 2.6.1001 | 3-cyclopropyl-4-methoxyphenyl | methyl | (ethyl butanoate)-3-yl | |
| 2.6.1002 | 3-cyano-4-methoxyphenyl | methyl | (ethyl butanoate)-3-yl | |
| 2.6.1003 | 3-trifluoromethyl-4-methoxyphenyl | methyl | (ethyl butanoate)-3-yl | |
| 2.6.1004 | 3,4-dimethoxyphenyl | methyl | (ethyl butanoate)-3-yl | |
| 2.6.1005 | 3-ethoxy-4-methoxyphenyl | methyl | (ethyl butanoate)-3-yl | |
| 2.6.1006 | 3-trifluoro-methoxy-4-methoxyphenyl | methyl | (ethyl butanoate)-3-yl | |
| 2.6.1007 | 3-nitro-4-methoxyphenyl | methyl | (ethyl butanoate)-3-yl | |
| 2.6.1008 | 3-fluoro-4-ethoxyphenyl | methyl | (ethyl butanoate)-3-yl | |
| 2.6.1009 | 3-chloro-4-ethoxyphenyl | methyl | (ethyl butanoate)-3-yl | |
| 2.6.1010 | 3-bromo-4-ethoxyphenyl | methyl | (ethyl butanoate)-3-yl | |
| 2.6.1011 | 3-methyl-4-ethoxyphenyl | methyl | (ethyl butanoate)-3-yl | |
| 2.6.1012 | 3-cyclopropyl-4-ethoxyphenyl | methyl | (ethyl butanoate)-3-yl | |
| 2.6.1013 | 3-cyano-4-ethoxyphenyl | methyl | (ethyl butanoate)-3-yl | |
| 2.6.1014 | 3-trifluoromethyl-4-ethoxyphenyl | methyl | (ethyl butanoate)-3-yl | |
| 2.6.1015 | 3-methoxy-4-ethoxyphenyl | methyl | (ethyl butanoate)-3-yl | |
| 2.6.1016 | 2,4-diethoxyphenyl | methyl | (ethyl butanoate)-3-yl | |
| 2.6.1017 | 3-trifluoro-methoxy-4-ethoxyphenyl | methyl | (ethyl butanoate)-3-yl | |
| 2.6.1018 | 3-nitro-4-ethoxyphenyl | methyl | (ethyl butanoate)-3-yl | |
| 2.6.1019 | 3-fluoro-4-isopropoxyphenyl | methyl | (ethyl butanoate)-3-yl | |
| 2.6.1020 | 3-chloro-4-isopropoxyphenyl | methyl | (ethyl butanoate)-3-yl | |
| 2.6.1021 | 3-bromo-4-isopropoxyphenyl | methyl | (ethyl butanoate)-3-yl | |
| 2.6.1022 | 3-methyl-4-isopropoxyphenyl | methyl | (ethyl butanoate)-3-yl | |
| 2.6.1023 | 3-cyclopropyl-4-isopropoxyphenyl | methyl | (ethyl butanoate)-3-yl | |
| 2.6.1024 | 3-cyano-4-isopropoxyphenyl | methyl | (ethyl butanoate)-3-yl | |
| 2.6.1025 | 3-trifluoromethyl-4-isopropoxy-phenyl | methyl | (ethyl butanoate)-3-yl | |
| 2.6.1026 | 3-methoxy-4-isopropoxyphenyl | methyl | (ethyl butanoate)-3-yl | |
| 2.6.1027 | 3-ethoxy-4-isopropoxyphenyl | methyl | (ethyl butanoate)-3-yl | |

TABLE 2.6-continued

Inventive compounds of the general formula (I) in which W* is COOY, R¹ and R² are each hydrogen, and aryl is the radical.

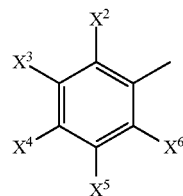

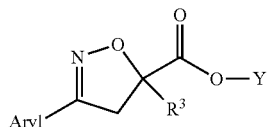

| No. | Aryl | R³ | Y | Physical data |
|---|---|---|---|---|
| 2.6.1028 | 3-trifluoro-methoxy-4-isopropoxyphenyl | methyl | (ethyl butanoate)-3-yl | |
| 2.6.1029 | 3-nitro-4-isopropoxyphenyl | methyl | (ethyl butanoate)-3-yl | |
| 2.6.1030 | 3-fluoro-4-trifluoro-methoxyphenyl | methyl | (ethyl butanoate)-3-yl | |
| 2.6.1031 | 3-chloro-4-trifluoro-methoxyphenyl | methyl | (ethyl butanoate)-3-yl | |
| 2.6.1032 | 3-bromo-4-trifluoro-methoxyphenyl | methyl | (ethyl butanoate)-3-yl | |
| 2.6.1033 | 3-methyl-4-trifluoro-methoxyphenyl | methyl | (ethyl butanoate)-3-yl | |
| 2.6.1034 | 3-cyclopropyl-4-trifluoromethoxy-phenyl | methyl | (ethyl butanoate)-3-yl | |
| 2.6.1035 | 3-cyano-4-trifluoro-methoxyphenyl | methyl | (ethyl butanoate)-3-yl | |
| 2.6.1036 | 3-trifluoromethyl-4-trifluoro-methoxyphenyl | methyl | (ethyl butanoate)-3-yl | |
| 2.6.1037 | 3-methoxy-4-trifluoromethoxy-phenyl | methyl | (ethyl butanoate)-3-yl | |
| 2.6.1038 | 3-ethoxy-4-trifluoro-methoxyphenyl | methyl | (ethyl butanoate)-3-yl | |
| 2.6.1039 | 3,4-bis(trifluoro-methoxy)phenyl | methyl | (ethyl butanoate)-3-yl | |
| 2.6.1040 | 3-nitro-4-trifluoro-methoxyphenyl | methyl | (ethyl butanoate)-3-yl | |
| 2.6.1041 | 3-fluoro-4-difluoromethoxy-phenyl | methyl | (ethyl butanoate)-3-yl | |
| 2.6.1042 | 3-chloro-4-difluoromethoxy-phenyl | methyl | (ethyl butanoate)-3-yl | |
| 2.6.1043 | 3-bromo-4-difluoromethoxy-phenyl | methyl | (ethyl butanoate)-3-yl | |
| 2.6.1044 | 3-methyl-4-difluoromethoxy-phenyl | methyl | (ethyl butanoate)-3-yl | |
| 2.6.1045 | 3-cyclopropyl-4-difluoromethoxy-phenyl | methyl | (ethyl butanoate)-3-yl | |
| 2.6.1046 | 3-cyano-4-difluoromethoxy-phenyl | methyl | (ethyl butanoate)-3-yl | |
| 2.6.1047 | 3-trifluoromethyl-4-difluoro-methoxyphenyl | methyl | (ethyl butanoate)-3-yl | |
| 2.6.1048 | 3-methoxy-4-difluoromethoxy-phenyl | methyl | (ethyl butanoate)-3-yl | |
| 2.6.1049 | 3-ethoxy-4-difluoromethoxy-phenyl | methyl | (ethyl butanoate)-3-yl | |
| 2.6.1050 | 3-trifluoro-methoxy-4-difluoromethoxy-phenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

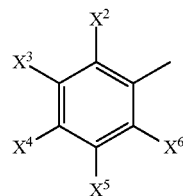

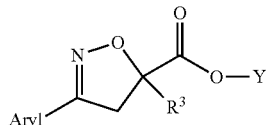

| No. | Aryl | $R^3$ | Y | Physical data |
|---|---|---|---|---|
| 2.6.1051 | 3-nitro-4-difluoromethoxy-phenyl | methyl | (ethyl butanoate)-3-yl | |
| 2.6.1052 | 3-fluoro-4-nitrophenyl | methyl | (ethyl butanoate)-3-yl | |
| 2.6.1053 | 3-chloro-4-nitrophenyl | methyl | (ethyl butanoate)-3-yl | |
| 2.6.1054 | 3-bromo-4-nitrophenyl | methyl | (ethyl butanoate)-3-yl | |
| 2.6.1055 | 3-methyl-4-nitrophenyl | methyl | (ethyl butanoate)-3-yl | |
| 2.6.1056 | 3-ethyl-4-nitrophenyl | methyl | (ethyl butanoate)-3-yl | |
| 2.6.1057 | 3-cyclopropyl-4-nitrophenyl | methyl | (ethyl butanoate)-3-yl | |
| 2.6.1058 | 3-cyano-4-nitrophenyl | methyl | (ethyl butanoate)-3-yl | |
| 2.6.1059 | 3-trifluoromethyl-4-nitrophenyl | methyl | (ethyl butanoate)-3-yl | |
| 2.6.1060 | 3-methoxy-4-nitrophenyl | methyl | (ethyl butanoate)-3-yl | |
| 2.6.1061 | 3-ethoxy-4-nitrophenyl | methyl | (ethyl butanoate)-3-yl | |
| 2.6.1062 | 3-trifluoro-methoxy-4-nitrophenyl | methyl | (ethyl butanoate)-3-yl | |
| 2.6.1063 | 3-fluoro-4-methylsulfanylphenyl | methyl | (ethyl butanoate)-3-yl | |
| 2.6.1064 | 3-chloro-4-methylsulfanyl-phenyl | methyl | (ethyl butanoate)-3-yl | |
| 2.6.1065 | 3-bromo-4-methylsulfanyl-phenyl | methyl | (ethyl butanoate)-3-yl | |
| 2.6.1066 | 3-methyl-4-methylsulfanyl-phenyl | methyl | (ethyl butanoate)-3-yl | |
| 2.6.1067 | 3-cyclopropyl-4-methylsulfanyl-phenyl | methyl | (ethyl butanoate)-3-yl | |
| 2.6.1068 | 3-cyano-4-methylsulfanyl-phenyl | methyl | (ethyl butanoate)-3-yl | |
| 2.6.1069 | 3-trifluoromethyl-4-methylsulfanyl-phenyl | methyl | (ethyl butanoate)-3-yl | |
| 2.6.1070 | 3-methoxy-4-methylsulfanyl-phenyl | methyl | (ethyl butanoate)-3-yl | |
| 2.6.1071 | 3-ethoxy-4-methylsulfanyl-phenyl | methyl | (ethyl butanoate)-3-yl | |
| 2.6.1072 | 3-trifluoro-methoxy-4-methylsulfanyl-phenyl | methyl | (ethyl butanoate)-3-yl | |
| 2.6.1073 | 3-nitro-4-methylsulfanyl-phenyl | methyl | (ethyl butanoate)-3-yl | |
| 2.6.1074 | 3,6-difluorophenyl | methyl | (ethyl butanoate)-3-yl | |
| 2.6.1075 | 3-chloro-6-fluorophenyl | methyl | (ethyl butanoate)-3-yl | |
| 2.6.1076 | 3-bromo-6-fluorophenyl | methyl | (ethyl butanoate)-3-yl | |
| 2.6.1077 | 3-methyl-6-fluorophenyl | methyl | (ethyl butanoate)-3-yl | |
| 2.6.1078 | 3-ethyl-6-fluorophenyl | methyl | (ethyl butanoate)-3-yl | |
| 2.6.1079 | 3-cyclopropyl-6-fluorophenyl | methyl | (ethyl butanoate)-3-yl | |
| 2.6.1080 | 3-cyano-6-fluorophenyl | methyl | (ethyl butanoate)-3-yl | |
| 2.6.1081 | 3-methoxy-6-fluorophenyl | methyl | (ethyl butanoate)-3-yl | |
| 2.6.1082 | 3-ethoxy-6-fluorophenyl | methyl | (ethyl butanoate)-3-yl | |
| 2.6.1083 | 3-trifluoro-methoxy-6-fluorophenyl | methyl | (ethyl butanoate)-3-yl | |
| 2.6.1084 | 3-nitro-6-fluorophenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

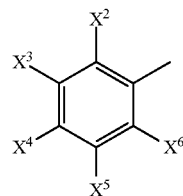

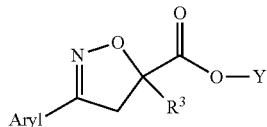

| No. | Aryl | $R^3$ | Y | Physical data |
|---|---|---|---|---|
| 2.6.1085 | 3-fluoro-6-chlorophenyl | methyl | (ethyl butanoate)-3-yl | |
| 2.6.1086 | 3,6-dichlorophenyl | methyl | (ethyl butanoate)-3-yl | |
| 2.6.1087 | 3-bromo-6-chlorophenyl | methyl | (ethyl butanoate)-3-yl | |
| 2.6.1088 | 3-methyl-6-chlorophenyl | methyl | (ethyl butanoate)-3-yl | |
| 2.6.1089 | 3-cyclopropyl-6-chlorophenyl | methyl | (ethyl butanoate)-3-yl | |
| 2.6.1090 | 3-cyano-6-chlorophenyl | methyl | (ethyl butanoate)-3-yl | |
| 2.6.1091 | 3-trifluoromethyl-6-chlorophenyl | methyl | (ethyl butanoate)-3-yl | |
| 2.6.1092 | 3-methoxy-6-chlorophenyl | methyl | (ethyl butanoate)-3-yl | |
| 2.6.1093 | 3-ethoxy-6-chlorophenyl | methyl | (ethyl butanoate)-3-yl | |
| 2.6.1094 | 3-trifluoro-methoxy-6-chlorophenyl | methyl | (ethyl butanoate)-3-yl | |
| 2.6.1095 | 3-nitro-6-chlorophenyl | methyl | (ethyl butanoate)-3-yl | |
| 2.6.1096 | 3-fluoro-6-bromophenyl | methyl | (ethyl butanoate)-3-yl | |
| 2.6.1097 | 3-chloro-6-bromophenyl | methyl | (ethyl butanoate)-3-yl | |
| 2.6.1098 | 3,6-dibromophenyl | methyl | (ethyl butanoate)-3-yl | |
| 2.6.1099 | 3-methyl-6-bromophenyl | methyl | (ethyl butanoate)-3-yl | |
| 2.6.1100 | 3-ethyl-6-bromophenyl | methyl | (ethyl butanoate)-3-yl | |
| 2.6.1101 | 3-cyclopropyl-6-bromophenyl | methyl | (ethyl butanoate)-3-yl | |
| 2.6.1102 | 3-cyano-6-bromophenyl | methyl | (ethyl butanoate)-3-yl | |
| 2.6.1103 | 3-trifluoromethyl-6-bromophenyl | methyl | (ethyl butanoate)-3-yl | |
| 2.6.1104 | 3-methoxy-6-phenyl | methyl | (ethyl butanoate)-3-yl | |
| 2.6.1105 | 3-ethoxy-6-bromophenyl | methyl | (ethyl butanoate)-3-yl | |
| 2.6.1106 | 3-trifluoro-methoxy-6-bromophenyl | methyl | (ethyl butanoate)-3-yl | |
| 2.6.1107 | 3-nitro-6-bromophenyl | methyl | (ethyl butanoate)-3-yl | |
| 2.6.1108 | 3-fluoro-6-iodophenyl | methyl | (ethyl butanoate)-3-yl | |
| 2.6.1109 | 3-chloro-6-iodophenyl | methyl | (ethyl butanoate)-3-yl | |
| 2.6.1110 | 3-bromo-6-iodophenyl | methyl | (ethyl butanoate)-3-yl | |
| 2.6.1111 | 3-methyl-6-iodophenyl | methyl | (ethyl butanoate)-3-yl | |
| 2.6.1112 | 3-cyclopropyl-6-iodophenyl | methyl | (ethyl butanoate)-3-yl | |
| 2.6.1113 | 3-cyano-6-iodophenyl | methyl | (ethyl butanoate)-3-yl | |
| 2.6.1114 | 3-trifluoromethyl-6-iodophenyl | methyl | (ethyl butanoate)-3-yl | |
| 2.6.1115 | 3-methoxy-6-iodophenyl | methyl | (ethyl butanoate)-3-yl | |
| 2.6.1116 | 3-ethoxy-6-iodophenyl | methyl | (ethyl butanoate)-3-yl | |
| 2.6.1117 | 3-trifluoro-methoxy-6-iodophenyl | methyl | (ethyl butanoate)-3-yl | |
| 2.6.1118 | 3-nitro-6-iodophenyl | methyl | (ethyl butanoate)-3-yl | |
| 2.6.1119 | 3-fluoro-6-methylphenyl | methyl | (ethyl butanoate)-3-yl | |
| 2.6.1120 | 3-chloro-6-methylphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

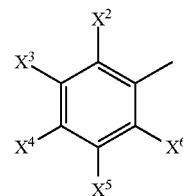

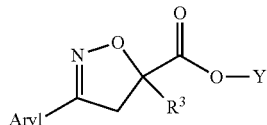

| No. | Aryl | $R^3$ | Y | Physical data |
|---|---|---|---|---|
| 2.6.1121 | 3-bromo-6-methylphenyl | methyl | (ethyl butanoate)-3-yl | |
| 2.6.1122 | 3,6-dimethylphenyl | methyl | (ethyl butanoate)-3-yl | |
| 2.6.1123 | 3-cyclopropyl-6-methylphenyl | methyl | (ethyl butanoate)-3-yl | |
| 2.6.1124 | 3-cyano-6-methylphenyl | methyl | (ethyl butanoate)-3-yl | |
| 2.6.1125 | 3-trifluoromethyl-6-methylphenyl | methyl | (ethyl butanoate)-3-yl | |
| 2.6.1126 | 3-methoxy-6-methylphenyl | methyl | (ethyl butanoate)-3-yl | |
| 2.6.1127 | 3-ethoxy-6-methylphenyl | methyl | (ethyl butanoate)-3-yl | |
| 2.6.1128 | 3-trifluoro-methoxy-6-methylphenyl | methyl | (ethyl butanoate)-3-yl | |
| 2.6.1129 | 3-nitro-6-methylphenyl | methyl | (ethyl butanoate)-3-yl | |
| 2.6.1130 | 3-fluoro-6-ethylphenyl | methyl | (ethyl butanoate)-3-yl | |
| 2.6.1131 | 3-chloro-6-ethylphenyl | methyl | (ethyl butanoate)-3-yl | |
| 2.6.1132 | 3-bromo-6-ethylphenyl | methyl | (ethyl butanoate)-3-yl | |
| 2.6.1133 | 3-methyl-6-ethylphenyl | methyl | (ethyl butanoate)-3-yl | |
| 2.6.1134 | 3,6-diethylphenyl | methyl | (ethyl butanoate)-3-yl | |
| 2.6.1135 | 3-cyclopropyl-6-ethylphenyl | methyl | (ethyl butanoate)-3-yl | |
| 2.6.1136 | 3-cyano-6-ethylphenyl | methyl | (ethyl butanoate)-3-yl | |
| 2.6.1137 | 3-trifluoromethyl-6-ethylphenyl | methyl | (ethyl butanoate)-3-yl | |
| 2.6.1138 | 3-methoxy-6-ethylphenyl | methyl | (ethyl butanoate)-3-yl | |
| 2.6.1139 | 3-ethoxy-6-ethylphenyl | methyl | (ethyl butanoate)-3-yl | |
| 2.6.1140 | 3-trifluoro-methoxy-6-ethylphenyl | methyl | (ethyl butanoate)-3-yl | |
| 2.6.1141 | 3-nitro-6-ethylphenyl | methyl | (ethyl butanoate)-3-yl | |
| 2.6.1142 | 3-fluoro-6-isopropylphenyl | methyl | (ethyl butanoate)-3-yl | |
| 2.6.1143 | 3-chloro-6-isopropylphenyl | methyl | (ethyl butanoate)-3-yl | |
| 2.6.1144 | 3-bromo-6-isopropylphenyl | methyl | (ethyl butanoate)-3-yl | |
| 2.6.1145 | 3-methyl-6-isopropylphenyl | methyl | (ethyl butanoate)-3-yl | |
| 2.6.1146 | 3-ethyl-6-isopropylphenyl | methyl | (ethyl butanoate)-3-yl | |
| 2.6.1147 | 3-cyclopropyl-6-isopropylphenyl | methyl | (ethyl butanoate)-3-yl | |
| 2.6.1148 | 3-cyano-6-isopropylphenyl | methyl | (ethyl butanoate)-3-yl | |
| 2.6.1149 | 3-trifluoromethyl-6-isopropylphenyl | methyl | (ethyl butanoate)-3-yl | |
| 2.6.1150 | 3-methoxy-6-isopropylphenyl | methyl | (ethyl butanoate)-3-yl | |
| 2.6.1151 | 3-thoxy-6-isopropylphenyl | methyl | (ethyl butanoate)-3-yl | |
| 2.6.1152 | 3-trifluoro-methoxy-6-isopropylphenyl | methyl | (ethyl butanoate)-3-yl | |
| 2.6.1153 | 3-nitro-6-isopropylphenyl | methyl | (ethyl butanoate)-3-yl | |
| 2.6.1154 | 3-fluoro-6-tert-butylphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

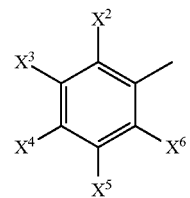

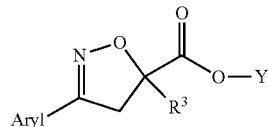

| No. | Aryl | $R^3$ | Y | Physical data |
|---|---|---|---|---|
| 2.6.1155 | 3-chloro-6-tert-butylphenyl | methyl | (ethyl butanoate)-3-yl | |
| 2.6.1156 | 3-bromo-6-tert-butylphenyl | methyl | (ethyl butanoate)-3-yl | |
| 2.6.1157 | 3-methyl-6-tert-butylphenyl | methyl | (ethyl butanoate)-3-yl | |
| 2.6.1158 | 3-cyclopropyl-6-tert-butylphenyl | methyl | (ethyl butanoate)-3-yl | |
| 2.6.1159 | 3-cyano-6-tert-butylphenyl | methyl | (ethyl butanoate)-3-yl | |
| 2.6.1160 | 3-trifluoromethyl-6-tert-butylphenyl | methyl | (ethyl butanoate)-3-yl | |
| 2.6.1161 | 3-methoxy-6-tert-butylphenyl | methyl | (ethyl butanoate)-3-yl | |
| 2.6.1162 | 3-ethoxy-6-tert-butylphenyl | methyl | (ethyl butanoate)-3-yl | |
| 2.6.1163 | 3-trifluoro-methoxy-6-tert-butylphenyl | methyl | (ethyl butanoate)-3-yl | |
| 2.6.1164 | 3-nitro-6-tert-butylphenyl | methyl | (ethyl butanoate)-3-yl | |
| 2.6.1165 | 3-fluoro-6-cyclopropylphenyl | methyl | (ethyl butanoate)-3-yl | |
| 2.6.1166 | 3-chloro-6-cyclopropylphenyl | methyl | (ethyl butanoate)-3-yl | |
| 2.6.1167 | 3-bromo-6-cyclopropylphenyl | methyl | (ethyl butanoate)-3-yl | |
| 2.6.1168 | 3-methyl-6-cyclopropylphenyl | methyl | (ethyl butanoate)-3-yl | |
| 2.6.1169 | 3-cyano-6-cyclopropylphenyl | methyl | (ethyl butanoate)-3-yl | |
| 2.6.1170 | 3-trifluoromethyl-6-cyclopropyl-phenyl | methyl | (ethyl butanoate)-3-yl | |
| 2.6.1171 | 3-methoxy-6-cyclopropylphenyl | methyl | (ethyl butanoate)-3-yl | |
| 2.6.1172 | 3-ethoxy-6-cyclopropylphenyl | methyl | (ethyl butanoate)-3-yl | |
| 2.6.1173 | 3-trifluoro-methoxy-6-cyclopropylphenyl | methyl | (ethyl butanoate)-3-yl | |
| 2.6.1174 | 3-fluoro-6-methoxycarbonyl-phenyl | methyl | (ethyl butanoate)-3-yl | |
| 2.6.1175 | 3-chloro-6-methoxycarbonyl-phenyl | methyl | (ethyl butanoate)-3-yl | |
| 2.6.1176 | 3-bromo-6-methoxycarbonyl-phenyl | methyl | (ethyl butanoate)-3-yl | |
| 2.6.1177 | 3-methyl-6-methoxycarbonyl-phenyl | methyl | (ethyl butanoate)-3-yl | |
| 2.6.1178 | 3-cyclopropyl-6-methoxycarbonyl-phenyl | methyl | (ethyl butanoate)-3-yl | |
| 2.6.1179 | 3-cyano-6-methoxycarbonyl-phenyl | methyl | (ethyl butanoate)-3-yl | |
| 2.6.1180 | 3-trifluoromethyl-6-methoxy-carbonylphenyl | methyl | (ethyl butanoate)-3-yl | |

TABLE 2.6-continued

Inventive compounds of the general formula (I) in which W* is COOY, R¹ and R² are each hydrogen, and aryl is the radical.

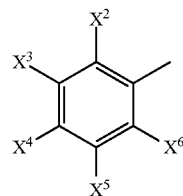

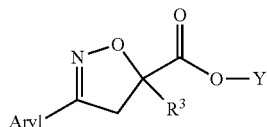

| No. | Aryl | R³ | Y | Physical data |
|---|---|---|---|---|
| 2.6.1181 | 3-methoxy-6-methoxycarbonyl-phenyl | methyl | (ethyl butanoate)-3-yl | |
| 2.6.1182 | 3-ethoxy-6-methoxycarbonyl-phenyl | methyl | (ethyl butanoate)-3-yl | |
| 2.6.1183 | 3-trifluoro-methoxy-6-methoxycarbonyl-phenyl | methyl | (ethyl butanoate)-3-yl | |
| 2.6.1184 | 3-nitro-6-methoxycarbonyl-phenyl | methyl | (ethyl butanoate)-3-yl | |
| 2.6.1185 | 3-fluoro-6-cyanophenyl | methyl | (ethyl butanoate)-3-yl | |
| 2.6.1186 | 3-chloro-6-cyanophenyl | methyl | (ethyl butanoate)-3-yl | |
| 2.6.1187 | 3-bromo-6-cyanophenyl | methyl | (ethyl butanoate)-3-yl | |
| 2.6.1188 | 3-methyl-6-cyanophenyl | methyl | (ethyl butanoate)-3-yl | |
| 2.6.1189 | 3-cyclopropyl-6-cyanophenyl | methyl | (ethyl butanoate)-3-yl | |
| 2.6.1190 | 3-cyano-6-cyanophenyl | methyl | (ethyl butanoate)-3-yl | |
| 2.6.1191 | 3-trifluoromethyl-6-cyanophenyl | methyl | (ethyl butanoate)-3-yl | |
| 2.6.1192 | 3-methoxy-6-cyanophenyl | methyl | (ethyl butanoate)-3-yl | |
| 2.6.1193 | 3-ethoxy-6-cyanophenyl | methyl | (ethyl butanoate)-3-yl | |
| 2.6.1194 | 3-trifluoro-methoxy-6-cyanophenyl | methyl | (ethyl butanoate)-3-yl | |
| 2.6.1195 | 3-nitro-6-cyanophenyl | methyl | (ethyl butanoate)-3-yl | |
| 2.6.1196 | 3-fluoro-6-methoxyphenyl | methyl | (ethyl butanoate)-3-yl | |
| 2.6.1197 | 3-chloro-6-methoxyphenyl | methyl | (ethyl butanoate)-3-yl | |
| 2.6.1198 | 3-bromo-6-methoxyphenyl | methyl | (ethyl butanoate)-3-yl | |
| 2.6.1199 | 3-methyl-6-methoxyphenyl | methyl | (ethyl butanoate)-3-yl | |
| 2.6.1200 | 3-cyclopropyl-6-methoxyphenyl | methyl | (ethyl butanoate)-3-yl | |
| 2.6.1201 | 3-cyano-6-methoxyphenyl | methyl | (ethyl butanoate)-3-yl | |
| 2.6.1202 | 3-trifluoromethyl-6-methoxyphenyl | methyl | (ethyl butanoate)-3-yl | |
| 2.6.1203 | 3,6-dimethoxyphenyl | methyl | (ethyl butanoate)-3-yl | |
| 2.6.1204 | 3-ethoxy-6-methoxyphenyl | methyl | (ethyl butanoate)-3-yl | |
| 2.6.1205 | 3-trifluoro-methoxy-6-methoxyphenyl | methyl | (ethyl butanoate)-3-yl | |
| 2.6.1206 | 3-nitro-6-methoxyphenyl | methyl | (ethyl butanoate)-3-yl | |
| 2.6.1207 | 3-fluoro-6-ethoxyphenyl | methyl | (ethyl butanoate)-3-yl | |
| 2.6.1208 | 3-chloro-6-ethoxyphenyl | methyl | (ethyl butanoate)-3-yl | |

TABLE 2.6-continued

Inventive compounds of the general formula (I) in which W* is COOY, R¹ and R² are each hydrogen, and aryl is the radical.

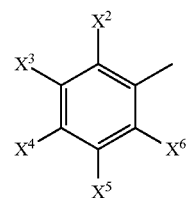

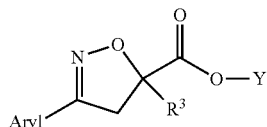

| No. | Aryl | R³ | Y | Physical data |
|---|---|---|---|---|
| 2.6.1209 | 3-bromo-6-ethoxyphenyl | methyl | (ethyl butanoate)-3-yl | |
| 2.6.1210 | 3-methyl-6-ethoxyphenyl | methyl | (ethyl butanoate)-3-yl | |
| 2.6.1211 | 3-cyclopropyl-6-ethoxyphenyl | methyl | (ethyl butanoate)-3-yl | |
| 2.6.1212 | 3-cyano-6-ethoxyphenyl | methyl | (ethyl butanoate)-3-yl | |
| 2.6.1213 | 3-trifluoromethyl-6-ethoxyphenyl | methyl | (ethyl butanoate)-3-yl | |
| 2.6.1214 | 3-methoxy-6-ethoxyphenyl | methyl | (ethyl butanoate)-3-yl | |
| 2.6.1215 | 2,6-diethoxyphenyl | methyl | (ethyl butanoate)-3-yl | |
| 2.6.1216 | 3-trifluoro-methoxy-6-ethoxyphenyl | methyl | (ethyl butanoate)-3-yl | |
| 2.6.1217 | 3-nitro-6-ethoxyphenyl | methyl | (ethyl butanoate)-3-yl | |
| 2.6.1218 | 3-fluoro-6-propoxyphenyl | methyl | (ethyl butanoate)-3-yl | |
| 2.6.1219 | 3-chloro-6-propoxyphenyl | methyl | (ethyl butanoate)-3-yl | |
| 2.6.1220 | 3-bromo-6-propoxyphenyl | methyl | (ethyl butanoate)-3-yl | |
| 2.6.1221 | 3-methyl-6-propoxyphenyl | methyl | (ethyl butanoate)-3-yl | |
| 2.6.1222 | 3-cyclopropyl-6-propoxyphenyl | methyl | (ethyl butanoate)-3-yl | |
| 2.6.1223 | 3-cyano-6-propoxyphenyl | methyl | (ethyl butanoate)-3-yl | |
| 2.6.1224 | 3-trifluoromethyl-6-propoxyphenyl | methyl | (ethyl butanoate)-3-yl | |
| 2.6.1225 | 3-methoxy-6-propoxy-phenyl | methyl | (ethyl butanoate)-3-yl | |
| 2.6.1226 | 3-ethoxy-6-propoxyphenyl | methyl | (ethyl butanoate)-3-yl | |
| 2.6.1227 | 3-trifluoro-methoxy-6-propoxyphenyl | methyl | (ethyl butanoate)-3-yl | |
| 2.6.1228 | 3-nitro-6-propoxyphenyl | methyl | (ethyl butanoate)-3-yl | |
| 2.6.1229 | 3-fluoro-6-isopropoxyphenyl | methyl | (ethyl butanoate)-3-yl | |
| 2.6.1230 | 3-chloro-6-isopropoxyphenyl | methyl | (ethyl butanoate)-3-yl | |
| 2.6.1231 | 3-bromo-6-isopropoxyphenyl | methyl | (ethyl butanoate)-3-yl | |
| 2.6.1232 | 3-methyl-6-isopropoxyphenyl | methyl | (ethyl butanoate)-3-yl | |
| 2.6.1233 | 3-cyclopropyl-6-isopropoxyphenyl | methyl | (ethyl butanoate)-3-yl | |
| 2.6.1234 | 3-cyano-6-isopropoxyphenyl | methyl | (ethyl butanoate)-3-yl | |
| 2.6.1235 | 3-trifluoromethyl-6-isopropoxy-phenyl | methyl | (ethyl butanoate)-3-yl | |
| 2.6.1236 | 3-methoxy-6-isopropoxyphenyl | methyl | (ethyl butanoate)-3-yl | |
| 2.6.1237 | 3-ethoxy-6-isopropoxyphenyl | methyl | (ethyl butanoate)-3-yl | |
| 2.6.1238 | 3-trifluoro-methoxy-6-isopropoxyphenyl | methyl | (ethyl butanoate)-3-yl | |

TABLE 2.6-continued

Inventive compounds of the general formula (I) in which W* is COOY, R¹ and R² are each hydrogen, and aryl is the radical.

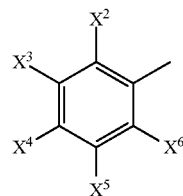

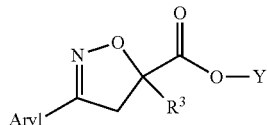

| No. | Aryl | R³ | Y | Physical data |
|---|---|---|---|---|
| 2.6.1239 | 3-nitro-6-isopropoxyphenyl | methyl | (ethyl butanoate)-3-yl | |
| 2.6.1240 | 3-fluoro-6-trifluoromethoxyphenyl | methyl | (ethyl butanoate)-3-yl | |
| 2.6.1241 | 3-chloro-6-trifluoromethoxyphenyl | methyl | (ethyl butanoate)-3-yl | |
| 2.6.1242 | 3-bromo-6-trifluoromethoxyphenyl | methyl | (ethyl butanoate)-3-yl | |
| 2.6.1243 | 3-methyl-6-trifluoromethoxyphenyl | methyl | (ethyl butanoate)-3-yl | |
| 2.6.1244 | 3-cyclopropyl-6-trifluoromethoxyphenyl | methyl | (ethyl butanoate)-3-yl | |
| 2.6.1245 | 3-cyano-6-trifluoromethoxyphenyl | methyl | (ethyl butanoate)-3-yl | |
| 2.6.1246 | 3-trifluoromethyl-6-trifluoromethoxyphenyl | methyl | (ethyl butanoate)-3-yl | |
| 2.6.1247 | 3-methoxy-6-trifluoromethoxyphenyl | methyl | (ethyl butanoate)-3-yl | |
| 2.6.1248 | 3-ethoxy-6-trifluoromethoxyphenyl | methyl | (ethyl butanoate)-3-yl | |
| 2.6.1249 | 3,6-bis(trifluoromethoxy)phenyl | methyl | (ethyl butanoate)-3-yl | |
| 2.6.1250 | 3-nitro-6-trifluoromethoxyphenyl | methyl | (ethyl butanoate)-3-yl | |
| 2.6.1251 | 3-fluoro-6-difluoromethoxyphenyl | methyl | (ethyl butanoate)-3-yl | |
| 2.6.1252 | 3-chloro-6-difluoromethoxyphenyl | methyl | (ethyl butanoate)-3-yl | |
| 2.6.1253 | 3-bromo-6-difluoromethoxyphenyl | methyl | (ethyl butanoate)-3-yl | |
| 2.6.1254 | 3-methyl-6-difluoromethoxyphenyl | methyl | (ethyl butanoate)-3-yl | |
| 2.6.1255 | 3-cyclopropyl-6-difluoromethoxyphenyl | methyl | (ethyl butanoate)-3-yl | |
| 2.6.1256 | 3-cyano-6-difluoromethoxyphenyl | methyl | (ethyl butanoate)-3-yl | |
| 2.6.1257 | 3-trifluoromethyl-6-difluoromethoxyphenyl | methyl | (ethyl butanoate)-3-yl | |
| 2.6.1258 | 3-methoxy-6-difluoromethoxyphenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

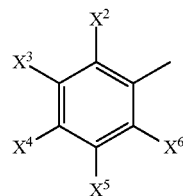

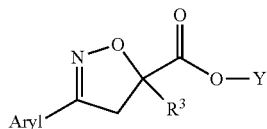

| No. | Aryl | $R^3$ | Y | Physical data |
|---|---|---|---|---|
| 2.6.1259 | 3-ethoxy-6-difluoromethoxy-phenyl | methyl | (ethyl butanoate)-3-yl | |
| 2.6.1260 | 3-trifluoro-methoxy-6-difluoromethoxy-phenyl | methyl | (ethyl butanoate)-3-yl | |
| 2.6.1261 | 3-nitro-6-difluoromethoxy-phenyl | methyl | (ethyl butanoate)-3-yl | |
| 2.6.1262 | 3-fluoro-6-nitrophenyl | methyl | (ethyl butanoate)-3-yl | |
| 2.6.1263 | 3-chloro-6-nitrophenyl | methyl | (ethyl butanoate)-3-yl | |
| 2.6.1264 | 3-bromo-6-nitrophenyl | methyl | (ethyl butanoate)-3-yl | |
| 2.6.1265 | 3-methyl-6-nitrophenyl | methyl | (ethyl butanoate)-3-yl | |
| 2.6.1266 | 3-cyclopropyl-6-nitrophenyl | methyl | (ethyl butanoate)-3-yl | |
| 2.6.1267 | 3-cyano-6-nitrophenyl | methyl | (ethyl butanoate)-3-yl | |
| 2.6.1268 | 3-trifluoromethyl-6-nitrophenyl | methyl | (ethyl butanoate)-3-yl | |
| 2.6.1269 | 3-methoxy-6-nitrophenyl | methyl | (ethyl butanoate)-3-yl | |
| 2.6.1270 | 3-ethoxy-6-nitrophenyl | methyl | (ethyl butanoate)-3-yl | |
| 2.6.1271 | 3-trifluoro-methoxy-6-nitrophenyl | methyl | (ethyl butanoate)-3-yl | |
| 2.6.1272 | 3-fluoro-6-methylsulfanyl-phenyl | methyl | (ethyl butanoate)-3-yl | |
| 2.6.1273 | 3-chloro-6-methylsulfanyl-phenyl | methyl | (ethyl butanoate)-3-yl | |
| 2.6.1274 | 3-bromo-6-methylsulfanyl-phenyl | methyl | (ethyl butanoate)-3-yl | |
| 2.6.1275 | 3-methyl-6-methylsulfanyl-phenyl | methyl | (ethyl butanoate)-3-yl | |
| 2.6.1276 | 3-cyclopropyl-6-methylsulfanyl-phenyl | methyl | (ethyl butanoate)-3-yl | |
| 2.6.1277 | 3-cyano-6-methylsulfanyl-phenyl | methyl | (ethyl butanoate)-3-yl | |
| 2.6.1278 | 3-trifluoromethyl-6-methylsulfanyl-phenyl | methyl | (ethyl butanoate)-3-yl | |
| 2.6.1279 | 3-methoxy-6-methylsulfanyl-phenyl | methyl | (ethyl butanoate)-3-yl | |
| 2.6.1280 | 3-ethoxy-6-methylsulfanyl-phenyl | methyl | (ethyl butanoate)-3-yl | |
| 2.6.1281 | 3-trifluoro-methoxy-6-methylsulfanyl-phenyl | methyl | (ethyl butanoate)-3-yl | |
| 2.6.1282 | 3-nitro-6-methylsulfanyl-phenyl | methyl | (ethyl butanoate)-3-yl | |
| 2.6.1283 | 2,3,4-trifluorophenyl | methyl | (ethyl butanoate)-3-yl | |
| 2.6.1284 | 2,3,4-trichlorophenyl | methyl | (ethyl butanoate)-3-yl | |
| 2.6.1285 | 2,3,4-trimethylphenyl | methyl | (ethyl butanoate)-3-yl | |
| 2.6.1286 | 2-fluoro-2-chloro-5-trifluoromethyl-phenyl | methyl | (ethyl butanoate)-3-yl | |
| 2.6.1287 | 2,3,5-trifluorophenyl | methyl | (ethyl butanoate)-3-yl | |
| 2.6.1288 | 2,3,5-trichlorophenyl | methyl | (ethyl butanoate)-3-yl | |
| 2.6.1289 | 2,3,5-trimethylphenyl | methyl | (ethyl butanoate)-3-yl | |
| 2.6.1290 | 2, 3-dichloro-5-methoxyphenyl | methyl | (ethyl butanoate)-3-yl | |
| 2.6.1291 | 2,3,6-trifluorophenyl | methyl | (ethyl butanoate)-3-yl | |
| 2.6.1292 | 2,3,6-trichlorophenyl | methyl | (ethyl butanoate)-3-yl | |
| 2.6.1293 | 2,3,6-trimethylphenyl | methyl | (ethyl butanoate)-3-yl | |
| 2.6.1294 | 3,4,5-trifluorophenyl | methyl | (ethyl butanoate)-3-yl | |

TABLE 2.6-continued

Inventive compounds of the general formula (I) in which W* is COOY, $R^1$ and $R^2$ are each hydrogen, and aryl is the radical.

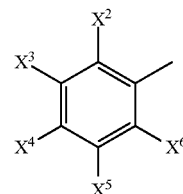

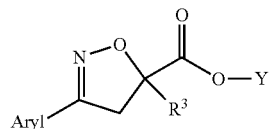

| No. | Aryl | $R^3$ | Y | Physical data |
|---|---|---|---|---|
| 2.6.1295 | 3,4,5-trichlorophenyl | methyl | (ethyl butanoate)-3-yl | |
| 2.6.1296 | 3,4,5-trimethylphenyl | methyl | (ethyl butanoate)-3-yl | |
| 2.6.1297 | 3,5-dimethyl-4-fluorophenyl | methyl | (ethyl butanoate)-3-yl | |
| 2.6.1298 | 3,5-dichloro-4-methoxyphenyl | methyl | (ethyl butanoate)-3-yl | |
| 2.6.1299 | 3,5-difluoro-4-chlorophenyl | methyl | (ethyl butanoate)-3-yl | |
| 2.6.1300 | 3,5-dichloro-4-hydroxyphenyl | methyl | (ethyl butanoate)-3-yl | |
| 2.6.1301 | 3,5-trifluoromethyl-4-chlorophenyl | methyl | (ethyl butanoate)-3-yl | |
| 2.6.1302 | 3,4,6-trifluorophenyl | methyl | (ethyl butanoate)-3-yl | |
| 2.6.1303 | 3,4,6-trichlorophenyl | methyl | (ethyl butanoate)-3-yl | |
| 2.6.1304 | 3,4,6-trimethylphenyl | methyl | (ethyl butanoate)-3-yl | |
| 2.6.1305 | 2,3,4,5-pentafluoro-phenyl | methyl | (ethyl butanoate)-3-yl | |

TABLE 3

Inventive compounds of the general formula (I) in which W* is CN, $R^1$ and $R^2$ are each hydrogen, and aryl is the radical.

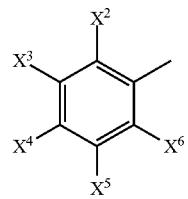

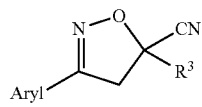

| No. | Aryl | $R^3$ | Physical data |
|---|---|---|---|
| 3.1 | 3-fluorophenyl | methyl | |
| 3.2 | 3-fluorophenyl | ethyl | |
| 3.3 | 3-fluorophenyl | CN | |
| 3.4 | 3-fluorophenyl | fluoromethyl | |
| 3.5 | 3-fluorophenyl | hydroxymethyl | |
| 3.6 | 3-fluorophenyl | vinyl | |
| 3.7 | 3-fluorophenyl | 1-chlorovinyl | |
| 3.8 | 3-fluorophenyl | ethynyl | |
| 3.9 | 3-chlorophenyl | methyl | |
| 3.10 | 3-chlorophenyl | ethyl | |
| 3.11 | 3-chlorophenyl | CN | |
| 3.12 | 3-chlorophenyl | fluoromethyl | |
| 3.13 | 3-chlorophenyl | hydroxymethyl | |
| 3.14 | 3-chlorophenyl | fluoromethyl | |
| 3.15 | 3-chlorophenyl | ethynyl | |

TABLE 3-continued

Inventive compounds of the general formula (I) in which W* is CN, $R^1$ and $R^2$ are each hydrogen, and aryl is the radical.

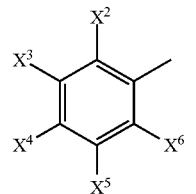

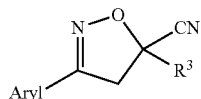

| No. | Aryl | $R^3$ | Physical data |
|---|---|---|---|
| 3.16 | 3-bromophenyl | methyl | |
| 3.17 | 3-bromophenyl | ethyl | |
| 3.18 | 3-bromophenyl | vinyl | |
| 3.19 | 3-iodophenyl | methyl | |
| 3.20 | 3-methylphenyl | methyl | |
| 3.21 | 3-ethylphenyl | methyl | |
| 3.22 | 3-propylphenyl | methyl | |
| 3.23 | 3-isopropylphenyl | methyl | |
| 3.24 | 3-n-butylphenyl | methyl | |
| 3.25 | 3-i-butylphenyl | methyl | |
| 3.26 | 3-tert-butylphenyl | methyl | |
| 3.27 | 3-cyclopropylphenyl | methyl | |
| 3.28 | 3-cyclobutylphenyl | methyl | |
| 3.29 | 3-cyclopentylphenyl | methyl | |
| 3.30 | 3-vinylphenyl | methyl | |
| 3.31 | 3-ethynylphenyl | methyl | |
| 3.32 | 3-cyanophenyl | methyl | |
| 3.33 | 3-trifluoromethylphenyl | methyl | |
| 3.34 | 3-difluoromethylphenyl | methyl | |
| 3.35 | 3-(hydroxycarbonyl)phenyl | methyl | |
| 3.36 | 3-(methoxycarbonyl)phenyl | methyl | |
| 3.37 | 3-(ethoxycarbonyl)phenyl | methyl | |
| 3.38 | 3-hydroxymethylphenyl | methyl | |
| 3.39 | 3-carbamoylphenyl | methyl | |
| 3.40 | 3-hydroxyphenyl | methyl | |
| 3.41 | 3-methoxyphenyl | methyl | |
| 3.42 | 3-methoxyphenyl | ethyl | |
| 3.43 | 3-methoxyphenyl | CN | |
| 3.44 | 3-methoxyphenyl | fluoromethyl | |
| 3.45 | 3-methoxyphenyl | hydroxymethyl | |
| 3.46 | 3-methoxyphenyl | ethynyl | |
| 3.47 | 3-ethoxyphenyl | methyl | |
| 3.48 | 3-propyloxyphenyl | methyl | |
| 3.49 | 3-isopropyloxyphenyl | methyl | |
| 3.50 | 3-n-butyloxyphenyl | methyl | |
| 3.51 | 3-i-butyloxyphenyl | methyl | |
| 3.52 | 3-t-butyloxyphenyl | methyl | |
| 3.53 | 3-difluoromethoxyphenyl | methyl | |
| 3.54 | 3-trifluoromethoxyphenyl | methyl | |
| 3.55 | 3-trifluoromethoxyphenyl | ethyl | |
| 3.56 | 3-trifluoromethoxyphenyl | CN | |
| 3.57 | 3-trifluoromethoxyphenyl | fluoromethyl | |
| 3.58 | 3-trifluoromethoxy | hydroxymethyl | |
| 3.59 | 3-trifluoromethoxyphenyl | ethynyl | |
| 3.60 | 3-(2,2,2-trifluoroethoxy)phenyl | methyl | |
| 3.61 | 3-nitrophenyl | methyl | |
| 3.62 | 3-acetoxyphenyl | methyl | |
| 3.63 | (3-[(tert-butoxycarbonyl)amino]phenyl} | methyl | |
| 3.64 | 3-methylsulfanylphenyl | methyl | |
| 3.65 | 3-ethylsulfanylphenyl | methyl | |
| 3.66 | 3-(pentafluoro-lambda$^6$-sulfanyl)phenyl | methyl | |
| 3.67 | 2,3-difluorophenyl | methyl | |
| 3.68 | 2,3-difluorophenyl | ethyl | |
| 3.69 | 2,3-difluorophenyl | CN | |
| 3.70 | 2,3-difluorophenyl | fluoromethyl | |
| 3.71 | 2,3-difluorophenyl | hydroxymethyl | |
| 3.72 | 2,3-difluorophenyl | ethynyl | |
| 3.73 | 2-chloro-3-fluorophenyl | methyl | |

TABLE 3-continued

Inventive compounds of the general formula (I) in which W* is CN, $R^1$ and $R^2$ are each hydrogen, and aryl is the radical.

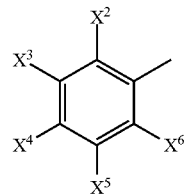

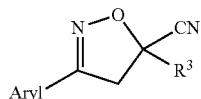

| No. | Aryl | $R^3$ | Physical data |
|---|---|---|---|
| 3.74 | 2-bromo-3-fluorophenyl | methyl | |
| 3.75 | 2-methyl-3-fluorophenyl | methyl | |
| 3.76 | 2-ethyl-3-fluorophenyl | methyl | |
| 3.77 | 2-cyclopropyl-3-fluorophenyl | methyl | |
| 3.78 | 2-cyano-3-fluorophenyl | methyl | |
| 3.79 | 2-methoxy-3-fluorophenyl | methyl | |
| 3.80 | 2-ethoxy-3-fluorophenyl | methyl | |
| 3.81 | 2-trifluoromethoxy-3-fluorophenyl | methyl | |
| 3.82 | 2-nitro-3-fluorophenyl | methyl | |
| 3.83 | 2-fluoro-3-chlorophenyl | methyl | |
| 3.84 | 2,3-dichlorophenyl | methyl | |
| 3.85 | 2,3-dichlorophenyl | ethyl | |
| 3.86 | 2,3-dichlorophenyl | CN | |
| 3.87 | 2,3-dichlorophenyl | fluoromethyl | |
| 3.88 | 2,3-dichlorophenyl | hydroxymethyl | |
| 3.89 | 2,3-dichlorophenyl | ethynyl | |
| 3.90 | 2-bromo-3-chlorophenyl | methyl | |
| 3.91 | 2-methyl-3-chlorophenyl | methyl | |
| 3.92 | 2-methyl-3-chlorophenyl | ethyl | |
| 3.93 | 2-methyl-3-chlorophenyl | CN | |
| 3.94 | 2-methyl-3-chlorophenyl | fluoromethyl | |
| 3.95 | 2-methyl-3-chlorophenyl | hydroxymethyl | |
| 3.96 | 2-methyl-3-chlorophenyl | ethynyl | |
| 3.97 | 2-ethyl-3-chlorophenyl | methyl | |
| 3.98 | 2-cyclopropyl-3-chlorophenyl | methyl | |
| 3.99 | 2-cyano-3-chlorophenyl | methyl | |
| 3.100 | 2-trifluoromethyl-2-chlorophenyl | methyl | |
| 3.101 | 2-methoxy-3-chlorophenyl | methyl | |
| 3.102 | 2-ethoxy-3-chlorophenyl | methyl | |
| 3.103 | 2-trifluoromethoxy-3-chlorophenyl | methyl | |
| 3.104 | 2-nitro-3-chlorophenyl | methyl | |
| 3.105 | 2-fluoro-3-bromophenyl | methyl | |
| 3.106 | 2-chloro-3-bromophenyl | methyl | |
| 3.107 | 2,3-dibromophenyl | methyl | |
| 3.108 | 2-methyl-3-bromophenyl | methyl | |
| 3.109 | 2-ethyl-3-bromophenyl | methyl | |
| 3.110 | 2-cyclopropyl-3-bromophenyl | methyl | |
| 3.111 | 2-cyano-3-bromophenyl | methyl | |
| 3.112 | 2-trifluoromethyl-3-bromophenyl | methyl | |
| 3.113 | 2-methoxy-3-phenyl | methyl | |
| 3.114 | 2-ethoxy-3-bromophenyl | methyl | |
| 3.115 | 2-trifluoromethoxy-3-bromophenyl | methyl | |
| 3.116 | 2-nitro-3-bromophenyl | methyl | |
| 3.117 | 2-fluoro-3-iodophenyl | methyl | |
| 3.118 | 2-chloro-3-iodophenyl | methyl | |
| 3.119 | 2-bromo-3-iodophenyl | methyl | |
| 3.120 | 2-methyl-3-iodophenyl | methyl | |
| 3.121 | 2-ethyl-3-iodophenyl | methyl | |
| 3.122 | 2-cyclopropyl-3-iodophenyl | methyl | |
| 3.123 | 2-cyano-3-iodophenyl | methyl | |
| 3.124 | 2-trifluoromethyl-3-iodophenyl | methyl | |
| 3.125 | 2-methoxy-3-iodophenyl | methyl | |
| 3.126 | 2-ethoxy-3-iodophenyl | methyl | |
| 3.127 | 2-trifluoromethoxy-3-iodophenyl | methyl | |
| 3.128 | 2-nitro-3-iodophenyl | methyl | |
| 3.129 | 2-fluoro-3-methylphenyl | methyl | |
| 3.130 | 2-fluoro-3-methylphenyl | ethyl | |
| 3.131 | 2-fluoro-3-methylphenyl | CN | |

TABLE 3-continued

Inventive compounds of the general formula (I) in which W* is CN, $R^1$ and $R^2$ are each hydrogen, and aryl is the radical.

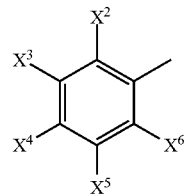

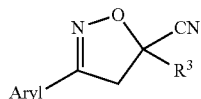

| No. | Aryl | $R^3$ | Physical data |
|---|---|---|---|
| 3.132 | 2-fluoro-3-methylphenyl | fluoromethyl | |
| 3.133 | 2-fluoro-3-methylphenyl | hydroxymethyl | |
| 3.134 | 2-fluoro-3-methylphenyl | ethynyl | |
| 3.135 | 2-chloro-3-methylphenyl | methyl | |
| 3.136 | 2-chloro-3-methylphenyl | ethyl | |
| 3.137 | 2-chloro-3-methylphenyl | CN | |
| 3.138 | 2-chloro-3-methylphenyl | fluoromethyl | |
| 3.139 | 2-chloro-3-methylphenyl | hydroxymethyl | |
| 3.140 | 2-chloro-3-methylphenyl | ethynyl | |
| 3.141 | 2-bromo-3-methylphenyl | methyl | |
| 3.142 | 2,3-dimethylphenyl | methyl | |
| 3.143 | 2-ethyl-3-methylphenyl | methyl | |
| 3.144 | 2-cyclopropyl-3-methylphenyl | methyl | |
| 3.145 | 2-cyano-3-methylphenyl | methyl | |
| 3.146 | 2-trifluoromethyl-3-methylphenyl | methyl | |
| 3.147 | 2-methoxy-3-methylphenyl | methyl | |
| 3.148 | 2-ethoxy-3-methylphenyl | methyl | |
| 3.149 | 2-trifluoromethoxy-3-methylphenyl | methyl | |
| 3.150 | 2-nitro-3-methylphenyl | methyl | |
| 3.151 | 2-fluoro-3-ethylphenyl | methyl | |
| 3.152 | 2-chloro-3-ethylphenyl | methyl | |
| 3.153 | 2-bromo-3-ethylphenyl | methyl | |
| 3.154 | 2-methyl-3-ethylphenyl | methyl | |
| 3.155 | 2,3-diethylphenyl | methyl | |
| 3.156 | 2-cyclopropyl-3-ethylphenyl | methyl | |
| 3.157 | 2-cyano-3-ethylphenyl | methyl | |
| 3.158 | 2-trifluoromethyl-3-ethylphenyl | methyl | |
| 3.159 | 2-methoxy-3-ethylphenyl | methyl | |
| 3.160 | 2-ethoxy-3-ethylphenyl | methyl | |
| 3.161 | 2-trifluoromethoxy-3-ethylphenyl | methyl | |
| 3.162 | 2-nitro-3-ethylphenyl | methyl | |
| 3.163 | 2-fluoro-3-propylphenyl | methyl | |
| 3.164 | 2-chloro-3-propylphenyl | methyl | |
| 3.165 | 2-bromo-3-propylphenyl | methyl | |
| 3.166 | 2-methyl-3-propylphenyl | methyl | |
| 3.167 | 2-methyl-3-propylphenyl | methyl | |
| 3.168 | 2-cyclopropyl-3-propylphenyl | methyl | |
| 3.169 | 2-cyano-3-propylphenyl | methyl | |
| 3.170 | 2-trifluoromethyl-3-propylphenyl | methyl | |
| 3.171 | 2-methoxy-3-propylphenyl | methyl | |
| 3.172 | 2-ethoxy-3-propylphenyl | methyl | |
| 3.173 | 2-trifluoromethoxy-3-propylphenyl | methyl | |
| 3.174 | 2-nitro-3-propylphenyl | methyl | |
| 3.175 | 2-fluoro-3-isopropylphenyl | methyl | |
| 3.176 | 2-chloro-3-isopropylphenyl | methyl | |
| 3.177 | 2-bromo-3- isopropylphenyl | methyl | |
| 3.178 | 2-methyl-3-isopropylphenyl | methyl | |
| 3.179 | 2-ethyl-3-isopropylphenyl | methyl | |
| 3.180 | 2-cyclopropyl-3-isopropylphenyl | methyl | |
| 3.181 | 2-cyano-3-isopropylphenyl | methyl | |
| 3.182 | 2-trifluoromethyl-3-isopropylphenyl | methyl | |
| 3.183 | 2- methoxy-3-isopropylphenyl | methyl | |
| 3.184 | 2-ethoxy-3-isopropylphenyl | methyl | |
| 3.185 | 2-trifluoromethoxy-3-isopropylphenyl | methyl | |
| 3.186 | 2-nitro-3-isopropylphenyl | methyl | |
| 3.187 | 2-fluoro-3-tert-butylphenyl | methyl | |
| 3.188 | 2-fluoro-3-tert-butylphenyl | ethyl | |
| 3.189 | 2-fluoro-3-tert-butylphenyl | CN | |

TABLE 3-continued

Inventive compounds of the general formula (I) in which W* is CN, $R^1$ and $R^2$ are each hydrogen, and aryl is the radical.

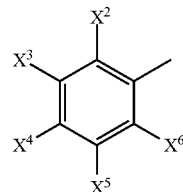

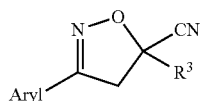

| No. | Aryl | $R^3$ | Physical data |
|---|---|---|---|
| 3.190 | 2-fluoro-3-tert-butylphenyl | fluoromethyl | |
| 3.191 | 2-fluoro-3-tert-butylphenyl | hydroxymethyl | |
| 3.192 | 2-fluoro-3-tert-butylphenyl | ethynyl | |
| 3.193 | 2-chloro-3-tert-butylphenyl | methyl | |
| 3.194 | 2-bromo-3-tert-butylphenyl | methyl | |
| 3.195 | 2-methyl-3-tert-butylphenyl | methyl | |
| 3.196 | 2-ethyl-3-tert-butylphenyl | methyl | |
| 3.197 | 2-cyclopropyl-3-tert-butylphenyl | methyl | |
| 3.198 | 2-cyano-3-tert-butylphenyl | methyl | |
| 3.199 | 2-trifluoromethyl-3-tert-butylphenyl | methyl | |
| 3.200 | 2- methoxy-3-tert-butylphenyl | methyl | |
| 3.201 | 2-ethoxy-3-tert-butylphenyl | methyl | |
| 3.202 | 2-trifluoromethoxy-3-tert-butylphenyl | methyl | |
| 3.203 | 2-nitro-3-tert-butylphenyl | methyl | |
| 3.204 | 2-fluoro-3-cyclopropylphenyl | methyl | |
| 3.205 | 2-chloro-3-cyclopropylphenyl | methyl | |
| 3.206 | 2-bromo-3-cyclopropylphenyl | methyl | |
| 3.207 | 2-methyl-3-cyclopropylphenyl | methyl | |
| 3.208 | 2-ethyl-3-cyclopropylphenyl | methyl | |
| 3.209 | 2-cyclopropyl-3-cyclopropyl phenyl | methyl | |
| 3.210 | 2-cyano-3-cyclopropylphenyl | methyl | |
| 3.211 | 2-trifluoromethyl-3-cyclopropylphenyl | methyl | |
| 3.212 | 2-methoxy-3-cyclopropylphenyl | methyl | |
| 3.213 | 2-ethoxy-3-cyclopropylphenyl | methyl | |
| 3.214 | 2-trifluoromethoxy-3-cyclopropylphenyl | methyl | |
| 3.215 | 2-fluoro-3-methoxycarbonylphenyl | methyl | |
| 3.216 | 2-chloro-3-methoxycarbonylphenyl | methyl | |
| 3.217 | 2-bromo-3-methoxycarbonylphenyl | methyl | |
| 3.218 | 2-methyl-3-methoxycarbonylphenyl | methyl | |
| 3.219 | 2-methyl-3-methoxycarbonylphenyl | ethyl | |
| 3.220 | 2-methyl-3-methoxycarbonylphenyl | CN | |
| 3.221 | 2-methyl-3-methoxycarbonylphenyl | vinyl | |
| 3.222 | 2-methyl-3-methoxycarbonylphenyl | fluoromethyl | |
| 3.223 | 2-methyl-3-methoxycarbonylphenyl | hydroxymethyl | |
| 3.224 | 2-methyl-3-methoxycarbonylphenyl | ethynyl | |
| 3.225 | 2-ethyl-3-methoxycarbonylphenyl | methyl | |
| 3.226 | 2-cyclopropyl-3-methoxycarbonyl-phenyl | methyl | |
| 3.227 | 2-cyano-3-methoxycarbonylphenyl | methyl | |
| 3.228 | 2-trifluoromethyl-3-methoxycarbonylphenyl | methyl | |
| 3.229 | 2-methoxy-3-methoxycarbonylphenyl | methyl | |
| 3.230 | 2-ethoxy-3-methoxycarbonylphenyl | methyl | |
| 3.231 | 2-trifluoromethoxy-3-methoxycarbonylphenyl | methyl | |
| 3.232 | 2-nitro-3-methoxycarbonylphenyl | methyl | |
| 3.233 | 2-fluoro-3-cyanophenyl | methyl | |
| 3.234 | 2-fluoro-3-cyanophenyl | ethyl | |
| 3.235 | 2-fluoro-3-cyanophenyl | CN | |
| 3.236 | 2-fluoro-3-cyanophenyl | vinyl | |
| 3.237 | 2-fluoro-3-cyanophenyl | fluoromethyl | |
| 3.238 | 2-fluoro-3-cyanophenyl | hydroxymethyl | |
| 3.239 | 2-fluoro-3-cyanophenyl | ethynyl | |
| 3.240 | 2-chloro-3-cyanophenyl | methyl | |
| 3.241 | 2-chloro-3-cyanophenyl | ethyl | |
| 3.242 | 2-chloro-3-cyanophenyl | CN | |
| 3.243 | 2-chloro-3-cyanophenyl | vinyl | |
| 3.244 | 2-chloro-3-cyanophenyl | fluoromethyl | |
| 3.245 | 2-chloro-3-cyanophenyl | hydroxymethyl | |

TABLE 3-continued

Inventive compounds of the general formula (I) in which W* is CN, $R^1$ and $R^2$ are each hydrogen, and aryl is the radical.

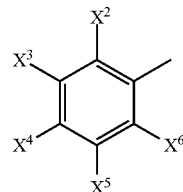

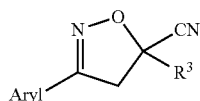

| No. | Aryl | $R^3$ | Physical data |
|---|---|---|---|
| 3.246 | 2-chloro-3-cyanophenyl | ethynyl | |
| 3.247 | 2-bromo-3-cyanophenyl | methyl | |
| 3.248 | 2-methyl-3-cyanophenyl | methyl | |
| 3.249 | 2-ethyl-3-cyanophenyl | methyl | |
| 3.250 | 2-cyclopropyl-3-cyanophenyl | methyl | |
| 3.251 | 2-cyano-3-cyanophenyl | methyl | |
| 3.252 | 2-trifluoromethyl-3-cyanophenyl | methyl | |
| 3.253 | 2-methoxy-3-cyanophenyl | methyl | |
| 3.254 | 2-ethoxy-3-cyanophenyl | methyl | |
| 3.255 | 2-trifluoromethoxy-3-cyanophenyl | methyl | |
| 3.256 | 2-nitro-3-cyanophenyl | methyl | |
| 3.257 | 2-chloro-3-methoxyphenyl | methyl | |
| 3.258 | 2-bromo-3-methoxyphenyl | methyl | |
| 3.259 | 2-methyl-3-methoxyphenyl | methyl | |
| 3.260 | 2-ethyl-3-methoxyphenyl | methyl | |
| 3.261 | 2-cyclopropyl-3-methoxyphenyl | methyl | |
| 3.262 | 2-cyano-3-methoxyphenyl | methyl | |
| 3.263 | 2-trifluoromethyl-3-methoxyphenyl | methyl | |
| 3.264 | 2,3-dimethoxyphenyl | methyl | |
| 3.265 | 2-ethoxy-3-methoxyphenyl | methyl | |
| 3.266 | 2-trifluoromethoxy-3-methoxyphenyl | methyl | |
| 3.267 | 2- nitro-3-methoxyphenyl | methyl | |
| 3.268 | 2-fluoro-3-ethoxyphenyl | methyl | |
| 3.269 | 2-chloro-3-ethoxyphenyl | methyl | |
| 3.270 | 2-bromo-3-ethoxyphenyl | methyl | |
| 3.271 | 2-methyl-3-ethoxyphenyl | methyl | |
| 3.272 | 2-ethyl-3-ethoxyphenyl | methyl | |
| 3.273 | 2-cyclopropyl-3-ethoxyphenyl | methyl | |
| 3.274 | 2-cyano-3-ethoxyphenyl | methyl | |
| 3.275 | 2-trifluoromethyl-3-ethoxyphenyl | methyl | |
| 3.276 | 2-methoxy-3-ethoxyphenyl | methyl | |
| 3.277 | 2,3-diethoxyphenyl | methyl | |
| 3.278 | 2-trifluoromethoxy-3-ethoxyphenyl | methyl | |
| 3.279 | 2-nitro-3-ethoxyphenyl | methyl | |
| 3.280 | 2-fluoro-3-propoxyphenyl | methyl | |
| 3.281 | 2-chloro-3-propoxyphenyl | methyl | |
| 3.282 | 2-bromo-3-propoxyphenyl | methyl | |
| 3.283 | 2-methyl-3-propoxyphenyl | methyl | |
| 3.284 | 2-ethyl-3-propoxyphenyl | methyl | |
| 3.285 | 2-cyclopropyl-3-propoxyphenyl | methyl | |
| 3.286 | 2-vinyl-3-propoxyphenyl | methyl | |
| 3.287 | 2-ethynyl-3-propoxyphenyl | methyl | |
| 3.288 | 2-cyano-3-propoxyphenyl | methyl | |
| 3.289 | 2-trifluoromethyl-3-propoxyphenyl | methyl | |
| 3.290 | 2-methoxy-3-propoxyphenyl | methyl | |
| 3.291 | 2-ethoxy-3-propoxyphenyl | methyl | |
| 3.292 | 2-trifluoromethoxy-3-propoxyphenyl | methyl | |
| 3.293 | 2-nitro-3-propoxyphenyl | methyl | |
| 3.294 | 2-fluoro-3-isopropoxyphenyl | methyl | |
| 3.295 | 2-chloro-3-isopropoxyphenyl | methyl | |
| 3.296 | 2-bromo-3-isopropoxyphenyl | methyl | |
| 3.297 | 2- methyl-3-isopropoxyphenyl | methyl | |
| 3.298 | 2-ethyl-3-isopropoxyphenyl | methyl | |
| 3.299 | 2-cyclopropyl-3-isopropoxyphenyl | methyl | |
| 3.300 | 2-vinyl-3-isopropoxyphenyl | methyl | |
| 3.301 | 2-ethynyl-3-isopropoxyphenyl | methyl | |
| 3.302 | 2-cyano-3-isopropoxyphenyl | methyl | |
| 3.303 | 2-trifluoromethyl-3-isopropoxyphenyl | methyl | |

TABLE 3-continued

Inventive compounds of the general formula (I) in which W* is CN, $R^1$ and $R^2$ are each hydrogen, and aryl is the radical.

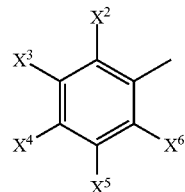

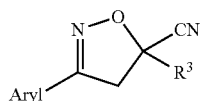

| No. | Aryl | $R^3$ | Physical data |
|---|---|---|---|
| 3.304 | 2-methoxy-3-isopropoxyphenyl | methyl | |
| 3.305 | 2-ethoxy-3-isopropoxyphenyl | methyl | |
| 3.306 | 2-trifluoromethoxy-3-isopropoxyphenyl | methyl | |
| 3.307 | 2-nitro-3-isopropoxyphenyl | methyl | |
| 3.308 | 2-fluoro-3-trifluoromethoxyphenyl | methyl | |
| 3.309 | 2-chloro-3-trifluoromethoxyphenyl | methyl | |
| 3.310 | 2-bromo-3-trifluoromethoxyphenyl | methyl | |
| 3.311 | 2-methyl-3-trifluoromethoxyphenyl | methyl | |
| 3.312 | 2-ethyl-3-trifluoromethoxyphenyl | methyl | |
| 3.313 | 2-cyclopropyl-3-trifluoromethoxyphenyl | methyl | |
| 3.314 | 2-cyano-3-trifluoromethoxyphenyl | methyl | |
| 3.315 | 2-trifluoromethyl-3-trifluoromethoxy-phenyl | methyl | |
| 3.316 | 2-methoxy-3-trifluoromethoxyphenyl | methyl | |
| 3.317 | 2-ethoxy-3-trifluoromethoxyphenyl | methyl | |
| 3.318 | 2,3-bis(trifluoromethoxy)phenyl | methyl | |
| 3.319 | 2-nitro-3-trifluoromethoxyphenyl | methyl | |
| 3.320 | 2-fluoro-3-difluoromethoxyphenyl | methyl | |
| 3.321 | 2-chloro-3-difluoromethoxyphenyl | methyl | |
| 3.322 | 2-bromo-3-difluoromethoxyphenyl | methyl | |
| 3.323 | 2-methyl-3-difluoromethoxyphenyl | methyl | |
| 3.324 | 2-ethyl-3-difluoromethoxyphenyl | methyl | |
| 3.325 | 2-cyclopropyl-3-difluoromethoxyphenyl | methyl | |
| 3.326 | 2-cyano-3-difluoromethoxyphenyl | methyl | |
| 3.327 | 2-trifluoromethyl-3-difluoromethoxyphenyl | methyl | |
| 3.328 | 2-methoxy-3-difluoromethoxyphenyl | methyl | |
| 3.329 | 2-ethoxy-3-difluoromethoxyphenyl | methyl | |
| 3.330 | 2-trifluoromethoxy-3-difluoromethoxy-phenyl | methyl | |
| 3.331 | 2-nitro-3-difluoromethoxyphenyl | methyl | |
| 3.332 | 2-fluoro-3-nitrophenyl | methyl | |
| 3.333 | 2-chloro-3-nitrophenyl | methyl | |
| 3.334 | 2-bromo-3-nitrophenyl | methyl | |
| 3.335 | 2-methyl-3-nitrophenyl | methyl | |
| 3.336 | 2-ethyl-3-nitrophenyl | methyl | |
| 3.337 | 2-cyclopropyl-3-nitrophenyl | methyl | |
| 3.338 | 2-cyano-3-nitrophenyl | methyl | |
| 3.339 | 2-trifluoromethyl-3-nitrophenyl | methyl | |
| 3.340 | 2-methoxy-3-nitrophenyl | methyl | |
| 3.341 | 2-ethoxy-3-nitrophenyl | methyl | |
| 3.342 | 2-trifluoromethoxy-3-nitrophenyl | methyl | |
| 3.343 | 2-fluoro-3-methylsulfanylphenyl | methyl | |
| 3.344 | 2-chloro-3-methylsulfanylphenyl | methyl | |
| 3.345 | 2-bromo-3-methylsulfanylphenyl | methyl | |
| 3.346 | 2-methyl-3-methylsulfanylphenyl | methyl | |
| 3.347 | 2-ethyl-3-methylsulfanylphenyl | methyl | |
| 3.348 | 2-cyclopropyl-3-methylsulfanylphenyl | methyl | |
| 3.349 | 2-cyano-3-methylsulfanylphenyl | methyl | |
| 3.350 | 2-trifluoromethyl-3-methylsulfanylpheny | lmethyl | |
| 3.351 | 2-methoxy-3-methylsulfanylphenyl | methyl | |
| 3.352 | 2-ethoxy-3-methylsulfanylphenyl | methyl | |
| 3.353 | 2-trifluoromethoxy-3-methylsulfanylphenyl | methyl | |
| 3.354 | 2-nitro-3-methylsulfanylphenyl | methyl | |
| 3.355 | 3,5-difluorophenyl | methyl | [$CDCl_3$] 1.91 (s, 3H), 3.38 (d, 1H), 3.81 (d, 1H), 6.93 (m, 1H), 7.18 (m, 2H) |
| 3.356 | 3,5-difluorophenyl | ethyl | |

TABLE 3-continued

Inventive compounds of the general formula (I) in which W* is CN, $R^1$ and $R^2$ are each hydrogen, and aryl is the radical.

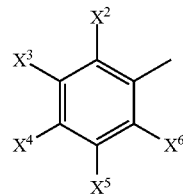

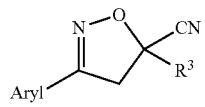

| No. | Aryl | $R^3$ | Physical data |
|---|---|---|---|
| 3.357 | 3,5-difluorophenyl | CN | |
| 3.358 | 3,5-difluorophenyl | vinyl | |
| 3.359 | 3,5-difluorophenyl | fluoromethyl | |
| 3.360 | 3,5-difluorophenyl | hydroxymethyl | |
| 3.361 | 3,5-difluorophenyl | ethynyl | |
| 3.362 | 3-chloro-5-fluorophenyl | methyl | |
| 3.363 | 3-chloro-5-fluorophenyl | ethyl | |
| 3.364 | 3-chloro-5-fluorophenyl | CN | |
| 3.365 | 3-chloro-5-fluorophenyl | vinyl | |
| 3.366 | 3-chloro-5-fluorophenyl | fluoromethyl | |
| 3.367 | 3-chloro-5-fluorophenyl | hydroxymethyl | |
| 3.368 | 3-chloro-5-fluorophenyl | ethynyl | |
| 3.369 | 3-bromo-5-fluorophenyl | methyl | |
| 3.370 | 3-iodo-5-fluorophenyl | methyl | |
| 3.371 | 3-methyl-5-fluorophenyl | methyl | |
| 3.372 | 3-methyl-5-fluorophenyl | ethyl | |
| 3.373 | 3-methyl-5-fluorophenyl | CN | |
| 3.374 | 3-methyl-5-fluorophenyl | vinyl | |
| 3.375 | 3-methyl-5-fluorophenyl | fluoromethyl | |
| 3.376 | 3-methyl-5-fluorophenyl | hydroxymethyl | |
| 3.377 | 3-methyl-5-fluorophenyl | ethynyl | |
| 3.378 | 3-ethyl-5-fluorophenyl | methyl | |
| 3.379 | 3-propyl-5-fluorophenyl | methyl | |
| 3.380 | 3-i-propyl-5-fluorophenyl | methyl | |
| 3.381 | 3-n-butyl-5-fluorophenyl | methyl | |
| 3.382 | 3-isobutyl-5-fluorophenyl | methyl | |
| 3.383 | 3-tert-butyl-5-fluorophenyl | methyl | |
| 3.384 | 3-tert-butyl-5-fluorophenyl | ethyl | |
| 3.385 | 3-tert-butyl-5-fluorophenyl | CN | |
| 3.386 | 3-tert-butyl-5-fluorophenyl | vinyl | |
| 3.387 | 3-tert-butyl-5-fluorophenyl | fluoromethyl | |
| 3.388 | 3-tert-butyl-5-fluorophenyl | hydroxymethyl | |
| 3.389 | 3-tert-butyl-5-fluorophenyl | ethynyl | |
| 3.390 | 3-cyclopropyl-5-fluorophenyl | methyl | |
| 3.391 | 3-cyano-5-fluorophenyl | methyl | |
| 3.392 | 3-cyano-5-fluorophenyl | ethyl | |
| 3.393 | 3-cyano-5-fluorophenyl | CN | |
| 3.394 | 3-cyano-5-fluorophenyl | vinyl | |
| 3.395 | 3-cyano-5-fluorophenyl | fluoromethyl | |
| 3.396 | 3-cyano-5-fluorophenyl | hydroxymethyl | |
| 3.397 | 3-cyano-5-fluorophenyl | ethynyl | |
| 3.398 | 3-trifluoromethyl-5-fluorophenyl | methyl | |
| 3.399 | 3-(methoxycarbonyl)-5-fluorophenyl | methyl | |
| 3.400 | 3-methoxy-5-fluorophenyl | methyl | |
| 3.401 | 3-methoxy-5-fluorophenyl | ethyl | |
| 3.402 | 3-methoxy-5-fluorophenyl | CN | |
| 3.403 | 3-methoxy-5-fluorophenyl | vinyl | |
| 3.404 | 3-methoxy-5-fluorophenyl | fluoromethyl | |
| 3.405 | 3-methoxy-5-fluorophenyl | hydroxymethyl | |
| 3.406 | 3-methoxy-5-fluorophenyl | ethynyl | |
| 3.407 | 3-ethoxy-5-fluorophenyl | methyl | |
| 3.408 | 3-n-propoxy-5-fluorophenyl | methyl | |
| 3.409 | 3-isopropoxy-5-fluorophenyl | methyl | |
| 3.410 | 3-n-butoxy-5-fluorophenyl | methyl | |
| 3.411 | 3-isobutoxy-5-fluorophenyl | methyl | |
| 3.412 | 3-difluoromethoxy-5-fluorophenyl | methyl | |
| 3.413 | 3-trifluoromethoxy-5-fluorophenyl | methyl | |
| 3.414 | 3-nitro-5-fluorophenyl | methyl | |

TABLE 3-continued

Inventive compounds of the general formula (I) in which W* is CN, $R^1$ and $R^2$ are each hydrogen, and aryl is the radical.

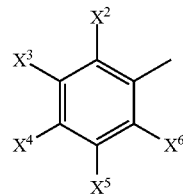

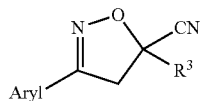

| No. | Aryl | $R^3$ | Physical data |
|---|---|---|---|
| 3.415 | 3-acetoxy-5-fluorophenyl | methyl | |
| 3.416 | 3-methylsulfanyl-5-fluorophenyl | methyl | |
| 3.417 | 3,5-dichlorophenyl | methyl | [CDCl$_3$] 1.91 (s, 3H); 3.38 (d, 1H); 3.80 (d, 1H); 7.45 (s, 1H); 7.52 (s, 1H). |
| 3.418 | 3,5-dichlorophenyl | ethyl | |
| 3.419 | 3,5-dichlorophenyl | isopropyl | [DMSO] 1.06 (d, 3H); 1.10 (d, 3H); 2.25 (m, 1H); 3.85 (d, 1H); 4.10 (d, 1H); 7.74 (d, 1H); 7.79 (d, 1H). |
| 3.420 | 3,5-dichlorophenyl | vinyl | |
| 3.421 | 3,5-dichlorophenyl | fluoromethyl | |
| 3.422 | 3,5-dichlorophenyl | hydroxymethyl | |
| 3.423 | 3,5-dichlorophenyl | ethynyl | |
| 3.424 | 3-bromo-5-chlorophenyl | methyl | |
| 3.425 | 3-iodo-5-chlorophenyl | methyl | |
| 3.426 | 3-methyl-5-chlorophenyl | methyl | |
| 3.427 | 3-methyl-5-chlorophenyl | ethyl | |
| 3.428 | 3-methyl-5-chlorophenyl | CN | |
| 3.429 | 3-methyl-5-chlorophenyl | vinyl | |
| 3.430 | 3-methyl-5-chlorophenyl | fluoromethyl | |
| 3.431 | 3-methyl-5-chlorophenyl | hydroxymethyl | |
| 3.432 | 3-methyl-5-chlorophenyl | ethynyl | |
| 3.433 | 3-ethyl-5-chlorophenyl | methyl | |
| 3.434 | 3-propyl-5-chlorophenyl | methyl | |
| 3.435 | 3-isopropyl-5-chlorophenyl | methyl | |
| 3.436 | 3-n-butyl-5-chlorophenyl | methyl | |
| 3.437 | 3-isobutyl-5-chlorophenyl | methyl | |
| 3.438 | 3-tert-butyl-5-chlorophenyl | methyl | |
| 3.439 | 3-cyclopropyl-5-chlorophenyl | methyl | |
| 3.440 | 3-cyano-5-chlorophenyl | methyl | |
| 3.441 | 3-cyano-5-chlorophenyl | ethyl | |
| 3.442 | 3-cyano-5-chlorophenyl | CN | |
| 3.443 | 3-cyano-5-chlorophenyl | vinyl | |
| 3.444 | 3-cyano-5-chlorophenyl | fluoromethyl | |
| 3.445 | 3-cyano-5-chlorophenyl | hydroxymethyl | |
| 3.446 | 3-cyano-5-chlorophenyl | ethynyl | |
| 3.447 | 3-trifluoromethyl-5-chlorophenyl | methyl | |
| 3.448 | 3-trifluoromethyl-5-chlorophenyl | ethyl | |
| 3.449 | 3-trifluoromethyl-5-chlorophenyl | CN | |
| 3.450 | 3-trifluoromethyl-5-chlorophenyl | vinyl | |
| 3.451 | 3-trifluoromethyl-5-chlorophenyl | fluoromethyl | |
| 3.452 | 3-trifluoromethyl-5-chlorophenyl | hydroxymethyl | |
| 3.453 | 3-trifluoromethyl-5-chlorophenyl | ethynyl | |
| 3.454 | 3-(methoxycarbonyl)-5-chlorophenyl | methyl | |
| 3.455 | 3-methoxy-5-chlorophenyl | methyl | |
| 3.456 | 3-methoxy-5-chlorophenyl | ethyl | |
| 3.457 | 3-methoxy-5-chlorophenyl | CN | |
| 3.458 | 3-methoxy-5-chlorophenyl | vinyl | |
| 3.459 | 3-methoxy-5-chlorophenyl | fluoromethyl | |
| 3.460 | 3-methoxy-5-chlorophenyl | hydroxymethyl | |
| 3.461 | 3-methoxy-5-chlorophenyl | ethynyl | |
| 3.462 | 3-ethoxy-5-chlorophenyl | methyl | |
| 3.463 | 3-n-propoxy-5-chlorophenyl | methyl | |
| 3.464 | 3-isopropoxy-5-chlorophenyl | methyl | |
| 3.465 | 3-isobutoxy-5-chlorophenyl | methyl | |

TABLE 3-continued

Inventive compounds of the general formula (I) in which W* is CN, $R^1$ and $R^2$ are each hydrogen, and aryl is the radical.

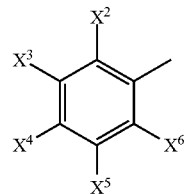

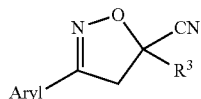

| No. | Aryl | $R^3$ | Physical data |
|---|---|---|---|
| 3.466 | 3-difluoromethoxy-5-chlorophenyl | methyl | |
| 3.467 | 3-trifluoromethoxy-5-chlorophenyl | methyl | |
| 3.468 | 3-trifluoromethoxy-5-chlorophenyl | ethyl | |
| 3.469 | 3-trifluoromethoxy-5-chlorophenyl | CN | |
| 3.470 | 3-trifluoromethoxy-5-chlorophenyl | vinyl | |
| 3.471 | 3-trifluoromethoxy-5-chlorophenyl | fluoromethyl | |
| 3.472 | 3-trifluoromethoxy-5-chlorophenyl | hydroxymethyl | |
| 3.473 | 3-trifluoromethoxy-5-chlorophenyl | ethynyl | |
| 3.474 | 3-nitro-5-chlorophenyl | methyl | |
| 3.475 | 3-acetoxy-5-chlorophenyl | methyl | |
| 3.476 | 3-methylsulfanyl-5-chlorophenyl | methyl | |
| 3.477 | 3,5-dibromophenylphenyl | methyl | |
| 3.478 | 3-iodo-5-bromophenyl | methyl | |
| 3.479 | 3-methyl-5-bromophenyl | methyl | |
| 3.480 | 3-ethyl-5-bromophenyl | methyl | |
| 3.481 | 3-propyl-5-bromophenyl | methyl | |
| 3.482 | 3-isopropyl-5-bromophenyl | methyl | |
| 3.483 | 3-n-butyl-5-bromophenyl | methyl | |
| 3.484 | 3-isobutyl-5-bromophenyl | methyl | |
| 3.485 | 3-tert-butyl-5-bromophenyl | methyl | |
| 3.486 | 3-cyclopropyl-5-bromophenyl | methyl | |
| 3.487 | 3-cyano-5-bromophenyl | methyl | |
| 3.488 | 3-trifluoromethyl-5-bromophenyl | methyl | |
| 3.489 | 3-(methoxycarbonyl)-5-bromophenyl | methyl | |
| 3.490 | 3-methoxy-5-bromophenyl | methyl | |
| 3.491 | 3-ethoxy-5-bromophenyl | methyl | |
| 3.492 | 3-n-propoxy-5-bromophenyl | methyl | |
| 3.493 | 3-isopropoxy-5-bromophenyl | methyl | |
| 3.494 | 3-n-butoxy-5-bromophenyl | methyl | |
| 3.495 | 3-isobutoxy-5-bromophenyl | methyl | |
| 3.496 | 3-difluoromethoxy-5-bromophenyl | methyl | |
| 3.497 | 3-trifluoromethoxy-5-bromophenyl | methyl | |
| 3.498 | 3-nitro-5-bromophenyl | methyl | |
| 3.499 | 3-acetoxy-5-bromophenyl | methyl | |
| 3.500 | 3-methylsulfanyl-5-bromophenyl | methyl | |
| 3.501 | 3,5-diiodophenyl | methyl | |
| 3.502 | 3-methyl-5-iodophenyl | methyl | |
| 3.503 | 3-ethyl-5-iodophenyl | methyl | |
| 3.504 | 3-propyl-5-iodophenyl | methyl | |
| 3.505 | 3-isopropyl-5-iodophenyl | methyl | |
| 3.506 | 3-n-butyl-5-iodophenyl | methyl | |
| 3.507 | 3-isobutyl-5-iodophenyl | methyl | |
| 3.508 | 3-tert-butyl-5-iodophenyl | methyl | |
| 3.509 | 3-cyclopropyl-5-iodophenyl | methyl | |
| 3.510 | 3-cyano-5-iodophenyl | methyl | |
| 3.511 | 3-trifluoromethyl-5-iodophenyl | methyl | |
| 3.512 | 3-(methoxycarbonyl)-5-iodophenyl | methyl | |
| 3.513 | 3-methoxy-5-iodophenyl | methyl | |
| 3.514 | 3-ethoxy-5-iodophenyl | methyl | |
| 3.515 | 3-n-propoxy-5-iodophenyl | methyl | |
| 3.516 | 3-isopropoxy-5-iodophenyl | methyl | |
| 3.517 | 3- n-butoxy-5-iodophenyl | methyl | |
| 3.518 | 3-isobutoxy-5-iodophenyl | methyl | |
| 3.519 | 3-difluoromethoxy-5-iodophenyl | methyl | |
| 3.520 | 3-trifluoromethoxy-5-iodophenyl | methyl | |
| 3.521 | 3-nitro-5-iodophenyl | methyl | |
| 3.522 | 3-acetoxy-5-iodophenyl | methyl | |
| 3.523 | 3-methylsulfanyl-5-iodophenyl | methyl | |

TABLE 3-continued

Inventive compounds of the general formula (I) in which W* is CN, R¹ and R² are each hydrogen, and aryl is the radical.

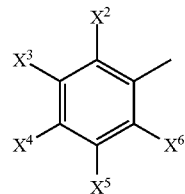

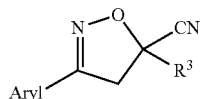

| No. | Aryl | R³ | Physical data |
|---|---|---|---|
| 3.524 | 3,5-dimethylphenyl | methyl | |
| 3.525 | 3-ethyl-5-methylphenyl | methyl | |
| 3.526 | 3-propyl-5-methylphenyl | methyl | |
| 3.527 | 3-isopropyl-5-methylphenyl | methyl | |
| 3.528 | 3-n-butyl-5-methylphenyl | methyl | |
| 3.529 | 3-isobutyl-5-methylphenyl | methyl | |
| 3.530 | 3-tert-butyl-5-methylphenyl | methyl | |
| 3.531 | 3-cyclopropyl-5-methylphenyl | methyl | |
| 3.532 | 3-cyano-5-methylphenyl | methyl | |
| 3.533 | 3-trifluoromethyl-5-methylphenyl | methyl | |
| 3.534 | 3-(methoxycarbonyl)-5-methylphenyl | methyl | |
| 3.535 | 3-methoxy-5-methylphenyl | methyl | |
| 3.536 | 3-ethoxy-5-methylphenyl | methyl | |
| 3.537 | 3-n-propoxy-5-methylphenyl | methyl | |
| 3.538 | 3-isobutoxy-5-methylphenyl | methyl | |
| 3.539 | 3-difluoromethoxy-5-methylphenyl | methyl | |
| 3.540 | 3-trifluoromethoxy-5-methylphenyl | methyl | |
| 3.541 | 3-nitro-5-methylphenyl | methyl | |
| 3.542 | 3-acetoxy-5-methylphenyl | methyl | |
| 3.543 | 3-methylsulfanyl-5-methylphenyl | methyl | |
| 3.544 | 3,5-diethylphenyl | methyl | |
| 3.545 | 3-propyl-5-ethylphenyl | methyl | |
| 3.546 | 3-isopropyl-5-ethylphenyl | methyl | |
| 3.547 | 3-n-butyl-5-ethylphenyl | methyl | |
| 3.548 | 3-isobutyl-5-ethylphenyl | methyl | |
| 3.549 | 3-cyclopropyl-5-ethylphenyl | methyl | |
| 3.550 | 3-cyano-5-ethylphenyl | methyl | |
| 3.551 | 3-trifluoromethyl-5-ethylphenyl | methyl | |
| 3.552 | 3-(methoxycarbonyl)-5-ethylphenyl | methyl | |
| 3.553 | 3-methoxy-5-ethylphenyl | methyl | |
| 3.554 | 3-ethoxy-5-ethylphenyl | methyl | |
| 3.555 | 3-n-propoxy-5-ethylphenyl | methyl | |
| 3.556 | 3-n-butoxy-5-ethylphenyl | methyl | |
| 3.557 | 3-isobutoxy-5-ethylphenyl | methyl | |
| 3.558 | 3-difluoromethoxy-5-ethylphenyl | methyl | |
| 3.559 | 3-trifluoromethoxy-5-ethylphenyl | methyl | |
| 3.560 | 3-nitro-5-ethylphenyl | methyl | |
| 3.561 | 3-acetoxy-5-ethylphenyl | methyl | |
| 3.562 | 3-methylsulfanyl-5-ethylphenyl | methyl | |
| 3.563 | 3,5-dipropylphenyl | methyl | |
| 3.564 | 3-isopropyl-5-propylphenyl | methyl | |
| 3.565 | 3-n-butyl-5-propylphenyl | methyl | |
| 3.566 | 3-isobutyl-5-propylphenyl | methyl | |
| 3.567 | 3-tert-butyl-5-propylphenyl | methyl | |
| 3.568 | 3-cyclopropyl-5-propylphenyl | methyl | |
| 3.569 | 3-cyano-5-propylphenyl | methyl | |
| 3.570 | 3-trifluoromethyl-5-propylphenyl | methyl | |
| 3.571 | 3-(methoxycarbonyl)-5-propylphenyl | methyl | |
| 3.572 | 3-methoxy-5-propylphenyl | methyl | |
| 3.573 | 3-ethoxy-5-propylphenyl | methyl | |
| 3.574 | 3-n-propoxy-5-propylphenyl | methyl | |
| 3.575 | 3-isobutoxy-5-propylphenyl | methyl | |
| 3.576 | 3-difluoromethoxy-5-propylphenyl | methyl | |
| 3.577 | 3-trifluoromethoxy-5-ethylphenyl | methyl | |
| 3.578 | 3-nitro-5-propylphenyl | methyl | |
| 3.579 | 3-acetoxy-5-propylphenyl | methyl | |
| 3.580 | 3-methylsulfanyl-5-propylphenyl | methyl | |
| 3.581 | 3,5-diisopropylphenyl | methyl | |

TABLE 3-continued

Inventive compounds of the general formula (I) in which W* is CN, $R^1$ and $R^2$ are each hydrogen, and aryl is the radical.

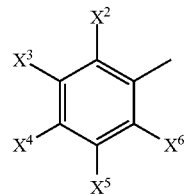

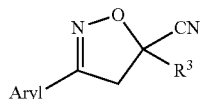

| No. | Aryl | $R^3$ | Physical data |
|---|---|---|---|
| 3.582 | 3-n-butyl-5-isopropylphenyl | methyl | |
| 3.583 | 3-isobutyl-5-isopropylphenyl | methyl | |
| 3.584 | 3-tert-butyl-5-isopropylphenyl | methyl | |
| 3.585 | 3-cyclopropyl-5-isopropylphenyl | methyl | |
| 3.586 | 3-cyano-5-isopropylphenyl | methyl | |
| 3.587 | 3-trifluoromethyl-5-isopropylphenyl | methyl | |
| 3.588 | 3-(methoxycarbonyl)-5-isopropylphenyl | methyl | |
| 3.589 | 3- methoxy-5-isopropylphenyl | methyl | |
| 3.590 | 3-ethoxy-5-isopropylphenyl | methyl | |
| 3.591 | 3-n-propoxy-5-isopropylphenyl | methyl | |
| 3.592 | 3-isobutoxy-5- isopropylphenyl | methyl | |
| 3.593 | 3-difluoromethoxy-5- isopropylphenyl | methyl | |
| 3.594 | 3-trifluoromethoxy-5-isopropylphenyl | methyl | |
| 3.595 | 3-nitro-5-isopropylphenyl | methyl | |
| 3.596 | 3-acetoxy-5-isopropylphenyl | methyl | |
| 3.597 | 3-methylsulfanyl-5-isopropylphenyl | methyl | |
| 3.598 | 3,5-diisobutylphenyl | methyl | |
| 3.599 | 3-tert-butyl-5-isobutylphenyl | methyl | |
| 3.600 | 3-cyclopropyl-5-isobutylphenyl | methyl | |
| 3.601 | 3-cyano-5-isobutylphenyl | methyl | |
| 3.602 | 3-trifluoromethyl-5-isobutylphenyl | methyl | |
| 3.603 | 3-(methoxycarbonyl)-5-isobutylphenyl | methyl | |
| 3.604 | 3-ethoxy-5-isobutylphenyl | methyl | |
| 3.605 | 3-n-propoxy-5-isobutylphenyl | methyl | |
| 3.606 | 3-isobutoxy-5-isobutylphenyl | methyl | |
| 3.607 | 3-difluoromethoxy-5-isobutylphenyl | methyl | |
| 3.608 | 3-trifluoromethoxy-5-isobutylphenyl | methyl | |
| 3.609 | 3-nitro-5- isobutylphenyl | methyl | |
| 3.610 | 3-acetoxy-5-isobutylphenyl | methyl | |
| 3.611 | 3-methylsulfanyl-5-isobutylphenyl | methyl | |
| 3.612 | 3,5-d i-tert-butylphenyl | methyl | |
| 3.613 | 3-cyclopropyl-5-tert-butylphenyl | methyl | |
| 3.614 | 3-cyano-5-tert-butylphenyl | methyl | |
| 3.615 | 3-trifluoromethyl-5-tert-butylphenyl | methyl | |
| 3.616 | 3-(methoxycarbonyl)-5-tert-butylphenyl | methyl | |
| 3.617 | 3-methoxy-5-tert-butylphenyl | methyl | |
| 3.618 | 3-ethoxy-5-tert-butylphenyl | methyl | |
| 3.619 | 3-n-propoxy-5-tert-butylphenyl | methyl | |
| 3.620 | 3-isobutoxy-5-tert-butylphenyl | methyl | |
| 3.621 | 3-difluoromethoxy-5-tert-butylphenyl | methyl | |
| 3.622 | 3-trifluoromethoxy-5-tert-butylphenyl | methyl | |
| 3.623 | 3-nitro-5-tert-butylphenyl | methyl | |
| 3.624 | 3-acetoxy-5-tert-butylphenyl | methyl | |
| 3.625 | 3-methylsulfanyl-5-tert-butylphenyl | methyl | |
| 3.626 | 3-tert-butyl-5-cyclopropylphenyl | methyl | |
| 3.627 | 3,5-dicyclopropylphenyl | methyl | |
| 3.628 | 3-cyano-5-cyclopropylphenyl | methyl | |
| 3.629 | 3-cyano-5-cyclopropylphenyl | ethyl | |
| 3.630 | 3-cyano-5-cyclopropylphenyl | CN | |
| 3.631 | 3-cyano-5-cyclopropylphenyl | vinyl | |
| 3.632 | 3-cyano-5-cyclopropylphenyl | fluoromethyl | |
| 3.633 | 3-cyano-5-cyclopropylphenyl | hydroxymethyl | |
| 3.634 | 3-cyano-5-cyclopropylphenyl | ethynyl | |
| 3.635 | 3-trifluoromethyl-5-cyclopropylphenyl | methyl | |
| 3.636 | 3-(methoxycarbonyl)-5-cyclopropylphenyl | methyl | |
| 3.637 | 3-methoxy-5-cyclopropylphenyl | methyl | |
| 3.638 | 3-ethoxy-5-cyclopropylphenyl | methyl | |
| 3.639 | 3-n-propoxy-5-cyclopropylphenyl | methyl | |

TABLE 3-continued

Inventive compounds of the general formula (I) in which W* is CN, $R^1$ and $R^2$ are each hydrogen, and aryl is the radical.

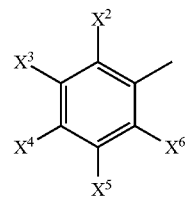

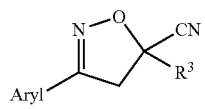

| No. | Aryl | $R^3$ | Physical data |
|---|---|---|---|
| 3.640 | 3-isobutoxy-5-cyclopropylphenyl | methyl | |
| 3.641 | 3-difluoromethoxy-5-cyclopropylphenyl | methyl | |
| 3.642 | 3-trifluoromethoxy-5-cyclopropylphenyl | methyl | |
| 3.643 | 3-nitro-5-cyclopropylphenyl | methyl | |
| 3.644 | 3-acetoxy-5-cyclopropylphenyl | methyl | |
| 3.645 | 3-methylsulfanyl-5-cyclopropylphenyl | methyl | |
| 3.646 | 3,5-dicyanophenyl | methyl | |
| 3.647 | 3-trifluoromethyl-5-cyanophenyl | methyl | |
| 3.648 | 3-(methoxycarbonyl)-5-cyanophenyl | methyl | |
| 3.649 | 3-methoxy-5-cyanophenyl | methyl | |
| 3.650 | 3-ethoxy-5-cyanophenyl | methyl | |
| 3.651 | 3-n-propoxy-5-cyanophenyl | methyl | |
| 3.652 | 3-isobutoxy-5-cyanophenyl | methyl | |
| 3.653 | 3-difluoromethoxy-5-cyanophenyl | methyl | |
| 3.654 | 3-trifluoromethoxy-5-cyanophenyl | methyl | |
| 3.655 | 3-nitro-5-cyanophenyl | methyl | |
| 3.656 | 3-acetoxy-5-cyanophenyl | methyl | |
| 3.657 | 3-methylsulfanyl-5-cyanophenyl | methyl | |
| 3.658 | 3,5-di(trifluoromethyl)phenyl | methyl | |
| 3.659 | 3,5-di(trifluoromethyl)phenyl | ethyl | |
| 3.660 | 3,5-di(trifluoromethyl)phenyl | CN | |
| 3.661 | 3,5-di(trifluoromethyl)phenyl | vinyl | |
| 3.662 | 3,5-di(trifluoromethyl)phenyl | fluoromethyl | |
| 3.663 | 3,5-di(trifluoromethyl)phenyl | hydroxymethyl | |
| 3.664 | 3,5-di(trifluoromethyl)phenyl | ethynyl | |
| 3.665 | 3-(methoxycarbonyl)-5-trifluoromethyl-phenyl | methyl | |
| 3.666 | 3-methoxy-5-trifluoromethylphenyl | methyl | |
| 3.667 | 3-ethoxy-5-trifluoromethylphenyl | methyl | |
| 3.668 | 3-n-propoxy-5-trifluoromethylphenyl | methyl | |
| 3.669 | 3-n-butoxy-5-trifluoromethylphenyl | methyl | |
| 3.670 | 3-isobutoxy-5-trifluoromethylphenyl | methyl | |
| 3.671 | 3-difluoromethoxy-5-trifluoromethylphenyl | methyl | |
| 3.672 | 3-trifluoromethoxy-5-trifluoromethylphenyl | methyl | |
| 3.673 | 3-nitro-5-trifluoromethylphenyl | methyl | |
| 3.674 | 3-acetoxy-5-trifluoromethylphenyl | methyl | |
| 3.675 | 3-methylsulfanyl-5-trifluoromethylphenyl | methyl | |
| 3.676 | 3,5-di(methoxycarbonyl)phenyl | methyl | |
| 3.677 | 3-methoxy-5-(methoxycarbonyl)phenyl | methyl | |
| 3.678 | 3-ethoxy-5-(methoxycarbonyl)phenyl | methyl | |
| 3.679 | 3-n-propoxy-5-(methoxycarbonyl)phenyl | methyl | |
| 3.680 | 3-isobutoxy-5-(methoxycarbonyl)phenyl | methyl | |
| 3.681 | 3-difluoromethoxy-5-(methoxycarbonyl)-phenyl | methyl | |
| 3.682 | 3-trifluoromethoxy-5-(methoxycarbonyl)-phenyl | methyl | |
| 3.683 | 3-nitro-5-(methoxycarbonyl)phenyl | methyl | |
| 3.684 | 3-acetoxy-5-(methoxycarbonyl)phenyl | methyl | |
| 3.685 | 3-methylsulfanyl-5-(methoxycarbonyl)-phenyl | methyl | |
| 3.686 | 3,5-dimethoxyphenyl | methyl | |
| 3.687 | 3,5-dimethoxyphenyl | ethyl | |
| 3.688 | 3,5-dimethoxyphenyl | CN | |
| 3.689 | 3,5-dimethoxyphenyl | vinyl | |
| 3.690 | 3,5-dimethoxyphenyl | fluoromethyl | |
| 3.691 | 3,5-dimethoxyphenyl | hydroxymethyl | |
| 3.692 | 3,5-dimethoxyphenyl | ethynyl | |
| 3.693 | 3-ethoxy-5-methoxyphenyl | methyl | |

TABLE 3-continued

Inventive compounds of the general formula (I) in which W* is CN, $R^1$ and $R^2$ are each hydrogen, and aryl is the radical.

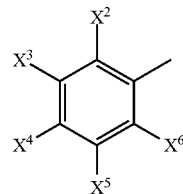

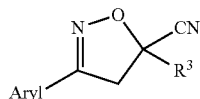

| No. | Aryl | $R^3$ | Physical data |
|---|---|---|---|
| 3.694 | 3-n-propoxy-5-methoxyphenyl | methyl | |
| 3.695 | 3-isobutoxy-5-methoxyphenyl | methyl | |
| 3.696 | 3-difluoromethoxy-5-methoxyphenyl | methyl | |
| 3.697 | 3-trifluoromethoxy-5-methoxyphenyl | methyl | |
| 3.698 | 3-nitro-5-methoxyphenyl | methyl | |
| 3.699 | 3-acetoxy-5-methoxyphenyl | methyl | |
| 3.700 | 3-methylsulfanyl-5-methoxyphenyl | methyl | |
| 3.701 | 3,5-diethoxyphenyl | methyl | |
| 3.702 | 3-n-propoxy-5-ethoxyphenyl | methyl | |
| 3.703 | 3-n-butoxy-5-ethoxyphenyl | methyl | |
| 3.704 | 3-isobutoxy-5-ethoxyphenyl | methyl | |
| 3.705 | 3-difluoromethoxy-5-ethoxyphenyl | methyl | |
| 3.706 | 3-trifluoromethoxy-5-ethoxyphenyl | methyl | |
| 3.707 | 3-nitro-5-ethoxyphenyl | methyl | |
| 3.708 | 3-acetoxy-5-ethoxyphenyl | methyl | |
| 3.709 | 3-methylsulfanyl-5-ethoxyphenyl | methyl | |
| 3.710 | 3,5-di(isopropoxy)phenyl | methyl | |
| 3.711 | 3-isobutoxy-5-isopropoxyphenyl | methyl | |
| 3.712 | 3-difluoromethoxy-5-isopropoxyphenyl | methyl | |
| 3.713 | 3-trifluoromethoxy-5-isopropoxyphenyl | methyl | |
| 3.714 | 3-nitro-5-isopropoxyphenyl | methyl | |
| 3.715 | 3-acetoxy-5-isopropoxyphenyl | methyl | |
| 3.716 | 3-methylsulfanyl-5-isopropoxyphenyl | methyl | |
| 3.717 | 3,5-di(trifluoro-methoxy)phenyl | methyl | |
| 3.718 | 3-nitro-5-trifluoro-methoxyphenyl | methyl | |
| 3.719 | 3-methylsulfany1-5-trifluoromethoxy-phenyl | methyl | |
| 3.720 | 3,5-bis(difluoro-methoxy)phenyl | methyl | |
| 3.721 | 3-nitro-5-difluoro-methoxyphenyl | methyl | |
| 3.722 | 3-acetoxy-5-difluoromethoxyphenyl | methyl | |
| 3.723 | 3-methylsulfanyl-5-acetoxyphenyl | methyl | |
| 3.724 | 3-acetoxy-5-nitrophenyl | methyl | |
| 3.725 | 3-methylsulfanyl-5-nitrophenyl | methyl | |
| 3.726 | 3,5-di(methylsulfanyl)phenyl | methyl | |
| 3.727 | 3,4-difluorophenyl | methyl | |
| 3.728 | 3,4-difluorophenyl | ethyl | |
| 3.729 | 3,4-difluorophenyl | CN | |
| 3.730 | 3,4-difluorophenyl | vinyl | |
| 3.731 | 3,4-difluorophenyl | fluoromethyl | |
| 3.732 | 3,4-difluorophenyl | hydroxymethyl | |
| 3.733 | 3,4-difluorophenyl | ethynyl | |
| 3.734 | 3-chloro-4-fluorophenyl | methyl | |
| 3.735 | 3-bromo-4-fluorophenyl | methyl | |
| 3.736 | 3-methyl-4-fluorophenyl | methyl | |
| 3.737 | 3-methyl-4-fluorophenyl | ethyl | |
| 3.738 | 3-methyl-4-fluorophenyl | CN | |
| 3.739 | 3-methyl-4-fluorophenyl | vinyl | |
| 3.740 | 3-methyl-4-fluorophenyl | fluoromethyl | |
| 3.741 | 3-methyl-4-fluorophenyl | hydroxymethyl | |
| 3.742 | 3-methyl-4-fluorophenyl | ethynyl | |
| 3.743 | 3-ethyl-4-fluorophenyl | methyl | |
| 3.744 | 3-cyclopropyl-4-fluorophenyl | methyl | |
| 3.745 | 3-cyano-4-fluorophenyl | methyl | |
| 3.746 | 3-methoxy-4-fluorophenyl | methyl | |
| 3.747 | 3-ethoxy-4-fluorophenyl | methyl | |
| 3.748 | 3-trifluoromethoxy-4-fluorophenyl | methyl | |
| 3.749 | 3-nitro-4-fluorophenyl | methyl | |
| 3.750 | 3-fluoro-4-chlorophenyl | methyl | |

TABLE 3-continued

Inventive compounds of the general formula (I) in which W* is CN, $R^1$ and $R^2$ are each hydrogen, and aryl is the radical.

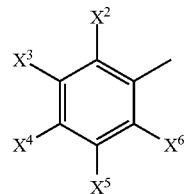

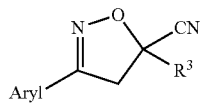

| No. | Aryl | $R^3$ | Physical data |
|---|---|---|---|
| 3.751 | 3,4-dichlorophenyl | methyl | [CDCl$_3$] 1.92 (s, 3H), 3.38 (d, 1H), 3.82 (d, 1H), 7.5 (m, 2H), 7.7 (d, 1H). |
| 3.752 | 3,4-dichlorophenyl | tert-butyl | [DMSO] 1.10 (s, 9H); 4.2 (dd, 2H); 7.75 (m, 2H); 7.95 (d, 1H). |
| 3.753 | 3-,4-dichlorophenyl | isopropyl | [DMSO] 1.09 (2d; 6H); 2.28 (m, 1H); 3.85 (d, 1H); 4.10 (d, 1H); 7.72 (dd, 1H); 7.78 (d, 1H); 7.93 (d, 1H). |
| 3.754 | 3-cyclopropyl-4-chlorophenyl | methyl | |
| 3.755 | 3-cyano-4-chlorophenyl | methyl | |
| 3.756 | 3-trifluoromethyl-4-chlorophenyl | methyl | |
| 3.757 | 3-methoxy-4-chlorophenyl | methyl | |
| 3.758 | 3-ethoxy-4-chlorophenyl | methyl | |
| 3.759 | 3-trifluoromethoxy-4-chlorophenyl | methyl | |
| 3.760 | 3-nitro-4-chlorophenyl | methyl | |
| 3.761 | 3-fluoro-4-bromophenyl | methyl | |
| 3.762 | 3-chloro-4-bromophenyl | methyl | |
| 3.763 | 3,4-dibromophenyl | methyl | |
| 3.764 | 3-methyl-4-bromophenyl | methyl | |
| 3.765 | 3-cyclopropyl-4-bromophenyl | methyl | |
| 3.766 | 3-cyano-4-bromophenyl | methyl | |
| 3.767 | 3-trifluoromethyl-4-bromophenyl | methyl | |
| 3.768 | 3-methoxy-4-phenyl | methyl | |
| 3.769 | 3-ethoxy-4-bromophenyl | methyl | |
| 3.770 | 3-trifluoromethoxy-4-bromophenyl | methyl | |
| 3.771 | 3-nitro-4-bromophenyl | methyl | |
| 3.772 | 3-fluoro-4-iodophenyl | methyl | |
| 3.773 | 3-chloro-4-iodophenyl | methyl | |
| 3.774 | 3-bromo-4-iodophenyl | methyl | |
| 3.775 | 3-methyl-4-iodophenyl | methyl | |
| 3.776 | 3-cyclopropyl-4-iodophenyl | methyl | |
| 3.777 | 3-cyano-4-iodophenyl | methyl | |
| 3.778 | 3-trifluoromethyl-4-iodophenyl | methyl | |
| 3.779 | 3-methoxy-4-iodophenyl | methyl | |
| 3.780 | 3-ethoxy-4-iodophenyl | methyl | |
| 3.781 | 3-trifluoromethoxy-4-iodophenyl | methyl | |
| 3.782 | 3-nitro-4-iodophenyl | methyl | |
| 3.783 | 3-fluoro-4-methylphenyl | methyl | |
| 3.784 | 3-chloro-4-methylphenyl | methyl | |
| 3.785 | 3-chloro-4-methylphenyl | ethyl | |
| 3.786 | 3-chloro-4-methylphenyl | CN | |
| 3.787 | 3-chloro-4-methylphenyl | vinyl | |
| 3.788 | 3-chloro-4-methylphenyl | fluoromethyl | |
| 3.789 | 3-chloro-4-methylphenyl | hydroxymethyl | |
| 3.790 | 3-chloro-4-methylphenyl | ethynyl | |
| 3.791 | 3-bromo-4-methylphenyl | methyl | |
| 3.792 | 3,4-dimethylphenyl | methyl | |
| 3.793 | 3-cyclopropyl-4-methylphenyl | methyl | |
| 3.794 | 3-cyano-4-methylphenyl | methyl | |
| 3.795 | 3-trifluoromethyl-4-methylphenyl | methyl | |
| 3.796 | 3-methoxy-4-methylphenyl | methyl | |
| 3.797 | 3-ethoxy-4-methylphenyl | methyl | |
| 3.798 | 3-trifluoromethoxy-4-methylphenyl | methyl | |
| 3.799 | 3-nitro-4-methylphenyl | methyl | |

TABLE 3-continued

Inventive compounds of the general formula (I) in which W* is CN, $R^1$ and $R^2$ are each hydrogen, and aryl is the radical.

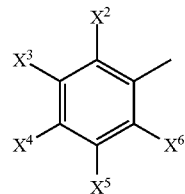

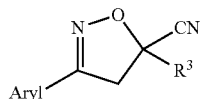

| No. | Aryl | $R^3$ | Physical data |
|---|---|---|---|
| 3.800 | 3-fluoro-4-ethylphenyl | methyl | |
| 3.801 | 3-chloro-4-ethylphenyl | methyl | |
| 3.802 | 3-bromo-4-ethylphenyl | methyl | |
| 3.803 | 3-methyl-4-ethylphenyl | methyl | |
| 3.804 | 3,4-diethylphenyl | methyl | |
| 3.805 | 3-cyclopropyl-4-ethylphenyl | methyl | |
| 3.806 | 3-cyano-4-ethylphenyl | methyl | |
| 3.807 | 3-trifluoromethyl-4-ethylphenyl | methyl | |
| 3.808 | 3-methoxy-4-ethylphenyl | methyl | |
| 3.809 | 3-ethoxy-4-ethylphenyl | methyl | |
| 3.810 | 3-trifluoromethoxy-4-ethylphenyl | methyl | |
| 3.811 | 3-nitro-4-ethylphenyl | methyl | |
| 3.812 | 3-fluoro-4-propylphenyl | methyl | |
| 3.813 | 3-chloro-4-propylphenyl | methyl | |
| 3.814 | 3-bromo-4-propylphenyl | methyl | |
| 3.815 | 3-methyl-4-propylphenyl | methyl | |
| 3.816 | 3-cyclopropyl-4-propylphenyl | methyl | |
| 3.817 | 3-cyano-4-propylphenyl | methyl | |
| 3.818 | 3-trifluoromethyl-4-propylphenyl | methyl | |
| 3.819 | 3-methoxy-4-propylphenyl | methyl | |
| 3.820 | 3-ethoxy-4-propylphenyl | methyl | |
| 3.821 | 3-trifluoromethoxy-4-propylphenyl | methyl | |
| 3.822 | 3-nitro-4-propylphenyl | methyl | |
| 3.823 | 3-fluoro-4-isopropylphenyl | methyl | |
| 3.824 | 3-chloro-4-isopropylphenyl | methyl | |
| 3.825 | 3-bromo-4- isopropylphenyl | methyl | |
| 3.826 | 3-methyl-4-isopropylphenyl | methyl | |
| 3.827 | 3-cyclopropyl-4-isopropylphenyl | methyl | |
| 3.828 | 3-cyano-4-isopropylphenyl | methyl | |
| 3.829 | 3-trifluoromethyl-4-isopropylphenyl | methyl | |
| 3.830 | 3- methoxy-4-isopropylphenyl | methyl | |
| 3.831 | 3-ethoxy-4-isopropylphenyl | methyl | |
| 3.832 | 3-trifluoromethoxy-4-isopropylphenyl | methyl | |
| 3.833 | 3-nitro-4-isopropylphenyl | methyl | |
| 3.834 | 3-fluoro-4-tert-butylphenyl | methyl | |
| 3.835 | 3-fluoro-4-tert-butylphenyl | ethyl | |
| 3.836 | 3-fluoro-4-tert-butylphenyl | CN | |
| 3.837 | 3-fluoro-4-tert-butylphenyl | vinyl | |
| 3.838 | 3-fluoro-4-tert-butylphenyl | fluoromethyl | |
| 3.839 | 3-fluoro-4-tert-butylphenyl | hydroxymethyl | |
| 3.840 | 3-fluoro-4-tert-butylphenyl | ethynyl | |
| 3.841 | 3-chloro-4-tert-butylphenyl | methyl | |
| 3.842 | 3-bromo-4-tert-butylphenyl | methyl | |
| 3.843 | 3-methyl-4-tert-butylphenyl | methyl | |
| 3.844 | 3-ethyl-4-tert-butylphenyl | methyl | |
| 3.845 | 3-cyclopropyl-4-tert-butylphenyl | methyl | |
| 3.846 | 3-cyano-4-tert-butylphenyl | methyl | |
| 3.847 | 3-trifluoromethyl-4-tert-butylphenyl | methyl | |
| 3.848 | 3-methoxy-4-tert-butylphenyl | methyl | |
| 3.849 | 3-ethoxy-4-tert-butylphenyl | methyl | |
| 3.850 | 3-trifluoromethoxy-4-tert-butylphenyl | methyl | |
| 3.851 | 3-nitro-4-tert-butylphenyl | methyl | |
| 3.852 | 3-fluoro-4-cyclopropylphenyl | methyl | |
| 3.853 | 3-chloro-4-cyclopropylphenyl | methyl | |
| 3.854 | 3-bromo-4-cyclopropylphenyl | methyl | |
| 3.855 | 3-methyl-4-cyclopropylphenyl | methyl | |
| 3.856 | 3-cyclopropyl-4-cyclopropylphenyl | methyl | |
| 3.857 | 3-cyano-4-cyclopropylphenyl | methyl | |

TABLE 3-continued

Inventive compounds of the general formula (I) in which W* is CN, $R^1$ and $R^2$ are each hydrogen, and aryl is the radical.

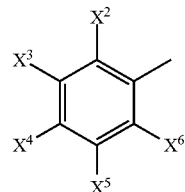

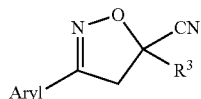

| No. | Aryl | $R^3$ | Physical data |
|---|---|---|---|
| 3.858 | 3-trifluoromethyl-4-cyclopropylphenyl | methyl | |
| 3.859 | 3-methoxy-4-cyclopropylphenyl | methyl | |
| 3.860 | 3-ethoxy-4-cyclopropylphenyl | methyl | |
| 3.861 | 3-trifluoromethoxy-4-cyclopropylphenyl | methyl | |
| 3.862 | 3-fluoro-4-methoxycarbonyl-phenyl | methyl | |
| 3.863 | 3-chloro-4-methoxycarbonylphenyl | methyl | |
| 3.864 | 3-bromo-4-methoxycarbonylphenyl | methyl | |
| 3.865 | 3-methyl-4-methoxycarbonylphenyl | methyl | |
| 3.866 | 3-cyclopropyl-4-methoxycarbonylphenyl | methyl | |
| 3.867 | 3-cyano-4-methoxycarbonylphenyl | methyl | |
| 3.868 | 3-trifluoromethyl-4-methoxycarbonyl-phenyl | methyl | |
| 3.869 | 3-methoxy-4-methoxycarbonylphenyl | methyl | |
| 3.870 | 3-ethoxy-4-methoxycarbonylphenyl | methyl | |
| 3.871 | 3-nitro-4-methoxycarbonylphenyl | methyl | |
| 3.872 | 3-fluoro-4-cyanophenyl | methyl | |
| 3.873 | 3-chloro-4-cyanophenyl | methyl | |
| 3.874 | 3-bromo-4-cyanophenyl | methyl | |
| 3.875 | 3-methyl-4-cyanophenyl | methyl | |
| 3.876 | 3-cyclopropyl-4-cyanophenyl | methyl | |
| 3.877 | 3-cyano-4-cyanophenyl | methyl | |
| 3.878 | 3-trifluoromethyl-4-cyanophenyl | methyl | |
| 3.879 | 3-methoxy-4-cyanophenyl | methyl | |
| 3.880 | 3-ethoxy-4-cyanophenyl | methyl | |
| 3.881 | 3-trifluoromethoxy-4-cyanophenyl | methyl | |
| 3.882 | 3-nitro-4-cyanophenyl | methyl | |
| 3.883 | 3-fluoro-4-methoxyphenyl | methyl | |
| 3.884 | 3-chloro-4-methoxyphenyl | methyl | |
| 3.885 | 3-bromo-4-methoxyphenyl | methyl | |
| 3.886 | 3-methyl-4-methoxyphenyl | methyl | |
| 3.887 | 3-cyclopropyl-4-methoxyphenyl | methyl | |
| 3.888 | 3-cyano-4-methoxyphenyl | methyl | |
| 3.889 | 3-trifluoromethyl-4-methoxyphenyl | methyl | |
| 3.890 | 3,4-dimethoxyphenyl | methyl | |
| 3.891 | 3-ethoxy-4-methoxyphenyl | methyl | |
| 3.892 | 3-trifluoromethoxy-4-methoxyphenyl | methyl | |
| 3.893 | 3-nitro-4-methoxyphenyl | methyl | |
| 3.894 | 3-fluoro-4-ethoxyphenyl | methyl | |
| 3.895 | 3-chloro-4-ethoxyphenyl | methyl | |
| 3.896 | 3-bromo-4-ethoxyphenyl | methyl | |
| 3.897 | 3-methyl-4-ethoxyphenyl | methyl | |
| 3.898 | 3-cyclopropyl-4-ethoxyphenyl | methyl | |
| 3.899 | 3-cyano-4-ethoxyphenyl | methyl | |
| 3.900 | 3-trifluoromethyl-4-ethoxyphenyl | methyl | |
| 3.901 | 3-methoxy-4-ethoxyphenyl | methyl | |
| 3.902 | 2,4-diethoxyphenyl | methyl | |
| 3.903 | 3-trifluoromethoxy-4-ethoxyphenyl | methyl | |
| 3.904 | 3-nitro-4-ethoxyphenyl | methyl | |
| 3.905 | 3-fluoro-4-isopropoxyphenyl | methyl | |
| 3.906 | 3-chloro-4-isopropoxyphenyl | methyl | |
| 3.907 | 3-bromo-4-isopropoxyphenyl | methyl | |
| 3.908 | 3-methyl-4-isopropoxyphenyl | methyl | |
| 3.909 | 3-cyclopropyl-4-isopropoxyphenyl | methyl | |
| 3.910 | 3-cyano-4-isopropoxyphenyl | methyl | |
| 3.911 | 3-trifluoromethyl-4-isopropoxyphenyl | methyl | |
| 3.912 | 3-methoxy-4-isopropoxyphenyl | methyl | |
| 3.913 | 3-ethoxy-4-isopropoxyphenyl | methyl | |
| 3.914 | 3-trifluoromethoxy-4-isopropoxyphenyl | methyl | |

TABLE 3-continued

Inventive compounds of the general formula (I) in which W* is CN, $R^1$ and $R^2$ are each hydrogen, and aryl is the radical.

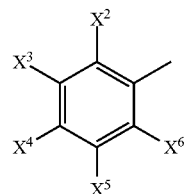

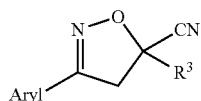

| No. | Aryl | $R^3$ | Physical data |
|---|---|---|---|
| 3.915 | 3-nitro-4-isopropoxyphenyl | methyl | |
| 3.916 | 3-fluoro-4-trifluoromethoxyphenyl | methyl | |
| 3.917 | 3-chloro-4-trifluoromethoxyphenyl | methyl | |
| 3.918 | 3-bromo-4-trifluoromethoxyphenyl | methyl | |
| 3.919 | 3-methyl-4-trifluoromethoxyphenyl | methyl | |
| 3.920 | 3-ethyl-4-trifluoromethoxyphenyl | methyl | |
| 3.921 | 3-cyclopropyl-4-trifluoromethoxyphenyl | methyl | |
| 3.922 | 3-cyano-4-trifluoromethoxyphenyl | methyl | |
| 3.923 | 3-trifluoromethyl-4-trifluoromethoxy-phenyl | methyl | |
| 3.924 | 3-methoxy-4-trifluoromethoxyphenyl | methyl | |
| 3.925 | 3-ethoxy-4-trifluoro-methoxyphenyl | methyl | |
| 3.926 | 3,4-bis(trifluoro-methoxy)phenyl | methyl | |
| 3.927 | 3-nitro-4-trifluoro- methoxyphenyl | methyl | |
| 3.928 | 3-fluoro-4-difluoromethoxyphenyl | methyl | |
| 3.929 | 3-chloro-4-difluoromethoxyphenyl | methyl | |
| 3.930 | 3-bromo-4-difluoromethoxyphenyl | methyl | |
| 3.931 | 3-methyl-4-difluoromethoxyphenyl | methyl | |
| 3.932 | 3-cyclopropyl-4-difluoromethoxyphenyl | methyl | |
| 3.933 | 3-cyano-4-difluoromethoxyphenyl | methyl | |
| 3.934 | 3-trifluoromethyl-4-difluoromethoxyphenyl | methyl | |
| 3.935 | 3-methoxy-4-difluoromethoxyphenyl | methyl | |
| 3.936 | 3-ethoxy-4-difluoromethoxyphenyl | methyl | |
| 3.937 | 3-nitro-4-difluoromethoxyphenyl | methyl | |
| 3.938 | 3-fluoro-4-nitrophenyl | methyl | |
| 3.939 | 3-chloro-4-nitrophenyl | methyl | |
| 3.940 | 3-bromo-4-nitrophenyl | methyl | |
| 3.941 | 3-methyl-4-nitrophenyl | methyl | |
| 3.942 | 3-cyclopropyl-4-nitrophenyl | methyl | |
| 3.943 | 3-cyano-4-nitrophenyl | methyl | |
| 3.944 | 3-trifluoromethyl-4-nitrophenyl | methyl | |
| 3.945 | 3-methoxy-4-nitrophenyl | methyl | |
| 3.946 | 3-ethoxy-4-nitrophenyl | methyl | |
| 3.947 | 3-trifluoromethoxy-4-nitrophenyl | methyl | |
| 3.948 | 3-fluoro-4-methylsulfanylphenyl | methyl | |
| 3.949 | 3-chloro-4-methylsulfanylphenyl | methyl | |
| 3.950 | 3-bromo-4-methylsulfanylphenyl | methyl | |
| 3.951 | 3-methyl-4-methylsulfanylphenyl | methyl | |
| 3.952 | 3-cyclopropyl-4-methylsulfanylphenyl | methyl | |
| 3.953 | 3-cyano-4-methylsulfanylphenyl | methyl | |
| 3.954 | 3-trifluoromethyl-4-methylsulfanylphenyl | methyl | |
| 3.955 | 3-methoxy-4-methylsulfanylphenyl | methyl | |
| 3.956 | 3-ethoxy-4-methylsulfanylphenyl | methyl | |
| 3.957 | 3-trifluoromethoxy-4-methylsulfanylphenyl | methyl | |
| 3.958 | 3-nitro-4-methylsulfanylphenyl | methyl | |
| 3.959 | 3,6-difluorophenyl | methyl | |
| 3.960 | 3,6-difluorophenyl | ethyl | |
| 3.961 | 3,6-difluorophenyl | CN | |
| 3.962 | 3,6-difluorophenyl | vinyl | |
| 3.963 | 3,6-difluorophenyl | fluoromethyl | |
| 3.964 | 3,6-difluorophenyl | hydroxymethyl | |
| 3.965 | 3,6-difluorophenyl | ethynyl | |
| 3.966 | 3-chloro-6-fluorophenyl | methyl | |
| 3.967 | 3-bromo-6-fluorophenyl | methyl | |
| 3.968 | 3-methyl-6-fluorophenyl | methyl | |
| 3.969 | 3-cyclopropyl-6-fluorophenyl | methyl | |
| 3.970 | 3-cyano-6-fluorophenyl | methyl | |
| 3.971 | 3-methoxy-6-fluorophenyl | methyl | |

TABLE 3-continued

Inventive compounds of the general formula (I) in which W* is CN, $R^1$ and $R^2$ are each hydrogen, and aryl is the radical.

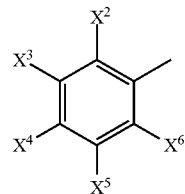

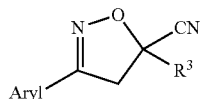

| No. | Aryl | $R^3$ | Physical data |
|---|---|---|---|
| 3.972 | 3-ethoxy-6-fluorophenyl | methyl | |
| 3.973 | 3-trifluoromethoxy-6-fluorophenyl | methyl | |
| 3.974 | 3-nitro-6-fluorophenyl | methyl | |
| 3.975 | 3-fluoro-6-chlorophenyl | methyl | |
| 3.976 | 3,6-dichlorophenyl | methyl | |
| 3.977 | 3-bromo-6-chlorophenyl | methyl | |
| 3.978 | 3-methyl-6-chlorophenyl | methyl | |
| 3.979 | 3-cyclopropyl-6-chlorophenyl | methyl | |
| 3.980 | 3-cyano-6-chlorophenyl | methyl | |
| 3.981 | 3-trifluoromethyl-6-chlorophenyl | methyl | |
| 3.982 | 3-methoxy-6-chlorophenyl | methyl | |
| 3.983 | 3-ethoxy-6-chlorophenyl | methyl | |
| 3.984 | 3-trifluoromethoxy-6-chlorophenyl | methyl | |
| 3.985 | 3-nitro-6-chlorophenyl | methyl | |
| 3.986 | 3-fluoro-6-bromophenyl | methyl | |
| 3.987 | 3-chloro-6-bromophenyl | methyl | |
| 3.988 | 3,6-dibromophenyl | methyl | |
| 3.989 | 3-methyl-6-bromophenyl | methyl | |
| 3.990 | 3-ethyl-6-bromophenyl | methyl | |
| 3.991 | 3-cyclopropyl-6-bromophenyl | methyl | |
| 3.992 | 3-cyano-6-bromophenyl | methyl | |
| 3.993 | 3-trifluoromethyl-6-bromophenyl | methyl | |
| 3.994 | 3-methoxy-6-phenyl | methyl | |
| 3.995 | 3-ethoxy-6-bromophenyl | methyl | |
| 3.996 | 3-trifluoromethoxy-6-bromophenyl | methyl | |
| 3.997 | 3-nitro-6-bromophenyl | methyl | |
| 3.998 | 3-fluoro-6-iodophenyl | methyl | |
| 3.999 | 3-chloro-6-iodophenyl | methyl | |
| 3.1000 | 3-bromo-6-iodophenyl | methyl | |
| 3.1001 | 3-methyl-6-iodophenyl | methyl | |
| 3.1002 | 3-cyclopropyl-6-iodophenyl | methyl | |
| 3.1003 | 3-cyano-6-iodophenyl | methyl | |
| 3.1004 | 3-trifluoromethyl-6-iodophenyl | methyl | |
| 3.1005 | 3-methoxy-6-iodophenyl | methyl | |
| 3.1006 | 3-ethoxy-6-iodophenyl | methyl | |
| 3.1007 | 3-trifluoromethoxy-6-iodophenyl | methyl | |
| 3.1008 | 3-nitro-6-iodophenyl | methyl | |
| 3.1009 | 3-fluoro-6-methylphenyl | methyl | |
| 3.1010 | 3-chloro-6-methylphenyl | methyl | |
| 3.1011 | 3-bromo-6-methylphenyl | methyl | |
| 3.1012 | 3,6-dimethylphenyl | methyl | |
| 3.1013 | 3,6-dimethylphenyl | ethyl | |
| 3.1014 | 3,6-dimethylphenyl | CN | |
| 3.1015 | 3,6-dimethylphenyl | vinyl | |
| 3.1016 | 3,6-dimethylphenyl | fluoromethyl | |
| 3.1017 | 3,6-dimethylphenyl | hydroxymethyl | |
| 3.1018 | 3,6-dimethylphenyl | ethynyl | |
| 3.1019 | 3-cyclopropyl-6-methylphenyl | methyl | |
| 3.1020 | 3-cyano-6-methylphenyl | methyl | |
| 3.1021 | 3-trifluoromethyl-6-methylphenyl | methyl | |
| 3.1022 | 3-methoxy-6-methylphenyl | methyl | |
| 3.1023 | 3-ethoxy-6-methylphenyl | methyl | |
| 3.1024 | 3-trifluoromethoxy-6-methylphenyl | methyl | |
| 3.1025 | 3-nitro-6-methylphenyl | methyl | |
| 3.1026 | 3-fluoro-6-ethylphenyl | methyl | |
| 3.1027 | 3-chloro-6-ethylphenyl | methyl | |
| 3.1028 | 3-bromo-6-ethylphenyl | methyl | |
| 3.1029 | 3-methyl-6-ethylphenyl | methyl | |

TABLE 3-continued

Inventive compounds of the general formula (I) in which W* is CN, $R^1$ and $R^2$ are each hydrogen, and aryl is the radical.

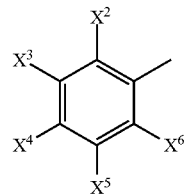

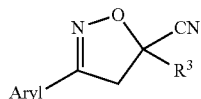

| No. | Aryl | $R^3$ | Physical data |
|---|---|---|---|
| 3.1030 | 3,6-diethylphenyl | methyl | |
| 3.1031 | 3-cyclopropyl-6-ethylphenyl | methyl | |
| 3.1032 | 3-cyano-6-ethylphenyl | methyl | |
| 3.1033 | 3-trifluoromethyl-6-ethylphenyl | methyl | |
| 3.1034 | 3-methoxy-6-ethylphenyl | methyl | |
| 3.1035 | 3-ethoxy-6-ethylphenyl | methyl | |
| 3.1036 | 3-trifluoromethoxy-6-ethylphenyl | methyl | |
| 3.1037 | 3-nitro-6-ethylphenyl | methyl | |
| 3.1038 | 3-fluoro-6-isopropylphenyl | methyl | |
| 3.1039 | 3-chloro-6-isopropylphenyl | methyl | |
| 3.1040 | 3-bromo-6-isopropylphenyl | methyl | |
| 3.1041 | 3-methyl-6-isopropylphenyl | methyl | |
| 3.1042 | 3-cyclopropyl-6-isopropylphenyl | methyl | |
| 3.1043 | 3-cyano-6-isopropylphenyl | methyl | |
| 3.1044 | 3-trifluoromethyl-6-isopropylphenyl | methyl | |
| 3.1045 | 3-methoxy-6-isopropylphenyl | methyl | |
| 3.1046 | 3-ethoxy-6-isopropylphenyl | methyl | |
| 3.1047 | 3-trifluoromethoxy-6-isopropylphenyl | methyl | |
| 3.1048 | 3-nitro-6-isopropylphenyl | methyl | |
| 3.1049 | 3-fluoro-6-tert-butylphenyl | methyl | |
| 3.1050 | 3-chloro-6-tert-butylphenyl | methyl | |
| 3.1051 | 3-bromo-6-tert-butylphenyl | methyl | |
| 3.1052 | 3-methyl-6-tert-butylphenyl | methyl | |
| 3.1053 | 3-cyclopropyl-6-tert-butylphenyl | methyl | |
| 3.1054 | 3-cyano-6-tert-butylphenyl | methyl | |
| 3.1055 | 3-trifluoromethyl-6-tert-butylphenyl | methyl | |
| 3.1056 | 3-methoxy-6-tert-butylphenyl | methyl | |
| 3.1057 | 3-ethoxy-6-tert-butylphenyl | methyl | |
| 3.1058 | 3-trifluoromethoxy-6-tert-butylphenyl | methyl | |
| 3.1059 | 3-nitro-6-tert-butylphenyl | methyl | |
| 3.1060 | 3-fluoro-6-cyclopropylphenyl | methyl | |
| 3.1061 | 3-chloro-6-cyclopropylphenyl | methyl | |
| 3.1062 | 3-bromo-6-cyclopropylphenyl | methyl | |
| 3.1063 | 3-methyl-6-cyclopropylphenyl | methyl | |
| 3.1064 | 3-ethyl-6-cyclopropylphenyl | methyl | |
| 3.1065 | 3-cyclopropyl-6-cyclopropylphenyl | methyl | |
| 3.1066 | 3-cyano-6-cyclopropylphenyl | methyl | |
| 3.1067 | 3-trifluoromethyl-6-cyclopropylphenyl | methyl | |
| 3.1068 | 3-methoxy-6-cyclopropylphenyl | methyl | |
| 3.1069 | 3-ethoxy-6-cyclopropylphenyl | methyl | |
| 3.1070 | 3-trifluoromethoxy-6-cyclopropylphenyl | methyl | |
| 3.1071 | 3-fluoro-6-methoxycarbonylphenyl | methyl | |
| 3.1072 | 3-chloro-6-methoxycarbonylphenyl | methyl | |
| 3.1073 | 3-bromo-6-methoxycarbonylphenyl | methyl | |
| 3.1074 | 3-methyl-6-methoxycarbonylphenyl | methyl | |
| 3.1075 | 3-cyclopropyl-6-methoxycarbonylphenyl | methyl | |
| 3.1077 | 3-trifluoromethyl-6-methoxycarbonyl-phenyl | methyl | |
| 3.1076 | 3-cyano-6-methoxycarbonylphenyl | methyl | |
| 3.1078 | 3-methoxy-6-methoxycarbonylphenyl | methyl | |
| 3.1079 | 3-ethoxy-6-methoxycarbonylphenyl | methyl | |
| 3.1080 | 3-trifluoromethoxy-6-methoxycarbonyl-phenyl | methyl | |
| 3.1081 | 3-nitro-6-methoxycarbonylphenyl | methyl | |
| 3.1082 | 3-fluoro-6-cyanophenyl | methyl | |
| 3.1083 | 3-chloro-6-cyanophenyl | methyl | |
| 3.1084 | 3-bromo-6-cyanophenyl | methyl | |
| 3.1085 | 3-methyl-6-cyanophenyl | methyl | |

TABLE 3-continued

Inventive compounds of the general formula (I) in which W* is CN, $R^1$ and $R^2$ are each hydrogen, and aryl is the radical.

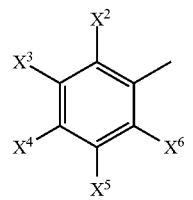

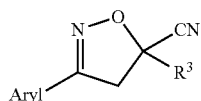

| No. | Aryl | $R^3$ | Physical data |
|---|---|---|---|
| 3.1086 | 3-cyclopropyl-6-cyanophenyl | methyl | |
| 3.1087 | 3-cyano-6-cyanophenyl | methyl | |
| 3.1088 | 3-trifluoromethyl-6-cyanophenyl | methyl | |
| 3.1089 | 3-methoxy-6-cyanophenyl | methyl | |
| 3.1090 | 3-ethoxy-6-cyanophenyl | methyl | |
| 3.1091 | 3-trifluoromethoxy-6-cyanophenyl | methyl | |
| 3.1092 | 3-nitro-6-cyanophenyl | methyl | |
| 3.1093 | 3-fluoro-6-methoxyphenyl | methyl | |
| 3.1094 | 3-chloro-6-methoxyphenyl | methyl | |
| 3.1095 | 3-bromo-6-methoxyphenyl | methyl | |
| 3.1096 | 3-methyl-6-methoxyphenyl | methyl | |
| 3.1097 | 3-cyclopropyl-6-methoxyphenyl | methyl | |
| 3.1098 | 3-cyano-6-methoxyphenyl | methyl | |
| 3.1099 | 3-trifluoromethyl-6-methoxyphenyl | methyl | |
| 3.1100 | 3,6-dimethoxy--phenyl | methyl | |
| 3.1101 | 3-ethoxy-6-methoxyphenyl | methyl | |
| 3.1102 | 3-trifluoromethoxy-6-methoxyphenyl | methyl | |
| 3.1103 | 3- nitro-6-methoxyphenyl | methyl | |
| 3.1104 | 3-fluoro-6-ethoxyphenyl | methyl | |
| 3.1105 | 3-chloro-6-ethoxyphenyl | methyl | |
| 3.1106 | 3-bromo-6-ethoxyphenyl | methyl | |
| 3.1107 | 3-methyl-6-ethoxyphenyl | methyl | |
| 3.1108 | 3-cyclopropyl-6-ethoxyphenyl | methyl | |
| 3.1109 | 3-cyano-6-ethoxyphenyl | methyl | |
| 3.1110 | 3-trifluoromethyl-6-ethoxyphenyl | methyl | |
| 3.1111 | 3-methoxy-6-ethoxyphenyl | methyl | |
| 3.1112 | 2,6-diethoxyphenyl | methyl | |
| 3.1113 | 3-trifluoromethoxy-6-ethoxyphenyl | methyl | |
| 3.1114 | 3-nitro-6-ethoxyphenyl | methyl | |
| 3.1115 | 3-fluoro-6-isopropoxyphenyl | methyl | |
| 3.1116 | 3-chloro-6-isopropoxyphenyl | methyl | |
| 3.1117 | 3-bromo-6-isopropoxyphenyl | methyl | |
| 3.1118 | 3-methy1-6-isopropoxyphenyl | methyl | |
| 3.1119 | 3-cyclopropyl-6-isopropoxyphenyl | methyl | |
| 3.1120 | 3-cyano-6-isopropoxyphenyl | methyl | |
| 3.1121 | 3-trifluoromethyl-6-isopropoxyphenyl | methyl | |
| 3.1122 | 3-methoxy-6-isopropoxyphenyl | methyl | |
| 3.1123 | 3-ethoxy-6-isopropoxyphenyl | methyl | |
| 3.1124 | 3-trifluoromethoxy-6-isopropoxyphenyl | methyl | |
| 3.1125 | 3-nitro-6-isopropoxyphenyl | methyl | |
| 3.1126 | 3-fluoro-6-trifluoromethoxyphenyl | methyl | |
| 3.1127 | 3-chloro-6-trifluoromethoxyphenyl | methyl | |
| 3.1128 | 3-bromo-6-trifl uoromethoxyphenyl | methyl | |
| 3.1129 | 3-methyl-6-trifluoromethoxyphenyl | methyl | |
| 3.1130 | 3-ethyl-6-trifluoromethoxyphenyl | methyl | |
| 3.1131 | 3-cyclopropyl-6-trifluoromethoxyphenyl | methyl | |
| 3.1132 | 3-cyano-6-trifluoromethoxyphenyl | methyl | |
| 3.1133 | 3-trifluoromethyl-6-trifluoromethoxy-phenyl | methyl | |
| 3.1134 | 3-methoxy-6-trifluoromethoxyphenyl | methyl | |
| 3.1135 | 3-ethoxy-6-trifluoromethoxyphenyl | methyl | |
| 3.1136 | 3,6-bis(trifluoro-methoxy)phenyl | methyl | |
| 3.1137 | 3-nitro-6-trifluoromethoxyphenyl | methyl | |
| 3.1138 | 3-fluoro-6-difluoromethoxyphenyl | methyl | |
| 3.1139 | 3-chloro-6-difluoromethoxyphenyl | methyl | |
| 3.1140 | 3-bromo-6-difluoromethoxyphenyl | methyl | |
| 3.1141 | 3-methyl-6-difluoromethoxyphenyl | methyl | |
| 3.1142 | 3-cyclopropyl-6-difluoromethoxyphenyl | methyl | |

TABLE 3-continued

Inventive compounds of the general formula (I) in which W* is CN, $R^1$ and $R^2$ are each hydrogen, and aryl is the radical.

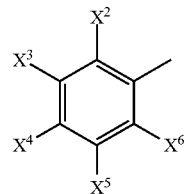

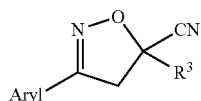

| No. | Aryl | $R^3$ | Physical data |
|---|---|---|---|
| 3.1143 | 3-cyano-6-difluoromethoxyphenyl | methyl | |
| 3.1144 | 3-trifluoromethyl-6-difluoromethoxyphenyl | methyl | |
| 3.1145 | 3-methoxy-6-difluoromethoxyphenyl | methyl | |
| 3.1146 | 3-ethoxy-6-difluoromethoxyphenyl | methyl | |
| 3.1147 | 3-nitro-6-difluoromethoxyphenyl | methyl | |
| 3.1148 | 3-fluoro-6-nitrophenyl | methyl | |
| 3.1149 | 3-chloro-6-nitrophenyl | methyl | |
| 3.1150 | 3-bromo-6-nitrophenyl | methyl | |
| 3.1151 | 3-methyl-6-nitrophenyl | methyl | |
| 3.1152 | 3-ethyl-6-nitrophenyl | methyl | |
| 3.1153 | 3-cyclopropyl-6-nitrophenyl | methyl | |
| 3.1154 | 3-cyano-6-nitrophenyl | methyl | |
| 3.1155 | 3-trifluoromethyl-6-nitrophenyl | methyl | |
| 3.1156 | 3-methoxy-6-nitrophenyl | methyl | |
| 3.1157 | 3-ethoxy-6-nitrophenyl | methyl | |
| 3.1158 | 3-trifluoromethoxy-6-nitrophenyl | methyl | |
| 3.1159 | 3-fluoro-6-methylsulfanylphenyl | methyl | |
| 3.1160 | 3-chloro-6-methylsulfanylphenyl | methyl | |
| 3.1161 | 3-bromo-6-methylsulfanylphenyl | methyl | |
| 3.1162 | 3-methyl-6-methylsulfanylphenyl | methyl | |
| 3.1163 | 3-cyclopropyl-6-methylsulfanylphenyl | methyl | |
| 3.1164 | 3-cyano-6-methylsulfanylphenyl | methyl | |
| 3.1165 | 3-trifluoromethyl-6-methylsulfanylphenyl | methyl | |
| 3.1166 | 3-methoxy-6-methylsulfanylphenyl | methyl | |
| 3.1167 | 3-ethoxy-6-methylsulfanylphenyl | methyl | |
| 3.1168 | 3-trifluoromethoxy-6-methylsulfanylphenyl | methyl | |
| 3.1169 | 3-nitro-6-methylsulfanylphenyl | methyl | |
| 3.1170 | 2,3,4-trifluorophenyl | methyl | |
| 3.1171 | 2,3,4-trichlorophenyl | methyl | |
| 3.1172 | 2,3,4-trimethylphenyl | methyl | |
| 3.1173 | 2-fluoro-2-chloro-5-trifluoromethylphenyl | methyl | |
| 3.1174 | 2,3,5-trifluorophenyl | methyl | |
| 3.1175 | 2,3,5-trichlorophenyl | methyl | [CDCl3] 1.92 (s, 3H); 3.40 (d, 1H); 3.95 (d, 1H); 7.58 (s, 1H); 7.85 (s, 1H) |
| 3.1176 | 2,3,5-trichlorophenyl | isopropyl | [DMSO] 1.10 (2d, 6H); 2.30 (m, 1H); 3.89 (d, 1H); 4.08 (d, 1H). |
| 3.1177 | 2,3,5-trichlorophenyl | tert-butyl | [CDCl3] 1.17 (s, 9H); 3.73 (dd, 2H); 7.57 (s, 1H); 7.80 (s, 1H) |
| 3.1178 | 2,3,6-trifluorophenyl | methyl | |
| 3.1179 | 2,3,6-trichlorophenyl | methyl | |
| 3.1180 | 2,3,6-trimethylphenyl | methyl | |
| 3.1181 | 3,4,5-trifluorophenyl | methyl | |
| 3.1182 | 3,4,6-trifluorophenyl | methyl | |
| 3.1183 | 3,4,6-trichlorophenyl | methyl | [CDCl$_3$] 1.94 (s, 3H), 3.51 (d, 1H), 3.95 (d, 1H), 7.58 (s, 1H), 7.83 (s, 1H). |
| 3.1184 | 3,4,6-trichlorophenyl | ethyl | |
| 3.1185 | 3,4,6-trichlorophenyl | CN | |
| 3.1186 | 3,4,6-trichlorophenyl | vinyl | |
| 3.1187 | 3,4,6-trichlorophenyl | fluoromethyl | |
| 3.1188 | 3,4,6-trichlorophenyl | hydroxymethyl | |
| 3.1189 | 3,4,6-trichlorophenyl | ethynyl | |
| 3.1190 | 3,4,5-trimethylphenyl | methyl | |

TABLE 3-continued

Inventive compounds of the general formula (I) in which W* is CN, $R^1$ and $R^2$ are each hydrogen, and aryl is the radical.

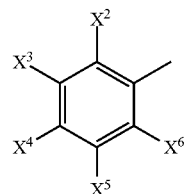

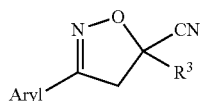

| No. | Aryl | $R^3$ | Physical data |
|---|---|---|---|
| 3.1191 | 3,5-dimethyl-4-fluorophenyl | methyl | |
| 3.1192 | 3,5-dichloro-4-methoxyphenyl | methyl | |
| 3.1193 | 3,5-difluoro-4-chlorophenyl | methyl | |
| 3.1194 | 3,5-dichloro-4-hydroxyphenyl | methyl | |
| 3.1195 | 3,5-trifluoromethyl-4-chlorophenyl | methyl | |
| 3.1196 | 3,4,6-trifluorophenyl | methyl | |
| 3.1197 | 3,4,6-trichlorophenyl | methyl | |
| 3.1198 | 3,4,6-trimethylphenyl | methyl | |
| 3.1199 | 2,3,4,5-pentafluoro-phenyl | methyl | |

TABLE 4

Inventive compounds of the general formula (I) in which W* is CHO, $R^1$ and $R^2$ are each hydrogen, and aryl is the radical.

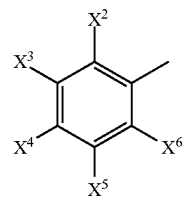

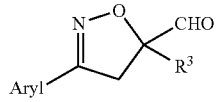

| No. | Aryl | $R^3$ | Physical data |
|---|---|---|---|
| 4.1 | 3-fluorophenyl | methyl | |
| 4.2 | 3-fluorophenyl | ethyl | |
| 4.3 | 3-fluorophenyl | CN | |
| 4.4 | 3-fluorophenyl | fluoromethyl | |
| 4.5 | 3-fluorophenyl | methylcarbonyl | |
| 4.6 | 3-fluorophenyl | hydroxymethyl | |
| 4.7 | 3-fluorophenyl | vinyl | |
| 4.8 | 3-fluorophenyl | 1-chlorovinyl | |
| 4.9 | 3-fluorophenyl | ethynyl | |
| 4.10 | 3-chlorophenyl | methyl | |
| 4.11 | 3-chlorophenyl | ethyl | |
| 4.12 | 3-chlorophenyl | CN | |
| 4.13 | 3-chlorophenyl | fluoromethyl | |
| 4.14 | 3-chlorophenyl | hydroxymethyl | |
| 4.15 | 3-chlorophenyl | methylcarbonyl | |
| 4.16 | 3-chlorophenyl | fluoromethyl | |
| 4.17 | 3-chlorophenyl | ethynyl | |
| 4.18 | 3-bromophenyl | methyl | |
| 4.19 | 3-bromophenyl | ethyl | |
| 4.20 | 3-bromophenyl | vinyl | |
| 4.21 | 3-iodophenyl | methyl | |
| 4.22 | 3-methylphenyl | methyl | |
| 4.23 | 3-ethylphenyl | methyl | |

TABLE 4-continued

Inventive compounds of the general formula (I) in which W* is CHO, $R^1$ and $R^2$ are each hydrogen, and aryl is the radical.

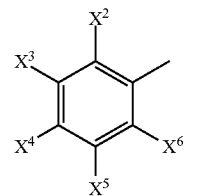

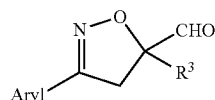

| No. | Aryl | $R^3$ | Physical data |
|---|---|---|---|
| 4.24 | 3-propylphenyl | methyl | |
| 4.25 | 3-isopropylphenyl | methyl | |
| 4.26 | 3-n-butylphenyl | methyl | |
| 4.27 | 3-i-butylphenyl | methyl | |
| 4.28 | 3-tert-butylphenyl | methyl | |
| 4.29 | 3-cyclopropylphenyl | methyl | |
| 4.30 | 3-cyclobutylphenyl | methyl | |
| 4.31 | 3-cyclopentylphenyl | methyl | |
| 4.32 | 3-vinylphenyl | methyl | |
| 4.33 | 3-ethynylphenyl | methyl | |
| 4.34 | 3-cyanophenyl | methyl | |
| 4.35 | 3-trifluoromethylphenyl | methyl | |
| 4.36 | 3-difluoromethylphenyl | methyl | |
| 4.37 | 3-(methoxycarbonyl)phenyl | methyl | |
| 4.38 | 3-(ethoxycarbonyl)phenyl | methyl | |
| 4.39 | 3-hydroxymethylphenyl | methyl | |
| 4.40 | 3-methoxyphenyl | methyl | |
| 4.41 | 3-methoxyphenyl | ethyl | |
| 4.42 | 3-methoxyphenyl | CN | |
| 4.43 | 3-methoxyphenyl | fluoromethyl | |
| 4.44 | 3-methoxyphenyl | methylcarbonyl | |
| 4.45 | 3-methoxyphenyl | hydroxymethyl | |
| 4.46 | 3-methoxyphenyl | ethynyl | |
| 4.47 | 3-ethoxyphenyl | methyl | |
| 4.48 | 3-propyloxyphenyl | methyl | |
| 4.49 | 3-isopropyloxyphenyl | methyl | |
| 4.50 | 3-i-butyloxyphenyl | methyl | |
| 4.51 | 3-t-butyloxyphenyl | methyl | |
| 4.52 | 3-difluoromethoxyphenyl | methyl | |
| 4.53 | 3-trifluoromethoxyphenyl | methyl | |
| 4.54 | 3-trifluoromethoxyphenyl | ethyl | |
| 4.55 | 3-trifluoromethoxyphenyl | CN | |
| 4.56 | 3-trifluoromethoxyphenyl | fluoromethyl | |
| 4.57 | 3-trifluoromethoxyphenyl | methylcarbonyl | |
| 4.58 | 3-trifluoromethoxy | hydroxymethyl | |
| 4.59 | 3-trifluoromethoxyphenyl | ethynyl | |
| 4.60 | 3-nitrophenyl | methyl | |
| 4.61 | 3-acetoxyphenyl | methyl | |
| 4.62 | 3-methylsulfanylphenyl | methyl | |
| 4.63 | 3-ethylsulfanylphenyl | methyl | |
| 4.64 | 3-(pentafluoro-lambda$^6$-sulfanyl)phenyl | methyl | |
| 4.65 | 2,3-difluorophenyl | methyl | |
| 4.66 | 2,3-difluorophenyl | ethyl | |
| 4.67 | 2,3-difluorophenyl | CN | |
| 4.68 | 2,3-difluorophenyl | fluoromethyl | |
| 4.69 | 2,3-difluorophenyl | methylcarbonyl | |
| 4.70 | 2,3-difluorophenyl | hydroxymethyl | |
| 4.71 | 2,3-difluorophenyl | ethynyl | |
| 4.72 | 2-chloro-3-fluorophenyl | methyl | |
| 4.73 | 2-bromo-3-fluorophenyl | methyl | |
| 4.74 | 2-methyl-3-fluorophenyl | methyl | |
| 4.75 | 2-ethyl-3-fluorophenyl | methyl | |
| 4.76 | 2-cyclopropyl-3-fluorophenyl | methyl | |
| 4.77 | 2-cyano-3-fluorophenyl | methyl | |
| 4.78 | 2-methoxy-3-fluorophenyl | methyl | |
| 4.79 | 2-trifluoromethoxy-3-fluorophenyl | methyl | |
| 4.80 | 2-nitro-3-fluorophenyl | methyl | |
| 4.81 | 2-fluoro-3-chlorophenyl | methyl | |
| 4.82 | 2,3-dichlorophenyl | methyl | |

TABLE 4-continued

Inventive compounds of the general formula (I) in which W* is CHO, $R^1$ and $R^2$ are each hydrogen, and aryl is the radical.

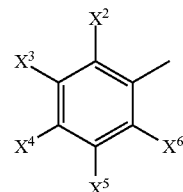

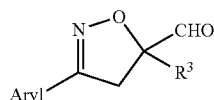

| No. | Aryl | $R^3$ | Physical data |
|---|---|---|---|
| 4.83 | 2,3-dichlorophenyl | ethyl | |
| 4.84 | 2,3-dichlorophenyl | CN | |
| 4.85 | 2,3-dichlorophenyl | fluoromethyl | |
| 4.86 | 2,3-dichlorophenyl | methylcarbonyl | |
| 4.87 | 2,3-dichlorophenyl | hydroxymethyl | |
| 4.88 | 2,3-dichlorophenyl | ethynyl | |
| 4.89 | 2-bromo-3-chlorophenyl | methyl | |
| 4.90 | 2-methyl-3-chlorophenyl | methyl | |
| 4.91 | 2-methyl-3-chlorophenyl | ethyl | |
| 4.92 | 2-methyl-3-chlorophenyl | CN | |
| 4.93 | 2-methyl-3-chlorophenyl | fluoromethyl | |
| 4.94 | 2-methyl-3-chlorophenyl | methylcarbonyl | |
| 4.95 | 2-methyl-3-chlorophenyl | hydroxymethyl | |
| 4.96 | 2-methyl-3-chlorophenyl | ethynyl | |
| 4.97 | 2-ethyl-3-chlorophenyl | methyl | |
| 4.98 | 2-cyclopropyl-3-chlorophenyl | methyl | |
| 4.99 | 2-cyano-3-chlorophenyl | methyl | |
| 4.100 | 2-trifluoromethyl-2-chlorophenyl | methyl | |
| 4.101 | 2-methoxy-3-chlorophenyl | methyl | |
| 4.102 | 2-ethoxy-3-chlorophenyl | methyl | |
| 4.103 | 2-trifluoromethoxy-3-chlorophenyl | methyl | |
| 4.104 | 2-nitro-3-chlorophenyl | methyl | |
| 4.105 | 2-fluoro-3-bromophenyl | methyl | |
| 4.106 | 2-chloro-3-bromophenyl | methyl | |
| 4.107 | 2,3-dibromophenyl | methyl | |
| 4.108 | 2-methyl-3-bromophenyl | methyl | |
| 4.109 | 2-ethyl-3-bromophenyl | methyl | |
| 4.110 | 2-cyclopropyl-3-bromophenyl | methyl | |
| 4.111 | 2-cyano-3-bromophenyl | methyl | |
| 4.112 | 2-trifluoromethyl-3-bromophenyl | methyl | |
| 4.113 | 2-methoxy-3-phenyl | methyl | |
| 4.114 | 2-trifluoromethoxy-3-bromophenyl | methyl | |
| 4.115 | 2-nitro-3-bromophenyl | methyl | |
| 4.116 | 2-fluoro-3-iodophenyl | methyl | |
| 4.117 | 2-chloro-3-iodophenyl | methyl | |
| 4.118 | 2-bromo-3-iodophenyl | methyl | |
| 4.119 | 2-methyl-3-iodophenyl | methyl | |
| 4.120 | 2-ethyl-3-iodophenyl | methyl | |
| 4.121 | 2-cyclopropyl-3-iodophenyl | methyl | |
| 4.122 | 2-cyano-3-iodophenyl | methyl | |
| 4.123 | 2-trifluoromethyl-3-iodophenyl | methyl | |
| 4.124 | 2-methoxy-3-iodophenyl | methyl | |
| 4.125 | 2-trifluoromethoxy-3-iodophenyl | methyl | |
| 4.126 | 2-nitro-3-iodophenyl | methyl | |
| 4.127 | 2-fluoro-3-methylphenyl | methyl | |
| 4.128 | 2-fluoro-3-methylphenyl | ethyl | |
| 4.129 | 2-fluoro-3-methylphenyl | CN | |
| 4.130 | 2-fluoro-3-methylphenyl | fluoromethyl | |
| 4.131 | 2-fluoro-3-methylphenyl | hydroxymethyl | |
| 4.132 | 2-fluoro-3-methylphenyl | ethynyl | |
| 4.133 | 2-chloro-3-methylphenyl | methyl | |
| 4.134 | 2-chloro-3-methylphenyl | ethyl | |
| 4.135 | 2-chloro-3-methylphenyl | CN | |
| 4.136 | 2-chloro-3-methylphenyl | fluoromethyl | |
| 4.137 | 2-chloro-3-methylphenyl | methylcarbonyl | |
| 4.138 | 2-chloro-3-methylphenyl | hydroxymethyl | |
| 4.139 | 2-chloro-3-methylphenyl | ethynyl | |
| 4.140 | 2-bromo-3-methylphenyl | methyl | |
| 4.141 | 2,3-dimethylphenyl | methyl | |

TABLE 4-continued

Inventive compounds of the general formula (I) in which W* is CHO, $R^1$ and $R^2$ are each hydrogen, and aryl is the radical.

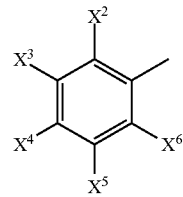

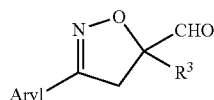

| No. | Aryl | $R^3$ | Physical data |
|---|---|---|---|
| 4.142 | 2-ethyl-3-methylphenyl | methyl | |
| 4.143 | 2-cyclopropyl-3-methylphenyl | methyl | |
| 4.144 | 2-cyano-3-methylphenyl | methyl | |
| 4.145 | 2-trifluoromethyl-3-methylphenyl | methyl | |
| 4.146 | 2-methoxy-3-methylphenyl | methyl | |
| 4.147 | 2-trifluoromethoxy-3-methylphenyl | methyl | |
| 4.148 | 2-nitro-3-methylphenyl | methyl | |
| 4.149 | 2-fluoro-3-ethylphenyl | methyl | |
| 4.150 | 2-chloro-3-ethylphenyl | methyl | |
| 4.151 | 2-bromo-3-ethylphenyl | methyl | |
| 4.152 | 2-methyl-3-ethylphenyl | methyl | |
| 4.153 | 2,3-diethylphenyl | methyl | |
| 4.154 | 2-cyclopropyl-3-ethylphenyl | methyl | |
| 4.155 | 2-cyano-3-ethylphenyl | methyl | |
| 4.156 | 2-trifluoromethyl-3-ethylphenyl | methyl | |
| 4.157 | 2-methoxy-3-ethylphenyl | methyl | |
| 4.158 | 2-trifluoromethoxy-3-ethylphenyl | methyl | |
| 4.159 | 2-nitro-3-ethylphenyl | methyl | |
| 4.160 | 2-fluoro-3-propylphenyl | methyl | |
| 4.161 | 2-chloro-3-propylphenyl | methyl | |
| 4.162 | 2-bromo-3-propylphenyl | methyl | |
| 4.163 | 2-methyl-3-propylphenyl | methyl | |
| 4.164 | 2-methyl-3-propylphenyl | methyl | |
| 4.165 | 2-cyclopropyl-3-propylphenyl | methyl | |
| 4.166 | 2-cyano-3-propylphenyl | methyl | |
| 4.167 | 2-trifluoromethyl-3-propylphenyl | methyl | |
| 4.168 | 2-methoxy-3-propylphenyl | methyl | |
| 4.169 | 2-trifluoromethoxy-3-propylphenyl | methyl | |
| 4.170 | 2-nitro-3-propylphenyl | methyl | |
| 4.171 | 2-fluoro-3-isopropylphenyl | methyl | |
| 4.172 | 2-chloro-3-isopropylphenyl | methyl | |
| 4.173 | 2-bromo-3-isopropylphenyl | methyl | |
| 4.174 | 2-methyl-3-isopropylphenyl | methyl | |
| 4.175 | 2-cyclopropyl-3-isopropylphenyl | methyl | |
| 4.176 | 2-cyano-3-isopropylphenyl | methyl | |
| 4.177 | 2-trifluoromethyl-3-isopropylphenyl | methyl | |
| 4.178 | 2-methoxy-3-isopropylphenyl | methyl | |
| 4.179 | 2-trifluoromethoxy-3-isopropylphenyl | methyl | |
| 4.180 | 2-nitro-3-isopropylphenyl | methyl | |
| 4.181 | 2-fluoro-3-tert-butylphenyl | methyl | |
| 4.182 | 2-fluoro-3-tert-butylphenyl | ethyl | |
| 4.183 | 2-fluoro-3-tert-butylphenyl | CN | |
| 4.184 | 2-fluoro-3-tert-butylphenyl | fluoromethyl | |
| 4.185 | 2-fluoro-3-tert-butylphenyl | methylcarbonyl | |
| 4.186 | 2-fluoro-3-tert-butylphenyl | hydroxymethyl | |
| 4.187 | 2-fluoro-3-tert-butylphenyl | ethynyl | |
| 4.188 | 2-chloro-3-tert-butylphenyl | methyl | |
| 4.189 | 2-bromo-3-tert-butylphenyl | methyl | |
| 4.190 | 2-methyl-3-tert-butylphenyl | methyl | |
| 4.191 | 2-cyclopropyl-3-tert-butylphenyl | methyl | |
| 4.192 | 2-cyano-3-tert-butylphenyl | methyl | |
| 4.193 | 2-trifluoromethyl-3-tert-butylphenyl | methyl | |
| 4.194 | 2-methoxy-3-tert-butylphenyl | methyl | |
| 4.195 | 2-trifluoromethoxy-3-tert-butylphenyl | methyl | |
| 4.196 | 2-nitro-3-tert-butylphenyl | methyl | |
| 4.197 | 2-fluoro-3-cyclopropylphenyl | methyl | |
| 4.198 | 2-chloro-3-cyclopropylphenyl | methyl | |
| 4.199 | 2-bromo-3-cyclopropylphenyl | methyl | |
| 4.200 | 2-methyl-3-cyclopropylphenyl | methyl | |

TABLE 4-continued

Inventive compounds of the general formula (I) in which W* is CHO, $R^1$ and $R^2$ are each hydrogen, and aryl is the radical.

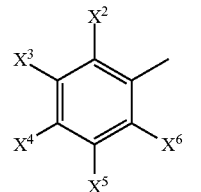

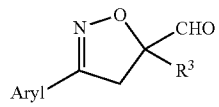

| No. | Aryl | $R^3$ | Physical data |
|---|---|---|---|
| 4.201 | 2-cyclopropyl-3-cyclopropylphenyl | methyl | |
| 4.202 | 2-cyano-3-cyclopropylphenyl | methyl | |
| 4.203 | 2-trifluoromethyl-3-cyclopropylphenyl | methyl | |
| 4.204 | 2-methoxy-3-cyclopropylphenyl | methyl | |
| 4.205 | 2-ethoxy-3-cyclopropylphenyl | methyl | |
| 4.206 | 2-trifluoromethoxy-3-cyclopropylphenyl | methyl | |
| 4.207 | 2-fluoro-3-methoxycarbonylphenyl | methyl | |
| 4.208 | 2-chloro-3-methoxycarbonylphenyl | methyl | |
| 4.209 | 2-bromo-3-methoxycarbonylphenyl | methyl | |
| 4.210 | 2-methyl-3-methoxycarbonylphenyl | methyl | |
| 4.211 | 2-methyl-3-methoxycarbonylphenyl | ethyl | |
| 4.212 | 2-methyl-3-methoxycarbonylphenyl | CN | |
| 4.213 | 2-methyl-3-methoxycarbonylphenyl | vinyl | |
| 4.214 | 2-methyl-3-methoxycarbonylphenyl | fluoromethyl | |
| 4.215 | 2-methyl-3-methoxycarbonylphenyl | methylcarbonyl | |
| 4.216 | 2-methyl-3-methoxycarbonylphenyl | hydroxymethyl | |
| 4.217 | 2-methyl-3-methoxycarbonylphenyl | ethynyl | |
| 4.218 | 2-cyclopropyl-3-methoxycarbonylphenyl | methyl | |
| 4.219 | 2-cyano-3-methoxycarbonylphenyl | methyl | |
| 4.220 | 2-trifluoromethyl-3-methoxycarbonylphenyl | methyl | |
| 4.221 | 2-methoxy-3-methoxycarbonylphenyl | methyl | |
| 4.222 | 2-ethoxy-3-methoxycarbonylphenyl | methyl | |
| 4.223 | 2-trifluoromethoxy-3-methoxycarbonylphenyl | methyl | |
| 4.224 | 2-nitro-3-methoxycarbonylphenyl | methyl | |
| 4.225 | 2-fluoro-3-cyanophenyl | methyl | |
| 4.226 | 2-fluoro-3-cyanophenyl | ethyl | |
| 4.227 | 2-fluoro-3-cyanophenyl | CN | |
| 4.228 | 2-fluoro-3-cyanophenyl | vinyl | |
| 4.229 | 2-fluoro-3-cyanophenyl | fluoromethyl | |
| 4.230 | 2-fluoro-3-cyanophenyl | methylcarbonyl | |
| 4.231 | 2-fluoro-3-cyanophenyl | hydroxymethyl | |
| 4.232 | 2-fluoro-3-cyanophenyl | ethynyl | |
| 4.233 | 2-chloro-3-cyanophenyl | methyl | |
| 4.234 | 2-chloro-3-cyanophenyl | ethyl | |
| 4.235 | 2-chloro-3-cyanophenyl | CN | |
| 4.236 | 2-chloro-3-cyanophenyl | vinyl | |
| 4.237 | 2-chloro-3-cyanophenyl | fluoromethyl | |
| 4.238 | 2-chloro-3-cyanophenyl | methylcarbonyl | |
| 4.239 | 2-chloro-3-cyanophenyl | hydroxymethyl | |
| 4.240 | 2-chloro-3-cyanophenyl | ethynyl | |
| 4.241 | 2-bromo-3-cyanophenyl | methyl | |
| 4.242 | 2-methyl-3-cyanophenyl | methyl | |
| 4.243 | 2-ethyl-3-cyanophenyl | methyl | |
| 4.244 | 2-cyclopropyl-3-cyanophenyl | methyl | |
| 4.245 | 2-cyano-3-cyanophenyl | methyl | |
| 4.246 | 2-trifluoromethyl-3-cyanophenyl | methyl | |
| 4.247 | 2-methoxy-3-cyanophenyl | methyl | |
| 4.248 | 2-trifluoromethoxy-3-cyanophenyl | methyl | |
| 4.249 | 2-nitro-3-cyanophenyl | methyl | |
| 4.250 | 2-fluoro-3-methoxyphenyl | methyl | |
| 4.251 | 2-chloro-3-methoxyphenyl | methyl | |
| 4.252 | 2-bromo-3-methoxyphenyl | methyl | |
| 4.253 | 2-methyl-3-methoxyphenyl | methyl | |
| 4.254 | 2-cyclopropyl-3-methoxyphenyl | methyl | |
| 4.255 | 2-cyano-3-methoxyphenyl | methyl | |
| 4.256 | 2-trifluoromethyl-3-methoxyphenyl | methyl | |
| 4.257 | 2,3-dimethoxyphenyl | methyl | |

TABLE 4-continued

Inventive compounds of the general formula (I) in which W* is CHO, R¹ and R² are each hydrogen, and aryl is the radical.

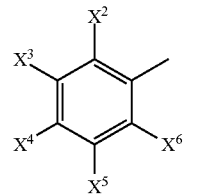

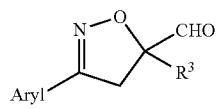

| No. | Aryl | R³ | Physical data |
|---|---|---|---|
| 4.258 | 2-ethoxy-3-methoxyphenyl | methyl | |
| 4.259 | 2-trifluoromethoxy-3-methoxyphenyl | methyl | |
| 4.260 | 2-nitro-3-methoxyphenyl | methyl | |
| 4.261 | 2-fluoro-3-ethoxyphenyl | methyl | |
| 4.262 | 2-chloro-3-ethoxyphenyl | methyl | |
| 4.263 | 2-bromo-3-ethoxyphenyl | methyl | |
| 4.264 | 2-methyl-3-ethoxyphenyl | methyl | |
| 4.265 | 2-cyclopropyl-3-ethoxyphenyl | methyl | |
| 4.266 | 2-cyano-3-ethoxyphenyl | methyl | |
| 4.267 | 2-trifluoromethyl-3-ethoxyphenyl | methyl | |
| 4.268 | 2-methoxy-3-ethoxyphenyl | methyl | |
| 4.269 | 2,3-diethoxyphenyl | methyl | |
| 4.270 | 2-trifluoromethoxy-3-ethoxyphenyl | methyl | |
| 4.271 | 2-nitro-3-ethoxyphenyl | methyl | |
| 4.272 | 2-fluoro-3-isopropoxyphenyl | methyl | |
| 4.273 | 2-chloro-3-isopropoxyphenyl | methyl | |
| 4.274 | 2-bromo-3-isopropoxyphenyl | methyl | |
| 4.275 | 2-methyl-3-isopropoxyphenyl | methyl | |
| 4.276 | 2-cyclopropyl-3-isopropoxyphenyl | methyl | |
| 4.277 | 2-cyano-3-isopropoxyphenyl | methyl | |
| 4.278 | 2-trifluoromethyl-3-isopropoxyphenyl | methyl | |
| 4.279 | 2-methoxy-3-isopropoxyphenyl | methyl | |
| 4.280 | 2-trifluoromethoxy-3-isopropoxyphenyl | methyl | |
| 4.281 | 2-nitro-3-isopropoxyphenyl | methyl | |
| 4.282 | 2-fluoro-3-trifluoromethoxyphenyl | methyl | |
| 4.283 | 2-chloro-3-trifluoromethoxyphenyl | methyl | |
| 4.284 | 2-bromo-3-trifluoromethoxyphenyl | methyl | |
| 4.285 | 2-methyl-3-trifluoromethoxyphenyl | methyl | |
| 4.286 | 2-cyclopropyl-3-trifluoromethoxyphenyl | methyl | |
| 4.287 | 2-cyano-3-trifluoromethoxyphenyl | methyl | |
| 4.288 | 2-trifluoromethyl-3-trifluoromethoxy-phenyl | methyl | |
| 4.289 | 2-methoxy-3-trifluoromethoxyphenyl | methyl | |
| 4.290 | 2,3-bis(trifluoromethoxy)phenyl | methyl | |
| 4.291 | 2-nitro-3-trifluoromethoxyphenyl | methyl | |
| 4.292 | 2-fluoro-3-difluoromethoxyphenyl | methyl | |
| 4.293 | 2-chloro-3-difluoromethoxyphenyl | methyl | |
| 4.294 | 2-bromo-3-difluoromethoxyphenyl | methyl | |
| 4.295 | 2-methyl-3-difluoromethoxyphenyl | methyl | |
| 4.296 | 2-cyclopropyl-3-difluoromethoxyphenyl | methyl | |
| 4.297 | 2-cyano-3-difluoromethoxyphenyl | methyl | |
| 4.298 | 2-trifluoromethyl-3-difluoromethoxyphenyl | methyl | |
| 4.299 | 2-methoxy-3-difluoromethoxyphenyl | methyl | |
| 4.300 | 2-ethoxy-3-difluoromethoxyphenyl | methyl | |
| 4.301 | 2-nitro-3-difluoromethoxyphenyl | methyl | |
| 4.302 | 2-fluoro-3-nitrophenyl | methyl | |
| 4.303 | 2-chloro-3-nitrophenyl | methyl | |
| 4.304 | 2-bromo-3-nitrophenyl | methyl | |
| 4.305 | 2-methyl-3-nitrophenyl | methyl | |
| 4.306 | 2-cyclopropyl-3-nitrophenyl | methyl | |
| 4.307 | 2-cyano-3-nitrophenyl | methyl | |
| 4.308 | 2-trifluoromethyl-3-nitrophenyl | methyl | |
| 4.309 | 2-methoxy-3-nitrophenyl | methyl | |
| 4.310 | 2-ethoxy-3-nitrophenyl | methyl | |
| 4.311 | 2-trifluoromethoxy-3-nitrophenyl | methyl | |
| 4.312 | 2-fluoro-3-methylsulfanylphenyl | methyl | |
| 4.313 | 2-chloro-3-methylsulfanylphenyl | methyl | |
| 4.314 | 2-bromo-3-methylsulfanylphenyl | methyl | |
| 4.315 | 2-methyl-3-methylsulfanylphenyl | methyl | |

TABLE 4-continued

Inventive compounds of the general formula (I) in which W* is CHO, $R^1$ and $R^2$ are each hydrogen, and aryl is the radical.

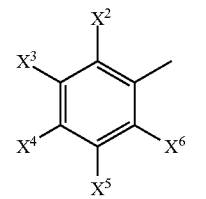

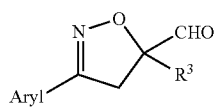

| No. | Aryl | $R^3$ | Physical data |
|---|---|---|---|
| 4.316 | 2-ethyl-3-methylsulfanylphenyl | methyl | |
| 4.317 | 2-cyclopropyl-3-methylsulfanylphenyl | methyl | |
| 4.318 | 2-cyano-3-methylsulfanylphenyl | methyl | |
| 4.319 | 2-trifluoromethyl-3-methylsulfanylphenyl | methyl | |
| 4.320 | 2-methoxy-3-methylsulfanylphenyl | methyl | |
| 4.321 | 2-ethoxy-3-methylsulfanylphenyl | methyl | |
| 4.322 | 2-trifluoromethoxy-3-methylsulfanylphenyl | methyl | |
| 4.323 | 2-nitro-3-methylsulfanylphenyl | methyl | |
| 4.324 | 3,5-difluorophenyl | methyl | [CDCl$_3$] 1.61 (s, 3H); 3.05 (d, 1H); 3.68 (d, 1H); 6.88 (m, 1H); 7.15 (m, 2H); 9.65 (s, 1H). |
| 4.325 | 3,5-difluorophenyl | ethyl | |
| 4.326 | 3,5-difluorophenyl | CN | |
| 4.327 | 3,5-difluorophenyl | vinyl | |
| 4.328 | 3,5-difluorophenyl | fluoromethyl | |
| 4.329 | 3,5-difluorophenyl | methylcarbonyl | |
| 4.330 | 3,5-difluorophenyl | hydroxymethyl | |
| 4.331 | 3,5-difluorophenyl | ethynyl | |
| 4.332 | 3-chloro-5-fluorophenyl | methyl | |
| 4.333 | 3-chloro-5-fluorophenyl | ethyl | |
| 4.334 | 3-chloro-5-fluorophenyl | CN | |
| 4.335 | 3-chloro-5-fluorophenyl | vinyl | |
| 4.336 | 3-chloro-5-fluorophenyl | fluoromethyl | |
| 4.337 | 3-chloro-5-fluorophenyl | methylcarbonyl | |
| 4.338 | 3-chloro-5-fluorophenyl | hydroxymethyl | |
| 4.339 | 3-chloro-5-fluorophenyl | ethynyl | |
| 4.340 | 3-bromo-5-fluorophenyl | methyl | |
| 4.341 | 3-iodo-5-fluorophenyl | methyl | |
| 4.342 | 3-methyl-5-fluorophenyl | methyl | |
| 4.343 | 3-methyl-5-fluorophenyl | ethyl | |
| 4.344 | 3-methyl-5-fluorophenyl | CN | |
| 4.345 | 3-methyl-5-fluorophenyl | vinyl | |
| 4.346 | 3-methyl-5-fluorophenyl | fluoromethyl | |
| 4.347 | 3-methyl-5-fluorophenyl | methylcarbonyl | |
| 4.348 | 3-methyl-5-fluorophenyl | hydroxymethyl | |
| 4.349 | 3-methyl-5-fluorophenyl | ethynyl | |
| 4.350 | 3-ethyl-5-fluorophenyl | methyl | |
| 4.351 | 3-propyl-5-fluorophenyl | methyl | |
| 4.352 | 3-i-propyl-5-fluorophenyl | methyl | |
| 4.353 | 3-n-butyl-5-fluorophenyl | methyl | |
| 4.354 | 3-isobutyl-5-fluorophenyl | methyl | |
| 4.355 | 3-tert-butyl-5-fluorophenyl | methyl | |
| 4.356 | 3-tert-butyl-5-fluorophenyl | ethyl | |
| 4.357 | 3-tert-butyl-5-fluorophenyl | CN | |
| 4.358 | 3-tert-butyl-5-fluorophenyl | vinyl | |
| 4.359 | 3-tert-butyl-5-fluorophenyl | fluoromethyl | |
| 4.360 | 3-tert-butyl-5-fluorophenyl | methylcarbonyl | |
| 4.361 | 3-tert-butyl-5-fluorophenyl | hydroxymethyl | |
| 4.362 | 3-tert-butyl-5-fluorophenyl | ethynyl | |
| 4.363 | 3-cyclopropyl-5-fluorophenyl | methyl | |
| 4.364 | 3-cyano-5-fluorophenyl | methyl | |
| 4.365 | 3-cyano-5-fluorophenyl | ethyl | |
| 4.366 | 3-cyano-5-fluorophenyl | CN | |
| 4.367 | 3-cyano-5-fluorophenyl | vinyl | |
| 4.368 | 3-cyano-5-fluorophenyl | fluoromethyl | |
| 4.369 | 3-cyano-5-fluorophenyl | methylcarbonyl | |
| 4.370 | 3-cyano-5-fluorophenyl | hydroxymethyl | |

TABLE 4-continued

Inventive compounds of the general formula (I) in which W* is CHO, $R^1$ and $R^2$ are each hydrogen, and aryl is the radical.

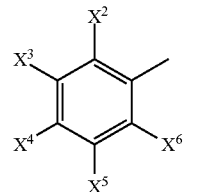

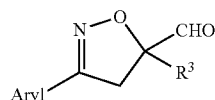

| No. | Aryl | $R^3$ | Physical data |
|---|---|---|---|
| 4.371 | 3-cyano-5-fluorophenyl | ethynyl | |
| 4.372 | 3-trifluoromethyl-5-fluorophenyl | methyl | |
| 4.373 | 3-(methoxycarbonyl)-5-fluorophenyl | methyl | |
| 4.374 | 3-methoxy-5-fluorophenyl | methyl | |
| 4.375 | 3-methoxy-5-fluorophenyl | ethyl | |
| 4.376 | 3-methoxy-5-fluorophenyl | CN | |
| 4.377 | 3-methoxy-5-fluorophenyl | vinyl | |
| 4.378 | 3-methoxy-5-fluorophenyl | fluoromethyl | |
| 4.379 | 3-methoxy-5-fluorophenyl | methylcarbonyl | |
| 4.380 | 3-methoxy-5-fluorophenyl | hydroxymethyl | |
| 4.381 | 3-methoxy-5-fluorophenyl | ethynyl | |
| 4.382 | 3-ethoxy-5-fluorophenyl | methyl | |
| 4.383 | 3-n-propoxy-5-fluorophenyl | methyl | |
| 4.384 | 3-isopropoxy-5-fluorophenyl | methyl | |
| 4.385 | 3-n-butoxy-5-fluorophenyl | methyl | |
| 4.386 | 3-isobutoxy-5-fluorophenyl | methyl | |
| 4.387 | 3-difluoromethoxy-5-fluorophenyl | methyl | |
| 4.388 | 3-trifluoromethoxy-5-fluorophenyl | methyl | |
| 4.389 | 3-nitro-5-fluorophenyl | methyl | |
| 4.390 | 3-acetoxy-5-fluorophenyl | methyl | |
| 4.391 | 3-methylsulfanyl-5-fluorophenyl | methyl | |
| 4.392 | 3,5-dichlorophenyl | methyl | |
| 4.393 | 3,5-dichlorophenyl | ethyl | |
| 4.394 | 3,5-dichlorophenyl | CN | |
| 4.395 | 3,5-dichlorophenyl | vinyl | |
| 4.396 | 3,5-dichlorophenyl | fluoromethyl | |
| 4.397 | 3,5-dichlorophenyl | methylcarbonyl | |
| 4.398 | 3,5-dichlorophenyl | hydroxymethyl | |
| 4.399 | 3,5-dichlorophenyl | ethynyl | |
| 4.400 | 3-bromo-5-chlorophenyl | methyl | |
| 4.401 | 3-iodo-5-chlorophenyl | methyl | |
| 4.402 | 3-methyl-5-chlorophenyl | methyl | |
| 4.403 | 3-methyl-5-chlorophenyl | ethyl | |
| 4.404 | 3-methyl-5-chlorophenyl | CN | |
| 4.405 | 3-methyl-5-chlorophenyl | vinyl | |
| 4.406 | 3-methyl-5-chlorophenyl | fluoromethyl | |
| 4.407 | -methyl-5-chlorophenyl | methylcarbonyl | |
| 4.408 | 3-methyl-5-chlorophenyl | hydroxymethyl | |
| 4.409 | 3-methyl-5-chlorophenyl | ethynyl | |
| 4.410 | 3-ethyl-5-chlorophenyl | methyl | |
| 4.411 | 3-propyl-5-chlorophenyl | methyl | |
| 4.412 | 3-isopropyl-5-chlorophenyl | methyl | |
| 4.413 | 3-isobutyl-5-chlorophenyl | methyl | |
| 4.414 | 3-tert-butyl-5-chlorophenyl | methyl | |
| 4.415 | 3-cyclopropyl-5-chlorophenyl | methyl | |
| 4.416 | 3-cyano-5-chlorophenyl | methyl | |
| 4.417 | 3-cyano-5-chlorophenyl | ethyl | |
| 4.418 | 3-cyano-5-chlorophenyl | CN | |
| 4.419 | 3-cyano-5-chlorophenyl | vinyl | |
| 4.420 | 3-cyano-5-chlorophenyl | fluoromethyl | |
| 4.421 | 3-cyano-5-chlorophenyl | methylcarbonyl | |
| 4.422 | 3-cyano-5-chlorophenyl | hydroxymethyl | |
| 4.423 | 3-cyano-5-chlorophenyl | ethynyl | |
| 4.424 | 3-trifluoromethyl-5-chlorophenyl | methyl | |
| 4.425 | 3-trifluoromethyl-5-chlorophenyl | ethyl | |
| 4.426 | 3-trifluoromethyl-5-chlorophenyl | CN | |
| 4.427 | 3-trifluoromethyl-5-chlorophenyl | vinyl | |
| 4.428 | 3-trifluoromethyl-5-chlorophenyl | fluoromethyl | |
| 4.429 | 3-trifluoromethyl-5-chlorophenyl | methylcarbonyl | |

TABLE 4-continued

Inventive compounds of the general formula (I) in which W* is CHO, $R^1$ and $R^2$ are each hydrogen, and aryl is the radical.

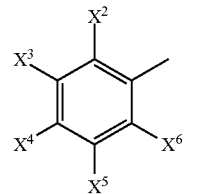

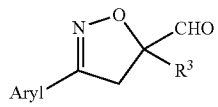

| No. | Aryl | $R^3$ | Physical data |
|---|---|---|---|
| 4.430 | 3-trifluoromethyl-5-chlorophenyl | hydroxymethyl | |
| 4.431 | 3-trifluoromethyl-5-chlorophenyl | ethynyl | |
| 4.432 | 3-(methoxycarbonyl)-5-chlorophenyl | methyl | |
| 4.433 | 3-methoxy-5-chlorophenyl | methyl | |
| 4.434 | 3-methoxy-5-chlorophenyl | ethyl | |
| 4.435 | 3-methoxy-5-chlorophenyl | CN | |
| 4.436 | 3-methoxy-5-chlorophenyl | vinyl | |
| 4.437 | 3-methoxy-5-chlorophenyl | fluoromethyl | |
| 4.438 | 3-methoxy-5-chlorophenyl | methylcarbonyl | |
| 4.439 | 3-methoxy-5-chlorophenyl | hydroxymethyl | |
| 4.440 | 3-methoxy-5-chlorophenyl | ethynyl | |
| 4.441 | 3-ethoxy-5-chlorophenyl | methyl | |
| 4.442 | 3-n-propoxy-5-chlorophenyl | methyl | |
| 4.443 | 3-isopropoxy-5-chlorophenyl | methyl | |
| 4.444 | 3-n-butoxy-5-chlorophenyl | methyl | |
| 4.445 | 3-isobutoxy-5-chlorophenyl | methyl | |
| 4.446 | 3-difluoromethoxy-5-chlorophenyl | methyl | |
| 4.447 | 3-trifluoromethoxy-5-chlorophenyl | methyl | |
| 4.448 | 3-trifluoromethoxy-5-chlorophenyl | ethyl | |
| 4.449 | 3-trifluoromethoxy-5-chlorophenyl | CN | |
| 4.450 | 3-trifluoromethoxy-5-chlorophenyl | vinyl | |
| 4.451 | 3-trifluoromethoxy-5-chlorophenyl | fluoromethyl | |
| 4.452 | 3trifluoromethoxy-5-chlorophenyl | methylcarbonyl | |
| 4.453 | 3-trifluoromethoxy-5-chlorophenyl | hydroxymethyl | |
| 4.454 | 3-trifluoromethoxy-5-chlorophenyl | ethynyl | |
| 4.455 | 3-nitro-5-chlorophenyl | methyl | |
| 4.456 | 3-acetoxy-5-chlorophenyl | methyl | |
| 4.457 | 3-methylsulfanyl-5-chlorophenyl | methyl | |
| 4.458 | 3,5-dibromophenylphenyl | methyl | |
| 4.459 | 3-iodo-5-bromophenyl | methyl | |
| 4.460 | 3-methyl-5-bromophenyl | methyl | |
| 4.461 | 3-ethyl-5-bromophenyl | methyl | |
| 4.462 | 3-propyl-5-bromophenyl | methyl | |
| 4.463 | 3-isopropyl-5-bromophenyl | methyl | |
| 4.464 | 3-isobutyl-5-bromophenyl | methyl | |
| 4.465 | 3-tert-butyl-5-bromophenyl | methyl | |
| 4.466 | 3-cyclopropyl-5-bromophenyl | methyl | |
| 4.467 | 3-cyano-5-bromophenyl | methyl | |
| 4.468 | 3-trifluoromethyl-5-bromophenyl | methyl | |
| 4.469 | 3-(methoxycarbonyl)-5-bromophenyl | methyl | |
| 4.470 | 3-methoxy-5-bromophenyl | methyl | |
| 4.471 | 3-ethoxy-5-bromophenyl | methyl | |
| 4.472 | 3-n-propoxy-5-bromophenyl | methyl | |
| 4.473 | 3-isopropoxy-5-bromophenyl | methyl | |
| 4.474 | 3-n-butoxy-5-bromophenyl | methyl | |
| 4.475 | 3-isobutoxy-5-bromophenyl | methyl | |
| 4.476 | 3-tert-butoxy-5-bromophenyl | methyl | |
| 4.477 | 3-difluoromethoxy-5-bromophenyl | methyl | |
| 4.478 | 3-trifluoromethoxy-5-bromophenyl | methyl | |
| 4.479 | 3-nitro-5-bromophenyl | methyl | |
| 4.480 | 3-acetoxy-5-bromophenyl | methyl | |
| 4.481 | 3-methylsulfanyl-5-bromophenyl | methyl | |
| 4.482 | 3,5-diiodophenyl | methyl | |
| 4.483 | 3-methyl-5-iodophenyl | methyl | |
| 4.484 | 3-ethyl-5-iodophenyl | methyl | |
| 4.485 | 3-propyl-5-iodophenyl | methyl | |
| 4.486 | 3-isopropyl-5-iodophenyl | methyl | |
| 4.487 | 3-n-butyl-5-iodophenyl | methyl | |
| 4.488 | 3-isobutyl-5-iodophenyl | methyl | |

TABLE 4-continued

Inventive compounds of the general formula (I) in which W* is CHO, R¹ and R² are each hydrogen, and aryl is the radical.

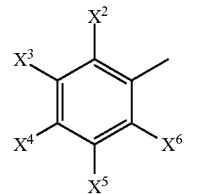

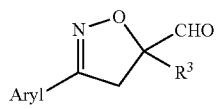

| No. | Aryl | R³ | Physical data |
|---|---|---|---|
| 4.489 | 3-tert-butyl-5-iodophenyl | methyl | |
| 4.490 | 3-cyclopropyl-5-iodophenyl | methyl | |
| 4.491 | 3-cyano-5-iodophenyl | methyl | |
| 4.492 | 3-trifluoromethyl-5-iodophenyl | methyl | |
| 4.493 | 3-(methoxycarbonyl)-5-iodophenyl | methyl | |
| 4.494 | 3-methoxy-5-iodophenyl | methyl | |
| 4.495 | 3-ethoxy-5-iodophenyl | methyl | |
| 4.496 | 3-n-propoxy-5-iodophenyl | methyl | |
| 4.497 | 3-isopropoxy-5-iodophenyl | methyl | |
| 4.498 | 3-n-butoxy-5-iodophenyl | methyl | |
| 4.499 | 3-isobutoxy-5-iodophenyl | methyl | |
| 4.500 | 3-difluoromethoxy-5-iodophenyl | methyl | |
| 4.501 | 3-trifluoromethoxy-5-iodophenyl | methyl | |
| 4.502 | 3-nitro-5-iodophenyl | methyl | |
| 4.503 | 3-acetoxy-5-iodophenyl | methyl | |
| 4.504 | 3-methylsulfanyl-5-iodophenyl | methyl | |
| 4.505 | 3,5-dimethylphenyl | methyl | |
| 4.506 | 3-ethyl-5-methylphenyl | methyl | |
| 4.507 | 3-propyl-5-methylphenyl | methyl | |
| 4.508 | 3-isopropyl-5-methylphenyl | methyl | |
| 4.509 | 3-n-butyl-5-methylphenyl | methyl | |
| 4.510 | 3-isobutyl-5-methylphenyl | methyl | |
| 4.511 | 3-tert-butyl-5-methylphenyl | methyl | |
| 4.512 | 3-cyclopropyl-5-methylphenyl | methyl | |
| 4.513 | 3-cyano-5-methylphenyl | methyl | |
| 4.514 | 3-trifluoromethyl-5-methylphenyl | methyl | |
| 4.515 | 3-(methoxycarbonyl)-5-methylphenyl | methyl | |
| 4.516 | 3-methoxy-5-methylphenyl | methyl | |
| 4.517 | 3-ethoxy-5-methylphenyl | methyl | |
| 4.518 | 3-n-propoxy-5-methylphenyl | methyl | |
| 4.519 | 3-n-butoxy-5-methylphenyl | methyl | |
| 4.520 | 3-isobutoxy-5-methylphenyl | methyl | |
| 4.521 | 3-difluoromethoxy-5-methylphenyl | methyl | |
| 4.522 | 3-trifluoromethoxy-5-methylphenyl | methyl | |
| 4.523 | 3-nitro-5-methylphenyl | methyl | |
| 4.524 | 3-acetoxy-5-methylphenyl | methyl | |
| 4.525 | 3-methylsulfanyl-5-methylphenyl | methyl | |
| 4.526 | 3,5-diethylphenyl | methyl | |
| 4.527 | 3-propyl-5-ethylphenyl | methyl | |
| 4.528 | 3-isopropyl-5-ethylphenyl | methyl | |
| 4.529 | 3-n-butyl-5-ethylphenyl | methyl | |
| 4.530 | 3-isobutyl-5-ethylphenyl | methyl | |
| 4.531 | 3-tert-butyl-5-ethylphenyl | methyl | |
| 4.532 | 3-cyclopropyl-5-ethylphenyl | methyl | |
| 4.533 | 3-cyano-5-ethylphenyl | methyl | |
| 4.534 | 3-trifluoromethyl-5-ethylphenyl | methyl | |
| 4.535 | 3-(methoxycarbonyl)-5-ethylphenyl | methyl | |
| 4.536 | 3-methoxy-5-ethylphenyl | methyl | |
| 4.537 | 3-ethoxy-5-ethylphenyl | methyl | |
| 4.538 | 3-n-propoxy-5-ethylphenyl | methyl | |
| 4.539 | 3-n-butoxy-5-ethylphenyl | methyl | |
| 4.540 | 3-isobutoxy-5-ethylphenyl | methyl | |
| 4.541 | 3-difluoromethoxy-5-ethylphenyl | methyl | |
| 4.542 | 3-trifluoromethoxy-5-ethylphenyl | methyl | |
| 4.543 | 3-nitro-5-ethylphenyl | methyl | |
| 4.544 | 3-acetoxy-5-ethylphenyl | methyl | |
| 4.545 | 3-methylsulfanyl-5-ethylphenyl | methyl | |
| 4.546 | 3,5-dipropylphenyl | methyl | |
| 4.547 | 3-isopropyl-5-propylphenyl | methyl | |

TABLE 4-continued

Inventive compounds of the general formula (I) in which W* is CHO, $R^1$ and $R^2$ are each hydrogen, and aryl is the radical.

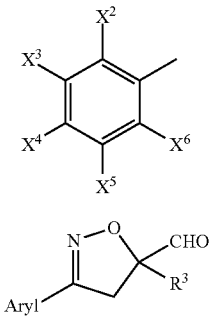

| No. | Aryl | $R^3$ | Physical data |
|---|---|---|---|
| 4.548 | 3-n-butyl-5-propylphenyl | methyl | |
| 4.549 | 3-isobutyl-5-propylphenyl | methyl | |
| 4.550 | 3-tert-butyl-5-propylphenyl | methyl | |
| 4.551 | 3-cyclopropyl-5-propylphenyl | methyl | |
| 4.552 | 3-cyano-5-propylphenyl | methyl | |
| 4.553 | 3-trifluoromethyl-5-propylphenyl | methyl | |
| 4.554 | 3-(methoxycarbonyl)-5-propylphenyl | methyl | |
| 4.555 | 3-methoxy-5-propylphenyl | methyl | |
| 4.556 | 3-ethoxy-5-propylphenyl | methyl | |
| 4.557 | 3-n-propoxy-5-propylphenyl | methyl | |
| 4.558 | 3-n-butoxy-5-propylphenyl | methyl | |
| 4.559 | 3-isobutoxy-5-propylphenyl | methyl | |
| 4.560 | 3-tert-butoxy-5-propylphenyl | methyl | |
| 4.561 | 3-difluoromethoxy-5-propylphenyl | methyl | |
| 4.562 | 3-trifluoromethoxy-5-ethylphenyl | methyl | |
| 4.563 | 3-nitro-5-propylphenyl | methyl | |
| 4.564 | 3-acetoxy-5-propylphenyl | methyl | |
| 4.565 | 3-methylsulfanyl-5-propylphenyl | methyl | |
| 4.566 | 3,5-diisopropylphenyl | methyl | |
| 4.567 | 3-n-butyl-5-isopropylphenyl | methyl | |
| 4.568 | 3-isobutyl-5-isopropylphenyl | methyl | |
| 4.569 | 3-tert-butyl-5-isopropylphenyl | methyl | |
| 4.570 | 3-cyclopropyl-5-isopropylphenyl | methyl | |
| 4.571 | 3-cyano-5-isopropylphenyl | methyl | |
| 4.572 | 3-trifluoromethyl-5-isopropylphenyl | methyl | |
| 4.573 | 3-(methoxycarbonyl)-5-isopropylphenyl | methyl | |
| 4.574 | 3-methoxy-5-isopropylphenyl | methyl | |
| 4.575 | 3-ethoxy-5-isopropylphenyl | methyl | |
| 4.576 | 3-n-propoxy-5-isopropylphenyl | methyl | |
| 4.577 | 3-n-butoxy-5-isopropylphenyl | methyl | |
| 4.578 | 3-isobutoxy-5-isopropylphenyl | methyl | |
| 4.579 | 3-tert-butoxy-5-isopropylphenyl | methyl | |
| 4.580 | 3-difluoromethoxy-5-isopropylphenyl | methyl | |
| 4.581 | 3-trifluoromethoxy-5-isopropylphenyl | methyl | |
| 4.582 | 3-nitro-5-isopropylphenyl | methyl | |
| 4.583 | 3-acetoxy-5-isopropylphenyl | methyl | |
| 4.584 | 3-methylsulfanyl-5-isopropylphenyl | methyl | |
| 4.585 | 3,5-diisobutylphenyl | methyl | |
| 4.586 | 3-tert-butyl-5-isobutylphenyl | methyl | |
| 4.587 | 3-cyclopropyl-5-isobutylphenyl | methyl | |
| 4.588 | 3-cyano-5-isobutylphenyl | methyl | |
| 4.589 | 3-trifluoromethyl-5-isobutylphenyl | methyl | |
| 4.590 | 3-(methoxycarbonyl)-5-isobutylphenyl | methyl | |
| 4.591 | 3-methoxy-5-isobutylphenyl | methyl | |
| 4.592 | 3-ethoxy-5-isobutylphenyl | methyl | |
| 4.593 | 3-n-propoxy-5-isobutylphenyl | methyl | |
| 4.594 | 3-n-butoxy-5-isobutylphenyl | methyl | |
| 4.595 | 3-isobutoxy-5-isobutylphenyl | methyl | |
| 4.596 | 3-tert-butoxy-5-isobutylphenyl | methyl | |
| 4.597 | 3-difluoromethoxy-5-isobutylphenyl | methyl | |
| 4.598 | 3-trifluoromethoxy-5-isobutylphenyl | methyl | |
| 4.599 | 3-nitro-5-isobutylphenyl | methyl | |
| 4.600 | 3-acetoxy-5-isobutylphenyl | methyl | |
| 4.601 | 3-methylsulfanyl-5-isobutylphenyl | methyl | |
| 4.602 | 3-tert-butyl-5-cyclopropylphenyl | methyl | |
| 4.603 | 3,5-dicyclopropylphenyl | methyl | |
| 4.604 | 3-cyano-5-cyclopropylphenyl | methyl | |
| 4.605 | 3-cyano-5-cyclopropylphenyl | ethyl | |
| 4.606 | 3-cyano-5-cyclopropylphenyl | CN | |

TABLE 4-continued

Inventive compounds of the general formula (I) in which W* is CHO, R¹ and R² are each hydrogen, and aryl is the radical.

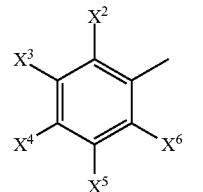

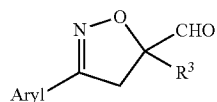

| No. | Aryl | R³ | Physical data |
|---|---|---|---|
| 4.607 | 3-cyano-5-cyclopropylphenyl | vinyl | |
| 4.608 | 3-cyano-5-cyclopropylphenyl | fluoromethyl | |
| 4.609 | 3-cyano-5-cyclopropylphenyl | methylcarbonyl | |
| 4.610 | 3-cyano-5-cyclopropylphenyl | hydroxymethyl | |
| 4.611 | 3-cyano-5-cyclopropylphenyl | ethynyl | |
| 4.612 | 3-trifluoromethyl-5-cyclopropylphenyl | methyl | |
| 4.613 | 3-(methoxycarbonyl)-5-cyclopropylphenyl | methyl | |
| 4.614 | 3-methoxy-5-cyclopropylphenyl | methyl | |
| 4.615 | 3-ethoxy-5-cyclopropylphenyl | methyl | |
| 4.616 | 3-n-propoxy-5-cyclopropylphenyl | methyl | |
| 4.617 | 3-n-butoxy-5-cyclopropylphenyl | methyl | |
| 4.618 | 3-isobutoxy-5-cyclopropylphenyl | methyl | |
| 4.619 | 3-difluoromethoxy-5-cyclopropylphenyl | methyl | |
| 4.620 | 3-trifluoromethoxy-5-cyclopropylphenyl | methyl | |
| 4.621 | 3-nitro-5-cyclopropylphenyl | methyl | |
| 4.622 | 3-acetoxy-5-cyclopropylphenyl | methyl | |
| 4.623 | 3-methylsulfanyl-5-cyclopropylphenyl | methyl | |
| 4.624 | 3,5-dicyanophenyl | methyl | |
| 4.625 | 3-trifluoromethyl-5-cyanophenyl | methyl | |
| 4.626 | 3-(methoxycarbonyl)-5-cyanophenyl | methyl | |
| 4.627 | 3-methoxy-5-cyanophenyl | methyl | |
| 4.628 | 3-ethoxy-5-cyanophenyl | methyl | |
| 4.629 | 3-n-propoxy-5-cyanophenyl | methyl | |
| 4.630 | 3-n-butoxy-5-cyanophenyl | methyl | |
| 4.631 | 3-isobutoxy-5-cyanophenyl | methyl | |
| 4.632 | 3-difluoromethoxy-5-cyanophenyl | methyl | |
| 4.633 | 3-trifluoromethoxy-5-cyanophenyl | methyl | |
| 4.634 | 3-nitro-5-cyanophenyl | methyl | |
| 4.635 | 3-acetoxy-5-cyanophenyl | methyl | |
| 4.636 | 3-methylsulfanyl-5-cyanophenyl | methyl | |
| 4.637 | 3,5-di(trifluoromethyl)phenyl | methyl | |
| 4.638 | 3,5-di(trifluoromethyl)phenyl | ethyl | |
| 4.639 | 3,5-di(trifluoromethyl)phenyl | CN | |
| 4.640 | 3,5-di(trifluoromethyl)phenyl | vinyl | |
| 4.641 | 3,5-di(trifluoromethyl)phenyl | fluoromethyl | |
| 4.642 | 3,5-di(trifluoromethyl)phenyl | methylcarbonyl | |
| 4.643 | 3,5-di(trifluoromethyl)phenyl | hydroxymethyl | |
| 4.644 | 3,5-di(trifluoromethyl)phenyl | ethynyl | |
| 4.645 | 3-(methoxycarbonyl)-5-trifluoromethyl-phenyl | methyl | |
| 4.646 | 3-methoxy-5-trifluoromethylphenyl | methyl | |
| 4.647 | 3-ethoxy-5-trifluoromethylphenyl | methyl | |
| 4.648 | 3-n-propoxy-5-trifluoromethylphenyl | methyl | |
| 4.649 | 3-n-butoxy-5-trifluoromethylphenyl | methyl | |
| 4.650 | 3-isobutoxy-5-trifluoromethylphenyl | methyl | |
| 4.651 | 3-difluoromethoxy-5-trifluoromethylphenyl | methyl | |
| 4.652 | 3-trifluoromethoxy-5-trifluoromethylphenyl | methyl | |
| 4.653 | 3-nitro-5-trifluoromethylphenyl | methyl | |
| 4.654 | 3-acetoxy-5-trifluoromethylphenyl | methyl | |
| 4.655 | 3-methylsulfanyl-5-trifluoromethylphenyl | methyl | |
| 4.656 | 3,5-di(methoxycarbonyl)phenyl | methyl | |
| 4.657 | 3-methoxy-5-(methoxycarbonyl)phenyl | methyl | |
| 4.658 | 3-ethoxy-5-(methoxycarbonyl)phenyl | methyl | |
| 4.659 | 3-n-propoxy-5-(methoxycarbonyl)phenyl | methyl | |
| 4.660 | 3-n-butoxy-5-(methoxycarbonyl)phenyl | methyl | |
| 4.661 | 3-isobutoxy-5-(methoxycarbonyl)phenyl | methyl | |
| 4.662 | 3-difluoromethoxy-5-(methoxycarbonyl)-phenyl | methyl | |

TABLE 4-continued

Inventive compounds of the general formula (I) in which W* is CHO, R¹ and R² are each hydrogen, and aryl is the radical.

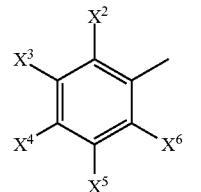

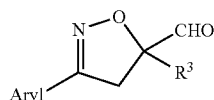

| No. | Aryl | R³ | Physical data |
|---|---|---|---|
| 4.663 | 3-trifluoromethoxy-5-(methoxycarbonyl)-phenyl | methyl | |
| 4.664 | 3-nitro-5-(methoxycarbonyl)phenyl | methyl | |
| 4.665 | 3-acetoxy-5-(methoxycarbonyl)phenyl | methyl | |
| 4.666 | 3-methylsulfanyl-5-(methoxycarbonyl)-phenyl | methyl | |
| 4.667 | 3,5-dimethoxyphenyl | methyl | |
| 4.668 | 3,5-dimethoxyphenyl | ethyl | |
| 4.669 | 3,5-dimethoxyphenyl | CN | |
| 4.670 | 3,5-dimethoxyphenyl | vinyl | |
| 4.671 | 3,5-dimethoxyphenyl | fluoromethyl | |
| 4.672 | 3,5-dimethoxyphenyl | methylcarbonyl | |
| 4.673 | 3,5-dimethoxyphenyl | hydroxymethyl | |
| 4.674 | 3,5-dimethoxyphenyl | ethynyl | |
| 4.675 | 3-ethoxy-5-methoxyphenyl | methyl | |
| 4.676 | 3-n-propoxy-5-methoxyphenyl | methyl | |
| 4.677 | 3-n-butoxy-5-methoxyphenyl | methyl | |
| 4.678 | 3-isobutoxy-5-methoxyphenyl | methyl | |
| 4.679 | 3-difluoromethoxy-5-methoxyphenyl | methyl | |
| 4.680 | 3-trifluoromethoxy-5-methoxyphenyl | methyl | |
| 4.681 | 3-nitro-5-methoxyphenyl | methyl | |
| 4.682 | 3-acetoxy-5-methoxyphenyl | methyl | |
| 4.683 | 3-methylsulfanyl-5-methoxyphenyl | methyl | |
| 4.684 | 3,5-diethoxyphenyl | methyl | |
| 4.685 | 3-n-propoxy-5-ethoxyphenyl | methyl | |
| 4.686 | 3-n-butoxy-5-ethoxyphenyl | methyl | |
| 4.687 | 3-isobutoxy-5-ethoxyphenyl | methyl | |
| 4.688 | 3-tert-butoxy-5-ethoxyphenyl | methyl | |
| 4.689 | 3-difluoromethoxy-5-ethoxyphenyl | methyl | |
| 4.690 | 3-trifluoromethoxy-5-ethoxyphenyl | methyl | |
| 4.691 | 3-nitro-5-ethoxyphenyl | methyl | |
| 4.692 | 3-acetoxy-5-ethoxyphenyl | methyl | |
| 4.693 | 3-methylsulfanyl-5-ethoxyphenyl | methyl | |
| 4.694 | 3,5-di(trifluoromethoxy)phenyl | methyl | |
| 4.695 | 3-nitro-5-trifluoromethoxyphenyl | methyl | |
| 4.696 | 3-methylsulfanyl-5-trifluoromethoxy-phenyl | methyl | |
| 4.697 | 3,5-bis(difluoromethoxy)phenyl | methyl | |
| 4.698 | 3-trifluoromethoxy-5-difluoromethoxy-phenyl | methyl | |
| 4.699 | 3-nitro-5-difluoromethoxyphenyl | methyl | |
| 4.700 | 3-acetoxy-5-difluoromethoxyphenyl | methyl | |
| 4.701 | 3-methylsulfanyl-5-difluoromethoxy-phenyl | methyl | |
| 4.702 | 3-methylsulfanyl-5-acetoxyphenyl | methyl | |
| 4.703 | 3-acetoxy-5-nitrophenyl | methyl | |
| 4.704 | 3-methylsulfanyl-5-nitrophenyl | methyl | |
| 4.705 | 3,5-di(methylsulfanyl)phenyl | methyl | |
| 4.706 | 3,4-difluorophenyl | methyl | |
| 4.707 | 3,4-difluorophenyl | ethyl | |
| 4.708 | 3,4-difluorophenyl | CN | |
| 4.709 | 3,4-difluorophenyl | vinyl | |
| 4.710 | 3,4-difluorophenyl | fluoromethyl | |
| 4.711 | 3,4-difluorophenyl | methylcarbonyl | |
| 4.712 | 3,4-difluorophenyl | hydroxymethyl | |
| 4.713 | 3,4-difluorophenyl | ethynyl | |
| 4.714 | 3-chloro-4-fluorophenyl | methyl | |
| 4.715 | 3-bromo-4-fluorophenyl | methyl | |
| 4.716 | 3-methyl-4-fluorophenyl | methyl | |

TABLE 4-continued

Inventive compounds of the general formula (I) in which W* is CHO, $R^1$ and $R^2$ are each hydrogen, and aryl is the radical.

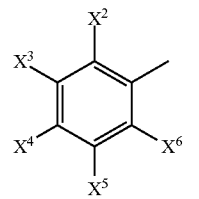

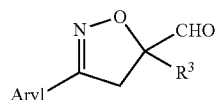

| No. | Aryl | $R^3$ | Physical data |
|---|---|---|---|
| 4.717 | 3-methyl-4-fluorophenyl | ethyl | |
| 4.718 | 3-methyl-4-fluorophenyl | CN | |
| 4.719 | 3-methyl-4-fluorophenyl | vinyl | |
| 4.720 | 3-methyl-4-fluorophenyl | fluoromethyl | |
| 4.721 | 3-methyl-4-fluorophenyl | methylcarbonyl | |
| 4.722 | 3-methyl-4-fluorophenyl | hydroxymethyl | |
| 4.723 | 3-methyl-4-fluorophenyl | ethynyl | |
| 4.724 | 3-ethyl-4-fluorophenyl | methyl | |
| 4.725 | 3-cyclopropyl-4-fluorophenyl | methyl | |
| 4.726 | 3-cyano-4-fluorophenyl | methyl | |
| 4.727 | 3-methoxy-4-fluorophenyl | methyl | |
| 4.728 | 3-ethoxy-4-fluorophenyl | methyl | |
| 4.729 | 3-trifluoromethoxy-4-fluorophenyl | methyl | |
| 4.730 | 3-nitro-4-fluorophenyl | methyl | |
| 4.731 | 3-fluoro-4-chlorophenyl | methyl | |
| 4.732 | 3,4-dichlorophenyl | methyl | |
| 4.733 | 3-bromo-4-chlorophenyl | methyl | |
| 4.734 | 3-methyl-4-chlorophenyl | methyl | |
| 4.735 | 3-cyclopropyl-4-chlorophenyl | methyl | |
| 4.736 | 3-cyano-4-chlorophenyl | methyl | |
| 4.737 | 3-trifluoromethyl-4-chlorophenyl | methyl | |
| 4.738 | 3-methoxy-4-chlorophenyl | methyl | |
| 4.739 | 3-ethoxy-4-chlorophenyl | methyl | |
| 4.740 | 3-trifluoromethoxy-4-chlorophenyl | methyl | |
| 4.741 | 3-nitro-4-chlorophenyl | methyl | |
| 4.742 | 3-fluoro-4-bromophenyl | methyl | |
| 4.743 | 3-chloro-4-bromophenyl | methyl | |
| 4.744 | 3,4-dibromophenyl | methyl | |
| 4.745 | 3-methyl-4-bromophenyl | methyl | |
| 4.746 | 3-cyclopropyl-4-bromophenyl | methyl | |
| 4.747 | 3-cyano-4-bromophenyl | methyl | |
| 4.748 | 3-trifluoromethyl-4-bromophenyl | methyl | |
| 4.749 | 3-methoxy-4-phenyl | methyl | |
| 4.750 | 3-ethoxy-4-bromophenyl | methyl | |
| 4.751 | 3-trifluoromethoxy-4-bromophenyl | methyl | |
| 4.752 | 3-nitro-4-bromophenyl | methyl | |
| 4.753 | 3-fluoro-4-iodophenyl | methyl | |
| 4.754 | 3-chloro-4-iodophenyl | methyl | |
| 4.755 | 3-bromo-4-iodophenyl | methyl | |
| 4.756 | 3-methyl-4-iodophenyl | methyl | |
| 4.757 | 3-cyclopropyl-4-iodophenyl | methyl | |
| 4.758 | 3-cyano-4-iodophenyl | methyl | |
| 4.759 | 3-trifluoromethyl-4-iodophenyl | methyl | |
| 4.760 | 3-methoxy-4-iodophenyl | methyl | |
| 4.761 | 3-ethoxy-4-iodophenyl | methyl | |
| 4.762 | 3-trifluoromethoxy-4-iodophenyl | methyl | |
| 4.763 | 3-nitro-4-iodophenyl | methyl | |
| 4.764 | 3-fluoro-4-methylphenyl | methyl | |
| 4.765 | 3-chloro-4-methylphenyl | methyl | |
| 4.766 | 3-chloro-4-methylphenyl | ethyl | |
| 4.767 | 3-chloro-4-methylphenyl | CN | |
| 4.768 | 3-chloro-4-methylphenyl | vinyl | |
| 4.769 | 3-chloro-4-methylphenyl | fluoromethyl | |
| 4.770 | 3-chloro-4-methylphenyl | methylcarbonyl | |
| 4.771 | 3-chloro-4-methylphenyl | hydroxymethyl | |
| 4.772 | 3-chloro-4-methylphenyl | ethynyl | |
| 4.773 | 3-bromo-4-methylphenyl | methyl | |
| 4.774 | 3,4-dimethylphenyl | methyl | |
| 4.775 | 3-ethyl-4-methylphenyl | methyl | |

TABLE 4-continued

Inventive compounds of the general formula (I) in which W* is CHO, $R^1$ and $R^2$ are each hydrogen, and aryl is the radical.

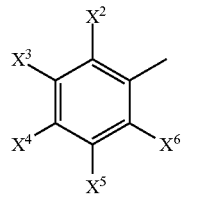

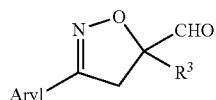

| No. | Aryl | $R^3$ | Physical data |
|---|---|---|---|
| 4.776 | 3-cyclopropyl-4-methylphenyl | methyl | |
| 4.777 | 3-cyano-4-methylphenyl | methyl | |
| 4.778 | 3-trifluoromethyl-4-methylphenyl | methyl | |
| 4.779 | 3-methoxy-4-methylphenyl | methyl | |
| 4.780 | 3-ethoxy-4-methylphenyl | methyl | |
| 4.781 | 3-trifluoromethoxy-4-methylphenyl | methyl | |
| 4.782 | 3-nitro-4-methylphenyl | methyl | |
| 4.783 | 3-fluoro-4-ethylphenyl | methyl | |
| 4.784 | 3-chloro-4-ethylphenyl | methyl | |
| 4.785 | 3-bromo-4-ethylphenyl | methyl | |
| 4.786 | 3-methyl-4-ethylphenyl | methyl | |
| 4.787 | 3,4-diethylphenyl | methyl | |
| 4.788 | 3-cyclopropyl-4-ethylphenyl | methyl | |
| 4.789 | 3-cyano-4-ethylphenyl | methyl | |
| 4.790 | 3-trifluoromethyl-4-ethylphenyl | methyl | |
| 4.791 | 3-methoxy-4-ethylphenyl | methyl | |
| 4.792 | 3-ethoxy-4-ethylphenyl | methyl | |
| 4.793 | 3-trifluoromethoxy-4-ethylphenyl | methyl | |
| 4.794 | 3-nitro-4-ethylphenyl | methyl | |
| 4.795 | 3-fluoro-4-propylphenyl | methyl | |
| 4.796 | 3-chloro-4-propylphenyl | methyl | |
| 4.797 | 3-bromo-4-propylphenyl | methyl | |
| 4.798 | 3-methyl-4-propylphenyl | methyl | |
| 4.799 | 3-cyclopropyl-4-propylphenyl | methyl | |
| 4.800 | 3-cyano-4-propylphenyl | methyl | |
| 4.801 | 3-trifluoromethyl-4-propylphenyl | methyl | |
| 4.802 | 3-methoxy-4-propylphenyl | methyl | |
| 4.803 | 3-ethoxy-4-propylphenyl | methyl | |
| 4.804 | 3-trifluoromethoxy-4-propylphenyl | methyl | |
| 4.805 | 3-nitro-4-propylphenyl | methyl | |
| 4.806 | 3-fluoro-4-isopropylphenyl | methyl | |
| 4.807 | 3-chloro-4-isopropylphenyl | methyl | |
| 4.808 | 3-bromo-4-isopropylphenyl | methyl | |
| 4.809 | 3-methyl-4-isopropylphenyl | methyl | |
| 4.810 | 3-cyclopropyl-4-isopropylphenyl | methyl | |
| 4.811 | 3-cyano-4-isopropylphenyl | methyl | |
| 4.812 | 3-trifluoromethyl-4-isopropylphenyl | methyl | |
| 4.813 | 3-methoxy-4-isopropylphenyl | methyl | |
| 4.814 | 3-ethoxy-4-isopropylphenyl | methyl | |
| 4.815 | 3-trifluoromethoxy-4-isopropylphenyl | methyl | |
| 4.816 | 3-nitro-4-isopropylphenyl | methyl | |
| 4.817 | 3-fluoro-4-tert-butylphenyl | methyl | |
| 4.818 | 3-fluoro-4-tert-butylphenyl | ethyl | |
| 4.819 | 3-fluoro-4-tert-butylphenyl | CN | |
| 4.820 | 3-fluoro-4-tert-butylphenyl | vinyl | |
| 4.821 | 3-fluoro-4-tert-butylphenyl | fluoromethyl | |
| 4.822 | 3-fluoro-4-tert-butylphenyl | methylcarbonyl | |
| 4.823 | 3-fluoro-4-tert-butylphenyl | hydroxymethyl | |
| 4.824 | 3-fluoro-4-tert-butylphenyl | ethynyl | |
| 4.825 | 3-chloro-4-tert-butylphenyl | methyl | |
| 4.826 | 3-bromo-4-tert-butylphenyl | methyl | |
| 4.827 | 3-methyl-4-tert-butylphenyl | methyl | |
| 4.828 | 3-cyclopropyl-4-tert-butylphenyl | methyl | |
| 4.829 | 3-cyano-4-tert-butylphenyl | methyl | |
| 4.830 | 3-trifluoromethyl-4-tert-butylphenyl | methyl | |
| 4.831 | 3-methoxy-4-tert-butylphenyl | methyl | |
| 4.832 | 3-ethoxy-4-tert-butylphenyl | methyl | |
| 4.833 | 3-trifluoromethoxy-4-tert-butylphenyl | methyl | |
| 4.834 | 3-nitro-4-tert-butylphenyl | methyl | |

TABLE 4-continued

Inventive compounds of the general formula (I) in which W* is CHO, R¹ and R² are each hydrogen, and aryl is the radical.

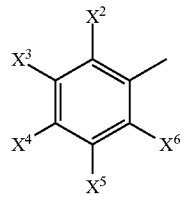

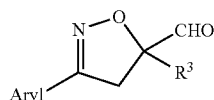

| No. | Aryl | R³ | Physical data |
|---|---|---|---|
| 4.835 | 3-fluoro-4-cyclopropylphenyl | methyl | |
| 4.836 | 3-chloro-4-cyclopropylphenyl | methyl | |
| 4.837 | 3-bromo-4-cyclopropylphenyl | methyl | |
| 4.838 | 3-methyl-4-cyclopropylphenyl | methyl | |
| 4.839 | 3-cyclopropyl-4-cyclopropylphenyl | methyl | |
| 4.840 | 3-cyano-4-cyclopropylphenyl | methyl | |
| 4.841 | 3-trifluoromethyl-4-cyclopropylphenyl | methyl | |
| 4.842 | 3-methoxy-4-cyclopropylphenyl | methyl | |
| 4.843 | 3-ethoxy-4-cyclopropylphenyl | methyl | |
| 4.844 | 3-trifluoromethoxy-4-cyclopropylphenyl | methyl | |
| 4.845 | 3-fluoro-4-methoxycarbonylphenyl | methyl | |
| 4.846 | 3-chloro-4-methoxycarbonylphenyl | methyl | |
| 4.847 | 3-bromo-4-methoxycarbonylphenyl | methyl | |
| 4.848 | 3-methyl-4-methoxycarbonylphenyl | methyl | |
| 4.849 | 3-cyclopropyl-4-methoxycarbonylphenyl | methyl | |
| 4.850 | 3-cyano-4-methoxycarbonylphenyl | methyl | |
| 4.851 | 3-trifluoromethyl-4-methoxycarbonylphenyl | methyl | |
| 4.852 | 3-methoxy-4-methoxycarbonylphenyl | methyl | |
| 4.853 | 3-ethoxy-4-methoxycarbonylphenyl | methyl | |
| 4.854 | 3-trifluoromethoxy-4-methoxycarbonylphenyl | methyl | |
| 4.855 | 3-nitro-4-methoxycarbonylphenyl | methyl | |
| 4.856 | 3-fluoro-4-cyanophenyl | methyl | |
| 4.857 | 3-chloro-4-cyanophenyl | methyl | |
| 4.858 | 3-bromo-4-cyanophenyl | methyl | |
| 4.859 | 3-methyl-4-cyanophenyl | methyl | |
| 4.860 | 3-cyclopropyl-4-cyanophenyl | methyl | |
| 4.861 | 3-cyano-4-cyanophenyl | methyl | |
| 4.862 | 3-trifluoromethyl-4-cyanophenyl | methyl | |
| 4.863 | 3-methoxy-4-cyanophenyl | methyl | |
| 4.864 | 3-ethoxy-4-cyanophenyl | methyl | |
| 4.865 | 3-trifluoromethoxy-4-cyanophenyl | methyl | |
| 4.866 | 3-nitro-4-cyanophenyl | methyl | |
| 4.867 | 3-fluoro-4-methoxyphenyl | methyl | |
| 4.868 | 3-chloro-4-methoxyphenyl | methyl | |
| 4.869 | 3-bromo-4-methoxyphenyl | methyl | |
| 4.870 | 3-methyl-4-methoxyphenyl | methyl | |
| 4.871 | 3-cyclopropyl-4-methoxyphenyl | methyl | |
| 4.872 | 3-cyano-4-methoxyphenyl | methyl | |
| 4.873 | 3-trifluoromethyl-4-methoxyphenyl | methyl | |
| 4.874 | 3,4-dimethoxyphenyl | methyl | |
| 4.875 | 3-ethoxy-4-methoxyphenyl | methyl | |
| 4.876 | 3-trifluoromethoxy-4-methoxyphenyl | methyl | |
| 4.877 | 3-nitro-4-methoxyphenyl | methyl | |
| 4.878 | 3-fluoro-4-ethoxyphenyl | methyl | |
| 4.879 | 3-chloro-4-ethoxyphenyl | methyl | |
| 4.880 | 3-bromo-4-ethoxyphenyl | methyl | |
| 4.881 | 3-methyl-4-ethoxyphenyl | methyl | |
| 4.882 | 3-cyclopropyl-4-ethoxyphenyl | methyl | |
| 4.883 | 3-cyano-4-ethoxyphenyl | methyl | |
| 4.884 | 3-trifluoromethyl-4-ethoxyphenyl | methyl | |
| 4.885 | 3-methoxy-4-ethoxyphenyl | methyl | |
| 4.886 | 2,4-diethoxyphenyl | methyl | |
| 4.887 | 3-trifluoromethoxy-4-ethoxyphenyl | methyl | |
| 4.888 | 3-nitro-4-ethoxyphenyl | methyl | |
| 4.889 | 3-fluoro-4-isopropoxyphenyl | methyl | |
| 4.890 | 3-chloro-4-isopropoxyphenyl | methyl | |
| 4.891 | 3-bromo-4-isopropoxyphenyl | methyl | |

TABLE 4-continued

Inventive compounds of the general formula (I) in which W* is CHO, $R^1$ and $R^2$ are each hydrogen, and aryl is the radical.

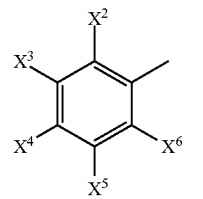

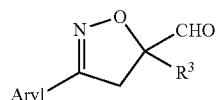

| No. | Aryl | $R^3$ | Physical data |
|---|---|---|---|
| 4.892 | 3-methyl-4-isopropoxyphenyl | methyl | |
| 4.893 | 3-cyclopropyl-4-isopropoxyphenyl | methyl | |
| 4.894 | 3-cyano-4-isopropoxyphenyl | methyl | |
| 4.895 | 3-trifluoromethyl-4-isopropoxyphenyl | methyl | |
| 4.896 | 3-methoxy-4-isopropoxyphenyl | methyl | |
| 4.897 | 3-ethoxy-4-isopropoxyphenyl | methyl | |
| 4.898 | 3-trifluoromethoxy-4-isopropoxyphenyl | methyl | |
| 4.899 | 3-nitro-4-isopropoxyphenyl | methyl | |
| 4.900 | 3-fluoro-4-trifluoromethoxyphenyl | methyl | |
| 4.901 | 3-chloro-4-trifluoromethoxyphenyl | methyl | |
| 4.902 | 3-bromo-4-trifluoromethoxyphenyl | methyl | |
| 4.903 | 3-methyl-4-trifluoromethoxyphenyl | methyl | |
| 4.904 | 3-cyclopropyl-4-trifluoromethoxyphenyl | methyl | |
| 4.905 | 3-cyano-4-trifluoromethoxyphenyl | methyl | |
| 4.906 | 3-trifluoromethyl-4-trifluoromethoxy-phenyl | methyl | |
| 4.907 | 3-methoxy-4-trifluoromethoxyphenyl | methyl | |
| 4.908 | 3-ethoxy-4-trifluoromethoxyphenyl | methyl | |
| 4.909 | 3,4-bis(trifluoromethoxy)phenyl | methyl | |
| 4.910 | 3-nitro-4-trifluoromethoxyphenyl | methyl | |
| 4.911 | 3-fluoro-4-difluoromethoxyphenyl | methyl | |
| 4.912 | 3-chloro-4-difluoromethoxyphenyl | methyl | |
| 4.913 | 3-bromo-4-difluoromethoxyphenyl | methyl | |
| 4.914 | 3-methyl-4-difluoromethoxyphenyl | methyl | |
| 4.915 | 3-cyclopropyl-4-difluoromethoxyphenyl | methyl | |
| 4.916 | 3-cyano-4-difluoromethoxyphenyl | methyl | |
| 4.917 | 3-trifluoromethyl-4-difluoromethoxyphenyl | methyl | |
| 4.918 | 3-methoxy-4-difluoromethoxyphenyl | methyl | |
| 4.919 | 3-ethoxy-4-difluoromethoxyphenyl | methyl | |
| 4.920 | 3-trifluoromethoxy-4-difluoromethoxy-phenyl | methyl | |
| 4.921 | 3-nitro-4-difluoromethoxyphenyl | methyl | |
| 4.922 | 3-fluoro-4-nitrophenyl | methyl | |
| 4.923 | 3-chloro-4-nitrophenyl | methyl | |
| 4.924 | 3-bromo-4-nitrophenyl | methyl | |
| 4.925 | 3-methyl-4-nitrophenyl | methyl | |
| 4.926 | 3-cyclopropyl-4-nitrophenyl | methyl | |
| 4.927 | 3-cyano-4-nitrophenyl | methyl | |
| 4.928 | 3-trifluoromethyl-4-nitrophenyl | methyl | |
| 4.929 | 3-methoxy-4-nitrophenyl | methyl | |
| 4.930 | 3-ethoxy-4-nitrophenyl | methyl | |
| 4.931 | 3-trifluoromethoxy-4-nitrophenyl | methyl | |
| 4.932 | 3-fluoro-4-methylsulfanylphenyl | methyl | |
| 4.933 | 3-chloro-4-methylsulfanylphenyl | methyl | |
| 4.934 | 3-bromo-4-methylsulfanylphenyl | methyl | |
| 4.935 | 3-methyl-4-methylsulfanylphenyl | methyl | |
| 4.936 | 3-cyclopropyl-4-methylsulfanylphenyl | methyl | |
| 4.937 | 3-cyano-4-methylsulfanylphenyl | methyl | |
| 4.938 | 3-trifluoromethyl-4-methylsulfanylphenyl | methyl | |
| 4.939 | 3-methoxy-4-methylsulfanylphenyl | methyl | |
| 4.940 | 3-ethoxy-4-methylsulfanylphenyl | methyl | |
| 4.941 | 3-trifluoromethoxy-4-methylsulfanylphenyl | methyl | |
| 4.942 | 3-nitro-4-methylsulfanylphenyl | methyl | |
| 4.943 | 3,6-difluorophenyl | methyl | |
| 4.944 | 3,6-difluorophenyl | ethyl | |
| 4.945 | 3,6-difluorophenyl | CN | |
| 4.946 | 3,6-difluorophenyl | vinyl | |
| 4.947 | 3,6-difluorophenyl | fluoromethyl | |
| 4.948 | 3,6-difluorophenyl | methylcarbonyl | |

TABLE 4-continued

Inventive compounds of the general formula (I) in which W* is CHO, $R^1$ and $R^2$ are each hydrogen, and aryl is the radical.

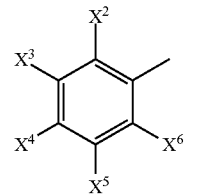

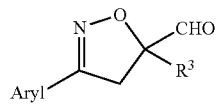

| No. | Aryl | $R^3$ | Physical data |
|---|---|---|---|
| 4.949 | 3,6-difluorophenyl | hydroxymethyl | |
| 4.950 | 3,6-difluorophenyl | ethynyl | |
| 4.951 | 3-chloro-6-fluorophenyl | methyl | |
| 4.952 | 3-bromo-6-fluorophenyl | methyl | |
| 4.953 | 3-methyl-6-fluorophenyl | methyl | |
| 4.954 | 3-cyclopropyl-6-fluorophenyl | methyl | |
| 4.955 | 3-cyano-6-fluorophenyl | methyl | |
| 4.956 | 3-methoxy-6-fluorophenyl | methyl | |
| 4.957 | 3-ethoxy-6-fluorophenyl | methyl | |
| 4.958 | 3-trifluoromethoxy-6-fluorophenyl | methyl | |
| 4.959 | 3-nitro-6-fluorophenyl | methyl | |
| 4.960 | 3-fluoro-6-chlorophenyl | methyl | |
| 4.961 | 3,6-dichlorophenyl | methyl | |
| 4.962 | 3-bromo-6-chlorophenyl | methyl | |
| 4.963 | 3-methyl-6-chlorophenyl | methyl | |
| 4.964 | 3-cyclopropyl-6-chlorophenyl | methyl | |
| 4.965 | 3-cyano-6-chlorophenyl | methyl | |
| 4.966 | 3-trifluoromethyl-6-chlorophenyl | methyl | |
| 4.967 | 3-methoxy-6-chlorophenyl | methyl | |
| 4.968 | 3-ethoxy-6-chlorophenyl | methyl | |
| 4.969 | 3-trifluoromethoxy-6-chlorophenyl | methyl | |
| 4.970 | 3-nitro-6-chlorophenyl | methyl | |
| 4.971 | 3-fluoro-6-bromophenyl | methyl | |
| 4.972 | 3-chloro-6-bromophenyl | methyl | |
| 4.973 | 3,6-dibromophenyl | methyl | |
| 4.974 | 3-methyl-6-bromophenyl | methyl | |
| 4.975 | 3-cyclopropyl-6-bromophenyl | methyl | |
| 4.976 | 3-cyano-6-bromophenyl | methyl | |
| 4.977 | 3-trifluoromethyl-6-bromophenyl | methyl | |
| 4.978 | 3-methoxy-6-phenyl | methyl | |
| 4.979 | 3-ethoxy-6-bromophenyl | methyl | |
| 4.980 | 3-trifluoromethoxy-6-bromophenyl | methyl | |
| 4.981 | 3-nitro-6-bromophenyl | methyl | |
| 4.982 | 3-fluoro-6-iodophenyl | methyl | |
| 4.983 | 3-chloro-6-iodophenyl | methyl | |
| 4.984 | 3-bromo-6-iodophenyl | methyl | |
| 4.985 | 3-methyl-6-iodophenyl | methyl | |
| 4.986 | 3-ethyl-6-iodophenyl | methyl | |
| 4.987 | 3-cyclopropyl-6-iodophenyl | methyl | |
| 4.988 | 3-cyano-6-iodophenyl | methyl | |
| 4.989 | 3-trifluoromethyl-6-iodophenyl | methyl | |
| 4.990 | 3-methoxy-6-iodophenyl | methyl | |
| 4.991 | 3-ethoxy-6-iodophenyl | methyl | |
| 4.992 | 3-trifluoromethoxy-6-iodophenyl | methyl | |
| 4.993 | 3-nitro-6-iodophenyl | methyl | |
| 4.994 | 3-fluoro-6-methylphenyl | methyl | |
| 4.995 | 3-chloro-6-methylphenyl | methyl | |
| 4.996 | 3-bromo-6-methylphenyl | methyl | |
| 4.997 | 3,6-dimethylphenyl | methyl | |
| 4.998 | 3,6-dimethylphenyl | ethyl | |
| 4.999 | 3,6-dimethylphenyl | CN | |
| 4.1000 | 3,6-dimethylphenyl | vinyl | |
| 4.1001 | 3,6-dimethylphenyl | fluoromethyl | |
| 4.1002 | 3,6-dimethylphenyl | methylcarbonyl | |
| 4.1003 | 3,6-dimethylphenyl | hydroxymethyl | |
| 4.1004 | 3,6-dimethylphenyl | ethynyl | |
| 4.1005 | 3-cyclopropyl-6-methylphenyl | methyl | |
| 4.1006 | 3-cyano-6-methylphenyl | methyl | |
| 4.1007 | 3-trifluoromethyl-6-methylphenyl | methyl | |

TABLE 4-continued

Inventive compounds of the general formula (I) in which W* is CHO, R¹ and R² are each hydrogen, and aryl is the radical.

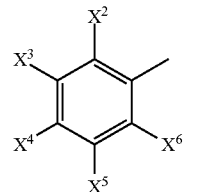

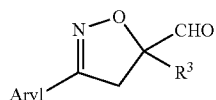

| No. | Aryl | R³ | Physical data |
|---|---|---|---|
| 4.1008 | 3-methoxy-6-methylphenyl | methyl | |
| 4.1009 | 3-ethoxy-6-methylphenyl | methyl | |
| 4.1010 | 3-trifluoromethoxy-6-methylphenyl | methyl | |
| 4.1011 | 3-nitro-6-methylphenyl | methyl | |
| 4.1012 | 3-fluoro-6-ethylphenyl | methyl | |
| 4.1013 | 3-chloro-6-ethylphenyl | methyl | |
| 4.1014 | 3-bromo-6-ethylphenyl | methyl | |
| 4.1015 | 3-methyl-6-ethylphenyl | methyl | |
| 4.1016 | 3,6-diethylphenyl | methyl | |
| 4.1017 | 3-cyclopropyl-6-ethylphenyl | methyl | |
| 4.1018 | 3-cyano-6-ethylphenyl | methyl | |
| 4.1019 | 3-trifluoromethyl-6-ethylphenyl | methyl | |
| 4.1020 | 3-methoxy-6-ethylphenyl | methyl | |
| 4.1021 | 3-ethoxy-6-ethylphenyl | methyl | |
| 4.1022 | 3-trifluoromethoxy-6-ethylphenyl | methyl | |
| 4.1023 | 3-nitro-6-ethylphenyl | methyl | |
| 4.1024 | 3-fluoro-6-isopropylphenyl | methyl | |
| 4.1025 | 3-chloro-6-isopropylphenyl | methyl | |
| 4.1026 | 3-bromo-6-isopropylphenyl | methyl | |
| 4.1027 | 3-methyl-6-isopropylphenyl | methyl | |
| 4.1028 | 3-cyclopropyl-6-isopropylphenyl | methyl | |
| 4.1029 | 3-cyano-6-isopropylphenyl | methyl | |
| 4.1030 | 3-trifluoromethyl-6-isopropylphenyl | methyl | |
| 4.1031 | 3-methoxy-6-isopropylphenyl | methyl | |
| 4.1032 | 3-ethoxy-6-isopropylphenyl | methyl | |
| 4.1033 | 3-trifluoromethoxy-6-isopropylphenyl | methyl | |
| 4.1034 | 3-nitro-6-isopropylphenyl | methyl | |
| 4.1035 | 3-fluoro-6-tert-butylphenyl | methyl | |
| 4.1036 | 3-chloro-6-tert-butylphenyl | methyl | |
| 4.1037 | 3-bromo-6-tert-butylphenyl | methyl | |
| 4.1038 | 3-methyl-6-tert-butylphenyl | methyl | |
| 4.1039 | 3-ethyl-6-tert-butylphenyl | methyl | |
| 4.1040 | 3-cyclopropyl-6-tert-butylphenyl | methyl | |
| 4.1041 | 3-cyano-6-tert-butylphenyl | methyl | |
| 4.1042 | 3-trifluoromethyl-6-tert-butylphenyl | methyl | |
| 4.1043 | 3-methoxy-6-tert-butylphenyl | methyl | |
| 4.1044 | 3-ethoxy-6-tert-butylphenyl | methyl | |
| 4.1045 | 3-trifluoromethoxy-6-tert-butylphenyl | methyl | |
| 4.1046 | 3-nitro-6-tert-butylphenyl | methyl | |
| 4.1047 | 3-fluoro-6-cyclopropylphenyl | methyl | |
| 4.1048 | 3-chloro-6-cyclopropylphenyl | methyl | |
| 4.1049 | 3-bromo-6-cyclopropylphenyl | methyl | |
| 4.1050 | 3-methyl-6-cyclopropylphenyl | methyl | |
| 4.1051 | 3-cyclopropyl-6-cyclopropylphenyl | methyl | |
| 4.1052 | 3-cyano-6-cyclopropylphenyl | methyl | |
| 4.1053 | 3-trifluoromethyl-6-cyclopropylphenyl | methyl | |
| 4.1054 | 3-methoxy-6-cyclopropylphenyl | methyl | |
| 4.1055 | 3-ethoxy-6-cyclopropylphenyl | methyl | |
| 4.1056 | 3-trifluoromethoxy-6-cyclopropylphenyl | methyl | |
| 4.1057 | 3-fluoro-6-methoxycarbonylphenyl | methyl | |
| 4.1058 | 3-chloro-6-methoxycarbonylphenyl | methyl | |
| 4.1059 | 3-bromo-6-methoxycarbonylphenyl | methyl | |
| 4.1060 | 3-methyl-6-methoxycarbonylphenyl | methyl | |
| 4.1061 | 3-cyclopropyl-6-methoxycarbonylphenyl | methyl | |
| 4.1062 | 3-cyano-6-methoxycarbonylphenyl | methyl | |
| 4.1063 | 3-trifluoromethyl-6-methoxycarbonyl-phenyl | methyl | |
| 4.1064 | 3-methoxy-6-methoxycarbonylphenyl | methyl | |
| 4.1065 | 3-ethoxy-6-methoxycarbonylphenyl | methyl | |

TABLE 4-continued

Inventive compounds of the general formula (I) in which W* is CHO, $R^1$ and $R^2$ are each hydrogen, and aryl is the radical.

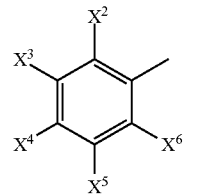

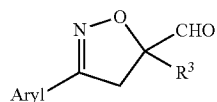

| No. | Aryl | $R^3$ | Physical data |
|---|---|---|---|
| 4.1066 | 3-trifluoromethoxy-6-methoxycarbonyl-phenyl | methyl | |
| 4.1067 | 3-nitro-6-methoxycarbonylphenyl | methyl | |
| 4.1068 | 3-fluoro-6-cyanophenyl | methyl | |
| 4.1069 | 3-chloro-6-cyanophenyl | methyl | |
| 4.1070 | 3-bromo-6-cyanophenyl | methyl | |
| 4.1071 | 3-methyl-6-cyanophenyl | methyl | |
| 4.1072 | 3-cyclopropyl-6-cyanophenyl | methyl | |
| 4.1073 | 3-cyano-6-cyanophenyl | methyl | |
| 4.1074 | 3-trifluoromethyl-6-cyanophenyl | methyl | |
| 4.1075 | 3-methoxy-6-cyanophenyl | methyl | |
| 4.1076 | 3-ethoxy-6-cyanophenyl | methyl | |
| 4.1077 | 3-trifluoromethoxy-6-cyanophenyl | methyl | |
| 4.1078 | 3-nitro-6-cyanophenyl | methyl | |
| 4.1079 | 3-fluoro-6-methoxyphenyl | methyl | |
| 4.1080 | 3-chloro-6-methoxyphenyl | methyl | |
| 4.1081 | 3-bromo-6-methoxyphenyl | methyl | |
| 4.1082 | 3-methyl-6-methoxyphenyl | methyl | |
| 4.1083 | 3-cyclopropyl-6-methoxyphenyl | methyl | |
| 4.1084 | 3-cyano-6-methoxyphenyl | methyl | |
| 4.1085 | 3-trifluoromethyl-6-methoxyphenyl | methyl | |
| 4.1086 | 3,6-dimethoxyphenyl | methyl | |
| 4.1087 | 3-ethoxy-6-methoxyphenyl | methyl | |
| 4.1088 | 3-trifluoromethoxy-6-methoxyphenyl | methyl | |
| 4.1089 | 3-nitro-6-methoxyphenyl | methyl | |
| 4.1090 | 3-fluoro-6-ethoxyphenyl | methyl | |
| 4.1091 | 3-chloro-6-ethoxyphenyl | methyl | |
| 4.1092 | 3-bromo-6-ethoxyphenyl | methyl | |
| 4.1093 | 3-methyl-6-ethoxyphenyl | methyl | |
| 4.1094 | 3-cyclopropyl-6-ethoxyphenyl | methyl | |
| 4.1095 | 3-cyano-6-ethoxyphenyl | methyl | |
| 4.1096 | 3-trifluoromethyl-6-ethoxyphenyl | methyl | |
| 4.1097 | 3-methoxy-6-ethoxyphenyl | methyl | |
| 4.1098 | 2,6-diethoxyphenyl | methyl | |
| 4.1099 | 3-trifluoromethoxy-6-ethoxyphenyl | methyl | |
| 4.1100 | 3-nitro-6-ethoxyphenyl | methyl | |
| 4.1101 | 3-fluoro-6-isopropoxyphenyl | methyl | |
| 4.1102 | 3-chloro-6-isopropoxyphenyl | methyl | |
| 4.1103 | 3-bromo-6-isopropoxyphenyl | methyl | |
| 4.1104 | 3-methyl-6-isopropoxyphenyl | methyl | |
| 4.1105 | 3-cyclopropyl-6-isopropoxyphenyl | methyl | |
| 4.1106 | 3-cyano-6-isopropoxyphenyl | methyl | |
| 4.1107 | 3-trifluoromethyl-6-isopropoxyphenyl | methyl | |
| 4.1108 | 3-methoxy-6-isopropoxyphenyl | methyl | |
| 4.1109 | 3-ethoxy-6-isopropoxyphenyl | methyl | |
| 4.1110 | 3-trifluoromethoxy-6-isopropoxyphenyl | methyl | |
| 4.1111 | 3-nitro-6-isopropoxyphenyl | methyl | |
| 4.1112 | 3-fluoro-6-trifluoromethoxyphenyl | methyl | |
| 4.1113 | 3-chloro-6-trifluoromethoxyphenyl | methyl | |
| 4.1114 | 3-bromo-6-trifluoromethoxyphenyl | methyl | |
| 4.1115 | 3-methyl-6-trifluoromethoxyphenyl | methyl | |
| 4.1116 | 3-cyclopropyl-6-trifluoromethoxyphenyl | methyl | |
| 4.1117 | 3-cyano-6-trifluoromethoxyphenyl | methyl | |
| 4.1118 | 3-trifluoromethyl-6-trifluoromethoxy-phenyl | methyl | |
| 4.1119 | 3-methoxy-6-trifluoromethoxyphenyl | methyl | |
| 4.1120 | 3-ethoxy-6-trifluoromethoxyphenyl | methyl | |
| 4.1121 | 3,6-bis(trifluoromethoxy)phenyl | methyl | |
| 4.1122 | 3-nitro-6-trifluoromethoxyphenyl | methyl | |

TABLE 4-continued

Inventive compounds of the general formula (I) in which W* is CHO, $R^1$ and $R^2$ are each hydrogen, and aryl is the radical.

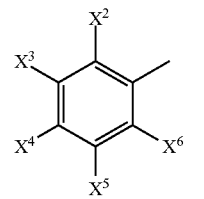

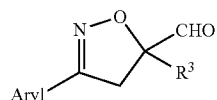

| No. | Aryl | $R^3$ | Physical data |
|---|---|---|---|
| 4.1123 | 3-fluoro-6-difluoromethoxyphenyl | methyl | |
| 4.1124 | 3-chloro-6-difluoromethoxyphenyl | methyl | |
| 4.1125 | 3-bromo-6-difluoromethoxyphenyl | methyl | |
| 4.1126 | 3-methyl-6-difluoromethoxyphenyl | methyl | |
| 4.1127 | 3-cyclopropyl-6-difluoromethoxyphenyl | methyl | |
| 4.1128 | 3-cyano-6-difluoromethoxyphenyl | methyl | |
| 4.1129 | 3-trifluoromethyl-6-difluoromethoxyphenyl | methyl | |
| 4.1130 | 3-methoxy-6-difluoromethoxyphenyl | methyl | |
| 4.1131 | 3-ethoxy-6-difluoromethoxyphenyl | methyl | |
| 4.1132 | 3-trifluoromethoxy-6-difluoromethoxy-phenyl | methyl | |
| 4.1133 | 3-nitro-6-difluoromethoxyphenyl | methyl | |
| 4.1134 | 3-fluoro-6-nitrophenyl | methyl | |
| 4.1135 | 3-chloro-6-nitrophenyl | methyl | |
| 4.1136 | 3-bromo-6-nitrophenyl | methyl | |
| 4.1137 | 3-methyl-6-nitrophenyl | methyl | |
| 4.1138 | 3-cyclopropyl-6-nitrophenyl | methyl | |
| 4.1139 | 3-cyano-6-nitrophenyl | methyl | |
| 4.1140 | 3-trifluoromethyl-6-nitrophenyl | methyl | |
| 4.1141 | 3-methoxy-6-nitrophenyl | methyl | |
| 4.1142 | 3-ethoxy-6-nitrophenyl | methyl | |
| 4.1143 | 3-trifluoromethoxy-6-nitrophenyl | methyl | |
| 4.1144 | 3-fluoro-6-methylsulfanylphenyl | methyl | |
| 4.1145 | 3-chloro-6-methylsulfanylphenyl | methyl | |
| 4.1146 | 3-bromo-6-methylsulfanylphenyl | methyl | |
| 4.1147 | 3-methyl-6-methylsulfanylphenyl | methyl | |
| 4.1148 | 3-ethyl-6-methylsulfanylphenyl | methyl | |
| 4.1149 | 3-cyclopropyl-6-methylsulfanylphenyl | methyl | |
| 4.1150 | 3-cyano-6-methylsulfanylphenyl | methyl | |
| 4.1151 | 3-trifluoromethyl-6-methylsulfanylphenyl | methyl | |
| 4.1152 | 3-methoxy-6-methylsulfanylphenyl | methyl | |
| 4.1153 | 3-ethoxy-6-methylsulfanylphenyl | methyl | |
| 4.1154 | 3-trifluoromethoxy-6-methylsulfanylphenyl | methyl | |
| 4.1155 | 3-nitro-6-methylsulfanylphenyl | methyl | |
| 4.1156 | 2,3,4-trifluorophenyl | methyl | |
| 4.1157 | 2,3,4-trichlorophenyl | methyl | |
| 4.1158 | 2,3,4-trimethylphenyl | methyl | |
| 4.1159 | 2-fluoro-2-chloro-5-trifluoromethylphenyl | methyl | |
| 4.1160 | 2,3,5-trifluorophenyl | methyl | |
| 4.1161 | 2,3,5-trichlorophenyl | methyl | |
| 4.1162 | 2,3,5-trimethylphenyl | methyl | |
| 4.1163 | 2,3-dichloro-5-methoxyphenyl | methyl | |
| 4.1164 | 2,3,6-trifluorophenyl | methyl | |
| 4.1165 | 2,3,6-trichlorophenyl | methyl | |
| 4.1166 | 2,3,6-trimethylphenyl | methyl | |
| 4.1167 | 3,4,5-trifluorophenyl | methyl | |
| 4.1168 | 3,4,6-trifluorophenyl | methyl | |
| 4.1169 | 3,4,6-trichlorophenyl | methyl | |
| 4.1170 | 3,4,6-trichlorophenyl | ethyl | |
| 4.1171 | 3,4,6-trichlorophenyl | CN | |
| 4.1172 | 3,4,6-trichlorophenyl | vinyl | |
| 4.1173 | 3,4,6-trichlorophenyl | fluoromethyl | |
| 4.1174 | 3,4,6-trichlorophenyl | methylcarbonyl | |
| 4.1175 | 3,4,6-trichlorophenyl | hydroxymethyl | |
| 4.1176 | 3,4,6-trichlorophenyl | ethynyl | |
| 4.1177 | 3,4,5-trimethylphenyl | methyl | |
| 4.1178 | 3,5-dimethyl-4-fluorophenyl | methyl | |
| 4.1179 | 3,5-dichloro-4-methoxyphenyl | methyl | |
| 4.1180 | 3,5-difluoro-4-chlorophenyl | methyl | |

TABLE 4-continued

Inventive compounds of the general formula (I) in which W* is CHO, $R^1$ and $R^2$ are each hydrogen, and aryl is the radical.

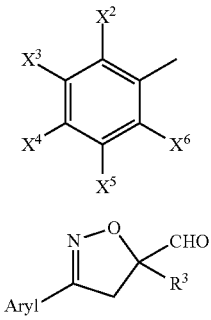

| No. | Aryl | $R^3$ | Physical data |
|---|---|---|---|
| 4.1181 | 3,5-dichloro-4-hydroxyphenyl | methyl | |
| 4.1182 | 3,5-trifluoromethyl-4-chlorophenyl | methyl | |
| 4.1183 | 3,4,6-trifluorophenyl | methyl | |
| 4.1184 | 3,4,6-trichlorophenyl | methyl | |
| 4.1185 | 3,4,6-trimethylphenyl | methyl | |
| 4.1186 | 2,3,4,5-pentafluorophenyl | methyl | |

B. FORMULATION EXAMPLES

1. Dusting Products

A dusting product is obtained by mixing 10 parts by weight of a compound of the formula (I) and 90 parts by weight of talc as an inert substance and comminuting the mixture in a hammer mill.

2. Dispersible Powder

A readily water-dispersible wettable powder is obtained by mixing 25 parts by weight of a compound of the formula (I), 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

3. Dispersion Concentrate

A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as a solvent and 10 parts by weight of ethoxylated nonylphenol as an emulsifier.

5. Water-Dispersible Granules

Water-dispersible granules are obtained by mixing
75 parts by weight of a compound of the formula (I),
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill, and granulating the powder in a fluidized bed by spray application of water as a granulating liquid.

Water-dispersible granules are also obtained by homogenizing and precomminuting, in a colloid mill,
25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
then grinding the mixture in a bead mill and atomizing and drying the suspension thus obtained in a spray tower by means of a one-phase nozzle.

C. BIOLOGICAL EXAMPLES

1. Pre-Emergence Herbicidal Action Against Harmful Plants

Seeds or rhizome pieces of mono- and dicotyledonous harmful plants are placed in sandy loam soil in pots having a diameter of 9 to 13 cm and covered with soil. The herbicides, formulated as emulsifiable concentrates or dusting products, are then applied in various dosages in the form of aqueous dispersions or suspensions or emulsions at an application rate of 300 to 800 l of water/ha (converted) to the surface of the covering soil. For further cultivation of the plants, the pots are then kept under optimal conditions in a greenhouse. After the test plants have been left to stand in the greenhouse for 3 to 4 weeks under optimal growth conditions, the activity of the inventive compounds is scored visually. For example, compounds No. 1.1.054, 1.1.2008, 1.1.462, 1.1.463, 1.1.494, 1.1.520, 1.1.527, 1.1.580, 1.1.603, 1.3.470, 1.2.471, 1.3.001, 1.3.473, 2.1.466, 2.1.478, 1.3.527, 2.1.522, 2.1.526, 2.1.546, 2.1.588, 2.2.472, 2.3.475, 2.3.528, 2.3.572, 2.6.462, 2.6.463, 2.6.464, 2.6.465, 2.6.467, 2.6.468, 2.6.469, 2.6.470, 2.6.471, 2.6.473, 2.6.474, 2.6.479, 2.6.480, 2.6.481, 2.6.486, 2.6.488, 2.6.489, 2.6.490, 2.6.541, 2.6.547, 2.6.553, 2.6.555 and 2.6.561 at an application rate of 320 grams per hectare each showed at least 80% efficacy against *Avena fatua*. Compounds No. 1.1.471, 1.1.519, 1.1.540, 1.1.580, 1.3.476, 1.3.571, 1.3.644, 2.1.523, 2.1.524, 2.1.532, 2.1.569, 2.2.530, 2.3.527, 2.3.534, 2.6.545, 2.6.548, 2.6.549, 2.6.550 and 2.6.552 at an application rate of 320 grams per hectare each showed at least 80% efficacy against *Stellaria media*. Compounds No. 1.1.566, 1.3.474, 2.1.531, 2.6.475 and 2.6.478 at an application rate of 320 grams per hectare each showed at least 80% efficacy against *Lolium multiflorum*.

2. Post-Emergence Herbicidal Action Against Harmful Plants

Seeds of monocotyledonous and dicotyledonous harmful plants are laid out in sandy loam in cardboard pots, covered with soil and cultivated in a greenhouse under good growth conditions. Two to three weeks after sowing, the test plants are treated at the three-leaf stage. The inventive compounds, formulated as wettable powders or as emulsion concentrates, are sprayed onto the surface of the green parts of the plants at an application rate of 600 to 800 l of water/ha (converted). After the test plants have been left to stand in the greenhouse for 3 to 4 weeks under optimal growth conditions, the activity of the inventive compounds is scored visually. For example, compounds No. 1.1.2009, 1.1.462, 1.1.463, 1.1.494, 1.1.519, 1.1.520, 1.1.529, 1.1.540, 1.1.566, 1.1.580, 1.2.470, 1.2.471, 1.2.525, 1.3.001, 1.3.004, 1.3.470, 1.3.472, 1.3.474, 1.3.473, 1.3.476, 1.3.486, 1.3.527, 1.3.528, 1.3.571, 1.3.644, 2.1.466, 2.1.478, 2.1.522, 2.1.526, 2.1.527, 2.1.530, 2.1.532, 2.1.546, 2.1.570, 2.1.588, 2.2.471, 2.2.472, 2.2.527, 2.3.475, 2.3.476, 2.3.527, 2.3.528, 2.3.534, 2.3.535, 2.3.572, 2.3.645, 2.6.009, 2.6.462, 2.6.463, 2.6.464, 2.6.467, 2.6.468, 2.6.469, 2.6.470, 2.6.471, 2.6.473, 2.6.474, 2.6.475, 2.6.476, 2.6.477, 2.6.478, 2.6.479, 2.6.480, 2.6.481, 2.6.486, 2.6.488, 2.6.489, 2.6.490, 2.6.494, 2.6.495, 2.6.541, 2.6.545, 2.6.546, 2.6.547, 2.6.548, 2.6.549, 2.6.552, 2.6.553, 2.6.554, 2.6.555 and 2.6.561 at an application rate of 320 grams per hectare each showed at least 80% efficacy against *Avena fatua*.

Compounds No. 1.1.2008, 1.1.1211, 1.1.527, 1.1.502, 1.1.925, 1.2.002, 1.2.528, 2.1.523, 2.1.524, 2.1.531, 2.1.670, 2.2.475, 2.6.465 and 2.6.550 at an application rate of 320 grams per hectare each showed at least 80% efficacy against *Veronica persica*.

The invention claimed is:
1. A 3-phenylisoxazoline derivative and/or salt thereof, of formula (I)

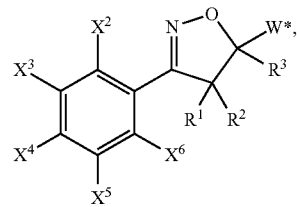

in which
R¹ and R² are each independently hydrogen, fluorine, chlorine, bromine, iodine, cyano, or $(C_1-C_4)$-alkyl or $(C_1-C_4)$-alkoxy each substituted by m radicals from the group consisting of fluorine, chlorine, bromine, iodine and cyano,
or
R¹ and R² together with the carbon atom to which they are bonded form a saturated or partly or fully unsaturated three-, four- or five-membered ring formed from q carbon atoms and p oxygen atoms;
R³ is fluorine, chlorine, cyano, $(C_1-C_3)$-alkylcarbonyloxy or $S(O)_nR^5$,
or $(C_1-C_6)$-alkyl, $(C_3-C_6)$-cycloalkyl, $(C_2-C_6)$-alkenyl or $(C_2-C_6)$-alkynyl each substituted by m radicals from the group consisting of fluorine, chlorine, bromine, iodine, cyano, $(C_1-C_4)$-alkoxy and hydroxyl,
or $(C_1-C_6)$-alkylcarbonyl, $(C_2-C_6)$-alkenylcarbonyl or $(C_3-C_6)$-cycloalkylcarbonyl each substituted by m radicals from the group consisting of fluorine, chlorine, bromine, iodine, and cyano;
R⁵ is $(C_1-C_6)$-alkyl or $(C_3-C_6)$-cycloalkyl each substituted by m radicals from the group consisting of fluorine, chlorine, bromine, iodine, cyano and hydroxyl;
R⁶ is hydrogen or R⁵;
R⁷ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;
R⁸ is R⁷;
W* is COOH, COOY, CN or CHO;
Y is $(C_1-C_8)$-alkyl which is substituted by m radicals from the group consisting of fluorine, chlorine, bromine, cyano, hydroxyl and COO—$(C_1-C_8)$-alkyl and which is interrupted by n heteroatoms from the group consisting of oxygen, sulfur and nitrogen, or
a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;
X², X⁴ and X⁶ are each independently hydrogen, fluorine, chlorine, bromine, iodine, cyano, nitro,
or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;
X³ is fluorine, chlorine, bromine, iodine, hydroxyl, cyano, nitro, SF₅, $CONR^8OSO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$,
or $(C_1-C_6)$-alkyl, $(C_2-C_6)$-alkenyl, $(C_2-C_6)$-alkynyl each substituted by m radicals from the group consisting of fluorine, chlorine, bromine, iodine, hydroxyl and cyano,
or $(C_1-C_6)$-alkoxy, $(C_3-C_6)$-cycloalkoxy $(C_2-C_6)$-alkenyloxy or $(C_2-C_6)$-alkynyloxy each substituted by m radicals from the group consisting of fluorine, chlorine, bromine, iodine, cyano and ($C_1$-$C_2$)-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;

m is 0, 1, 2, 3, 4 or 5;
n is 0, 1 or 2;
p is 0 or 1;
q is 3, 4 or 5;
with the proviso that
a) $X^3$ and $X^4$ are not both substituted or unsubstituted alkoxy,
b) in the compounds in which $R^3$ is methyl and W* is COOH, $X^5$ is not hydrogen, and
c) the compounds methyl 3-(3-cyanophenyl)-5-(isopropoxymethyl)-4,5-dihydro-1,2-oxazole-5-carboxylate, methyl 5-(butoxymethyl)-3-(3-cyanophenyl)-4,5-dihydro-1,2-oxazole-5-carboxylate, methyl 3-(3-cyanophenyl)-5-(methoxymethyl)-4,5-dihydro-1,2-oxazole-5-carboxylate, methyl 3-(3-cyanophenyl)-5-(2-methoxyethyl)-4,5-dihydro-1,2-oxazole-5-carboxylate, 3-(3-cyanophenyl)-5-(trifluoromethyl)-4,5-dihydro-1,2-oxazole-5-carboxylic acid, methyl 3-(3-cyanophenyl)-5-methyl-4,5-dihydro-1,2-oxazole-5-carboxylate, ethyl 3-(3-cyanophenyl)-5-methyl-4,5-dihydro-1,2-oxazole-5-carboxylate, methyl 5-methyl-3-(3-nitrophenyl)-4,5-dihydro-1,2-oxazole-5-carboxylate, methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

2. A 3-phenylisoxazoline derivative and/or salt as claimed in claim 1, in which $R^1$ and $R^2$ are each hydrogen, $R^3$ is ($C_1$-$C_6$)-alkyl, ($C_1$-$C_4$)-alkoxy-($C_1$-$C_4$)-alkyl, ($C_2$-$C_6$)-alkenyl, ($C_2$-$C_6$)-alkynyl, halo-($C_1$-$C_6$)-alkyl or halo-($C_2$-$C_6$)-alkenyl;

$R^5$ is ($C_1$-$C_6$)-alkyl or ($C_3$-$C_6$)-cycloalkyl each substituted by m radicals from the group consisting of fluorine, chlorine, bromine, iodine, cyano and hydroxyl;

$R^6$ is hydrogen or $R^5$;

$R^7$ is hydrogen or ($C_1$-$C_6$)-alkyl, ($C_3$-$C_6$)-cycloalkyl, ($C_2$-$C_4$)-alkenyl or ($C_2$-$C_4$)-alkynyl each substituted by m radicals from the group consisting of fluorine, chlorine, bromine, cyano and ($C_1$-$C_2$)-alkoxy;

$R^8$ is $R^7$;

W* is COOH or COOP;

Y is ($C_1$-$C_6$)-alkyl which is substituted by m radicals from the group consisting of fluorine, chlorine, bromine, cyano, hydroxyl and COO—($C_1$-$C_4$)-alkyl and which is interrupted by n oxygen atoms, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl each substituted by m radicals from the group consisting of fluorine, chlorine, bromine, iodine, cyano and ($C_1$-$C_4$)-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;

m is 0, 1, 2, 3, 4 or 5;
n is 0, 1 or 2;
with the proviso that
a) $X^3$ and $X^4$ are not both substituted or unsubstituted alkoxy,
b) in the compounds in which $R^3$ is methyl and W* is COOH, $X^5$ is not hydrogen, and
c) the compounds methyl 3-(3-cyanophenyl)-5-(isopropoxymethyl)-4,5-dihydro-1,2-oxazole-5-carboxylate, methyl 5-(butoxymethyl)-3-(3-cyanophenyl)-4,5-dihydro-1,2-oxazole-5-carboxylate, methyl 3-(3-cyanophenyl)-5-(methoxymethyl)-4,5-dihydro-1,2-oxazole-5-carboxylate, methyl 3-(3-cyanophenyl)-5-(2-methoxyethyl)-4,5-dihydro-1,2-oxazole-5-carboxylate, 3-(3-cyanophenyl)-5-(trifluoromethyl)-4,5-dihydro-1,2-oxazole-5-carboxylic acid, methyl 3-(3-cyanophenyl)-5-methyl-4,5-dihydro-1,2-oxazole-5-carboxylate, ethyl 3-(3-cyanophenyl)-5-methyl-4,5-dihydro-1,2-oxazole-5-carboxylate, methyl 5-methyl-3-(3-nitrophenyl)-4,5-dihydro-1,2-oxazole-5-carboxylate, methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

3. A 3-phenylisoxazoline derivative and/or salt as claimed in claim 1, in which
R$^1$ and R$^2$ are each hydrogen,
R$^3$ is (C$_1$-C$_4$)-alkyl, (C$_1$-C$_4$)-alkoxy-(C$_1$-C$_4$)-alkyl, vinyl, (C$_2$-C$_4$)-alkynyl, halo-(C$_1$-C$_4$)-alkyl or halo-(C$_2$-C$_4$)-alkenyl;
R$^5$ is methyl or ethyl;
R$^6$ is hydrogen or R$^5$;
R$^7$ is hydrogen or (C$_1$-C$_6$)-alkyl substituted by m radicals from the group consisting of fluorine and chlorine;
R$^8$ is R$^7$;
W* is COOH or COOP;
Y is (C$_1$-C$_6$)-alkyl which is substituted by m radicals from the group consisting of fluorine, chlorine, bromine, cyano, hydroxyl and COO—(C$_1$-C$_4$)-alkyl and which is interrupted by n oxygen atoms, or
a radical from the group consisting of (cyclohex-2-en-1-one)-3-yl, (propan-1-ol)-3-yl, (2,2-dimethyl propan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;
X$^2$, X$^4$ and X$^6$ are each independently hydrogen, fluorine, or chlorine,
or (C$_1$-C$_4$)-alkyl or (C$_1$-C$_4$)-alkoxy each substituted by m radicals from the group consisting of fluorine, chlorine, cyano and (C$_1$-C$_4$)-alkoxy;
X$^3$ is fluorine, chlorine, bromine, cyano,
or (C$_1$-C$_6$)-alkyl substituted by m radicals from the group consisting of fluorine and chlorine,
or (C$_1$-C$_6$)-alkoxy substituted by m radicals from the group consisting of fluorine and chlorine;
X$^5$ is hydrogen, fluorine, chlorine, bromine, cyano,
or (C$_1$-C$_6$)-alkyl substituted by m radicals from the group consisting of fluorine and chlorine,
or (C$_1$-C$_6$)-alkoxy substituted by m radicals from the group consisting of fluorine and chlorine;
m is 0, 1, 2 or 3;
n is 0, 1 or 2;
with the proviso that
a) X$^3$ and X$^4$ are not both substituted or unsubstituted alkoxy,
b) in the compounds in which R$^3$ is methyl and W* is COOH, X$^5$ is not hydrogen, and
c) the compounds methyl 3-(3-cyanophenyl)-5-(isopropoxymethyl)-4,5-dihydro-1,2-oxazole-5-carboxylate, methyl 5-(butoxymethyl)-3-(3-cyanophenyl)-4,5-dihydro-1,2-oxazole-5-carboxylate, methyl 3-(3-cyanophenyl)-5-(methoxymethyl)-4,5-dihydro-1,2-oxazole-5-carboxylate, methyl 3-(3-cyanophenyl)-5-(2-methoxyethyl)-4,5-dihydro-1,2-oxazole-5-carboxylate, 3-(3-cyanophenyl)-5-(trifluoromethyl)-4,5-dihydro-1,2-oxazole-5-carboxylic acid, methyl 3-(3-cyanophenyl)-5-methyl-4,5-dihydro-1,2-oxazole-5-carboxylate, ethyl 3-(3-cyanophenyl)-5-methyl-4,5-dihydro-1,2-oxazole-5-carboxylate, methyl 5-methyl-3-(3-nitrophenyl)-4,5-dihydro-1,2-oxazole-5-carboxylate, methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

4. A 3-phenylisoxazoline derivative and/or salt as claimed in claim 3, in which
X$^5$ is fluorine, chlorine, bromine, cyano,
or (C$_1$-C$_6$)-alkyl substituted by m radicals from the group consisting of fluorine and chlorine,
or (C$_1$-C$_6$)-alkoxy substituted by m radicals from the group consisting of fluorine and chlorine.

5. A herbicidal composition, comprising a herbicidally active content of at least one compound of the formula (I) and/or salt

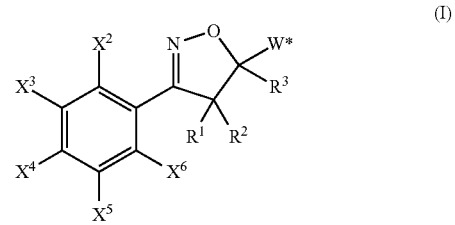

(I)

in which
R$^1$ and R$^2$ are each independently hydrogen, fluorine, chlorine, bromine, iodine, cyano, or (C$_1$-C$_4$)-alkyl or (C$_1$-C$_4$)-alkoxy each substituted by m radicals from the group consisting of fluorine, chlorine, bromine, iodine and cyano,
or
R$^1$ and R$^2$ together with the carbon atom to which they are bonded form a saturated or partly or fully unsaturated three-, four- or five-membered ring formed from q carbon atoms and p oxygen atoms;
R$^3$ is fluorine, chlorine, cyano, (C$_1$-C$_3$)-alkylcarbonyloxy or S(O)$_n$R$^5$,
or (C$_1$-C$_6$)-alkyl, (C$_3$-C$_6$)-cycloalkyl, (C$_2$-C$_6$)-alkenyl or (C$_2$-C$_6$)-alkenyl each substituted by m radicals from the group consisting of fluorine, chlorine, bromine, iodine, cyano, (C$_1$-C$_4$)-alkoxy and hydroxyl,
or (C$_1$-C$_6$)-alkylcarbonyl, (C$_2$-C$_6$)-alkenylcarbonyl or (C$_3$-C$_6$)-cycloalkylcarbonyl each substituted by m radicals from the group consisting of fluorine, chlorine, bromine, iodine, cyano and (C$_1$-C$_6$)-alkoxy;
R$^5$ is (C$_1$-C$_6$)-alkyl or (C$_3$-C$_6$)-cycloalkyl each substituted by m radicals from the group consisting of fluorine, chlorine, bromine, iodine, cyano and hydroxyl;
R$^6$ is hydrogen or R$^5$,
R$^7$ is hydrogen or (C$_1$-C$_6$)-alkyl, (C$_3$-C$_6$)-cycloalkyl, (C$_2$-C$_4$)-alkenyl or (C$_2$-C$_4$)-alkenyl each substituted by m radicals from the group consisting of fluorine, chlorine, bromine, cyano and (C$_1$-C$_2$)-alkoxy;
R$^8$ is R$^7$,
W* is COOH, COOY, CN or CHO;
Y is (C$_1$-C$_8$)-alkyl which is substituted by m radicals from the group consisting of fluorine, chlorine, bromine, cyano, hydroxyl and COO—(C$_1$-C$_8$)-alkyl and which is interrupted by n heteroatoms from the group consisting of oxygen, sulfur and nitrogen, or
a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

m is 0, 1, 2, 3, 4 or 5;
n is 0, 1 or 2;
p is 0 or 1;
q is 3, 4 or 5;

with the proviso that
a) $X^3$ and $X^4$ are not both substituted or unsubstituted alkoxy,
b) in the compounds in which $R^3$ is methyl and W* is COOH, $X^5$ is not hydrogen, and
c) the compounds methyl 3-(3-cyanophenyl)-5-(isopropoxymethyl)-4,5-dihydro-1,2-oxazole-5-carboxylate, methyl 5-(butoxymethyl)-3-(3-cyanophenyl)-4,5-dihydro-1,2-oxazole-5-carboxylate, methyl 3-(3-cyanophenyl)-5-(methoxymethyl)-4,5-dihydro-1,2-oxazole-5-carboxylate, methyl 3-(3-cyanophenyl)-5-(2-methoxyethyl)-4,5-dihydro-1,2-oxazole-5-carboxylate, 3-(3-cyanophenyl)-5-(trifluoromethyl)-4,5-dihydro-1,2-oxazole-5-carboxylic acid, methyl 3-(3-cyanophenyl)-5-methyl-4,5-dihydro-1,2-oxazole-5-carboxylate, ethyl 3-(3-cyanophenyl)-5-methyl-4,5-dihydro-1,2-oxazole-5-carboxylate, methyl 5-methyl-3-(3-nitrophenyl)-4,5-dihydro-1,2-oxazole-5-carboxylate, methyl 3-(3,5-di-tert-butyl-4-hydroxyphenyl)-5-methyl-4,5-dihydro-1,2-oxazole-5-carboxylate and ethyl 3-(3-chlorophenyl)-5-methyl-4,5-dihydro-1,2-oxazole-5-carboxylate are excluded.

6. The herbicidal composition as claimed in claim 5 in a mixture with one or more formulation auxiliaries.

7. The herbicidal composition as claimed in claim 5, comprising at least one further pesticidally active substance selected from the group consisting of insecticides, acaricides, herbicides, fungicides, safeners and growth regulators.

8. The herbicidal composition as claimed in claim 7, comprising a safener.

9. The herbicidal composition as claimed in claim 8, in which the safener is selected from the group consisting of mefenpyr-diethyl, cyprosulfamide, isoxadifen-ethyl, cloquintocet-mexyl, benoxacor and dichlormid.

10. The herbicidal composition as claimed in claim 7, comprising a further herbicide.

11. A method for controlling one or more unwanted plants comprising applying an effective amount of at least one compound of formula (Ia) to the one or more plants and/or a site of unwanted vegetation, wherein the compound of formula (Ia) is a 3-phenylisoxazoline derivative of formula (Ia)

(Ia)

in which
$R^1$ and $R^2$ are each independently hydrogen, fluorine, chlorine, bromine, iodine, cyano, or $(C_1-C_4)$-alkyl or $(C_1-C_4)$-alkoxy each substituted by m radicals from the group consisting of fluorine, chlorine, bromine, iodine and cyano, or
$R^1$ and $R^2$ together with the carbon atom to which they are bonded form a saturated or partly or fully unsaturated three-, four- or five-membered ring formed from q carbon atoms and p oxygen atoms;

$R^3$ is fluorine, chlorine, cyano, $(C_1-C_3)$-alkylcarbonyloxy or $S(O)_nR^5$, or $(C_1-C_6)$-alkyl, $(C_3-C_6)$-cycloalkyl, $(C_2-C_6)$-alkenyl or $(C_2-C_6)$-alkynyl each substituted by m radicals from the group consisting of fluorine, chlorine, bromine, iodine, cyano, $(C_1-C_4)$-alkoxy and hydroxyl, or $(C_1-C_6)$-alkylcarbonyl, $(C_2-C_6)$-alkenylcarbonyl or $(C_3-C_6)$-cycloalkylcarbonyl each substituted by m radicals from the group consisting of fluorine, chlorine, bromine, iodine, cyano and $(C_1-C_6)$-alkoxy;

$R^5$ is $(C_1-C_6)$-alkyl or $(C_3-C_6)$-cycloalkyl each substituted by m radicals from the group consisting of fluorine, chlorine, bromine, iodine, cyano and hydroxyl;

$R^6$ is hydrogen or $R^5$;

$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;

$R^8$ is $R^7$;

W* is COOH, COOY, CN or CHO;

Y is $(C_1-C_8)$-alkyl which is substituted by m radicals from the group consisting of fluorine, chlorine, bromine, cyano, hydroxyl and COO—$(C_1-C_8)$-alkyl and which is interrupted by n heteroatoms from the group consisting of oxygen, sulfur and nitrogen, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl each substituted by m radicals from the group consisting of fluorine, chlorine, bromine iodine, cyano and ($C_1$-$C_4$)-alkoxy;

$X^3$ is fluorine, chlorine, bromine, iodine, hydroxyl, cyano, nitro, $SF_5$, $CONR^8SO_2R^5$, $CONR^6R^8$, $COR^E$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^E$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_n R^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;

m is 0, 1, 2, 3, 4 or 5;
n is 0, 1 or 2;
p is 0 or 1;
q is 3, 4 or 5.

12. The method as claimed in claim 11, in which
$R^1$ and $R^2$ are each hydrogen,
$R^3$ is ($C_1$-$C_6$)-alkyl, ($C_1$-$C_4$)-alkoxy-($C_1$-$C_4$)-alkyl, ($C_2$-$C_6$)-alkenyl, ($C_2$-$C_6$)-alkynyl, halo-($C_1$-$C_6$)-alkyl or halo-($C_2$-$C_6$)-alkenyl;
$R^5$ is ($C_1$-$C_6$)-alkyl or ($C_3$-$C_6$)-cycloalkyl each substituted by m radicals from the group consisting of fluorine, chlorine, bromine, iodine, cyano and hydroxyl;
$R^6$ is hydrogen or $R^5$;
$R^7$ is hydrogen or ($C_1$-$C_6$)-alkyl, ($C_3$-$C_6$)-cycloalkyl, ($C_2$-$C_4$)-alkenyl or ($C_2$-$C_4$)-alkynyl each substituted by m radicals from the group consisting of fluorine, chlorine, bromine, cyano and ($C_1$-$C_2$)-alkoxy;
$R^8$ is $R^7$;
W* is COOH or COOP;

Y is ($C_1$-$C_6$)-alkyl which is substituted by m radicals from the group consisting of fluorine, chlorine, bromine, cyano, hydroxyl and COO—($C_1$-$C_4$)-alkyl and which is interrupted by n oxygen atoms, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl each substituted by m radicals from the group consisting of fluorine, chlorine, bromine, iodine, cyano and ($C_1$-$C_4$)-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;

m is 0, 1, 2, 3, 4 or 5;
n is 0, 1 or 2.

13. The method as claimed in claim 11, in which
$R^1$ and $R^2$ are each hydrogen,
$R^3$ is ($C_1$-$C_4$)-alkyl, ($C_1$-$C_4$)-alkoxy-($C_1$-$C_4$)-alkyl, vinyl, ($C_2$-$C_4$)-alkynyl, halo-($C_1$-$C_4$)-alkyl or halo-($C_2$-$C_4$)-alkenyl;
$R^5$ is methyl or ethyl,
$R^6$ is hydrogen or $R^5$;
$R^7$ is hydrogen or ($C_1$-$C_6$)-alkyl substituted by m radicals from the group consisting of fluorine and chlorine;
$R^8$ is $R^7$;
W* is COOH or COOP;
Y is ($C_1$-$C_6$)-alkyl which is substituted by m radicals from the group consisting of fluorine, chlorine, bromine, cyano, hydroxyl and COO—$(C_1$-$C_4)$-alkyl and which is interrupted by n oxygen atoms;

$X^2$, $X^4$ and $X^6$ are each independently hydrogen, fluorine, or chlorine, or $(C_1$-$C_4)$-alkyl or $(C_1$-$C_4)$-alkoxy each substituted by m radicals from the group consisting of fluorine, chlorine, cyano and $C_1$-$C_4)$-alkoxy;

$X^3$ is fluorine, chlorine, bromine, cyano, or $(C_1$-$C_6)$-alkyl substituted by m radicals from the group consisting of fluorine and chlorine, or $(C_1$-$C_6)$-alkoxy substituted by m radicals from the group consisting of fluorine and chlorine;

$X^5$ is hydrogen, fluorine, chlorine, bromine, cyano, or $(C_1$-$C_6)$-alkyl substituted by m radicals from the group consisting of fluorine and chlorine, or $(C_1$-$C_6)$-alkoxy substituted by m radicals from the group consisting of fluorine and chlorine;

m is 0, 1, 2 or 3;

n is 0, 1 or 2.

14. The method as claimed in claim 13, in which $X^5$ is fluorine, chlorine, bromine, cyano, or $(C_1$-$C_6)$-alkyl substituted by m radicals from the group consisting of fluorine and chlorine, or $(C_1$-$C_6)$-alkoxy substituted by m radicals from the group consisting of fluorine and chlorine.

15. A method for preparing a herbicidally active 3-phenylisoxazoline-5-carboxamide and/or 3-phenylisoxazoline-5-thioamide comprising employing a 3 phenylisoxazoline derivative of formula (Ia)

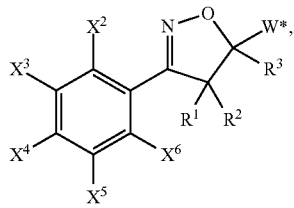

(Ia)

in which $R^1$ and $R^2$ are each independently hydrogen, fluorine, chlorine, bromine, iodine, cyano, or $(C_1$-$C_4)$-alkyl or $(C_1$-$C_4)$-alkoxy each substituted by m radicals from the group consisting of fluorine, chlorine, bromine, iodine and cyano, or $R^1$ and $R^2$ together with the carbon atom to which they are bonded form a saturated or partly or fully unsaturated three-, four- or five-membered ring formed from q carbon atoms and p oxygen atoms;

$R^3$ is fluorine, chlorine, cyano, $(C_1$-$C_3)$-alkylcarbonyloxy or $S(O)_nR^5$, or $(C_1$-$C_6)$-alkyl, $(C_3$-$C_6)$-cycloalkyl, $(C_2$-$C_6)$-alkenyl or $(C_2$-$C_6)$-alkynyl each substituted by m radicals from the group consisting of fluorine, chlorine, bromine, iodine, cyano, $(C_1$-$C_4)$-alkoxy and hydroxyl, or $(C_1$-$C_6)$-alkylcarbonyl, $(C_2$-$C_6)$-alkenylcarbonyl or $(C_3$-$C_6)$-cycloalkylcarbonyl each substituted by m radicals from the group consisting of fluorine, chlorine, bromine, iodine, cyano and $(C_1$-$C_6)$-alkoxy;

$R^5$ is $(C_1$-$C_6)$-alkyl or $(C_3$-$C_6)$-cycloalkyl each substituted by m radicals from the group consisting of fluorine, chlorine, bromine, iodine, cyano and hydroxyl;

$R^6$ is hydrogen or $R^5$;

$R^7$ is hydrogen or $(C_1$-$C_6)$-alkyl, $(C_3$-$C_6)$-cycloalkyl, $(C_2$-$C_4)$-alkenyl or $(C_2$-$C_4)$-alkynyl each substituted by m radicals from the group consisting of fluorine, chlorine, bromine, cyano and $(C_1$-$C_2)$-alkoxy;

$R^8$ is $R^7$;

W* is COOH, COOY, CN or CHO;

Y is $(C_1$-$C_8)$-alkyl which is substituted by m radicals from the group consisting of fluorine, chlorine, bromine, cyano, hydroxyl and COO—$(C_1$-$C_8)$-alkyl and which is interrupted by n heteroatoms from the group consisting of oxygen, sulfur and nitrogen, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or $(C_1$-$C_4)$-alkyl, $(C_3$-$C_5)$-cycloalkyl, $(C_2$-$C_4)$-alkenyl, $(C_2$-$C_4)$-alkynyl, $(C_1$-$C_4)$-alkoxy, $(C_2$-$C_4)$-alkenyloxy, $(C_2$-$C_4)$-alkynyloxy or $(C_1$-$C_4)$-alkylcarbonyl each substituted by m radicals from the group consisting of fluorine, chlorine, bromine iodine, cyano and $(C_1$-$C_4)$-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1$-$C_6)$-alkyl, $(C_2$-$C_6)$-alkenyl, $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1$-$C_6)$-alkyl, $(C_3$-$C_5)$-cycloalkyl, $(C_2$-$C_6)$-alkenyl, $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

m is 0, 1, 2, 3, 4 or 5;

n is 0, 1 or 2;

p is 0 or 1;

q is 3, 4 or 5.

16. The method as claimed in claim 15, in which $R^1$ and $R^2$ are each hydrogen, $R^3$ is $(C_1$-$C_6)$-alkyl, $(C_1$-$C_4)$-alkoxy-$(C_1$-$C_4)$-alkyl, $(C_2$-$C_6)$-alkenyl, $(C_2$-$C_6)$-alkynyl, halo-$(C_1$-$C_4)$-alkyl or halo-$(C_2$-$C_4)$-alkenyl;

$R^5$ is $(C_1-C_6)$-alkyl or $(C_3-C_6)$-cycloalkyl each substituted by m radicals from the group consisting of fluorine, chlorine, bromine, iodine, cyano and hydroxyl;

$R^6$ is hydrogen or $R^5$;

$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;

$R^8$ is $R^7$;

W* is COOH or COOP;

Y is $(C_1-C_6)$-alkyl which is substituted by m radicals from the group consisting of fluorine, chlorine, bromine, cyano, hydroxyl and COO—$(C_1-C_4)$-alkyl and which is interrupted by n oxygen atoms, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;

$X^3$ is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$X^5$ is hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

m is 0, 1, 2, 3, 4 or 5;

n is 0, 1 or 2.

17. The method as claimed in claim 15, in which $R^1$ and $R^2$ are each hydrogen, $R^3$ is $(C_1-C_4)$-alkyl, $(C_1-C_4)$-alkoxy-$(C_1-C_4)$-alkyl, vinyl, $(C_2-C_4)$-alkynyl, halo-$(C_1-C_4)$-alkyl or halo-$(C_2-C_4)$-alkenyl;

$R^5$ is methyl or ethyl, $R^6$ is hydrogen or $R^5$;

$R^7$ is hydrogen or $(C_1-C_6)$-alkyl substituted by m radicals from the group consisting of fluorine and chlorine;

$R^8$ is $R^7$;

W* is COOH or COOP;

Y is $(C_1-C_6)$-alkyl which is substituted by m radicals from the group consisting of fluorine, chlorine, bromine, cyano, hydroxyl and COO—$(C_1-C_4)$-alkyl and which is interrupted by n oxygen atoms, or a radical from the group consisting of (cyclohex-2-en-1-one)-3-yl, (propan-1-ol)-3-yl, (2,2-dimethylpropan-1-ol)-3-yl, (methyl 2,2-dimethylpropanoate)-3-yl, (methyl propanoate)-3-yl, (ethyl propanoate)-3-yl, (ethyl butanoate)-3-yl, (ethyl (3R)-4,4,4-trifluorobutanoate)-3-yl, (butan-2-one)-4-yl, (3-methylbutan-2-one)-4-yl, (pent-3-en-2-one)-4-yl,((2S)-dimethyl butanedioate)-2-yl, (dimethyl pentanedioate)-3-yl, (methyl (2R)-2-methylpropanoate)-3-yl, 4-methoxycarbonylbenzyl, 3,5-difluorobenzyl, 3,4-difluorobenzyl, 2,6-difluorobenzyl, 5-methylpyridin-3-ylmethyl, tetrahydrofuran-3-yl and (butan-1-ol)-4-yl;

$X^2$, $X^4$ and $X^6$ are each independently hydrogen, fluorine, or chlorine, or $(C_1-C_4)$-alkyl or $(C_1-C_4)$-alkoxy each substituted by m radicals from the group consisting of fluorine, chlorine, cyano and $(C_1-C_4)$-alkoxy;

$X^3$ is fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine;

$X^5$ is hydrogen, fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine;

m is 0, 1, 2 or 3;

n is 0, 1 or 2.

18. The method as claimed in claim 17, in which $X^5$ is fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine.

19. A method for controlling one or more unwanted plants, comprising applying an effective amount of at least one compound of formula (I) as claimed in claim 1 to the one or more plants and/or a site of unwanted vegetation.

20. A method for controlling one or more unwanted plants, comprising applying an effective amount of the composition as claimed in claim 5 to the one or more unwanted plants and/or site of unwanted vegetation.

21. A method for controlling one or more unwanted plants in one or more crops of one or more useful plants, comprising applying an effective amount of the compound as claimed in claim 2 to the one or more unwanted plants and/or site of unwanted vegetation.

22. The method as claimed in claim 21, wherein the one or more useful plants are one or more transgenic useful plants.

23. The 3-phenylisoxazoline derivative as claimed in claim 1, which is compound 1.1.462, in which
$R^1$ and $R^2$ are each hydrogen,
$R^3$ is methyl;
W* is COOH;
$X^2$, $X^4$ and $X^6$ are each independently hydrogen; and
$X^3$ and $X^5$ are each independently fluorine.

24. The 3-phenylisoxazoline derivative as claimed in claim 1, which is compound 1.1.519, in which
$R^1$ and $R^2$ are each hydrogen,
$R^3$ is methyl;
W* is COOH;
$X^2$, $X^4$ and $X^6$ are each independently hydrogen; and
$X^3$ and $X^5$ are each independently chlorine.

25. The 3-phenylisoxazoline derivative as claimed in claim 1, which is compound 1.1.580, in which
$R^1$ and $R^2$ are each hydrogen,
$R^3$ is methyl;
W* is COOH;
$X^2$, $X^4$ and $X^6$ are each independently hydrogen;
$X^3$ is trifluoromethyl; and
$X^5$ is bromine.

26. The 3-phenylisoxazoline derivative as claimed in claim 1, which is compound 1.3.4, in which
$R^1$ and $R^2$ are each hydrogen,
$R^3$ is 1-chlorovinyl;
W* is COOH;
$X^4$, $X^5$ and $X^6$ are each independently hydrogen; and
$X^3$ is fluorine.

27. The 3-phenylisoxazoline derivative as claimed in claim 1, which is compound 1.3.470, in which
$R^1$ and $R^2$ are each hydrogen,
$R^3$ is vinyl;
W* is COOH;
$X^2$, $X^4$ and $X^6$ are each independently hydrogen; and
$X^3$ and $X^5$ are each independently fluorine.

28. The 3-phenylisoxazoline derivative as claimed in claim 1, which is compound 2.1.33, in which
$R^1$ and $R^2$ are each hydrogen,
$R^3$ is methyl;
W* is COOP;
$X^2$, $X^4$, $X^5$ and $X^6$ are each independently hydrogen;
$X^3$ is acetyl; and
Y is ethyl.

29. The 3-phenylisoxazoline derivative as claimed in claim 1, which is compound 2.2.472, in which
$R^1$ and $R^2$ are each hydrogen,
$R^3$ is difluoromethyl;
W* is COOP;
$X^2$, $X^4$ and $X^6$ are each independently hydrogen;
$X^3$ and $X^5$ are each independently fluorine; and
Y is ethyl.

30. The 3-phenylisoxazoline derivative as claimed in claim 1, which is compound 2.2.527, in which
$R^1$ and $R^2$ are each hydrogen,
$R^3$ is chloromethyl;
W* is COOP;
$X^2$, $X^4$ and $X^6$ are each independently hydrogen;
$X^3$ and $X^5$ are each independently chlorine; and
Y is ethyl.

31. The 3-phenylisoxazoline derivative as claimed in claim 1, which is compound 2.3.475, in which
$R^1$ and $R^2$ are each hydrogen,
$R^3$ is vinyl;
W* is COOP;
$X^2$, $X^4$ and $X^6$ are each independently hydrogen;
$X^3$ is chlorine;
$X^5$ is fluorine; and
Y is methyl.

32. The 3-phenylisoxazoline derivative as claimed in claim 1, which is compound 2.6.546, in which
$R^1$ and $R^2$ are each hydrogen,
$R^3$ is methyl;
W* is COOP;
$X^2$, $X^4$ and $X^6$ are each independently hydrogen;
$X^3$ and $X^5$ are each independently chlorine; and
Y is (ethyl propanoate)-3-yl.

* * * * *